US008236826B2

(12) United States Patent
Matsuyama et al.

(10) Patent No.: US 8,236,826 B2
(45) Date of Patent: Aug. 7, 2012

(54) DIARYLETHER DERIVATIVES AS ANTITUMOR AGENTS

(75) Inventors: Hironori Matsuyama, Otsu (JP); Kenji Ohnishi, Otsu (JP); Takashi Nakagawa, Otsu (JP); Hideki Takasu, Otsu (JP); Makoto Sakamoto, Otsu (JP); Kumi Higuchi, Otsu (JP); Keisuke Miyajima, Otsu (JP); Satoshi Yamada, Otsu (JP); Masaaki Motoyama, Otsu (JP); Yutaka Kojima, Otsu (JP); Koichi Yasumura, Otsu (JP); Takeshi Kodama, Otsu (JP); Shun Otsuji, Otsu (JP); Keizo Kan, Tokushima (JP); Takumi Sumida, Otsu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 695 days.

(21) Appl. No.: 12/095,930

(22) PCT Filed: Dec. 4, 2006

(86) PCT No.: PCT/JP2006/324610

§ 371 (c)(1), (2), (4) Date: May 15, 2009

(87) PCT Pub. No.: WO2007/066784

PCT Pub. Date: Jun. 14, 2007

(65) Prior Publication Data

US 2010/0004438 A1 Jan. 7, 2010

(30) Foreign Application Priority Data

Dec. 5, 2005 (JP) ................................ 2005-351255

(51) Int. Cl.
*A61K 31/44* (2006.01)

(52) U.S. Cl. ......... 514/349; 514/619; 546/297; 564/123

(58) Field of Classification Search .................. 540/575; 544/130, 169, 360, 391; 546/194, 224, 297
See application file for complete search history.

(56) References Cited

U.S. PATENT DOCUMENTS

| | | | |
|---|---|---|---|
| 3,182,085 A | 5/1965 | Pitchforth et al. | |
| 3,715,375 A | 2/1973 | Shen et al. | |
| 4,153,775 A | 5/1979 | Winkelmann et al. | |
| 4,211,699 A | 7/1980 | Winkelmann et al. | |
| 4,482,721 A | 11/1984 | Wegner et al. | |
| 4,978,672 A | 12/1990 | Bowman et al. | |
| 5,210,169 A | 5/1993 | Mühlebach et al. | |
| 5,401,772 A | 3/1995 | Yokoyama et al. | |
| 6,511,995 B1 | 1/2003 | Edamatsu et al. | |
| 2001/0029250 A1 | 10/2001 | Karras | |
| 2002/0065296 A1 | 5/2002 | Dumas et al. | |
| 2007/0270422 A1* | 11/2007 | Fukushima et al. | 514/235.5 |
| 2010/0210661 A1* | 8/2010 | Sekiguchi et al. | 514/252.11 |
| 2010/0261720 A1* | 10/2010 | Sumida et al. | 514/230.8 |

FOREIGN PATENT DOCUMENTS

| | | | |
|---|---|---|---|
| DE | 2146450 | | 9/1971 |
| EP | 0 580 550 | A1 | 1/1994 |
| EP | 1 101 755 | A1 | 5/2001 |
| EP | 1 211 235 | A2 | 6/2002 |
| EP | 1 256 341 | A1 | 11/2002 |
| EP | 1 604 981 | A1 | 12/2005 |
| GB | 1 353 520 | | 5/1974 |
| GB | 1 494 117 | | 12/1977 |
| GB | 2 374 009 | A | 10/2002 |
| JP | 2001-89412 | | 4/2001 |
| JP | 2001-89450 | | 4/2001 |

(Continued)

OTHER PUBLICATIONS

A.M. Traynor et al., Drugs of Today, 40(8), 697-710, 698 (2004).*
F.F. De Arruda, et al., Int. J. Radiation Oncology Biol. Phys., 64(2), 363-373 (2006).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
B.C. Bastian, Genetic Progression, in From Melanocytes to Melanoma the Progression to Malignancy 197, 201 (V. J. Hearing et al., eds., 2006).*
L. Pusztai, Histopathologic and Molecular Markers of Prognosis and Response to Therapy, in Breast Cancer 324, 326-328 (Kelly k. Hunt et al., ed., 2nd ed., 2008).*

(Continued)

*Primary Examiner* — James O Wilson
*Assistant Examiner* — Alexander R Pagano
(74) *Attorney, Agent, or Firm* — Finnegan, Henderson, Farabow, Garrett & Dunner, L.L.P.

(57) ABSTRACT

An object of the present invention is to provide a medicinal drug much improved in anti tumor activity and excellent in safety. According to the present invention, there is provided a medicinal drug containing a compound represented by the following general formula (1) or a salt thereof as an active ingredient: [Formula 1] wherein $X_1$ represents a nitrogen atom or a group —CH═, $R^1$ represents a group —Z—$R^6$, in which Z represents a group —CO—, a group —CH(OH)— or the like, $R^6$ represents a 5- to 15-membered monocyclic, dicyclic or tricyclic saturated or unsaturated heterocyclic group having 1 to 4 nitrogen atoms, oxygen atoms or sulfur atoms, $R^2$ represents a hydrogen atom or a halogen atom, Y represents a group —O—, a group —CO—, a group —CH(OH)— or a lower alkylene group, and A represents [Formula 2] wherein $R^3$ represents a hydrogen atom, a lower alkoxy group or the like, p represents 1 or 2, $R^4$ represents an imidazolyl lower alkyl group or the like.

[1]

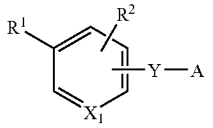

[2]

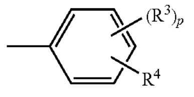

6 Claims, No Drawings

FOREIGN PATENT DOCUMENTS

| | | | | |
|---|---|---|---|---|
| JP | 2002-507601 | | | 3/2002 |
| JP | 2004-35475 | | | 2/2004 |
| RU | 2003101342 | | | 7/2004 |
| WO | WO-95/01326 | | | 1/1995 |
| WO | WO-96/40620 | | | 12/1996 |
| WO | WO-99/24404 | | | 5/1999 |
| WO | WO-99/40073 | | | 8/1999 |
| WO | WO-99/40083 | | | 8/1999 |
| WO | WO-99/48871 | | | 9/1999 |
| WO | WO-00/00470 | | | 1/2000 |
| WO | WO-02/32408 | A2 | | 4/2000 |
| WO | WO-00/42012 | | | 7/2000 |
| WO | WO-00/46203 | | | 8/2000 |
| WO | WO-00/58279 | | | 10/2000 |
| WO | WO-01/02359 | A1 | | 11/2001 |
| WO | WO 01/90101 | A1 | | 11/2001 |
| WO | WO-01/98256 | A1 | | 12/2001 |
| WO | WO-02/16358 | A2 | | 2/2002 |
| WO | WO-02/26191 | A2 | | 4/2002 |
| WO | WO-02/053150 | A1 | | 7/2002 |
| WO | WO-02/102787 | A2 | | 12/2002 |
| WO | WO-03/018586 | A1 | | 3/2003 |
| WO | WO-03/035602 | A1 | | 5/2003 |
| WO | WO-03/035627 | A1 | | 5/2003 |
| WO | WO-03/070728 | A2 | | 8/2003 |
| WO | WO-03/076406 | A1 | | 9/2003 |
| WO | WO-2004/080966 | A1 | | 9/2004 |
| WO | WO 2004080966 | A1 | * | 9/2004 |
| WO | WO-2005/007621 | A2 | | 1/2005 |
| WO | WO-2005/009940 | A1 | | 2/2005 |
| WO | WO-2006/014012 | A2 | | 2/2006 |
| WO | WO 2006014012 | A2 | * | 2/2006 |

OTHER PUBLICATIONS

S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
K. Odunsi et al, Molecular Biology of Gynecological Cancers, in 2 Cancer Principles & Practice of Oncology 1487, 1492 (V.T. DeVita, Jr. et al. eds., 8th ed., 2008).*
S.K. Libutti, Colon Cancer in, 1 Cancer Principles & Practice of Oncology 1232, 1243 (V.T. DeVita, Jr. et al. eds., 8th ed., 2008).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
A. Kamb, Nature Reviews Drug Discovery 2, 161-165 (2005).*
N.F. Smith, Molecular Cancer Therapeutics, 6, 428-440, 428 (2007).*
N.E. Sharpless et al., Nature Reviews Drug Discovery 5, 741-754, 742 (2006).*
K.P. Olive et al., Clinical Cancer Research 12, 5277-5287 (2006).*
C. Abad-Zapatero, Drug Discovery Today, 1-8 (2010).*
Collins, Current Signal Transduction Therapy, 1, 13-14 (2006).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
P. Kumar et al, Journal of Thoracic and Cardiovascular Surgery, 125(6) 1321-1327, 1322 (2003).*
Machine translation of R. Nishizawa et al. WO2004/080966 (Sep. 23, 2004).*
A.T. Hawley et al., Etiology of Cancer: Cancer Susceptibility Syndromes, in 2 Cancer Principles & Practice of Oncology 157-168, 157 (V.T. DeVita, Jr. et al. eds., 8th ed., 2008).*
Q. Lin et al., 11 Organic Letters, 1999 (2009).*
Balcells et al.; "Synthesis of Phenoxyphenyl Pyride and Pyrazine Carboxamides. Activity Against *Cydia pomonella* (L.) Eggs"; J. Agric Food Chem., vol. 48, No. 1, pp. 83-87, (2000).
Mühlebach; "Pyrazoles—A Novel Class of Blocking Agents for Isocyanates"; Journal of Polymer Science, vol. 32, No. 4, pp. 735-765, (1994).
Bethegnies et al.; "Substituted Phenylthiophenylamines With Antiinflammatory Activity"; IL Farmaco, vol. 44, Nos. 7-8, pp. 683-694, (1989).
Anagnostou et al.; "Synthesis of Blocked MDI Adducts, Their DSC Evaluation and Effect of Pigmentation"; Journal of Coating Technology, vol. 53, No. 673, pp. 35-45, (1981).
Molina, Vered et al., "Intravenous Immunoglobulin and Fibrosis," Clinical Reviews in Allergy & Immunology, vol. 29, No. 3, pp. 321-326 (2005).
Korean Office Action for Korean Patent Application No. 10-2009-7006358 dated Apr. 1, 2011.
English Translation of Korean Office Action for Korean Patent Application No. 10-2009-7006358 dated Apr. 1, 2011.
George et al., "Metabolic Activation Stimulates Acid Secretion and Expression of Matrix Degrading Proteases in Human Osteoblasts", Annals of the Rheumatic Diseases, vol. 63, No. 1, pp. 67-70, (2004).
Barnstein et al., "STAT5 Expression Is Required for IgE-Mediated Mast Cell Function", The Journal of Immunology, vol. 177, pp. 3421-3426, (2006).
Gao et al., "Disruption of Neural Signal Transducer and Activator of Transcription 3 Causes Obesity, Diabetes, Infertility, and Thermal Dysregulation", PNAS, vol. 101, No. 13, pp. 4661-4666, (2004).
Sano et al., "STAT3 Links Activated Keratinocytes and Immunocytes Required for Development of Psoriasis in a Novel Transgenic Mouse Model", Nature Medicine, vol. 11, No. 1, pp. 43-49, (2005).
Yoshida et al., "Activation of STAT3 by the Hepatitis C Virus Core Protein Leads to Cellular Transformation", The Journal of Experimental Medicine, vol. 196, No. 5, pp. 641-653, (2002).
Maggio et al., "Interleukin-6 in Aging and Chronic Disease: A Magnificent Pathway", The Journal of Gerontology, vol. 61A, No. 6, pp. 575-584, (2006).
Decision of Grant for Russian Application No. 2007-108298 dated Oct. 13, 2010.
Belikov, V.G., "Pharmaceutical Chemistry," Highest School, Moscow, pp. 43-47 (1993).
European Office Action for EP Application No. 05 780 290.2-1521 dated Sep. 15, 2011.
Final Office Action for copending U.S. Appl. No. 11/659,689 dated Dec. 22, 2010.
Final Office Action in U.S. Appl. No. 12/311,500 dated Oct. 5, 2011.
Gao, H. et al. "Stat3 and Suppressor of Cytokine Signaling 3: Potential Targets in Lung Inflammatory Responses," Expert Opin. Ther. Targets 11:869-880 (2007).
Kholodov, L.E. et al., "Clinic Pharmacokinetics," Manual, Medicine, Moscow, pp. 83-98, 134-138, 160, 378-380, (1985).
Levinthal, MD., G.N. et al., "Liver Disease and Diabetes Mellitus," Clinical Diabetes 17(2) (1999).
Montori, V. et al., "Waking Up From the DREAM of Preventing Diabetes With Drugs," BMJ 334:882-884 (2007).
Mosby Medical Encyclopedia, Revised Edition, p. 320 (1996).
Notice of Allowance in U.S. Appl. No. 11/659,689 mailed Sep. 26, 2011.
Office Action for copending U.S. Appl. No. 11/659,689 dated May 25, 2011.
Office Action for copending U.S. Appl. No. 12/311,500 dated Oct. 5, 2011.
Restriction Requirement in U.S. Appl. No. 11/659,689 mailed Dec. 30, 2009.
Restriction Requirement in U.S. Appl. No. 11/659,689 mailed Sep. 18, 2009.
Restriction Requirement in U.S. Appl. No. 12/311,500 dated Dec. 9, 2010.
Russian Office Action for Russian Application No. 2009116653 dated Oct. 21, 2011.
Sergeev, Professor, "Short Course of Molecular Pharmacology," Moscow Medical Institute, Moscow, p. 10, (1975).

* cited by examiner

DIARYLETHER DERIVATIVES AS ANTITUMOR AGENTS

BACKGROUND OF THE INVENTION (1) Field of the Invention

The present invention relates to a medicinal drug.

(2) Description of Related Art

Since the clinical use of nitrogen mustard as an anticancer agent was started in the 1940s for the first time in the world, numerous anticancer drugs have ever been developed. Actually, for example, antimetabolites such as 5-fluorouracil, antitumor antibiotics such as adriamycin, platinum complex such as cisplatin, and plant-derived carcinostatics such as vindesine have been subjected to clinical use.

However, most of these carcinostatics have significant side effects such as digestive disorders, myelosuppression and alopecia since they are cytotoxic also to normal cells. Due to the side effects, their range of application is limited. In addition, the therapeutic effects themselves are partial and short, in most cases.

Developments of new carcinostatics in place of these has been made; however, satisfactory results have not yet been obtained. Patent documents 1 and 2 disclose that certain kinds of compounds have fibrosing inhibitory actions. However, it is not known whether the compounds have antitumor actions.

[Patent Document 1] WO/2006/014012

[Patent Document 2] JP-A-2004-35475

BRIEF SUMMARY OF THE INVENTION

An object of the present invention is therefore to provide an excellent medicinal drug such as a therapeutic drug for a tumor, particularly, a therapeutic drug for a malignant tumor.

The present inventors intensively conducted studies with the view to attaining the aforementioned object. As a result, they found that a compound represented by the general formula (1) below and a salt thereof have an excellent antitumor effect. The present invention has been achieved based on the finding.

More specifically, the present invention provides medicinal drugs shown in items 1 to 58.

Item 1: An antitumor agent comprising a compound represented by the general formula (1) below or a salt thereof as an active ingredient:

(1)

[Formula 1]

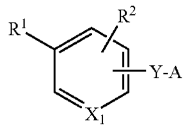

wherein $X_1$ represents a nitrogen atom or a group —CH═, $R^1$ represents a group —Z—$R^6$, Z represents a group —N($R^8$)—B—, a group —B—N($R^8$)—, a group —$B_0$—O—, a group

[Formula 2]

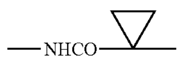

a group —CO—, a group —CH(OH)—, a group N($R^{9a}$—CO—N—($R^{9b}$)—, a group —N═CH—, a group —N($R^{10a}$)—$SO_2$—($B_{22a}$)e-, a lower alkenylene group, a group —NHCO—$B_1$—, a group —NHCO—$B_2$—(W)u-, a group —$B_0$—$B_{19a}$—, a group

[Formula 3]

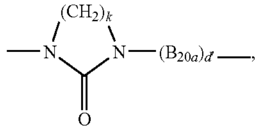

a group

[Formula 4]

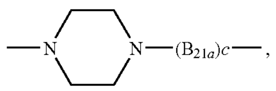

a group —$SO_2$—N($R^{10b}$)—, a group —S—, a lower alkynylene group, a lower alkylene group, a group —N($R^{8d}$)— or a group —CO—NH—$B_{18a}$—, $R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, $B_0$ represents a lower alkylene group, $B_1$ represents a lower alkenylene group that may have a phenyl group as a substituent, $B_2$ represents a lower alkylene group that may be substituted by a group selected from the group consisting of a lower alkoxy group and a phenyl group, $R^{9a}$ represents a hydrogen atom or a lower alkyl group, $R^{9b}$ represents a hydrogen atom or a lower alkyl group, $R^{10}$ represents a hydrogen atom or a lower alkyl group, $B_{22a}$ represents a lower alkylene group or a lower alkenylene group, e represents 0 or 1, $B_{18}$ represents a lower alkylene group, $B_{19a}$ represents a lower alkylene group, $B_{20a}$ represents a lower alkylene group, $B_{21a}$ represents a lower alkylene group, k represents 2 or 3, c represents 0 or 1, d' represents 0 or 1, $R^{10b}$ represents a hydrogen atom or a lower alkyl group, $R^{8d}$ represents a hydrogen atom or a lower alkyl group, W represents an oxygen atom, a group —NH—, or a sulfur atom, u represents 0 or 1, $R^6$ represents 5- to 15-membered monocyclic, dicyclic or tricyclic saturated or unsaturated heterocyclic group having 1 to 4 nitrogen atoms, oxygen atoms or sulfur atoms (that may have 1 to 3 substituents, which are selected from the group consisting of an oxo group; a lower alkoxy group that may have a halogen atom as a substituent; a lower alkyl group that may have a halogen atom as a substituent; a halogen atom; a lower alkylsulfonyl group; a phenyl group that may be substituted by a lower alkyl group that may have a halogen atom on the phenyl ring; a lower alkylthio group, a pyrrolyl group, a benzoyl group; a lower alkanoyl group; lower alkoxycarbonyl group; and an amino group that may have a group selected from the group consisting of a lower alkyl group and a lower alkanoyl group as a substituent, on the heterocyclic ring), an adamantly group, a naphthyl group (that may have 1 to 3 groups selected from the group consisting of a lower alkyl group, a halogen atom, and an amino group that may have a group selected from the group consisting of a lower alkyl group and a lower alkanoyl group as a substituent, on the naphthalene ring), an alkyl group that may have a lower alkoxy group as a substituent, a cycloalkyl group that may be substituted by a group selected from the group consisting of an amino substituted lower alkyl group that may have a lower alkyl group and a lower alkyl group that may have a halogen atom as a substituent, on the cycloalkyl ring, a lower alkenyl group that may have a halogen atom as a substituent, a lower alkanoyl group, a benzoyl group (that may have 1 to 3 groups selected from the group consisting of a lower alkyl group that may have a halogen atom and halogen atom, as a substituents, on the phenyl ring), a halogen atom substituted lower alkyl group, cycloalkyl lower alkyl group or a group

[Formula 5]

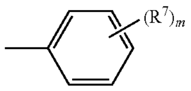

$R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group or a 5- or 6-membered saturated or unsaturated heterocyclic group having 1 to 4 nitrogen atoms, oxygen atoms, or sulfur atoms (that may have an oxo group on the heterocyclic ring), m represents an integer from 1 to 5 (when m represents 2 to 5, two to five $R^7$s may be identical or different) and $R^2$ represents a hydrogen atom, a halogen atom, or a lower alkyl group, Y represents a group —O—, a group —$N(R^5)$—, a group —CO—, a group —CH(OH)—, a lower alkylene group, a group —

S(O)n-, or a group —C(=N—OH)—, $R^5$ represents a hydrogen atom, a lower alkyl group, a lower alkanoyl group, a benzoyl group, a phenyl lower alkyl group, or a cycloalkyl group, n represents 0, 1, or 2, A represents a group

[Formula 6]

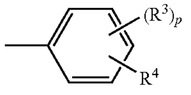

or a group

[Formula 7]

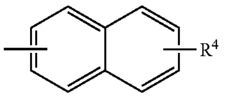

p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —$CONR^{11}R^{12}$, or a cyano group, wherein $R^{11}$ and $R^{12}$ may be identical or different and each represent a hydrogen atom, a lower alkyl group, a cycloalkyl group, or a phenyl group, and $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring, $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

[Formula 8]

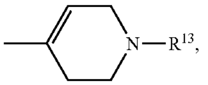

a group

[Formula 9]

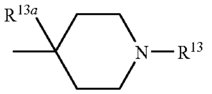

or a group $-(T)_1-N(R^{14})R^{15}$, $R^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, $R^{13a}$ represents a hydrogen atom or a hydroxyl group, T represents a lower alkylene group, a group —$N(R^{17})$—$B_3$—CO—, a group —$B_{19}$—$N(R^{18})$—CO—, a group —$B_4$—CO—, a group -Q-$B_5$—CO—, a group —$B_6$—N $(R^{19})$—$B_7$—CO—, a group —CO—$B_8$—, a group —CH(OH)—$B_9$—, a group —CO—$B_{10}$—CO—, a group —CH(OH)—$B_{11}$—CO—, a group —CO—, a group —$SO_2$—, or a group —$B_{23a}$—CO—CO—, wherein $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, $B_3$ represents a lower alkylene group, $B_{19}$ represents a lower alkylene group, $R^{18}$ represents a hydrogen atom or a lower alkyl group, $B_4$ represents a lower alkenylene group or a lower alkylene group that may have a hydroxyl group as a substituent, Q represents an oxygen atom or a group —S(O)n- (wherein n is the same as described above), $B_5$ represents a lower alkylene group, $B_6$ represents a lower alkylene group, $R^{19}$ represents a hydrogen atom or a lower alkanoyl group, $B_7$ represents a lower alkylene group, $B_8$ represents a lower alkylene group, $B_9$ represents a lower alkylene group, $B_{10}$ represents a lower alkylene group, $B_{11}$ represents a lower alkylene group, $B_{23a}$ represents a lower alkylene group, l represents 0 or 1, $R^{14}$ represents a hydrogen atom or an alkyl group that may have a hydroxyl group as a substituent, $R^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

[Formula 10]

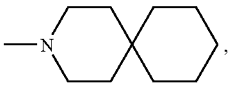

(26) a carbonyl lower alkyl group substituted by a group

[Formula 11]

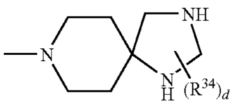

(27) a group —CO—$B_{20}$—$N(R^{36})R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group, d represents an integer from 0 to 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 phenyl lower alkyl groups that may have a lower alkylenedioxy group on the phenyl ring, may be present as a substituent(s), $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

[Formula 12]

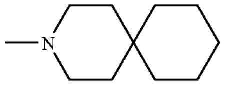

wherein, on the heterocyclic ring, 1 to 3 substituents may be present which are selected from the group consisting of (28) a phenyl-substituted lower alkyl group, which has 1 to 2 phenyl groups that may be substituted by 1 to 3 groups on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, and that may have a pyridyl group on the lower alkyl group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

[Formula 13]

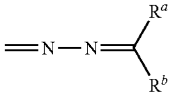

(wherein $R^a$ and $R^b$ each represent a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group $-(B_{12}CO)t\text{-}N(R^{20})R^{21}$, (50) a group $-(CO)o\text{-}B_{13}-N(R^{22})R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadizole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group $-(O-B_{15})s\text{-}CO-N(R^{26})R^{27}$, (85) a group $-N(R^{28})-CO-B_{16}-N(R^{29})R^{30}$, (86) a group $-N(R^{31})-B_{17}-CO-N(R^{32})R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, $R^{20}$ and $R^{21}$ may be identical or different and each represent a hydrogen atom; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or a cycloalkyl group; and $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring), o represents 0 or 1, $B_{13}$ represents a lower alkylene group, $R^{22}$ and $R^{23}$ may be identical or different and each represent a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group and a phenyl lower alkyl group that may have a lower alkylenedioxy group as a substituent on the phenyl ring), $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, (wherein, on the heterocyclic ring, 1 to 3 phenyl lower alkyl groups that may have a lower alkylenedioxy group as a substituent, may be present on the phenyl ring, as a substituent(s)), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, (wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring), provided that the aforementioned compound or a salt thereof satisfies the following requirements (i) to (v):

(i) when $X_1$ represents a group —CH=, then $R^3$ represents a hydrogen atom;

(ii) when $X_1$ represents a group —CH=, l represents 1, T represents —CO—, and $R^{14}$ represents a hydrogen atom or an alkyl group that may have a hydroxyl group as a substituent, $R^{15}$ represents the group (24);

(iii) when $X_1$ represents a group —CH=, l represents 1, and T represents —N($R^{17}$)—$B_3$—CO—, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein, on the heterocyclic ring, 1 to 3 groups of (28) are present as a substituent(s);

(iv) when $X_1$ represents a nitrogen atom, and l represents 0, or when $X_1$ represents a nitrogen atom, l represents 1, and T represents —CO— or —$SO_2$, $R^{15}$ is not a group (5), (7), (19), or (20); and (v) when $R^6$ represents a cycloalkyl group that may have on the cycloalkyl ring, a substituent selected from the group consisting of an amino-substituted lower alkyl group that may have a lower alkyl group and a lower alkyl group that may have a halogen atom as a substituent, $R^4$ represents a group -$(T)_l$-N($R^{14}$)$R^{15}$ (wherein T and l are the same as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group

[Formula 14]

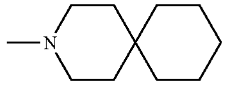

Item 2: The antitumor agent according to item 1, comprising a compound selected from the group consisting of the compounds represented by the general formulas (1-1) to (1-7) below or a salt thereof as an active ingredient:

[Formula 15]

(1-1)

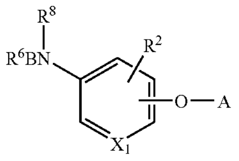

(1-2)

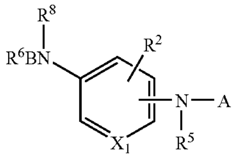

(1-3)

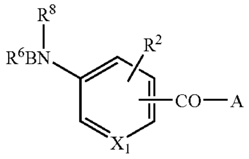

(1-4)

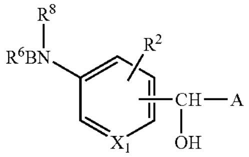

(1-5)

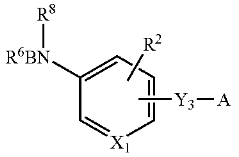

(1-6)

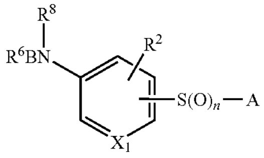

(1-7)

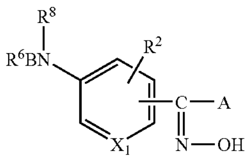

wherein $Y_3$ represents a lower alkylene group.

Item 3: The antitumor agent according to item 1, comprising a compound selected from the group consisting of the compounds represented by the general formulas (1-8) to (1-14) below or a salt thereof as an active ingredient:

[Formula 16]

(1-8)

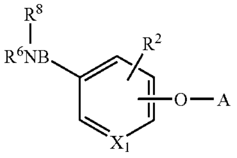

(1-9)

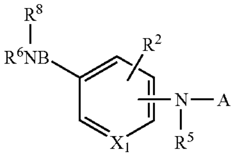

(1-10)

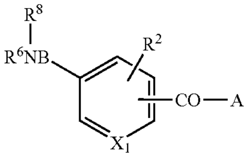

(1-11)

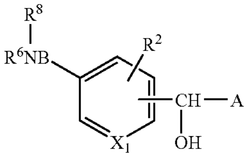

(1-12)

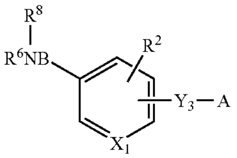

(1-13)

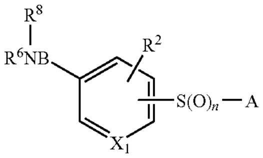

(1-14)

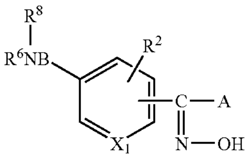

wherein $Y_3$ represents a lower alkylene group.

Item 4: The antitumor agent according to item 1, comprising a compound selected from the group consisting of the compounds represented by the general formulas (1-15) to (1-21) below or a salt thereof as an active ingredient:

[Formula 17]

(1-15)

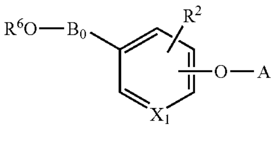

-continued (1-16)

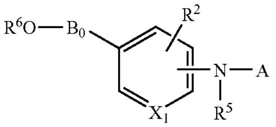

(1-17)

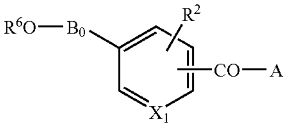

(1-18)

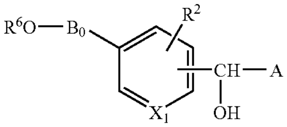

(1-19)

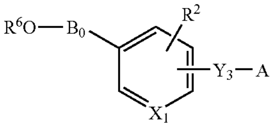

(1-20)

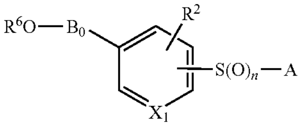

(1-21)

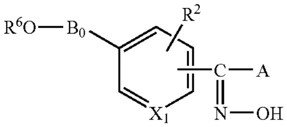

wherein $Y_3$ represents a lower alkylene group.

Item 5: The antitumor agent according to item 1, comprising a compound selected from the group consisting of the compounds represented by the general formulas (1-22) to (1-28) below or a salt thereof as an active ingredient:

[Formula 18]

(1-22)

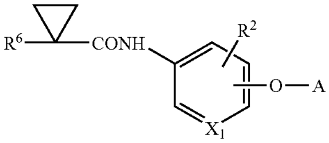

(1-23)

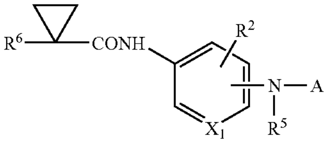

(1-24)

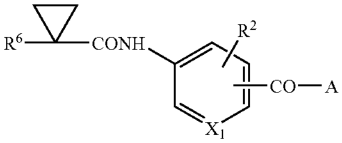

-continued (1-25)

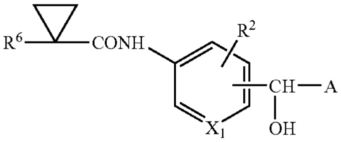

(1-26)

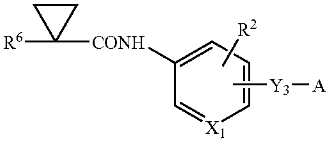

(1-27)

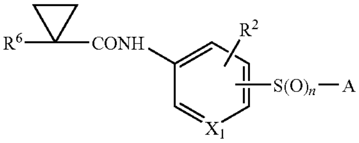

(1-28)

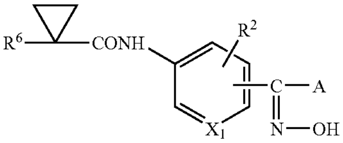

wherein $Y_3$ represents a lower alkylene group.

Item 6: The antitumor agent according to item 1, comprising a compound selected from the group consisting of the compounds represented by the general formulas (1-29) to (1-35) below or a salt thereof as an active ingredient:

[Formula 19]

(1-29)

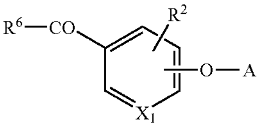

(1-30)

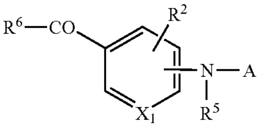

(1-31)

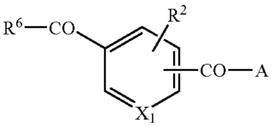

(1-32)

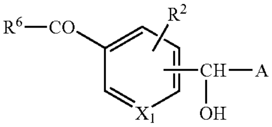

(1-33)

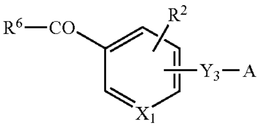

-continued (1-34)

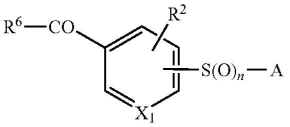

(1-35)

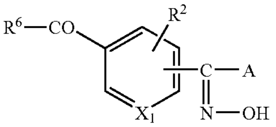

wherein $Y_3$ represents a lower alkylene group.

Item 7: The antitumor agent according to item 1, comprising a compound selected from the group consisting of the compounds represented by the general formulas (1-36) to (1-42) below or a salt thereof as an active ingredient:

[Formula 20]

(1-36)

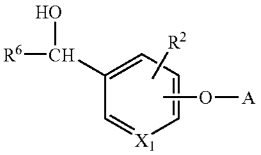

(1-37)

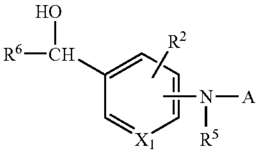

(1-38)

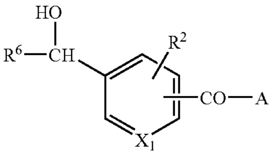

(1-39)

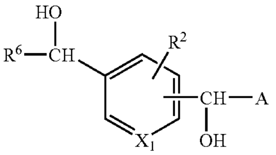

(1-40)

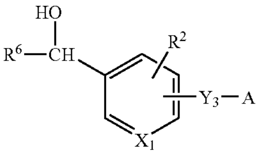

(1-41)

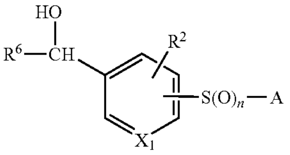

-continued (1-42)

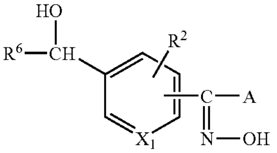

wherein $Y_3$ represents a lower alkylene group.

Item 8: The antitumor agent according to item 1, comprising a compound selected from the group consisting of the compounds represented by the general formulas (1-43) to (1-49) below or a salt thereof as an active ingredient:

[Formula 21]

(1-43)

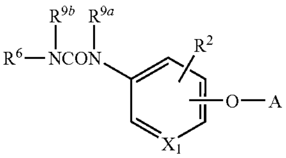

(1-44)

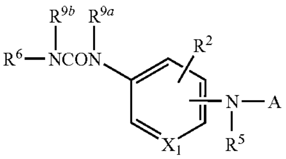

(1-45)

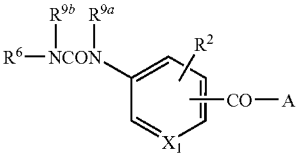

(1-46)

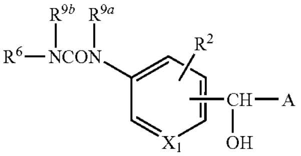

(1-47)

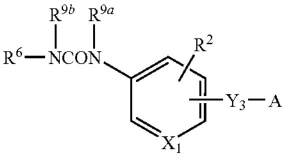

(1-48)

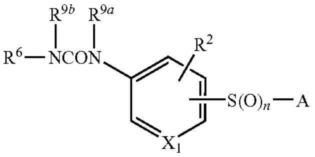

(1-49)

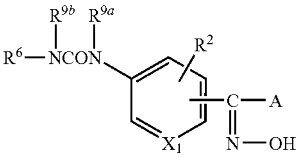

wherein $Y_3$ represents a lower alkylene group.

Item 9: The antitumor agent according to item 1, comprising a compound selected from the group consisting of the compounds represented by the general formulas (1-50) to (1-56) below or a salt thereof as an active ingredient:

[Formula 22]

(1-50)

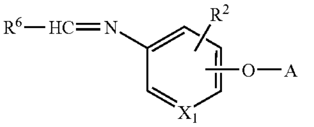

(1-51)

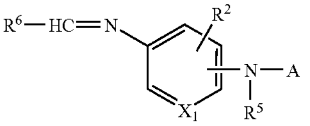

(1-52)

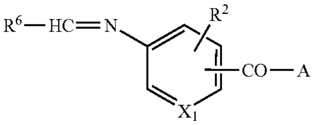

(1-53)

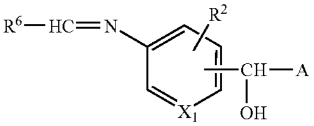

(1-54)

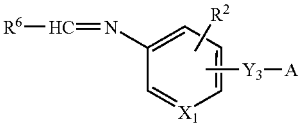

(1-55)

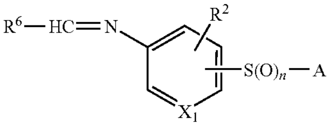

(1-56)

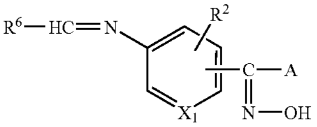

wherein $Y_3$ represents a lower alkylene group.

Item 10: The antitumor agent according to item 1, comprising a compound selected from the group consisting of the compounds represented by the general formulas (1-57) to (1-63) below or a salt thereof as an active ingredient:

[Formula 23]

(1-57)

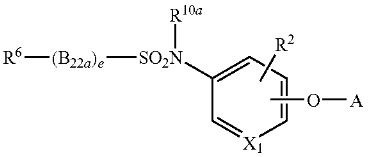

-continued (1-58)

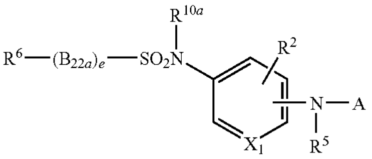

(1-59)

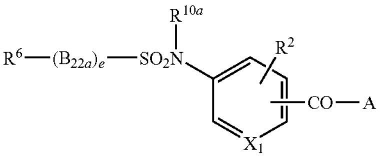

(1-60)

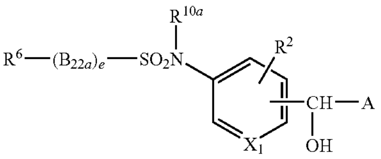

(1-61)

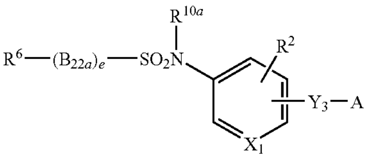

(1-62)

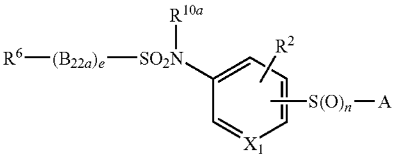

(1-63)

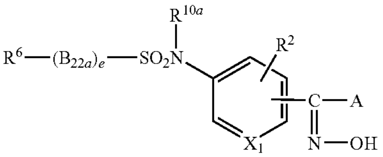

wherein $Y_3$ represents a lower alkylene group.

Item 11: the antitumor agent according to item 1, comprising a compound selected from the group consisting of the compounds represented by the general formulas (1-64) to (1-70) below or a salt thereof as an active ingredient:

[Formula 24]

(1-64)

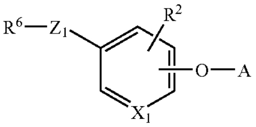

(1-65)

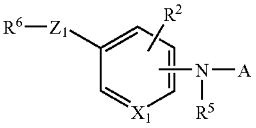

-continued (1-66)

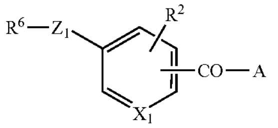

(1-67)

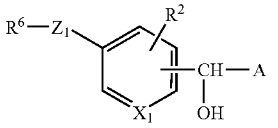

(1-68)

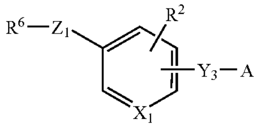

(1-69)

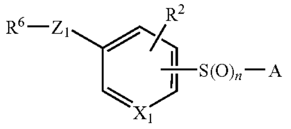

(1-70)

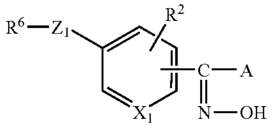

wherein $Y_3$ represents a lower alkylene group, and $Z_1$ represents a lower alkenylene group.

Item 12: The antitumor agent according to item 1, comprising a compound selected from the group consisting of the compounds represented by the general formulas (1-71) to (1-77) below or a salt thereof as an active ingredient:

[Formula 25]

(1-71)

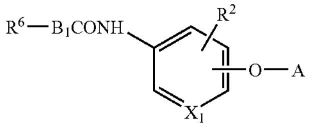

(1-72)

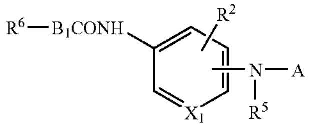

(1-73)

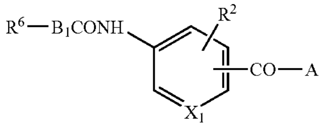

(1-74)

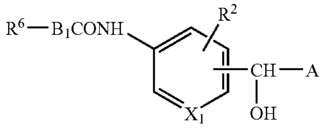

-continued (1-75)

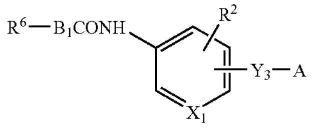

(1-76)

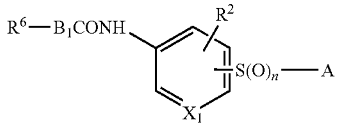

(1-77)

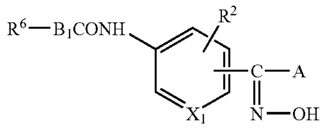

wherein $Y_3$ represents a lower alkylene group.

Item 13: The antitumor agent according to item 1, comprising a compound selected from the group consisting of the compounds represented by the general formulas (1-78) to (1-84) below or a salt thereof as an active ingredient:

[Formula 26]

(1-78)

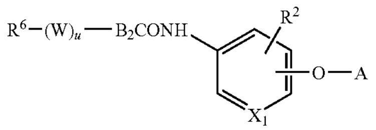

(1-79)

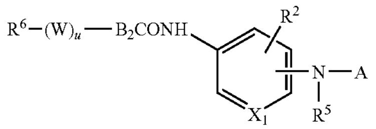

(1-80)

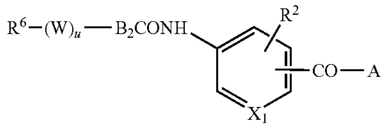

(1-81)

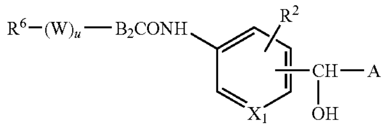

(1-82)

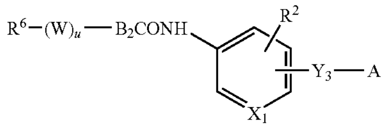

(1-83)

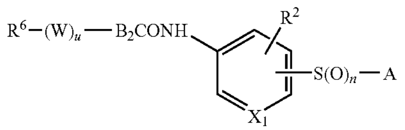

-continued (1-84)

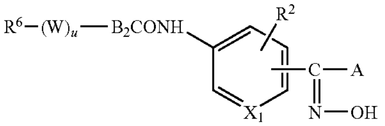

wherein $Y_3$ represents a lower alkylene group.

Item 14: The antitumor agent according to item 1, comprising a compound selected from the group consisting of the compounds represented by the general formulas (1-85) to (1-91) below or a salt thereof as an active ingredient:

[Formula 27]

(1-85)

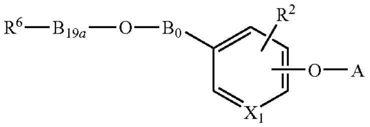

(1-86)

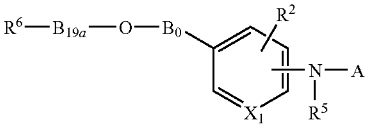

(1-87)

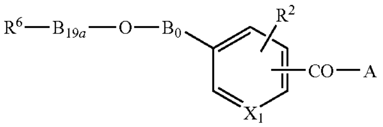

(1-88)

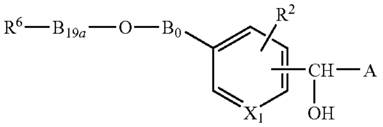

(1-89)

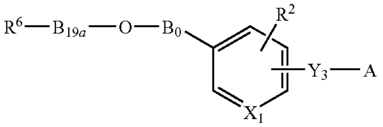

(1-90)

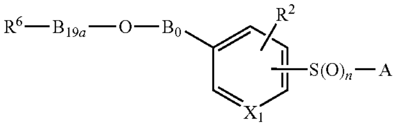

(1-91)

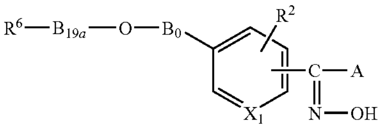

wherein $Y_3$ represents a lower alkylene group.

Item 15: The antitumor agent according to item 1, comprising a compound selected from the group consisting of the compounds represented by the general formulas (1-92) to (1-98) below or a salt thereof as an active ingredient:

[Formula 28]

(1-92)

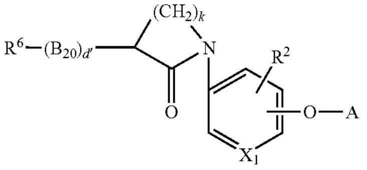

(1-93)

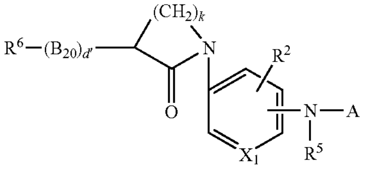

(1-94)

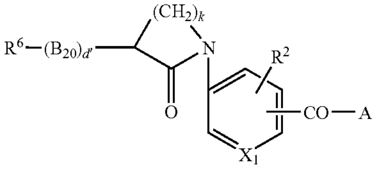

(1-95)

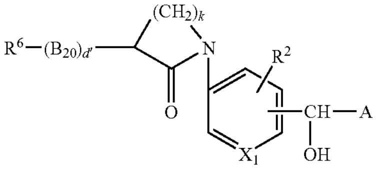

(1-96)

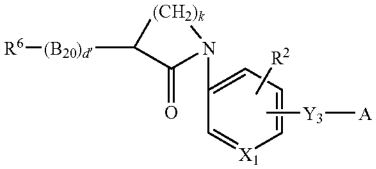

(1-97)

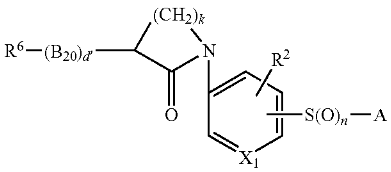

(1-98)

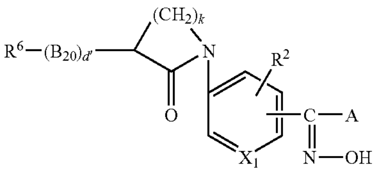

wherein $Y_3$ represents a lower alkylene group.

Item 16: The antitumor agent according to item 1, comprising a compound selected from the group consisting of the compounds represented by the general formulas (1-99) to (1-105) below or a salt thereof as an active ingredient:

[Formula 29]

(1-99)

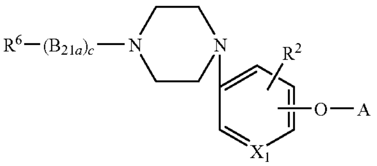

(1-100)

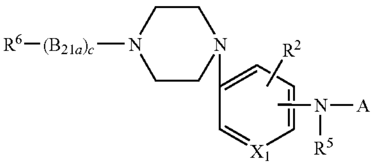

(1-101)

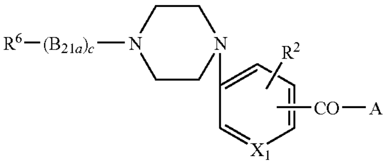

(1-102)

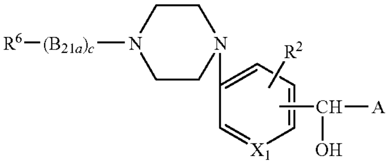

(1-103)

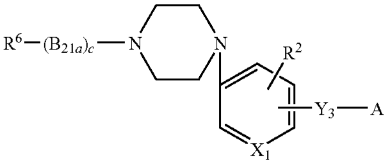

(1-104)

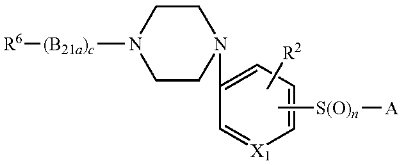

(1-105)

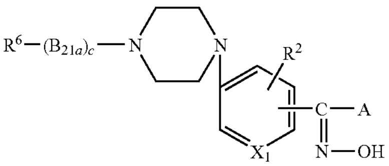

wherein $Y_3$ represents a lower alkylene group.

Item 17: The antitumor agent according to item 1, comprising a compound selected from the group consisting of the compounds represented by the general formulas (1-106) to (1-112) below or a salt thereof as an active ingredient:

[Formula 30]

(1-106)

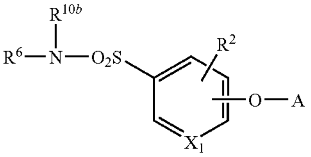

(1-107)

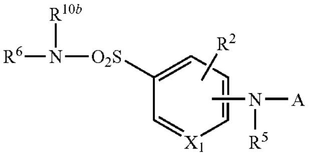

(1-108)

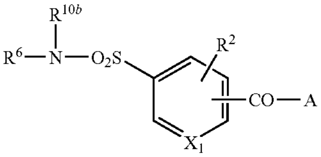

(1-109)

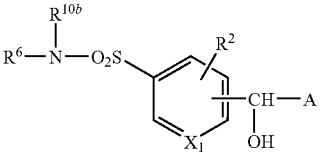

(1-110)

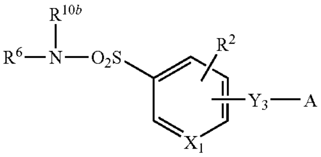

(1-111)

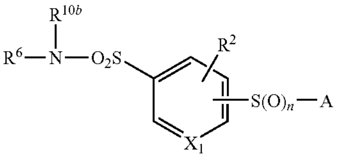

(1-112)

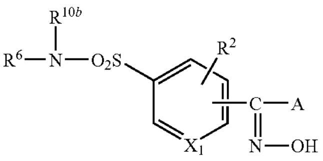

wherein $Y_3$ represents a lower alkylene group.

Item: 18 The antitumor agent according to item 1, comprising a compound selected from the group consisting of the compounds represented by the general formulas (1-113) to (1-119) below or a salt thereof as an active ingredient:

[Formula 31]

(1-113)

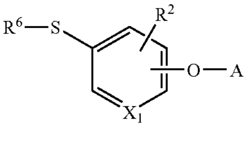

-continued (1-114)

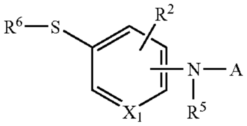

(1-115)

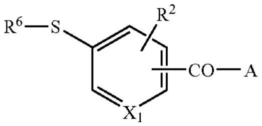

(1-116)

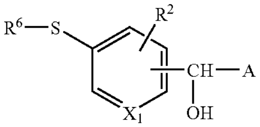

(1-117)

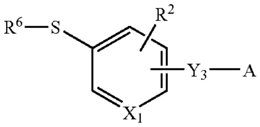

(1-118)

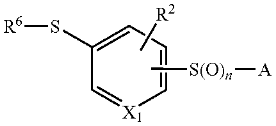

(1-119)

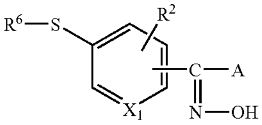

wherein $Y_3$ represents a lower alkylene group.

Item: 19 The antitumor agent according to item 1, comprising a compound selected from the group consisting of the compounds represented by the general formulas (1-120) to (1-126) below or a salt thereof as an active ingredient:

[Formula 32]

(1-120)

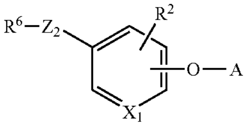

(1-121)

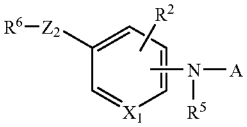

(1-122)

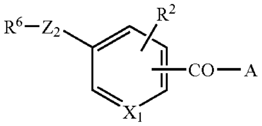

(1-123)

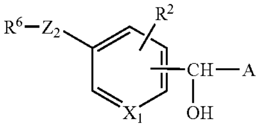

-continued (1-124)

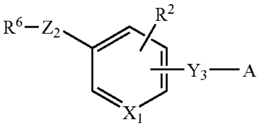

(1-125)

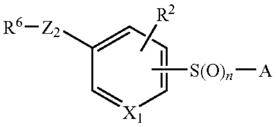

(1-126)

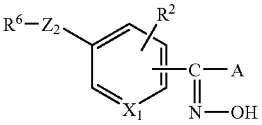

wherein $Y_3$ represents a lower alkylene group, and $Z_2$ represents a lower alkynylene group.

Item: 20 The antitumor agent according to item 1, comprising a compound selected from the group consisting of the compounds represented by the general formulas (1-127) to (1-133) below or a salt thereof as an active ingredient:

[Formula 33]

(1-127)

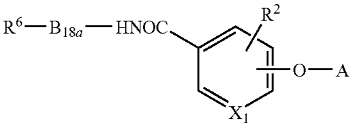

(1-128)

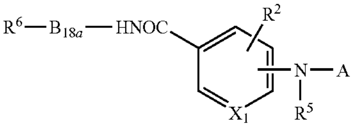

(1-129)

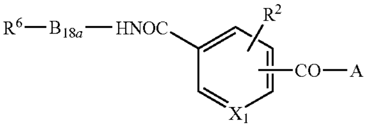

(1-130)

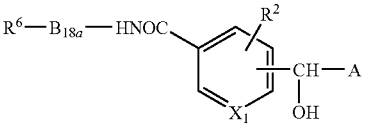

(1-131)

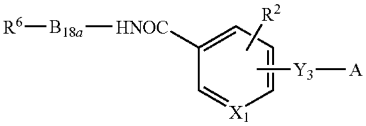

(1-132)

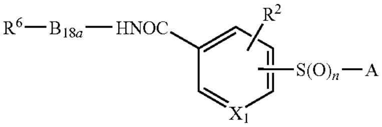

-continued (1-133)

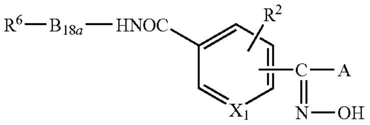

wherein $Y_3$ represents a lower alkylene group.

Item: 21 The antitumor agent according to item 1, comprising a compound selected from the group consisting of the compounds represented by the general formulas (1-134) to (1-140) below or a salt thereof as an active ingredient:

[Formula 34]

(1-134)

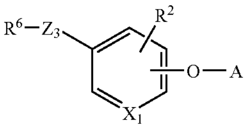

(1-135)

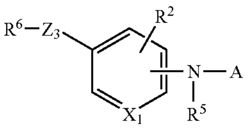

(1-136)

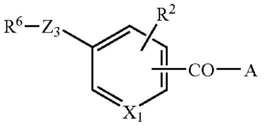

(1-137)

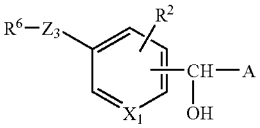

(1-138)

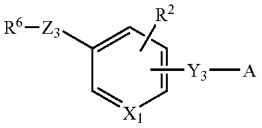

(1-139)

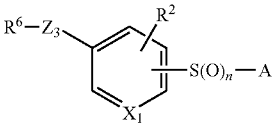

(1-140)

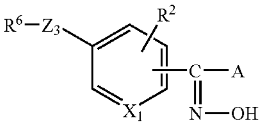

wherein $Y_3$ represents a lower alkylene group, and $Z_3$ represents a lower alkylene group or a group —N($R^{8d}$)—.

Item 22: The antitumor agent according to any one of items 1 to 21, wherein Y is a group —O—.

Item 23: The antitumor agent according to any one of items 1 to 21, wherein Y is a group —N($R^5$)—.

Item 24: The antitumor agent according to any one of items 1 to 21, wherein Y is a group —CO—, a group —CH(OH)—, a lower alkylene group, a group —S(O)n-, or a group —C(═N—OH)—.

Item 25: The antitumor agent according to any one of items 1 to 21, wherein A is a group

[Formula 35]

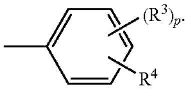

Item 26: The antitumor agent according to any one of items 1 to 21, wherein A is a group

[Formula 36]

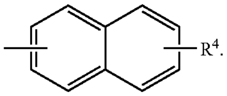

Item 27: The antitumor agent according to any one of items 1 to 21, wherein $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

[Formula 37]

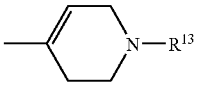

or a group

[Formula 38]

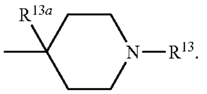

Item 28: The antitumor agent according to any one of items 1 to 21, wherein $R^4$ is a group $-(T)_l-N(R^{14})R^{15}$, and l is 0.

Item 29: The antitumor agent according to any one of items 1 to 21, wherein $R^4$ is a group $-(T)_l-N(R^{14})R^{14}R^{15}$, and l is 1.

Item 30: The antitumor agent according to any one of items 1 to 21, wherein $R^4$ is a group $-(T)_l-N(R^{14})R^{15}$, l is 1, and T is a group —N($R^{17}$)—$B_3$—CO—.

Item 31: The antitumor agent according to any one of items 1 to 21, wherein $R^4$ is a group $-(T)_l-N(R^{14})R^{15}$, l is 1, and T is a group —$B_{19}$—N($R^{18}$)—CO—.

Item 32: The antitumor agent according to any one of items 1 to 21, wherein $R^4$ is a group $-(T)_l-N(R^{14})R^{15}$, l is 1, and T is a group —$B_4$—CO—.

Item 33: The antitumor agent according to any one of items 1 to 21, wherein $R^4$ is a group $-(T)_l-N(R^{14})R^{15}$, l is 1, and T is a group -Q-$B_5$—CO—.

Item 34: The antitumor agent according to any one of items 1 to 21, wherein $R^4$ is a group $-(T)_l-N(R^{14})R^{15}$, l is 1, and T is a group —$B_6$—N($R^{19}$)—$B_7$—.

Item 35: The antitumor agent according to any one of items 1 to 21, wherein $R^4$ is a group $-(T)_l-N(R^{14})R^{15}$, l is 1, and T is a group —CO—$B_8$—.

Item 36: The antitumor agent according to any one of Items 1 to 21, wherein $R^4$ is a group $-(T)_l-N(R^{14})R^{15}$, l is 1, and T is a group —CH(OH)—$B_9$—.

Item 37: The antitumor agent according to any one of items 1 to 21, wherein $R^4$ is a group $-(T)_l-N(R^{14})R^{15}$, l is 1, and T is a group —CO—$B_{10}$—CO—.

Item 38: The antitumor agent according to any one of items 1 to 21, wherein $R^4$ is a group $-(T)_l-N(R^{14})R^{15}$, l is 1, and T is a group —CH(OH)—$B_{11}$—CO—.

Item 39: The antitumor agent according to any one of items 1 to 21, wherein $R^4$ is a group $-(T)_l-N(R^{14})R^{15}$, l is 1, and T is a group —CO—.

Item 40: The antitumor agent according to any one of items 1 to 21, wherein $R^4$ is a group $-(T)_l-N(R^{14})R^{15}$, l is 1, and T is a group —$SO_2$—.

Item 41: The antitumor agent according to any one of items 1 to 21, wherein $R^4$ is a group $-(T)_l-N(R^{14})R^{15}$, l is 1, and T is a group —$B_{23a}$—CO—CO—.

Item 42: The antitumor agent according to any one of items 1 to 21, wherein $R^4$ is a group $-(T)_l-N(R^{14})R^{15}$, l is 1, and T is a lower alkylene group.

Item 43: The antitumor agent according to item 1, comprising a compound selected from the group consisting of the compounds represented by the general formulas (1-1), (1-2), (1-8), (1-9), (1-15), (1-16), (1-29), (1-30), (1-43), (1-44), (1-57), (1-58), (1-64) and (1-65) or a salt thereof as an active ingredient, wherein Y is a group —O— or a group —$N(R^5)$—, A is a group

[Formula 39-1]

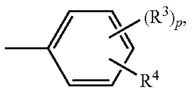

and $R^4$ is a group $-(T)_l-N(R^{14})R^{15}$.

Item 44: The antitumor agent according to item 43, wherein l is 1, and T is a group —$N(R^7)$—$B_3$—CO—.

Item 45: The antitumor agent according to item 43, wherein l is 1, and T is a group —$B_4$—CO—.

Item 46: The antitumor agent according to item 43, wherein l is 1, and T is a group —CO—.

Item 47: The antitumor agent according to item 43, wherein l is 0.

Item 48: The antitumor agent according to item 1, comprising a compound selected from the group consisting of N-[6-(4-{[2-(4-piperonylpiperazin-1-yl)-2-oxoethyl]ethylamino}-2-methoxyphenoxy)pyridin-3-yl]-3,4-dichlorobenzamide, N-[6-(4-{[2-(4-piperonylpiperazin-1-yl)-2-oxoethyl] ethylamino}phenoxy)pyridin-3-yl]-4-trifluoromethylbenzamide, N-[6-(4-{[2-(4-piperonylpiperazin-1-yl)-2-oxoethyl] ethylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methylphenoxy)pyridin-3-yl]-3,4-dichlorobenzamide, N-[6-(4-{[2-(4-piperonylpiperazin-1-yl)-2-oxoethyl] methylamino}-2-methylphenoxy)pyridin-3-yl]-4-trifluoromethylbenzamide, N-(6-{4-[3-(4-piperonylpiperazin-1-yl)-3-oxopropyl]phenoxy}pyridin-3-yl)-3,4-dichlorobenzenesulfonamide, N-[6-(4-{4-[2-(4-piperonylpiperazin-1-yl)-2-oxoethyl]piperazin-1-yl}phenoxy)pyridin-3-yl]-4-trifluoromethylbenzamide, N-[6-(4-{4-[2-(4-piperonylpiperazin-1-yl)-2-oxoethyl]piperidin-1-yl}phenoxy)pyridin-3-yl]-4-trifluoromethylbenzamide, N-{6-[(4-{4-[2-(4-piperonylpiperazin-1-yl)-2-oxoethyl]piperidin-1-yl}phenyl)methylamino]pyridin-3-yl}-4-trifluoromethylbenzamide, N-[6-(4-{4'-[2-(4-benzylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-3,4-dichlorobenzamide, N-{6-[4-(4-benzylpiperazine-1-carbonyl)phenoxy]pyridin-3-yl}-4-trifluoromethylbenzamide, N-{6-[4-(4-benzylpiperazine-1-carbonyl)phenoxy]pyridin-3-yl}-3,4-dichlorobenzamide, N-[6-({4-[3-(4-piperonylpiperazin-1-yl)-3-oxopropyl] phenyl}methylamino)pyridin-3-yl]-4-trifluoromethylbenzamide, N-[6-(4-{[2-(4-piperonylpiperazin-1-yl)-2-oxoethyl] ethylamino}-2-fluorophenoxy)pyridin-3-yl]-3,4-dichlorobenzamide, N-[6-(4-{[2-(4-piperonylpiperazin-1-yl)-2-oxoethyl]methylamino}-2-fluorophenoxy)pyridin-3-yl]-3,4-dichlorobenzamide, N-[6-(4-{[2-(4-piperonylpiperazin-1-yl)-2-oxoethyl]methylamino}-2-methoxyphenoxy)pyridin-3-yl]-3,4-dichlorobenzamide, N-[6-(4-{[2-(4-piperonylpiperazin-1-yl)-2-oxoethyl] methylamino}phenoxy)pyridin-3-yl]-3,4-dichlorobenzamide, 1-(6-{4-[3-(4-piperonylpiperazin-1-yl)-3-oxopropyl] phenoxy}pyridin-3-yl)-3-(3,4-dichlorophenyl)-1-ethylurea, N-(6-{4-[3-(4-piperonylpiperazin-1-yl)-3-oxopropyl] phenoxy}pyridin-3-yl)-4-trifluoromethylbenzamide, N-[6-(4-{[2-(4-benzylpiperazin-1-yl)-2-oxoethyl]methylamino}-2-methylphenoxy)pyridin-3-yl]-4-trifluoromethylrobenzamide, N-[6-(4-{4-[2-(4-benzylpiperazin-1-yl)-2-oxoethyl]piperidin-1-yl}phenoxy) pyridin-3-yl]-3,4-dichlorobenzamide, N-(6-{4-[3-(4-piperonylpiperazine-1-carbonyl)piperidin-1-yl] phenoxy}pyridin-3-yl)-3,4-dichlorobenzamide, N-[6-(4-{4-[2-(4-benzylrupiperazin-1-yl)-2-oxoethyl]piperidin-1-yl}phenoxy)pyridin-3-yl]-4-trifluoromethylbenzamide, N-{6-[(4-{4-[2-(4-benzylpiperazin-1-yl)-2-oxoethyl]piperidin-1-yl}phenyl)methylamino]pyridin-3-yl}-4-trifluoromethylbenzamide, N-(6-{4-[(2-{4-[4-(4-fluorobenzoyl)phenyl]piperazin-1-yl}-2-oxoethyl)methylamino]-2-methoxyphenoxy}pyridin-3-yl)-4-trifluoromethylbenzamide, 2-(4-piperonylpiperazin-1-yl)-N-{3-methyl-4-[5-(4-trifluoromethylphenoxymethyl)pyridin-2-yloxy]phenyl}-2-oxoacetamide, N-[6-(4-{[2-(4-piperonylpiperazin-1-yl)-2-oxoethyl]methylamino}-2-methylphenoxy)pyridin-3-yl]-2-fluoro-4-trifluoromethylbenzamide, N-[6-(4-{4-[2-(4-piperonylpiperazin-1-yl)-2-oxoethyl]piperidin-1-yl}-2-methoxyphenoxy)pyridin-3-yl]-4-trifluoromethylbenzamide and 4-(3-{3-methyl-4-[5-(4-trifluoromethylbenzoylamino)-pyridin-2-yloxy]phenyl}-2-oxohexahydropyrimidin-1-yl) benzoic acid ethyl ester, or a salt thereof as an active ingredient.

Item 49: The antitumor agent according to any one of items 1 to 48, wherein a target of the antitumor agent is a malignant tumor.

Item 50: The antitumor agent according to item 49, wherein the malignant tumor is a solid tumor.

Item 51: The antitumor agent according to item 49, wherein the malignant tumor is a hematological cancer.

Item 52: The antitumor agent according to item 49, wherein the malignant tumor is lymphoma, leukemia, or myeloma.

Item 53: A method for treating or preventing tumor comprising an administration of a compound represented by the general formula (1) below or a salt thereof:

[Formula 39-2]

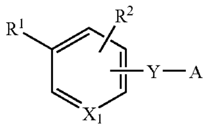

wherein $X_1$ represents a nitrogen atom or a group —CH═, $R^1$ represents a group —Z—$R^6$, Z represents a group —N($R^8$)—B—, a group —B—N($R^8$)—, a group —$B_0$—O—, a group

[Formula 39-3]

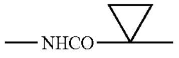

a group —CO—, a group —CH(OH)—, a group —N($R^{9a}$)—CO—N—($R^{9b}$)—, a group —N═CH—, a group —N($R^{10a}$)—$SO_2$—($B_{22a}$) e-, a lower alkenylene group, a group —NHCO—$B_1$—, a group —NHCO—$B_2$—(W)u-, a group —BO—O—$B_{19a}$—, a group

[Formula 39-4]

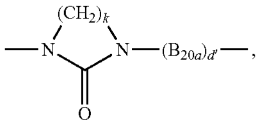

a group

[Formula 39-5]

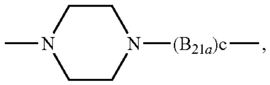

a group —$SO_2$—N($R^{10b}$)—, a group —S—, a lower alkynylene group, a lower alkylene group, a group —N($R^{8d}$)— or a group —CO—NH—$B_{18a}$—.

$R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, $B_0$ represents a lower alkylene group, $B_1$ represents a lower alkenylene group that may have a phenyl group as a substituent, $B_2$ represents a lower alkylene group that may be substituted by a group selected from the group consisting of a lower alkoxy group and a phenyl group, $R^{9a}$ represents a hydrogen atom or a lower alkyl group, $R^{9b}$ represents a hydrogen atom or a lower alkyl group, $R^{10a}$ represents a hydrogen atom or a lower alkyl group, $B_{22a}$ represents a lower alkylene group or a lower alkenylene group, e represents 0 or 1, $B_{18a}$ represents a lower alkylene group, $B_{19a}$ represents a lower alkylene group, $B_{20a}$ represents a lower alkylene group, $B_{21a}$ represents a lower alkylene group, k represents 2 or 3, c represents 0 or 1, d' represents 0 or 1, $R^{10b}$ represents a hydrogen atom or a lower alkyl group, $R^{8d}$ represents a hydrogen atom or a lower alkyl group, W represents an oxygen atom, a group —NH—, or a sulfur atom, u represents 0 or 1, $R^6$ represents 5- to 15-membered monocyclic, dicyclic or tricyclic saturated or unsaturated heterocyclic group having 1 to 4 nitrogen atoms, oxygen atoms or sulfur atoms (that may have 1 to 3 substituents, which are selected from the group consisting of an oxo group; a lower alkoxy group that may have a halogen atom as a substituent; a lower alkyl group that may have a halogen atom as a substituent; a halogen atom; a lower alkylsulfonyl group; a phenyl group that may be substituted by a lower alkyl group that may have a halogen atom on the phenyl ring; a lower alkylthio group, a pyrrolyl group, a benzoyl group; a lower alkanoyl group; lower alkoxycarbonyl group; and an amino group that may have a group selected from the group consisting of a lower alkyl group and a lower alkanoyl group as a substituent, on the heterocyclic ring), an adamantly group, a naphthyl group (that may have 1 to 3 groups selected from the group consisting of a lower alkyl group, a halogen atom, and an amino group that may have a group selected from the group consisting of a lower alkyl group and a lower alkanoyl group as a substituent, on the naphthalene ring), an alkyl group that may have a lower alkoxy group as a substituent, a cycloalkyl group that may be substituted by a group selected from the group consisting of an amino substituted lower alkyl group that may have a lower alkyl group and a lower alkyl group that may have a halogen atom as a substituent, on the cycloalkyl ring, a lower alkenyl group that may have a halogen atom as a substituent, a lower alkanoyl group, a benzoyl group (that may have 1 to 3 groups selected from the group consisting of a lower alkyl group that may have a halogen atom and halogen atom, as a substituents, on the phenyl ring), a halogen atom substituted lower alkyl group, cycloalkyl lower alkyl group or a group

[Formula 39-6]

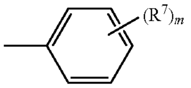

$R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group or a 5- or 6-membered saturated or unsaturated heterocyclic group having 1 to 4 nitrogen atoms, oxygen atoms, or sulfur atoms (that may have an oxo group on the heterocyclic ring), m represents an integer from 1 to 5 (when m represents 2 to 5, two to five $R^7$s may be identical or different) and $R^2$ represents a hydrogen atom, a halogen atom, or a lower alkyl group, Y represents a group —O—, a group —N($R^5$)—, a group —CO—, a group —CH(OH)—, a lower alkylene group, a group —S(O)n-, or a group —C(=N—OH)—, $R^5$ represents a hydrogen atom, a lower alkyl group, a lower alkanoyl group, a benzoyl group, a phenyl lower alkyl group, or a cycloalkyl group, n represents 0, 1, or 2, A represents a group

[Formula 39-7]

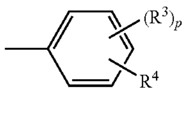

or a group

[Formula 39-8]

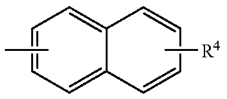

p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —CON$R^{11}R^{12}$, or a cyano group, wherein $R^{11}$ and $R^{12}$ may be identical or different and each represent a hydrogen atom, a lower alkyl group, a cycloalkyl group, or a phenyl group, and $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring, $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

[Formula 39-9]

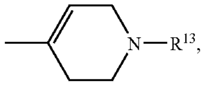

a group

[Formula 39-10]

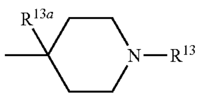

or a group -$(T)_l$-N($R^{14}$)$R^{15}$, $R^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, $R^{13a}$ represents a hydrogen atom or a hydroxyl group, T represents a lower alkylene group, a group —N($R^{17}$)—$B_3$—CO—, a group —$B_{19}$—N($R^{18}$)—CO—, a group —$B_4$—CO—, a group -Q-$B_5$—CO—, a group —$B_6$—N($R^{19}$)—$B_7$—CO—, a group —CO—$B_8$—, a group —CH(OH)—$B_9$—, a group —CO—$B_{10}$—CO—, a group —CH(OH)—$B_{11}$—CO—, a group —CO—, a group —$SO_2$—, or a group —$B_{23a}$—CO—CO—, wherein $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, $B_3$ represents a lower alkylene group, $B_{19}$ represents a lower alkylene group, $R^{18}$ represents a hydrogen atom or a lower alkyl group, $B_4$ represents a lower alkenylene group or a lower alkylene group that may have a hydroxyl group as a substituent, Q represents an oxygen atom or a group —S(O)n- (wherein n is the same as described above), $B_5$ represents a lower alkylene group, $B_6$ represents a lower alkylene group, $R^{19}$ represents a hydrogen atom or a lower alkanoyl group, $B_7$ represents a lower alkylene group, $B_8$ represents a lower alkylene group, $B_9$ represents a lower alkylene group, $B_{10}$ represents a lower alkylene group, $B_{11}$ represents a lower alkylene group, $B_{23a}$ represents a lower alkylene group, l represents 0 or 1, $R^{14}$ represents a hydrogen atom or an alkyl group that may have a hydroxyl group as a substituent, $R^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

[Formula 39-11]

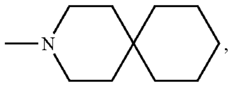

(26) a carbonyl lower alkyl group substituted by a group

[Formula 39-12]

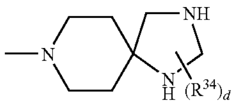

27) a group —CO—$B_2$O—N($R^{36}$)$R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group, d represents an integer from 0 to 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 phenyl lower alkyl groups that may have a lower alkylenedioxy group on the phenyl ring, may be present as a substituent(s), $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

[Formula 39-13]

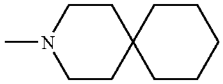

wherein, on the heterocyclic ring, 1 to 3 substituents may be present which are selected from the group consisting of (28) a phenyl-substituted lower alkyl group, which has 1 to 2 phenyl groups that may be substituted by 1 to 3 groups on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, and that may have a pyridyl group on the lower alkyl group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

[Formula 39-14]

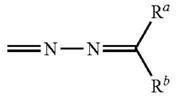

(wherein $R^a$ and $R^b$ each represent a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group $—(B_{12}CO)t\text{-}N(R^{20})R^{21}$, (50) a group $—(CO)o\text{-}B_{13}—N(R^{22})R^{22}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadizole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group $—(O—B_{15})s\text{-}CO—N(R^{26})R^{27}$, (85) a group $—N(R^{28})—CO—B_{16}—N(R^{29})R^{30}$, (86) a group $—N(R^{31})—B_{17}—CO—N(R^{32})R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, $R^{20}$ and $R^{21}$ may be identical or different and each represent a hydrogen atom; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or a cycloalkyl group; and $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring), o represents 0 or 1, $B_{13}$ represents a lower alkylene group, $R^{22}$ and $R^{23}$ may be identical or different and each represent a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group and a phenyl lower alkyl group that may have a lower alkylenedioxy group as a substituent on the phenyl ring), $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, (wherein, on the heterocyclic ring, 1 to 3 phenyl lower alkyl groups that may have a lower alkylenedioxy group as a substituent, may be present on the phenyl ring, as a substituent(s)), $R^{27}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, (wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring), provided that the aforementioned compound or a salt thereof satisfies the following requirements (i) to (v):

(i) when $X_1$ represents a group —CH═, then $R^3$ represents a hydrogen atom;

(ii) when $X_1$ represents a group —CH═, l represents 1, T represents —CO—, and $R^{14}$ represents a hydrogen atom or an alkyl group that may have a hydroxyl group as a substituent, $R^{15}$ represents the group (24);

(iii) when $X_1$ represents a group —CH═, l represents 1, and T represents —N($R^{17}$)—$B_3$—CO—, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein, on the heterocyclic ring, 1 to 3 groups of (28) are present as a substituent(s);

(iv) when $X_1$ represents a nitrogen atom, and l represents 0, or when $X_1$ represents a nitrogen atom, l represents 1, and T represents —CO— or —$SO_2$, $R^{15}$ is not a group (5), (7), (19), or (20); and (v) when $R^6$ represents a cycloalkyl group that may have on the cycloalkyl ring, a substituent selected from the group consisting of an amino-substituted lower alkyl group that may have a lower alkyl group and a lower alkyl group that may have a halogen atom as a substituent, $R^4$ represents a group -$(T)_l$-N($R^{14}$)$R^{15}$ (wherein T and l are the same as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group

[Formula 39-15]

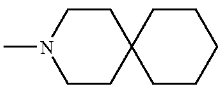

Item 54: Use of a compound represented by the general formula (1) below or a salt thereof for manufacturing an antitumor agent:

[Formula 39-16]

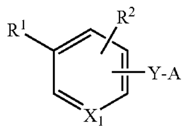

wherein $X_1$ represents a nitrogen atom or a group —CH═, $R^1$ represents a group —Z—$R^6$, Z represents a group —N($R^8$)—B—, a group —B—N($R^8$)—, a group —$B_0$—O—, a group

[Formula 39-17]

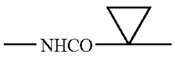

a group —CO—, a group —CH(OH)—, a group —N($R^{9a}$)—CO—N—($R^{9b}$)—, a group —N═CH—, a group —N($R^{10a}$)—$SO_2$—$(B_{22a})$e-, a lower alkenylene group, a group —NHCO—$B_1$—, a group —NHCO—$B_2$—(W)u-, a group —BO—O—$B_{19a}$—, a group

[Formula 39-18]

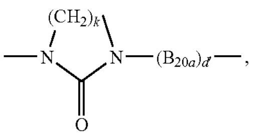

a group

[Formula 39-19]

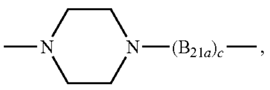

a group —$SO_2$—N($R^{10b}$)—, a group —S—, a lower alkynylene group, a lower alkylene group, a group —N($R^{8d}$)— or a group —CO—NH—$B_{18a}$—.

$R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, $B_0$ represents a lower alkylene group, $B_1$ represents a lower alkenylene group that may have a phenyl group as a substituent, $B_2$ represents a lower alkylene group that may be substituted by a group selected from the group consisting of a lower alkoxy group and a phenyl group, $R^{9a}$ represents a hydrogen atom or a lower alkyl group, $R^{9b}$ represents a hydrogen atom or a lower alkyl group, $R^{10a}$ represents a hydrogen atom or a lower alkyl group, $B_{22a}$ represents a lower alkylene group or a lower alkenylene group, e represents 0 or 1, $B_{18a}$ represents a lower alkylene group, $B_{19a}$ represents a lower alkylene group, $B_{20a}$ represents a lower alkylene group, $B_{21a}$ represents a lower alkylene group, k represents 2 or 3, c represents 0 or 1, d' represents 0 or 1, $R^{10b}$ represents a hydrogen atom or a lower alkyl group, $R^{8d}$ represents a hydrogen atom or a lower alkyl group, W represents an oxygen atom, a group —NH—, or a sulfur atom, u represents 0 or 1, $R^6$ represents 5- to 15-membered monocyclic, dicyclic or tricyclic saturated or unsaturated heterocyclic group having 1 to 4 nitrogen atoms, oxygen atoms or sulfur atoms (that may have 1 to 3 substituents, which are selected from the group consisting of an oxo group; a lower alkoxy group that may have a halogen atom as a substituent; a lower alkyl group that may have a halogen atom as a substituent; a halogen atom; a lower alkylsulfonyl group; a phenyl group that may be substituted by a lower alkyl group that may have a halogen atom on the phenyl ring; a lower alkylthio group, a pyrrolyl group, a benzoyl group; a lower alkanoyl group; lower alkoxycarbonyl group; and an amino group that may have a group selected from the group consisting of a lower alkyl group and a lower alkanoyl group as a substituent, on the heterocyclic ring), an adamantly group, a naphthyl group (that may have 1 to 3 groups selected from the group consisting of a lower alkyl group, a halogen atom, and an amino group that may have a group selected from the group consisting of a lower alkyl group and a lower alkanoyl group as a substituent, on the naphthalene ring), an alkyl group that may have a lower alkoxy group as a substituent, a cycloalkyl group that may be substituted by a group selected from the group consisting of an amino substituted lower alkyl group that may have a lower alkyl group and a lower alkyl group that may have a halogen atom as a substituent, on the cycloalkyl ring, a lower alkenyl group that may have a halogen atom as a substituent, a lower alkanoyl group, a benzoyl group (that may have 1 to 3 groups selected from the group consisting of a lower alkyl group that may have a halogen atom and halogen atom, as a substituents, on the phenyl ring), a halogen atom substituted lower alkyl group, cycloalkyl lower alkyl group or a group

[Formula 39-20]

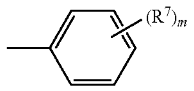

$R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group or a 5- or 6-membered saturated or unsaturated heterocyclic group having 1 to 4 nitrogen atoms, oxygen atoms, or sulfur atoms (that may have an oxo group on the heterocyclic ring), m represents an integer from 1 to 5 (when m represents 2 to 5, two to five $R^7$s may be identical or different) and $R^2$ represents a hydrogen atom, a halogen atom, or a lower alkyl group, Y represents a group —O—, a group —N($R^5$)—, a group —CO—, a group —CH(OH)—, a lower alkylene group, a group —S(O)n-, or a group —C(=N—OH)—, $R^5$ represents a hydrogen atom, a lower alkyl group, a lower alkanoyl group, a benzoyl group, a phenyl lower alkyl group, or a cycloalkyl group, n represents 0, 1, or 2, A represents a group

[Formula 39-21]

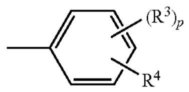

or a group

[Formula 39-22]

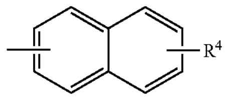

p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —CON$R^{11}R^{12}$, or a cyano group, wherein $R^{11}$ and $R^{12}$ may be identical or different and each represent a hydrogen atom, a lower alkyl group, a cycloalkyl group, or a phenyl group, and $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring, $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

[Formula 39-23]

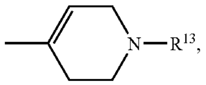

a group

[Formula 39-24]

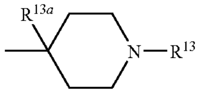

or a group $-(T)_l-N(R^{14})R^{15}$, $R^{13}$ represents a hydrogen atom, a lower alkyl group that may have a halogen atom as a substituent, a lower alkanoyl group that may have a halogen atom as a substituent, a lower alkoxy-carbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, $R^{13a}$ represents a hydrogen atom or a hydroxyl group, T represents a lower alkylene group, a group $—N(R^{17})—B_3—CO—$, a group $—B_{19}—N(R^{18})—CO—$, a group $—B_4—CO—$, a group $Q-B_5—CO—$, a group $—B_6—N(R^{19})—B_7—CO—$, a group $—CO—B_8—$, a group $—CH(OH)—B_9—$, a group $—CO—B_{10}—CO—$, a group $—CH(OH)—B_{11}—CO—$, a group —CO—, a group $—SO_2—$, or a group $—B_{23a}—CO—CO—$, wherein $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, $B_3$ represents a lower alkylene group, $B_{19}$ represents a lower alkylene group, $R^{18}$ represents a hydrogen atom or a lower alkyl group, $B_4$ represents a lower alkenylene group or a lower alkylene group that may have a hydroxyl group as a substituent, Q represents an oxygen atom or a group —S(O)n- (wherein n is the same as described above), $B_5$ represents a lower alkylene group, $B_6$ represents a lower alkylene group, $R^{19}$ represents a hydrogen atom or a lower alkanoyl group, $B_7$ represents a lower alkylene group, $B_8$ represents a lower alkylene group, $B_9$ represents a lower alkylene group, $B_{10}$ represents a lower alkylene group, $B_{11}$ represents a lower alkylene group, $B_{23a}$ represents a lower alkylene group, l represents 0 or 1, $R^{14}$ represents a hydrogen atom or an alkyl group that may have a hydroxyl group as a substituent, $R^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydro-quinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolyl-carbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

[Formula 39-25]

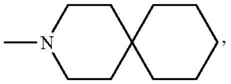

(26) a carbonyl lower alkyl group substituted by a group

[Formula 39-26]

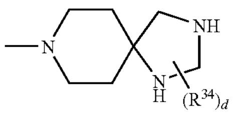

27) a group —CO—$B_{20}$—N($R^{36}$)$R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an Oxo group or a phenyl group, d represents an integer from 0 to 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 phenyl lower alkyl groups that may have a lower alkylenedioxy group on the phenyl ring, may be present as a substituent(s), $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

[Formula 39-27]

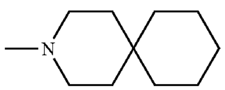

wherein, on the heterocyclic ring, 1 to 3 substituents may be present which are selected from the group consisting of (28) a phenyl-substituted lower alkyl group, which has 1 to 2 phenyl groups that may be substituted by 1 to 3 groups on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, and that may have a pyridyl group on the lower alkyl group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

[Formula 39-28]

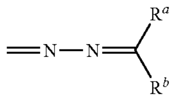

(wherein $R^a$ and $R^b$ each represent a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group —$(B_{12}CO)t$-N($R^{20}$)$R^{21}$, (50) a group —(CO)o-$B_{13}$—N($R^{22}$)$R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadizole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group —(O—$B_{15}$)s-CO—N($R^{26}$)$R^{27}$, (85) a group —N($R^{28}$)—CO—$B_{16}$—N($R^{29}$)$R^{30}$, (86) a group —N($R^{31}$)—$B_{17}$—CO—N($R^{32}$)$R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, $R^{20}$ and $R^{21}$ may be identical or different and each represent a hydrogen atom; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or a cycloalkyl group; and $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring), o represents 0 or 1, $B_{13}$ represents a lower alkylene group, $R^{22}$ and $R^{23}$ may be identical or different and each represent a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group and a phenyl lower alkyl group that may have a lower alkylenedioxy group as a substituent on the phenyl ring), $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, (wherein, on the heterocyclic ring, 1 to 3 phenyl lower alkyl groups that may have a lower alkylenedioxy group as a substituent, may be present on the phenyl ring, as a substituent(s)), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, (wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring), provided that the aforementioned compound or a salt thereof satisfies the following requirements (i) to (v):

(i) when $X_1$ represents a group —CH═, then $R^3$ represents a hydrogen atom;

(ii) when $X_1$ represents a group —CH═, l represents 1, T represents —CO—, and $R^{14}$ represents a hydrogen atom or an alkyl group that may have a hydroxyl group as a substituent, $R^{15}$ represents the group (24);

(iii) when $X_1$ represents a group —CH═, l represents 1, and T represents —N($R^{17}$)—$B_3$—CO—, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein, on the heterocyclic ring, 1 to 3 groups of (28) are present as a substituent(s);

(iv) when $X_1$ represents a nitrogen atom, and l represents 0, or when $X_1$ represents a nitrogen atom, l represents 1, and T represents —CO— or —$SO_2$, $R^{15}$ is not a group (5), (7), (19), or (20); and (v) when $R^6$ represents a cycloalkyl group that may have on the cycloalkyl ring, a substituent selected from the group consisting of an amino-substituted lower alkyl group that may have a lower alkyl group and a lower alkyl group that may have a halogen atom as a substituent, $R^4$ represents a group -$(T)_l$-N($R^{14}$)$R^{15}$ (wherein T and l are the same as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group

[Formula 39-29]

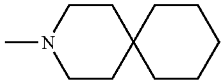

Item 55: The use according to item 54, wherein a target of the antitumor agent is a malignant tumor.

Item 56: The use according to item 55, wherein the malignant tumor is a solid tumor.

Item 57: The use according to item 55, wherein the malignant tumor is a hematological cancer.

Item 58: The use according to item 55, wherein the malignant tumor is lymphoma, leukemia, or myeloma.

Item 59: The antitumor agent according to any one of items 44 to 47, wherein $R^{14}$ and $R^{15}$, together with the nitrogen atom to which they bind, bind to each other, directly or via a nitrogen atom to form a 6-membered saturated heterocyclic group that is substituted, on the heterocyclic ring, by a phenyl-substituted lower alkyl group that may be substituted, on the phenyl ring, by 1 or 2 group(s), as substituent(s), selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group.

Item 60: The antitumor agent according to item 59, wherein the saturated heterocyclic group is a piperazinyl group that is substituted by a phenyl-substituted lower alkyl group that is substituted by a lower alkylenedioxy group on the phenyl ring.

Item 61: The antitumor agent according to item 59 or 60, wherein $X_1$ is a nitrogen atom and Y is an oxygen atom.

Specific examples of individual groups shown in the general formula (1) are as follows.

Examples of the lower alkenylene group include linear or branched alkenylene groups having 2 to 6 carbon atoms and 1 to 3 double bonds such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, and 1,4-hexadienylene groups.

Examples of the lower alkynylene group include linear or branched alkynylene groups having 2 to 6 carbon atoms and 1 to 3 triple bonds such as ethynylene, 1-propynylene, 1-methyl-1-propynylene, 2-methyl-1-propynylene, 2-propynylene, 2-butynylene, 1-butynylene, 3-butynylene, 2-pentynylene, 1-pentynylene, 3-pentynylene, 4-pentynylene, 2-pentyn-4-ynylene, 2-hexynylene, 1-hexynylene, 5-hexynylene, 3-hexynylene, 4-hexynylene, 3,3-diethyl-1-propynylene, and 2-ethyl-1-propynylene groups.

Examples of the lower alkoxy group include linear or branched alkoxy groups having 1 to 6 carbon atoms such as methoxy, ethoxy, propoxy, isopropoxy, butoxy, tert-butoxyl, pentyloxy, and hexyloxy groups.

Examples of the lower alkyl group include linear or branched alkyl groups having 1 to 6 carbon atoms such as methyl, ethyl, propyl, isopropyl, 2,2-dimethylpropyl, 1-ethylpropyl, butyl, isobutyl, tert-butyl, isopentyl, pentyl, and hexyl groups.

Examples of the lower alkyl group which may have a lower alkoxy group as a substituent include, in addition to the above described lower alkyl groups, linear or branched alkyl groups having 1 to 6 carbon atoms which may have a linear or branched alkoxy group having 1 to 6 carbon atoms as a substituent such as methoxymethyl, 1-ethoxyethyl, 27-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the lower alkanoyl group include linear or branched alkanoyl groups having 1 to 6 carbon atoms such as formyl, acetyl, propionyl, butyryl, isobutyryl, pentanoyl, tert-butylcarbonyl, and hexanoyl groups.

Examples of the phenyl lower alkyl group include phenylalkyl groups whose alkyl moiety is a linear or branched alkyl group having 1 to 6 carbon atoms such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, and 2-methyl-3-phenylpropyl groups.

Examples of the lower alkylene group include linear or branched alkylene groups having 1 to 6 carbon atoms such as methylene, ethylene, trimethylene, 2-methyltrimethylene, 2,2-dimethylethylene, 2,2-dimethyltrimethylene, 1-methyltrimethylene, methylmethylene, ethylmethylene, tetramethylene, pentamethylene, and hexamethylene groups.

Examples of the lower alkenylene group which may have a phenyl group as a substituent include linear or branched alkenylene groups, which have 2 to 6 carbon atoms and 1 to 3 double bonds, and which may have a phenyl group as a substituent such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-pentene-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene, 1-phenylvinylene, 3-phenyl-1-propenylene, 3-phenyl-1-methyl-1-propenylene, 3-phenyl-2-methyl-1-propenylene, 1-phenyl-2-propenylene, 1-phenyl-2-butenylene, 3-phenyl-1-butenylene, 1-phenyl-3-butenylene, 5-phenyl-2-pentenylene, 4-phenyl-1-pentenylene, 2-phenyl-3-pentenylene, 1-phenyl-4-pentenylene, 1-phenyl-1,3-butadienylene, 1-phenyl-1,3-pentadienylene, 1-phenyl-2-penten-4-ynylene, 1-phenyl-2-hexenylene, 3-phenyl-1-hexenylene, 4-phenyl-5-hexenylene, 6-phenyl-3-hexenylene, 5-phenyl-4-hexenylene, 1-phenyl-3,3-dimethyl-1-propenylene, 1-phenyl-2-ethyl-1-propenylene, 6-phenyl-1,3,5-hexatrienylene, 1-phenyl-1,3-hexadienylene, and 2-phenyl-1,4-hexadienylene groups.

Examples of the lower alkylene group which may be substituted with a group selected from the group consisting of a lower alkoxy group and a phenyl group include, in addition to the above described lower alkylene groups, linear or branched alkylene groups having 1 to 6 carbon atoms which may be substituted with 1 or 2 groups selected from the group consisting of a linear or branched alkoxy group having 1 to 6 carbon atoms and a phenyl group such as methoxymethylene, 2-phenylethylene, 3-ethoxytrimethylene, 1-propoxy-2-methyltrimethylene, 1-phenyl-2,2-dimethylethylene, 3-phenyl-2, 2-dimethyltrimethylene, 2-butoxy-1-methyltrimethylene, phenylmethylmethylene, 2-pentyloxyethylmethylene, 4-phenyl-2-hexyloxytetramethylene, 3-phenylpentamethylene, 5-phenylhexamethylene, ethoxymethylene, 1-phenylethylene, 3-phenyltrimethylene, and 2-phenyl-1-methoxyethylene groups.

Examples of the 5- to 15-membered monocyclic, bicyclic or tricyclic saturated or unsaturated heterocyclic group which has 1 to 4 nitrogen atoms, oxygen atoms or sulfur atoms include pyrrolidinyl, piperidinyl, piperazinyl, morpholino, pyridyl, 1,2,5,6-tetrahydropyridyl, 1,2,4-triazolyl, 1,2,3-triazolyl, 1,2,5-triazolyl, thiazolidinyl, 1,2,3,4-tetrazolyl, thienyl, quinolyl, 1,4-dihydroquinolyl, benzothiazolyl, pyrazyl, pyrimidyl, pyridazyl, 2H-pyrrolyl, pyrrolyl, 1,3,4-oxadiazolyl, tetrahydropyranyl, tetrahydrofuryl, furazanyl, carbostyryl, 3,4-dihydrocarbostyryl, 1,2,3,4-tetrahydroquinolyl, 1,2,3,4-tetrahydroisoquinolyl, indolyl, isoindolyl, indolinyl, benzoimidazolyl, benzooxazolyl, imidazolidinyl, isoquinolyl, quinazolidinyl, quinoxalinyl, cinnolinyl, phthalazinyl, carbazoyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxathiinyl, phenoxazinyl, 4H-chromenyl, 1H-indazolyl, phenazinyl, xanthenyl, thianthrenyl, 2-imidazolinyl, 2-pyrrolinyl, furyl, oxazolyl, isooxazolyl, isooxazolidinyl, thiazolyl, isothiazolyl, pyranyl, 2-thiazolinyl, 2-pyrazolinyl, quinuclidinyl, 1,4-benzooxadinyl, 3,4-dihydro-2H-1,4-benzooxadinyl, 3,4-dihydro-2H-1,4-benzothiazinyl, 1,4-benzothiazinyl, 1,2,3,4-tetrahydroquinoxalinyl, 1,3-dithia-2, 4-dihydronaphthalenyl, phenalthridinyl, 1,4-dithianaphthalenyl, dibenz[b,e]azepine, and 6,11-dihydro-5H-dibenz[b,e]azepine groups.

Examples of the halogen atom include a fluorine atom, chlorine atom, bromine atom and iodine atom.

Examples of the lower alkoxy group which may have a halogen atom as a substituent include linear or branched alkoxy groups having 1 to 6 carbon atoms which may have 1 to 3 halogen atoms as substituents such as methoxy, ethoxy, propoxy, isopropoxy, butoxy, tert-butoxy, pentyloxy, hexyloxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, and 5,6-dichlorohexyloxy groups.

Examples of the lower alkyl group which may have a halogen atom as a substituent include, in addition to the above described lower alkyl groups, linear or branched alkyl groups having 1 to 6 carbon atoms which may have 1 to 3 halogen atoms as substituents such as trifluoromethyl, trichloromethyl, chloromethyl, bromomethyl, fluoromethyl, iodomethyl, difluoromethyl, dibromomethyl, dichloromethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the lower alkylsulfonyl group include linear or branched alkylsulfonyl groups having 1 to 6 carbon atoms such as methylsulfonyl, ethylsulfonyl, propylsulfonyl, isopropylsulfonyl, butylsulfonyl, tert-butylsulfonyl, pentylsulfonyl, and hexylsulfonyl groups.

Examples of the phenyl group which may be substituted, on the phenyl ring, with a lower alkyl group which may have a halogen atom include phenyl groups which may be substituted, on the phenyl ring, with 1 to 3 linear or branched alkyl groups having 1 to 6 carbon atoms which may have 1 to 3 halogen atoms such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, and 3-ethyl-4-trichloromethyl groups.

Examples of the lower alkylthio group include linear or branched alkylthio groups having 1 to 6 carbon atoms such as methylthio, ethylthio, propylthio, isopropylthio, butylthio, tert-butylthio, pentylthio, and hexylthio groups.

Examples of the amino group which may have a group selected from the group consisting of a lower alkyl group and a lower alkanoyl group as a substituent include amino groups which may have 1 or 2 groups selected from the group consisting of linear or branched alkyl groups having 1 to 6 carbon atoms and linear or branched alkanoyl groups having 1 to 6 carbon atoms as substituents such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-acetylamino, N-formylamino, N-propionylamino, N-butyrylamino, N-isobutyrylamino, N-pentanoylamino, N-tert-butylcarbonylamino, N-hexanoylamino, diacetylamino, N-acetyl-N-methylamino, and N-acetyl-N-ethylamino groups.

Examples of the naphthyl group which may be substituted on the naphthalene ring with 1 to 3 substituents selected from the group consisting of a lower alkyl group, a halogen atom, and an amino group which may have a group selected from the group consisting of a lower alkyl group and a lower alkanoyl group include naphthyl groups which may have, on the naphthalene ring, 1 to 3 substituents selected from the group consisting of a linear or branched alkyl group having 1 to 6 carbon atoms, a halogen atom, and an amino group which may have 1 or 2 substituents selected from the group consisting of a linear or branched alkyl group having 1 to 6 carbon atoms and a linear or branched alkanoyl group having 1 to 6 carbon atoms such as (1- or 2-)naphthyl, 1-methyl-(2-, 3-, 4-, 5-, 6-, 7- or 8-)naphthyl, 2-ethyl-(1-, 3-, 4-, 5-, 6-, 7- or 8-)naphthyl, 3-n-propyl-(1-, 2-, 4-, 5-, 6-, 7- or 8-)naphthyl, 4-n-butyl-(1-, 2-, 3-, 5-, 6-, 7- or 8-)naphthyl, 4-methyl-(1-, 2-, 3-, 5-, 6-, 7- or 8-)naphthyl, 5-n-pentyl-(1-, 2-, 3-, 4-, 6-, 7- or 8-)naphthyl, 6-n-hexyl-(1-, 2-, 3-, 4-, 5-, 7- or 8-)naphthyl, 1,7-dimethyl-(2-, 3-, 4-, 5-, 6- or 8-)naphthyl, 1,2,8-trimethyl-(3-, 4-, 5-, 6- or 7-)naphthyl, 1-dimethylamino-(2-, 3-, 4-, 5-, 6-, 7- or 8-)naphthyl, 2-dimethylamino-(1-, 3-, 4-, 5-, 6-, 7- or 8-)naphthyl, 3-methylamino-(1-, 2-, 4-, 5-, 6-, 7- or 8-)naphthyl, 5-amino-(1-, 2-, 3-, 4-, 6-, 7- or 8-)naphthyl, 5-dimethylamino-(1-, 2-, 3-, 4-, 6-, 7- or 8-)naphthyl, 4-(N-methyl-N-ethylamino)-(1-, 2-, 3-, 5-, 6-, 7- or 8-)naphthyl, 1-methyl-2-dimethylamino-(3-, 4-, 5-, 6-, 7- or 8-)naphthyl, 1-chloro-(2-, 3-, 4-, 5-, 6-, 7- or 8-)naphthyl, and 1-acetylamino-(2-, 3-, 4-, 5-, 6-, 7- or 8-)naphthyl groups.

Examples of the alkyl group which may have a lower alkoxy group as a substituent include, in addition to the above described lower alkyl groups which may have a lower alkoxy group as a substituent, linear or branched alkyl groups having 1 to 8 carbon atoms which may have a linear or branched alkoxy group having 1 to 6 carbon atoms as a substituent such as heptyl, 1-ethylpentyl, octyl, 7-methoxyheptyl, 1-ethoxyheptyl, 2-propoxyl-1-ethylpentyl, 3-isopropoxyoctyl, 7-butoxyheptyl, 8-pentyloxyoctyl, and 5-hexyloxy-1-ethylpentyl groups.

Examples of the amino substituted lower alkyl group which may have a lower alkyl group include linear or branched alkyl groups having 1 to 6 carbon atoms substituted with an amino group which may have 1 or 2 linear or branched alkyl groups having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-diisopropylaminoethyl, (N-ethyl-N-propylamino)methyl, and 2-(N-methyl-N-hexylamino)ethyl groups.

Examples of the cycloalkyl group include cycloalkyl groups having 3 to 16 carbon atoms such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cycloteradecyl, cyclopentadecyl, and cyclohexadecyl groups.

Examples of the cycloalkyl group which may be substituted with a group selected from the group consisting of an amino substituted lower alkyl group which may have a lower alkyl group and a lower alkyl group which may have a halogen atom as a substituent on the cycloalkyl ring include, in addition to the above described cycloalkyl groups, cycloalkyl groups having 3 to 16 carbon atoms which may be substituted, on the cycloalkyl ring, with 1 to 3 groups selected from the group consisting of a linear or branched alkyl group having 1 to 6 carbon atoms substituted with an amino group which may have 1 or 2 linear or branched alkyl groups having 1 to 6 carbon atoms and a linear or branched alkyl group having 1 to 6 carbon atoms which may have 1 to 3 halogen atoms as substituents such as 4-dimethylaminomethylcyclohexyl, 2-(aminomethyl)cyclopropyl, 3-(2-aminomethyl)cyclobutyl, 2-(1-aminoethyl)cyclopentyl, 3-(3-aminopropyl)cyclohexyl, 3-(4-aminobutyl)cycloheptyl, 4-(5-aminopentyl)cyclooctyl, 4-(6-aminohexyl)cyclohexyl, 2-(1,1-dimethyl-2-aminoethyl)cycloheptyl, 3-(2-methyl-3-aminopropyl)cyclopentyl, 3-(methylaminomethyl)cyclohexyl, 2-(1-ethylaminoethyl)cyclooctyl, 2-(2-propylaminoethyl)cyclohexyl, 3-(3-isopropylaminopropyl)cyclopentyl, 4-(4-butylaminobutyl)cycloheptyl, 2-(5-pentylaminopentyl)cyclohexyl, 2-(6-hexylaminohexyl)cyclopentyl, 3-(dimethylaminomethyl)cyclohexyl, 3-[(N-ethyl-N-propylamino)methyl]cycloheptyl, 4-[2-(N-methyl-N-hexylamino)ethyl]cyclooctyl, 4-dimethylaminomethylcyclononyl, 2-(aminomethyl)cyclodecyl, 3-(2-aminomethyl)cycloundecyl, 2-(1-aminoethyl)cyclododecyl, 3-(3-aminopropyl)cyclotridecyl, 3-(4-aminobutyl)cyclotetradecyl, 4-(5-aminopentyl)cyclopentadecyl, 4-(6-aminohexyl)cyclohexadecyl, 2-(1,1-dimethyl-2-aminoethyl)cyclononyl, 3-(2-methyl-3-aminopropyl)cyclodecyl, 3-(methylaminomethyl)cycloundecyl, 2-(1-ethylaminoethyl)cyclododecyl, 2-(2-propylaminoethyl)cyclotridecyl, 3-(3-isopropylaminopropyl)cyclotetradecyl, 4-(4-butylaminobutyl)cyclopentadecyl, 2-(5-pentylaminopentyl)cyclohexadecyl, 2-(6-hexylaminohexyl)cyclononyl, 3-(dimethylaminomethyl)cyclododecyl, 3-[(N-ethyl-N-propylamino)methyl]cyclodecyl, 4-[2-(N-methyl-N-hexylamino)ethyl]cyclohexadecyl, 2,2-dimethylcyclopropyl, and 2-trifluoromethylcyclopropyl groups.

Examples of the lower alkenyl group include linear or branched alkenyl groups having 2 to 6 carbon atoms and 1 to 3 double bonds such as vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl groups.

Examples of the lower alkenyl group which may have a halogen atom as a substituent include, in addition to the above described lower alkenyl groups, linear or branched alkenyl groups having 2 to 6 carbon atoms which may have 1 to 3 halogen atoms as substituents and which have 1 to 3 double bonds such as 3,3,3-trifluoro-1-propenyl, 2-bromovinyl, 3-chloro-1-propenyl, 3-iodo-1-methyl-1-propenyl, 3-fluoro-2-methyl-1-propenyl, 2-butenyl, 4,4,3-trichloro-1-butenyl, 4,4-difluoro-3-butenyl, 5-fluoro-2-pentenyl, 5,5,3-tribromo-1-pentenyl, 5-chloro-3-pentenyl, 5,5,5-trifluoro-4-pentenyl, 4-chloro-1,3-butadienyl, 5-fluoro-1,3-pentadienyl, 5-bromo-2-penten-4-ynyl, 6-fluoro-2-hexenyl, 6,6,5-trifluoro-1-hexenyl, 6-chloro-5-hexenyl, 5-bromo-3-hexenyl, 6-chloro-4-hexenyl, 3,3-dimethyl-2-chloro-1-propenyl, 3-fluoro-2-ethyl-1-propenyl, 6-chloro-1,3,5-hexatrienyl, 6-bromo-1,3-hexadienyl, and 6-fluoro-1,4-hexadienyl groups.

Examples of the benzoyl group (which may have, on the phenyl ring, 1 to 3 substituents selected from the group consisting of a lower alkyl group which may have a halogen atom as a substituent and a halogen atom) include benzoyl groups (which may have, on the phenyl ring, with 1 to 3 substituents selected from the group consisting of a linear or branched alkyl group having 1 to 6 carbon atoms and which may have 1 to 3 halogen atoms as substituents and a halogen atom) such as benzoyl, 3,4-difluorobenzoyl, 2-fluorobenzoyl, 3-bromobenzoyl, 4-iodobenzoyl, 4-methylbenzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl)benzoyl, 4-(2,2,2-trichloroethyl)benzoyl, 2-methyl-4-trifluoromethylbenzoyl, 3-ethyl-4-trichloromethylbenzoyl, 2-chloro-4-trifluoromethylbenzoyl, 3-ethyl-4-fluorobenzoyl, 3-fluoro-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, and 2,4-difluorobenzoyl groups.

Examples of the halogen substituted lower alkyl group include linear or branched alkyl groups having 1 to 6 carbon atoms which have 1 to 3 halogen atoms as substituents such as trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the lower alkylenedioxy group include linear or branched alkylene groups having 1 to 4 carbon atoms such as methylenedioxy, ethylenedioxy, trimethylenedioxy, and tetramethylenedioxy groups.

Examples of the amino group which may have a substituent selected from the group consisting of a lower alkyl group, a lower alkanoyl group, a benzoyl group and a cycloalkyl group include amino groups which may have 1 or 2 substituents selected from the group consisting of a linear or branched alkyl group having 1 to 6 carbon atoms, a linear or branched alkanoyl group having 1 to 6 carbon atoms, a benzoyl group, and a cycloalkyl group having 3 to 16 carbon atoms such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, N-benzoylamino, N-ethyl-N-benzoylamino, N-methyl-N-benzoylamino, N-acetyl-N-benzoylamino, cyclopropylamino, cyclobutylamino, cyclopentylamino, cyclohexylamino, cycloheptylamino, cyclooctylamino, N-methyl-N-cyclohexylamino, N-methyl-N-cyclopentylamino, N-methyl-N-cycloheptylamino, N-cyclohexyl-N-acetylamino, N-cyclopentyl-N-benzoylamino, cyclononylamino, cyclodecylamino, cyclododecylamino, cyclotridecylamino, cyclotetradecylamino, cyclopentadecylamino, N-methyl-N-cyclohexadecylamino, N-methyl-N-cyclononylamino, N-methyl-N-cyclodecylamino, N-cycloundecyl-N-acetylamino, and N-cyclohexadecyl-N-benzoyl groups.

Examples of the lower alkanoyl group which may have a halogen atom as a substituent include, in addition to the above described lower alkanoyl groups, linear or branched alkanoyl groups having 2 to 6 carbon atoms which may have 1 to 3 halogen atoms as substituents such as 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, and 5,6-dibromohexanoyl groups.

Examples of the lower alkoxycarbonyl group include linear or branched alkoxycarbonyl groups having 1 to 6 carbon atoms such as methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl groups.

Examples of the lower alkanoyloxy group include linear or branched alkanoyloxy groups having 2 to 6 carbon atoms such as acetyloxy, propionyloxy, butyryloxy, isobutyryloxy, pentanoyloxy, tert-butylcarbonyloxy, and hexanoyloxy groups.

Examples of the 5- or 6-membered saturated or unsaturated heterocyclic group having 1 to 4 nitrogen atoms, oxygen atoms or sulfur atoms include pyrrolidinyl, piperidinyl, piperazinyl, morpholino, thiomorpholino, pyridyl, 1,2,5,6-tetrahydropyridyl, thienyl, pyrazyl, pyrimidyl, pyridazyl, pyrrolyl, 2H-pyrrolyl, imidazolidinyl, pyrazolyl, imidazolyl, pyrazolidinyl, furazanyl, 2-imidazolinyl, imidazolidinyl, 2-pyrrolinyl, furyl, oxazolyl, isooxazolidinyl, isooxazolyl, thiazolyl, isothiazolyl, pyranyl, 2-pyrazolidinyl, 1,2,4-triazolyl, 1,2,3-triazolyl, 1,2,5-triazolyl, thiazolidinyl, 2-thiazolinyl, 1,2,3,4-tetrazolyl, 1,3,4-oxadiazolyl, tetrahydropyranyl, and tetrahydrofuryl groups.

Examples of the 5- to 7-membered saturated heterocyclic ring formed by binding $R^{11}$ and $R^{12}$ each other, together with nitrogen atoms bound to them, through or not through a nitrogen atom, a sulfur atom or an oxygen atom, include pyrrolidinyl, piperidinyl, piperazinyl, morpholino, thiomorpholino, and homopiperazinyl groups.

Examples of the imidazolyl lower alkyl group include imidazolylalkyl groups whose alkyl moiety is a linear or branched alkyl group having 1 to 6 carbon atoms such as (1, 2, 4 or 5-)imidazolylmethyl, 2-[(1, 2, 4 or 5-)imidazolyl]ethyl, 1-[(1, 2, 4 or 5-)imidazolyl]ethyl, 3-[(1, 2, 4 or 5-)imidazolyl]propyl, 4-[(1, 2, 4 or 5-)imidazolyl]butyl, 5-[(1, 2, 4 or 5-)imidazolyl]pentyl, 6-[(1, 2, 4 or 5-)imidazolyl]hexyl, 1,1-dimethyl-2-[(1, 2, 4 or 5-)imidazolyl]ethyl, and 2-methyl-3-[(1, 2, 4 or 5-)imidazolyl]propyl groups.

Examples of the 1,2,4-triazolyl lower alkyl group include 1,2,4-triazolylalkyl groups whose alkyl moiety is a linear or branched alkyl group having 1 to 6 carbon atoms such as (1, 3 or 5-)1,2,4-triazolylmethyl, 2-[(1, 3 or 5-)1,2,4-triazolyl]ethyl, 1-[(1, 3 or 5-)1,2,4-triazolyl]ethyl, 3-[(1, 3 or 5-)1,2,4-triazolyl]propyl, 4-[(1, 3 or 5-)1,2,4-triazolyl]butyl, 5-[(1, 3 or 5-)1,2,4-triazolyl]pentyl, 6-[(1, 3 or 5-)1,2,4-triazolyl]hexyl, 1,1-dimethyl-2-[(1, 3 or 5-)1,2,4-triazolyl]ethyl, and 2-methyl-3-[(1, 3 or 5-)1,2,4-triazolyl]propyl groups.

Examples of the 1,2,3-triazolyl lower alkyl group include 1,2,3-triazolylalkyl groups whose alkyl moiety is a linear or branched alkyl group having 1 to 6 carbon atoms such as (1, 4 or 5-)1,2,3-triazolylmethyl, 2-[(1, 4 or 5-)1,2,3-triazolyl]ethyl, 1-[(1, 4 or 5-)1,2,3-triazolyl]ethyl, 3-[(1, 4 or 5-)1,2,3-triazolyl]propyl, 4-[(1, 4 or 5-)1,2,3-triazolyl]butyl, 5-[(1, 4 or 5-)1,2,3-triazolyl]pentyl, 6-[(1, 4 or 5-)1,2,3-triazolyl]hexyl, 1,1-dimethyl-2-[(1, 4 or 5-)1,2,3-triazolyl]ethyl, and 2-methyl-3-[(1, 4 or 5-)1,2,3-triazolyl]propyl groups.

Examples of the 1,2,5-triazolyl lower alkyl group include 1,2,5-triazolylalkyl groups whose alkyl moiety is a linear or branched alkyl group having 1 to 56 carbon atoms such as (1, 3 or 4-)1,2,5-triazolylmethyl, 2-[(1, 3 or 4-)1,2,5-triazolyl]ethyl, 1-[(1, 3 or 4-)1,2,5-triazolyl]ethyl, 3-[(1, 3 or 4-)1,2,5-triazolyl]propyl, 4-[(1, 3 or 4-)1,2,5-triazolyl]butyl, 5-[(1, 3 or 4-)1,2,5-triazolyl]pentyl, 6-[(1, 3 or 4-)1,2,5-triazolyl]hexyl, 1,1-dimethyl-2-[(1, 3 or 4-)1,2,5-triazolyl]ethyl, and 2-methyl-3-[(1, 3 or 4-)1,2,5-triazolyl]propyl groups.

Examples of the pyrazolyl lower alkyl group include pyrazolylalkyl groups whose alkyl moiety is a linear or branched alkyl group having 1 to 6 carbon atoms such as (1, 3, 4 or 5-)pyrazolylmethyl, 2-[(1, 3, 4 or 5-)pyrazolyl]ethyl, 1-[(1, 3, 4 or 5-)pyrazolyl]ethyl, 3-[(1, 3, 4 or 5-)pyrazolyl]propyl, 4-[(1, 3, 4 or 5-)pyrazolyl]butyl, 5-[(1, 3, 4 or 5-)pyrazolyl]pentyl, 6-[(1, 3, 4 or 5-)pyrazolyl]hexyl, 1,1-dimethyl-2-[(1, 3, 4 or 5-)pyrazolyl]ethyl, and 2-methyl-3-[(1, 3, 4 or 5-)pyrazolyl]propyl groups.

Examples of the pyrimidinyl lower alkyl group which may have an oxo group as a substituent on the pyrimidine ring include pyrimidinylalkyl groups which may have 1 to 3 oxo groups as substituents on the pyrimidine ring and whose alkyl moiety is a linear or branched alkyl group having 1 to 6 carbon atoms such as (2, 4, 5 or 6-)pyrimidinylmethyl, 2-[(2, 4, 5 or 6-)pyrimidinyl]ethyl, 1-[(2, 4, 5 or 6-)pyrimidinyl]ethyl, 3-[(2, 4, 5 or 6-)pyrimidinyl]propyl, 4-[(2, 4, 5 or 6-)pyrimidinyl]butyl, 5-[(2, 4, 5 or 6-)pyrimidinyl]pentyl, 6-[(2, 4, 5 or 6-)pyrimidinyl]hexyl, 1,1-dimethyl-2-[(2, 4, 5 or 6-)pyrimidinyl]ethyl, 2-methyl-3-[(2, 4, 5 or 6-)pyrimidinyl]propyl, [(1, 3, 4 or 5-)2,6-dioxopyrimidinyl]methyl, [(1, 3, 4, 5 or 6-)2-oxopyrimidinyl]methyl, [(1, 2, 4 or 5-)6-oxopyrimidinyl]methyl, [(1, 2, 5 or 6-)4-oxopyrimidinyl]methyl, [(1, 3, 5 or 6-)2,4-dioxopyrimidinyl]methyl, 2-[(4 or 6-)2,5-dioxopyrimidinyl]ethyl, 1-[(1, 3, 4 or 5-)2,6-dioxopyrimidinyl]ethyl, 3-[(1, 3 or 5-)2,4,6-trioxopyrimidinyl]propyl, 4-[(1, 3, 4 or 5-)2,6-dioxopyrimidinyl]butyl, 5-[(4 or 6-)2,5-dioxopyrimidinyl]pentyl, 6-[(1, 3, 5 or 6-)2,4-dioxopyrimidinyl]hexyl, 1,1-dimethyl-[(1, 3, 4 or 5-)2,6-dioxopyrimidinyl]ethyl, and 2-methyl-3-[(1, 3, 4 or 5-)2,6-dioxopyrimidinyl]propyl groups.

Examples of the 3,5-dioxoisoxazolidin-4-ylidene lower alkyl group include 3,5-dioxoisoxazolidin-4-ylidenealkyl groups whose alkyl moiety is a linear or branched alkyl group having 1 to 6 carbon atoms such as 3,5-dioxoisoxazolidin-4-ylidenemethyl, 3,5-dioxoisoxazolidin-4-ylideneethyl, 3,5-dioxoisoxazolidin-4-ylidenepropyl, 3,5-dioxoisoxazolidin-4-ylideneisopropyl, 3,5-dioxoisoxazolidin-4-ylidenebutyl, 3,5-dioxoisoxazolidin-4-ylidenepentyl, and 3,5-dioxoisoxazolidin-4-ylidenehexyl groups.

Examples of the 1,2,4-oxadiazolyl lower alkyl group which may have a lower alkyl group as a substituent on the 1,2,4-oxadiazol ring include 1,2,4-oxadiazolylalkyl groups which may have a linear or branched alkyl group having 1 to 6 carbon atoms as a substituent on the 1,2,4-oxadiazol ring and whose alkyl moiety is a linear or branched alkyl group having 1 to 6 carbon atoms such as (3 or 5-)1,2,4-oxadiazolylmethyl, 2-[(3 or 5-)1,2,4-oxadiazolyl]ethyl, 1-[(3 or 5-)1,2,4-oxadiazolyl]ethyl, 3-[(3 or 5-)1,2,4-oxadiazolyl]propyl, 4-[(3 or 5-)1,2,4-oxadiazolyl]butyl, 5-[(3 or 5-)1,2,4-oxadiazolyl]pentyl, 6-[(3 or 5-)1,2,4-oxadiazolyl]hexyl, 1,1-dimethyl-2-[(3 or 5-)1,2,4-oxadiazolyl]ethyl, 2-methyl-3-[(3 or 5-)1,2,4-oxadiazolyl]propyl, 5-methyl-3-(1,2,4-oxadiazolyl)methyl, 3-ethyl-2-[5-(1,2,4-oxadiazolyl)]ethyl, 1-[3-propyl-5-(1,2,4-oxadiazolyl)]ethyl, 3-[5-butyl-3-(1,2,4-oxadiazolyl)]propyl, 4-[3-pentyl-5-(1,2,4-oxadiazolyl)]butyl, 5-[5-hexyl-3-(1,2,4-oxadiazolyl)]pentyl, 6-[3-methyl-5-(1,2,4-oxadiazolyl)]hexyl, 1,1-dimethyl-2-[5-isopropyl-3-(1,2,4-oxadiazolyl)]ethyl, and 2-methyl-3-[3-isobutyl-5-(1,2,4-oxadiazolyl)]propyl groups.

Examples of the thiazolydinyl lower alkyl group which may have an oxo group as a substituent on the thiazolydine ring include thiazolydinylalkyl groups which may have 1 to 3 oxo groups as substituents on the thiazolydine ring and whose alkyl moiety is a linear or branched alkyl group having 1 to 6 carbon atoms such as (2, 3, 4 or 5-)thiazolidinylmethyl, 2-[(2, 3, 4 or 5-)thiazolidinyl]ethyl, 1-[(2, 3, 4 or 5-)thiazolidinyl]ethyl, 3-[(2, 3, 4 or 5-)thiazolidinyl]propyl, 4-[(2, 3, 4 or 5-)thiazolidinyl]butyl, 5-[(2, 3, 4 or 5-)thiazolidinyl]pentyl, 6-[(2, 3, 4 or 5-)thiazolidinyl]hexyl, 1,1-dimethyl-2-[(2, 3, 4 or 5-)thiazolidinyl]ethyl, 2-methyl-3-[(2, 3, 4 or 5-)thiazolidinyl]propyl, 2,4-dioxo-5-thiazolidinylmethyl, 2-[2-oxo-(3, 4 or 5-)thiazolidinyl]ethyl, 1-[4-oxo-(2, 3 or 5-)thiazolidinyl]ethyl, 3-[5-oxo-(2, 3 or 4-)thiazolidinyl]propyl, 4-[2,5-dioxo-(3 or 4-)thiazolidinyl]butyl, 5-[2,4,5-trioxo-3-thiazolidinyl]pentyl, 6-[4,5-dioxo-(2 or 3-)thiazolidinyl]hexyl, 1,1-dimethyl-2-[2,4-dioxo-(3 or 5-)thiazolidinyl]ethyl, 2-methyl-3-[2,4-dioxo-(3 or 5-)thiazolidinyl]propyl, and 3-[2,4-dioxo-(3 or 5-)thiazolidinyl]propyl groups.

Examples of the phenyl lower alkyl group which may have a lower alkylenedioxy group as a substituent on the phenyl ring include, in addition to the above described phenyl lower alkyl groups, phenylalkyl groups which may have a linear or branched alkylenedioxy group having 1 to 4 carbon atoms as a substituent on the phenyl ring and whose alkyl moiety is a linear or branched alkyl group having 1 to 6 carbon atoms such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, and 2-methyl-3-(3,4-ethylenedioxyphenyl)propyl groups.

Examples of the lower alkoxycarbonyl lower alkyl group include alkoxycarbonylalkyl groups whose alkoxy moiety is a linear or branched alkoxy group having 1 to 6 carbon atoms and whose alkyl moiety is a linear or branched alkyl group having 1 to 6 carbon atoms such as methoxycarbonylmethyl, ethoxycarbonylmethyl, 2-methoxycarbonylethyl, 2-ethoxycarbonylethyl, 1-ethoxycarbonylethyl, 3-methoxycarbonylpropyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, and hexyloxycarbonylmethyl groups.

Examples of the carboxy lower alkyl group include carboxyalkyl groups whose alkyl moiety is a linear or branched alkyl group having 1 to 6 carbon atoms such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, and 2-methyl-3-carboxypropyl groups.

Examples of the morpholino substituted lower alkanoyl group include morpholino substituted alkanoyl groups whose alkanoyl moiety is a linear or branched alkanoyl group having 2 to 6 carbon atoms such as 2-[(2, 3 or 4-)morpholino]acetyl group, 3-[(2, 3 or 4-)morpholino]propionyl, 2-[(2, 3 or 4-)morpholino]propionyl, 4-[(2, 3 or 4-)morpholino]butyryl, 5-[(2, 3 or 4-)morpholino]pentanoyl, 6-[(2, 3 or 4-)morpholino]hexanoyl, 2,2-dimethyl-2-[(2, 3 or 4-)morpholino]propionyl, and 2-methyl-3-[(2, 3 or 4-)morpholino]propionyl groups.

Examples of the piperazinylcarbonyl lower alkyl group which may be substituted on the piperazine ring with a phenyl lower alkyl group which may have a lower alkylenedioxy group as a substituent on the phenyl ring include piperazinylcarbonylalkyl groups whose alkyl moiety is a linear or branched alkyl group having 1 to 6 carbon atoms and which may be substituted on the piperazine ring with 1 to 3 phenylalkyl groups which may have a linear or branched alkylenedioxy group having 1 to 4 carbon atoms as a substituent on the phenyl group and whose alkyl moiety is a linear or branched alkyl group having 1 to 6 carbon atoms such as [(1, 2 or 3-)piperazinyl]carbonylmethyl, 2-[(1, 2 or 3-)piperazinyl]carbonylethyl, 1-[(1, 2 or 3-)piperazinyl]carbonylethyl, 3-[(1, 2 or 3-)piperazinyl]carbonylpropyl, 4-[(1, 2 or 3-)piperazinyl]carbonylbutyl, 5-[(1, 2 or 3-)piperazinyl]carbonylpentyl, 6-[(1, 2 or 3-)piperazinyl]carbonylhexyl, 1,1-dimethyl-2-[(1, 2 or 3-)piperazinyl]carbonylethyl, 2-methyl-3-[(1, 2 or 3-)piperazinyl]carbonylpropyl, (4-benzyl-1-piperazinylcarbonyl)methyl, 2-[4-(2-phenylethyl)-1-piperazinylcarbonyl]ethyl, 1-[4-(3-phenylpropyl)-1-piperazinylcarbonyl]ethyl, 3-[4-(4-phenylbutyl)-1-piperazinylcarbonyl]propyl, 4-[4-(5-phenylpentyl)-1-piperazinylcarbonyl]butyl, 5-[4-(6-phenylpropyl)-1-piperazinylcarbonyl]pentyl, 6-(4-benzyl-1-piperazinylcarbonyl)hexyl, 1,1-dimethyl-2-(4-benzyl-1-piperazinylcarbonyl)ethyl, 2-methyl-3-(4-benzyl-1-piperazinylcarbonyl)propyl, [4-(3,4-methylenedioxybenzyl)-1-piperazinylcarbonyl]methyl, 2-{4-[2-(2,3-ethylenedioxyphenyl)ethyl]-1-piperazinylcarbonyl}ethyl, 1-{4-[3-(3,4-trimethylenedioxyphenyl)propyl]-1-piperazinylcarbonyl}ethyl, 3-{4-[4-(2,3-tetramethylenedioxyphenyl)butyl]-1-piperazinylcarbonyl}propyl, 4-{4-[5-(3,4-methylenedioxyphenyl)pentyl]-1-piperazinylcarbonyl}butyl, 5-{4-[3-(2,3-ethylenedioxyphenyl)propyl]-1-piperazinylcarbonyl}pentyl, 6-[4-(3,4-trimethylenedioxybenzyl)-1-piperazinylcarbonyl]hexyl, 1,1-dimethyl-2-[4-(2,3-tetramethylenedioxybenzyl)-1-piperazinylcarbonyl]ethyl, 2-methyl-3-[4-(3,4-methylenedioxybenzyl)-1-piperazinylcarbonyl]propyl, (3,4-dibenzyl-1-piperazinylcarbonyl)methyl, (3,4,5-tribenzyl-1-piperazinylcarbonyl)methyl, [2,4-di(3,4-methylenedioxybenzyl)-1-piperazinylcarbonyl]methyl, [2,4,6-tri(3,4-methylenedioxybenzyl)-1-piperazinylcarbonyl]methyl, and [3-benzyl-4-(3,4-methylenedioxybenzyl)-1-piperazinylcarbonyl]methyl groups.

Examples of the piperazinyl lower alkanoyl group which may be substituted on the piperazine ring with a phenyl lower alkyl group which may have a lower alkylenedioxy group as a substituent on the phenyl ring include piperazinylalkanoyl groups whose alkanoyl moiety is a linear or branched alkanoyl group having 2 to 6 carbon atoms and which may be substituted on the piperazine ring with 1 to 3 phenylalkyl groups which may have a linear or branched alkylenedioxy group having 1 to 4 carbon atoms as a substituent on the phenyl ring and whose alkyl moiety is a linear or branched alkyl group having 1 to 6 carbon atoms, such as 2-[(1, 2 or 3-)piperazinyl]acetyl, 3-[(1, 2 or 3-)piperazinyl]propionyl, 2-[(1, 2 or 3-)piperazinyl]propionyl, 4-[(1, 2 or 3-)piperazinyl]butyryl, 5-[(1, 2 or 3-)piperazinyl]pentanoyl, 6-[(1, 2 or 3-)piperazinyl]hexanoyl, 2,2-dimethyl-3-[(1, 2 or 3-)piperazinyl]propionyl, 2-methyl-3-[(1, 2 or 3-)piperazinyl]propionyl, 2-(4-benzyl-1-piperazinyl)acetyl, 3-[4-(2-phenylethyl)-1-piperazinyl]propionyl, 2-[4-(3-phenylpropyl)-1-piperazinyl]propionyl, 4-[4-(4-phenylbutyl)-1-piperazinyl]butyryl, 5-[4-(5-phenylpentyl)-1-piperazinyl]pentanoyl, 6-[4-(6-phenylpropyl)-1-piperazinyl]hexanoyl, 6-(4-benzyl-1-piperazinyl)hexanoyl, 2,2-dimethyl-3-(4-benzyl-1-piperazinyl)propionyl, 2-methyl-3-(4-benzyl-1-piperazinyl)propionyl, 2-[4-(3,4-methylenedioxybenzyl)-1-piperazinyl]acetyl, 3-{4-[2-(2,3-ethylenedioxyphenyl)ethyl]-1-piperazinyl}propionyl, 2-{4-[3-(3,4-trimethylenedioxyphenyl)propyl]-1-piperazinyl}propionyl, 4-{4-[4-(2,3-tetramethylenedioxyphenyl)butyl]-1-piperazinyl}butyryl, 5-{4-[5-(3,4-methylenedioxyphenyl)pentyl]-1-piperazinyl}pentanoyl, 5-{4-[3-(2,3-ethylenedioxyphenyl)propyl]-1-piperazinyl}pentanoyl, 6-[4-(3,4-trimethylenedioxybenzyl)-1-piperazinyl]hexanoyl, 2,2-dimethyl-3-[4-(2,3-tetramethylenedioxybenzyl)-1-piperazinyl]propionyl, 2-methyl-3-[4-(3,4-methylenedioxybenzyl)-1-piperazinyl]propionyl, 2-(3,4-dibenzyl-1-piperazinyl)acetyl, 2-(3,4,5-tribenzyl-1-piperazinyl)acetyl, 2-[2,4-di(3,4-methylenedioxybenzyl)-1-piperazinyl]acetyl, 2-[2,4,6-tri(3,4-methylenedioxybenzyl)-1-piperazinyl]acetyl, and 2-[3-benzyl-4-(3,4-methylenedioxybenzyl)-1-piperazinyl]acetyl groups.

Examples of the morpholinocarbonyl substituted lower alkyl group include morpholinocarbonylalkyl groups whose alkyl moiety is a linear or branched alkyl group having 1 to 6 carbon atoms such as [(2, 3 or 4-)morpholino]carbonylmethyl, 2-[(2, 3 or 4-)morpholino]carbonylethyl, 1-[(2, 3 or 4-)morpholino]carbonylethyl, 3-[(2, 3 or 4-)morpholino]carbonylpropyl, 4-[(2, 3 or 4-)morpholino]carbonylbutyl, 5-[(2, 3 or 4-)morpholino]carbonylpentyl, 6-[(2, 3 or 4-)morpholino]carbonylhexyl, 1,1-dimethyl-2-[(2, 3 or 4-)morpholino]carbonylethyl, and 2-methyl-3-[(2, 3 or 4-)morpholino]carbonylpropyl groups.

Examples of the imidazolyl lower alkanoyl group include imidazolylalkanoyl groups whose alkanoyl moiety is a linear or branched alkanoyl group having 2 to 6 carbon atoms such as 2-[(1, 2, 4 or 5-)imidazolyl]acetyl, 3-[(1, 2, 4 or 5-)imidazolyl]propionyl, 2-[(1, 2, 4 or 5-)imidazolyl]propionyl, 4-[(1, 2, 4 or 5-)imidazolyl]butyryl, 5-[(1, 2, 4 or 5-)imidazolyl]pentanoyl, 6-[(1, 2, 4 or 5-)imidazolyl]hexanoyl, 2,2-dimethyl-3-[(1, 2, 4 or 5-)imidazolyl]propionyl, and 2-methyl-3-[(1, 2, 4 or 5-)imidazolyl]propionyl groups.

Examples of the cycloalkylcarbonyl group include cycloalkylcarbonyl groups whose cycloalkyl moiety is a cycloalkyl group having 3 to 16 carbon atoms such as cyclopropylcarbonyl, cyclobutylcarbonyl, cyclopentylcarbonyl, cyclohexylcarbonyl, cycloheptylcarbonyl, cyclooctylcarbonyl, cyclononylcarbonyl, cyclodecylcarbonyl, cycloundecylcarbonyl, cyclododecylcarbonyl, cyclotridecylcarbonyl, cyclotetradecylcarbonyl, cyclopentadecylcarbonyl, and cyclohexadecylcarbonyl groups.

Examples of the amino substituted lower alkanoyl group which may have a lower alkyl group as a substituent include linear or branched alkanoyl groups having 2 to 6 carbon atoms substituted with an amino group which may have 1 or 2 linear or branched alkyl groups having 1 to 6 carbon atoms as substituents such as aminoacetyl, 2-aminopropionyl, 3-aminopropionyl, 4-aminobutyryl, 5-aminopentanoyl, 6-aminohexanoyl, 2,2-dimethyl-3-aminopropionyl, 2-methyl-3-aminopropionyl, methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, dimethylaminoacetyl, 3-diisopropylaminopropionyl, (N-ethyl-N-propylamino)acetyl, and 2-(N-methyl-N-hexylamino)acetyl groups.

Examples of the lower alkylene group which may have a hydroxyl group as a substituent include, in addition to the above described lower alkylene groups, linear or branched alkylene groups having 1 to 6 carbon atoms which may have 1 to 3 hydroxyl groups as substituents such as 1-hydroxymethylene, 2-hydroxyethylene, 1-hydroxyethylene, 2-hydroxytrimethylene, 3-hydroxytrimethylene, 1-hydroxytrimethylene, 3-hydroxy-2-methyltrimethylene, 1-hydroxy-2-methyltrimethylene, 3-hydroxy-2,2-dimethyltrimethylene, 1-hydroxy-2,2-dimethyltrimethylene, 3-hydroxy-1-methyltrimethylene, 2-hydroxy-1-methyltrimethylene, 1-hydroxymethylmethylene, hydroxymethylmethylene, 2-hydroxymethyltrimethylene, 2-hydroxymethyl-2-methyltrimethylene, (2-hydroxyethyl)methylene, (1-hydroxyethyl)methylene, 4-hydroxytetramethylene, 2-hydroxytetramethylene, 3-hydroxytetramethylene, 1-hydroxytetramethylene, 5-hydroxypentamethylene, 4-hydroxypentamethylene, 3-hydroxypentamethylene, 2-hydroxypentamethylene, 1-hydroxypentamethylene, 6-hydroxyhexamethylene, 5-hydroxyhexamethylene, 4-hydroxyhexamethylene, 3-hydroxyhexamethylene, 2-hydroxyhexamethylene, 1-hydroxyhexamethylene, 1,2-dihydroxytrimethylene, 2,2,4-trihydroxytetramethylene, 1,2,6-trihydroxyhexamethylene, and 3,4,5-trihydroxypentamethylene groups.

Examples of the alkyl group which may have a hydroxyl group as a substituent include, in addition to the above described lower alkyl groups, linear or branched alkyl groups having 1 to 16 carbon atoms which may have 1 to 3 hydroxyl groups as substituents such as heptyl, octyl, nonyl, decyl, undecyl, dodecyl, tridecyl, tetradecyl, pentadecyl, 1-methylhexyl, hexadecyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the hydroxyl group substituted alkyl group include linear or branched alkyl groups having 1 to 16 carbon atoms and 1 to 3 hydroxyl groups as substituents such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the cycloalkyl group which may have a substituent selected from the group consisting of a hydroxyl group and a lower alkyl group include, in addition to the above described cycloalkyl groups, cycloalkyl groups having 3 to 16 carbon atoms which may have 1 to 3 substituents selected from the group consisting of a hydroxyl group and a linear or branched alkyl group having 1 to 6 carbon atoms such as 2-hydroxycyclopropyl, 3-hydroxycyclobutyl, 3-hydroxycyclopentyl, 2-hydroxycyclohexyl, 4-hydroxycyclohexyl, 3-hydroxycycloheptyl, 4-hydroxycyclooctyl, 5-hydroxycyclononyl, 3-hydroxycyclodecyl, 4-hydroxycycloundecyl, 5-hydroxycyclododecyl, 6-hydroxycyclotridecyl, 7-hydroxycyclotetradecyl, 6-hydroxycyclopentadecyl, 8-hydroxycyclohexadecyl, 2,4-dihydroxycyclohexyl, 2,4,6-trihydroxycyclohexyl, 1-methylcyclopentyl, 2-ethylcyclopropyl, 3-n-propylcyclobutyl, 2-n-butylcyclohexyl, 4-n-pentylcycloheptyl, 4-n-hexylcyclooctyl, 2,3-dimethylcyclohexyl, 2,3,4-trimethylcyclohexyl, and 2-methyl-4-hydroxycyclohexyl groups.

Examples of the phenoxy lower alkyl group include phenoxyalkyl groups whose alkyl moiety is a linear or branched alkyl group having 1 to 6 carbon atoms such as phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 1-phenoxyisopropyl, and 2-methyl-3-phenoxypropyl groups.

Examples of the amino lower alkoxy group which may have a lower alkyl group as a substituent include linear or branched alkoxy groups having 1 to 6 carbon atoms substituted with an amino group which may have 1 or 2 linear or branched alkyl groups having 1 to 6 carbon atoms such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, 2-diethylaminoethoxy, 2-diisopropylaminoethoxy, (N-ethyl-N-propylamino)methoxy, and 2-(N-methyl-N-hexylamino)ethoxy groups.

Examples of the hydroxyl group substituted lower alkyl group include linear or branched alkyl groups having 1 to 6 carbon atoms which have 1 to 3 hydroxyl groups as substituents such as hydroxymethyl, 1-hydroxyethyl, 2-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the amino group which may have a lower alkylsulfonyl as a substituent include amino groups which may have 1 or 2 linear or branched alkylsulfonyl groups having 1 to 6 carbon atoms as substituents such as amino, methylsulfonylamino, ethylsulfonylamino, propylsulfonylamino, isopropylsulfonylamino, butylsulfonylamino, tert-butylsulfonylamino, pentylsulfonylamino, hexylsulfonylamino, dimethylsulfonylamino, diethylsulfonylamino, dipropylsulfonylamino, dibutylsulfonylamino, dipentylsulfonylamino, dihexylsulfonylamino, N-methylsulfonyl-N-ethylsulfonylamino, N-ethylsulfonyl-N-propylsulfonylamino, N-methylsulfonyl-N-butylsulfonylamino, and N-methylsulfonyl-N-hexylsulfonylamino groups.

Examples of the lower alkynyl group include linear or branched alkynyl groups having 2 to 6 carbon atoms such as ethynyl, 2-propynyl, 2-butynyl, 3-butynyl, 1-methyl-2-propynyl, 2-pentynyl, and 2-hexynyl groups.

Examples of the anilino group which may have a halogen atom as a substituent on the phenyl ring include anilino groups which may have 1 to 3 halogen atoms as substituents on the phenyl ring such as anilino, 2-fluoroanilino, 3-fluoroanilino, 4-fluoroanilino, 2-bromoanilino, 3-bromoanilino, 4-bromoanilino, 2-iodoanilino, 3-iodoanilino, 4-iodoanilino, 2,3-dibromoanilino, 2,4-diiodoanilino, 2,5-difluoroanilino, 2,6-dichloroanilino, 2,4,6-trichloroanilino, 2,6-difluoroanilino, 3,5-difluoroanilino, 2,6-difluoroanilino, 2-chloroanilino, 3-chloroanilino, 4-chloroanilino, 2,3-dichloroanilino, 2,4-dichloroanilino, 2,5-dichloroanilino, 3,4-dichloroanilino, 2,6-dichloroanilino, 3,5-dichloroanilino, 2,4,6-trifluoroanilino, 2,4-difluoroanilino, and 3,4-difluoroanilino groups.

Examples of the piperazinyl group which may have a lower alkyl group as a substituent on the piperazine ring include piperazinyl groups which may have 1 to 3 linear or branched alkyl groups having 1 to 6 carbon atoms as substituents on the piperazine ring such as (1-, 2- or 3-)piperazinyl, 4-methyl-(1-, 2- or 3-)piperazinyl, 2,3-dimethyl-(1- or 5-)piperazinyl, and 2,3,4-trimethyl-(1-, 5- or 6-)piperazinyl groups.

Examples of the pyrrolidinyl group which may have an oxo group as a substituent on the pyrrolidine ring include pyrrolidinyl groups which may have 1 or 2 oxo groups as substituents on the pyrrolidine ring such as (1-, 2- or 3-)pyrrolidinyl, 2-oxo-(1-, 3-, 4- or 5-)pyrrolidinyl, 3-oxo-(1-, 2-, 4- or 5-)pyrrolidinyl, 2,3-dioxo-(1-, 4- or 5-)pyrrolidinyl, and 2,5-dioxo-(1-, 3- or 4-)pyrrolidinyl groups.

Examples of the lower alkanoyl amino group include linear or branched alkanoyl amino groups having 2 to 6 carbon atoms which have 1 to 3 halogen atoms as substituents such as acetyl amino, propionyl amino, butyryl amino, pentanoyl amino, 2-methylpropionyl amino, and hexanoyl amino groups.

Examples of the phenyl group which may be substituted on the phenyl ring with 1 to 3 groups selected from the group consisting of a lower alkyl group; a lower alkoxy group which may have a halogen atom as a substituent; a halogen atom; an amino lower alkoxy group which may have a lower alkyl group as a substituent; a hydroxyl group substituted lower alkyl group; a phenyl lower alkyl group; a lower alkynyl group; an amino group which may have a lower alkylsulfonyl group as a substituent; a lower alkylthio group; a cycloalkyl group; a phenylthio group; an adamantyl group; an anilino group which may have a halogen atom as a substituent on the phenyl ring; a lower alkoxycarbonyl group; a piperazinyl group which may have a lower alkyl group as a substituent on the piperazine ring; a lower alkanoylamino group; a cyano group; a pyrrolidinyl group which may have an oxo group as a substituent on the pyrrolidine ring; and a phenoxy group include phenyl groups which may be substituted on the phenyl ring with 1 to 3 groups selected from the group consisting of a linear or branched alkyl group having 1 to 6 carbon atoms; a linear or branched alkoxy group having 1 to 6 carbon atoms which may have 1 to 3 halogen atoms; a halogen atom; an aminoalkoxy group whose alkoxy moiety is a linear or branched alkoxy group having 1 to 6 carbon atoms and which may have 1 or 2 linear or branched alkyl groups having 1 to 6 carbon atom as substituents; a linear or branched alkyl group having 1 to 6 carbon atoms and 1 to 3 hydroxyl groups as substituents; a phenylalkyl group whose alkyl moiety is a linear or branched alkyl group having 1 to 6 carbon atoms; a linear or branched alkynyl group having 2 to 6 carbon atoms; an amino group which may have 1 or 2 linear or branched alkylsulfonyl groups having 1 to 6 carbon atoms as substituents; a linear or branched alkylthio group having 1 to 6 carbon atoms; a cycloalkyl group having 3 to 16 carbon atoms; a phenylthio group; an adamantyl group; an anilino group which may have 1 to 3 halogen atoms as substituents on the phenyl ring; a linear or branched alkoxycarbonyl group having 1 to 6 carbon atoms; an amino group which may have 1 or 2 linear or branched alkanoyl groups having 2 to 6 carbon atoms; a cyano group; a piperazinyl group which may have 1 to 3 linear or branched alkyl groups having 1 to 6 carbon atoms as substituents on the piperazine ring; a pyrrolidinyl group which may have 1 or 2 oxo groups as substituents on the pyrrolidine ring; and a phenoxy group such as phenyl, 2-methylphenyl, 3-methylphenyl, 4-methylphenyl, 2-ethylphenyl, 3-ethylphenyl, 4-ethylphenyl, 2-isopropylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-triflupromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-methyl-3-trifluoromethoxy-4-trifluoromethoxyphenyl, 2-phenoxyphenyl, 3-phenoxyphenyl, 4-phenoxyphenyl, 2,3-diphenoxyphenyl, 3,4-diphenoxyphenyl, 2,6-diphenoxyphenyl, 3,4,5-triphenoxyphenyl, 2-methyl-4-phenoxyphenyl, 3-ethyl-4-phenoxyphenyl, 2-methoxy-4-phenoxyphenyl, 3-ethoxy-4-phenoxyphenyl, 2-methyl-3-phenoxy-4-trifluoromethoxyphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 4-methylthiophenyl, 4-cyclohexylphenyl, 4-chloro-2-anilinophenyl, 2-(4-chloro anilino)-5-ethoxy carbonylphenyl, 4-[2-(N,N-diethylamino)ethoxy]phenyl, 4-(4-methyl-1-piperazinyl)phenyl, 4-(2-oxo-1-pyrrolidinyl)phenyl, 4-methylsulfonylaminophenyl, 4-(2-hydroxyethyl)phenyl, 4-benzylphenyl, 4-ethynylphenyl, 4-phenylthiophenyl, 4-(1-adamantyl)phenyl, 5-acetylamino-2-chlorophenyl, 2-propanoylaminophenyl, 3-cyanophenyl, 2-cyanophenyl, 4-cyanophenyl, 3,4-dicyanophenyl, and 3,4,5-tricyanophenyl groups.

Examples of the phenyl lower alkyl group which may be substituted on the phenyl ring with 1 to 3 groups selected from the group consisting of a halogen atom, a lower alkoxy group which may have a halogen atom as a substituent, and a lower alkyl group include, in addition to the above described phenyl lower alkyl groups, phenylalkyl groups whose alkyl moiety is a linear or branched alkyl group having 1 to 6 carbon atoms and which may be substituted on the phenyl ring with 1 to 3 groups selected from the group consisting of a halogen atom, a linear or branched alkoxy group having 1 to 6 carbon atoms which may have 1 to 3 halogen atoms as substituents, and a linear or branched alkyl group having 1 to 6 carbon atoms such as 4-fluorobenzyl, 2-chlorobenzyl, 3-chlorobenzyl, 4-chlorobenzyl, 2-(2-fluorophenyl)ethyl, 2-(4-fluorophenyl)ethyl, 2-(4-chlorophenyl)ethyl, 3,4-dibromobenzyl, 3,4-diiodobenzyl, 2,4-difluorobenzyl, 2,5-dichlorobenzyl, 2,6-dichlorobenzyl, 3,4,5-trifluorobenzyl, 3-(4-chlorophenyl)propyl, 1-(2-bromophenyl)ethyl, 4-(3-fluorophenyl)butyl, 5-(4-iodophenyl)pentyl, 6-(4-chlorophenyl)hexyl, 1,1-dimethyl-2-(3-fluorophenyl)ethyl, 2-methyl-3-(4-chlorophenyl)propyl, 2-methylbenzyl, 2-(3-methylphenyl)ethyl, 3-(4-methylphenyl)propyl, 1-(2-ethylphenyl)ethyl, 4-(3-ethylphenyl)butyl, 5-(4-ethylphenyl)pentyl, 6-(4-isopropylphenyl)hexyl, 1,1-dimethyl-2-(3-butylphenyl)ethyl, 2-methyl-3-(4-pentylphenyl)propyl, 4-hexylbenzyl, 3,4-dimethylbenzyl, 3,4-diethylbenzyl, 2,4-dimethylbenzyl, 2,5-dimethylbenzyl, 2,6-dimethylbenzyl, 3,4,5-trimethylbenzyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, 3,4,5-trimethoxybenzyl, 2-trifluoromethoxybenzyl, 3-trifluoromethoxybenzyl, 4-trifluoromethoxybenzyl, 2-[2-(bromomethoxy)phenyl]ethyl, 1-[3'-(2-chloroethoxy)phenyl]ethyl, 3-[4-(2,3-dichloropropoxy)phenyl]propyl, 4-[4-(4-fluorobutoxy)phenyl]butyl, 5-[3-(5-chloropentyloxy)phenyl]pentyl, 6-[4-(5-bromohexyloxy)phenyl]hexyl, 1,1-dimethyl-2-[4-(5,6-dibromohexyloxy)phenyl]ethyl, 3,4-di(trifluoromethoxy)benzyl, 3,4-di(4,4,4-trichlorobutoxy)benzyl, 2,4-di(3-chloro-2-methoxypropyl)benzyl, 2,5-di(3-chloropropoxy)benzyl, 2,6-di(2,2,2-trifluoroethoxy)benzyl, 3,4,5-tri(trifluoromethoxy)benzyl, 4-(2,2,2-trichloroethoxy)benzyl, 2-methyl-4-trifluoromethoxybenzyl, 3-ethyl-4-trichloromethoxybenzyl, 2-methoxy-4-trifluoromethoxybenzyl, 3-ethoxy-4-trichloromethoxybenzyl, 2-methyl-3-trifluoromethoxy-4-trifluoromethoxybenzyl, 2-chloro-3-methylbenzyl, 4-fluoro-2-trifluoromethoxybenzyl, and 3-chloro-2-methyl-4-methoxybenzyl groups.

Examples of the phenyl lower alkyl group which has a lower alkylenedioxy group as a substituent on the phenyl ring include phenylalkyl groups which have a linear or branched alkylenedioxy group having 1 to 4 carbon atoms as a substituent on the phenyl ring and whose alkyl moiety is a linear or branched alkyl group having 1 to 6 carbon atoms such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, and 2-methyl-3-(3,4-ethylenedioxyphenyl)propyl groups.

Examples of the amino group which may have a lower alkanoyl group as a substituent include amino groups which may have a linear or branched alkanoyl group having 1 to 6 carbon atoms as a substituent such as amino, N-acetylamino, N-formylamino, N-propionylamino, N-butyrylamino, N-isobutyrylamino, N-pentanoylamino, N-tert-butylcarbonylamino, and N-hexanoylamino groups.

Examples of the 1,2,3,4-tetrahydroquinolyl group which may have, on the tetrahydroquinoline ring, 1 to 3 substituents selected from the group consisting of an oxo group, a lower alkoxy group, and a lower alkylenedioxy group include 1,2,3,4-tetrahydroquinolyl groups which may have, on the tetrahydroquinoline ring, 1 to 3 substituents selected from the group consisting of an oxo group, a linear or branched alkoxy group having 1 to 6 carbon atoms, and a linear or branched alkylenedioxy group having 1 to 4 carbon atoms such as (1, 2, 3, 4, 5, 6, 7 or 8-)1,2,3,4-tetrahydroquinolyl, 2-oxo-(1, 3, 4, 5, 6, 7 or 8-)1,2,3,4-tetrahydroquinolyl, 2-oxo-6,7-methylenedioxy-(1, 3, 4, 5 or 8-)1,2,3,4-tetrahydroquinolyl, 4-oxo-(1, 2, 3, 5, 6, 7 or 8-)1,2,3,4-tetrahydroquinolyl, 2,4-dioxo-(1, 3, 5, 6, 7 or 8-)1,2,3,4-tetrahydroquinolyl, 2,4-dioxo-6,7-methylenedioxy-(1, 3, 5 or 8-)2,3,4-tetrahydroquinolyl, 5,6-ethylenedioxy-(1, 2, 3, 4, 7 or 8-)1,2,3,4-tetrahydroquinolyl, 7,8-trimethylenedioxy-(1, 2, 3, 4, 5 or 6-)1,2,3,4-tetrahydroquinolyl, 6,7-tetramethylenedioxy-(1, 2, 3, 4, 5 or 8-)1,2,3,4-tetrahydroquinolyl, 5-methoxy-2-oxo-(1, 3, 4, 6, 7 or 8-)1,2,3,4-tetrahydroquinolyl, and 2-oxo-6,7-ethylenedioxy-(1, 3, 4, 5 or 8-)1,2,3,4-tetrahydroquinolyl groups.

Examples of the cycloalkyl lower alkyl group include cycloalkylalkyl groups having 3 to 16 carbon atoms whose alkyl moiety is a linear or branched alkyl group having 1 to 6 carbon atoms such as cyclopropylmethyl, cyclohexylmethyl, 2-cyclopropylethyl, 1-cyclobutylethyl, 3-cyclopentylpropyl, 4-cyclohexylbutyl, 5-cycloheptylpentyl, 6-cyclooctylhexyl, 1,1-dimethyl-2-cyclononylethyl, 2-methyl-3-cyclodecylpropyl, cycloundecylmethyl, 2-cyclododecylethyl, 1-cyclotridecylethyl, 3-cyclotetradecylpropyl, 4-cyclopentadecylbutyl, and 5-cyclohexadecylpentyl groups.

Examples of the pyridyl lower alkyl group include pyridylalkyl groups whose alkyl moiety is a linear or branched alkyl group having 1 to 6 carbon atoms such as (2, 3 or 4-)pyridylmethyl, 2-[(2, 3 or 4-)pyridyl]ethyl, 1-[(2, 3 or 4-)pyridyl]ethyl, 3-[(2, 3 or 4-)pyridyl]propyl, 4-[(2, 3 or 4-)pyridyl]butyl, 1,1-dimethyl-2-[(2, 3 or 4-)pyridyl]ethyl, 5-[(2, 3 or 4-)pyridyl]pentyl, 6-[(2, 3 or 4-)pyridyl]hexyl, 1-[(2, 3 or 4-)pyridyl]isopropyl, and 2-methyl-3-[(2, 3 or 4-)pyridyl]propyl groups.

Examples of the amino group substituted lower alkyl group which may have a substituent selected from the group consisting of a lower alkyl group and a lower alkanoyl group include linear or branched alkyl groups having 1 to 6 carbon atoms and an amino group which may have 1 or 2 substituents selected from the group consisting of a linear or branched alkyl group having 1 to 6 carbon atoms and a linear or branched alkanoyl group having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N,N-dimethylamino)ethyl, 2-(N-methyl-N-hexylamino)ethyl, formylaminomethyl, acetylaminomethyl, 1-propionylaminoethyl, 2-acetylaminoethyl, 3-butyrylaminopropyl, 4-pentanoylaminobutyl, 5-hexanoylaminopentyl, 6-acetylaminohexyl, N-methyl-N-acetylaminomethyl, 2-(N-ethyl-N-propanoylamino)ethyl, (N-ethyl-N-butyrylamino)methyl, 2-(N-methyl-N-hexanoylamino)ethyl, and 3-(N,N-dimethylamino)propyl groups.

Examples of the lower alkoxy lower alkyl group include linear or branched alkyl groups having 1 to 6 carbon atoms which have a linear or branched alkoxy group having 1 to 6 carbon atoms, as a substituent such as methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the 1,2,3,4-tetrahydroisoquinolylcarbonyl substituted lower alkyl group include 1,2,3,4-tetrahydroisoquinolylcarbonyl-alkyl groups whose alkyl moiety is a linear or branched alkyl group having 1 to 6 carbon atoms such as (1, 2, 3, 4, 5, 6, 7 or 8-)1,2,3,4-tetrahydroisoquinolylcarbonylmethyl, 2-[(1, 2, 3, 4, 5, 6, 7or 8-)1,2,3,4-tetrahydroisoquinolylcarbonyl]ethyl, 1-[((1, 2, 3, 4, 5, 6, 7 or 8-)1, 2, 3, 4-tetrahydroisoquinolylcarbonyl)ethyl, 3-[(1, 2, 3, 4, 5, 6, 7 or 8-)1,2,3,4-tetrahydroisoquinolylcarbonyl]propyl, 4-[(1, 2, 3, 4, 5, 6, 7 or 8-)1,2,3,4-tetrahydroisoquinolylcarbonyl]butyl, 1,1-dimethyl-2-[(1, 2, 3, 4, 5, 6, 7 or 8-)1,2,3,4-tetrahydroisoquinolylcarbonyl]ethyl, 5-[(1, 2, 3, 4, 5, 6, 7 or 8-)1,2,3,4-tetrahydroisoquinolylcarbonyl]pentyl, 6-[(1, 2, 3, 4, 5, 6, 7 or 8-) 1,2,3,4-tetrahydroisoquinolylcarbonyl]hexyl, 1-[(1, 2, 3, 4, 5, 6, 7 or 8-)1,2,3,4-tetrahydroisoquinolylcarbonyl]isopropyl, and 2-methyl-3-[(1, 2, 3, 4, 5, 6, 7 or 8-)1,2,3,4-tetrahydroisoquinolylcarbonyl]propyl groups.

Examples of the piperidinylcarbonyl group which may have, on the piperidine ring, a substituent selected from the group consisting of a lower alkoxycarbonyl group, a phenyl lower alkyl group, and a furyl lower alkyl group include piperidinylcarbonyl groups which may have, on the piperidine ring, 1 to 3 substituents selected from the group consisting of an alkoxycarbonyl group whose alkoxy moiety is a linear or branched alkoxy group having 1 to 6 carbon atoms, a phenylalkyl group whose alkyl moiety is a linear or branched alkyl group having 1 to 6 carbon atoms, and a furylalkyl group whose alkyl moiety is a linear or branched alkyl group having 1 to 6 carbon atoms such as (1, 2, 3 or 4-)piperidinylcarbonyl, 1-benzyl-(2, 3 or 4-)piperidinylcarbonyl, 1-(2 or 3-)furylmethyl-(2, 3 or 4-)piperidinylcarbonyl, 1-(2-phenylethyl)-(2, 3 or 4-)piperidinylcarbonyl, 1-{2-[(1 or 2-)furyl]ethyl}-(2, 3 or 4-)piperidinylcarbonyl, 1-(1-phenylethyl)-(2, 3 or 4-)piperidinylcarbonyl, 1-{3-[(1 or 2-)furyl]propyl]}-(2, 3 or 4-)piperidinylcarbonyl, 1-(3-phenylpropyl)-(2, 3 or 4-)piperidinylcarbonyl, 1-{1-[(1 or 2-)furyl]ethyl]}-(2, 3 or 4-)piperidinylcarbonyl, 1-(4-phenylbutyl)-(2, 3 or 4-)piperidinylcarbonyl, 1-{4-[(1 or 2-)furyl]butyl]}-(2, 3 or 4-)piperidinylcarbonyl, 1-(5-phenylpentyl)-(2, 3 or 4-)piperidinylcarbonyl, 1-{5-[(1 or 2-)furyl]pentyl]}-(2, 3 or 4-)piperidinylcarbonyl, 1-(6-phenylhexyl)-(2, 3 or 4-)piperidinylcarbonyl, 1-{6-[(1 or 2-)furyl]hexyl]}-(2, 3 or 4-)piperidinylcarbonyl, 1,2-dibenzyl-(3, 4, 5 or 6-)piperidinylcarbonyl, 1,3-di(1 or 2-)furylmethyl-(2, 4, 5 or 6-)piperidinylcarbonyl, 1,3,5-tribenzyl-(2, 4 or 6-)piperidinylcarbonyl, 1,2,6-tri(1 or 2-)furylmethyl-(3, 4 or 5-)piperidinylcarbonyl, 1-benzyl-3-(1 or 2-)furylmethyl-(2, 4, 5 or 6-)piperidinylcarbonyl, 1-{1-[(1 or 2-)furyl]ethyl]}-(2, 3 or 4-)piperidinylcarbonyl, 1-methoxycarbonyl-(2, 3 or 4-)piperidinylcarbonyl, 1-ethoxycarbonyl-(2, 3 or 4-)piperidinylcarbonyl, 1-propoxycarbonyl-(2, 3 or 4-)piperidinylcarbonyl, 1-butoxycarbonyl-(2, 3 or 4-)piperidinylcarbonyl, 1-tert-butoxycarbonyl-(2, 3 or 4-)piperidinylcarbonyl, 1-pentyloxycarbonyl-(2, 3 or 4-)piperidinylcarbonyl, 1-hexyloxycarbonyl-(2, 3 or 4-)piperidinylcarbonyl, 1,2-dimethoxycarbonyl-(3, 4, 5 or 6-)piperidinylcarbonyl, 1,2,6-triethoxycarbonyl-(3, 4 or 5-)piperidinylcarbonyl, 1-(1 or 2-)furylmethyl-3-tert-butoxycarbonyl-(3, 4, 5 or 6-)piperidinylcarbonyl, 1-benzyl-2-methoxycarbonyl-(2, 4, 5 or 6-)piperidinylcarbonyl, and 1-(1 or 2-)furylmethyl-2,4-dimethoxycarbonyl-(3, 5 or 6-)piperidinylcarbonyl groups.

Examples of the thiazolidinyl lower alkanoyl group which may have an oxo group as a substituent on the thiazolidine ring include thiazolidinylalkanoyl groups which may have 1 to 3 oxo groups as substituents on the thiazolidine ring and whose alkanoyl moiety is a linear or branched alkanoyl group having 2 to 6 carbon atoms such as 2-[(2, 3, 4 or 5-)thiazolidinyl]acetyl, 3-[(2, 3, 4 or 5-)thiazolidinyl]propionyl, 2-[(2, 3, 4 or 5-)thiazolidinyl]propionyl, 4-[(2, 3, 4 or 5-)thiazolidinyl]butyryl, 5-[(2, 3, 4 or 5-)1,2,4-thiazolidinyl]pentanoyl, 6-[(2, 3, 4 or 5-)thiazolidinyl]hexanoyl, 2,2-dimethyl-3-[(2, 3, 4 or 5-)thiazolidinyl]propionyl, 2-methyl-3-[(2, 3, 4 or 5-)thiazolidinyl]propionyl, 2,4-dioxo-(3 or 5-)thiazolidinylacetyl, 3-[2-oxo-(3, 4 or 5-)thiazolidinyl]propionyl, 2-[4-oxo-(2, 3 or 5-)thiazolidinyl]propionyl, 4-[5-oxo-(2, 3 or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, and 2-methyl-3-[2,4-dioxo-(3 or 5-)thiazolidinyl]propionyl groups.

Examples of the piperidinyl group which may be substituted on the piperidine ring with a group selected from the group consisting of a lower alkoxycarbonyl group, a phenyl lower alkyl group, a lower alkyl group, a benzoyl group and a furyl lower alkyl group include piperidinyl groups which may be substituted on the piperidine ring with 1 to 3 groups selected from the group consisting of an alkoxycarbonyl group whose alkoxy moiety is a linear or branched alkoxy group having 1 to 6 carbon atoms, a phenylalkyl group whose alkyl moiety is a linear or branched alkyl group having 1 to 6 carbon atoms, a linear or branched alkyl group having 1 to 6 carbon atoms, a benzoyl group, and a furylalkyl group whose alkyl moiety is a linear or branched alkyl group having 1 to 6 carbon atoms such as (1, 2, 3 or 4-)piperidinyl, 1-benzyl-(2, 3 or 4-)piperidinyl, 1-(2 or 3-)furylmethyl-(2, 3 or 4-)piperidinyl, 1-(2-phenylethyl)-(2, 3 or 4-)piperidinyl, 1-(2-[(1 or 2-)furyl]ethyl}-(2, 3 or 4-)piperidinyl, 1-(1-phenylethyl)-(2, 3 or 4-)piperidinyl, 1-{3-[(1 or 2-)furyl]propyl]}-(2, 3 or 4-)piperidinyl, 1-(3-phenylpropyl)-(2, 3 or 4-)piperidinyl, 1-{1-[(1 or 2-)furyl]ethyl]}-(2, 3 or 4-)piperidinyl, 1-(4-phenylbutyl)-(2, 3 or 4-)piperidinyl, 1-{4-[(1 or 2-)furyl]butyl]}-(2, 3 or 4-)piperidinyl, 1-(5-phenylpentyl)-(2, 3 or 4-)piperidinyl, 1-{5-[(1 or 2-)furyl]pentyl]}-(2, 3 or 4-)piperidinyl, 1-(6-phenylhexyl)-(2, 3 or 4-)piperidinyl, 1-{6-[(1 or 2-)furyl]hexyl]}-(2, 3 or 4-)piperidinyl, 1,2-dibenzyl-(3, 4, 5 or 6-)piperidinyl, 1,3-di(1 or 2-)furylmethyl-(2, 4, 5 or 6-)piperidinyl, 1,3,5-tribenzyl-(2, 4 or 6-)piperidinyl, 1,2,6-tri(1 or 2-)furylmethyl-(3, 4 or 5-)piperidinyl, 1-benzyl-3-(1 or 2-)furylmethyl-(2, 4, 5 or 6-)piperidinyl, 1-{1-[(1 or 2-)furyl]ethyl]}-(2, 3 or 4-)piperidinyl, 1-benzoyl-(2, 3 or 4-)piperidinyl, 1,2-dibenzoyl-(3, 4, 5 or 6-)piperidinyl, 1,3,5-tribenzoyl-(2, 4 or 6-)piperidinyl, 1-methyl-(2, 3 or 4-)piperidinyl, 1-ethyl-(2, 3 or 4-)piperidinyl, 1-propyl-(2, 3 or 4-)piperidinyl, 1-isopropyl-(2, 3 or 4-)piperidinyl, 1-butyl-(2, 3 or 4-)piperidinyl, 1-isobutyl-(2, 3 or 4-)piperidinyl, 1-tert-butyl-(2, 3 or 4-)piperidinyl, 1-pentyl-(2, 3 or 4-)piperidinyl, 1-hexyl-(2, 3 or 4-)piperidinyl, 1,2-dimethyl-(3, 4, 5 or 6-)piperidinyl, 1,2,6-trimethyl-(3, 4 or 5-)piperidinyl, 1-methyl-3-benzyl-(3, 4, 5 or 6-)piperidinyl, 1-benzoyl-2-methyl-(2, 4, 5 or 6-)piperidinyl, 1-(1 or 2-)furylmethyl-2,4-dimethyl-(3, 5 or 6-)piperidinyl, 1-methoxycarbonyl-(2, 3 or 4-)piperidinyl, 1-ethoxycarbonyl-(2, 3 or 4-)piperidinyl, 1-propoxycarbonyl-(2, 3 or 4-)piperidinyl, 1-butoxycarbonyl-(2, 3 or 4-)piperidinyl, 1-tert-butoxycarbonyl-(2, 3 or 4-)piperidinyl, 1-pentyloxycarbonyl-(2, 3 or 4-)piperidinyl, 1-hexyloxycarbonyl-(2, 3 or 4-)piperidinyl, 1,2-dimethoxycarbonyl-(3, 4, 5 or 6-)piperidinyl, 1,2,6-triethoxycarbonyl-(3, 4 or 5-)piperidinyl, 1-methyl-3-tert-butoxycarbonyl-(3, 4, 5 or 6-)piperidinyl, 1-benzoyl-2-methoxycarbonyl-(2, 4, 5 or 6-)piperidinyl, 1-(1 or 2-)furylmethyl-2,4-dimethoxycarbonyl-(3, 5 or 6-)piperidinyl, and 1-benzyl-2,4-dimethoxycarbonyl-(3, 5 or 6-)piperidinyl groups.

Examples of the carbonyl lower alkyl group substituted with a group:

[Formula 40]

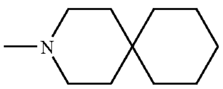

(hereinafter called "A group") include A group substituted carbonylalkyl groups whose alkyl moiety is a linear or branched alkyl group having 1 to 6 carbon atoms such as A group substituted carbonylmethyl, 2-A group substituted carbonylethyl, 1-A group substituted carbonylethyl, 3-A group substituted carbonylpropyl, 4-A group substituted carbonylbutyl, 1,1-dimethyl-2-A group substituted carbonylethyl, 5-A group substituted carbonylpentyl, 6-A group substituted carbonylhexyl, 1-A group substituted carbonylisopropyl, and 2-methyl-3-A group substituted carbonylpropyl groups.

Examples of the carbonyl lower alkyl group substituted with a group:

[Formula 41]

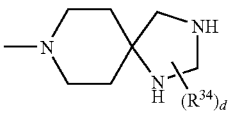

wherein $R^{34}$ is an oxo group or a phenyl group, and d is an integer of 0 to 3 (hereinafter called. "B group"), include B group substituted carbonylalkyl groups whose alkyl moiety is a linear or branched alkyl group having 1 to 6 carbon atoms such as B group substituted carbonylmethyl, 2-B group substituted carbonylethyl, 1-B group substituted carbonylethyl, 3-B group substituted carbonylpropyl, 4-B group substituted carbonylbutyl, 1,1-dimethyl-2-B group substituted carbonylethyl, 5-B group substituted carbonylpentyl, 6-B group substituted carbonylhexyl, 1-B group substituted carbonylisopropyl, and 2-methyl-3-B group substituted carbonylpropyl groups.

Examples of the pyrrolidinyl lower alkyl group include pyrrolidinylalkyl groups whose alkyl moiety is a linear or branched alkyl group having 1 to 6 carbon atoms such as (1-, 2-, or 3-)pyrrolidinylmethyl, 2-[(1-, 2-, or 3-)pyrrolidinyl]ethyl, 1-[(1-, 2-, or 3-)pyrrolidinyl]ethyl, 3-[(1-, 2-, or 3-)pyrrolidinyl]propyl, 4-[(1-, 2-, or 3-)pyrrolidinyl]butyl, 5-[(1-, 2-, or 3-)pyrrolidinyl]pentyl, 6-[(1-, 2-, or 3-)pyrrolidinyl]hexyl, 1,1-dimethyl-2-[(1-, 2-, or 3-)pyrrolidinyl]ethyl, and 2-methyl-3-[(1-, 2-, or 3-)pyrrolidinyl]propyl groups.

Examples of the morpholino lower alkyl group include morpholinoalkyl groups whose alkyl moiety is a linear or branched alkyl group having 1 to 6 carbon atoms such as (2-, 3- or 4-)morpholinomethyl, 2-[(2-, 3- or 4-)morpholino]ethyl, 1-[(2-, 3- or 4-)morpholino]ethyl, 3-[(2-, 3- or 4-)morpholino]propyl, 4-[(2-, 3- or 4-)morpholino]butyl, 5-[(2-, 3- or 4-)morpholino]pentyl, 6-[(2-, 3- or 4-)morpholino]hexyl, 1,1-dimethyl-2-[(2-, 3- or 4-)morpholino]ethyl, and 2-methyl-3-[(2-, 3- or 4-)morpholino]propyl groups.

Examples of the phenyl lower alkenyl group include phenylalkenyl groups whose alkenyl moiety is a linear or branched alkenyl group having 2 to 6 carbon atoms and which have 1 to 3 double bonds such as styryl, 3-phenyl-2-propenyl group (trivial name: cinnamyl group), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, and 6-phenyl-1,3,5-hexatrienyl groups.

Examples of the anilinocarbonyl lower alkyl group which may have a lower alkyl group as a substituent on the phenyl ring include anilinocarbonylalkyl groups whose alkyl moiety is a linear or branched alkyl group having 1 to 6 carbon atoms and which may have 1 to 3 linear or branched alkyl groups having 1 to 6 carbon atoms as substituents on the phenyl ring such as anilinocarbonylmethyl, 2-anilinocarbonylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl-2-anilinocarbonylethyl, 2-methyl-3-anilinocarbonylpropyl, (4-methylanilinocarbonyl)methyl, 2-(3-methylanilinocarbonyl)ethyl, 3-(4-methylanilinocarbonyl)propyl, 1-(2-ethylanilinocarbonyl)ethyl, 4-(3-ethylanilinocarbonyl)butyl, 5-(4-ethylanilinocarbonyl)pentyl, 6-(4-isopropylanilinocarbonyl)hexyl, 1,1-dimethyl-2-(3-butylanilinocarbonyl)ethyl, 2-methyl-3-(4-pentylanilinocarbonyl)propyl, 4-hexylanilinocarbonylmethyl, 3,4-dimethylanilinocarbonylmethyl, 3,4-diethylanilinocarbonylmethyl, 2,4-dimethylanilinocarbonylmethyl, 2,5-dimethylanilinocarbonylmethyl, 2,6-dimethylanilinocarbonylmethyl, and 3,4,5-trimethylanilinocarbonylmethyl groups.

Examples of the piperazinyl lower alkyl group which may have, on the piperazine ring, a substituent selected from the group consisting of a lower alkyl group and a phenyl lower alkyl group which may have a lower alkylenedioxy group as a substituent on the phenyl ring include piperazinylalkyl groups whose alkyl moiety is a linear or branched alkyl group having 1 to 6 carbon atoms and which may have, on the piperazine ring, 1 to 3 substituents selected from the group consisting of a linear or branched alkyl group having 1 to 6 carbon atoms and a phenylalkyl group which may have a linear or branched alkylenedioxy group having 1 to 4 carbon atoms as a substituent on the phenyl ring and whose alkyl moiety is a linear or branched alkyl group having 1 to 6 carbon atoms such as [(1-, 2- or 3-)piperazinyl]methyl, 2-[(1-, 2- or 3-)piperazinyl]ethyl, 1-[(1-, 2- or 3-)piperazinyl]ethyl, 3-[(1-, 2- or 3-)piperazinyl]propyl, 4-[(1-, 2- or 3-)piperazinyl]butyl, 5-[(1-, 2- or 3-)piperazinyl]pentyl, 6-[(1-, 2- or 3-)piperazinyl]hexyl, 1,1-dimethyl-2-[(1-, 2- or 3-)piperazinyl]ethyl, 2-methyl-3-[(1-, 2- or 3-)piperazinyl]propyl, [1-methyl-(2-, 3- or 4-)piperazinyl]methyl, 2-[1-ethyl-(2-, 3- or 4-)piperazinyl]ethyl, 1-[4-propyl-(1-, 2- or 3-)piperazinyl]ethyl, 3-[3-isopropyl-(1-, 2-, 4-, 5- or 6-)piperazinyl]propyl, 4-[2-butyl-(1-, 3-, 4-, 5- or 6-)piperazinyl]butyl, 5-[1-isobutyl-(2-, 3- or 4-)piperazinyl]pentyl, 3-[4-methyl-(1-, 2- or 3-)piperazinyl]propyl, 6-[1-tert-butyl-(2-, 3- or 4-)piperazinyl]hexyl, 1,1-dimethyl-2-[4-pentyl-(1-, 2- or 3-)piperazinyl]ethyl, [1,2-dimethyl-(3-, 4-, 5- or 6-)piperazinyl]methyl, [1,2,6-trimethyl-(3-, 4- or 5-)piperazinyl]methyl, and 2-[4-(3,4-methylenedioxybenzyl)-(1-, 2- or 3-)piperazinyl]ethyl groups.

Examples of the amidino lower alkyl group which may have a lower alkyl group as a substituent include amidinoalkyl groups whose alkyl moiety is a linear or branched alkyl group having 1 to 6 carbon atoms and which may have 1 or 2 linear or branched alkyl groups having 1 to 6 carbon atoms such as amidinomethyl, 2-amidinoethyl, 1-amidinoethyl, 3-amidinopropyl, 4-amidinobutyl, 5-amidinopentyl, 6-amidinohexyl, 1,1-dimethyl-2-amidinoethyl, 2-methyl-3-amidinopropyl, N,N-dimethylamidinomethyl, 2-(N,N-dimethylamidino)ethyl, 1-(N-methylamidino)ethyl, 3-(N-ethylamidino)propyl, 4-(N-n-propylamidino)propyl, 5-(N-n-pentylamidino)pentyl, 6-(N-n-hexylamidino)hexyl, and (N-methyl-N-ethylamidino)methyl groups.

Examples of the carbazolyl group which may have a lower alkyl group as a substituent on the carbazole ring include carbazolyl groups which may have 1 to 3 linear or branched alkyl groups having 1 to 6 carbon atoms as substituents on the carbazole ring such as (1-, 2-, 3- or 4-)carbazolyl, 9-methyl-(1-, 2-, 3- or 4-)carbazolyl, 9-ethyl-(1-, 2-, 3- or 4-)carbazolyl, 1-ethyl-(2-, 3-, 4-, 5-, 6-, 7-, 8- or 9-)carbazolyl, 2-n-propyl-(1-, 3-, 4-, 5-, 6-, 8- or 9-)carbazolyl, 3-n-butyl-(1-, 2-, 4-, 5-, 6-, 7-, 8- or 9-)carbazolyl, 4-n-pentyl-(1-, 2-, 3-, 5-, 6-, 7-, 8- or 9-)carbazolyl, 5-n-hexyl-(1-, 2-, 3-, 4-, 6-, 7-, 8- or 9-)carbazolyl, 6,9-dimethyl-(1-, 2-, 3-, 4-, 5-, 7- or 8-)carbazolyl, and 1,7,8-trityl-(2-, 3-, 4-, 5-, 6-, 7-, 8- or 9-)carbazolyl groups.

Examples of the amidino group which may have a lower alkyl group as a substituent include amidino groups which may have 1 or 2 linear or branched alkyl groups having 1 to 6 carbon atoms as substituents such as amidino, N,N-dimethylamidino, N-methylamidino, N-ethylamidino, N-n-propylamidino, N-n-butylamidino, N-n-pentylamidino, N-n-hexylamidino, N,N-diethylamidino, and N-methyl-N-ethylamidino groups.

Examples of the phenyl lower alkyl group (which may have, on the phenyl ring, 1 to 3 substituents selected from the group consisting of a lower alkylenedioxy group and a lower alkoxy group), include, in addition to the above described phenyl lower alkyl groups, phenylalkyl groups whose alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, 2-methyl-3-(3,4-ethylenedioxyphenyl)propyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, and 3,4,5-trimethoxybenzyl groups.

Examples of the piperazinyl substituted oxalyl group which may have, on the piperazine ring, 1 to 3 substituents selected from the group consisting of a phenyl lower alkyl group (which may have, on the phenyl ring, 1 to 3 substituents selected from the group consisting of a lower alkylenedioxy group and a lower alkoxy group) and a pyridyl lower alkyl group include piperazinyl substituted oxalyl groups which may have, on the piperazine ring, 1 to 3 substituents selected from the group consisting of a phenylalkyl group whose alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) and a pyridylalkyl group whose alkyl moiety is a linear or branched alkyl group having 1 to 6 carbon atoms such as 4-(3,4-methylenedioxybenzyl)-(1-, 2- or 3-)piperazinyloxalyl, 4-(2-, 3- or 4-pyridylmethyl)-(1-, 2- or 3-)piperazinyloxalyl, 4-(3,4-dimethoxybenzyl)-(1-, 2- or 3-)piperazinyloxalyl, 4-(2,3-methylenedioxybenzyl)-(1-, 2- or 3-)piperazinyloxalyl, 4-(3,4-ethylenedioxybenzyl)-(1-, 2- or 3-)piperazinyloxalyl, 4-[2-(2-, 3- or 4-pyridyl)ethyl]-(1-, 2- or 3-)piperazinyloxalyl, 4-[3-(2-, 3- or 4-pyridyl)propyl-(1-, 2- or 3-)piperazinyloxalyl, 2,4-bis(2-, 3- or 4-pyridylmethyl)-(1-, 2- or 3-)piperazinyloxalyl, 2-(3,4-methylenedioxybenzyl)-4-(2-, 3- or 4-pyridylmethyl)-(1-, 2- or 3-)piperazinyloxalyl, and 2,3,4-tri(2-, 3- or 4-pyridylmethyl)-(1-, 2- or 3-)piperazinyloxalyl groups.

Examples of the cyano substituted lower alkyl group include cyanoalkyl groups whose alkyl moiety is a linear or branched alkyl group having 1 to 6 carbon atoms such as cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, and 2-methyl-3-cyanopropyl groups.

Examples of the 5- to 7-membered saturated heterocyclic ring formed by binding $R^{36}$ and $R^{37}$ each other, together with nitrogen atoms bound to them, through or not through a nitrogen atom, an oxygen atom, or a sulfur atom include pyrrolidinyl, piperidinyl, piperazinyl, morpholino, thiomorpholino, and homopiperazinyl groups.

Examples of the 5- to 10-membered saturated or unsaturated heterocyclic ring formed by binding $R^{14}$ and $R^{15}$ each other, together with nitrogen atoms bound to them, through or not through a nitrogen atom, an oxygen atom, or a sulfur atom include 1,2,3,4,5,6-hexahydropyrimidinyl, pyrrolidinyl, piperidinyl, piperazinyl, morpholino, thiomorpholino, homopiperazinyl, homopiperidinyl, thiazolidinyl, 1,2,5,6-tetrahydropyridyl, pyrrolyl, pyrazolyl, imidazolyl, 2-pyrrolinyl, 2-imidazolinyl, imidazolidinyl, 2-pyrazolinyl, pyrazolidinyl, 1,2-dihydropyridyl, 1,2-dihydroquinolyl, 1,2,3,4-tetrahydroquinolyl, 1,2,3,4-tetrahydroisoquinolyl, 1,2-dihydroisoquinolyl, indolyl, isoindolyl, indolinyl, isoindolinyl, 3,4-dihydro-2H-1,4-benzooxazinyl, 3,4-dihydro-2H-1,4-benzothiazolidinyl, 1,4-benzothiazinyl, 1,2,3,4-tetrahydroquinoxalinyl, 1,2,3,4-tetrahydrocinnolinyl, 1,2,3,4-tetrahydrophthalazinyl, 1,2,3,4-tetrahydroquinazolinyl, 1,2-dihydroquinoxalinyl, 3,4-dihydroquinoxalinyl, 1,4-dihydroquinoxalinyl, 1,2-dihydrocinnolinyl, 1,2-dihydrophthalazinyl, 3,4-dihydrophthalazinyl, 1,2-dihydroquinazolinyl, 3,4-dihydroquinazolinyl, indazolyl, indazolinyl, 6-azabicyclo[3,2,1]octyl, 3-aza-spiro[5,5]undecyl, and thiazolidinyl groups. Preferably, $R^{14}$ and $R^{15}$, together with the nitrogen atom to which they bind, bind to each other, directly or via a nitrogen atom to form a 6-membered saturated heterocyclic group. Most preferably, they include piperidinyl and piperazinyl groups.

Examples of the phenyl lower alkoxy group include phenylalkoxy groups whose alkoxy moiety is a linear or branched alkoxy group having 1 to 6 carbon atoms such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, and 2-methyl-3-phenylpropoxy groups.

Examples of the phenyl substituted lower alkyl group which has 1 or 2 phenyl groups which may be substituted on the phenyl ring with 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy groups; and which may have a pyridyl group on the lower alkyl group include in addition to the above described phenyl lower alkyl groups, phenyl substituted alkyl groups which have 1 or 2 phenyls which may be substituted on the phenyl ring with 1 to 3 substituents selected from the group consisting of a linear or branched alkanoyl group having 1 to 6 carbon atoms, an amino group which may have 1 or 2 linear or branched alkanoyl groups having 1 to 6 carbon atoms as substituents, a linear or branched alkoxycarbonyl group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, a phenylalkoxy groups whose alkoxy moiety is a linear or branched alkoxy group having 1 to 6 carbon atoms, a hydroxy group, and a linear or branched alkylenedioxy group having 1 to 4 carbon atoms; which may have a pyridyl group on the alkyl group, and whose alkyl moiety is a linear or branched alkyl group having 1 to 6 carbon atoms, such as 1-phenyl-1-(2, 3 or 4-)pyridyl methyl, 1,1-diphenylmethyl, 1,1-di(4-fluorophenyl)methyl, 1-phenyl-1-(4-methoxyphenyl)methyl, 3,4-methylenedioxybenzyl, 3,4-ethylenedioxybenzyl, 3,4-trimethylenedioxybenzyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butoxycarbonylbenzyl, 3-chloro-6-methoxybenzyl, 4-acetylaminobenzyl, 4-nitro-3-methylbenzyl, 4-hydroxybenzyl, 3-hydroxybenzyl, 2-hydroxybenzyl, 4-tert-butyrylbenzyl, 4-benzyloxybenzyl, 4-pivaloylbenzyl, 2-(4-acetylphenyl)ethyl, 1-(3-propionylphenyl)ethyl, 3-(2-butyrylphenyl)propyl, 4-(4-pentanoylphenyl)butyl, 5-(3-hexanoylphenyl)pentyl, 6-(2,4-diacetylphenyl)hexyl, 1,1-dimethyl-2-(2,4,6-triacetylphenyl)ethyl, 2-methyl-3-(3,4-diacetylphenyl)propyl, 2-(4-aminophenyl)ethyl, 1-(3-propionylaminophenyl)ethyl, 3-(2-butyrylaminophenyl)propyl, 4-(4-pentanoylamino)phenylbutyl, 5-(hexanoylaminophenyl)pentyl, 6-(N-acetyl-N-propionylaminophenyl)hexyl, 1,1-dimethyl-2-(3,4-diaminophenyl)ethyl, 2-methyl-3-(3,4,5-triacetylaminophenyl)propyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-triethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(4-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl)ethyl, 2-methyl-3-(2,4,6-trifluorophenyl)propyl, 2-(2-ethylphenyl)ethyl; 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-(2-benzyloxyphenyl)ethyl, 1-[3-(2-phenylethoxy)phenyl]ethyl, 3-[4-(3-phenylpropoxy)phenyl]propyl, 4-[2-(4-phenylbutoxy)phenyl]butyl, 5-[3-(5-phenylpentyloxy)phenyl]pentyl, 6-[4-(6-phenylhexyloxy)phenyl]hexyl, 1,1-dimethyl-2-(2,4-dibenzyloxyphenyl)ethyl, 2-methyl-3-(2,4,6-tribenzyloxyphenyl)propyl, 2-(2-hydroxyphenyl)ethyl, 1-(3-hydroxyphenyl)ethyl, 3-(4-hydroxyphenyl)propyl, 4-(2-hydroxyphenyl)butyl, 5-(3-hydroxyphenyl)pentyl, 6-(4-hydroxyphenyl)hexyl, 1,1-dimethyl-2-(2,4-dihydroxyphenyl)ethyl, 2-methyl-3-(2,4,6-trihydroxyphenyl)propyl, 2-(3,4-methylenedioxyphenyl)ethyl, 1-(2,3-ethylenedioxyphenyl)ethyl, 3-(3,4-trimethylenedioxyphenyl)propyl, 4-(3,4-tetramethylenedioxyphenyl)butyl, 5-(3,4-methylenedioxyphenyl)pentyl, 6-(3,4-ethylenedioxyphenyl)hexyl, 1,1-dimethyl-2-(3,4-methylenedioxy)ethyl, and 2-methyl-3-(3,4-methylenedioxyphenyl)propyl groups. Preferably, they include phenyl substituted lower alkyl groups which may be substituted on the phenyl ring with group(s), as substituent(s), selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy groups.

Examples of the pyridyl lower alkyl group which may have, on the pyridine ring, 1 to 3 substituents selected from the group consisting of a hydroxyl group and a lower alkyl group which may have a hydroxyl group as a substituent include, in addition to the above described pyridyl lower alkyl groups, pyridylalkyl groups which may have, on the pyridine ring, 1 to 3 substituents selected from the group consisting of a hydroxy group and a linear or branched alkyl group having 1 to 6 carbon atoms which may have 1 to 3 hydroxy groups as substituents, and whose alkyl moiety is a linear or branched alkyl group having 1 to 6 carbon atoms such as [2-methyl-(3, 4, 5 or 6-)pyridyl]methyl, [2-methyl-3-hydroxy-5-hydroxymethyl-(4 or 6-)pyridyl]methyl, 2-[3-ethyl-(2, 4, 5 or 6-)pyridyl]ethyl, 1-[4-propyl-(2, 3, 5 or 6-)pyridyl]ethyl, 3-[2-butyl-(3, 4, 5 or 6-)pyridyl]propyl, 4-[3-pentyl-(2, 4, 5 or 6-)pyridyl]butyl, 1,1-dimethyl-2-[4-hexyl-(2, 3, 5 or 6-)pyridyl]ethyl, 5-[2,3-dimethyl-(4, 5 or 6-)pyridyl]pentyl, 6-[2,4,6-trimethyl-(3 or 5-)pyridyl]hexyl, 1-[2-hydroxy-(2, 3, 5 or 6-)pyridyl]isopropyl, 2-methyl-3-[3-hydroxy-(2, 4, 5 or 6-)pyridyl]propyl, [2-hydroxy-(3, 4, 5 or 6-)pyridyl]methyl, 2-[3-hydroxy-(2, 4, 5 or 6-)pyridyl]ethyl, 1-[4-hydroxy-(2, 3, 5 or 6-)pyridyl]ethyl, 3-[2-hydroxy-(3, 4, 5 or 6-)pyridyl]propyl, 4-[3-hydroxy-(2, 4, 5 or 6-)pyridyl]butyl, 1,1-dimethyl-2-[4-hydroxy-(2, 3, 5 or 6-)pyridyl]ethyl, 5-[2,3-dihydroxy-(4, 5 or 6-)pyridyl]pentyl, 6-[2,4,6-trihydroxy-(3 or 5-)pyridyl]hexyl, [2-hydroxymethyl-(3, 4, 5 or 6-)pyridyl]methyl, 2-[3-(2-hydroxyethyl)-(2, 4, 5 or 6-)pyridyl]ethyl, 1-[4-(3-hydroxypropyl)-(2, 3, 5 or 6-)pyridyl]ethyl, 3-[2-(4-hydroxybutyl)-(3, 4, 5 or 6-)pyridyl]propyl, 4-[3-(5-hydroxypentyl)-(2, 4, 5 or 6-)pyridyl]butyl, 1,1-dimethyl-2-[4-(6-hydroxyhexyl)-(2, 3, 5 or 6-)pyridyl]ethyl, 5-[2,3-di(hydroxymethyl)-(4, 5 or 6-)pyridyl]pentyl, 6-[2,4,6-tri(hydroxymethyl)-(3 or 5-)pyridyl]hexyl, 1-[2-hydroxymethyl-(2, 3, 5 or 6-)pyridyl]isopropyl, 2-methyl-3-[3-(2,3-dihydroxypropyl)-(2, 4, 5 or 6-)pyridyl]propyl, [2-methyl-3-(2,2,4-trihydroxybutyl)-(4, 5 or 6-)pyridyl]methyl, and [2-methyl-5-hydroxymethyl-(3, 4 or 6-)pyridyl]methyl groups.

Examples of the pyrrolyl lower alkyl group which may have 1 to 3 lower alkyl groups as substituents on the pyrrole ring include pyrrolylalkyl groups which may have 1 to 3 linear or branched alkyl groups having 1 to 6 carbon atoms on the pyrrole ring and whose alkyl moiety is a linear or branched alkyl group having 1 to 6 carbon atoms such as [(1, 2 or 3-)pyrrolyl]methyl, 2-[(1, 2 or 3-)pyrrolyl]ethyl, 1-[(1, 2 or 3-)pyrrolyl]ethyl, 3-[(1, 2 or 3-)pyrrolyl]propyl, 4-[(1, 2 or 3-)pyrrolyl]butyl, 5-[(1, 2 or 3-)pyrrolyl]pentyl, 6-[(1, 2 or 3-)pyrrolyl]hexyl, 1,1-dimethyl-2-[(1, 2 or 3-)pyrrolyl]ethyl, 2-methyl-3-[(1, 2 or 3-)pyrrolyl]propyl, [1-methyl-(2 or 3-)pyrrolyl]methyl, 2-[2-ethyl-(1, 3, 4 or 5-)pyrrolyl]ethyl, 1-[3-propyl-(1, 2, 4 or 5-)pyrrolyl]ethyl, 3-[1-butyl-(2, 3 or 4-)pyrrolyl]propyl, 4-[2-pentyl-(1, 3, 4 or 5-)pyrrolyl]butyl, 5-[3-hexyl-(1, 2, 4 or 5-)pyrrolyl]pentyl, 6-[1,2-dimethyl-(3, 4 or 5-)pyrrolyl]hexyl, 1,1-dimethyl-2-[1,2,3-trimethyl-(4 or 5-)pyrrolyl]ethyl, and 2-methyl-3-[1-ethyl-2-methyl-(3, 4 or 5-)pyrrolyl]propyl groups.

Examples of the benzoxazolyl lower alkyl group include benzoxazolylalkyl groups whose alkyl moiety is a linear or branched alkyl group having 1 to 6 carbon atoms such as [(2, 4, 5, 6 or 7-)benzooxazolyl]methyl, 2-[(2, 4, 5, 6 or 7-)benzooxazolyl]ethyl, 1-[(2, 4, 5, 6 or 7-)benzooxazolyl]ethyl, 3-[(2, 4, 5, 6 or 7-)benzooxazolyl]propyl, 4-[(2, 4, 5, 6 or 7-)benzooxazolyl]butyl, 5-[(2, 4, 5, 6 or 7-)benzooxazolyl]pentyl, 6-[(2, 4, 5, 6 or 7-)benzooxazolyl]hexyl, 1,1-dimethyl-2-[(2, 4, 5, 6 or 7-)benzooxazolyl]ethyl, and 2-methyl-3-[(2, 4, 5, 6 or 7-)benzooxazolyl]propyl groups.

Examples of the benzothiazolyl lower alkyl group include benzothiazolylalkyl groups whose alkyl moiety is a linear or branched alkyl group having 1 to 6 carbon atoms such as [(2, 4, 5, 6 or 7-)benzothiazolyl]methyl, 2-[(2, 4, 5, 6 or 7-)benzothiazolyl]ethyl, 1-[(2, 4, 5, 6 or 7-)benzothiazolyl]ethyl, 3-[(2, 4, 5, 6 or 7-)benzothiazolyl]propyl, 4-[(2, 4, 5, 6 or 7-)benzothiazolyl]butyl, 5-[(2, 4, 5, 6 or 7-)benzothiazolyl]pentyl, 6-[(2, 4, 5, 6 or 7-)benzothiazolyl]hexyl, 1,1-dimethyl-2-[(2, 4, 5, 6 or 7-)benzothiazolyl]ethyl, and 2-methyl-3-[(2, 4, 5, 6 or 7-)benzothiazolyl]propyl groups.

Examples of the furyl lower alkyl group include furylalkyl groups whose alkyl moiety is a linear or branched alkyl group having 1 to 6 carbon atoms such as [(2 or 3-)furyl]methyl, 2-[(2 or 3-)furyl]ethyl, 1-[(2 or 3-)furyl]ethyl, 3-[(2 or 3-)furyl]propyl, 4-[(2 or 3-)furyl]butyl, 5-[(2 or 3-)furyl]pentyl, 6-[(2 or 3-)furyl]hexyl, 1,1-dimethyl-2-[(2 or 3-)furyl]ethyl, and 2-methyl-3-[(2 or 3-)furyl]propyl groups.

Examples of the thiazolidinyl lower alkyl group which may have an oxo group as a substituent on the thiazolidine ring include thiazolidinylalkyl groups which may have 1 to 3 oxo groups as substituents on the thiazolidine ring and whose alkyl moiety is a linear or branched alkyl group having 1 to 6 carbon atoms such as (2, 3, 4 or 5-)thiazolidinylmethyl, 2-[(2, 3, 4 or 5-)thiazolidinyl]ethyl, 1-[(2, 3, 4 or 5-)thiazolidinyl]ethyl, 3-[(2, 3, 4 or 5-)thiazolidinyl]propyl, 4-[(2, 3, 4 or 5-)thiazolidinyl]butyl, 5-[(2, 3, 4 or 5-)thiazolidinyl]pentyl, 6-[(2, 3, 4 or 5-)thiazolidinyl]hexyl, 1,1-dimethyl-2-[(2, 3, 4 or 5-)thiazolidinyl]ethyl, 2-methyl-3-[(2, 3, 4 or 5-)thiazolidinyl]propyl, [2,4-dioxo-(3 or 5-)thiazolidinyl]methyl, 2-[2-oxo-(3, 4 or 5-)thiazolidinyl]ethyl, 1-[4-oxo-(2, 3 or 5-)thiazolidinyl]ethyl, 3-[2-oxo-(3, 4 or 5-)thiazolidinyl]propyl, 4-[5-oxo-(2, 3 or 4-)thiazolidinyl]butyl, 5-[2,5-dioxo-(3 or 4-)thiazolidinyl]pentyl, 6-[2,4,5-trioxo-3-thiazolidinyl]hexyl, 1-[4,5-dioxo-(2 or 3-)thiazolidinyl]ethyl, 2-[4,5-dioxo-(2- or 3-)thiazolidinyl]ethyl, 1,1-dimethyl-2-[2,4-dioxo-(3 or 5-)thiazolidinyl]ethyl, and 2-methyl-3-[2,4-dioxo-(3 or 5-)thiazolidinyl]propyl groups.

Examples of the thiazolidinylidene lower alkyl group which may have an oxo group as a substituent on the thiazolidine ring include thiazolidinylidenealkyl groups which may have 1 to 3 oxo groups as substituents on the thiazolidine ring and whose alkyl moiety is a linear or branched alkyl group having 1 to 6 carbon atoms such as (2, 4 or 5-)thiazolidinylidenemethyl, (2, 4 or 5-)thiazolidinylideneethyl, (2, 4 or 5-)thiazolidinylidenepropyl, (2, 4 or 5-)thiazolidinylideneisopropyl, (2, 4 or 5-)thiazolidinylidenebutyl, (2, 4 or 5-)thiazolidinylidenepentyl, (2, 4 or 5-)thiazolidinylidenehexyl, 4,5-dioxo-2-thiazolidinylidenemethyl, 2,5-dioxo-4-thiazolidinylidenemethyl, 2,4-dioxo-5-thiazolidinylidenemethyl, 4-oxo-(2 or 5-)thiazolidinylideneethyl, 5-oxo-(2 or 4-)thiazolidinylidenepropyl, and 2-oxo-(4 or 5-)thiazolidinylidenebutyl groups.

Examples of the benzoyl group which may be substituted on the phenyl ring with 1 to 3 groups selected from the group consisting of a cyano group, an amino group which may have a lower alkylsulfonyl group as a substituent, a halogen atom, a lower alkoxy group, a lower alkyl group which may have a halogen atom as a substituent, a thiazolidinyl lower alkyl group which may have an oxo group as a substituent on the thiazolidine ring, a thiazolidinylidene lower alkyl group which may have an oxo group as a substituent on the thiazolidine ring, and a lower alkylenedioxy group include benzoyl groups which may be substituted on the phenyl ring with 1 to 3 groups selected from the group consisting of a cyano group; an amino group which may have 1 or 2 linear or branched alkylsulfonyl groups having 1 to 6 carbon atoms as substituents; a halogen atom; a linear or branched alkoxy group having 1 to 6 carbon atoms; a linear or branched alkyl group having 1 to 6 carbon atoms which may have 1 to 3 halogen atoms as substituents; a thiazolidinylalkyl group which may have 1 to 3 oxo groups as substituents on the thiazolidine ring and whose alkyl moiety is a linear or branched alkyl group having 1 to 6 carbon atoms; a thiazolidinylidenealkyl group which may have 1 to 3 oxo groups as substituents on the thiazolidine ring and whose alkyl moiety is a linear or branched alkyl group having 1 to 6 carbon atoms; and a linear or branched alkylenedioxy group having 1 to 4 carbon atoms such as benzoyl, 4-cyanobenzoyl, 3,4-methylenedioxybenzoyl, 2-aminobenzoyl, 3-aminobenzoyl, 4-aminobenzoyl, 3,4-diaminobenzoyl, 2,4,6-triaminobenzoyl, 4-methoxybenzoyl, 4-trifluoromethylbenzoyl, 4-chlorobenzoyl, 3,4-difluorobenzoyl, 2-fluorobenzoyl, 3-bromobenzoyl, 4-iodobenzoyl, 3,4-dimethoxybenzoyl, 4-fluorobenzoyl, 3-cyanobenzoyl, 2-cyanobenzoyl, 2,3-dicyanobenzoyl, 3,4,5-tricyanobenzoyl, 4-methylbenzoyl, 4-(2,4-dioxothiazolidinylmethyl)benzoyl, 4-(2,4-dioxothiazolidinylidenemethyl)benzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-methoxybenzoyl, 3-methoxybenzoyl, 2-ethoxybenzoyl, 3-ethoxybenzoyl, 4-ethoxybenzoyl, 4-isopropoxybenzoyl, 3-butoxybenzoyl, 4-pentyloxybenzoyl, 4-hexyloxybenzoyl, 3,4-diethoxybenzoyl, 2,4-dimethoxybenzoyl, 2,5-dimethoxybenzoyl, 2,6-dimethoxybenzoyl, 3,4,5-trimethoxybenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl)benzoyl, 4-(2,2,2-trichloroethyl)benzoyl, 2-methyl-4-trifluoromethylbenzoyl, 3-ethyl-4-trichloromethylbenzoyl, 2-methoxy-4-trifluoromethylbenzoyl, 3-ethyl-4-fluorobenzoyl, 3-ethoxy-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4- dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, 2,4-difluorobenzoyl, 3,4-difluorobenzoyl, 3,4-methylenedioxybenzoyl, 3,4-trimethylenedioxybenzoyl, 2,3-ethylenedioxybenzoyl, 3,4-trimethylenedioxybenzoyl, 2,3-tetramethylenedioxybenzoyl, 2,3-methylenedioxybenzoyl, 3,4-ethylenedioxybenzoyl, and 2-methanesulfonylaminobenzoyl groups.

Examples of the thiazolidinyl lower alkanoyl group which may be substituted on the thiazolidine ring with a group selected from the group consisting of an oxo group and a group of the formula:

[Formula 42]

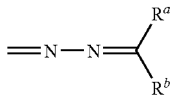

wherein $R^a$ and $R^b$ each represent a lower alkyl group, include thiazolidinylalkanoyl groups which may be substituted on the thiazolidine ring with 1 to 3 substituents selected from the group consisting of an oxo group and a group of the formula:

[Formula 43-1]

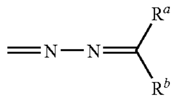

wherein $R^a$ and $R^b$ each represent a linear or branched alkyl group having 1 to 6 carbon atoms, and whose alkanoyl moiety is a linear or branched alkanoyl group having 2 to 6 carbon atoms such as 2-[(2, 3, 4 or 5-)thiazolidinyl]acetyl, 3-[(2, 3, 4 or 5-)thiazolidinyl]propionyl, 2-[(2, 3, 4 or 5-)thiazolidinyl] propionyl, 4-[(2, 3, 4 or 5-)thiazolidinyl]butyryl, 5-[(2, 3, 4 or 5-)thiazolidinyl]pentanoyl, 6-[(2, 3, 4 or 5-)thiazolidinyl] hexanoyl, 2,2-dimethyl-3-[(2, 3, 4 or 5-)thiazolidinyl]propionyl, 2-methyl-3-[(2, 3, 4 or 5-)thiazolidinyl]propionyl, [2,4-dioxo-(3 or 5-)thiazolidinyl]acetyl, 3-[2-oxo-(3, 4 or 5-)thiazolidinyl]propionyl, 2-[4-oxo-(2, 3 or 5-)thiazolidinyl]propionyl, 4-[5-oxo-(2, 3 or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, 2-methyl-3-[2,4-dioxo-(3 or 5-)thiazolidinyl] propionyl, 2-[4-oxo-2-isopropylidenehydrazono-(3 or 5-)thiazolidinyl]acetyl, 2-[2-oxo-5-isopropylidenehydrazono-(3 or 4-)thiazolidinyl]acetyl, 2-[2,4-di(isopropylidenehydrazono)-(3 or 5-)thiazolidinyl]acetyl, 3-[2-methylidenehydrazono-(3, 4 or 5-)thiazolidinyl]propionyl, 2-[4-ethylidenehydrazono-(2, 3 or 5-)thiazolidinyl]propionyl, 4-[5-propylidenehydrazono-(2, 3 or 4-)thiazolidinyl]butyryl, 5-[2,5-di(isopropylidenehydrazono)-(3 or 4-)thiazolidinyl] pentanoyl, 6-[2,4,5-tri(isopropylidenehydrazono)-3-thiazolidinyl]hexanoyl, 2-[4,5-di(isopropylidenehydrazono)-(2 or 3-)thiazolidinyl]acetyl, 2,2-dimethyl-3-[4-butylidenehydrazono(2, 3 or 5-)thiazolidinyl]propionyl, 2-methyl-3-[5-pentylidene-(2, 3 or 4-)thiazolidinyl]propionyl, and 2-(hexylidenehydrazono)-(3, 4 or 5-)thiazolidinylacetyl groups.

Examples of the lower alkyl group which may have a substituent selected from the group consisting of a hydroxyl group and a halogen atom include, in addition to the above described lower alkyl groups, linear or branched alkyl groups having 1 to 6 carbon atoms which may have 1 to 3 substituents selected from the group consisting of a hydroxy group and a halogen atom such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, 2-hydroxy-3-fluoropropyl, and 2,2-dichloro-3-hydroxybutyl groups.

Examples of the carbamoyl group which may have a group selected from the group consisting of a lower alkoxy lower alkyl group and a lower alkyl group include carbamoyl groups which may have 1 or 2 groups selected from the group consisting of a linear or branched alkyl group having 1 to 6 carbon atoms and which has a linear or branched alkoxy group having 1 to 6 carbon atoms and a linear or branched alkyl group having 1 to 6 carbon atoms such as carbamoyl, N-(2-methoxyethyl)carbamoyl, methylcarbamoyl, ethylcarbamoyl, propylcarbamoyl, isopropylcarbamoyl, butylcarbamoyl, tert-butylcarbamoyl, pentylcarbamoyl, hexylcarbamoyl, dimethylcarbamoyl, diethylcarbamoyl, dipropylcarbamoyl, dibutylcarbamoyl, dipentylcarbamoyl, dihexylcarbamoyl, N-methyl-N-ethylcarbamoyl, N-ethyl-N-propylcarbamoyl, N-methyl-N-butylcarbamoyl, N-methyl-N-hexylcarbamoyl, N-(methoxymethyl)carbamoyl, N-(3-propoxypropyl)carbamoyl, N-(4-butoxybutyl)carbamoyl, N-(4-ethoxybutyl) carbamoyl, N-(5-pentyloxypentyl)carbamoyl, N-(5-methoxypentyl)carbamoyl, N-(6-hexyloxyhexyl)carbamoyl, di(2-methoxyethyl)carbamoyl, N-(2-methoxyethyl)-N-methylcarbamoyl, and N-(2-methoxyethyl)-N-ethylcarbamoyl groups.

Examples of the phenyl group which may be substituted on the phenyl ring with 1 to 3 groups selected from the group consisting of a carbamoyl group which may have a group selected from the group consisting of a lower alkoxy lower alkyl group and a lower alkyl group, a lower alkoxycarbonyl group, a carboxy group, a cyano group, a phenyl group, a halogen atom, a lower alkyl group which may have a halogen atom as a substituent, a lower alkoxy group which may have a halogen atom as a substituent, a benzoyl group which may have a halogen atom as a substituent on the phenyl ring, a phenyl lower alkyl group which may have a halogen atom as a substituent on, the phenyl ring, and a hydroxyl group include phenyl groups which may be substituted on the phenyl ring with 1 to 3 groups selected from the group consisting of a carbamoyl group which may have 1 or 2 groups selected from the group consisting of an alkoxyalkyl group whose alkoxy moiety is a linear or branched alkoxy group having 1 to 6 carbon atoms and whose alkyl moiety is a linear or branched alkyl group having 1 to 6 carbon atoms and a linear or branched alkyl group having 1 to 6 carbon atoms; a linear or branched alkoxycarbonyl group having 1 to 6 carbon atoms; a carboxy group; a cyano group; a phenyl group; a halogen atom; a linear or branched alkyl group having 1 to 6 carbon atoms which may have 1 to 3 halogen atoms as substituents; a linear or branched alkoxy group having 1 to 6 carbon atoms which may have 1 to 3 halogen atoms as substituents; a benzoyl group which may have 1 to 3 halogen atoms as substituents on the phenyl ring; a phenylalkyl group which may have 1 to 3 halogen atoms as substituents on the phenyl ring and whose alkyl moiety is a linear or branched alkyl group having 1 to 6 carbon atoms, and a hydroxyl group such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,3-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluorbmethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 4-isopropoxycarbonylphenyl, 3-butoxycarbonylphenyl, 4-tert-butoxycarbonylphenyl, 4-pentyloxycarbonylphenyl, 4-hexyloxycarbonylphenyl, 3,4-dimethoxycarbonylphenyl, 3,4-diethoxycarbonylphenyl, 2,4-dimethoxycarbonylphenyl, 2,5-diethoxycarbonylphenyl, 2,6-dimethoxycarbonylphenyl, 3,4,5-triethoxycarbonylphenyl, 2-cyanophenyl, 3-cyanophenyl, 4-cyanophenyl, 3,4-dicyanophenyl, 3,5-dicyanophenyl, 2,4-dicyanophenyl, 2,5-dicyanophenyl, 2,6-dicyanophenyl, 3,4,5-tricyanophenyl, 2-phenylphenyl, 3-phenylphenyl, 4-phenylphenyl, 3,4-diphenylphenyl, 3,5-diphenylphenyl, 2,4-diphenylphenyl, 2,5-diphenylphehyl, 2,6-diphenylphenyl, 3,4,5-triphenylphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 2-hydroxyphenyl, 3-hydroxyphenyl, 4-hydroxyphenyl, 3,4-dihydroxyphenyl, 3,5-dihydroxyphenyl, 2,4-dihydroxyphenyl, 2,5-dihydroxyphenyl, 2,6-dihydroxyphenyl, 3,4,5-trihydroxyphenyl, 3-benzylphenyl, 2-(2-phenylethyl)phenyl, 4-(1-phenylethyl)phenyl, 2-(3-phenylpropyl)phenyl, 3-(4-phenylbutyl)phenyl, 4-(5-phenylpentyl)phenyl, 2-(6-phenylhexyl)phenyl, 4-(1,1-dimethyl-2-phenylethyl)phenyl, 3-(2-methyl-3-phenylpropyl)phenyl, 2-(4-fluorobenzyl)phenyl, 2-methyl-5-chlorophenyl, 2-methoxy-5-chlorophenyl, 4-(4-fluorobenzoyl)phenyl, 4-(4-fluorobenzyl)phenyl, 3-(2-chlorobenzyl)phenyl, 4-(3-chlorobenzyl)phenyl, 2-(4-chlorobenzyl)phenyl, 3-[2-(4-fluorophenyl)ethyl]phenyl, 4-[2-(4-chlorophenyl)ethyl]phenyl, 2-(3,4-dibromobenzyl)phenyl, 3-(3,4-diiodobenzyl)phenyl, 4-(2,4-difluorobenzyl)phenyl, 2-(2,5-dichlorobenzyl)phenyl, 3-(2,6-dichlorobenzyl)phenyl, 4-(3,4,5-trifluorobenzyl)phenyl, 2-[3-(4-chlorophenyl)propyl]phenyl, 3-[1-(2-bromophenyl)ethyl]phenyl, 4-[4-(3-fluorophenyl)butyl]phenyl, 2-[5-(4-iodophenyl)pentyl]phenyl, 3-[6-(4-chlorophenyl)hexyl]phenyl, 2-[1,1-dimethyl-2-(3-fluorophenyl)ethyl]phenyl, 4-[2-methyl-3-(4-chlorophenyl)propyl]phenyl, 2,4-dibenzylphenyl, 2,4,6-tribenzylphenyl, 2-chloro-4-cyanophenyl, 3-hydroxy-4-phenylphenyl, 3-ethoxycarbonyl-2-benzoylphenyl, 2-benzyl-4-methyl-6-methoxyphenyl, 4-[(2-methoxyethyl)carbamoyl]phenyl, 3-(N-ethyl-N-isopropylcarbamoyl)phenyl, 4-dimethylcarbamoylphenyl, 2-carboxyphenyl, 3-carboxyphenyl, and 4-carboxyphenyl groups.

Examples of the phenyl group which has a lower alkylenedioxy group as a substituent on the phenyl ring include phenyl groups which has a linear or branched alkylenedioxy group having 1 to 4 carbon atom as a substituent on the phenyl ring such as 3,4-methylenedioxyphenyl, 3,4-trimethylenedioxyphenyl, 2,3-ethylenedioxyphenyl, 2,3-tetramethylenedioxyphenyl, 2,3-methylenedioxyphenyl, 3,4-ethylenedioxyphenyl, and 2,3-trimethylenedioxyphenyl groups.

Examples of the naphthyl lower alkyl group include naphthylalkyl groups whose alkyl moiety is a linear or branched alkyl group having 1 to 6 carbon atoms such as (1 or 2-)naphthylmethyl, 2-[(1 or 2-)naphthyl]ethyl, 1-[(1 or 2-)naphthyl]ethyl, 3-[(1 or 2-)naphthyl]propyl, 4-[(1 or 2-)naphthyl]butyl, 5-[(1 or 2-)naphthyl]pentyl, 6-[(1 or 2-)naphthyl]hexyl, 1,1-dimethyl-2-[(1 or 2-)naphthyl]ethyl, and 2-methyl-3-[(1 or 2-)naphthyl]propyl groups.

Examples of the phenoxy group which may be substituted on the phenyl ring with 1 to 3 groups selected from the group consisting of a cyano group, a lower alkyl group which may have a halogen atom as a substituent, and a lower alkoxy group which may have a halogen atom as a substituent include phenoxy groups which may be substituted on the phenyl group with 1 to 3 groups selected from the group consisting of a cyano group, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents such as phenoxy, 2-methylphenoxy, 3-methylphenyl, 4-methylphenoxy, 2-ethylphenoxy, 3-ethylphenoxy, 4-ethylphenoxy, 4-isopropylphenoxy, 3-butylphenoxy, 4-pentylphenoxy, 4-hexylphenoxy, 3,4-dimethylphenoxy, 3,4-diethylphenoxy, 2,4-dimethylphenoxy, 2,5-dimethylphenoxy, 2,6-dimethylphenoxy, 3,4,5-trimethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 4-isopropoxyphenoxy, 3-butoxyphenoxy, 4-pentyloxyphenoxy, 4-hexyloxyphenoxy, 3,4-dimethoxyphenoxy, 3,4-diethoxyphenoxy, 2,4-dimethoxyphenoxy, 2,5-dimethoxyphenoxy, 2,6-dimethoxyphenoxy, 3,4,5-trimethoxyphenoxy, 2-trifluoromethoxyphenoxy, 3-trifluoromethoxyphenoxy, 4-trifluoromethoxyphenoxy, 2-(bromomethoxy)phenoxy, 3-(2-chloroethoxy)phenoxy, 4-(2,3-dichloropropoxy)phenoxy, 4-(4-fluorobutoxy)phenoxy, 3-(5-chloropentyloxy)phenoxy, 4-(5-bromohexyloxy)phenoxy, 4-(5,6-dibromohexyloxy)phenoxy, 3,4-di(trifluoromethoxy)phenoxy, 3,4-di(4,4,4-trichlorobutoxy)phenoxy, 2,4-di(3-chloro-2-methoxypropyl)phenoxy, 2,5-di(3-chloropropoxy)phenoxy, 2,6-di(2,2,2-trifluoroethoxy)phenoxy, 3,4,5-tri(trifluoromethoxy)phenoxy, 4-(2,2,2-trichloroethoxy)phenoxy, 2-methyl-4-trifluoromethoxyphenoxy, 3-ethyl-4-trichloromethoxyphenoxy, 2-methoxy-4-trifluoromethoxyphenoxy, 3-ethoxy-4-trichloromethoxyphenoxy, 2-trifluoromethylphenoxy, 3-trifluoromethylphenoxy, 4-trifluoromethylphenoxy, 2-(bromomethyl)phenoxy, 3-(2-chloroethyl)phenoxy, 4-(2,3-dichloropropyl)phenoxy, 4-(4-fluorobutyl)phenoxy, 3-(5-chloropentyl)phenoxy, 4-(5-bromohexyl)phenoxy, 4-(5,6-dibromohexyl)phenoxy, 3,4-di(trifluoromethyl)phenoxy, 3,4-di(4,4,4-trichlorobutyl)phenoxy, 2,4-di(3-chloro-2-methylpropyl)phenoxy, 2,5-di(3-chloropropyl)phenoxy, 2,6-di(2,2,2-trifluoroethyl)phenoxy, 3,4,5-tri(trifluoromethyl)phenoxy, 4-(2,2,2-trichloroethyl)phenoxy, 2-methyl-4-trifluoromethylphenoxy, 3-ethyl-4-trichloromethylphenoxy, 2-cyanophenoxy, 3-cyanophenoxy, 4-cyanophenoxy, 3,4-dicyanophenoxy, 3,5-dicyanophenoxy, 2,3-dicyanophenoxy, 2,4-dicyanophenoxy, 2,5-dicyanophenoxy, 2,6-dicyanophenoxy, 3,4,5-tricyanophenoxy, 2-cyano-4-methylphenoxy, 3-cyano-4-methoxyphenoxy, 3-cyano-5-trifluoromethylphenoxy, and 4-cyano-3-trifluoromethoxyphenoxy groups.

Examples of the phenyl lower alkoxy group which may be substituted on the phenyl ring with 1 to 3 groups selected from the group consisting of a halogen atom, a lower alkyl group which may have a halogen atom as a substituent, and a lower alkoxy group which may have a halogen atom as a substituent include, in addition to the above described phenyl lower alkoxy groups, phenylalkoxy groups which may be substituted on the phenyl ring with 1 to 3 groups selected from the group consisting of a halogen atom, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents, and whose alkoxy moiety is a linear or branched alkoxy group having 1 to 6 carbon atoms such as 2,5-difluorobenzyloxy, 2,4-difluorobenzyloxy, 3,4-difluorobenzyloxy, 3,5-difluorobenzyloxy, 2,6-difluorobenzyloxy, 3-trifluoromethylbenzyloxy, 2-trifluoromethylbenzyloxy, 4-trifluoromethylbenzyloxy, 3,4-dimethoxybenzyloxy, 3,5-dimethoxybenzyloxy, 2-chlorobenzyloxy, 3-chlorobenzyloxy, 4-chlorobenzyloxy, 2-methylbenzyloxy, 3-methylbenzyloxy, 4-methylbenzyloxy, 3,4-dimethylbenzyloxy, 2,3-dimethylbenzyloxy, 2-methoxybenzyloxy, 3-methoxybenzyloxy, 4-methoxybenzyloxy, 2,3-dichlorobenzyloxy, 2,4-dichlorobenzyloxy, 2,5-dichlorobenzyloxy, 3,4-dichlorobenzyloxy, 2,6-dichlorobenzyloxy, 4-fluorobenzyloxy, 3-fluorobenzyloxy, 2-fluorobenzyloxy, 3-trifluoromethoxybenzyloxy, 4-trifluoromethoxybenzyloxy, 2-trifluoromethoxybenzyloxy, 4-tert-butylbenzyloxy, 4-ethylbenzyloxy, 4-isopropylbenzyloxy, 4-methoxy-3-chlorobenzyloxy, 2-(4-methoxyphenyl)ethoxy, 2-(4-fluorophenyl)ethoxy, 2-(4-chlorophenyl)ethoxy, 2-(3-methoxyphenyl)ethoxy, 2-(4-methylphenyl)ethoxy, 3-methyl-4-chlorobenzyloxy, 4-(4-methoxyphenyl)butoxy, 2-(4-methylphenyl)ethoxy, 4-tert-butitocybenzyloxy, 3-chloro-6-methoxybenzyloxy, 4-methoxy-3-methylbenzyloxy, 2-(2-fluorophenyl)ethoxy, 1-(3-bromophenyl)ethoxy, 3-(4-iodophenyl)propoxy, 4-(2-bromophenyl)butoxy, 5-(3-chlorophenyl)pentyloxy, 6-(4-bromophenyl)hexyloxy, 1,1-dimethyl-2-(2,4-dichlorophenyl)ethoxy, 2-methyl-3-(2,4,6-trifluorophenyl)propoxy, 2-(2-ethylphenyl)ethoxy, 1-(3-propylphenyl)ethoxy, 3-(4-butylphenyl)propoxy, 4-(2-pentylphenyl)butoxy, 5-(3-hexylphenyl)pentyloxy, 6-(4-trifluoromethylphenyl)hexyloxy, 1,1-dimethyl-2-(2,4-dimethylphenyl)ethoxy, 2-methyl-3-[2,4,6-tri(trifluoromethyl)phenyl]propoxy, 2-(2-ethoxyphenyl)ethoxy, 1-(3-propoxyphenyl)ethoxy, 3-(4-butoxyphenyl)propoxy, 4-(2-pentyloxyphenyl)butoxy, 5-(3-hexyloxyphenyl)pentyloxy, 6-(4-trifluoromethoxyphenyl)hexyloxy, 1,1-dimethyl-2-(2,4-dimethoxyphenyl)ethoxy, and 2-methyl-3-[2,4,6-tri(trifluoromethoxy)phenyl]propoxy groups.

Examples of the 1,2,3,4-tetrahydronaphthyl substituted lower alkyl group which may have 1 to 5 lower alkyl groups as substituents on the 1,2,3,4-tetrahydronaphthalene ring include 1,2,3,4-tetrahydronaphthyl substituted alkyl groups which may have 1 to 5 linear or branched alkyl groups having 1 to 6 carbon atoms as substituents on the 1,2,3,4-tetrahydronaphthalene ring, and whose alkyl moiety is a linear or branched alkyl group having 1 to 6 carbon atoms such as (1, 2, 5 or 6-)1,2,3,4-tetrahydronaphthylmethyl, 2-[(1, 2, 5 or 6-)1,2,3,4-tetrahydronaphthyl]ethyl, 1-[(1, 2, 5 or 6-)1,2,3,4-tetrahydronaphthyl]ethyl, 3-[(1, 2, 5 or 6-)1,2,3,4-tetrahydronaphthyl]propyl, 4-[(1, 2, 5 or 6-)1,2,3,4-tetrahydronaphthyl]butyl, 5-[(1, 2, 5 or 6-)1,2,3,4-tetrahydronaphthyl]pentyl, 6-[(1, 2, 5 or 6-)1,2,3,4-tetrahydronaphthyl]hexyl, 1,1-dimethyl-2-[(1, 2, 5 or 6-)1,2,3,4-tetrahydronaphthyl]ethyl, 2-methyl-3-[(1, 2, 5 or 6-)1,2,3,4-tetrahydronaphthyl]propyl, 1,1,4,4-tetramethyl(2, 3, 5 or 6-)1,2,3,4-tetrahydronaphthylmethyl, 1,1,4,4,5-pentamethyl(2, 3, 6, 7 or 8-)1,2,3,4-tetrahydronaphthylmethyl, 1,4,4-trimethyl(2, 3, 5, 6, 7 or 8-)1,2,3,4-tetrahydronaphthylmethyl, 5,6-dimethyl(2, 3, 7 or 8-)1,2,3,4-tetrahydronaphthylmethyl, 2-[1-methyl-(1, 2, 3, 4, 5, 6, 7 or 8-)1,2,3,4-tetrahydronaphthyl]ethyl, 1-[2-ethyl-(1, 2, 3, 4, 5, 6, 7 or 8-)1,2,3,4-tetrahydronaphthyl]ethyl, 3-[3-propyl-(1, 2, 3, 4, 5, 6, 7 or 8-)1,2,3,4-tetrahydronaphthyl]propyl, 4-[(4-butyl-(1, 2, 3, 4, 5, 6, 7 or 8-)1,2,3,4-tetrahydronaphthyl]butyl, 5-[5-pentyl-(1, 2, 3, 4, 6, 7 or 8-)1,2,3,4-tetrahydronaphthyl]pentyl, 6-[6-hexyl-(1, 2, 3, 4, 5, 7 or 8-)1,2,3,4-tetrahydronaphthyl]hexyl, 1,1-dimethyl-2-[1,7-dimethyl-(1, 2, 3, 4, 5, 6 or 8-)1,2,3,4-tetrahydronaphthyl]ethyl, and 2-methyl-3-[1,1,4-trimethyl-(2, 3, 4, 5, 6, 7 or 8-)1,2,3,4-tetrahydronaphthyl]propyl groups.

Examples of the piperidinyl group which may have 1 to 3 lower alkyl groups as substituents on the piperidine ring include piperidinyl group which may have 1 to 3 linear or branched alkyl groups having 1 to 6 carbon atoms as substituents on the piperidine ring such as (1, 2, 3 or 4-)piperidinyl, 1-methyl-(2, 3 or 4-)piperidinyl, 1-ethyl-(2, 3 or 4-)piperidinyl, 1-propyl-(2, 3 or 4-)piperidinyl, 1-isopropyl-(2, 3 or 4-)piperidinyl, 1-butyl-(2, 3 or 4-)piperidinyl, 1-isobutyl-(2, 3 or 4-)piperidinyl, 1-tert-butyl-(2, 3 or 4-)piperidinyl, 1-pentyl-(2, 3 or 4-)piperidinyl, 1-hexyl-(2, 3 or 4-)piperidinyl, 1,2-dimethyl-(3, 4, 5 or 6-)piperidinyl, and 1,2,6-trimethyl-(3, 4 or 5-)piperidinyl groups.

Examples of the quinolyl lower alkyl group include quinolylalkyl groups whose alkyl moiety is a linear or branched alkyl group having 1 to 6 carbon atoms such as (2, 3, 4, 5, 6, 7 or 8-)quinolylmethyl, 2-[(2, 3, 4, 5, 6, 7 or 8-)quinolyl]ethyl, 1-[(2, 3, 4, 5, 6, 7 or 8-)quinolyl]ethyl, 3-[(2, 3, 4, 5, 6, 7 or 8-)quinolyl]propyl, 4-[(2, 3, 4, 5, 6, 7 or 8-)quinolyl]butyl, 5-[(2, 3, 4, 5, 6, 7 or 8-)pentyl, and 6-[(2, 3, 4, 5, 6, 7 or 8-)hexyl groups.

Examples of the 1,2,3,4-tetrazolyl lower alkyl group which may have, on the tetrazole ring, a substituent selected from the group consisting of a lower alkyl group and a phenyl lower alkyl group include 1,2,3,4-tetrazolylalkyl groups whose alkyl moiety is a linear or branched alkyl group having 1 to 6 carbon atoms and which may have, on the tetrazole ring, a substituent selected from the group consisting of a linear or branched alkyl group having 1 to 6 carbon atoms and a phenyl alkyl group whose alkyl moiety is a linear or branched alkyl group having 1 to 6 carbon atoms, such as [(1 or 5-)1,2,3,4-tetrazolyl]methyl, 2-[(1 or 5-)1,2,3,4-tetrazolyl]ethyl, 1-[(1 or 5-)1,2,3,4-tetrazolyl]ethyl, 3-[(1 or 5-)1,2,3,4-tetrazolyl]propyl, 4-[(1 or 5-)1,2,3,4-tetrazolyl]butyl, 5-[(1 or 5-)1,2,3, 4-tetrazolyl]pentyl, 6-[(1 or 5-)1,2,3,4-tetrazolyl]hexyl, 5-[1-methyl-5-(1,2,3,4-tetrazolyl)]pentyl, 6-[1-methyl-5-(1,2,3,4-tetrazolyl)]hexyl, 5-methyl-1-(1,2,3,4-tetrazolyl)methyl, 2-[5-ethyl-1-(1,2,3,4-tetrazolyl]hexyl, 1,1-dimethyl-2-[(1 or 5-)1,2,3,4-tetrazolyl)]ethyl, 2-methyl-3-[(1 or 5-)1,2,3,4-tetrazolyl]propyl, [1-methyl-5-(1,2,3,4-tetrazolyl)]methyl, [1-ethyl-5-(1,2,3,4-tetrazolyl)]methyl, 2-[1-propyl-5-(1,2,3,4-tetrazolyl)]ethyl, 1-[1-butyl-5-(1,2,3,4-tetrazolyl)]ethyl, 3-[1-pentyl-5-(1,2,3,4-tetrazolyl)]propyl, 3-[5-propyl-1-(1,2,3,4-tetrazolyl)]propyl, 4-[5-butyl-1-(1,2,3,4-tetrazolyl)]butyl, 5-[5-pentyl-1-(1,2,3,4-tetrazolyl)]pentyl, 6-[5-hexyl-1-(1,2,3,4-tetrazolyl)]hexyl, [1-ethyl-5-(1,2,3,4-tetrazolyl)]methyl, [1-benzyl-5-(1,2,3,4-tetrazolyl)]methyl, 1-[(2-phenylethyl)-5-(1,2,3,4-tetrazolyl)]methyl, 2-[1-(3-phenylpropyl)-5-(1,2,3,4-tetrazolyl)]ethyl, 1-[1-(4-phenylbutyl)-5-(1,2,3,4-tetrazolyl)]ethyl, 3-[1-(5-phenylpentyl)-5-(1,2,3,4-tetrazolyl)]propyl, 4-[1-(6-phenylhexyl)-5-(1,2,3,4-tetrazolyl)]butyl, 5-[1-(1,1-dimethyl-2-phenylethyl)-5-(1,2,3,4-tetrazolyl)]methyl, 6-[1-(2-methyl-3-phenylpropyl)-5-(1,2,3,4-tetrazolyl)]hexyl, 5-benzyl-1-(1,2,3,4-tetrazolyl)methyl, 2-[5-(1-phenylethyl)-1-(1,2,3,4-tetrazolyl)]ethyl, 3-[5-(3-phenylpropyl)-1-(1,2,3,4-tetrazolyl)]propyl, 4-[5-(4-phenylbutyl)-1-(1,2,3,4-tetrazolyl)]butyl, 5-[5-(5-phenylpentyl)-1-(1,2,3,4-tetrazolyl)]pentyl, and 6-[5-(6-phenylhexyl)-1-(1,2,3,4-tetrazolyl)]hexyl groups.

Examples of the thiazolyl lower alkyl group which may have a phenyl group as a substituent on the thiazole ring include thiazolylalkyl groups which may have 1 or 2 phenyl groups as substituents on the thiazole ring and whose alkyl moiety is a linear or branched alkyl group having 1 to 6 carbon atoms such as [(2, 4 or 5-)thiazolyl]methyl, 2-[(2, 4 or 5-)thiazolyl]ethyl, 1-[(2, 4 or 5-)thiazolyl]ethyl, 3-[(2, 4 or 5-)thiazolyl]propyl, 4-[(2, 4 or 5-)thiazolyl]butyl, 5-[(2, 4 or 5-)thiazolyl]pentyl, 6-[(2, 4 or 5-)thiazolyl]hexyl, 1,1-dimethyl-2-[(2, 4 or 5-)thiazolyl]ethyl, 2-methyl-3-[(2, 4 or 5-)thiazolyl]propyl, [2-phenyl-(4 or 5-)thiazolyl]methyl, 2-[4-phenyl-(2 or 5-)thiazolyl]ethyl, 1-[5-phenyl-(2 or 4-)thiazolyl]ethyl, 3-[2-phenyl-(2 or 5-)thiazolyl]propyl, 4-(2,4-diphenyl-5-thiazolyl)butyl, 5-(2,5-diphenyl-4-thiazolyl)pentyl, 6-(4,5-diphenyl-2-thiazolyl)hexyl, 1,1-dimethyl-2-[2-phenyl-(4 or 5-)thiazolyl]ethyl, 2-methyl-3-[4-phenyl-(2 or 5-)thiazolyl]propyl, [4-phenyl-(2 or 5-)thiazolyl]methyl, [5-phenyl-(2 or 4-)thiazolyl]methyl, (2,4-diphenyl-5-thiazolyl)methyl, (2,5-diphenyl-4-thiazolyl)methyl, and (4,5-diphenyl-2-thiazolyl)methyl groups.

Examples of the benzoyl lower alkyl group which may have, on the phenyl ring, 1 to 3 substituents selected from the group consisting of a lower alkoxy group and a halogen atom include benzoylalkyl groups which may have, on the phenyl ring, 1 to 3 substituents selected from the group consisting of a linear or branched alkoxy group having 1 to 6 carbon atoms and a halogen atom and whose alkyl moiety is a linear or branched alkyl group having 1 to 6 carbon atoms such as benzoylmethyl, 2-benzoylethyl, 1-benzoylethyl, 3-benzoylpropyl, 4-benzoylbutyl, 5-benzoylpentyl, 6-benzoylhexyl, 1,1-dimethyl-2-benzoylethyl, 2-methyl-3-benzoylpropyl, 4-fluorobenzoylmethyl, 2-chlorobenzoylmethyl, 3-chlorobenzoylmethyl, 4-chlorobenzoylmethyl, 2-(4-fluorobenzoyl)ethyl, 2-(4-chlorobenzoyl)ethyl, 3,4-dibromobenzoylmethyl, 3,4-diiodobenzoylmethyl, 2,4-difluorobenzoylmethyl, 2,5-dichlorobenzoylmethyl, 2,6-dichlorobenzoylmethyl, 3,4,5-trifluorobenzoylmethyl, 3-(4-chlorobenzoyl)propyl, 1-(2-bromobenzoyl)ethyl, 4-(3-fluorobenzoyl)butyl, 5-(4-iodobenzoyl)pentyl, 6-(4-chlorobenzoyl)hexyl, 1,1-dimethyl-2-(3-fluorobenzoyl)ethyl, 2-methyl-3-(4-chlorobenzoyl)propyl, 2-methoxybenzoylmethyl, 2-(3-methoxybenzoyl)ethyl, 2-(4-methoxybenzoyl)ethyl, 4-methoxybenzoylmethyl, 1-(2-ethoxybenzoyl)ethyl, 3-(3-ethoxybenzoyl)propyl, 4-(4-ethoxybenzoyl)butyl, 5-(4-isopropoxybenzoyl)pentyl, 6-(3-butoxybenzoyl)hexyl, 1,1-dimethyl-2-(4-pentyloxybenzoyl)ethyl, 2-methyl-3-(4-hexyloxybenzoyl)propyl, 3,4-dimethoxybenzoylmethyl, 3,4-diethoxybenzoylmethyl, 2,4-dimethoxybenzoylmethyl, 2,5-dimethoxybenzoylmethyl, 2,6-dimethoxybenzoylmethyl, 3,4,5-trimethoxybenzoylmethyl, 2-chloro-4-methoxybenzoylmethyl, and 3-fluoro-5-ethoxybenzoylmethyl groups.

Examples of the piperidinyl lower alkyl group which may have a lower alkyl group as a substituent on the piperidine ring include piperidinylalkyl groups which may have 1 to 3 linear or branched alkyl groups having 1 to 6 carbon atoms as substituents on the piperidine ring and whose alkyl moiety is a linear or branched alkyl group having 1 to 6 carbon atoms such as [(1, 2, 3 or 4-)piperidinyl]methyl, 2-[(1, 2, 3 or 4-)piperidinyl]ethyl, 1-[(1, 2, 3 or 4-)piperidinyl]ethyl, 3-[(1, 2, 3 or 4-)piperidinyl]propyl, 4-[(1, 2, 3 or 4-)piperidinyl]butyl, 5-[(1, 2, 3 or 4-)piperidinyl]pentyl, 6-[(1, 2, 3 or 4-)piperidinyl]hexyl, 1,1-dimethyl-2-[(1, 2, 3 or 4-)piperidinyl]ethyl, 2-methyl-3-[(1, 2, 3 or 4-)piperidinyl]propyl, [1-methyl-(2, 3 or 4-)piperidinyl]methyl, 2-[1-ethyl-(2, 3 or 4-)piperidinyl]ethyl, 1-[4-propyl-(1, 2 or 3-)piperidinyl]ethyl, 3-[3-isopropyl-(1, 2, 4, 5 or 6-)piperidinyl]propyl, 4-[2-butyl-(1, 3, 4, 5 or 6-)piperidinyl]butyl, 5-[1-isobutyl-(2, 3 or 4-)piperidinyl]pentyl, 6-[1-tert-butyl-(2, 3 or 4-)piperidinyl]hexyl, 1,1-dimethyl-2-[4-pentyl-(1, 2 or 3-)piperidinyl]ethyl, 2-methyl-3-[1-hexyl-(2, 3 or 4-)piperidinyl]propyl, [1,2-dimethyl-(3, 4, 5 or 6-)piperidinyl]methyl, and [1,2,6-trimethyl-(3, 4 or 5-)piperidinyl]methyl groups.

Examples of the imidazolyl group which may have 1 to 3 phenyl groups as substituents on the imidazole ring include imidazolyl groups which may have 1 to 3 phenyl groups as substituents on the imidazole ring such as 1, 2, 4 or 5-)imidazolyl, 1-phenyl-(2, 4 or 5-)imidazolyl, 2-phenyl-(1, 4 or 5-)imidazolyl, 4-phenyl-(1, 2 or 5-)imidazolyl, 5-phenyl-(1, 2 or 4-)imidazolyl, 1,2-diphenyl-(4 or 5-)imidazolyl, 2,4-diphenyl-(1 or 5-)imidazolyl, 4,5-diphenyl-(1 or 2-)imidazolyl, 2,5-diphenyl-(1 or 4-)imidazolyl, and 2,4,5-triphenyl-1-imidazolyl groups.

Examples of the benzimidazolyl group which may have 1 to 3 lower alkyl groups as substituents on the benzimidazole ring include benzimidazolyl group which may have 1 to 3 linear or branched alkyl groups having 1 to 6 carbon atoms as substituents on the benzimidazole ring such as (1, 2, 4, 5, 6 or 7-)benzimidazolyl, 1-methyl-(2, 4, 5, 6 or 7-)benzimidazolyl, 2-ethyl-(1, 4, 5, 6 or 7-)benzimidazolyl, 4-propyl-(1, 2, 5, 6 or 7-)benzimidazolyl, 5-butyl-(1, 2, 4, 6 or 7-)benzimidazolyl, 6-pentyl-(1, 2, 4, 5 or 7-)benzimidazolyl, 7-hexyl-(1, 2, 4, 5 or 6-)benzimidazolyl, 1-ethyl-(2, 4, 5, 6 or 7-)benzimidazolyl]hexyl, 1-butyl-(2, 4, 5, 6 or 7-)benzimidazolyl, 1-isopropyl-(1, 2, 4, 5, 6 or 7-)benzimidazolyl, 1,2-dimethyl-(4, 5, 6 or 7-)benzimidazolyl, 1-methyl-4-ethyl-(2, 5, 6 or 7-)benzimidazolyl, 1-propyl-5-methyl-(2, 4, 6 or 7-)benzimidazolyl, and 1,2,5-trimethyl-(2, 4, 5, 6 or 7-)benzimidazolyl groups.

Examples of the pyridyl lower alkoxy group include pyridylalkoxy groups whose alkyl moiety is a linear or branched alkyl group having 1 to 6 carbon atoms such as (2, 3 or 4-)pyridylmethoxy, 2-[(2, 3 or 4-)pyridyl]ethoxy, 1-[(2, 3 or 4-)pyridyl]ethoxy, 3-[(2, 3 or 4-)pyridyl]propoxy, 4-[(2, 3 or 4-)pyridyl]butoxy, 1-1-dimethyl-2-[(2, 3 or 4-)pyridyl]ethoxy, 5-[(2, 3 or 4-)pyridyl]pentyloxy, 6-[(2, 3 or 4-)pyridyl]hexyloxy, 1-[(2, 3 or 4-)pyridyl]isopropoxy, and 2-methyl-3-[(2, 3 or 4-)pyridyl]propoxy groups.

Examples of the 1,2,3,4-tetrahydroquinolyl lower alkyl group which may have an oxo group as a substituent on the tetrahydroquinoline ring include 1,2,3,4-tetrahydroquinolylalkyl groups which may have 1 or 2 oxo groups as substituents on the tetrahydroquinoline ring and whose alkyl moiety is a linear or branched alkyl group having 1 to 6 carbon atoms such as (1, 2, 3, 4, 5, 6, 7 or 8-)1,2,3,4-tetrahydroquinolylmethyl, 2-[(1, 2, 3, 4, 5, 6, 7 or 8-)1,2,3,4-tetrahydroquinolyl]ethyl, 1-[(1, 2, 3, 4, 5, 6, 7 or 8-)1,2,3,4-tetrahydroquinolyl]ethyl, 3-[(1, 2, 3, 4, 5, 6, 7 or 8-)1,2,3,4-tetrahydroquinolyl]propyl, 4-[(1, 2, 3, 4, 5, 6, 7 or 8-)1,2,3,4-tetrahydroquinolyl]butyl, 5-[(1, 2, 3, 4, 5, 6, 7 or 8-)1,2,3,4-tetrahydroquinolyl]pentyl, 6-[(1, 2, 3, 4, 5, 6, 7 or 8-)1,2,3,4-tetrahydroquinolyl]hexyl, 1,1-dimethyl-2-[(1, 2, 3, 4, 5, 6, 7 or 8-)1,2,3,4-tetrahydroquinolyl]ethyl, 2-methyl-3-[(1, 2, 3, 4, 5, 6, 7 or 8-)1,2,3,4-tetrahydroquinolyl]propyl, [2-oxo-(1, 3, 4, 5, 6, 7 or 8-)1,2,3,4-tetrahydroquinolyl]methyl, [4-oxo-(1, 2, 3, 5, 6, 7 or 8-)1,2,3,4-tetrahydroquinolyl]methyl, [2,4-dioxo-(1, 3, 5, 6, 7 or 8-)1,2,3,4-tetrahydroquinolyl]methyl, 2-[2-oxo-(1, 3, 4, 5, 6, 7 or 8-)1,2,3,4-tetrahydroquinolyl]ethyl, 3-(4-oxo-(1, 2, 3, 5, 6, 7 or 8-)1,2,3,4-tetrahydroquinolyl]propyl, 4-[2, 4-dioxo-(1, 3, 5, 6, 7 or 8-)1,2,3,4-tetrahydroquinolyl]butyl, 5-[2-oxo-(1, 3, 4, 5, 6, 7 or 8-)1,2,3,4-tetrahydroquinolyl]pentyl, and 6-[4-oxo-(1, 2, 3, 5, 6, 7 or 8-)1,2,3,4-tetrahydroquinolyl]hexyl groups.

Examples of the 1,3,4-oxadiazolyl lower alkyl group which may have an oxo group as a substituent on the 1,3,4-oxadiazole ring include 1,3,4-oxadiazolylalkyl groups which may have an oxo group as a substituent on the 1,3,4-oxadiazole ring and whose alkyl moiety is a linear or branched alkyl group having 1 to 6 carbon atoms such as (2 or 5-)1,3,4-oxadiazolylmethyl, 2-[(2 or 5-)1,3,4-oxadiazolyl]ethyl, 1-[(2 or 5-)1,3,4-oxadiazolyl]ethyl, 3-[(2 or 5-)1,3,4-oxadiazolyl]propyl, 4-[(2 or 5-)1,3,4-oxadiazolyl]butyl, 5-[(2 or 5-)1,3,4-oxadiazolyl]pentyl, 6-[(2 or 5-)1,3,4-oxadiazolyl]hexyl, 1,1-dimethyl-2-[(2 or 5-)1,3,4-oxadiazolyl]ethyl, 2-methyl-3-[(2 or 5-)1,3,4-oxadiazolyl]propyl, 2-oxo-[(3 or 5-)1,3,4-oxadiazolyl]methyl, 5-oxo-[(2 or 3-)1,3,4-oxadiazolyl]methyl, 2-[2-oxo-(3 or 5-)(1,3,4-oxadiazolyl)]ethyl, 1-[5-oxo-(2 or 3-)1,3,4-oxadiazolyl]ethyl, 3-[(2 or 5-)1,3,4-oxadiazolyl]propyl, 4-[2-oxo(3 or 5-)1,3,4-oxadiazolyl]butyl, 5-[5-oxo(2 or 3-)1,3,4-oxadiazolyl]pentyl, 6-[2-oxo(3 or 5-)1,3,4-oxadiazolyl]hexyl, 1,1-dimethyl-2-[5-oxo(2 or 3-)1,3,4-oxadiazolyl]ethyl, and 2-methyl-3-[2-oxo(3 or 5-)1,3,4-oxadiazolyl]propyl groups.

Examples of the thienyl lower alkyl group include thienylalkyl groups whose alkyl moiety is a linear or branched alkyl group having 1 to 6 carbon atoms such as (2 or 3-)thienylmethyl, 2-[(2 or 3-)thienyl]ethyl, 1-[(2 or 3-)thienyl]ethyl, 3-[(2 or 3-)thienyl]propyl, 4-[(2 or 3-)thienyl]butyl, 5-[(2 or 3-)thienyl]pentyl, 6-[(2 or 3-)thienyl]hexyl, 1,1-dimethyl-2-[(2 or 3-)thienyl]ethyl, and 2-methyl-3-[(2 or 3-)thienyl]propyl groups.

Examples of the pyrimidinylcarbonyl group which may have an oxo group as a substituent on the pyrimidine ring include pyrimidinylcarbonyl groups which may have 1 to 3 oxo groups as substituents on the pyrimidine ring such as (2, 3, 4 or 6-)pyrimidinylcarbonyl, 2,6-dioxo-(1, 3, 4 or 5-)pyrimidinylcarbonyl, 2-oxo-(1, 3, 4, 5 or 6-)pyrimidinylcarbonyl, 6-oxo-(1, 2, 3, 4 or 5-)pyrimidinylcarbonyl, 4-oxo-(1, 2, 3, 5 or 6-)pyrimidinylcarbonyl, 2,4-dioxo-(1, 3, 4 or 6-)pyrimidinylcarbonyl, and 2,4,6-trioxo-(1, 3 or 5-)pyrimidinylcarbonyl groups.

Examples of the lower alkoxy lower alkoxy group include linear or branched alkoxy groups having 1 to 6 carbon atoms which may have a linear or branched alkoxy group having 1 to 6 carbon atoms as a substituent such as methoxymethoxy, 1-ethoxyethoxy, 2-methoxyethoxy, 2-propoxyethoxy, 3-isopropoxypropoxy, 4-butbxybutoxy, 5-pentyloxypentyloxy, 6-hexyloxyhexyloxy, 1,1-dimethyl-2-methoxyethoxy, 2-methyl-3-ethoxypropoxy, and 3-methoxypropoxy groups.

Examples of the lower alkoxycarbonyl lower alkoxy group include alkoxycarbonylalkoxy groups whose two alkoxy moieties are linear or branched alkoxy groups having 1 to 6 carbon atoms such as methoxycarbonylmethoxy, ethoxycarbonylmethoxy, 2-methoxycarbonylethoxy, 2-ethoxycarbonylethoxy, 1-ethoxycarbonylethoxy, 3-methoxycarbonylpropoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, and hexyloxycarbonylmethoxy groups.

Examples of the carboxy lower alkoxy group include carboxyalkoxy groups whose alkoxy moiety is a linear or branched alkoxy group having 1 to 6 carbon atoms such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, and 2-methyl-3-carboxypropoxy groups.

Examples of the phenoxy lower alkanoyl group include phenoxyalkanoyl groups whose alkanoyl moiety is a linear or branched alkanoyl group having 2 to 6 carbon atoms such as 2-phenoxyacetyl, 3-phenoxypropionyl, 2-phenoxypropionyl, 4-phenoxybutyryl, 5-phenoxypentanoyl, 6-phenoxyhexanoyl, 2,2-dimethyl-2-phenoxypropionyl, and 2-methyl-3-phenoxypropionyl groups.

Examples of the 1,2,3,4-tetrahydroquinolylcarbonyl group which may have an oxo group as a substituent on the tetrahydroquinoline ring include 1,2,3,4-tettahydroquinolylcarbonyl groups which may have 1 or 2 oxo groups as substituents on the tetrahydroquinoline ring such as [(1, 3, 4, 5, 6, 7 or 8-)1,2,3,4-tetrahydroquinolyl]carbonyl, [2-oxo-(1, 3, 4, 5, 6, 7 or 8-)1,2,3,4-tetrahydroquinolyl]carbonyl, [4-oxo-(1, 2, 3, 5, 6, 7 or 8-)1,2,3,4-tetrahydroquinolyl]carbonyl, and [2,4-dioxo-(1, 3, 5, 6, 7 or 8-)1,2,3,4-tetrahydroquinolyl]carbonyl groups.

Examples of the 1,2,3,4-tetrahydroquinolyl group which may have an oxo group as a substituent on the tetrahydroquinoline ring include 1,2,3,4-tetrahydroquinolyl groups which may have 1 or 2 oxo groups as substituents on the tetrahydroquinoline ring such as (1, 2, 3, 4, 5, 6, 7 or 8-)1,2,3,4-tetrahydroquinolyl, 2-oxo-(1, 3, 4, 5, 6, 7 or 8-)1,2,3,4-tetrahydroquinolyl, 4-oxo-(1, 2, 3, 5, 6, 7 or 8-)1,2,3,4-tetrahydroquinolyl, and 2,4-dioxo-(1, 3, 5, 6, 7 or 8-)1,2,3,4-tetrahydroquinolyl groups.

Examples of the amino group which may have a lower alkoxycarbonyl group as a substituent include amino groups which may have a linear or branched alkoxycarbonyl group having 1 to 6 carbon atoms such as amino, methoxycarbonylamino, ethoxycarbonylamino, propoxycarbonylamino, isopropoxycarbonylamino, butoxycarbonylamino, tert-butoxycarbonylamino, pentyloxycarbonylamino, and hexyloxycarbonylamino groups.

Examples of the benzoyl group which may have 1 to 3 lower alkoxy groups as substituents on the phenyl ring include benzoyl groups which may have 1 to 3 linear or branched alkoxy groups having 1 to 6 carbon atoms as substituents on the phenyl ring such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 3-butoxybenzoyl, 4-pentyloxybenzoyl, 4-hexyloxybenzoyl, 3,4-dimethoxybenzoyl, 3,4-diethoxybenzoyl, 2,4-dimethoxybenzoyl, 2,5-dimethoxybenzoyl, 2,6-dimethoxybenzoyl, and 3,4,5-trimethoxybenzoyl groups.

Examples of the lower alkyl group which have 1 or 2 phenyls which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent, and a lower alkylthio group include, in addition to the above described phenyl lower alkyl groups, linear or branched alkyl groups which have 1 to 6 carbon atoms and 1 to 2 phenyls which may have, on the phenyl ring, 1 to 3 substituents selected from the group consisting of a linear or branched alkoxycarbonyl group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, and a linear or branched alkylthio group having 1 to 6 carbon atoms such as 1,1-diphenylmethyl, 1,1-di(4-fluorophenyl)methyl, 1-phenyl-1-(4-methoxyphenyl)methyl, 3,3-diphenylpropyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 37-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butitocycarbonylbenzyl, 3-chloro-6-methoxybenzyl, 4-nitro-3-methylbenzyl, 4-tert-butyrylbenzyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-diethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(4-iodoruphenyl)propyl, 4-(2-bromophenyl)butyl, 5-(3-chlorophenyl)pentyl, 6-(4-bromoruphenyl)hexyl, 1,1-dimethyl-2-(2,4-dichlorophenyl)ethyl, 2-methyl-3-(2,4,6-trifluorophenyl)propyl, 2-(2-ethylphenyl)ethyl, 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-methylthiobenzyl, 3-methylthiobenzyl, 4-methylthiobenzyl, 3,4-dimethylthiobenzyl, 2,3-dimethylthiobenzyl, 2-(2-ethylthiophenyl)ethyl, 2-(4-methylthiophenyl)ethyl, 1-(3-propylthiophenyl)ethyl, 3-(4-butylthiophenyl)propyl, 4-(2-pentylthiophenyl)butyl, 5-(3-hexylthiophenyl)pentyl, 6-(4-methylthiophenyl)hexyl, 1,1-dimethyl-2-(2,4-dimethylthiophenyl)ethyl, 2-methyl-3-[2,4,6-trimethylthiophenyl]propyl, 2-methyl-4-cyanobenzyl, 3-ethoxy-4-ethoxycarbonylbenzyl, 4-phenyl-3-nitrobenzyl, 3-fluoro-4-methoxybenzyl, 4-trifluoromethyl-3-cyanobenzyl, and 3-trifluoromethoxy-3-fluorobenzyl groups.

Examples of the phenyl group which may have, on the phenyl ring, 1 to 3 groups selected from the group consisting of a lower alkoxy group which may have a halogen atom as a substituent and a lower alkyl group which may have a halogen atom as a substituent include phenyl groups which may have, on the phenyl ring, 1 to 3 groups selected from the group consisting of a linear or branched alkoxy group having 1 to 6 carbon atoms which may have 1 to 3 halogen atoms as substituents and a linear or branched alkyl group having 1 to 6 carbon atoms and which may have 1 to 3 halogen atoms as substituents such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxylphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromoethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2, 2,2-trichloroethyl)phenyl, 2-methyl-4-trifluoromethylphenyl, and 3-ethyl-4-trichloromethylphenyl groups.

Examples of the pyrrolidinyl lower alkyl group which may have, on the pyrrolidine ring, 1 to 3 lower alkyl groups which may have a hydroxyl group as a substituent include pyrrolidinylalkyl groups which may have, on the pyrrolidine ring, 1 to 3 linear or branched alkyl groups having 1 to 6 carbon atoms which may have 1 to 3 hydroxyl groups as substituents and whose alkyl moiety is a linear or branched alkyl group having 1 to 6 carbon atoms such as [(1, 2 or 3-)pyrrolidinyl]methyl, 2-[(1, 2 or 3-)pyrrolidinyl]ethyl, 1-[(1, 2 or 3-)pyrrolidinyl]ethyl, 3-[(1, 2 or 3-)pyrrolidinyl]propyl, 4-[(1, 2 or 3-)pyrrolidinyl]butyl, 5-[(1, 2 or 3-)pyrrolidinyl]pentyl, 6-[(1, 2 or 3-)pyrrolidinyl]hexyl, 1,1-dimethyl-2-[(1, 2 or 3-)pyrrolidinyl]ethyl, 2-methyl-3-[(1, 2 or 3-)pyrrolidinyl]propyl, [1-methyl-(2 or 3-)pyrrolidinyl]methyl, 2-[2-ethyl-(1, 3, 4 or 5-)pyrrolidinyl]ethyl, 1-[3-propyl-(1, 2, 4 or 5-)pyrrolidinyl-ethyl, 3-[1-butyl-(2 or 3-)pyrrolidinyl]propyl, 4-[2-pentyl-(1, 3, 4 or 5-)pyrrolidinyl]butyl, 5-[3-hexyl-(1, 2, 4 or 5-)pyrrolidinyl]pentyl, 6-[1,2-dimethyl-(3, 4 or 5-)pyrrolidinyl]hexyl, 1,1-dimethyl-2-[1,2,3-trimethyl-(4 or 5-)pyrrolidinyl]ethyl, 2-methyl-3-[1-ethyl-2-methyl-(3, 4 or 5-)pyrrolidinyl]propyl, [1-(2-hydroxyethyl)-(2 or 3-)pyrrolidinyl]methyl, [2-hydroxymethyl-(1, 3, 4 or 5-)pyrrolidinyl]methyl, 2-[2-hydroxymethyl-(1, 3, 4 or 5-)pyrrolidinyl]ethyl, 1-[3-(3-hydroxypropyl)-(1, 2, 4 or 5-)pyrrolidinyl]ethyl, 3-[1-(4-hydroxybutyl)-(2 or 3-)pyrrolidinyl]propyl, 4-[2-(5-hydroxypentyl)-(1, 3, 4 or 5-)pyrrolidinyl]butyl, 5-[3-(6-hydroxyhexyl)-(1, 2, 4 or 5-)pyrrolidinyl]pentyl, 6-[1,2-dihydroxymethyl-(3, 4 or 5-)pyrrolidinyl]hexyl, 1,1-dimethyl-2-[1,2,3-trihydroxymethyl-(4 or 5-)pyrrolidinyl]ethyl, 2-methyl-3-[2-(1,2-hydroxyethyl)-(1, 3, 4 or 5-)pyrrolidinyl]propyl, and [2-(2,3,4-trihydroxybutyl)-(1, 3, 4 or 5-)pyrrolidinyl]methyl groups.

Examples of the amino substituted lower alkyl group which may have a substituent selected from the group consisting of a phenyl group and a lower alkyl group include linear or branched alkyl groups having 1 to 6 carbon atoms substituted with an amino group which may have 1 or 2 substituents selected from the group consisting of a phenyl group and a linear or branched alkyl group having 1 to 6 carbon atoms such as aminomethyl, 2-aminomethyl, 1-aminoethyl, 3-aminopropyl, 4-aminobutyl, 5-aminopentyl, 6-aminohexyl, 1,1-dimethyl-2-aminoethyl, N,N-diethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N-methyl-N-hexylamino)ethyl, phenylaminomethyl, 1-phenylaminoethyl, 2-phenylaminoethyl, 3-phenylaminopropyl, 4-phenylaminobutyl, 5-phenylaminopentyl, 6-phenylaminohexyl, N-methyl-N-phenylaminomethyl, 2-(N-ethyl-N-phenylamino)ethyl, (N-ethyl-N-phenylamino)methyl, and 2-(N-methyl-N-phenylamino)ethyl groups.

Examples of the tetrahydrofuryl lower alkyl group which may have a hydroxyl group as a substituent on the lower alkyl group include tetrahydrofurylalkyl groups which may have a hydroxyl group as a substituent on the lower alkyl group and whose alkyl moiety is a linear or branched alkyl group having 1 to 6 carbon atoms such as [(2 or 3-)tetrahydrofuryl]methyl, 2-[(2 or 3-)tetrahydrofuryl]ethyl, 1-[(2 or 3-)tetrahydrofuryl]ethyl, 3-[(2 or 3-)tetrahydrofuryl]propyl, 4-[(2 or 3-)tetrahydrofuryl]butyl, 5-[(2 or 3-)tetrahydrofuryl]pentyl, 6-[(2 or 3-)tetrahydrofuryl]hexyl, 1,1-dimethyl-2-[(2 or 3-)tetrahydrofuryl]ethyl, 2-methyl-3-[(2 or 3-)tetrahydrofuryl]propyl, 1-hydroxy-1-[(2 or 3-)tetrahydrofuryl]methyl, 2-hydroxy-2-[(2 or 3-)tetrahydrofuryl]ethyl, 2-hydroxy-1-[(2 or 3-)tetrahydrofuryl]ethyl, 3-hydroxy-3-[(2 or 3-)tetrahydrotetrahydrofuryl]propyl, 4-hydroxy-4-[(2 or 3-)tetrahydrofuryl]butyl, 5-hydroxy-5-[(2 or 3-)tetrahydrofuryl]pentyl, 6-hydroxy-6-[(2 or 3-)tetrahydrofuryl]hexyl, 2-hydroxy-1,1-dimethyl-2-[(2 or 3-)tetrahydrofuryl]ethyl, and 3-hydroxy-2-methyl-3-[(2 or 3-)tetrahydrofuryl]propyl groups.

Examples of the phenoxy lower alkyl group which may have, on the phenyl ring, 1 to 3 substituents selected from the group consisting of a lower alkyl group and a nitro group include, in addition to the above described phenoxy lower alkyl groups, phenoxyalkyl groups which may have, on the phenyl ring, 1 to 3 substituents selected from the group consisting of a linear or branched alkyl group having 1 to 6 carbon atoms and a nitro group and whose alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(3-methylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, 2-methyl-3-(2,4,6-trimethylphenoxy)propyl, 2-(4-nitro-3-methylphenoxy)ethyl, 4-nitrophenoxymethyl, 3-nitrophenoxymethyl, 2-nitrophenoxymethyl, 2-(2-nitrophenoxy)ethyl, 2-(4-nitrophenoxy)ethyl, 1-(3-nitrophenoxy)ethyl, 3-(4-nitrophenoxy)propyl, 4-(2-nitrophenoxy)butyl, 5-(3-nitrophenoxy)pentyl, 6-(4-nitrophenoxy)hexyl, 1,1-dimethyl-2-(2,4-dinitrophenoxy)ethyl, and 2-methyl-3-(2,4,6-trinitrophenoxy)propyl groups.

Examples of the phenyl lower alkanoyl group include phenylalkanoyl groups whose alkanoyl moiety is a linear or branched alkanoyl group having 2 to 6 carbon atoms such as 2-phenylacetyl, 3-phenylpropionyl, 2-phenylpropionyl, 4-phenylbutyryl, 5-phenylpentanoyl, 6-phenylhexanoyl, 2,2-dimethyl-3-phenylpropionyl, and 2-methyl-3-phenylpropionyl groups.

Examples of the phenyl group which may have, on the phenyl ring, 1 to 3 substituents selected from the group consisting of a halogen atom and a lower alkyl group which may have a halogen atom include phenyl groups which may have, on the phenyl ring, 1 to 3 substituents selected from the group consisting of a halogen atom and a linear or branched alkyl group having 1 to 6 carbon atoms which may have 1 to 3 halogen atoms such as phenyl, 3,4-difluorophenyl, 2-fluorophenyl, 3-bromophenyl, 4-iodophenyl, 4-methylphenyl, 2-methylphenyl, 3-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-chloro-4-trifluoromethylphenyl, 3-ethyl-4-fluorophenyl, 3-fluoro-4-trichloromethylphenyl, 2-methyl-3-trifluoromethyl-4-trifluoromethylphenyl, 3-fluorophenyl, 4-fluorophenyl, 2-bromophenyl, 4-bromophenyl, 2-iodophenyl, 3-iodophenyl, 2,3-dibromophenyl, 2,4-diiodophenyl, 2,5-difluorophenyl, 2,6-dichlorophenyl, 2,4,6-trichlorophenyl, 2,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trifluorophenyl, and 2,4-difluorophenyl groups.

Examples of the 5- to 7-membered saturated heterocyclic group formed by mutually binding $R^{20}$ and $R^{21}$, $R^{22}$ and $R^{23}$, $R^{26}$ and $R^{27}$, $R^{29}$ and $R^{30}$ or $R^{32}$ and $R^{33}$ together with the nitrogen atoms bound to them, through or not through a nitrogen atom, an oxygen atom or a sulfur atom, include pyrrolidinyl, piperidinyl, piperazinyl, morpholino, thiomorpholino, and homopiperazinyl groups.

Examples of the phenoxy lower alkyl group which may have, on the phenyl ring, a lower alkyl group as a substituent include, in addition to the above described phenoxy lower alkyl groups, phenoxyalkyl groups which may have, on the phenyl ring, 1 to 3 linear or branched alkyl groups having 1 to 6 carbon atoms as substituents and whose alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, and 2-methyl-3-(2,4,6-trimethylphenoxy)propyl groups.

A compound represented by the general formula (I) or a salt thereof is more preferred, wherein $X_1$ represents a nitrogen atom or a group —CH═, $R^1$ represents a group —Z—$R^6$ Z represents a group —N($R^8$)—B—, a group —B—N($R^8$)—, a group —$B_0$—O— or a group —N($R^{9a}$)—CO—N—($R^{9b}$)—, $R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, $B_0$ represents a lower alkylene group, $R^{9a}$ represents a hydrogen atom or a lower alkyl group, $R^{9b}$ represents a hydrogen atom or a lower alkyl group, $R^6$ represents a group

[Formula 43-2]

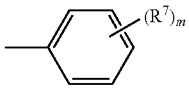

$R^7$ represents a halogen atom or a lower alkyl group that may have a halogen atom as a substituent, m represents an integer of 1 or 2 (when m represents 2, two $R^7$s may be identical or different) and $R^2$ represents a hydrogen atom, a halogen atom, or a lower alkyl group, Y represents a group —O—, or a group —N($R^5$)—, $R^5$ represents a hydrogen atom, or a lower alkyl group, A represents a group

[Formula 43-3]

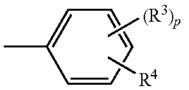

p represents 1 or 2, $R^3$ represents a hydrogen atom, a lower alkoxy group, a halogen atom, or a lower alkyl group that may have a halogen atom as a substituent, $R^9$ represents a group -$(T)_l$-N($R^{14}$)$R^{15}$, T represents a group —N($R^{17}$)—$B_3$—CO—, a group —$B_4$—CO—, or a group —CO—, $R^{17}$ represents a hydrogen atom, or a lower alkyl group, $B_3$ represents a lower alkylene group, $B_4$ represents a lower alkenylene group or a lower alkylene group that may have a hydroxyl group as a substituent, l represents 0 or 1', $R^{14}$ represents a hydrogen atom or an alkyl group that may have a hydroxyl group as a substituent, $R^{15}$ represents (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, $R^{14}$ and $R^{15}$, together with the nitrogen atom to which they bind, form a heterocyclic group which is piperidinyl or piperazinyl group, wherein the heterocyclic ring may be substituted by a group selected from the group consisting of (28) a phenyl-substituted lower alkyl group that may be substituted by a group, on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group (49) a group —($B_{12}$CO)t-N($R^{20}$)$R^{21}$, or (84) a group —(O—$B_{15}$)s-CO—N($R^{26}$)$R^{27}$, $B_{12}$ represents a lower alkylene group, t represents 0 or 1, $R^{20}$ and $R^{21}$, together with the nitrogen atom to which they bind, form a saturated heterocyclic group which is piperidinyl or piperazinyl group that, on the heterocyclic ring, may be substituted by a phenyl lower alkyl group that may have a lower alkylenedioxy group as a substituent on the phenyl ring, $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, (wherein the heterocyclic ring may be substituted by 1 to 3 phenyl lower alkyl groups that may have a lower alkylenedioxy group on the phenyl ring).

For example, a compound represented by the general formula (1) or a salt thereof is further more preferred, wherein $X_1$ represents a nitrogen atom, $R^1$ represents a group —Z—$R^6$, Z represents a group —N($R^8$)—B—, $R^8$ represents a hydrogen atom, or a lower alkyl group that may have a lower alkoxy group as a substituent, B represents a group —CO—, $R^6$ represents a group

[Formula 43-4]

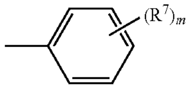

$R^7$ represents a halogen atom or a lower alkyl group that may have a halogen atom as a substituent, m represents an integer of 1 or 2 (when m represents 2, two $R^7$s may be identical or different) and $R^2$ represents a hydrogen atom, Y represents a group —O—, or a group —N($R^5$)—, $R^5$ represents a hydrogen atom, or a lower alkyl group, A represents a group

[Formula 43-5]

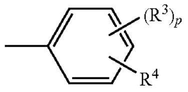

p represents 1 or 2, $R^3$ represents a hydrogen atom, a lower alkoxy group, a halogen atom, or a lower alkyl group that may have a halogen atom as a substituent, $R^4$ represents a group $-(T)_l-N(R^{14})R^{15}$, T represents a group —N($R^{17}$)—$B_3$—CO—, a group —$B_4$—CO—, or a group —CO—, $R^{17}$ represents a hydrogen atom, or a lower alkyl group, $B_3$ represents a lower alkylene group, $B_4$ represents a lower alkylene group that may have a hydroxyl group as a substituent, l represents 0 or 1, $R^{14}$ and $R^{15}$, together with the nitrogen atom to which they bind, form a heterocyclic group which is piperidinyl or piperazinyl group that, on the heterocyclic ring, may be substituted by (28) a phenyl-substituted lower alkyl group that may be substituted by a lower alkylenedioxy group on the phenyl ring.

Another more preferred example is a compound represented by the general formula (1) or a salt thereof, wherein $X_1$ represents a nitrogen atom, $R^1$ represents a group —Z—$R^6$ Z represents a group N($R^8$)—B—, $R^8$ represents a hydrogen atom, or a lower alkyl group that may have a lower alkoxy group as a substituent, B represents a group —CO—, $R^6$ represents a group

[Formula 43-6]

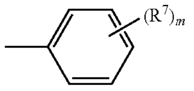

$R^7$ represents a halogen atom or a lower alkyl group that may have a halogen atom as a substituent, m represents an integer of 1 or 2 (when m represents 2, two $R^7$s may be identical or different) and $R^2$ represents a hydrogen atom, Y represents a group —O—, or a group —N($R^5$)—, $R^5$ represents a hydrogen atom, or a lower alkyl group, A represents a group

[Formula 43-7]

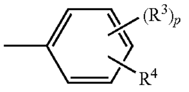

represents 1 or 2, $R^3$ represents a hydrogen atom, a lower alkoxy group, a halogen atom, or a lower alkyl group that may have a halogen atom as a substituent, $R^4$ represents a group $-(T)_l-N(R^{14})R^{15}$, $R^{17}$ represents a hydrogen atom, or a lower alkyl group, $B_3$ represents a lower alkylene group, $B_4$ represents a lower alkylene group that may have a hydroxyl group as a substituent, l represents 0, $R^{14}$ and $R^{15}$, together with the nitrogen atom to which they bind, form a heterocyclic group which is piperidinyl or piperazinyl group wherein, on the heterocyclic ring, one substituent may be present which is selected from the group consisting of (49) a group —($B_{12}$CO)t-N($R^{20}$)$R^{21}$, and (84) a group —(O—$B_{15}$)s-CO—N($R^{26}$)$R^{27}$, $B_{12}$ represents a lower alkylene group, t represents 0 or 1, $R^{20}$ and $R^{21}$, together with the nitrogen atom to which they bind, form a saturated heterocyclic group which is piperazine or piperidine wherein, on the heterocyclic ring, one substituent may be present which is a phenyl lower alkyl group that may have a lower alkylenedioxy group as a substituent on the phenyl ring, $B_{15}$ represents a lower alkylene group, s represents 0 or 1, $R^{26}$ and $R^{27}$, together with the nitrogen atom to which they bind, bind to each other, directly or via an oxygen atom or nitrogen atom to form a 6-membered saturated heterocyclic ring, (wherein the heterocyclic ring may be substituted by 1 to 3 phenyl lower alkyl groups that may have a lower alkylenedioxy group as a substituent on the phenyl ring).

Methods for producing compounds according to the present invention will be described below.

A compound according to the present invention represented by the general formula (1), in which various groups may be used as Y, is produced, for example, in accordance with reaction formulas 1 to 4 below.

[Reaction formula 1]

[Formula 44]

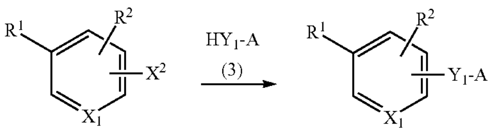

(2) (1a)

wherein, $R^1$, $R^2$, $X_1$ and A are the same as described above, $Y_1$ represents a group —O—, a group —S— or a group —NH—, and $X_2$ represents a halogen atom.

The reaction between the compound (2) and the compound (3) is generally carried out in the presence or absence of an appropriate solvent and in the presence or absence of a basic compound.

Examples of the inert solvent to be used include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethylsulfoxide, N,N-dimethylformamide, N-methylpyrrolidone, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, and sodium n-butoxide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

When the reaction is carried out in the presence of a basic compound, the basic compound is used typically in an equimolar amount to that of the compound (2) and preferably 1 to 10 times that of the compound (2) on a molar basis.

The compound (3) is used typically in at least equimolar amount to that of the compound (2) and preferably 1 to 10 times that of the compound (2) on a molar basis.

The reaction is carried out typically at −30 to 200° C., and preferably at about −30 to 150° C., and generally completed in about 5 minutes to 80 hours.

To this reaction system, an alkali metal halide such as sodium iodide or potassium iodide may be added, and a phase-transfer catalyst may be added.

Examples of the phase-transfer catalyst include quaternary ammonium salts substituted with a group selected from the group consisting of a linear or branched alkyl group having 1 to 18 carbon atoms, a phenyl alkyl group whose alkyl moiety is a linear or branched alkyl group having 1 to 6 carbon atoms and a phenyl group, such as tetrabutylammonium chloride, tetrabutylammonium bromide, tetrabutylammonium fluoride, tetrabutylammonium iodide, tetrabutylammonium hydroxide, tetrabutylammonium hydrogensulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride; phosphonium salts substituted with a linear or branched alkyl group having 1 to 18 carbon atoms such as tetrabutylphosphonium chloride; and pyridinium salts substituted with a linear or branched alkyl group having 1 to 18 carbon atoms such as 1-dodecanylpyridinium chloride. These phase-transfer catalysts are used singly or in a combination of two types or more.

Typically the phase-transfer catalyst is used in an equimolar amount of 0.1 to 1 times that of the compound (2) and preferably 0.1 to 0.5 times that of the compound (2) on a molar basis.

A compound (1a) wherein $Y_1$ represents a group —NH—, may be produced also by reacting a compound (2) with a compound (3) in the presence of an acid in place of a basic compound. Examples of the acid used herein include mineral acids such as hydrochloric acid, sulfuric acid, and hydrobromic acid, and organic acids such as acetic acid, trifluoroacetic acid, and p-toluenesulfonic-acid. These acids are used singly or in a mixture of two types or more.

A compound (1) wherein Y represents a group —N($R^5$)— group, and $R^5$ represents a group other than a hydrogen atom, may be produced from a compound (1) wherein Y represents a group —NH— in accordance with reaction formula 2.

[Reaction formula 2]

[Formula 45]

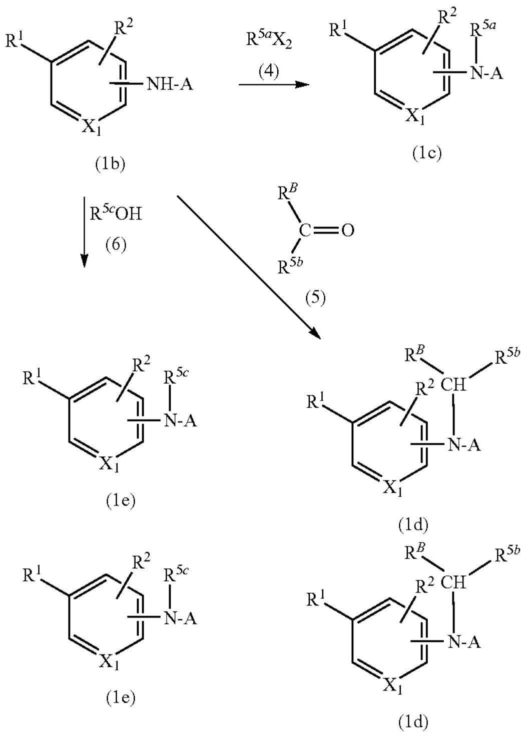

(1b) (1c) (5) (1e) (1d) (1e) (1d)

wherein $R^1$, $R^2$, $X_1$, A and $X_2$ are the same as described above, $R^{5a}$ represents a lower alkyl group, phenyl lower alkyl group or cycloalkyl group, $R^{5b}$ represents a hydrogen atom, lower alkyl group, phenyl group or phenyl lower alkyl group, $R^{5c}$ represents a lower alkanoyl group or benzoyl group, $R^B$ represents a hydrogen atom or lower alkyl group, and $R^{5b}$ and $R^B$ may bind to each other together with carbon atoms bound to these groups to form a cycloalkyl ring, provided that the carbon number of the alkyl moiety in the group —$CHR^BR^{5b}$ of the compound (1d) is 1 to 6.

The reaction of the compound (1b) and the compound (4) is carried out under the same conditions as in the reaction of the compound (2) and the compound (3) shown in reaction formula 1 above.

The reaction of the compound (1b) and the compound (5) is carried out, for example, in the presence of a reducing agent and in the presence or absence of an appropriate solvent. Hereinafter, this method is called "method A".

Examples of the solvent used herein include water, lower alcohols such as, methanol, ethanol, isopropanol, butanol, tert-butanol, and ethylene glycol, acetonitrile, fatty acids such as formic acid, and acetic acid, ethers such as diethyl ether, tetrahydrofuran, dioxane, monoglyme, and diglyme, aromatic hydrocarbons such as benzene, toluene, and xylene, and halogenated hydrocarbons such as dichloromethane, dichloroethane, chloroform, and carbon tetrachloride, and a mixture thereof.

Examples of the reducing agent include fatty acids and alkali metal salts thereof such as formic acid, sodium formate, and sodium acetate, hydride reducing agents such as sodium borohydride, sodium cyanoborohydride, sodium triacetyloxyborohydride, and aluminum lithium hydride, or a mixture of these hydride reducing agents, and catalytic hydrogen reducing agents such as palladium black, palladium-carbon, platinum oxide, platinum black, and Raney nickel.

In using a fatty acid or an alkali metal salt thereof such as formic acid, sodium formate, or sodium acetate as a reducing agent, the appropriate reaction temperature is typically from room temperature to about 200° C., and preferably about 50 to about 150° C. The reaction is completed generally in about 10 minutes to 10 hours. It is preferable to use a fatty acid or an alkali metal salt thereof in a large excess amount with respect to the compound (1b).

In using a hydride reducing agent, the appropriate reaction temperature is typically −80 to 100° C., and preferably −80 to 70° C. The reaction is completed generally in about 30 minutes to 60 hours. The hydride reducing agent is used typically in an equimolar amount 1 to 20 times that of the compound (1b), and preferably 1 to 6 times that of the compound (1b) on a molar basis. Especially in using aluminum lithium hydride as a hydride reducing agent, it is preferable to employ an ether such as diethyl ether, tetrahydrofuran, dioxane, monoglyme, or diglyme, or an aromatic hydrocarbon such as benzene, toluene, or xylene, as a solvent. To the reaction system, an amine such as trimethylamine, triethylamine, and N-ethyldiisopropylamine, or molecular sieves such as Molecular Sieves 3A (MS-3A) or Molecular Sieves 4A (MS-4A) may be added.

In using a catalytic hydrogen reducing agent, the reaction is preferably carried out in a hydrogen atmosphere typically at a normal pressure to about 20 atm, and preferably at a normal pressure to about 10 atm, or in the presence of a hydrogen donor such as formic acid, ammonium formate, cyclohexene, or hydrazine hydrate, at a temperature of typically −30 to 100° C., and preferably 0 to 60° C. The reaction is generally completed in about 1 to 12 hours. The catalytic hydrogen reducing agent is used typically in an amount of about 0.1% to 40% by weight, and preferably about 1 to 20% by weight based on the compound (1b).

In the reaction of the compound (1b) and the compound (5), the compound (5) is used typically in at least an equimolar amount to that of the compound (1b), and preferably in an equal amount to a large excess amount on a molar basis.

The reaction is carried out using a compound (5), whose $R^B$ and $R^{5b}$ (bound to a carbon atom) are mutually bound to form a cycloalkyl ring together with the carbon atom in the presence of a hydride reducing agent, as a starting material. In this case, in place of the compound (5), cycloalkyloxytrialkylsilane such as [(1-ethoxycyclopropyl)oxy]trimethylsilane may be used as the starting material to produce the above described compound (5) in the reaction system.

The compound (1d) may be also produced by reacting the compound (1b) with the compound (5) under the same conditions as in the reaction between the compound (1f) with hydroxylamine of the later described reaction formula 3, and then reducing the resulting compound represented by the general formula:

[Formula 46]

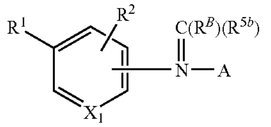

wherein $R^1$, $R^2$, $X_1$, $R^B$ and $R^{5b}$ are the same as described above.

The same reaction conditions as in the method A may be applied to this reducing reaction.

The reaction of the compound (1b) and the compound (6) is carried out by a method for reacting the compound (1b) with the carboxylic acid of the compound (6) in accordance with a general reaction for producing an amide bond. This reaction may be performed by any known reaction for producing an amide bond. Specific examples of the method include: (a) a mixed acid anhydride method, specifically, a method of reacting an alkylhalocarboxylic acid with the carboxylic acid (6) to prepare a mixed acid anhydride, and then reacting the amine (1b) with the mixed acid anhydride; (b) an active ester method, specifically, a method of preparing, from the carboxylic acid (6), an active ester such as a phenyl ester, p-nitrophenyl ester, N-hydroxysuccinimide ester, or 1-hydroxybenzotriazole ester, or an active amide with benzoxazoline-2-thione, and then reacting the active ester or amide with the amine (1b); (c) a carbodiimide method, specifically, a method of condensating the carboxylic acid (6) with the amine (1b) in the presence of an activator such as dicyclohexylcarbodiimide, 1-(3-dimethylaminopropyl)-3-ethylcarbodiimide (WSC), or carbonyldiimidazole; (d) other methods, for example, a method of preparing a carboxylic anhydride from the carboxylic acid (6) by the action of a dehydrator such as acetic anhydride, and then reacting the carboxylic anhydride with the amine (1b), a method of reacting an ester of the carboxylic acid (6) with a lower alcohol with the amine (1b) at a high pressure and a high temperature, and a method of reacting an acid halide of the carboxylic acid (6), that is, carboxylic acid halide, with the amine (1b).

The mixed acid anhydride used in the mixed anhydride method (a) described above, which is obtained by a general Schotten-Baumann reaction, is used as it is without isolation in the reaction with the amine (2) to produce the compound of the present invention represented by the general formula (1e).

The Schotten-Baumann reaction described above is carried out in the presence of a basic compound.

Examples of the basic compound to be used include compounds commonly used in the Schotten-Baumann reaction, for example, organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and inorganic bases including carbonates such as sodium carbonate, potassium carbonate, sodium bicarbonate, and potassium bicarbonate, metal hydroxides such as sodium hydroxide, potassium hydroxide, and calcium hydroxide, potassium hydride, sodium hydride, potassium, sodium, sodium amide, and metal alcoholates such as sodium methylate and sodium ethylate. These basic compounds are used singly or in a combination of two types or more. The reaction is carried out at typically about −20 to 100° C., and preferably about 0 to 50° C. The reaction time is about 5 minutes to 10 hours, and preferably about 5 minutes to 2 hours.

The resulting mixed acid anhydride is reacted with the amine (1b) typically at about −20 to 150° C. and preferably about 10 to 50° C. The reaction time is about 5 minutes to 10 hours and preferably about 5 minutes to 5 hours.

The mixed acid anhydride method is generally carried out in a solvent. Any solvent may be used as long as it is conventionally used in the mixed acid anhydride method. Specific examples of the solvent include halogenated hydrocarbons such as chloroform, dichloromethane, dichloroethane, and carbon tetrachloride, aromatic hydrocarbons such as benzene, toluene and xylene, ethers such as diethyl ether, diisopropyl ether, tetrahydrofuran, and dimethoxyethane, esters such as methyl acetate, ethyl acetate, and isopropyl acetate, and aprotic polar solvents such as N,N-dimethylformamide, dimethylsulfoxide, and hexamethylphosphoric acid triamide, and a mixture thereof.

Examples of the alkylhalocarboxylic acid used in the mixed acid anhydride method include methyl chloroformate, methyl bromoformate, ethyl chloroformate, ethyl bromoformate, and isobutyl chloroformate.

In the mixed acid anhydride method, the carboxylic acid (6), alkylhalocarboxylic acid, and the amine (1b) may be preferably used in equimolar amounts to each other. However, each of alkyl halocarboxylic acid and the carboxylic acid (6) may be used 1 to 1.5 times that of the amine (1b) on a molar basis, respectively.

In the method (c) of performing a condensation reaction in the presence of an activator, the reaction is carried out in an appropriate solvent in the presence or absence of a basic compound. Any of the solvents and basic compounds used in the reaction in the methods (d) of reacting the amine (1b) with a carboxylic acid halide described below may be used for this reaction. It is appropriate to use the activator typically in at least an equimolar amount to that of the compound (1b), and preferably 1 to 5 times that of the compound (1b) on a molar basis. When WSC is used as an activator, the reaction may be carried out advantageously if 1-hydroxybenzotriazole and/or an acid such as hydrochloric acid is added to the reaction system. This reaction is carried out typically at about −20 to 180° C. and preferably at about 0 to 150° C., and completed typically in about 5 minutes to 90 hours.

When a method (d) of reacting the amine (1b) with a carboxylic acid halide is employed, the reaction is carried out in an appropriate solvent in the presence of a basic compound. Any basic compound may be used as long as it is widely known in the art. Any basic compound may be used as long as it is used in, for example, the Shotten-Baumann reaction. Examples of the solvent include, in addition to the solvents used in the mixed acid anhydride method, alcohols such as methanol, ethanol, isopropanol, propanol, butanol, 3-methoxy-1-butanol, ethyl cellosolve, and methyl cellosolve, acetonitrile, pyridine, acetone, and water. The ratio of the amine (1b) to the carboxylic acid halide is not particularly limited and may be appropriately selected in a wide range. Typically, the latter one may be used in an amount at least about equimolar to that of the former one, and preferably about 1 to 5 times that of the former one on a molar basis. This reaction is carried out typically at about −20 to 180° C. and preferably at about 0 to 150° C., and completed typically in 5 minutes to 50 hours.

Further, the reaction for producing an amide bond shown in reaction formula 2 may be carried out also by reacting the carboxylic acid (6) and the amine (1b) in the presence of a condensation agent of a phosphorus compound such as triphenylphosphine, diphenylphosphinyl chloride, phenyl-N-phenylphosphoramide chloridate, diethyl chlorophosphate, diethyl cyanophosphate, diphenylphosphoric acid azide, or bis(2-oxo-3-oxazolidinyl)phosphinic chloride. The condensation agent is used singly or in a mixture of two types or more.

The reaction is carried out, in the presence of the solvent and the basic compound which are used in the method for reacting the amine (1b) with the carboxylic acid halide described above, typically at about −20 to 150° C., and preferably at about 0 to 100° C., and completed typically in 5 minutes to about 30 hours. The condensation agent and the carboxylic acid (6) each may be used approximately in at least an equimolar amount to that of the amine (1b), and preferably about 1 to 2 times that of the amine (1b) on a molar basis.

The compound (1), wherein Y represents a group —CH(OH)— or a group —C(=N—OH), is produced from a compound wherein Y represents a group —CO—, in accordance with reaction formula 3.

[Reaction formula 3]

[Formula 47]

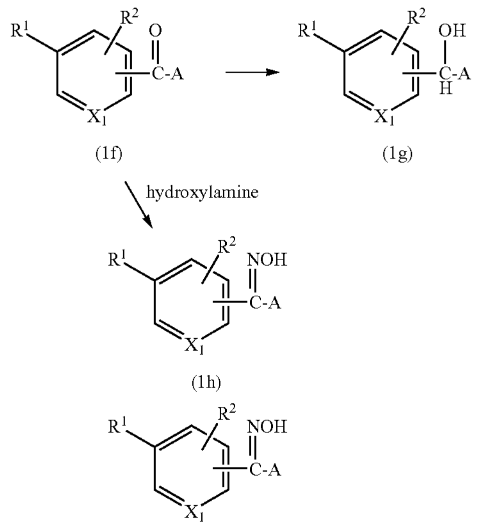

(1f) (1g) (1h) (1h)

wherein $R^1$, $R^2$, $X_1$ and A are the same as described above.

The compound (1g) is produced by reducing the compound (1f).

In the reducing reaction described above, a reducing method employing a hydride reducing agent is favorably used. Examples of the reducing agent to be used include aluminum lithium hydride, sodium borohydride, borane, diborane, and lithium borohydride-trimethoxyborane. These reducing agents are used singly or in a mixture of two types or more. The reducing agent is used typically in at least an equimolar amount to that of the compound (1f), and preferably 1 to 15 times that of the compound (1f) on a molar basis. This reducing reaction is typically carried out in an appropriate solvent, for example, water, a lower alcohol such as methanol, ethanol, or isopropanol, an ether such as tetrahydrofuran, diethyl ether, diisopropyl ether, or diglyme, or a halogenated hydrocarbon such as dichloromethane, chloroform, or carbon tetrachloride, or a mixture thereof, at about −60 to 150° C. preferably about −30 to 100° C. and generally for about 10 minutes to 40 hours. In the case where aluminum lithium hydride or borane is used as the reducing agent, it is preferable to use an anhydrous solvent such as tetrahydrofuran, diethyl ether, diisopropyl ether, or diglyme.

The compound (1h) is produced by reacting the compound (1f) and hydroxylamine in an appropriate inert solvent in the presence or absence of a basic compound.

Examples of the basic compound used herein include inorganic basic compounds such as sodium hydroxide, potassium hydroxide, calcium hydroxide, sodium carbonate, and potassium carbonate, fatty acid alkali metal salts such as sodium acetate, organic bases such as piperidine, piperidinium acetate, triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO). These basic compounds may be used singly or in a mixture of two types or more.

Any inert solvent may be used as long as it does not negatively affect the reaction. Examples of the inert solvent include water, aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethyl sulfoxide, N,N-dimethylformamide, and hexamethyl phosphate triamide, and a mixture thereof.

Hydroxylamine is used typically in at least an equimolar amount to that of the compound (1f), and preferably 1 to 5 times that of the compound (1f) on a molar basis. The reaction temperature is typically at room temperature to 200° C. and preferably about 50 to 150° C. The reaction is generally completed in about 5 minutes to 30 hours.

The compound (1), wherein Y represents a group —S(O)n- (n=1 or 2), is produced from a compound wherein Y represents a group —S—, in accordance with reaction formula 4.

[Reaction formula 4]

[Formula 48]

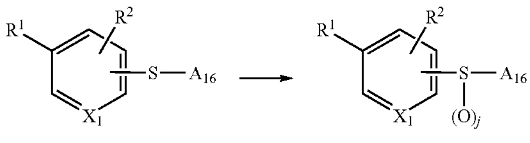

(1zzzz) (1aaaaa)

wherein $R^1$, $R^2$, $X_1$ and A are the same as described above, $A_{16}$ represents a group -A or a group $-A_{10}-T_2-COOR^{59a}$, $T_2$ represents a group $—N(R^{17})—B_3—$, a group $—B^{19}—N(R^{18})—$, a group $—B_4—$, a group $-Q-B_5—$, a group $—B_6—N—(R^{19})—B_7—$, a group $—CO—B_{10}—$, a group $—CH(OH)—B_{11}—$, a group $—B_{23a}—CO—$ group, or a direct bond, wherein $R^{17}$, $B_3$, $B_{19}$, $R^{18}$, $B_4$, $B_5$, $B_6$, $R^{19}$, $B_7$, $B_{10}$ and $B_{11}$ are the same as described above, $A^{10}$ represents

[Formula 49]

group 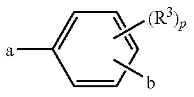 or group 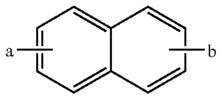

wherein $R^3$ and p are the same as described above, provided that a is bound to a group —S or a group —S(O)j, and b is bound to group $-T_2$, $R^{59a}$ is a hydrogen atom or a lower alkyl group, and j is 1 or 2.

The reaction for converting the compound (1zzzz) into the compound (1aaaaa) is carried out in an appropriate solvent in the presence of an oxidizing agent.

Examples of the solvent include water, fatty acids such as formic acid, acetic acid, and trifluoroacetic acid, alcohols such as methanol and ethanol, and halogenated hydrocarbons such as chloroform and dichloromethane, and a mixture thereof.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperidodate, dichromic acid, dichromates such as sodium dichromate and potassium dichromate, permanganic acid, permanganates such as sodium permanganate and potassium permanganate, and lead salts such as lead tetraacetate. These oxidizing agents are used singly or in a mixture of two types or more.

The oxidizing agent is appropriately used typically in at least an equimolar amount to that of the compound (1zzzz), and preferably 1 to 2 times that of the compound (1zzzz) on a molar basis. In the oxidizing reaction which converts a sulfur atom into a sulfonyl group (j=2), the oxidizing agent is preferably used typically in an amount at least two times that of the compound (1zzzz) and preferably 2 to 4 times that of the compound (1zzzz) on a molar basis.

The reaction is carried out at typically −10 to 150° C., and preferably about −10 to 100° C. and generally completed in about 1 to 100 hours.

The compound of the present invention represented by the general formula (1) wherein various groups may be used as A, is produced, for example, in accordance with the following reaction formulas 5 to 36.

The compound (1), wherein A represents:

[Formula 50]

group 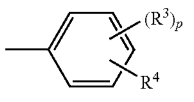 or group 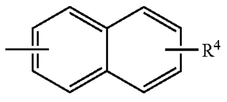

wherein $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group which may have an oxo group as a substituent on the pyrimidine ring, a 1,2,4-oxadiazolyl lower alkyl group which may have an lower alkyl group as a substituent on the 1,2,4-oxadiazole ring, a thiazolidinyl lower alkyl group which may have an oxo group as a substituent on the thiazolidine ring, or a group $-(T)_l-NR^{14}R^{15}$, (T is a lower alkylene group and l is 1) is produced by reacting the compound (7) with the compound (8) as shown in reaction formula 5.

[Reaction formula 5]

[Formula 51]

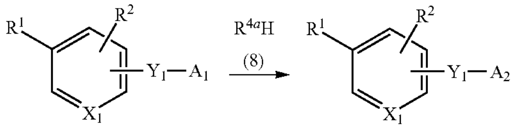

(7) (1i)

wherein $R^1$, $R^2$ $Y_1$ and $X_1$ are the same as described above, $A_1$ represents

[Formula 52]

group 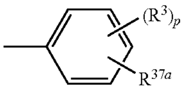 or group 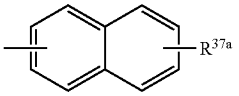

wherein $R^3$ and p are the same as described above, $R^{37a}$ represents a group —$B_{21}$—$X_2$, $B_{21}$ represents a lower alkylene group, and $X_2$ is the same as described above, and $A_2$ represents

[Formula 53]

group 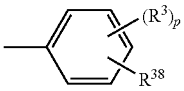 or group 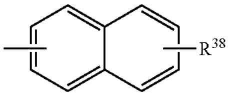

wherein $R^3$ and p are the same as described above, $R^{38}$ represents a group —$B_{21}$—$R^{4a}$, $B_{21}$ is the same as described above, $R^{4a}$ represents an imidazolyl group, a 1,2,4-triazolyl group, a 1,2,3-triazolyl group, a 1,2,5-triazolyl group, a pyrazolyl group, a pyrimidynyl group which has an oxo group as a substituent on the pyrimidine ring, a 1,2,4-oxadiazolyl group which may have a lower alkyl group as a substituent on the 1,2,4-oxadiazole ring, a thiazolidinyl group which may have an oxo group as a substituent on the thiazolidine ring, or an —$NR^{14}R^{15}$ group, and $R^{14}$ and $R^{15}$ are the same as described above:

The reaction of the compound (7) with the compound (8) is carried out under the same conditions as in the reaction between the compound (2) and the compound (3) in accordance with reaction formula 1.

The compound (1), wherein A represents

[Formula 54]

group 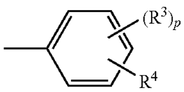 or group 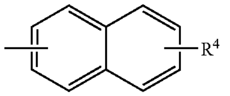

wherein $R^4$ is an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group which has an oxo group as a substituent on the pyrimidine ring, a 1,2,4-oxadiazolyl lower alkyl group which may have a lower alkyl group as a substituent on the 1,2,4-oxadiazole ring, a thiazolidinyl lower alkyl group which may have an oxo group as a substituent on the thiazolidine ring, or a group $-(T)_l-NR^{14}R^{15}$ (T is a lower alkylene group and l is 1)

is also produced by reacting the compound (8) with the compound (9) in accordance with reaction formula 6.

[Reaction formula 6]

[Formula 55]

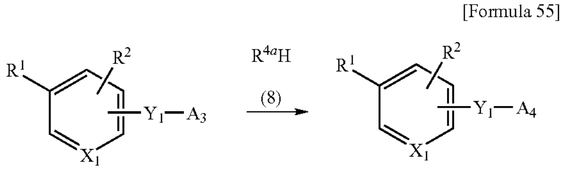

(9) (1j)

wherein $R^1$, $R^2$, $X_1$ and $Y_1$, and $R^{4a}$ are the same as described above, $A_3$ represents

[Formula 56]

group 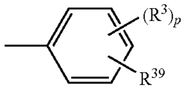 or group 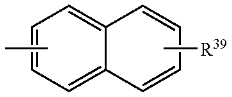

wherein $R^3$ and p are the same as described above, $R^{39}$ represents a —$(B_{21})_f COR^4$ group, $B_{21}$ is the same as described above, $R^4$ represents a hydrogen atom or a lower alkyl group, and f represents 0 or 1, and $A_4$ represents

[Formula 57]

group 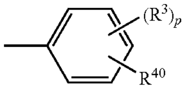 or group

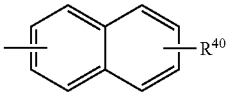

wherein $R^3$ and p are the same as described above, $R^{40}$ represents a group —$(B_{21})_f CHR^4R^{4a}$, and $B_{21}$, $R^4$, f and $R^{4a}$ are the same as described above, provided that the alkyl moiety of the group —$(B_{21})_f CHR^4R^{4a}$ has not more than 6 carbon atoms.

The reaction of the compound (9) with the compound (8) is carried out under the same conditions as in the reaction between the compound (1b) and the compound (5) of reaction formula 2.

The compound (1), wherein A represents

[Formula 58]

group 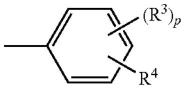 or group

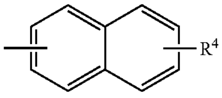

wherein $R^4$ represents a 3,5-dioxoisooxazolidinyl lower alkylidene group which may have an oxo group as a substituent on the 3,5-dioxoisooxazolidine ring, is produced by reacting the compound (11) with the compound (10) in accordance with reaction formula 7.

[Reaction formula 7]

[Formula 59]

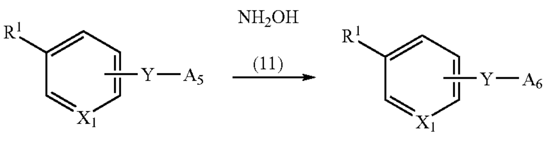

(10) (1k)

wherein $R^1$, $R^2$, $X_1$ and Y are the same as described above, and $A^5$ represents

[Formula 60]

group 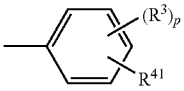 or group

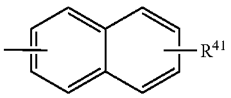

wherein $R^3$ and p are the same as described above, $R^{41}$ represents a group —$B_{22}$ ($CO_2R^{43}$)($CO_2R^{44}$), $B_{22}$ represents a lower alkylidene group, and $R^{43}$ and $R^{44}$ each represent a lower alkyl group, and $A^6$ represents

[Formula 61]

group 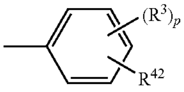 or group

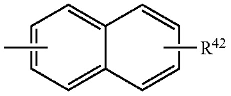

wherein $R^3$ and p are the same as described above, and $R^{42}$ is a group represented by

[Formula 62]

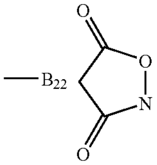

wherein $B_{22}$ is the same as described above.

The reaction of the compound (10) with the compound (11) is carried out under the same condition as in the reaction for converting the compound (1f) into the compound (1h) in accordance with reaction formula 3.

The compound (1), wherein A represents

[Formula 63]

group 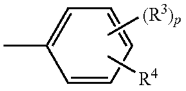 or group

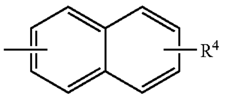

wherein $R^4$ represents

[Formula 64]

group 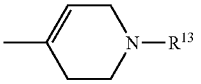 or group

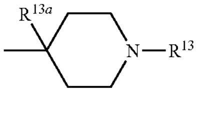

is produced from the compound (13), as shown in reaction formula 8.

[Reaction formula 8]

[Formula 65]

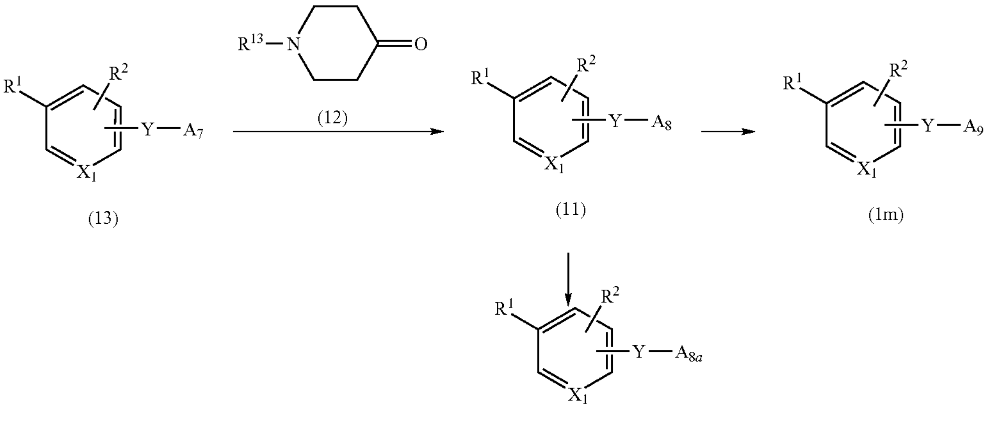

(13) (11) (1m)

(11')

wherein $R^1$, $R^2$, $X_1$, Y and $R^{13}$ are the same as described above, $A_7$ represents

[Formula 66]

group 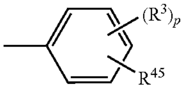 or group 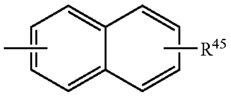

wherein $R^3$ and p are the same as described above, and $R^{45}$ represents a halogen atom, $A_8$ represents

[Formula 67]

group 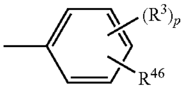 or group 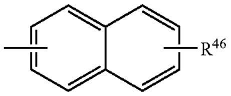

wherein $R^3$ and p are the same as described above, and $R^{46}$ represents

[Formula 68]

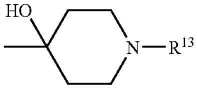

wherein $R^{13}$ is the same as described above, $A_9$ represents:

[Formula 69]

group 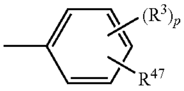 or group 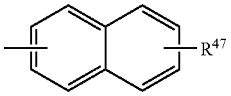

wherein $R^3$ and p are the same as described above, and $R^{47}$ represents a group

[Formula 70]

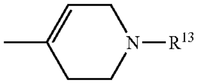

wherein $R^{13}$ is the same as described above, and $A_{8a}$ represents

[Formula 71]

group 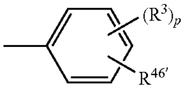 or group 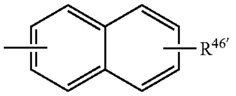

wherein $R^3$ and p are the same as described above, and $R^{46}$ represents a group

[Formula 72]

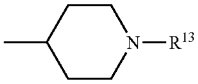

wherein $R^{13}$ is the same as described above.

The reaction of the compound (13) with the compound (12) is carried out in an appropriate inert solvent in the presence of a basic compound.

Examples of the basic compound used herein include such as metal sodium, metal potassium, metal magnesium, sodium hydride, sodium amide, metal alcoholates such as sodium methylate, sodium ethylate, and potassium tert-butoxide, and alkyl and aryl lithiums or lithium amides such as methyl lithium, n-butyl lithium, phenyl lithium, and lithium diisopropylamide. These basic compounds are used singly or in a mixture of two types or more.

The basic compound is appropriately used typically in at least an equimolar amount to that of the compound (13), and preferably 1 to 5 times that of the compound (13) on a molar basis.

Examples of the inert solvent to be used include aromatic hydrocarbons such as benzene, toluene, and xylene, ethers such as diethyl ether, tetrahydrofuran, dioxane, monoglyme, and diglyme, aliphatic hydrocarbons such as n-hexane, heptane, and cyclohexane, halogenated hydrocarbons such as chloroform, dichloromethane, dichloroethane, and carbon tetrachloride, dimethylsulfoxide, and N,N-dimethylformamide, and a mixture thereof.

The reaction is carried out typically at about −90 to 150° C. and preferably at about −90 to 120° C., and completed generally in about 10 minutes to 10 hours.

The compound (12) is appropriately used typically in at least an equimolar amount to that of the compound (13) and preferably 1 to 5 times that of the compound (13) on a molar basis.

The reaction for converting the compound (1l) into the compound (1m) is carried out in an appropriate inert solvent and in the presence of an acid.

Examples of the acid used herein include mineral acids such as hydrochloric acid, sulfuric acid, and hydrobromic acid, and organic acids such as sulfonic acids including p-toluenesulfonic acid. These acids are used singly or in a mixture of two types or more.

The acid is preferably used typically in at least an equimolar amount to that of the compound (1l) and preferably in an equal amount to a large excess amount with respect to the compound (1l) on a molar basis.

Any solvent may be used in this reaction as long as it is used in the reaction between the compound (13) and the compound (12).

This reaction is carried out typically at room temperature to 200° C., preferably at room temperature to about 150° C., and completed generally in about 1 to 20 hours.

The reaction for converting the compound (11) into the compound (11') is carried out in an appropriate solvent and in the presence of an acid and a catalyst.

Examples of the solvent used herein include water, lower alcohols such as methanol, ethanol, and isopropanol, ketones such as acetone and methyl ethyl ketone, halogenated hydrocarbons such as dichloromethane, dichloroethane, chloroform, and carbon tetrachloride, ethers such as diethyl ether, dimethoxyethane, tetrahydrofuran, diisopropyl ether, diglyme, and 1,4-dioxane, aromatic hydrocarbons such as benzene, toluene, and xylene, acetonitrile, dimethyl sulfoxide, N,N-dimethylacetamide, N,N-dimethylformamide, and N-methylpyrrolidone, and a mixture thereof.

Examples of the acid used herein include inorganic acids such as hydrochloric acid, sulfuric acid, and hydrobromic acid, and organic acids such as boron trifluoride diethyl etherate, formic acid, acetic acid, trifluoroacetic acid, and p-toluenesulfonic acid.

Examples of the catalyst include alkylsilane compounds such as triethylsilane.

The acid and the catalyst described above each are used typically in an amount about 0.01 to 5 times that of the compound (11), and preferably about 0.01 to 1 times to that of the compound (11) on a molar basis.

The reaction is carried out at about room temperature to 200° C., and preferably about room temperature to 150° C., and completed generally in about 1 to 10 hours.

The reaction which converts the compound (11) into the compound (11') may be carried out in an appropriate solvent and in the presence of a catalytic hydrogen reducing agent.

Examples of the solvent to be used include water, fatty acids such as acetic acid, alcohols such as methanol, ethanol, and isopropanol, aliphatic hydrocarbons such as n-hexane, alicyclic hydrocarbons such as cyclohexane, ethers such as diethyl ether, dimethoxyethane, tetrahydrofuran, monoglyme, diglyme, and 1,4-dioxane, esters such as methyl acetate, ethyl acetate, and butyl acetate, and aprotic polar solvents such as N,N-dimethylformamide, N,N-dimethylacetamide, N-methylpyrrolidone, and a mixture thereof.

Examples of the catalytic hydrogen reducing agent include palladium, palladium-black, palladium-carbon, palladium hydroxide-carbon, rhodium-alumina, platinum, platinum oxide, copper chromite, Raney nickel, and palladium acetate.

The catalytic hydrogen reducing agent is used typically in an amount of 0.01 to 1 times that of the compound (11) on a weight basis.

The reaction favorably proceeds typically at about −20 to 100° C. and preferably at about 0 to 80° C., and completed generally in about 0.5 to 20 hours. The hydrogen pressure is typically at 1 to 10 atm.

It is preferable to add a mineral acid such as hydrochloric acid to this reaction system.

The compound (1), wherein A represents

[Formula 73]

group

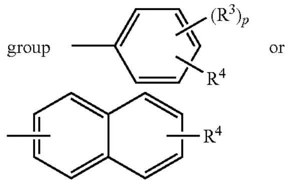

or group wherein $R^4$ represents

[Formula 74]

group

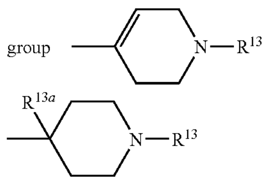

or group wherein $R^{13}$ represents a group other than a hydrogen atom, is produced from a compound wherein $R^{13}$ is a hydrogen atom, in accordance with the following reaction formula 9.

[Reaction formula 9]

[Formula 75]

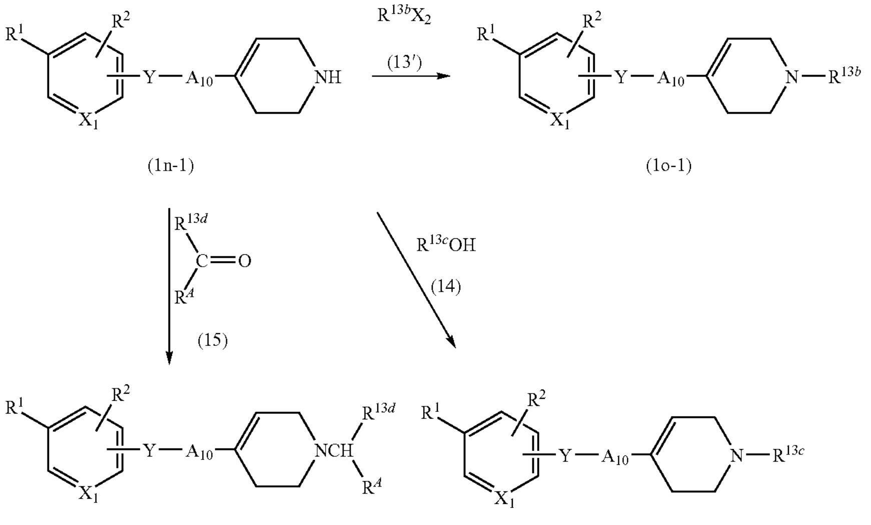

(1n-1) (1o-1)

(1q-1) (1p-1)

-continued

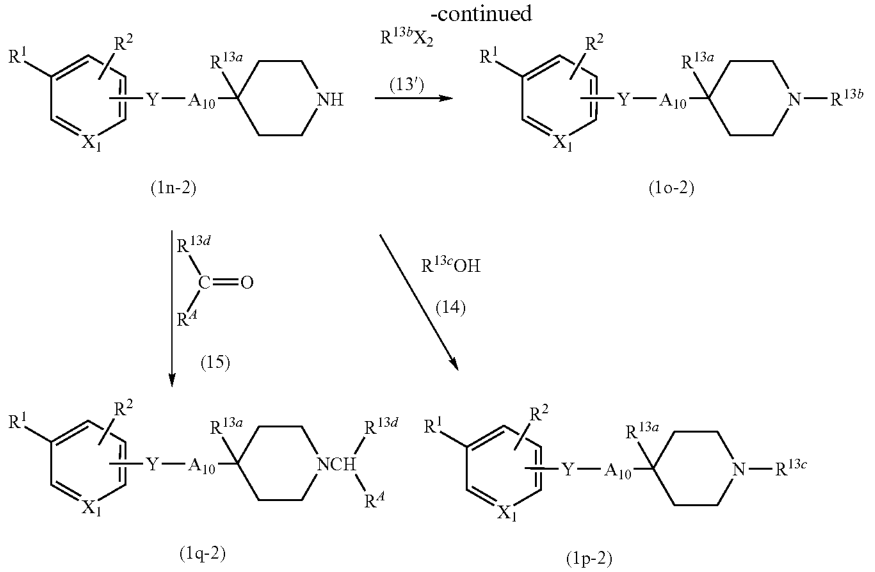

(1n-2) (1o-2) (1q-2) (1p-2)

wherein $R^1$, $R^2$, $X_1$, Y, $A_{10}$, $R^A$, $R^{13a}$ and $X_2$ are the same as described above, provided that a and b of $A_{10}$ are bound to Y and a piperidinyl group, respectively, $R^{13b}$ represents a lower alkyl group which may have a halogen atom as a substituent, a phenyl lower alkyl group which may have a lower alkylenedioxy group as a substituent on the phenyl ring, an imidazolyl lower alkyl group, a lower alkoxycarbonyl lower alkyl group, a carboxy lower alkyl group, a piperazinylcarbonyl lower alkyl group which may be substituted, on the piperazine ring, with a phenyl lower alkyl group which may have a lower alkylenedioxy group as a substituent on the phenyl ring, or a morpholinocarbonyl substituted lower alkyl group, $R^{13c}$ represents a lower alkanoyl group which may have a halogen atom as a substituent, a lower alkoxy carbonyl group, a benzoyl group, a morpholino substituted lower alkanoyl group, a piperazinyl lower alkanoyl group which may be substituted, on the piperazine ring, with a phenyl lower alkyl group which may have a lower alkylenedioxy group as a substituent on the phenyl ring; or an imidazolyl lower alkanoyl group, and $R^{13d}$ represents a hydrogen atom, a lower alkyl group which may have a halogen atom as a substituent, a phenyl lower alkyl group which may have a lower alkylenedioxy group as a substituent on the phenyl ring, a phenyl group which may have a lower alkylenedioxy group as a substituent on the phenyl ring, an imidazolyl group, an imidazolyl lower alkyl group, a lower alkoxycarbonyl lower alkyl group, a carboxy lower alkyl group, a piperazinylcarbonyl lower alkyl group which may be substituted, on the piperazine ring, with a phenyl lower alkyl group which may have a lower alkylenedioxy group as a substituent on the phenyl ring, or a morpholinocarbonyl substituted lower alkyl group, provided that the alkyl moiety of the side chain (group —$CHR^AR^{13d}$) of the compound (1q) has not more than 6 carbon atoms.

The reaction of the compound (1n-1) with the compound (13') is carried out under the same conditions as in the reaction between the compound (1b) and the compound (4) in accordance with reaction formula 2.

The reaction between the compound (1n-1) and the compound (14) is carried out under the same conditions as in the reaction between the compound (1b) and the compound (6) in accordance with reaction formula 2.

The reaction between the compound (1n-1) and the compound (15) is carried out under the same conditions as in the reaction between the compound (1b) and the compound (5) of reaction formula 2.

Also, the reaction between the compound (1n-2) and the compound (13') is carried out under the same conditions as in the reaction between the compound (1b) and the compound (4) in accordance with reaction formula 2, the reaction between the compound (1n-2) and the compound (14) is carried out under the same conditions as in the reaction between the compound (1b) and the compound (6) in accordance with reaction formula 2, and the reaction between the compound (1n-2) and the compound (15) is carried out under the same conditions as in the reaction between the compound (1b) and the compound (5) in accordance with reaction formula 2.

In reaction formula 9, the hydrolysis of the compounds (1o-1) and (1o-2) wherein $R^{13b}$ represents a lower alkoxycarbonyl lower alkyl group may produce the corresponding compounds (1o-1) and (1o-2) wherein $R^{13b}$ represents a carboxy lower alkyl group.

In reaction formula 9, the hydrolysis of compounds (1p-1) and (1p-2), wherein $R^{13c}$ represents a lower alkoxycarbonyl group, may produce the corresponding compounds (1p-1) and (1p-2), wherein $R^{13c}$ is a hydrogen atom.

The hydrolysis reaction (hereinafter, this hydrolysis reaction will be called "hydrolysis B") may be carried out in the presence or absence of an appropriate solvent and in the presence of an acidic or basic compound.

Examples of the solvent to be used herein include water, lower alcohols such as methanol, ethanol, isopropanol, and tert-butanol, ketones such as acetone and methyl ethyl ketone, ethers such as diethyl ether, dioxane, tetrahydrofuran, monoglyme, and diglyme, fatty acids such as acetic acid and formic acid, esters such as methyl acetate and ethyl acetate, halogenated hydrocarbons such as chloroform, dichloromethane, dichloroethane, and carbon tetrachloride, dimethylsulfoxide, N,N-dimethylformamide, and hexamethylphosphoric acid triamide, and a mixture thereof.

Examples of the acid include mineral acids such as hydrochloric acid, sulfuric acid, and hydrobromic acid, organic acids such as formic acid, acetic acid, trifluoroacetic acid, sulfonic acids including p-toluenesulfonic acid, and Lewis acids such as boron tribromide and boron trichloride. These acids are used singly or in a mixture of two types or more.

Examples of the basic compound include carbonates such as sodium carbonate, potassium carbonate, sodium bicarbonate, and potassium bicarbonate, and metal hydroxides such as sodium hydroxide, potassium hydroxide, calcium hydroxide, and lithium hydroxide. These basic compounds are used singly or in a mixture of two types or more.

The hydrolysis reaction favorably proceeds typically at about 0 to about 200° C. and preferably at about 0 to 150° C., and is completed generally in about 10 minutes to 50 hours.

The compound (1) wherein A represents

[Formula 76]

group 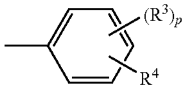 or group 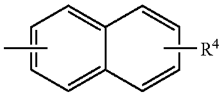

wherein $R^4$ represents

[Formula 77]

group 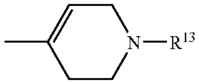 or group 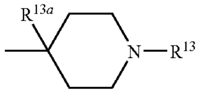

wherein $R^{13}$ represents an imidazolyl lower alkyl group, is produced as shown in reaction formula 10 below.

[Reaction formula 10]

[Formula 78]

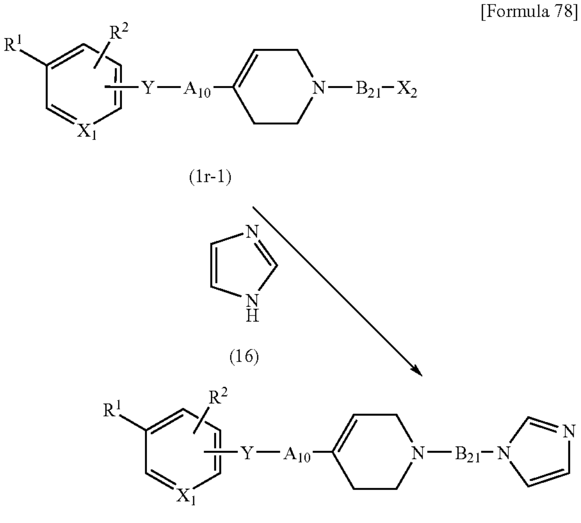

(1r-1)

(16)

(1s-1)

-continued

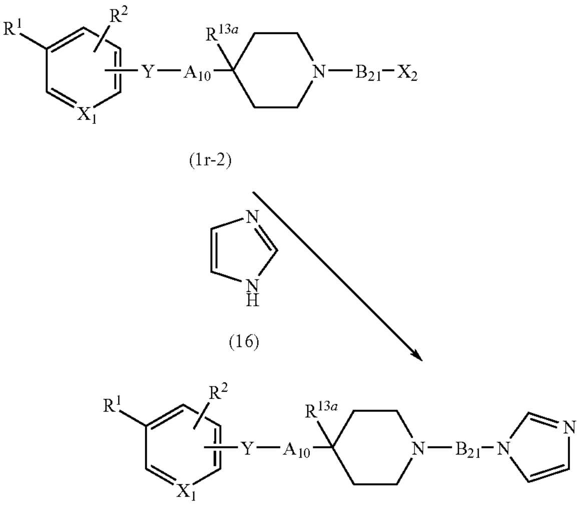

(1r-2)

(16)

(1s-2)

wherein $R^1$, $R^2$, $X_1$, Y, $A_{10}$, $R^{13a}$, $B_2$, and $X_2$ are the same as described above, provided that a and b of $A_{10}$ are bound to Y and a piperidinyl group, respectively.

The reaction of the compound (1r-1) and the compound (16) and the reaction of the compound (1r-2) and the compound (16) are carried out under the same conditions as in the reaction of the compound (2) and the compound (3) shown in reaction formula 1 above.

The compound (1) wherein A represents

[Formula 79]

group 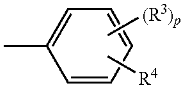 or group 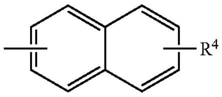

wherein $R^4$ represents

[Formula 80]

group 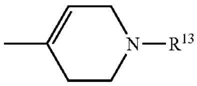 or group 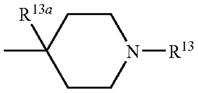

wherein $R^{13}$ represents a morpholino substituted lower alkanoyl group, a piperazinyl lower alkanoyl group which may be substituted on the piperazine ring with a phenyl lower alkyl group which may have a lower alkylenedioxy group as a substituent on the phenyl ring, or an imidazolyl lower alkanoyl group, may be produced from the corresponding compound, wherein $R^{13}$ represents a lower alkanoyl group which may have a halogen atom as a substituent, as shown in reaction formula 11 below.

[Reaction formula 11]

[Formula 81]

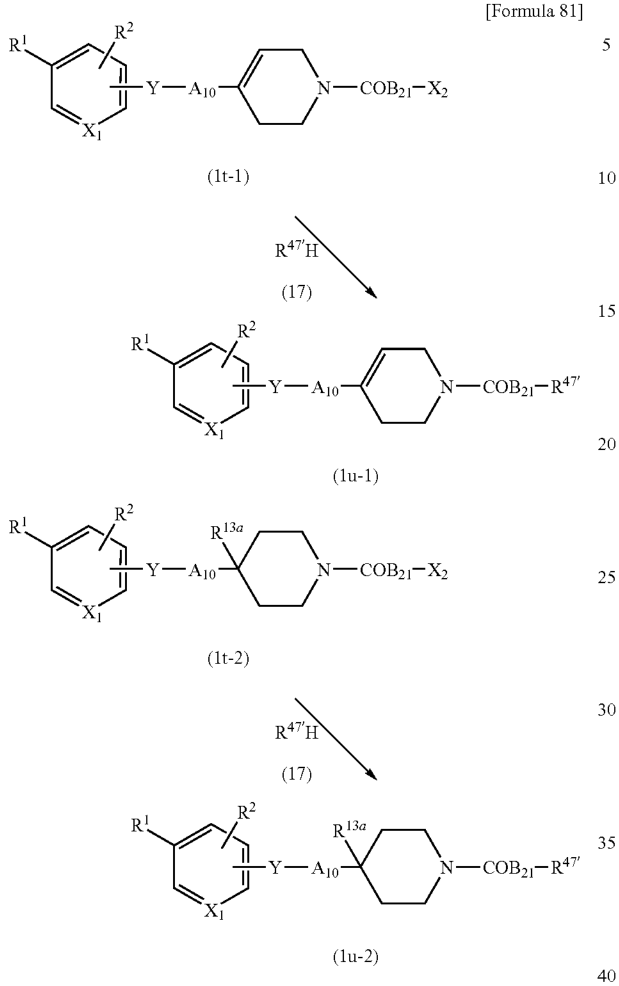

(1t-1)

(1u-1)

(1t-2)

(1u-2)

wherein $R^1$, $R^2$, $X_1$, Y, $R^{13a}$, $B_{21}$ and $X_2$ are the same as described above, and $R^{47'}$ is a morpholino group, a piperazinyl group which may be substituted, on the piperazine ring, with a phenyl lower alkyl group which may have a lower alkylenedioxy group as a substituent on the phenyl ring, or an imidazolyl group, provided that a and b of $A_{10}$ are bound to Y and a piperidinyl group, respectively.

The reaction of the compound (1t-1) and the compound (17) and the reaction of the compound (1t-2) and the compound (17) are carried out under the same conditions as in the reaction of the compound (2) and the compound (3) shown in reaction formula 1 above.

The compound (1) wherein A represents

[Formula 82]

group 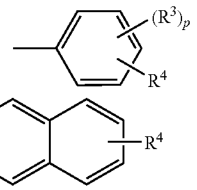 or group wherein $R^4$ represents

[Formula 83]

group 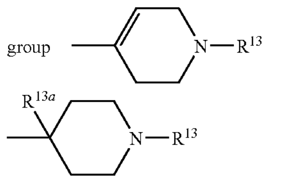 or group wherein $R^{13}$ represents a piperazinylcarbonyl lower alkyl group which is substituted, on the piperazine ring, with a phenyl lower alkyl group which may have a lower alkylenedioxy group as a substituent on the phenyl ring, or a morpholinocarbonyl substituted lower alkyl group, is produced from the corresponding compound wherein $R^{13}$ is a carboxy group, as shown in reaction formula 12 below.

[Reaction formula 12]

[Formula 84]

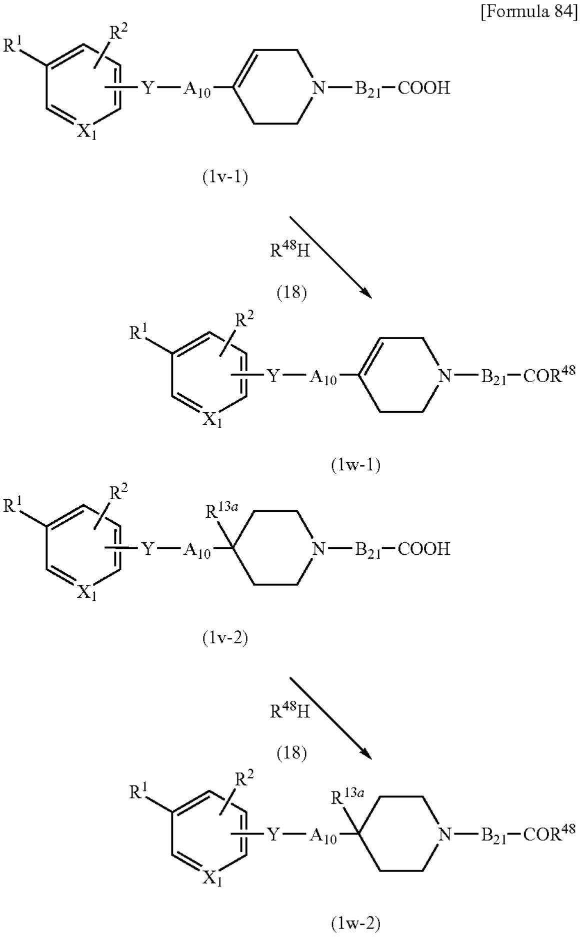

(1v-1)

(1w-1)

(1v-2)

(1w-2)

wherein $R^1$, $R^2$, $X_1$, Y, $A_{10}$, $R^{13a}$ and $B_{21}$ are the same as described above, $R^{48}$ is a piperazinyl group which may be substituted, on the piperazine ring, with a phenyl lower alkyl group which may have a lower alkylenedioxy group as a substituent on the phenyl ring, or a morpholino group, provided that a and b of $A_{10}$ are bound to Y and a piperidinyl group, respectively.

The reaction of the compound (1v-1) and the compound (18) and the reaction of the compound (1v-2) and the compound (18) are carried out under the same conditions as in the reaction of the compound (1b) and the compound (6) shown in reaction formula above.

The compound (1) wherein A represents

[Formula 85]

group 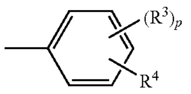 or group

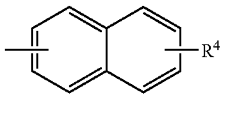

wherein $R^4$ represents a group $-(T)_l-NR^{14}R^{15}$, is produced as shown in reaction formulas 13 and 14 below.

[Reaction formula 13]

[Formula 86]

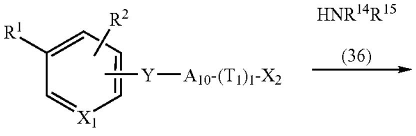

(35)

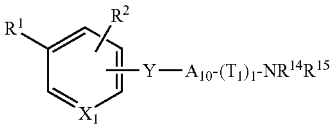

(1pp)

wherein $R^1$, $R^2$, $X_1$, Y, $A_{10}$, $X_2$, l, $R^{14}$ and $R^{15}$ are the same as described above, $T_1$ is a lower alkylene group, a group $—COB_8—$, a group $—SO_2—$ or a group $—CH(OH)—B_9—$, and $B_8$ and $B_9$ are the same as described above, provided that, in the compounds (35) and (1pp), a and b of $A_{10}$ are bound to Y and $-(T_l)_l$, respectively.

The reaction of the compound (35) and the compound (36) is carried out under the same reaction conditions as in the reaction of the compound (2) and the compound (3) shown in reaction formula 1 above.

The compound (35) wherein l is 0 may also be produced by reacting the corresponding compound (35) with the compound (36) in an appropriate solvent in the presence of a basic compound and a catalyst.

Any solvent and basic compound may be used as long as they are used in the reaction of the compound (2) and the compound (3) shown in reaction formula 1 above.

Examples of the catalyst include various metal complexes as well as various combinations of a metal complex with a ligand. Examples of the metal complex include palladium acetate (II), tetrakis(triphenylphosphine)palladium(0), and tris(dibenzylideneacetone)dipalladium(0). Examples of the ligand include R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), t-butylphosphine, and 4,5-bis(diphenylphosphino)-9,9-dimethylxanthene.

The catalyst is appropriately used typically in at least an equimolar amount to the compound (35) and preferably 1 to 5 times that of the compound (35) on a molar basis.

This reaction is carried out typically at about 0 to 200° C. and preferably at about 0 to 150° C., and completed generally in about 1 to 60 hours. This reaction will be hereinafter called "reaction C".

[Reaction formula 14]

[Formula 87]

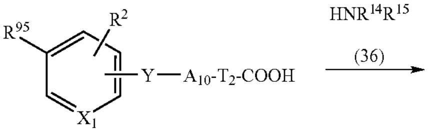

(37)

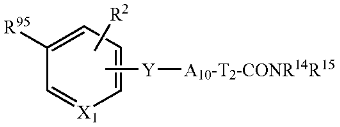

(1qq)

wherein $R^2$, $X_1$, Y, $A_{10}$, $T_2$, $R^{14}$ and $R^{15}$ are the same as described above, provided that, in the compounds (37) and (1qq), a and b of $A_{10}$ are bound to Y and $T_2$, respectively, and $R^{95}$ represents a group $R^1$ or a halogen atom. The $R^1$ used herein is the same as described above.

The reaction of the compound (37) and the compound (36) is carried out in the same reaction conditions as in the reaction of the compound (1b) and the compound (6) shown in reaction formula 2 above.

The compound (1) wherein A represents

[Formula 88]

group 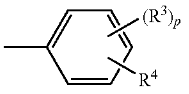 or group

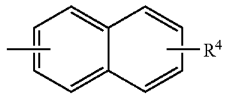

wherein $R^4$ represents a group $-(T)_l-NR^{14}R^{15}$, and l represents 0, may also be produced by the method shown in reaction formula 15.

[Reaction formula 15]

[Formula 89]

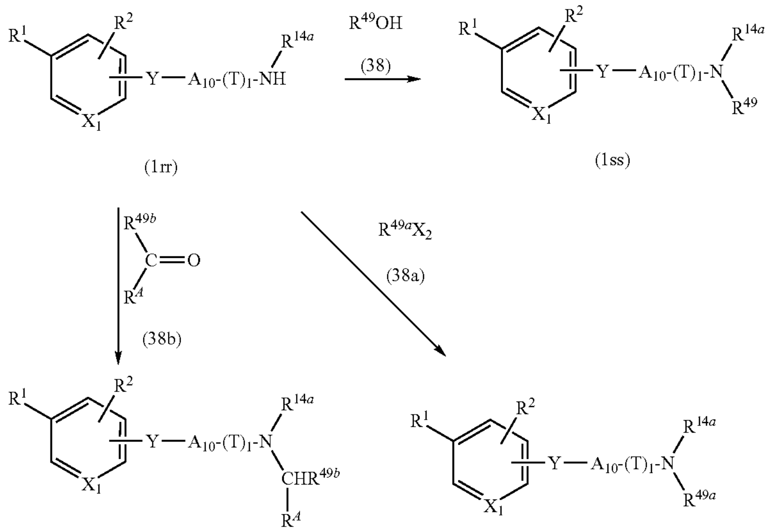

(1rr) (1ss) (1ss″) (1ss′)

wherein $R^1$, $R^2$, $X_1$, Y, $R^A$, $X_2$, T, l and $A_{10}$ are the same as described above, $R^{49}$ is the same group as $R^{15}$ defined in (15), (22), (23), (27) and (36a), $R^{49a}$ is $R^{15}$ defined in (2) to (5), (7), (8), (10), (11), (13), (14), (16) to (21), (24), (25), (26), (26a), (27a), (28a), (29a), (30a), (31a), (32a), (33a), (34a), (35a), or (37a), a phenoxycarbonyl group and a lower alkylsulfonyl group, $R^{49b}$ represents a hydrogen atom, an alkyl group which may have a hydroxyl group as a substituent, a phenoxy lower alkyl group, a phenyl lower alkyl group which may have, on the phenyl ring, with 1 to 3 substituents selected from the group consisting of a halogen atom, a lower alkoxy group which may have a halogen atom as a substituent, and a lower alkyl group, a phenyl group which may have, on the phenyl ring, with 1 to 3 substituents selected from the group consisting of a halogen atom, a lower alkoxy group which may have a halogen atom as a substituent, and a lower alkyl group, a phenyl lower alkyl group which may have a lower alkylenedioxy group as a substituent on the phenyl ring, a phenyl group which may have a lower alkylenedioxy group on the phenyl ring, a lower alkoxycarbonyl substituted lower alkyl group, a carboxy substituted lower alkyl group, a cycloalkyl lower alkyl group, a cycloalkyl group, a pyridyl lower alkyl group, a pyridyl group, an amino group substituted lower alkyl group which may have a substituent selected from the group consisting of a lower alkyl group and a lower alkanoyl group, a lower alkoxy lower alkyl group, an imidazolyl group, an imidazolyl lower alkyl group, a 1,2,3,4-tetrahydroisoquinolylcarbonyl substituted lower alkyl group, an A group-substituted carbonyl lower alkyl group, a pyrrolidinyl group, a pyrrolidinyl lower alkyl group, a morpholino group, a morpholino lower alkyl group, an anilinocarbonyl lower alkyl group which may have a lower alkyl group as a substituent on the phenyl ring, a piperazinyl group which may have, on the piperazine ring, a substituent selected from the group consisting of a lower alkyl group and a phenyl lower alkyl group which may have a lower alkylenedioxy group as a substituent on the phenyl ring, a piperazinyl lower alkyl group which may have, on the piperazine ring, a substituent selected from the group consisting of a lower alkyl group and a phenyl lower alkyl group which may have a lower alkylenedioxy group as a substituent on the phenyl ring, an amidino group which may have a lower alkyl group as a substituent, an amidino lower alkyl group which may have a lower alkyl group as a substituent, a B group substituted carbonyl lower alkyl group, or a cyano substituted lower alkyl group, $R^{14a}$ represents a hydrogen atom or a lower alkyl group which may have a hydroxyl group as a substituent, and $R^{34}$, d, $R^{36}$, $R^{37}$ and $B_{20}$ are the same as described above, provided that, in the compounds (1rr), (1ss), (1ss') and (1ss"), a and b of $A_{10}$ are bound to Y and N, respectively, and, in the compound (1ss"), the $CHR^AR^{49b}$ moiety of the side chain (—Y-$A_{10}$N($R^{14a}$)($CHR^AR^{49b}$) has not more than 6 carbon atoms.

The reaction of the compound (1rr) and the compound (38a) is carried out under the same conditions as in the reaction of the compound (1b) and the compound (4) shown in reaction formula 2 above.

The reaction of the compound (1rr) with the compound (38) is carried out under the same conditions as in the reaction of the compound (1b) and the compound (6) shown in reaction formula 2 above.

The reaction of the compound (1rr) with the compound (38b) is carried out under the condition similar to that of the reaction of the compound (1b) and the compound (5) shown in reaction formula 2 above.

The compound (1) wherein A represents

[Formula 90]

group 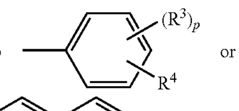 or group 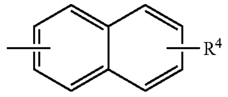

wherein $R^4$ represents a group -$(T)_l$-$NR^{14}R^{15}$, l represents 1, and T represents a group —CH(OH)—$B_9$—, may also be produced by the method shown in reaction formula 16 below.

[Reaction formula 16]

[Formula 91]

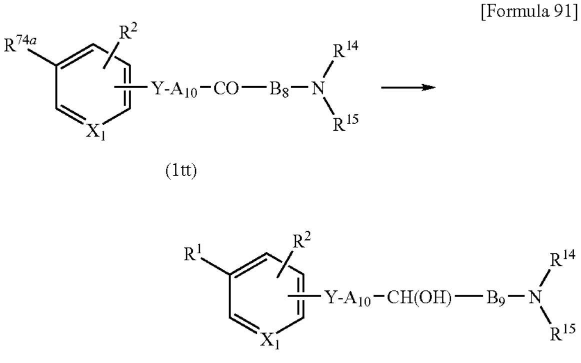

(1tt)

(1uu)

wherein $R^1$, $R^2$, $X_1$, $A_{10}$, Y, $B_8$, $B_9$, $R^{14}$ and $R^{15}$ are the same as described above, provided that, in the compounds (1tt) and (1uu), a and b of $A_{10}$ are bound to Y and $B_8$ or $B_9$, respectively.

The reaction which converts the compound (1tt) into the compound (1uu) is carried out under the same condition as in the reaction which converts the compound (1f) into the compound (1g) shown in reaction formula 3 above.

The compound (1) wherein A represents

[Formula 92]

group 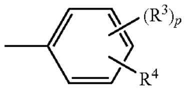 or group

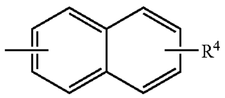

wherein $R^4$ represents a group -$(T)_l$-$NR^{14}R^{15}$, l represents 1, and T represents a group —CH(OH)—$B_{11}$, —CO—, may also be produced by the method shown in reaction formula 17 below.

[Reaction formula 17]

[Formula 93]

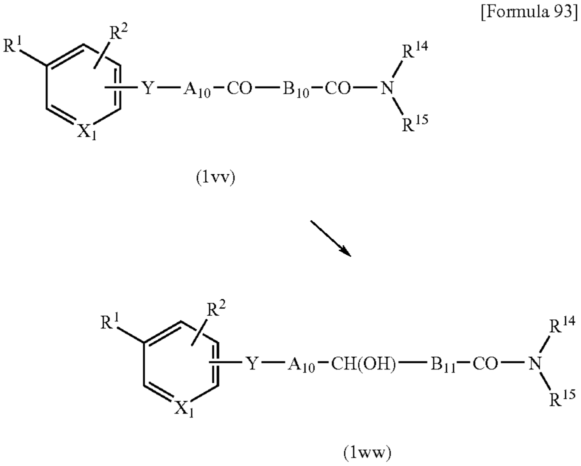

(1vv)

(1ww)

wherein $R^1$, $R^2$, $X_1$, $A_{10}$, Y, $B_{10}$, $B_{11}$, $R^{14}$ and $R^{15}$ are the same as described above, provided that, in the compounds (1vv) and (1ww), a and b of $A_{10}$ are bound to Y and a group —$COB_{10}$ or —$CH(OH)B_{11}$—, respectively.

The reaction which converts the compound (1vv) into the compound (1ww) is carried out under the same conditions as in the reaction which converts the compound (1f) into the compound (1g) shown in reaction formula 3 above.

The compound (1) wherein A represents

[Formula 94]

group 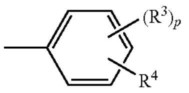 or group

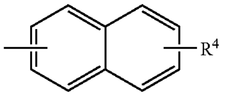

wherein $R^4$ is a group -$(T)_1NR^{14}R^{15}$, and $R^{14}$ and $R^{15}$ are bound with each other to form a 5- to 10-membered saturated or unsaturated heterocyclic group which has various substituents thereon, may be produced as shown in reaction formulas 18 to 20, 22, 24 to 31, and 34 to 36 below.

[Reaction formula 18]

[Formula 95]

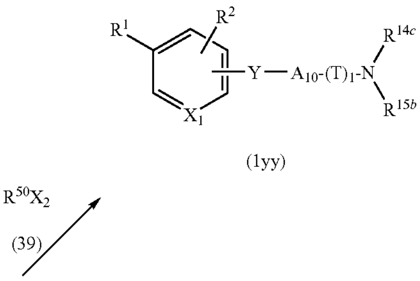

(1yy)

$R^{50}X_2$ (39)

-continued

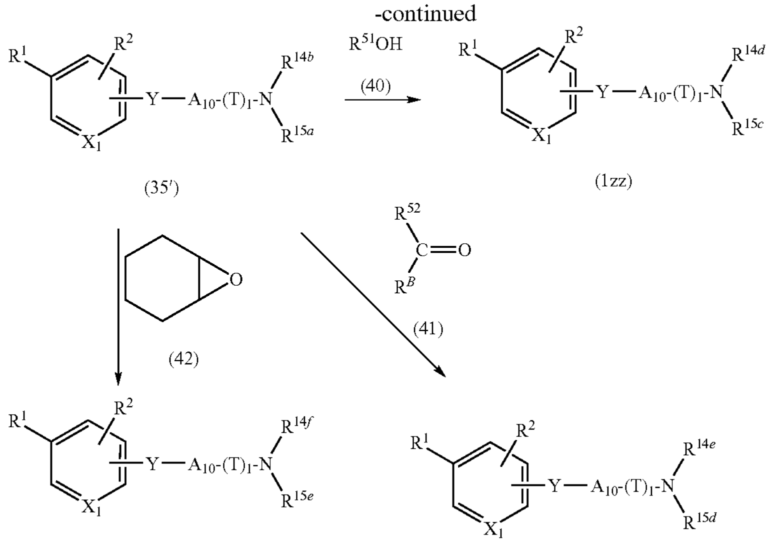

(35') (1zz) (1bbb) (1aaa)

wherein $R^1$, $R^2$, $R^B$, $X_1$, Y, T, l, $A_{10}$ and $X_2$ are the same as described above, provided that a and b of $A_{10}$ are bound to a group Y and a group (T)l, respectively;

$R^{14b}$ and $R^{15a}$ represent the same 5- to 10-membered saturated or unsaturated heterocyclic groups as defined in $R^{14}$ and $R^{15}$ above, respectively, except that each of the heterocyclic groups has at least one secondary amine thereon;

$R^{14c}$ and $R^{15b}$ represent the same 5- to 10-membered saturated or unsaturated heterocyclic groups as defined in $R^{14}$ and $R^{15}$ above respectively, except that each of the heterocyclic groups has at least one tertiary amine substituted with $R^{50}$ thereon;

$R^{14d}$ and $R^{15c}$ represent the same 5- to 10-membered saturated or unsaturated heterocyclic group defined in $R^{14}$ and $R^{15}$ above, respectively, except that each of the heterocyclic groups has at least one tertiary amine substituted with $R^{51}$ thereon;

$R^{14e}$ and $R^{15d}$ represent the same 5- to 10-membered saturated or unsaturated heterocyclic groups as defined in $R^{14}$ and $R^{15}$ above, respectively, except that each of the heterocyclic groups has at least one tertiary amine substituted with a $R^{52}$ ($R^B$)CH— group thereon;

$R^{14f}$ and $R^{15e}$ represent the same 5- to 10-membered saturated or unsaturated heterocyclic groups as defined in $R^{14}$ and $R^{15}$ above, respectively, except that each of the heterocyclic groups has at least one tertiary amine thereon substituted with a group

[Formula 96]

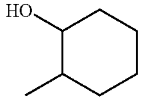

wherein $R^{50}$ is the same substituent for the heterocyclic ring, which is formed by binding $R^{14}$ and $R^{15}$ to each other, as (28), (30), (31), (32), (33), (34), (36), (37), (38), (41), (43), (44), (45), (47), (49) (provided that t is 1), (50) (provided that o is 0), (51), (52), (53), (54), (55), (56), (57), (58), (59), (60), (62), (63), (64), (65), (66), (70), (77), (79), (82), (83), (87), (88a), or (90a) described above;

$R^{51}$ is the same substituent for the heterocyclic group, which is formed by binding $R^{14}$ and $R^{15}$ to each other, as (35), (39), (40), (42), (50) (provided that o is 1), (67), (75), (76), (77), (78), (80), (81) or (84) (provided that s is 0) described above;

$R^{52}$ is a hydrogen atom, a lower alkyl group which has 1 or 2 phenyls which may have, on the phenyl ring, 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy group, (the lower alkyl group optionally having a pyridyl group on the lower alkyl group), a phenyl group which may have, on the phenyl ring 1 to 3 substituents selected from the group consisting of a lower alkanoyl group, an amino group which have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxy group, and a lower alkylenedioxy group, a pyridyl lower alkyl group which may have, on the pyridine ring, 1 to 3 substituents selected from the group consisting of a hydroxyl group and a lower alkyl group which may have a hydroxyl group as a substituent, a pyridyl group which may have, on the pyridine ring, 1 to 3 substituents selected from the group consisting of a hydroxyl group and a lower alkyl group which may have a hydroxyl group as a substituent, a pyrrolyl lower alkyl group which may have 1 to 3 lower alkyl groups as substituents on the pyrrole ring, a pyrrolyl group which may have 1 to 3 lower alkyl groups as substituents on the pyrrole ring, a benzoxazolyl lower alkyl group, a benzoxazolyl group, a benzothiazolyl lower alkyl group, a benzothiazolyl group, a furyl lower alkyl group, a furyl group, a lower alkyl group which may have a substituent selected from the group consisting of a hydroxyl group and a halogen atom, a naphthyl lower alkyl group, a naphthyl group, a phenoxy lower alkyl group, a group —$B_{12}CO$—$NR^{20}R^{21}$; a group —$B_{13}NR^{22}R^{23}$ group, a group 1,2,3,4-tetrahydronaphthyl substituted lower alkyl group which may have 1 to 5 lower alkyl groups as substituents on the 1,2,3,4-tetrahydronaphthalene ring, a 1,2,3,4-tetrahydronaphthyl group which may have 1 to 5 lower alkyl groups as substituents on the 1,2,3,4-tetrahydronaphthalene ring, a quinolyl lower alkyl group, a quinolyl group, a 1,2,3,4-tetrazolyl lower alkyl group which may have, on the tetrazole ring, a substituent selected from the group consisting of a lower alkyl group and a phenyl lower alkyl group, a 1,2,3,4-tetrazolyl group which may have, on the tetrazole ring, a substituent selected from the group consisting of a lower alkyl group and a phenyl lower alkyl group, a thiazolyl lower alkyl group which may have a phenyl group as a substituent on the thiazole ring, a thiazolyl group which may have a phenyl group as a substituent on the thiazole ring, a benzoyl lower alkyl group which may have, on the phenyl ring, 1 to 3 substituents selected from the group consisting of a lower alkoxy group and a halogen atom, a piperidinyl lower alkyl group which may have a lower alkyl group as a substituent on the piperidine ring, a benzoyl lower alkyl group which may have, on the phenyl ring, 1 to 3 substituents selected from the group consisting of a lower alkoxy group and a halogen atom, a piperidinyl group which may have a lower alkyl group on the piperidine ring, a 1,2,3,4-tetrahydroquinolyl lower alkyl group which may have an oxo group as a substituent on the tetrahydroquinoline ring, a 1,2,3,4-tetrahydroquinolyl group which may have an oxo group as a substituent on the tetrahydroquinoline ring, a 1,3,4-oxadiazolyl lower alkyl group which may have an oxo group as a substituent on the 1,3,4-oxadiazole ring, a 1,3,4-oxadiazolyl group which may have an oxo group as a substituent on the 1,3,4-oxadiazole ring, a cycloalkyl lower alkyl group, a cycloalkyl group, a thienyl lower alkyl group, a thienyl group, a lower alkoxy lower alkyl group, a carboxy lower alkyl group, a lower alkoxycarbonyl lower alkyl group, an imidazolyl lower alkyl group, or an imidazolyl group; and $R^B$ and $R^{52}$, together with carbon atoms to which they bind, may form a cycloalkyl group or a tetrahydro-4H-pyranyl group;

provided that the alkyl moiety of the $R^{52}(R^B)CH$— group in the compound (1aaa) has not more than six carbon atoms.

The reaction of the compound (35') and the compound (39) is carried out under the same conditions as in the reaction of the compound (1b) with the compound (4) shown in reaction formula 2 above.

The reaction of the compound (35') and the compound (40) is carried out under the same conditions as in the reaction of the compound (1b) and the compound (6) shown in reaction formula 2 above.

The reaction of the compound (35') and the compound (41) is carried out under the same conditions as in the reaction of the compound (1b) and the compound (5) shown in reaction formula 2 above.

The reaction is carried out using a compound (41), whose $R^B$ and $R^{52}$ (bound to a carbon atom) are mutually bound to form a cycloalkyl ring or a tetrahydro-4H-pyran ring together with the carbon atom in the presence of a hydride reducing agent, as a starting material. In this case, in place of the compound (41), cycloalkyloxytrialkylsilane such as [(1-ethoxycyclopropyl)oxy]trimethylsilane may be used as the starting material (to produce the above described compound (41) in the reaction system).

The reaction of the compound (35') and the compound (42) is carried out under the same conditions as in the reaction of the compound (2) and the compound (3) shown in reaction formula 1 above.

The compound (35') may also be produced from the compound (1yy), (1zz) or (1aaa) under the same reaction conditions as in the reaction which converts the compound (1iii') into the compound (1hhh') shown in reaction formula 24 below.

[Reaction formula 19]

[Formula 97]

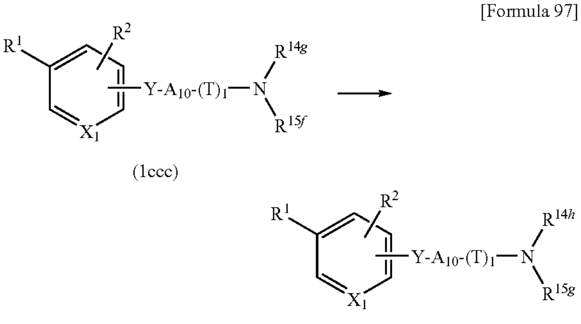

(1ccc)

(1ddd)

wherein $R^1$, $R^2$, $X_1$, Y, T, l, $A_{10}$ and $X_2$ are the same as described above, provided that a and b of $A_{10}$ are bound to Y and (T)l, respectively;

$R^{14g}$ and $R^{15f}$ are the same 5- to 10-membered saturated or unsaturated heterocyclic groups as defined in $R^{14}$ and $R^{15}$ above, respectively, except that each of the heterocyclic groups has at least one tertiary amine substituted with a lower alkoxycarbonyl group thereon; and $R^{14h}$ and $R^{15g}$ are the same 5- to 10-membered saturated or unsaturated heterocyclic groups as defined in $R^{14}$ and $R^{15}$ above, respectively, except that each of the heterocyclic groups has at least one secondary amine thereon.

The reaction which converts the compound (1ccc) into the compound (1ddd) may be carried out under the same reaction conditions as in hydrolysis B as described in reaction formula 9 above.

[Reaction formula 20]

[Formula 98]

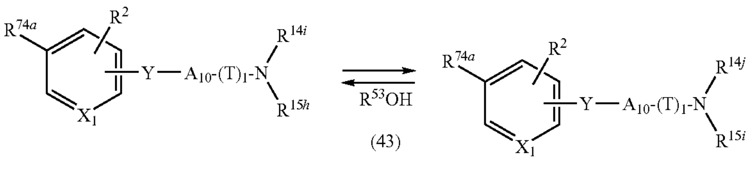

(1eee)

(1fff)

wherein $R^1$, $R^2$, $X_1$, Y, T, l and $A_{10}$ are the same as described above, provided that a and b of $A_{10}$ are bound to a group Y and a group (T)l, respectively, $R^{74a}$ represents a nitro group or a group —$R^1$, and;

$R^{14i}$ and $R^{15i}$ are the same 5- to 10-membered saturated or unsaturated heterocyclic groups as defined in $R^{14}$ and $R^{15}$ above, respectively, except that each of the heterocyclic groups has at least one lower alkoxycarbonyl lower alkoxy group, lower alkoxycarbonyl group, lower alkoxycarbonyl lower alkyl group, or a group —$(B_{12}CO)t$-$N(R^{20a})R^{51'}$ thereon;

$R^{14j}$ and $R^{15i}$ are the same 5- to 10-membered saturated or unsaturated heterocyclic groups as defined in $R^{14}$ and $R^{15}$ above, respectively, except that each of the heterocyclic groups has at least one carboxy lower alkoxy group, carboxy group, carboxy lower alkyl group, or a group —$(B_{12}CO)t$-$N(R^{20a})R^{52'}$ group thereon;

$B_{12}$ and t are the same as described above;

$R^{20a}$ represents a hydrogen atom, a cycloalkyl group, an amino group which may have a lower alkoxycarbonyl group as a substituent, a benzoyl group which may have 1 to 3 alkoxy groups as substituents on the phenyl ring, a lower alkyl group, a lower alkyl group which may have, on the phenyl ring, substituents selected from the group consisting of an lower alkoxycarbonyl group, a cyano group, a nitro group, a phenyl group, and a halogen atom, a lower alkyl group which may have a halogen atom as a substituent, a lower alkoxy group which may have a halogen atom as a substituent, and a lower alkylthio group, a phenyl group which may have, on the phenyl ring, 1 to 3 substituents selected from the group consisting of a lower alkoxy group which may have a halogen atom as a substituent and a lower alkyl group which may have a halogen atom as a substituent, a lower alkoxycarbonyl group, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a phenyl lower alkanoyl group, a lower alkanoyl group which may have a halogen atom as a substituent, an imidazolyl lower alkanoyl group, a lower alkoxycarbonyl lower alkyl group, a pyridyl group, or a carboxy lower alkyl group;

$R^{51'}$ is a lower alkdxycarbonyl group or a lower alkoxycarbonyl lower alkyl group;

$R^{52}$ is a hydrogen atom or a carboxy lower alkyl group; and $R^{53}$ is a lower alkyl group.

The reaction which converts the compound (1eee) into the compound (1fff) may be carried out under the same reaction conditions as described in hydrolysis B as described in reaction formula 9 above.

The reaction of the compound (1fff) and the compound (43) may be carried out under any conditions of a typical esterification reaction. For example, the reaction is carried out in the presence of a mineral acid such as hydrochloric acid or sulfuric acid, and a halogenating agent such as thionylchloride, phosphorus oxychloride, phosphorus pentachloride, or phosphorus trichloride. The compound (43) is used in a large excess amount of that of the compound (1fff). The reaction favorably proceeds typically at about 0 to 150° C. and preferably at about 50 to 100° C., and is completed generally in about 1 to 10 hours.

The esterification reaction may be carried out using a condensation agent such as carbodiimide in the presence of a basic compound such as dimethylaminopyridine. Typical reaction conditions for producing an amide bond, which are used in the reaction of the compound (1b) and the compound (6) shown in reaction formula 2, may also be used.

The reaction of the compound (1fff) and compound (43) is carried out in the presence of the same basic compound and the solvent as those used in the reaction of the compound (2) and the compound (3) of reaction formula 1. The reaction is carried out typically at about 0 to 100° C. and preferably at about 0 to 70° C., and completed generally in about 1 to 30 hours.

The compound (1eee) may also be produced using a halogenated lower alkyl such as methyl iodide in place of the compound (43) under the same conditions as in the reaction of the compound (2) and the compound (3) shown in reaction formula 1.

[Reaction formula 21]

[Formula 99]

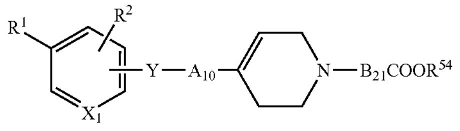

(1ggg-1)

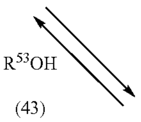

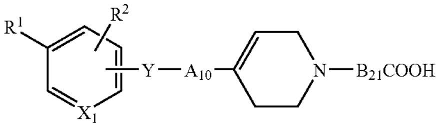

(1v-1)

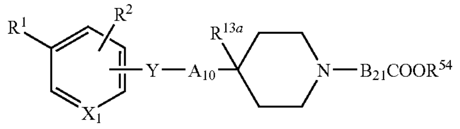

(1ggg-2)

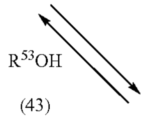

-continued

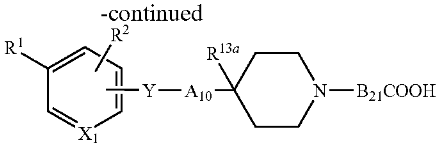

(1v-2)

wherein $R^1$, $R^2$, $X_1$, Y, $A_{10}$, $R^{13a}$, $B_{21}$ and $R^{53}$ are the same as described above, and $R^{54}$ is a lower alkyl group, provided that a and b of $A_{10}$ are bound to a group Y and a piperidinyl group, respectively.

The reaction which converts the compound (1ggg-1) into the compound (1v-1) and the reaction which converts the compound (1ggg-2) into the compound (1v-2) is carried out under the same reaction conditions as in hydrolysis B as described in reaction formula 9.

The reaction of the compound (1v-1) and the compound (43) and the reaction of the compound (1v-2) and the compound (43) are carried out under the same reaction conditions as in the reaction of the compound (1fff) and the compound (43) shown in reaction formula above.

The compound (1ggg-1) may also be produced using a halogenated lower alkyl such as methyl iodide in place of the compound (43) under the same conditions as in the reaction of the compound (2) and the compound (3) shown in reaction formula 1 above.

Similarly, the compound (1ggg-2) may also be produced using a halogenated lower alkyl such as methyl iodide in place of the compound (43) under the same conditions as in the reaction of the compound (2) and the compound (3) shown in reaction formula 1 above.

[Reaction formula 22]

[Formula 100]

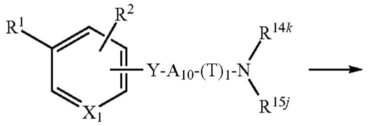

(1hhh)

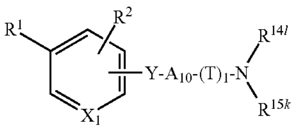

(1iii)

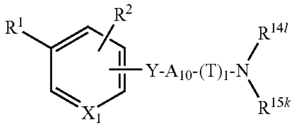

(1iii)

wherein $R^1$, $R^2$, $X_1$, Y, T, l and $A_{10}$ are the same as described above, provided that a and b of $A_{10}$ are bound to a group Y and a group (T)l, respectively;

$R^{14k}$ and $R^{15j}$ are the same 5- to 10-membered saturated or unsaturated heterocyclic groups as defined in $R^{14}$ and $R^{15}$ above, respectively, except that each of the heterocyclic groups has at least one group $—B_{21}CONHNH_2$ (wherein $B_{21}$ is the same as described above) thereon; and $R^{14l}$ and $R^{15k}$ are the same 5- to 10-membered saturated or unsaturated heterocyclic groups as defined in $R^{14}$ and $R^{15}$ above, respectively, except that each of the heterocyclic groups has at least one group

[Formula 101]

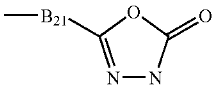

thereon.

The reaction which converts the compound (1hhh) into compound (1iii) is carried out under the same conditions as in the reaction of the compound (1b) and the compound (6) shown in reaction formula 2 above.

[Reaction formula 23]

[Formula 102]

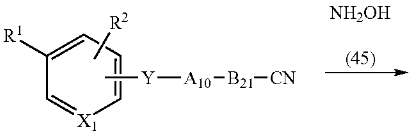

(44)

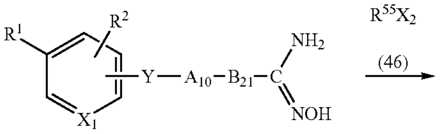

(44a)

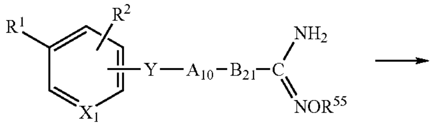

(47)

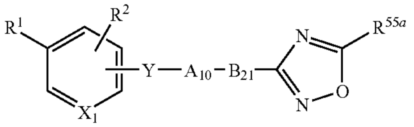

(1rrr)

wherein $R^1$, $R^2$, $X_1$, Y, $A_{10}$, $B_{21}$ and $X_2$ are the same as described above, provided that a and b of $A_{10}$ are bound to a group Y and a group (T)l, respectively, $R^{55}$ is a lower alkanoyl group, and $R^{55a}$ is a lower alkyl group.

The reaction of the compound (44) and the compound (45) is carried out under the same conditions as in the reaction which converts the compound (1f) into the compound (1h) shown in reaction formula 3 above.

The reaction of the compound (44a) and the compound (46) is carried out under the same conditions as in the reaction of the compound (2) and the compound (3) shown in reaction formula 1 above.

The reaction which converts the compound (47) into the compound (1rrr) is carried out under the same conditions as in the reaction which converts the compound (1f) into the compound (1h) shown in reaction formula 3 above.

[Reaction formula 24]

[Formula 103]

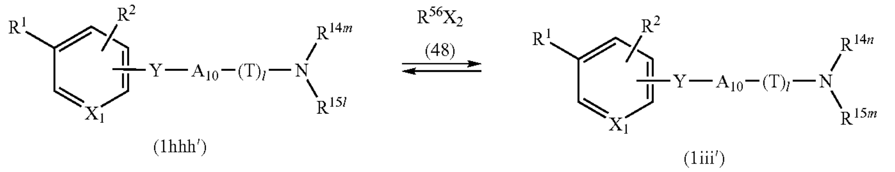

(1hhh') (1iii')

wherein $R^1$, $R^2$, $X_1$, Y, T, l, $A_{10}$ and $X_2$ are the same as described above, provided that a and b of $A_{10}$ are bound to a group Y and a group (T)l, respectively;

$R^{14m}$ and $R^{15l}$ are the same 5- to 10-membered saturated or unsaturated heterocyclic groups as defined in $R^{14}$ and $R^{15}$ above, respectively, except that each of the heterocyclic groups has at least one hydroxyl group or hydroxyl group substituted lower alkyl group thereon;

$R^{14n}$ and $R^{15m}$ are the same 5- to 10-membered saturated or unsaturated heterocyclic groups as defined in $R^{14}$ and $R^{15}$ above, respectively, except that each of the heterocyclic groups has at least one group —$OR^{56}$ thereon;

$R^{56}$ represents a phenyl group which have, on the phenyl ring, with 1 to 3 substituents selected from the group consisting of a cyano group, a lower alkyl group which may have a halogen atom as a substituent, and a lower alkoxy group which may have a halogen atom as a substituent, a phenyl lower alkyl group which may have, on the phenyl ring, with 1 to 3 substituents selected from the group consisting of a halogen atom, a lower alkyl group which may have a halogen atom as a substituent, and a lower alkoxy group which may have a halogen atom as a substituent, a pyridyl lower alkyl group, a lower alkyl group, a lower alkoxy lower alkyl group, a benzoyl group, a lower alkoxycarbonyl lower alkyl, a carboxy lower alkyl group; or a group —$B_{15}$—CO—$NR^{26}R^{27}$ group (wherein $B_{15}$, $R^{26}$ and $R^{27}$ are the same as described above), provided that, the $R^{56}$ of the compound (48), which reacts with the heterocyclic group substituted with at least one hydroxyl group substituted lower alkyl group of the compound (1hhh'), is an unsubstituted phenyl group or a lower alkyl group.

The reaction of the compound (1hhh') and the compound (48) is carried out under the same conditions as in the reaction of the compound (2) and the compound (3) shown in reaction formula 1 above.

The reaction which converts the compound (1iii') into the compound (1hhh') is carried out under the same conditions as in hydrolysis B as described in reaction formula 9 above.

The compound (1iii') may be converted into the compound (1hhh') by a reduction reaction. This reduction reaction is, for example, carried out in an appropriate solvent in the presence of a catalytic hydrogen reducing agent.

Examples of the solvent include water, fatty acids such as acetic acid, alcohols such as methanol, ethanol, and isopropanol, aliphatic hydrocarbons such as hexane and cyclohexane, ethers such as dioxane, tetrahydrofuran, diethyl ether, monoglyme, and diglyme, esters such as ethyl acetate and methyl acetate, aprotic polar solvents such as N,N-dimethylformamide, and a mixture thereof.

Examples of the catalytic hydrogen reducing agent include palladium, palladium black, palladium-carbon, platinum, platinum oxide, copper chromite, and Raney nickel. These reducing agents may be used singly or as a mixture of two types or more.

The catalytic hydrogen reducing agent is preferably used generally in an amount of 0.02 to 1 times that of the compound (1iii') on a weight basis.

The reaction temperature is typically set at about −20 to 100° C. and preferably at about 0 to about 80° C. The reaction is preferably carried out at a hydrogen pressure of typically 1-10 atm, and completed generally in about 0.5 to 20 hours.

[Reaction formula 25]

[Formula 104]

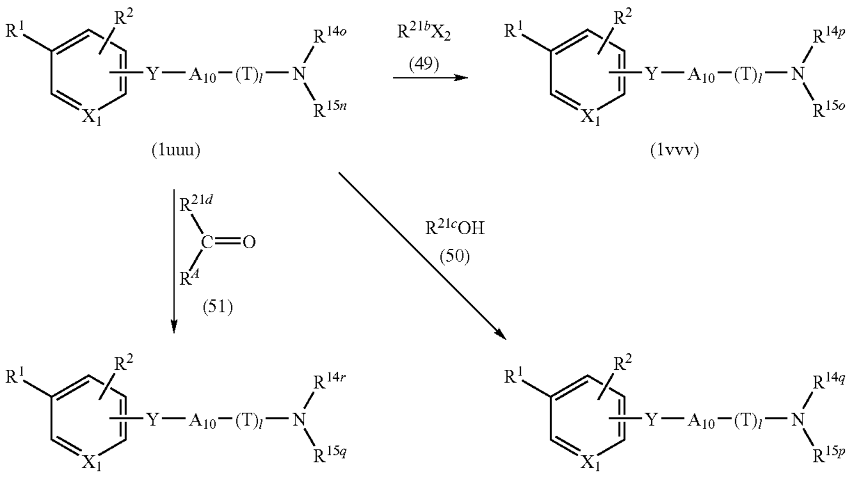

(1uuu) (1vvv) (1xxx) (1www)

wherein $R^1$, $R^2$, $X_1$, Y, T, l, $A_{10}$, $R^A$ and $X_2$ are the same as described above, provided that a and b of $A_{10}$ are bound to a group Y and a group (T)l, respectively; $R^{14o}$ and $R^{15n}$ are the same 5- to 10-membered saturated or unsaturated heterocyclic groups as defined in $R^{14}$ and $R^{15}$ above, respectively, except that each of the heterocyclic groups has at least one group —$(B_{12}CO)tNHR^{20a}$ thereon;

$R^{14p}$ and $R^{15o}$ are the same 5- to 10-membered saturated or unsaturated heterocyclic groups as defined in $R^{14}$ and $R^{15}$ above, respectively, except that each of the heterocyclic groups has at least one group —$(B_{12}CO)tN(R^{20a})R^{21b}$ thereon; and $R^{14q}$ and $R^{15p}$ are the same 5- to 10-membered saturated or unsaturated heterocyclic groups as defined in $R^{14}$ and $R^{15}$ above, respectively, except that each of the heterocyclic groups has at least one group —$(B_{12}CO)tN(R^{20a})R^{21c}$ thereon;

$R^{14r}$ and $R^{15q}$ represent the same 5- to 10-membered saturated or unsaturated heterocyclic groups as defined in $R^{14}$ and $R^{15}$ above, respectively, except that each of the heterocyclic groups has at least one group —$(B_{12}CO)tN(R^{20a})(CHR^AR^{21d})$ thereon, wherein $B_{12}$, t and $R^{20a}$ are the same as described above;

$R^{21b}$ represents a lower alkyl group, a cycloalkyl group, a lower alkyl group which may have 1 or 2 phenyls which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group, a phenyl group which may have, on the phenyl ring, 1 to 3 groups selected from the group consisting of a lower alkoxy group which may have a halogen atom as a substituent and a lower alkyl group which may have a halogen atom as a substituent, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a lower alkoxycarbonyl lower alkyl group, a pyridyl group, or a carboxy lower alkyl group;

$R^{21c}$ represents a benzoyl group which may have 1 to 3 lower alkoxy groups as substituents on the phenyl ring, a lower alkoxycarbonyl group, a phenyl lower alkanoyl group, a lower alkanoyl group which may have a halogen atom as a substituent or an imidazolyl lower alkanoyl group; and $R^{21d}$ represents a hydrogen atom, a lower alkyl group, a lower alkyl group which have 1 or 2 phenyl groups which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group, a phenyl group which may have, on the phenyl ring, 1 to 3 substituents selected from the group consisting of a lower alkoxycarbonyl group, a cyano group, a nitro group, a phenyl group, a halogen atom, a lower alkyl group which may be substituted with a halogen atom, a lower alkoxy group which may be substituted with a halogen atom and a lower alkylthio group, a cycloalkyl lower alkyl group, a cycloalkyl group, a pyrrolidinyl lower alkyl group which may have, on the pyrrolidine ring, 1 to 3 lower alkyl groups which may have a hydroxyl group as a substituent, a pyrrolidinyl group which may have, on the pyrrolidine ring, 1 to 3 lower alkyl groups which may have a hydroxyl group as a substituent, an amino substituted lower alkyl group which may have a group selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a 1,2,3,4-tetrahydronaphthyl group which may have 1 to 5 lower alkyl groups as substituents on the 1,2,3,4-tetrahydronaphthalene ring, a naphthyl lower alkyl group, a naphthyl group, a pyridyl lower alkyl group, a pyridyl group, a quinolyl lower alkyl group, a quinolyl group, a 1,2,3,4-tetrazolyl lower alkyl group which may have, on the tetrazole ring, 1 to 3 substituents selected from the group consisting of a lower alkyl group and a phenyl lower alkyl group, a 1,2,3,4-tetrazolyl group which may have, on the tetrazole ring, 1 to 3 substituents selected from the group consisting of a lower alkyl group and a phenyl lower alkyl group, a 1,2,4-triazolyl lower alkyl group, a 1,2,4-triazolyl group, a tetrahydrofuryl lower alkyl group which may have a hydroxyl group as a substituent on the lower alkyl group, a tetrahydrofuryl group which may have a hydroxyl group as a substituent on the lower alkyl group, a phenoxy lower alkyl group which may have, on the phenyl ring, 1 to 3 substituents selected from the group consisting of a lower alkyl group and a nitro group, a lower alkoxycarbonyl lower alkyl group or a carboxy lower alkyl group;

provided that the alkyl moiety of $CHR^AR^{21d}$ in the side chain (—$(B_{21}CO)tN(R^{20a})(CHR^AR^{21d})$) has not more than 6 carbon atoms.

The reaction of the compound (1uuu) with the compound (49) is carried out under the same reaction conditions as in the reaction of the compound (1b) and the compound (4) shown in reaction formula 2 above.

The reaction of the compound (1uuu) and the compound (51) is carried out under the same reaction conditions as in the reaction of the compound (1b) and the compound (5) shown in reaction formula 2 above.

The reaction of the compound (1uuu) and the compound (50) is carried out under the same reaction conditions as in the reaction of the compound (1b) and the compound (6) shown in reaction formula 2 above.

[Reaction formula 26]

[Formula 105]

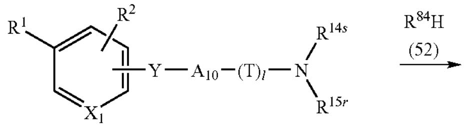

(1yyy)

-continued

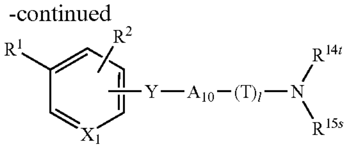

(1zzz)

wherein $R^1$, $R^2$, $X_1$, Y, T, l, and $A_{10}$ are the same as described above, provided that a and b of $A_{10}$ are bound to Y and (T)l, respectively;

$R^{14s}$ and $R^{15r}$ represent the same 5- to 10-membered saturated or unsaturated heterocyclic groups as defined in $R^{14}$ and $R^{15}$ above, respectively, except that each of the heterocyclic groups has at least one group —(CO)o$B_{13}X_2$ thereon;

$R^{14t}$ and $R^{15s}$ represent the same 5- to 10-membered saturated or unsaturated heterocyclic groups as defined in $R^{14}$ and $R^{15}$ above, respectively, except that each of the heterocyclic groups has at least one group —(CO)o $B_{13}R^{84}$ thereon; and $R^{84}$ is a group —$NR^{22}R^{23}$ or an imidazolyl group (wherein $B_{13}$, o, $X_2$, $R^{22}$ and $R^{23}$ are the same as described above).

The reaction of the compound (1yyy) and the compound (52) is carried out under the same reaction conditions as in the reaction of the compound (1b) and the compound (4) shown in reaction formula 2 above.

[Reaction formula 27]

[Formula 106]

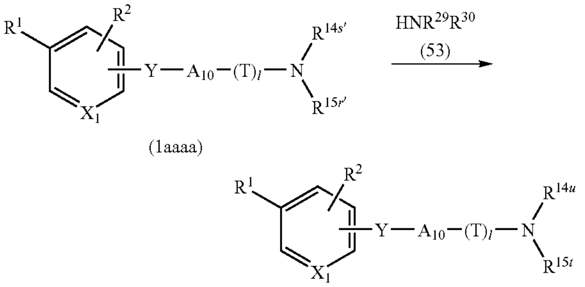

(1aaaa)

(1bbbb)

wherein $R^1$, $R^2$, $X_1$, Y, T, l, and $A_{10}$ are the same as described above, provided that a and b of $A_{10}$ are bound to a group Y and group (T)l, respectively;

$R^{14s'}$ and $R^{15r'}$ represent the same 5- to 10-membered saturated or unsaturated heterocyclic groups as defined in $R^{14}$ and $R^{15}$ above, respectively, except that each of the heterocyclic groups has at least one group —N($R^{28}$)—CO—$B_{16}X_2$ thereon; and $R^{14u}$ and $R^{15t}$ represent the same 5- to 10-membered saturated or unsaturated heterocyclic groups as defined in $R^{14}$ and $R^{15}$ above, respectively, except that each of the heterocyclic groups has at least one group —N($R^{28}$)—CO—$B_{16}NR^{29}R^{30}$ thereon;

(wherein $R^{28}$, $B_{16}$, $X_2$, $R^{29}$ and $R^{30}$ represent the same as described above).

The reaction of the compound (1aaaa) and the compound (53) is carried out under the same reaction conditions as in the reaction of the compound (1b) and the compound (4) shown in reaction formula 2 above.

[Reaction formula 28]

[Formula 107]

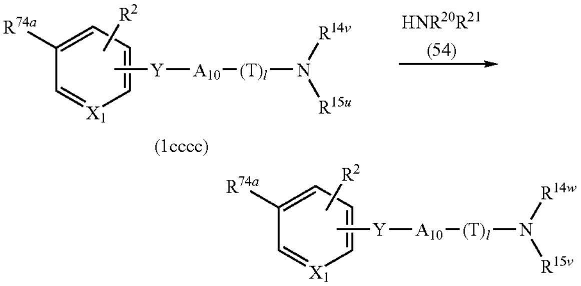

(1cccc)

(1dddd)

wherein $R^{74a}$, $R^2$, $X_1$, Y, T, l, and $A_{10}$ are the same as described above, provided that a and b of $A_{10}$ are bound to a group Y and a group (T)l, respectively;

$R^{14v}$ and $R^{15u}$ represent the same 5- to 10-membered saturated or unsaturated heterocyclic groups as defined in $R^{14}$ and $R^{15}$ above, respectively, except that each of the heterocyclic groups has at least one group —$B_{12}$COOH thereon; and $R^{14w}$ and $R^{15v}$ represent the same 5- to 10-membered saturated or unsaturated heterocyclic groups as defined in $R^{14}$ and $R^{15}$ above, respectively, except that each of the heterocyclic groups has at least one group —$B_{12}CONR^{20}R^{21}$ thereon;

(wherein $B_{12}$, $R^{20}$ and $R^{21}$ are the same as described above).

The reaction of the compound (1cccc) and the compound (54) is carried out under the same reaction conditions as in the reaction of the compound (1b) and the compound (6) shown in reaction formula 2 above.

[Reaction formula 29]

[Formula 108]

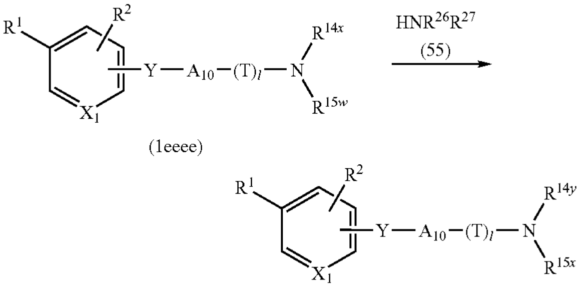

(1eeee)

(1ffff)

wherein $R^1$, $R^2$, $X_1$, Y, T, l, and $A_{10}$ are the same as described above, provided that a and b of $A_{10}$ are bound to a group Y and a group $(T)_l$, respectively;

$R^{14x}$ and $R^{15w}$ represent the same 5- to 10-membered saturated or unsaturated heterocyclic groups as defined in $R^{14}$ and $R^{15}$ above, respectively, except that each of the heterocyclic groups has at least one group —O—$B_{15}$COOH; and $R^{14y}$ and $R^{15x}$ represent the same 5- to 10-membered saturated or unsaturated heterocyclic groups as defined in $R^{14}$ and $R^{15}$ above, respectively, except that each of the heterocyclic groups has at least one group —O—$B_{15}CONR^{26}R^{27}$ thereon;

(wherein $B_{15}$, $R^{26}$ and $R^{27}$ are the same as described above).

The reaction of the compound (1eeee) and the compound (55) is carried out under the same reaction conditions as in the reaction of the compound (1b) and the compound (6) shown in reaction formula 2 above.

[Reaction formula 30]

[Formula 109]

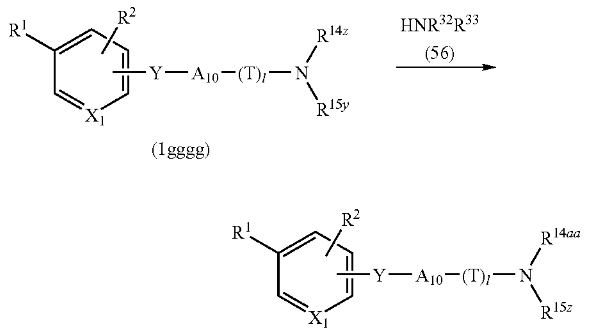

(1gggg)

(1hhhh)

wherein $R^1$, $R^2$, $X_1$, Y, T, l, and $A_{10}$ are the same as described above, provided that a and b of $A_{10}$ are bound to a group Y and (T)l, respectively;

$R^{14z}$ and $R^{15y}$ represent the same 5- to 10-membered saturated or unsaturated heterocyclic groups as defined in $R^{14}$ and $R^{15}$ above, respectively, except that each of the heterocyclic groups has at least one group —$N(R^{31})$—$B_{17}$—COOH thereon; and $R^{14aa}$ and $R^{15z}$ represent the same 5- to 10-membered saturated or unsaturated heterocyclic groups as defined in $R^{14}$ and $R^{15}$ above, respectively, except that each of the heterocyclic groups has at least one group —$N(R^{31})$—$B_{17}CONR^{32}R^{33}$ thereon;

(wherein $R^{31}$, $B_{17}$, and $R^{32}$, $R^{33}$ are the same as described above).

The reaction of the compound (1gggg) and the compound (56) is carried out under the same reaction conditions as in the reaction of the compound (1b) and the compound (6) of reaction formula 2 above.

[Reaction formula 31]

[Formula 110]

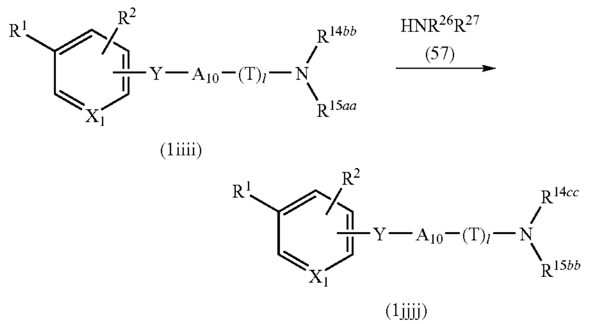

(1iiii)

(1jjjj)

wherein $R^1$, $R^2$, $X_1$, Y, T, l, and $A_{10}$ are the same as described above, provided that a and b of $A_{10}$ are bound to a group Y and a group (T)l, respectively;

$R^{14bb}$ and $R^{15aa}$ represent the same 5- to 10-membered saturated or unsaturated heterocyclic groups as defined in $R^{14}$ and $R^{15}$ above, respectively, except that each of the heterocyclic groups has at least one group —COOH thereon; and $R^{14cc}$ and $R^{15bb}$ represent the same 5- to 10-membered saturated or unsaturated heterocyclic groups as defined in $R^{14}$ and $R^{15}$ above, respectively, except that each of the heterocyclic groups has at least one group —$CONR^{26}R^{27}$ thereon;

wherein $R^{26}$ and $R^{27}$ are the same as described above.

The reaction of the compound (1iiii) and the compound (57) is carried out under the same reaction conditions as in the reaction of the compound (1b) and the compound (6) shown in reaction formula 2 above.

[Reaction formula 32]

[Formula 111]

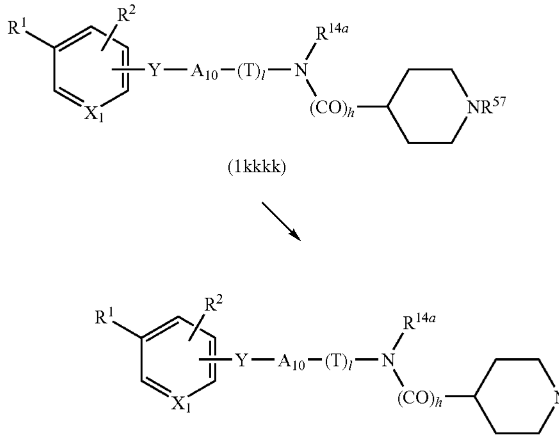

(1kkkk)

(1llll)

wherein $R^1$, $R^2$, $X_1$, Y, T, l, $R^{14a}$ and $A_{10}$ are the same as described above, provided that a and b of $A_{10}$ are bound to a group Y and a group $(T)_l$, respectively;

h represents 0 or 1; and $R^{57}$ represents a lower alkoxycarbonyl group.

The reaction which converts the compound (1kkkk) into the compound (1llll) may be carried out under the same reaction conditions as in hydrolysis B described in reaction formula 9 above.

[Reaction formula 33]

[Formula 112]

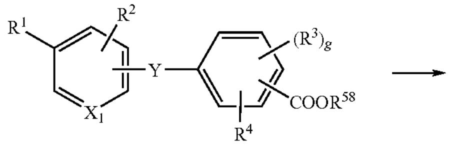

(1mmmm)

-continued

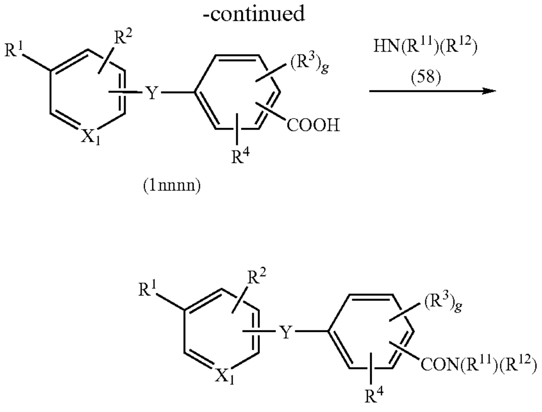

(1nnnn)

(1oooo)

wherein $R^1$, $R^2$, $X_1$, $R^3$, $R^4$, Y, $R^{11}$ and $R^{12}$ are the same as described above, $R^{58}$ represents a lower alkyl group, and g represents 0 or 1.

The reaction which converts the compound (1mmmm) into the compound (1nnnn) may be carried out under the same reaction conditions as in hydrolysis B as described in reaction formula 9 above.

The reaction of the compound (1nnnn) with the compound (58) is carried out under the same reaction conditions as in the reaction of the compound (1b) and the compound (6) shown in reaction formula 2 above.

$R^{14ii}$ and $R^{15hh}$ represent the same 5- to 10-membered saturated or unsaturated heterocyclic groups as defined in $R^{14}$ and $R^{15}$ above, respectively, except that each of the heterocyclic groups has at least one group —(CO)o-$B_{13}$N($R^{22a}$)$R^{23b}$ thereon;

$R^{14kk}$ and $R^{15jj}$ represent the same 5- to 10-membered saturated or unsaturated heterocyclic groups as defined in $R^{14}$ and $R^{15}$ above, respectively, except that each of the heterocyclic ring has at least one —(CO)o-$B_{13}$N($R^{22a}$)(CH$R^A$$R^{23c}$) group thereon, (wherein $R^A$, $B_{13}$ and o are the same as described above);

$R^{22a}$ is a hydrogen atom, a lower alkyl group, a benzoyl group which may have 1 to 3 lower alkoxy groups as substituents on the phenyl ring, a phenoxy lower alkyl group which may have a lower alkyl group as a substituent on the phenyl ring, a phenyl lower alkyl group or a phenyl group;

$R^{23a}$ represents a lower alkyl group, a phenoxy lower alkyl group which may have a lower alkyl group as a substituent on the phehyl ring, a phenyl lower alkyl group or a phenyl group;

$R^{23b}$ represents a benzoyl group which may have 1 to 3 lower alkoxy groups as substituents on the phenyl ring; and $R^{23c}$ represents a hydrogen atom, a lower alkyl group, a phenoxy lower alkyl group which may have a lower alkyl group as a substituent on the phenyl ring, a phenyl lower alkyl group or a phenyl group; provided that the alkyl moiety of the —CH$R^A$$R^{23c}$ group in the side chain (—(CO)o-$B_{13}$—N($R^{22a}$)(CH$R^A$$R^{23c}$)) of the compound (1ssss) has not more than 6 carbon atoms.

[Reaction formula 34]

[Formula 113]

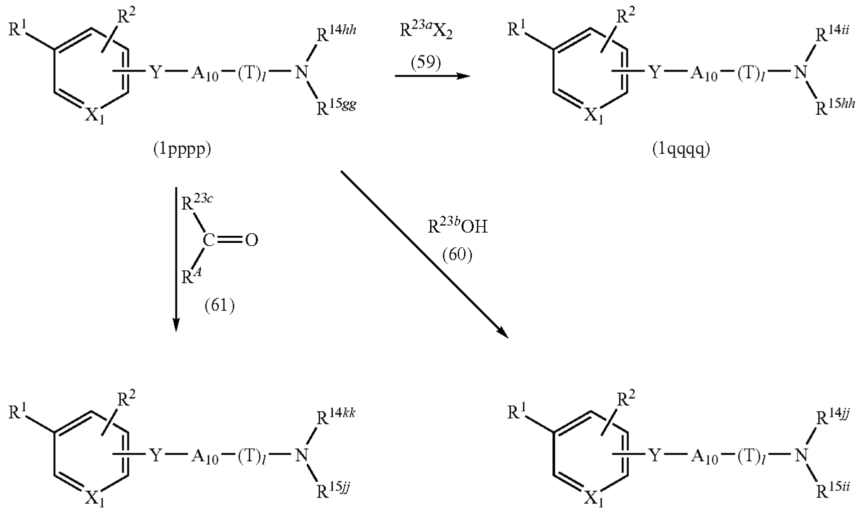

(1pppp) (1qqqq) (1ssss) (1rrrr)

wherein $R^1$, $R^2$, $X_1$, Y, T, l, $A_{10}$ and $X_2$ are the same as described above, provided that a and b of $A_{10}$ are bound to a group Y and a group (T)l, respectively;

$R^{14hh}$ and $R^{15gg}$ represent the same 5- to 10-membered saturated or unsaturated heterocyclic groups as defined in $R^{14}$ and $R^{15}$ above, respectively, except that each of the heterocyclic groups has at least one group —(CO)o-$B_{13}$NH($R^{22a}$) thereon;

$R^{14ii}$ and $R^{15hh}$ represent the same 5- to 10-membered saturated or unsaturated heterocyclic groups as defined in $R^{14}$ and $R^{15}$ above respectively, except that each of the heterocyclic groups has at least one group —(CO)o-$B_{13}$N($R^{22a}$) thereon;

The reaction of the compound (1pppp) and the compound (59) is carried out under the same reaction conditions as in the reaction of the compound (1b) and the compound (4) shown in reaction formula 2 above.

The reaction of the compound (1pppp) and the compound (61) is carried out under the same reaction conditions as in the reaction of the compound (1b) and the compound (5) shown in reaction formula 2 above.

The reaction of the compound (1pppp) and the compound (60) is carried out under the same reaction conditions as in the reaction of the compound (1b) and the compound (6) shown in reaction formula 2 above.

[Reaction formula 35]

[Formula 114]

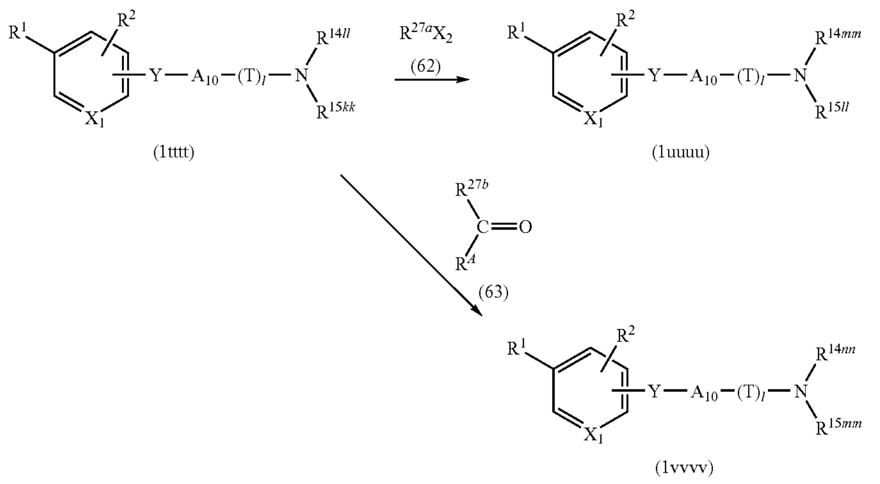

wherein $R^1$, $R^2$, $X_1$, Y, T, l, $A_{10}$ and $X_2$ are the same as described above, provided that a and b of $A_{10}$ are bound to a group Y and a group (T)l, respectively;

$R^{14ll}$ and $R^{15kk}$ represent the same 5- to 10-membered saturated or unsaturated heterocyclic groups as defined in $R^{14}$ and $R^{15}$ above, respectively, except that each of the heterocyclic groups has at least one group —(O—$B_{15}$)s-CONH($R^{26a}$) thereon;

$R^{14mm}$ and $R^{15ll}$ represent the same 5- to 10-membered saturated or unsaturated heterocyclic groups as defined in $R^{14}$ and $R^{15}$ above, respectively, except that each of the heterocyclic groups has at least one group —(O—$B_{15}$)s-CON($R^{26a}$)($R^{27a}$) thereon;

$R^{14nn}$ and $R^{15mm}$ represent the same 5- to 10-membered saturated or unsaturated heterocyclic group as defined in $R^{14}$ and $R^{15}$ above, respectively, except that each of the heterocyclic rings has at least one group —(O—$B_{15}$)s-CON($R^{26a}$)($CHR^AR^{27b}$)

(wherein $B_{15}$, s and $R^A$ are the same as described above);

$R^{26a}$ represents a hydrogen atom, a lower alkyl group, a phenyl lower alkyl group or an imidazolyl lower alkyl group;

$R^{27a}$ represents a lower alkyl group, a phenyl lower alkyl group or an imidazolyl lower alkyl group; and $R^{27b}$ represents a hydrogen atom, a lower alkyl group, a phenyl lower alkyl group, a phenyl group, an imidazolyl group or an imidazolyl lower alkyl group;

provided that the alkyl moiety of the —$CHR^AR^{27b}$ group in the side chain (—(O—$B_{15}$)s-CO($R^{26a}$)($CHR^AR^{27b}$)) of the compound (1vvvv) has not more than 6 carbon atoms.

The reaction of the compound (1tttt) and the compound (62) is carried out under the same reaction conditions as in the reaction of the compound (1b) and the compound (4) shown in reaction formula 2 above.

The reaction of the compound (1tttt) and the compound (63) is carried out under the same reaction conditions as in the reaction of the compound (1b) and the compound (5) shown in reaction formula 2 above.

[Reaction formula 36]

[Formula 115]

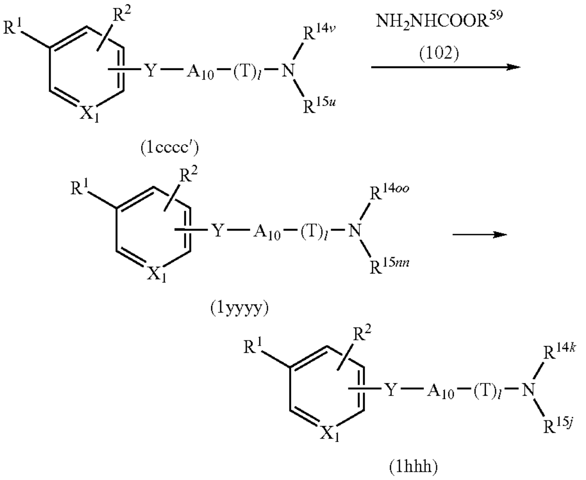

wherein $R^1$, $R^2$, $X_1$, Y, T, l, $A_{10}$, $R^{14v}$, $R^{15u}$, $R^{14k}$ and $R^{14j}$ are the same as described above, provided that a and b of $A_{10}$ are bound to a group Y and a group (T)l, respectively;

$R^{59}$ represents a lower alkyl group; and $R^{14oo}$ and $R^{15nn}$ represent the same 5- to 10-membered saturated or unsaturated heterocyclic groups as defined in $R^{14}$ and $R^{15}$ above, respectively, except that each of the heterocyclic groups has at least one group —$B_{21}CONHNHCOOR^{59}$, (wherein $B_{21}$ is the same as described above).

The reaction of the compound (1cccc') and the compound (102) is carried out under the same reaction conditions as in the reaction of the compound (1b) and the compound (6) shown in reaction formula 2 above.

The reaction which converts the compound (1yyyy) into the compound (1hhh) may be carried out under the same reaction conditions as in hydrolysis B as described in reaction formula 9 above.

The compound of the present invention of the general formula (1) in which various groups are taken as $R^1$ is produced, for example, as shown by reaction formulas 37 to 46 below.

[Reaction formula 37]

[Formula 116]

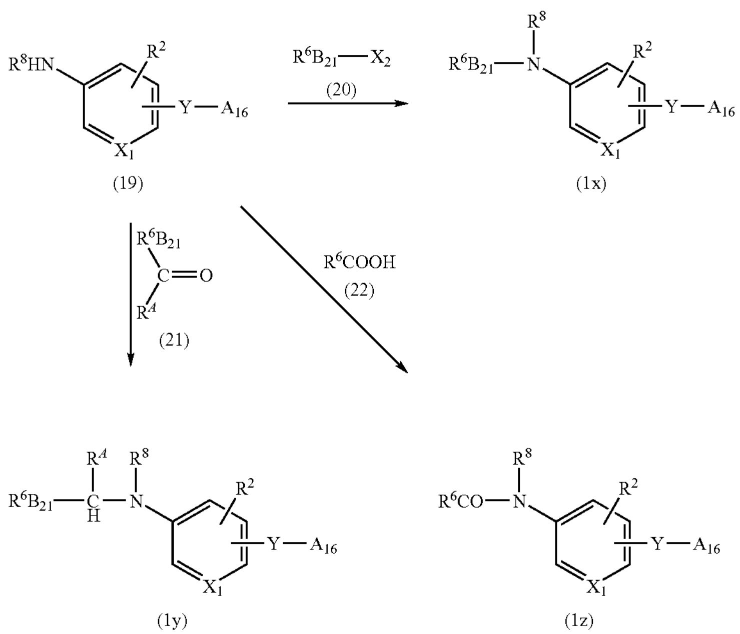

wherein $R^2$, $X_1$, Y, $A_{16}$, $R^6$, $R^8$, $B_{21}$, $R^A$ and $X_2$ are the same as described above, provided that the $B_{21}CHR^A$ moiety of the ($R^6$—$B_{21}CHR^A$—) group of the compound (1y) has hot more than 6 carbon atoms.

The reaction of the compound (19) and the compound (20) is carried out under the same reaction conditions as in the reaction of the compound (1b) and the compound (4) shown in reaction formula 2 above.

The reaction of the compound (19) and the compound (21) is carried out under the same reaction conditions as in the reaction of the compound (1b) and the compound (5) of reaction formula 2 above.

The reaction of the compound (19) and the compound (22) is carried out under the same reaction conditions as in the reaction of the compound (1b) and the compound (6) of reaction formula 2 above.

[Reaction formula 38]

[Formula 117]

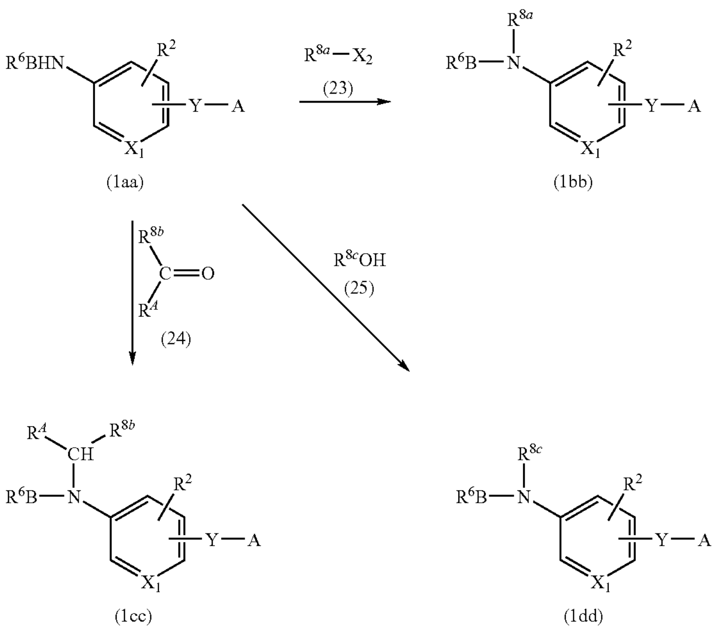

wherein $R^2$, $X_1$, Y, A, $R^6$, B, $R^A$ and $X_2$ are the same as described above, $R^{8a}$ represents a lower alkyl group which may have a lower-alkoxy group as a substituent, a lower alkylsulfonyl group or a phenyl lower alkyl group, $R^{8b}$ represents a hydrogen atom, a phenyl group, phenyl lower alkyl group or a lower alkyl group which may have a lower alkoxy group as a substituent, and $R^{8c}$ represents a lower alkanoyl group, provided that the alkyl moiety of the —$CHR^AR^{8b}$ group of the compound (1cc) has not more than 6 carbon atoms.

The reaction of the compound (1aa) and the compound (23) is carried out under the same reaction conditions as in the reaction of the compound (1b) and the compound (4) shown in reaction formula 2 above.

The reaction of the compound (1aa) and the compound (24) is carried out under the same reaction conditions as in the reaction of the compound (1b) and the compound (5) shown in reaction formula 2 above.

The reaction of the compound (1aa) and the compound (25) is carried out under the same reaction conditions as in the reaction of the compound (1b) and the compound (6) shown in reaction formula 2 above.

[Reaction formula 39]

[Formula 118]

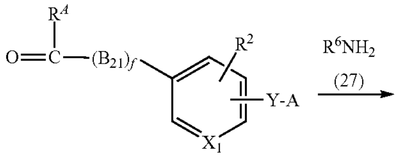

(26)

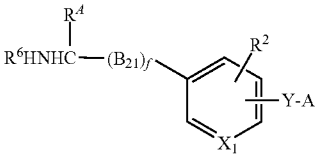

(1ee)

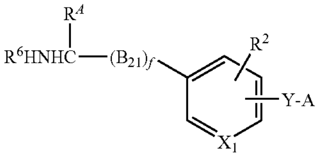

(1ee)

wherein $R^2$, $X_1$, Y, A, $B_{21}$, f, $R^A$ and $R^6$ are the same as described above, provided that the $(B_{21})fCHR^A$ moiety of the side chain (—$(B_{21})fCHR^ANHR^6$) of the compound (1ee) has not more than 6 carbon atoms.

The reaction of the compound (26) and the compound (27) is carried out under the same reaction conditions as in the reaction of the compound (1b) and the compound (5) shown in reaction formula 2 above.

[Reaction formula 40]

[Formula 119]

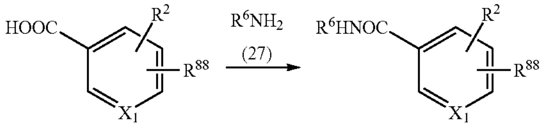

(28) 1ff wherein $R^{88}$ represents a group —Y-A or a halogen atom, and $R^2$, $X_1$, Y, A, and $R^6$ are the same as described above.

The reaction of the compound (28) and the compound (27) is carried out under the same reaction conditions as in the reaction of the compound (1b) and the compound (6) shown in reaction formula 2 above.

[Reaction formula 41]

[Formula 120]

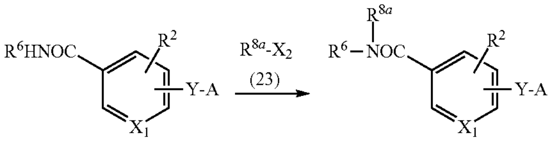

(1ff') (1gg)

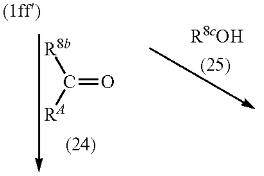

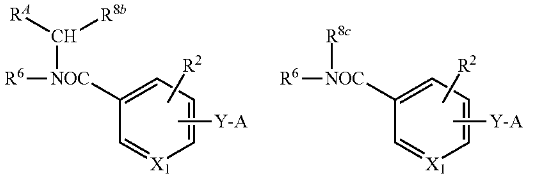

(1hh) (1ii)

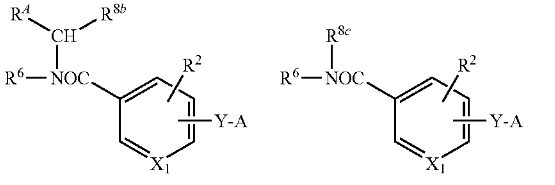

(1hh) (1ii)

wherein $R^2$, $X_1$, Y, A, $R^6$, $R^{8a}$, $R^{8b}$, $R^{8c}$, $R^A$ and $X_2$ are the same as described above, provided that the alkyl moiety of the group —$CHR^AR^{8b}$ of the compound (1hh) has not more than 6 carbon atoms.

The reaction of the compound (1ff') and the compound (23) is carried out under the same reaction conditions similar as in the reaction of the compound (1b) and the compound (4) shown in reaction formula 2 above.

The reaction of the compound (1ff') and the compound (24) is carried out under the same reaction conditions as in the reaction of the compound (1b) and the compound (5) shown in reaction formula 2 above.

The reaction of the compound (1ff') and the compound (25) is carried out under the same reaction conditions as in the reaction of the compound (1b) and the compound (6) shown in reaction formula 2 above.

[Reaction formula 42]

[Formula 121]

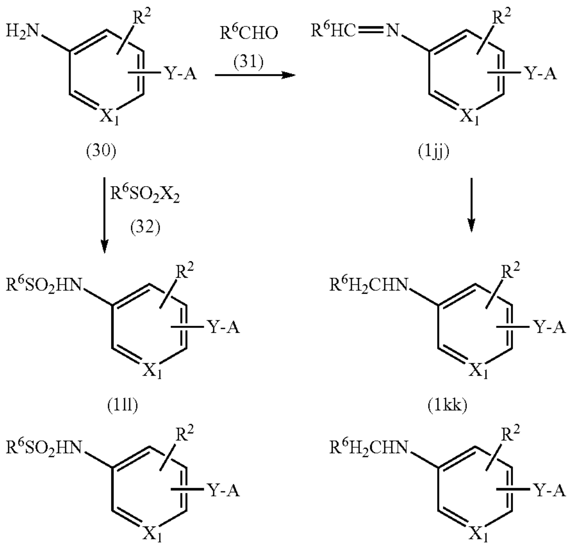

(30) (1jj) (1ll) (1kk) (1ll) (1kk)

wherein $R^2$, $X_1$, Y, A, $R^6$ and $X_2$ are the same as described above.

The reaction which converts the compound (30) into the compound (1jj) is carried out under the same reaction conditions as in the reaction which converts the compound (1f) into the compound (1h) shown in reaction formula 3 above.

The reaction which converts the compound (1jj) into the compound (1kk) is carried out under the same reaction conditions as in the reaction of the compound (1b) and the compound (5) shown in reaction formula 2 above.

The reaction of the compound (30) and the compound (32) is carried out under the same reaction conditions as in the reaction of the compound (1b) and the compound (4) shown in reaction formula 2 above.

[Reaction formula 43]

[Formula 122]

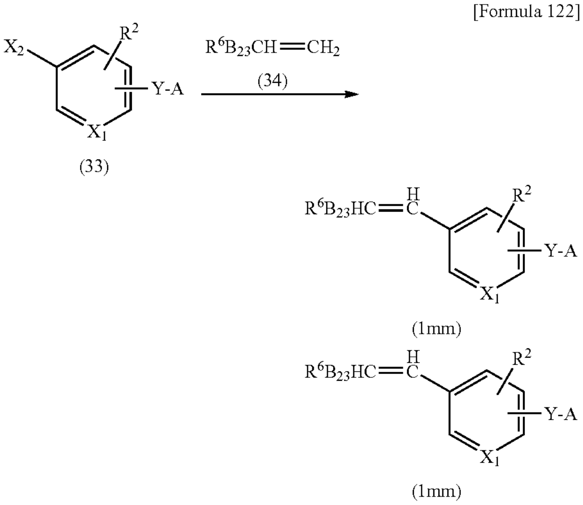

(33) (1mm) (1mm)

wherein $R^2$, $X_1$, Y, A, $X_2$ and $R^6$ are the same as described above, $B_{23}$ represents a lower alkylene group or a lower alkenylene group, and the $B_{23}$—HC═CH— moiety in the side chain ($R^6B_{23}$—HC═CH—) of the compound (1 mm) has 1 to 3 double bonds and has not more than 6 carbon atoms.

The reaction of the compound (33) and the compound (34) is carried out in an appropriate inert solvent and in the presence of a condensation agent.

Examples of the inert solvent to be used in the above described reaction include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as α-dimethylaminoacetic acid and acetic acid, esters such as ethyl acetate and methyl acetate, ketones such as acetone and methyl ethyl ketone, acetonitrile, 1-methyl-2-pyrrolidone, pyridine, dimethyl sulfoxide, dimethylformamide, and hexamethylphosphoric acid triamide, and a mixture thereof.

Examples of the condensation agent include palladium complexes such as bis(benzonitrile)dichloropalladium(II).

The condensation agent is favorably used typically in an amount 0.01 to 1 times and preferably 0.01 to 0.5 times that of the compound (33) on a molar basis.

The above described reaction favorably proceeds typically at 0 to 200° C. and preferably at about room temperature to about 150° C. and is generally completed in about 10 minutes to 20 hours.

The above described reaction proceeds advantageously by adding an alkali metal salt of a fatty acid such as sodium acetate to the reaction system.

[Reaction formula 44]

[Formula 123]

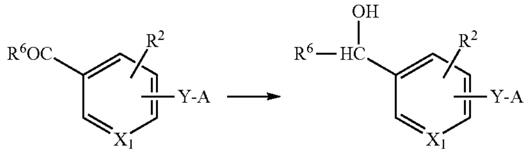

(1nn) (1oo)

wherein $R^2$, $X_1$, Y, A and $R^6$ are the same as described above.

The reaction which converts the compound (1nn) into the compound (1oo) is carried out under the same reaction conditions as in the reaction which converts the compound (1f) into the compound (1g) shown in reaction formula 3 above.

[Reaction Formula 45]

[Formula 124]

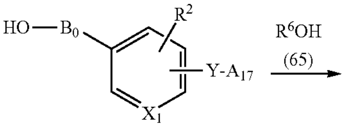

(64)

-continued

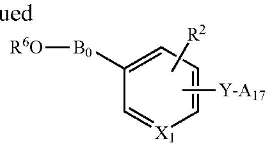

(1wwww)

wherein $A_{17}$ represents a group

[Formula 125]

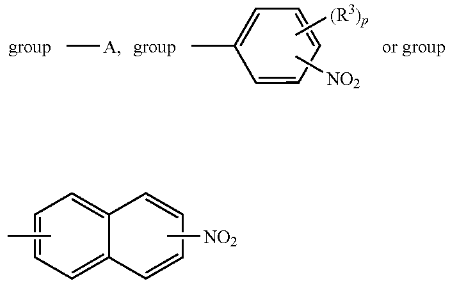

wherein $R^2$, $R^3$, p, $X_1$, Y, A, Bo and $R^6$ are the same as described above.

The reaction of the compound (64) and the compound (65) is carried out in an appropriate solvent in the presence of a condensation agent.

Any solvent may be used as long as it is used in the reaction of a carboxylic acid halide with an amine (1b) of the reactions between the compound (1b) and the compound (6) (an amide bond generation reaction) shown in reaction formula 2.

Examples of the condensation agent include a mixture of an azocarboxylate (such as diethyl azodicarboxylate) and a phosphorus compound (such as triphenylphosphine).

The condensation agent is favorably used typically in at least an equimolar amount to the compound (64) and preferably 1 to 2 times that of the compound (64) on a molar basis.

The compound (65) is favorably used typically in an amount of at least an equimolar to the compound (64) and preferably 1 to 2 times that of the compound (64) on a molar basis.

The above described reaction favorably proceeds typically at 0 to 200° C., preferably at about 0 to 150° C. and is generally completed in about 1 to 10 hours.

[Reaction formula 46]

[Formula 126]

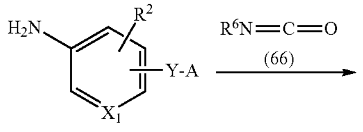

(30)

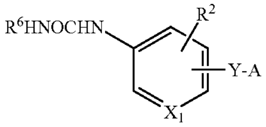

(1xxxx)

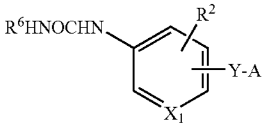

(1xxxx)

wherein $R^2$, $X_1$, Y, A, and $R^6$ are the same as described above.

The reaction of the compound (30) and the compound (66) is carried out in the presence or absence of a basic compound and preferably in the absence of the basic compound and in the presence or absence of an appropriate solvent.

Any inert solvent and basic compound may be used as long as they are used in the reaction of a carboxylic acid halide and an amine (1b) of the reactions between the compound (1b) and the compound (6) (an amide bond generation reaction) shown in reaction formula 2.

The compound (66) may be used typically in an amount of about 1 to 5 times and preferably about 1 to 3 times that of the compound (30) on a molar basis.

The above described reaction is carried out typically at 0 to 200° C. and preferably at about room temperature to 150° C. and is generally completed in about minutes to 50 hours.

A boron compound such as a boron trifluoride-diethyl ether complex may be added to the reaction system of the above described reaction.

[Reaction formula 47]

[Formula 127]

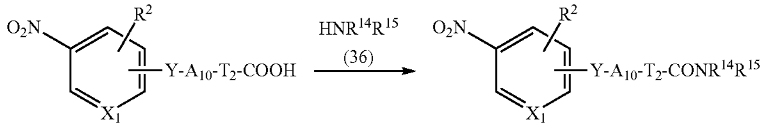

(71) (72)

-continued

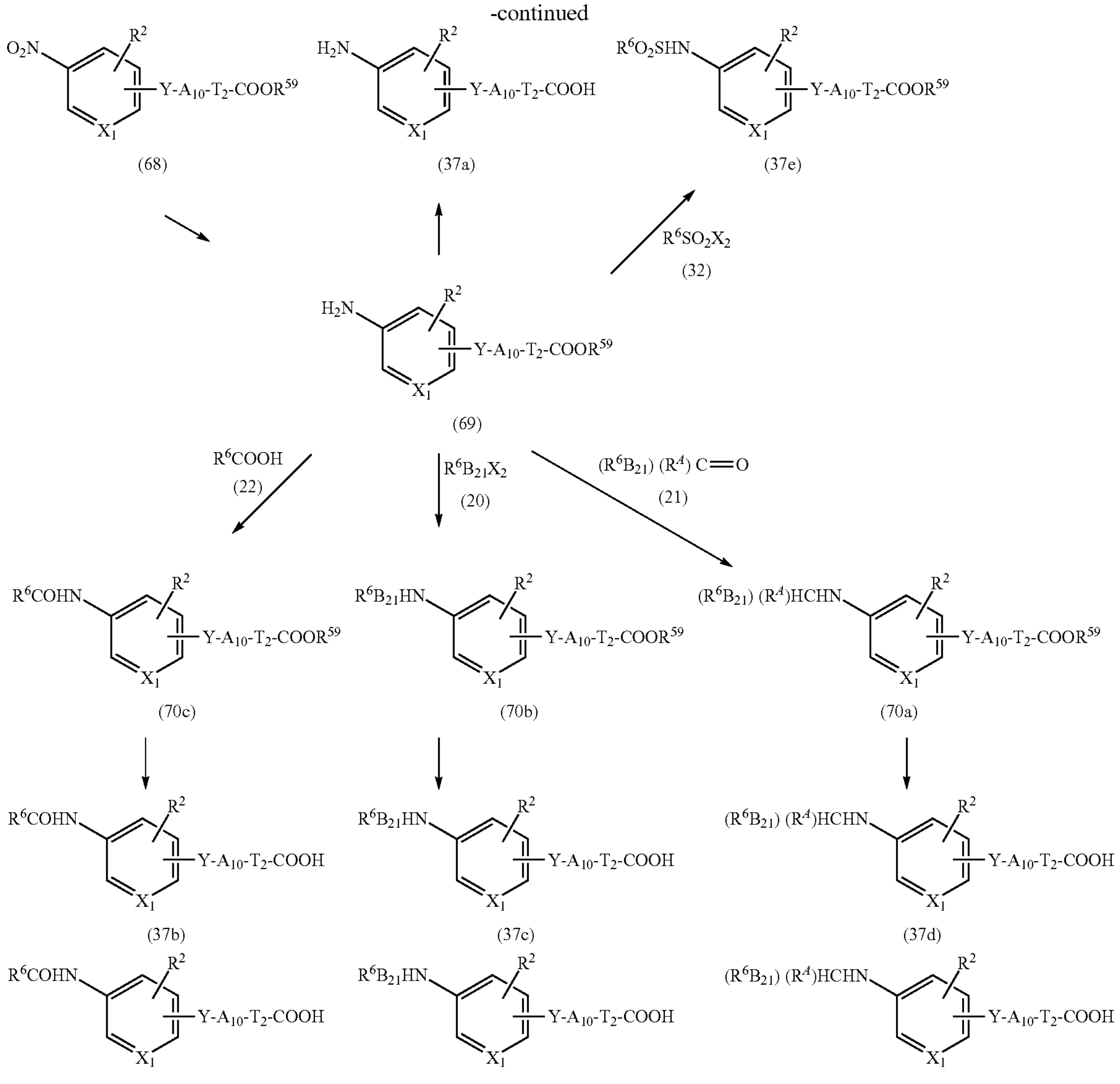

(68) (37a) (37e)

(69)

(70c) (70b) (70a)

(37b) (37c) (37d)

(37b) (37c) (37d)

wherein $R^2$, $X_1$, Y, $T_2$, $A_{10}$, $R^{14}$, $R^{15}$, $B_{21}$, $R^4$, $X_2$, $R^6$ and $R^{59}$ are the same as described above, provided that a and b of $A_{10}$ are bound to a group Y and a group $T_2$, respectively.

The reaction which converts the compound (68) into the compound (71) may be carried out under the same reaction conditions as in hydrolysis B as described in reaction formula 9 above.

The reaction of the compound (71) and the compound (100) is carried out under the same reaction conditions as in the reaction of the compound (1fff) and the compound (43) shown in reaction formula 20 above.

The compound (68) may also be produced using a halogenated lower alkyl group such as methyl iodide in place of the compound (100) in the same as in the reaction of the compound (2) and the compound (3) shown in reaction formula 1 above.

The reaction which converts the compound (68) into the compound (69) may be carried out, for example, (1) by reducing the compound (68) with a catalytic hydride reducing agent in an appropriate solvent, or (2) by reducing the compound (68) with a reducing agent such as a mixture of a metal or a metal salt with an acid, or a mixture of a metal or a metal salt with an alkali metal hydroxide, a sulfide, an ammonium salt or the like, in an appropriate inert solvent.

Examples of the solvent for use in the method (1) include water, acetic acid, alcohols such as methanol, ethanol, and isopropanol, hydrocarbons such as n-hexane and cyclohexane, ethers such as dioxane, tetrahydrofuran, diethyl ether, and diethylene glycol dimethyl ether, esters such as ethyl acetate and methyl acetate, and aprotic polar solvents such as N,N-dimethylformamide, and a mixture thereof. Examples of the catalytic hydride reducing agent include palladium, palladium black, palladium-carbon, platinum-carbon, platinum, platinum oxide, copper chromite, and Raney nickel. These reducing agents may be used singly or in a mixture of two types or more. The reducing agent may be used generally in an amount 0.02 to 1 times that of the compound (68) on a weight basis. The reaction temperature is set typically at about −20 to 150° C. and preferably at about 0 to 100° C., and the hydrogen pressure is set typically at 1 to 10 atm. Generally, the above described reaction is completed in about 0.5 to 100 hours. An acid such as hydrochloric acid may be added to the reaction system.

The reducing agent for use in the method (2) is a mixture of iron, zinc, tin or stannous chloride with a mineral acid such as hydrochloric acid or sulfuric acid; or a mixture of iron, ferrous sulfate, zinc or tin with an alkali metal hydroxide such as sodium hydroxide, a sulfate such as ammonium sulfate or an ammonium salt such as ammonium hydroxide or ammonium chloride. Examples of the inert solvent include water, acetic acid, alcohols such as methanol and ethanol, and ethers such as dioxane, and a mixture thereof. The reducing reaction conditions may be chosen appropriately depending on the reducing agent to be used. For example, when stannous chloride or hydrochloric acid is used as the reducing agent, the reaction is favorably carried out advantageously at about 0 to 150° C., for about 0.5 to 10 hours. The reducing agent is used in an amount at least an equimolar to the compound (68) and typically 1 to 5 times that of the compound (68) on a molar basis.

The reaction of the compound (69) and the compound (20) is carried out under the same reaction conditions as in the reaction of the compound (1b) and the compound (4) shown in reaction formula 2 above.

The reaction of the compound (69) and the compound (22) is carried out under the same reaction conditions as in the reaction of the compound (1b) and the compound (6) shown in reaction formula 2 above.

The reaction of the compound (69) and the compound (21) is carried out under the same reaction conditions as in the reaction of the compound (1b) and the compound (5) shown in reaction formula 2 above.

The reaction which converts the compound (69) into the compound (37a), the reaction which converts the compound (70a) into the compound (37d), the reaction which converts the compound (70b) into the compound (37c) and the reaction which converts the compound (70c) into the compound (37b) is carried out under the same reaction conditions as in hydrolysis B as described in reaction formula 9.

The reaction of the compound (71) and the compound (36) is carried out under the same reaction conditions as in the reaction of the compound (1b) and the compound (6) shown in reaction formula 2.

The reaction of the compound (69) and the compound (32) is carried out under the same reaction conditions as in the reaction of the compound (30) and the compound (32) shown in reaction formula 42 above.

[Reaction formula 48]

[Formula 128]

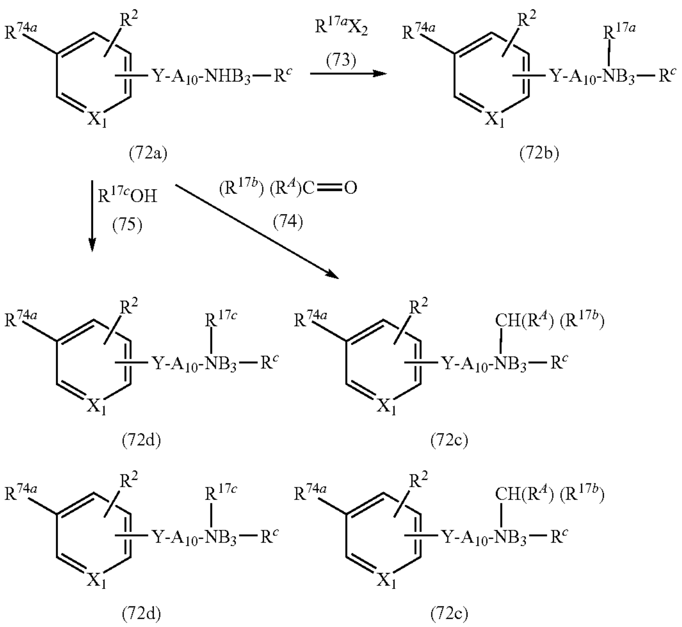

wherein $R^2$, $X_1$, Y, $A_{10}$, $B_3$, $R^{14}$, $R^{15}$, $R^4$, $R^{74a}$ and $X_2$ are the same as described above;

$R^c$ represents a group —$CONR^{14}R^{15}$ or a group —$COOR^{59b}$, $R^{59b}$ represents a lower alkyl group or a phenyl lower alkyl group;

$R^{17a}$ represents a lower alkyl group, a cycloalkyl group, a lower alkyl sulfonyl group or a lower alkenyl group;

$R^{17b}$ represents a hydrogen atom or a lower alkyl group; and $R^{17c}$ represents a cycloalkylcarbonyl group, a lower alkanoyl group which may have a halogen atom as a substituent or an amino substituted lower alkanoyl group which may have a lower alkyl group as a substituent (wherein a of $A_{10}$ is bound to a group Y and b is bound to a group —$NHB_3$—Rc, a group —$N(R^{17a})B_3$—Rc, a group —$N(CH(R^4)(R^{17b}))B_3$—Rc or a group —$N(R^{17c})B_3$—Rc.

The reaction of the compound (72a) and the compound (73) is carried out under the same reaction conditions as in the reaction of the compound (1b) and the compound (4) shown in reaction formula 2 above The reaction of the compound (72a) and the compound (75) is carried out under the same reaction conditions as in the reaction of the compound (1b) and the compound (6) shown in reaction formula 2 above.

The reaction of the compound (72a) and the compound (74) is carried out under the same reaction conditions as in the reaction of the compound (1b) and the compound (5) shown in reaction formula 2 above.

[Reaction formula 49]

[Formula 129]

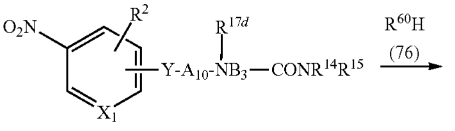

(72e)

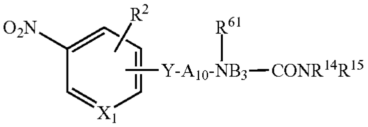

(72f)

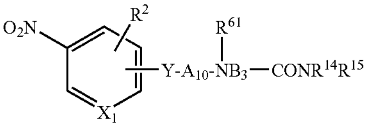

(72f)

wherein $R^2$, $X_1$, Y, $A_{10}$, $B_3$, $R^{14}$ and $R^{15}$ are the same as described above, $R^{17d}$ represents a lower alkanoyl group which has a halogen atom as a substituent, $R^{60}$ represents an amino group which may be substituted with a lower alkyl group, and $R^{61}$ represents an amino substituted lower alkanoyl group which may be substituted with a lower alkyl group, wherein a of $A_{10}$ is bound to a group Y and b is bound to a group $—N(R^{17d})B_3—CONR^{14}R^{15}$ or a group $—NR^{61}B_3—CONR^{14}R^{15}$.

The reaction of the compound (72e) and the compound (76) is carried out under the same reaction conditions as in the reaction of the compound (2) and the compound (3) shown in reaction formula 1 above.

wherein $R^2$, $X_1$, Y, $R^6$, $B_{21}$, $R^A$ and $X_2$ are the same as described above, and $A_{11}$ represents

[Formula 131]

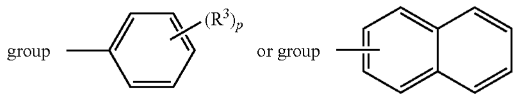

wherein $R^3$ and p are the same as described above, provided that the alkyl moiety in the side chain $(—NHCH(R^A)(B_{21}R^6)$ group) of the compound (78b) has not more than 6 carbon atoms.

The reaction which converts the compound (77a) into the compound (77b) is carried out under the same reaction conditions as in the reaction which converts the compound (68) into the compound (69) shown in reaction formula 47 above.

The reaction of the compound (77b) and the compound (20) is carried out under the same reaction conditions as in the reaction of the compound (1b) and the compound (4) shown in reaction formula 2 above.

The reaction of the compound (77b) and the compound (22) is carried out under the same reaction conditions as in the reaction of the compound (1b) and the compound (6) shown in reaction formula 2 above.

The reaction of the compound (77b) and the compound (21) is carried out under the same reaction conditions as in the reaction of the compound (1b) and the compound (5) shown in reaction formula 2 above.

[Reaction formula 50]

[Formula 130]

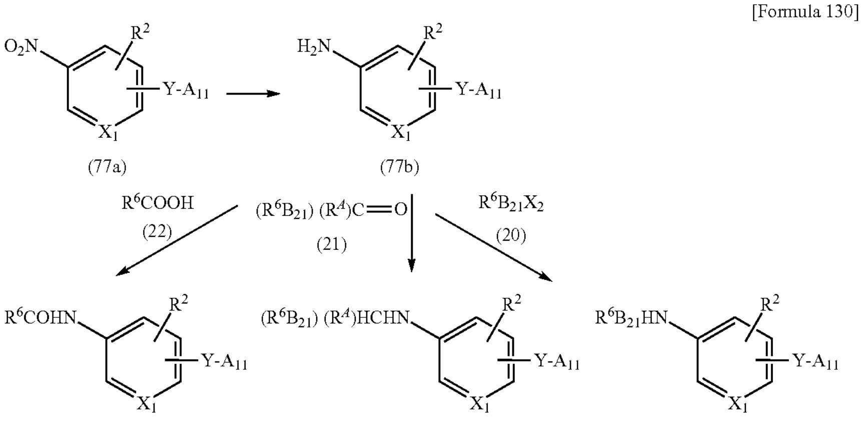

(77a)

(77b)

(78c)

(78b)

(78a)

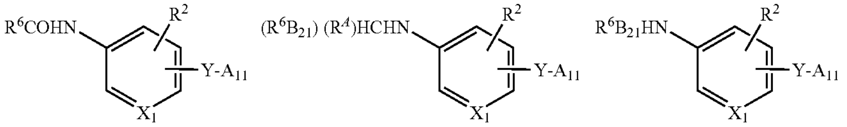

(78c)

(78b)

(78a)

[Reaction formula 51]

[Formula 132]

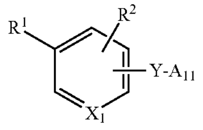

(77c)

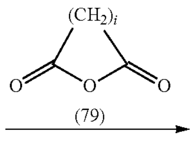

(79)

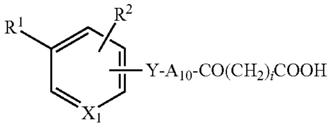

(37e')

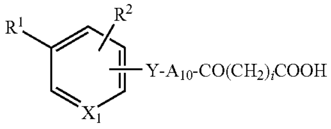

(37e')

wherein $R^1$, $R^2$, $X_1$, Y and $A_{11}$ are the same as described above, and i represents an integer of 2 to 4.

The reaction of the compound (77c) and the compound (79) is generally called Friedel-Crafts reaction and carried out in an appropriate solvent in the presence of a Lewis acid.

Any Lewis acid may be used herein as long as it is typically used in the Friedel-Crafts reaction. Examples of the Lewis acid include aluminum chloride, zinc chloride, iron chloride, tin chloride, boron tribromide, and concentrated sulfuric acid. These Lewis acids are used singly or in a mixture of two types or more. The Lewis acid is used typically in an amount 2 to 6 times that of the compound (77c) on a molar basis.

Examples of the solvent to be used herein include aromatic hydrocarbons such as carbon disulfide, nitrobenzene, and chlorobenzene, and halogenated hydrocarbons such as dichloromethane, dichloroethane, carbon tetrachloride, and tetrachloroethane, and a mixture thereof.

The compound (7 g) is used typically in at least an equimolar amount to the compound (77c) and preferably 1 to 5 times that of the compound (77c) on a molar basis.

The above described reaction favorably proceeds typically at 0 to 120° C. and preferably at about 0 to 70° C., and is generally completed in about 0.5 to 24 hours.

[Reation formula 52]

[Formula 133]

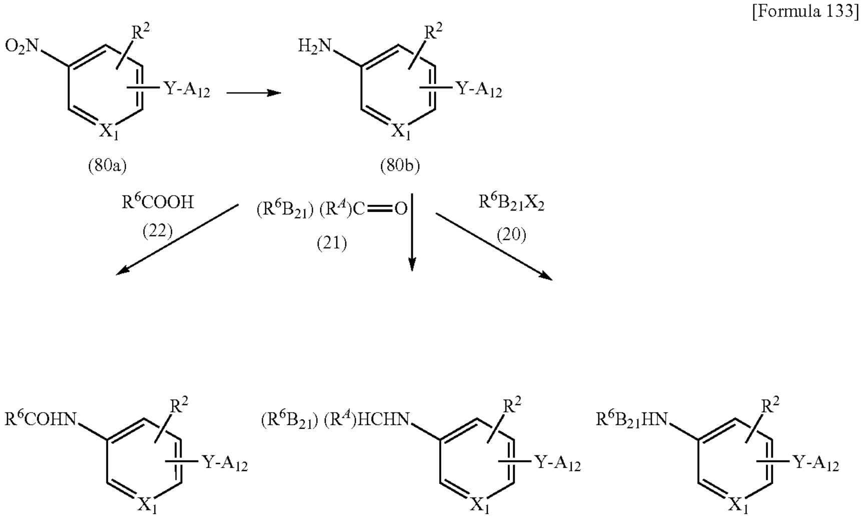

(81c) (81b) (81a)

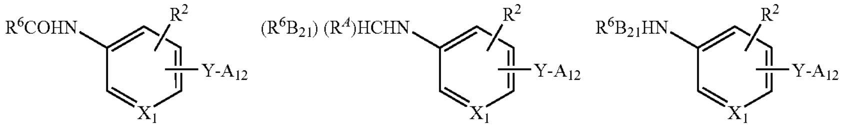

(81c) (81b) (81a)

wherein $R^2$, $X_1$, Y, $R^6$, $X_2$, $B_{21}$ and $R^4$ are the same as described above. $A_{12}$ represents a group

[Formula 134]

group 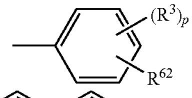 or group

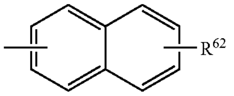

wherein $R^3$ and p are the same as defined above, and $R^{62}$ represents a lower alkanoyl group or a hydroxyl group substituted lower alkyl group, provided that the alkyl moiety in the side chain (—NHCH($R^4$)($B_{21}R^6$) group) of the compound (81b) has not more than 6 carbon atoms.

The reaction which converts the compound (80a) into the compound (80b) is carried out under the same reaction conditions as in the reaction which converts the compound (68) into the compound (69) shown in reaction formula 47 above.

The reaction of the compound (80b) and the compound (20) is carried out under the same reaction conditions as in the reaction of the compound (1b) and the compound (4) shown in reaction formula 2 above.

The reaction of the compound (80b) and the compound (22) is carried out under the same reaction conditions as in the reaction of the compound (1b) and the compound (6) shown in reaction formula 2 above.

The reaction of the compound (80b) and the compound (21) is carried out under the same reaction conditions as in the reaction of the compound (1b) and the compound (5) shown in reaction formula 2 above.

[Reaction formula 53]

[Formula 135]

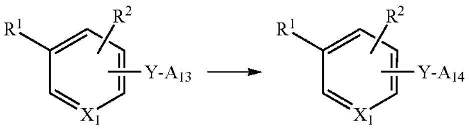

(80b') (35a)

wherein $R^1$, $R^2$, $X_1$, and Y are the same as above, $A_{13}$ represents a group

[Formula 136]

group 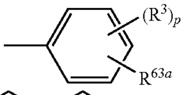 or group

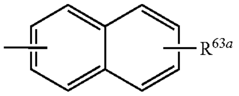

wherein $R^3$ and p are the same as described above, and $R^{63a}$ represents a lower alkanoyl group or a lower alkyl group, and $A_{14}$ represents a group

[Formula 137]

group 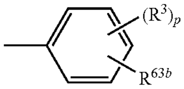 or group

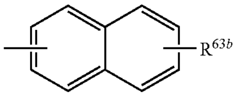

wherein $R^{63b}$ represents a lower alkanoyl group which is substituted with a halogen atom at the α-position or a lower alkyl group which is substituted with a halogen atom at the 2 position.

The reaction which converts the compound (80b') into the compound (35a) is carried out in the presence of a halogenating agent in an appropriate solvent.

Examples of the halogenating agent include halogen molecules such as bromine and chlorine, iodine chloride, sulfuryl chloride, copper compounds such as cupric bromide, and N-halogenated succinic acid imides such as N-bromosuccinic acid imide and N-chlorosuccinic acid imide.

Examples of the solvent to be used herein include halogenated hydrocarbons such as dichloromethane, dichloroethane, chloroform, and carbon tetrachloride, fatty acids such as acetic acid and propionic acid, and carbon disulfide.

The halogenating agent is favorably used typically in an amount 1 to 10 times and preferably 1 to 5 times that of the compound (80b') on a molar basis.

The above described reaction is carried out typically at 0° C. to the boiling point of the solvent and preferably at about 0 to 100° C., and completed typically for about 5 minutes to 30 hours.

When an N-halogenated succinic acid imide is used as a halogenating agent, a peroxide such as benzoyl peroxide may be added to the reaction system as a radical reaction initiator.

[Reaction formula 54]

[Formula 138]

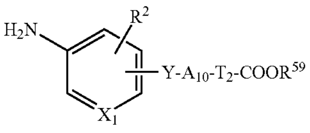

(69)

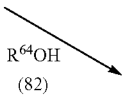

-continued

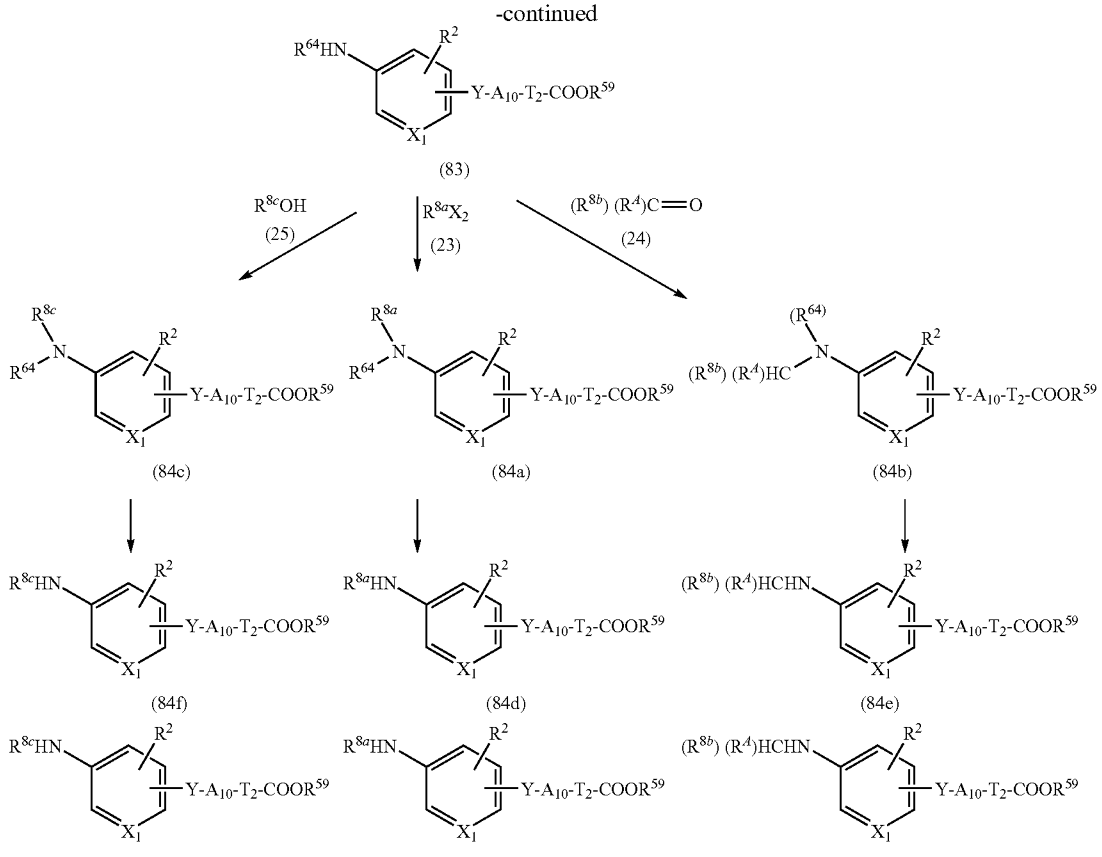

(83)

(84c) (84a) (84b)

(84f) (84d) (84e)

(84f) (84d) (84e)

wherein $R^2$, $X_1$, Y, $A_{10}$, $T_2$, $R^{59}$, $R^{8a}$, $R^{8b}$, $R^{8c}$, $X_2$ and $R^A$ are the same as described above, and $R^{64}$ represents a phenyl lower alkoxycarbonyl group, provided that each of the alkyl moieties in the side chain ($-N(CHR^AR^{8b})(R^{64})$ group) of the compound (84b) and the side chain ($-NH(CHR^AR^{8b})$ group) of the compound (84e) has not more than 6 carbon atoms and a and b of $A_{10}$ are bound to a group Y and a group $T_2$, respectively.

The reaction of the compound (83) and the compound (23) is carried out under the same reaction conditions as in the reaction of the compound (1b) and the compound (4) shown in reaction formula 2 above.

The reaction of the compound (69) and the compound (82), and the reaction of the compound (83) and the compound (25) are carried out under the same reaction conditions as in the reaction of the compound (1b) and the compound (6) shown in reaction formula 2 above.

The reaction of the compound (83) and the compound (24) is carried out under the same reaction conditions as in the reaction of the compound (1b) and the compound (5) shown in reaction formula 2 above.

The reactions which convert the compound (84a) into the compound (84d), the compound (84b) into the compound (84e), and the compound (84c) into the compound (84f) are carried out under the same reaction conditions as in the reaction in which the compound (1iii') is reduced to convert into the compound (1hhh') as described in reaction formula 24 above.

[Reaction formula 55]

[Formula 139]

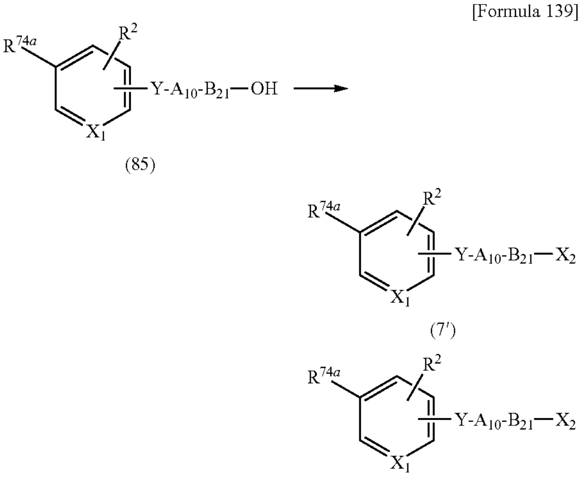

(85)

(7')

(7')

wherein $R^2$, $X_1$, Y, $A_{10}$, $B_{21}$, $R^{74a}$ and $X_2$ are the same as described above, provided that a and b of $A_{10}$ are bound to a group Y and a group $B_{21}$, respectively.

The reaction which converts the compound (85) into the compound (7') is carried out by reacting compound (85) with a halogenating agent in the presence or absence of an appropriate solvent.

Examples of the halogenating agent include mineral acids such as hydrochloric acid and hydrobromic acid, N,N-diethyl-1,2,2-trichlorovinyl azide, phosphorus pentachloride, phosphorus pentabromide, phosphorus oxychloride, sulfonyl halide compounds such as thionyl chloride, mesyl chloride, and tosyl chloride, and a mixture of carbon tetra bromide with triphenylphosphine. The sulfonyl halide compound may be used together with a basic compound.

Any basic compound may be used as long as it is used in the reaction of the compound (2) and the compound (3) shown in reaction formula 1 above.

Examples of the solvent to be used include ethers such as dioxane, tetrahydrofuran, and diethyl ether, halogenated hydrocarbons such as chloroform, methylene chloride, and carbon tetrachloride, and dimethylformamide, and a mixture thereof.

When a sulfonyl halide compound serving as a halogenating agent is used together with a basic compound, the sulfonyl halide compound is favorably used typically in at least an equimolar amount to the compound (85) and preferably 1 to 2 times that of the compound (85) on a molar basis. The basic compound is used typically in a catalytic amount of the compound (85) and preferably in a catalytic amount to an equimolar amount to the compound (85). When a halogenating agent other than sulfonyl halide compound is used, the halogenating agent is used in at least an equimolar amount to the compound (85) and typically used in a large excess amount.

The above described reaction favorably proceeds typically at room temperature to 200° C. and preferably at room temperature to 150° C., and is generally completed in about 1 to 80 hours.

[Reaction formula 56]

[Formula 140]

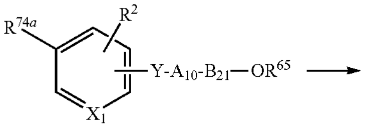

(86)

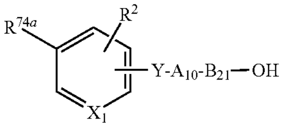

(85)

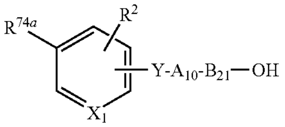

(85)

wherein $R^{74a}$, $R^2$, $X_1$, Y, $A_{10}$ and $B_2$, are the same as described above, and $R^{65}$ represents a tri-lower alkyl silyl group, provided that a and b of $A_{10}$ are bound to a group Y and a group $B_{21}$, respectively.

Examples of the tri-lower alkyl silyl group to be used herein include trialkylsilyl groups whose alkyl moiety is a linear or branched alkyl group having 1 to 6 carbon atoms such as tert-butyldimethylsilyl, trimethylsilyl, and diethylmethylsilyl groups.

The reaction which converts the compound (86) into the compound (85) may be carried out under the same reaction conditions as in hydrolysis B as described in reaction formula 9 above.

[Reaction formula 57]

[Formula 141]

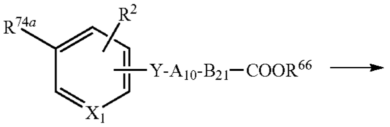

(69a)

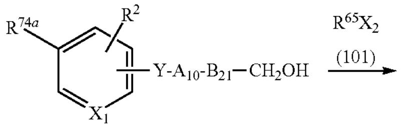

(85a)

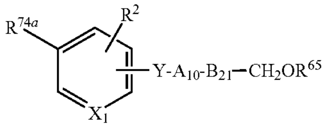

(86a)

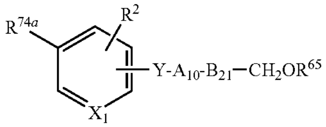

(86a)

wherein $R^{74a}$, $R^2$, $X_1$, Y, $A_{10}$, $B_{21}$, $R^{65}$ and $X_2$ are the same as described above, and $R^{66}$ represents a hydrogen atom, a lower alkyl group or a lower alkoxycarbonyl group, provided that a and b of $A_{10}$ are bound to a group Y and a group $B_{21}$, respectively, and each of the alkyl moieties in the side chain (—Y-$A_{10}$-$B_{21}CH_2OH$) of the compound (85a) and the side chain (—Y-$A_{10}$-$B_{21}CH_2OR^{65}$) of the compound (86a) has not more than 6 carbon atoms.

The reaction which converts the compound (69a) into the compound (85a) is carried out under the same reaction conditions as in the reaction which converts the compound (1f) into the compound (1g) shown in reaction formula 3 above.

The reaction of the compound (85a) and the compound (101) is carried out under the same reaction conditions as in the reaction which converts the compound (2) into the compound (3) shown in reaction formula 1 above.

[Reaction formula 58]

[Formula 142]

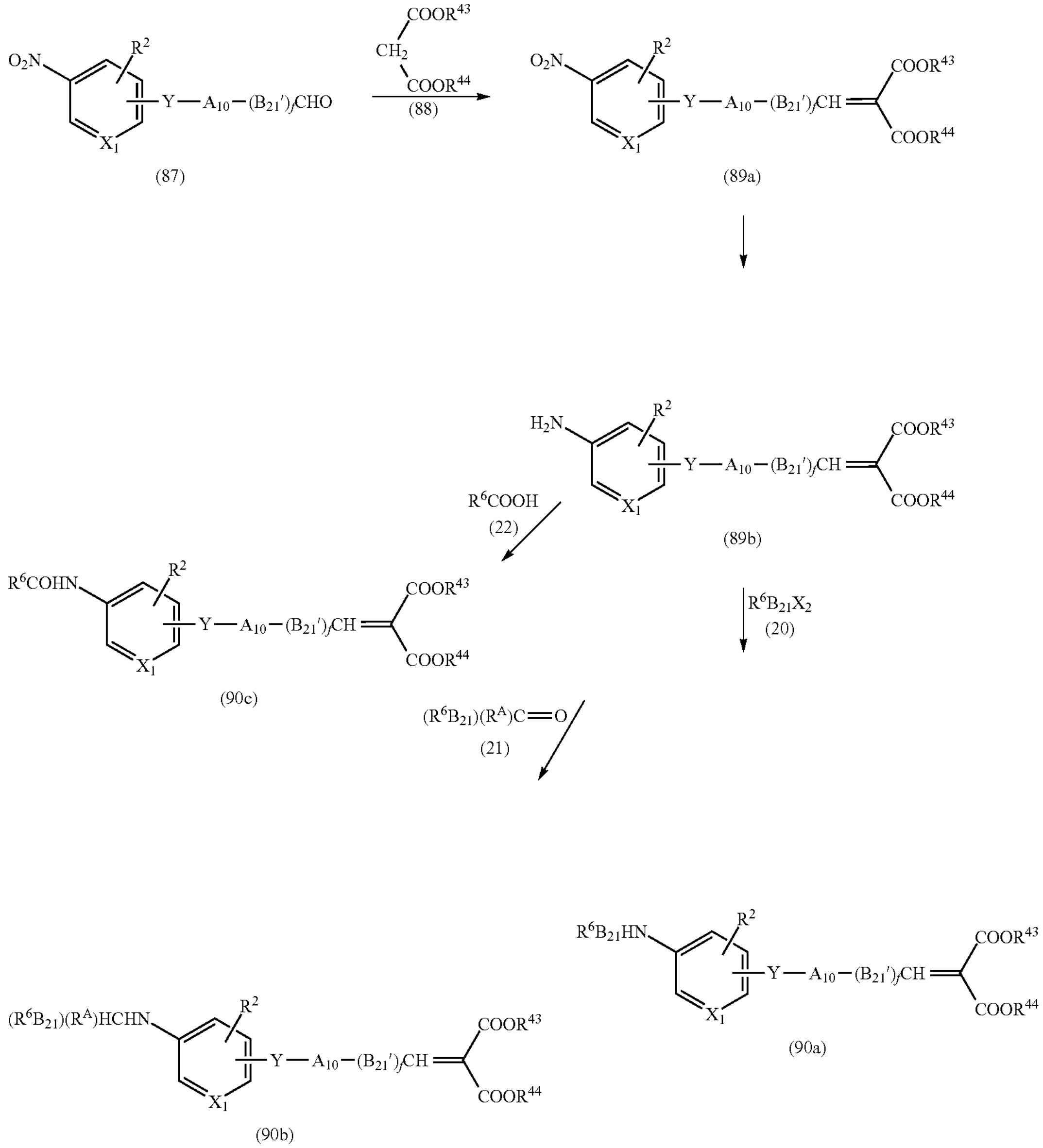

wherein $R^2$, $X_1$, Y, $A_{10}$, $B_{21}$, $R^6$, $R^A$, f, $R^{43}$, $R^{44}$ and $X_2$ are the same as described above, and $B_{21}$ represents a lower alkylene group, provided that a and b of $A_{10}$ are bound to a group Y and a group $B_{21'}$, respectively, and each of the $(B_{21'})$f-CH═C moiety in the side chain (—Y-$A_{10}$-$(B_{21'})$f-CH═C($COOR^{43}$)($COOR^{44}$)) of the compound (90c) and the alkyl moiety in the side chain (—NHCH($R^A$)$B_{21}R^6$)) of the compound (90b) have not more than 6 carbon atoms, respectively.

The reaction of the compound (87) and the compound (88) is carried out under the same reaction conditions as in the reaction of the compound (1f) and a hydroxylamine shown in reaction formula 3 above.

The reaction which converts the compound (89a) into the compound (89b) is carried out under the same reaction conditions as in the reaction which converts the compound (68) into the compound (69) shown in reaction formula 47 above.

The reaction of the compound (89b) and the compound (20) is carried out under the same reaction conditions as in the reaction of the compound (1b) and the compound (4) shown in reaction formula 2 above.

The reaction of the compound (89b) and the compound (22) is carried out under the same reaction conditions as in the reaction of the compound (1b) and the compound (6)shown in reaction formula 2 above.

The reaction of the compound (89b) and the compound (21) is carried out under the same reaction conditions as in the reaction of the compound (1b) and the compound (5) shown in reaction formula 2 above.

[Reaction formula 59]

[Formula 143]

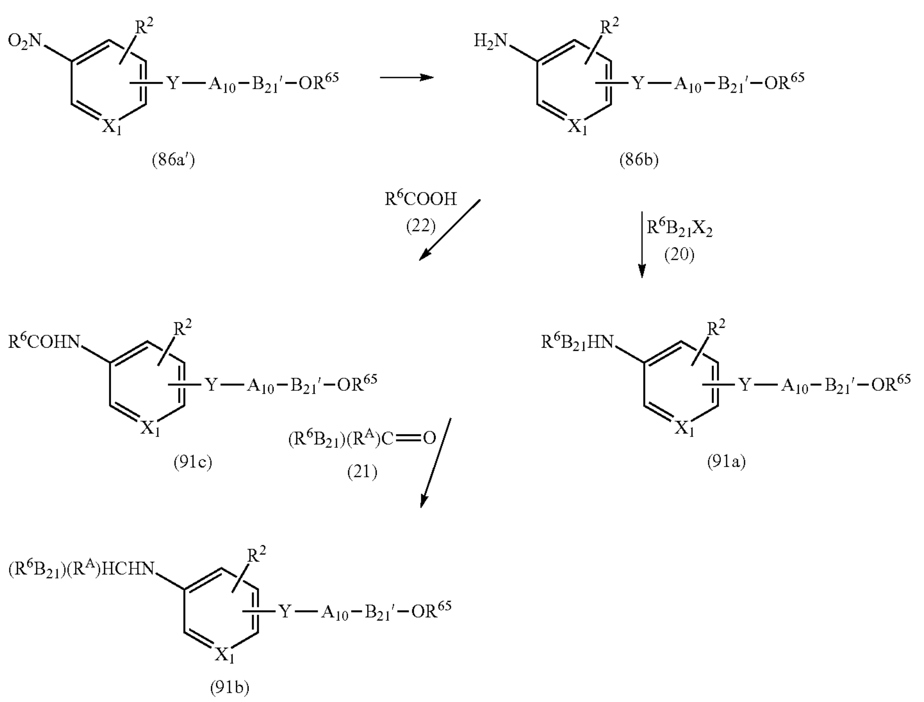

wherein $R^2$, $X_1$, Y, $A_{10}$, $B_{21'}$, $R^{65}$, $R^6$, $B_{21}$, $R^A$ and $X_2$ are the same as defined above, provided that a and b of $A_{10}$ are bound to a group Y and a group $B_{21'}$, respectively, and the alkyl moiety in the side chain (—NHCH($R^A$)($B_{21}R^6$)) of the compound (91b) has not more than 6 carbon atoms.

The reaction which converts the compound (86a') into the compound (86b) is carried out under the same reaction conditions as in the reaction which converts the compound (68) into the compound (69) shown in reaction formula 47 above.

The reaction of the compound (86b) and the compound (20) is carried out under the same reaction conditions as in the reaction of the compound (1b) and the compound (4) shown in reaction formula 2 above.

The reaction of the compound (86b) and the compound (22) is carried out under the same reaction conditions as in the reaction of the compound (1b) and the compound (6) shown in reaction formula 2 above.

The reaction of the compound (86b) and the compound (21) is carried out under the same reaction conditions as in the reaction of the compound (1b) and the compound (5) shown in reaction formula 2 above.

[Reaction formula 60]

[Formula 144]

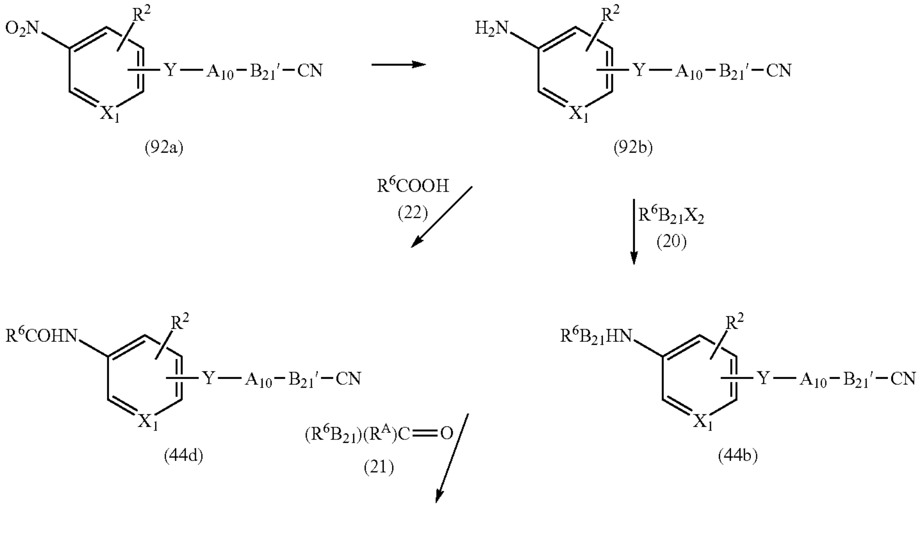

-continued

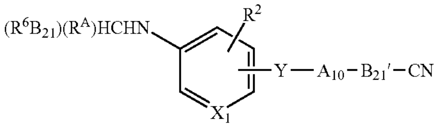

(44c)

wherein $R^2$, $X_1$, Y, $A_{10}$, $B_{21}$, $B_{21'}$, $R^6$, $R^A$ and $X_2$ are the same as described above, provided that a and b of $A_{10}$ are bound to a group Y and a group $B_{21'}$, respectively, and the alkyl moiety in the side chain (—$NHCH(R^A)(B_{21}R^6)$) of the compound (44c) has not more than 6 carbon atoms.

The reaction which converts the compound (92a) into the compound (92b) is carried out under the same reaction conditions as in the reaction which converts the compound (68) into the compound (69) shown in reaction formula 47 above.

The reaction of the compound (92b) and the compound (20) is carried out under the same reaction conditions as in the reaction of the compound (1b) and the compound (4) shown in reaction formula 2 above.

The reaction of the compound (92b) and the compound (22) is carried out under the same reaction conditions as in the reaction of the compound (1b) and the compound (6) shown in reaction formula 2 above.

The reaction of the compound (92b) and the compound (21) is carried out under the same reaction conditions as in the reaction of the compound (1b) and the compound (5) shown in reaction formula 2 above.

[Reaction formula 61]

[Formula 145]

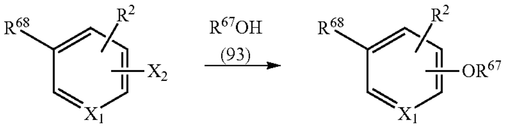

(94) (95)

[Formula 145]

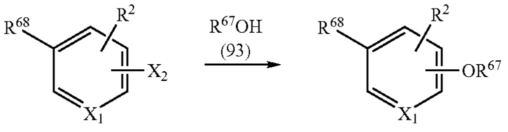

(94) (95)

wherein $R^2$, $X_1$, and $X_2$ are the same as described above, $R^{67}$ represents a group -$A_{10}B_{21}CN$, a group -$A_{10}$-$R^{59d}$ a group -$A_{10}$-$T_2$-$COOR^{59a}$ or a group -A, $R^{59d}$ represents a lower alkyl group, $A_{10}$, $B_{21}$, $T_2$ and $R^{59a}$ are the same as described above, and $R^{68}$ represents a nitro group or a halogen atom.

The reaction of the compound (93) and the compound (94) is carried out under the same reaction conditions as in the reaction of the compound (2) and the compound (3) shown in reaction formula 1 above.

[Reaction formula 62]

[Formula 146]

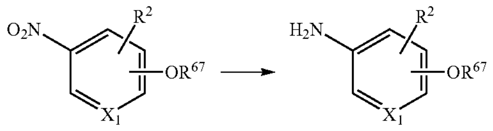

(95a) (95b)

wherein $R^2$, $R^{67}$ and $X_1$ are the same as described above.

The reaction which converts the compound (95a) into the compound (95b) is carried out under the same reaction conditions as in the reaction which converts the compound (68) into the compound (69) shown in reaction formula 47 above.

[Reaction formula 63]

[Formula 147]

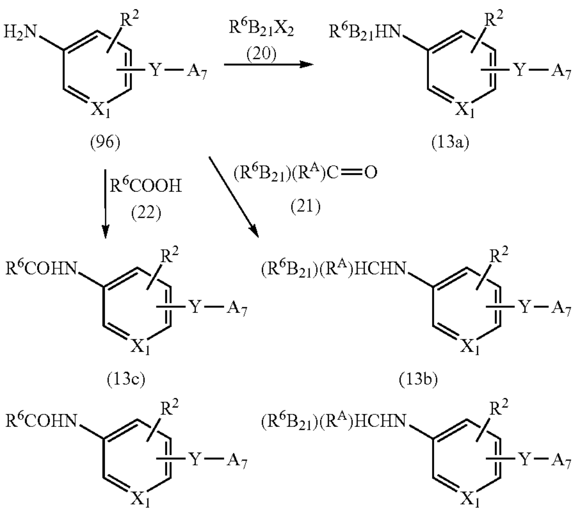

wherein $R^2$, $X_1$, Y, $A_7$, $R^6$, $B_{21}$, $R^A$ and $X_2$ are the same as described above, provided that the alkyl moiety in the side chain (—$NHCH(R^A)(B_{21}R^6)$) of the compound (13b) has not more than 6 carbon atoms.

The reaction of the compound (96) and the compound (20) is carried out under the same reaction conditions as in the reaction of the compound (1b) and the compound (4) shown in reaction formula 2.

The reaction of the compound (96) and the compound (22) is carried out under the same reaction conditions as in the reaction of the compound (1b) and the compound (6) shown in reaction formula 2 above.

The reaction of the compound (96) and the compound (21) is carried out under the same reaction conditions as in the reaction of the compound (1b) and the compound (5) shown in reaction formula 2 above.

The reaction of the compound (97b) and the compound (21) is carried out under the same reaction conditions as in the reaction of the compound (1b) and the compound (5) shown in reaction formula 2.

[Reaction formula 64]

[Formula 148]

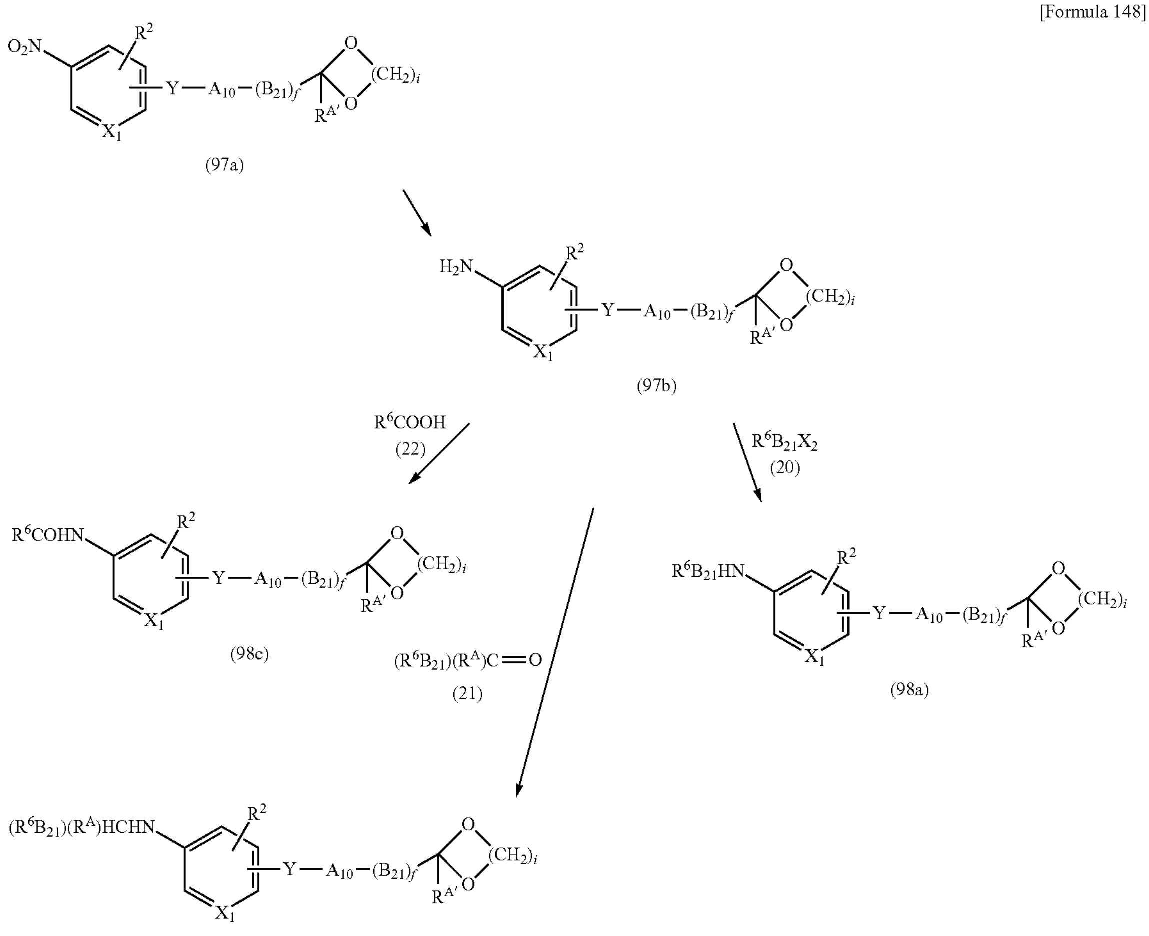

(97a)

(97b)

(98c)

(98a)

(98b)

wherein $R^2$, $X_1$, Y, $B_{21}$, f, i, $R^6$, $B_{21}$, $A_{10}$, $R^A$ and $X_2$ are the same as described above, and $R^{A'}$ represents a hydrogen atom or a lower alkyl group, provided that the alkyl moiety in the side chain (—NHCH($R^A$)($B_{21}R^6$)) in compound (98b) has not more than 6 carbon atoms, and a and b of $A_{10}$ are bound to a group Y and a group $(B_{21})$f, respectively.

The reaction which converts the compound (97a) into the compound (97b) is carried out under the same reaction conditions as in the reaction which converts the compound (68) into the compound (69) shown in reaction formula 47 above.

The reaction of the compound (97b) and the compound (20) is carried out under the same reaction conditions as in the reaction of the compound (1b) and the compound (4) shown in reaction formula 2 above.

The reaction of the compound (97b) and the compound (22) is carried out under the same reaction conditions as in the reaction of the compound (1b) and the compound (6) shown in reaction formula 2 above.

[Reaction formula 65]

[Formula 149]

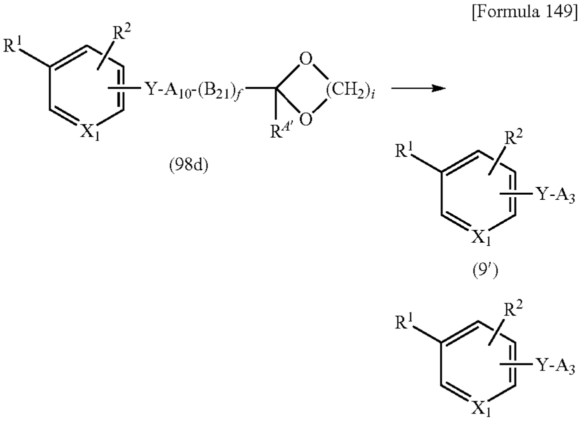

(98d)

(9')

(9')

wherein $R^1$, $R^2$, $X_1$, Y, $A_{10}$, $B_{21}$, f, $R^{A'}$ and $A_3$ are the same as described above, provided that a and b of $A_{10}$ are bound to a group Y and a group $(B_{21})$f, respectively.

The reaction which converts the compound (98d) into the compound (9') may be carried out under the same reaction conditions as in hydrolysis B described in reaction formula 9 above.

[Reaction formula 66]

[Formula 150]

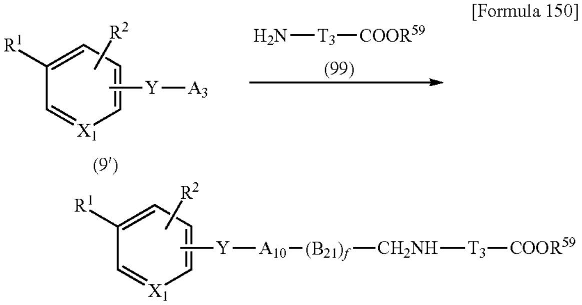

(9')

(69b)

wherein $R^1$, $R^2$, $X_1$, Y, $A_3$, $R^{59}$, $A_{10}$, $B_{21}$ and f are the same as described above, $T_3$ represents a direct bond or group $B_7$, and $B_7$ represents the same as described above, provided that a and b of $A_{10}$ are bound to a group Y and a group $(B_{21})$f, respectively.

The reaction of the compound (9') and the compound (99) is carried out under the same reaction conditions as in the reaction of the compound (1b) and the compound (5) shown in reaction formula 2 above.

wherein $R^3$, $X_1$, Y, $A_{10}$, $R^{14a}$, $R^{49a}$, $R^{49}$, $R^{49b}$, T, l, $R^A$ and $X_2$ are the same as described above, provided that the $CHR^A$ moiety in the side chain (—$N(R^{14a})(CHR^AR^{49b})$) of the compound (104c) has not more than 6, a of $A_{10}$ is bound to a group Y, and b of $A_{10}$ is bound to a group —$NR^{14a}H$, a group $NR^{14a}R^{49a}$ a group —$NR^{14a}R^{49}$, or a group —$NR^{14a}(CHR^AR^{49b})$.

The reaction of the compound (103) and the compound (38a) is carried out under the same reaction conditions as in the reaction of the compound (1b) and the compound (4) shown in reaction formula 2 above.

The reaction of the compound (103) and the compound (38) is carried out under the same reaction conditions as in the reaction of the compound (1b) and the compound (6) shown in reaction formula 2 above.

The reaction of the compound (103) and the compound (38b) is carried out under the same reaction conditions as in the reaction of the compound (1b) and the compound (5) shown in reaction formula 2 above.

[Reaction formula 68]

[Formula 152]

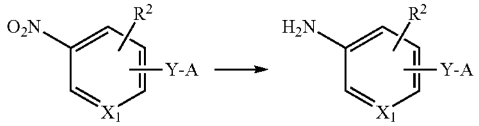

(105) (19a)

wherein $R^2$, $X_1$, Y and A are the same as described above.

The reaction which converts the compound (105) into the compound (19a) is carried out under the same reaction con ditions as in the reaction which converts the compound (68) into the compound (69) shown in reaction formula 47 above. The compound (19a) can be subjected to the following reaction without isolation.

[Reaction formula 67]

[Formula 151]

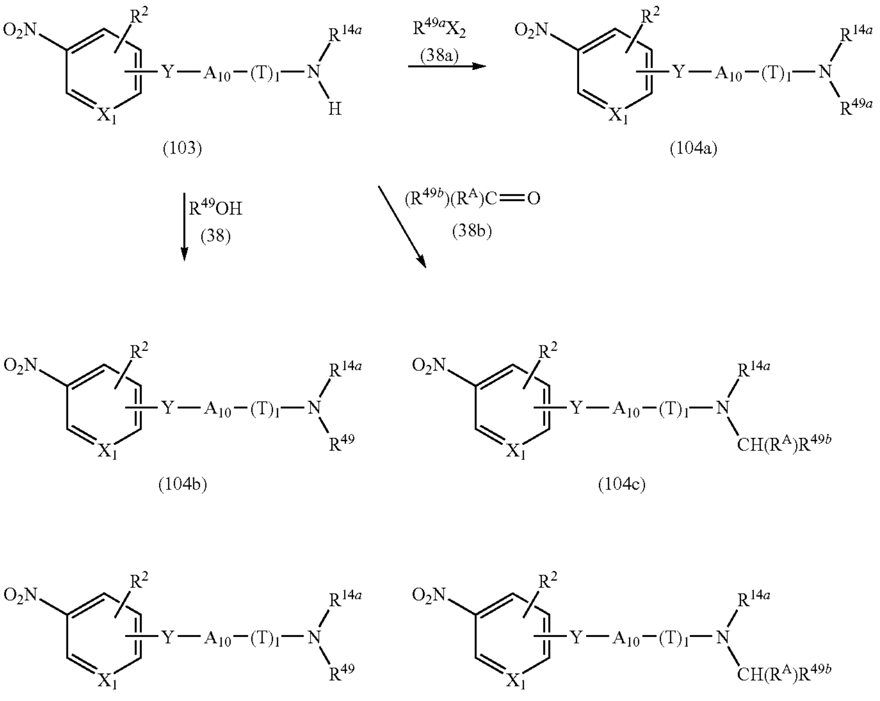

(103) (104a)

(104b) (104c)

(104b) (104c)

[Reaction formula 69]

[Formula 153]

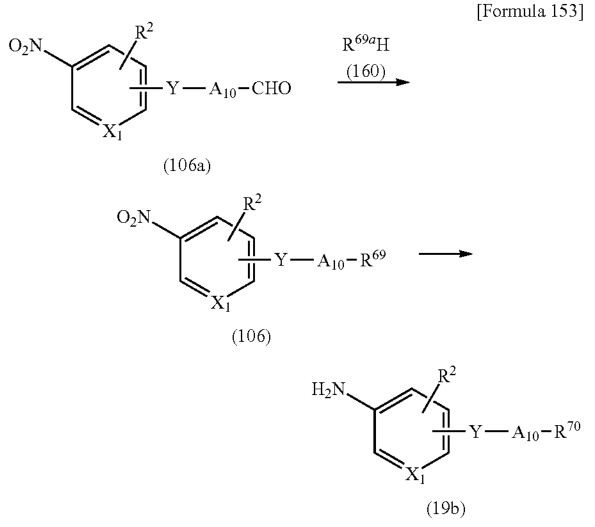

wherein $R^2$, $X_1$, Y and $A_{10}$ are the same as described above, $R^{69a}$ represents a thiazolidinyl group which may have an oxo group as a substituent on the thiazolidine ring, $R^{69}$ represents a thiazolidinylidene lower alkyl group which may have an oxo group as a substituent on the thiazolidine ring, and $R^{70}$ represents a thiazolidinyl lower alkyl group which may have an oxo group as a substituent on the thiazolidine ring, provided that a of $A_{10}$ is bound to a group Y and b of $A_{10}$ is bound to a group —$R^{69}$ or a group —$R^{70}$.

The reaction of the compound (106a) and the compound (160) is carried out under the same reaction conditions as in the reaction of the compound (87) and the compound (88) shown in reaction formula 58 above.

The reaction which converts the compound (106) into the compound (19b) is carried out under the same reaction conditions as in the reaction which converts the compound (68) into the compound (69) shown in reaction formula 47 above.

[Reaction formula 70]

[Formula 154]

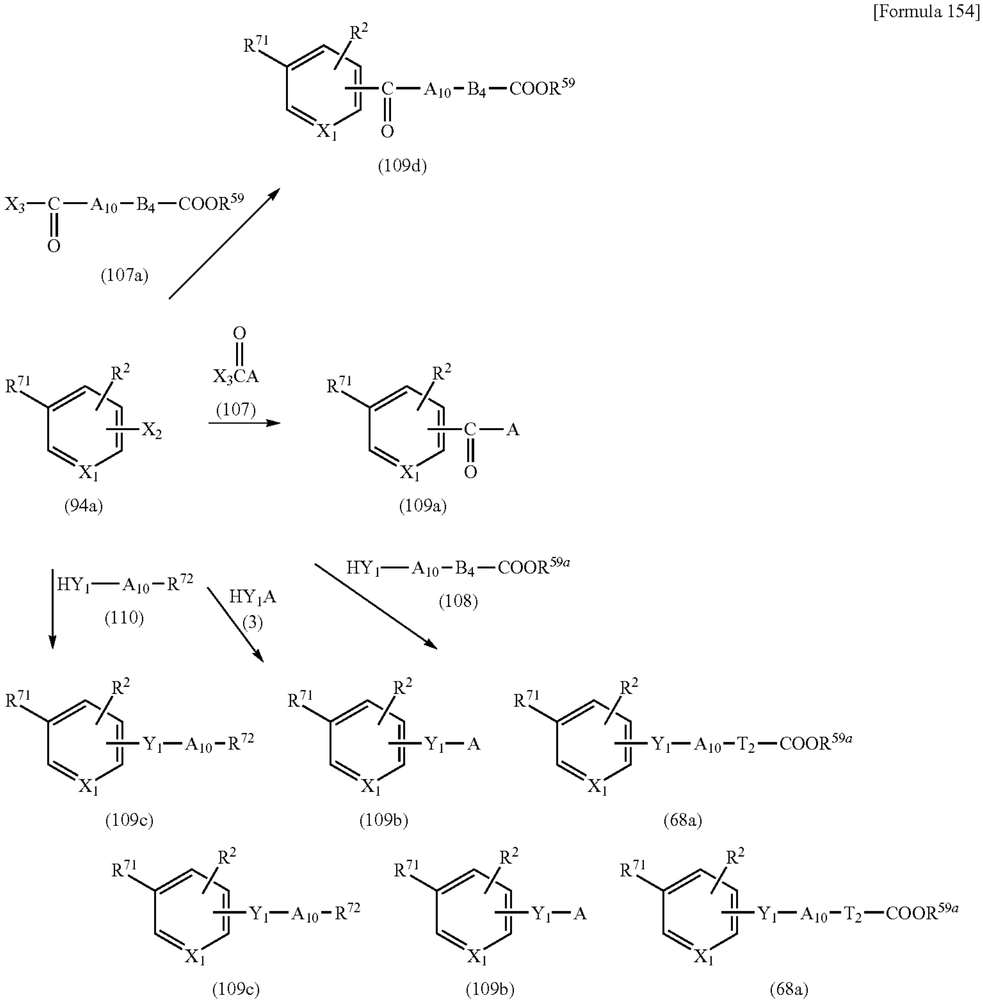

wherein $R^2$, $X_1$, $X_2$, A, $Y_1$, $A_{10}$, $T_2$, $R^{59}$ and $R^{59a}$ are the same as described above, $R^{71}$ represents a group —$R^1$ (wherein $R^1$ is the same as described above), a nitro group or a lower alkoxycarbonyl group, $X_3$ represents a halogen atom, and $R^{72}$ represents a lower alkyl group which may have a hydroxyl group as a substituent, a nitro group, an amino group which may have a lower alkanoyl group, a carboxy lower alkyl group, a —$(B_{21})fC(=O)R^A$ group (wherein $B_{21}$, f and $R^A$ are the same as described above), a lower alkanoyl group, a lower alkoxy group or a hydrogen atom; provided that a of $A_{10}$ is bound to a group $Y_1$ and b of $A_{10}$ is bound to a group -$T_2$ or a group —$R^{72}$.

The reaction of the compound (94a) and the compound (107), and the reaction of the compound (94a) and the compound (107a) each are carried out in an appropriate solvent and in the presence of a catalyst.

Any solvent may be used herein as long as it is used in the reaction of the compound (2) and the compound (3) shown in reaction formula 1.

As the catalyst to be used herein, various metal complexes as well as various combinations of a metal complex and a ligand may be used. Examples of the metal complexes include, palladium acetate (II), tetrakis(triphenylphosphine) palladium(0), and tris(dibenzylideneacetone)dipalladium(0). Examples of the ligand include. R-2,2'-bis(diphenylphosphino)-1,1'-binaphthyl (R-BINAP), S-2,2'-bis(diphenylphosphino)-1,1'-binaphthyl (S-BINAP), RAC-2,2'-bis (diphenylphosphino)-1,1'-binaphthyl (RAC-BINAP), t-butylphosphine, and 4,5-bis(diphenylphosphino)-9,9-dimethylxanthene.

Such a catalyst is favorably used typically in at least an equimolar amount to the compound (94a) and preferably 1 to 5 times that of the compound (94a) on a molar basis.

The above described reaction is carried out typically at about 0 to 200° C. and preferably at about 0 to 150° C., and generally completed in about 30 minutes to 10 hours.

When molecular sieves such as Molecular Sieves 3A (MS3A) or Molecular Sieves 4A (MS4A) or a phosphorus compound such as triphenylphosphine or tri(2-furyl)phosphine are added in the reaction system, the reaction proceeds advantageously.

The reaction of the compound (94a) and the compound (108), compound (3) or compound (110) is carried out under the same reaction conditions as in the reaction of the compound (2) and the compound (3) shown in reaction formula 1 above.

The compound (109c) wherein $R^{71}$ represents a lower alkoxycarbonyl group, may be converted into the corresponding compound (109c) wherein $R^7$ represents a carboxy group, by hydrolyzing it under the same reaction conditions as in hydrolysis B described in reaction formula 9 above.

[Reaction formula 71]

[Formula 155]

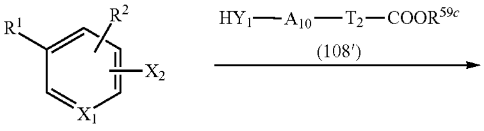

(2)

-continued

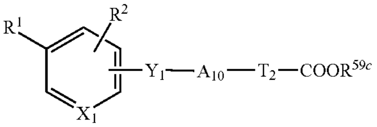

(68b)

wherein $R^1$, $R^2$, $X_1$, $X_2$, $Y_1$, $A_{10}$ and $T_2$ are the same as described above, and $R^c$ represents a hydrogen atom, a lower alkyl or a phenyl lower alkyl group, provided that a and b of $A_{10}$ are bound to a group Y, and a group -$T_2$, respectively.

The reaction of the compound (2) and the compound (108') is carried out under the same reaction conditions as in the reaction of the compound (2) and the compound (3) shown in reaction formula 1 above.

[Reaction formula 72]

[Formula 156]

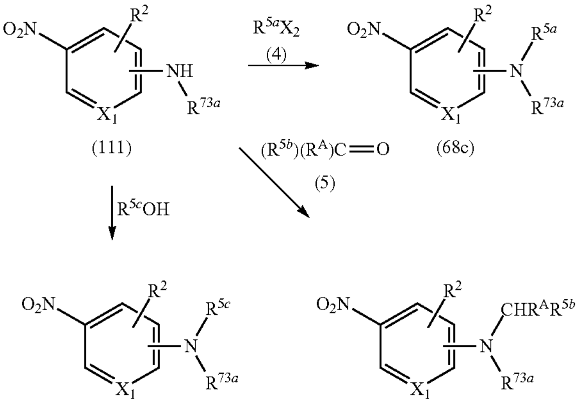

(111) (68c) (68e) (68d)

wherein $R^2$, $X_1$, $R^{5a}$, $R^{5b}$, $R^A$, $R^{5c}$ and $X_2$ are the same as described above, and $R^{73a}$ represents a group -$A_{10}$-$T_2$-$COOR^{59}$ (wherein $A_{10}$, $T_2$ and $R^{59}$ are the same as described above) or a group -A (wherein A is the same as described above), provided that a of $A_{10}$ is bound to a group —NH—, group —$NR^{5a}$—, group —$N(CHR^AR^{5b})$— or a group —$NR^{5c}$—, and b of $A_{10}$ is bound to a group -$T_2$, and the alkyl moiety in the side chain (—$N(R^{73a})(CHR^AR^{5b})$) of the compound (68d) has not more than 6 carbon atoms.

The reaction of the compound (111) and the compound (4) is carried out under the same reaction conditions as in the reaction of the compound (1b) and the compound (4) shown in reaction formula 2 above.

The reaction of the compound (111) and the compound (6) is carried out under the same reaction conditions as in the reaction of the compound (1b) and the compound (6) shown in reaction formula 2 above.

The reaction of the compound (111) and the compound (5) is carried out under the same reaction conditions as in the reaction of the compound (1b) and the compound (5) shown in reaction formula 2 above.

[Reaction formula 73]

[Formula 157]

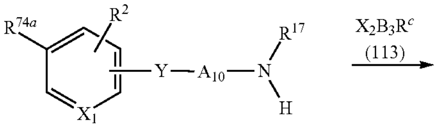

(112)

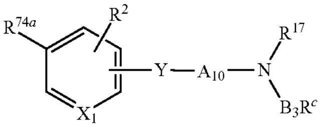

(109d')

wherein $R^2$, $X_1$, Y, $A_{10}$, $X_2$, $R^{17}$, $B_3$, $R^{74a}$ and $R^c$ are the same as described above, provided that a of $A_{10}$ is bound to a group —Y and b of $A_{10}$ is bound to a group —$NHR^{17}$ or a group —$NR^{17}B_3R^c$.

The reaction of the compound (112) and the compound (113) is carried out under the same reaction conditions as in the reaction of the compound (1b) and the compound (4) shown in reaction formula 2 above.

[Reaction formula 74]

[Formula 158]

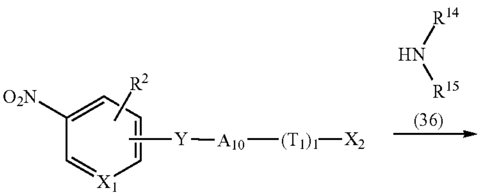

(114)

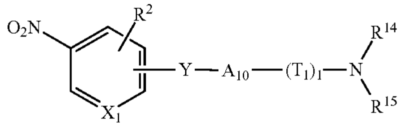

(109e)

wherein $R^2$, $X_1$, Y, $A_{10}$, $T_1$, l, $R^{14}$ and $R^{15}$ are the same as described above, provided that a and b of $A_{10}$ are bound to a group —Y and a group -$(T_1)$l, respectively.

The reaction of the compound (114) and the compound (36) is carried out under the same reaction conditions as in the reaction of the compound (1b) and the compound (5) shown in reaction formula 2 above.

The compound (109e) in which l is 0 may also be produced by reacting the corresponding compound (114) and the compound (36) in an appropriate solvent in the presence of a basic compound and a catalyst.

The above described reaction is carried out under the same reaction conditions as in reaction C described in reaction formula 13 above.

[Reaction formula 75]

[Formula 159]

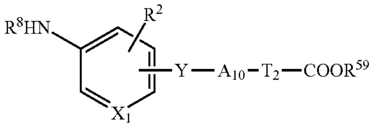

(84g)

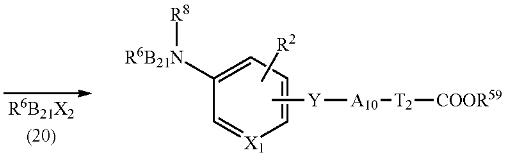

(84h)

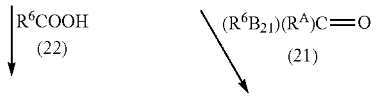

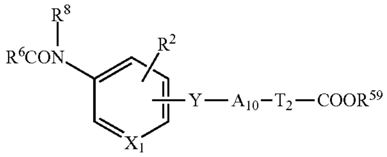

(84j)

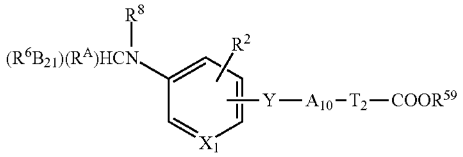

(84i)

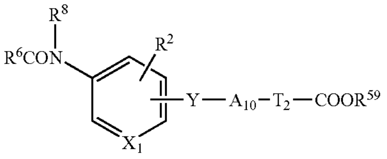

(84j)

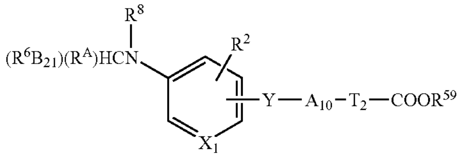

(84i)

wherein $R^2$, $X_1$, Y, $R^8$, $B_{21}$, $R^6$, $A_{10}$, $T_2$, $R^{59}$, $R^A$ and $X_2$ are the same as described above, provided that the $CHR^AB_{21}$ moiety in the side chain (—$N(R^8)(CH(R^A)B_{21}R^6)$) of the compound (84i) has not more than 6 carbon atoms, and a and b of $A_{10}$ are bound to a group —Y and a group -$T_2$, respectively.

The reaction of the compound (84g) and the compound (20) is carried out under the same reaction conditions as in the reaction of the compound (1b) and the compound (4) shown in reaction formula 2 above.

The reaction of the compound (84g) and the compound (22) is carried out under the same reaction conditions as in the reaction of the compound (1b) and the compound (6) shown in reaction formula 2 above.

The reaction of the compound (84g) and the compound (21) is carried out under the same reaction conditions as in the reaction of the compound (1b) and the compound (5) shown in reaction formula 2 above.

[Reaction formula 76]

[Formula 160]

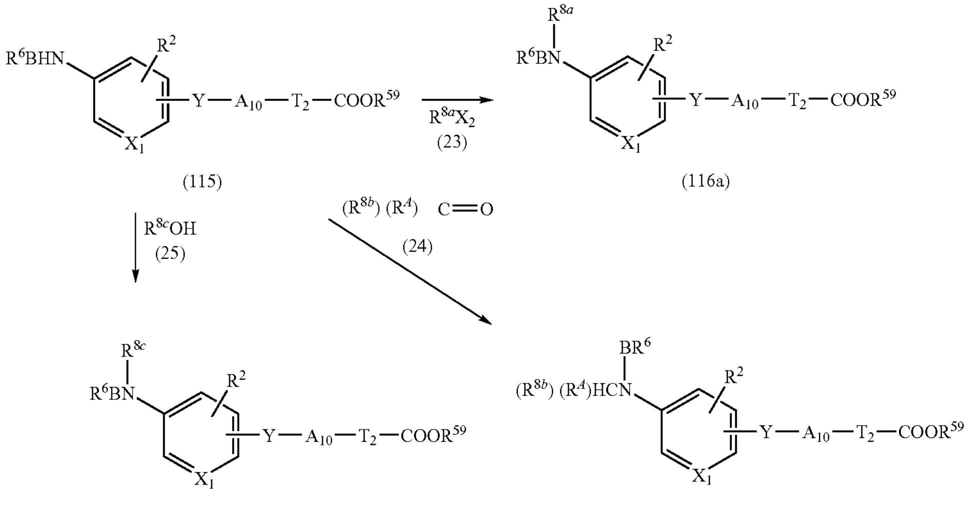

(115) (116a) (116c) (116b)

wherein $R^2$, $X_1$, Y, $R^{8a}$, $R^{8b}$, $R^{8c}$, B, $R^6$, $A_{10}$, $T_2$, $R^{59}$, $R^A$ and $X_2$ are the same as described above, provided that the $CHR^A$ moiety in the side chain (—$NB(R^6)(CH(R^A)R^{8b})$) of the compound (116b) has not more than 6 carbon atoms, and a and b of $A_{10}$ are bound to a group —Y and a group -$T_2$, respectively.

The reaction of the compound (115) and the compound (23) is carried out under the same reaction conditions as in the reaction of the compound (1b) and the compound (4) shown in reaction formula 2 above.

The reaction of the compound (115) and the compound (25) is carried out under the same reaction conditions as in the reaction of the compound (1b) and the compound (6) shown in reaction formula 2 above.

The reaction of the compound (115) and the compound (24) is carried out under the same reaction conditions as in the reaction of the compound (1b) and the compound (5) shown in reaction formula 2 above.

[Reaction formula 77]

[Formula 161]

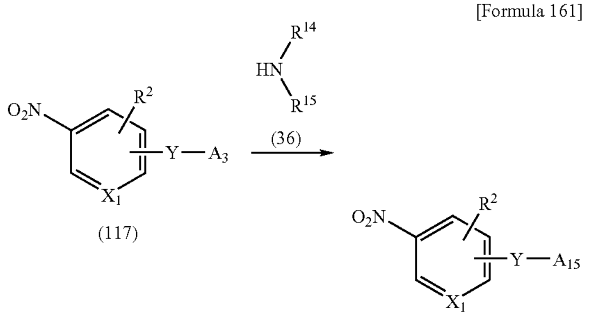

(117) (118)

wherein $R^2$; $X_1$, Y, $A_3$, $R^{14}$ and $R^{15}$ are the same as described above, and $A_{15}$ represents a group

[Formula 162]

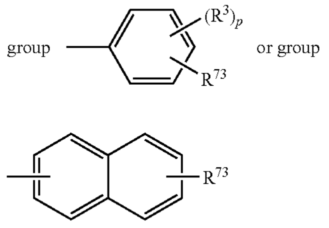

wherein $R^{73}$ represents a group —$(B_{21})fCH(R^A)(NR^{14}R^{15})$, and $B_{21}$, f and $R^A$ are the same as described above, provided that the $(B_{21})fCH(R^A)$ moiety has not more than 6 carbon atoms.

The reaction of the compound (117) and the compound (36) is carried out the same reaction conditions as in the reaction of the compound (1b) and the compound (5) shown in reaction formula 2.

[Reaction formula 78]

[Formula 163]

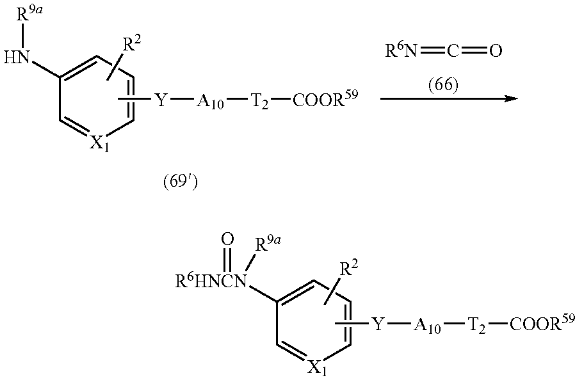

(69')

(119)

wherein, $R^2$, $X_1$, Y, $A_{10}$, $T_2$, $R^6$, $R^{9a}$ and $R^{59}$ are the same as described above, provided that a and b of $A_{10}$ are bound to a group —Y and a -$T_2$ group, respectively.

The reaction of the compound (69') and the compound (66) is carried out under the same reaction conditions as in the reaction of the compound (30) and the compound (66) shown in reaction formula 46 above.

[Reaction formula 79]

[Formula 164]

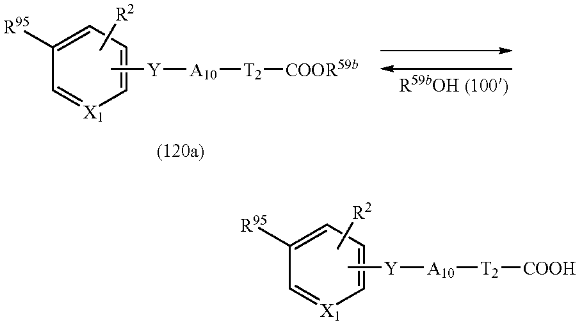

(120a)

(120b)

wherein $R^{95}$, $R^2$, $X_1$, Y, $A_{10}$, $T_2$, and $R^{59b}$ are the same as described above, provided that a and b of $A_{10}$ are bound to a group —Y and a group -$T_2$, respectively.

The reaction which converts the compound (120a) into the compound (120b) may be carried out under the same reaction conditions as in hydrolysis B described for reaction formula 9 above.

The reaction of the compound (120b) and the compound (100') is carried out under the same reaction conditions as in the reaction of the compound (1fff) and the compound (43) in reaction formula 20 above.

The compound (120a) may also be produced using a lower alkyl halide such as methyl iodide in place of the compound (100') under the same reaction conditions as in the reaction of the compound (2) and the compound (3) shown in reaction formula 1 above.

[Reaction formula 80]

[Formula 165]

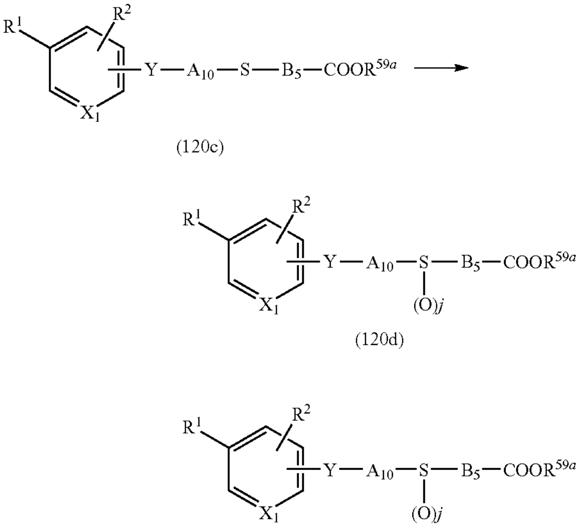

(120c)

(120d)

(120d)

wherein $R^1$, $R^2$, $X_1$, Y, $A_{10}$, $B_5$, $R^{59a}$ and j are the same as described above, provided that a and b of $A_{10}$ are bound to a group —Y and a group —S, respectively.

The reaction which converts the compound (120c) into the compound (120d) is carried out under the same reaction conditions as in the reaction which converts the compound (1zzzz) into the compound (1aaaaa) in reaction formula 4 above.

[Reaction formula 81]

[Formula 166]

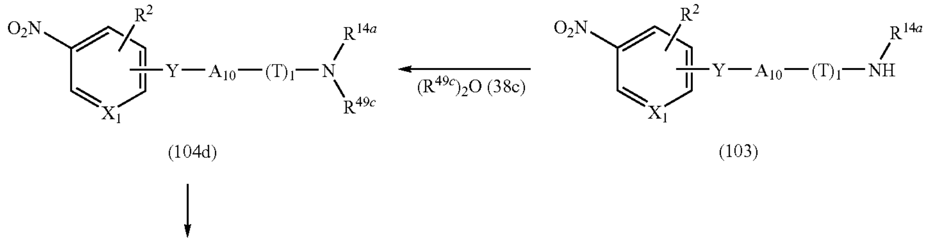

(104d)

(103)

-continued

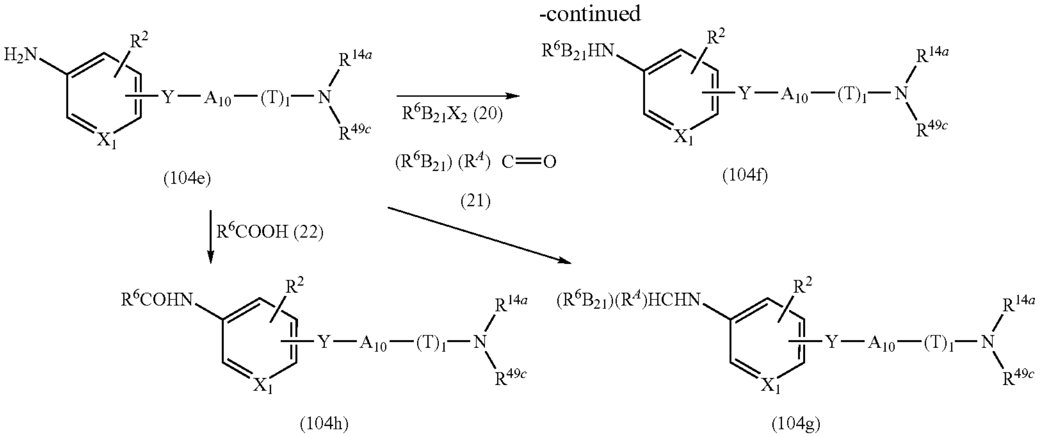

(104e) (104f) (104h) (104g)

wherein $R^2$, $X_1$, Y, $A_{10}$, T, l, $R^6$, $X_2$, $R^A$, $B_{21}$ and $R^{14a}$ are the same as described above, and $R^{49c}$ represents a lower alkoxycarbonyl group, provided that a and b of $A_{10}$ are bound to a group —Y and a group -$(T)_l$, respectively.

The reaction of the compound (103) and the compound (38c) is carried out under the same reaction conditions as in the reaction of the compound (2) and the compound (3) shown in reaction formula 1 above.

The reaction which converts the compound (104d) into the compound (104e) is carried out under the same reaction conditions as in the reaction which converts the compound (68) into the compound (69) shown in reaction formula 47 above.

The reaction of the compound (104e) and the compound (20) is carried out under the same reaction conditions as in the reaction of the compound (1b) and the compound (4) shown in reaction formula 2 above.

The reaction of the compound (104e) and the compound (22) is carried out under the same reaction conditions as in the reaction of the compound (1b) and the compound (6) shown in reaction formula 2 above.

The reaction of the compound (104e) and the compound (21) is carried out under the same reaction conditions as in the reaction of the compound (1b) and the compound (5) shown in reaction formula 2 above.

[Reaction formula 82]

[Formula 167]

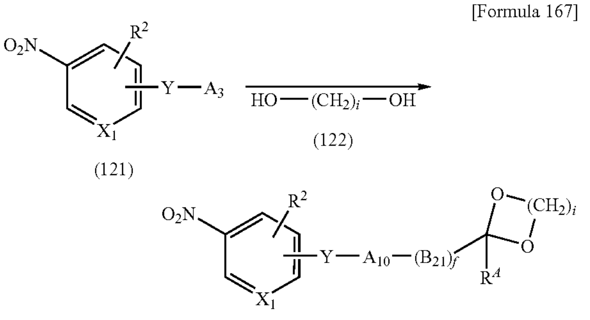

(121) (122) (123a)

wherein $R^2$, $X_1$, Y, $A_3$, $A_{10}$, $B_{21}$, f, $R^A$ and i are the same as described above, provided that a and b of $A_{10}$ are bound to a group —Y and a group —$(B_{21})$f, respectively, and the moiety $(B_{21})$f$C(R^A)$ in the side chain of the compound (123a) has not more than 6 carbon atoms in total.

The reaction of the compound (121) and the compound (122) may be carried out in an appropriate solvent in the presence of an acid.

Any solvent may be used herein as long as it is used in the reaction of the compound (2) and the compound (3) shown in reaction formula 1 above.

Examples of the acid include mineral acids such as hydrochloric acid, sulfuric acid, and hydrobromic acid, and organic acids such as acetic acid, trifluoroacetic acid, and sulfonic acids including p-toluenesulfonic acid. These acids may be used singly or in a mixture of two type's or more. The acid is favorably used typically in an amount at least 0.01 to 5 times and preferably 0.01 to 2 times that of the compound (121) on a molar basis. The compound (122) is favorably used typically in at least an equimolar amount to the compound (121) and preferably 1 to 10 times that of the compound (121) on a molar basis.

The above described reaction is carried out typically at 0 to 200° C. and preferably at about 0 to 150° C. and generally completed in about 30 minutes to 10 hours.

[Reaction formula 83]

[Formula 168]

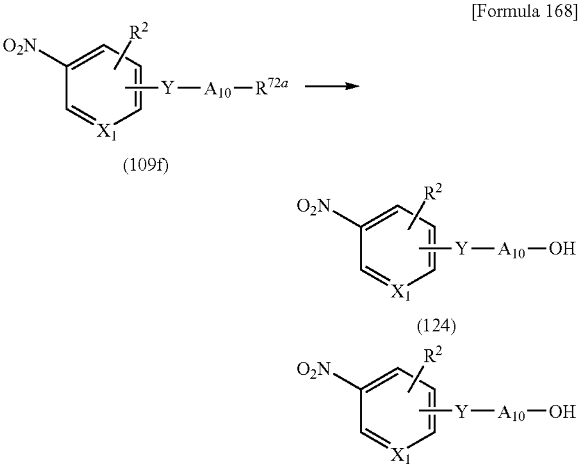

(109f) (124) (124)

wherein $R^2$, $X_1$, Y and $A_{10}$ are the same as described above, and $R^{72a}$ represents a lower alkoxy group, provided that a of $A_{10}$ is bound to a group —Y and b of $A_{10}$ is bound to a group —$R^{72}$ or a hydroxyl group.

The reaction which converts the compound (109f) into the compound (124) may be carried out in an appropriate solvent in the presence of an acid.

As the solvent, in addition to water, any solvent may be used herein as long as it is used in the reaction of the compound (2) and the compound (3) shown in reaction formula 1 above.

Examples of the acid include mineral acids such as hydrobromic acid, hydrochloric acid, and concentrated sulfuric acid, fatty acids such as formic acid and acetic acid, organic acids such as p-toluenesulfonic acid, Lewis acids such as aluminum chloride, zinc chloride, iron chloride, tin chloride, boron trifluoride, and boron tribromide, iodides such as sodium iodide and potassium iodide, a mixture of a Lewis acid and an iodide as described above. The acid is favorably used typically in an amount 0.1 to 5 times and preferably 0.5 to 3 times that of the compound (109f) on a molar basis.

The above described reaction is carried out typically at 0 to 150° C. and preferably at about 0 to 100° C. and generally completed in about 0.5 to 15 hours.

[Reaction formula 84]

[Formula 169]

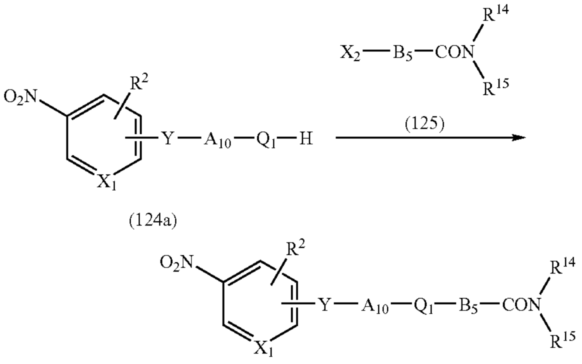

(125)

(124a)

(72g)

wherein $R^2$, $X_1$, Y, $A_{10}$, $B_5$, $X_2$, $R^{14}$ and $R^{15}$ are the same as described above, and $Q_1$ represents an oxygen atom or a sulfur atom, provided that a and b of $A_{10}$ are bound to a group —Y and a group -$Q_1$, respectively.

The reaction of the compound (124a) and the compound (125) is carried out under the same reaction conditions as in the reaction of the compound (2) and the compound (3) shown in reaction formula 1 above.

[Reaction formula 85]

[Formula 170]

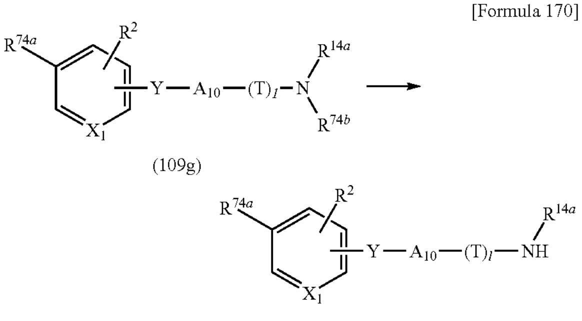

(109g)

(109h)

-continued

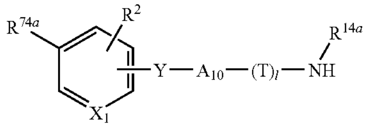

(109h)

wherein $R^2$, $X_1$, Y, $A_{10}$, $R^{14a}$, $R^{74a}$, T and l are the same as described above, and $R^{74b}$ represents a lower alkanoyl group or a lower alkoxycarbonyl group, provided that a and b of $A_{10}$ are bound to a group —Y and a group -(T)l, respectively.

The reaction which converts the compound (109g) into the compound (109h) may be carried out under the same reaction conditions as in hydrolysis B described in reaction formula 9 above.

[Reaction formula 86]

[Formula 171]

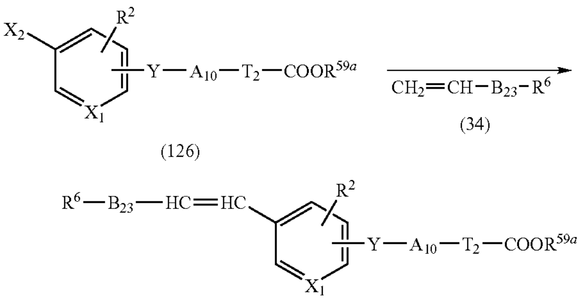

(126)

(34)

(127)

wherein $R^2$, $X_1$, Y, $A_{10}$, $T_2$, $X_2$, $R^{59a}$, $B_{23}$ and $R^6$ are the same as described above, provided that a and b of $A_{10}$ are bound to —Y group and a group -$T_2$, respectively.

The reaction of the compound (126) and the compound (34) is carried out under the same reaction conditions as in the reaction of the compound (33) and the compound (34) in reaction formula 43 above.

[Reaction formula 87]

[Formula 172]

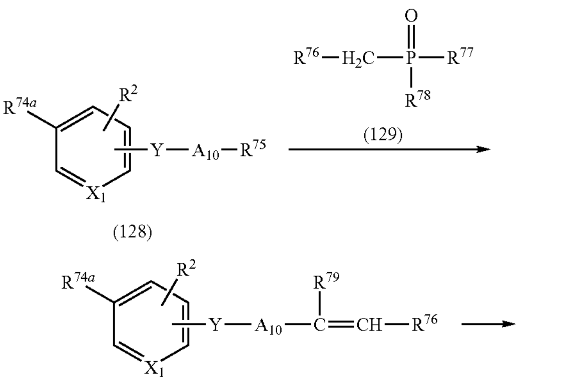

(129)

(128)

(130)

-continued

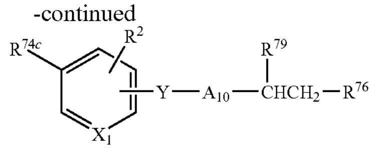

(131)

wherein $R^2$, $X_1$, Y, $R^{74}$ and $A_{10}$ are the same as described above, $R^{74c}$ represents an amino group or a group —$R^1$ (wherein $R^1$ is the same as described above), $R^{75}$ represents a lower alkanoyl group, $R^{76}$ represents a lower alkoxycarbonyl group, $R^{77}$ and $R^{78}$ are both lower alkoxy groups, and $R^{79}$ represents a hydrogen atom or a lower alkyl group, provided that a of $A_{10}$ is bound to a group —Y, and b of $A_{10}$ is bound to a group —$R^{75}$, a group —$C(R^{79})$═$CHR^{76}$ or a group —$CH(R^{79})CH_2R^{76}$, and each of the $C(R^{79})$═CH moiety and the $CH(R^{79})CH_2$ moiety has not more than 6 carbon atoms.

The reaction of the compound (128) and the compound (129) is carried out in an appropriate solvent in the presence of a basic compound.

Any conventional solvent may be used as long as it does not affect the reaction. Examples of such a solvent include ethers such as diethyl ether, dioxane, tetrahydrofuran, monoglyme, and diglyme, aromatic hydrocarbons such as benzene, toluene, and xylene, aliphatic hydrocarbons such as n-hexane, heptane, and cyclohexane, amines such as pyridine and N,N-dimethylaniline, aprotic polar solvents such as acetonitrile, N,N-dimethylformamide, dimethyl sulfoxide, and hexamethylphosphoric acid triamide, and alcohols such as methanol, ethanol, and isopropanol, and a mixture thereof.

Examples of the basic compound include metal sodium, metal potassium, sodium hydride, sodium amide, metal hydroxides such as sodium hydroxide, potassium hydroxide, and calcium hydroxide, carbonates such as sodium carbonate, potassium carbonate, and sodium bicarbonate, metal alcoholates such as sodium methylate, sodium ethylate, and potassium tert-butoxide, alkyl and aryl lithiums or lithium amides such as methyl lithium, n-butyryl lithium, phenyl lithium, and lithium diisopropylamide, and organic bases such as pyridine, piperidine, quinoline, trimethylamine, diisopropylethylamine, and N,N-dimethylaniline. These basic compounds are used singly or in a mixture of two types or more. The basic compound is favorably used typically in an amount 0.1 to 10 times and preferably 0.5 to 5 times that of the compound (128) on a molar basis.

The compound (129) is favorably used typically in at least an equimolar amount to the compound (128) and preferably 1 to 5 times that of the compound (128) on a molar basis.

The above described reaction is carried out typically at −80 to 150° C. and preferably at about −80 to 120° C. and generally completed in, about 0.5 to 40 hours.

When an organic base is used as the basic compound, the reaction advantageously proceeds by adding a lithium salt such as lithium chloride to the reaction system.

The reaction which converts the compound (130) into the compound (131) is carried out under the same reaction conditions as in the reaction which converts the compound (68) into the compound (69) shown in reaction formula 47 above.

[Reaction formula 88]

[Formula 173]

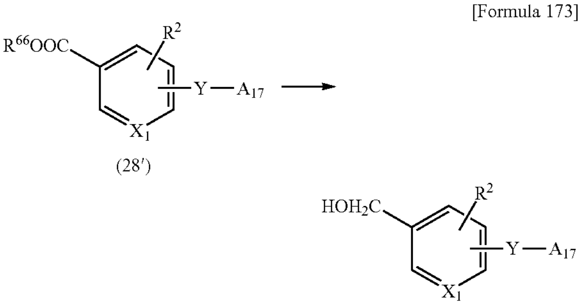

(28')

(64a)

(64a)

wherein $R^2$, $X_1$, Y, $R^{66}$ and $A_{17}$ are the same as described above.

The reaction which converts the compound (28') into the compound (64a) is carried out under the same reaction conditions as in the reaction which converts the compound (1f) into the compound (1g) shown in reaction formula 3 above.

[Reaction formula 89]

[Formula 174]

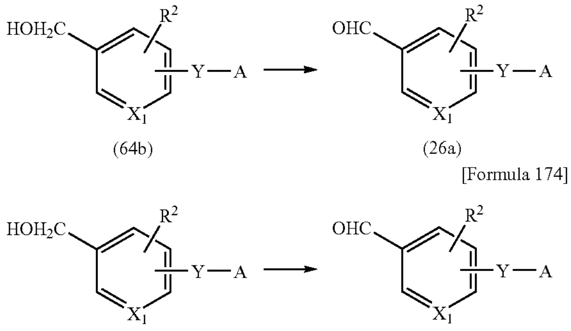

(64b) (26a)

[Formula 174]

(64b) (26a)

wherein $R^2$, $X_1$, Y and A are the same as described above.

The reaction which converts the compound (64b) into the compound (26a) is carried out in an appropriate solvent in the presence of an oxidizing agent.

Examples of the solvent include water, fatty acids such as formic acid, acetic acid, trifluoroacetic acid, and propionic acid, esters such as ethyl acetate and methyl acetate, alcohols such as methanol, ethanol, and isopropanol, ethers such as dioxane, tetrahydrofuran, and diethyl ether, ketones such as acetone and methyl ethyl ketone, aromatic hydrocarbons such as benzene, toluene, chlorobenzene, and xylene, and halogenated hydrocarbons such as chloroform and dichloromethane, hexamethylphosphoric acid triamide, N,N-dimethylformamide, dimethyl sulfoxide, and pyridine, and a mixture thereof.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperidodate, dichromic acid, dichromates such as sodium dichromate and potassium dichromate, manganese dioxide, permanganic acid, permanganates such as sodium permanganate and potassium permanganate, lead salts such as lead tetraacetate, silver oxide, and a Dess-Martin reagent (Dess-Martin periodinane). These oxidizing agents are used singly or in a mixture of two or more. The oxidizing agent is used typically in at least an equimolar amount to the compound (64b) and preferably 1 to 3 times that of the compound (64b) on a molar basis.

The above described reaction is carried out typically at -10 to 100° C. and preferably at about 0 to 50° C. and completed in about 30 minutes to 24 hours.

[Reaction formula 90]

[Formula 175]

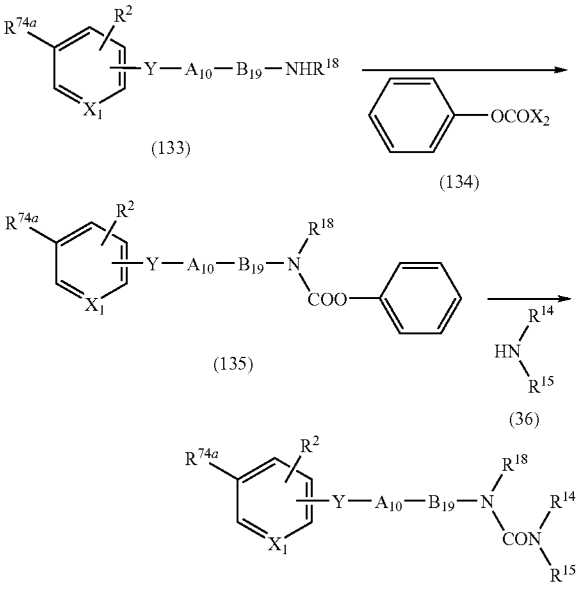

(133) (134) (135) (36) (136)

wherein $R^2$, $X_1$, Y, $A_{10}$, $B_{19}$, $R^{18}$, $X_2$, $R^{14}$, $R^{74a}$ and $R^{15}$ are the same as described above, provided that a and b of $A_{10}$ are bound to a group —Y and a group —$B_{19}$, respectively.

The reactions between compound (133) and the compound (134), and compound (135) and the compound (36) each are carried out under the same reaction conditions as in the reaction of the compound (2) and the compound (3) shown in reaction formula 1 above.

[Reaction formula 91]

[Formula 176]

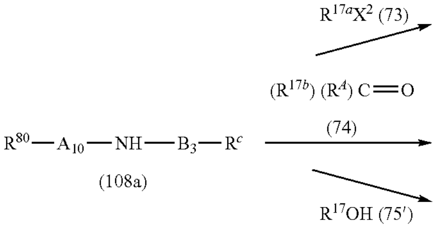

(108a)

-continued

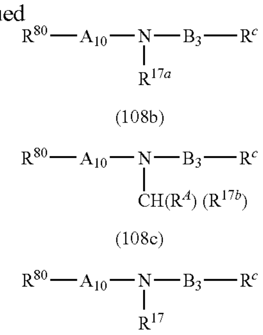

(108b)

(108c)

(108d)

wherein $A_{10}$, $B_3$, $R^{17a}$, $R^{17b}$, $R^A$, $R^{17}$, $Y_1$, $R^c$ and $X_2$ are the same as described above, and $R^{80}$ represents group —$Y_1$H or group —$OR^{81}$, $R^{81}$ represents a protective group of the hydroxyl group, provided that the $CHR^A$ moiety in the side chain (—$N(B_3R^c)(CHR^AR^{17b})$) of the compound (108c) has not more than 6 carbon atoms, a of $A_{10}$ is bound to a group —$R^{80}$, and b is bound to a group —$NHB_3R^c$, a group —$N(R^{17a})B_3R^c$, a group —$N(CHR^AR^{17b})B_3R^c$ or a group —$N(R_{17})B_3R^c$.

Examples of the protective group of the hydroxyl group include a phenyl lower alkyl group, a lower alkoxy lower alkyl group, tetrahydropyranyl group, tri lower alkylsilyl group, a lower alkanoyl group, and a lower alkyl group described above.

The reaction of the compound (108a) and the compound (73) is carried out under the same reaction conditions as in the reaction of the compound (1b) and the compound (4) shown in reaction formula 2 above.

The reaction of the compound (108a) and the compound (75') is carried out under the same reaction conditions as in the reaction of the compound (1b) and the compound (6) shown in reaction formula 2 above.

The reaction of the compound (108a) and the compound (74) is carried out under the same reaction conditions as in the reaction of the compound (1b) and the compound (5) shown in reaction formula 2 above.

The reaction is carried out using a compound (74), whose $R^A$ and $R^{17b}$ (bound to a carbon atom) are mutually bound to form a cycloalkyl ring together with the carbon atom in the presence of a hydride reducing agent, as a starting material. In this case, in place of the compound (74), cycloalkyloxytrialkylsilane such as [(1-ethoxycyclopropyl)oxy]trimethylsilane may be used as the starting material (to produce the above described compound (74) in the reaction system).

[Reaction formula 92]

[Formula 177]

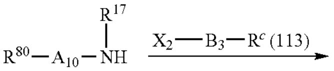

(108e)

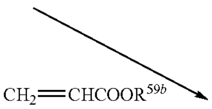

$CH_2{=}CHCOOR^{59b}$ (137)

-continued

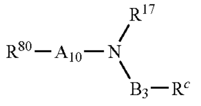

(108f)

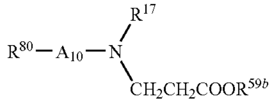

(108g)

wherein $R^{80}$, $A_{10}$, $R^{17}$, $B_3$, $R^c$, $X_2$ and $R^{59b}$ are the same as described above, provided that a of $A_{10}$ is bound to a group —$R^{80}$ and b is bound to a group —$NHR^{17}$, a group —$N(R^{17})B_3R^c$ or a group —$N(R^{17})CH_2CH_2COOR^{59}$.

The reaction of the compound (108e) and the compound (113) is carried out under the same reaction conditions as in the reaction of the compound (1b) and the compound (4) shown in reaction formula 2 above.

The reaction of the compound (108e) and the compound (137) is carried out in an appropriate solvent in the presence of an acid.

Any solvent may be used as long as it is used in the reaction of the compound (2) and the compound (3) shown in reaction formula 1 above.

Examples of the acid include mineral acids such as hydrochloric acid, sulfuric acid, and hydrobromic acid, organic acids such as acetic acid, trifluoroacetic acid, and sulfonic acids including p-toluenesulfonic acid, and Lewis acids such as aluminum chloride, zinc chloride, iron chloride, tin chloride, boron tribromide, and a boron trifluoride/diethyl ether complex. These acids may be used singly or in a mixture of two types or more. The acid is favorably used typically in an amount at least 0.01 to 5 times and preferably 0.1 to 2 times that of the compound (108e) on a molar basis. The compound (137) is favorably used typically in at least an equimolar amount to the compound (108e) and preferably 1 to 10 times that of the compound (108e) on a molar basis.

The above described reaction is carried out typically at 0 to 200° C. and preferably at about 0 to 150° C. and generally completed in about 30 minutes to 80 hours.

[Reaction formula 93]

[Formula 178]

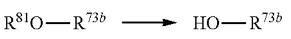

(138) (139)

wherein $R^{81}$ is the same as described above, $R^{73b}$ represents a group $A_{10}$-$T_2$-$COOR^{59a}$ or a group -A, and $A_{10}$, $T_2$, $R^{59a}$ and A are the same as described above, provided that a of $A_{10}$ is bound to a group —$OR^{81}$ group or a hydroxyl group, and b of $A_{10}$ is bound to a group -$T_2$.

When $R^{81}$ of the starting compound (138) represents a phenyl lower alkyl group, the reaction which converts the compound (138) into the compound (139) may be carried out under the same reaction conditions as in the reduction reaction (1) (method using a catalytic hydrogen reducing agent), which is one of the reactions which convert the compound (68) into the compound (69) shown in reaction formula 47 above.

The starting compound (138), in which $R^{81}$ represents a tetrahydropyranyl group or a tri-lower alkylsilyl group is converted into the compound (139), may be carried out under the same reaction conditions as in hydrolysis reaction B described in reaction formula 9 above. In the reaction which converts the compound (138) into the compound (139), hydrolysis is favorably carried out by use of an acid. The acid is favorably used typically in an amount 1 to 10 times and preferably 1 to 2 times that of the compound (138) on a molar basis.

The compound (138) in which $R^{81}$ represents a tri-lower alkylsilyl group, may be treated with a fluorine compound such as tetra-n-butyl ammonium fluoride, hydrogen fluoride or cesium fluoride.

The starting compound (138) in which $R^{81}$ represents a lower alkoxy lower alkyl group or a lower alkyl group, may be treated in an appropriate solvent in the presence of an acid. Examples of the solvent include water, lower alcohols such as methanol, ethanol, and isopropanol, ethers such as dioxane, tetrahydrofuran, and diethyl ether, halogenated hydrocarbons such as dichloromethane, chloroform, and carbon tetrachloride, and polar solvents such as acetonitrile, and a mixture thereof. Examples of the acid include mineral acids such as hydrochloric acid, sulfuric acid, and hydrobromic acid, fatty acids such as formic acid and acetic acid, sulfonic acids such as p-toluenesulfonic acid, Lewis acids such as boron trifluoride, aluminum chloride, and boron tribromide, iodides such as sodium iodide and potassium iodide, and a mixture of an iodide with a Lewis acid as described above. The above described reaction is carried out typically at 0 to 200° C. and preferably at about room temperature to 150° C. and generally completed in about 0.5- to 25 hours.

Furthermore, the hydrolysis may be carried out using a basic compound under the same reaction conditions as in hydrolysis reaction B described in reaction formula 9 above. In this case, an amine such as triethylamine may be used other than the basic compounds used in hydrolysis reaction B, as the basic compound.

The material compound (138), in which $R^{81}$ represents a lower alkanoyl group, is converted into the compound (139) under the same reaction conditions as in hydrolysis reaction B described in reaction formula 9 above.

The compound (138) in which $R^{73a}$ represents a group

[Formula 179]

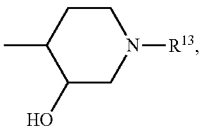

a dehydration reaction takes place under the hydrolysis conditions above, with the result that the compound (138), in which the corresponding $R^{73a}$ represents a group

[Formula 180]

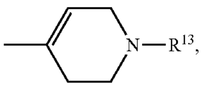

may be obtained in some cases.

[Reaction formula 94]

[Formula 181]

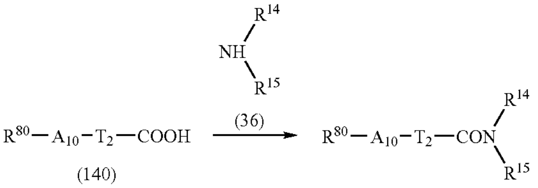

(140) (108h)

wherein $R^{80}$, $A_{10}$, $T_2$, $R^{14}$ and $R^{15}$ are the same as described above, provided that a and b of $A_{10}$ are to a group —$R^{80}$ and a group -$T_2$, respectively.

The reaction of the compound (140) and the compound (36) is carried out under the same reaction conditions as in the reaction of the compound (1b) and the compound (6) shown in reaction formula 2 above.

[Reaction formula 95]

[Formula 182]

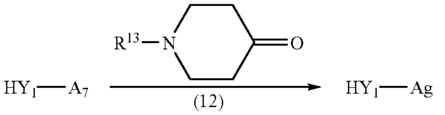

(141) (142)

wherein $Y_1$, $A_7$, $R^{13}$ and $A_9$ are the same as described above.

The reaction of the compound (141) and the compound (12) is carried out under the same reaction conditions as in the reaction of the compound (13) and the compound (12) shown in reaction formula 8 above.

[Reaction formula 96]

[Formula 183]

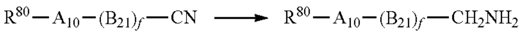

(143) (144)

wherein $R^{80}$, $A_{10}$, $B_{21}$ and f are the same as described above, provided that the alkyl moiety in the side chain (—$(B_{21})$f-$CH_2NH_2$) of the compound (144) has not more than 6 carbon atoms.

The reaction which converts the compound (143) into the compound (144) is carried out under the same reaction conditions as in the reaction using a hydride reducing agent, which is one of the reactions of the compound (1b) and the compound (5) shown in reaction formula 2.

[Reaction formula 97]

[Formula 184]

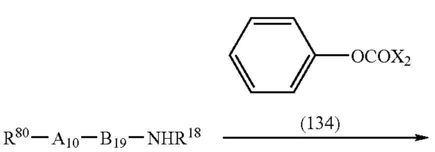

(145)

-continued

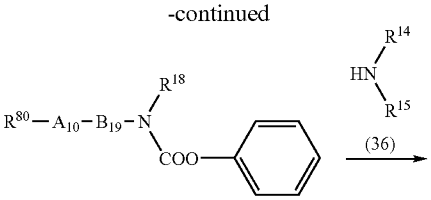

(146)

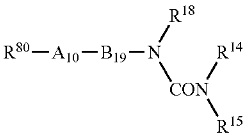

(108i)

wherein $R^{80}$, $A_{10}$, $B_{19}$, $X_2$, $R^{18}$, $R^{14}$ and $R^{15}$ are the same as described above, provided that a of $A_{10}$ is bound to a group —$R^{80}$ and b is bound to a group —$B_{19}$.

The reaction of the compound (145) and the compound (134) is carried out under the same reaction conditions as in the reaction of the compound (133) and the compound (134) shown in reaction formula 90 above.

The reaction of the compound (146) and the compound (36) is carried out under the same reaction conditions as in the reaction of the compound (1b) and the compound (6) shown in reaction formula 2 above.

[Reaction formula 98]

[Formula 185]

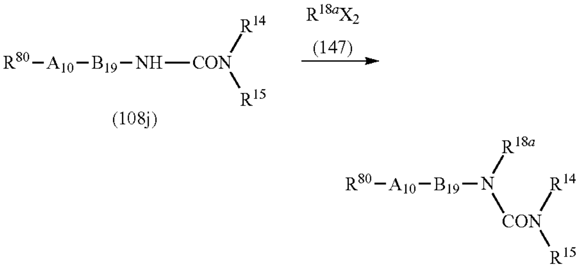

(108j)

(108k)

wherein, $A_{10}$, $B_{19}$, $R^{14}$, $R^{15}$, $R^{80}$, and $X_2$ are the same as described above, and $R^{18a}$ represents a lower alkyl group, provided that a and b of $A_{10}$ are bound to a group —$R^{80}$ and a group —$B_{19}$, respectively.

The reaction of the compound (108j) and the compound (147) is carried out under the same-reaction conditions as in the reaction of the compound (1b) and the compound (4 shown in reaction formula 2 above.

[Reaction formula 99]

[Formula 186]

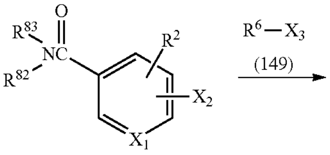

(148)

-continued

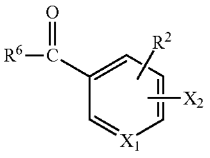

(2a)

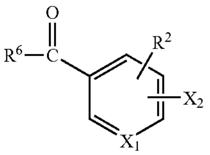

(2a)

wherein $R^2$, $X_1$, $X_2$, $X_3$ and $R^6$ are the same as described above, $R^{82}$ represents a lower alkyl group, and $R^{83}$ represents a lower alkoxy group.

The reaction of the compound (148) and the compound (149) is carried out in an appropriate solvent in the presence of a catalyst.

Any solvent may be used herein as long as it is used in the reaction of the compound (2) and the compound (3) shown in reaction formula 1.

Examples of the catalyst include magnesium. The catalyst is favorably used typically in at least an equimolar amount to the compound (148) and preferably 1 to 5 times that of the compound (148) on a molar basis.

The above described reaction is carried out typically at 0 to 200° C. and preferably at about 0 to 150° C. and generally completed in about 30 minutes to 10 hours.

Reaction formula 100

[Formula 187]

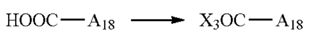

(150) (107')

wherein $A_{18}$ represents a group -A or a group $-A_{10}-T_2-COOR^{59b}$, and A, $A_{10}$, $T_2$, $R^{59b}$ and $X_3$ are the same as described above.

The reaction which converts the compound (150) into the compound (107') is carried out under the same reaction conditions as in the reaction which converts the compound (85) into the compound (7') shown in reaction formula 55 above.

Reaction formula 101

[Formula 188]

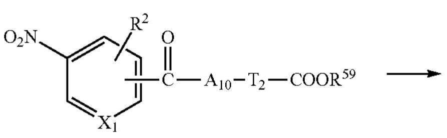

(109a')

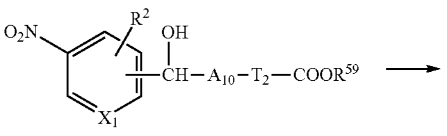

(151)

-continued

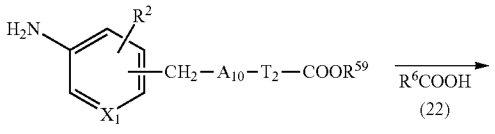

(152)

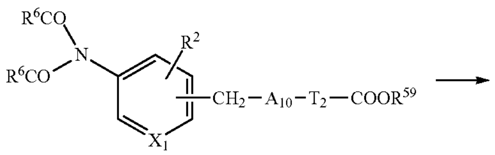

(153)

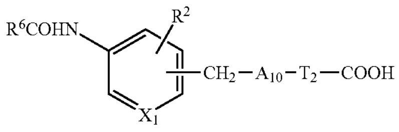

(154)

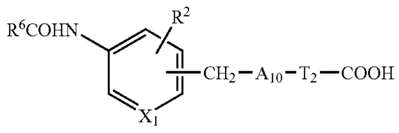

(154)

wherein $R^2$, $X_1$, $A_{10}$, $T_2$ and $R^6$ are the same as described above, provided that a of $A_{10}$ is bound to a —CO group, a —CH(OH) group or —$CH_2$ group, and b of $A_{10}$ is bound to a group $-T_2$.

The reaction which converts the compound (109a') into the compound (151) is carried out under the same reaction conditions as in the reaction using a hydride reducing agent which is one of the reactions of the compound (1b) and the compound (5) shown in reaction formula 2 above.

The reaction which converts the compound (151) into the compound (152) is carried out under the same reaction conditions as in the reaction which converts the compound (68) into the compound (69) shown in reaction formula 47 above.

The reaction of the compound (152) and the compound (22) is carried out under the same reaction conditions as in the reaction of the compound (1b) and the compound (6) shown in reaction formula 2 above.

The reaction which converts the compound (153) into the compound (154) may be carried out under the same react-ion conditions as in hydrolysis B reaction described in reaction formula 9 above.

[Reaction formula 102]

[Formula 189]

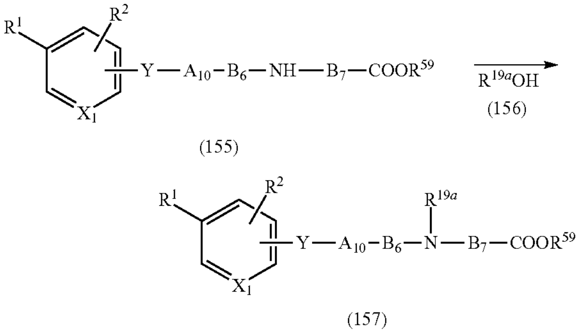

wherein $R^1$, $R^2$, $X_1$, Y, $A_{10}$, $B_6$, $B_7$ or $R^{59}$ are the same as described above, and $R^{19a}$ represents a lower alkanoyl group, provided that a and b of $A_{10}$ are bound to a group —Y and a group —$B_6$, respectively.

The reaction of the compound (155) and the compound (156) is carried out under the same reaction conditions as in the reaction of the compound (1b) and the compound (6) shown in reaction formula 2 above.

[Reaction formula 103]

[Formula 190]

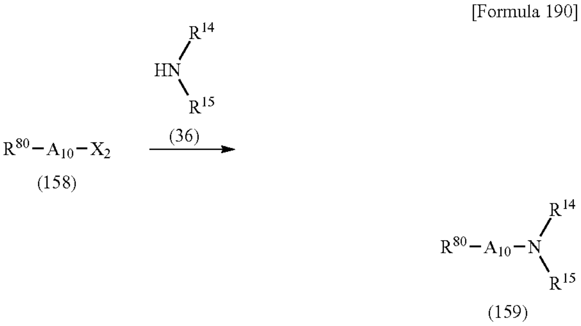

wherein $R^{80}$, $A_{10}$, $X_2$, $R^{14}$ and $R^{15}$ are the same as described above.

The reaction of the compound (158) and the compound (36) is carried out under the same reaction conditions as the reaction of the compound (114) and the compound (36) shown in reaction formula 74 in which l is 0.

[Reaction formula 104]

[Formula 191]

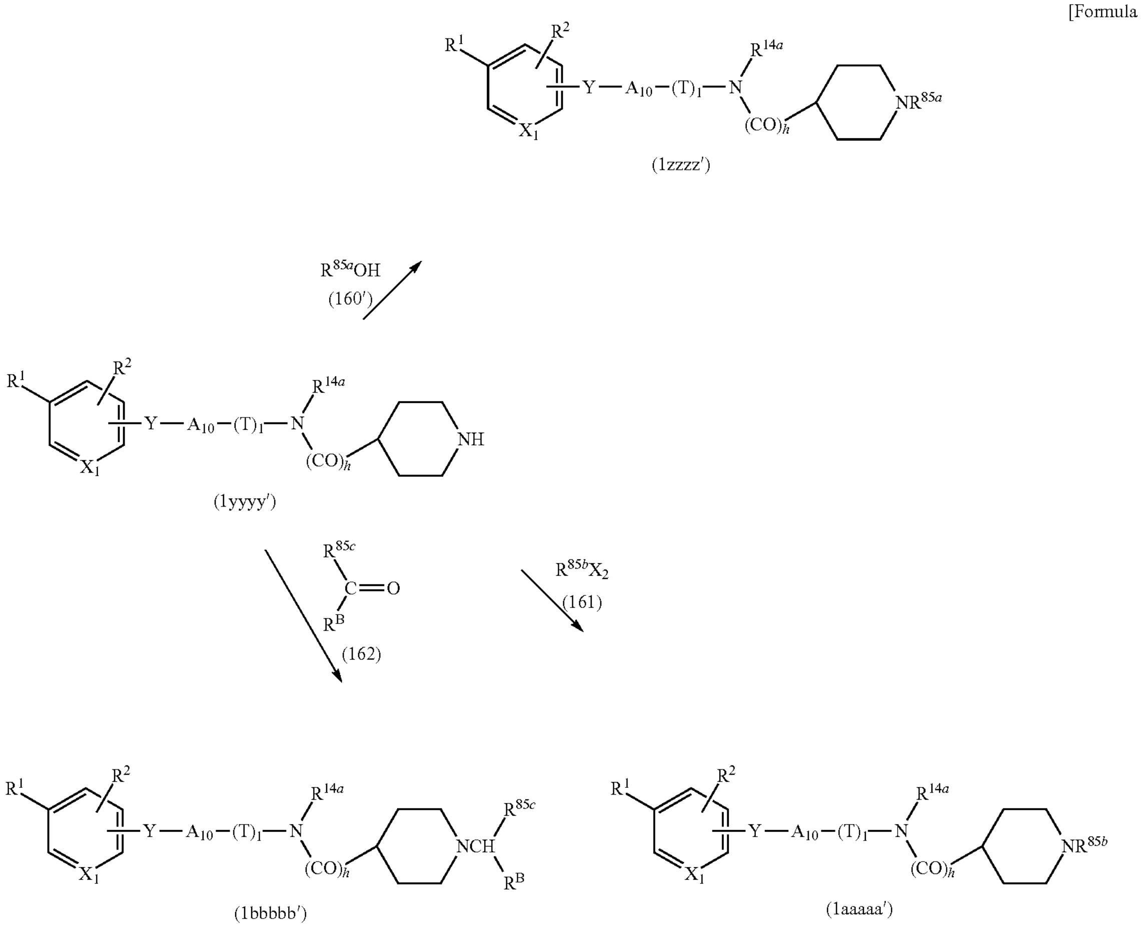

wherein $R^1$, $R^2$, Y, $A_{10}$, $R^{14a}$, h, T, l, $R^B$, $X_1$ and $X_2$ are the same as described above, $R^{85a}$ represents a benzoyl group, $R^{85b}$ represents a lower alkoxy carbonyl group, a phenyl lower alkyl group, a lower alkyl group or furyl lower alkyl group, and $R^{85c}$ represents a hydrogen atom, a lower alkyl group, a phenyl group, phenyl lower alkyl group, a furyl group or a furyl lower alkyl group, provided that the a group —$CH(R^B)R^{85c}$ of the compound (1bbbbb) has not more than 6 carbon atoms.

The reaction of the compound (1yyyy') and the compound (160') is carried out under the same reaction conditions as in the reaction of the compound (1b) and the compound (6) shown in reaction formula 2 above.

The reaction of the compound (1yyyy') and the compound (161) is carried out under the same reaction conditions as in the reaction of the compound (1b) and the compound (4) shown in reaction formula 2 above.

The reaction of the compound (1yyyy') and the compound (162) is carried out under the same reaction conditions as in the reaction of the compound (1b) and the compound (5) shown in reaction formula 2 above.

[Reaction formula 105]

[Formula 192]

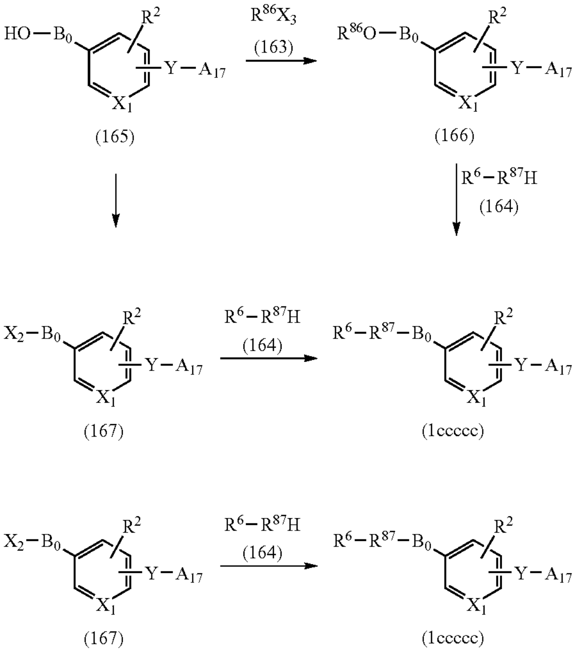

wherein $R^2$, $B_0$, Y, $X_1$, $A_{17}$, $R^8$, $X_2$, $X_3$ and $R^6$ are the same as described above, $R^{86}$ represents a lower alkylsulfonyl group, and $R^{87}$ represents an oxygen atom or a group —$N(R^8)$—.

The reaction of the compound (165) and the compound (163) is carried out under the same reaction conditions as in the reaction of the compound (2) and the compound (3) shown in reaction formula 1 above.

The reaction which converts the compound (165) into the compound (167) is carried out under the same reaction conditions as in the reaction which converts the compound (85) into the compound (7') of the above described formula 55.

The reaction of the compound (166) or the compound (167) and the compound (164) is carried out under the same reaction conditions as in the reaction of the compound (2) and the compound (3) shown in reaction formula 1 above.

[Reaction formula 106]

[Formula 193]

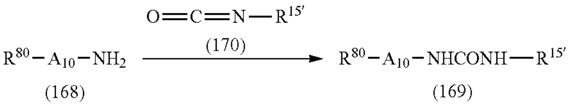

wherein $R^{80}$ and $A_{10}$ are the same as described above, $R^{15}$ represents the same group as that of (5) in $R^{15}$ described above.

The reaction of the compound (168) and the compound (170) is carried out under the same reaction conditions as in the reaction of the compound (30) and the compound (66) shown in reaction formula 46 above.

[Reaction formula 107]

[Formula 194]

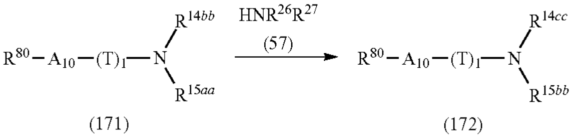

wherein $R^{80}$, $A_{10}$, T, l, $R^{14bb}$, $R^{15aa}$, $R^{14cc}$, $R^{15bb}$, $R^{26}$ and $R^{27}$ are the same as described above.

The reaction of the compound (171) and the compound (57) is carried out under the same reaction conditions as in the reaction of the compound (1iiii) and the compound (57) shown in reaction formula 31 above.

[Reaction formula 108]

[Formula 195]

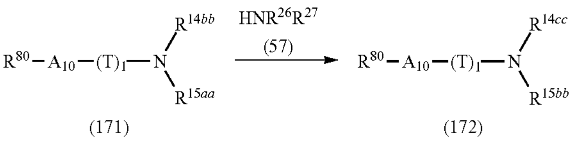

wherein $R^1$, $R^2$, $X_1$, Y, $A_{10}$, $R^{15'}$ and $X_2$ are the same as described above, and $R^{89}$ represents a lower alkyl group.

The reaction of the compound (173) and the compound (170) is carried out under the same reaction conditions as in the reaction of the compound (30) and the compound (66) shown in reaction formula 46 above.

The reaction of the compound (1ddddd) and the compound (173) is carried out under the same reaction conditions as in the reaction of the compound (2) and the compound (3) shown in reaction formula 1 above.

[Reaction formula 109]

[Formula 196]

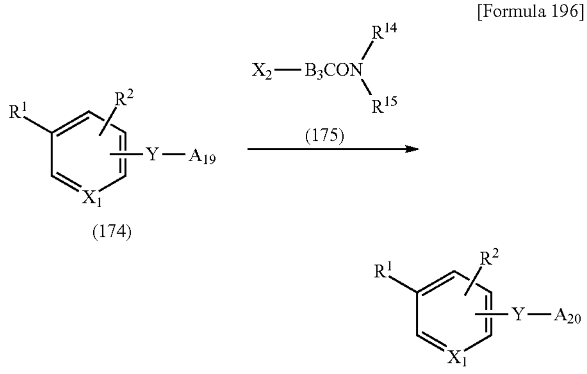

(174)

(1fffff)

wherein $R^1$, $R^2$, $X_1$, Y, $X_2$, $B_3$, $R^{14}$ and $R^{15}$ are the same as described above, and $A_{19}$ represents a group

[Formula 197]

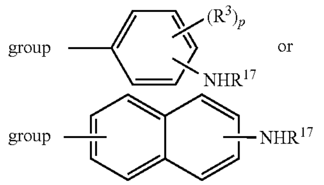

$A_{20}$ represents a group

[Formula 198]

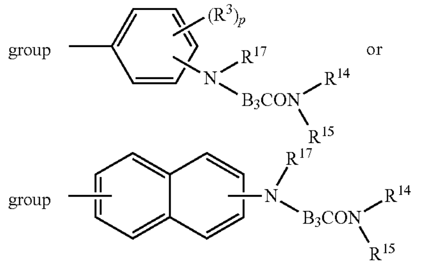

wherein $R^3$, p, $R^{17}$, $B_3$, $R^{14}$ and $R^{15}$ are the same as described above.

The reaction of the compound (174) and the compound (175) is carried out under the same reaction conditions as in the reaction of the compound (2) and the compound (3) shown in reaction formula 1 above.

[Reaction formula 110]

[Formula 199]

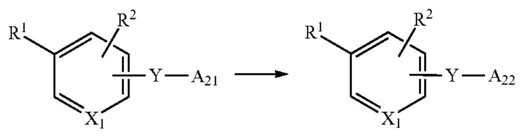

(1ggggg) (1hhhhh)

-continued

[Formula 199]

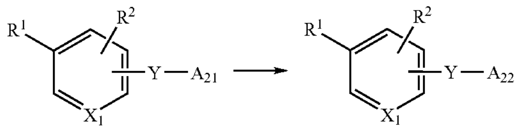

(1ggggg) (1hhhhh)

wherein $R^1$, $R^2$, $X_1$, and Y are the same as described above, $A_{21}$ represents a group

[Formula 200]

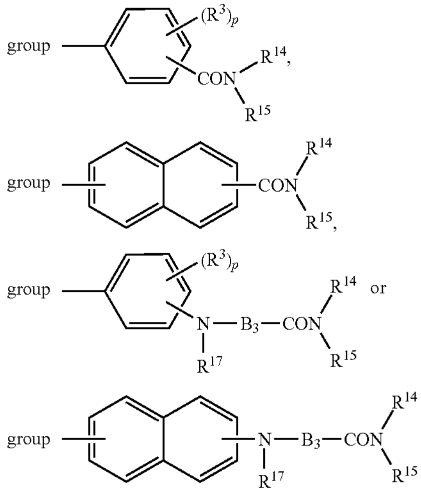

and $A_{22}$ represents a group

[Formula 201]

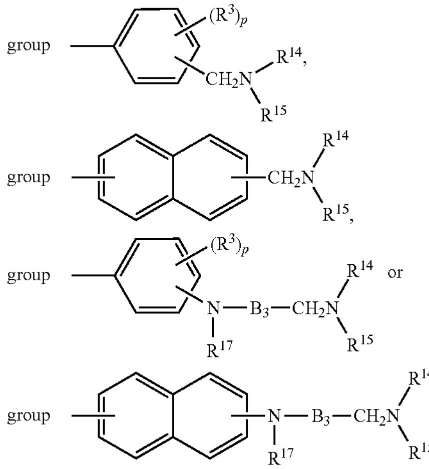

wherein $R^3$, p, $R^{17}$, $B_3$, $R^{14}$ and $R^{15}$ are the same as described above.

The reaction which converts the compound (1ggggg) into the compound (1hhhhh) is carried out under the same reaction conditions as in the reaction of the compound (1b) and the compound (5) shown in reaction formula 2 in which a hydride reducing agent is used.

[Reaction formula 111]

[Formula 202]

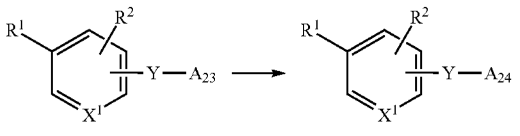

(1iiiii) (1jjjjj)

wherein $R^1$; $R^2$, $X_1$ and Y are the same as described above, $A_{23}$ represents a group

[Formula 203]

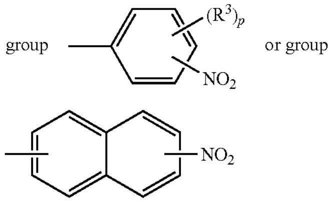

and $A_{24}$ represents a group

[Formula 204]

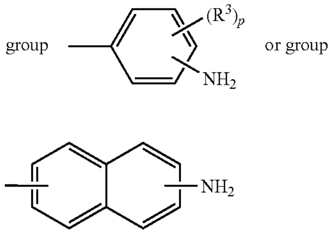

wherein $R^3$ and p are the same as described above.

The reaction which converts the compound (1iiiii) into the compound (1jjjjj) is carried out under the same reaction conditions as in the reaction which converts the compound (68) into the compound (69) shown in reaction formula 47.

[Reaction formula 112]

[Formula 205]

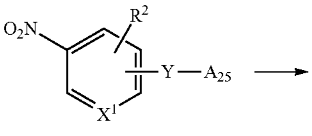

(1kkkkk)

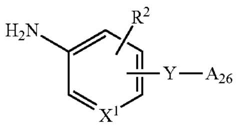

(1lllll)

wherein $R^2$, $X_1$ and Y are the same as described above, $A_{25}$ represents a group

[Formula 206]

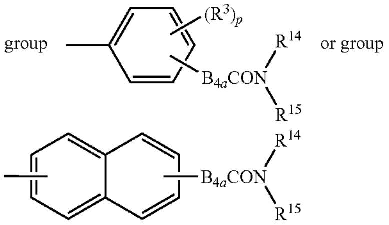

and $A_{26}$ represents a group

[Formula 207]

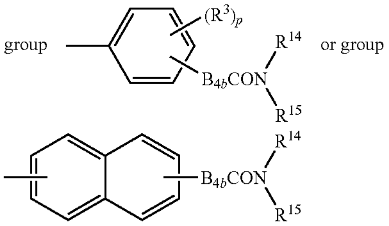

wherein $B_{4a}$ represents a lower alkenylene group, $B_{4b}$ represents a lower alkylene group, and $R^3$, p, $R^{14}$ and $R^{15}$ are the same as described above.

The reaction which converts the compound (1kkkkk) into the compound (1lllll) is carried out the same as in the reaction of the method (1) of the reactions which convert the compound (68) into the compound (69) shown in reaction formula 47 above.

[Reaction formula 113]

[Formula 208]

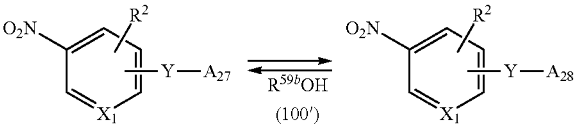

(1mmmmm) (1nnnnn)

[Formula 208]

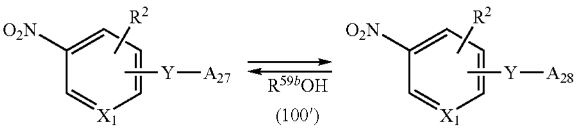

(1mmmmm) (1nnnnn)

wherein $R^2$, $X_1$, Y, and $R^{59b}$ are the same as described above, and $A_{28}$ represents a group

[Formula 209]

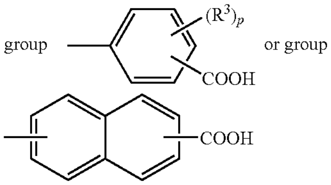

and $A_{27}$ represents a group

[Formula 210]

group 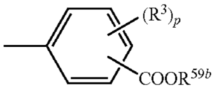 or group

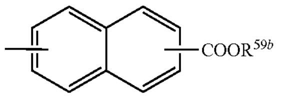

wherein $R^3$, p and $R^{59b}$ are the same as described above.

The reaction which converts the compound (1mmmmm) into the compound (1nnnnn) is carried out under the same reaction conditions as in hydrolysis B described in reaction formula 9 above.

The reaction of the compound (1nnnnn) and the compound (100') is carried out under the same reaction conditions as in the reaction of the compound (1fff) and the compound (43) shown in reaction formula 20 above.

[Reaction formula 114]

[Formula 211]

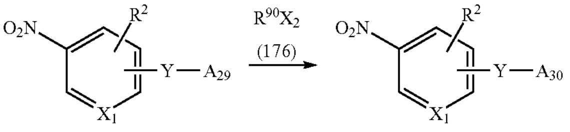

(1ooooo) (1ppppp)

[Formula 211]

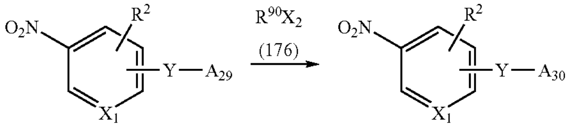

(1ooooo) (1ppppp)

wherein $R^2$, $X_1$, $X_2$ and Y are the same as described above, $A_{29}$ represents a group

[Formula 212]

group 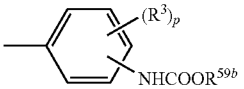 or group

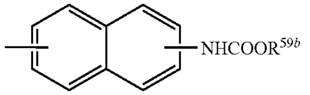

and $A_{30}$ represents

[Formula 213]

group 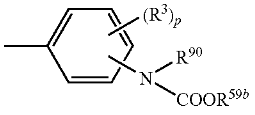 or group

-continued

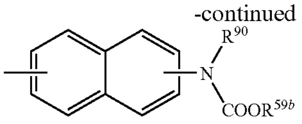

wherein $R^{90}$ represents a lower alkyl group which may have a hydroxyl group as a substituent, and $R^3$, p and $R^{59b}$ are the same as described above.

The reaction of the compound (1ooooo) and the compound (176) is carried out under the same reaction conditions as in the reaction of the compound (1b) and the compound (4) shown in reaction formula 2 above.

[Reaction formula 115]

[Formula 214]

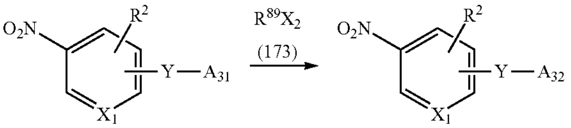

(1qqqqq) (1rrrrr)

[Formula 214]

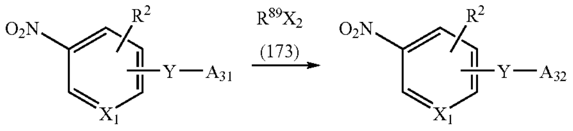

(1qqqqq) (1rrrrr)

wherein $R^2$, $X_1$, $X_2$ and Y are the same as described above, $A_{31}$ represents a group

[Formula 215]

group 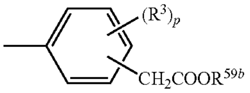 or group

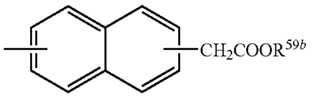

wherein $A_{32}$ represents a group

{Formula 216]

group 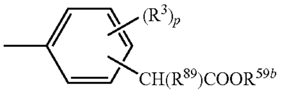 or group

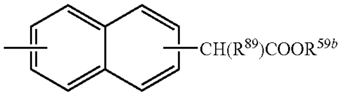

wherein $R^3$, p, $R^{59b}$ and $R^{89}$ are the same as described above.

The reaction of the compound (1qqqqq) and the compound (173) is carried out under the same reaction conditions as in the reaction of the compound (2) and the compound (3) shown in reaction formula 1 above.

[Reaction formula 116]

[Formula 217]

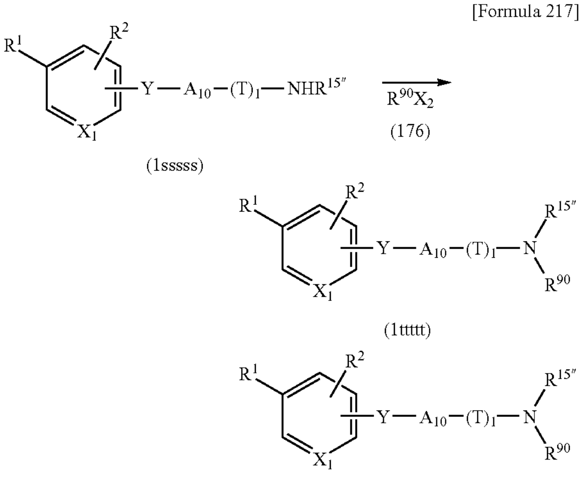

(1sssss)

(1ttttt)

(1ttttt)

wherein $R^1$, $R^2$, $X_1$, Y, $A_{10}$, T, l, $R^{90}$ and $X_2$ are the same as described above.

$R^{15''}$ represents the group (2), (3), (4), (5), (6), (7), (8), (10), (11), (12), (13), (14), (15), (16), (17), (18), (19), (20), (21), (22), (23), (24), (25), (26), (27), (26a), (27a), (28a), (29a), (30a), (31a), (32a), (33a), (34a), (35a), (36a), or (37a), which is defined in $R^{15}$ described above.

The reaction of the compound (1sssss) and the compound (176) is carried out under the same reaction conditions as in the reaction of the compound (2) and the compound (3) shown in reaction formula 1 above.

[Reaction formula 117]

[Formula 218]

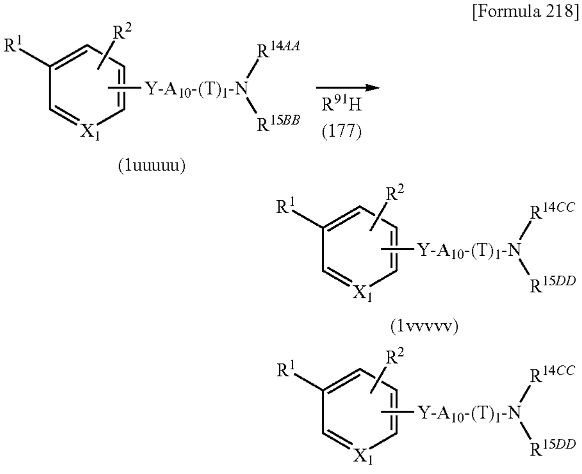

(1uuuuu)

(1vvvvv)

(1vvvvv)

wherein $R^1$, $R^2$, $X_1$, Y, $A_{10}$, T and l are the same as described above, $R^{14AA}$ and $R^{15BB}$ each represent the same 5- to 10-membered saturated or unsaturated heterocyclic group as defined in $R^{14}$ and $R^{15}$ described above except that the heterocyclic ring has at least one group —$(B_{12}CO)t$-$N(R^{20})$—CO—$B_{16}X_2$ thereon, $R^{14CC}$ and $R^{15DD}$ each represent the same 5- to 10-membered saturated or unsaturated heterocyclic group as defined in $R^{14}$ and $R^{15}$ described above except that the heterocyclic ring has at least one group —$(B_{12}CO)t$-$N(R^{20'})$—CO—$B_{16}R^{91}$ thereon, wherein $B_{12}$, t, $B_{16}$ and $X_2$ are the same as described above, $R^{91}$ represents an imidazolyl group, and $R^{20'}$ represents a hydrogen atom, a cycloalkyl group, an amino group which may have a lower alkoxycarbonyl group as a substituent, a benzoyl group which may have 1 to 3 lower alkoxy groups as substituents on the phenyl ring, a lower alkyl group, a lower alkyl group which have 1 or 2 phenyls which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent and a lower alkylthio group which may have a halogen atom as a substituent, a phenyl group which may be substituted, on the phenyl ring, with 1 to 3 groups selected from the group consisting of a lower alkoxy group which may have a halogen atom as a substituent and a lower alkyl group which may have a halogen atom as a substituent, a lower alkoxycarbonyl group, a cycloalkyl lower alkyl group, a pyrrolidinyl lower alkyl group which may have, on the pyrrolidine ring, 1 to 3 lower alkyl groups which may have a hydroxyl group as a substituent, an amino substituted lower alkyl group which may have a substituent selected from the group consisting of a phenyl group and a lower alkyl group, a 1,2,3,4-tetrahydronaphthyl substituted lower alkyl group which may have 1 to 5 lower alkyl groups as substituents on the 1,2,3,4-tetrahydronaphthalene ring, a naphthyl lower alkyl group, a pyridyl lower alkyl group, a quinolyl lower alkyl group, a 1,2,3,4-tetrazolyl lower alkyl group which may have, on the tetrazole ring, 1 to 3 substituents selected from the group consisting of a lower alkyl group and a phenyl lower alkyl group, a 1,2,4-triazolyl lower alkyl group, a tetrahydrofuryl lower alkyl group which may have a hydroxyl group as a substituent on the lower alkyl group, a phenoxy lower alkyl group which may have, on the phenyl ring, 1 to 3 substituents selected from the group consisting of a lower alkyl group and a nitro group, a phenyl lower alkanoyl group, a lower alkanoyl group which may have a halogen atom as a substituent, an imidazolyl lower alkanoyl group, a lower alkoxycarbonyl lower alkyl group, a pyridyl group or a carboxy lower alkyl group.

The reaction of the compound (1uuuuu) and the compound (177) is carried out under the same reaction conditions as in the reaction of the compound (1b) and the compound (4) shown in reaction formula 2 above.

[Reaction formula 118]

[Formula 219]

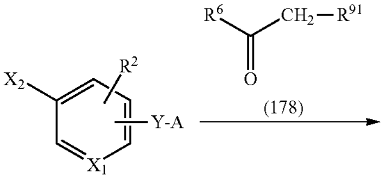

(33)

-continued

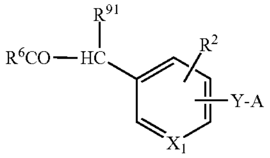

(1wwwwww)

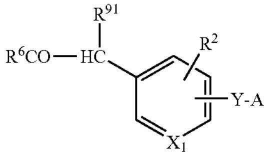

(1wwwwww)

wherein $X_1$, $X_2$, $R^2$, Y, A and $R^6$ are the same as described above, and $R^{91}$ represents a hydrogen atom or a lower alkyl group.

The reaction of the compound (33) and the compound (178) is carried out in an appropriate solvent in the presence of a basic compound and a catalyst.

As the solvent, an inert solvent selected from a wide range may be used. Examples of the inert solvent include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, N-methylpyrrolidone, dimethyl sulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, potassium phosphate, sodium phosphate, sodium hydride, potassium hydride, potassium, sodium, sodium amide, metal alcoholates such as sodium methylate, sodium ethylate, sodium n-butoxide, sodium tert-butoxide, and potassium tert-butoxide, alkylsilylamide alkali metal salts such as potassium bis(trimethylsilyl)amide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst may include palladium compounds such as palladium acetate, bis(tributyltin)/bis(dibenzylideneacetone)palladium, copper iodide/2,2'-bipyridyl, bis(dibenzylideneacetone)palladium, copper iodide/bis(triphenylphosphine)palladium dichloride, tris(dibenzylideneacetone)dipalladium, R-tris(dibenzylideneacetone)-dipalladium, S-tris(dibenzylideneacetone)dipalladium, palladium(II) acetate, [1,1'-bis(diphenylphosphino)ferrocene]dichloropalladium (II), and tetrakis(triphenylphosphine)palladium, compounds such as R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl-(RAC-BINAP), and 2,2-bis(diphenylimidazolidinylidene), xanthene compounds such as 4,5-bis(diphenylphosphino)-9,9-dimethylxanthene, and borates such as tri-tert-butylphosphine tetrafluoroborate, and a mixture thereof.

The basic compound is favorably used in an amount at least 0.5 times and preferably 0.5 to 40 times that of the compound (33) on a molar basis. The catalyst is favorably used in a typical catalyst amount based on the compound (33).

The compound (178) is favorably used in an amount at least in 0.5 times and preferably 0.5 to 3 times that of the compound (33) on a molar basis.

The above described reaction is carried out typically at room temperature to 200° C., preferably at room temperature to about 150° C., and completed in about 0.5 to 20 hours.

[Reaction formula 119]

[Formula 220]

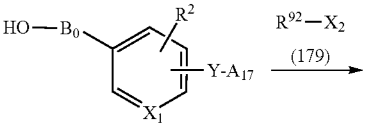

(64)

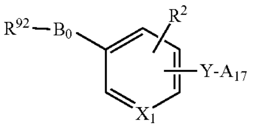

(1aaaaaa)

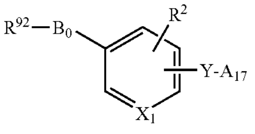

(1aaaaaa)

wherein $B_o$, $X_1$, $R^2$, Y, $A_{17}$, $R^6$ and $X_2$ are the same as described above, $R^{92}$ represents a group $R^6$—$Z_4$— or a group $R^6$— and $Z_4$ represents a lower alkylene group.

The reaction of the compound (64) and the compound (179) is carried out under the same reaction conditions as in the reaction of the compound (2) and the compound (3) shown in reaction formula 1.

[Reaction formula 120]

[Formula 221]

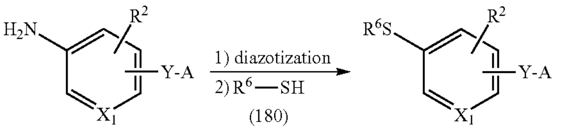

(30) (1bbbbbb)

wherein $R^2$, $X_1$, Y, A and $R^6$ are the same as described above.

The method for converting the compound (30) into the compound (1bbbbbb) is carried out by subjecting the compound (30) to diazotization to obtain a diazonium salt and reacting the diazonium salt with the compound (180).

The diazotization reaction 1) is carried out in an appropriate solvent in the presence of an acid and a diazotizing agent. Examples of the solvent to be used herein include water and acetonitrile. Examples of the acid include hydrochloric acid, hydrobromic acid, sulfuric acid, tetrafluoroboric acid, and hexafluorophosophoric acid. Examples of the diazotizing-agent include metal nitrites such as sodium nitrite and potassium nitrite, lower alkyl nitrites such as t-butyl nitrite and isoamyl nitrite.

The acid is favorably used typically in an amount about 1 to 10 times that of the compound (30) and preferably about 1 to 5 times that of the compound (30) on a molar basis. The diazotizing agent is used typically in at least about equimolar amount to the compound (30) and preferably 1 to 3 times that of the compound (30) on a molar basis.

The above described reaction is carried out typically at about 0 to 70° C. and preferably at about 0° C. to room temperature, and completed in about a few minutes to 5 hours.

The reaction of the diazonium salt obtained in the diazotination reaction and the compound (180) is carried out in the same solvent as in the diazotization reaction 1) and in the presence of a basic compound.

Any basic compound may be used herein as long as it is used in the reaction of the compound (2) and the compound (3) shown in reaction formula 1.

The basic compound is favorably used in at least an equimolar amount to the compound (30) and preferably 1 to 5 times that of the compound (30) on a molar basis.

The compound (180) is favorably used in at least an equimolar amount to the compound (30) and preferably 1 to 5 times that of the compound (30) on a molar basis.

The above described reaction is carried out typically at about 0 to 70° C., preferably at about 0° C. to room temperature, and completed in about a few minutes to 5 hours.

[Reaction formula 121]

[Formula 222]

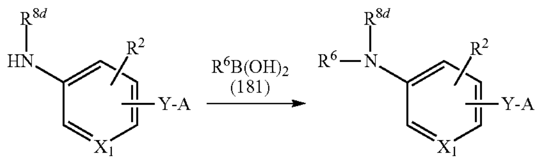

(30a) (1cccccc)

wherein $X^1$, $R^{8d}$, Y, A, $R^2$ and $R^6$ are the same as described above.

The reaction of the compound (30a) and the compound (181) may be carried out in an appropriate solvent in the presence of a basic compound and a catalyst.

Examples of the solvent used herein include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methylethyl ketone, acetonitrile, pyridine, dimethylsulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, sodium n-butoxide, sodium tert-butoxide, and potassium tert-butoxide, organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst include palladium compounds such as tetrakis(triphenylphosphine)palladium(0) and dichlorobis(triphenylphosphine)palladium(II), and copper compounds such as copper (II) acetate.

The basic compound is favorably used in at least an equimolar amount to the compound (30a) and preferably 1 to 5 times that of the compound (30a) on a molar basis.

The catalyst is favorably used in an amount 0.001 to 1 times and preferably 0.01 to 0.5 times that of the compound (30a) on a molar basis.

The compound (181) is favorably used in at least an equimolar amount to the compound (30a) and preferably 1 to 5 times that of the compound (30a) on a molar basis.

The above described reaction is carried out typically at −30 to 200° C. and preferably at 0 to 150° C. and generally completed in 0.5 to about 30 hours. A molecular sieve such as Molecular Sieves 3A (MS-3A), Molecular Sieves 4A (MS-4A) may be added to the reaction.

[Reaction formula 122]

[Formula 223]

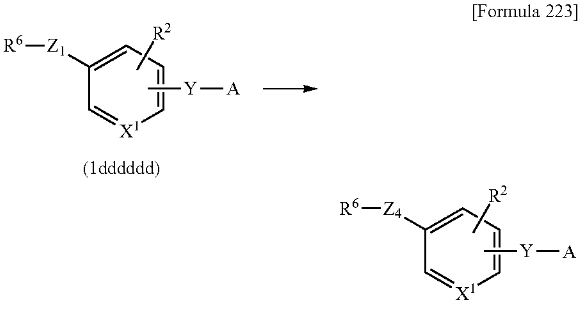

(1dddddd)

(1eeeeee)

wherein $R^6$, $Z_1$, $X^1$, $R^2$, $Y_4$ and A are the same as described above.

The reaction which converts the compound (1dddddd) into the compound (1eeeeee) is carried out in an appropriate solvent in the presence of a catalytic hydrogen reducing agent.

Examples of the solvent include water, fatty acids such as acetic acid, alcohols such as methanol, ethanol, and isopropanol, aliphatic hydrocarbons such as n-hexane, alicyclic hydrocarbons such as cyclohexane, ethers such as diethyl ether, dimethoxyethane, tetrahydrofuran, monoglyme, diglyme, and 1,4-dioxane, esters such as methyl acetate, ethyl acetate, and butyl acetate, and aprotic polar solvents such as N,N-dimethylformamide, N,N-dimethylacetoamide, and N-methylpyrrolidone, and a mixture thereof.

Examples of the catalytic hydrogen reducing agent include palladium, palladium-black, palladium-carbon, palladium hydroxide-carbon, rhodium-alumina, platinum, platinum oxide, copper chromite, Raney nickel, and palladium acetate.

The above described catalytic hydrogen reducing agent is used typically in an amount 0.01 to 1 times that of the compound (1dddddd) on a molar basis.

The above reaction favorably proceeds typically at about −20 to 150° C., and preferably at 0 to 100° C. and generally completed in 0.5 to 20 hours. The hydrogen pressure may be applied typically at 1 to 10 atm.

[Reaction formula 123]

[Formula 224]

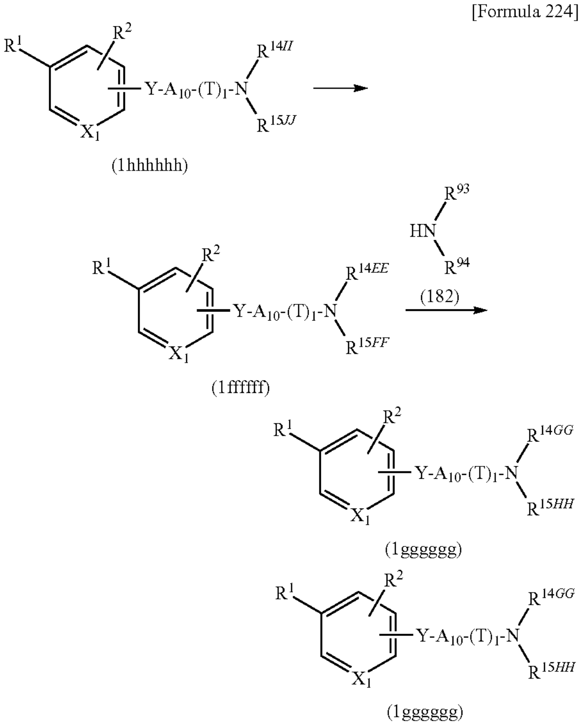

(1hhhhhh) (1ffffff) (1gggggg) (1gggggg)

wherein $R^1$, $R^2$, $X_1$, Y, $A_{10}$, T and l are the same as described above; $R^{14II}$ and $R^{15JJ}$ each represent the same 5- to 10-membered saturated or unsaturated heterocyclic group as defined in $R^{14}$ and $R^{15}$ above, except that they have at least one phenyl group which has a lower alkoxycarbonyl group on the heterocyclic ring; $R^{14EE}$ and $R^{15FF}$ each represent the same 5- to 10-membered saturated or unsaturated heterocyclic group as defined in $R^{14}$ and $R^{15}$ above, except that they have at least one phenyl group which has a carboxy group on the heterocyclic ring;

$R^{14GG}$ and $R^{15HH}$ each represent the same 5- to 10-membered saturated or unsaturated heterocyclic group as defined in $R^{14}$ and $R^{15}$ above, except that they have, on the heterocyclic ring, at least one phenyl group which may have a carbamoyl group which may have a group selected from the group consisting of a lower alkoxy lower alkyl group and a lower alkyl group; and $R^{93}$ and $R^{94}$ each represent a hydrogen atom, a lower alkyl group or a lower alkoxy lower alkyl group.

The reaction which converts the compound (1hhhhhh) into the compound (1ffffff) may be carried out the under the same reaction conditions as in the hydrolysis B described in reaction formula 9 above.

The reaction of the compound (1ffffff) and the compound (182) is carried out under the same reaction conditions as in the reaction of the compound (1b) and the compound (6) shown in reaction formula 2 above.

[Reaction formula 124]

[Formula 225]

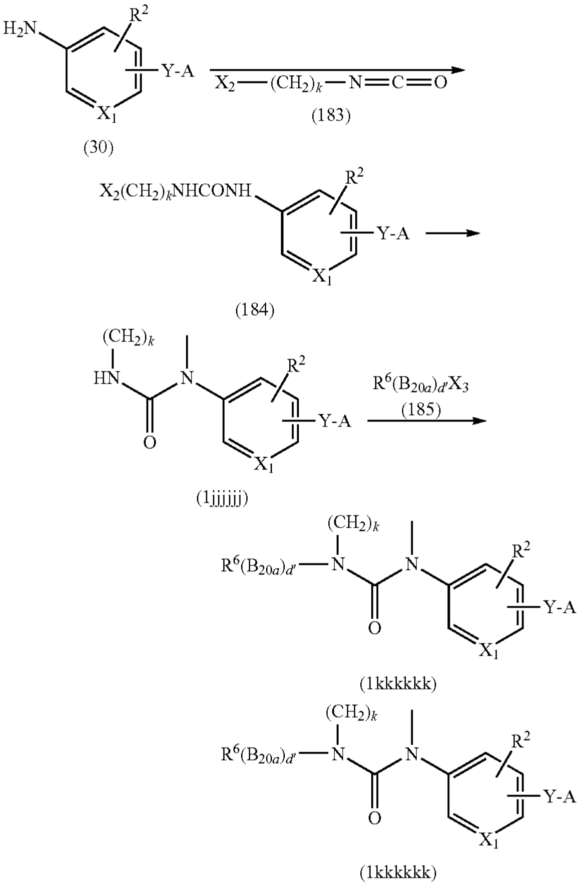

(30) (184) (1jjjjjj) (1kkkkkk) (1kkkkkk)

wherein $X_1$, $R^2$, Y, A, $X_2$, k, $X_3$, $R^6$, $B_{20a}$ and d' are the same as described above.

The reaction of the compound (30) and the compound (183) is carried out under the same reaction conditions as in the reaction of the compound (30) and the compound (66) shown in reaction formula 46 above.

The reaction which converts the compound (184) into the compound (1jjjjjj) is carried out under the same reaction conditions as in the reaction of the compound (2) and the compound (3) shown in reaction formula 1 above.

The reaction of the compound (1jjjjjj) and the compound (185) is carried out under the same reaction conditions as in the reaction of the compound (2) and the compound (3) shown in reaction formula 1 above.

When the compound (185) wherein d' represents 0, the reaction which converts the compound (1jjjjjj) into the compound (1kkkkkk) may be carried out in an appropriate solvent in the presence of a halogenated copper such as copper iodide, an alkylglycine such as N,N-dimethylglycine, or an alkali metal phosphate such as potassium phosphate.

Any solvent may be used herein as long as it is used in the reaction of the compound (2) and the compound (3) shown in reaction formula 1 above.

A halogenated copper or an alkylglycine is used in a typical catalyst amount. The alkali metal phosphate is favorably used typically in at least an equimolar amount to the compound (1jjjjjj) and preferably 1 to 5 times that of the compound (1jjjjjj) on a molar basis. The compound (185) is used in an amount typically 0.5 to 5 times and preferably 0.5 to 3 times that of the compound (1jjjjjj) on a molar basis. The above described reaction is carried out typically at room temperature to 200° C. preferably at about room temperature to 150° C. and generally completed in about 1 to 30 hours.

[Reaction formula 125]

[Formula 226]

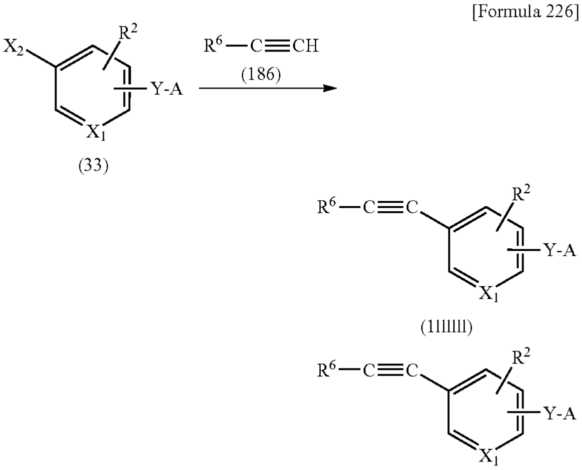

(33)

(186)

(1lllllll)

(1lllllll)

wherein $X_2$, $R^2$, $X_1$, Y, A and $R^6$ are the same as described above.

The reaction of the compound (33) and the compound (186) is carried out under the same reaction conditions as in the reaction of the compound (33) and the compound (178) shown in reaction formula 118 above.

Reaction formula 126]

[Formula 227]

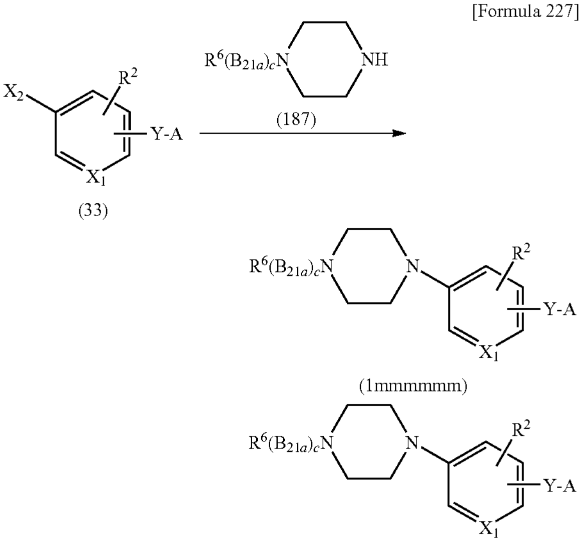

(33)

(187)

(1mmmmmmm)

(1mmmmmmm)

wherein $X_1$, $X_2$, $R^2$, Y, A, $B_{21a}$, $R^6$, and c are the same as described above.

The reaction of the compound (33) and the compound (187) is carried out under the same reaction conditions as in the reaction of the compound (33) and the compound (178) shown in reaction formula 118 above.

[Reaction formula 127]

[Formula 228]

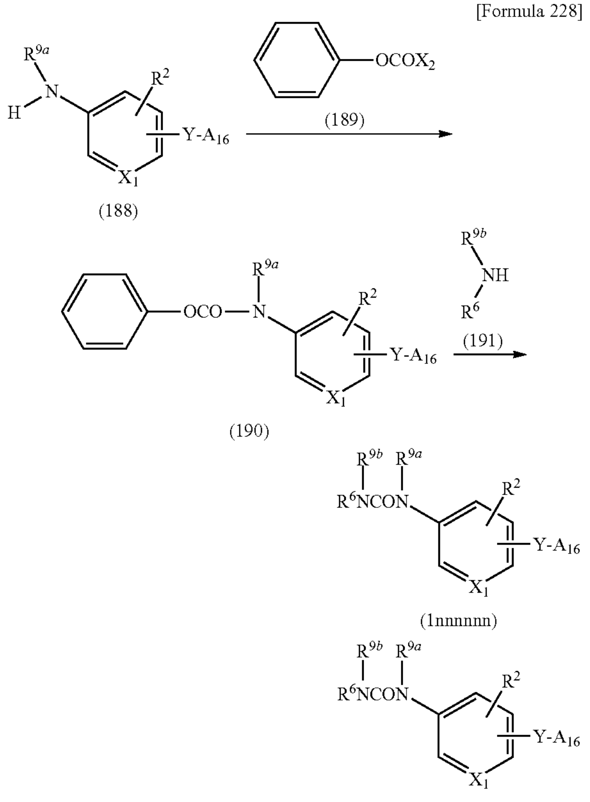

(188)

(189)

(190)

(191)

(1nnnnnn)

(1nnnnnn)

wherein $R^{9a}$, $R^2$, $R^6$, $X_1$, Y, $A_{16}$, $X_2$ and $R^{9b}$ are the same as described above.

The reaction of the compound (188) and the compound (189) is carried out under the same reaction conditions as in the reaction in which an amine is reacted with a carboxylic acid halide among the methods (d) in which the compound (1b) is reacted with the compound (6) shown in reaction formula 2.

The reaction of the compound (190) and the compound (191) is carried out under the same reaction conditions as in the reaction of the compound (2) and the compound (3) shown in reaction formula 1 above.

[Reaction formula 128]

[Formula 229]

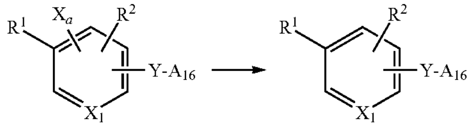

(1oooooo)

(1pppppp)

wherein $R^1$, $R^2$, $X_1$, Y and $A_{16}$ are the same as described above. Xa represents a halogen atom.

The reaction which converts the compound (1oooooo) into the compound (1pppppp) is carried out in an appropriate solvent in the presence of a catalytic hydrogen reducing agent and a hydrogen donor such as formic acid, ammonium formate, cyclohexene, or hydrazine hydrate.

Any solvent and catalytic hydrogen reducing agent may be used as long as they are used in the reaction which converts the compound (1dddddd) into the compound (1eeeeee) shown in reaction formula 122 above.

The catalytic hydrogen reducing agent is typically used in an amount of 0.01 to 40 wt % and preferably 0.01 to 20 wt % of the compound (1oooooo).

The hydrogen donor is used typically in at least an equimolar amount to the compound (1oooooo) and preferably 1 to 10 times that of the compound (1oooooo) on a molar basis.

The above described reaction is carried out under a hydrogen atmosphere typically at about normal pressure to 20 atm and preferably at normal pressure to 10 atm, and at a temperature of about −30 to 150° C. and preferably at about 0 to 100° C. The reaction is generally completed in about 1 to 12 hours.

[Reaction formula 129]

[Formula 230]

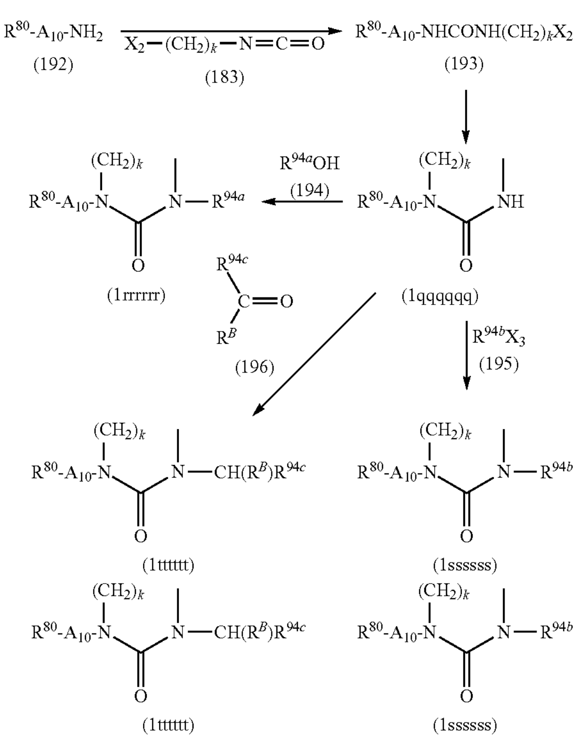

wherein $A_{10}$, $X_2$, k, $X_3$, $R^{80}$ and $R^B$ are the same as described above; $R^{94a}$ represents a group defined as a substituent present on a heterocyclic group formed by binding $R^{14}$ and $R^{15}$ to each other, and include a substituent represented by (35), (40), (42), (67), (75), (76), (78), (80) or (81) in which o is 1, or (84) in which s is 0.

$R^{94b}$ represents a group defined as a substituent present on a heterocyclic ring formed by binding $R^{14}$ and $R^{15}$ to each other, and include a substituent represented by (28), (30) to (34), (36) to (39), (41), (43) to (45), (47), (52) to (60), (62) to (66), (70), (77), (79), (82), (83), (87), (88a) or (90a), a substituent represented by (49) in which t is 1, or a substituent represented by (50) in which o is 0;

and $R^{94c}$ represents a group defined as a substituent present on a heterocyclic ring formed by binding $R^{14}$ and $R^{15}$ to each other and include a substituent represented by (28), (30) to (34), (39), (41), (45), (47), (54) to (58), (62) to (64), (66), (70), (79), (82) or (83), a substituent represented by (49) in which t is 1, or a substituent represented by (50) in which o is 0; a phenyl group which may have, on the phenyl ring, 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxy group and a lower alkylenedioxy group, a pyridyl group which may have, on the pyridine ring, 1 to 3 substituents selected from the group consisting of a hydroxy group and a lower alkyl group which may have a hydroxyl group as a substituent, a pyrrolyl group which may have 1 to 3 lower alkyl groups as substituents on a pyrrolyl group, a benzoxazolyl group, a benzothiazolyl group, a furyl group, a lower alkyl group which may have a substituent selected from the group consisting of a hydroxy group and a halogen atom, a naphthyl group, a 1,2,3,4-tetrahydronaphthyl group which may have 1 to 5 lower alkyl groups as substituents on the 1,2,3,4-tetrahydronaphthalene ring, a quinolyl group, a 1,2,3,4-tetrazolyl group which may have, on the tetrazole ring, a substituent selected from the group consisting of a lower alkyl group and a phenyl lower alkyl group; a thiazolyl group which may have a phenyl group as a substituent on the thiazole ring; a benzoyl group which may have, on the phenyl ring, 1 to 3 substituents selected from the group consisting of a lower alkoxy group and a halogen atom, a piperidinyl group which may have a lower alkyl group as a substituent on the piperidine ring, a 1,2,3,4-tetrahydroquinolyl group which may have an oxo group as a substituent on the tetrahydroquinoline ring, a 1,3,4-oxadiazolyl group which may have an oxo group as a substituent on the 1,3,4 oxadiazole ring, a cycloalkyl group, a thienyl group, or an imidazolyl group.

The reaction of the compound (192) and the compound (183) is carried out under the same reaction conditions as in the reaction of the compound (30) and the compound (183) shown in reaction formula 124 above.

The reaction which converts the compound (193) into the compound (1qqqqqq) is carried out under the same reaction conditions as in the reaction which converts the compound (184) into the compound (1jjjjjj) shown in reaction formula 124 above.

The reaction of the compound (1qqqqqq) and the compound (195) is carried out under the same reaction conditions as in the reaction of the compound (1b) and the compound (4) shown in reaction formula 2 above.

The compound (195), in which $R^{94b}$ is a group represented by (36) to (38), (43), (44), (53), (59), (60), (87), (88a) or (90a), is reacted with the compound (1qqqqqq) in an appropriate solvent in the presence of a copper halide such as copper iodide, an alkylglycine such as N,N-dimethylglycine, and an alkyl metal phosphate such as potassium phosphate.

Any solvent may be used herein as long as it is used in the reaction of the compound (2) and the compound (3) shown in reaction formula 1 above. The copper halide and alkyliglycine are used in a normal catalyst amount. The alkali metal phosphate is favorably used typically in at least an equimolar amount to the compound (1qqqqqq) and preferably 1 to 5 times that of the compound (1qqqqqq) on a molar basis. The compound (195) is favorably used typically in an amount 0.5 to 5 times and preferably 0.5 to 3 times that of the compound (1qqqqqq) on a molar basis. The above described reaction is carried out typically at room temperature to 200° C. and preferably about room temperature to 150° C. and completed in about 1 to 30 hours.

The reaction of the compound (1qqqqqq) and the compound (194) is carried out under the same reaction conditions as in the reaction of the compound (1b) and the compound (6) shown in reaction formula 2 above.

The reaction of the compound (1qqqqqq) and the compound (196) is carried out under the same reaction conditions as in the reaction of the compound (1b) and the compound (5) of the above described formula 2 above.

[Reaction formula 130]

[Formula 231]

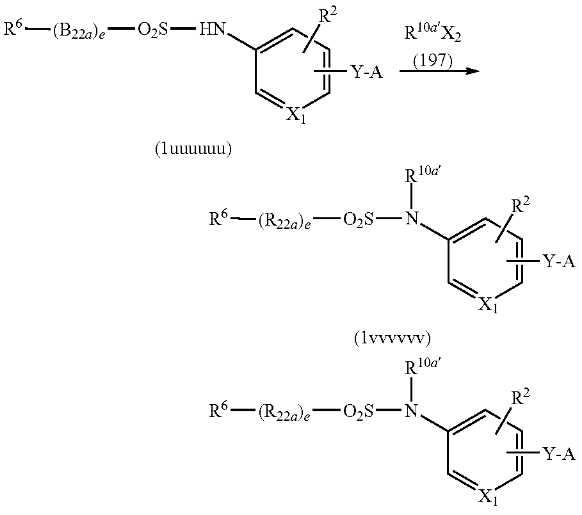

(1uuuuuu)

(1vvvvvv)

(1vvvvvv)

wherein $X_1$, Y, A, $R^2$, $R^6$, $B_{22a}$, e and $X_2$ are the same as described above, and $R^{10a'}$ represents a lower alkyl group.

The reaction of the compound (1uuuuuu) and the compound (197) is carried out under the same reaction conditions as in the reaction of the compound (1b) and the compound (4) of reaction formula 2 above.

[Reaction formula 131]

[Formula 232]

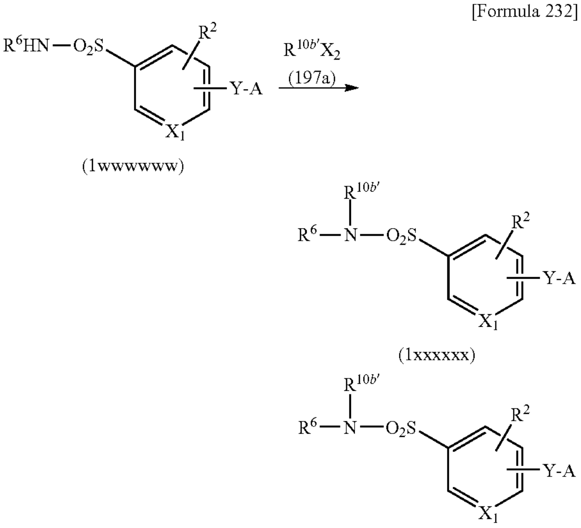

(1wwwwww)

(1xxxxxx)

(1xxxxxx)

wherein $X_1$, Y, A, $R^2$, $R^6$ and $X_2$ are the same as described above. $R^{10b'}$ represents a lower alkyl group.

The reaction of the compound (1wwwwww) and the compound (197a) is carried out under the same reaction conditions as in the reaction of the compound (1b) and the compound (4) shown in reaction formula 2 above.

[Reaction formula 132]

[Formula 233]

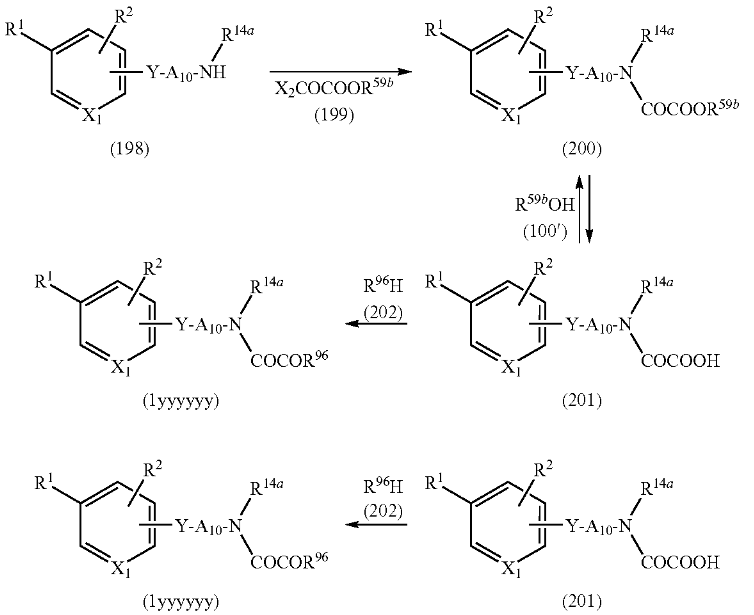

(198)

(200)

(201)

(1yyyyyy)

(201)

(1yyyyyy)

wherein $R^1$, $X_1$, Y, $X_2$, $R^{14a}$ and $R^{59b}$ are the same as described above, and $R^{96}$ represents a piperazinyl group which may have, on the piperazine ring, 1 to 3 substituents selected from the group consisting of a phenyl lower alkyl group (which may have, on the phenyl ring, 1 to 3 substituents selected from the group consisting of a lower alkylenedioxy group and a lower alkoxy group) and a pyridyl lower alkyl group.

The reaction of the compound (198) and the compound (199) is carried out under the same reaction conditions as in the reaction of the compound (2) and the compound (3) shown in reaction formula 1 above.

The reaction which converts the compound (200) into the compound (201) may be carried out under the same reaction conditions as in hydrolysis B described in reaction formula 9 above.

The reaction of the compound (201) and the compound (100') is carried out under the same reaction conditions as in the reaction of the compound (120b) and the compound (100') shown in reaction formula 79 above.

The reaction of the compound (201) and the compound (202) is carried out under the same reaction conditions as in the reaction of the compound (1b) and the compound (6) shown in reaction formula 2 above.

The compound (200) may also be produced by the method shown in the following reaction formula 133:

[Reaction formula 133]

[Formula 234]

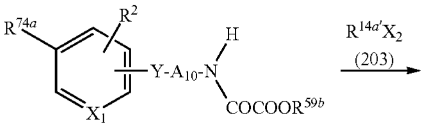

(200a)

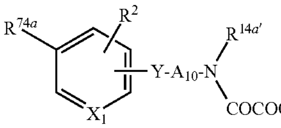

(200b)

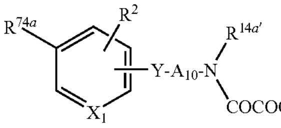

(200b)

wherein $R^{74a}$, $R^2$, $X_1$, Y. $A_{10}$, $R^{59b}$ and $X_2$ are the same as described above, and $R^{14a'}$ represents a lower alkyl group which may have a hydroxyl group as a substituent.

The reaction of the compound (200a) and the compound (203) is carried out under the same reaction conditions as in the reaction of the compound (2) and the compound (3) shown in reaction formula 1 above.

The compound (3) may also be produced by the method of the following reaction formula 134:

[Reaction formula 134]

[Formula 235]

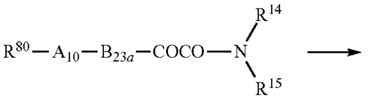

(1081)

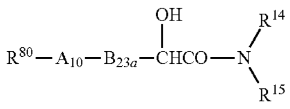

(108m)

wherein $R^{80}$, $A_{10}$, $B_{23a}$, $R^{14}$ and $R^{15}$ are the same as described above.

The reaction which converts the compound (1081) into the compound (108m) is carried out under the same reaction conditions as in the reaction which converts the compound (1f) into the compound (1g) shown in reaction formula 3 above.

[Reaction formula 135]

[Formula 236]

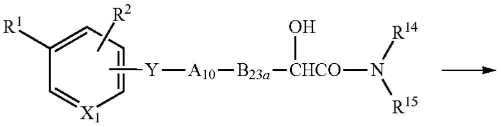

(1zzzzzz)

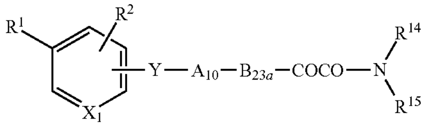

(1AAAAAA)

wherein $R^1$, $R^2$, $X_1$, Y, $A_{10}$, $B_{23a}$, $R^{14}$ and $R^{15}$ are the same as described above.

The reaction which converts the compound (1zzzzzz) into the compound (1AAAAAA) is carried out under the same reaction conditions as in the reaction which converts the compound (64b) into the compound (26a) shown in reaction formula 89 above.

A reaction mixture containing each of the target compounds obtained by reaction formulas shown above is cooled, and thereafter, a crude reaction product can be isolated from the reaction mixture cooled by an isolation operation such as filtration, concentration, or extraction, and purified by a conventional purification operation such as column chromatography or re-crystallization.

The compound of the present invention represented by the general formula (1) includes a stereoisomer, an optical isomer, a solvate (hydrate and ethanolate, etc.)

Of the compounds of the present invention, a compound having a basic group may be easily reacted with a conventional pharmacologically acceptable acid to form a salt. Examples of such an acid include mineral acids such as hydrochloric acid, hydrobromic acid, nitric acid, sulfuric acid, and phosphoric acid, and organic acids such as methanesulfonic acid, p-toluenesulfonic acid, acetic acid, citric acid, tartaric acid, maleic acid, fumaric acid, malonic acid, and lactic acid.

Of the compounds of the present invention, a compound having an acidic group may be easily reacted with a conventional pharmacologically acceptable basic compound to form a salt. Examples of such a basic compound include sodium hydroxide, potassium hydroxide, calcium hydroxide, sodium carbonate, potassium carbonate, sodium bicarbonate, and potassium bicarbonate.

Next, a medical formulation containing a compound according to the present invention as an active ingredient will be described.

The medical formulation is obtained by formulating a compound according to the present invention in the form of pharmaceutical preparation, and more specifically, prepared using a diluent or an excipient such as a filler, expander, binder, moistener, disintegrator, surfactant, or lubricant.

The form of such a medicinal formulation may be chosen from various forms depending upon the therapeutic purpose, and typical forms include tablets, pills, powders, liquids, suspensions, emulsions, granules, capsules, suppositories, and injections (liquids, suspensions).

The carrier to be used in forming tablets may be chosen widely from conventionally known ones. Examples of the carrier include excipients such as lactose, saccharose, sodium chloride, glucose, urea, starch, calcium carbonate, kaolin, and crystalline cellulose, binders such as water, ethanol, propanol, simple syrup, a glucose solution, a starch solution, a gelatin solution, carboxymethylcellulose, shellac, methylcellulose, potassium phosphate, and polyvinylpyrrolidone, disintegrators such as dried starch, sodium arginate, agar powder, laminaran powder, sodium bicarbonate, calcium carbonate, polyoxyethylene sorbitan fatty acid ester, sodium lauryl sulfate, stearic acid monoglyceride, starch, and lactose, anti-disintegrators such as saccharose, stearine, cacao butter, and hydrogenated oil, absorbefacients such as quartenary ammonium base and sodium lauryl sulfate, wetting agents such as glycerol and starch, adsorbents such as starch, lactose, kaolin, bentonite, and colloidal silicate, and lubricants such as purified talc, stearate, boric acid powder, and polyethylene glycol.

Further, tablets may be coated in a conventional manner as needed. Examples of coated tablets include sugar-coated tablets, gelatin-coated tablets, enteric-coated tablets, film-coated tablets, or double or multi-layered tablets.

The carriers to be used in forming pills may be chosen widely from the conventionally known ones. Examples of the carrier include excipients such as glucose, lactose, starch, cacao butter, hydrogenated vegetable oil, kaolin, and talc, binders such as gum arabic powder, tragacanth powder, gelatin, and ethanol, and disintegrators such as laminaran and agar.

The carriers to be used in forming suppositories may be chosen widely from the conventionally known ones. Examples of the carrier include polyethylene glycol, cacao butter, higher alcohols, esters of higher alcohols, gelatin, and semi-synthetic glycerides.

When liquid, emulsion and suspension are prepared as injection preparations, they are preferably sterilized and controlled to be isotonic with the blood. Diluents to be used in forming these liquid, emulsion and suspension preparations may be chosen widely from the conventionally known ones. Examples of the diluents include water, ethanol, propylene glycol, ethoxylated isostearyl alcohol, polyoxylated isostearyl alcohol, and polyoxyethylene sorbitan fatty acid ester. In this case, the medical formulations may contain sodium chloride, glucose or glycerol in a sufficient amount to prepare isotonic solutions. Also, conventional solubilizers, buffers, analgesics, and the like, and, as necessary, coloring agents, preservatives, spices, flavors, sweets and the like, or other pharmaceuticals may be contained.

Although the amount of a compound according to the present invention contained in a medical formulation is not particularly limited and may be appropriately selected from a wide range of compounds. It is preferable that a compound according to the present invention is contained in an amount of 1 to 70 wt % in a medical formulation.

The method for administrating a medical formulation according to the present invention is not particularly limited. The medical formulation can be administered by a method determined depending upon the form of medical formulation, patient's age, sex, severity of the disease and other conditions. For example, tablets, pills, liquids, suspensions, emulsions, granules and capsules are administered orally. The injection formulations are administered singly or by mixing with a conventional fluid replacement such as a glucose solution or amino acid solution, intravenously or, as necessary, singly administered intramuscularly, intradermally, subcutaneously or intraperitoneally. Suppositories are administered into the rectum.

The dosage for the above mentioned medical formulation may be chosen appropriately depending upon the usage, patient's age, sex and severity of the disease and other conditions. Typically, 0.001 to 100 mg per kg (body weight) per day, preferably 0.001 to 50 mg per kg (body weight) per day, is administered once or in several times a day.

Since the above described dosage varies depending upon various conditions, the dosage may be smaller than the lower limit of the range described above or larger than the upper limit of the range described above.

The medicinal drug has an excellent antitumor effect and thus useful as a tumor therapeutic drug.

As a tumor upon which antitumor effect is exerted, for example, a malignant tumor and the like may be mentioned.

As such a malignant tumor, for example, a solid tumor (cancer, sarcoma and the like), blood cancers (lymphoma, leukemia, myeloma and the like) may be mentioned.

Specific examples of the malignant tumor include brain tumors of an infant such as astroglioma, malignant medulloblastoma, germ cell tumor, craniopharyngioma, and ependymoma; brain tumors of an adult such as glioma, meningioma, pituitary gland adenoma, and neurilemma; head cervix cancers such as cancer of maxillary sinus, pharyngeal cancer (nasopharyngeal carcinoma, mesopharyngeal carcinoma, hypopharyngeal carcinoma), laryngeal cancer, oral cavity cancer, labial cancer, tongue cancer, and parotoid cancer; chest cancers and tumors, such as cellule lung cancer, non-small-cell lung cancer, chest adenoma, and mesotheliomas; digestive organ cancers and tumors such as esophagus cancer, liver cancer, primary hepatic cancer, gallbladder cancer, bile duct cancer, stomach cancer, large bowel cancer, colonic cancer, rectal cancer, anal cancer, pancreatic cancer, and pancreas internal secretion tumor; urinary organ cancers and tumors such as penile cancer, renal pelvic/ureteral cancer, renal cell cancer, testicular tumor, prostatic cancer, bladder cancer, Wilms tumor, and urothelial cancer; gynecologic cancers and tumors such as vulvar cancer, cancer of the uterine cervix, corpus uteri cancer, endometrial cancer, uterine sarcoma, chorioma, vaginal cancer, breast cancer, ovary cancer, ovary germ cell tumor;

a soft part sarcoma of an infant and adult; tumors of bones such as osteosarcoma and Ewing tumor; cancers and tumors of the endocrine tissue such as adrenocortical cancer, thyroid cancer;

malignancy lymphoma and leukemia such as malignant lymphoma, non-Hodgkin's lymphoma, Hodgkin's disease, multiple myeloma, plasmacytic tumor, acute myelogenous leukemia, acute lymphatic leukemia, adult T cell leukemia lymphoma, chronic myelogenous leukemia, and chronic lymphatic leukemia; cancers and tumors of skin such as chronic myeloproliferative disorders, malignant melanoma, prickle cell cancer, basal cell cancer, and mycosis fungoides; and metastatic foci of tumors and cancers mentioned above. Of them, the medicinal drug of the present invention have an effect upon liver cancer, chronic myelogenous leukemia, acute myelogenous leukemia, lymphoma, and multiple myeloma.

The medical drug of the present invention has less side effects and excellent safety and is thus more excellent tumor therapeutic agent.

DETAILED DESCRIPTION OF THE INVENTION

The present invention will be explained more specifically by way of Reference Examples, Examples, Preparation Examples and Pharmacological Tests.

Reference Example 1

Production of 1-(t-butoxycarbonyl)-4-(4-hydroxyphenyl)-1,2,5,6-tetrahydropyridine

Step 1

Production of 1-(t-butoxycarbonyl)-4-[(4-methoxymethoxy)phenyl]-4-hydroxypiperidine A solution of 1-bromo-4-methoxymethoxybenzene (5.43 g, 25.0 mmol) in tetrahydrofuran (THF) (100 mL) was stirred at −85° C., and a 2.46 M n-butyllithium hexane solution (10.2 mL, 25.0 mmol) was added dropwise to the stirred solution over 10 minutes. The resulting solution was stirred at the same temperature for 40 minutes. To the reaction solution was added dropwise for 10 minutes a solution of 1-(t-butoxycarbonyl)-4-piperidone (5.20 g, 26.0 mmol) in THF (30 mL). The temperature of the resulting solution was raised to 25° C. over 4 hours, and then the solution was stirred at that temperature for 2 hours. An aqueous solution of saturated ammonium chloride was then added to this solution. The reaction solution was extracted with ethyl acetate and dried over anhydrous magnesium sulfate, after which the solvent was evaporated. The residue was purified by silica gel column chromatography (ethyl acetate:n-hexane=2:3, in ratio by volume; hereinafter the same), to thereby yield 7.63 g of the title compound.

Appearance: Colorless oil $^1$H NMR ($CDCl_3$) δ 1.49 (9H, s), 1.73 (2H, d, J=12.0 Hz), 1.97 (2H, brs), 3.24 (2H, brs), 3.48 (3H, s), 4.00 (2H, brs), 5.17 (2H, s), 7.03 (2H, d, J=9.0 Hz), 7.39 (2H, d, J=9.0 Hz).

Step 2

Production of 1-(t-butoxycarbonyl)-4-(4-hydroxyphenyl)-1,2,5,6-tetrahydropyridine To a solution of 1-(t-butoxycarbonyl)-4-[(4-methoxymethoxy)phenyl]-4-hydroxypiperidine (5.32 g, 15.8 mmol) in toluene (100 mL) was added p-toluenesulfonic acid monohydrate (0.56 g, 2.95 mmol), and the resulting solution was refluxed for 21 hours. The reaction solution was cooled to room temperature, and evaporated under reduced pressure. To this crude product were added ethanol (60 mL) and 2 M hydrochloric acid (40 mL, 80 mmol), and the resulting solution was stirred for 2 hours at 60° C. The reaction solution was again cooled to room temperature, and evaporated under reduced pressure. To the residue were added methanol (100 mL), triethylamine (9.0 mL, 64.6 mmol) and di-t-butyl dicarbonate (5.20 g, 23.8 mmol), and the resulting solution was stirred for 24 hours at room temperature. The solvent was evaporated under reduced pressure, after which to the residue was added 100 mL of ethyl acetate. Insoluble matter was removed by filtration, after which the filtrate was evaporated under reduced pressure. To the residue were added 1,4-dioxane (50 mL) and a 1 M aqueous solution of sodium hydroxide (50 mL, 50 mmol) and stirred for 14 hours at 60° C. To the resulting reaction solution was added at room temperature 2 M hydrochloric acid (25 mL, 50 mmol) to neutralize, and then extracted with ethyl acetate. The ethyl acetate layer was washed with water, dried over anhydrous magnesium sulfate, and evaporated to thereby yield 4.10 g of the title compound.

Appearance: Brown amorphous $^1$H NMR ($CDCl_3$) δ 1.49 (9H, s), 2.47 (2H, brs), 3.62 (2H, t, J=5.5 Hz), 4.05 (2H, brs), 5.91 (1H, brs), 6.81 (2H, d, J=9.0 Hz), 7.25 (2H, d, J=9.0 Hz).

Reference Example 2

Production of methyl 5-(4-benzylpiperazin-1-yl)-2-methoxymethoxybenzoate

To a solution of methyl 5-chloro-2-methoxymethoxybenzoate (1.45 g, 6.29 mmol) and 1-benzylpiperazine (1.66 g, 9.43 mmol) in toluene (50 mL) were added palladium acetate (28 mg, 0.126 mmol), 2,2'-bis(diphenylphosphino)-1,1'-binaphthyl (157 mg, 0.252 mmol) and cesium carbonate (3.07 g, 9.43 mmol), and the resulting solution was refluxed for 3 hours. Water was added to the resulting solution, and extracted with ethyl acetate. The ethyl acetate layer was dried over anhydrous magnesium sulfate, and evaporated. The residue was purified by silica gel column chromatography (ethyl acetate:n-hexane=1:2), to thereby yield 400 mg of the title compound.

Appearance: Yellow oil $^1$H NMR ($CDCl_3$) δ 2.59-2.62 (4H, m), 3.12-3.16 (4H, m), 3.51 (3H, s), 3.57 (2H, s), 3.88 (3H, s), 5.16 (2H, s), 7.01 (1H, dd, J=9.1 Hz, 3.1 Hz), 7.10 (1H, d, J=9.1 Hz), 7.28-7.35 (6H, m).

The following compounds were produced in the same manner as in Reference Example 2.

TABLE 1

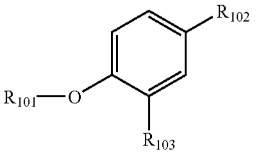

| Reference Example No. | $R_{101}$ | $R_{102}$ | $R_{103}$ | $^1H$ NMR ($CDCl_3$) δ ppm |
|---|---|---|---|---|
| 3 | $-CH_2OCH_3$ | 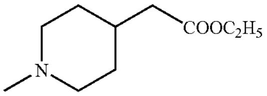 | —H | 1.27 (3H, t, J = 7.0 Hz), 1.43-1.48 (2H, m), 1.83 (2H, brd, J = 13.0 Hz), 1.90 (1H, m), 2.28 (2H, d, J = 7.0 Hz), 2.66 (2H, dt, J = 2.5 Hz, 12.0 Hz), 3.47 (3H, s), 3.50 (2H, brd, J = 12.0 Hz), 4.15 (2H, q, J = 7.0 Hz), 5.10 (2H, s), 6.89 (2H, d, J = 9.0 Hz), 6.95 (2H, d, J = 9.0 Hz). |
| 4 | $-CH_2OCH_3$ | 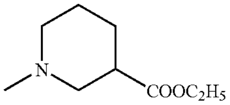 | —H | 1.27 (3H, t, J = 7.0 Hz), 1.57-1.75 (2H, m), 1.82 (1H, m), 2.00 (1H, m), 2.68-2.75 (2H, m), 2.93 (1H, dd, J = 10.0 Hz, 12.0 Hz), 3.34 (1H, d, J = 12.0 Hz), 3.48 (3H, s), 3.56 (1H, brd, J = 10.0 Hz), 4.16 (2H, q, J = 7.0 Hz), 5.11 (2H, s), 6.91 (2H, d, J = 9.0 Hz), 6.96 (2H, d, J = 9.0 Hz). |
| 5 | $-CH_3$ | 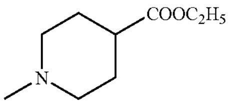 | —H | 1.27 (3H, t, J = 7.0 Hz), 1.91 (2H, dq, J = 3.0 Hz, 13.5 Hz), 2.02 (2H, dd, J = 13.5 Hz, 3.0 Hz), 2.38 (1H, m), 2.69 (2H, dt, J = 3.0 Hz, 12.0 Hz), 3.48 (2H, dt, J = 12.0 Hz, 3.0 Hz), 3.37 (3H, s), 4.16 (2H, q, J = 7.0 Hz), 6.83 (2H, d, J = 9.0 Hz), 6.91 (2H, d, J = 9.0 Hz). |
| 6 | $-CH_2OCH_3$ | 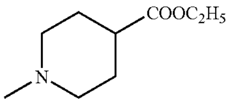 | $-CH_3$ | 1.27 (3H, t, J = 7.1 Hz), 1.82-1.99 (4H, m), 2.22 (3H, s), 2.33-2.42 (1H, m), 2.64-2.73 (2H, m), 3.50-3.52 (5H, m), 4.15 (2H, q, J = 7.1 Hz), 5.12 (2H, s), 6.70 (1H, dd, J = 8.9 Hz, 3.1 Hz), 6.78 (1H, d, J = 3.0 Hz), 6.95 (1H, d, J = 8.7 Hz). |
| 7 | $-CH_2OCH_3$ | 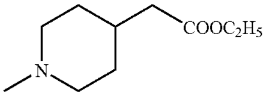 | $-OCH_3$ | 1.27 (3H, t, J = 7.1 Hz), 1.37-1.47 (2H, m), 1.81-1.94 (3H, m), 2.29 (2H, d, J = 6.9 Hz), 2.64-2.73 (2H, m), 3.51 (3H, s), 3.54 (2H, brs), 3.85 (3H, s), 4.15 (2H, q, J = 7.1 Hz), 5.13 (2H, s), 6.44 (1H, dd, J = 8.7 Hz, 2.6 Hz), 6.56 (1H, d, J = 2.6 Hz), 7.02 (1H, d, J = 8.7 Hz). |
| 8 | $-CH_2OCH_3$ | 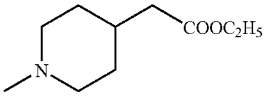 | $-CH_3$ | 1.27 (3H, t, J = 7.1 Hz), 1.37-1.49 (2H, m), 1.80-2.04 (3H, m), 2.22 (3H, s), 2.27 (2H, d, J = 6.9 Hz), 2.60-2.68 (2H, m), 3.48 (3H, s), 3.52 (2H, brs), 4.14 (2H, q, J = 7.1 Hz), 5.11 (2H, s), 6.69-6.79 (2H, m), 6.94 (1H, d, J = 8.7 Hz). |

TABLE 2

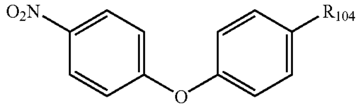

| Reference Example No. | $R_{104}$ | $^1H$ NMR ($CDCl_3$) δ ppm |
|---|---|---|
| 9 | 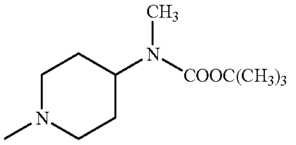 | 1.48 (9H, s), 1.76-1.89 (4H, m), 2.78 (3H, brs), 2.81 (2H, brt, J = 12.0 Hz), 3.71 (2H, brd, J = 12.0 Hz), 4.15 (1H, brs), 6.96 (2H, d, J = 9.0 Hz), 6.98 (4H, s), 8.17 (2H, d, J =9.0 Hz). |
| 10 | 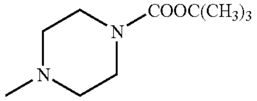 | 1.49 (9H, s), 3.13 (4H, t, J = 5.0 Hz), 3.60 (4H, t, J = 5.0 Hz), 6.96-7.00 (6H, m), 8.18 (2H, d, J = 9.0 Hz). |
| 11 | 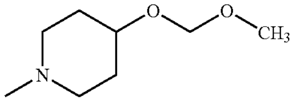 | 1.79 (2H, m), 2.03 (2H, m), 2.96 (2H, m), 3.41 (3H, s), 3.51 (2H, m), 3.73 (1H, m), 4.74 (2H, s), 6.95-6.98 (6H, m), 8.17 (2H, d, J = 9.0 Hz). |
| 12 | 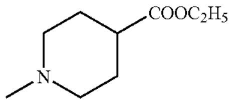 | 1.28 (3H, t, J = 7.0 Hz), 1.90 (2H, dq, J = 4.0 Hz, 13.0 Hz), 2.05 (2H, dd, J = 13.0 Hz, 4.0 Hz), 2.45 (1H, m), 2.82 (2H, dt, J = 2.5 Hz, 12.0 Hz), 3.62 (2H, brd, J = 12.5 Hz), 4.17 (2H, q, J = 7.0 Hz), 6.95-6.98 (6H, m), 8.17 (2H, d, J = 9.0 Hz). |
| 13 | 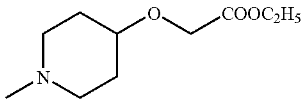 | 1.31 (3H, t, J = 7.0 Hz), 1.83 (2H, m), 2.05 (2H, m), 2.96 (1H, m), 3.07 (1H, m), 3.46 (1H, m), 3.53 (1H, m), 3.60 (1H, m), 4.16 (2H, s), 4.24 (2H, q, J = 7.0 Hz), 6.95-7.01 (6H, m), 8.17 (2H, d, J = 9.0 Hz). |

Reference Example 14

Production of methyl 5-(4-benzylpiperazin-1-yl)-2-hydroxybenzoate

To a solution of 400 mg of methyl 5-(4-benzylpiperazin-1-yl)-2-methoxymethoxybenzoate (1.1 mmol) in 1,4-dioxane (20 mL) was added a solution of 4 N hydrogen chloride in 1,4-dioxane (4 mL, 16 mmol), and the resulting solution was stirred for 2 hours at 100° C. The resulting reaction solution was subjected to distillation under reduced pressure to obtain a residue. This residue was purified by silica gel column chromatography (dichloromethane:methanol=30:1), to thereby yield 353 mg of the title compound.

Appearance: Pale yellow powder $^1H$ NMR ($CD_3OD$) δ 3.29-3.40 (8H, m), 3.94 (3H, s), 4.39 (2H, s), 6.91 (1H, d, J=8.9 Hz), 7.28 (1H, dd, J=8.9 Hz, 3.0 Hz), 7.42 (1H, d, J=3.0 Hz), 7.49-7.60 (5H, m).

The following compounds were produced in the same manner as in Reference Example 14.

TABLE 3

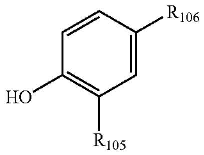

| Reference Example No. | $R_{105}$ | $R_{106}$ | Form | $^1H$ NMR (solvent) δ ppm |
|---|---|---|---|---|
| 15 | —H | 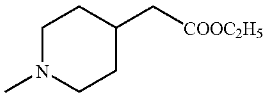 | free | ($DMSO-d_6$) 1.20 (3H, t, J = 7.0 Hz), 1.78 (2H, brs), 1.91 (2H, brs), 2.10 (1H, brs), 2.34 (2H, brs), 3.45 (2H, brs), 3.55 (2H, brs), 4.09 (2H, q, J = 7.0 Hz), 6.88 (2H, brs), 7.60 (2H, brs), 10.05 (1H, brs), 11.75 (1H, brs). |

TABLE 3-continued

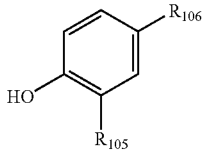

| Reference Example No. | $R_{105}$ | $R_{106}$ | Form | $^1$H NMR (solvent) δ ppm |
|---|---|---|---|---|
| 16 | —H | 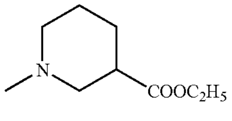 | free | (DMSO-$d_6$) 1.20 (3H, t, J = 7.0 Hz), 1.64 (1H, brs), 1.93 (2H, brs), 2.08 (2H, brs), 3.30 (1H brs), 3.45 (2H, brs), 3.48 (2H, brs), 4.10 (2H, q, J = 7.0 Hz), 6.88 (2H, brs), 7.66 (2H, brs), 10.05 (1H, brs), 12.60 (1H, brs). |
| 17 | —$CH_3$ | 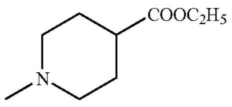 | hydro-chloride | (DMSO-$d_6$) 1.22 (3H, t, J = 7.1 Hz), 2.03-2.13 (4H, m), 2.14 (3H, s), 2.75 (1H, brs), 3.38-3.57 (4H, m), 4.12 (2H, q, J = 7.1 Hz), 6.89 (1H, d, J = 8.6 Hz), 7.46-7.53 (2H, m), 9.99 (1H, brs). |
| 18 | —$OCH_3$ | 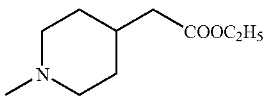 | free | ($CDCl_3$) 1.27 (3H, t, J = 7.1 Hz), 1.98-2.18 (3H,.m), 2.41-2.44 (4H, m), 3.30 (2H, t, J = 12.0 Hz), 3.66 (2H, d, J = 11.9 Hz), 3.95 (3H, s), 4.15 (2H, q, J = 7.1 Hz), 6.26 (1H, brs), 6.96-7.03 (2H, m), 7.85 (1H, s). |
| 19 | —$CH_3$ | 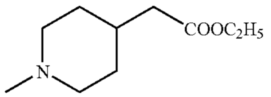 | hydro-chloride | (DMSO-$d_6$) 1.20 (3H, t, J = 7.1 Hz), 1.87 (4H, brs), 2.14 (4H, brs), 2.33 (2H, d, J = 6.4 Hz), 2.52 (2H, brs), 3.44 (2H, brs), 4.19 (2H, q, J = 7.1 Hz), 6.88 (1H, d, J = 8.6 Hz), 7.46-7.57 (2H, m), 9.98 (1H, brs), 12.04 (1H, brs). |

Reference Example 20

Production of ethyl N-(4-hydroxyphenyl)isonipecotate

To a solution of ethyl N-(4-methoxyphenyl)-isonipecotate (2.63 g, 10 mmol) in dichloromethane (100 mL) was added a solution of 2 M boron tribromide in dichloromethane (20 mL, 40 mmol), and the resulting solution was stirred for 0.5 hours at room temperature. The resulting reaction solution was poured into ice water, then an aqueous solution of 1 M sodium hydroxide (110 mL) was added to the solution. After stirring, the resulting solution was separated. The organic layer was washed with water, dried over anhydrous magnesium sulfate, and evaporated under reduced pressure to thereby yield 2.43 g of the title compound.

Appearance: Yellow oil $^1$H NMR ($CDCl_3$) δ 1.27 (3H, t, J=7.0 Hz), 1.91 (2H, m), 2.02 (2H, brd, J=11.5 Hz), 2.38 (1H, m), 2.68 (2H, dt, J=2.0 Hz, 11.5 Hz), 3.46 (2H, dt, J=12.0 Hz, 3.0 Hz), 4.16 (2H, q, J=7.0 Hz), 4.45 (1H, brs), 6.75 (2H, d, J=9.0 Hz), 6.86 (2H, d, J=9.0 Hz).

The following compounds were produced in the same manner as in Reference Example 20.

Reference Example 21

4-(2-Fluoro-4-nitrophenoxy)phenol $^1$H NMR (DMSO-$d_6$) δ 6.80-7.10 (5H, m), 8.04 (1H, ddd, J=1.4 Hz, 2.7 Hz, 9.2 Hz), 8.29 (1H, dd, J=2.7 Hz, 10.9 Hz), 9.59 (1H, s).

Reference Example 22

1-Benzyl-3-(4-hydroxyphenyl)imidazolidin-2-one $^1$H NMR (DMSO-$d_6$) δ 3.18-3.40 (2H, m), 3.61-3.80 (2H, m), 4.35 (2H, s), 6.71 (2H, d, J=8.8 Hz), 7.15-7.48 (7H, m), 9.10 (1H, s).

Reference Example 23

Production of 2-(4-hydroxyphenylamino)-1-(4-piperonylpiperazin-1-yl)ethanone To a solution of N-(4-hydroxyphenyl)glycine (11.38 g, 68.1 mmol) in N,N-dimethylformamide (DMF) (150 mL) were added under ice cooling 1-piperonylpiperazine (15.0 g, 68.1 mmol), 1-hydroxybenzotriazole monohydrate (10.43 g, 68.1 mmol) and 1-ethyl-3-(3-dimethylaminopropyl)carbodiimide hydrochloride (15.66 g, 81.7 mmol), and the resulting solution was stirred for 30 minutes under ice cooling and for 4.5 hours at room temperature. The reaction solution was concentrated under reduced pressure. To the residue was added a saturated sodium bicarbonate solution (400 mL), and extracted with ethyl acetate (400 mL). The ethyl acetate layer was washed with a saturated sodium bicarbonate solution and brine. The ethyl acetate layer was dried over anhydrous magnesium sulfate, and evaporated, to leave the resulting product solidified in a powdered form. Ethyl acetate was added, and the resulting product was filtered off and washed with ethyl acetate, to thereby yield 18.58 g of the title compound.

Appearance: Brown powder $^1$H NMR (DMSO-$d_6$) δ 2.30 (2H, brs), 2.36 (2H, brs), 3.40 (2H, s), 3.47 (4H, t, J=14.5 Hz), 4.03 (2H, d, J=7.0 Hz), 4.90 (1H, brs), 5.99 (2H, s), 6.49 (2H, d, J=8.9 Hz), 6.54 (2H, d, J=8.9 Hz), 6.75 (1H, dd, J=8.0 Hz, 1.1 Hz), 6.85 (1H, d, J=8.0 Hz), 6.87 (1H, s), 8.42 (1H, s).

The following compounds were produced in the same manner as in Reference Example 23.

Reference Example 24

6-Chloro-N-(3,4-dichlorophenyl)nicotinamide $^1$H NMR ($CDCl_3$) δ 7.64 (1H, d, J=8.9 Hz), 7.72 (1H, dd, J=8.7 Hz, 2.3 Hz), 7.73 (1H, dd, J=8.3 Hz, 0.7 Hz), 8.12 (1H, d, J=2.3 Hz), 8.35 (1H, dd, J=8.3 Hz, 2.5 Hz), 8.95 (1H, dd, J=2.5 Hz, 0.7 Hz), 10.71 (1H, brs).

Reference Example 25

4-(4-Piperonylpiperazine-1-carbonyl)-1-(4-hydroxyphenyl)pyrrolidin-2-one $^1$H NMR ($CDCl_3$) δ 2.43-2.45 (4H, m), 2.73-2.95 (2H, m), 3.45 (2H, s), 3.49-3.54 (4H, m), 3.65-3.72 (1H, m), 3.78-3.87 (1H, m), 4.17-4.23 (1H, m), 5.96 (2H, s), 6.71-6.80 (4H, m), 6.84-6.85 (1H, m), 7.29 (2H, d, J=8.9 Hz).

TABLE 4

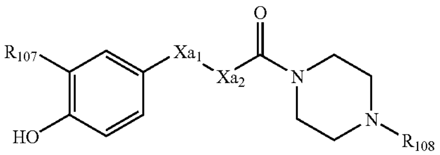

| Reference Example No. | $Xa_1$ | $Xa_2$ | $R_{107}$ | $R_{108}$ | Form | $^1$H NMR (solvent) δ ppm |
|---|---|---|---|---|---|---|
| 26 | —NH— | —$CH_2$— | —H | benzyl | free | ($CDCl_3$) 2.46-2.48 (4H, m), 3.45 (2H, t, J = 5.0 Hz), 3.54 (2H, s), 3.68 (2H, t, J = 5.0 Hz), 3.82 (2H, s), 6.53 (2H, d, J = 8.7 Hz), 6.70 (2H, d, J = 8.7 Hz), 7.27-7.34 (5H, m). |
| 27 | —$CH_2$— | —$CH_2$— | —H | benzyl | free | ($CDCl_3$) 2.30-2.33 (2H, m), 2.41-2.45 (2H, m), 2.55-2.60 (2H, m), 2.85-2.91 (2H, m), 3.36-3.40 (2H, m), 3.52 (2H, s), 3.62-3.66 (2H, m), 5.10 (1H, brs), 6.74-6.77 (2H, m), 7.03 (2H, d, J = 8.6 Hz), 7.27-7.32 (5H, m). |
| 28 | —$CH_2$— | —$CH_2$— | —H | piperonyl | hydro-chloride | (DMSO-$d_6$) 2.56-3.47 (10H, m), 4.01-4.07 (1H, m), 4.18-4.48 (3H, m), 6.07 (2H, s), 6.65-6.68 (2H, m), 7.00-7.03 (4H, m), 7.21 (1H, s), 9.18 (1H, brs), 11.04 (1H, brs). |
| 29 | —O— | —$CH_2$— | —H | piperonyl | free | ($CDCl_3$) 2.31-2.50 (4H, m), 3.41 (2H, s), 3.52-3.72 (4H, m), 4.63 (2H, s), 5.94 (2H, s), 6.25 (1H, brs), 6.70 (2H, d, J = 9.1 Hz), 6.69-6.77 (1H, m), 6.73 (1H, s), 6.77 (2H, d, J = 9.1 Hz), 6.83 (1H, d, J = 0.9 Hz). |
| 30 | —O— | —$CH_2$— | —H | benzyl | free | ($CDCl_3$) 2.40-2.52 (4H, m), 3.51 (2H, s), 3.53-3.73 (4H, m), 4.63 (2H, s), 5.89 (1H, brs), 6.70 (2H, d, J = 9.2 Hz), 6.78 (2H, d, J = 9.2 Hz), 7.22-7.43 (5H, m). |
| 31 | —CH(OH)— | none | —H | benzyl | free | ($CDCl_3$) 1.89-2.03 (1H, m), 2.21-2.32 (1H, m), 2.32-2.57 (2H, m), 3.00-3.18 (1H, m), 3.20-3.35 (1H, m), 3.40 (1H, d, J = 13.1 Hz), 3.46 (1H, d, J = 13.1 Hz), 3.60-3.83 (2H, m), 5.13 (1H, s), 6.71 (2H, d, J = 8.6 Hz), 7.09 (2H, d, J = 8.6 Hz), 7.18-7.35 (5H, m). |
| 32 | none | none | —H | 3-pyridyl | free | (DMSO-$d_6$) 3.18-3.35 (4H, m), 3.64 (4H, brs), 6.82 (2H, d, J = 8.4 Hz), 7.21-7.37 (4H, m), 8.02-8.03 (1H, m), 8.32 (1H, d, J = 2.4 Hz), 9.90 (1H, brs). |
| 33 | —$CH_2$— | —CO— | —H | —$CO_2C(CH_3)_3$ | free | ($CDCl_3$) 1.44 (9H, s), 2.93-3.15 (4H, m), 3.32 (2H, t, J = 5.2 Hz), 3.50 (2H, t, J = 5.2 Hz), 3.97 (2H, s), 5.48 (1H, brs), 6.81 (2H, d, J = 8.6 Hz), 7.11 (2H, d, J = 8.6 Hz). |

TABLE 4-continued

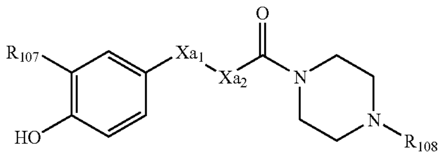

| Reference Example No. | $Xa_1$ | $Xa_2$ | $R_{107}$ | $R_{108}$ | Form | $^1H$ NMR (solvent) δ ppm |
|---|---|---|---|---|---|---|
| 34 | —NH— | $—CH_2—$ | $—CH_3$ | piperonyl | free | ($CDCl_3$) 2.20 (3H, s), 2.41-2.46 (4H, m), 3.44 (4H, brs), 3.67 (2H, t, J = 4.8 Hz), 3.81 (2H, s), 4.34 (1H, brs), 4.52 (1H, brs), 5.95 (2H, s), 6.37 (1H, dd, J = 8.4 Hz, 2.6 Hz), 6.44 (1H, d, J = 2.8 Hz), 6.64 (1H, d, J = 8.4 Hz), 6.70-6.77 (2H, m), 6.85 (1H, s). |

Reference Example 35

Production of ethyl(4-hydroxy-3-methylphenylamino)acetate

Potassium carbonate (5.04 g, 36.5 mmol) was added at room temperature to a solution of 4-amino-o-cresol (3.00 g, 24.4 mmol) and ethyl bromoacetate (2.70 mL, 24.4 mmol) in DMF (30 mL). The resulting solution was stirred at room temperature for 1.5 hours. Water was added to the reaction mixture, and extracted with ethyl acetate. The ethyl acetate layer was washed with brine. The ethyl acetate layer was dried over anhydrous sodium sulfate, and evaporated. The residue was purified by silica gel column chromatography (n-hexane:ethyl acetate=3:1), to thereby yield 5.10 g of the title compound.

Appearance: Yellow solid $^1H$ NMR ($CDCl_3$) δ 1.28 (3H, t, J=7.1 Hz), 2.19 (3H, s), 3.84 (2H, s), 3.95 (1H, brs), 4.22 (2H, q, J=7.1 Hz), 4.59 (1H, brs), 6.36 (1H, dd, J=8.4 Hz, 2.9 Hz), 6.44 (1H, d, J=2.9 Hz), 6.63 (1H, d, J=8.4 Hz).

The following compounds were produced in the same manner as in Reference Example 35.

Reference Example 36

Ethyl(3-hydroxyphenylamino)acetate $^1H$ NMR ($CDCl_3$) δ 1.30 (3H, t, J=7.1 Hz), 3.88 (2H, s), 4.25 (2H, q, J=7.1 Hz), 4.29 (1H, brs), 4.85 (1H, s), 6.08-6.10 (1H, m), 6.18-6.24 (2H, m), 7.01-7.07 (1H, m).

Reference Example 37

Benzyl(4-hydroxy-3-methoxyphenylamino)acetate $^1H$ NMR ($CDCl_3$) δ 3.81 (3H, s), 3.92 (2H, brs), 4.01 (1H, brs), 5.09 (1H, brs), 5.20 (2H, s), 6.11 (1H, dd, J==8.4 Hz, 2.6 Hz), 6.23 (1H, d, J=2.6 Hz), 6.76 (1H, d, J=58.4 Hz), 7.31-7.38 (5H, m).

Reference Example 38 t-Butyl[3-(4-benzyloxy-3-methylphenyl)-2-oxotetrahydropyrimidin-1-yl]acetate $^1H$ NMR ($CDCl_3$) δ 1.47 (9H, s), 2.04-2.21 (2H, m), 2.25 (3H, s), 3.45 (2H, t, J=5.9 Hz), 3.67 (2H, t, J=5.9 Hz), 4.04 (2H, s), 5.06 (2H, s), 6.82 (1H, d, J=8.6 Hz), 7.01 (1H, dd, J=2.6 Hz, 8.6 Hz), 7.06-7.12 (1H, m), 7.26-7.48 (5H, m).

TABLE 5

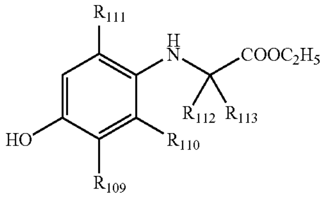

| Reference Example No. | $R_{109}$ | $R_{110}$ | $R_{111}$ | $R_{112}$ | $R_{113}$ | $^1H$ NMR ($CDCl_3$) δ ppm or MS |
|---|---|---|---|---|---|---|
| 39 | $—CH_3$ | $—CH_3$ | —H | —H | —H | $^1H$ NMR 1.30 (3H, t, J = 7.1 Hz), 2.14 (3H, s), 2.20 (3H, s), 3.87 (2H, s), 4.24 (2H, q, J = 7.1 Hz), 4.42 (1H, brs), 6.29 (1H, d, J = 8.6 Hz), 6.58 (1H, d, J = 8.6 Hz). |
| 40 | —F | —H | —F | —H | —H | $^1H$ NMR 1.30 (3H, t, J = 7.1 Hz), 3.85 (2H, s), 4.25 (2H, q, J = 7.1 Hz), 4.77 (1H, s), 6.37 (1H, dd, J = 7.9 Hz, 11.8 Hz), 6.73 (1H, dd, J = 7.9 Hz, 11.6 Hz). |

TABLE 5-continued

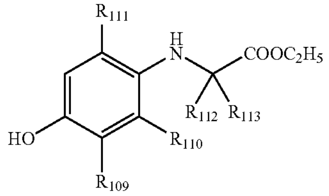

| Reference Example No. | $R_{109}$ | $R_{110}$ | $R_{111}$ | $R_{112}$ | $R_{113}$ | $^1$H NMR ($CDCl_3$) δ ppm or MS |
|---|---|---|---|---|---|---|
| 41 | —$CH_3$ | —H | —$CH_3$ | —H | —H | $^1$H NMR 1.30 (3H, t, J = 7.1 Hz), 2.15 (3H, s), 2.19 (3H, s), 3.84 (1H, brs), 3.89 (2H, s), 4.17 (1H, s), 4.25 (2H, q, J = 7.1 Hz), 6.28 (1H, s), 6.57 (1H, s). |
| 42 | —H | —$CH_3$ | —$CH_3$ | —H | —H | MS 223 ($M^+$) |
| 43 | —$OCH_3$ | —H | —H | —H | —H | $^1$H NMR 1.29 (3H, t, J = 7.1 Hz), 3.82 (3H, s), 3.85 (2H, s), 4.23 (2H, q, J = 7.1 Hz), 5.26 (1H, brs), 6.11 (1H, dd, J = 8.4 Hz, 2.6 Hz), 6.25 (1H, d, J = 2.6 Hz), 6.76 (1H, d, J = 8.4 Hz). |
| 44 | —F | —H | —H | —H | —H | $^1$H NMR 1.30 (3H, t, J = 7.1 Hz), 3.83 (2H, s), 4.08 (1H, brs), 4.24 (2H, q, J = 7.1 Hz), 4.62 (1H, d, J = 3.3 Hz), 6.30-6.41 (2H, m), 6.85 (1H, t, J = 8.9 Hz). |
| 45 | —H | —H | —H | —$CH_3$ | —$CH_3$ | $^1$H NMR 1.20 (3H, t, J = 7.1 Hz), 1.48 (6H, s), 4.15 (2H, q, J = 7.1 Hz), 6.60-6.69 (4H, m). |
| 46 | —$CH_3$ | —H | —H | —$CH_3$ | —H | $^1$H NMR 1.24 (3H, t, J = 7.3 Hz), 1.44 (3H, d, J = 6.9 Hz), 2.18 (3H, s), 3.80 (1H, brs), 4.03 (1H, q, J = 6.9 Hz), 4.17 (2H, q, J = 7.3 Hz), 4.25 (1H, brs), 6.37 (1H, dd, J = 8.4 Hz, 3.0 Hz), 6.45 (1H, d, J = 2.8 Hz), 6.62 (1H, d, J = 8.4 Hz). |
| 47 | —H | —H | —H | —$CH_3$ | —H | $^1$H NMR 1.24 (3H, t, J = 7.1 Hz), 1.44 (3H, d, J = 6.7 Hz), 3.88 (1H, brs), 4.04 (1H, q, J = 6.9 Hz), 4.17 (2H, q, J = 7.1 Hz), 4.59 (1H, brs), 6.54 (2H, d, J = 8.9 Hz), 6.68 (2H, d, J = 8.9 Hz). |
| 48 | —$CF_3$ | —H | —H | —H | —H | MS 263 ($M^+$) |

TABLE 6

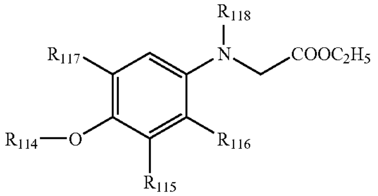

| Reference Example No. | $R_{114}$ | $R_{115}$ | $R_{116}$ | $R_{117}$ | $R_{118}$ | $^1$H NMR (solvent) δ ppm or MS |
|---|---|---|---|---|---|---|
| 49 | 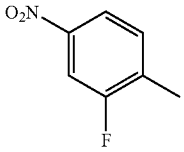 | —H | —H | —H | —H | $^1$H NMR (DMSO-$d_6$) 1.18 (3H, t, J = 7.1 Hz), 3.89 (2H, d, J = 6.2 Hz), 4.11 (2H, q, J = 7.1 Hz), 6.14 (1H, t, J = 6.2 Hz), 6.62 (2H, d, J = 8.8 Hz), 6.90 (1H, t, J = 9.0 Hz), 6.97 (2H, d, J = 8.8 Hz), 8.03 (1H, dd, J = 2.6 Hz, 9.0 Hz), 8.24 (1H, dd, J = 2.6 Hz, 10.9 Hz). |
| 50 | 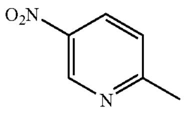 | —F | —H | —F | —$CH_3$ | $^1$H NMR ($CDCl_3$) 1.29 (3H, t, J = 7.1 Hz), 3.07 (3H, s), 4.03 (2H, s), 4.22 (2H, q, J = 7.1 Hz), 6.22-6.35 (2H, m), 7.15 (1H, d, J = 9.0 Hz), 8.49 (1H, dd, J = 2.8 Hz, 9.0 Hz), 9.01 (1H, d, J = 2.8 Hz). |

TABLE 6-continued

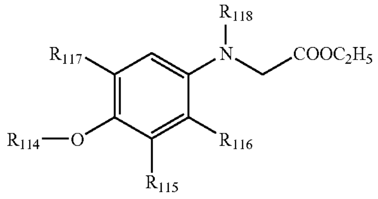

| Reference Example No. | $R_{114}$ | $R_{115}$ | $R_{116}$ | $R_{117}$ | $R_{118}$ | $^1H$ NMR (solvent) δ ppm or MS |
|---|---|---|---|---|---|---|
| 51 | 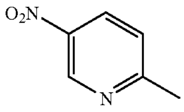 | —F | —F | —H | $—CH_3$ | $^1H$ NMR ($CDCl_3$) 1.28 (3H, t, J = 7.1 Hz), 3.05 (3H, s), 4.06 (2H, s), 4.20 (2H, q, J = 7.1 Hz), 6.72 (1H, td, J = 2.2 Hz, 9.0 Hz), 6.90 (1H, td, J = 1.8 Hz, 9.4 Hz), 7.11 (1H, d, J = 9.0 Hz), 8.50 (1H, dd, J = 2.7 Hz, 9.0 Hz), 9.02 (1H, d, J = 2.7 Hz). |
| 52 | 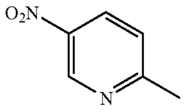 | —H | —H | —H | $—SO_2CH_3$ | $^1H$ NMR ($CDCl_3$) 1.31 (3H, t, J = 7.1 Hz), 3.17 (3H, s), 4.25 (2H, q, J = 7.1 Hz), 4.47 (2H, s), 7.09 (1H, d, J = 8.9 Hz), 7.20 (2H, d, J = 8.7 Hz), 7.60 (2H, d, J = 8.9 Hz), 8.51 (1H, dd, J = 9.1 Hz, 2.8 Hz), 9.03 (1H, d, J = 2.8 Hz). |
| 53 | 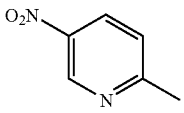 | $—CH_3$ | —H | —H | $—SO_2CH_3$ | $^1H$ NMR ($CDCl_3$) 1.31 (3H, t, J = 7.1 Hz), 2.16 (3H, s), 3.17 (3H, s), 4.25 (2H, q, J = 7.1 Hz), 4.46 (2H, s), 7.07 (1H, dd, J = 9.1 Hz, 0.7 Hz), 7.08 (1H, d, J = 7.3 Hz), 7.40 (1H, d, J = 2.6 Hz), 7.44 (1H, dd, J = 7.3 Hz, 2.6 Hz), 8.50 (1H, dd, J = 9.1 Hz, 2.8 Hz), 9.01 (1H, dd, J = 2.8 Hz, 0.7 Hz). |
| 54 | —H | $—CF_3$ | —H | —H | $—C_2H_5$ | MS 291 ($M^+$) |

TABLE 7

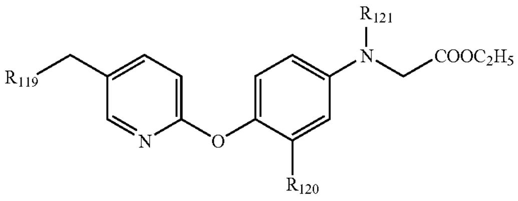

| Reference Example No. | $R_{119}$ | $R_{120}$ | $R_{121}$ | $^1H$ NMR ($CDCl_3$) δ ppm |
|---|---|---|---|---|
| 55 | $4-CF_3Ph-$ | —H | —H | 1.30 (3H, t, J = 7.1 Hz), 3.89 (2H, d, J = 4.6 Hz), 3.95 (2H, s), 4.20 (1H, brs), 4.25 (2H, q, J = 7.1 Hz), 6.62 (2H, d, J = 8.9 Hz), 6.77 (1H, d, J = 8.4 Hz), 6.97 (2H, d, J = 8.9 Hz), 7.27 (2H, d, J = 7.9 Hz), 7.39 (1H, dd, J = 8.4 Hz, 2.5 Hz), 7.54 (2H, d, J = 7.9 Hz), 8.03 (1H, d, J = 2.5 Hz). |
| 56 | $4-CF_3PhO—$ | —H | $—SO_2CH_3$ | 1.30 (3H, t, J = 7.1 Hz), 3.15 (3H, s), 4.23 (2H, q, J = 7.1 Hz), 4.45 (2H, s), 5.06 (2H,s), 6.99-7.04 (3H, m), 7.16 (2H, d, J = 8.9 Hz), 7.54 (2H, d, J = 8.9 Hz), 7.56 (2H, d, J = 9.2 Hz), 7.79-7.83 (1H, m), 8.23 (1H, d, J = 2.0 Hz). |
| 57 | $4-CF_3PhO—$ | $—CH_3$ | $—SO_2CH_3$ | 1.30 (3H, t, J = 7.1 Hz), 2.19 (3H, s), 3.16 (3H, s), 4.24 (2H, q, J = 7.1 Hz), 4.44 (2H, s), 5.05 (2H, s), 6.96-7.07 (4H, m), 7.36 (1H, dd, J = 8.7 Hz, 2.6 Hz), 7.42 (1H, d, J = 2.3 Hz), 7.56 (2H, d, J = 8.9 Hz), 7.80 (1H, dd, J = 8.6 Hz, 2.3 Hz), 8.20 (1H, d, J = 2.3 Hz). |

(Ph means a benzene ring having 1 to 4 free valences. Hereinafter Ph indicates the same meaning.)

Reference Example 58 t-Butyl(3-cyano-4-hydroxyphenylamino)acetate

MS 248 ($M^+$)

Reference Example 59

Production of 2-[4-(2-fluoro-4-nitrophenoxy)phenoxy]-1-(4-piperonylpiperazin-1-yl)ethanone Potassium carbonate (0.350 g, 2.53 mmol) was added to a solution of 4-(2-fluoro-4-nitrophenoxy)phenol (0.420 g, 1.69 mmol) and 1-chloroacetyl-4-piperonylpiperazine (0.500 g, 1.70 mmol) in DMF (8 mL). The resulting reaction mixture was stirred for 40 minutes at 100° C. Water was added to the reaction mixture, and extracted with ethyl acetate. The ethyl acetate layer was washed with brine, dried over anhydrous sodium sulfate, and evaporated, to thereby yield 0.860 of the title compound.

Appearance: Brown oil $^1$H NMR ($CDCl_3$) δ 2.50-2.60 (4H, m), 3.43 (2H, s), 3.50-3.70 (4H, m), 4.71 (2H, s), 5.95 (2H, s), 6.65-6.75 (2H, m), 6.80-7.05 (6H, m), 7.94 (1H, dd, J=2.3 Hz, 9.1 Hz), 8.06 (1H, dd, J=2.3 Hz, 10.4 Hz).

The following compound was produced in the same manner as in Reference Example 59.

Reference Example 60

2-[4-(2-fluoro-4-nitrophenoxy)phenylamino]-1-(4-piperonylpiperazin-1-yl)ethanone $^1$H NMR (DMSO-$d_6$) δ 2.25-2.40 (4H, m), 3.43 (2H, s), 3.45-3.50 (4H, m), 3.90 (2H, d, J=5.1 Hz), 5.75 (1H, t, J=5.1 Hz), 5.99 (2H, s), 6.70-6.75 (3H, m), 6.80-7.00 (5H, m), 8.05 (1H, ddd, J=1.4 Hz, 2.7 Hz, 10.5 Hz), 8.27 (1H, dd, J=2.7 Hz, 11.0 Hz).

Reference Example 61

Production of methyl 3-(4-benzyloxyphenylamino)-propionate

Under nitrogen, 4-benzyloxyaniline (13.0 g, 65 mmol) was dissolved by heating at 70° C., and a boron trifluoride-diethyl ether complex (0.82 mL, 6.5 mmol) was added dropwise at the same temperature to the dissolved solution. Methyl acrylate (5.85 mL, 65 mmol) was then slowly added dropwise to the resulting solution. This solution was stirred for 10 hours at 70° C. After cooling with ice, ethyl acetate was added to the reaction mixture and washed with aqueous 1 N sodium hydroxide and brine. The organic layer was dried over anhydrous magnesium sulfate, evaporated, and the residue was purified by silica gel column chromatography (n-hexane: ethyl acetate=5:1), to thereby yield 17.5 g of the title compound.

Appearance: Brown powder $^1$H NMR ($CDCl_3$) δ 2.60 (2H, t, J=6.4 Hz), 3.39 (2H, t, J=6.4 Hz), 3.69 (3H, s), 3.77 (1H, brs), 4.98 (2H, s), 6.58 (2H, d, J=8.9 Hz), 6.85 (2H, d, J=8.9 Hz), 7.30-7.44 (5H, m).

Reference Example 62

Production of ethyl 3-(4-Methoxyphenylamino)propionate 3-(4-hydroxyphenylamino)propionic acid (4.00 g, 20.5 mmol) was added to 48% hydrobromic acid (50 mL), and the resulting solution was stirred for 2.5 hours at 100° C. After concentration under reduced pressure, ethanol (10 mL) was added to the residue, and concentrated under reduced pressure. A saturated sodium bicarbonate solution was added to the residue, and extracted with dichloromethane. The dichloromethane layer was dried over anhydrous sodium sulfate and evaporated. The residue was purified by silica gel column chromatography (n-hexane:ethyl acetate=2:1), to thereby yield 1.27 g of the title compound.

Appearance: Yellow oil $^1$H NMR ($CDCl_3$) δ 1.27 (3H, t, J=7.2 Hz), 2.59 (2H, t, J=6.4 Hz), 3.38 (2H, t, J=6.4 Hz), 4.15 (2H, q, J=7.2 Hz), 6.55 (2H, d, J=8.8 Hz), 6.70 (2H, d, J=8.8 Hz).

Reference Example 63

Production of ethyl[(3-fluoro-4-hydroxyphenyl)methyl-amino]acetate

Ethyl(3-fluoro-4-hydroxyphenylamino)acetate (1.06 g, 5.1 mmol) was dissolved in methanol (150 mL) and the resulting solution was cooled with ice. To the resulting solution were added aqueous 37% formaldehyde (1.5 mL), sodium triacetoxyborohydride (1 g, 16 mmol) and acetic acid (0.9 mL, 15 mmol), and then stirred at room temperature under a nitrogen atmosphere for 14 hours. The solvent was evaporated under reduced pressure. Water was added to the residue, and the resulting solution was neutralized with a saturated sodium bicarbonate solution and extracted with ethyl acetate. The organic layer was washed with brine, and then dried over anhydrous sodium sulfate. The solvent was evaporated under reduced pressure, and the residue was purified by silica gel column chromatography (ethyl acetate:n-hexane=1:2), to thereby yield 0.93 g of the title compound.

Appearance: Light brown oil $^1$H NMR ($CDCl_3$) δ 1.24 (3H, t, J=7.1 Hz), 3.00 (3H, s), 3.98 (2H, s), 4.17 (2H, q, J=7.1 Hz), 4.68 (1H, brs), 6.31-6.52 (2H, m), 6.87 (1H, t, J=8.9 Hz).

The following compounds were produced in the same manner as in Reference Example 63.

Reference Example 64

Ethyl(methyl{4-[5-(4-trifluoromethylbenzyl)pyridin-2-yloxy]phenyl}amino)acetate $^1$H NMR ($CDCl_3$) δ 1.25 (3H, t, J=7.1 Hz), 3.07 (3H, s), 3.95 (2H, s), 4.04 (2H, s), 4.18 (2H, q, J=7.1 Hz), 6.69 (2H, d, J=–9.1 Hz), 6.75 (1H, d, J=8.5 Hz), 7.00 (2H, d, J=9.1 Hz), 7.27 (2H, d, J=8.1 Hz), 7.39 (1H, dd, J=8.5 Hz, 2.5 Hz), 7.54 (2H, d, J=8.1 Hz) 8.04 (1H, d, J=2.5 Hz).

Reference Example 65

Ethyl[(4-hydroxy-2-trifluoromethylphenyl)methylamino]-acetate MS 277 ($M^+$)

TABLE 8

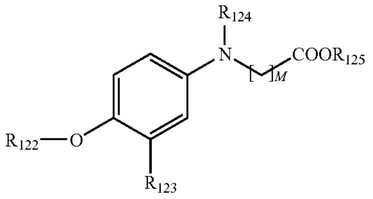

| Reference Example No. | $R_{122}$ | $R_{123}$ | $R_{124}$ | $R_{125}$ | M | $^1H$ NMR ($CDCl_3$) δ ppm |
|---|---|---|---|---|---|---|
| 66 | —H | —H | $—CH_3$ | $—CH_3$ | 1 | 3.00 (3H, s), 3.71 (3H, s), 4.01 (2H, s), 4.55 (1H, brs), 6.62 (2H, d, J = 9.2 Hz), 6.75 (2H, d, J = 9.2 Hz). |
| 67 | Benzyl | —H | $—CH_3$ | $—CH_3$ | 2 | 2.51-2.57 (2H, m), 2.86 (3H, s), 3.56-3.62 (2H, m) 3 66 (3H, s), 5.00 (2H, s), 6.72 (2H, d, J = 9.1 Hz), 6.91 (2H, d, J = 9.1 Hz), 7.30-7.45 (5H, m). |
| 68 | —H | —F | $—C_2H_5$ | $—C_2H_5$ | 1 | 1.18 (3H, t, J = 7 1 Hz), 1.26 (3H, t, J = 7.1 Hz), 3.38 (2H, q, J = 7.1 Hz) 3.94 (2H, s), 4.19 (2H, q, J = 7.1 Hz), 4.61 (1H, brs), 630-6.35 (1H, m), 6.43 (1H, dd, J = 13.7 Hz, 3.0 Hz), 6.86 (1H, t, J = 8.9 Hz). |
| 69 | —H | $—OCH_3$ | $—C_2H_5$ | $—C_2H_5$ | 1 | 1.17 (3H, t, J = 7.1 Hz), 1.25 (3H, t, J = 7.1 Hz), 3.39 (2H, q, J = 7.1 Hz), 3.85 (3H, s), 3.95 (2H, s) 4.18 (2H, q, J = 7.1 Hz), 5.30 (1H, brs), 6.21 ( 1H, dd, J = 8.6 Hz, 2.8 Hz), 6.33 (1H, d, J = 2.8 Hz), 6.79 (1H, d, J = 8.7 Hz). |
| 70 | 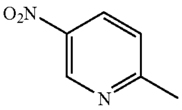 | $—CH_3$ | $—C_2H_5$ | $—C_2H_5$ | 1 | 1.23 (3H, t, J = 7.1 Hz), 1.28 (3H, t, J = 7.1 Hz), 2.08 (3H, s), 3.47 (2H, q, J = 7.1 Hz), 4.01 (2H, s), 4.22 (2H, q, J = 7.1 Hz) 6.40-6.59 (2H, m), 6.81-7.00 (2H, m), 8.43 (1H, dd, J = 9.1 Hz, 2.8 Hz), 9.06 (1H, d, J = 2.8 Hz). |
| 71 | 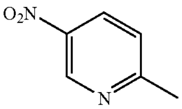 | $—CH_3$ | $—CH_3$ | $—C_2H_5$ | 1 | 1.27 (3H, t, J = 7.1 Hz), 2.10 (3H, s), 3.08 (3H, s), 4.06 (2H, s), 4.21 (2H, q, J = 7.1 Hz), 6.50-6.62 (2H, m), 6.85-6.99 (2H, m), 8.43 (1H, dd, J = 9.1 Hz, 2.8 Hz), 9.05 (1H, d, J = 2.8 Hz). |
| 72 | 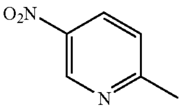 | $—OCH_3$ | $—CH_3$ | $—C_2H_5$ | 1 | 1.27 (3H, t, J = 7.1 Hz), 3.11 (3H, s), 3.74 (3H, s), 4.07 (2H, s), 4.21 (2H, q, J = 7.1 Hz), 6.27 (1H, dd, J = 8.7 Hz, 2.8 Hz), 6.34 (1H, d, J = 2.8 Hz), 6.95-7.01 (2H, m), 8.42 (1H, dd, J = 9.2 Hz, 3.0 Hz), 9.03 (1H, d, J = 2.8 Hz). |

(M means the number of the methylene groups. Hereinafter M indicates the same meaning.)

TABLE 9

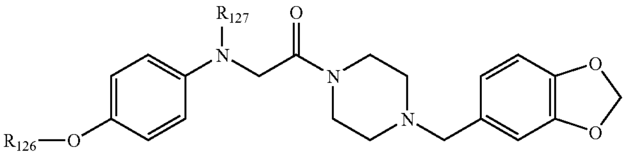

| Reference Example No. | $R_{126}$ | $R_{127}$ | $^1H$ NMR ($CDCl_3$) δ ppm |
|---|---|---|---|
| 73 | —H | $—CH_3$ | 2.41 (4H, brs), 2.88 (3H, s), 3.42 (2H, s), 3.50 (2H, brs), 3.60 (2H, brs), 3.94 (2H, s), 5.92 (2H, s), 6.55-6.69 (4H, m), 6.72 (2H, s), 6.82 (1H, s), 7.47 (1H, brs). |

TABLE 9-continued

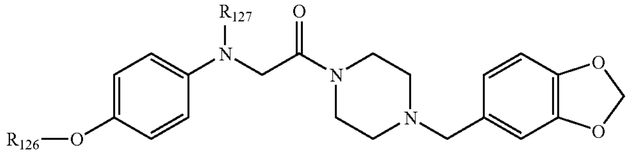

| Reference Example No. | $R_{126}$ | $R_{127}$ | $^1H$ NMR ($CDCl_3$) δ ppm |
|---|---|---|---|
| 74 | —H | —$C_2H_5$ | 1.05 (3H, t, J = 7.1 Hz), 2.44 (4H, brs), 3.25 (2H, q, J = 7.1 Hz), 3.46 (2H, s), 3.60 (4H, brs), 3.91 (2H, s), 5.94 (2H, s), 6.63 (4H, s), 6.72-6.74 (2H, m), 6.82 (1H, s), 7.43 (1H, brs). |
| 75 | 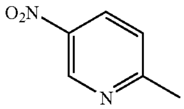 | —$CH_3$ | 2.44 (4H, brs), 3.06 (3H, s), 3.44 (2H, s), 3.49 (2H, brs), 3.63 (2H, brs), 4.11 (2H, s), 5.94 (2H, s), 6.69-6.77 (4H, m), 6.85 (1H, s), 6.92-7.02 (3H, m), 8.41 (1H, dd, J = 9.1 Hz, 2.8 Hz), 9.04 (1H, d, J = 3.0 Hz). |
| 76 | 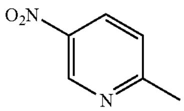 | —$C_2H_5$ | 1.20 (3H, t, J = 7.1 Hz), 2.42-2.46 (4H, m), 3.44-3.51 (6H, m), 3.64 (2H, q, J = 7.1 Hz), 4.06 (2H, s), 5.95 (2H, s), 6.67 (2H, d, J = 9.2 Hz), 6.74 (2H, brs), 6.85 (1H, brs), 6.94 (1H, d, J = 9.1 Hz), 6.99 (2H, d, J = 9.1 Hz), 8.42 (1H, dd, J = 9.1 Hz, 2.8 Hz), 9.05 (1H, d, J = 2.8 Hz). |

Reference Example 77

Production of 1-(4-piperonylpiperazin-1-yl)-2-[cyclopropyl(4-hydroxyphenyl)amino]ethanone To a solution of 1-(4-piperonylpiperazin-1-yl)-2-(4-hydroxyphenylamino)ethanone (1.00 g, 2.7 mmol) in methanol (10 mL) were added acetic acid (1.55 mL, 27 mmol), molecular sieves 3A1/16 (1.00 g), [(1-ethoxycyclopropyl)oxy]trimethylsilane (0.653 mL, 3.2 mmol) and sodium cyanoborohydride (770 mg, 12 mmol). The resulting solution was stirred for 16 hours at 60° C. This reaction solution was filtered and concentrated, and to the residue were added ethyl acetate and water. The aqueous layer was adjusted to pH 10 using aqueous 6 N sodium hydroxide. This layer was stirred for some time, and once insoluble matter had dissolved, the ethyl acetate layer was removed, and washed with aqueous 2 N sodium hydroxide and a saturated sodium bicarbonate solution, then dried over anhydrous magnesium sulfate. The solvent was evaporated, to thereby yield 770 mg of the title compound.

Appearance: White powder $^1H$ NMR ($CDCl_3$) δ 0.54-0.59 (2H, m), 0.72-0.79 (2H, m), 2.39-2.45 (4H, m), 2.70-2.77 (1H, m), 3.44 (2H, s), 3.48-3.51 (2H, m), 3.57-3.60 (2H, m), 4.12 (2H, s), 5.95 (2H, s), 6.62-6.67 (2H, m), 6.74-6.85 (5H, m).

The following compound was produced in the same manner as in Reference Example 77.

Reference Example 78

Ethyl{cyclopropyl[3-methyl-4-(5-nitropyridin-2-yloxy)phenyl]amino}acetate $^1H$ NMR ($CDCl_3$) δ 0.66-0.72 (2H, m), 0.83-0.89 (2H, m), 1.26 (3H, t, J=7.3 Hz), 2.10 (3H, s), 2.71-2.79 (1H, m), 4.08-4.22 (4H, m), 6.77-6.82 (2H, m), 6.91-6.95 (2H, m), 8.40-8.45 (1H, m), 9.05 (1H, d, J=2.8 Hz).

Reference Example 79

Production of ethyl[(3-hydroxyphenyl)methylamino]-acetate

Potassium bicarbonate (1.42 mL, 14.19 mmol) was added to a solution of ethyl(3-hydroxyphenylamino)acetate (2.77 g, 14.19 mmol) in DMF (15 mL). To the resulting solution was further added methyl iodide (1.77 mL, 28.38 mmol), and then stirred at room temperature for 18 hours. To the resulting reaction solution was added brine (150 mL), and the obtained mixture was extracted with ethyl acetate (150 mL). The ethyl acetate layer was dried over anhydrous sodium sulfate, after which solvent was evaporated, to thereby yield 2.48 g of the title compound.

Appearance: Pale yellow oil $^1H$ NMR ($CDCl_3$) δ 1.24 (3H, t, J=7.1 Hz), 3.04 (3H, s), 4.03 (2H, s), 4.18 (2H, q, J=7.1 Hz), 5.17 (1H, brs), 6.17-6.27 (3H, m), 7.04-7.10 (1H, m).

The following compounds were produced in the same manner as in Reference Example 79.

TABLE 10

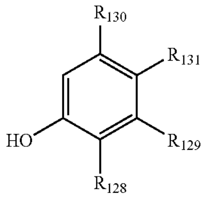

| Reference Example No. | $R_{128}$ | $R_{129}$ | $R_{130}$ | $R_{131}$ | $^1$H NMR ($CDCl_3$) δ ppm or MS |
|---|---|---|---|---|---|
| 80 | —H | —H | —H | 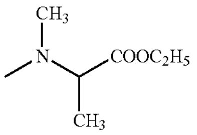 | $^1$H NMR 1.22 (3H, t, J = 7.1 Hz), 1.43 (3H, d, J = 7.1 Hz), 2.83 (3H, s), 4.16 (2H, q, J = 7.1 Hz), 4.33 (1H, q, J = 7.1 Hz), 4.84 (1H, brs), 6.75 (4H, s). |
| 81 | —$CH_3$ | —H | —H | 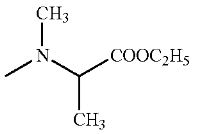 | $^1$H NMR 1.23 (3H, t, J = 7.3 Hz), 1.42 (3H, d, J = 7.1 Hz), 2.22 (3H, s), 2.82 (3H, s), 4.08-4.21 (2H, m), 4.30 (1H, s), 4.33 (1H, q, J = 7.1 Hz), 6.58 (1H, dd, J = 8.6 Hz, 3.0 Hz), 6.65 (1H, d, J = 2.8 Hz), 6.68 (1H, d, J = 8.6 Hz). |
| 82 | —$OCH_3$ | —H | —H | 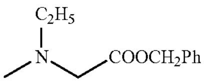 | $^1$H NMR 1.17 (3H, t, J = 7.1 Hz), 3.39 (2H, q, J = 7.1 Hz), 3.75 (3H, s), 4.00 (2H, brs), 5.11 (1H, brs), 5.15 (2H, s), 6.21 (1H, dd, J = 8.6 Hz, 2.8 Hz), 6.27 (1H, d, J = 2.8 Hz), 6.77 (1H, d, J = 8.6 Hz), 7.27-7.37 (5H, m). |
| 83 | —F | —H | —F | 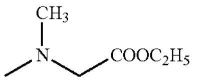 | $^1$H NMR 1.24 (3H, t, J = 7.1 Hz), 2.92 (3H, s), 3.93 (2H, s), 4.15 (2H, q, J = 7.1 Hz), 4.96 (1H, d, J = 2.8 Hz), 6.70 (1H, d, J = 8.2 Hz, 12.9 Hz), 6.77 (1H, d, J = 8.1 Hz, 12.2 Hz). |
| 84 | —$CH_3$ | —H | —$CH_3$ | 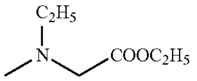 | $^1$H NMR 0.99 (3H, t, J = 7.1 Hz), 1.21 (3H, t, J = 7.1 Hz), 2.18 (3H, s), 2.24 (3H, s), 3.10 (2H, q, J = 7.1 Hz), 3.68 (2H, s), 4.11 (2H, q, J = 7.1 Hz), 4.47 (1H, s), 6.59 (1H, s), 6.94 (1H, s). |
| 85 | —H | —H | —H | 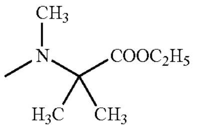 | $^1$H NMR 1.26 (3H, t, J = 7.3 Hz), 1.33 (6H, s), 2.80 (3H, s), 4.18 (2H, q, J = 7.3 Hz), 5.15 (1H, brs), 6.71 (2H, d, J = 8.9 Hz), 7.00 (2H, d, J = 8.9 Hz). |
| 86 | —H | —$CH_3$ | —$CH_3$ | 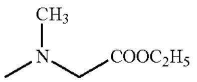 | MS 237 ($M^+$) |
| 87 | —$CH_3$ | —H | —$CH_3$ | 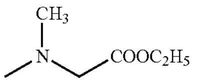 | $^1$H NMR 1.24 (3H, t, J = 7.1 Hz), 2.19 (3H, s), 2.24 (3H, s), 2.79 (3H, s), 3.64 (2H, s), 4.15 (2H, q, J = 7.1 Hz), 4.45 (1H, brs), 6.59 (1H, s), 6.89 (1H, s). |
| 88 | —$CF_3$ | —H | —H | 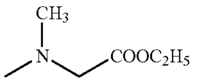 | MS 277 ($M^+$) |
| 89 | —CN | —H | —H | 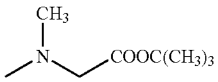 | MS 262 ($M^+$) |

TABLE 11

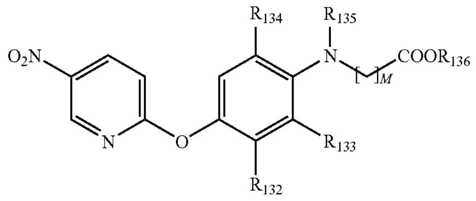

| Reference Example No. | $R_{132}$ | $R_{133}$ | $R_{134}$ | $R_{135}$ | $R_{136}$ | M | $^1$H NNMR ($CDCl_3$) δ ppm |
|---|---|---|---|---|---|---|---|
| 90 | —H | —H | —H | —$C_2H_5$ | —$C_2H_5$ | 1 | 1.24 (3H, t, J = 7.1 Hz), 1.28 (3H, t, J = 7.0 Hz), 3.48 (2H, q, J = 7.1 Hz), 4.02 (2H, s), 4.21 (2H, q, J = 7.0 Hz), 6.67 (2H, d, J = 8.9 Hz), 6.95 (1H, d, J = 9.1 Hz), 7.00 (2H, d, J = 8.9 Hz), 8.42 (1H, dd, J = 2.8 Hz, 9.1 Hz), 9.06 (1H, d, J = 2.8 Hz). |
| 91 | —H | —H | —H | —$CH_3$ | —$C_2H_5$ | 1 | 1.27 (3H, t, J = 7.2 Hz), 3.10 (3H, s), 4.07 (2H, s), 4.20 (2H, q, J = 7.2 Hz), 6.71 (2H, d, J = 9.2 Hz), 6.95 (1H, d, J = 9.1 Hz), 7.02 (2H, d, J = 9.2 Hz), 8.43 (1H, dd, J = 2.8 Hz, 9.1 Hz), 9.05 (1H, d, J = 2.8 Hz). |
| 92 | —F | —H | —H | allyl | —$C_2H_5$ | 1 | 1.29 (3H, t, J = 7.1 Hz), 4.02 (4H, brs), 4.23 (2H, q, J = 7.1 Hz), 5.21-5.30 (2H, m), 5.84-5.94 (1H, m), 6.40-6.52 (2H, m), 7.01-7.08 (2H, m), 8.47 (1H, dd, J = 8.9 Hz, 2.8 Hz), 9.03 (1H, d, J = 2.6 Hz). |
| 93 | —F | —H | —F | —$C_2H_5$ | —$C_2H_5$ | 1 | 1.22 (3H, t, J = 7.1 Hz), 1.27 (3H, t, J = 7.1 Hz), 3.37 (2H, q, J = 7.1 Hz), 4.02 (2H, s), 4.20 (2H, q, J = 7.1 Hz), 6.77 (1H, dd, J = 8.1 Hz, 12.3 Hz), 6.92 (1H, dd, J = 7.3 Hz, 12.7 Hz), 7.09 (1H, d, J = 9.0 Hz), 8.49 (1H, dd, J = 2.8 Hz, 9.0 Hz), 9.02 (1H, d, J = 2.8 Hz). |
| 94 | —F | —F | —H | —$CH_3$ | —$C(CH_3)_3$ | 0 | 1.45 (9H, s), 3.26 (3H, s), 6.90-7.11 (2H, m), 7.16 (1H, d, J = 9.0 Hz), 8.53 (1H, dd, J = 2.8 Hz, 9.0 Hz), 9.01 (1H, d, J = 2.8 Hz). |

TABLE 12

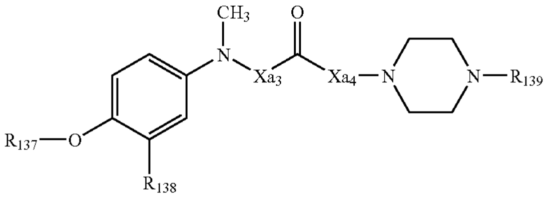

| Reference Example No. | $R_{137}$ | $R_{138}$ | $R_{139}$ | $Xa_3$ | $Xa_4$ | $^1$H NMR ($CDCl_3$) δ ppm |
|---|---|---|---|---|---|---|
| 95 | 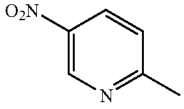 | —H | piperonyl | none | —$CH_2$— | 2.44 (8H, brs), 2.96 (2H, s), 3.30 (3H, s), 3.38 (2H, s), 5.92 (2H, s), 6.72 (2H, brs), 6.82 (1H, s), 7.09 (1H, d, J = 9.1 Hz), 7.20 (2H, d, J = 8.9 Hz), 7.29 (2H, d, J = 8.9 Hz), 8.51 (1H, dd, J = 9.1 Hz, 2.8 Hz), 9.04 (1H, d, J = 2.8 Hz). |

TABLE 12-continued

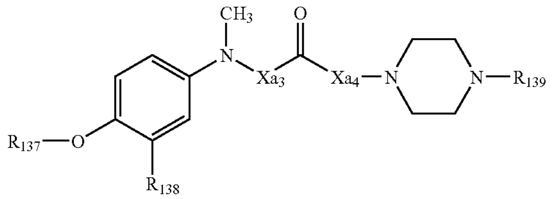

| Reference Example No. | $R_{137}$ | $R_{138}$ | $R_{139}$ | $Xa_3$ | $Xa_4$ | $^1$H NMR ($CDCl_3$) δ ppm |
|---|---|---|---|---|---|---|
| 96 | 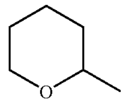 | —H | benzyl | none | none | 1.55-1.80 (3H, m), 1.81-2.15 (3H, m), 2.23 (4H, t, J = 5.0 Hz), 3.16 (3H, s), 3.20 (4H, t, J = 5.0 Hz), 3.42 (2H, s), 3.55-3.69 (1H, m), 3.85-4.00 (1H, m), 5.36 (1H, t, J = 3.2 Hz), 6.99 (4H, s), 7.16-7.36 (5H, m). |
| 97 | —H | $—CH_3$ | piperonyl | $—CH_2—$ | none | 2.18 (3H, s), 2.38-2.42 (4H, m), 2.89 (3H, s), 3.41 (2H, s), 3.50 (2H, brs), 3.61 (2H, brs), 3.95 (2H, brs), 5.93 (2H, s), 6.44-6.57 (3H, m), 6.73-6.76 (2H, m), 6.83 (1H, s). |

TABLE 13

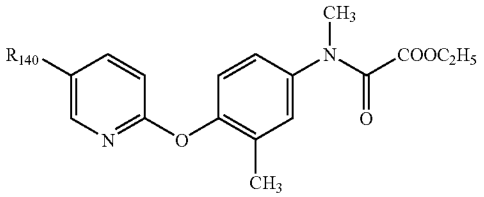

| Reference Example No. | $R_{140}$ | $^1$H NMR ($CDCl_3$) δ ppm |
|---|---|---|
| 98 | $—NO_2$ | 1.07 (3H, t, J = 7.1 Hz), 2.15 (3H, s), 3.38 (3H, s), 4.19 (2H, q, J = 7.1 Hz), 7.06-7.20 (4H, m), 8.51 (1H, dd, J = 9.1 Hz, 2.8 Hz), 8.97 (1H, d, J = 2.8 Hz). |
| 99 | $4-CF_3PhOCH_2—$ | 1.07 (3H, t, J = 7.1 Hz), 2.18 (3H, s), 3.36 (3H, s), 4.08 (2H, q, J = 7.1 Hz), 5.04 (2H, s), 6.97 (1H, d, J = 8.6 Hz), 7.01-7.13 (4H, m), 7.16 (1H, d, J = 2.3 Hz), 7.57 (2H, d, J = 8.6 Hz), 7.80 (1H, dd, J = 8.6 Hz, 2.3 Hz), 8.17 (1H, d, J = 2.3 Hz). |

Reference Example 100

Production of ethyl[acetyl(3-fluoro-4-hydroxyphenyl)amino]acetate

Ethyl(3-fluoro-4-hydroxyphenylamino)acetate (0.84 g, 4 mmol) was dissolved in N,N-dimethylacetamide (4 mL). To the resulting solution was added acetyl chloride (0.6 mL, 10 mmol), and the resulting solution was stirred at room temperature for 1 hour. Water (1 mL), methanol (10 mL) and saturated sodium carbonate (10 mL) were added, and the mixture was stirred at room temperature for 1 hour. Water was added to the solution. 10% hydrochloric acid was employed to turn the solution acidic, and then the solution was extracted with ethyl acetate. The organic layer was washed with water and brine, then dried over anhydrous sodium sulfate. The solvent was evaporated under reduced pressure, and the obtained residue was purified by silica gel column chromatography (ethyl acetate: n-hexane 2:1), to thereby yield 0.84 g of the title compound.

Appearance: Colorless powder $^1$H NMR ($CDCl_3$) δ 1.28 (3H, t, J=7.3 Hz), 1.94 (3H, s), 4.20 (2H, q, J=7.3 Hz), 4.32 (2H, s), 6.02 (1H, brs), 6.99-7.07 (2H, m), 7.13-7.18 (1H, m).

The following compounds were produced in the same manner as in Reference Example 100.

TABLE 14

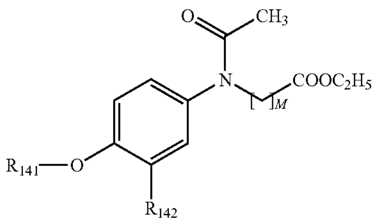

| Reference Example No. | $R_{141}$ | $R_{142}$ | M | $^1H$ NMR ($CDCl_3$) δ ppm |
|---|---|---|---|---|
| 101 | —H | —$CH_3$ | 1 | 1.26 (3H, t, J = 7.1 Hz), 1.92 (3H, s), 2.24 (3H, s), 4.19 (2H, q, J = 7.1 Hz), 4.32 (2H, s), 5.38 (1H, brs), 6.78 (1H, d, J = 8.4 Hz), 7.04 (1H, dd, J = 8.4 Hz, 2.5 Hz), 7.10 (1H, d, J = 2.5 Hz). |
| 102 | —H | —H | 2 | 1.21 (3H, t, J = 7.2 Hz), 1.83 (3H, s), 2.56 (2H, t, J = 7.4 Hz), 3.97 (2H, t, J = 7.4 Hz), 4.06 (2H, q, J = 7.2 Hz), 6.05 (1H, brs), 6.87 (2H, d, J = 8.7 Hz), 7.03 (2H, d, J = 8.7 Hz). |
| 103 | benzyl | —H | 1 | 1.26 (3H, t, J = 7.1 Hz), 1.91 (3H, s), 4.18 (2H, q, J = 7.1 Hz), 4.33 (2H, s), 5.07 (2H, s), 6.98 (2H, d, J = 8.9 Hz), 7.26 (2H, d, J = 8.9 Hz), 7.35-7.45 (5H, m). |
| 104 | 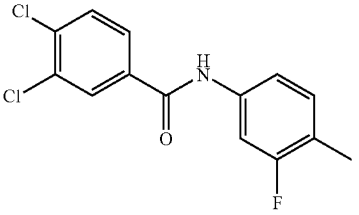 | —H | 1 | 1.24 (3H, t, J = 7.1 Hz), 1.89 (3H, s), 4.15 (2H, q, J = 7.1 Hz), 4.32 (2H, s), 6.95 (2H, d, J = 8.9 Hz), 7.12 (1H, t, J = 9.0 Hz), 7.27-7.32 (3H, m), 7.52-7.60 (1H, m), 7.70-7.80 (2H, m), 7.99 (1H, s), 8.05 (1H, s). |

TABLE 15

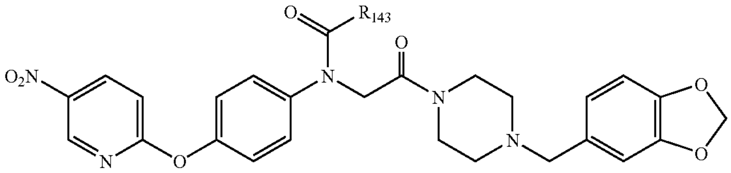

| Reference Example No. | $R_{143}$ | $^1H$ NMR ($CDCl_3$) δ ppm |
|---|---|---|
| 105 | —$C_2H_5$ | 1.09 (3H, t, J = 7.4 Hz), 2.20 (2H, q, J = 7.4 Hz), 2.40-2.45 (4H, m), 3.43 (4H, brs), 3.61 (2H, brs), 4.47 (2H, s), 5.94 (2H, s), 6.70-6.76 (2H, m), 6.84 (1H, s), 7.08 (1H, d, J = 9.0 Hz), 7.19 (2H, d, J = 8.7 Hz), 7.52 (2H, d, J = 8.7 Hz), 8.51 (1H, dd, J = 2.8 Hz, 9.0 Hz), 9.04 (1H, d, J = 2.8 Hz). |
| 106 | —$CH_2Cl$ | 2.40-2.48 (4H, m), 3.43 (4H, s), 3.62 (2H, brs), 3.97 (2H, s), 4.49 (2H, s), 5.95 (2H, s), 6.70-6.77 (2H, m), 6.84 (1H, s), 7.11 (1H, d, J = 9.0 Hz), 7.23 (2H, d, J = 8.7 Hz), 7.59 (2H, d, J = 8.7 Hz), 8.52 (1H, dd, J = 2.8 Hz, 9.0 Hz), 9.04 (1H, d, J = 2.8 Hz). |
| 107 | cyclopropyl | 0.65-1.52 (5H, m), 2.43 (4H, brs), 3.43 (4H, brs), 3.61 (2H, brs), 4.50 (2H, brs), 5.95 (2H, s), 6.72-6.75 (2H, m), 6.84 (1H, s), 7.08 (1H, d, J = 9.1 Hz), 7.20 (1H, d, J = 8.8 Hz), 7.59 (2H, d, J = 8.8 Hz), 8.50 (1H, dd, J = 2.9 Hz, 9.1 Hz), 9.04 (1H, d, J = 2.9 Hz). |

TABLE 16

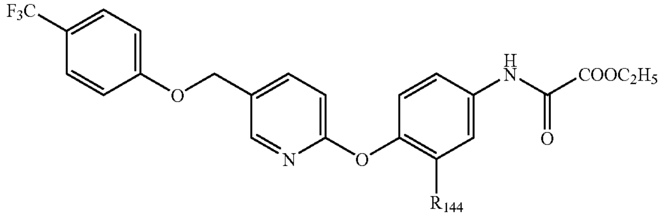

| Reference Example No. | $R_{144}$ | $^1H$ NMR ($CDCl_3$) δ ppm |
|---|---|---|
| 108 | —H | 1.44 (3H, t, J = 7.1 Hz), 4.43 (2H, q, J = 7.1 Hz), 5.05 (2H, s), 6.93 (1H, d, J = 8.6 Hz), 7.02 (2H, d, J = 8.6 Hz), 7.17 (2H, d, J = 8.9 Hz), 7.56 (2H, d, J = 8.4 Hz), 7.69 (2H, d, J = 8.9 Hz), 7.79 (1H, dd, J = 8.4 Hz, 2.5 Hz), 8.22 (1H, d, J = 2.5 Hz), 8.90 (1H, brs). |
| 109 | —$CH_3$ | 1.44 (3H, t, J = 7.1 Hz), 2.19 (3H, s), 4.43 (2H, q, J = 7.1 Hz), 5.03 (2H, s), 6.94 (1H, d, J = 8.4 Hz), 7.02 (2H, d, J = 8.4 Hz), 7.07 (1H, d, J = 8.6 Hz), 7.51-7.58 (4H, m), 7.78 (1H, dd, J = 8.6 Hz, 2.5 Hz), 8.20 (1H, d, J = 2.5 Hz), 8.84 (1H, brs). |

Reference Example 110

Production of (6-chloropyridin-3-yl)(4-trifluoromethylphenyl)methanone

Under an argon gas flow, half of a solution of 4-bromobenzotrifluoride (1.20 g, 5.33 mmol) in THF (6 mL) was added to magnesium (156 mg, 6.41 mmol). The resulting solution was stirred, and further 1,2-dibromoethane (3 drops) was added. Once the reaction began, the balance of the 4-bromobenzotrifluoride in THF solution was added dropwise, and once dropping had finished, the resulting solution was stirred for 30 minutes at 60° C. A solution of 6-chloro-N-methoxy-N-methylnicotinamide (990 mg, 5.36 mmol) in THF (3 mL) was charged into a separate reaction vessel, into which the above reaction solution was added dropwise under an argon gas flow and ice cooling. After dropping had finished, the resulting solution was stirred for 30 minutes at room temperature, and then heated to reflux for 1 hour. The reaction solution was cooled with ice, then aqueous ammonium chloride and water were added. The resulting solution was extracted with ethyl acetate, and washed with brine. The ethyl acetate layer was dried over anhydrous magnesium sulfate, evaporated, and the residue was purified by silica gel column chromatography (n-hexane:ethyl acetate=10:1), to thereby yield 610 mg of the title compound.

Appearance: White powder $^1H$ NMR ($CDCl_3$) δ 7.52 (1H, d, J=8.3 Hz), 7.80 (2H, d, J=8.0 Hz), 7.90 (2H, d, J=8.0 Hz), 8.11 (1H, dd, J=8.3 Hz, 2.0 Hz), 8.77 (1H, d, J=2.0 Hz).

Reference Example 111

Production of ethyl 3-[4-(4-nitrophenoxy)phenyl]-propionate

To a solution of ethyl 3-(4-hydroxyphenyl)-propionate (6.00 g, 30.9 mmol) in DMF (60 mL) were added 4-fluoronitrobenzene (6.54 g, 46.3 mmol) and potassium carbonate (5.12 g, 37.1 mmol). The resulting reaction solution was stirred for 1 hour at 80° C. To the reaction solution was added water and extracted with ethyl acetate. The resulting ethyl acetate layer was washed with water and then with brine. The ethyl acetate layer was dried over anhydrous magnesium sulfate, evaporated, and the residue was purified by silica gel column chromatography (n-hexane:ethyl acetate=5:1), to thereby yield 9.64 g of the title compound.

Appearance: Pale yellow oil $^1H$ NMR ($CDCl_3$) δ 1.23 (3H, t, J=7.1 Hz), 2.62 (2H, t, J=7.7 Hz), 2.96 (2H, t, J=7.7 Hz), 4.12 (2H, q, J=7.1 Hz), 6.93-7.06 (4H, m), 7.24 (2H, d, J=8.5 Hz), 8.17 (2H, d, J=9.2 Hz).

The following compounds were produced in the same manner as in Reference Example 111.

TABLE 17

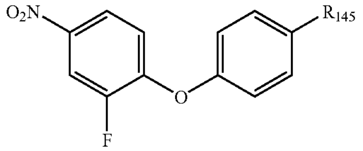

| Reference Example No. | $R_{145}$ | $^1H$ NMR (solvent) δ ppm |
|---|---|---|
| 112 | -Ac | (DMSO-$d_6$) 2.58(3 H, s), 7.26(2 H, d, J = 8.8 Hz), 7.40(1 H, t, J = 8.4 Hz), 8.04(2 H, d, J = 8.8 Hz), 8.15(1 H, ddd, J = 1.4 Hz, 2.6 Hz, 8.4 Hz), 8.39(1 H, dd, J = 2.6 Hz, 10.7 Hz). |

TABLE 17-continued

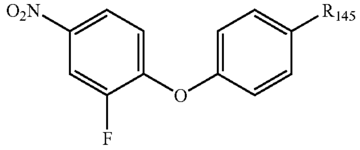

| Reference Example No. | $R_{145}$ | $^1$H NMR (solvent) δ ppm |
|---|---|---|
| 113 | —$CH_2COOCH_3$ | (DMSO-$d_6$) 3.63(3 H, s), 3.72(2 H, s), 7.11-7.17(3 H, m), 7.38(2 H, d, J = 8.4 Hz), 8.09(1 H, ddd, J = 1.4 Hz, 2.7 Hz, 9.1 Hz), 8.33(1 H, dd, J = 2.7 Hz, 10.2 Hz). |
| 114 | —$(CH_2)_2COOC_2H_5$ | ($CDCl_3$) 1.22(3 H, t, J = 7.1 Hz), 2.62(2 H, t, J = 7.6 Hz), 2.96(2 H, t, J = 7.6 Hz), 4.12(2 H, q, J = 7.1 Hz), 6.92(1 H, dd, J = 9.0 Hz, 8.0 Hz), 6.99(2 H, d, J = 8.6 Hz), 7.24(2 H, d, J = 8.6 Hz), 7.90-8.00(1 H, m), 8.06(1 H, dd, J = 10.3 Hz, 2.7 Hz). |
| 115 | —NHAc | (DMSO-$d_6$) 2.05(3 H, s), 7.07(1 H, t, J = 8.6 Hz), 7.16(2 H, d, J = 9.0 Hz), 7.67(2 H, d, J = 9.0 Hz), 8.06(1 H, ddd, J = 1.4 Hz, 2.7 Hz, 8.6 Hz), 8.31(1 H, dd, 2.7 Hz, 10.9 Hz), 10.06(1 H, s). |
| 116 | —$SCH_2COOC_2H_5$ | ($CDCl_3$) 1.24(3 H, t, J = 7.1 Hz), 3.62(2 H, s), 4.18(2 H, q, J = 7.1 Hz), 6.95-7.05(3 H, m), 7.49(2 H, d, J = 8.8 Hz), 8.00(1 H, ddd, J = 1.5 Hz, 2.6 Hz, 9.1 Hz), 8.08(1 H, dd, J = 2.6 Hz, 10.2 Hz). |
| 117 | —$OCH_3$ | (DMSO-$d_6$) 3.77(3 H, s), 6.90-7.10(3 H, m), 7.16(2 H, d, J = 9.1 Hz), 8.03(1 H, ddd, J = 1.4 Hz, 2.6 Hz, 9.2 Hz), 8.27(1 H, dd, J = 2.6 Hz, 10.9 Hz). |
| 118 | —H | ($CDCl_3$) 6.95(1 H, dd, J = 9.0 Hz, 8.0 Hz), 7.07(2 H, d, J = 7.9 Hz), 7.24(2 H, t, J = 7.9 Hz), 7.42(2 H, t, J = 7.9 Hz), 7.91-8.02(1 H, m), 8.07(1 H, dd, J = 10.3 Hz, 2.7 Hz). |
| 119 | —$(CH_2)_3COOC_2H_5$ | ($CDCl_3$) 1.25(3 H, t, J = 7.1 Hz), 1.88-2.03(2 H, m), 2.32(2 H, t, J = 7.4 Hz), 2.66(2 H, t, J = 7.4 Hz), 4.12(2 H, q, J = 7.1 Hz), 6.91(1 H, dd, J = 9.0 Hz, 8.0 Hz), 6.99(2 H, d, J = 8.5 Hz), 7.22(2 H, d, J = 8.5 Hz), 7.91-7.98(1 H, m), 8.06(1 H, dd, J = 10.3 Hz, 2.7 Hz) |
| 120 | —CHO | (DMSO-$d_6$) 7.33(2 H, d, J = 8.7 Hz), 7.47(1 H, t, J = 9.0 Hz), 8.00(2 H, d, J = 8.7 Hz), 8.16(1 H, ddd, J = 1.4 Hz, 2.7 Hz, 9.0 Hz), 8.40(1 H, dd, J = 2.7 Hz, 10.6 Hz), 9.99(1 H, s). |
| 121 | —$COOC_2H_5$ | (DMSO-$d_6$) 1.32(3 H, t, J = 7.1 Hz), 4.31(2 H, q, J = 7.1 Hz), 7.26(2 H, d, J = 8.9 Hz), 7.41(1 H, t, J = 8.4 Hz), 8.03(2 H, d, J = 8.9 Hz), 8.14(1 H, ddd, J = 1.4 Hz, 2.6 Hz, 8.4 Hz), 8.39(1 H, dd, J = 2.6 Hz, 10.6 Hz). |

(Ac means an acetyl group. Hereinafter Ac indicates the same meaning.)

TABLE 18

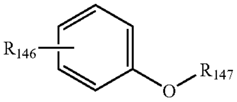

| Reference Example No. | $R_{146}$ | $R_{147}$ | $^1$H NMR (solvent) δ ppm |
|---|---|---|---|
| 122 | 4-$NO_2$ | 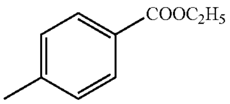 | (DMSO-$d_6$) 1.33(3 H, t, J = 7.1 Hz), 4.32(2 H, q, J = 7.1 Hz), 7.24-7.31(4 H, m), 8.05(2 H, d, J = 8.9 Hz), 8.29(2 H, d,J = 9.3 Hz). |
| 123 | 4-$NO_2$ | 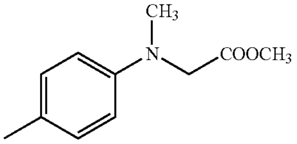 | ($CDCl_3$) 3.10(3 H, s), 3.75(3 H, s), 4.10(2 H, s), 6.71(2 H, d, J = 9.2 Hz), 6.96(2 H, d, J = 9.2 Hz), 6.98(2 H, d, J = 9.2 Hz), 8.17(2 H, d, J = 9.2 Hz). |
| 124 | 2-$NO_2$ | 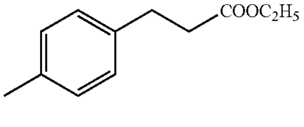 | ($CDCl_3$) 1.22(3 H, t, J = 7.1 Hz), 2.60(2 H, t, J = 7.7 Hz), 2.93(2 H, t, J = 7.7 Hz), 4.11(2 H, q, J = 7.1 Hz), 6.92-6.99(3 H, m), 7.13-7.23(3 H, m), 7.45(1 H, dt, J = 1.6 Hz, 8.2 Hz), 7.92(1 H, dd, J = 8.2 Hz, 1.6 Hz). |

TABLE 18-continued

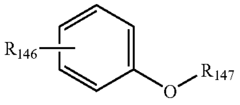

| Reference Example No. | $R_{146}$ | $R_{147}$ | $^{1}$H NMR (solvent) δ ppm |
|---|---|---|---|
| 125 | 4-$NO_2$ | 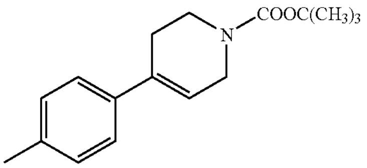 | ($CDCl_3$) 1.50(9 H, s), 2.53(2 H, brs), 3.66(2 H, m), 4.10 (2 H, brs), 6.05(1 H, brs), 7.02(2 H, d, J = 9.0 Hz), 7.06 (2 H, d, J = 8.5 Hz), 7.43(2 H, d, J = 8.5 Hz), 8.21(2 H, d, J = 9.0 Hz). |
| 126 | 4-$NO_2$ | 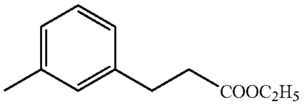 | ($CDCl_3$) 1.21(3 H, t, J = 7.1 Hz), 2.61(2 H, t, J = 7.7 Hz), 2.95(2 H, t, J = 7.7 Hz), 4.10(2 H, q, J = 7.1 Hz), 6.88-6.94(2 H, m), 6.98(2 H, d, J = 9.2 Hz), 7.08(1 H, d, J = 7.6 Hz), 7.32(1 H, t, J = 7.6 Hz), 8.18(2 H, d, J = 9.2 Hz). |
| 127 | 4-$NO_2$ | 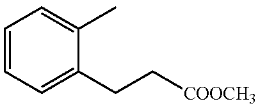 | ($CDCl_3$) 2.58(2 H, t, J = 7.7 Hz), 2.87(2 H, t, J = 7.7 Hz), 3.62(3 H, s), 6.89-7.01(3 H, m), 7.13-7.37(3 H, m), 8.18(2 H, d, J = 9.2 Hz). |

TABLE 19

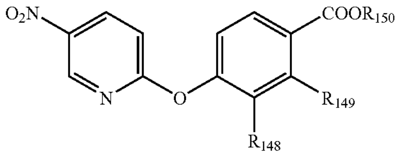

| Reference Example No. | $R_{148}$ | $R_{149}$ | $R_{150}$ | $^{1}$H NMR ($CDCl_3$) δ ppm |
|---|---|---|---|---|
| 128 | —H | —H | —$C_2H_5$ | 1.41(3 H, t, J = 7.3 Hz), 4.40(2 H, q, J = 7.3 Hz), 7.09(1 H, d, J = 8.9 Hz), 7.22-7.26(2 H, m), 8.14-8.17(2 H, m), 8.52(1 H, dd, J = 8.9 Hz, 3.0 Hz), 9.04(1 H, d, J = 3.0 Hz). |
| 129 | —H | —H | —$CH_3$ | 3.94(3 H, s), 7.10(1 H, d, J = 8.9 Hz), 7.22-7.26(2 H, m), 8.13-8.16(2 H, m), 8.52(1 H, dd, J = 8.9 Hz, 2.7 Hz), 9.04(1 H, d, J = 2.7 Hz). |
| 130 | —F | —H | —$CH_3$ | 3.95(3 H, s), 7.18(1 H, d, J = 8.8 Hz), 7.29-7.35(1 H, m), 7.87-7.96(2 H, m), 8.54(1 H, dd, J = 8.8 Hz, 2.6 Hz), 8.99(1 H, d, J = 2.6 Hz). |
| 131 | —F | —H | —$C_2H_5$ | 1.41(3 H, t, J = 7.1 Hz), 4.41(2 H, q, J = 7.1 Hz), 7.18(1 H, d, J = 9.1 Hz), 7.29-7.35(1 H, m), 7.88-7.96(2 H, m), 8.54(1 H, dd, J = 9.1 Hz, 2.8 Hz), 8.99(1 H, d, J = 2.8 Hz). |
| 132 | —$CH_3$ | —H | —$CH_3$ | 2.21(3 H, s), 3.93(3 H, s), 7.08-7.15(2 H, m), 7.97(1 H, dd, J = 8.4 Hz, 2.2 Hz), 8.02(1 H, d, J = 2.2 Hz), 8.52(1 H, dd, J = 8.9 Hz, 2.7.Hz), 9.01(1 H, d, J = 2.7 Hz). |
| 133 | —$OCH_3$ | —H | —$C_2H_5$ | 1.41(3 H, t, J = 7.1 Hz), 3.80(3 H, s), 4.40(2 H, q, J = 7.1 Hz), 7.09(1 H, d, J = 8.9 Hz), 7.21(1 H, d, J = 8.2 Hz), 7.71-7.77(2 H, m), 8.49(1 H, dd, J = 8.9 Hz, 2.8 Hz), 8.97(1 H, a, J = 2.8 H). |
| 134 | —H | —$OCH_3$ | —$CH_3$ | 3.90(3 H, s), 3.91(3 H, s), 6.77-6.81(2 H, m), 7.11(1 H, dd, J = 9.1 Hz, 0.5 Hz), 7.91-7.95(1 H, m), 8.53(1 H, dd, J = 9.1 Hz, 2.7 Hz), 9.06(1 H, d, J = 2.7 Hz). |
| 135 | —H | —$CH_3$ | —$CH_3$ | 2.64(3 H, s), 3.91(3 H, s), 7.02-7.10(3 H, m), 8.03-8.06(1 H, m), 8.52(1 H, dd, J = 8.9 Hz, 2.7 Hz), 9.05(1 H, dd, J = 2.7 Hz, 0.5 Hz). |
| 136 | —Cl | —H | —$CH_3$ | 3.95(3 H, s), 7.17-7.20(1 H, m), 7.31(1 H, d, J = 8.6 Hz), 8.03-8.07(1 H, m), 8.20(1 H, a, J = 2.0 Hz), 8.55(1 H, dd, J = 9.1 Hz, 2.8 Hz), 8.98(1 H, dd, J = 2.8 Hz, 0.5 Hz). |

TABLE 19-continued

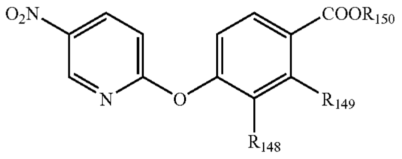

| Reference Example No. | $R_{148}$ | $R_{149}$ | $R_{150}$ | $^1H$ NMR ($CDCl_3$) δ ppm |
|---|---|---|---|---|
| 137 | —F | —F | $—CH_3$ | 3.97(3 H, s), 7.06-7.16(1 H, m), 7.21(1 H, dd, J = 0.3 Hz, 9.0 Hz), 7.77-7.88(1 H, m), 8.56(1 H, dd, J = 2.8 Hz, 9.0 Hz), 8.99(1 H, dd, J = 0.3 Hz, 2.8 Hz) |

TABLE 20

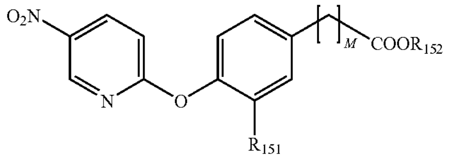

| Reference Example No. | $R_{151}$ | $R_{152}$ | M | $^1H$ NMR (CD $Cl_3$) δ ppm |
|---|---|---|---|---|
| 138 | —H | $—CH_3$ | 2 | 2.64-2.70(2 H, m), 2.97-3.02(2 H, m), 3.69(3 H, s), 7.01-7.10(3 H, m), 7.26-7.30(2 H, m), 8.47(1 H, dd, J = 8.9 Hz, 2.6 Hz), 9.04(1 H, d, J = 2.6 Hz). |
| 139 | $—OCH_3$ | $—C_2H_5$ | 2 | 1.26(3 H, t, J = 7.1. Hz), 2.67(2 H, t, J = 7.5 Hz), 2.99(2 H, t, J = 7.5 Hz), 3.74(3 H, s), 4.16(2 H, q, J = 7.1 Hz), 6.76-6.91(2 H, m), 7.02(1 H, d, J = 9.1 Hz), 7.06(1 H, d, J = 8.0 Hz), 8.45(1 H, dd, J = 9.1 Hz, 2.6 Hz), 9.01(1 H, d, J = 2.6 Hz). |
| 140 | —H | $—CH_3$ | 1 | 3.67(2 H, s), 3.72(3 H, s), 7.04(1 H, d, J = 8.9 Hz), 7.12(2 H, d, J = 8.6 Hz), 7.38(2 H, d, J = 8.6 Hz), 8.45-8.50(1 H, m), 9.04(1 H, d, J = 3.0 Hz). |
| 141 | —H | $—C_2H_5$ | 2 | 1.23(3 H, t, J = 7.1 Hz), 2.63(2 H, t, J = 7.8 Hz), 2.97(2 H, t, J = 7.8 Hz), 4.11(2 H, q, J = 7.1 Hz), 7.00(1 H, d, J = 9.1 Hz), 7.06(2 H, d, J = 8.5 Hz), 7.26(2 H, d, J = 8.5 Hz), 8.45(1 H, dd, J = 9.1 Hz, 2.8 Hz), 9.02(1 H, d, J = 2.8 Hz). |
| 142 | $—OCH_3$ | $—CH_3$ | 2 | 2.66-2.71(2 H, m), 2.97-3.02(2 H, m), 3.70(3 H, s), 3.74(3 H, s), 6.83-6.88(2 H, m), 7.01-7.08(2 H, m), 8.45(1 H, dd, J = 9.1 Hz, 2.8 Hz), 9.01(1 H, d, J = 2.8 Hz). |
| 143 | $—OC_2H_5$ | $—C_2H_5$ | 2 | 1.15(3 H, t, J = 7.0 Hz), 1.26(3 H, t, J = 7.1 Hz), 2.53-2.72(2 H, m), 2.87-3.05(2 H, m), 3.98(2 H, q, J = 7.0 Hz), 4.15(2 H, q, J = 7.1 Hz), 6.73-6.93(2 H, m), 7.02(1 H, d, J = 9.0 Hz), 7.07(1 H, d, J = 8.0 Hz), 8.45(1 H, dd, J = 9.0 Hz, 2.8 Hz), 9.01(1 H, d, J = 2.8 Hz). |
| 144 | —F | $—C_2H_5$ | 2 | 1.26(3 H, t, J = 7.1 Hz), 2.57-2.71(2 H, m), 2.89-3.06(2 H, m), 4.15(2 H, q, J = 7.1 Hz), 6.98-7.21(4 H, m), 8.50(1 H, dd, J = 9.0 Hz, 2.8 Hz), 9.01(1 H, d, J = 2.8 Hz). |
| 145 | —H | $—C_2H_5$ | 4 | 1.26(3 H, t, J = 7.3 Hz), 1.60-1.80(4 H, m), 2.30-2.40(2 H, m), 2.60-2.75(2 H, m), 4.13(2 H, q, J = 7.3 Hz), 7.01(1 H, d, J = 9.0 Hz), 7.06(2 H, d, J = 8.6 Hz), 7.25(2 H, d, J = 8.6 Hz), 8.46(1 H, dd, J = 9.0 Hz, 3.0 Hz), 9.04(1 H, d, J = 3.0 Hz). |

TABLE 21

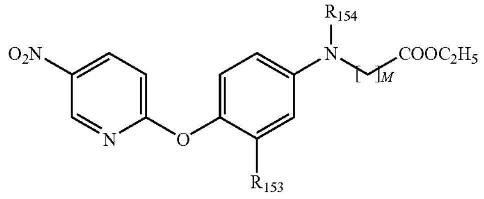

| Reference Example No. | $R_{153}$ | $R_{154}$ | M | $^1$H NMR ($CDCl_3$) δ ppm or MS |
|---|---|---|---|---|
| 146 | —$CH_3$ | —H | 1 | $^1$H NMR 1.32(3 H, t, J = 7.1 Hz), 2.08(3 H, s), 3.90(2 H, d, J = 5.3 Hz), 4.15-4.39 (3 H, m), 6.39-6.59(2 H, m), 6.81-7.01(2 H, m), 8.44(1 H, dd, J = 9.1 Hz, 2.8 Hz), 9.05(1 H, dd, J = 2.8 Hz, 0.4 Hz). |
| 147 | —$CH_3$ | -Ac | 1 | $^1$H NMR 1.29(3 H, t, J = 7.1 Hz), 1.99(3 H, s), 2.17(3 H, s), 4.22(2 H, q, J = 7.1 Hz), 4.38(2 H, s), 7.05-7.12(2 H, m), 7.22-7.28(2 H, m), 7.31(1 H, s), 8.50(1 H, d, J = 9.0 Hz), 9.01(1 H, s). |
| 148 | —H | —H | 1 | $^1$H NMR 1.32(3 H, t, J = 7.1 Hz), 3.91(2 H, d, J = 5.4 Hz), 4.27(2 H, q, J = 7.1 Hz), 4.37(1 H, t, J = 5.4 Hz), 6.66(2 H, d, J = 8.9 Hz), 6.96(1 H, d, J = 9.1 Hz), 6.98(2 H, d, J = 8.9 Hz), 8.43(1 H, dd, J = 2.8 Hz, 9.1 Hz), 9.05(1 H, d, J = 2.8 Hz). |
| 149 | —H | -Ac | 2 | $^1$H NMR 1.23(3 H, t, J = 7.1 Hz), 1.90(3 H, s), 2.62(2 H, t, J = 7.3 Hz), 4.03(2 H, t, J = 7.3 Hz), 4.08(2 H, q, J = 7.1 Hz), 7.10(1 H, d, J = 9.0 Hz), 7.21-7.28(4 H, m), 8.52(1 H, dd, J = 2.8 Hz, 9.0 Hz), 9.04(1 H, d, J = 2.8 Hz). |
| 150 | —F | —$C_2H_5$ | 1 | $^1$H NMR 1.21-1.32(6 H, m), 3.47(2 H, q, J = 7.1 Hz), 4.01(2 H, s), 4.23(2 H, q, J = 7.1 Hz), 6.38-6.49(2 H, m), 7.01-7.07(2 H, m), 8.46(1 H, dd, J = 9.1 Hz, 2.8 Hz), 9.03(1 H, d, J = 2.8 Hz). |
| 151 | —$OCH_3$ | —$C_2H_5$ | 1 | $^1$H NMR 1.25(3 H, t, J = 7.1 Hz), 1.28(3 H, t, J = 7.1 Hz), 3.50(2 H, q, J = 7.1 Hz), 3.72(3 H, s), 4.03(2 H, s), 4.22(2 H, q, J = 7.1 Hz), 6.23(1 H, dd, J = 8.9 Hz, 2.8 Hz), 6.30(1 H, d, J = 2.6 Hz), 6.95-6.99(2 H, m), 8.42(1 H, dd, J = 9.1 Hz, 2.8 Hz), 9.04(1 H, d, J = 2.8 Hz). |
| 152 | —F | —$CH_3$ | 1 | $^1$H NMR 1.28(3 H, t, J = 7.1 Hz), 3.09(3 H, s), 4.06(2 H, s), 4.21(2 H, q, J = 7.1 Hz), 6.42-6.54(2 H, m), 7.03-7.10(2 H, m), 8.47(1 H, dd, J = 9.1 Hz, 2.8 Hz), 9.03(1 H, d, J = 2.8 Hz). |
| 153 | —$OCH_3$ | —H | 1 | $^1$H NMR 1.32(3 H, t, J = 7.1 Hz), 3.72(3 H, s), 3.92(2 H, d J = 5.3 Hz), 4.27(2 H, q, J = 7.1 Hz), 4.41(1 H, brt), 6.19(1 H, dd, J = 8.4 Hz, 2.5 Hz), 6.29(1 H, d, J = 2.5 Hz), 6.96-7.00(2 H, m), 8.42(1 H, dd, J = 9.1 Hz, 2.8 Hz), 9.03(1 H, d, J = 2.8 Hz). |
| 154 | —F | -Ac | 1 | $^1$H NMR 1.30 (3 H, t, J = 7.1 Hz), 2.02(3 H, s), 4.23(2 H, q, J = 7.1 Hz), 4.38(2 H, s), 7.16-7.33(4 H, m), 8.54(1 H, dd, J = 9.1 Hz, 2.8 Hz), 9.01(1 H, dd, J = 2.8 Hz, 0.5 Hz). |
| 155 | —F | —H | 1 | $^1$H NMR 1.32(3 H, t, J = 7.1 Hz), 3.89(2 H, d, J = 5.3 Hz), 4.28(2 H, q, J = 7.1 Hz), 4.35-4.55(1 H, m), 6.31-6.50(2 H, m), 6.91-7.11(2 H, m), 8.47(1 H, dd, J = 9.1 Hz, 2.8 Hz), 9.02(1 H, dd, J = 2.8 Hz, 0.4 Hz). |
| 156 | —$CF_3$ | —$CH_3$ | 1 | MS 399($M^+$) |
| 157 | —$CF_3$ | —$C_2H_5$ | 1 | MS 413($M^+$) |

TABLE 22

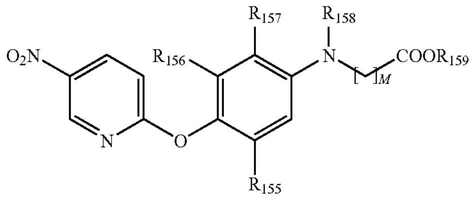

| Reference Example No. | $R_{155}$ | $R_{156}$ | $R_{157}$ | $R_{158}$ | $R_{159}$ | M | $^1$H NMR or MS |
|---|---|---|---|---|---|---|---|
| 158 | —H | —H | —H | —$CH_3$ | —$CH_3$ | 1 | $^1$H NMR ($CDCl_3$) δ 3.10(3 H, s), 3.74(3 H, s), 4.09(2 H, s), 6.72(2 H, |

TABLE 22-continued

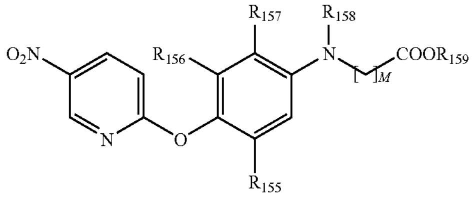

| Reference Example No. | $R_{155}$ | $R_{156}$ | $R_{157}$ | $R_{158}$ | $R_{159}$ | M | $^1$H NMR or MS |
|---|---|---|---|---|---|---|---|
| | | | | | | | d, J = 9.1 Hz), 6.96 (1 H, d, J = 9.0 Hz), 7.03(2 H, d, J = 9.1 Hz), 8.43(1 H, dd, J = 9.0 Hz, 2.9 Hz), 9.06(1 H, d, J = 2.9 Hz). |
| 159 | —H | —H | —H | -Ac | —$C_2H_5$ | 1 | $^1$H NMR (DMSO-$d_6$) δ 1.20(3 H, t, J = 7.1 Hz), 1.87(3 H, s), 4.12(2 H, q, J = 7.1 Hz), 4.37 (2 H, s), 7.28-7.35(3 H, m), 7.48(2 H, d, J = 8.7 Hz), 8.65(1 H, dd, J = 2.9 Hz, 9.1 Hz), 9.05 (1 H, d, J = 2.9 Hz). |
| 160 | —H | —H | —H | —$CH_3$ | —$CH_3$ | 2 | $^1$H NMR ($CDCl_3$) δ 2.59-2.64(2 H, m), 2.96 (3 H, s), 3.67-3.72(5 H, m), 6.76(2 H, d, J = 9.1 Hz), 6.97(1 H, d, J = 9.1 Hz), 7.05(2 H, d, J = 8.9 Hz), 8.43(1 H, dd, J = 9.1 Hz, 3.0 Hz), 9.06(1 H, d, J = 2.8 Hz). |
| 161 | —F | —H | —F | —H | —$C_2H_5$ | 1 | $^1$H NMR ($CDCl_3$) δ 1.32(3 H, t, J = 7.1 Hz), 3.91(2 H, d, J = 5.5 Hz), 4.28(2 H, q, J = 7.1 Hz), 4.57-4.71(1 H, m), 6.43(1 H, dd, J = 7.9 Hz, 11.6 Hz), 6.94(1 H, dd, J = 7.0 Hz 11.0 Hz), 7.08(1 H, d, J = 9.0 Hz), 8.49(1 H, dd, J = 2.8 Hz, 9.0 Hz), 9.01(1 H, d, J = 2.8 Hz). |
| 162 | —F | —F | —H | —$CH_3$ | —$C(CH_3)_3$ | 0 | $^1$H NMR ($CDCl_3$) δ 1.51(9 H, s), 3.30(3 H, s), 6.95-7.10(2 H, m), 7.21(1 H, d, J = 9.1 Hz), 8.54(1 H, dd, J = 2.8 Hz, 9.1 Hz), 9.00(1 H, d, J = 2.8 Hz). |
| 163 | —$CH_3$ | —H | —$CH_3$ | —$C_2H_5$ | —$C_2H_5$ | 1 | $^1$H NMR ($CDCl_3$) δ 1.08(3 H, t, J = 7.1 Hz), 1.24(3 H, t, J = 7.1 Hz), 2.07(3 H, s), 2.28(3 H, s), 3.21(2 H, q, J = 7.1 Hz), 3.78(2 H, s), 4.15 (2 H, q, J = 7.1 Hz), 6.86(1 H, s), 6.95(1 H, d, J = 9.1 Hz), 7.07(1 H, s), 8.45(1 H, dd, J = 9.1 Hz, 2.8 Hz), 9.06(1 H, d, J = 2.8 Hz). |
| 164 | —$COOCH_3$ | —H | —H | —$C_2H_5$ | —$C(CH_3)_3$ | 1 | MS 431($M^+$) |
| 165 | —$CH_3$ | —H | —$CH_3$ | —$CH_3$ | —$C_2H_5$ | 1 | $^1$H NMR ($CDCl_3$) δ 1.27(3 H, t, J = 7.1 Hz), 2.08(3 H, s), 2.28(3 H, s), 2.89(3 H, s), 3.73(2 H, s), 4.19(2 H, q, J = 7.1 Hz), 6.85(1 H, s), 6.96 (1 H,d, J = 9.1 Hz), 7.01(1 H, s), 8.45(1 H, dd, J = 9.1 Hz, 2.8 Hz), 9.06(1 H, d, J = 2.8 Hz). |
| 166 | —CN | —H | —H | —$CH_3$ | —$C(CH_3)_3$ | 1 | MS 384($M^+$) |
| 167 | —H | —H | —$CF_3$ | —$C_2H_5$ | —$C_2H_5$ | 1 | MS 413($M^+$) |

TABLE 23

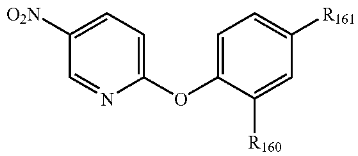

| Reference Example No. | $R_{160}$ | $R_{161}$ | $^1H$ NMR ($CDCl_3$) δ ppm |
|---|---|---|---|
| 168 | —H | 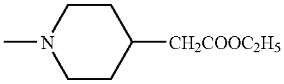 | 1.27(3 H, t, J = 7.0 Hz), 1.41-1.48(2 H m), 1.85 (2 H, brd, J = 13.0 Hz), 1.95(1 H, m), 2.29(2 H, d, J = 7.0 Hz) 2 76(2 H, dt, J = 2.5 Hz, 12.0 Hz), 3.65 (2 H, brd, J = 12.0 Hz), 4.16(2 H, q, J = 7.0 Hz), 6.96-6.99(3 H, m), 7.03(2 H, d, J = 9.0 Hz), 8.44 (1 H, dd, J = 9.0 Hz, 3.0 Hz), 9.05(1 H, d, J = 3.0 Hz). |
| 169 | —H | morpholino | 3.16-3.19(4 H, m), 3.86-3.89(4 H, m), 6.94-7.01 (3 H, m), 7.05-7.11(2 H, m), 8.45(1 H, dd, J = 9.2 Hz, 3.0 Hz), 9.05(1 H, d, J = 3.0 Hz). |
| 170 | —H | 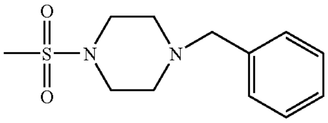 | 2.47-2.62(4 H, m) 2 96-3.14(4 H, m), 3.49(2 H, s), 7.11(1 H, d, J = 9.0 Hz), 7.19-7.37(7 H, m), 7.81 (2 H, d, J = 8.7 Hz), 8.52(1 H, dd, J = 9.0 Hz, 2.0 Hz), 9.02(1 H, d, J = 2.0 Hz). |
| 171 | —H | 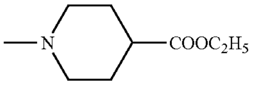 | 1.28(3 H, t, J = 7.0 Hz), 1.90(2 H, dq, J = 4.0 Hz, 11.5 Hz), 2.04(2 H, brd, J = 13.0 Hz), 2.43(1 H, m), 2.82(2 H, dt, J = 3.0 Hz, 12.0 Hz), 3.63(2 H, dt, J = 13.0 Hz, 3.0 Hz), 4.17(2 H, q, J = 7.0 Hz), 6.97-6.99(3 H, m), 7.04(2 H, d, J = 9.0 Hz), 8.44(1 H, dd, J = 9.0 Hz, 3.0 Hz), 9.05(1 H, d, J = 3.0 Hz). |
| 172 | —H | 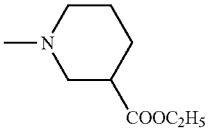 | 1.28(3 H, t, J = 7.0 Hz), 1.70(2 H, m), 1.84(1 H, m), 2.04(1 H, m), 2.69(1 H, m), 2.86(1 H, m), 3.08(1 H, dd, J = 12.0 Hz, 10.0 Hz), 3.46(1 H, brd, J = 12.0 Hz), 3.69(1 H, dd, J = 12.0 Hz, 4.0 Hz), 4.18(2 H, q, J = 7.0 Hz), 6.97-7.05(5 H, m), 8.45(1 H, dd, J = 9.0 Hz, 3.0 Hz), 9.06(1 H, d, J = 3.0 Hz). |
| 173 | —$COOCH_3$ | 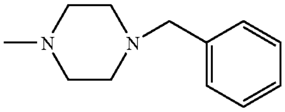 | 2.61-2.64(4 H, m) 3.24-3.28(4 H, m), 3.58(2 H; s), 3.68(3 H, s), 7.03-7.16(3 H, m), 7.26-7.36(5 H, m), 7.54(1 H, d, J = 2.8 Hz), 8.46(1 H, d.d, J = 9.1 Hz, 2.8 Hz), 8.97(1 H, d, J = 2.8 Hz). |
| 174 | —H | 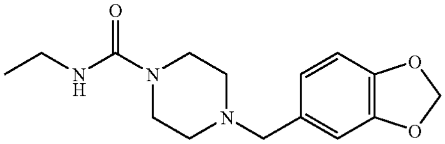 | 2.43(4 H, t, J = 5.1 Hz), 3.40(4 H, t, J = 5.1 Hz), 3.43(2 H, s), 4.46(2 H, t, J = 5.5 Hz), 4.79(1 H, t, J = 5.5 Hz), 5.95(2 H, s), 6.74(2 H, s), 6.85(1 H, s), 7.05(1 H, d, J = 9.1 Hz), 7.12(2 H, d, J = 8.4 Hz), 7.40(2 H, d, J = 8.4 Hz), 8.48(1 H, dd, J = 9.1 Hz, 2.8 Hz), 9.03(1 H, d, J = 2.8 Hz). |
| 175 | —$CH_3$ | —$NHCOCOOC_2H_5$ | 1.33(3 H, t, J = 7.1 Hz), 2.07(3 H, s), 4.32(2 H, q, J = 7.1 Hz), 7.15(1 H, d, J = 8.7 Hz), 7.27(1 H, cld, J = 9.2 Hz, 0.5 Hz), 7.63(1 H, cM, J = 8.6 Hz, 2.5 Hz), 7.71(1 H, d, J = 2.5 Hz), 8.62(1 H, dd, J = 9.1 Hz, 2 8 Hz), 9.01(1 H, dd, J = 2.8 Hz, 0.5 Hz), 10.82(1 H, brs). |

TABLE 24

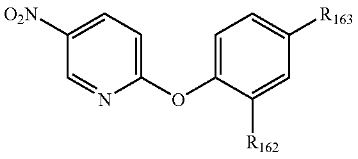

| Reference Example No. | $R_{162}$ | $R_{163}$ | $^1H$ NMR (solvent) δ ppm |
|---|---|---|---|
| 176 | —H | —Ac | ($CDCl_3$ ) 2.60 (3H, s), 7.10-9.00 (7H, m). |
| 177 | —H | —CHO | ($CDCl_3$) 7.14 (1H, d, J = 9.0 Hz), 7.35 (2H, d, J = 8.7 Hz), 8.00 (2H, d, J = 8.7 Hz), 8.54 (1H, dd, J = 9.0 Hz, 1.8 Hz), 9.04 (1H, d, J = 1.8 Hz), 10.03 (1H, s). |
| 178 | —H | —$C_2H_5$ | ($CDCl_3$) 1.28 (3H, t, J = 7.6 Hz), 2.70 (2H, q, J = 7.6 Hz), 7.01 (1H, dd, J = 9.1 Hz, 0.7 Hz), 7.07 (2H, d, J = 8.7 Hz), 7.28 (2H, d, J = 8.7 Hz), 8.46 (1H, dd, J = 9.1 Hz, 2.8 Hz), 9.05 (1H, dd, J = 2.8 Hz, 0.7 Hz). |
| 179 | —$CH_3$ | —CHO | ($CDCl_3$) 2.25 (3H, s), 7.14 (1H, d, J = 8.9 Hz), 7.24 (1H, d, J = 8.2 Hz), 7.81 (1H, dd, J = 8.2 Hz, 2.0 Hz), 7.85 (1H, s), 8.53 (1H, dd, J = 8.9 Hz, 2.6 Hz), 9.00 (1H, d, J = 2.6 Hz), 10.00 (1H, s). |
| 180 | —H | 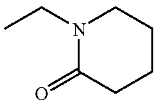 | ($CDCl_3$) 1.70-1.93 (4H, m), 2.45-2.56 (2H, m), 3.22-3.36 (2H, m), 4.62 (2H, s), 7.03 (1H, d, J = 9.2 Hz), 7.12 (2H, d, J = 8.6 Hz), 7.35 (2H, d, J = 8.6 Hz), 8.47 (1H, dd, J = 9.2 Hz, 2.6 Hz), 9.04 (1H, d, J = 2.6 Hz). |
| 181 | —H | 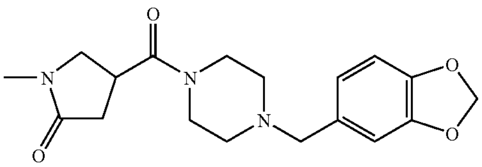 | ($CDCl_3$) 2.46-2.47 (4H, m), 2.77-2.99 (2H, m), 3.46 (2H, s), 3.51-3.57 (4H, m), 3.64-3.73 (1H, m), 3.90-3.96 (1H, m), 4.30-4.36 (1H, m), 5.96 (2H, s), 6.75-6.86 (3H, m), 7.04 (1H, d, J = 9.1 Hz), 7.17 (2H, d, J = 9.1 Hz), 7.70 (2H, d, J = 8.9 Hz), 8.48 (1H, dd, J = 2.8 Hz, 9.1 Hz), 9.03 (1H, d, J = 2.8 Hz). |
| 182 | —H | 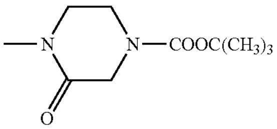 | ($CDCl_3$) 1.51 (9H, s), 3.80 (4H, m), 4.27 (2H, s), 7.07 (1H, d, J = 9.1 Hz), 7.21 (2H, dd, J = 6.8 Hz, 2.1 Hz), 7.38 (2H, dd, J = 6.8 Hz, 2.1 Hz), 8.49 (1H, dd, J = 9.1 Hz, 2.8 Hz), 9.04 (1H, d, J = 2.8 Hz). |
| 183 | —H | 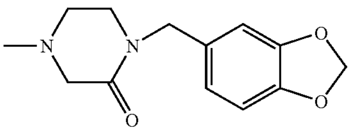 | ($CDCl_3$) 3.35-3.55 (4H, m), 3.96 (2H, s), 4.58 (2H, s), 5.96 (2H, s), 6.73-6.78 (2H, m), 6.81 (1H, s), 6.91 (2H, d, J = 9.1 Hz), 7.00 (1H, d, J = 9.1 Hz), 7.09 (2H, d, J = 9.1 Hz), 8.45 (1H, dd, J = 9.1 Hz, 2.8 Hz), 9.04 (1H, d, J = 2.8 Hz). |
| 184 | —H | —NHCONHPh | (DMSO-$d_6$) 6.96 (1H, t, J = 6.5 Hz), 7.14 (2H, d, J = 8.8 Hz), 7.21 (1H, d, J = 9.1 Hz), 7.27 (2H, t, J = 8.3 Hz), 7.45 (2H, d, J = 8.3 Hz), 7.52 (2H, d, J = 8.8 Hz), 8.60 (1H, dd, J = 2.8 Hz, 9.1 Hz), 8.70 (1H, s), 8.77 (1H, s), 9.02 (1H, d, J = 2.8 Hz). |

TABLE 25

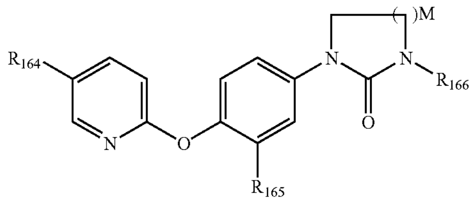

| Reference Example No. | $R_{164}$ | $R_{165}$ | $R_{166}$ | M | mp (° C.) or $^1$H NMR (solvent) δ ppm |
|---|---|---|---|---|---|
| 185 | —$NO_2$ | —$CH_3$ | piperonyl | 2 | mp 142.0-143.0 |
| 186 | —$NO_2$ | —H | benzyl | 1 | $^1$H NMR (DMSO-$d_6$) 3.36 (2H, t, J = 8.1 Hz), 3.84 (2H, t, J = 8.1 Hz), 4.40 (2H, s), 7.15-7.25 (3H, m), 7.26-7.34 (3H, m), 7.35-7.41 (2H, m), 7.61-7.71 (2H, m), 8.59 (1H, dd, J = 2.9 Hz, 9.1 Hz), 9.02 (1H, d, J = 9.1 Hz). |
| 187 | —$NO_2$ | —$CH_3$ | piperonyl | 1 | $^1$H NMR (DMSO-$d_6$) 2.05 (3H, s), 3.29-3.41 (2H, m), 3.71-3.88 (2H, m), 4.29 (2H, s), 5.60 (2H, s), 6.74-6.81 (1H, m), 6.82-6.92 (2H, m), 7.09 (1H, d, J = 8.8 Hz), 7.21 (1H, d, J = 9.1 Hz), 7.49 (1H, d, J = 2.6 Hz, 8.8 Hz), 7.51-7.57 (1H, m), 8.60 (1H, d, J = 9.1 Hz), 9.00 (1H, d, J = 2.9 Hz). |
| 188 | —$NO_2$ | —$CH_3$ | 3,4-$(CH_3O)_2PhCH_2$— | 2 | $^1$H NMR ($CDCl_3$) 2.00-2.15 (2H, m), 2.14 (3H, s), 3.31 (2H, t, J = 6.0 Hz), 3.73 (2H, d, J = 6.0 Hz), 3.88 (3H, s), 3.89 (3H, s), 4.57 (2H, s), 6.83 (1H, d, J = 8.1 Hz), 6.87 (1H, dd, J = 1.9 Hz, 8.1 Hz), 6.91 (1H, d, J = 1.9 Hz), 6.98-7.06 (2H, m), 7.20 (1H, dd, J = 2.4 Hz, 8.6 Hz), 7.29 (1H, d, J = 2.4 Hz), 8.46 (1H, dd, J = 2.8 Hz, 9.1 Hz), 9.04 (1H, d, J = 2.8 Hz). |
| 189 | —$NO_2$ | —$CH_3$ | —$CH_2COOC(CH_3)_3$ | 2 | $^1$H NMR ($CDCl_3$) 1.48 (9H, s), 2.12 (3H, s), 2.12-2.24 (2H, m), 3.48 (2H, t, J = 5.9 Hz), 3.77 (2H, t, J = 5.9 Hz), 4.05 (2H, s), 6.92-7.06 (2H, m), 7.17 (1H, dd, J = 2.6 Hz, 8.6 Hz), 8.45 (1H, dd, J = 2.9 Hz, 9.1 Hz), 9.04 (1H, d, J = 2.9 Hz). |
| 190 | —Br | —$CH_3$ | piperonyl | 2 | $^1$H NMR ($CDCl_3$) 1.94-2.18 (2H, m), 2.15 (3H, s), 3.30 (2H, d, J = 6.0 Hz), 3.71 (2H, d, J = 6.0 Hz), 4.52 (2H, s), 5.95 (2H, s), 6.69-6.82 (3H, m), 6.88 (1H, s), 7.00 (1H, d, J = 8.6 Hz), 7.15 (1H, dd, J = 2.6 Hz, 8.6 Hz), 7.24 (1H, d, J = 2.6 Hz), 7.73 (1H, dd, J = 2.5 Hz, 8.6 Hz), 8.20 (1H, d, J = 2.5 Hz). |
| 191 | —Br | —$CH_3$ | 3,4-$(CH_3O)_2PhCH_2$— | 2 | $^1$H NMR ($CDCl_3$) 1.95-2.11 (2H, m), 2.14 (3H, s), 3.30 (2H, t, J = 5.9 Hz), 3.70 (2H, t, J = 5.9 Hz), 3.88 (3H, s), 3.88 (3H, s), 4.56 (2H, s), 6.74-6.92 (4H, s), 7.00 (1H, d, J = 8.5 Hz), 7.15 (1H, dd, J = 2.4 Hz, 8.5 Hz), 7.24 (1H, d, J = 2.4 Hz), 7.73 (1H, dd, J = 2.6 Hz, 8.8 Hz), 8.19 (1H, dd, J = 0.5 Hz, 2.6 Hz). |

TABLE 26

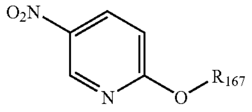

| Reference Example No. | $R_{167}$ | $^1H$ NMR ($CDCl_3$) δ ppm or MS |
|---|---|---|
| 192 | 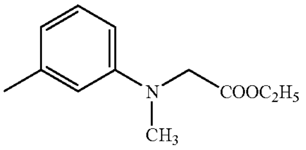 | $^1H$ NMR 1.24 (3H, t, J = 7.1 Hz), 3.07 (3H, s), 4.05 (2H, s), 4.18 (2H, q, J = 7.1 Hz), 6.44-6.45 (1H, m), 6.49-6.53 (1H, m), 6.57-6.61 (1H, m), 6.97 (1H, d, J = 9.1 Hz), 7.25-7.31 (1H, m), 8.44 (1H, dd, J = 9.1 Hz, 2.8 Hz), 9.07 (1H, d, J = 2.8 Hz). |
| 193 | 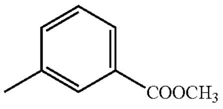 | $^1H$ NMR 3.93 (3H, s), 7.08-7.11 (1H, m), 7.26-7.40 (1H, m), 7.51-7.57 (1H, m), 7.83-7.84 (1H, m), 7.96-8.00 (1H, m), 8.49-8.53 (1H, m), 9.02-9.03 (1H, m). |
| 194 | 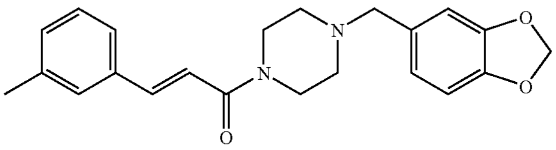 | MS 488 ($M^+$) |
| 195 | 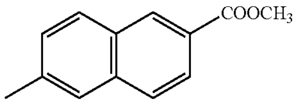 | $^1H$ NMR 4.00 (3H, s), 7.14 (1H, d, J = 8.9 Hz), 7.37 (1H, dd, J = 8.9 Hz, 2.3 Hz), 7.67 (1H, d, J = 2.3 Hz), 7.87 (1H, d, J = 8.6 Hz), 8.04 (1H, d, J = 8.9 Hz), 8.11 (1H, dd, J = 8.6 Hz, 1.7 Hz), 8.51-8.55 (1H, m), 8.64 (1H, brs), 9.05 (1H, d, J = 2.8 Hz). |
| 196 | 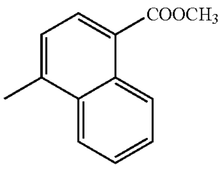 | $^1H$ NMR 4.03 (3H, s), 7.20 (1H, d, J = 9.1 Hz), 7.31 (1H, d, J = 8.1 Hz), 7.51-7.57 (1H, m), 7.65-7.71 (1H, m), 7.94 (1H, d, J = 8.4 Hz), 8.29 (1H, d, J = 8.1 Hz), 8.55 (1H, dd, J = 9.1 Hz, 2.8 Hz), 8.99 (1H, d, J = 2.8 Hz), 9.05 (1H, d, J = 8.7 Hz). |
| 197 | 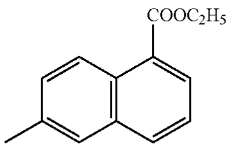 | $^1H$ NMR 1.47 (3H, t, J = 7.1 Hz), 4.49 (2H, t, J = 7.1 Hz), 7.11 (1H, d, J = 8.9 Hz), 7.42 (1H, dd, J = 9.4 Hz, 2.5 Hz), 7.52-7.58 (1H, m), 7.67 (1H, d, J = 2.5 Hz), 7.99 (1H, d, J = 8.2 Hz), 8.21 (1H, dd, J = 7.3 Hz, 1.2 Hz), 8.51 (1H, dd, J = 9.1 Hz, 2.8 Hz), 9.04-9.08 (2H, m). |
| 198 | 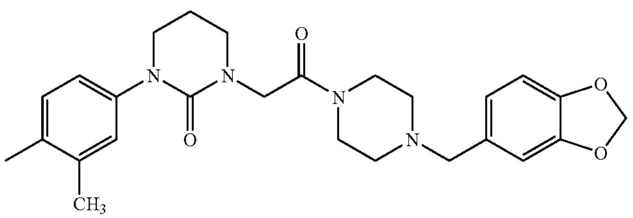 | $^1H$ NMR ($CDCl_3$) 2.11 (3H, s), 2.19 (2H, t, J = 5.9 Hz), 2.34-2.50 (4H, m), 3.42 (2H, s), 3.40-3.47 (2H, m), 3.51 (2H, t, J = 5.9 Hz), 3.56-3.76 (2H, m), 3.78 (2H, t, J = 5.7 Hz), 4.20 (2H, s), 5.94 (2H, s), 6.69-6.77 (2H, m), 6.84 (1H, d, J = 1.0 Hz), 6.96-7.02 (2H, m), 7.17 (1H, dd, J = 2.6 Hz, 8.5 Hz), 7.24-7.28 (1H, m), 8.45 (1H, dd, J = 2.8 Hz, 9.1 Hz), 9.04 (1H, d, J = 2.8 Hz). |

TABLE 27

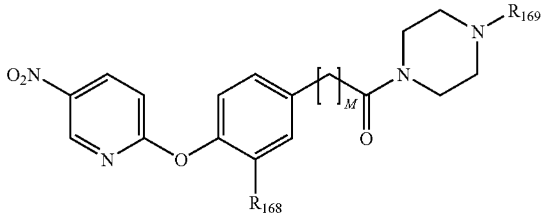

| Reference Example No. | $R_{168}$ | $R_{169}$ | M | $^1$H NMR (solvent) δ ppm |
|---|---|---|---|---|
| 199 | —H | benzyl | 2 | ($CDCl_3$) 2.36-2.45 (4H, m), 2.63-2.68 (2H, m), 2.99-3.05 (2H, m), 3.41-3.45 (2H, m), 3.52 (2H, s), 3.64-3.67 (2H, m), 7.01-7.11 (3H, m), 7.29-7.34 (7H, m), 8.47 (1H, dd, J = 9.1 Hz, 2.8 Hz), 9.05 (1H, d, J = 2.8 Hz). |
| 200 | —H | piperonyl | 2 | ($CDCl_3$) 2.33-2.41 (4H, m), 2.62-2.67 (2H, m), 2.98-3.04 (2H, m), 3.39-3.43 (4H, m), 3.62-3.65 (2H, m), 5.94 (2H, s), 6.73-6.77 (2H, m), 6.84 (1H, s), 7.00-7.10 (3H, m), 7.26-7.31 (2H, m), 8.44-8.48 (1H, m), 9.03 (1H, dd, J = 3.0 Hz, 0.5 Hz). |
| 201 | —F | benzyl | 0 | ($CDCl_3$) 2.49 (4H, brs), 3.49-3.56 (4H, m), 3.79 (2H, brs), 7.15 (1H, d, J = 8.9 Hz), 7.24-7.38 (8H, m), 8.53 (1H, dd, J = 9.1 Hz, 2.8 Hz), 8.99 (1H, d, J = 2.8 Hz). |
| 202 | —H | benzyl | 0 | (DMSO-$d_6$) 2.41 (4H, brs), 3.33 (2H, brs), 3.52 (4H, brs), 7.24-7.27 (8H, m), 7.50 (2H, d, J = 7.9 Hz), 8.64 (1H, dd, J = 9.1 Hz, 2.8 Hz), 9.04 (1H, d, J = 2.8 Hz). |
| 203 | —H | 4-$CH_3OPhCH_2$— | 0 | ($CDCl_3$) 2.46 (4H, brs), 3.44-3.90 (4H, m), 3.49 (2H, s), 3.81 (3H, s), 6.85-6.89 (2H, m), 7.06 (1H, d, J = 8.9 Hz), 7.18-7.27 (4H, m), 7.48-7.53 (2H, m), 8.48-8.52 (1H, m), 9.03 (1H, d, J = 2.8 Hz). |
| 204 | —H | piperonyl | 0 | ($CDCl_3$) 2.46 (4H, brs), 3.46 (2H, s), 3.52 (2H, brs), 3.77 (2H, brs), 5.95 (2H, s), 6.75 (2H, s), 6.86 (1H, s), 7.07 (1H, dd, J = 9.1 Hz, 0.5 Hz), 7.20 (2H, d, J = 8.6 Hz), 7.51 (2H, d, J = 8.6 Hz), 8.50 (1H, dd, J = 8.9 Hz, 2.8 Hz), 9.03 (1H, dd, J = 2.8 Hz, 0.5 Hz). |
| 205 | —H | 3-pyridyl | 0 | ($CDCl_3$) 3.27 (4H, brs), 3.84 (4H, brs), 7.08-7.12 (1H, m), 7.21-7.27 (4H, m), 7.54-7.59 (2H, m), 8.16-8.18 (1H, m), 8.34 (1H, brs), 8.52 (1H, dd, J = 9.1 Hz, 2.8 Hz), 9.05 (1H, dd, J = 2.8 Hz, 0.5 Hz). |

TABLE 28

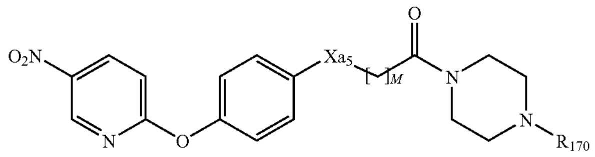

| Reference Example No. | $Xa_5$ | $R_{170}$ | M | $^1$H NMR ($CDCl_3$) δ ppm |
|---|---|---|---|---|
| 206 | —O— | piperonyl | 1 | 2.43 (4H, brs), 3.42 (2H, s), 3.58 (2H, t, J = 5.0 Hz), 3.64 (2H, t, J = 5.0 Hz), 4.70 (2H, s), 5.95 (2H, s), 6.70-6.79 (2H, m), 6.84 (1H, d, J = 0.6 Hz), 7.01 (3H, d, J = 9.1 Hz), 7.09 (2H, d, J = 9.1 Hz), 8.46 (1H, dd, J = 9.1 Hz, 2.8 Hz), 9.04 (1H, d, J = 2.8 Hz). |
| 207 | —CH(OH)— | benzyl | 0 | 1.90-2.05 (1H, m), 2.21-2.68 (3H, m), 3.11-3.25 (1H, m), 3.28-3.40 (1H, m), 3.45 (2H, s), 3.73 (2H, t, J = 5.1 Hz), 4.77 (1H, d, J = 6.3 Hz), 5.24 (1H, d, J = 6.3 Hz), 7.04 (1H, d, J = 8.9 Hz), 7.16 (2H, d, J = 8.7 Hz), 7.21-7.35 (5H, m), 7.38 (2H, d, J = 8.7 Hz), 8.48 (1H, dd, J = 8.9 Hz, 2.8 Hz), 9.03 (1H, d, J = 2.8 Hz). |

TABLE 28-continued

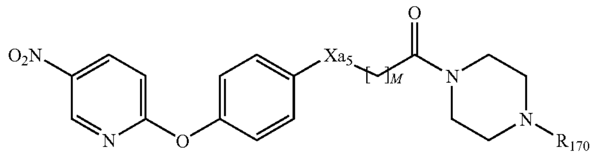

| Reference Example No. | $Xa_5$ | $R_{170}$ | M | $^1$H NMR ($CDCl_3$) δ ppm |
|---|---|---|---|---|
| 208 | 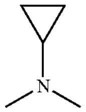 | piperonyl | 1 | 0.65-0.70 (2H, m), 0.81-0.88 (2H, m), 2.41-2.48 (4H, m), 2.77-2.85 (1H, m), 3.45 (2H, s), 3.49-3.52 (2H, m), 3.60-3.63 (2H, m), 4.20 (2H, s), 5.95 (2H, s), 6.71-6.78 (2H, m), 6.86 (1H, brs), 6.90-7.02 (5H, m), 8.39-8.44 (1H, m), 9.06 (1H, d, J = 2.8 Hz). |
| 209 | —O— | benzyl | 1 | 2.45 (4H, t, J = 4.5 Hz), 3.52 (2H, s), 3.59 (2H, t, J = 4.9 Hz), 3.65 (2H, t, J = 4.9 Hz), 4.70 (2H, s), 7.00 (2H, d, J = 9.2 Hz), 7.01 (1H, d, J = 9.0 Hz), 7.08 (2H, d, J = 9.2 Hz), 7.21-7.40 (5H, m), 8.46 (1H, dd, J = 9.0 Hz, 2.8 Hz), 9.04 (1H, d, J = 2.8 Hz). |
| 210 | —N($CH_3$)— | benzyl | 0 | 2.32 (4H, brs), 3.24 (3H, s), 3.28 (4H, brs), 3.48 (2H, brs), 7.04 (1H, d, J = 9.1 Hz), 7.11 (2H, d, J = 9.0 Hz), 7.15 (2H, d, J = 9.0 Hz), 7.22-7.40 (5H, m), 8.48 (1H, dd, J = 9.1 Hz, 2.8 Hz), 9.04 (1H, d, J = 2.8 Hz). |

TABLE 29

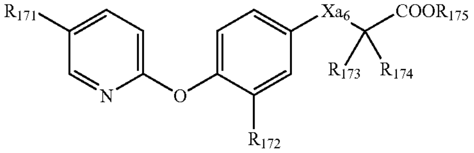

| Reference Example No. | $R_{171}$ | $R_{172}$ | $Xa_6$ | $R_{173}$ | $R_{174}$ | $R_{175}$ | $^1$H NMR ($CDCl_3$) δ ppm or MS |
|---|---|---|---|---|---|---|---|
| 211 | —$NO_2$ | —H | —N($CH_3$)— | —$CH_3$ | —H | —$C_2H_5$ | $^1$H NMR 1.25 (3H, t, J = 7.1 Hz), 1.50 (3H, d, J = 7.1 Hz), 2.93 (3H, s), 4.18 (2H, q, J = 7.1 Hz), 4.48 (1H, q, J = 7.3 Hz), 6.82 (2H, d, J = 9.2 Hz), 6.97 (1H, d, J = 9.1 Hz), 7.03 (2H, d, J = 9.0 Hz), 8.43 (1H, dd, J = 9.1 Hz, 2.8 Hz), 9.06 (1H, d, J = 2.8 Hz). |
| 212 | —$NO_2$ | —H | —N($CH_3$)— | —$CH_3$ | —$CH_3$ | —$C_2H_5$ | $^1$H NMR 1.24 (3H, t, J = 7.1 Hz), 1.46 (6H, s), 2.94 (3H, s), 4.18 (2H, q, J = 7.1 Hz), 6.97 (1H, dd, J = 9.1 Hz, 0.5 Hz), 7.00-7.08 (4H, m), 8.45 (1H, dd, J = 9.1 Hz, 3.0 Hz), 9.05 (1H, dd, J = 2.8 Hz, 0.5 Hz). |
| 213 | —$NO_2$ | —$CH_3$ | —N($CH_3$)— | —$CH_3$ | —H | —$C_2H_5$ | $^1$H NMR 1.26 (3H, t, J = 7.1 Hz), 1.49 (3H, d, J = 7.3 Hz), 2.10 (3H, s), 2.91 (3H, s), 4.13-4.24 (2H, m), 4.48 (1H, q, J = 7.3 Hz), 6.64-6.68 (2H, m), 6.91-6.96 (2H, m), 8.43 (1H, dd, J = 9.1 Hz, 2.8 Hz), 9.06 (1H, dd, J = 2.8 Hz, 0.5 Hz). |
| 214 | —$NO_2$ | —H | none | —$CH_3$ | —$CH_3$ | —$CH_3$ | MS 316 ($M^+$) |
| 215 | —Br | —$OCH_3$ | —$CH_2$— | —H | —H | —$C_2H_5$ | $^1$H NMR 1.26 (3H, t, J = 7.1 Hz), 2.63-2.68 (2H, m), 2.94-3.00 (2H, m), 3.75 (3H, s), 4.15 (2H, q, J = 7.1 Hz), 6.80-6.86 (3H, m), 7.03 (1H, d, J = 7.9 Hz), 7.73 (1H, dd, J = 8.7 Hz, 2.6 Hz), 8.16 (1H, dd, J = 2.6 Hz, 0.7 Hz). |
| 216 | 3,4-$Cl_2PhCH_2NHCO$— | —H | —$CH_2$— | —H | —H | —$C_2H_5$ | MS 472 ($M^+$) |
| 217 | 4-$CF_3PhCH_2NHCO$— | —H | —$CH_2$— | —H | —H | —$C_2H_5$ | MS 472 ($M^+$) |

TABLE 30

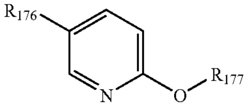

| Reference Example No. | $R_{176}$ | $R_{177}$ | $^1H$ NMR ($CDCl_3$) δ ppm or MS |
|---|---|---|---|
| 218 | 4-$CF_3$PhCO— | 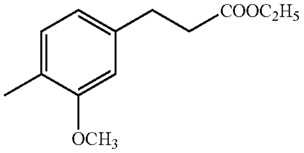 | $^1H$ NMR 1.26 (3H, t, J = 7.1 Hz), 2.64-2.69 (2H, m), 2.95-3.01 (2H, m), 3.76 (3H, s), 4.15 (2H, q, J = 7.1 Hz), 6.83-6.89 (2H, m), 7.03-7.10 (2H, m), 7.73-7.76 (2H, m), 7.86-7.89 (2H, m), 8.21 (1H, dd, J = 8.6 Hz, 2.5 Hz), 8.55 (1H, dd, J = 2.5 Hz, 0.7 Hz). |
| 219 | 3.4-$Cl_2$PhNHCO— | 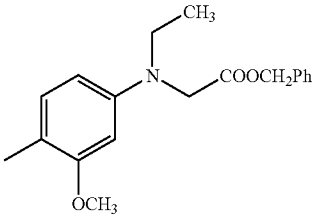 | $^1H$ NMR 1.20 (3H, t, J = 7.1 Hz), 3.44 (2H, q, J = 7.1 Hz), 3.56 (3H, s), 4.04 (2H, s), 5.17 (2H, s), 6.15-6.18 (2H, m), 6.83 (1H, d, J = 8.7 Hz), 6.88 (1H, d, J = 8.9 Hz), 7.29-7.35 (6H, m), 7.44 (1H, dd, J = 8.7 Hz, 2.5 Hz), 7.82 (1H, d, J = 2.3 Hz), 8.10 (1H, dd, J = 8.7 Hz, 2.5 Hz), 8.59 (1H, d, J = 2.5 Hz), 8.72 (1H, brs). |
| 220 | 3,4-$Cl_2$PhNHCO— | 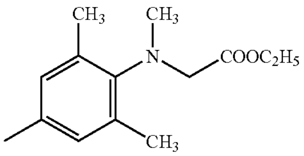 | MS 501 ($M^+$) |
| 221 | 4-$CF_3$PhNHCO— | 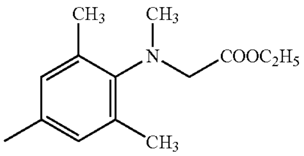 | MS 501 ($M^+$) |
| 222 | —$COOC_2H_5$ | 4-$NO_2$Ph- | $^1H$ NMR 1.40 (3H, t, J = 7.1 Hz), 4.40 (2H, q, J = 7.1 Hz), 7.08 (1H, d, J = 8.6 Hz), 7.32 (2H, d, J = 9.0 Hz), 8.31 (2H, d, J = 9.0 Hz), 8.37 (1H, dd, J = 8.6 Hz, 2.3 Hz), 8.82 (1H, d, J = 2.3 Hz). |
| 223 | 4-$CF_3$PhNHCO— | 4-CHOPh- | MS 386 ($M^+$) |
| 224 | —$COOC_2H_5$ | 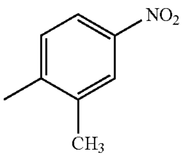 | $^1H$ NMR 1.39 (3H, t, J = 7.1 Hz), 2.28 (3H, s), 4.39 (2H, q, J = 7.1 Hz), 7.07 (1H, dd, J = 8.6 Hz, 0.5 Hz), 7.21 (1H, d, J = 8.9 Hz), 8.13 (1H, dd, J = 8.9 Hz, 2.8 Hz), 8.20 (1H, d, J = 2.8 Hz), 8.36 (1H, dd, J = 8.6 Hz, 2.3 Hz), 8.78 (1H, dd, J = 2.8 Hz, 0.5 Hz). |

(CHOPh means a formylphenyl group. Hereinafter CHOPh indicates the same meaning.)

TABLE 31

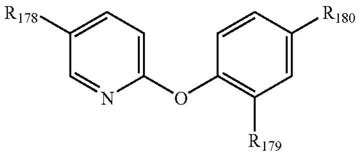

| Reference Example No. | $R_{178}$ | $R_{179}$ | $R_{180}$ | Form | mp (° C.) or $^1$H NMR (solvent) δ ppm |
|---|---|---|---|---|---|
| 225 | 4-$CF_3$PhNHCO— | —$CH_3$ | —$NHCOCOOC_2H_5$ | free | $^1$H NMR (DMSO-$d_6$) 1.33 (3H, t, J = 7.1 Hz), 2.08 (3H, s), 4.33 (2H, q, J = 7.1 Hz), 7.12 (1H, d, J = 8.7 Hz), 7.17 (1H, d, J = 8.6 Hz), 7.63 (1H, dd, J = 8.7 Hz, 2.5 Hz), 7.72-7.75 (3H, m), 7.98 (2H, d, J = 8.7 Hz), 8.37 (1H, dd, J = 8.6 Hz, 2.5 Hz), 8.69 (1H, d, J = 2.5 Hz), 10.62 (1H, brs), 10.81 (1H, brs). |
| 226 | 3,4-$Cl_2$PhNHCO— | —$CH_3$ | 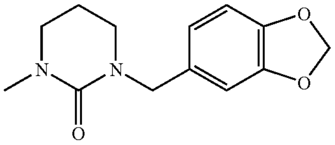 | hydro-bromide | mp 132.0-134.0 |
| 227 | —$NO_2$ | —$CH_3$ | 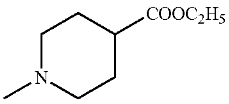 | free | $^1$H NMR ($CDCl_3$) 1.28 (3H, t, J = 7.1 Hz), 1.86-1.95(2H, m), 2.02-2.06 (2H, m), 2.10 (3H, s), 2.40-2.48 (1H, m), 2.76-2.85 (2H, m), 3.61-3.65 (2H, m), 4.17 (2H, q, J = 7.1 Hz), 6.79-6.97 (4H, m), 8.43 (1H, dd, J = 9.1 Hz, 3.0 Hz), 9.04 (1H, d, J = 2.8 Hz). |
| 228 | —$NO_2$ | —$OCH_3$ | 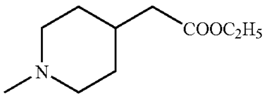 | free | $^1$H NMR ($CDCl_3$) 1.28 (3H, t, J = 7.1 Hz), 1.41-1.50 (2H, m), 1.84-2.04 (3H, m), 2.30 (2H, d, J = 6.9 Hz), 2.78 (2H, dd, J = 12.0 Hz, 9.7 Hz), 3.65 (2H, d, J = 12.4 Hz), 3.73 (3H, s) 4.16 (2H, q, J = 7.3 Hz), 6.53 (1H, dd, J = 8.7 Hz, 2.6 Hz), 6.59 (1H, d, J = 2.6 Hz), 6.96-7.02 (2H, m), 8.42 (1H, dd, J = 9.1 Hz, 2.8 Hz), 9.03 (1H, d, J = 2.8 Hz). |
| 229 | —$NO_2$ | —$CH_3$ | 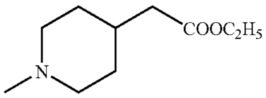 | free | $^1$H NMR ($CDCl_3$) 1.27 (3H, t, J = 7.1 Hz), 1.37-1.49 (2H, m), 1.83-2.03 (3H, m), 2.10 (3H, s), 2.29 (2H, d, J = 6.9 Hz), 2.74 (2H, dd, J = 12.2 Hz, 10.1 Hz), 3.64 (2H, d, J = 12.4 Hz), 4.15 (2H, q, J = 7.3 Hz), 6.77-6.83 (2H, m), 6.91-6.97 (2H, m), 8.42 (1H, dd, J = 9.1 Hz, 2.8 Hz), 9.02 (1H, d, J = 2.8 Hz). |

TABLE 32

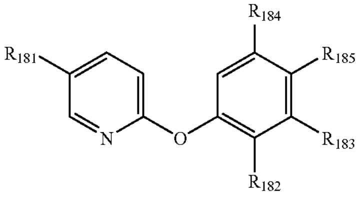

| Reference Example No. | $R_{181}$ | $R_{182}$ | $R_{183}$ | $R_{184}$ | $R_{185}$ | $^1$H NMR ($CDCl_3$) δ ppm or MS |
|---|---|---|---|---|---|---|
| 230 | —Br | $—CH_3$ | —H | —H | 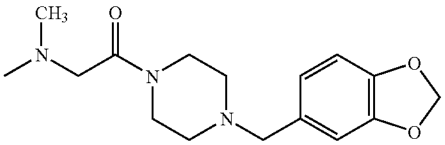 | $^1$H NMR 2.09 (3H, s), 2.41-2.45 (4H, m), 3.01 (3H, s), 3.43 (2H, s), 3.49 (2H, brs), 3.63 (2H, brs), 4.07 (2H, brs), 5.93 (2H, s), 6.51-6.56 (2H, m), 6.68-6.77 (3H, m), 6.85-6.91 (2H, m), 7.68 (1H, dd, J = 8.7 Hz, 2.5 Hz), 8.19 (1H, d, J = 2.5 Hz). |
| 231 | $3,4-Cl_2PhNHCO—$ | —H | $—CF_3$ | —H | $—N(CH_3)CH_2COOC_2H_5$ | MS 541 ($M^+$) |
| 232 | $4-CF_3PhNHCO—$ | —H | $—CF_3$ | —H | $—N(CH_3)CH_2COOC_2H_5$ | MS 541 ($M^+$) |
| 233 | $3,4-Cl_2PhCH_2NHCO—$ | —H | $—CF_3$ | —H | $—N(CH_3)CH_2COOC_2H_5$ | MS 555 ($M^+$) |
| 234 | $4-CF_3CH_2NHCO—$ | —H | $—CF_3$ | —H | $—N(CH_3)CH_2COOC_2H_5$ | MS 555 ($M^+$) |
| 235 | —Br | —F | —H | —F | $—N(CH_3)CH_2COOC_2H_5$ | $^1$H NMR 1.26 (3H, t, J = 7.1 Hz), 2.99 (3H, s), 4.03 (2H, s), 4.18 (2H, q J = 7.1 Hz), 6.76 (1H, d, J = 8.2 Hz, 12.1 Hz), 6.84-6.95 (2H, m), 7.77 (1H, dd, J = 2.6 Hz, 8.7 Hz), 8.17 (1H, d, J = 2.6 Hz). |

TABLE 33

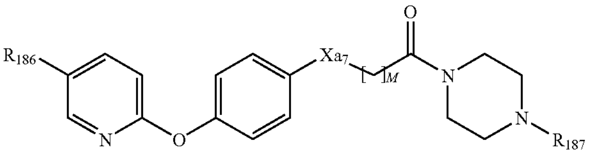

| Reference Example No. | $R_{186}$ | $Xa_7$ | $R_{187}$ | M | $^1$H NMR (solvent) δ ppm |
|---|---|---|---|---|---|
| 236 | $—COOC_2H_5$ | $—CH_2—$ | piperonyl | 1 | (DMSO-$d_6$) 1.31 (3H, t, J = 7.0 Hz), 2.28 (4H, brs), 2.60-2.66 (2H, m), 2.80-2.86 (2H, m), 3.38 (2H, s), 3.40-3.46 (4H, m), 4.31 (2H, q, J = 7.0 Hz), 5.98 (2H, s), 6.72-6.76 (1H, m), 6.84 (2H, d, J = 8.4 Hz), 7.06-7.11 (3H, m), 7.30 (2H, d, J = 8.4 Hz), 8.30 (1H, dd, J = 8.6 Hz, 2.4 Hz), 8.68 (1H, d, J = 2.4 Hz). |
| 237 | $—COOC_2H_5$ | none | benzyl | 0 | ($CDCl_3$) 1.39 (3H, t, J = 7.3 Hz), 2.48 (4H, brs), 3.55-3.91 (6H, m), 4.38 (2H, q, J = 7.3 Hz), 6.97 (1H, d, J = 8.6 Hz), 7.17-7.19 (2H, m), 7.20-7.34 (5H, m), 7.46-7.49 (2H, m), 8.31 (1H, dd, J = 8.6 Hz, 2.4 Hz), 8.82 (1H, d, J = 2.4 Hz). |
| 238 | —Br | $—N(CH_3)—$ | piperonyl | 1 | ($CDCl_3$) 2.41-2.45 (4H, m), 3.03 (3H, s), 3.43 (2H, s), 3.47-3.51 (2H, m), 3.61-3.65 (2H, m), 4.09 (2H, s), 5.95 (2H, s), 6.68-6.85 (6H, m), 6.96-7.02 (2H, m), 7.70 (1H, dd, J = 8.7 Hz, 2.5 Hz), 8.20 (1H, d, J = 2.5 Hz). |

TABLE 33-continued

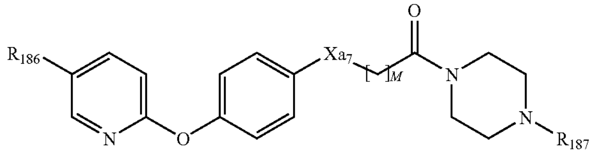

| Reference Example No. | $R_{186}$ | $Xa_7$ | $R_{187}$ | M | $^1$H NMR (solvent) δ ppm |
|---|---|---|---|---|---|
| 239 | —Br | —$CH_2$— | piperonyl | 1 | ($CDCl_3$) 2.31-2.41 (4H, m), 2.59-2.65 (2H, m), 2.95-3.00 (2H, m), 3.38-3.42 (4H, m), 3.61-3.65 (2H, m), 5.95 (2H, s), 6.70-6.77 (2H, m), 6.81-6.84 (2H, m), 7.01-7.06 (2H, m), 7.22-7.27 (2H, m), 7.76 (1H, dd, J = 8.7 Hz, 2.6 Hz), 8.20-8.21 (1H, m). |
| 240 | —Br | none | benzyl | 0 | ($CDCl_3$) 2.47 (4H, brs), 3.49-3.55 (6H, m), 6.86 (1H, d, J = 8.6 Hz), 7.14 (2H, d, J = 8.6 Hz), 7.28-7.33 (5H, m), 7.45 (2H, d, J = 8.6 Hz), 7.80 (1H, dd, J = 8.6 Hz, 2.5 Hz), 8.22 (1H, d, J = 2.5 Hz). |
| 241 | —$COOCH_3$ | —$N(CH_3)$— | piperonyl | 1 | ($CDCl_3$) 2.41-2.45 (4H, m), 3.04 (3H, s), 3.43 (2H, s), 3.47-3.49 (2H, m), 3.63 (2H, s), 3.91 (3H, s), 4.10 (2H, s), 5.95 (2H, s), 6.69-6.75 (4H, m), 6.84 (1H, dd, J = 8.7 Hz, 0.7 Hz), 6.85 (1H, brs), 7.02 (2H, d, J = 9.2 Hz), 8.21 (1H, dd, J = 8.7 Hz, 2.5 Hz), 8.82 (1H, dd, J = 2.5 Hz, 0.7 Hz). |
| 242 | —$COOC_2H_5$ | none | piperonyl | 0 | ($CDCl_3$) 1.39 (3H, t, J = 7.1 Hz), 2.45 (4H, brs), 3.45 (2H, s), 3.54-3.75 (4H, m), 4.38 (2H, q, J = 7.1 Hz), 5.95 (2H, s), 6.71-6.75 (2H, m), 6.86 (1H, s), 6.97 (1H, d, J = 8.6 Hz), 7.19 (2H, d, J = 8.6 Hz), 7.48 (2H, d, J = 8.7 Hz), 8.30 (1H, dd, J = 2.3 Hz, 8.6 Hz), 8.82 (1H, d, J = 2.3 Hz). |

TABLE 34

| Reference Example No. | Chemical Structure | MS ($M^+$) |
|---|---|---|
| 243 | 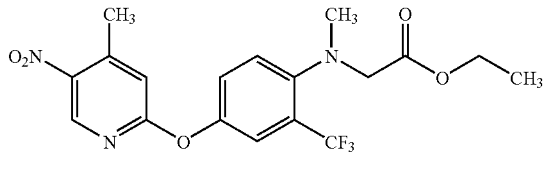 | 413 |
| 244 | 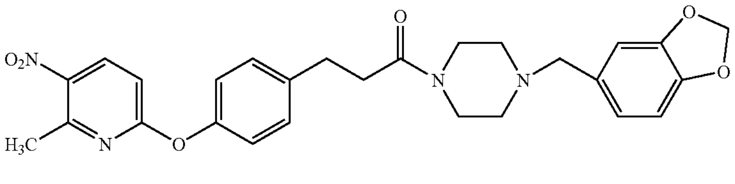 | 504 |
| 245 | 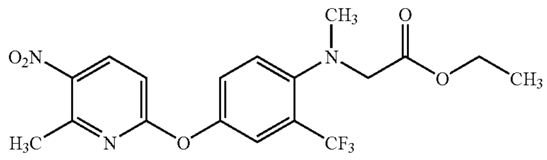 | 413 |

TABLE 34-continued

| Reference Example No. | Chemical Structure | MS ($M^+$) |
| --- | --- | --- |
| 246 | 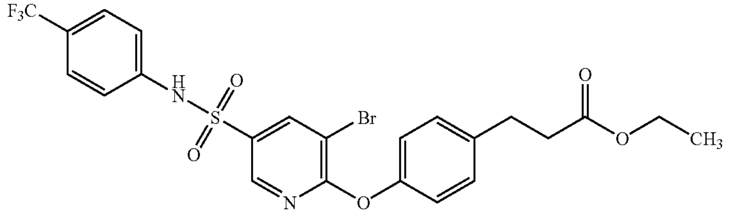 | 574 |

Reference Example 247

Production of 4-(5-nitropyridin-2-yloxy)phenylamine

To a solution of sodium hydroxide (730 mg, 18.25 mmol) in methanol was added 4-aminophenol (2.00 g, 18.32 mmol). After the resulting mixture was made to dissolve, methanol was evaporated under reduced pressure. To the residue was added DMF (20 mL), and then 2-chloro-5-nitropyridine (2.91 g, 18.35 mmol). The reaction solution was stirred for 1.5 hours at 70° C., and then concentrated under reduced pressure. Water was added to the residue, and the resulting solution was extracted with ethyl acetate. The ethyl acetate layer was washed with brine. The ethyl acetate layer was dried over anhydrous magnesium sulfate, after which solvent was evaporated, and the residue was purified by silica gel column chromatography (n-hexane:ethyl acetate=1:1), to thereby yield 3.37 g of the title compound.

Appearance: Black-red powder $^1$H NMR (DMSO-$d_6$) δ 5.10 (2H, s), 6.61 (2H, d, J=8.9 Hz), 6.85 (2H, d, J=8.9 Hz), 7.08 (1H, d, J=9.0 Hz), 8.55 (1H, dd, J=9.0 Hz, 3.0 Hz), 9.01 (1H, d, J=3.0 Hz).

The following compounds were produced in the same manner as in Reference Example 247.

TABLE 35

| Reference Example No. | Chemical Structure | $^1$H NMR (solvent) δ ppm |
| --- | --- | --- |
| 248 | 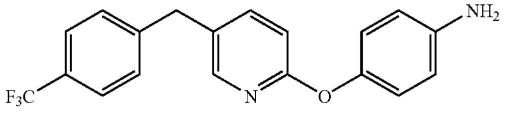 | (DMSO-$d_6$) 4.03 (2H, s), 6.96 (1H, d, J = 8.4 Hz), 7.10 (2H, d, J = 8.9 Hz), 7.17 (2H, d, J = 8.9 Hz), 7.48 (2H, d, J = 8.1 Hz), 7.66 (2H, d, J = 8.1 Hz), 7.71 (1H, dd, J = 8.4 Hz, 2.5 Hz), 8.08 (1H, d, J = 2.5 Hz), 9.12 (2H, brs). |
| 249 | 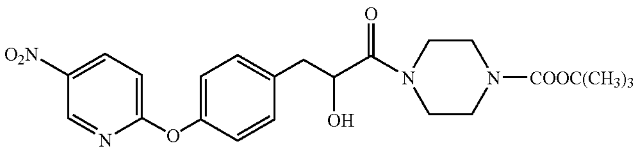 | ($CDCl_3$) 1.47 (9H, s), 2.94 (2H, d, J = 5.1 Hz), 3.10-3.80 (9H, m), 4.62 (1H, d, J = 5.1 Hz), 7.03 (1H, d, J = 9.1 Hz), 7.10 (2H, d, J = 8.5 Hz), 7.31 (2H, d, J = 8.5 Hz), 8.46 (1H, dd, J = 9.1 Hz, 2.8 Hz), 9.01 (1H, d, J = 2.8 Hz). |

TABLE 36

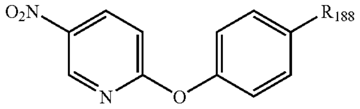

| Reference Example No. | $R_{188}$ | $^1$H NMR (solvent) δ ppm |
| --- | --- | --- |
| 250 | $-CH_2OH$ | ($CDCl_3$) 4.74 (2H, s), 7.04 (1H, d, J = 8.9 Hz), 7.13-7.18 (2H, m), 7.46 (2H, d, J = 8.3 Hz), 8.48 (1H, dd, J = 8.9 Hz, 2.6 Hz), 9.03 (1H, d, J = 2.6 Hz). |

TABLE 36-continued

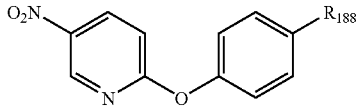

| Reference Example No. | $R_{188}$ | $^1H$ NMR (solvent) δ ppm |
|---|---|---|
| 251 | $—(CH_2)_2OH$ | ($CDCl_3$) 2.91 (2H, t, J = 6.6 Hz), 3.91 (2H, t, J = 6.6 Hz), 7.03 (1H, d, J = 9.2 Hz), 7.09-7.13 (2H, m), 7.32 (2H, d, J = 8.6 Hz), 8.47 (1H, dd, J = 9.2 Hz, 3.0 Hz), 9.04 (1H, d, J = 3.0 Hz). |
| 252 | $—(CH_2)_2COOH$ | ($CDCl_3$) 2.73 (2H, t, J = 7.9 Hz), 3.01 (2H, t, J = 7.9 Hz), 7.03 (1H, d, J = 8.9 Hz), 7.09 (2H, d, J = 8.6 Hz), 7.30 (2H, d, J = 8.6 Hz), 8.47 (1H, dd, J = 9.2 Hz, 3.0 Hz), 9.04 (1H, d, J = 2.6 Hz). |
| 253 | $—(CH_2)_3COOH$ | (DMSO-$d_6$) 2.01 (2H, dq, J = 15.0 Hz, 7.2 Hz), 2.46 (2H, t, J = 7.2 Hz), 2.72 (2H, t, J = 7.2 Hz), 7.02 (1H, d, J = 8.6 Hz), 7.08 (2H, d, J = 8.6 Hz), 7.27 (2H, d, J = 8.6 Hz), 8.46 (1H, dd, J = 8.6 Hz, 3.0 Hz), 9.04 (1H, d, J = 3.0 Hz). |

Reference Example 254

Production of ethyl 3-[4-(3-nitrophenoxy)phenyl]-propionate

Under argon; to a solution of 3-iodonitrobenzene (3.00 g, 12.0 mmol) in pyridine (15 mL) were added ethyl 3-(4-hydroxyphenyl)propionate (2.81 g, 14.5 mmol), copper oxide (3.35 g, 42.2 mmol), and potassium carbonate (4.16 g, 30.1 mmol), and the resulting solution was heated to reflux for 40 hours. The reaction solution was concentrated under reduced pressure. Water and ethyl acetate were added to the residue, and once insoluble matter had been filtered off, and the filtrate was extracted with ethyl acetate out. The ethyl acetate layer was washed with 1 M hydrochloric acid, water and a saturated sodium bicarbonate solution, and then washed with brine. The ethyl acetate layer was dried over anhydrous magnesium sulfate, evaporated, and the residue was purified by silica gel column chromatography (n-hexane:ethyl acetate=9:1→6:1), to thereby yield 1.12 g of the title compound.

Appearance: Pale yellow oil $^1H$ NMR ($CDCl_3$) δ 1.23 (3H, t, J=7.1 Hz), 2.62 (2H, t, J=7.7 Hz), 2.95 (2H, t, J=7.7 Hz), 4.12 (2H, q, J=7.1 Hz), 6.96 (2H, d, J=8.6 Hz), 7.22 (2H, d, J=8.6 Hz), 7.29 (1H, dd, J=8.2 Hz, 2.3 Hz), 7.43 (1H, t, J=8.2 Hz), 7.74 (1H, s), 7.90 (1H, dd, J=8.2 Hz, 2.3 Hz).

Reference Example 255

Production of 1-(t-butoxycarbonyl)-4-[4-(4-nitrophenoxy)phenyl]piperazine

Potassium carbonate (15.7 g, 114 mmol) was added to a solution of 2-chloro-5-nitropyridine (4.50 g, 28.4 mmol) and 1-(4-hydroxyphenyl)piperazine dihydrochloride (7.13 g, 28.4 mmol) in DMF (80 mL). The resulting solution was stirred at room temperature for 8 hours. To this reaction solution was added di-t-butyl dicarbonate (6.81 g, 31.2 mmol), and stirred at room temperature for 2.5 days. To the reaction solution was charged with ethyl acetate, washed with water, and dried with anhydrous magnesium sulfate, and evaporated. The residue was purified by silica gel column chromatography (ethyl acetate:n-hexane=1:3), to thereby yield 7.05 g of the title compound.

Appearance: Yellow needles $^1H$ NMR ($CDCl_3$) δ 1.49 (9H, s), 3.15 (4H, t, J=5.0 Hz), 3.59 (4H, t, J=5.0 Hz), 6.98 (2H, d, J=9.0 Hz), 7.00 (1H, d, J=9.0 Hz), 7.07 (2H, d, J=9.0 Hz), 8.45 (1H, dd, J=9.0 Hz, 2.5 Hz), 9.05 (1H, d, J=2.5 Hz).

Reference Example 256

Production of (ethyl{3-methoxy-4-[5-(4-trifluoromethylphenylcarbamoyl)pyridin-2-yloxy]phenyl}amino)acetate Benzyl[ethyl(4-hydroxy-3-methoxyphenyl)amino]acetate (9.46 g, 30 mmol) and 6-chloro-N-(4-trifluoromethylphenyl)nicotinamide (9.02 g, 30 mmol) were dissolved in DMF (100 mL). To the resulting solution was added potassium carbonate (6.22 g, 45 mmol), and then stirred for 12 hours at 120° C. The reaction solution was concentrated under reduced pressure. To the residue was added ethyl acetate and extracted with water. The pH of the aqueous layer was adjusted from 3 to 4 with 1 M hydrochloric acid, after which the mixture was extracted with ethyl acetate. The organic layer was washed with brine and dried over anhydrous magnesium sulfate, and evaporated to thereby yield 4.2 g of the title compound.

Appearance: Brown powder $^1H$ NMR (DMSO-$d_6$) δ 1.19 (3H, t, J=7.1 Hz), 3.40 (2H, q, J=7.1 Hz), 3.63 (3H, s), 4.01 (2H, s), 6.17 (1H, d, J=8.9 Hz), 6.22 (1H, brs), 6.25 (1H, d, J=2.5 Hz), 6.87-6.90 (2H, m), 7.53 (2H, d, J=8.6 Hz), 7.76 (2H, d, J=8.4 Hz), 8.18 (1H, dd, J=8.7 Hz, 2.3 Hz), 8.67 (1H, d, J=2.1 Hz), 8.88 (1H, brs).

Reference Example 257

Production of ethyl methyl[2,5-difluoro-4-(5-nitropyridin-2-yloxy)phenyl]aminoacetate To a solution of ethyl(2,5-difluoro-4-hydroxyphenyl)aminoacetate (1.1 g, 4.8 mmol) in DMF (25 mL) were added sodium bicarbonate (0.44 g, 5.2 mmol) and methyl iodide (1.69 mL, 28.6 mmol), and the resulting reaction solution was stirred for 2 days at room temperature. Water was added to the reaction mixture, and extracted with ethyl acetate. Once the ethyl acetate layer had been washed with water, the ethyl acetate layer was dried with anhydrous magnesium sulfate, and evaporated. The residue was dissolved in DMF (30 mL), and to this resulting solution were added potassium carbonate (0.72 g, 5.2 mmol) and 2-chloro-5-nitropyridine (0.79 g, 5.0 mmol). The reaction solution was stirred for 2.5 days at room temperature. Water was added to the reaction mixture, and extracted with ethyl acetate. The ethyl acetate layer was washed with water, and dried over anhydrous magnesium sulfate. The solvent was then evaporated, and the residue was purified by silica gel chromatography (n-hexane:ethyl acetate=8:1), to thereby yield 1.41 g of the title compound.

Appearance: Yellow oil $^1$H NMR ($CDCl_3$) δ 1.27 (3H, t, J=7.1 Hz), 3.01 (3H, s), 4.05 (2H, s), 4.19 (2H, q, J=7.1 Hz), 6.77 (1H, dd, J=8.2 Hz, 12.2 Hz), 6.92 (1H, dd, J=7.2 Hz, 12.8 Hz), 8.49 (1H, dd, J=2.8 Hz, 9.0 Hz), 9.02 (1H, d, J=2.8 Hz).

The following compounds were produced in the same manner as in Reference Example 257.

TABLE 37

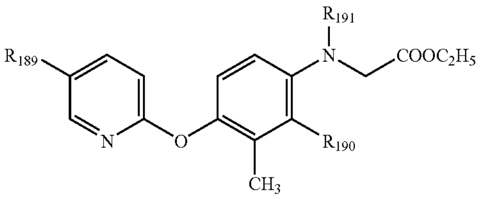

| Reference Example No. | $R_{189}$ | $R_{190}$ | $R_{191}$ | $^1$H NMR ($CDCl_3$) δ ppm |
|---|---|---|---|---|
| 258 | —$NO_2$ | —$CH_3$ | —$CH_3$ | 1.27 (3H, t, J = 7.1 Hz), 2.05 (3H, s), 2.29 (3H, s), 2.87 (3H, s), 3.71 (2H, s), 4.18 (2H, q, J = 7.1 Hz), 6.87 (1H, d, J = 8.7 Hz), 6.97 (1H, dd, J = 9.1 Hz, 0.3 Hz), 7.08 (1H, d, J = 8.7 Hz), 8.45 (1H, dd, J = 9.1 Hz, 2.8 Hz), 9.04 (1H, dd, J = 2.8 Hz, 0.3 Hz). |
| 259 | 4-$CF_3$PhCO— | —H | —$C_2H_5$ | 1.23 (3H, t, J = 7.1 Hz), 1.28 (3H, t, J = 7.1 Hz), 2.12 (3H, s), 3.46 (2H, q, J = 7.1 Hz), 4.01 (2H, s), 4.21 (2H, q, J = 7.1 Hz), 6.49-6.53 (2H, m), 6.92-6.96 (2H, m), 7.73-7.77 (2H, m), 7.86-7.89 (2H, m), 8.17 (1H, dd, J = 8.7 Hz, 2.5 Hz), 8.59 (1H, dd, J = 2.5 Hz, 0.7 Hz). |

Reference Example 260

Production of ethyl 4-{3-[3-methyl-4-(5-nitropyridin-2-yloxy)phenyl]-2-oxotetrahydropyrimidin-1-yl}benzoate Under a nitrogen atmosphere, to a solution of ethyl 4-[3-(4-benzyloxy-3-methyl)phenyl-2-oxotetrahydropyrimidin-1-yl]benzoate (1.82 g, 3.1 mmol) in ethanol-DMF (70 mL-30 mL) was added 10% palladium-carbon (0.4 g), and the resulting solution was stirred under a hydrogen atmosphere for 4 hours at room temperature. The resulting solution was filtered through Celite, and ethanol was evaporated under reduced pressure so as to give a DMF (30 mL) solution. To this solution was addde 2-chloro-5-nitropyridine (0.52 g, 3.3 mmol) and stirred under a nitrogen atmosphere for 14 hours at room temperature, and then for 3 hours at 40° C. Water was added to the reaction mixture, and extracted with ethyl acetate. The ethyl acetate layer was washed with water, dried over anhydrous magnesium sulfate, and evaporated. The residue was purified by silica gel chromatography (n-hexane: ethyl acetate=10:1), to thereby yield 1.8 g of the title compound.

Appearance: White powder $^1$H NMR ($CDCl_3$) δ 1.39 (3H, t, J=7.1 Hz), 2.14 (3H, s), 2.21-2.40 (2H, m), 3.75-3.97 (4H, m), 4.36 (2H, q, J=7.1 Hz), 7.01 (1H, d, J=9.1 Hz), 7.06 (1H, d, J=8.6 Hz), 7.23 (1H, dd, J=2.6 Hz, 8.6 Hz), 7.32 (1H, d, J=2.6 Hz), 7.40-7.49 (2H, m), 7.97-8.07 (2H, m), 8.46 (1H, dd, J=2.8 Hz, 9.1 Hz), 9.04 (1H, d, J=2.8 Hz).

Reference Example 261

Production of 3-[4-(5-nitropyridin-2-ylsulfanyl)phenyl]propionic acid

To a solution of 2-chloro-5-nitropyridine (1.74 g, 11.0 mmol) and 4-mercaptohydrocinnamic acid (2.00 g, 11.0 mmol) in DMF (30 mL) was added potassium carbonate (4.55 g, 32.9 mmol), and the resulting solution was stirred for 1 hour at 80° C. To the reaction solution were added water and concentrated hydrochloric acid, and then cooled with ice. The precipitated solid matter was collected by filtration, to thereby yield 3.29 g of the title compound.

Appearance: Pale yellow powder $^1$H NMR (DMSO-$d_6$) δ 2.60 (2H, t, J=7.5 Hz), 2.91 (2H, t, J=7.5 Hz), 7.07 (1H, d, J=9.0 Hz), 7.43 (2H, d, J=8.2 Hz), 7.57 (2H, d, J=8.2 Hz), 8.39 (1H, dd, J=2.8 Hz, 9.0 Hz), 9.17 (1H, d, J=2.8 Hz), 12.19 (1H, s).

Reference Example 262

Production of ethyl 3-[3-methoxy-4-(5-nitropyridin-2-ylamino)phenyl]propionate

To 2-chloro-5-nitropyridine (3.11 g, 20 mmol) were added ethyl 3-(4-amino-3-methoxyphenyl)propionate (4.38 g, 20 mmol) and acetic acid (10 mL), and the resulting solution was stirred for 13 hours at 100° C. To the reaction solution were added ethyl acetate and water. The ethyl acetate layer was separated, washed with brine, a saturated sodium bicarbonate solution and brine, and dried over anhydrous magnesium sulfate. The solvent was evaporated, and the residue was purified by silica gel column chromatography (n-hexane: ethyl acetate=2:1), to thereby yield 3.78 g of the title compound.

Appearance: Yellow powder $^{1}$H NMR ($CDCl_3$) δ 1.26 (3H, t, J=7.1 Hz), 2.61-2.67 (2H, m), 2.93-2.99 (2H, m), 3.89 (3H, s), 4.15 (2H, q, J=7.1 Hz), 6.73 (1H, d, J=9.2 Hz), 6.81-6.87 (2H, m), 7.43 (1H, brs), 7.92 (1H, d, J=8.1 Hz), 8.23 (1H, dd, J=9.2 Hz, 2.8 Hz), 9.11 (1H, d, J=2.8 Hz).

The following compounds were produced in the same manner as in Reference Example 262.

TABLE 38

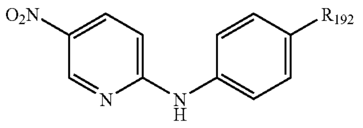

| Reference Example No. | $R_{192}$ | $^{1}$H NMR (solvent) δ ppm |
|---|---|---|
| 263 | —$COOC_2H_5$ | ($DMSO-d_6$) 1.32 (3H, t, J = 7.1 Hz), 4.29 (2H, q, J = 7.1 Hz), 7.01 (1H, d, J = 9.3 Hz), 7.89 (2H, d, J = 8.9 Hz), 8.36 (1H, dd, J = 2.9 Hz, 9.3 Hz), 9.09 (1H, d, J = 2.9 Hz), 10.43 (1H, s). |
| 264 | —$(CH_2)_2COOC_2H_5$ | ($CDCl_3$) 1.25 (3H, t, J = 7.1 Hz), 2.64 (2H, t, J = 7.6 Hz), 2.97 (2H, t, J = 7.6 Hz), 4.14 (2H, q, J = 7.1 Hz), 6.73 (1H, d, J = 9.3 Hz), 7.20-7.40 (4H, m), 8.23 (1H, dd, J = 2.7 Hz, 9.3 Hz), 9.07 (1H, d, J = 2.7 Hz). |
| 265 | 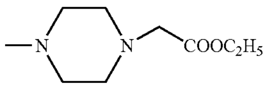 | ($CDCl_3$) 1.30 (3H, t, J = 7.1 Hz), 2.77 (4H, t, J = 5.0 Hz), 3.28 (4H, t, J = 5.0 Hz), 3.28 (2H, s), 4.22 (2H, q, J = 7.1 Hz), 6.61 (1H, d, J = 9.4 Hz), 6.95 (2H, d, J = 9.0 Hz), 7.11 (1H, brs), 7.22 (2H, d, J = 9.0 Hz), 8.18 (1H, dd, J = 9.4 Hz, 2.5 Hz), 9.05 (1H, d, J = 2.5 Hz). |
| 266 | 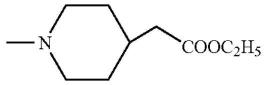 | ($CDCl_3$) 1.28 (3H, t, J = 7.1 Hz), 1.32-1.60 (2H, m), 1.75-2.12 (3H, m), 2.29 (2H, d, J = 6.9 Hz), 2.77 (2H, td, J = 12.4 Hz, 2.4 Hz), 3.68 (2H, d, J = 12.4 Hz), 4.16 (2H, q, J = 7.1 Hz), 6.60 (1H, d, J = 9.2 Hz), 6.96 (2H, d, J = 8.9 Hz), 7.16 (1H, brs), 7.20 (2H, d, J = 8.9 Hz), 8.18 (1H, dd, J = 9.2 Hz, 2.6 Hz), 9.05 (1H, d, J = 2.6 Hz). |

Reference Example 267

Production of 4-[(5-nitro-2-pyridyl)oxy]benzaldehyde ethylene acetal

To a solution of 4-[(5-nitro-2-pyridyl)oxy]benzaldehyde (5.00 g, 20.5 mmol) in benzene (100 mL) were added ethylene glycol (2.28 mL, 41.0 mmol) and p-toluenesulfonic acid (0.50 g), and the resulting solution was heated to reflux for 3 hours while removing water with a Dean-Stark. The reaction solution was washed with a saturated sodium bicarbonate solution, and subsequently washed with brine. The benzene layer was dried over anhydrous magnesium sulfate, and evaporated, to thereby yield 5.88 g of the title compound.

Appearance: Yellow powder $^{1}$H NMR ($CDCl_3$) δ 4.00-4.19 (4H, m), 5.83 (1H, s), 7.00 (1H, d, J=9.0 Hz), 7.15 (2H, d, J=8.5 Hz), 7.55 (2H, d, J=8.5 Hz), 8.45 (1H, dd, J=9.0 Hz, 2.0 Hz), 9.01 (1H, d, J=2.0 Hz).

The following compound was produced in the same manner as in Reference Example 267.

Reference Example 268

4-(2-Fluoro-4-nitrophenoxybenzaldehyde ethylene acetal $^{1}$H NMR ($DMSO-d_6$) δ 3.90-4.10 (4H, m), 5.76 (1H, s), 7.15-7.25 (3H, m), 7.54 (2H, d, J=8.7 Hz), 8.10 (1H, ddd, J=1.3 Hz, 2.7 Hz, 9.1 Hz), 8.35 (1H, dd, J=2.7 Hz, 10.8 Hz).

Reference Example 269

Production of t-butyl[4-(5-nitropyridin-2-yloxy)phenyl]carbamate

To a solution of 4-(5-nitropyridin-2-yloxy)phenylamine (2.97 g, 12.85 mmol) in THF was added di-t-butyl dicarbonate (5.60 g, 25.66 mmol), and the resulting solution was stirred under reflux for 4 hours. The reaction solution was concentrated under reduced pressure. Water was added to the residue, and extracted with ethyl acetate. The ethyl acetate layer was washed with brine, dried over anhydrous magnesium sulfate, evaporated, and to the resulting product was added diethyl ether. The obtained white powder was filtered, and the resulting product was washed with diethyl ether, to thereby yield 3.04 g of the title compound.

Appearance: Yellow powder $^{1}$H NMR ($CDCl_3$) δ 1.53 (9H, s), 6.53 (1H, brs), 7.00 (1H, d, J=9.2 Hz), 7.09 (2H, d, J=8.9 Hz), 7.45 (2H, d, J=8.9 Hz), 8.46 (1H, dd, J=9.2 Hz, 3.0 Hz), 9.03 (1H, d, J=3.0 Hz).

Reference Example 270

Production of 5-[3-methyl-4-(5-nitropyridin-2-yloxy)benzylidene]thiazolidine-2,4-dione To a solution of 3-methyl-4-(5-nitropyridin-2-yloxy)benzaldehyde (600 mg, 2.32 mmol) in toluene (35 mL) were added 2,4-thiazolidinedione (270 mg, 2.31 mmol) and piperidine acetate (135 mg, 0.93 mmol). The resulting solution was attached to a Dean Stark, and stirred under reflux for 1.5 hours. After being left to cool for 17 hours at room temperature, the precipitated yellow powder was filtered, to thereby yield 600 mg of the title compound.

Appearance: Yellow powder $^1$H NMR (DMSO-$d_6$) δ 2.15 (3H, s), 7.33 (1H, d, J=8.4 Hz), 7.35 (1H, d, J=9.1 Hz), 7.52 (1H, dd, J=8.4 Hz, 2.0 Hz), 7.59 (1H, d, J=2.0 Hz), 7.79 (1H, s), 8.65 (1H, dd, J=9.1 Hz, 3.0 Hz), 9.02 (1H, d, J=3.0 Hz), 12.63 (1H, brs).

The following compounds were produced in the same manner as in Reference Example 270.

TABLE 39

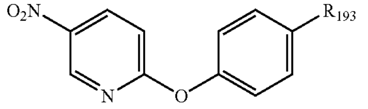

| Reference Example No. | $R_{193}$ | $^1$H NMR (solvent) δ ppm |
|---|---|---|
| 271 | 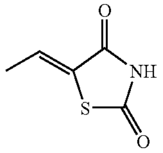 | (DMSO-$d_6$) 7.35 (1H, d, J = 9.0 Hz), 7.42 (2H, d, J = 8.6 Hz), 7.71 (2H, d, J = 8.6 Hz), 7.84 (1H, s), 8.65 (1H, dd, J = 9.0 Hz, 2.9 Hz), 9.04 (1H, d, J = 2.9 Hz), 12.64 (1H, brs). |
| 272 | —CH═C(COOCH$_3$)$_2$ | ($CDCl_3$) 3.87 (6H, s), 7.09 (1H, d, J = 9.0 Hz), 7.20 (2H, d, J = 8.5 Hz), 7.53 (2H, d, J = 8.5 Hz), 7.77 (1H, s), 8.51 (1H, dd, J = 9.0 Hz, 2.8 Hz), 9.04 (1H, d, J = 2.8 Hz). |

Reference Example 273

Production of N-[4-(2-fluoro-4-nitrophenoxy)phenyl]-N-[2-(4-piperonylpiperazin-1-yl)-2-oxyethyl] acetamide To a solution of N-[4-(2-fluoro-4-nitrophenoxy)phenyl] acetamide (0.800 g, 2.76 mmol) in DMF (5 mL) was added 60% sodium hydride (0.118 g, 2.95 mmol). The resulting solution was stirred for 10 minutes at room temperature, after which a solution of 1-chloroacetyl-4-piperonylpiperazine (0.870 g, 2.96 mmol) in DMF (4 mL) was added to the reaction solution. The reaction solution was stirred for 2 hours at 60° C., and then for 1 hour at 100° C. Water was added to the reaction mixture, and extracted with ethyl acetate. The ethyl acetate layer was washed with brine, dried over anhydrous sodium sulfate, evaporated, and the residue was purified by silica gel column chromatography (dichloromethane:methanol=5:1), to thereby yield 0.730 g of the title compound.

Appearance: Yellow oil $^1$H NMR (DMSO-$d_6$) δ 1.82 (3H, s), 2.20-2.40 (4H, m), 3.30-3.50 (6H, m), 4.43 (2H, s), 5.98 (2H, s), 6.70-6.85 (3H, m), 7.20-7.30 (3H, m), 7.48 (2H, d, J=8.8 Hz), 8.12 (1H, ddd, J=1.4 Hz, 2.7 Hz, 10.5 Hz), 8.36 (1H, dd, J=2.7 Hz, 10.7 Hz).

The following compound was produced in the same manner as in Reference Example 273.

Reference Example 274

3-(4-Benzyloxy-3-methylphenyl)-1-[2-oxo-2-(4-piperonylpiperazin-1-yl)ethyl]tetrahydropyrimidin-2-one $^1$H NMR (DMSO-$d_6$) δ 1.92-2.08 (2H, m), 2.15 (3H, s), 2.22-2.40 (4H, m), 3.25-3.49 (8H, m), 3.56 (2H, d, J=5.6 Hz), 4.08 (2H, s), 5.09 (2H, s), 5.97 (2H, s), 6.74 (1H, dd J=1.3 Hz, 7.9 Hz), 6.84 (1H, d, J=7.9 Hz), 6.85 (1H, d, J=1.3 Hz), 6.91 (1H, d, J=8.7 Hz), 6.95 (1H, dd, J=2.5 Hz, 8.6 Hz), 7.01 (1H, d, J=2.5 Hz), 7.28-7.34 (1H, m), 7.36-7.41 (2H, m), 7.42-7.48 (2H, m).

Reference Example 275

Production of 2-dimethylamino-N-[4-(5-nitropyridin-2-yloxy)phenyl]-N-[2-(4-piperonylpiperazin-1-yl)-2-oxoethyl]acetamide To a solution of 2-chloro-N-[4-(5-nitropyridin-2-yloxy) phenyl]-N-[2-(4-piperonylpiperazin-1-yl)-2-oxoethyl]acetamide (0.300 g, 0.528 mmol) in acetonitrile (3 mL) was added at room temperature dimethylamine (0.150 mL, 1.63 mmol), and the resulting solution was stirred for 2 hours at 50° C. Water was added to the reaction mixture, and extracted with ethyl acetate. The ethyl acetate layer was washed with brine, dried over anhydrous sodium sulfate, evaporated, and the residue was purified by silica gel column chromatography (dichloromethane:methanol=10:1), to thereby yield 0.270 g of the title compound.

Appearance: Yellow powder $^1$H NMR ($CDCl_3$) δ 2.29 (6H, s), 2.40-2.45 (4H, m), 3.02 (2H, s), 3.40-3.46 (4H, m), 3.61 (2H, s), 4.48 (2H, s), 5.95 (2H, s), 6.70-6.77 (2H, m), 6.84 (1H, s), 7.09 (1H, d, J=9.0 Hz), 7.19 (2H, d, J=8.7 Hz), 7.51 (2H, d, J=8.7 Hz), 8.51 (1H, dd, J=2.8 Hz, 9.0 Hz), 9.04 (1H, d, J=2.8 Hz).

Reference Example 276

Production of methyl 2-[4-(5-nitropyridin-2-yloxy)phenyl]propionate

To a solution of methyl 2-[4-(5-nitropyridin-2-yloxy)phenyl]acetate (0.50 g, 1.7 mmol) in DMF (10 mL) were added 60% sodium hydride (0.153 g, 3.8 mmol) and methyl iodide (0.13 mL, 2.1 mmol), and the resulting reaction solution was stirred for 1 hour at 0° C. To the reaction solution was added saturated aqueous ammonium chloride, and extracted with ethyl acetate. The ethyl acetate layer was washed with water and saturated aqueous sodium chloride. The ethyl acetate layer was dried over anhydrous magnesium sulfate, evaporated, and the residue was purified by silica gel chromatography (n-hexane:ethyl acetate=8:1), to thereby yield 0.32 g of the title compound.

Appearance: Colorless oil $^1$H NMR ($CDCl_3$) δ 1.54 (3H, d, J=7.4 Hz), 3.69 (3H, s), 3.78 (1H, q, J=7.2 Hz), 7.03 (1H, d, J=9.1 Hz), 7.09-7.15 (2H, m), 7.36-7.41 (2H, m), 8.48 (1H, dd, J=9.1, 2.8 Hz), 9.05 (1H, d, J=2.8 Hz).

Reference Example 277

Production of ethyl 3-{3-methoxy-4-[methyl(5-nitropyridin-2-yl)amino]phenyl}propionate To a solution of ethyl 3-[3-methoxy-4-(5-nitropyridin-2-ylamino)phenyl]propionate (3.70 g, 11 mmol) in DMF (60 mL) were added under ice-cooling sodium hydride (60%, 490 mg, 12 mmol) and methyl iodide (0.77 mL, 12 mmol), and the resulting reaction solution was stirred for 2 hours gradually warming up to room temperature. The reaction solution was concentrated under reduced pressure. To the residue was added ethyl acetate, washed with water and brine, and then dried with anhydrous magnesium sulfate. The solvent was evaporated, to thereby yield 4.27 g of the title compound.

Appearance: Yellow oil substance $^1$H NMR ($CDCl_3$) δ 1.27 (3H, t, J=7.1 Hz), 2.66-2.71 (2H, m), 2.98-3.04 (2H, m), 3.46 (3H, s), 3.78 (3H, s), 4.17 (2H, q, J=7.1 Hz), 6.12 (1H, brd, J=9.5 Hz), 6.87-6.90 (2H, m), 7.11-7.14 (1H, m), 7.97-8.02 (1H, m), 9.11 (1H, d, J=2.7 Hz).

The following compounds were produced in the same manner as in Reference Example 277.

TABLE 40

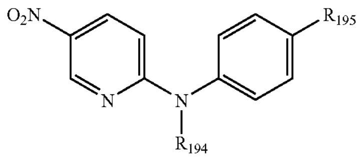

| Reference Example No. | $R_{194}$ | $R_{195}$ | $^1$H NMR (solvent) δ ppm |
|---|---|---|---|
| 278 | $—CH_3$ | $—COOC_2H_5$ | (DMSO-$d_6$) 1.34 (3H, t, J = 7.1 Hz), 3.56 (3H, s), 4.34 (2H, q, J = 7.1 Hz), 6.70 (1H, d, J = 9.5 Hz), 7.55 (2H, d, J = 8.6 Hz), 8.06 (2H, d, J = 8.6 Hz), 8.21 (1H, dd, J = 2.8 Hz, 9.5 Hz), 9.05 (1H, d, J = 2.8 Hz). |
| 279 | $—CH_3$ | $—(CH_2)_2COOC_2H_5$ | ($CDCl_3$) 1.26 (3H, t, J = 7.1 Hz), 2.67 (2H, t, J = 7.6 Hz), 3.01 (2H, t, J = 7.6 Hz), 3.55 (3H, s), 4.15 (2H, q, J = 7.1 Hz), 6.32 (1H, d, J = 9.5 Hz), 7.17 (2H, d, J = 8.3 Hz), 7.32 (2H, d, J = 8.3 Hz), 8.01 (1H, dd, J = 2.7 Hz, 9.5 Hz), 9.11 (1H, d, J = 2.7 Hz). |
| 280 | benzyl | $—(CH_2)_2COOC_2H_5$ | ($CDCl_3$) 1.24 (3H, t, J = 7.2 Hz), 2.64 (2H, t, J = 7.7 Hz), 2.97 (2H, t, J = 7.7 Hz), 4.14 (2H, q, J = 7.2 Hz), 5.27 (2H, s), 6.26 (1H, d, J = 9.5 Hz), 7.06 (2H, d, J = 8.3 Hz), 7.20-7.30 (7H, m), 8.02 (1H, dd, J = 2.7 Hz, 9.5 Hz), 9.12(1H, d, J = 2.7 Hz). |
| 281 | $—CH_3$ | 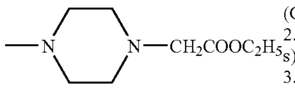 | ($CDCl_3$) 1.30 (3H, t, J = 7.1 Hz), 2.78 (4H, t, J = 5.0 Hz), 3.30 (2H, s), 3.31 (4H, t, J = 5.0 Hz), 3.53 (3H, s), 4.22 (2H, q, J = 7.1 Hz), 6.30 (1H, d, J = 9.5 Hz), 6.99 (2H, d, J = 8.9 Hz), 7.12 (2H, d, J = 8.9 Hz), 7.99 (1H, dd, J = 9.5 Hz, 2.8 Hz), 9.10 (1H, d, J = 2.8 Hz). |
| 282 | $—CH_3$ | 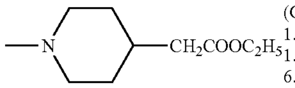 | ($CDCl_3$) 1.28 (3H, t, J = 7.1 Hz), 1.45 (2H, qd, J = 12.2 Hz, 3.7 Hz), 1.80-2.17 (3H, m), 2.30 (2H, d, J = 6.9 Hz), 2.80 (2H, td, J = 12.2 Hz, 2.3 Hz), 3.52 (3H, s), 3.72 (2H, d, J = 12.4 Hz), 4.16 (2H, q, J = 7.1 Hz), 6.30 (1H, d, J = 9.5 Hz), 6.98 (2H, d, J = 8.9 Hz), 7.10 (2H, d, J = 8.9 Hz), 7.98 (1H, dd, J = 9.5 Hz, 2.8 Hz), 9.10 (1H, d, J = 2.8 Hz). |

TABLE 41

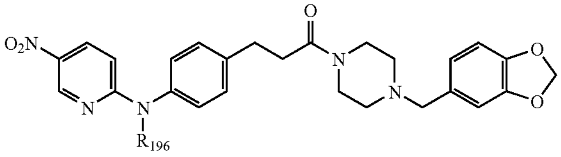

| Reference Example No. | $R_{196}$ | $^1H$ NMR ($CDCl_3$) δ ppm |
|---|---|---|
| 283 | $—(CH_2)_2CH_3$ | 0.93 (3H, t, J = 7.4 Hz), 1.60-1.70 (2H, m), 2.35-2.43 (4H, m), 2.66 (2H, t, J = 8.1 Hz), 3.03 (2H, t, J = 8.1 Hz), 3.42 (2H, s), 3.43-3.45 (2H, m), 3.62-3.65 (2H, m), 3.96 (2H, t, J = 7.7 Hz), 5.95 (2H, s), 6.16 (1H, d, J = 9.5 Hz), 6.70-6.80 (2H, m), 6.84 (1H, d, J = 1.3 Hz), 7.14 (2H, d, J = 8.3 Hz), 7.33 (2H, d, J = 8.3 Hz), 7.96 (1H, dd, J = 2.8 Hz, 9.5 Hz), 9.08 (1H, d, J = 2.8 Hz). |
| 284 | cyclopentyl | 1.30-1.40 (2H, m), 1.55-1.65 (4H, m), 1.95- |

TABLE 41-continued

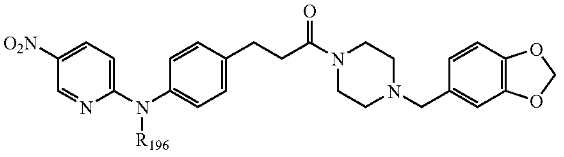

| Reference Example No. | $R_{196}$ | $^1H$ NMR ($CDCl_3$) δ ppm |
|---|---|---|
| | | 2.00 (2H, m), 2.35-2.45 (4H, m), 2.67 (2H, t, J = 7.4 Hz), 3.04 (2H, t, J = 7.4 Hz), 3.42 (2H, s), 3.43-3.47 (2H, m), 3.55-3.68 (2H, m), 5.18-5.28(1H, m), 5.88 (1H, d, J = 9.5 Hz), 5.95 (2H, s), 6.70-6.78 (2H, m), 6.84 (1H, s), 7.04 (2H, d, J = 8.2 Hz), 7.34 (2H, d, J = 8.2 Hz), 7.92 (1H, dd, J = 2.8 Hz, 9.5 Hz), 9.09 (1H, d, J = 2.8 Hz). |

TABLE 42

| Reference Example No. | Chemical Structure | $^1H$ NMR (solvent) δ ppm |
|---|---|---|
| 285 | 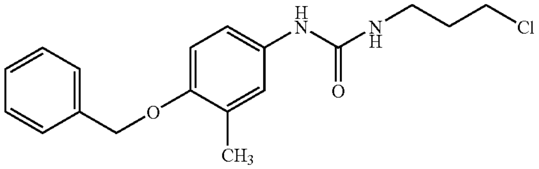 | ($CDCl_3$) 1.91-2.06 (2H, m), 2.27 (3H, s), 3.31-3.44 (2H, m), 3.58 (2H, t, J = 6.3 Hz), 4.69-4.85 (1H, m), 5.07 (2H, s), 6.04 (1H, s), 6.84 (1H, d, J = 10.1 Hz), 7.01 (1H, dd, J = 8.5 Hz, 2.5 Hz), 7.04 (1H, d, J = 2.5 Hz), 7.30-7.36 (1H, m), 7.37-7.46 (4H, m). |
| 286 | 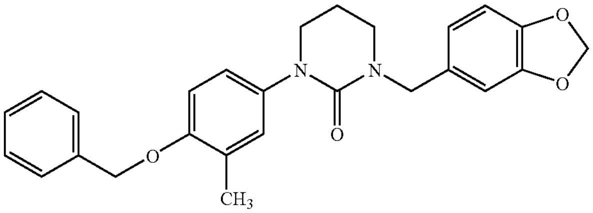 | ($CDCl_3$) 1.96-2.11 (2H, m), 2.27 (3H, s), 3.20-3.34 (2H, m), 3.56-3.68 (2H, m), 4.50 (2H, s), 5.07 (2H, s), 5.94 (2H, s), 6.72-6.80 (2H, m), 6.84 (1H, d, J = 8.6 Hz), 6.88 (1H, d, J = 1.2 Hz), 7.04 (1H, dd, J = 2.6 Hz, 8.6 Hz), 7.11 (1H, d, J = 2.6 Hz), 7.28-7.34 (1H, m), 7.35-7.41 (2H, m), 7.42-7.48 (2H, m). |
| 287 | 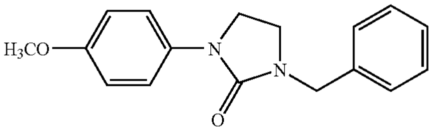 | (DMSO-$d_6$) 3.20-3.40 (2H, m), 3.71 (3H, s), 3.64-3.83 (2H, m), 4.36 (2H, s), 6.84-6.95 (2H, m), 7.22-7.41 (5H, m), 7.42-7.53 (2H, m). |
| 288 | 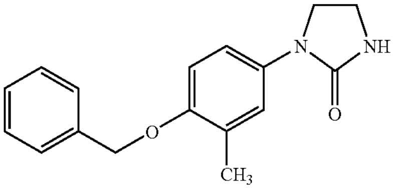 | (DMSO-$d_6$) 2.18 (3H, s), 3.35 (2H, t, J = 8.7 Hz), 3.69-3.84 (2H, m), 5.05 (2H, s), 6.74 (1H, s), 6.93 (1H, d, J = 8.9 Hz), 7.23 (1H, dd, J = 2.8 Hz, 8.9 Hz), 7.27-7.48 (6H, m). |
| 289 | 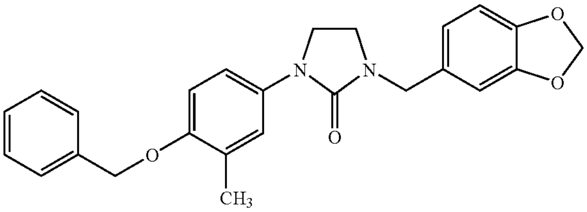 | ($CDCl_3$) 2.29 (3H, s), 3.28-3.39 (2H, m), 3.68-3.81 (2H, m), 4.36 (2H, s), 5.06 (2H, s), 5.95 (2H, s), 6.77 (2H, s), 6.78-6.91 (2H, m), 7.20-7.35 (2H, m), 7.36-7.51 (5H, m). |

TABLE 42-continued

| Reference Example No. | Chemical Structure | $^1H$ NMR (solvent) δ ppm |
|---|---|---|
| 290 | 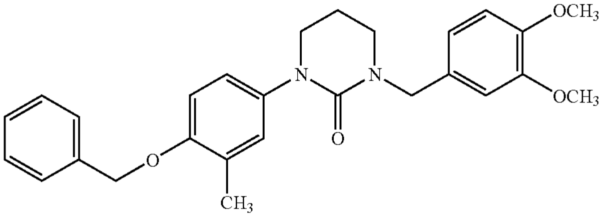 | ($CDCl_3$) 1.93-2.12 (2H, m), 2.27 (3H, s), 3.28 (2H, t, J = 5.9 Hz), 3.63 (2H, t, J = 5.9 Hz), 3.88 (6H, s), 4.55 (2H, s), 5.07 (2H, s), 6.71-6.92 (4H, m), 6.96-7.08 (1H, m), 7.11 (1H, d, J = 2.1 Hz), 7.25-7.51 (5H, m). |

Reference Example 291

Production of N-[4-(5-nitropyridin-2-yloxy)phenyl]-2-(4-piperonylpiperazin-1-yl)acetamide A solution of (4-piperonylpiperazin-1-yl)acetic acid (13.9 g, 50 mmol) was suspended in DMF (400 mL), and to the resulting suspension were added 1-hydroxybenzotriazole monohydrate (8.42 g, 55 mmol), 1-ethyl-3-(3-dimethylaminopropyl)carbodiimide hydrochloride (10.5 g, 55 mmol) and 4-(5-nitropyridin-2-yloxy)phenylamine (11.6 g, 50 mmol) under ice cooling. The resulting solution was stirred for 6 hours at room temperature. The reaction solution was concentrated under reduced pressure. To the residue was added ethyl acetate, and washed with a saturated sodium bicarbonate solution and brine. The organic layer was left for standing overnight at room temperature, and the resulting precipitated crystals were collected by suction filtration, to thereby yield 12.8 g of the title compound.

Appearance: White powder $^1H$ NMR ($CDCl_3$) δ 2.53 (4H, brs), 2.64-2.65 (4H, m), 3.15 (2H, s), 3.46 (2H, s), 5.95 (2H, s), 6.76 (2H, brs), 6.86 (1H, s), 7.04 (1H, d, J=9.1 Hz), 7.14 (2H, d, J=8.7 Hz), 7.67 (2H, d, J=8.9 Hz), 8.47 (1H, dd, J=9.1 Hz, 2.8 Hz), 9.03 (1H, d, J=2.8 Hz), 9.24 (1H, brs).

Reference Example 292

Production of ethyl{methanesulfonyl[3-methoxy-4-(5-nitropyridin-2-yloxy)phenyl]amino}acetate A solution of ethyl[3-methoxy-4-(5-nitropyridin-2-yloxy)phenylamino]acetate (2.43 g, 7.00 mmol) was dissolved in THF (15 mL), dichloromethane (20 mL) and DMF (10 mL), and to the resulting solution were added triethylamine (1.95 mL, 13.99 mmol), 4-dimethylaminopyridine (0.86 g, 7.00 mmol) and methanesulfonyl chloride (1.08 mL, 13.99 mmol) under ice cooling. The resulting solution was stirred for 14 hours at 30° C. Water was added to the reaction mixture, and extracted with dichloromethane. The dichloromethane layer was washed with water and brine. The dichloromethane layer was dried over anhydrous magnesium sulfate, evaporated, and the residue was purified by silica gel column chromatography (ethyl acetate:n-hexane=1:2), to thereby yield 1.10 g of the title compound.

Appearance: Yellow oil

1H NMR ($CDCl_3$) δ 1.32 (3H, t, J=7.3 Hz), 3.18 (3H, s), 3.75 (3H, s), 4.26 (2H, q, J=7.3 Hz), 4.49 (2H, s), 7.09 (1H, d, J=9.1 Hz), 7.15 (2H, d, J=1.2 Hz), 7.25 (1H, s), 8.48 (1H, dd, J=9.1 Hz, 2.8 Hz), 8.98 (1H, d, J=2.8 Hz).

The following compounds were produced in the same manner as in Reference Example 292.

TABLE 43

| Reference Example No. | Chemical Structure | $^1H$ NMR (solvent) δ ppm or MS |
|---|---|---|
| 293 | 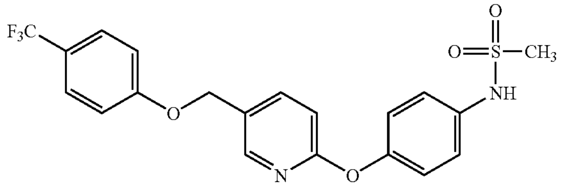 | $^1H$ NMR (DMSO-$d_6$) 3.00 (3H, s), 5.17 (2H, s), 7.05 (1H, d, J = 8.4 Hz), 7.12 (2H, d, J = 8.9 Hz), 7.19-7.26 (4H, m), 7.67 (2H, d, J = 8.9 Hz), 7.95 (1H, dd, J = 8.4 Hz, 2.5 Hz), 8.25 (1H, d, J = 2.3 Hz), 9.69 (1H, brs). |
| 294 | 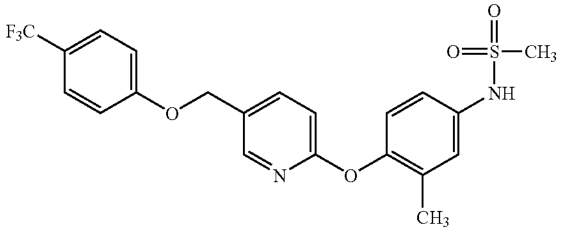 | $^1H$ NMR ($CDCl_3$) 2.18 (3H, s), 3.04 (3H, s), 5.04 (2H, s), 6.56 (1H, brs), 6.96 (1H, d, J = 8.6 Hz), 7.01-7.09 (4H, m), 7.15 (1H, d, J = 2.6 Hz), 7.56 (2H, d, J = 8.4 Hz), 7.79 (1H, dd, J = 8.6 Hz, 2.5 Hz), 8.19 (1H, d, J = 2.5 Hz). |

TABLE 43-continued

| Reference Example No. | Chemical Structure | $^1$H NMR (solvent) δ ppm or MS |
|---|---|---|
| 295 | 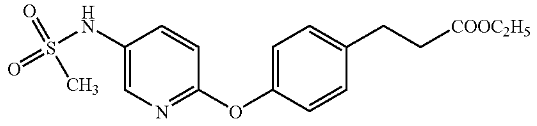 | MS 364 ($M^+$) |

Reference Example 296

Production of 3-[4-(5-nitropyridin-2-yloxy)phenyl]-n-propanol

To a solution of 3-[4-(5-nitropyridin-2-yloxy)phenyl]propionic acid (2.64 g, 9.2 mmol) in THF (50 mL) was added dropwise a 1 M borane-THF complex THF solution (38.4 mL, 38.4 mmol) under ice cooling. The reaction solution was stirred for 2 hours at room temperature. Water was added to the reaction mixture, and extracted with ethyl acetate, and the ethyl acetate layer was washed with water and then brine. The ethyl acetate layer was dried over anhydrous magnesium sulfate, after which solvent was evaporated, and the residue was purified by silica gel column chromatography (n-hexane: ethyl acetate=1:1), to thereby yield 1.17 g of the title compound.

Appearance: Green oil $^1$H NMR ($CDCl_3$) δ 1.90-1.96 (2H, m), 2.73-2.79 (2H, m), δ 3.69-3.74 (2H, m), 7.00-7.09 (3H, m), 7.26-7.30 (2H, m), 8.44-8.49 (1H, m), 9.05 (1H, d, J=2.6 Hz).

Reference Example 297

Production of 2-{4-[3-(t-butyldimethylsilanyloxy)-propyl]phenoxy}-5-nitropyridine To a solution of 3-[4-(5-nitropyridin-2-yloxy)phenyl]-n-propanol (1.17 g, 4.3 mmol) in DMF (10 mL) were added imidazole (580 mg, 8.5 mmol) and t-butylchlorodimethylsilane (640 mg, 4.2 mmol), and the resulting solution was stirred for 13 hours at room temperature. Water was added to the reaction mixture, and extracted with diethyl ether, and the diethyl ether layer was washed with water and then brine. The diethyl ether layer was dried over anhydrous magnesium sulfate, evaporated, and the residue was purified by silica gel column chromatography (n-hexane:ethyl acetate=5:1), to thereby yield 1.14 g of the title compound.

Appearance: Pale yellow powder $^1$H NMR ($CDCl_3$) δ 0.07 (6H, s), 0.92 (9H, s), 1.84-1.89 (2H, m), 2.69-2.75 (2H, m), 3.66 (2H, t, J=6.3 Hz), 6.99-7.08 (3H, m), 7.27 (2H, d, J=7.6 Hz), 8.46 (1H, dd, J=8.9 Hz, 3.0 Hz), 9.05 (1H, d, J=3.0 Hz).

The following compound was produced in the same manner as in Reference Example 297.

Reference Example 298

2-{4-[2-(t-Butyldimethylsilanyloxy)ethyl]phenoxy}-5-nitropyridine $^1$H NMR ($CDCl_3$) δ 0.00 (6H, s), 0.88 (9H, s), 2.86 (2H, t, J=6.9 Hz), 3.84 (2H, t, J=6.9 Hz), 7.00 (1H, d, J=9.2 Hz), 7.05-7.08 (2H, m), 7.26-7.31 (2H, m), 8.46 (1H, dd, J=9.2 Hz, 3.0 Hz), 9.05 (1H, d, J=3.0 Hz).

Reference Example 299

Production of ethyl 4-[4-(5-nitropyridin-2-yloxy)phenyl]butanoate

To a solution of 4-[4-(5-nitropyridin-2-yloxy)phenyl]butanoic acid (9.98 g, 33.01 mmol) in dichloromethane were added ethanol (5.59 mL, 99.01 mmol), 4-dimethylaminopyridine (400 mg, 3.27 mmol), triethylamine (13.81 mL, 99.08 mmol) and 1-ethyl-3-(3-dimethylaminopropyl)carbodiimide hydrochloride (7.6 g, 39.65 mmol) under ice cooling, and the resulting solution was stirred for 20 minutes under ice cooling and then for 1 hour at room temperature. The reaction solution was concentrated under reduced pressure. Water was added to the residue, and extracted with ethyl acetate, and the ethyl acetate layer was washed with 1 N hydrochloric acid, a saturated sodium bicarbonate solution and brine. The ethyl acetate layer was dried over anhydrous magnesium sulfate, evaporated, and the residue was purified by silica gel column chromatography (n-hexane:ethyl acetate=5:1), to thereby yield 6.77 g of the title compound.

Appearance: Colorless oil $^1$H NMR ($CDCl_3$) δ 1.27 (3H, t, J=7.0 Hz), 1.99 (2H, dt, J=15.0 Hz, 7.5 Hz), 2.36 (2H, t, J=7.5 Hz), 2.70 (2H, t, J=7.5 Hz), 4.14 (2H, q, J=7.0 Hz), 7.01 (1H, d, J=9.0 Hz), 7.08 (2H, d, J=8.5 Hz), 7.26 (2H, d, J=8.5 Hz), 8.46 (1H, dd, J=9.0 Hz, 3.0 Hz), 9.04 (1H, d, J=3.0 Hz).

Reference Example 300

Production of methyl 3-[4-(5-nitropyridin-2-ylsulfanyl)phenyl]propionate

To a solution of 3-[4-(5-nitropyridin-2-ylsulfanyl)phenyl] propionic acid (86.0 g, 0.283 mmol) in DMF (1 mL) were added potassium carbonate (59.0 mg, 0.424 mmol) and methyl iodide (0.0260 mL, 0.424 mmol), and the resulting solution was stirred for 1 hour at room temperature. Water was added to the reaction mixture, and then cooled with ice. The precipitated solid matter was collected by filtration, to thereby yield 76.9 mg of the title compound.

Appearance: Light brown powder $^1$H NMR (DMSO-$d_6$) δ 2.70 (2H, t, J=7.6 Hz), 2.94 (2H, t, J=7.6 Hz), 3.60 (3H, s), 7.07 (1H, d, J=8.9 Hz), 7.43 (2H, d, J=8.1 Hz), 7.57 (2H, d, J=8.1 Hz), 8.39 (1H, dd, J=2.7 Hz, 8.9 Hz), 9.17 (1H, d, J=2.7 Hz).

Reference Example 301

Production of ethyl(Z)-3-[4-(5-nitro-2-pyridyloxy) phenyl]-2-butenoate

To a suspension of 60% sodium hydride (1.28 g, 32.0 mmol) in THF (80 mL) was added dropwise a solution of triethyl phosphonoacetate (8.71 g, 38.8 mmol) in THF (40 mL) under ice cooling, and the resulting solution was stirred for 10 minutes at the same temperature. To the reaction solution was added 4-[(5-nitro-2-pyridyl)oxy]acetophenone (5.90 g, 22.8 mmol) and the resulting solution was stirred at the same temperature for 10 minutes, and then stirred at room temperature for 60 hours. To the reaction solution was added saturated ammonium chloride and extracted with ethyl acetate. The ethyl acetate layer was washed with a saturated sodium bicarbonate solution, and then washed with brine. The ethyl acetate layer was dried over anhydrous magnesium sulfate, evaporated, and the residue was purified by silica gel column chromatography (n-hexane:ethyl acetate=5:1), to thereby yield 1.17 g of the title compound.

Appearance: Colorless needles $^1$H NMR ($CDCl_3$) δ 1.13 (3H, t, J=7.1 Hz), 2.20 (3H, d, J=1.4 Hz), 4.02 (2H, q, J=7.1 Hz), 5.93 (1H, q, J=1.4 Hz), 7.02 (1H, d, J=9.0 Hz), 7.12 (2H, d, J=8.6 Hz), 7.29 (2H, d, J=8.6 Hz), 8.45 (1H, dd, J=9.0 Hz, 2.8 Hz), 9.03 (1H, d, J=2.8 Hz).

The following compounds were produced in the same manner as in Reference Example 301.

Reference Example 302

Ethyl(E)-3-{4-[4-(3,4-dichlorobenzoylamino)-2-fluorophenoxy]phenyl}acrylate

Melting point: 166-167° C.

TABLE 44

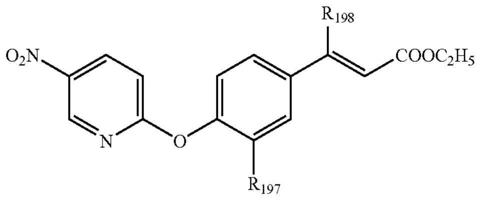

| Reference Example No. | $R_{197}$ | $R_{198}$ | $^1$H NMR ($CDCl_3$) δ ppm or MS |
|---|---|---|---|
| 303 | —H | —H | $^1$H NMR 1.35 (3H, t, J = 7.1 Hz), 4.28 (2H, q, J = 7.1 Hz), 6.43 (1H, d, J = 16.0 Hz), 7.09 (1H, d, J = 8.9 Hz), 7.20 (2H, d, J = 8.7 Hz), 7.62 (2H, d, J = 8.7 Hz), 7.70 (1H, d, J = 16.0 Hz), 8.50 (1H, dd, J = 8.9 Hz, 2.5 Hz), 9.04 (1H, d, J = 2.5 Hz). |
| 304 | —H | —$CH_3$ | $^1$H NMR 1.31 (3H, t, J = 7.1 Hz), 2.58 (3H, d, J = 1.2 Hz), 4.21 (2H, q, J = 7.1 Hz), 6.14 (1H, q, J = 1.2 Hz), 7.05 (1H, d, J = 9.0 Hz), 7.16 (2H, d, J = 8.7 Hz), 7.55 (2H, d, J = 8.7 Hz), 8.48 (1H, dd, J = 9.0 Hz, 2.8 Hz), 9.03 (1H, d, J = 2.8 Hz). |
| 305 | —$CH_3$ | —H | MS 328 ($M^+$) |

Reference Example 306

Production of ethyl 3-[4-(5-nitropyridine-2-carbonyl)phenyl]propionate

A solution of bis(tributyltin) (1.37 g, 2.36 mmol) in toluene (7 mL) was added under an argon atmosphere to 2-chloro-5-nitropyridine (0.325 g, 2.05 mmol), bis(dibenzylideneacetone)palladium(0) (18.1 mg, 0.0315 mmol), tri(2-furyl) phosphine (29.3 mg, 0.126 mmol) and molecular sieves 4A (1.90 g), and the resulting solution was heated to reflux for 1 hour. To the reaction solution was added bis(dibenzylideneacetone)palladium(0) (27.2 mg, 0.0472 mmol) and tri(2-furyl)phosphine (43.9 mg, 0.189 mmol), and subsequently added a solution of 4-[2-ethoxycarbonyl]ethyl]benzoyl chloride (0.379 g, 1.57 mmol) in toluene (5 mL). The resulting reaction solution was stirred for 4 hours at 80° C. To the reaction solution was added saturated aqueous potassium fluoride and stirred for 0.5 hours at room temperature. Insoluble matter was then filtered off. The filtrate was extracted with ethyl acetate, and the ethyl acetate layer was washed with brine. The ethyl acetate layer was dried over anhydrous magnesium sulfate, evaporated, and the residue was purified by silica gel column chromatography (n-hexane→n-hexane:ethyl acetate=4:1), to thereby yield 0.323 g of the title compound.

Appearance: Pale yellow powder $^1$H NMR ($CDCl_3$) δ 1.22 (3H, t, J=7.1 Hz), 2.65 (2H, t, J=7.7 Hz), 3.03 (2H, t, J=7.7 Hz), 4.12 (2H, q, J=7.1 Hz), 7.34 (2H, d, J=8.3 Hz), 8.00 (2H, d, J=8.3 Hz), 8.18 (1H, d, J=8.5 Hz), 8.65 (1H, dd, J=8.5 Hz, 2.6 Hz), 9.49 (1H, d, J=2.6 Hz).

Reference Example 307

Production of ethyl 3-[4-(4-aminophenoxy)phenyl]propionate

To a suspension of 5% palladium-carbon (0.50 g) in ethanol (50 mL) was added ethyl 3-[4-(4-nitrophenoxy)phenyl] propionate (5.00 g, 15.9 mmol), and the resulting solution was subjected to catalytic reduction at atmospheric pressure and at room temperature. Once the absorption of hydrogen had stopped, the catalyst was removed by filtration, and the filtrate was concentrated under reduced pressure, to thereby yield 4.52 g of the title compound.

Appearance: Light brown oil $^1$H NMR ($CDCl_3$) δ 1.22 (3H, t, J=7.1 Hz), 2.57 (2H, t, J=7.8 Hz), 2.88 (2H, t, J=7.8 Hz), 3.55 (2H, brs), 4.10 (2H, q, J=7.1 Hz), 6.64 (2H, d, J=8.8 Hz), 6.78-6.86 (4H, m), 7.08 (2H, d, J=8.6 Hz).

The following compounds were produced in the same manner as in Reference Example 307.

TABLE 45

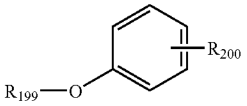

| Reference Example No. | $R_{199}$ | $R_{200}$ | $^1$H NMR ($CDCl_3$) δ ppm |
|---|---|---|---|
| 308 | 4-$NH_2$Ph- | 2-$(CH_2)_2COOCH_3$ | 2.66 (2H, t, J = 7.8 Hz), 3.00 (2H, t, J = 7.8 Hz), 3.54 (2H, brs), 3.63 (3H, s), 6.65 (2H, d, J = 8.8 Hz), 6.70 (1H, d, J = 8.1 Hz), 6.79 (2H, d, J = 8.8 Hz), 6.94 (1H, t, J = 8.1 Hz), 7.08 (1H, t, J = 8.1 Hz), 7.19 (1H, d, J = 8.1 Hz). |
| 309 | 4-$NH_2$Ph- | 3-$(CH_2)_2COOC_2H_5$ | 1.21 (3H, t, J = 7.2 Hz), 2.56 (2H, t, J = 7.9 Hz), 2.87 (2H, t, J = 7.9 Hz), 3.54 (2H, brs), 4.10 (2H, q, J = 7.2 Hz), 6.66 (2H, d, J = 8.8 Hz), 6.70-6.76 (2H, m), 6.79-6.87 (3H, m), 7.16 (1H, t, J = 7.8 Hz). |
| 310 | 2-$NH_2$Ph- | 4-$(CH_2)_2COOC_2H_5$ | 1.22 (3H, t, J = 7.2 Hz), 2.56 (2H, t, J = 7.8 Hz), 2.89 (2H, t, J = 7.8 Hz), 3.55 (2H, brs), 4.11 (2H, q, J = 7.2 Hz), 6.72 (1H, t, J = 7.8 Hz), 6.79-6.92 (4H, m), 6.93 (1H, t, J = 7.8 Hz), 7.12 (2H, d, J = 8.5 Hz). |
| 311 | 4-$NH_2$Ph- | 4-$COOC_2H_5$ | 1.37 (3H, t, J = 7.1 Hz), 4.36 (2H, q, J = 7.1 Hz), 4.00-4.50 (2H, m), 6.78 (2H, d, J = 8.9 Hz), 6.89-6.95 (4H, m), 7.97 (2H, d, J = 8.9 Hz). |
| 312 | 3-$NH_2$Ph- | 4-$(CH_2)_2COOC_2H_5$ | 1.22 (3H, t, J = 7.2 Hz), 2.59 (2H, t, J = 7.8 Hz), 2.91 (2H, t, J = 7.8 Hz), 3.65 (2H, brs), 4.12 (2H, q, J = 7.2 Hz), 6.29 (1H, t, J = 2.2 Hz), 6.32-6.41 (2H, m), 6.92 (2H, d, J = 8.6 Hz), 7.06 (1H, t, J = 8.0 Hz), 7.13 (2H, d, J = 8.6 Hz). |
| 313 | 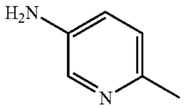 | 3-$COOCH_3$ | 3.56 (2H, brs), 3.89 (3H, s), 6.80 (1H, dd, J = 8.6 Hz, 0.7 Hz), 7.11 (1H, dd, J = 8.6 Hz, 3.0 Hz), 7.25-7.29 (1H, m), 7.39-7.44 (1H, m), 7.69-7.72 (2H, m), 7.78-7.82 (1H, m). |

TABLE 46

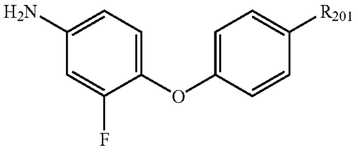

| Reference Example No. | $R_{201}$ | Form | $^1$H NMR (solvent) δ ppm |
|---|---|---|---|
| 314 | —Ac | hydrochloride | (DMSO-$d_6$) 2.53 (3H, s), 3.30-4.20 (3H, m), 6.88 (1H, d, J = 8.8 Hz), 6.99-7.05 (3H, m), 7.22 (1H, t, J = 8.8 Hz), 7.96 (1H, d, J = 8.9 Hz). |
| 315 | —$CH_2COOCH_3$ | free | ($CDCl_3$) 3.57 (2H, s), 3.60-3.80 (5H, m), 6.41 (1H, ddd, J = 1.2 Hz, 2.6 Hz, 8.6 Hz), 6.50 (1H, dd, J = 2.6 Hz, 12.0 Hz), 6.80-6.95 (3H, m), 7.18 (2H, d, J = 8.4 Hz). |
| 316 | —$(CH_2)_2COOC_2H_5$ | free | ($CDCl_3$) 1.21 (3H, t, J = 7.1 Hz), 2.56 (2H, t, J = 7.8 Hz), 2.87 (2H, t, J = 7.8 Hz), 3.66 (2H, brs), 4.10 (2H, q, J = 7.1 Hz), 6.34-6.43 (1H, m), 6.48 (1H, dd, J = 12.0 Hz, 2.7 Hz), 6.77-6.93 (3H, m), 7.08 (2H, d, J = 8.7 Hz). |
| 317 | —H | free | ($CDCl_3$) 3.66 (2H, brs), 6.35-6.44 (1H, m), 6.49 (1H, dd, J = 12.0 Hz, 2.7 Hz), 6.83-6.96 (3H, m), 7.01 (1H, dd, J = 9.0 Hz, 8.0 Hz), 7.26 (2H, t, J = 8.0 Hz). |
| 318 | —$(CH_2)_3COOC_2H_5$ | free | ($CDCl_3$) 1.23 (3H, t, J = 7.1 Hz), 1.83-1.97 (2H, m), 2.28 (2H, t, J = 7.5 Hz), 2.57 (2H, t, J = 7.6 Hz), 3.66 (2H, brs), 4.09 (2H, q, J = 7.1 Hz), 6.34-6.43 (1H, m), 6.48 (1H, dd, J = 12.0 Hz, 2.7 Hz), 6.81 (2H, |

TABLE 46-continued

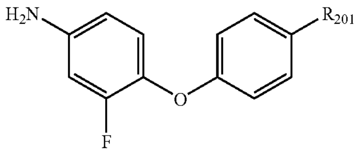

| Reference Example No. | $R_{201}$ | Form | $^1H$ NMR (solvent) δ ppm |
|---|---|---|---|
| | | | d, J = 8.5 Hz), 6.88 (1H, dd, J = 9.0 Hz, 8.0 Hz), 7.05 (2H, d, J = 8.5 Hz). |
| 319 | $-COOC_2H_5$ | free | ($DMSO-d_6$) 1.29 (3H, t, J = 7.1 Hz), 4.27 (2H, q, J = 7.1 Hz), 5.42 (2H, brs), 6.41 (1H, dt, J = 1.6 Hz, 8.6 Hz), 6.50 (1H, dd, J = 2.5 Hz, 13.3 Hz), 6.90-7.00 (3H, m), 7.91 (2H, d, J = 9.7 Hz). |
| 320 | $-NHCH_2COOC_2H_5$ | free | ($CDCl_3$) 1.29 (3H, t, J = 7.1 Hz), 3.62 (2H, s), 3.86 (2H, s), 4.12 (1H, s), 4.23 (2H, q, J = 7.1 Hz), 6.35-6.39 (1H, m), 6.48 (1H, dd, J = 2.7 Hz, 12.1 Hz), 6.55 (2H, d, J = 8.9 Hz), 6.80-6.85 (3H, m). |
| 321 | 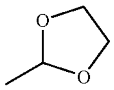 | free | ($CDCl_3$) 3.70 (2H, brs), 3.95-4.15 (4H, m), 5.76 (1H, s), 6.38-6.42 (1H, m), 6.49 (1H, dd, J = 2.7 Hz, 14.7 Hz), 6.85-6.93 (3H, m), 7.39 (2H, d, J = 8.7 Hz). |

TABLE 47

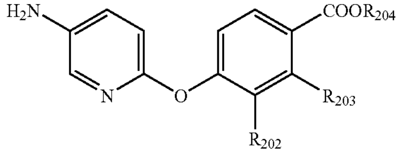

| Reference Example No. | $R_{202}$ | $R_{203}$ | $R_{204}$ | $^1H$ NMR ($CDCl_3$) δ ppm |
|---|---|---|---|---|
| 322 | —H | —H | $-C_2H_5$ | 1.38 (3H, t, J = 7.3 Hz), 4.35 (2H, q, J = 7.3 Hz), 6.82 (1H, d, J = 8.6 Hz), 7.04-7.14 (3H, m), 7.75 (1H, d, J = 3.0 Hz), 8.01-8.04 (2H, m). |
| 323 | —H | —H | $-CH_3$ | 3.30 (2H, brs), 3.89 (3H, s), 6.82 (1H, d, J = 8.6 Hz), 7.04-7.13 (3H, m), 7.75 (1H, d, J = 3.0 Hz), 8.02 (2H, dd, J = 6.6 Hz, 2.0 Hz). |
| 324 | —F | —H | $-CH_3$ | 3.57 (2H, brs), 3.91 (3H, s), 6.87 (1H, d, J = 8.6 Hz), 7.10-7.23 (2H, m), 7.64 (1H, d, J = 3.0 Hz), 7.80-7.82 (1H, m), 7.83-7.85 (1H, m). |
| 325 | —F | —H | $-C_2H_5$ | 1.38 (3H, t, J = 7.1 Hz), 4.37 (2H, q, J = 7.1 Hz), 6.87 (1H, d, J = 8.6 Hz), 7.12 (1H, dd, J = 8.6 Hz, 3.0 Hz), 7.15-7.22 (1H, m), 7.64 (1H, d, J = 3.0 Hz), 7.81-7.86 (2H, m). |
| 326 | $-CH_3$ | —H | $-CH_3$ | 2.29 (3H, s), 3.56 (2H, brs), 3.89 (3H, s), 6.79 (1H, d, J = 8.6 Hz), 6.92 (1H, d, J = 8.6 Hz), 7.11 (1H, dd, J = 8.6 Hz, 3.0 Hz), 7.71 (1H, d, J = 3.0 Hz), 7.85 (1H, dd, J = 8.6 Hz, 2.4 Hz), 7.94 (1H, d, J = 2.4 Hz). |
| 327 | $-OCH_3$ | —H | $-C_2H_5$ | 1.38 (3H, t, J = 7.1 Hz), 3.55 (2H, brs), 3.85 (3H, s), 4.37 (2H, q, J = 7.1 Hz), 6.79-6.83 (1H, m), 7.02 7.10 (2H, m), 7.63-7.67 (3H, m). |
| 328 | —H | $-OCH_3$ | $-CH_3$ | 3.63 (2H, brs), 3.86 (6H, s), 6.54-6.58 (1H, m), 6.68 (1H, d, J = 2.2 Hz), 6.81-6.84 (1H, m), 7.13 (1H, dd, J = 8.6 Hz, 3.0 Hz), 7.77 (1H, dd, J = 3.0 Hz, 0.5 Hz), 7.83 (1H, d, J = 8.9 Hz). |
| 329 | —H | $-CH_3$ | $-CH_3$ | 2.58 (3H, s), 3.63 (2H, brs), 3.86 (3H, s), 6.80-6.88 (3H, m), 7.13 (1H, dd, J = 8.6 Hz, 3.0 Hz), 7.75 (1H, d, J = 3.0 Hz), 7.92-7.96 (1H, m). |
| 330 | —Cl | —H | $-CH_3$ | 3.62 (2H, brs), 3.91 (3H, s), 6.88 (1H, d, J = 8.6 Hz), 7.08-7.15 (2H, m), 7.68 (1H, d, J = 3.0 Hz), 7.91 (1H, dd, J = 8.6 Hz, 2.1 Hz), 8.13 (1H, d, J = 2.1 Hz). |

TABLE 48

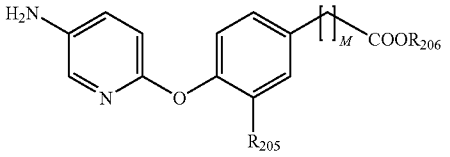

| Reference Example No. | $R_{205}$ | $R_{206}$ | M | $^1H$ NMR ($CDCl_3$) δ ppm or MS |
|---|---|---|---|---|
| 331 | —H | —$CH_3$ | 2 | MS 272 ($M^+$) |
| 332 | —$OCH_3$ | —$C_2H_5$ | 2 | $^1H$ NMR 1.25 (3H, t, J = 7.1 Hz), 2.63 (2H, t, J = 7.5 Hz), 2.94 (2H, t, J = 7.5 Hz), 3.43 (2H, brs), 3.77 (3H, s), 4.14 (2H, q, J = 7.1 Hz), 6.71-6.86 (3H, m), 6.98 (1H, d, J = 8.0 Hz), 7.06 (1H, dd, J = 8.6 Hz, 2.9 Hz), 7.65 (1H, d, J = 2.9 Hz). |
| 333 | —H | —$CH_3$ | 1 | $^1H$ NMR 3.60 (2H, s), 3.69 (3H, s), 6.76 (1H, d, J = 8.6 Hz), 6.99-7.10 (3H, m), 7.24-7.27 (2H, m), 7.71 (1H, d, J = 3.0 Hz). |
| 334 | —H | —$C_2H_5$ | 2 | $^1H$ NMR 1.21 (3H, t, J = 7.1 Hz), 2.58 (2H, t, J = 7.7 Hz), 2.90 (2H, t, J = 7.7 Hz), 4.11 (2H, q, J = 7.1 Hz), 6.72 (1H, d, J = 8.6 Hz), 6.95 (2H, d, J = 8.5 Hz), 7.05 (1H, dd, J = 8.6 Hz, 3.0 Hz), 7.14 (2H, d, J = 8.5 Hz), 7.68 (1H, d, J = 3.0 Hz). |
| 335 | —$OCH_3$ | —$CH_3$ | 2 | $^1H$ NMR 2.62-2.68 (2H, m), 2.91-2.97 (2H, m), 3.45 (2H, brs), 3.69 (3H, s), 3.77 (3H, s), 6.74-6.79 (2H, m), 6.82 (1H, d, J = 1.8 Hz), 6.98 (1H, d, J = 7.9 Hz), 7.04-7.26 (1H, m), 7.64 (1H, d, J = 3.0 Hz). |
| 336 | —$OC_2H_5$ | —$C_2H_5$ | 2 | $^1H$ NMR 1.20 (3H, t, J = 7.0 Hz), 1.25 (3H, t, J = 7.1 Hz), 2.51-2.68 (2H, m), 2.81-3.01 (2H, m), |

TABLE 48-continued

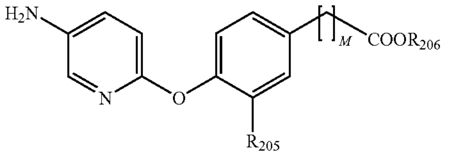

| Reference Example No. | $R_{205}$ | $R_{206}$ | M | $^1H$ NMR ($CDCl_3$) δ ppm or MS |
|---|---|---|---|---|
| | | | | 3.19-3.63 (2H, m), 3.98 (2H, q, J = 7.0 Hz), 4.14 (2H, q, J = 7.1 Hz), 6.69-6.83 (3H, m), 6.95-7.09 (2H, m), 7.60-7.67 (1H, m). |
| 337 | —F | —$C_2H_5$ | 2 | $^1H$ NMR 1.25 (3H, t, J = 7.1 Hz), 2.52-2.71 (2H, m), 2.86-3.02 (2H, m), 3.47 (2H, brs), 4.14 (2H, q, J = 7.1 Hz), 6.81 (1H, d, J = 8.6 Hz), 6.93-7.04 (2H, m), 7.05-7.13 (2H, m), 7.63 (1H, d, J = 2.9 Hz). |
| 338 | —H | —$C_2H_5$ | 4 | $^1H$ NMR 1.25 (3H, t, J = 7.2 Hz), 1.55-1.80 (4H, m), 2.32 (2H, t, J = 7.0 Hz), 2.60 (2H, t, J = 7.0 Hz), 3.49 (2H, brs), 4.12 (2H, q, J = 7.2 Hz), 6.74 (1H, d, J = 8.5 Hz), 6.97 (2H, d, J = 8.5 Hz), 7.06 (1H, dd, J = 8.5 Hz, 3.0 Hz), 7.14 (2H, d, J = 8.5 Hz), 7.71 (1H, d, J = 3.0 Hz). |
| 339 | —H | —$C_2H_5$ | 3 | $^1H$ NMR 1.26 (3H, t, J = 7.5 Hz), 1.94 (2H, dt, J = 15.0 Hz, 7.5 Hz), 2.33 (2H, t, J = 7.5 Hz), 2.63 (2H, t, J = 7.5 Hz), 3.50 (2H, brs), 4.13 (2H, q, J = 7.0 Hz), 6.75 (1H, d, J = 8.5 Hz), 6.98 (2H, d, J = 8.5 Hz), 7.07 (1H, dd, J = 8.5 Hz, 3.0 Hz), 7.15 (2H, d, J = 8.5 Hz), 7.72 (1H, d, J = 3.0 Hz). |

TABLE 49

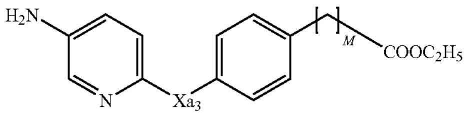

| Reference Example No. | $Xa_8$ | M | Form | $^1H$ NMR (solvent) δ ppm |
|---|---|---|---|---|
| 340 | —NH— | 2 | free | ($CDCl_3$) 1.24 (3H, t, J = 7.1 Hz), 2.60 (2H, t, J = 7.6 Hz), 2.90 (2H, t, J = 7.6 Hz), 3.35 (2H, brs), 4.13 (2H, q, J = 7.1 Hz), 6.16 (1H, brs), 6.77 (1H, d, J = 8.6 Hz), 6.98 (1H, dd, J = 2.9 Hz, 8.6 Hz), 7.00-7.15 (4H, m), 7.78 (1H, d, J = 2.9 Hz). |
| 341 | —N($CH_3$)— | 0 | hydrochloride | ($DMSO-d_6$) 1.30 (3H, t, J = 7.1 Hz), 3.43 (3H, s), 4.28 (2H, q, J = 7.1 Hz), 7.03 (1H, d, J = 9.1 Hz), 7.30 (2H, d, J = 8.6 Hz), 7.55 (1H, d, J = 9.1 Hz), 7.93 (2H, d, J = 8.6 Hz), 8.05 (1H, s). |
| 342 | —N($CH_3$)— | 2 | free | ($CDCl_3$) 1.24 (3H, t, J = 7.2 Hz), 2.63 (2H, t, J = 7.7 Hz), 2.95 (2H, t, J = 7.7 Hz), 3.53 (3H, s), 4.14 (2H, q, J = 7.2 Hz), 6.52 (1H, d, J = 9.5 Hz), 7.07 (1H, dd, J = 2.7 Hz, 9.5 Hz), 7.10 (2H, d, J = 8.3 Hz), 7.22 (2H, d, J = 8.3 Hz), 7.83 (1H, d, J = 2.7 Hz). |
| 343 | —N($CH_2Ph$)— | 2 | dihydrochloride | ($CDCl_3$) 1.22 (3H, t, J = 7.1 Hz), 2.57 (2H, t, J = 7.7 Hz), 2.90 (2H, t, J = 7.7 Hz), 4.11 (2H, q, J = 7.1 Hz), 5.28 (2H, s), 6.65 (1H, d, J = 8.8 Hz), 7.08 (2H, d, J = |

TABLE 49-continued

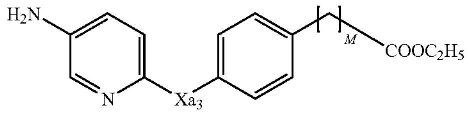

| Reference Example No. | $Xa_8$ | M | Form | $^1$H NMR (solvent) δ ppm |
|---|---|---|---|---|
| | | | | 7.8 Hz), 7.15-7.24 (7H, m), 8.27 (1H, d, J = 8.8 Hz), 8.80 (1H, s). |
| 344 | —CO— | 2 | free | ($CDCl_3$) 1.21 (3H, t, J = 7.1 Hz), 2.63 (2H, t, J = 7.7 Hz), 2.98 (2H, t, J = 7.7 Hz), 4.10 (2H, q, J = 7.1 Hz), 7.18 (2H, brs), 7.27 (2H, d, J = 8.1 Hz), 7.32 (1H, d, J = 8.3 Hz), 7.88-7.99 (3H, m), 8.27 (1H, s). |

(——CO—— means a group of  .

Hereinafter ——CO—— indicates the same meaning.)

TABLE 50

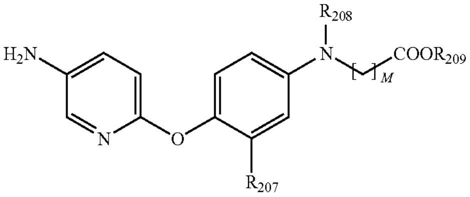

| Reference Example No. | $R_{207}$ | $R_{208}$ | $R_{209}$ | M | $^1$H NMR (solvent) δ ppm |
|---|---|---|---|---|---|
| 345 | —H | —H | —$C(CH_3)_3$ | 0 | ($CDCl_3$) 1.51 (9H, s), 3.49 (2H, brs) 641 (1H, brs), 6.72 (1H, d, J = 8.6 Hz), 7.00 (2H, d, J = 8.9 Hz), 7.06 (1H, dd, J = 8.6 Hz, 3 0 Hz) 7 32 (2H, d, J = 8.9 Hz), 7.69 (1H, d, J = 3.0 Hz). |
| 346 | —H | —Ac | —$C_2H_5$ | 1 | ($CDCl_3$) 1.27 (3H, t, J = 7.1 Hz), 1.94 (3H, s) 3.60 (2H, brs), 4.18 (2H q, J = 7.1 Hz), 4.35 (2H, s), 6.82 (1H, d, J = 8.6 Hz), 7.07 (2H, d, J = 8.8 Hz), 7.12 (1H, dd, J = 3.0 Hz, 8.6 Hz) 7.31 (2H, d, J = 8.8 Hz), 7.73 (1H, d, J = 3.0 Hz), |
| 347 | —H | —Ac | —$C_2H_5$ | 2 | ($CDCl_3$) 1.23 (3H, t, J = 7.1 Hz), 1.85 (3H, s), 2.57 (2H, t, J = 7.4 Hz), 3.60 (2H, s), 3.98 (2H, t, J = 7.4 Hz), 4.07 (2H, q, J = 7.1 Hz), 6.82 (1H, d, J = 8.6 Hz), 7.08 (2H, d, J = 8.8 Hz), 7.10-7.15 (3H, m), 7.74 (1H, d, J = 3.0 Hz). |
| 348 | —$CH_3$ | —Ac | —$C_2H_5$ | 1 | ($CDCl_3$) 1.28 (3H, t, J = 7.1 Hz), 1.95 (3H, s), 2.23 (3H, s), 3.52 (2H, s), 4.19 (2H, q, J = 7.1 Hz), 4.34 (2H, s), 6.73 (1H, d, J = 8.6 Hz) 6.91 (1H, d, J = 8.4 Hz), 7.05-7.15 (2H, m), 7.20 (1H, s), 7.66 (1H, s). |
| 349 | —H | —$CH_3$ | —$CH_3$ | 1 | ($CDCl_3$) 3.05 (3H, s), 3.45 (2H, brs), 3.72 (3H, s), 4.05 (2H, s), 6.67 (3H, d, J = 9.0 Hz), 6.98 (2H, d, J = 2.0 Hz), 7.04 (1H, dd, J = 8.6 Hz, 3.0 Hz), 7.69 (1H, d, J = 2.0 Hz). |
| 350 | —H | —$CH_3$ | —$C_2H_5$ | 1 | ($CDCl_3$) 1.25 (3H, t, J = 7.1 Hz), 3.05 (3H, s), 3.45 (2H, brs), 4.03 (2H, s), 4.18 (2H, q, J = 7.1. Hz), 6.65-6.69 (3H, m), 6.96 (2H, d, J = 9.0 Hz), 7.04 (1H, dd, J = 2.9 Hz, 8.6 Hz), 7.69 (1H, d, J = 2.9 Hz). |
| 351 | —H | —$C_2H_5$ | —$C_2H_5$ | 1 | ($CDCl_3$) 1.20 (3H, t, J = 7.2 Hz), 1.26 (3H, t, J = 7.2 Hz), 3.40-3.46 (4H, m), 3.99 (2H, s), 4.19 (2H, q, J = 7.2 Hz), 6.63 (2H, d, J = 9.1 Hz), 6.67 (1H, d, J = 8.6 Hz), 6.95 (2H, d, J = 9.1 Hz), 7.04 (1H, dd, J = 3.2 Hz, 8.6 Hz), 7.69 (1H, d, J = 3.2 Hz). |
| 352 | —$CH_3$ | —$CH_3$ | —$C_2H_5$ | 1 | ($CDCl_3$) 1.26 (3H, t, J = 7.1 Hz), 2.13 (3H, s), 3.05 (3H, s), 3.41 (2H, brs), 4.02 (2H, s), 4.19 (2H, q, J = 7.1 Hz), 6.46-6.68 (3H, m), 6.89 (1H, d, J = |

TABLE 50-continued

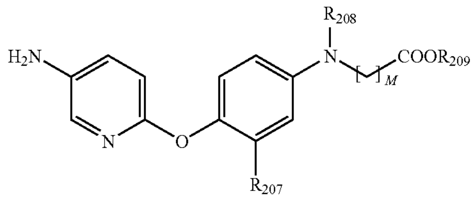

| Reference Example No. | $R_{207}$ | $R_{208}$ | $R_{209}$ | M | $^1$H NMR (solvent) δ ppm |
|---|---|---|---|---|---|
| | | | | | 8.6 Hz), 7.03 (1H, dd, J = 8.6 Hz, 3.0 Hz), 7.67 (1H, d, J = 3.0 Hz). |
| 353 | —$OCH_3$ | —$CH_3$ | —$C_2H_5$ | 1 | ($CDCl_3$) 1.26 (3H, t, J = 7.1 Hz), 3.07 (3H, s), 3.42 (2H, brs), 3.75 (3H, s), 4.04 (2H, s), 4.19 (2H, q, J = 7.1 Hz), 6.24 (1H, dd, J = 8.7 Hz, 2.8 Hz), 6.33 (1H, d, J = 2.8 Hz), 6.67 (1H, d, J = 8.6 Hz), 6.95 (1H, d, J = 8.7 Hz), 7.02 (1H, dd, J = 8.6 Hz, 3.0 Hz), 7.63 (1H, d, J = 2.8 Hz). |
| 354 | —$OCH_3$ | —$C_2H_5$ | —$C_2H_5$ | 1 | (DMSO-$d_6$) 1.13 (3H, t, J = 7.1 Hz), 1.20 (3H, t, J = 7.1 Hz), 3.41 (2H, q, J = 7.1 Hz), 3.63 (3H, s), 4.09-4.17 (4H, m), 4.81 (2H, brs), 6.11 (1H, dd, J = 8.7 Hz, 2.8 Hz), 6.26 (1H d, J = 2.8 Hz), 6.55 (1H, d, J = 8.6 Hz), 6.79 (1H, d, J = 8.7 Hz), 6.99 (1H, dd, J = 8.7 Hz, 3.0 Hz), 7.40 (1H, d, J = 2.3 Hz). |

TABLE 51

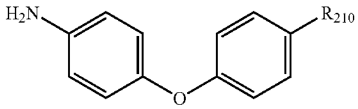

| Reference Example No. | $R_{210}$ | $^1$H NMR ($CDCl_3$) δ ppm |
|---|---|---|
| 355 | 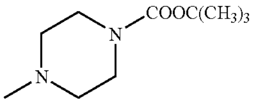 | 1.48 (9H, s), 3.04 (4H, t, J = 5.0 Hz), 3.54 (2H, brs), 3.57 (4H, t, J = 5.0 Hz), 6.65 (2H, d, J = 9.0 Hz), 6.82 (2H, d, J = 9.0 Hz), 6.88 (4H, ABq, J = 9.0 Hz). |
| 356 | 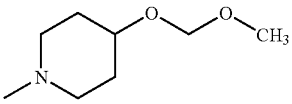 | 1.78 (2H, m), 2.03 (2H, m), 2.86 (2H, m), 3.39 (3H, s), 3.42 (2H, m), 3.52 (2H, brs), 3.70 (1H, m), 4.72 (2H; s), 6.64 (2H, d, J = 9.0 Hz), 6.82 (2H, d, J = 9.0 Hz), 6.88 (4H, ABq, J = 9.0 Hz). |
| 357 | 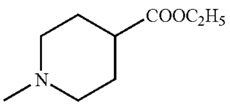 | 1.27 (3H, t, J = 7.0 Hz), 1.88 (2H, dq, J = 3.5 Hz, 12.5 Hz), 2.03 (2h, dd, J = 12.5 Hz, 3.0 Hz), 2.40 (1H, m), 2.72 (2H, dt, J = 2.5 Hz, 12.0 Hz), 3.51-3.53 (4H, m), 4.16 (2H, q, J = 7.0 Hz), 6.65 (2H, d, J = 8.5 Hz), 6.82 (2H, d, J = 8.5 Hz), 6.88 (4H, s). |
| 358 | 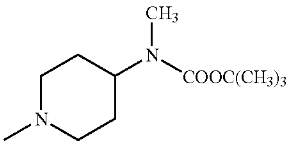 | 1.48 (9H, s), 1.74 (2H, brd, J = 11.5 Hz), 1.85 (2H, m), 2.74 (2H, m), 2.77 (3H, s), 3.53 (2H, brs), 3.60 (2H, brd, J = 12.0 Hz), 4.12 (1H, brs), 6.65 (2H, d, J = 8.5 Hz), 6.82 (2H, d, J = 8.5 Hz), 6.87 (4H, s). |
| 359 | 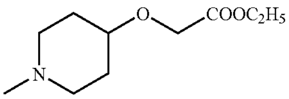 | 1.30 (3H, t, J = 7.0 Hz), 1.81 (2H, m), 2.03 (2H, m), 2.84 (1H, m), 2.95 (1H, m), 3.35 (1H, m), 3.44 (1H, m), 3.54 (3H, m), 4.15 (2H, s), 4.23 (2H, q, J = 7.0 Hz), 6.65 (2H, d, J = 9.0 Hz), 6.82 (2H, d, J = 9.0 Hz), 6.88 (4H, s). |

TABLE 51-continued

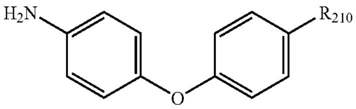

| Reference Example No. | $R_{210}$ | $^1H$ NMR ($CDCl_3$) δ ppm |
|---|---|---|
| 360 | 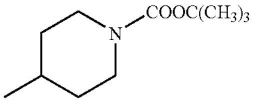 | 1.48 (9H, s), 1.60 (2H, m), 1.80 (2H, m), 2.59 (1H, m), 2.78 (2H, brs), 3.57 (2H, brs), 4.23 (2H, brs), 4.12 (1H, brs), 6.67 (2H, d, J = 9.0 Hz), 6.86 (2H, d, J = 9.0 Hz), 6.87 (2H, d, J = 9.0 Hz), 7.09 (2H, d, J = 9.0 Hz). |

TABLE 52

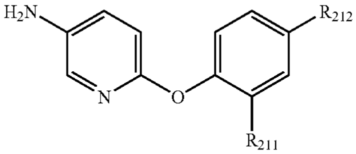

| Reference Example No. | $R_{211}$ | $R_{212}$ | $^1H$ NMR ($CDCl_3$) δ ppm or MS |
|---|---|---|---|
| 361 | —H | —Ac | $^1H$ NMR 2.50 (3H, s), 3.60 (2H, brs), 6.80-7.90 (7H, m). |
| 362 | —H | —NHCONHPh | $^1H$ NMR 3.55 (2H, s), 6.76 (1H, d, J = 8.6 Hz), 6.89 (1H, s), 6.95-7.02 (3H, m), 7.03-7.12 (2H, m), 7.21-7.36 (6H, m), 6.68 (1H, d, J = 2.9 Hz). |
| 363 | —H | 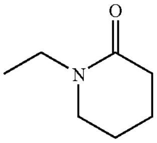 | $^1H$ NMR 1.70-1.90 (4H, m), 2.18 (2H, brs), 2.40-2.50 (2H, m), 3.13-3.29 (2H, m), 4.56 (2H, s), 6.76 (1H, d, J = 8.6 Hz), 7.01 (2H, d, J = 8.6 Hz), 7.09 (1H, dd, J = 8.6 Hz, 3.0 Hz), 7.23 (2H, d, J = 8.6 Hz), 7.72 (1H, d, J = 3.0 Hz). |
| 364 | —H | $—CH(CH_3)COOCH_3$ | MS 272 ($M^+$) |
| 365 | —H | $—C(CH_3)_2COOCH_3$ | MS 286 ($M^+$) |
| 366 | —H | 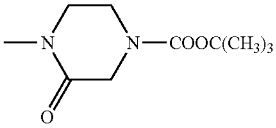 | $^1H$ NMR 1.50 (9H, s), 3.55 (2H, brs), 3.72 (2H, m), 3.78 (2H, m), 4.25 (2H, s), 6.80 (1H, d, J = 8.6 Hz), 7.08 (2H, d, J = 8.9 Hz), 7.10 (1H, dd, J = 8.6 Hz, 3.0 Hz), 7.24 (2H, d, J = 8.9 Hz), 7.72 (1H, d, J = 3.0 Hz). |
| 367 | —H | 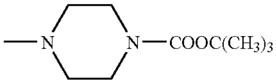 | $^1H$ NMR 1.48 (9H, s), 3.07 (4H, brs), 3.47 (2H, brs), 3.57 (4H, t, J = 5.0 Hz), 6.72 (1H, d, J = 8.5 Hz), 6.92 (2H, d, J = 9.0 Hz), 7.00 (2H, d, J = 9.0 Hz), 7.06 (1H, dd, J = 8.5 Hz, 3.0 Hz), 7.70 (1H, d, J = 3.0 Hz). |
| 368 | —H | 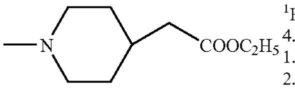 | $^1H$ NMR 1.27 (3H, t, J = 7.0 Hz), 1.44 (2H, dq, J = 4.0 Hz, 12.5 Hz), 1.83 (2H, brd, J = 13.0 Hz), 1.91 (1H, m), 2.28 (2H, d, J = 7.0 Hz), 2.70 (2H, dt, J = 2.5 Hz, 12.0 Hz), 3.46 (2H, brs), 3.57 (2H, brd, J = 12.0 Hz), 4.15 (2H, q, J = 7.0 Hz), 6.69 (1H, d, J = 8.5 Hz), 6.92 (2H, d, J = 9.0 Hz), 6.97 (2H, d, J = 9.0 Hz), 7.05 (2H, dd, J = 8.5 Hz, 3.0 Hz), 7.70 (1H, d, J = 3.0 Hz). |
| 369 | $—CH_3$ | 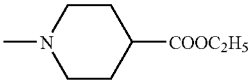 | $^1H$ NMR 1.27 (3H, t, J = 7.1 Hz), 1.86-2.05 (4H, m), 2.14 (3H, s), 2.35-2.44 (1H, m), 2.69-2.79 (2H, m), 3.43 (2H, brs), 3.55-3.59 (2H, m), 4.16 (2H, q, J = 7.1 Hz), 6.62 (1H, d, J = 8.6 Hz), 6.74-6. 82 (2H, m), 6.89 (1H, d, J = 8.6 Hz), 7.03 (1H, dd, J = 8.6 Hz, 3.0 Hz), 7.68 (1H, d, J = 3.0 Hz). |

TABLE 52-continued

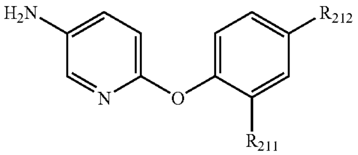

| Reference Example No. | $R_{211}$ | $R_{212}$ | $^1H$ NMR ($CDCl_3$) δ ppm or MS |
|---|---|---|---|
| 370 | —$OCH_3$ | 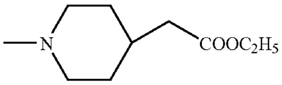 | $^1H$ NMR 1.27 (3H, t, J = 7.1 Hz), 1.38-1.50 (2H, m), 1.87-2.06 (3H, m), 2.29 (2H, d, J = 7.1 Hz), 2.69-2.77 (2H, m), 3.42 (2H, brs), 3.58 (2H, d, J = 12.2 Hz), 3.75 (3H, s), 4.15 (2H, q, J = 7.1 Hz), 6.49 (1H, dd, J = 8.6 Hz, 2.6 Hz), 6.59 (1H, d, J = 2.6 Hz), 6.70 (1H, d, J = 8.6 Hz), 6.96 (1H, d, J = 8.6 Hz), 7.04 (1H, dd, J = 8.6 Hz, 3.0 Hz), 7.65 (1H, d, J = 3.0 Hz). |
| 371 | —$CH_3$ | 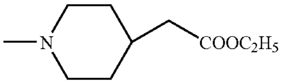 | $^1H$ NMR 1.27 (3H, t, J = 7.1 Hz), 1.37-1.49 (2H, m), 1.80-2.04 (3H, m), 2.13 (3H, s), 2.28 (2H, d, J = 6.9 Hz), 2.69 (2H, dd, J = 12.0 Hz, 9.9 Hz), 3.41-3.59 (4H, m), 4.15 (2H, q, J = 7.3 Hz), 6.60 (1H, d, J = 8.6 Hz), 6.73-6.81 (2H, m), 6.88 (1H, d, J = 8.6 Hz), 7.02 (1H, dd, J = 8.6 Hz, 3.0 Hz), 7.66 (1H, d, J = 2.8 Hz). |

TABLE 53

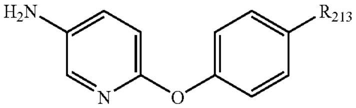

| Reference Example No. | $R_{213}$ | $^1H$ NMR ($CDCl_3$) δ ppm |
|---|---|---|
| 372 | 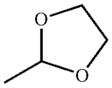 | 3.51 (2H, brs), 3.94-4.12 (4H, m), 5.78 (1H, s), 6.73 (1H, d, J = 8.6 Hz), 6.99-7.09 (3H, m), 7.43 (2H, d, J = 8.5 Hz), 7.70 (1H, d, J = 2.7 Hz). |
| 373 | 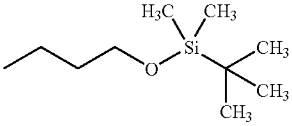 | 0.05 (6H, s), 0.91 (9H, s), 1.77-1.88 (2H, m), 2.62-2.68 (2H, m), 3.62-3.66 (2H, m), 6.73 (1H, d, J = 8.9 Hz), 6.95-7.17 (5H, m), 7.72 (1H, d, J = 3.0 Hz). |
| 374 | 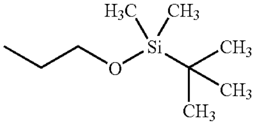 | −0.07 (6H, s), 0.81 (9H, s), 2.73 (2H, t, J = 7.3 Hz), 3.72 (2H, t, J = 7.3 Hz), 6.66 (1H, dd, J = 8.6 Hz, 0.7 Hz), 6.88-6.92 (2H, m), 6.99 (1H, dd, J = 8.6 Hz, 3.0 Hz), 7.10 (2H, d, J = 8.6 Hz), 7.64 (1H, d, J = 3.0 Hz). |
| 375 | morpholino | 3.09-3.13 (4H, m), 3.84-3.87 (4H, m), 6.71 (1H, d, J = 8.6 Hz), 6.90 (2H, d, J = 8.9 Hz), 7.02 (2H, d, J = 9.2 Hz), 7.05 (1H, dd, J = 8.6 Hz, 3.0 Hz), 7.69 (1H, d, J = 3.0 Hz) |
| 376 | 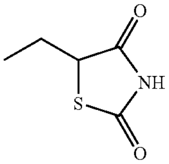 | 3.12 (1H, dd, J = 14.2 Hz, 9.8 Hz), 3.52 (1H, dd, J = 14.2 Hz, 3.8 Hz), 3.70 (2H, s), 4.51 (1H, dd, J = 9.8 Hz, 3.8 Hz), 6.78 (1H, d, J = 8.6 Hz), 7.02 (2H, d, J = 8.6 Hz), 7.09 (1H, dd, J = 8.6 Hz, 3.1 Hz), 7.20 (2H, d, J = 8.6 Hz), 7.71 (1H, d, J = 3.1 Hz), 7.98 (1H, brs). |
| 377 | —$CH{=}C(COOCH_3)_2$ | 3.84 (3H, s), 3.85 (3H, s), 6.82 (1H, d, J = 8.3 Hz), 7.03 (2H, d, J = 8.9 Hz), 7.02-7.10 (1H, m), 7.42 (2H, d, J = 8.9 Hz), 7.70-7.76 (2H, m). |

TABLE 53-continued

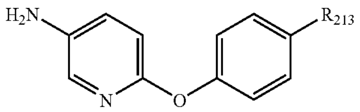

| Reference Example No. | $R_{213}$ | $^1H$ NMR ($CDCl_3$) δ ppm |
|---|---|---|
| 378 | 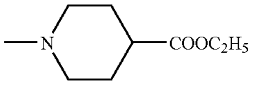 | 1.27 (3H, t, J = 7.0 Hz), 1.88 (2H, m), 2.02 (2H, m), 2.40 (1H, m), 2.75 (2H, dt, J = 3.0 Hz, 12.0 Hz), 3.46 (2H, brs), 3.56 (2H, dt, J = 13.0 Hz, 3.0 Hz), 4.15 (2H, q, J = 7.0 Hz), 6.70 (1H, d, J = 8.5 Hz), 6.92 (2H, d, J = 9.0 Hz), 6.98 (2H, d, J = 9.0 Hz), 7.05 (1H, dd, J = 8.5 Hz, 3.0 Hz), 7.70 (1H, d, J = 3.0 Hz). |
| 379 | 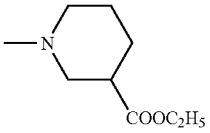 | 1.28 (3H, t, J = 7.0 Hz), 1.66-1.72 (2H, m), 1.82 (1H, m), 2.01 (1H, m), 2.68 (1H, m), 2.78 (1H, m), 2.99 (1H, dd, J = 12.0 Hz, 10.0 Hz), 3.39 (1H, brd, J = 12.0 Hz), 3.47 (2H, brs), 3.62 (1H, dd, J = 12.0 Hz, 4.0 Hz), 4.17 (2H, q, J = 7.0 Hz), 6.70 (1H, d, J = 8.5 Hz), 6.94 (2H, d, J = 9.0 Hz), 6.98 (2H, d, J = 9.0 Hz), 7.06 (1H, dd, J = 8.5 Hz, 3.0 Hz), 7.70 (1H, d, J = 3.0 Hz). |
| 380 | $-CH(CH_3)CH_2COOC_2H_5$ | 1.18 (3H, t, J = 7.2 Hz), 1.27 (3H, d, J = 7.0 Hz), 2.43-2.60 (2H, m), 3.19-3.29 (1H, m), 3.48 (2H, brs), 4.06 (2H, q, J = 7.2 Hz), 6.72 (1H, d, J = 8.7 Hz), 6.96 (2H, d, J = 8.6 Hz), 7.05 (1H, dd, J = 8.7 Hz, 3.0 Hz), 7.16 (2H, d, J = 8.6 Hz), 7.70 (1H, d, J = 3.0 Hz). |

TABLE 54

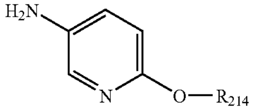

| Reference Example No. | $R_{214}$ | $^1H$ NMR ($CDCl_3$) δ ppm or MS |
|---|---|---|
| 381 | 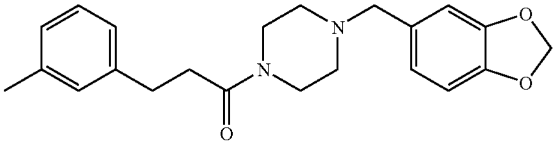 | MS 460 ($M^+$) |
| 382 | 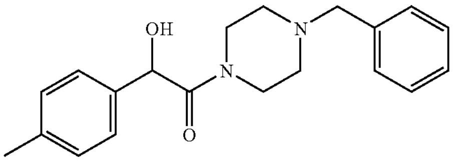 | $^1H$ NMR 1.90-2.03 (1H, m), 2.20-2.55 (3H, m), 3.11-3.25 (1H, m) 3.25-3.38 (1H, m), 3.43 (2H, s), 3.57 (2H, s), 3.60-3.88 (2H, m), 4.70 (1H, d, J = 6.5 Hz), 5.18 (1H, d, J = 6.5 Hz), 6.76 (1H, d, J = 8.6 Hz), 7.02 (2H, d, J = 8.5 Hz), 7.08 (1H, dd, J = 8.5 Hz, 3.0 Hz), 7.20-7.35 (7H, m), 7.73 (1H, dd, J = 3.1 Hz, 0.5 Hz). |
| 383 | 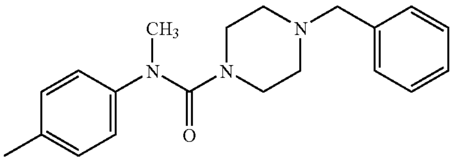 | $^1H$ NMR 2.25 (4H, t, J = 5.0 Hz), 3.19 (3H, s), 3.22 (4H, t, J = 5.0 Hz), 3.43 (2H, s), 3.56 (2H, brs), 6.77 (1H, d, J = 8.6 Hz), 7.00 (2H, d, J = 9.2 Hz), 7.05 (2H, d, J = 9.2 Hz), 7.09 (1H, dd, J = 8.6 Hz, 2.8 Hz), 7.17-7.35 (5H, m), 7.72 (1H, d, J = 2.8 Hz). |

TABLE 54-continued

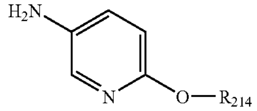

| Reference Example No. | $R_{214}$ | $^1H$ NMR ($CDCl_3$) δ ppm or MS |
|---|---|---|
| 384 | 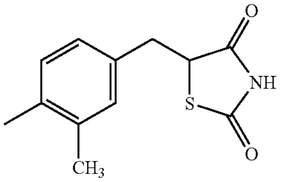 | $^1H$ NMR 2.20 (3H, s), 3.07 (1H, dd, J = 14.2 Hz, 10.1 Hz), 3.50 (2H, brs), 3.52 (1H, dd, J = 14.2 Hz, 3.8 Hz), 4.51 (1H, dd, J = 10.1 Hz, 3.8 Hz), 6.73 (1H, d, J = 8.5 Hz), 6.90 (1H, d, J = 8.5 Hz), 7.03 (1H, dd, J = 8.5 Hz, 3.0 Hz), 7.08 (1H, dd, J = 8.5 Hz, 3.0 Hz), 7.10 (1H, d, J = 3.0 Hz), 7.67 (1H, d, J = 3.0 Hz), 8.10 (1H, brs). |
| 385 | 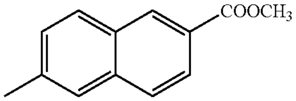 | $^1H$ NMR 3.62 (2H, brs), 3.97 (3H, s), 6.86 (1H, d, J = 8.6 Hz), 7.12 (1H, dd, J = 8.6 Hz, 3.0 Hz), 7.32 (1H, dd, J = 8.9 Hz, 2.5 Hz), 7.41 (1H, d, J = 2.1 Hz), 7.72-7.75 (2H, m), 7.92 (1H, d, J = 8.9 Hz), 8.02 (1H, dd, J = 8.6 Hz, 1.7 Hz), 8.56 (1H, s). |
| 386 | 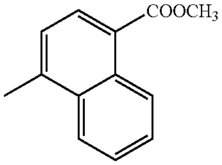 | $^1H$ NMR 3.63 (2H, brs), 3.98 (3H, s), 6.90 (1H, d, J = 8.6 Hz), 6.94 (1H, d, J = 8.2 Hz), 7.15 (1H, dd, J = 8.7 Hz, 3.0 Hz), 7.54-7.57 (1H, m), 7.62-7.68 (1H, m), 7.77 (1H, d, J = 3.0 Hz), 8.18 (1H, d, J = 8.2 Hz), 8.32-8.35 (1H, m), 9.03 (1H, d, J = 8.7 Hz). |
| 387 | 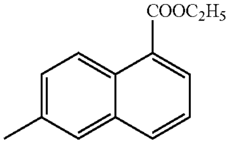 | $^1H$ NMR 1.45 (3H, t, J = 7.1 Hz), 3.57 (2H, brs), 4.47 (2H, q, J = 7.1 Hz), 6.83 (1H, d, J = 8.6 Hz), 7.12 (1H, dd, J = 8.6 Hz, 3.1 Hz), 7.38 (1H, dd, J = 9.4 Hz, 2.6 Hz), 7.43-7.49 (2H, m, 7.75 (1H, d, J = 3.0 Hz), 7.89 (1H, d, J = 8.2 Hz), 8.10 (1H, dd, J = 7.3 Hz, 1.3 Hz), 8.93 (1H, d, J = 9.4 Hz). |

TABLE 55

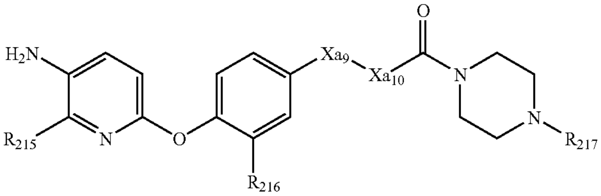

| Reference Example No. | $R_{215}$ | $R_{216}$ | $R_{217}$ | $Xa_9$ | $Xa_{10}$ | $^1H$ NMR ($CDCl_3$) δ ppm or MS |
|---|---|---|---|---|---|---|
| 388 | —H | $—CH_3$ | piperonyl | $—CH_2—$ | $—CH_2—$ | MS 474 ($M^+$) |
| 389 | —H | —F | benzyl | none | none | $^1H$ NMR 2.46 (4H, brs), 3.54 (6H, brs), 6.83 (1H, d, J = 8.7 Hz), 7.09 (1H, dd, J = 8.6 Hz, 3.0 Hz), 7.16-7.36 (8H, m), 7.61 (1H, d, J = 3.0 Hz). |
| 390 | —H | $—OCH_3$ | piperonyl | $—CH_2—$ | $—CH_2—$ | $^1H$ NMR 2.31-2.41 (4H, m), 2.59-2.65 (2H, m), 2.92-2.98 (2H, m), 3.41 (4H, brs), 3.62-365 (2H, m), 3.76 (3H, s), 5.95 (2H, s), 6.71-6.79 (4H, m), 6.83-6.85 (2H, m), 6.97 (1H, d, J = 8.1 Hz), 7.06 (1H, dd, J = 8.7 Hz, 3.0 Hz), 7.63 (1H, d, J = 2.8 Hz). |

TABLE 55-continued

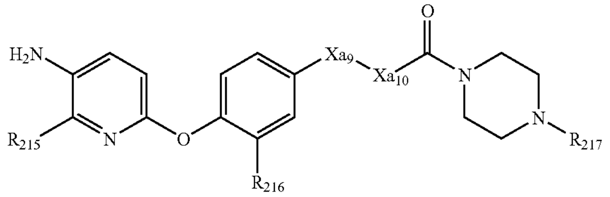

| Reference Example No. | $R_{215}$ | $R_{216}$ | $R_{217}$ | $Xa_9$ | $Xa_{10}$ | $^1H$ NMR ($CDCl_3$) δ ppm or MS |
|---|---|---|---|---|---|---|
| 391 | —H | —H | —COOC($CH_3$)$_3$ | —$CH_2$— | —CH(OH)— | $^1H$ NMR 1.47 (9H, s), 2.81-2.98 (2H, m), 301-3.20 (1H, m), 3.29 (3H, brs), 3.39 (2H, brs), 3.51 (2H, brs), 3.58-3.78 (3H, m), 4.58 (1H, q, J = 7.0 Hz), 6.75 (1H, d, J = 8.8 Hz), 6.99 (2H, d, J = 8.6 Hz), 7.07 (1H, dd, J = 8.8 Hz, 3.0 Hz), 7.19 (2H, d, J = 8.6 Hz), 7.67 (1H, d, J = 3.0 Hz). |
| 392 | —$CH_3$— | —H | piperonyl | —$CH_2$— | —$CH_2$— | MS 474 ($M^+$) |

TABLE 56

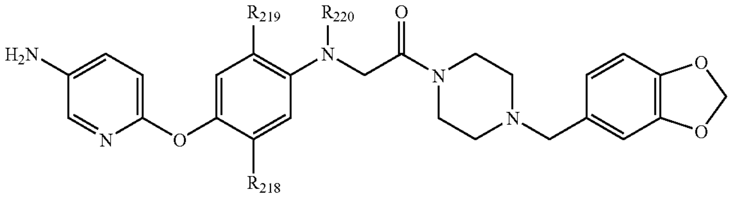

| Reference Example No. | $R_{218}$ | $R_{219}$ | $R_{220}$ | $^1H$ NMR ($CDCl_3$) δ ppm or MS |
|---|---|---|---|---|
| 393 | —H | —H | —H | $^1H$ NMR 2.42-2.49 (4H, m), 3.42-3.48 (4H, m), 3.66-3.72 (2H, m), 3.86 (2H, d, J = 4.3 Hz), 4.82 (1H, t, J = 4.3 Hz), 5.96 (2H, s), 6.62 (2H, d, J = 8.8 Hz), 6.68 (1H, d, J = 8.6 Hz), 6.73-6.78 (2H, m), 6.86 (1H, d, J = 1.0 Hz), 6.95 (1H, d, J = 8.8 Hz), 7.05 (1H, dd, J = 3.0 Hz, 8.6 Hz), 7.69 (1H, d, J = 3.0 Hz) |
| 394 | —H | —H | —Ac | $^1H$ NMR 1.94 (3H, s), 2.45-2.55 (4H, m), 3.45-3.70 (8H, m), 4.42 (2H, s), 5.95 (2H, s), 6.75-6.85 (3H, m, 6.92 (1H, s), 7.04 (2H, d, J = 8.8 Hz), 7.12 (1H, dd, J = 3.0 Hz, 8.6 Hz), 7.36 (2H, d, J = 8.8 Hz), 7.72 (1H, d, J = 3.0 Hz). |
| 395 | —H | —H | —$COC_2H_5$ | $^1H$ NMR 1.06 (3H, t, J = 7.5 Hz), 2.17 (2H, q, J = 7.5 Hz), 2.40-2.45 (4H, m), 3.41 (4H, s), 3.59 (2H, d), 4.42 (2H, s), 5.94 (2H, s), 6.70-6.75 (2H, m), 6.80-6.85 (2H, m), 7.04 (2H, d, J = 8.7 Hz), 7.11 (1H, dd, J = 3.1 Hz, 8.6 Hz), 7.36 (2H, d, J = 8.7 Hz), 7.72 (1H, d, J = 3.1 Hz). |
| 396 | —H | —H | 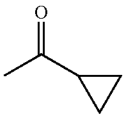 | $^1H$ NMR 0.60-1.55 (5H, m), 2.39 (4H, brs), 3.42 (4H1, brs), 3.55 (2H, brs), 4.46 (2H, brs), 5.94 (2H, s), 6.69-6.75 (2H, m), 6.77-6.85 (2H, m,) 7.00-7.15 (2H, m), 7.40-7.46 (2H, m), 7.72 (1H, s). |
| 397 | —H | —H | cyclopropyl | $^1H$ NMR 0.60-0.66 (2H, m), 0.77-0.83 (2H, m), 2.42-2.44 (4H, m), 2.77-2.79 (1H, m), 3.43-3.52 (6H, m), 3.59-3.62 (2H, m), 4.16 (2H, s), 5.95 (2H, s), 6.66 (1H, d, J = 8.6 Hz), 6.75 (2H, s), 6.86-6.97 (5H, m), 7.03 (1H, dd, J = 8.6 Hz, 2.8 Hz), 7.70 (1H, d, J = 2.8 Hz). |

TABLE 56-continued

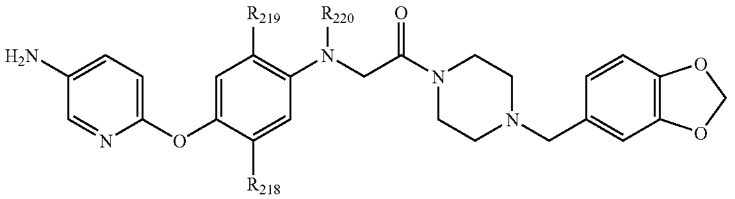

| Reference Example No. | $R_{218}$ | $R_{219}$ | $R_{220}$ | $^1H$ NMR ($CDCl_3$) δ ppm or MS |
|---|---|---|---|---|
| 398 | $-CH_3$ | $-CH_3$ | $-C_2H_5$ | MS 517($M^+$) |
| 399 | $-COOCH_3$ | —H | $-C_2H_5$ | MS 547($M^+$) |

TABLE 57

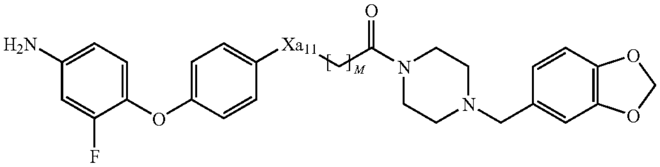

| Reference Example No. | $Xa_{11}$ | M | $^1H$ NMR ($CDCl_3$) δ ppm |
|---|---|---|---|
| 400 | —NH— | 0 | 2.40-2.50 (4H; m), 3.40-3.55 (6H, m), 3.68 (2H, brs), 5.95 (2H, s), 6.27 (1H, s), 6.30-6.55 (2H, m), 6.65-6.95 (5H, m), 7.20-7.30 (2H, m). |
| 401 | —NH— | 1 | 2.40-2.50 (4H, m), 3.35-3.45 (4H, m), 3.55-3.70 (4H, m), 3.83 (2H, d, J = 4.4 Hz), 4.72 (1H, t, J = 4.4 Hz), 5.95 (2H, s), 6.30-6.40 (1H, m), 6.45-6.60 (3H, m), |
| 402 | —N(Ac)— | 1 | 1.91 (3H, s), 2.40-2.50 (4H, m), 3.45-3.75 (8H, m), 4.41 (2H, s), 5.94 (2H, s), 6.40-6.52 (2H, m), 6.70-6.75 (2H, m), 6.80-6.95 (4H, m), 7.28 (2H, d, J = 9.0 Hz). |
| 403 | —O— | 1 | 2.41 (4H, brs), 3.42 (2H, s), 3.50-3.80 (6H, m), 4.63 (2H, s), 5.94 (2H, s), 6.40 (1H, ddd, J = 1.2 Hz, 2.6 Hz, 7.4 Hz), 6.50 (1H, dd, J = 2.6 Hz, 12.1 Hz), 6.65-6.75 (2H, m), 6.80-6.95 (6H, m). |

Reference Example 404

Production of methyl 3-[(4-hydroxyphenyl)methylamino]-propionate

Methyl 3-[(4-benzyloxyphenyl)methylamino]-propionate (27.3 g, 91.1 mmol) was dissolved in ethanol (300 mL), and the resulting solution was cooled with ice and 10% palladium-carbon (3.0 g) was added. The resulting solution was stirred for 4.5 hours at room temperature under a hydrogen atmosphere. The reaction solution was filtered through Celite to remove insoluble matter, and the filtrate was concentrated under reduced pressure to thereby yield 19.1 g of the title compound.

Appearance: Red oil $^1H$ NMR ($CDCl_3$) δ 2.51-2.56 (2H, m), 2.83 (3H, brs), 3.57 (2H, brs), 3.66 (3H, s), 4.99 (1H, brs), 6.71-6.74 (4H, m).

The following compounds were produced in the same manner as in Reference Example 404.

Reference Example 405

Ethyl[acetyl(4-hydroxyphenyl)amino]acetate $^1H$ NMR ($CDCl_3$) δ 1.26 (3H, t, J=7.1 Hz), 1.92 (3H, s), 4.19 (2H, q, J=7.1 Hz), 4.34 (2H, s), 6.16 (1H, s), 6.87 (2H, d, J=8.8 Hz), 7.21 (2H, d, J=8.8 Hz).

TABLE 58

| Reference Example No. | Chemical Structure | mp (° C.) or $^1$H NMR ($CDCl_3$) δ ppm |
| --- | --- | --- |
| 406 | 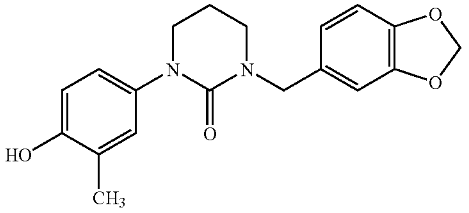 | mp 172.0-173.0 |
| 407 | 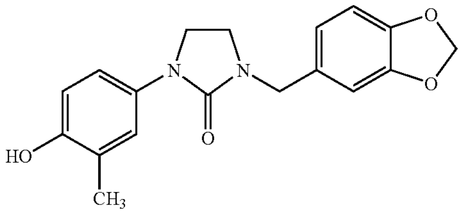 | $^1$H NMR 2.24 (3H, s), 3.25-3.39 (2H, m), 3.66-3.81 (2H, m), 4.36 (2H, s), 4.93 (1H, s), 5.95 (2H, s), 6.71 (1H, d, J = 8.6 Hz), 6.77 (2H, d, J = 0.6 Hz), 6.83 (1H, s), 7.15 (1H, dd, J = 2.8 Hz, 8.6 Hz), 7.32 (1H, d, J = 2.8 Hz). |
| 408 | 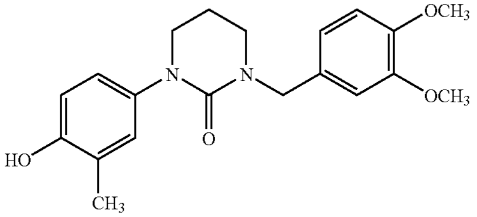 | $^1$H NMR 1.94-2.12 (2H, m), 2.08 (3H, s), 3.29 (2H, t, J = 6.0 Hz), 3.58 (2H, t, J = 6.0 Hz), 3.89 (3H, s), 3.93 (3H, s), 4.57 (2H, s), 6.34 (1H, d, J = 8.4 Hz), 6.71 (1H, dd, J = 2.6 Hz, 8.4 Hz), 6.75-6.93 (3H, m), 6.96 (1H, d, J = 1.3 Hz), 7.61 (1H, s). |
| 409 | 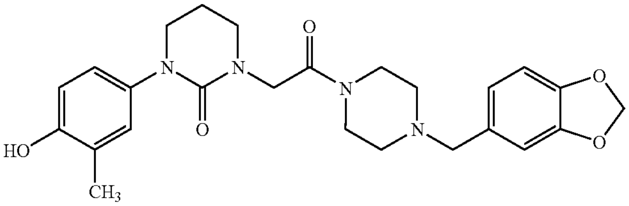 | $^1$H NMR 2.07 (3H, s), 2.09-2.18 (2H, m), 2.37-2.50 (4H, m), 3.41 (2H, s), 3.43-3.54 (4H, m), 3.54-3.68 (4H, m), 4.22 (2H, s), 5.94 (2H, s), 6.35 (1H, d, J = 8.4 Hz), 6.62-6.77 (3H, m), 6.83 (1H, d, J = 1.1 Hz), 6.88 (1H, d, J = 2.4 Hz). |
| 410 | 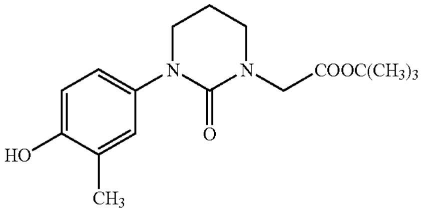 | $^1$H NMR 1.49 (9H, s), 2.07 (3H, s), 2.07-2.21 (2H, m), 3.45 (2H, t, J = 5.9 Hz), 3.61 (2H, t, J = 5.9 Hz), 4.07 (2H, s), 6.33 (1H, d, J = 8.4 Hz), 6.71 (1H, dd, J = 2.6 Hz, 8.4 Hz), 6.87 (1H, d, J = 2.6 Hz), 7.26 (1H, s). |

Reference Example 411

Production of [4-(5-aminopyridin-2-yloxy)phenyl](4-piperonylpiperazin-1-yl)methanone

[4-(5-nitropyridin-2-yloxy)phenyl](4-piperonylpiperazin-1-yl)methanone (0.36 g, 0.78 mmol) was dissolved in a mixed solvent consisting of ethanol (5 mL) and THF (5 mL). To the resulting solution was added 5% platinum-carbon (0.06 g), and stirred at room temperature under a hydrogen atmosphere. Two hours later, the 5% platinum-carbon was removed by filtration, and the solvent was evaporated under reduced pressure, to thereby yield 0.32 g of the title compound.

Appearance: Pale yellow amorphous powder $^1$H NMR ($CDCl_3$) δ 2.43 (4H, brs), 3.44 (2H, s), 3.58 (6H, brs), 5.95 (2H, s), 6.74 (2H, s), 6.80 (1H, d, J=8.6 Hz), 6.85 (1H, s), 7.05 (2H, d, J=8.6 Hz), 7.10 (1H, dd, J=8.6 Hz, 3.0° Hz), 7.40 (2H, d, J=8.7 Hz), 7.74 (1H, d, J=2.6 Hz).

The following compounds were produced in the same manner as in Reference Example 411.

Reference Example 412

4-[5-(4-Trifluoromethylphenoxymethyl)pyridin-2-yloxy]phenylamine $^1$H NMR ($CDCl_3$) δ 3.63 (2H, brs), 5.02 (2H, s), 6.70 (2H, d, J=8.9 Hz), 6.88 (1H, d, J=8.4 Hz), 6.94 (2H, d, J=8.9 Hz), 7.01 (2H, d, J=8.6 Hz), 7.55 (2H, d, J=8.4 Hz), 7.72 (1H, dd, J=8.4 Hz, 2.5 Hz), 8.22 (1H, d, J=2.3 Hz).

Reference Example 413

3-Methyl-4-[5-(4-trifluoromethylphenoxymethyl)pyridin-2-yloxy]phenylamine $^1$H NMR ($CDCl_3$) δ 2.08 (3H, s), 3.58 (2H, brs), 5.02 (2H, s), 6.65 (1H, dd, J=8.2 Hz, 2.8 Hz), 6.60 (1H, d, J=2.8 Hz), 6.83-6.87 (2H, m), 7.02 (2H, d, J=8.9 Hz), 7.56 (2H, d, J=9.1 Hz), 7.72 (1H, dd, J=8.6 Hz, 2.5 Hz), 8.21 (1H, d, J=2.5 Hz).

Reference Example 414

2-{[4-(4-Aminophenoxy)phenyl]methylamino}-1-(4-piperonylpiperazin-1-yl)ethanone $^1$H NMR ($CDCl_3$) δ 2.41 (4H, t, J=5.1 Hz), 2.99 (3H, s), 3.42 (2H, s), 3.48 (2H, t, J=4.8 Hz), 3.50 (2H, brs), 3.62 (2H, t, J=4.8 Hz), 4.04 (2H, s), 5.95 (2H, s), 6.61-6.68 (4H, m), 6.73-6.88 (7H, m).

Reference Example 415

2-{[3-(5-Aminopyridin-2-yloxy)phenyl]methylamino}-1-(4-piperonylpiperazin-1-yl)ethanone $^1$H NMR ($CDCl_3$) δ 2.40 (4H, t, J=4.9 Hz), 3.00 (3H, s), 3.41 (2H, s), 3.44-3.46 (2H, m), 3.51 (2H, brs), 3.59-3.61 (2H, m), 4.06 (2H, s), 5.95 (2H, s), 6.35-6.45 (3H, m), 6.70-6.74 (3H, m), 6.85 (1H, s), 7.05 (1H, dd, J=8.6 Hz, 3.1 Hz), 7.12-7.18 (1H, m), 7.73 (1H, d, J=3.1 Hz).

The following compound were produced in the same manner as in Reference Example 415.

TABLE 59

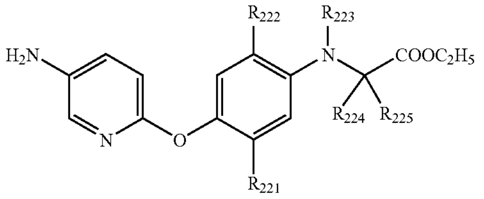

| Reference Example No. | $R_{221}$ | $R_{222}$ | $R_{223}$ | $R_{224}$ | $R_{225}$ | $^1$H NMR ($CDCl_3$) δ ppm or MS |
|---|---|---|---|---|---|---|
| 416 | —H | —H | —$CH_3$ | —$CH_3$ | —$CH_3$ | $^1$H NMR 1.25 (3H, t, J = 7.1 Hz), 1.38 (6H, s), 2.86 (3H, s), 3.50 (2H, brs), 4.17 (2H, q, J = 7.1 Hz), 6.73 (1H, dd, J = 8.6 Hz, 0.3 Hz), 6.93 (2H, d, J = 9.1 Hz), 7.02-7.09 (3H, m), 7.73 (1H, d, J = 3.0 Hz). |
| 417 | —F | —H | —$CH_3$ | —H | —H | $^1$H NMR 1.26 (3H, t, J = 7.1 Hz), 3.05 (3H, s), 3.44 (2H, brs), 4.02 (2H, s), 4.19 (2H, q, J = 7.1 Hz), 6.38-6.51 (2H, m), 6.75 (1H, d, J = 8.6 Hz), 7.01-7.13 (2H, m), 7.63 (1H, d, J = 3.0 Hz). |
| 418 | —F | —H | —$C_2H_5$ | —H | —H | $^1$H NMR 1.16-1.30 (6H, m), 3.43 (2H, brs), 3.43 (2H, q, J = 7.1 Hz), 3.98 (2H, s), 4.21 (2H, q, J = 7.1 Hz), 6.33-6.47 (2H, m), 6.75 (1H, d, J = 8.6 Hz), 6.99-7.09 (2H, m), 7.64 (1H, d, J = 3.0 Hz). |
| 419 | —F | —H | —$(CH_2)_2CH_3$ | —H | —H | $^1$ H NMR 0.95 (3H, t, J = 7.4 Hz), 1.27 (3H, t, J = 7.3 Hz), 1.59-1.70 (2H, m), 3.31 (2H, t, J = 7.6 z), 3.45 (2H, brs), 3.99 (2H, s), 4.20 (2H, q, J = 7.1 Hz), 6.32-6.45 (2H, m), 6.75 (1H, dd, J = 8.7 Hz, 0.7 Hz), 7.04 (1H, t, J = 9.1 Hz), 7.05 (1H, dd, J = 7.4 Hz, 5.8 Hz), 7.64 (1H, dd, J = 3.0 Hz, 0.7 Hz). |
| 420 | —F | —H | —Ac | —H | —H | $^1$H NMR 1.29 (3H, t, J = 7.1 Hz), 1.98 (3H, s), 3.55 (2H, brs), 4.21 (2H, q, J = 7.1 Hz), 4.35 (2H, s), 6.87 (1H, d, J = 8.7 Hz), 7.10-7.29 (4H, m), 7.63 (1H, d, J = 3.0 Hz). |
| 421 | —H | —$CF_3$ | —$C_2H_5$ | —H | —H | MS 383 ($M^+$) |

TABLE 60

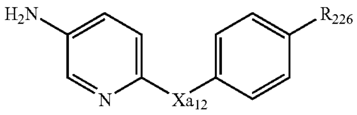

| Reference Example No. | $Xa_{12}$ | $R_{226}$ | $^1H$ NMR ($CDCl_3$) δ ppm |
| --- | --- | --- | --- |
| 422 | —O— | $—CH_2CN$ | 3.54 (2H, brs), 3.72 (2H, s), 6.79 (1H, d, J = 8.5 Hz), 7.06 (2H, d, J = 8.9 Hz), 7.09 (1H, dd, J = 8.5 Hz, 3.0 Hz), 7.30 (2H, d, J = 8.9 Hz), 7.71 (1H, d, J = 3.0 Hz). |
| 423 | —O— | 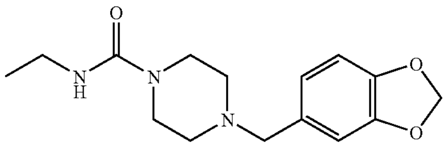 | 2.41 (4H, t, J = 5.1 Hz),3.38 (4H, t, J = 5.1 Hz), 3.42 (2H, s), 3.54 (2H, brs), 4.37 (2H, d, J = 5.1 Hz), 4.72 (1H, t, J = 5.1 Hz), 5.94 (2H, s), 6.74 (2H, s), 6.77 (1H, d, J = 8.7 Hz), 6.85 (1H, s), 7.01 (2H, d, J = 8.5 Hz), 7.08 (1H, dd, J = 8.7 Hz, 3.0 Hz), 7.28 (2H, d, J = 8.5 Hz), 7.68 (1H, d, J = 2.8 Hz). |
| 424 | —O— | 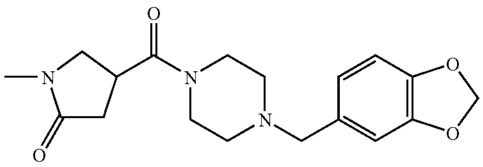 | 2.45-2.47 (4H, m), 2.73-2.98 (2H, m), 3.45 (2H, s), 3.49-3.72 (7H, m), 3.85-3.91 (1H, m), 4.24-4.30 (1H, m), 5.96 (2H, s), 6.74-6.78 (3H, m), 6.86 (1H, s), 7.05-7.11 (3H, m), 7.53-7.58 (2H, m), 7.70 (1H, d, J = 3.0 Hz). |
| 425 | —O— | 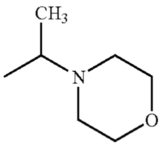 | 1.35 (3H, d, J = 6.6 Hz), 2.37-2.52 (4H, m), 3.31 (1H, q, J = 6.6 Hz), 3.67-3.72 (4H, m), 6.76 (1H, d, J = 8.6 Hz), 6.99 (2H, d, J = 8.3 Hz), 7.08 (1H, dd, J = 8.6 Hz, 2.3 Hz), 7.27 (2H, d, J = 8.4 Hz), 7.72 (1H, d, J = 3.0 Hz). |
| 426 | $—N(CH_3)—$ | 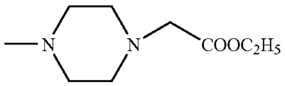 | 1.30 (3H, t, J = 7.1 Hz), 2.76 (4H, t, J = 5.0 Hz), 3.24 (4H, t, J = 5.0 Hz), 3.28 (3H, s), 3.35 (4H, s), 4.21 (2H, q, J = 7.1 Hz), 6.42 (1H, dd, J = 8.8 Hz, 0.7 Hz), 6.83 (1H, dd, J = 8.8 Hz, 2.9 Hz), 6.92 (2H, d, J = 8.9 Hz), 7.10 (2H, d, J = 8.9 Hz), 7.79 (1H, dd, J = 2.9 Hz, 0.7 Hz). |
| 427 | $—N(CH_3)—$ | 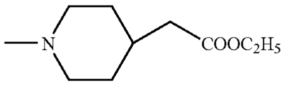 | 1.28 (3H, t, J = 7.1 Hz), 1.46 (2H, qd, J = 12.3 Hz, 3.6 Hz), 1.77-2.10 (3H, m), 2.29 (2H, d, J = 6.9 Hz), 2.73 (2H, td, J = 12.3 Hz, 2.4 Hz), 3.23 (2H, brs), 3.35 (3H, s), 3.63 (2H, d, J = 12.3 Hz), 4.15 (2H, q, J = 7.1 Hz), 6.41 (1H, d, J = 8.9 Hz), 6.82 (1H, dd, J = 8.9 Hz, 3.0 Hz), 6.92 (2H, d, J = 8.9 Hz), 7.09 (2H, d, J = 8.9 Hz), 7.79 (1H, d, J = 2.5 Hz). |
| 428 | —O— | 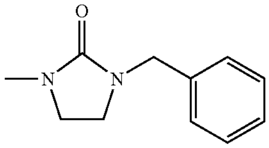 | 3.28-3.42 (2H, m), 3.43-3.59 (2H, m), 3.71-3.88 (2H, m), 4.47 (2H, s), 6.73 (1H, d, J = 8.6 Hz), 7.01-7.11 (3H, m), 7.25-7.39 (5H, m), 7.51-7.59 (2H, m), 7.70 (1H, d, J = 2.9 Hz). |

TABLE 61

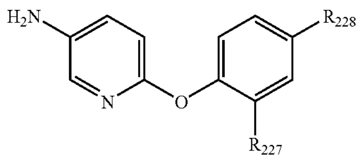

| Reference Example No. | $R_{227}$ | $R_{228}$ | $^1H$ NMR ($CDCl_3$) δ ppm or MS |
|---|---|---|---|
| 429 | —F | 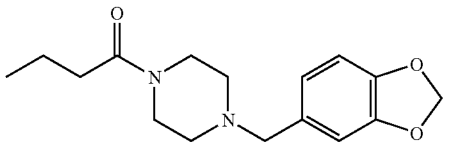 | MS 478 ($M^+$) |
| 430 | —$CH_3$ | 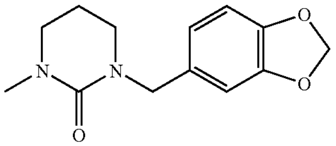 | $^1H$ NMR 1.96-2.11 (2H, m), 2.19 (3H, s), 3.29 (2H, t, J = 5.9 Hz), 3.46 (2H, s), 3.68 (2H, t, J = 5.9 Hz), 4.52 (2H, s), 5.95 (2H, s), 6.67 (1H, d, J = 8.6 Hz), 6.73-6.81 (2H, m), 6.88 (1H, s), 6.93 (1H, d, J = 8.6 Hz), 7.05 (1H, dd, J = 3.0 Hz, 8.6 Hz), 7.09 (1H, dd, J = 2.6 Hz, 8.6 Hz), 7.18-7.22 (1H, m), 7.00 (1H, d, J =3.0 Hz). |
| 431 | —$CH_3$ | 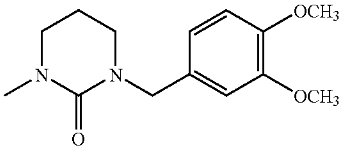 | $^1H$ NMR 1.99-2.11 (2H, m), 2.19 (3H, s), 3.29 (2H, t, J = 6.0 Hz), 3.47 (2H, s), 3.68 (2H, d, J = 6.0 Hz), 3.88 (3H, s), 3.88 (3H, s), 4.56 (2H, s), 6.68 (1H, d, J = 8.6 Hz), 6.82 (1H, d, J = 8.1 Hz), 6.86 (1H, dd, J = 1.8 Hz, 8.1 Hz), 6.91 (1H, d, J = 1.8 Hz), 6.93 (1H, d, J = 8.6 Hz), 7.05 (1H, dd, J = 3.0 Hz, 8.6 Hz), 7.09 (1H, dd, J = 2.6 Hz, 8.6 Hz), 7.19 (1H, d, J = 2.6 Hz), 7.69 (1H, d, J = 3.0 Hz). |
| 432 | —$CH_3$ | 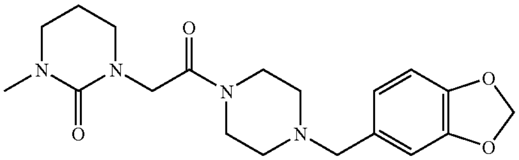 | $^1H$ NMR 2.10-2.21 (2H, m), 2.35-2.48 (4H, m), 3.42 (2H, s), 3.43-3.54 (6H, m), 3.57-3.66 (2H, m), 3.73 (2H, t, J = 5.7 Hz), 4.21 (2H, s), 5.95 (2H, s), 6.66 (1H, d, J = 8.6 Hz), 6.69-6.77 (2H, m), 6.84 (1H, d, J = 1.2 Hz), 6.92 (1H, d, J = 8.6 Hz), 7.02-7.09 (2H, m), 7.17 (1H, d, J = 2.4 Hz), 7.69 (1H, d, J = 2.8 Hz). |
| 433 | —$CH_3$ | 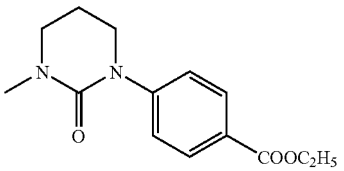 | $^1H$ NMR 1.38 (3H, t, J = 7.1 Hz), 2.19 (3H, s), 2.19-2.38 (2H, m), 3.47 (2H, s), 3.73-3.93 (4H, m), 4.36 (2H, q, J = 7.1 Hz), 6.67 (1H, d, J = 8.6 Hz), 6.94 (1H, d, J = 8.6 Hz), 7.05 (1H, dd, J = 3.0 Hz, 8.6 Hz), 7.12 (1H, dd, J = 2.6 Hz, 8.6 Hz), 7.22 (1H, d, J = 2.6 Hz), 7.40-7.48 (2H, m), 7.69 (1H, d, J = 3.0 Hz), 7.95 8.04 (2H, m). |
| 434 | —$CH_3$ | 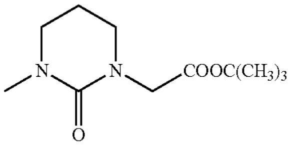 | $^1H$ NMR 1.47 (9H, s), 2.05-2.24 (5H, m), 3.34-3.54 (4H, m), 3.77 (2H, t, J = 5.8 Hz), 4.04 (2H, s), 6.65 (1H, d, J = 8.6 Hz), 6.90 (1H, d, J = 8.6 Hz), 6.99-7.10 (2H, m), 7.17 (1H, d, J = 2.4 Hz), 7.68 (1H, d, J = 3.0 Hz). |

TABLE 62

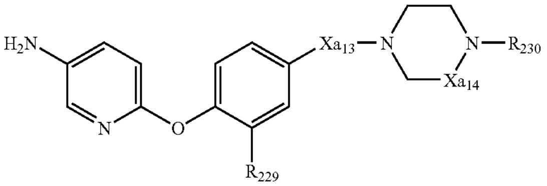

| Reference Example No. | $R_{229}$ | $Xa_{13}$ | $R_{230}$ | $Xa_{14}$ | $^1H$ NMR ($CDCl_3$) δ ppm |
|---|---|---|---|---|---|
| 435 | —H | —CO— | 3-pyridyl | $—CH_2—$ | 3.23 (4H, brs), 3.62 (2H, brs), 3.81 (4H, brs), 6.83 (1H, d, J = 8.6 Hz), 7.09 (2H, d, J 8.6 Hz), 7.12 (1H, dd, J = 8.6 Hz, 3.1 Hz), 7.20-7.21 (2H, m), 7.45 (2H, d, J = 8.7 Hz), 7.55 (1H, d, J = 3.0 Hz), 8.14-8.17 (1H, m), 8.31-8.33 (1H, m). |
| 436 | —H | none | piperonyl | —CO— | 3.37 (4H, s), 3.48 (2H, brs), 3.90 (2H, s), 4.57 (2H, s), 5.95 (2H, s), 6.72 (1H, dd, J = 8.5 Hz, 0.7 Hz), 6.74-6.78 (2H, m), 6.78-6.82 (1H, m), 6.86 (2H, d, J = 9.1 Hz), 7.02 (2H, d, J = 9.1 Hz), 7.06 (1H, dd, 4 = 8.5 Hz, 2.9 Hz), 7.69 (1H, d, J = 2.9 Hz). |
| 437 | $—COOCH_3$ | none | benzyl | $—CH_2—$ | 2.58-2.62 (4H, m), 3.14-3.18 (4H, m), 3.61 (2H, s), 3.65 (3H, s), 6.63 (1H, d, J = 8.7 Hz), 6.95 (1H, d, J = 8.9 Hz), 7.12-7.18 (2H, m), 7.25-7.36 (5H, m, 7.41 (1H, d, J = 3.0 Hz), 7.51 (1H, d, J = 2.8 Hz). |
| 438 | —H | $—CH_2—$ | $—COOC(CH_3)_3$ | $—CH_2—$ | 1.45 (9H, s), 2.36-2.40 (4H, m), 3.40-3.44 (4H, m), 3.47 (2H, s), 3.56 (2H, brs), 6.76 (1H, d, J = 8.6 Hz), 6.97-7.02 (2H, m), 7.08 (1H, dd, J = 8.6 Hz, 3.0 Hz), 7.25-7.29 (2H, m), 7.71 (1H, d J = 3.0 Hz). |
| 439 | —H | —CO— | benzyl | $—CH_2—$ | 2.38 4H, brs); 3.33 2H, brs), 3.50 (4H, brs), 5.17 (2H, brs), 6.82 (1H, d, J = 8.6 Hz), 6.96 (2H, d, J = 8.7 Hz), 7.10 (1H, dd, J = 8.6 Hz, 3.0 Hz), 7.27-7.33 (5H, m), 7.36 (2H, d, J = 8.7 Hz), 7.57 (1H, d, J = 3.0 Hz). |
| 440 | —H | —CO— | $4-CH_3OPhCH_2—$ | $—CH_2—$ | 2.44 (4H, brs), 3.48 (2H, s), 3.59 (4H, brs), 3.81 (3H, s), 6.80 (1H, dd, J = 8.6 Hz, 0.7 Hz), 6.85-6.89 (2H, m), 7.03-7.08 (2H, m), 7.11 (1H, dd, J = 8.6 Hz, 3.0 Hz), 7.21-7.26 (2H, m), 7.38-7.43 (2H, m), 7.73-7.75 (1H, m). |
| 441 | —H | $—SO_2—$ | benzyl | $—CH_2$13 | 2.42-2.57 (4H, m), 2.91-3.10 (4H, m), 3.47 (2H, s), 3.63 (2H, brs), 6.83 (1H, d, J = 8.6 Hz), 7.07-7.14 (3H, m), 7.18-7.31 (5H, m), 7.68 (2H, d, J = 8.8 Hz), 7.74 (1H, d, J = 2.0 Hz). |

TABLE 63

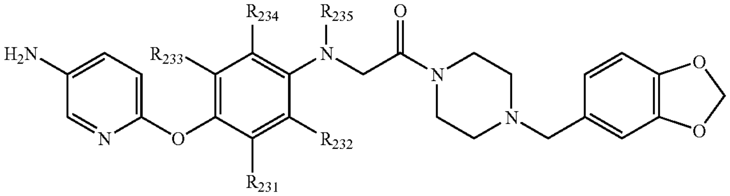

| Reference Example No. | $R_{231}$ | $R_{232}$ | $R_{233}$ | $R_{234}$ | $R_{235}$ | 'H NMR ($CDCl_3$) δ ppm |
|---|---|---|---|---|---|---|
| 442 | —F | —H | —H | —H | —H | 2.43-2.48 (4H, m), 3.44-3.47 (6H, m) 3.67-3.68 (2H, m), 3.82 (2H, d, J = 4.1 Hz), |

TABLE 63-continued

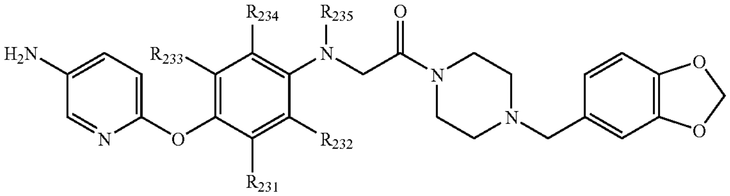

| Reference Example No. | $R_{231}$ | $R_{232}$ | $R_{233}$ | $R_{234}$ | $R_{235}$ | $^1H$ NMR ($CDCl_3$) δ ppm |
|---|---|---|---|---|---|---|
| | | | | | | 4.96 (1H, brs), 5.96 (2H, s), 6.36-6.43 (2H, m), 6.71-6.78 (3H, m), 6.86 (1H, brs), 6.97-7.03 (1H, m), 7.06 (1H, dd, J = 8.7 Hz, 3.0 Hz), 7.63 (1H, d, J = 3.0 Hz). |
| 443 | —F | —H | —H | —H | $—CH_3$ | 2.43-2.45 (4H, m), 3.01 (3H, s), 3.44 (2H, s), 3.47 (2H, brs), 3.63 (2H, brs), 4.07 (2H, s), 5.95 (2H, s), 6.39-6.50 (2H, m), 6.72-6.76 (3H, m), 6.85 (1H, s), 7.00-7.08 (2H, m), 7.63 (1H, dd, J = 3.0 Hz, 0.5 Hz). |
| 444 | —F | —H | —H | —H | $—C_2H_5$ | 1.18 (3H, t, J = 7.1 Hz), 2.43 (4H, t, J = 5.0 Hz), 3.37-3.48 (8H, m), 3.63 (2H, brs), 4.01 (2H, s), 5.95 (2H, s), 6.35-6.46 (2H, m), 6.72-6.77 (3H, m), 6.85 (1H, s), 6.99 (1H d, J = 8.9 Hz), 7.05 (1H, dd, J = 8.7 Hz, 3.0 Hz), 7.63 (1H, d, J = 3.0 Hz). |
| 445 | —F | —H | —H | —F | $CH_3$ | 2.33-2.49 (4H, m), 2.93 (3H s), 3.38-3.68 (8H, m), 4.00 (2H, s), 5.95 (2H, s), 6.71-6.77 (2H, s), 6.78-6.82 (2H, m), 6.83-6.91 (2H, m), 7.08 (1H, dd, J = 2.9 Hz, 8.6 Hz), 7.62 (1H, d, J = 2.9 Hz). |
| 446 | —F | —H | —H | —F | $—C_2H_5$ | 1.11 (3H, t, J = 7.1 Hz), 2.31-2.49 (4H, m), 3.29 (2H, q, J = 7.1 Hz), 3.41 (2H, s), 3.42-3.69 (6H, m), 3.96 (2H, s), 6.70-6.78 (2H, m), 6.79-6.91 (4H m), 7.08 (1H, dd, J = 2.9 Hz, 8.6 Hz), 7.62 (1H, d, J = 2.9 Hz). |
| 447 | —F | —H | —F | —H | $—CH_3$ | 2.36-2.52 (4H, m), 3.01 (3H, s), 3.34-3.54 (6H, m), 3.55-3.71 (2H, m), 4.05 (2H, s), 5.95 (2H, s), 6.18-6.29 (2H, m), 6.70-6.79 (2H, m), 6.82 (1H, d, J = 8.6 Hz), 6.85 (1H, d, J = 0.98 Hz), 7.07 (1H, dd, J = 2.9 Hz, 8.6 Hz), 7.59 (1H, d, J = 2.9 Hz). |
| 448 | —F | —F | —H | —H | $—CH_3$ | 2.29-2.55 (4H, m), 2.95 (3H s), 3.30-3.75 (8H, m), 4.01 (2H, s), 5.95 (2H, s), 6.60-6.95 (6H, m), 7.09 (1H, dd, J = 3.0 Hz, 8.6 Hz), 7.62 (1H, d, J = 3.0 Hz). |
| 449 | $—CH_3$ | $—CH_3$ | —H | —H | $—CH_3$ | 2.11 (3H, s), 2.25 (3H, s), 2.36-2.42 (4H, m), 2.66 (3H, s) 3.41 (2H, s), 3.45 (2H, brs), 3.53-3.56 (2H, m), 3.61-3.64 (2H, m), 3.73 (2H, s), 5.95 (2H, s) 6.67 (1H, d, J = 8.7 Hz) 6.70-6.85 (4H, m), 6.95 (1H, d, J = 8.7 Hz), 7.03-7.08 (1H, m), 7.67 (1H, d, J = 3.0 Hz). |
| 450 | $—CH_3$ | —H | —H | —H | 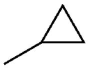 | 0.62-0.66 (2H, m), 0.76-0.83 (2H, m), 2.12 (3H, s), 2.40-2.46 (4H, m), 2.73-2.81 (1H, m), 3.43 (2H, s), 3.48-3.63 (4H, m), 4.15 (2H, s), 5.94 (2H, s) 6.58 (1H, d, J = 8.7 Hz), 6.68-6.77 (4H, m), 6.87 (2H, d, J = 8.6 Hz), 7.01 (1H, dd, J = 8.7 Hz, 3.0 Hz), 7.67 (1H, d, J = 3.0 Hz). |

TABLE 64

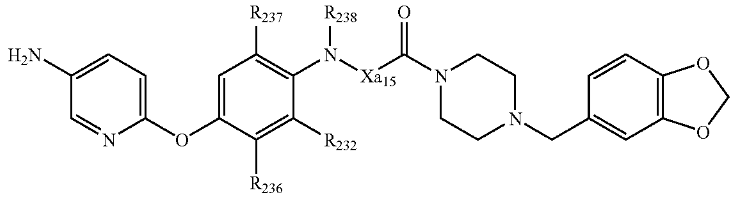

| Reference Example No. | $R_{236}$ | $R_{237}$ | $R_{238}$ | $Xa_{15}$ | $^1$H NMR ($CDCl_3$) δppm or MS |
|---|---|---|---|---|---|
| 451 | —$CH_3$ | —H | —H | —CO— | $^1$H NMR 2.20 (3H, s), 2.48-2.54 (4H, m), 3.44 (4H, s), 3.67-3.75 (2H, m), 4.23-4.27 (2H, m), 5.95 (2H, s), 6.68-6.78 (3H, m), 6.86 (1H, brs), 6.95 (1H, d, J = 8.7 Hz), 7.07 (1H, dd, J = 8.6 Hz, 3.0 Hz), 7.37 (1H, dd, J = 8.7 Hz, 2.6 Hz), 7.52 (1H, d, J = 2.5 Hz), 7.66 (1H, d, J = 3.0 Hz), 9.13 (1H, brs). |
| 452 | —$CH_3$ | —H | —$CH_3$ | —CO— | $^1$H NMR 2.21-2.31 (7H, m), 3.28-3.40 (9H, m), 3.53 (2H, brs), 5.93 (2H, s), 6.66-6.80 (4H, m,) 6.91 (1H, d, J = 8.6 Hz), 7.03-7.12 (3H, m), 7.66 (1H, d, J = 3.0 Hz). |
| 453 | —H | —H | —$SO_2CH_3$ | —$CH_2$— | $^1$H NMR 2.41 (4H, brs), 3.19 (3H, s), 3.34-3.38 (2H, m), 3.42 (2H, s), 3.57-3.60 (4H, m), 4.51 (2H, s), 5.95 (2H, s), 6.70-6.77 (2H, m), 6.80 (1H, d, J = 8.6 Hz), 6.84 (1H, brs), 7.02 (2H, d, J = 8.7 Hz), 7.10 (1H, dd, J = 8.6 Hz, 3.0 Hz), 7.59 (2H, d, J = 8.7 Hz), 7.71 (1H, d, J = 3.0 Hz). |
| 454 | —$CH_3$ | —H | —$SO_2CH_3$ | —$CH_2$— | $^1$H NMR 2.21 (3H, s), 2.41 (4H, brs), 3.20 (3H, s), 3.34-3.38 (2H, m), 3.42 (2H, s), 3.53 (2H, brs), 3.59-3.61 (2H, m), 4.51 (2H, s), 5.94 (2H, s), 6.70-6.77 (3H, m), 6.83 (1H, brs), 6.90 (1H, d, J = 8.6 Hz), 7.09 (1H, dd, J = 8.6 Hz, 3.0 Hz), 7.36 (1H, dd, J = 8.6 Hz, 2.1 Hz), 7.42 (1H, d, J = 2.3 Hz), 7.66 (1H, d, J = 3.0 Hz). |
| 455 | —$CF_3$ | —H | —$C_2H_5$ | —$CH_2$— | MS 557 ($M^+$) |
| 456 | —$CF_3$ | —H | —$CH_3$ | —$CH_2$— | MS 543 ($M^+$) |
| 457 | —CN | —H | —$CH_3$ | —$CH_2$— | MS 500 ($M^+$) |
| 458 | —$OCH_3$ | —H | —$SO_2CH_3$ | —$CH_2$— | $^1$H NMR 2.48 (4H, brs), 3.26 (3H, s), 3.42-3.66 (8H, m), 3.82 (3H, s), 4.58 (2H, s), 5.99 (2H, s), 6.77-6.79 (2H, m), 6.81-6.88 (2H, m), 7.06-7.30 (4H, m), 7.67 (1H, d, J = 2.3 Hz). |
| 459 | —$CH_3$ | —$CH_3$ | —$CH_3$ | —$CH_2$— | MS 503 ($M^+$) |

TABLE 65

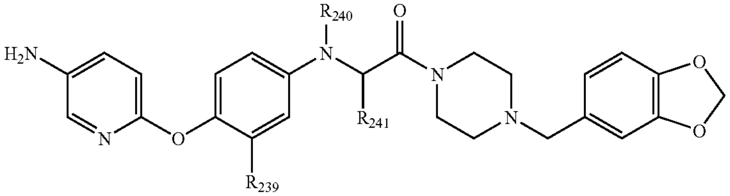

| Reference Example No. | $R_{239}$ | $R_{240}$ | $R_{241}$ | $^1$H NMR ($CDCl_3$) δ ppm |
|---|---|---|---|---|
| 460 | —H | —$CH_3$ | —H | 2.40-2.44 (4H, m), 3.00 (3H, s), 3.49 (4H, brs), 3.63 (2H, brs), 4.05 (2H, s), 5.95 (2H, s), 6.67 (1H, d, J = 8.6 Hz), 6.69 (2H, d, J = 9.1 Hz), 6.74 (2H, brs), 6.85 (1H, brs), 6.97 (2H, d, J = 9.1 Hz), 7.03 (1H, dd, J = 8.6 Hz, 3.0 Hz), 7.68 (1H, d, J = 3.0 Hz). |
| 461 | —H | —$CH_3$ | —$CH_3$ | 1.28 (3H, d, J = 6.6 Hz, 2.14-2.21 1H, m), 2.28-2.35 (2H, m) 2.47-2.49 (1H, m), 2.75 (3H, s), 3.24-3.54 (3H, m), 3.38 (2H, s), 3.45 (2H, s), 3.78-3.84 (1H, m), 4.54 (1H, q, J = 6.8 Hz), 5.93 (2H, s), 6.68-6.75 (5H, m), 6.82 (1H, s), 6.99 (2H, d, J = 9.1 Hz), 7.05 (1H, dd, J = 8.6 Hz, 3.0 Hz), 7.69 (1H, dd, J = 3.1 Hz, 0.7 Hz). |

TABLE 65-continued

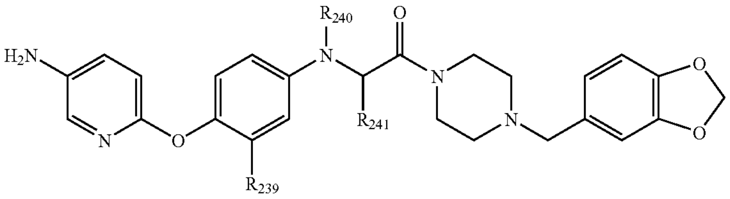

| Reference Example No. | $R_{239}$ | $R_{240}$ | $R_{241}$ | $^1H$ NMR ($CDCl_3$) δ ppm |
|---|---|---|---|---|
| 462 | —$CH_3$ | —$CH_3$ | —$CH_3$ | 1.28(3H, d, J 6.6 Hz), 2.15(3H, s), 2.15-2.21(1H, in), 2.33-2.36 (2H, m), 2.49 (1H, brs), 2.74 (3H, s), 3.25-3.55 (3H, m), 3.39 (2H, s), 3.42 (2H, s), 3.80 (1H, brs), 4.55 (1H, q, J = 6.4 Hz), 5.93 (2H, s), 6.55-6.59 (2H, m), 6.64 (1H, dd, J = 8.6 Hz, 0.5 Hz), 6.69-6.75 (2H, m), 6.83 (1H, brs), 6.90 (1H, d, J = 8.7 Hz), 7.04 (1H, dd, J = 8.7 Hz, 3.0 Hz), 7.67 (1H, dd, J = 3.0 Hz, 0.7 Hz). |
| 463 | —$OCH_3$ | —$CH_3$ | —H | 2.31-2.50 (4H, m), 3.02 (3H, s), 3.31-3.57 (6H, m), 3.58-3.70 (2H, m), 3.76 (3H, s), 4.06 (2H, s), 5.95 (2H, s), 6.24 (1H, dd, J = 8.7 Hz, 2.8 Hz), 6.37 (1H, d, J = 2.8 Hz), 6.68 (1H, d, J = 8.6 Hz), 6.69-6.79 (2H, m), 6.85 (1H, s), 6.94 (1H, d, J = 8.7 Hz), 7.02 (1H, dd, J = 8.6 Hz, 3.0 Hz), 7.65 (1H, d, J = 3.0 Hz). |
| 464 | —$OCH_3$ | —$C_2H_5$ | —H | 1.18 (3H, t, J = 7.0 Hz), 2.31-2.51 (4H, m), 3.28-3.70 (10 H, m), 3.74 (3H, s), 4.01 (2H, s), 5.95 (2H, s), 6.22 (1H, dd, J = 8.7 Hz, 2.8 Hz), 6.35 (1H, d, J = 2.8 Hz), 6.68 (1H dd, J = 8.7 Hz, 0.5 Hz), 6.69-6.79 (2H, m), 6.81-6.88 (1H, m), 6.93 (1H, d, J = 8.7 Hz), 7.03 (1H, dd, J = 8.7 Hz, 3.0 Hz), 7.65 (1H, dd, J = 3.0 Hz, 0.5 Hz). |
| 465 | —$CH_3$ | —$CH_3$ | —H | 2.13 (3H, s), 2.42 (4H, t, J = 3.0 Hz), 2.99 (3H, s), 3.35-3.57 (6H, m), 3.58-3.70 (2H, m), 4.05 (2H, s), 5.95 (2H, s), 6.53 (1H, dd, J = 8.8 Hz, 3.1 Hz), 6.57 (1H, d, J = 3.1 Hz), 6.60 (1H, d, J = 8.8 Hz), 6.71-6.78 (2H, m), 6.85 (1H, brs), 6.88 (1H, d, J = 8.7 Hz), 7.02 (1H, dd, J = 8.7 Hz, 3.0 Hz), 7.67 (1H, d, J = 3.0 Hz). |
| 466 | —$CH_3$ | —$C_2H_5$ | —H | 1.15 (3H, t, J = 7.0 Hz), 2.12 (3H, s), 2.42 (4H, t, J = 5.1 Hz), 3.27-3.70 (10H, m), 4.00 (2H, s), 5.95 (2H, s), 6.46-6.57 (2H, m), 6.60 (1H, dd, J = 8.7 Hz, 0.5 Hz), 6.69-6.78 (2H, m), 6.82-6.90 (2H, m), 7.02 (1H, dd, J = 8.7 Hz, 3.0 Hz), 7.68 (1H, dd, J = 3.0 Hz, 0.5 Hz). |
| 467 | —$CH_3$ | —Ac | —H | 1.95 (3H, s), 2.23 (3H, s), 2.31-2.52 (4H, m), 3.29-3.70 (8H, m), 4.43 (2H, s), 5.94 (2H, s), 6.69-6.79 (3H, m), 6.84 (1H, s), 6.92 (1H, d, J = 8.5 Hz), 7.10 (1H, dd, J = 8.6 Hz, 3.0 Hz), 7.19 (1H, dd, J = 8.5 Hz, 2.5 Hz), 7.28 (1H, d, J = 2.2 Hz), 7.68 (1H, d, J = 2.5 Hz). |

TABLE 66

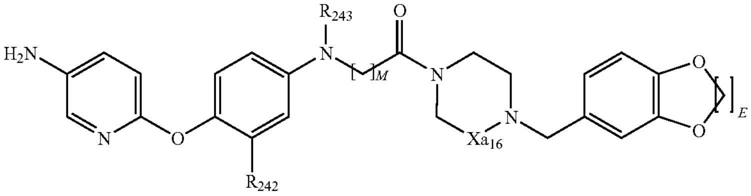

| Reference Example No. | $R_{242}$ | $R_{243}$ | $Xa_{16}$ | M | E | $^1H$ NMR (solvent) δ ppm |
|---|---|---|---|---|---|---|
| 468 | —$OCH_3$ | —H | —$CH_2$— | 1 | 1 | (DMSO-$d_6$) 2.32-2.40 (4H, m), 3.32 (2H, brs), 3.50 (4H, brs), 3.61 (3H, s), 3.88 (2H, brs), 4.88 (2H, brs), 5.44 (1H, brs), 5.99 (2H, s), 6.15 (1H, dd, J = 8.6 Hz, 2.5 Hz), 6.44 (1H, d, J = 2.3 Hz), 6.51 (1H, d, J = 8.6 Hz), 6.71-6.88 (4H, m), 6.98 (1H, dd, J = 8.6 Hz, 2.8 Hz), 7.40 (1H, d, J = 2.6 Hz). |
| 469 | —$OCR_3$ | —H | —$CH_2$— | 1 | 2 | (DMSO-$d_6$) 2.32 (2H, brs), 2.40 (2R, brs), 3.39 (2H, s), 3.49 (4H, brs), 3.61 (3H s), 3.89 (2H, brd), 4.22 (4H, s), 4.82 (2R, brs), 5.44 (1R, brt), 6.15 (1H, dd, J = 8.6 Hz, 2.5 |

TABLE 66-continued

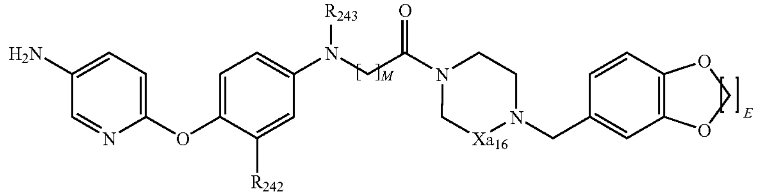

| Reference Example No. | $R_{242}$ | $R_{243}$ | $Xa_{16}$ | M | E | $^1H$ NMR (solvent) δ ppm |
|---|---|---|---|---|---|---|
| | | | | | | Hz), 6.44-6.52 (2H, m), 6.70-6.81 (4H, m), 6.98 (1H, dd, J = 8.7 Hz, 3.0 Hz), 7.39 (1H, d, J = 2.8 Hz). |
| 470 | —H | —$CH_3$ | —$CH_2$— | 2 | 1 | ($CDCl_3$) 2.35 (4H, tt, J = 5.0 Hz, 5.0 Hz), 2.52-2.58 (2R, m), 2.91 (3H, s), 3.36-3.39 (4R, m), 3.59-3.62 (2H, m), 3.65-3.73 (4R, m), 5.93 (2H, s), 6.64-6.76 (5H, m), 6.83 (1H, d, J = 1.0 Hz), 6.97 (2H, d, J = 9.1 Hz), 7.03 (1H, dd, J = 8.6 Hz; 3.1 Hz), 7.66 (1H, dd, J = 3.1 Hz, 0.5 Hz). |
| 471 | —$CH_3$ | —$CH_3$ | —CO— | 1 | 1 | ($CDCl_3$) 2.12 (3R, s), 2.88-3.10 (3H, m), 3.26 (2H, t, J = 5.3 Hz), 340 (2H, brs), 3.60-3.90 (2H, m), 4.00-4.15 (2R, m), 4.20-4.40 (2H, m), 4.52 (2H, s), 5.95 (2H, s), 6.53 (1H, dd, J = 8.5 Hz, 3.0 Hz), 6.60 (1H, s), 6.60 (1H, d, J = 8.5 Hz), 6.71 (1H, d, J = 8.5 Hz), 6.74 (1R, s), 6.76 (1H, d, J = 8.5 Hz), 6.88 (1H, d, J = 8.8 Hz), 7.02 (1R, dd, J = 8.5 Hz, 2.8 Hz), 7.66 (1H, d, J = 2.8 Hz). |
| 472 | —$OCH_3$ | —$C_2H_5$ | —CO— | 1 | 1 | ($CDCl_3$) 1.17 (3H, t, J = 7.0 Hz), 3.20-3.31 (2H, m), 3.40-3.60 (2H, m), 3.41 (2H, q, J = 7.0 Hz), 3.61-3.82 (2H, m), 3.74 (3R, s), 4.02 (2R, s), 4.30 (2R, s), 4.50 (2H, s), 5.95 (2R, s), 6.24 (1H, dd, J = 8.7 Hz, 2.8 Hz), 6.40 (1H, s), 6.68 (1H, d, J = 8.6 Hz), 6.70 (1H, dd, J = 7.9 Hz, 1.5 Hz), 6.76 (1H, s, J = 1.5 Hz), 6.76 (1H, d, J = 7.9 Hz), 6.93 (1H, d, J = 8.6 Hz), 7.03 (1H, dd, J = 8.5 Hz, 2.8 Hz), 7.64 (1H, d, J = 2.8 Hz). |

(E means the number of the methylene groups. Hereinafter E indicates the same meaning.)

TABLE 67

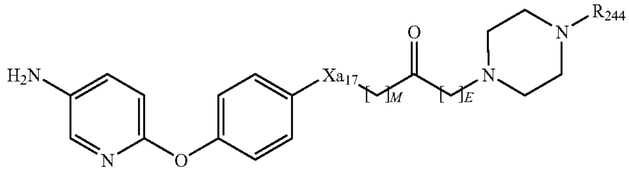

| Reference Example No. | $Xa_{17}$ | M | E | $R_{244}$ | Form | mp (° C.) or $^1H$ NMR ($CDCl_3$) δ ppm |
|---|---|---|---|---|---|---|
| 473 | —$CH_2$— | 1 | 0 | benzyl | free | $^1H$ NMR 2.33-2.43 (4H, m), 2.57-2.63 (2H, m), 2.91-2.97 (2H, m), 3.38-3.42 (4H, m), 3.50 (2H, s), 3.62-3.65 (2H, m), 6.75 (1H, dd, J = 8.6 Hz, 0.5 Hz), 6.95-7.00 (2H, m), 7.07 (1H, dd, J = 8.6 Hz, 3.0 Hz), 7.15-7.20 (2H, m), 7.28-7.33 (5H, m), 7.70 (1H, dd, J = 3.0 Hz, 0.5 Hz). |
| 474 | —$CH_2$— | 1 | 0 | piperonyl | trihydro-chloride | mp 179-180 dec |
| 475 | —O— | 1 | 0 | piperonyl | free | $^1H$ NMR 2.41 (4H, brs), 3.42 (2H, s), 3.48 (2H, brs), 3.50-3.70 (4H, m), 4.65 (2H, s), 5.95 (2H, s), 6.72 (1H, d, J = 8.6 Hz), 6.74 (2H, brs), 6.85 (1H, brs, 6.91 (2H, d, J = 9.2 Hz), 7.00 (2H, d, J = 9.2 Hz), 7.06 (1H, dd, |

TABLE 67-continued

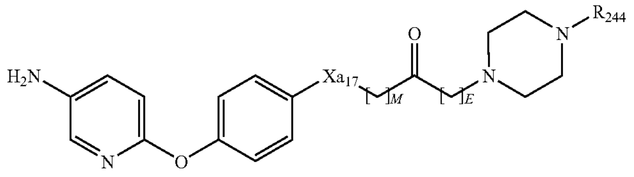

| Reference Example No. | $Xa_{17}$ | M | E | $R_{244}$ | Form | mp (° C.) or $^1H$ NMR ($CDCl_3$) δ ppm |
|---|---|---|---|---|---|---|
| | | | | | | J = 8.6 Hz, 3.0 Hz), 7.69 (1H, d, J = 3.0 Hz). |
| 476 | —O— | 1 | 0 | benzyl | free | $^1H$ NMR 2.44 (4H, t, J = 5.0 Hz), 3.51 (4H, s), 3.58 (2H, t, J = 5.0 Hz), 3.64 (2H, t, J = 5.0 Hz), 4.65 (2H, s), 6.72 (1H, d, J = 8.5 Hz), 6.92 (2H, d, J = 9.2 Hz), 7.00 (2H, d, J = 9.2 Hz), 7.06 (1H, dd, J = 8.5 Hz, 3.0 Hz), 7.22-7.35 (5H, m), 7.69 (1H, d, J = 3.0 Hz). |
| 477 | —NH— | 0 | 1 | piperonyl | free | $^1H$ NMR 2.51 (4H, brs), 2.62-2.63 (4H, m), 3.12 (2H, s), 3.45 (2H, s), 3.52 (2H, brs), 5.94 (2H, s), 6.74 (1H, dd, J = 8.7 Hz, 0.7 Hz), 6.75 (2H, brs), 6.85 (1H, s), 7.03 (2H, d, J = 8.9 Hz), 7.07 (1H, dd, J = 8.7 Hz, 3.0 Hz), 7.54 (2H, d, J = 9.1 Hz), 7.69 (1H, dd, J = 3.0 Hz, 0.7 Hz), 9.10 (1H, brs). |
| 478 | —N($CH_3$)— | 0 | 1 | piperonyl | free | $^1H$ NMR 2.44 (8H, brs), 2.93 (2H, s), 3.24 (3H, s), 3.38 (2H, s), 3.62 (2H, brs), 5.92 (2H, s), 6.72 (2H, brs), 6.80-6.84 (2H, m), 7.06 (2H, d, J = 9.1 Hz), 7.12 (1H, dd, J = 8.6 Hz, 3.1 Hz), 7.15 (2H, d, J = 8.9 Hz), 7.73 (1H, d, J = 3.0 Hz). |

TABLE 68

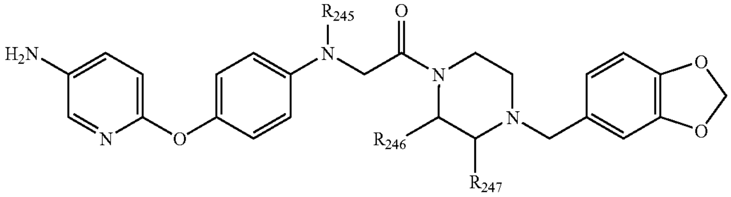

| Reference Example No. | $R_{245}$ | $R_{246}$ | $R_{247}$ | $^1H$ NMR ($CDCl_3$) δ ppm |
|---|---|---|---|---|
| 479 | —$CH_3$ | —H | —$CH_3$ | 1.12 (3H, d, J = 6.3 Hz), 2.10-2.12 (1H, m), 2.47 (1H, brs), 2.67-2.72 (1H, m), 2.80-3.11 (6H, m), 3.47-3.60 (3H, m), 3.84-4.10 (4H, m), 5.94 (2H, s), 6.64-6.74 (5H, m), 6.85 (1H, brs), 6.94-6.98 (2H, m), 7.00-7.05 (1H, m), 7.68 (1H, d, J = 2.8 Hz). |
| 480 | —$CH_3$ | —$CH_3$ | —H | 1.28-1.37 (3H, m), 1.94-2.03 (1H, m), 2.11-2.15 (1H, m), 2.63-2.67 (1H, m), 2.79-2.82 (1H, m), 2.95-3.00 (4H, m), 3.30-3.46 (5H, m), 4.03-4.69 (3H, m), 5.94 (2H, s), 6.66 (1H, d, J = 8.7 H), 6.68 (2H, d, J = 9.1 H), 6.74 (2H, brs), 6.87 (1H, brs), 6.96 (2H, d, J = 9.1 Hz), 7.03 (1H, dd, J = 8.7 Hz, 3.0 Hz), 7.68 (1H, d, J = 3.0 Hz). |
| 481 | —$C_2H_5$ | —H | —$CH_3$ | 1.11-1.18 (6H, m), 2.04-2.13 (1H, m), 2.45-2.47 (1H, m), 2.66-2.73 (1H, m), 2.85-3.64 (8H, m), 3.84-4.11 (4H, m), 5.94 (2H, s), 6.64-6.69 (3H, m), 6.74 (2H, brs), 6.85 (1H, brs), 6.93-6.96 (2H, m), 7.03 (1H, dd, J = 8.7 Hz, 3.0 Hz), 7.69 (1H, d, J = 3.0 Hz). |
| 482 | —$C_2H_5$ | —$CH_3$ | —H | 1.15 (3H, t, J = 7.1 Hz), 1.26-1.70 (3H, m), 1.94-2.04 (1H, m), 2.14-2.17 (1H, m), 2.63-2.67 (1H, m), 2.80 (1H, brs), 3.01-3.59 (8H, m), 3.73-4.71 (3H, m), 5.95 (2H, s), 6.63-6.70 (3H, m), 6.74 (2H, brs), 6.87 (1H, brs), 6.95 (2H, d, J = 9.1 Hz), 7.03 (1H, dd, J = 8.6 Hz, 3.0 Hz), 7.69 (1H, dd, J = 3.0 Hz, 0.7 Hz). |

TABLE 69

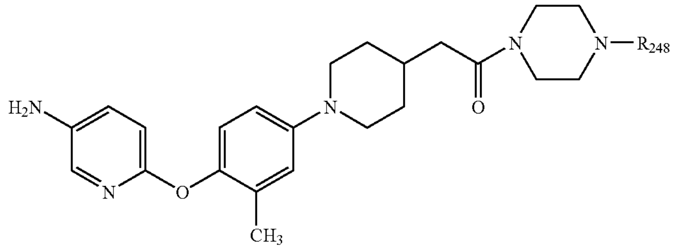

| Reference Example No. | $R_{248}$ | $^1H$ NMR ($CDCl_3$) δ ppm |
|---|---|---|
| 483 | piperonyl | 1.36-1.46 (2H, m), 1.82-1.99 (3H, m), 2.13 (3H, s), 2.28 (2H, d, J = 6.8 Hz), 2.41 (4H, brs), 2.70 (2H, t, J = 12.0 Hz), 3.41-3.76 (10 H, m), 5.94 (2H, s), 6.59-6.89 (7H, m), 7.03 (1H, dd, J = 8.6 Hz, 3.0 Hz), 7.67-7.69 (1H, m). |
| 484 | benzyl | 1.33-1.42 (2H, m), 1.82-1.98 (3H, m), 2.04 (3H, s), 2.28 (2H, d, J = 6.8 Hz), 2.41-2.45 (4H, m), 2.70 (2H, t, J = 12.0 Hz), 3.51-3.78 (10 H, m), 6.60 (1H, d, J = 8.6 Hz), 6.69-6.92 (3H, m), 7.03 (1H, dd, J = 8.6 Hz, 3.0 Hz), 7.28-7.33 (5H, m), 7.67 (1H, d, J = 2.5 Hz). |

TABLE 70

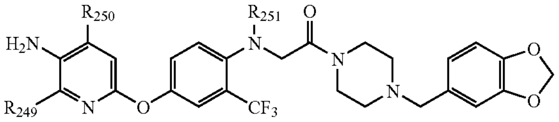

| Reference Example No. | $R_{249}$ | $R_{250}$ | $R_{251}$ | MS ($M^+$) |
|---|---|---|---|---|
| 485 | —H | —H | —$C_2H_5$ | 557 |
| 486 | —H | —$CH_3$ | —$CH_3$ | 557 |
| 487 | —$CH_3$ | —H | —$CH_3$ | 557 |

Reference Example 488

Production of ethyl[4-(4-amino-2-fluorophenoxy)phenylsulfanyl]acetate

To a solution of ethyl[4-(2-fluoro-4-nitrophenoxy)phenylsulfanyl]acetate (4.93 g, 14.0 mmol) in ethanol (100 mL) was added tin chloride dihydrate (9.50 g, 42.1 mmol), and the resulting solution was stirred for 8 hours at 50° C. Water was added to the reaction mixture and extracted with ethyl acetate. The ethyl acetate layer was washed with 1 M hydrochloric acid, a saturated sodium bicarbonate solution, and brine, dried over anhydrous sodium sulfate, and evaporated, to thereby yield 3.45 g of the title compound.

Appearance: Brown oil $^1H$ NMR ($CDCl_3$) δ 1.20 (3H, t, J=7.1 Hz), 3.53 (2H, s), 3.80-4.20 (4H, m), 6.37-6.45 (1H, m), 6.49 (1H, dd, J=2.6 Hz, 12.0 Hz), 6.80-7.00 (3H, m>, 7.38 (2H, d, J=8.9 Hz).

The following compounds were produced in the same manner as in Reference Example 488.

Reference Example 489

2-{Allyl[4-(5-aminopyridin-2-yloxy)-3-fluorophenyl]amino}-1-(4-piperonylpiperazin-1-yl)ethanone $^1H$ NMR ($CDCl_3$) δ 2.44-2.46 (4H, m), 3.44 (4H, brs), 3.44 (2H, s), 3.83 (2H, brs), 3.98 (2H, d, J=4.8 Hz), 4.03 (2H, s), 5.16-5.30 (2H, m), 5.82-5.95 (1H, m), 5.95 (2H, s), 6.35-6.46 (2H, m), 6.71-6.74 (3H, m), 6.85-6.87 (1H, m), 6.96-7.07 (2H, m), 7.63-7.64 (1H, m).

Reference Example 490

(E)-3-[3-(5-Aminopyridin-2-yloxy)phenyl]-1-(4-piperonylpiperazin-1-yl)propenone

MS 458 ($M^+$).

Reference Example 491

Production of methyl 3-[4-(5-aminopyridin-2-ylsulfanyl)phenyl]propionate

To a solution of methyl 3-[4-(5-nitropyridin-2-ylsulfanyl)phenyl]propionate (2.97 g, 9.33 mmol) in methanol (50 mL) were added sodium borohydride (0.590 g, 15.6 mmol) and 10% palladium-carbon (1.80 g), and the resulting solution was stirred for 24 hours at room temperature under a hydrogen atmosphere at atmospheric pressure. The reaction solution was filtered through Celite, and to the resulting filtrate was added concentrated hydrochloric acid (1.5 mL), and concentrated under reduced pressure. To the residue was added a saturated sodium bicarbonate solution, and extracted with ethyl acetate, and the ethyl acetate layer was washed with brine. The ethyl acetate layer was dried over anhydrous magnesium sulfate, and evaporated, to thereby yield 2.49 g of the title compound.

Appearance: Yellow powder $^1H$ NMR ($CDCl_3$) δ 2.62 (2H, t, J=7.6 Hz), 2.93 (2H, t, J=7.6 Hz), 3.67 (3H, s), 6.87 (1H, dd, J=2.9 Hz, 8.4 Hz), 6.98 (1H, d, J=8.4 Hz), 7.15 (2H, d, J=8.2 Hz), 7.35 (2H, d, J=>8.2 Hz), 8.01 (1H, d, J=2.9 Hz).

Reference Example 492

Production of ethyl 3-[4-(5-aminopyridin-2-yloxy)phenyl]acrylate

To a solution of ethyl 3-[4-(5-nitropyridin-2-yloxy)phenyl]acrylate (2.02 g, 6.43 mmol) in methanol (100 mL) were added zinc (6.3 g, 96.3 mmol) and ammonium chloride (710 mg, 13.27 mmol). The resulting reaction solution was stirred for 2.5 hours under reflux, then acetic acid (5 mL) was added, and stirred for 20 minutes under reflux. Insoluble matter was filtered off through Celite, after which the filtrate was concentrated under reduced pressure. To the residue was added 5% potassium hydrogensulfate (150 mL), the mixture was extracted with dichloromethane, and the dichloromethane layer was washed with a saturated sodium bicarbonate solution and brine. The dichloromethane layer was dried over anhydrous magnesium sulfate, and evaporated, to thereby yield 1.78 g of the title compound.

Appearance: Yellow oil $^1$H NMR ($CDCl_3$) δ 1.34 (3H, t, J=7.1 Hz), 3.58 (2H, brs), 4.26 (2H, q, J=7.1 Hz), 6.35 (1H, dd, J=16.0 Hz, 2.0 Hz), 6.81 (1H, d, J=8.6 Hz), 7.05 (2H, d, J=8.6 Hz), 7.10 (1H, dd, J=8.6 Hz, 3.0 Hz), 7.50 (2H, d, J=8.6 Hz), 7.66 (1H, dd, J=16.0 Hz, 3.0 Hz), 7.73 (1H, d, J=3.0 Hz).

Reference Example 493

Production of 3-(4-(5-amino-4-methylpyridin-2-yloxy)phenyl)-1-(4-piperonylpiperazin-1-yl)propan-1-one 3-(4-hydroxyphenyl)-1-(4-piperonylpiperazin-1-yl)propan-1-one (0.38 g, 1.0 mmol) was dissolved in DMF (6 mL). To the resulting solution was added 60% sodium hydride (0.05 g, 1.2 mmol) and 2-chloro-4-methyl-5-nitropyridine (0.196 g, 1.1 mmol), and the resulting reaction solution was stirred overnight at room temperature. To the reaction solution was added saturated aqueous ammonium chloride, and extracted with ethyl acetate. The ethyl acetate layer was washed with water and brine. The ethyl acetate layer was dried over anhydrous magnesium sulfate, evaporated, and the residue was purified by silica gel column chromatography (ethyl acetate), to thereby yield the intermediate product 3-(4-(4-methyl-5-nitropyridin-2-yloxy)phenyl)-1-(4-piperonylpiperazin-1-yl)propan-1-one.

The 3-(4-(4-methyl-5-nitropyridin-2-yloxy)phenyl)-1-(4-piperonylpiperazin-1-yl)propan-1-one was dissolved in a mixed solvent consisting of ethanol (4 mL) and dioxane (1 mL). To this solution was added 10% palladium-carbon (0.034 g), and the resulting solution was subjected to catalytic reduction for 8 hours at atmospheric pressure and room temperature. The catalyst was removed by filtration, and the filtrate was concentrated under reduced pressure, and the residue was purified by silica gel chromatography (dichloromethane:methanol=20:1), to thereby yield 0.22 g of the title compound.

Appearance: Slightly yellow oil $^1$H NMR ($CDCl_3$) δ 2.18 (3H, s), 2.30-2.45 (4H, m), 2.56-2.63 (2H, m), 2.91-2.97 (2H, m), 3.30-3.50 (6H, m), 3.55-3.70 (2H, m), 5.95 (2H, s), 6.65-6.80 (3H, m), 6.84 (1H, s), 6.95-7.05 (2H, m), 7.15-7.20 (2H, m), 7.64 (1H, s).

Reference Example 494

Production of ethyl 3-{4-[4-(3,4-dichlorobenzoylamino)-phenoxy]phenyl}propionate A solution of 3,4-dichlorobenzoyl chloride (3.65 g, 17.4 mmol) was added dropwise under ice cooling to a solution of ethyl 3-[4-(4-aminophenoxy)phenyl]propionate (4.52 g, 15.9 mmol) and triethylamine (2.65 mL, 19.0 mmol) in THF (80 mL), and the resulting solution was stirred for 1 hour at the same temperature. Water was added to the reaction mixture, and extracted with ethyl acetate. The ethyl acetate layer was washed with a saturated sodium bicarbonate solution and brine. The ethyl acetate layer was dried over anhydrous magnesium sulfate and evaporated. The residue was recrystallized from water-containing ethanol to thereby yield 6.67 g of the title compound.

Appearance: Colorless needles

Melting point: 139-141° C.

The following compounds were produced in the same manner as in Reference Example 494.

Reference Example 495

Ethyl 3-[4-(5-phenoxycarbonylaminopyridin-2-yloxy)phenyl]propionate

MS 406 ($M^+$).

TABLE 71

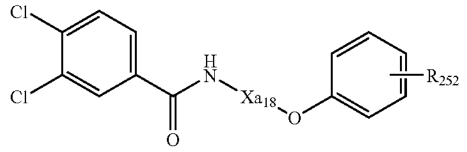

| Reference Example No. | $Xa_{18}$ | $R_{252}$ | mp.(° C.) or $^1$H NMR ($CDCl_3$) δ ppm |
|---|---|---|---|
| 496 | p-phenylene | 2-$(CH_2)_2COOCH_3$ | mp 117-119 |
| 497 | p-phenylene | 3-$(CH_2)_2COOC_2H_5$ | mp 111-113 |
| 498 | o-phenylene | 4-$(CH_2)_2COOC_2H_5$ | mp 72-73 |
| 499 | m-phenylene | 4-$(CH_2)_2COOC_2H_5$ | $^1$H NMR 1.22 (3H, t, J = 7.2 Hz), 2.59 (2H, t, J = 7.7 Hz), 2.91 (2H, t, J = 7.7 Hz), 4.10 (2H, q, J = 7.2 Hz), 6.78 (1H, dt, J = 8.1 Hz, 1.1 Hz), 6.93 (2H, d, J =8.5 Hz), 7.14 (2H, d, J = 8.5 Hz), 1H, d, J = 8.3 Hz), 7.81 (1H; brs), 7.91 (1H, d, J = 2.1 Hz). |

TABLE 72

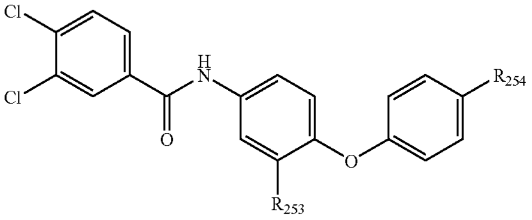

| Reference Example No. | $R_{253}$ | $R_{254}$ | mp (° C.) or $^1$H NMR (solvent) δ ppm |
|---|---|---|---|
| 500 | —F | —H | mp 168-169 |
| 501 | —H | —$COOC_2H_5$ | mp 144-145 |
| 502 | —F | —$COOC_2H_5$ | mp 145-146 |
| 503 | —F | —$CH_2COOCH_3$ | mp 127-129 |
| 504 | —F | —$(CH_2)_2COOC_2H_5$ | mp 131-133 |
| 505 | —F | —$(CH_2)_3COOC_2H_5$ | mp 110-111 |
| 506 | —F | —$SCH_2COOC_2H_5$ | $^1$H NMR ($CDCl_3$) 1.23 (3H, t, J = 7.1 Hz), 3.56 (2H, s), 4.15 (2H, q, J = 7.1 Hz), 6.90 (2H, d, J = 8.7 Hz), 7.08 (1H, t, J = 8.7 Hz), 7.20-7.30 (1H, m), 7.42 (2H, d, J = 8.7 Hz), 7.58 (1H, d, J = 8.3 Hz), 7.65-7.80 (2H, m), 7.82 (1H, s), 7.96 (1H, d, J = 2.1 Hz). |
| 507 | —F | —$NHCH_2COOC_2H_5$ | $^1$ H NMR (DMSO-$d_6$) 1.19 (3H, t, J = 7.1 Hz), 3.87 (2H, d, J = 6.4 Hz), 4.11 (2H, q, J = 7.1 Hz), 5.93 (1H, t, J = 6.4 Hz), 6.56 (2H, d, J = 9.0 Hz), 6.81 (2H, d, J = 9.0 Hz), 6.98 (1H, t, J = 9.2 Hz), 7.44-7.47 (1H, m), 7.82-7.86 (2H, m), 7.93 (1H, dd, J = 2.0 Hz, 8.4 Hz), 8.20 (1H, d, J = 2.0 Hz), 10.50 (1H, s). |
| 508 | —H | —Br | $^1$H NMR (DMSO-$d_6$) 6.96 (2H, d, J = 9.0 Hz), 7.08 (2H, d, J = 9.0 Hz), 7.55 (2H, d, J = 8.5 Hz), 7.79 (2H, d, J = 8.5 Hz), 7.83 (1H, d, J = 8.5 Hz), 7.94 (1H, dd, J = 8.5 Hz, 2.0 Hz), 8.21 (1H, d, J = 2.0 Hz), 10.44 (1H, brs). |
| 509 | —F | —Ac | mp 143 |
| 510 | —F | 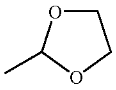 | $^1$H NMR ($CDCl_3$) 4.00-4.15 (4H, m), 5.78 (1H, s), 6.96 (2H, d, J = 8.7 Hz), 7.00-7.10 (1H, m), 7.20-7.30 (1H, m), 7.43 (2H, d, J = 8.7 Hz), 7.57 (1H, d, J = 8.3 Hz), 7.82 (1H, s), 7.95 (1H, d, J = 2.1 Hz). |

TABLE 73

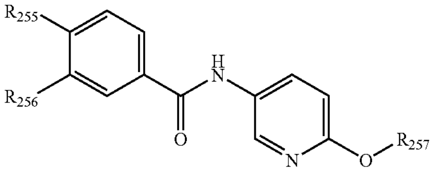

| Reference Example No. | $R_{255}$ | $R_{256}$ | $R_{257}$ | $^1$H NMR ($CDCl_3$) δ ppm |
|---|---|---|---|---|
| 511 | —Cl | —Cl | 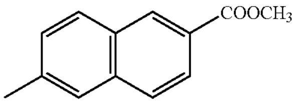 | 3.98 (3H, s), 7.06 (1H, d, J = 8.7 Hz), 7.33-7.37 (1H, m), 7.56-7.59 (2H, m, 7.70-7.73 (1H, m), 7.80 (1H, d, J = 8.5 Hz), 7.95-8.07 (4H, m), 8.23-8.30 (2H, m), 8.60 (1H, s). |
| 512 | —$CF_3$ | —H | 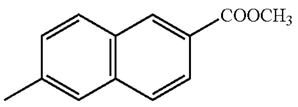 | 3.98 (3H, s), 7.07-7.10 (1H, m), 7.37 (1H, dd, J = 8.9 Hz, 2.3 Hz), 7.58 (1H, d, J = 2.3 Hz), 7.76-7.82 (3H, m), 7.93-8.08 (5H, m), 8.27-8.31 (2H, m), 8.60 (1H, s). |

TABLE 73-continued

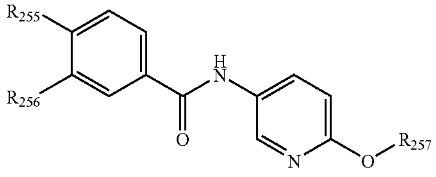

| Reference Example No. | $R_{255}$ | $R_{256}$ | $R_{257}$ | $^1H$ NMR ($CDCl_3$) δ ppm |
|---|---|---|---|---|
| 513 | —Cl | —Cl | 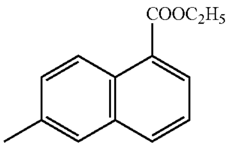 | 1.46 (3H, t, J = 7.1 Hz), 4.47 (2H, q, J = 7.1 Hz), 7.04 (1H, d, J = 8.7 Hz), 7.41 (1H, dd, J = 9.4 Hz, 2.5 Hz), 7.47-7.60 (3H, m), 7.70 (1H, dd, J = 8.4 Hz, 2.1 Hz), 7.82 (1H, brs), 7.94 (1H, d, J = 8.6 Hz), 7.98 (1H, d, J = 2.1 Hz), 8.14 (1H, dd, J = 7.3 Hz, 1.2 Hz), 8.20-8.27 (2H, m), 8.92 (1H, d, J = 9.4 Hz). |
| 514 | —$CF_3$ | —H | 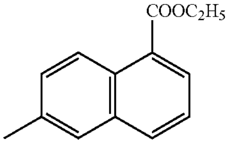 | 1.46 (3H, t, J = 7.1 Hz), 4.47 (2H, q, J = 7.1 Hz), 7.04 (1H, d, J = 8.7 Hz), 7.40 (1H, dd, J = 9.4 Hz, 2.5 Hz), 7.47-7.53 (1H, m), 7.59 (1H, d, J = 2.5 Hz), 7.75 (2H, d, J = 8.2 Hz), 7.92-8.00 (4H, m), 8.14 (1H, dd, J = 7.3 Hz, 1.2 Hz), 8.23-8.29 (2H, m), 8.97 (1H, d, J = 9.4 Hz). |
| 515 | —Cl | —Cl | 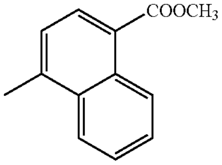 | 4.00 (3H, s), 7.09 (1H, d, J = 9.6 Hz), 7.16 (1H, d, J = 8.1 Hz), 7.50-7.57 (2H, m), 7.62-7.72 (2H, m), 7.98 (2H, d, J = 2.1 Hz), 8.15-8.29 (4H, m), 9.01 (1H, d, J = 8.7 Hz). |

TABLE 74

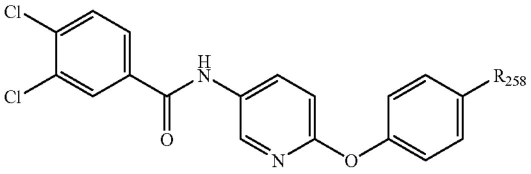

| Reference Example No. | $R_{258}$ | $^1H$ NMR ($CDCl_3$) δ ppm |
|---|---|---|
| 516 | —$COOCH_3$ | 3.91 (3H, s), 7.03 (1H, d, J = 8.9 Hz), 7.15-7.18 (2H, m), 7.58 (1H, d, J = 8.3 Hz), 7.69-7.73 (1H, m), 7.89 (1H, brs), 7.99 (1H, d, J = 2.0 Hz), 8.06-8.09 (2H, m), 8.23-8.30 (2H, m). |
| 517 | —$COOC_2H_5$ | 1.39 (3H, t, J = 7.3 Hz), 4.37 (2H, q, J = 7.3 Hz), 7.02 (1H, d, J = 8.6 Hz), 7.15-7.18 (2H, m), 7.57 (1H, d, J = 8.6 Hz); 7.70-7.73 (1H, m), 7.97-7.99 (2H, m), 8.06-8.09 (2H, m), 8.23-8.30 (2H, m). |
| 518 | —$CH_2COOCH_3$ | 3.63 (2H, s), 3.71 (3H, s), 6.94 (1H, d, J = 8.9 Hz), 7.07 (2H, d, J = 8.2 Hz), 7.30 (2H, d, J = 8.6 Hz), 7.55 (1H, d, J = 8.6 Hz), 7.70 (1H, dd, J = 8.2 Hz, 2.0 Hz), 7.97-8.08 (2H, m), 8.17 (1H, dd, J = 8.9 Hz, 2.6 Hz), 8.24 (1H, d, J = 2.6 Hz). |
| 519 | —$(CH_2)_2COOCH_3$ | 2.62-2.67 (2H, m), 2.93-2.98 (2H, m), 3.68 (3H, s), 6.93 (1H, d, J = 8.9 Hz), 7.03-7.06 (2H, m), 7.20-7.23 (2H, m), 7.56 (1H, d, J = 8.3 Hz), 7.68-7.72 (1H, m), 7.96-7.98 (2H, m), 8.17 (1H, dd, J = 8.9 Hz, 2.6 Hz), 8.24 (1H, d, J = 2.6 Hz). |
| 520 | —$(CH_2)_3COOC_2H_5$ | 1.26 (3H, t, J = 7.0 Hz), 1.96 (2H, dt, J = 15.0 Hz, 7.5 Hz), 2.34 (2H, t, J = 7.5 Hz), 2.66 (2H, t, J = 7.5 Hz), 4.13 (2H, q, J = 7.0 Hz), 6.93 (1H, d, J = 8.8 Hz), 7.04 (2H, d, J = 8.6 Hz), 7.20 (2H, d, J = 8.6 Hz), 7.56 (1H, d, J = 8.3 Hz), 7.70 (1H, dd, J = 8.3 Hz, 2.0 Hz), 7.89 (1H, s), 7.98 (1H, d, |

TABLE 74-continued

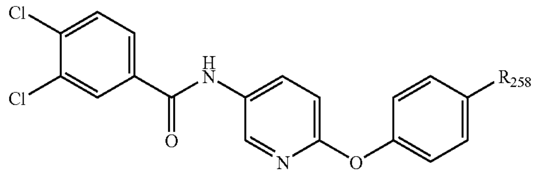

| Reference Example No. | $R_{258}$ | $^1H$ NMR ($CDCl_3$) δ ppm |
|---|---|---|
| | | J = 2.0 Hz), 8.16 (1H, dd, J = 8.8 Hz, 2.6 Hz), 8.24 (1H, d, J = 2.6 Hz). |
| 521 | —$(CH_2)_4COOC_2H_5$ | 1.26 (3H, t, J = 7.2 Hz), 1.60-1.75 (4H, m), 2.33 (2H, t, J = 7.0 Hz), 2.64 (2H, t, J = 7.0 Hz), 4.13 (2H, q, J = 7.2 Hz), 6.94 (1H, d, J = 8.9 Hz), 7.04 (2H, d; J = 8.5 Hz), 7.20 (2H, d, J = 8.5 Hz), 7.58 (1H, d, J = 8.3 Hz), 7.70 (1H, dd, J = 8.3 Hz, 2.3 Hz), 7.78 (1H, brs), 7.98 (1H, d, J = 2.3 Hz), 8.16 (1H, dd, J = 8.9 Hz, 2.6 Hz), 8.24 (1H, d, J = 2.6 Hz). |
| 522 | —$CH_2CN$ | 3.76 (2H, s), 7.00 (1H, d, J = 8.8 Hz), 7.16 (2H, d, J = 8.7 Hz), 7.37 (2H, d, J = 8.7 Hz), 7.58 (1H, d, J = 8.4 Hz), 7.70 (1H, dd, J = 8.4 Hz, 2.1 Hz), 7.81 (1H, s), 7.98 (1H, d, J = 2.1 Hz), 8.20 (1H, dd, J = 8.8 Hz, 2.3 Hz), 8.25 (1H, d, J =2.3 Hz). |
| 523 | —$NHCOOC(CH_3)_3$ | 1.52 (9H, s), 6.49 (1H, brs), 6.90 (1H, d, J = 8.6 Hz), 7.05 (2H, d, J = 8.9 Hz), 7.37 (2H, d, J = 8.9 Hz), 7.56 (1H, d, J = 8.6 Hz), 7.69 (1H, dd, J = 8.6 Hz, 2.3 Hz), 7.92 (1H, brs), 7.97 (1H, d, J = 2.3 Hz), 8.14 (1H, dd, J = 8.6 Hz, 2.6 Hz), 8.22 (1H, d, J = 2.6 Hz). |
| 524 | —$CH{=}C(COOCH_3)_2$ | 3.85 (3H, s), 3.86 (3H, s), 7.02 (1H, d, J = 8.8 Hz), 7.13 (2H, d, J = 8.5 Hz), 7.46 (2H, d, J = 8.5 Hz), 7.59 (1H, d, J = 8.2 Hz), 7.70 (1H, dd, J = 8.2 Hz, 2.0 Hz), 7.74 (1H, s), 7.88 (1H, brs), 7.97 (1H, d, J = 2.0 Hz), 8.22 (1H, dd, J = 8.8 Hz, 2.5 Hz), 8.24 (1H, d, J = 2.5 Hz). |

TABLE 75

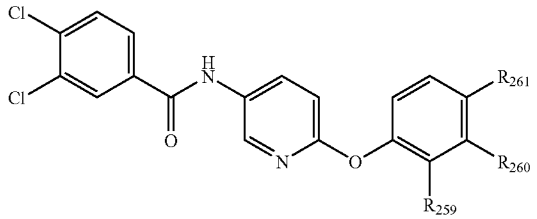

| Reference Example No. | $R_{259}$ | $R_{260}$ | $R_{261}$ | $^1H$ NMR (solvent) δ ppm |
|---|---|---|---|---|
| 525 | —$OCH_3$ | —H | —$COOC_2H_5$ | ($CDCl_3$) 1.40 (3H, t, J = 7.1 Hz), 3.81 (3H, s), 4.39 (2H, q, J = 7.1 Hz), 6.99-7.02 (1H, m), 7.16 (1H, d, J = 8.1 Hz), 7.56 (1H, d, J = 8.4 Hz), 7.67-7.72 (3H, m), 7.97-8.01 (2H, m), 8.17- 8.22 (2H, m). |
| 526 | —$CH_3$ | —H | —$COOCH_3$ | ($CDCl_3$) 2.24 (3H, s), 3.91 (3H, s), 6.97-7.01 (1H, m), 7.07 (1H, d, J = 8.4 Hz), 7.57 (1H, d, J = 8.4 Hz), 7.69-7.73 (1H, m), 7.91 (1H, dd, J = 8.4 Hz, 2.4 Hz), 7.97-7.99 (3H, m), 8.21-8.26 (2H, m). |
| 527 | —Cl | —H | —$COOCH_3$ | ($ODCl_3$) 3.93 (3H, s), 7.08 (1H, d, J = 8.7 Hz), 7.26 (1H, d, J = 1.7 Hz), 7.56 (1H, d, J = 8.2 Hz), 7.69-7.73 (1H, m), 7.95-7.99 (2H, m), 8.10 (1H, brs), 8.15 (1H, d, J = 2.0 Hz), 8.22-8.24 (1H, m), 8.27 (1H, d, J = 2.8 Hz). |
| 528 | —F | —H | —$COOCH_3$ | ($CDCl_3$) 3.92 (3H, s), 7.07 (1H, dd, J = 7.8 Hz, 1.8 Hz), 7.25-7.31 (1H, m), 7.56 (1H, d, J = 8.4 Hz), 7.71 (1H, dd, J = 8.2 Hz, 2.1 Hz), 7.82-7.89 (2H, m), 7.97 (1H, d, J = 2.1 Hz), 8.08 (1H, brs), 8.21-8.25 (2H, m). |
| 529 | —H | —$OCH_3$ | —$COOCH_3$ | ($ODCl_3$) 3.83 (3H, s), 3.87 (3H, s), 6.70 (1H, dd, J = 8.6 Hz, 2.2 Hz), 6.74 (1H, d, J = 2.2 Hz), 7.01 (1H, d, J = 8.6 Hz), 7.56 (1H, d, J = 8.1 |

TABLE 75-continued

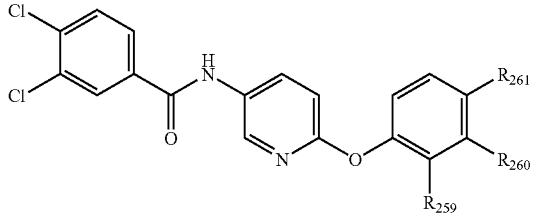

| Reference Example No. | $R_{259}$ | $R_{260}$ | $R_{261}$ | $^1H$ NMR (solvent) δ ppm |
|---|---|---|---|---|
| | | | | Hz), 7.75 (1H, dd, J = 8.6 Hz, 2.2 Hz), 7.87 (1H, d, J = 8.6 Hz), 8.01 (1H, d, J = 2.2 Hz), 8.25-8.33 (3H, m). |
| 530 | —H | —$CH_3$ | —$COOCH_3$ | ($ODCl_3$) 2.63 (3H, s), 3.91 (3H, s), 6.98-7.05 (3H, m), 7.60 (1H, d, J = 8.4 Hz), 7.75 (1H, dd, J = 8.4 Hz, 2.2 Hz), 7.97-8.03 (3H, m), 8.23-8.28 (1H, m), 8.30-8.32 (1H, m). |
| 531 | —H | —$COOCH_3$ | —H | (DMSO-$d6_6$) 3.85 (3H, s), 7.17 (1H, d, J = 8.9 Hz), 7.43-7.47 (1H, m), 7.56-7.62 (2H, m), 7.78-7.86 (2H, m), 7.93-7.97 (1H, m), 8.22-8.27 (2H, m), 8.50 (1H, d, J = 2.3 Hz), 10.60 (1H, s). |

TABLE 76

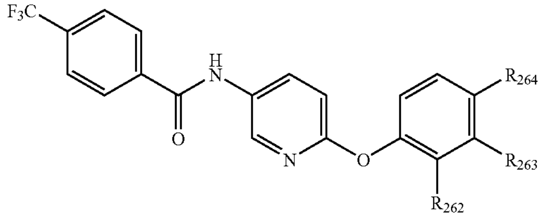

| Reference Example No. | $R_{262}$ | $R_{263}$ | $R_{264}$ | $^1H$ NMR ($CDCl_3$) δ ppm |
|---|---|---|---|---|
| 532 | —$OCH_3$ | —H | —$COOC_2H_5$ | 1.40 (3H, t, J = 7.1 Hz), 3.82 (3H, s), 4.39 (2H, q, J = 7.1 Hz), 7.00-7.03 (1H, m), 7.17 (1H, d, J = 8.1 Hz), 7.68-7.76 (4H, m), 8.01 (2H, d, J = 8.1 Hz), 8.16 (1H, brs), 8.22-8.25 (2H, m). |
| 533 | —$OCH_3$ | —H | —$(CH_2)_2COOCH_3$ | 2.63-2.69 (2H, m), 2.93-2.99 (2H, m), 3.69 (3H, s), 3.74 (3H, s), 6.78-6.84 (2H, m), 6.93 (1H, d, J = 8.7 Hz), 7.03 (1H, d, J =8.1 Hz), 7.73 (2H, d, J = 8.1 Hz), 7.96-7.99 (3H, m), 8.14-8.20 (2H, m). |
| 534 | —$CH_3$ | —H | —$COOCH_3$ | 2.25 (3H, s), 3.91 (3H, s), 6.99-7.03 (1H, m), 7.07 (1H, d, J = 8.4 Hz), 7.75-7.78 (2H, m), 7.88-7.92 (1H, m), 7.98-8.01 (4H, m), 8.26-8.29 (2H, m). |
| 535 | —Cl | —H | —$COOCH_3$ | 3.93 (3H, s), 7.09 (1H, d, J = 8.7 Hz), 7.24-7.27 (1H, m), 7.76 (2H, d, J = 8.7 Hz), 7.96-8.03 (4H, m), 8.16 (1H, d, J = 2.1 Hz), 8.24 (1H, d, J = 2.6 Hz), 8.29 (1H, dd, J = 8.7 Hz, 2.6 Hz). |
| 536 | —F | —H | —$COOCH_3$ | 3.92 (3H, s), 7.08 (1H, d, J = 8.7 Hz), 7.26-7.32 (1H, m), 7.75 (2H, d, J = 8.4 Hz), 7.83-7.90 (2H, m), 7.98 (3H, d, J = 8.2 Hz), 8.22-8.28 (2H, m). |
| 537 | —H | —$OCH_3$ | —$COOCH_3$ | 3.87 (3H, s), 3.88 (3H, s), 6.71 (1H, dd, J = 8.6 Hz, 2.2 Hz), 6.77 (1H, d, J = 2.2 Hz), 7.04 (1H, d, J = 8.9 Hz), 7.77 (2H, d, J = 8.1 Hz), 7.88 (1H, d, J = 8.6 Hz), 8.02 (2H, d, J = 8.1 Hz), 8.17 (1H, brs), 8.29-8.35 (2H, m). |
| 538 | —H | —$CH_3$ | —$COOCH_3$ | 2.63 (3H, s), 3.91 (3H, s), 6.98-7.06 (3H, m), 7.79 (2H, d, J = 8.1 Hz), 8.00-8.04 (4H, m), 8.27-8.34 (2H, m). |

TABLE 76-continued

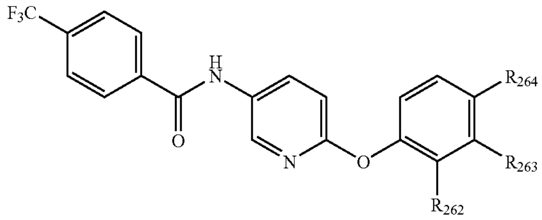

| Reference Example No. | $R_{262}$ | $R_{263}$ | $R_{264}$ | $^1H$ NMR ($CDCl_3$) δ ppm |
|---|---|---|---|---|
| 539 | —H | —$COOCH_3$ | —H | 3.91 (3H, s), 6.99-7.04 (1H, m), 7.32-7.37 (1H, m), 7.45-7.50 (1H, m, 7.74-7.80 (3H, m), 7.86-7.90 (1H, m), 7.96-8.01 (3H, m), 8.22-8.27 (2H, m). |

TABLE 77

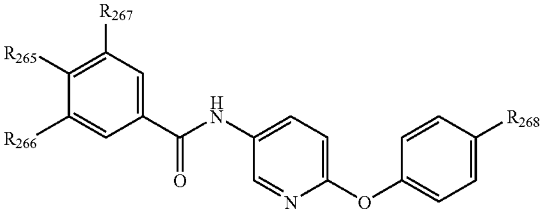

| Reference Example No. | $R_{265}$ | $R_{266}$ | $R_{267}$ | $R_{268}$ | $^1H$ NMR ($CDCl_3$) δ ppm or mp (° C.) |
|---|---|---|---|---|---|
| 540 | —$CF_3$ | —H | —H | 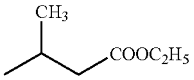 | $^1H$ NMR 1.17 (3H, t, J = 7.1 Hz) 1.26 (3H, d, J = 7.0 Hz), 2.44-2.61 (2H, m), 3.19-3.29 (1H, m), 4.05 (2H, q, J = 7.1 Hz), 6.88 (1H, d, J = 8.8 Hz), 7.01 (2H, d, J =8.5 Hz), 7.19 (2H, d, J = 8.5 Hz), 7.68 (2H, d, J =8.3 Hz), 7.94 (2H, d, J = 8.3 Hz), 8.15 (1H, dd, J = 8.8 Hz, 2.7 Hz), 8.23 (1H, d, J = 2.7 Hz), 8.29 (1H, brs). |
| 541 | —Cl | —Cl | —H | 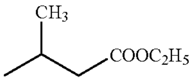 | $^1H$ NMR 1.17 (3H, t, J = 7.1 Hz), 1.26 (3H, d, J = 7.0 Hz), 2.43-2.60 (2H, m), 3.18-3.28 (1H, m), 4.05 (2H, q, J = 7.1 Hz), 6.85 (1H, d, J = 8.9 Hz), 6.99 (2H, d, J =8.4 Hz), 7.18 (2H, d, J = 8.4 Hz), 7.48 (1H, d, J = 8.3 Hz), 7.66 (1H, dd, J = 8.3 Hz, 2.0 Hz), 7.92 (1H, d, J = 2.0 Hz), 8.10 (1H, dd, J = 8.9 Hz, 2.7 Hz), 8.20 (1H, d, J =2.7 Hz), 8.39 (1H, brs). |
| 542 | —$CF_3$ | —H | —H | 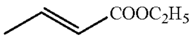 | $^1H$ NMR 1.35 (3H, t, J = 7.1 Hz), 4.27 (2H, q, J = 7.1 Hz), 6.39 (1H, dd, J = 16.0 Hz, 2.6 Hz), 7.03 (1H, d, J = 8.9 Hz), 7.16 (2H, d, J = 8.8 Hz), 7.56 (2H, d, J = 8.8 Hz), 7.68 (1H, dd, J = 16.0 Hz, 3.2 Hz), 7.77 (2H, d, J = 8.1 Hz), 7.93 (1H, brs), 8.01 (2H, d, J = 8.1 Hz), 8.26 (1H, dd, J =8.9 Hz, 2.6 Hz) 8.29 (1H, d, J = 2.6 Hz). |
| 543 | —$CF_3$ | —H | —H | —$CH_2COOCH_3$ | $^1H$ NMR 3.62 (2H, s), 3.70 (3H, s,) 6.94 (1H, d, J = 8.7 Hz), 7.05-7.09 (2H, m), 7.26-7.32 (2H, m), 7.72 (2H, d, J =8.6 Hz), 7.97 (2H, d, J = 8.2 Hz), 8.17-8.26 (3H, m). |
| 544 | —$CF_3$ | —H | —H | —$(CH_2)_2COOC_2H_5$ | $^1H$ NMR 1.25 (3H, t, J = 7.1 Hz), 2.62 (2H, t, J = 7.7 Hz), 2.95 (2H, t, J = 7.7 Hz), 4.13 (2H, q, J = 7.1 Hz), 6.94 (1H, d, J = 8.8 Hz), 7.04 (2H, d, J = 8.6 Hz), 7.22 (2H, d, J = 8.6 Hz), 7.75 (2H, d, J = 8.3 |

TABLE 77-continued

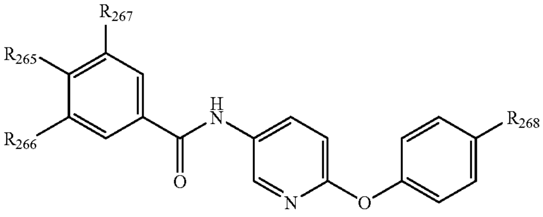

| Reference Example No. | $R_{265}$ | $R_{266}$ | $R_{267}$ | $R_{268}$ | $^1$H NMR ($CDCl_3$) δ ppm or mp (° C.) |
|---|---|---|---|---|---|
| | | | | | Hz), 7.98 (2H, d, J = 8.3 Hz), 8.03 (1H, brs), 8.19 (1H, dd, J = 8.8 Hz, 2.6 Hz), 8.26 (1H, d, J = 2.6 Hz). |
| 545 | —Cl | —Cl | —H | 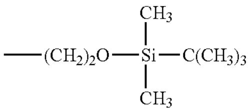 | $^1$H NMR 0.01 (3H, s), 0.89 (9H, s), 2.83 (2H, t, J = 6.9 Hz), 3.82 (2H, t, J = 6.9 Hz), 6.92 (1H, d, J = 8.9 Hz), 7.05 (2H, dd, J = 6.3 Hz, 2.0 Hz), 7.24 (2H, d, J = 8.6 Hz), 7.58 (1H, d, J = 8.3 Hz), 7.71 (1H, dd, J = 8.3 Hz, 2.0 Hz), 7.80 (1H, brs), 7.98 (1H, d, J = 2.0 Hz), 8.15-8.19 (1H, m), 8.25 (1H, d, J = 2.6 Hz). |
| 546 | —Cl | —Cl | —H | 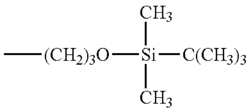 | $^1$H NMR 0.07 (6H, s), 0.91 (9H, s), 1.82-1.87 (2H, m), 2.65-2.71 (2H, m), 3.63-3.68 (2H, m), 6.92 (1H, d, J = 8.9 Hz), 7.02-7.05 (2H, m), 7.21 (2H, d, J = 8.6 Hz) 7.57 (1H, d, J = 8.3 Hz), 7.68-7.72 (1H, m), 7.86 (1H, brs), 7.97 (1H, d, J = 2.0 Hz), 8.14-8.18 (1H, m), 8.24 (1H, d, J = 2.3 Hz). |
| 547 | —H | —F | —$CF_3$ | —$COOC_2H_5$ | mp 133-134 |

TABLE 78

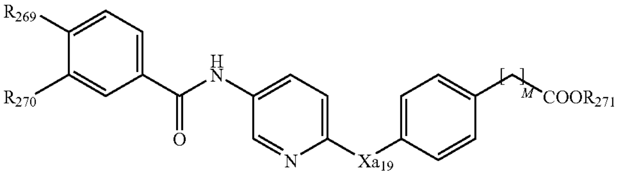

| Reference Example No. | $R_{269}$ | $R_{270}$ | $Xa_{19}$ | $R_{271}$ | M | mp (° C.) or $^1$H NMR (solvent) δ ppm |
|---|---|---|---|---|---|---|
| 548 | —Cl | —Cl | —S— | —$CH_3$ | 2 | mp 141-142 |
| 549 | —Cl | —Cl | —NH— | —$C_2H_5$ | 2 | mp 170-171 |
| 550 | —Cl | —Cl | —N($CH_3$)— | —$C_2H_5$ | 2 | $^1$H NMR DMSO-$d_6$) 1.17 (3H, t, J = 7.1 Hz), 2.63 (2H, t, J = 7.7 Hz), 2.85 (2H, t, J = 7.7 Hz), 3.36 (3H, s), 4.07 (2H, d, J = 7.1 Hz), 6.56 (1H, d, J = 9.5 Hz), 7.18 (2H, d, J = 8.3 Hz), 7.27 (2H, d, J = 8.3 Hz), 7.75-7.95 (3H, m), 8.20 (1H, s), 8.47 (1H, s), 10.26 (1H, s). |
| 551 | —$CF_3$ | —H | —N($CH_3$)— | —$C_2H_5$ | 0 | mp 135-136 |
| 552 | —$CF_3$ | —H | —N($CH_3$)— | —$C_2H_5$ | 2 | $^1$H NMR ($CDCl_3$) 1.26 (3H, t, J = 7.2 Hz), 2.65 (2H, t, J = 8.0 Hz), 2.97 (2H, t, J = 8.0 Hz), 3.45 (3H, s), 4.16 (2H, q, J = 7.2 Hz), 6.57 (1H, d, J = 9.1 Hz), 7.18 (2H, d, J = 8.3 Hz), 7.24 (2H, d, J = 8.3 Hz), 7.35-7.45 (1H, m), 7.65-7.78 (3H, m), 7.98 (2H, d, J = 8.1 Hz), 8.28 (1H, d, J = 2.5 Hz). |
| 553 | —Cl | —Cl | —N($CH_2$Ph)— | —$C_2H_5$ | 2 | $^1$H NMR ($CDCl_3$) 1.23 (3H, t, J = 7.2 Hz), 2.61 (2H, t, J = 7.6 Hz), 2.92 (2H, t, J = 7.6 Hz), 4.12 (2H, q, J = 7.2 Hz), 5.20 (2H, s), 6.54 (1H, d, J = 9.1 Hz), 7.10-7.30 (8H, m), 7.53 (1H, d, J = 8.4 |

TABLE 78-continued

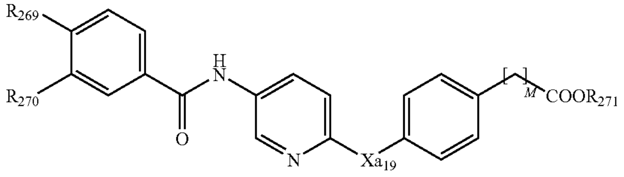

| Reference Example No. | $R_{269}$ | $R_{270}$ | $Xa_{19}$ | $R_{271}$ | M | mp (° C.) or $^1$H NMR (solvent) δ ppm |
|---|---|---|---|---|---|---|
| | | | | | | Hz), 7.60-7.75 (3H, m), 7.94 (1H, d, J = 1.3 Hz), 8.22 (1H, d, J = 2.3 Hz). |
| 554 | —Cl | —H | —O— | $—CH_3$ | 0 | $^1$H NMR ($CDCl_3$) 3.91 (3H, s), 7.04 (1H, d, J = 9.9 Hz), 7.17 (2H, d, J = 8.6 Hz), 7.49 (2H, d, J = 8.6 Hz), 7.79 (1H, brs), 7.83 (2H, d, J = 8.6 Hz), 8.08 (2H, d, J = 8.6 Hz), 8.27-8.29 (2H, m). |
| 555 | $—CF_3$ | —H | —O— | $—C_2H_5$ | 0 | $^1$H NMR ($CDCl_3$) 1.39 (3H, t, J = 7.3 Hz), 4.37 (2H, q, J = 7.3 Hz), 7.04 (1H, dd, J = 8.3 Hz, 1.3 Hz), 7.15-7.19 (2H, m), 7.78 (2H, d, J = 8.3 Hz), 7.91 (1H, brs), 8.00 (2H, d, J = 6.9 Hz), 8.07-8.10 (2H, m), 8.27-8.31 (2H, m). |
| 556 | —H | $—OCF_3$ | —O— | $—CH_3$ | 0 | $^1$H NMR ($CDCl_3$) 3.91 (3H, s), 7.04 (1H, d, J = 8.7 Hz), 7.16 (2H, d, J = 8.7 Hz), 7.42 (1H, d, J = 8.2 Hz), 7.53 (1H, t, J = 8.1 Hz), 7.76-7.81 (2H, m), 8.05-8.08 (3H, m), 8.25-8.31 (2H m). |
| 557 | —H | $—CF_3$ | —O— | $—C_2H_5$ | 0 | $^1$H NMR $CDCl_3$ 1.39 (3H, t, J = 7.2 Hz), 4.37 (2H, q, J = 7.2 Hz), 7.40 (1H, d, J = 8.7 Hz), 7.09-7.20 (2H, m), 7.66 (1H, t, J = 7.8 Hz), 7.76-7.90 (1H, m), 8.00 (1H, brs), 8.00-8.10 (3H, m), 8.10-8.18 (1H, m), 8.20-8.35 (2H, m). |

TABLE 79

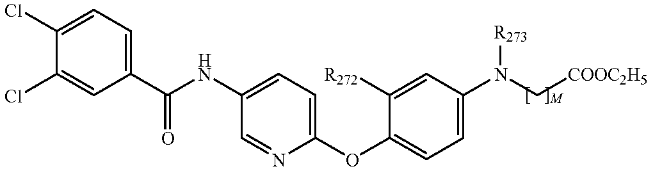

| Reference Example No. | $R_{272}$ | $R_{273}$ | M | mp (° C.) or $^1$H NMR ($CDCl_3$) δ ppm |
|---|---|---|---|---|
| 558 | —H | —Ac | 1 | mp 178-179 |
| 559 | —H | —Ac | 2 | $^1$H NMR 1.22 (3H, t, J = 7.2 Hz), 1.86 (3H, s), 2.58 (2H, t, J = 7.3 Hz), 3.99 (2H, t, J = 7.3 Hz), 4.07 (2H, q, J = 7.2 Hz), 7.02 (1H, d, J = 8.9 Hz), 7.15-7.20 (4H, m), 7.58 (1H, d, J = 8.4 Hz), 7.75 (1H, dd, J = 2.1 Hz, 8.4 Hz), 8.02 (1H, d, J = 2.1 Hz), 8.24 (1H, dd, J = 2.7 Hz, 8.9 Hz), 8.28 (1H, s), 8.32 (1H, d, J = 2.7 Hz). |
| 560 | —H | $—CH_3$ | 1 | $^1$H NMR 1.26 (3H, t, J = 7.1 Hz), 3.06 (3H, s), 4.04 (2H, s), 4.18 (2H; q, J = 7.1 Hz), 6.68 (2H, d, J = 9.1 Hz), 6.85 (1H, d, J = 8.9 Hz), 7.00 (2H, d, J = 9.1 Hz), 7.55 (1H, d, J = 8.4 Hz), 7.70 (1H, dd, J = 1.9 Hz, 8.4 Hz), 7.94 (1H, s), 7.97 (1H, d, J = 1.9 Hz), 8.10 (1H, dd, J = 2.6 Hz, 8.9 Hz), 8.21 (1H, d, J = 2.6 Hz). |
| 561 | —H | $—C_2H_5$ | 1 | $^1$H NMR 1.22 (3H, t, J = 7.1 Hz), 1.27 (3H, t, J = 7.1 Hz), 3.46 (2H, q, J = 7.1 Hz), 4.01 (2H, s), 4.20 (2H; q, J = 7.1 Hz), 6.64 (2H, d, 4 = 9.1 Hz), 6.86 (1H, d, J = 8.9 Hz), 6.98 (2H, d, J = 9.1 Hz), 7.56 (1H, d, J = 8.4 Hz), 7.70 (1H, dd, J = 1.9 Hz, 8.4 Hz), 7.82 (1H, s), 7.97 (1H, d, J = 1.9 Hz), 8.11 (1H, dd, J = 2.6 Hz, 8.9 Hz), 8.22 (1H, d, J = 2.6 Hz). |
| 562 | $—OCH_3$ | $—CH_3$ | 1 | $^1$H NMR 1.25 (3H, t, J = 7.1 Hz) 3.03 (3H, s), 3.65 (3H, s), 4.01 (2H, s), 4.17 (2H, q, J = 7.1 Hz), 6.16 (1H, d, J = 8.7 Hz), 6.21 (1H, s), 6.76 (1H, d, J = 8.9 Hz), 6.88 (1H, d, J = 8.6 Hz), 7.43 (1H, d, J = 8.4 Hz), 7.67 (1H, d, J = 8.4 Hz), 7.94 (1H, d, J = 1.8 Hz), 8.02 (1H, d, J = 8.9 Hz), 8.13 (1H, d, J = 2.3 Hz), 8.88 (1H, s). |
| 563 | $—OCH_3$ | $—C_2H_5$ | 1 | $^1$H NMR 1.21 (3H, t, J = 7.1 Hz), 1.27 (3H, t, J = 7.1 Hz), 3.44 (2H, q, J = 7.1 Hz), 3.68 (3H, s), 3.98 (2H, s), 4.20 (2H, q, J = 7.1 Hz), |

TABLE 79-continued

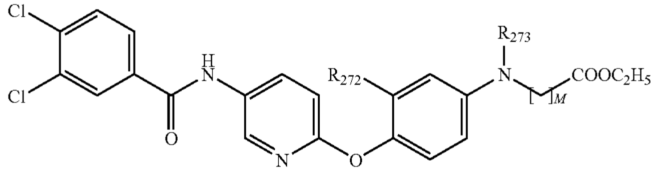

| Reference Example No. | $R_{272}$ | $R_{273}$ | M | mp (° C.) or $^1H$ NMR ($CDCl_3$) δ ppm |
|---|---|---|---|---|
| | | | | 6.17 (1H, dd, J = 8.9 Hz, 3.0 Hz), 6.24 (1H, d, J = 2.8 Hz), 6.81 (1H, d, J = 8.9 Hz), 6.91 (1H, d, J = 8.7 Hz), 7.48 (1H, d, J = 8.4 Hz), 7.68 (1H, dd, J = 8.4 Hz, 2.2 Hz), 7.96 (1H, d, J = 2.0 Hz), 8.04 (1H, dd, J = 8.9 Hz), 2.8 Hz), 8.15 (1H, d, J = 2.3 Hz), 8.34 (1H, s). |
| 564 | —$CH_3$ | —Ac | 1 | $^1H$ NMR 1.26 (3H, t, J = 7.1 Hz), 1.96 (3H, s), 2.22 (3H, s), 4.20 (2H, q, J = 7.1 Hz), 4.37 (2H, s), 6.99 (1H, d, J = 8.9 Hz), 7.07 (1H, d, J = 8.4 Hz), 7.19 (1H, dd, J = 2.4 Hz, 8.4 Hz), 7.59 (1H, d, J = 8.4 Hz), 7.72 (1H, d, J = 8.4 Hz), 7.90-8.12 (2H, m), 8.21 (1H, dd, J = 2.0 Hz, 8.4 Hz), 8.27 (1H, s). |
| 565 | —$CH_3$ | —$CH_3$ | 1 | $^1H$ NMR 1.26 (3H, t, J = 7.1 Hz), 2.12 (3H, s), 3.06 (3H, s), 4.04 (2H, s), 4.20 (2H, q, J = 7.1 Hz), 6.49-6.61 (2H, m), 6.83 (1H, d, J = 8.9 Hz), 6.93 (1H, d, J = 8.5 Hz), 7.57 (1H, d, J = 8.5 Hz), 7.70 (1H, dd, J = 8.5 Hz, 2.1 Hz), 7.73 (1H, s), 7.97 (1H, d, J = 2.1 Hz), 8.12 (1H, dd, J = 8.9 Hz, 2.8 Hz), 8.21 (1H, d, J = 2.8 Hz). |
| 566 | —F | —Ac | 1 | $^1H$ NMR 1.29 (3H, t, J = 7.1 Hz), 2.00 (3H, s), 4.21 (2H, q, J = 7.1 Hz), 4.37 (2H, s), 7.09 (1H, dd, J = 7.9 Hz, 1.8 Hz), 7.18-7.32 (3H, m), 7.59 (1H, d, J = 8.4 Hz), 7.72 (1H, dd, J = 8.3 Hz, 2.1 Hz), 7.83 (1H, brs), 7.99 (1H, d, J = 2.0 Hz), 8.20-8.24 (2H, m). |
| 567 | —F | —$CH_3$ | 1 | $^1H$ NMR 1.27 (3H, t, J = 7.1 Hz), 3.06 (3H, s), 4.04 (2H, s), 4.20 (2H, q, J = 7.1 Hz), 6.40-6.52 (2H, m), 6.96 (1H, d, J = 9.2 Hz), 7.07 (1H, t, 4 = 9.1 Hz), 7.57 (1H, d, J = 8.2 Hz), 7.70 (1H, dd, J = 8.2 Hz, 2.0 Hz), 7.82 (1H, brs), 7.97 (1H, d, J = 2.1 Hz), 8.13-8.19 (2H, m). |
| 568 | —F | —$C_2H_5$ | 1 | $^1H$ NMR 1.23 (3H, t, J = 7.1 Hz), 1.28 (3H, t, J = 7.1 Hz), 3.45 (2H, q, J = 7.1 Hz), 4.00 (2H, s), 4.22 (2H, q, J = 7.1 Hz), 6.37-6.48 (2H, m), 6.97 (1H, d, J = 8.7 Hz), 7.05 (1H, t, J = 9.1 Hz), 7.57 (1H, d, J = 8.4 Hz), 7.70 (1H, dd, J = 8.4 Hz, 2.2 Hz), 7.79 (1H, brs), 7.98 (1H, d, J = 2.0 Hz), 8.13-8.20 (2H, m). |

TABLE 80

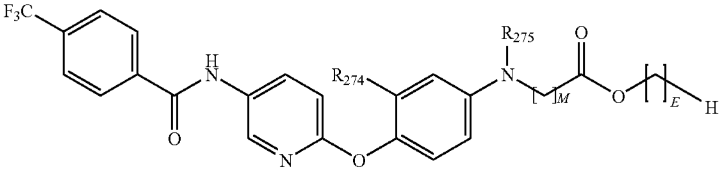

| Reference Example No. | $R_{274}$ | $R_{275}$ | M | E | mp (° C.) or $^1H$ NMR ($CDCl_3$) δ ppm |
|---|---|---|---|---|---|
| 569 | —H | -Ac | 1 | 2 | mp 163-164 |
| 570 | —H | -Ac | 2 | 2 | $^1H$ NMR 1.22(3 H, t, J = 7.2 Hz), 1.87(3 H, s), 2.59(2 H, t, J = 7.3 Hz), 4.00(2 H, t, J = 7.3 Hz), 4.08(2 H, q, J = 7.2 Hz), 7.03(1 H, d, J = 8.8 Hz), 7.19(4 H, s), 7.78(2 H, d, J = 8.3 Hz), 7.95(1 H, brs), 8.01(2 H, d, J = 8.3 Hz), 8.27(1 H, d, J = 8.8 Hz), 8.31(1 H, s). |
| 571 | —H | —$CH_3$ | 1 | 1 | $^1H$ NMR 3.06(3 H, s), 3.73(3 H, s), 4.07(2 H, s), 6.68(2 H, d, J = 9.1 Hz), 6.86 (1 H, d, J = 8.9 Hz), 7.00(2 H, d, J = 9.1 Hz), 7.74(2 H, d, J = 8.0 Hz), 7.98(2 H, d, J = 8.0 Hz), 8.07(1 H, s), 8.15(1 H, dd, J = 8.9 Hz, 2.5 Hz), 8.24(1 H, d, J = 2.5 Hz). |
| 572 | —H | —$C_2H_5$ | 1 | 2 | $^1H$ NMR 1.18(3 H, t, J = 7.1 Hz), 1.25(3 H, t, J = 7.1 Hz), 3.41(2 H, q, J = 7.1 Hz), 3.98(2 H, s), 4.17(2 H, q, J = 7.1 Hz), 6.59(2 H, d, J = 9.1 Hz), 6.79(1 H, d, J = 8.7 Hz), 6.92(2 H, d, J = 9.1 Hz), 7.64(2 H, d, J = 8.4 Hz), 7.94(2 H, d, J = 8.1 Hz), 8.07(1 H, dd, J = 8.9 Hz, 2.6 Hz), 8.22(1 H, d, J = 2.8 Hz), 8.75(1 H, s). |

TABLE 80-continued

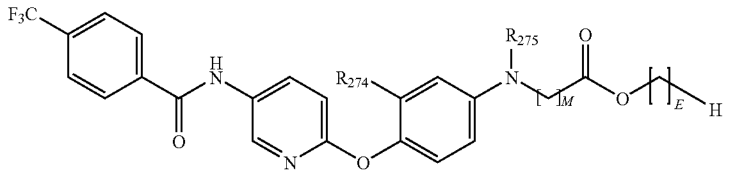

| Reference Example No. | $R_{274}$ | $R_{275}$ | M | E | mp (° C.) or $^1$H NMR ($CDCl_3$) δ ppm |
|---|---|---|---|---|---|
| 573 | —$OCH_3$ | —$CH_3$ | 1 | 2 | $^1$H NMR 1.24(3 H, t, J = 7.1 Hz), 3.03(3 H, s), 3.65(3 H, s), 4.01(2 H, s), 4.17 (2 H, q, J = 7.1 Hz), 6.17(1 H, dd, J = 8.7 Hz, 2.6 Hz), 6.24(1 H, d, J = 2.5 Hz), 6.77(1 H, d, J = 8.9 Hz), 6.89(1 H, d, J = 8.7 Hz), 7.63(2 H, d, J = 8.3 Hz), 7.96(2 H, d, J = 8.1 Hz), 8.06(1 H, d, J = 8.7 Hz), 8.16(1 H, d, J = 2.5 Hz), 8.91(1 H, s). |
| 574 | —$OCH_3$ | —$C_2H_5$ | 1 | 2 | $^1$H NMR 1.19 3 H, t, J = 7.1 Hz, 1.26 3 H, t, J = 7.1 Hz 3.42(2 H, q, J = 7.1 Hz), 3.64(3 H, s), 3.97(2 H, s), 4.18(2 H, q, J = 7.1 Hz), 6.14(1 H, dd, J = 8.7 Hz, 2.8 Hz), 6.21(1 H, d, J = 2.8 Hz), 6.76(1 H, d, J = 8.9 Hz), 6.87(1 H, d, J = 8.7 Hz), 7.62(2 H, d, J = 8.4 Hz), 7.96(2 H, d, J = 8.3 Hz), 8.05(1 H, dd, J = 8.9 Hz, 2.5 Hz), 8.18(1 H, d, J = 2.6 Hz), 9.01(1 H, s). |
| 575 | —$CH_3$ | -Ac | 1 | 2 | $^1$H NMR 1.25(3 H, t, J = 7.0 Hz), 1.93(3 H s) 2.21(3 H, s), 4.18(2 H, q, J = 7.0 Hz), 4.35(2 H, s), 6.98(1 H, d, J = 8.7 Hz), 7.06(1 H, d, J = 8.5 Hz), 7.18(1 H, d, J = 8.5 Hz), 7.23-7.28(1 H, m), 7.75(2 H, d, J = 7.8 Hz), 8.02(2 H, d, J = 7.8 Hz), 8.22-8.33(2 H, m). |
| 576 | —$CH_3$ | —$CH_3$ | 1 | 2 | $^1$H NMR 1.26(3 H, t, J = 7.1 Hz), 2.11(3 H, s), 3.05(3 H, s), 4.04(2 H, s), 4.19 (2 H, q, J = 7.1 Hz), 6.46-6.60(2 H, m), 6.80(1 H, d, J = 8.9 Hz), 6.91(1 H, d, J = 8.5 Hz), 7.74(2 H, d, J = 8.4 Hz), 7.98(2 H, d, J = 8.2 Hz), 8.07(1 H, s), 8.15 (1 H, dd, J = 8.9 Hz, 2.7 Hz), 8.23(1 H, d, J = 2.7 Hz). |
| 577 | —F | -Ac | 1 | 2 | $^1$H NMR 1.28(3 H, t, J = 7.1 Hz), 1.98(3 H, s), 4.20(2 H, q, J = 7.1 Hz), 4.36 (2 H, s), 7.09(1 H, dd, J = 6.4 Hz, 3.5 Hz), 7.13-7.32(3 H, m), 7.77(2 H, d, J = 8.3 Hz), 8.01(2 H, d, J = 8.1 Hz), 8.12(1 H, s), 8.23-8.28(2 H, m). |
| 578 | —F | —$CH_3$ | 1 | 2 | $^1$H NMR 1.27(3 H, t, J = 7.1 Hz), 3.07(3 H, s), 4.04(2 H, s), 4.20(2 H, q, J = 7.1 Hz), 6.41-6.53(2 H, m), 6.98(1 H, d, J = 9.7 Hz), 7.07(1 H, t, J = 9.1 Hz), 7.76 (2 H, d, J = 8.6 Hz), 7.84(1 H, s), 7.99(2 H, d, J = 8.1 Hz), 8.19-8.21(2 H, m). |
| 579 | —F | —$C_2H_5$ | 1 | 2 | $^1$H NMR 1.20-1.31(6 H, m), 3.45(2 H, q, J = 7.3 Hz), 4.00(2 H, s), 4.22(2 H, q, J = 7.1 Hz), 6.37-6.49(2 H, m), 6.97-7.09(2 H, m), 7.76-7.79(3 H, m), 7.99(2 H, d, J = 7.9 Hz), 8.19-8.21(2 H, m). |

Reference Example 580

Production of ethyl 3-{4-[5-(3,4-dichlorobenzoylamino)-pyridin-2-yloxy]-3-methoxyphenyl}propionate Under ice cooling, to a solution of ethyl 3-(4-(5-aminopyridin-2-yloxy)-3-methoxyphenyl)propionate (1.43 g, 4.5 mmol) in dichloromethane (30 mL) was added pyridine (0.44 mL, 5.4 mmol), and then 3,4-dichlorobenzoyl chloride (0.99 g, 4.7 mmol). The resulting solution was stirred for 1 hour under ice cooling, and then for 10 hours at room temperature. To the resulting reaction solution was added 10% hydrochloric acid, and extracted with dichloromethane. The dichloromethane layer was washed with water, dried over anhydrous magnesium sulfate, and evaporated. To the residue was added diethyl ether, and stirred. The precipitates were collected by filtration. After washing with water and diethyl ether, the precipitates were air dried at 60° C., to thereby yield 0.52 g of the title compound.

Appearance: White powder $^1$H NMR ($CDCl_3$) δ 1.26 (3H, t, J=7.1 Hz), 2.56-2.79 (2H, m), 2.91-3.09 (2H, m), 3.75 (3H, s), 4.15 (2H, q, J=7.1 Hz), 6.75 (3H, m), 7.10 (1H, d, J=8.0 Hz), 7.56 (1H, d, J=8.2 Hz), 7.99 (1H, d, J=8.1 Hz), 8.17 (1H, s), 8.69 (1H, d, J=9.2 Hz), 8.79 (1H, s), 9.52 (1H, brs).

The following compounds were produced in the same manner as in Reference Example 580.

TABLE 81

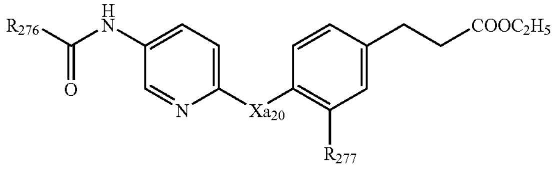

| Reference Example No. | $R_{276}$ | $R_{277}$ | $Xa_{20}$ | $^1H$ NMR ($CDCl_3$) δ ppm |
|---|---|---|---|---|
| 581 | 3,4-$Cl_2$Ph- | —H | —CO— | 1.23 (3H, t, J = 7.2 Hz), 2.64 (2H, t, J = 7.6 Hz), 3.01 (2H, t, J = 7.6 Hz), 4.12 (2H, q, J = 7.2 Hz), 7.30 (2H, d, J = 8.2 Hz), 7.57 (1H, d, J = 8.3 Hz), 7.73 (1H, dd, J = 8.3 Hz, 2.2 Hz), 7.95-8.04 (3H, m), 8.09 (1H, d, J = 8.6 Hz), 8.16 (1H, brs), 8.41 (1H, dd, J = 8.6 Hz, 2.6 Hz), 8.80 (1H, d, J = 2.6 Hz). |
| 582 | 4-$CF_3$Ph- | —$OC_2H_5$ | —O— | 1.22 (3H, t, J = 6.9 Hz), 1.26 (3H, t, J = 7.2 Hz), 251-2.73 (2H, m), 2.87-3.06 (2H, m), 4.02 (2H, q, J = 6.9 Hz), 4.15 (2H, q, J = 7.2 Hz), 6.71-6.96 (3H, m), 7.17 (1H, d, J = 7.9 Hz), 7.75 (2H, d, J = 7.6 Hz), 8.43 (2H, d, J = 7.6 Hz), 9.15-9.32 (1H, m), 9.42 (1H, s), 11.14 (1H, brs). |
| 583 | 3,4-$Cl_2$Ph- | —F | —O— | 1.26 (3H, t, J = 7.1 Hz), 2.53-2.70 (2H, m), 2.85-3.03 (2H, m), 4.15 (2H, q, J = 7.1 Hz), 6.97-7.09 (3H, m), 7.10-7.19 (1H, m), 7.58 (1H, d, J = 8.3 Hz), 7.70 (1H, dd, J = 8.3 Hz, 2.1 Hz), 7.72 (1H, brs), 7.97 (1H, d, J = 2.1 Hz), 8.15-8.23 (2H, m). |
| 584 | Ph$CH_2$O— | —H | —O— | 1.25 (3H, t, J = 7.1 Hz), 2.53-2.71 (2H, m), 2.84-3.04 (2H, m), 4.14 (2H, q, J = 7.1 Hz), 6.51-6.64 (1H, m), 6.88 (1H, d, J = 8.8 Hz), 6.98-7.06 (2H, m), 7.17-7.24 (2H, m), 7.30-7.43 (5H, m), 7.87-8.02 (1H, m), 8.05 (1H, d, J = 2.5 Hz). |
| 585 | 4-$CF_3$Ph- | —F | —O— | 1.26 (3H, t, J = 7.1 Hz), 2.56-2.71 (2H, m), 2.89-3.02 (2H, m), 4.15 (2H, q, J = 7.1 Hz), 6.97-7.08 (3H, m), 7.10-7.19 (1H, m), 7.77 (2H, d, J = 8.2 Hz), 7.82 (1H, brs), 7.99 (2H, d, J = 8.2 Hz), 8.17-8.26 (2H, m). |

TABLE 82

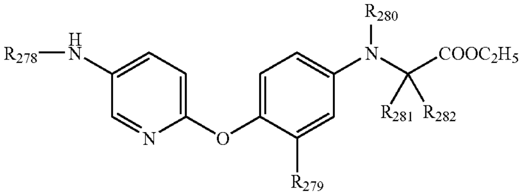

| Reference Example No. | $R_{278}$ | $R_{279}$ | $R_{280}$ | $R_{281}$ | $R_{282}$ | $^1H$ NMR ($CDCl_3$) δ ppm |
|---|---|---|---|---|---|---|
| 586 | 4-$CF_3$PhCO— | —F | —$(CH_2)_2CH_3$ | —H | —H | 0.96 (3H, t, J = 7.3 Hz), 1.28 (3H, t, J = 7.1 Hz), 1.63-1.74 (2H, m), 3.32 (2H, t, J = 7.6 Hz), 4.01 (2H, s), 4.21 (2H, q, J = 7.1 Hz), 6.35-6.47 (2H, m), 6.97 (1H, d, J = 7.8 Hz), 7.01 (1H, t, J = 8.9 Hz), 7.77 (2H, d, J = 8.2 Hz), 7.81 (1H, s), 7.99 (2H, d, J = 8.2 Hz), 8.19-8.22 (2H, m). |
| 587 | 4-$CF_3$PhCO— | —H | —$CH_3$ | —$CH_3$ | —$CH_3$ | 1.25 (3H, t, J = 7.1 Hz), 1.42 (6H, s), 2.91 (3H, s), 4.18 (2H, q, J = 7.1 Hz), 6.92 (1H, d, J = 8.7 Hz), 7.00 (2H, d, J = 9.2 Hz), 7.07 (2H, d, J = 9.1 Hz), 7.77 (2H, d, J = 8.2 Hz), |

TABLE 82-continued

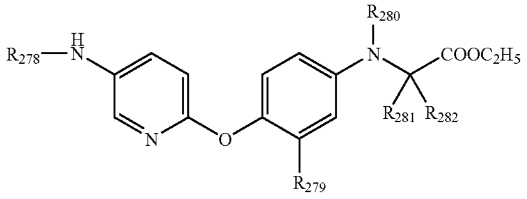

| Reference Example No. | $R_{278}$ | $R_{279}$ | $R_{280}$ | $R_{281}$ | $R_{282}$ | $^1H$ NMR ($CDCl_3$) δ ppm |
|---|---|---|---|---|---|---|
| 588 | 3,4-$Cl_2PhSO_2$— | —F | —$CH_3$ | —H | —H | 7.81 (1H, s), 8.00 (2H, d, J = 8.1 Hz), 8.20 (1H, dd, J = 8.7 Hz, 2.8 Hz), 8.28 (1H, d, J = 2.5 Hz). 1.29 (3H, t, J = 7.1 Hz), 3.05 (3H, s), 4.03 (2H, s), 4.22 (2H, q, J = 7.1 Hz), 6.38-6.49 (2H, m), 6.82 (1H, brs), 6.88 (1H, d, J = 8.7 Hz), 7.02 (1H, t, J = 8.8 Hz), 7.48 (1H, dd, J = 8.4, 1.6 Hz), 7.52 (1H, d, J = 8.4 Hz), 7.57 (1H, dd, J = 8.7 Hz, 2.6 Hz), 7.70 (1H, d, J = 2.6 Hz), 7.82 (1H, d, J = 1.8 Hz). |

Reference Example 589

Production of ethyl 4-[5-(3,4-dimethylbenzoylamino)-pyridin-2-yloxy]benzoate To a solution of ethyl 4-(5-aminopyridin-2-yloxy)benzoate (14.15 g, 54.8 mmol) in DMF (100 mL) were added 3,4-dimethylbenzoic acid (8.23 g, 54.8 mmol), 1-hydroxybenzotriazole monohydrate (8.4 g, 54.8 mmol), 1-ethyl-3-(3-dimethylaminopropyl)carbodiimide hydrochloride (12.6 g, 65.7 mmol) under ice cooling, and then stirred for 30 minutes under ice cooling and for 17 hours at room temperature. The reaction solution was concentrated under reduced pressure. To the residue was added water (200 mL), and extracted with ethyl acetate (250 mL). The ethyl acetate layer was washed with a saturated sodium bicarbonate solution and brine, dried over anhydrous magnesium sulfate, and evaporated. The residue was purified by silica gel column chromatography (n-hexane:ethyl acetate=2:1), to thereby yield 16.15 g of the title compound.

Appearance: White powder $^1H$ NMR ($CDCl_3$) δ 1.39 (3H, t, J=7.1 Hz), 2.33 (6H, s), 4.37 (2H, q, J=7.1 Hz), 6.99 (1H, d, J=9.7 Hz), 7.15 (2H, d, J=8.7 Hz), 7.24 (1H, d, J=7.7 Hz), 7.59 (1H, dd, J=7.7 Hz, 2.0 Hz), 7.65 (1H, d, J=2.0 Hz), 7.90 (1H, brs), 8.07 (2H, d, J=8.7 Hz), 8.25-8.35 (2H, m).

The following compounds were produced in the same manner as in Reference Example 589.

TABLE 83

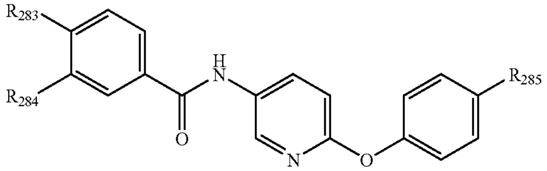

| Reference Example No. | $R_{283}$ | $R_{284}$ | $R_{285}$ | $^1H$ NMR ($CDCl_3$) δ ppm |
|---|---|---|---|---|
| 590 | —Cl | —Cl | —Ac | 2.58 (3H, s), 7.19 (1H, d, J = 8.7 Hz), 7.22 (2H, d, J = 8.7 Hz), 6.06 (2H, s), 7.84 (1H, d, J = 8.4 Hz), 7.97 (1H, dd, J = 8.4 Hz, 2.1 Hz), 8.01 (1H; d, J = 8.7 Hz), 8.24 (1H, d, J = 2.1 Hz), 8.28 (1H, dd, J = 8.7 Hz, 2.6 Hz), 8.56 (1H, d, J = 2.6 Hz), 10.64 (1H, brs). |
| 591 | —CN | —H | —$COOCH_3$ | 3.92 (3H, s), 7.05 (1H, d, J = 8.9 Hz), 7.18 (2H, d, J = 8.6 Hz), 7.81 (2H, d, J = 8.6 Hz), 7.90 (1H, brs), 8.00 (2H, d, J = 8.6 Hz), 8.08 (2H, d, J = 8.6 Hz), 8.27 (1H, dd, J = 8.6 Hz, 2.6 Hz), 8.30 (1H, d, J = 2.3 Hz). |

Reference Example 592

Production of ethyl 3-{4-[5-(3,4-dichlorobenzoylamino)-pyridin-2-yloxy]-3-ethoxyphenyl}propionate To a solution of ethyl 3-[3-ethoxy-4-(5-nitropyridin-2-yloxy)phenyl]propionate (0.82 g, 2.3 mmol) in ethanol (40 mL) was added 10% palladium-carbon (0.15 g) under a nitrogen atmosphere, and the resulting solution was stirred under a hydrogen atmosphere at atmospheric pressure for 1 hour at room temperature. The palladium-carbon was removed by filtration, and the filtrate was concentrated. The obtained filtrate (0.58 g) was dissolved in dichloromethane (30 mL), and to the resulting solution were added pyridine (0.17 mL, 2.1 mmol) and 3,4-dichlorobenzoyl chloride (0.39 g, 1.84 mmol) under ice cooling. The resulting solution was stirred under ice cooling for 1 hour, and then stirred for 12 hours at room temperature. The reaction solution was made acidic by adding 10% hydrochloric acid, and extracted with dichloromethane. The dichloromethane layer was washed with a saturated sodium bicarbonate solution, dried over anhydrous magnesium sulfate, and evaporated, to thereby yield 0.94 g of the title compound.

Appearance: Yellow amorphous powder $^1$H NMR ($CDCl_3$) δ 1.18 (3H, t, J=7.0 Hz), 1.26 (3H, t, J=7.1 Hz), 2.53-2.71 (2H, m), 2.86-3.01 (2H, m), 3.98 (2H, q, J=7.0 Hz), 4.15 (2H, q, J=7.1 Hz), 6.78-6.88 (2H, m), 6.95 (1H, d, J=8.8 Hz), 7.06 (1H, d, J=7.9 Hz), 7.58 (1H, d, J=8.3 Hz), 7.65-7.77 (2H, m), 7.98 (1H, d, J=2.1 Hz), 8.14 (1H, dd, J=8.8 Hz, 2.7 Hz), 8.19 (1H, d, J=2.3 Hz).

The following compound was produced in the same manner as in Reference Example 592.

Reference Example 593

N-{6-[4-(3-hydroxypropyl)phenoxy]pyridin-3-yl}-4-trifluoromethylbenzamide $^1$H NMR ($CDCl_3$) δ 1.86-1.97 (2H, m), 2.70-2.75 (2H, m), 3.68-3.73 (2H, m), 6.95 (1H, d, J=8.7 Hz), 7.03-7.08 (2H, m), 7.23 (2H, d, J=8.4 Hz), 7.77 (2H, d, J=8.2 Hz), 7.84 (1H, brs), 7.99 (2H, d, J=8.2 Hz), 8.20-8.23 (1H, m), 8.26 (1H, d, J=2.6 Hz).

Reference Example 594

Production of methyl 2-(4-{5-[3-(3,4-dichlorophenyl)-ureido]pyridin-2-yloxy}phenyl)acetate To a solution of methyl 2-[4-(5-aminopyridin-2-yloxy)phenyl]acetate (0.44 g, 1.7 mmol) in dichloro-methane (7 mL) was added 3,4-dichlorophenylisocyanate (0.353 g, 1.9 mmol), and the resulting reaction solution was stirred for 1 hour at room temperature. To the reaction solution was added diisopropyl ether. Insoluble matter was removed by filtration, to thereby yield 0.60 g of the title compound.

Appearance: White powder $^1$H NMR (DMSO-$d_6$) δ 3.63 (3H, s), 3.69 (2H, s), 6.99-7.05 (3H, m), 7.26-7.30 (2H, m), 7.35 (1H, dd, J=8.8, 2.4 Hz), 7.52 (1H, d, J=8.8 Hz), 7.86 (1H, d, J=2.4 Hz), 7.98 (1H, dd, J=8.8, 2.8 Hz), 8.18 (1H, d, J=2.7 Hz), 8.91 (1H, s), 9.10 (1H, s).

The following compounds were produced in the same manner as in Reference Example 594.

TABLE 84

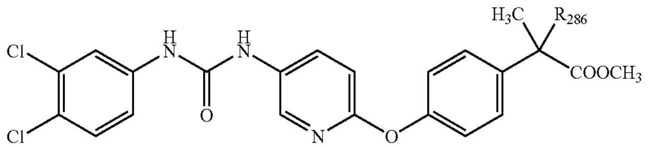

| Reference Example No. | $R_{286}$ | MS ($M^+$) |
|---|---|---|
| 595 | —H | 459 |
| 596 | —$CH_3$ | 473 |

TABLE 85

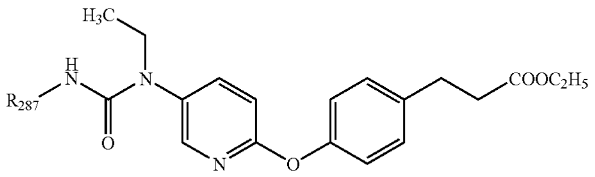

| Reference Example No. | $R_{287}$ | $^1$H NMR ($CDCl_3$) δ ppm or MS |
|---|---|---|
| 597 | 4-$CF_3$Ph- | $^1$H NMR 1.18(3 H, t, J = 7.1 Hz), 1.25(3 H, t, J = 7.1 Hz), 2.62-2.68(2 H, m), 2.96-3.01(2 H, m), 3.76(2 H, q, J = 7.1 Hz), 4.14(2 H, q, J = 7.1 Hz), 6.17(1 H, brs), 7.05(1 H, dd, J = 8.7 Hz, 0.7 Hz), 7.11(2 H, d, J = 8.6 Hz), 7.28(2 H, d, J = 8.6 Hz), 7.40(2 H, d, J = 8.7 Hz), 7.49(2 H, d,J = 8.6 Hz), 7.63(1 H, dd, J = 8.7 Hz, 2.6 Hz), 8.14(1 H, dd, J = 2.6 Hz, 0.7 Hz). |
| 598 | 3,4-$Cl_2$Ph- | MS 501($M^+$) |

TABLE 86

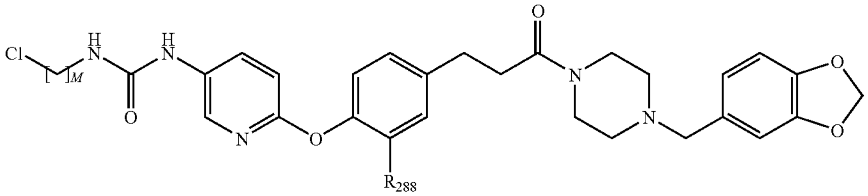

| Reference Example No. | $R_{288}$ | M | $^1$H NMR ($CDCl_3$) δ ppm |
|---|---|---|---|
| 599 | —H | 3 | 1.90-2.11(2 H, m), 2.28-2.50(4 H, m), 2.51-2.72(2 H, m), 2.82-3.07(2 H, m), 3.28-3.51(4 H, m), 3.52-3.78(4 H, m), 5.25-5.40(1 H, m), 5.96(2 H, s), 6.69-6.81(2 H, m), 6.82-6.94(2 H, m), 6.95-7.08(2 H, m), 7.09-7.26(3 H, m), 7.88-8.07(2 H, m). |
| 600 | —H | 2 | 2.20-2.46(4 H, m), 2.52-2.70(2 H, m), 2.82-3.02(2 H, m), 3.28-3.50(4 H, m), 3.51-3.72(6 H, m), 5.52-5.71(1 H, m), 5.95(1 H, s), 6.68-6.78(2 H, m), 6.80-6.89(2 H, m), 6.91(2 H, d, J = 8.4 Hz), 7.17(2 H, d, J = 8.4 Hz), 7.36(1 H, s), 7.89-8.01(2 H, m). |
| 601 | —$OCH_3$ | 3 | 1.85-2.08(2 H, m), 2.27-2.46(4 H, m), 2.55-2.71(2 H, m), 2.88-3.03(2 H, m), 3.30-3.46(6 H, m), 3.56(2 H, t, J = 6.3 Hz), 3.63(2 H, t, J = 4.9 Hz), 3.71(3 H, s), 5.20-5.36(1 H, m), 5.95(2 H, s), 6.68-6.89(6 H, m), 7.00(1 H, d, J = 8.0 Hz), 7.15(1 H, s), 7.87(1 H, d, J = 2.4 Hz), 7.92(1 H, dd J = 2.8 Hz, 8.8 Hz). |
| 602 | —$OCH_3$ | 2 | 2.25-2.49(4 H, m), 2.58-2.72(2 H, m), 2.87-3.05(2 H, m), 3.30-3.71(10 H, m), 3.7.1(3 H, s), 5.40-5.52(1 H, m), 5.95(2 H, s), 6.66-6.91(6 H, m), 7.00(1 H, d, J = 8.0 Hz), 7.07(1 H, s), 7.85-7.99 (2 H, m). |

TABLE 87

| Reference Example No. | Chemical Structure | $^1$H NMR (solvent) δ ppm |
|---|---|---|
| 603 | 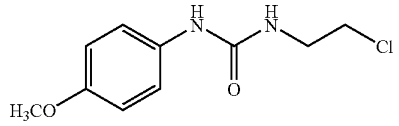 | (DMSO-$d_6$) 3.38(2 H, t, J = 6.1 Hz), 3.63(2 H, t, J = 6.1 Hz), 3.68(3 H, s), 6.27(1 H, t, J = 6.1 Hz), 6.76-6.84(2 H, m), 7.22-7.31(2 H, m), 8.41(1 H, s). |
| 604 | 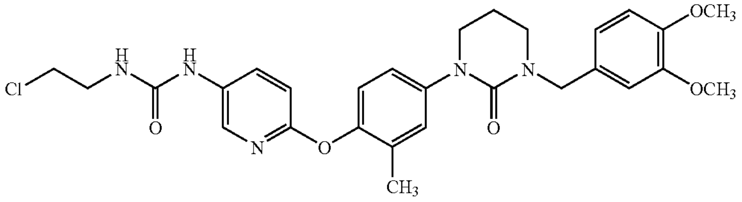 | ($CDCl_3$) 2.00-2.20(5 H, m), 3.27-3.47 (4 H, m), 3.48-3.60(2 H, m), 3.61-3.78 (2 H, m), 3.88(3 H, s), 3.89(3 H, s) 4 59 (2 H, s), 5.94-6.12(1 H, m), 6.66(1 H, d, J = 8.8 Hz), 6.83(1 H, d, J = 8.6 Hz), 6.80-6.92(3 H, m), 7.04(1 H, dd, J = 2.6 Hz, 8.6 Hz), 7.19(1 H, d, J = 2.6 Hz), 7.50(1 H, d, J = 2.8 Hz, 8.8 Hz), 7.73(1 H, s), 7.95(1 H, d, J = 2.8 Hz). |
| 605 | 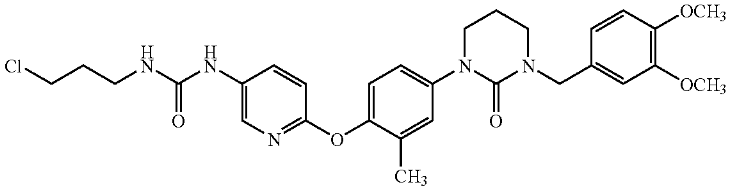 | ($CDCl_3$) 1.76-1.93(2 H, m), 2.00-2.20 (5 H, m), 3.11-3.28(2 H, m), 3.29-3.41 (2 H, m), 3.42-3.57(2 H, m), 3.60-3.78 (2 H, m), 3.87(3 H, s), 3.88(3 H, s), 4.57 (2 H, s), 5.70-5.88(1 H, m), 6.67(1 H, d, J = 8.8 Hz), 6.83(1 H, d, J = 8.6 Hz), 6.86(3 H, m), 7.04(1 H, dd, J = 2.6 Hz, 8.6 Hz), 7.17(1 H, d, J = 2.6 Hz), 7.56(1 H, dd, J = 2.8 Hz, 8.8 Hz), 7.68(1 H, s), 7.93(1 H, d, J =2.8 Hz). |

Reference Example 606

Production of methyl 3-(4-{5-[3-(4-trifluoromethylphenyl)ureido]pyridin-2-yloxy}phenyl)propionate Methyl 3-[4-(5-nitropyridin-2-yloxy)phenyl]propionate (1.00 g, 3.3 mmol) was dissolved in a mixed solvent consisting of THF (1 mL) and ethanol (120 mL). To the resulting solution was added 10% palladium-carbon (100 mg), and stirred for 23 hours at room temperature under a hydrogen atmosphere. The reaction solution was filtered and the filtrate was concentrated. To the residue were added THF (20 mL), triethylamine (0.917 mL, 6.6 mmol) and phenyl 4-trifluoromethylisocyanate (0.61 mL, 4.3 mmol), and the resulting solution was stirred for 20 hours at room temperature. The reaction solution was evaporated under reduced pressure. The residue was washed with ethyl acetate, to thereby yield 850 mg of the title compound.

Appearance: White powder $^1$H NMR (DMSO-$d_6$) δ 2.62-2.68 (2H, m), 2.83-2.88 (2H, m), 3.60 (3H, s), 6.97-7.02 (3H, m), 7.24 (2H, d, J=8.4 Hz), 7.65-7.69 (4H, m), 7.99 (1H, dd, J=8.9 Hz, 2.8 Hz), 8.19 (1H, d, J=2.8 Hz), 8.88 (1H, s), 9.20 (1H, s).

Reference Example 607

Production of methyl 3-fluoro-4-{5-[(4-trifluoromethyl-benzylidene)amino]pyridin-2-yloxy}benzoate Methyl 4-(5-aminopyridin-2-yloxy)-3-fluorobenzoate (2.0 g, 7.63 mmol) was dissolved in methanol (50 mL). To the resulting solution was added 4-trifluoromethylbenzaldehyde (1.04 mL, 7.63 mmol), and refluxed for 6 hours. The reaction solution was cooled to room temperature, and the resulting precipitated crystals were collected by suction filtration. The collected crystals were washed with methanol, to thereby yield 2.81 g of the title compound.

Appearance: Pale grey powder $^1$H NMR (DMSO-$d_6$) δ 3.89 (3H, s), 7.32 (1H, d, J=8.7 Hz), 7.48-7.54 (1H, m), 7.85-7.92 (4H, m), 8.01 (1H, dd, J=8.7 Hz, 2.6 Hz), 8.13-8.16 (3H, m), 8.86 (1H, s).

The following compounds were produced in the same manner as in Reference Example 607.

TABLE 88

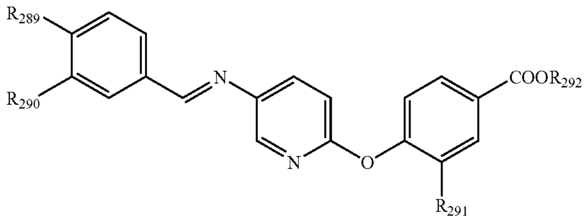

| Reference Example No. | $R_{289}$ | $R_{290}$ | $R_{291}$ | $R_{292}$ | $^1$H NMR (solvent) δ ppm |
|---|---|---|---|---|---|
| 608 | —$CF_3$ | —H | —H | —$CH_3$ | (DMSO-$d_6$) 3.86 (3H, s), 7.24-7.30 (3H, m), 7.92 (2H, d, J = 8.1 Hz), 7.98-8.05 (3H, m), 8.16 (2H, d, J = 8.1 Hz), 8.24 (1H, d, J = 2.1 Hz), 8.88 (1H, s). |
| 609 | —$CF_3$ | —H | —H | —$C_2H_5$ | (DMSO-$d_6$) 1.33 (3H, t, J = 7.1 Hz), 4.32 (2H, q, J = 7.1 Hz), 7.24-7.30 (3H, m), 7.92 (2H, d, J = 8.3 Hz), 8.00 (1H, dd, J = 8.7 Hz, 2.6 Hz), 8.02 (2H, d, J = 8.7 Hz), 8.16 (2H, d, J = 7.9 Hz), 8.24 (1H, d, J = 2.6 Hz), 8.88 (1H, s). |
| 610 | —Cl | —Cl | —F | —$CH_3$ | (DMSO-$d_6$) 3.89 (3H, s), 7.21 (1H, d, J = 8.6 Hz), 7.48-7.54 (1H, m), 7.80-7.94 (4H, m), 7.97 (1H, dd, J = 8.7 Hz, 2.8 Hz), 8.12-8.15 (2H, m), 8.75 (1H, s). |
| 611 | —Cl | —Cl | —F | —$C_2H_5$ | ($CDCl_3$) 1.40 (3H, t, J = 7.1 Hz), 4.39 (2H, q, J = 7.1 Hz), 7.09 (1H, d, J = 8.6 Hz), 7.26-7.35 (1H, m), 7.55-7.57 (1H, m), 7.66-7.73 (2H, m), 7.86-7.92 (2H, m), 8.02-8.03 (2H, m), 8.40 (1H, s). |

Reference Example 612

Production of ethyl 4-{5-[1-(4-trifluoromethylphenyl)-ethylideneamino]pyridin-2-yloxy}benzoate Ethyl 4-(5-aminopyridin-2-yloxy)benzoate (16.0 g, 62 mmol) was dissolved in toluene (300 mL). To the resulting solution were added 4-trifluoromethylacetophenone (11.7 g, 62 mmol) and (±)-camphor-10-sulfonic acid (1.08 g, 4.65 mmol), and refluxed overnight. The reaction solution was concentrated under reduced pressure, to thereby yield 26.5 g of the title compound.

Appearance: Dark green oil $^1$H NMR ($CDCl_3$) δ 1.35-1.41 (3H, m), 2.34 (3H, s), 4.36 (2H, d, J=7.1 Hz), 7.01-7.31 (4H, m), 7.70-7.77 (3H, m), 8.01-8.11 (4H, m).

Reference Example 613

Production of methyl 4-[5-(4-trifluoromethylbenzyl-amino)pyridin-2-yloxy]benzoate Methyl 4-{5-[(4-trifluoromethylbenzylidene)-amino]pyridin-2-yloxy}benzoate (2.64 g, 6.59 mmol) was suspended in methanol (25 mL), and to the resulting suspension was slowly added sodium borohydride (1.25 g, 33.0 mmol). The resulting solution was stirred at room temperature for 3 days. The reaction solution was concentrated under reduced pressure. To the residue was added ethyl acetate, and washed with water and brine. The organic layer was dried over anhydrous magnesium sulfate, and evaporated. The residue was washed with diethyl ether, to thereby yield 2.65 g of the title compound.

Appearance: White powder $^1$H NMR ($CDCl_3$) δ 3.89 (3H, s), 4.16 (1H, brs), 4.42 (2H, s), 6.84 (1H, d, J=8.7 Hz), 7.01 (1H, dd, J=8.6 Hz, 3.0 Hz), 7.05 (2H, d, J=8.4 Hz), 7.49 (2H, d, J=8.4 Hz), 7.62 (2H, d, J=8.3 Hz), 7.67 (1H, d, J=3.1 Hz), 8.01 (2H, d, J=8.6 Hz).

The following compounds were produced in the same manner as in Reference Example 613.

2-yloxy)phenyl]propionate (2.1 g, 7.3 mmol) in ethanol (20 mL), and the resulting solution was stirred for 2 hours at 40° C. To the resulting reaction solution was added sodium borohydride (0.55 g, 15.7 mmol) under ice cooling, and stirred at the same temperature for 1 hour. To the solution was added water and extracted with ethyl acetate. The ethyl acetate layer was washed with water, dried over anhydrous magnesium sulfate. The solvent was evaporated, and the residue was purified by silica gel column chromatography (n-hexane: ethyl acetate=4:1), to thereby yield 2.71 g of the title compound.

TABLE 89

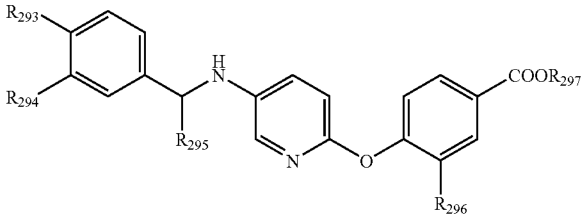

| Reference Example No. | $R_{293}$ | $R_{294}$ | $R_{295}$ | $R_{296}$ | $R_{297}$ | $^1$H NMR ($CDCl_3$) δ ppm |
|---|---|---|---|---|---|---|
| 614 | $—CF_3$ | —H | —H | —H | $—C_2H_5$ | 1.37 (3H, t, J = 7.1 Hz), 4.19 (1H, brs), 4.35 (2H, q, J = 7.1 Hz), 4.41 (2H, brs), 6.83 (1H, d, J = 8.7 Hz), 7.01 (1H, dd, J = 8.6 Hz, 3.0 Hz), 7.04 (2H, d, J = 8.6 Hz), 7.48 (2H, d, J = 8.1 Hz), 7.61 (2H, d, J = 8.3 Hz), 7.66 (1H, d, J = 3.0 Hz), 8.02 (2H, d, J = 8.7 Hz). |
| 615 | —CF | —H | $—CH_3$ | —H | $—C_2H_5$ | 1.37 (3H, t, J = 7.1 Hz), 1.56 (3H, d, J = 6.8 Hz), 4.06 (1H, brs), 4.34 (2H, q, J = 7.1 Hz), 4.49 (1H, q, J = 6.6 Hz), 6.75 (1H, d, J = 8.7 Hz), 6.87 (1H, dd, J = 8.7 Hz, 3.0 Hz), 7.01 (2H, d, J = 8.6 Hz), 7.47 (2H, d, J = 8.1 Hz), 7.53 (1H, d, J = 3.0 Hz), 7.60 (2H, d, J = 8.3 Hz), 8.00 (2H, d, J = 8.7 Hz). |
| 616 | $—CF_3$ | —H | —H | —F | $—CH_3$ | 3.90 (3H, s), 4.40 (2H, brs), 6.89 (1H, d, J = 8.1 Hz), 7.03 (1H, dd, J = 8.7 Hz, 3.0 Hz), 7.15-7.21 (1H, m), 7.47 (2H, d, J = 8.1 Hz), 7.55 (1H, d, J = 3.0 Hz), 7.61 (2H, d, J = 8.1 Hz), 7.80-7.84 (2H, m). |
| 617 | —Cl | —Cl | —H | —F | $—CH_3$ | 3.91 (3H, s), 4.29 (2H, brs), 6.88 (1H, d, J = 8.7 Hz), 7.02 (1H, dd, J = 8.7 Hz, 3.0 Hz), 7.15-7.21 (2H, m), 7.41 (1H, d, J = 8.3 Hz), 7.46 (1H, d, J = 2.0 Hz), 7.53 (1H, d, J = 3.0 Hz), 7.81-7.84 (2H, m). |

Reference Example 618

Production of ethyl 3-{4-[5-(3,4-dichlorobenzylamino)-pyridin-2-yloxy]phenyl}propionate A solution of 3,4'-dichlorobenzaldehyde (1.28 g, 7.3 mmol) was added to a solution of ethyl 3-[4-(5-aminopyridin- Appearance: Colorless oil $^1$H NMR ($CDCl_3$) δ 1.24 (3H, t, J=7.1 Hz), 2.50-2.68 (2H, m), 2.81-3.01 (2H, m), 3.71-4.20 (3H, m), 4.28 (2H, s), 6.76 (1H, d, J=8.7 Hz), 6.88-7.02 (3H, m), 7.06-7.23 (3H, m), 7.41 (1H, d, J=8.2 Hz), 7.46 (1H, d, J=2.0 Hz), 7.60 (1H, d, J=3.0 Hz).

The following compounds were produced in the same manner as in Reference Example 618.

TABLE 90

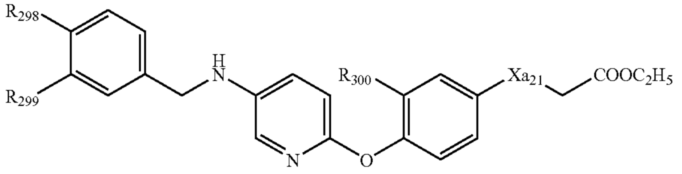

| Reference Example No. | $R_{298}$ | $R_{299}$ | $R_{300}$ | $Xa_{21}$ | $^1$H NMR ($CDCl_3$) δ ppm |
|---|---|---|---|---|---|
| 619 | —$CF_3$ | —H | —H | —$CH_2$— | 1.24 (3H, t, J = 7.3 Hz), 2.60 (2H, t, J = 8.1 Hz) 2.92 (2H, t, J = 8.1 Hz), 4.13 (2H, q, J = 7.3 Hz), 4.39 (2H, s), 6.76 (1H, d, J = 8.7 Hz), 6.97 (2H, d, J = 8.4 Hz), 6.98 (1H, dd, J = 8.6 Hz, 3.1 Hz), 7.17 (2H, d, J = 8.4 Hz), 7.47 (2H, d, J = 8.1 Hz), 7.60 (2H, d, J = 7.9 Hz), 7.61 (1H, d, J = 3.1 Hz). |
| 620 | —Cl | —Cl | —$OCH_3$ | —$CH_2$— | 1.25 (3H, t, J = 7.1 Hz), 2.65-2.74 (2H, m), 2.94 (2H, t, J = 8.2 Hz), 3.76 (3H, s), 3.93 (1H, brs), 4.14 (2H q, J =7.1 Hz), 4.22-4.34 (2H, m), 6.70-6.85 (3H, m), 6.85-7.02 (2H, m), 7.10-7.25 (1H m), 7.39 (1H, d, J = 8.2 Hz), 7.44 (1H, d, J = 2.0 Hz), 7.53 (1H, d, J = 2.7 Hz). |
| 621 | —$CF_3$ | —H | —$OCH_3$ | —$CH_2$— | 1.25 (3H, t, J = 7.1 Hz), 2.52-2.68 (2H, m), 2.81-3.01 (2H, m) 3.76 (3H s), 3.93 (1H, brs), 4.14 (2H, q, J = 7.1 Hz), 4.30-4.40 (2H, m), 6.72-6.84 (3H, m), 6.96 (1H, d, J = 8.0 Hz), 6.98 (1H, dd, J = 8.0 Hz, 3.0 Hz), 7.40 (2H, d, J = 8.0 Hz), 7.55 (1H, d, J = 3.0 Hz), 7.59 (2H, d, J = 8.0 Hz). |
| 622 | —Cl | —Cl | —$OC_2H_5$ | —$CH_2$— | 1.18 (3H, t, J = 7.0 Hz), 1.25 (3H, t, J = 7.1 Hz), 2.52-2.69 (2H, m), 2.82-3.00 (2H, m), 3.81-4.02 (3H, m), 4.14 (2H, q, J = 7.1 Hz), 4.27 (2H, d, J = 4.7 Hz), 6.72-6.82 (3H, m), 6.93-7.02 (2H, m), 7.18 (1H, dd, J = 8.2 Hz, 2.0 Hz), 7.39 (1H, d, J = 8.4 Hz), 7.45 (1H, d, J = 2.0 Hz), 7.52 (1H, d, J = 3.0 Hz). |
| 623 | —$CF_3$ | —H | —$OC_2H_5$ | —$CH_2$— | 1.18 (3H, t, J = 7.0 Hz), 1.25 (3H, t, J = 7.1 Hz), 2.51-2.72 (2H, m), 2.83-3.01 (2H, m), 3.87-4.06 (3H, m), 4.16 (2H, q, J = 7.1 Hz), 4.30-4.42 (2H, m), 6.72-6.83 (3H, m), 6.94-7.02 (2H, m), 7.46 (2H, d, J = 8.1 Hz), 7.54 (1H, d, J = 3.0 Hz), 7.59 (2H, d, J = 8.1 Hz). |
| 624 | —Cl | —Cl | —F | —$CH_2$— | 1.12-1.35 (3H, m), 2.50-2.74 (2H, m), 2.93 (2H, t, J = 7.7 Hz), 3.95 (1H, brs), 4.05-4.20 (2H, m), 4.27 (2H, s), 6.82 (1H, d, J = 8.4 Hz), 6.90-7.15 (4H, m), 7.18 (1H, dd, J = 8.4 Hz, 2.0 Hz), 7.35-7.60 (3H, m). |
| 625 | —$CF_3$ | —H | —F | —$CH_2$— | 1.13-1.35 (3H, m), 2.65-2.70 (2H, m), 2.93 (2H, t, J = 7.7 Hz), 4.01 (1H, brs), 4.05-4.23 (2H, m), 4.37 (2H, s), 6.82 (1H, d, J = 8.8Hz), 6.90-7.15 (4H, m), 7.37-7.55 (3H, m) 7.55-7.70 (2H, m). |
| 626 | —Cl | —Cl | —H | —N(Ac)— | 1.27 (3H, t, J = 7.1 Hz), 1.94 (3H, s), 4.10 (1H, brs), 4.19 (2H, q, J = 7.1 Hz), 4.31 (2H, s), 4.34 (2H, s), 6.84 (1H, d, J = 8.5 Hz), 7.00 (1H, dd, J = 8.5 Hz, 3.0 Hz), 7.06 (2H, d, J = 8.7 Hz), 7.20 (1H, dd, J = 8.2 Hz, 2.2 Hz), 7.31 (2H, d, J = 8.7 Hz), 7.42 (1H, d, J = 8.2 Hz), 7.47 (1H, d, J = 2.2 Hz), 7.62 (1H, d, J = 3.0 Hz). |
| 627 | —$CF_3$ | —H | —H | —N(Ac)— | 1.27 (3H, t, J = 7.1 Hz), 1.93 (3H, s) 4.15 (1H, brs), 4.18 (2H, q, J = 7.1 Hz), 4.34 (2H, s), 4.35-4.50 (2H, m), 6.83 (1H, d, J = 8.6 Hz), 7.01 (1H, dd, J = 8.6 Hz, 3.0 Hz), 7.06 (2H, d, J = 8.9 Hz), 7.31 (2H, d, J = 8.9 Hz), 7.48 (2H, d, J = 8.1 Hz), 7.62 (2H, d, J = 8.1 Hz), 7.64 (1H, d, J = 3.6 Hz). |

Reference Example 628

Production of ethyl 3-(4-{5-[benzyloxycarbonyl(2-methoxyethyl)amino]pyridin-2-yloxy}phenyl)propionate Under a nitrogen atmosphere, to a solution of ethyl 3-[4-(5-benzyloxycarbonylaminopyridin-2-yloxy)phenyl]propionate (1.7 g, 4.0 mmol) in DMF (50 mL) was added 60% sodium hydride (0.19 g, 4.9 mmol) under ice cooling, and the resulting solution was stirred for 35 minutes at the same temperature. 2-Bromoethylmethyl ether (0.4 mL, 4.2 mmol) was added dropwise to the solution. The reaction solution was stirred for 2 hours under ice cooling, and then stirred for 2 days at room temperature. To the reaction solution was added water, and extracted with ethyl acetate. The ethyl acetate layer was washed with water, and then dried over anhydrous magnesium sulfate. The solvent was evaporated, and the residue was purified by silica gel column chromatography (n-hexane: ethyl acetate=4:1), to thereby yield 1.6 g of the title compound.

Appearance: Pale yellow oil $^1$H NMR ($CDCl_3$) δ 1.25 (3H, t, J=7.1 Hz), 2.57-2.70 (2H, m), 2.89-3.02 (2H, m), 3.52 (2H, t, J=5.4 Hz), 3.79 (2H, t, J=5.4 Hz), 4.14 (2H, q, J=7.1 Hz), 5.14 (2H, brs), 6.87 (1H, d, J=8.7 Hz), 6.89-7.10 (2H, m), 7.11-7.41 (7H, m), 7.47-7.69 (1H, m), 8.10 (1H, brs).

The following compounds were produced in the same manner as in Reference Example 628.

Reference Example 629

Ethyl[(4-{5-[(3,4-dichlorophenyl)methylamino]pyridin-2-yloxy}-2-trifluoromethylphenyl)ethylamino] acetate

MS 541 ($M^+$)

TABLE 91

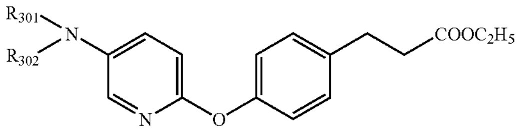

| Reference Example No. | $R_{301}$ | $R_{302}$ | $^1H$ NMR ($CDCl_3$) δ ppm or MS |
|---|---|---|---|
| 630 | $4\text{-}CF_3PhCH_2$— | $-(CH_2)_2OCH_3$ | $^1H$ NMR 1.24 (3H, t, J = 7.1 Hz), 2.54-2.67 (2H, m), 2.76-2.98 (2H, m), 4.13 (2H, q, J = 7.1 Hz), 4.61 (2H, s), 6.76 (1H, d, J = 8.9 Hz), 6.93-7.01 (2H, m), 7.07 (1H, dd, J = 8.9 Hz, 3.3 Hz), 7.12-7.20 (2H, m), 7.33 (2H, d, J = 8.0 Hz), 7.56 (2H, d, J = 8.0 Hz), 7.65 (1H, d, J = 2.9 Hz). |
| 631 | $4\text{-}CF_3PhCH_2$— | $—C_2H_5$ | $^1H$ NMR 1.09-1.32 (6H, m), 2.53-2.66 (2H, m), 2.84-2.98 (2H, m), 3.45 (2H, q, J = 7.1 Hz), 4.13 (2H, q, J = 7.1 Hz), 4.49 (2H, s), 6.77 (1H, d, J = 8.5 Hz), 6.93-7.01 (2H, m), 7.02-7.09 (1H, m), 7.12-7.20 (2H, m), 7.11-7.39 (2H, m), 7.53-7.61 (2H, m), 7.66 (1H, d, J = 3.0 Hz). |
| 632 | $PhCH_2OCO$— | $—C_2H_5$ | $^1H$ NMR 1.15 (3H, t, J = 7.1 Hz), 1.25 (3H, t, J = 7.1 Hz), 2.54-2.71 (2H, m), 2.83-3.04 (2H, m), 3.69 (2H, q, J = 7.1 Hz), 4.14 (2H, q, J = 7.1 Hz), 5.14 (2H, brs), 6.88 (1H, d, J = 8.7 Hz), 7.02-7.11 (2H, m), 7.18-7.40 (7H, m), 7.44-7.59 (1H, m), 7.98-8.08 (1H, m). |
| 633 | $4\text{-}CF_3PhCH_2$— | $—SO_2CH_3$ | MS 522($M^+$) |
| 634 | $3,4\text{-}Cl_2PhCH_2$— | $—SO_2CH_3$ | MS 522($M^+$) |
| 635 | $3,4\text{-}Cl_2Ph$- | $—CH_3$ | MS 444($M^+$) |

Reference Example 636

Production of ethyl 3-{4-[5-(2-methoxyethylamino)-pyridin-2-yloxy]phenyl}propionate To a solution of ethyl 3-(4-{5[benzyloxycarbonyl(2-methoxyethyl)amino]pyridin-2-yloxy}phenyl}propionate (1.82 g, 3.8 mmol) in ethanol-ethyl acetate (10 mL-10 mL) was added under a nitrogen atmosphere 10% palladium-carbon (0.2 g), and the resulting solution was stirred for 3 hours under a hydrogen atmosphere at atmospheric pressure. The palladium-carbon was filtered off through Celite, and the filtrate was evaporated to yield 1.23 g of the title compound.

Appearance: Blue oil $^1H$ NMR ($CDCl_3$) δ 1.24 (3H, t, J=7.1 Hz), 2.55-2.68 (2H, m), 2.87-2.98 (2H, m), 3.20-3.31 (2H, m), 3.56-3.66 (2H, m), 4.13 (2H, q, J=7.1 Hz), 6.77 (1H, d, J=8.7 Hz), 6.93-7.01 (2H, m), 7.03 (1H, dd, J=8.7 Hz, 3.0 Hz), 7.13-7.22 (2H, m), 7.66 (1H, d, J=3.0 Hz).

The following compound was produced in the same manner as in Reference Example 636.

Reference Example 637

Ethyl 3-[4-(5-ethylaminopyridin-2-yloxy)phenyl]-propionate $^1H$ NMR ($CDCl_3$) δ 1.29-1.32 (6H, m), 2.55-2.67 (2H, m), 2.87-2.99 (2H, m), 3.14 (2H, q, J=7.1 Hz), 4.13 (2H, q, J=7.1 Hz), 6.77 (1H, d, J=8.7 Hz), 6.89-7.02 (3H, m), 7.09-7.25 (3H, m), 7.63 (1H, d, J=3.0 Hz).

Reference Example 638

Production of ethyl 3-(3-methoxy-4-{5-[methyl-(4-trifluoromethylbenzyl)amino]pyridin-2-yloxy}phenyl)-propionate To a solution of ethyl 3-{3-methoxy-4-[5-(4-trifluoromethylbenzylamino]pyridin-2-yloxy}phenyl}-propionate (0.8 g, 1.7 mmol) in methanol (15 mL) were added a 37% aqueous formaldehyde solution (0.38 mL, 5.1 mmol) and acetic acid (0.1 mL, 1.7 mmol). The reaction solution was stirred for 30 minutes at room temperature. After that, sodium cyanoborohydride (0.24 g, 3.4 mmol) was added to the reaction solution under ice cooling, and the mixture was stirred under ice cooling for 40 minutes. To the reaction solution was added water, and extracted with ethyl acetate. The ethyl acetate layer was washed with water, and then dried over anhydrous magnesium sulfate. The solvent was evaporated, and the residue was purified by silica gel column chromatography (n-hexane: ethyl acetate=4:1), to thereby yield 0.62 g of the title compound.

Appearance: Pale yellow oil

$^1$H NMR ($CDCl_3$) δ 1.25 (3H, t, J=7.1 Hz), 2.52-2.70 (2H, m), 2.87-3.02 (5H, m), 3.77 (3H, s), 4.14 (2H, q, J=7.1 Hz), 4.40-4.50 (2H, m), 6.74-6.86 ((3H, m), 6.97 (1H, d, J=8.0 Hz), 7.11 (1H, dd, J=8.9 Hz, 3.2 Hz), 7.34 (2H, d, J=8.1 Hz), 7.57 (2H, d, J=8.1 Hz), 7.65 (1H, d, J=3.2 Hz).

The following compounds were produced in the same manner as in Reference Example 638.

TABLE 92

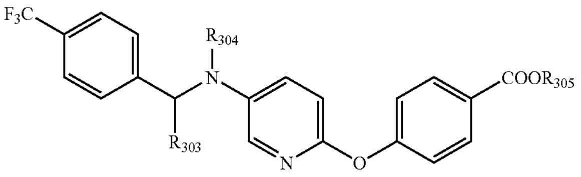

| Reference Example No. | $R_{303}$ | $R_{304}$ | $R_{305}$ | $^1$H NMR (CD $Cl_3$) δ ppm |
|---|---|---|---|---|
| 639 | —H | —$CH_3$ | —$CH_3$ | 3.07(3 H, s), 3.89(3 H, s), 4.56(2 H, s), 6.87(1 H, d, J = 8.9 Hz), 7.06(2 H, d, J = 8.6 Hz), 7.13(1 H, dd, J = 8.9 Hz, 3.3 Hz), 7.35(2 H, d, J = 8.1 Hz), 7.60(2 H, d, J = 8.3 Hz), 7.75(1 H, d, J = 3.1 Hz), 8.02(2 H, d, J = 8.6 Hz). |
| 640 | —H | —$C_2H_5$ | —$C_2H_5$ | 1.24(3 H, t, J = 7.1 Hz), 1.37(3 H, t, J = 7.1 Hz), 3.49(2 H, q, J = 7.1 Hz), 4.35(2 H, q, J = 7.1 Hz), 4 53(2 H, s), 6.84(1 H, d, J = 8.9 Hz), 7.05(2 H, d, J = 8.6 Hz), 7.06(1 H, dd, J = 8.9 Hz, 3.1 Hz), 7.36(2 H, d, J = 8.4 Hz), 7.58(2 H, d, J = 8.3 Hz), 7.69(1 H, d, J = 3.1 Hz), 8.02(2 H, d, J = 8.6 Hz). |
| 641 | —$CH_3$ | —$CH_3$ | —$C_2H_5$ | 1.38(3 H, t, J = 7.1 Hz), 1.59(3 H, d, J = 6.9 Hz), 2.74(3 H, s), 4.36(2 H, q, J = 7.1 Hz), 4.49(1 H, q, J = 6.9 Hz), 6.89(1 H, d, J = 8.9 Hz), 7.08 (2 H, d, J = 8.9 Hz), 7.24(1 H, dd, J = 8.9 Hz, 3.1 Hz), 7.43(2 H, d, J = 8.6 Hz), 7.61(2 H, d, J = 8.3 Hz), 7.84(1 H, d, J = 3.1 Hz), 8.03(2 H, d, J = 8.9 Hz). |

TABLE 93

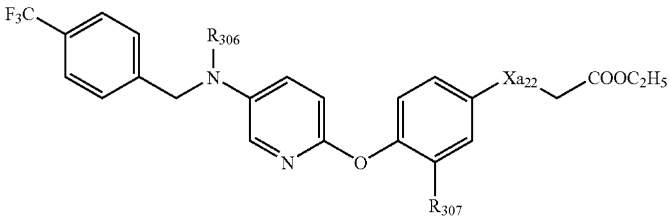

| Reference Example No. | $R_{306}$ | $R_{307}$ | $Xa_{22}$ | $^1$H NMR ($CDCl_3$) δ ppm |
|---|---|---|---|---|
| 642 | —$CH_3$ | —H | —$CH_2$— | 1.24(3 H, t, J = 7.1 Hz), 2.60(2 H, t, J = 7.8 Hz), 2.92(2 H, t, J = 7.8 Hz), 3.02(3 H, s), 4.12(2 H, q, J = 7.1 Hz), 4.51(2 H, s), 6.79(1 H, d, J = 8.9 Hz), 6.97(2 H, d, J = 8.4 Hz), 7.10(1 H, dd, J = 8.9 Hz, 3.3 Hz), 7.17(2 H, d, J = 8.3 Hz), 7.34(2 H, d, J = 8.1 Hz), 7.58(2 H, d, J = 8.3 Hz), 7.69(1 H, d, J = 3.1 Hz). |
| 643 | -$CH_3$ | —H | —N(Ac)- | 1.27(3 H, t, J = 7.1 Hz), 1.94(3 H, s), 3.06(3 H, s), 4.18(2 H, q, J = 7.1 Hz), 4.34(2 H, s), 4.55(2 H, s), 6.87(1 H, d, J = 8.9 Hz), 7.07(2 H, d, J = 83 Hz), 7.13(1 H, dd, J = 8.9 Hz, 3.1 Hz), 7.31(2 H, d, J = 8.7 Hz), 7.35(2 H, d, J = 8.0 Hz), 7.59(2 H, d, J = 8.0 Hz), 7.72(1 H, d, J = 3.1 Hz). |
| 644 | —$CH_3$ | —F | —$CH_2$— | 1.25(3 H, t, J = 7.1 Hz), 2.55-2.70(2 H, m), 2.93(2 H, t, J = 7.9 Hz), 3.00(3 H, s), 4.13(2 H, q, J = 7.1 Hz), 4.49(2 H, s), 6.86(1 H, d, J = 8.9 Hz), 6.90-7.16(4 H, m), 7.33(2 H, d, J = 8.1 Hz), 7.57(2 H, d, J = 8.1 Hz), 7.62(1 H, d, J = 3.2 Hz). |
| 645 | —$CH_3$ | —$OC_2H_5$ | —$CH_2$— | 1.19(3 H, t, J = 7.0 Hz), 1.25(3 H, t, J = 7.1 Hz), 2.50-2.69(2 H, m), 2.81-2.99(2 H, m), 2.98(3 H, s), 3.98(2 H, q, J = 7.0 Hz), 4.14(2 H, q, J = 7.1 Hz), 4.48(2 H, s), 6.68-6.88(3 H, m), 7.00(1 H, d, J = 8.0 Hz), 7.11(1 H, dd, J = 8.0 Hz, 3.0 Hz), 7.33(2 H, d, J = 8.0 Hz), 7.56(2 H, d, J = 8.0 Hz), 7.64(1 H, d, J = 3.0 Hz). |

TABLE 93-continued

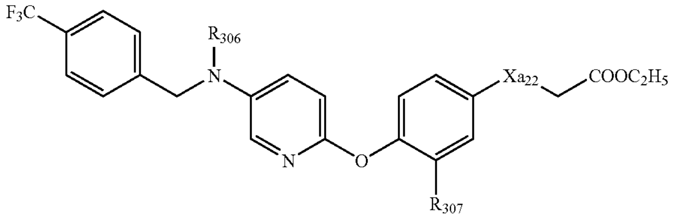

| Reference Example No. | $R_{306}$ | $R_{307}$ | $Xa_{22}$ | $^1H$ NMR ($CDCl_3$) δ ppm |
|---|---|---|---|---|
| 646 | —$C_2H_5$ | —F | —$CH_2$— | 1.19(3 H, t, J = 7.1 Hz), 1.10-1.35(3 H, m), 2.50-2.70(2 H, m), 2.93 (2 H, t, J = 8.0 Hz), 3.43(2 H, q, J = 7.1 Hz), 4.02-4.22(2 H, m), 4.47 (2 H, s), 6.83(1 H, d, J = 9.0 Hz), 6.88-7.15(4 H, m), 7.34(2 H, d, J = 8.0 Hz), 7.41-7.70(3 H, m). |
| 647 | —$C_2H_5$ | —$OCH_3$ | —$CH_2$— | 1.18(3 H, t, J = 7.0 Hz), 1.25(3 H, t, J = 7.1 Hz), 2.57-2.68(2 H, m), 2.88-2.99(2 H, m), 3.42(2 H, q, J = 7.0 Hz), 3.77(3 H, s), 4.14(2 H, q, 4 7.1 Hz), 4.42-4.50(2 H, m), 6.72-6.86((3 H, m), 6.97(1 H, d, J = 8.0 Hz), 7.05(1 H, 4d, J = 9.0 Hz, 3.2 Hz), 7.30-7.38(2 H, m), 7.51-7.59 (2 H, m), 7.60(1 H, d, J = 3.2 Hz). |
| 648 | —$C_2H_5$ | —$OC_2H_5$ | —$CH_2$— | 1.17(3 H, t, J = 7.0 Hz), 1.18(3 H, t, J = 7.0 Hz), 1.25(3 H, t, J = 7.1 Hz), 2.55-2.69(2 H, m), 2.84-2.98(2 H, m), 3.42(2 H, q, J = 7.1 Hz), 3.97(2 H, q, J = 7.0 Hz), 4.13(2 H, q, J = 7.0 Hz), 4.46(2 H, s), 6.71-6.82(3 H, m), 6.99(1 H, d, J = 8.0 Hz), 7.05(1 H, dd, J = 8.9 Hz, 3.1 Hz), 7.34(2 H, d, J = 8.0 Hz), 7.55(2 H, d, J = 8.0 Hz), 7.59(1 H, d, J = 3.1 Hz). |

TABLE 94

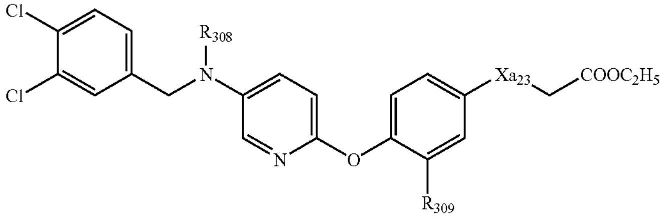

| Reference Example No. | $R_{308}$ | $R_{309}$ | $Xa_{23}$ | $^1H$ NMR (CD $Cl_3$) δ ppm |
|---|---|---|---|---|
| 649 | —$CH_3$ | —H | —N(Ac)- | 1.27(3 H, t, J = 7.1 Hz), 1.94(3 H, s); 3.03(3 H, s), 4.19(2 H, q, J = 7.1 Hz), 4.34(2 H, s), 4.43(2 H, s), 6 87(1 H, d, J = 9.0 Hz), 7.03-7.11(1 H, m), 7.07(2 H d, J = 8.7 Hz), 7.13(1 H, dd, J = 9.0 Hz, 3.1 Hz), 7.27-7.35(1 H, m), 7.31(2 H, d, J = 8.7 Hz), 7.40(1 H, d, J = 8.2 Hz), 7.71(1 H, d, J = 3.1 Hz). |
| 650 | —$CH_3$ | —F | —$CH_2$— | 1.15-1.30(3 H, m), 2.53-2.70(2 H, m), 2.93(2 H, t, J = 7.9 Hz), 2.97(3 H, s), 4.02-4.20(2 H, m), 4.37(2 H, s), 6.86(1 H, d, J = 8.9 Hz), 6.91-7.18(5 H, m), 7.32(1 H, d, J = 2.0 Hz), 7.38(1 H, d, J = 8.2 Hz), 7.61(1 H, d, J = 2.9 Hz). |
| 651 | —$CH_3$ | —$OCH_3$ | —$CH_2$— | 1.25(3 H, t, J = 7.1 Hz), 2.55-2.75(2 H, m), 2.85-3.05(2 H, m), 2.95(3 H, s), 3.77(3 H, s), 4.14(2 H, q, J = 7.1 Hz), 4.36(2 H, s), 6.71-6.88(3 H, m), 6.98(1 H, d, J = 8.1 Hz), 7.00-7.15(2 H, m), 7.32(1 H, d, J = 2.0 Hz), 7.38(1 H, d, J = 8.1 Hz), 7.64(1 H, d, J = 3.1 Hz). |
| 652 | —$CH_3$ | —$OC_2H_5$ | —$CH_2$— | 1.19(3 H, t, J = 7.0 Hz), 1.25(3 H, t, J = 7.1 Hz), 2.55-2.72(2 H, m), 2.84-3.01(5 H, m), 3.98(2 H, q, J = 7.0 Hz), 4.14(2 H, q, 4 7.1 Hz), 4.29-4.40(2 H, m), 6.74-6.83(3 H, m), 7.00(1 H, d, J = 8.0 Hz), 7.06(1 H, dd, J = 8.2 Hz, 2.0 Hz), 7.10(1 H, dd, J = 9.0 Hz, 3.2 Hz), 7.31(1 H, d, J = 2.0 Hz), 7.37(1 H, d, J = 8.2 Hz), 7.63(1 H, d, J = 3.2 Hz). |
| 653 | —$C_2H_5$ | —F | —$CH_2$— | 1.17(3 H, t, J = 7.1 Hz), 1.20-1.30(3 H, m), 2.50-2.72(2 H, m), 2.93(2 H, t, J = 7.8 Hz), 3.40(2 H, q, J = |

TABLE 94-continued

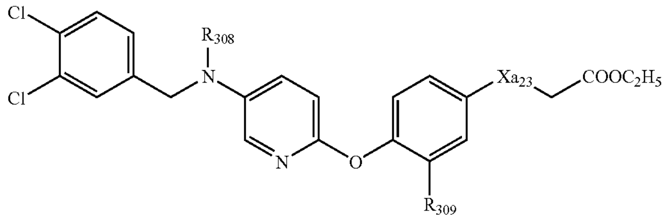

| Reference Example No. | $R_{308}$ | $R_{309}$ | $Xa_{23}$ | $^1H$ NMR (CD $Cl_3$) δ ppm |
|---|---|---|---|---|
| | | | | 7.1 Hz), 4.00-4.22(2 H, m), 4.36(2 H, s), 6.83(1 H, d, J = 8.9 Hz), 6.85-7.15(5 H, m), 7.28-7.32(1 H, m), 7.37(1 H, d, J = 8.2 Hz), 7.56(1 H, d, J = 3.2 Hz). |
| 654 | —$C_2H_5$ | —$OCH_3$ | —$CH_2$— | 1.16(3 H, t, J = 7.1 Hz), 1.21-1.35(3 H, m), 2.50-2.75(2 H, m), 2.82-3.05(2 H, m), 3.39(2 H, q, J = 7.1 Hz), 3.77(3 H, s), 4.05-4.25 (2 H, m), 4.35(2 H, s), 6.68-6.88(3 H, m), 6.90-7.00(1 H, m), 7.00-7.11(2 H, m), 7.31(1 H, d, J = 2.0 Hz), 7.37(1 H, d, J = 8.2 Hz), 7.59(1 H, d, J = 3.0 Hz). |
| 655 | —$C_2H_5$ | —$OC_2H_5$ | —$CH_2$— | 1.11-1.22(6 H, m), 1.25(3 H, t, J = 7.1 Hz), 2.56-2.67(2 H, m), 2.86-2.97(2 H, m), 3.39(2 H, q, J = 7.1 Hz), 3.97(2 H, q, J = 7.0 Hz), 4.14(2 H, q, J = 7.1 Hz), 4.34(2 H, s), 6.736.82(3 H, m), 6.99 (1 H, d, J = 8.0 Hz), 7.02-7.10(2 H, m), 7.32(1 H, d, J = 1.9 Hz), 7.36(1 H, d, J = 8.2 Hz), 7.58(1 H, d, J = 3.1 Hz). |

Reference Example 656

Production of ethyl 3-(4-(5-(3,4-dichloropheny-lamino)pyridin-2-yloxy)phenyl)propionate Triethylamine (1.2 mL, 8.4 mmol) was added to a suspension of ethyl 3-(4-(5-aminopyridin-2-yloxy)phenyl)propionate (1.2 g, 4.2 mmol), 3,4-dichlorophenylboronic acid (1.6 g, 8.4 mmol), anhydrous copper acetate (0.762 g, 4.2 mmol) and molecular sieves 4A (5 g) in dichloromethane (24 mL), and the resulting reaction solution was stirred overnight at room temperature. After the resulting solution was filtered through Celite, the filtrate was concentrated under reduced pressure. The residue was purified by silica gel chromatography (n-hexane:ethyl acetate=4:1), to thereby yield 1.5 g of the title compound.

Appearance: Slightly brown solid $^1$H NMR ($CDCl_3$) δ 1.25 (3H, t, J=7.1 Hz), 2.60-2.66 (2H, m), 2.93-2.99 (2H, m), 4.14 (2H, q, J=7.1 Hz), 5.52 (1H, brs), 6.71 (1H, dd, J=8.7 Hz, 2.7 Hz), 6.90 (1H, d, J=8.7 Hz), 6.97 (1H, d, J=2.7 Hz), 7.04-7.08 (2H, m), 7.21-7.26 (3H, m), 7.49 (1H, dd, J=8.7 Hz, 2.9 Hz), 8.01 (1H, d, J=2.8 Hz).

The following compound was produced in the same manner as in Reference Example 656.

Reference Example 657

Ethyl({4-[5-(3,4-dichlorophenylamino)pyridin-2-yloxy]-2-trifluoromethylphenyl}ethylamino)acetate

MS 527 ($M^+$)

Reference Example 658

Production of ethyl 4-[3-(4-benzyloxy-3-methyl)phenyl-2-oxotetrahydropyrimidin-1-yl]benzoate Under a nitrogen atmosphere, to a solution of 1-(4-benzyloxy-3-methyl)phenyltetrahydropyrimidin-2-one (0.5 g, 1.7 mmol) in dioxane (5 mL) were added copper (I) iodide (16 mg, 0.08 mmol) and N,N-dimethylglycine hydrochloride (47 mg, 0.34 mmol). The resulting solution was stirred for 5 minutes, and then ethyl 4-iodobenzoate (0.39 g, 1.4 mmol) and potassium (III) phosphate (1.04 g, 4.9 mmol) were added to the reaction mixture. The resulting solution was stirred for 20 hours at 100° C., after which the resulting solution was sprinkled with silica gel. The residue was purified by silica gel chromatography (n-hexane:ethyl acetate=3:1→dichloromethane:methanol=40:1), to thereby yield 0.43 g of the title compound.

Appearance: White powder $^1$H NMR (DMSO-$d_6$) δ 1.30 (3H, t, J=7.1 Hz), 2.08-2.22 (5H, m), 3.66 (2H, t, J=5.9 Hz), 3.81 (2H, t, J=5.9 Hz), 4.28 (2H, q, J=7.1 Hz), 5.10 (2H, s), 6.86-7.14 (3H, m), 7.26-7.51 (7H, m), 7.82-7.92 (2H, m).

Reference Example 659

Production of ethyl(E)-3-(3-methoxy-4-{5-[2-(4-trifluoromethylphenyl)vinyl]pyridin-2-yloxy}phenyl)propionate To ethyl 3-[4-(5-bromopyridin-2-yloxy)-3-methoxyphenyl]propionate (610 mg, 1.6 mmol) were added 4-trifluoromethylstyrene (0.332 mL, 2.2 mmol), dichlorobis(benzonitrile) palladium(II) (33 mg, 0.082 mmol), N,N-dimethylglycine hydrochloride (17 mg, 0.16 mmol), sodium acetate (263 mg, 3.2 mmol) and N-methylpyrrolidone (5 mL) under an argon atmosphere. The resulting solution was stirred under an argon atmosphere for 17 hours at 130° C. To the reaction solution was added ethyl acetate and filtered. The filtrate was washed with water, and then dried over anhydrous sodium sulfate. The solvent was evaporated, and the residue was purified by silica gel column chromatography (n-hexane:ethyl acetate=3:1), to thereby yield 500 mg of the title compound.

Appearance: Pale yellow oil $^1$H NMR ($CDCl_3$) δ 1.27 (3H, t, J=7.1 Hz), 2.64-2.69 (2H, m), 2.95-3.01 (2H, m), 3.76 (3H, s), 4.05 (2H, q, J=7.1 Hz), 6.71-6.88 (2H, m), 6.95 (1H, d, J=8.6 Hz), 6.98-7.08 (2H, m), 7.11 (1H, d, J=16.5 Hz), 7.56-7.63 (4H, m), 7.87-7.91 (1H, m), 8.23 (1H, d, J=2.3 Hz).

The following compound was produced in the same manner as in Reference Example 659.

Reference Example 660

Ethyl 3-(4-{5-[(E)-2-(3,4-dichlorophenyl)vinyl]pyridin-2-yloxy}-3-methoxyphenyl)propionate $^1$H NMR ($CDCl_3$) δ 1.26 (3H, t, J=7.1 Hz), 2.63-2.69 (2H, m), 2.94-3.00 (2H, m), 3.76 (3H, s), 4.15 (2H, q, J=7.1 Hz), 6.81-6.90 (3H, m), 6.93 (1H, d, J=8.6 Hz), 6.99 (1H, d, J=15.3 Hz), 7.06 (1H, d, J=9.1 Hz), 7.27-7.31 (1H, m), 7.40 (1H, d, J=8.2 Hz), 7.55 (1H, d, J=2.0 Hz), 7.82-7.86 (1H, m), 8.19 (1H, d, J=2.5 Hz).

Reference Example 661

Production of ethyl{4-[4-(3,4-dichlorobenzoylamino)-2-fluorophenoxy]benzenesulfonyl}acetate To a solution of ethyl{4-[4-(3,4-dichlorobenzoylamino)-2-fluorophenoxy]phenylsulfanyl}-acetate (1.20 g, 2.43 mmol) in dichloromethane (20 mL) was added m-chloroperbenzoic acid (1.45 g, 6.06 mmol) at 0° C. The resulting solution was stirred for 2 hours at room temperature. To the reaction solution was added methanol and stirred for some time. To the resulting solution was then added water, and extracted with dichloromethane. The dichloromethane layer was washed with a saturated sodium bicarbonate solution and brine, dried over anhydrous sodium sulfate, and evaporated. The obtained residue was purified by silica gel column chromatography (n-hexane:ethyl acetate=1:1), to thereby yield 1.28 g of the title compound.

Appearance: Yellow amorphous powder $^1$H NMR ($CDCl_3$) δ 1.22 (3H, t, J=7.1 Hz), 4.11 (2H, s), 4.16 (2H, q, J=7.1 Hz), 7.06 (2H, d, J=8.9 Hz), 7.19 (1H, t, J=8.7 Hz), 7.30 (1H, d, J=8.7 Hz), 7.59 (1H, d, J=8.3 Hz), 7.71 (1H, dd, J=2.0 Hz, 8.3 Hz), 7.75-7.85 (1H, m), 7.86-7.95 (3H, m), 7.98 (1H, d, J=2.0 Hz).

Reference Example 662

Production of methyl 3-{4-[5-(3,4-dichlorobenzoylamino)pyridine-2-sulfinyl]phenyl}propionate To a solution of methyl 3-{4-[5-(3,4-=dichlorobenzoylamino)pyridin-2-ylsulfanyl]phenyl}propionate (1.00 g, 2.17 mmol) in dichloromethane (20 mL) was added m-chloroperbenzoic acid (0.620 g, 2.60 mmol) at 0° C. The resulting solution was stirred for 1 hour at 0° C. To the reaction solution was added methanol and stirred for some time. To the resulting solution was then added water, and extracted with dichloromethane. The dichloromethane layer was washed with water, a saturated sodium bicarbonate solution and brine, dried over anhydrous sodium sulfate, and evaporated. The obtained residue was recrystallized from ethanol 3 times, to thereby yield 0.790 g of the title compound.

Appearance: White powder

Melting point: 164-166° C.

Reference Example 663

Production of methyl 3-{4-[5-(3,4-dichlorobenzoylamino)pyridine-2-sulfonyl]phenyl}propionate To a solution of methyl 3-{4-[5-(3,4-dichlorobenzoylamino)pyridin-2-ylsulfanyl]phenyl}-propionate (1.00 g, 2.17 mmol) in dichloromethane (20 mL) was added m-chloroperbenzoic acid (1.29 g, 5.42 mmol) at 0° C. The resulting solution was stirred for 1.5 hours at 0° C. To the reaction solution was added methanol and stirred for some time. To the resulting solution was then added water, and extracted with dichloromethane. The dichloromethane layer was washed with brine, dried over anhydrous sodium sulfate, and evaporated. The obtained residue was recrystallized from ethanol, to thereby yield 0.890 g of the title compound.

Appearance: White powder

Melting point: 165-166° C.

Reference Example 664

Production of ethyl{4-[4-(3,4-dichlorobenzoylamino)-2-fluorophenoxy]benzenesulphenyl}acetate To a solution of ethyl{4-[4-(3,4-dichloro-benzoylamino)-2-fluorophenoxy]phenylsulfanyl}acetate (0.800 g, 1.61 mmol) in methanol (20 mL) was added a 31% hydrogen peroxide solution (2.08 mL, 18.5 mmol). The resulting solution was refluxed for 16 hours. The reaction solution was cooled with ice, and the resulting precipitated solid was collected by filtration, to thereby yield 0.651 g of the title compound.

Appearance: White powder $^1$H NMR (DMSO-$d_6$) δ 1.13 (3H, t, J=7.1 Hz), 3.90-4.10 (4H, m), 7.14 (2H, d, J=8.8 Hz), 7.34 (1H, t, J=9.0 Hz), 7.55-7.65 (1H, m), 7.72 (2H, d, J=8.8 Hz), 7.84 (1H, d, J=8.4 Hz), 7.90-8.00 (2H, m), 8.22 (1H, d, J=2.0 Hz), 10.63 (1H, s).

Reference Example 665

Production of ethyl 3-(4-{5-[4-(trifluoromethyl)phenyl-carbomoyl]pyridin-2-yloxy}phenyl)butyrate To a suspension of 60% sodium hydride (0.133 g, 3.3 mmol) in THF (6 mL) was added dropwise triethylphosphono acetate (0.53 mL, 2.7 mmol) under ice cooling, and the resulting solution was stirred for 1 hour at room temperature. To the reaction solution was added a solution of 6-(4-acetylphenoxy)-N-[4-(trifluoromethyl]phenyl]nicotinamide (0.53 g, 1.3 mmol) in THF (6 mL), and the resulting solution was stirred for 10 hours at 60° C. To the reaction solution was added saturated aqueous ammonium chloride, and extracted with ethyl acetate. The ethyl acetate layer was washed with brine, dried over anhydrous magnesium sulfate, evaporated, and the residue was purified by silica gel chromatography (n-hexane:ethyl acetate=4:1), to thereby yield 0.57 g of the intermediate product ethyl 3-(4-{5-[4-(trifluoromethyl)phenyl-carbamoyl]pyridin-2-yloxy}phenyl)-2-butenoate.

10% palladium-carbon (0.057 g) was suspended in a mixed solvent consisting of ethanol (8 mL) and dioxane (2 mL), and to this suspension was added ethyl 3-(4-{5-[4-(trifluoromethyl)phenylcarbamoyl]pyridin-2-yloxy}phenyl)-2-butenoate (0.57 g, 1.2 mmol). The resulting product was subjected to catalytic reduction at atmospheric pressure and room temperature. Once the absorption of hydrogen had stopped, the catalyst was removed by filtration, and the filtrate was concentrated under reduced pressure, to thereby yield 0.56 g of the title compound.

Appearance: White solid $^1$H NMR ($CDCl_3$) δ 1.21 (3H, t, J=7.1 Hz), 1.33 (3H, d, J=7.0 Hz), 2.51-2.67 (2H, m), 3.28-3.37 (1H, m), 4.10 (2H, q, J=7.1 Hz), 7.00 (1H, d, J=8.6 Hz), 7.07-7.12 (2H, m), 7.26-7.31 (2H, m), 7.60-7.65 (2H, m), 7.73-7.77 (2H, m), 7.81 (1H, brs), 8.21 (1H, dd, J=8.6, 2.6 Hz), 8.68 (1H, d, J=2.3 Hz).

The following compound was produced in the same manner as in Reference Example 665.

Reference Example 666

Ethyl 2-methyl-3-{4-[5-(4-trifluoromethylphenyl-carbamoyl)pyridin-2-yloxy]phenyl}propionate

MS 472 ($M^+$)

Reference Example 667

Production of 3,4-dichloro-N-{6-[4-(N-hydroxy-carbamimidoylmethyl)phenoxy]pyridin-3-yl}benzamide To a solution of 3,4-dichloro-N-[6-(4-cyanomethylphenoxy)pyridin-3-yl]benzamide (700 mg, 1.76 mmol) in ethanol (30 mL) were added water (2 mL), hydroxylamine (420 mg, 12.71 mmol) and potassium carbonate (1.76 g, 12.73 mmol). Under argon, the resulting solution was stirred under reflux for 4 hours. The resulting reaction solution was concentrated under reduced pressure. To the residue was added water, and extracted with ethyl acetate. The ethyl acetate layer was washed with brine, dried over anhydrous magnesium sulfate, evaporated, and the residue was purified by silica gel column chromatography (dichloromethane:methanol=10:1), to thereby yield 510 mg of the title compound.

Appearance: White powder $^1$H NMR (DMSO-$d_6$) δ 3.27 (2H, s), 5.41 (2H, brs), 7.03 (2H, d, J=8.4 Hz), 7.05 (1H, d, J=8.8 Hz), 7.31 (2H, d, J=8.4 Hz), 7.84 (1H, d, J=8.4 Hz), 7.94 (1H, dd, J=8.4 Hz, 2.0 Hz), 8.18 (1H, dd, J=8.8 Hz, 2.6 Hz), 8.22 (1H, d, J=2.0 Hz), 8.46 (1H, d, J=2.6 Hz), 8.88 (1H, s), 10.53 (1H, s).

Reference Example 668

Production of 3,4-dichloro-N-{6-[4-(N-acetoxy-carbamimidoylmethyl)phenoxy]pyridin-3-yl}benzamide To a solution of 3,4-dichloro-N-{6-[4-(N-hydroxycarbamimidoylmethyl)phenoxy]pyridin-3-yl}benzamide (510 mg, 1.18 mmol) in dioxane (8 mL) was added potassium carbonate (163 mg, 1.18 mmol). While stirring under ice cooling, to the resulting solution was added dropwise acetyl chloride (0.084 mL, 1.18 mmol), and the resulting solution was stirred for 15 minutes at room temperature. To the reaction solution was added THF (10 mL), and then water, and extracted with ethyl acetate. The ethyl acetate layer was washed with brine, dried over anhydrous magnesium sulfate, evaporated. The residue was washed with ethyl acetate to yield 340 mg of the title compound.

Appearance: White powder $^1$H NMR (DMSO-$d_6$) δ 2.05 (3H, s), 3.35 (2H, s), 6.43 (2H, brs), 7.06 (1H, d, J=9.0 Hz), 7.06 (2H, d, J=8.6 Hz), 7.36 (2H, d, J=8.6 Hz), 7.84 (1H, d, J=8.3 Hz), 7.94 (1H, dd, J=8.3 Hz, 2.0 Hz), 8.18 (1H, dd, J=9.0 Hz, 2.5 Hz), 8.22 (1H, d, J=2.0 Hz), 8.47 (1H, d, J=2.5 Hz), 10.54 (1H, s).

Reference Example 66.9

Production of 4-{4-[4-(3,4-dichlorobenzoylamino)-2-fluorophenoxy]phenyl}-4-oxobutyric acid To a suspension consisting of 3,4-dichloro-3'-fluoro-4'-phenoxybenzanilide (5.05 g, 13.4 mmol) and succinic anhydride (1.48 g, 14.8 mmol) in 1,2-dichloroethane (25 mL) was added aluminum chloride (6.26 g, 47.0 mmol) under ice cooling, and the resulting mixture was stirred at the same temperature for 5 minutes, and then at room temperature for 1.5 hours. The resulting reaction solution was poured into ice water, and the resulting solid was collected by filtration. To the solid was added 50% aqueous acetone (200 mL), and the resulting solution was refluxed for 0.5 hours, then cooled. The obtained solid was collected by filtration, to thereby yield 6.30 g of the title compound.

Appearance: White powder

Melting point: 205-208° C.

Reference Example 670

Production of ethyl 3-{4-[hydroxy(5-nitro-2-pyridyl)-methyl]phenyl}propionate

To a solution of ethyl 3-[4-(5-nitropyridine-2-carbonyl)phenyl]propionate (1.52 g, 4.63 mmol) in dichloromethane (15 mL) and ethanol (15 mL) was added sodium borohydride (0.175 g, 4.63 mmol) under ice cooling, and the resulting solution was stirred at the same temperature for 1 hour. The reaction solution was concentrated under reduced pressure. The residue was dissolved in water and ethyl acetate. To the solution was added acetic acid and extracted with ethyl acetate. The ethyl acetate layer was washed with a saturated sodium bicarbonate solution and brine, and then dried over anhydrous magnesium sulfate. The solvent was evaporated, and the residue was purified by silica gel column chromatography (n-hexane:ethyl acetate=3:1), to thereby yield 0.264 g of the title compound.

Appearance: Brown powder $^1$H NMR ($CDCl_3$) δ 1.19 (3H, t, J=7.2 Hz), 2.56 (2H, t, J=7.8 Hz), 2.91 (2H, t, J=7.8 Hz), 4.09 (2H, q, J=7.2 Hz), 4.35 (1H, brs), 5.84 (1H, s), 7.17 (2H, d, J=8.1 Hz), 7.26 (2H, d, J=8.1 Hz), 7.46 (1H, d, J=8.7 Hz), 8.40 (1H, dd, J=8.7 Hz, 2.5 Hz), 9.36 (1H, d, J=2.5 Hz).

The following compound was produced in the same manner as in Reference Example 670.

Reference Example 671 t-Butyl 4-[2-hydroxy-3-(4-hydroxyphenyl)propionyl]-piperazine-1-carboxylate $^1$H NMR ($CDCl_3$) δ 1.47 (9H, s), 1.62 (1H, brs), 2.85 (2H, d, J=6.0 Hz), 3.00-3.80 (8H, m), 4.56 (1H, t, J=6.0 Hz), 5.35 (1H, brs), 6.74 (2H, d, J 8.4 Hz), 7.06 (2H, d, J=8.4 Hz).

Reference Example 672

Production of ethyl 3-(4-{5-[bis(3,4-dichlorobenzoyl)-amino]-2-pyridylmethyl}phenyl)propionate To a suspension of 10% palladium-carbon (27 mg) in ethanol (5 mL) were added a solution of ethyl 3-{4-[hydroxy(5- nitro-2-pyridyl)-methyl]phenyl}propionate (0.264 g, 0.799 mmol) and 0.5 M hydrogen chloride in ethanol (2 mL), and the resulting solution was subjected to catalytic reduction at atmospheric pressure at 50° C. Once the absorption of hydrogen had stopped, the catalyst was removed by filtration, and the filtrate was concentrated under reduced pressure. The residue was suspended in THF (5 mL), and triethylamine (0.267 mL, 2.40 mmol) was added. To the solution was added dropwise a solution of 3,4-dichlorobenzoyl chloride (0.255 g, 0.879 mmol) in THF (1 mL) under ice cooling, and stirred for 1 hour at the same temperature. To the resulting solution was added water and extracted with ethyl acetate. The ethyl acetate layer was washed with a saturated sodium bicarbonate solution and brine, dried over anhydrous magnesium sulfate, and evaporated. The residue was purified by silica gel column chromatography (n-hexane:ethyl acetate=5:1), to thereby yield 0.177 g of the title compound.

Appearance: Pale yellow oil $^1$H NMR ($CDCl_3$) δ 1.20 (3H, t, J=7.2 Hz), 2.56 (2H, t, J=7.8 Hz), 2.89 (2H, t, J=7.8 Hz), 4.09 (2H, q, J=7.2 Hz), 6.99 (1H, s), 7.17 (2H, d, J=8.2 Hz), 7.35 (2H, d, J=8.2 Hz), 7.42 (1H, d, J=8.6 Hz), 7.43-7.56 (2H, m), 7.63 (1H, dd, J=8.6 Hz, 2.1 Hz), 7.85-7.94 (2H, m), 8.15 (1H, d, J=2.0 Hz), 8.20-8.32 (2H, m), 8.57 (1H, d, J=2.5 Hz).

Reference Example 673

Production of ethyl 3-(4-(5-(N-(4-(trifluoromethyl)-phenyl)sulfamoyl)pyridin-2-yloxy)phenyl)propionate To a solution of ethyl 3-(4-(3-bromo-5-(N-(4-(trifluoromethyl)phenyl)sulfamoyl)pyridin-2-yloxy)phenyl)propionate (0.41 g, 0.7 mmol) in ethanol (10 mL) were added 10% palladium-carbon (0.041 g) and ammonium formate (0.226 g, 3.6 mmol), and the resulting solution was heated to reflux for 2 hours. The catalyst was removed by filtration, and the filtrate was concentrated under reduced pressure. The residue was then purified by silica gel chromatography (n-hexane: ethyl acetate=4:1), to thereby yield 0.28 g of the title compound.

Appearance: White solid $^1$H NMR ($CDCl_3$) δ 1.24 (3H, t, J=7.1 Hz), 2.60-2.66 (2H, m), 2.93-2.99 (2H, m), 4.14 (2H, q, J=7.1 Hz), 6.95 (1H, d, J=8.8 Hz), 7.01-7.05 (2H, m), 7.20-7.26 (3H, m), 7.50-7.54 (3H, m), 8.03 (1H, dd, J=8.8 Hz, 2.6 Hz), 8.59 (1H, d, J=2.6 Hz).

Reference Example 674

Production of 1-(4-methoxyphenyl)imidazolin-2-one

To a suspension of 1-(2-chloroethyl)-3-(4-methoxyphenyl)urea (7.0 g, 30.6 mmol) in t-butanol (120 mL) was added potassium t-butoxide (6.4 g, 57.0 mmol) under a nitrogen atmosphere. The resulting solution was stirred for 10 minutes, and then potassium t-butoxide (3.0 g, 26.7 mmol) was added. This solution was stirred for 10 minutes, and then potassium t-butoxide (4.3 g, 38.3 mmol) was added. The resulting solution was stirred for 16 hours at room temperature. The pH was adjusted to between 2 and 3 with 10% hydrochloric acid, and the solvent was evaporated under reduced pressure. To the residue were added water (100 mL) and ethyl acetate (100 mL), and stirred for 1 hour at room temperature. Resulting precipitates were filtered, washed with diethyl ether, and then dried under reduced pressure, to thereby yield 5.1 g of the title compound.

Appearance: White powder $^1$H NMR (DMSO-$d_6$) δ 3.29-3.44 (2H, m), 3.70 (3H, s), 3.71-3.88 (2H, m), 6.77 (1H, s), 6.81-6.95 (2H, m), 7.35-7.50 (2H, m).

The following compounds were produced in the same manner as in Reference Example 674.

Reference Example 675

1-(4-Benzyloxy-3-methylphenyl)tetrahydropyrimidin-2-one $^1$H NMR (DMSO-$d_6$) δ 1.81-1.96 (2H, m), 2.16 (3H, s), 3.11-3.25 (2H, m), 3.51 (2H, t, J=5.6 Hz), 5.09 (2H, s), 6.42 (1H, s), 6.91 (1H, d, J=8.7 Hz), 6.98 (1H, dd, J=2.6 Hz, 8.7 Hz), 7.04 (1H, d, J=2.6 Hz), 7.28-7.34 (1H, m), 7.36-7.41 (2H, m), 7.42-7.48 (2H, m).

TABLE 95

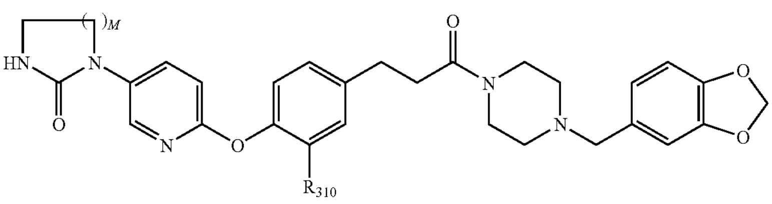

| Reference Example No. | $R_{310}$ | M | mp (°C.) or $^1$H NMR ($CDCl_3$) δ ppm |
|---|---|---|---|
| 676 | —H | 1 | mp 162.0-163.0 |
| 677 | —H | 2 | mp 179.0-180.0 |
| 678 | —$OCH_3$ | 1 | $^1$H NMR 2.29-2.45 (4H, m), 2.59-2.69 (2H, m), 2.91-3.04 (2H, m), 3.34-3.47 (4H, m), 3.53-1.69 (4H, m), 3.75 (3H, s), 3.85-3.96 (2H, m), 4.58 (1H, s), 5.95 (2H, s), 6.69-6.78 (2H, m), 6.79-6.89 (3H, m), 6.91 (1H, d, J = 9.0 Hz), 7.02 (1H, d, J = 8.0 Hz), 7.99 (1H, d, J = 2.9 Hz), 8.25 (1H, dd, J = 2.9 Hz, 9.0 Hz). |
| 679 | —$OCH_3$ | 2 | mp 140.0-141.5 |

TABLE 96

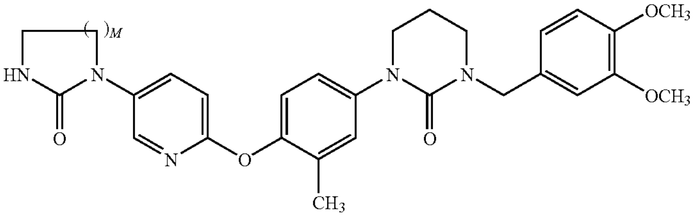

| Reference Example No. | M | $^1H$ NMR ($CDCl_3$) δ ppm |
|---|---|---|
| 680 | 1 | 1.98-2.14 (2H, m), 2.18 (3H, s), 3.30 (2H, d, J = 6.0 Hz), 3.51-3.66 (2H, m), 3.67-3.78 (2H, m), 3.80-4.05 (8H, m), 4.57 (2H, s), 4.79 (1H, s), 6.78-6.94 (4H, m), 6.99 (1H, d, J = 8.6 Hz), 7.13 (1H, dd, J = 2.6 Hz, 8.6 Hz), 7.22 (1H, d, J = 2.6 Hz), 8.05 (1H, d, J = 2.9 Hz), 8.22 (1H, dd, J = 2.9 Hz, 9.0 Hz). |
| 681 | 2 | 1.91-2.15 (4H, m), 2.18 (3H, s), 3.18-3.36 (2H, m), 3.37-3.51 (2H, m), 3.58-3.78 (2H, m), 3.88 (3H, s), 3.88 (3H, s), 4.56 (2H, s), 4.89 (1H, s), 6.76-6.94 (4H, m), 7.00 (1H, d, J = 8.7 Hz), 7.13 (1H, dd, J = 2.6 Hz, 8.7 Hz), 7.23 (1H, d, J = 2.6 Hz), 7.67 (1H, dd, J = 2.8 Hz, 8.8 Hz), 8.08 (1H, d, J = 2.8 Hz). |

Reference Example 682

Production of 3-{4-[4-(3,4-dichlorobenzoylamino)-phenoxy]phenyl}propionic acid

To a solution of ethyl 3-{4-[4-(3,4-dichlorobenzoylamino) phenoxy]phenyl}propionate (6.00 g, 13.1 mmol) in THF (60 mL) and ethanol (30 mL) were added 5 M aqueous sodium hydroxide (3.14 mL, 15.7 mmol) and water (30 mL) and the resulting solution was refluxed for 1 hour. The reaction solution was cooled with ice. To the reaction solution were added 5 M hydrochloric acid (4.0 mL, 20.0 mmol) and water (100 mL). The obtained solid was collected by filtration, and recrystallized from water-containing acetone, to thereby yield 5.60 g of the title compound.

Appearance: White powder

Melting point: 188-190° C.

The following compounds were produced in the same manner as in Reference Example 682.

TABLE 97

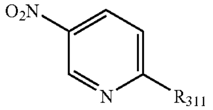

| Reference Example No. | $R_{311}$ | $^1H$ NMR (solvent) δ ppm or MS |
|---|---|---|
| 683 | 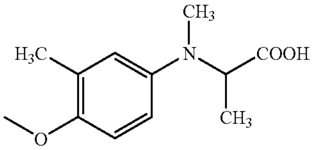 | $^1H$ NMR ($CDCl_3$) 1.51 (3H, d, J = 7.1 Hz), 2.12 (3H, s), 2.91 (3H, s), 4.49 (1H, q, J = 7.1 Hz), 6.71-6.75 (2H, m), 6.95-7.00 (2H, m), 8.45 (1H, dd, J = 9.1 Hz, 2.8 Hz), 9.04 (1H, dd, J = 2.8 Hz, 0.5 Hz). |
| 684 | 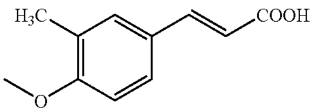 | MS 300 ($M^+$) |
| 685 | 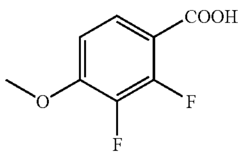 | $^1H$ NMR (DMSO-$d_6$) 7.39 (1H, td, J = 2.0 Hz, 8.9 Hz), 7.50 (1H, d, J = 9.0 Hz), 7.78 (1H, td, J = 2.1 Hz, 8.9 Hz), 8.70 (1H, dd, J = 2.8 Hz, 9.0 Hz), 9.04 (1H, d, J = 2.8 Hz), 11.35-11.91 (1H, m). |
| 686 | 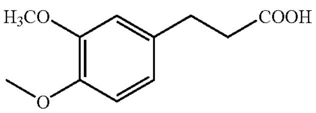 | $^1H$ NMR ($CDCl_3$) 2.72-2.77 (2H, m), 2.98-3.03 (2H, m), 3.74 (3H, s), 6.85-6.89 (2H, m), 7.03 (1H, d, J = 9.1 Hz), 7.06-7.09 (1H, m), 8.45 (1H, dd, J = 9.1 Hz, 2.8 Hz), 9.01. (1H, d, J = 2.8 Hz). |

TABLE 97-continued

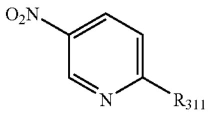

| Reference Example No. | $R_{311}$ | $^1H$ NMR (solvent) δ ppm or MS |
|---|---|---|
| 687 | 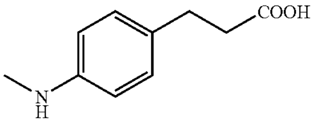 | $^1H$ NMR (DMSO-$d_6$) 2.52 (2H, t, J = 7.6 Hz), 2.80 (2H, t, J = 7.6 Hz), 6.86 (1H, d, J = 9.4 Hz), 7.21 (2H, d, J = 8.5 Hz), 7.58 (2H, d, J = 8.5 Hz), 8.26 (1H, dd, J = 2.9 Hz, 9.4 Hz), 9.01 (1H, d, J = 2.9 Hz), 10.06 (1H, s). |
| 688 | 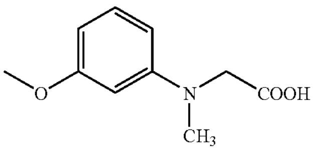 | $^1H$ NMR (DMSO-$d_6$) 2.96 (3H, s), 4.09 (2H, s), 6.44-6.49 (2H, m), 6.56 (1H, dd, J = 8.3 Hz, 2.4 Hz), 7.15 (1H, d, J = 9.1 Hz), 7.20-7.26 (1H, m), 8.59 (1H, dd, J = 9.1 Hz, 2.8 Hz), 9.05 (1H, d, J = 2.8 Hz). |
| 689 | 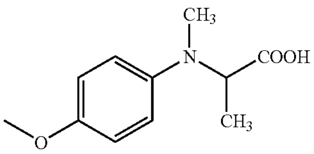 | $^1H$ NMR ($CDCl_3$) 1.53 (3H, d, J = 7.1 Hz), 2.93 (3H, s), 4.51 (1H, q, J = 7.1 Hz); 6.87 (2H, d, J = 9.2 Hz), 6.98 (1H, d, J = 9.1 Hz), 7.05 (2H, d, J = 9.1 Hz), 8.44 (1H, dd, J = 9.1 Hz, 2.8 Hz), 9.05 (1H, d, J = 2.6 Hz). |
| 690 | 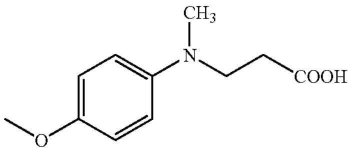 | $^1H$ NMR ($CDCl_3$) 2.63-2.69 (2H, m), 2.97 (3H, s), 3.68 (2H, t, J = 7.1 Hz), 6.81 (2H, d, J = 9.1 Hz), 6.98 (1H, d, J = 9.1 Hz), 7.05 (2H, d, J = 9.2 Hz), 8.44 (1H, dd, J = 9.1 Hz, 2.8 Hz), 9.06 (1H, d, J = 2.8 Hz). |
| 691 | 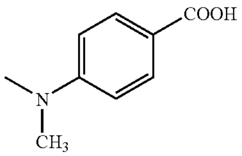 | $^1H$ NMR (DMSO-$d_6$) 3.55 (3H, s), 6.67 (1H, d, J = 9.5 Hz), 7.52 (2H, d, J = 8.5 Hz), 8.04 (2H, d, J = 8.5 Hz), 8.21 (1H, dd, J = 2.8 Hz, 9.5 Hz), 9.05 (1H, d, J = 2.8 Hz), 13.10 (1H, brs). |
| 692 | 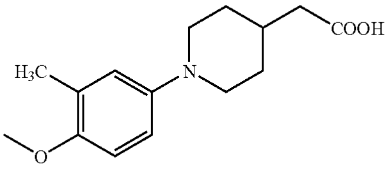 | $^1H$ NMR (DMSO-$d_6$) 1.28-1.32 (2H, m), 1.75-1.79 (3H, m), 2.01 (3H, s), 2.19 (2H, d, J = 6.8 Hz), 2.65 (2H, t, J = 12.0 Hz), 3.65 (2H, d, J = 12.4 Hz), 6.80-6.96 (3H, m), 7.15 (1H, d, J = 9.2 Hz), 8.58 (1H, dd, J = 9.1 Hz, 2.8 Hz), 9.01 (1H, d, J = 2.8 Hz), 10.71 (1H, brs). |
| 693 | 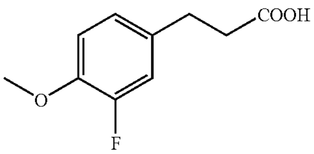 | MS 306 ($M^+$) |

TABLE 98

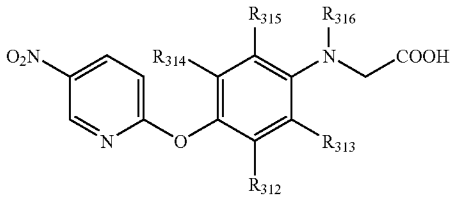

| Reference Example No. | $R_{312}$ | $R_{313}$ | $R_{314}$ | $R_{315}$ | $R_{316}$ | $^1H$ NMR (solvent) δ ppm |
|---|---|---|---|---|---|---|
| 694 | —F | —H | —H | —H | $—CH_3$ | ($CDCl_3$) 3.09 (3H, s), 4.12 (2H, s), 6.45-6.57 (2H, m), 7.05-7.12 (2H, m), 8.47 (1H, dd, J = 9.1 Hz, 2.8 Hz), 9.02 (1H, dd, J = 2.8 Hz, 0.7 Hz). |
| 695 | —F | —H | —H | —H | $—C_2H_5$ | ($CDCl_3$) 1.25 (3H, t, J = 7.1 Hz), 3.47 (2H, q, J = 7.1 Hz), 4.06 (2H, s), 6.42-6.53 (2H, m), 7.04-7.10 (2H, m), 8.47 (1H, dd, J = 9.1 Hz, 2.8 Hz), 9.02 (1H, dd, J = 2.8 Hz, 0.5 Hz). |
| 696 | —F | —H | —H | —H | allyl | ($CDCl_3$) 4.03 (2H, d, J = 5.0 Hz), 4.09 (2H, s), 5.25-5.32 (2H, m), 5.82-5.96 (1H, m), 6.44-6.56 (2H, m), 7.04-7.10 (2H, m), 8.47 (1H, dd, J = 9.1 Hz, 2.8 Hz), 9.02 (1H, d, J = 2.6 Hz). |
| 697 | —F | —H | —H | —F | $—CH_3$ | (DMSO-$d_6$) 2.94 (3H, s), 4.04 (3H, s), 6.92 (1H, dd, J = 8.5 Hz, 12.9 Hz), 7.30 (1H, dd, J = 7.5 Hz, 13.7 Hz), 7.35 (1H, d, J = 9.1 Hz), 8.63 (1H, dd, d = 2.8 Hz, 9.1 Hz), 9.04 (1H, d, J = 2.8 Hz), 12.41-12.82 (1H, m). |
| 698 | —F | —H | —H | —F | $—C_2H_5$ | (DMSO-$d_6$) 1.10 (3H, t, J = 7.0 Hz), 3.12-3.48 (2H, m), 4.01 (2H, s), 6.90 (1H, dd, J = 8.4 Hz, 13.1 Hz), 7.29 (1H, dd, J = 7.6 Hz, 13.7 Hz), 7.35 (1H, d, J = 9.0 Hz), 8.63 (1H, dd, J = 2.8 Hz, 9.0 Hz), 9.04 (1H, d, J = 2.8 Hz), 12.41-12.70 (1H, m). |
| 699 | —F | —H | —F | —H | $—CH_3$ | (DMSO-$d_6$) 2.96 (3H, s), 4.26 (2H, s), 6.41-6.61 (2H, m), 7.43 (1H, d, J = 9.1 Hz), 8.65 (1H, dd, J = 2.8 Hz, 9.1 Hz), 9.05 (1H, d, J = 2.8 Hz), 12.56-12.90 (1H, m). |
| 700 | $—CH_3$ | $—CH_3$ | —H | —H | $—CH_3$ | ($CDCl_3$) 2.07 (3H, s), 2.32 (3H, s), 2.85 (3H, s), 3.76 (2H, s), 6.91 (1H, d, J = 8.7 Hz), 7.00 (1H, dd, J = 9.1 Hz, 0.6 Hz), 7.09 (1H, d, J = 8.7 Hz), 8.46 (1H, dd, J = 9.1 Hz, 2.8 Hz), 9.04 (1H, dd, J = 2.8 Hz, 0.6 Hz). |
| 701 | $—CH_3$ | —H | —H | $—CH_3$ | $—C_2H_5$ | (DMSO-$d_6$) 0.98 (3H, t, J = 7.1 Hz), 1.98 (3H, s), 2.20 (3H, s), 3.09 (2H, q, J = 7.1 Hz), 3.70 (2H, s), 6.91 (1H, s), 7.06 (1H, s), 7.18 (1H, d, J = 9.1 Hz), 8.59 (1H, dd, J = 9.1 Hz, 2.9 Hz), 9.03 (1H, d, J = 2.9 Hz), 12.30 (1H, brs). |
| 702 | —H | —H | —H | —H | $—SO_2CH_3$ | (DMSO-$d_6$) 3.17 (3H, s), 4.43 (2H, s), 7.29 (2H, d, J = 8.7 Hz), 7.31 (1H, d, J = 9.1 Hz), 7.55 (2H, d, J = 8.9 Hz), 8.64 (1H, dd, J = 9.1 Hz, 2.8 Hz), 9.05 (1H, d, J = 2.8 Hz). |
| 703 | $—CH_3$ | —H | —H | —H | $—SO_2CH_3$ | (DMSO-$d_6$) 2.09 (3H, s), 3.11 (3H, s), 4.42 (2H, s), 7.20 (1H, d, J = 8.6 Hz), 7.31 (1H, d, J = 9.1 Hz), 7.37 (1H, dd, J = 8.6 Hz, 2.5 Hz), 7.44 (1H, d, J = 2.3 Hz), 8.64 (1H, dd, J = 9.1 Hz, 2.8 Hz), 9.03 (1H, d, J = 2.8 Hz), 12.88 (1H, brs). |

TABLE 99

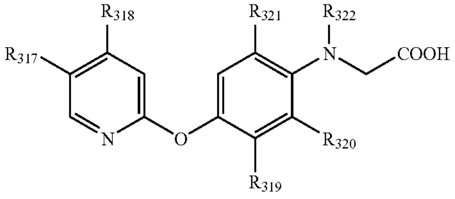

| Reference Example No. | $R_{317}$ | $R_{318}$ | $R_{319}$ | $R_{320}$ | $R_{321}$ | $R_{322}$ | $^1H$ NMR (solvent) δ ppm or MS |
|---|---|---|---|---|---|---|---|
| 704 | $-NO_2$ | —H | $-CH_3$ | —H | $-CH_3$ | $-CH_3$ | MS 331 ($M^+$) |
| 705 | $-NO_2$ | —H | $-CF_3$ | —H | —H | $-CH_3$ | MS 371 ($M^+$) |
| 706 | $-NO_2$ | —H | $-CF_3$ | —H | —H | $-C_2H_5$ | MS 385 ($M^+$) |
| 707 | $-NO_2$ | $-CH_3$ | —H | $-CF_3$ | —H | $-CH_3$ | MS 385 ($M^+$) |
| 708 | $-NO_2$ | —H | —F | —F | —H | $-CH_3$ | $^1H$ NMR (DMSO-$d_6$) 2.98 (3H, s), 4.05 (2H, s), 6.64-6.88 (1H, m), 6.96-7.20 (1H, m), 7.38 (1H, d, J = 9.1 Hz), 8.64 (1H, dd, J = 2.7 Hz, 9.1 Hz), 9.04 (1H, d, J = 2.7 Hz), 12.24-12.95 (1H, m). |
| 709 | $-NO_2$ | —H | $-OCH_3$ | —H | —H | $-SO_2CH_3$ | $^1H$ NMR (DMSO-$d_6$) 3.16 (3H, s), 3.70 (3H, s), 4.45 (2H, s), 7.10-7.30 (4H, m), 8.61 (1H, dd, J = 9.1 Hz, 2.8 Hz), 9.02 (1H, d, J = 2.8 Hz), 12.97 (1H, brs). |
| 710 | —Br | —H | —F | —H | —F | $-CH_3$ | $^1H$ NMR (DMSO-$d_6$) 2.92 (3H, s), 4.01 (2H, s), 6.80-6.93 (1H, m), 7.11 (1H, d, J = 8.8 Hz), 7.14-7.26 (1H, m), 8.06 (1H, dd, J = 2.6 Hz, 8.8 Hz), 8.25 (1H, d, J = 2.6 Hz), 12.18-12.89 (1H, m). |
| 711 | $4-CF_3PhCH_2-$ | —H | —H | —H | —H | $-CH_3$ | $^1H$ NMR ($CDCl_3$) 3.04 (3H, s), 3.93 (2H, s), 4.04 (2H, s), 6.69 (2H, d, J = 9.1 Hz), 6.70 (1H, d, J = 8.5 Hz), 6.97 (2H, d, J = 9.1 Hz), 7.25 (2H, d, J = 8.6 Hz), 7.39 (1H, dd, J = 8.5 Hz, 2.5 Hz), 7.52 (2H, d, J = 8.6 Hz), 8.09 (1H, d, J = 2.5 Hz), 11.26 (1H, brs). |
| 712 | $4-CF_3PhOCH_2-$ | —H | —H | —H | —H | $-SO_2CH_3$ | $^1H$ NMR (DMSO-$d_6$) 3.11 (3H, s), 4.40 (2H, s), 5.18 (2H, s), 7.12 (1H, d, J = 8.9 Hz), 7.15-7.23 (4H, m), 7.49 (2H, d, J = 8.9 Hz), 7.67 (2H, d, J = 8.6 Hz), 7.98 (1H, dd, J = 8.4 Hz, 2.5 Hz), 8.28 (1H, d, J = 2.0 Hz), 12.41 (1H, brs). |
| 713 | $4-CF_3PhOCH_2-$ | —H | $-CH_3$ | —H | —H | $-SO_2CH_3$ | $^1H$ NMR (DMSO-$d_6$) 2.06 (3H, s), 3.18 (3H, s), 3.89 (2H, s), 5.15 (2H, s), 7.02 (1H, d, J = 8.4 Hz), 7.07 (1H, d, J = 8.6 Hz), 7.21 (2H, d, J = 8.4 Hz), 7.44 (1H, dd, J = 8.6 Hz, 2.6 Hz), 7.49 (1H, d, J = 2.3 Hz), 7.67 (2H, d, J = 8.9 Hz), 7.95 (1H, dd, J = 8.4 Hz, 2.5 Hz), 8.24 (1H, d, J = 2.5 Hz). |

TABLE 100

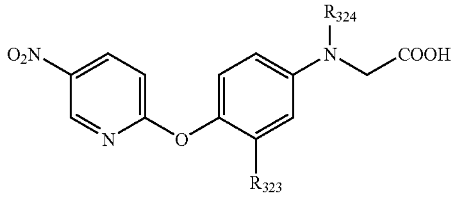

| Reference Example No. | $R_{323}$ | $R_{324}$ | $^1H$ NMR (solvent) δ ppm |
|---|---|---|---|
| 714 | —H | —H | (DMSO-$d_6$) 3.35 (1H, brs), 3.84 (2H, s), 6.63 (2H, d, J = 8.9 Hz), 6.96 (2H, d, J = 8.9 Hz), 7.14 (1H, d, J = 9.1 Hz), 8.59 (1H, dd, J = 2.9 Hz, 9.1 Hz), 9.05 (1H, d, J = 2.9 Hz). |
| 715 | —H | —$CH_3$ | ($CDCl_3$) 3.09 (3H, s), 4.11 (2H, s), 6.74 (2H, d, J = 9.1 Hz), 6.97 (1H, dd, J = 9.1 Hz, 0.5 Hz), 7.04 (2H, d, J = 9.1 Hz), 8.43 (1H, dd, J = 9.1 Hz, 2.8 Hz), 9.04 (1H, dd, J = 2.8 Hz, 0.5 Hz). |
| 716 | —H | —$C_2H_5$ | ($CDCl_3$) 1.24 (3H, t, J = 7.1 Hz), 3.48 (2H, q, J = 7.1 Hz), 4.07 (2H, s), 6.73 (2H, d, J = 9.2 Hz), 6.98 (1H, d, J = 9.1 Hz), 7.04 (2H, d, J = 9.2 Hz), 8.44 (1H, dd, J = 9.1 Hz, 2.8 Hz), 9.05 (1H, d, J = 2.8 Hz). |
| 717 | —$OCH_3$ | —H | (DMSO-$d_6$) 3.62 (3H, s), 3.83 (2H, s), 6.13 (1H, dd, J = 8.6 Hz, 2.5 Hz), 6.41 (1H, d, J = 2.5 Hz), 6.90 (1H, d, J = 8.6 Hz), 7.09 (1H, d, J = 8.6 Hz), 8.54 (1H, dd, J = 9.1 Hz, 3.0 Hz), 9.00 (1H, d, J =3.0 Hz). |
| 718 | —$OCH_3$ | —$CH_3$ | (DMSO-$d_6$) 3.00 (3H, s), 3.65 (3H, s), 4.12 (2H, s), 6.21 (1H, dd, J = 8.8 Hz, 2.8 Hz), 6.39 (1H, d, J = 2.8 Hz), 6.96 (1H, d, J = 8.8 Hz), 7.11 (1H, d, J = 9.1 Hz), 8.54 (1H, dd, J = 9.1 Hz, 2.8 Hz), 9.00 (1H, d, J = 2.8 Hz), 12.57 (1H, s). |
| 719 | —$OCH_3$ | —$C_2H_5$ | (DMSO-$d_6$) 1.13 (3H, t, J = 7.0 Hz), 3.42 (2H, q, J = 7.0 Hz), 3.64 (3H, s), 4.05 (2H, s), 6.14 (1H, dd, J = 8.8 Hz, 2.8 Hz), 6.31 (1H, d, J = 2.8 Hz), 6.95 (1H, d, J = 8.8 Hz), 7.12 (1H, d, J = 9.1 Hz), 8.53 (1H, dd, J = 9.1 Hz, 2.8 Hz), 9.00 (1H, d, J = 2.8 Hz), 12.59 (1H, brs). |
| 720 | —$CH_3$ | —Ac | (DMSO-$d_6$) 1.86 (3H, s), 2.08 (3H, s), 4.26 (2H, s), 7.05-7.50 (4H, m), 8.63 (1H, dd, J = 9.1 Hz, 2.9 Hz), 9.02 (1H, dd, J = 2.9 Hz, 0.4 Hz), 12.72 (1H, brs). |
| 721 | —$CH_3$ | —H | ($CDCl_3$) 2.09 (3H, s), 3.98 (2H, s), 5.26 (1H, brs), 6.50-6.55 (2H, m), 6.92 (1H, d, J = 8.4 Hz), 6.98 (1H, d, J = 8.1 Hz), 8.45 (1H, dd, J = 8.1 Hz, 2.8 Hz), 9.04 (1H, d, J = 2.8 Hz). |
| 722 | —$CH_3$ | —$CH_3$ | (DMSO-$d_6$) 1.99 (3H, s), 2.97 (3H, s), 4.09 (2H, s), 6.52 (1H, dd, J = 8.8 Hz, 3.0 Hz), 6.59 (1H, d, J = 3.0 Hz), 6.92 (1H, d, J = 8.8 Hz), 7.13 (1H, dd, J = 9.1 Hz, 0.3 Hz), 8.57 (1H, dd, J = 9.1 Hz, 2.9 Hz), 9.01 (1H, d, J = 2.9 Hz), 12.54 (1H, brs). |
| 723 | —$CH_3$ | —$C_2H_5$ | (DMSO-$d_6$) 1.11 (3H, t, J = 7.0 Hz), 1.98 (3H, s), 3.89 (2H, q, J = 7.0 Hz), 4.02 (2H, s), 6.44 (1H, dd, J = 8.8 Hz, 2.9 Hz), 6.51 (1H, d, J = 2.9 Hz), 6.90 (1H, d, J = 8.8 Hz), 7.13 (1H, d, J = 9.1 Hz), 8.56 (1H, dd, J = 9.1 Hz, 2.9 Hz), 9.0 1 (1H, d, J = 2.9 Hz), 12.53 (1H, brs). |
| 724 | —$CH_3$ | 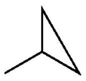 | (DMSO-$d_6$) 0.54-0.59 (2H, m), 0.80-0.87 (2H, m), 2.02 (3H, s), 2.64-2.71 (1H, m), 4.11 (2H, s), 6.77-6.81 (1H, m), 6.85 (1H, d, J = 2.8 Hz), 6.96 (1H, d, J = 8.7 Hz), 7.17 (1H, dd, J = 9.2 Hz, 0.5 Hz), 8.59 (1H, dd, J = 9.1 Hz, 3.0 Hz), 9.04 (1H, dd, J = 3.0 Hz, 0.5 Hz), 12.56 (1H, brs). |
| 725 | —F | —H | (DMSO-$d_6$) 3.82 (2H, s), 6.43 (1H, dd, J = 8.7 Hz, 2.8 Hz), 6.53 (1H, dd, J = 13.4 Hz, 2.6 Hz), 7.07 (1H, t, J = 8.9 Hz), 7.28 (1H, dd, J = 9.1 Hz, 0.5 Hz), 8.61 (1H, dd, J = 9.1 Hz, 2.8 Hz), 9.03 (1H, dd, J = 2.8 Hz, 0.5 Hz). |

TABLE 101

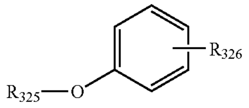

| Reference Example No. | $R_{325}$ | $R_{326}$ | mp (° C.) or $^1$H NMR (solvent) δ ppm |
|---|---|---|---|
| 726 | 4-$NO_2$Ph- | 4-$N(CH_3)CH_2COOH$ | $^1$H NMR ($CDCl_3$) 3.10 (3H, s), 4.13 (2H, s), 6.74 (2H, d, J = 9.2 Hz), 6.95 (2H, d, J = 9.2 Hz), 7.00 (2H, d, J = 9.2 Hz), 8.17 (2H, d, J = 9.2 Hz). |
| 727 | 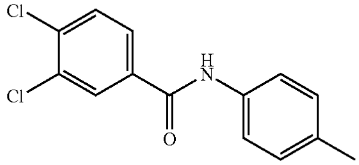 | 2-$(CH_2)_2COOH$ | mp 157-159 |
| 728 | 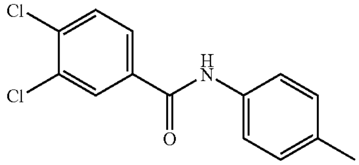 | 3-$(CH_2)_2COOH$ | mp 192-194 |
| 729 | 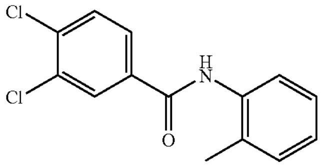 | 4-$(CH_2)_2COOH$ | $^1$H NMR ($CDCl_3$) 2.67 (2H, t, J = 7.7 Hz), 2.94 (2H, t, J = 7.7 Hz), 6.78 (1H, dd, J = 8.2 Hz, 1.2 Hz), 6.97 (2H, d, J = 8.6 Hz), 7.02-7.19 (2H, m), 7.20 (2H, d, J = 8.6 Hz), 7.48 (1H, d, J = 8.3 Hz), 7.56 (1H, dd, J = 8.3 Hz, 2.1 Hz), 7.84 (1H, d, J = 2.1 Hz), 8.38 (1H, brs), 8.49 (1H, dd, J = 8.3 Hz, 2.1 Hz), 10.46 (1H, brs). |
| 730 | 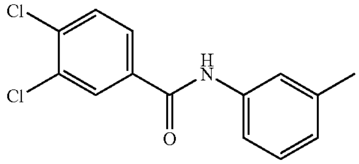 | 4-$(CH_2)_2COOH$ | $^1$H NMR ($CDCl_3$) 2.67 (2H, t, J = 7.6 Hz), 2.93 (2H, t, J = 7.6 Hz), 6.78 (1H, dt, J = 8.1 Hz, 1.2 Hz), 6.95 (2H, d, J = 8.5 Hz), 7.16 (2H, d, J = 8.5 Hz), 7.22-7.34 (3H, m), 7.53 (1H, d, J = 8.3 Hz), 7.64 (1H, dd, J = 8.3 Hz, 2.1 Hz), 7.73 (1H, brs), 7.90 (1H, d, J = 2.1 Hz), 10.23 (1H, brs). |
| 731 | 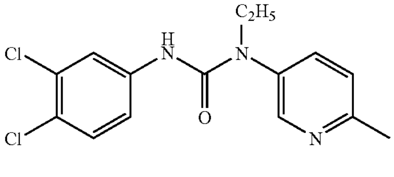 | 4-$(CH_2)_2COOH$ | $^1$H NMR (DMSO-$d_6$) 1.05 (3H, t, J = 7.1 Hz), 2.56 (2H, t, J = 7.6 Hz), 2.84 (2H, t, J = 7.6 Hz), 3.64 (2H q, J = 7.1 Hz), 7.05-7.10 (3H, m), 7.28 (2H, d, J = 8.6 Hz), 7.45 (2H, brs), 7.76-7.80 (2H, m), 8.08 (1H, dd J = 2.8 Hz, 0.5 Hz), 8.27 (1H, brs), 12.10 (1H, brs). |
| 732 | 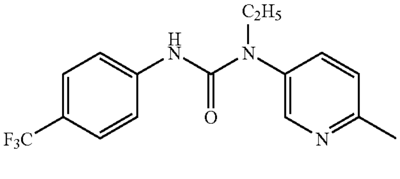 | 4-$(CH_2)_2COOH$ | $^1$H NMR (DMSO-$d_6$) 1.06 (3H, t, J = 7.1 Hz), 2.53-2.59 (2H, m), 2.81-2.87 (2H, m), 3.67 (2H, q, J = 7.1 Hz), 7.05-7.10 (3H, m), 7.29 (2H, d, J = 8.7 Hz), 7.56 (2H, d, J = 8.7 Hz), 7.66 (2H, d, J = 8.7 Hz), 7.78 (1H, dd, J = 8.6 Hz, 2.8 Hz), 8.09 (1H, d, J = 2.8 Hz), 8.41 (1H, brs), 12.14 (1H, brs). |

TABLE 102

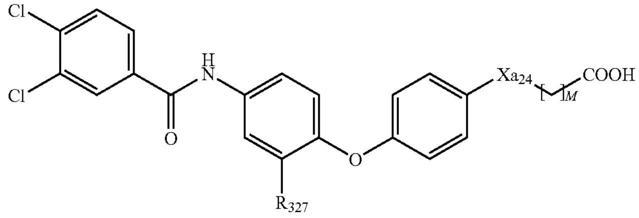

| Reference Example No. | $R_{327}$ | $Xa_{24}$ | M | Form | mp (° C.) or $^1$H NMR (DMSO-$d_6$) δ ppm |
|---|---|---|---|---|---|
| 733 | —H | none | 0 | free | mp 252-255 |
| 734 | —F | none | 0 | free | mp 257-259 |
| 735 | —F | none | 1 | free | mp 204-206 |
| 736 | —F | none | 2 | free | mp 173-174 |
| 737 | —F | none | 3 | free | mp 175-177 |
| 738 | —F | —S— | 1 | Na salt | $^1$H NMR 3.86 (2H, s), 6.86 (2H, d, J = 8.7 Hz), 7.15 (1H, t, J = 9.0 Hz), 7.25 (2H, d, J = 8.7 Hz), 7.55 (1H, d, J = 9.0 Hz), 7.80 (1H, d, J = 8.4 Hz), 7.91 (1H, dd, J = 2.4 Hz, 13.3 Hz), 7.98 (1H, dd, J = 2.0 Hz, 8.4 Hz), 8.25 (1H, d, J = 2.0 Hz). |
| 739 | —F | —SO— | 1 | free | $^1$H NMR 3.79 (1H, d, J = 14.3 Hz), 3.97 (1H, d, J = 14.3 Hz), 7.12 (2H, d, J = 8.8 Hz), 7.33 (1H, t, J = 9.1 Hz), 7.55-7.65 (1H, m), 7.71 (2H, d, J = 8.8 Hz), 7.84 (1H, d, J = 8.4 Hz), 7.90-7.95 (2H, m), 8.20 (1H, d, J = 2.0 Hz), 10.63 (1H, s), 13.20 (1H, brs). |
| 740 | —F | —$SO_2$— | 1 | free | mp 214-216 |
| 741 | —F | —N(Ac)— | 1 | free | $^1$H NMR 1.80 (3H, s), 4.22 (2H, s), 7.00 (1H, d, J = 8.9 Hz), 7.25-7.30 (1H, m), 7.38 (2H, d, J = 8.9 Hz), 7.50-7.60 (1H, m), 7.84 (1H, d, J = 8.4 Hz), 7.90-7.96 (2H, m), 8.21 (1H, d, J = 2.0 Hz), 10.61 (1H, s), 12.68 (1H, s). |
| 742 | —F | 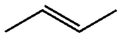 | 0 | free | mp 241-243 |

(—SO— means a group of

and —$SO_2$— means a group of

.

.

Hereinafter —SO— and —$SO_2$— indicate the same meanings.)

TABLE 103

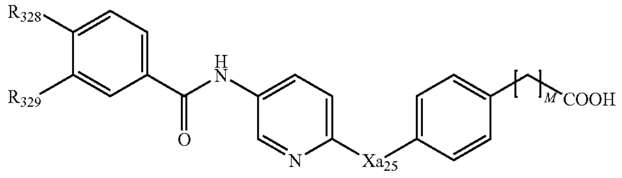

| Reference Example No. | $R_{328}$ | $R_{329}$ | $Xa_{25}$ | M | mp (° C.) or $^1$H NMR (DMSO-$d_6$) δ ppm |
|---|---|---|---|---|---|
| 743 | —Cl | —Cl | —CO— | 2 | $^1$H NMR 2.60 (2H, t, J = 7.6 Hz), 2.91 (2H, t, J = 7.6 Hz), 7.39 (2H, d, J = 8.2 Hz), 7.82-8.20 (4H, m), 8.07 (1H, d, J = 8.6 Hz), 8.25 (1H, dd, J = 7.5 Hz, 2.1 Hz), 8.45 (1H, dd, J = 8.6 Hz, 2.5 Hz), 9.03 (1H, d, J = 2.5 Hz), 10.91 (1H, s), 12.16 (1H, brs). |
| 744 | —Cl | —Cl | —S— | 2 | mp 201-202 |
| 745 | —Cl | —Cl | —SO— | 2 | mp 202-205 |
| 746 | —Cl | —Cl | —$SO_2$— | 2 | mp 172-173 |
| 747 | —Cl | —Cl | —NH— | 2 | $^1$H NMR 2.76 (2H, t, J = 7.6 Hz), 3.20-3.40 (2H, m), 6.86 (1H, d, J = 8.8 Hz), 7.12 (2H, d, |

TABLE 103-continued

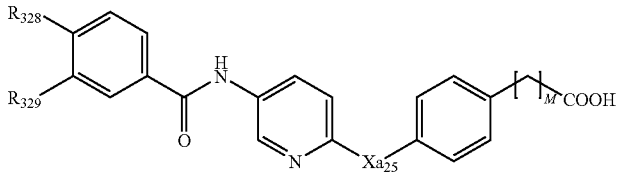

| Reference Example No. | $R_{328}$ | $R_{329}$ | $Xa_{25}$ | M | mp (° C.) or $^1$H NMR (DMSO-$d_6$) δ ppm |
|---|---|---|---|---|---|
| | | | | | J = 8.3 Hz), 7.52 (2H, d, J = 8.3 Hz), 7.83 (1H, d, J =8.4 Hz), 7.90-7.96 (2H, m), 8.21 (1H, d, J =1.3 Hz), 8.45 (1H, d, J = 2.4 Hz), 9.03 (1H, brs), 10.37 (1H, s), 12.11 (1H, brs). |
| 748 | —Cl | —Cl | —N($CH_3$)— | 2 | mp 158-160 |
| 749 | —$CF_3$ | —H | —N($CH_3$)— | 0 | mp 240-243 |
| 750 | —$CF_3$ | —H | —N($CH_3$)— | 2 | $^1$H NMR 2.57 (2H, t, J = 7.5 Hz), 2.84 (2H, t, J = 7.5 Hz), 3.38 (3H, s), 6.61 (1H, d, J = 9.1 Hz), 7.22 (2H, d, J = 8.3 Hz), 7.29 (2H, d, J = 8.3 Hz), 7.80-7.85 (1H, m), 7.91 (2H, d, J = 8.3 Hz), 8.15 (2H, d, J = 8.3 Hz), 8.51 (1H, d, J = 2.5 Hz), 10.42 (1H, s), 12.10 (1H, brs). |
| 751 | —Cl | —Cl | —N($CH_2$Ph)- | 2 | $^1$H NMR 2.53 (2H, t, J = 7.9 Hz), 2.80 (2H, t, J = 7.9 Hz), 5.21 (2H, s), 6.63 (1H, d, J = 9.1 Hz), 7.15-7.30 (9 H, m), 7.75-7.95 (3H, m), 8.19 (1H, d, J = 2.1 Hz), 8.45 (1H, d, J = 2.5 Hz), 10.34 (1H, s), 12.10 (1H, brs). |

TABLE 104

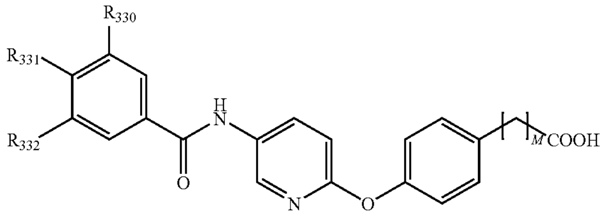

| Reference Example No. | $R_{330}$ | $R_{331}$ | $R_{332}$ | M | mp (° C.) or $^1$H NMR (DMSO-$d_6$) δ ppm |
|---|---|---|---|---|---|
| 752 | —H | —CN | —H | 0 | $^1$H NMR 7.18-7.21 (3H, m), 7.98 (2H, d, J = 8.2 Hz), 8.05 (2H, d, J = 8.9 Hz), 8.13 (2H, d, J = 8.2 Hz), 8.28 (1H, dd, J = 8.6 Hz, 2.6 Hz), 8.57 (1H, d, J = 2.6 Hz), 10.70 (1H, s), 12.87 (1H, brs). |
| 753 | —Cl | —Cl | —H | 0 | $^1$H NMR 7.17-7.22 (3H, m), 7.85 (1H, d, J = 8.2 Hz), 7.94-8.01 (3H, m), 8.23-8.29 (2H, m), 8.55 (1H, d, J = 2.6 Hz), 10.01 (1H, s), 12.87 (1H, brs). |
| 754 | —H | —Cl | —H | 0 | $^1$H NMR 7.16-7.21 (3H, m), 7.63 (2H, d, J = 8.6 Hz), 7.97-8.02 (4H, m), 8.28 (1H, dd, J = 8.6 Hz, 2.6 Hz), 8.57 (1H, d, J = 2.6 Hz), 10.53 (1H, s), 12.86 (1H, brs). |
| 755 | —H | —$CF_3$ | —H | 0 | $^1$H NMR 7.18-7.22 (3H, m), 7.93-8.00 (4H, m), 8.18 (2H, d, J = 8.4 Hz), 8.30 (1H, dd, J = 8.9 Hz, 2.7 Hz), 8.58 (1H, d, J = 2.7 Hz), 10.69 (1H, s), 12.91 (1H, brs). |
| 756 | —$CH_3$ | —$CH_3$ | —H | 0 | $^1$H NMR 2.30 (3H, s), 2.31 (3H, s), 7.16 (1H, d, J = 8.9 Hz), 7.18 (2H, d, J = 8.7 Hz), 7.31 (1H, d, J = 7.6 Hz), 7.72 (1H, d, J = 7.6 Hz), 7.77 (1H, s), 7.98 (2H, d, J = 8.7 Hz), 8.28 (1H, dd, J = 8.9 Hz, 2.7 Hz), 8.58 (1H, d, J = 2.7 Hz), 10.35 (1H, s), 12.88 (1H, brs). |
| 757 | —$CF_3$ | —H | —F | 0 | mp 238-239 |
| 758 | —$OCF_3$ | —H | —H | 0 | $^1$H NMR 7.18-7.22 (3H, m), 7.61-7.81 (2H, m), 7.89-8.06 (4H, m), 8.28 (1H, dd, J = 8.7 Hz, 2.6 Hz), 8.57 (1H, d, J = 2.3 Hz), 10.62 (1H, s), 12.95 (1H, brs). |
| 759 | —$CF_3$ | —H | —H | 0 | $^1$H NMR 7.11-7.22 (3H, m), 7.70-7.85 (1H, m), 7.90-8.05 (3H, m), 8.2-8.35 (3H, m), 8.56 (1H, d, J = 2.4 Hz), 10.70 (1H, s), 12.90 (1H, brs). |

TABLE 104-continued

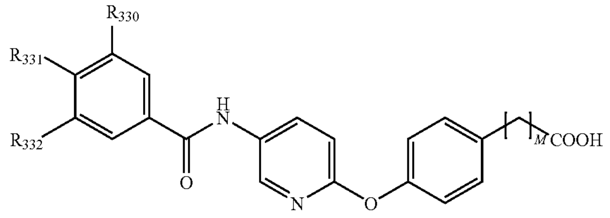

| Reference Example No. | $R_{330}$ | $R_{331}$ | $R_{332}$ | M | mp (° C.) or $^1$H NMR (DMSO-$d_6$) δ ppm |
|---|---|---|---|---|---|
| 760 | —H | —$CF_3$ | —H | 1 | $^1$H NMR 3.59 (2H, s), 7.04-7.10 (3H, m), 7.27-7.33 (2H, m), 7.94 (2H, d, J = 8.4 Hz), 8.17 (2H, d, J = 8.1 Hz), 8.21-8.25 (1H, m), 8.51 (1H, d, J = 2.6 Hz), 10.64 (1H, s), 12.43 (1H, brs). |
| 761 | —Cl | —Cl | —H | 1 | $^1$H NMR 3.59 (2H, s), 7.04-7.09 (3H, m), 7.27-7.32 (2H, m), 7.83 (1H, d, J = 8.4 Hz), 7.95 (1H, dd, J = 8.4 Hz, 2.1 Hz), 8.18-8.23 (2H, m), 8.48 (1H, d, J = 2.6 Hz), 10.55 (1H, s), 12.37 (1H, brs). |
| 762 | —Cl | —Cl | —H | 2 | $^1$H NMR 2.51-2.58 (2H, m), 2.81-2.86 (2H, m), 7.01-7.06 (3H, m), 7.26 (2H, d, J = 8.6 Hz), 7.84 (1H, d, J = 8.4 Hz), 7.93-7.97 (1H, m), 8.16-8.23 (2H, m), 8.47 (1H, d, J = 2.7 Hz), 10.54 (1H, s), 12.13 (1H, brs). |
| 763 | —H | —$CF_3$ | —H | 2 | $^1$H NMR 2.56 (2H, t, J = 7.5 Hz), 2.84 (2H, t, J = 7.5 Hz), 7.03 (2H, d, J = 8.6 Hz), 7.05 (1H, d, J = 8.8 Hz), 7.27 (2H, d, J = 8.6 Hz), 7.93 (2H, d, J = 8.2 Hz), 8.17 (2H, d, J = 8.2 Hz), 8.21 (1H, dd, J = 8.8 Hz, 2.6 Hz), 8.50 (1H, d, J = 2.6 Hz), 10.63 (1H, s), 12.16 (1H, s). |

TABLE 105

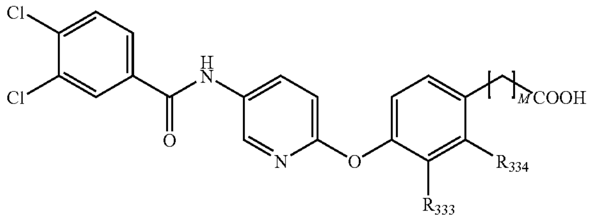

| Reference Example No. | $R_{333}$ | $R_{334}$ | M | $^1$H NMR (DMSO-$d_6$) δ ppm |
|---|---|---|---|---|
| 764 | —$OCH_3$ | —H | 0 | 3.76 (3H, s), 7.09 (1H, d, J = 8.9 Hz), 7.23 (1H, d, J = 8.1 Hz), 7.59-7.63 (2H, m), 7.84 (1H, d, J = 8.4 Hz), 7.93-7.96 (1H, m), 8.16-8.22 (2H, m), 8.39 (1H, d, J = 2.7 Hz), 10.53 (1H, s), 13.00 (1H, brs). |
| 765 | —H | —$OCH_3$ | 0 | 3.80 (3H, s), 6.69 (1H, dd, J = 8.4 Hz, 2.2 Hz), 6.90 (1H, d, J = 2.2 Hz), 7.17 (1H, d, J = 8.9 Hz), 7.73 (1H, d, J = 8.4 Hz), 7.85 (1H, d, J = 8.4 Hz), 7.97 (1H, dd, J = 8.4 Hz, 2.2 Hz), 8.23-8.28 (2H, m), 8.56 (1H, d, J = 2.4 Hz), 10.62 (1H, s), 12.56 (1H, brs). |
| 766 | —$CH_3$ | —H | 0 | 2.18 (3H, s), 7.09-7.16 (2H, m), 7.79-7.97 (4H, m), 8.21-8.26 (2H, m), 8.47 (1H, d, J = 2.2 Hz), 10.57 (1H, s), 12.86 (1H, brs). |
| 767 | —H | —$CH_3$ | 0 | 2.53 (3H, s), 6.97-7.04 (2H, m), 7.16 (1H, d, J = 8.7 Hz), 7.77-7.98 (3H, m), 8.23-8.27 (2H, m), 8.54 (1H, d, J = 2.6 Hz), 10.62 (1H, s), 12.79 (1H, brs). |
| 768 | —F | —H | 0 | 7.24 (1H, d, J = 8.9 Hz), 7.39-7.45 (1H, m), 7.70-8.05 (4H, m), 8.23-8.28 (2H, m), 8.46 (1H, d, J = 2.6 Hz), 10.64 (1H, s), 13.55 (1H, brs). |
| 769 | —Cl | —H | 0 | 7.25 (1H, d, J = 8.9 Hz), 7.39 (1H, d, J = 8.6 Hz), 7.84 (1H, d, J = 8.4 Hz), 7.93-7.97 (2H, m), 8.06 (1H, d, J = 2.0 Hz), 8.22 (1H, d, J = 2.0 Hz), 8.25-8.29 (1H, m), 8.47 (1H, d, J = 2.6 Hz), 10.61 (1H, s), 13.31 (1H, brs). |
| 770 | —$OCH_3$ | —H | 2 | 2.50-2.65 (2H, m), 2.71-2.92 (2H, m), 3.67 (3H, s), 6.81 (1H, dd, J = 8.1 Hz, 1.9 Hz), 6.95 (1H, d, J = 8.9 Hz), 6.99-7.05 (2H, m), 7.82 (1H, d, J = 8.4 Hz), 7.93 (1H, dd, J = 8.4 Hz, 2.0 Hz), 8.10 (1H, dd, J = 8.9 Hz, 2.7 Hz), 8.20 (1H, d, J = 2.0 Hz), 8.35 (1H, m), 10.47 (1H, s), 12.15 (1H, brs). |

TABLE 105-continued

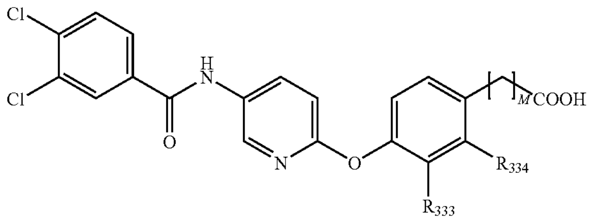

| Reference Example No. | $R_{333}$ | $R_{334}$ | M | $^1$H NMR (DMSO-$d_6$) δ ppm |
|---|---|---|---|---|
| 771 | —$OC_2H_5$ | —H | 2 | 1.06 (3H, t, J = 7.0 Hz), 2.51-2.62 (2H, m), 2.74-2.88 (2H, m), 3.94 (2H, q, J = 7.0 Hz), 6.80 (1H, dd, J = 8.1 Hz, 1.8 Hz), 6.92-7.04 (3H, m), 7.82 (1H, d, J = 8.4 Hz), 7.93 (1H, dd, J = 8.4 Hz, 2.0 Hz), 8.11 (1H, dd, J = 8.9 Hz, 2.7 Hz), 8.20 (1H, d, J = 2.0 Hz), 8.36 (1H, d, J = 2.7 Hz), 10.47 (1H, s), 12.14 (1H, brs). |
| 772 | —F | —H | 2 | 2.50-2.67 (2H, m), 2.75-2.93 (2H, m), 7.03-7.29 (4H, m), 7.82 (1H, d, J = 8.4 Hz), 7.93 (1H, dd, J = 8.4 Hz, 2.0 Hz), 8.12-8.24 (2H, m), 8.39 (1H, d, J = 2.5 Hz), 10.53 (1H, s), 12.18 (1H, brs). |

TABLE 106

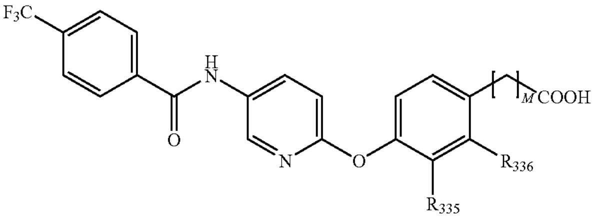

| Reference Example No. | $R_{335}$ | $R_{336}$ | M | $^1$H NMR (DMSO-$d_6$) δ ppm |
|---|---|---|---|---|
| 773 | —$OCH_3$ | —H | 0 | 3.76 (3H, s), 7.10 (1H, d, J = 8.9 Hz), 7.23 (1H, d, J = 8.1 Hz), 7.59-7.64 (2H, m), 7.93 (2H, d, J = 8.1 Hz), 8.15-8.23 (3H, m), 8.42 (1H, d, J = 2.2 Hz), 10.60 (1H, s), 13.00 (1H, brs). |
| 774 | —H | —$OCH_3$ | 0 | 3.80 (3H, s), 6.69 (1H, dd, J = 8.6 Hz, 2.2 Hz), 6.90 (1H, d, J = 2.2 Hz), 7.17 (1H, d, J = 8.6 Hz), 7.73 (1H, d, J = 8.4 Hz), 7.95 (2H, d, J = 8.4 Hz), 8.18 (2H, d, J = 8.4 Hz), 8.29 (1H, dd, J = 8.6 Hz, 2.7 Hz), 8.58 (1H, d, J = 2.7 Hz), 10.69 (1H, s), 12.51 (1H, brs). |
| 775 | —$CH_3$ | —H | 0 | 1.99 (3H, s), 7.09-7.17 (2H, m), 7.79-7.83 (1H, m), 7.91-7.95 (3H, m), 8.12-8.18 (2H, m), 8.27 (1H, dd, J = 8.9 Hz, 2.7 Hz), 8.49 (1H, d, J = 2.7 Hz), 10.64 (1H, s), 12.87 (1H, brs). |
| 776 | —H | —$CH_3$ | 0 | 2.54 (3H, s), 6.98-7.05 (2H, m), 7.17 (1H, d, J = 8.7 Hz), 7.87-7.97 (3H, m), 8.13-8.19 (2H, m), 8.26-8.30 (1H, m), 8.57 (1H, d, J = 2.8 Hz), 10.70 (1H, s), 12.81 (1H, brs). |
| 777 | —F | —H | 0 | 7.26 (1H, d, J = 8.9 Hz), 7.40-7.46 (1H, m), 7.82-7.85 (2H, m), 7.94 (2H, d, J = 8.2 Hz), 8.17 (2H, d, J = 8.2 Hz), 8.30 (1H, dd, J = 8.9 Hz, 2.1 Hz), 8.49 (1H, d, J = 2.1 Hz), 10.70 (1H, s), 13.39 (1H, brs). |
| 778 | —Cl | —H | 0 | 7.14 (1H, d, J = 8.9 Hz), 7.19 (1H, d, J = 8.2 Hz), 7.82-7.86 (1H, m), 7.92 (2H, d, J = 8.4 Hz), 7.96 (1H, d, J = 1.8 Hz), 8.20 (2H, d, J = 8.2 Hz), 8.29 (1H, dd, J = 8.9 Hz, 2.6 Hz), 8.47 (1H, d, J = 2.6 Hz), 10.86 (1H, s). |
| 779 | —$OCH_3$ | —H | 2 | 2.57-2.63 (2H, m), 2.83-2.89 (2H, m), 3.69 (3H, s), 6.84 (1H, dd, J = 8.1 Hz, 1.8 Hz), 6.97 (1H, d, J = 8.9 Hz), 7.01-7.04 (2H, m), 7.92 (2H, d, J = 8.4 Hz), 8.14-8.18 (3H, m), 8.40 (1H, d, J = 2.5 Hz), 10.58 (1H, s). |
| 780 | —$OC_2H_5$ | —H | 2 | 1.06 (3H, t, J = 7.0 Hz), 2.47-2.67 (2H, m), 2.72-2.91 (2H, m), 3.94 (2H, q, J = 7.0 Hz), 6.80 (1H, dd, J = 8.0 Hz, 1.8 Hz), 6.94-7.05 (3H, m), 7.91 (2H, d, J = 8.3 Hz), 8.09-8.19 (3H, m), 8.38 (1H, d, J = 2.6 Hz), 10.55 (1H, s), 12.14 (1H, brs) |

TABLE 106-continued

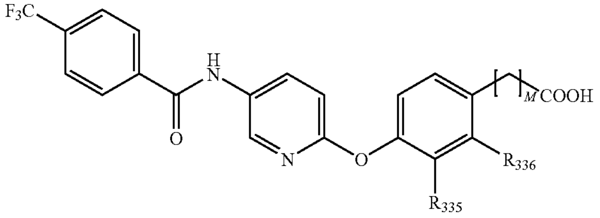

| Reference Example No. | $R_{335}$ | $R_{336}$ | M | $^1$H NMR (DMSO-$d_6$) δ ppm |
|---|---|---|---|---|
| 781 | —F | —H | 2 | 2.49-2.63 (2H, m), 2.71-2.93 (2H, m), 7.09 (1H, dd, J = 8.3 Hz, 1.5 Hz), 7.14 (1H, d, J = 8.9 Hz), 7.17-7.28 (2H, m), 7.92 (2H, d, J = 8.2 Hz), 8.15 (2H, d, J = 8.2 Hz), 8.21 (1H, dd, J = 8.9 Hz, 2.7 Hz), 8.38-8.44 (1H, m), 10.60 (1H, s), 12.17 (1H, brs). |

TABLE 107

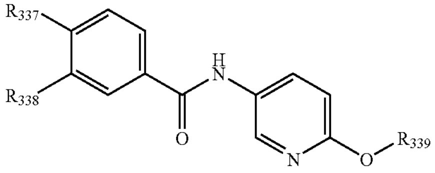

| Reference Example No. | $R_{337}$ | $R_{338}$ | $R_{339}$ | $^1$H NMR (DMSO-$d_6$) δ ppm |
|---|---|---|---|---|
| 782 | —Cl | —Cl | 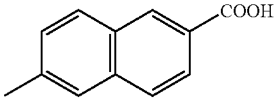 | 7.20 (1H, d, J = 8.7 Hz), 7.40 (1H, dd, J = 8.7 Hz, 2.3 Hz), 7.60-7.67 (1H, m), 7.82-8.03 (4H, m), 8.15 (1H, d, J = 8.9 Hz), 8.26-8.32 (2H, m), 8.56-8.60 (2H, m), 10.78 (1H, s). |
| 783 | —$CF_3$ | —H | 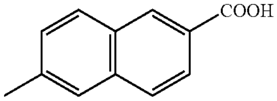 | 7.18 (1H, d, J = 8.7 Hz), 7.36 (1H, dd, J = 8.7 Hz, 2.3 Hz), 7.63 (1H, d, J = 2.0 Hz), 7.84-8.11 (5 H, m), 8.23 (2H, d, J = 8.1 Hz), 8.34 (1H, dd, J = 8.9 Hz, 2.5 Hz), 8.54-8.60 (2H, m), 10.98 (1H, s). |
| 784 | —Cl | —Cl | 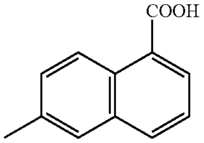 | 7.19 (1H, d, J = 8.7 Hz), 7.47 (1H, dd, J = 9.4 Hz, 2.5 Hz), 7.57-7.63 (1H, m), 7.73 (1H, d, J = 2.5 Hz), 7.85 (1H, d, J = 8.4 Hz), 7.96 (1H, dd, J = 8.4 Hz, 2.0 Hz), 8.10-8.14 (2H, m), 8.23-8.28 (2H, m), 8.52 (1H, d, J = 2.5 Hz), 8.92 (1H, d, J = 9.4 Hz), 10.60 (1H, s), 13.20 (1H, brs). |
| 785 | —$CF_3$ | —H | 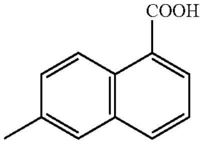 | 7.20 (1H, d, J = 8.7 Hz), 7.48 (1H, dd, J = 9.4 Hz, 2.6 Hz), 7.57-7.63 (1H, m), 7.73 (1H, d, J = 2.5 Hz), 7.94 (2H, d, J = 8.2 Hz), 8.11-8.19 (4H, m), 8.29 (1H, dd, J = 8.7 Hz, 2.6 Hz), 8.55 (1H, d, J = 2.5 Hz), 8.93 (1H, d, J = 9.4 Hz), 10.68 (1H, s), 13.21 (1H, brs). |
| 786 | —Cl | —Cl | 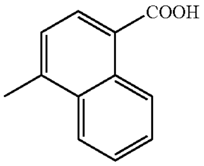 | 7.24 (1H, d, J = 8.1 Hz), 7.32 (1H, d, J = 8.7 Hz), 7.58-7.64 (1H, m), 7.69-7.77 (1H, m), 7.85 (1H, d, J = 8.4 Hz), 7.97 (1H, dd, J = 8.4 Hz, 2.1 Hz), 8.06-8.12 (1H, m), 8.20-8.23 (2H, m), 8.30 (1H, dd, J = 8.7 Hz, 2.6 Hz), 8.48 (1H, d, J = 2.6 Hz), 9.02 (1H, d, J = 8.7 Hz), 10.63 (1H, s), 13.11 (1H, brs). |
| 787 | —Cl | —Cl | 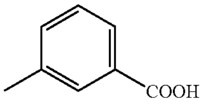 | 7.17 (1H, d, J = 8.9 Hz), 7.38-7.43 (1H, m), 7.53-7.59 (2H, m), 7.76-7.86 (2H, m), 7.93-7.97 (1H, m), 8.22-8.27 (2H, m), 8.51 (1H, d, J = 2.0 Hz), 10.60 (1H, s), 13.15 (1H, brs). |

TABLE 108

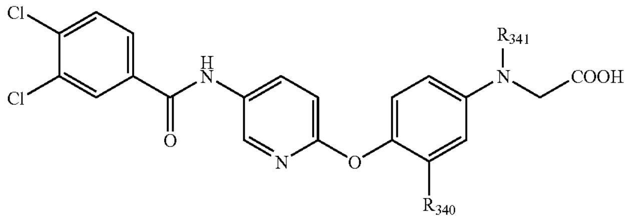

| Reference Example No. | $R_{340}$ | $R_{341}$ | $^1H$ NMR (solvent) δ ppm |
|---|---|---|---|
| 788 | —H | —Ac | (DMSO-$d_6$) 1.85 (3H, s), 4.26 (2H, s), 7.13 (1H, d, J = 8.8 Hz), 7.19 (2H, d, J = 8.7 Hz), 7.42 (2H, d, J = 8.7 Hz), 7.85 (1H, d, J = 8.4 Hz), 7.95 (1H, dd, J = 1.9 Hz, 8.4 Hz), 8.20-8.24 (2H, m), 8.51 (1H, d, J = 2.5 Hz), 12.77 (1H, brs). |
| 789 | —H | —$CH_3$ | (DMSO-$d_6$) 2.98 (3H, s), 4.01 (2H, s), 6.65 (1H, d, J = 9.1 Hz), 6.90-6.95 (3H, m), 7.82 (1H, d, J = 8.4 Hz), 7.94 (1H, dd, J = 2.1 Hz, 8.4 Hz), 8.13 (1H, dd, J = 2.7 Hz, 8.9 Hz), 8.22 (1H, d, J = 2.1 Hz), 8.43 (1H, d, J = 2.7 Hz), 10.54 (1H, s). |
| 790 | —H | —$C_2H_5$ | (DMSO-$d_6$) 1.11 (3H, t, d = 7.1 Hz), 3.39 (2H, q, J = 7.1 Hz), 4.01 (2H, s), 6.58 (2H, d, J = 9.1 Hz), 6.90-6.95 (3H, m), 7.81 (1H, d, J = 8.4 Hz), 7.92 (1H, dd, J = 2.0 Hz, 8.4 Hz), 8.11 (1H, dd, J = 2.7 Hz, 8.9 Hz), 8.19 (1H, d, J = 2.0 Hz), 8.41 (1H, d, J = 2.7 Hz), 10.48 (1H, s), 12.53 (1H, brs). |
| 791 | —$OCH_3$ | —$CH_3$ | (DMSO-$d_6$) 3.01 (3H, s), 3.67 (3H, s), 4.12 (2H, s), 6.20 (1H, dd, J = 8.7 Hz, 2.8 Hz), 6.39 (1H, d, J = 2.8 Hz), 6.85-6.94 (2H, m), 7.83 (1H, d, J = 8.4 Hz), 7.94 (1H, dd, J = 8.4 Hz, 2.1 Hz), 8.08 (1H, dd, J = 8.7 Hz, 2.6 Hz), 8.21 (1H, d, J = 2.0 Hz), 8.36 (1H, d, J = 2.5 Hz), 10.47 (1H, s), 12.58 (1H, brs). |
| 792 | —$OCH_3$ | —$C_2H_5$ | (DMSO-$d_6$) 1.15 (3H, t, J = 7.1 Hz), 3.43 (2H, q, J = 7.1 Hz), 3.65 (3H, s), 4.06 (2H, s), 6.13 (1H, dd, J = 8.7 Hz, 2.6 Hz), 6.30 (1H, d, J = 2.6 Hz), 6.87-6.91 (2H, m), 7.83 (1H, d, J = 8.4 Hz), 7.94 (1H, dd, J = 8.4 Hz, 2.0 Hz), 8.08 (1H, dd, J = 8.9 Hz, 2.6 Hz), 8.21 (1H, d, J = 2.0 Hz), 8.36 (1H, d, J = 2.6 Hz), 10.48 (1H, s), 12.58 (1H, brs). |
| 793 | —$CH_3$ | —Ac | (DMSO-$d_6$) 1.84 (3H, s), 2.11 (3H, s), 4.23 (2H, s), 7.05-7.10 (2H, m), 7.20-7.25 (1H, m), 7.32 (1H, d, J = 2.2 Hz), 7.75-7.85 (1H, m), 7.92 (1H, dd, J = 2.2 Hz, 8.4 Hz), 8.10-8.20 (2H, m), 8.43 (1H, d, J = 2.6 Hz), 10.53 (1H, s), 12.66 (1H, brs). |
| 794 | —$CH_3$ | —$CH_3$ | (DMSO-$d_6$) 2.01 (3H, s), 2.97 (3H, s), 4.07 (2H, s), 6.49 (1H, dd, J = 8.8 Hz, 3.0 Hz), 6.57 (1H, d, J = 3.0 Hz), 6.85 (1H, d, J = 8.8 Hz), 6.90 (1H, d, J = 8.9 Hz), 7.82 (1H, d, J = 8.4 Hz), 7.93 (1H, dd, J = 8.4 Hz, 2.0 Hz), 8.11 (1H, dd, J = 8.9 Hz, 2.7 Hz), 8.20 (1H, d, J = 2.0 Hz), 8.39 (1H, d, J = 2.7 Hz), 10.47 (1H, s), 12.51 (1H, brs). |
| 795 | —F | —Ac | ($CDCl_3$ + DMSO-$d_6$) 1.99 (3H, s), 4.35 (2H, s), 7.03 (1H, d, J = 8.9 Hz), 7.21-7.31 (3H, m), 7.57 (1H, d, J = 8.4 Hz), 7.90 (1H, dd, J = 8.4 Hz, 2.1 Hz), 8.19 (1H, d, J = 2.0 Hz), 8.32 (1H, dd, J = 8.9 Hz, 2.6 Hz), 8.46 (1H, d, J = 2.5 Hz), 10.12 (1H, s). |
| 796 | —F | —$CH_3$ | ($CDCl_3$ + DMSO-$d_6$) 3.04 (3H, s), 3.98 (2H, s), 6.40-6.49 (2H, m), 6.90 (1H, d, J = 8.9 Hz), 7.02 (1H, t, J = 8.7 Hz), 7.52 (1H, d, J = 8.4 Hz), 7.85 (1H, dd, J = 8.4 Hz, 2.1 Hz), 8.14 (1H, d, J = 2.0 Hz), 8.23 (1H, dd, J = 8.9 Hz, 2.6 Hz), 8.34 (1H, d, J = 2.5 Hz), 9.77 (1H, s). |
| 797 | —F | —$C_2H_5$ | ($CDCl_3$) 1.26 (3H, t, J = 7.1 Hz), 3.44 (2H, q, J = 7.1 Hz), 4.03 (2H, s), 6.39-6.52 (2H, m), 6.96 (1H, d, J = 9.7 Hz), 7.06 (1H, t, J = 8.9 Hz), 7.55 (1H, d, J = 8.4 Hz), 7.69 (1H, dd, J = 8.6 Hz, 2.1 Hz), 7.96-7.97 (2H, m), 8.15-8.18 (2H, m). |

TABLE 109

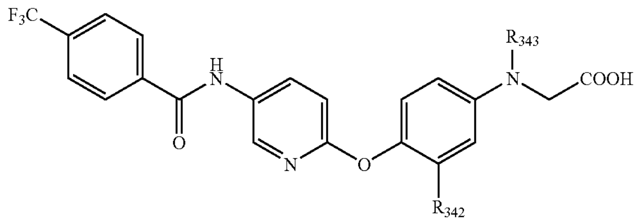

| Reference Example No. | $R_{342}$ | $R_{343}$ | $^1$H NMR (solvent) δ ppm |
|---|---|---|---|
| 798 | —H | —Ac | (DMSO-$d_6$) 1.85 (3H, s), 4.26 (2H, s), 7.13 (1H, d, J = 8.8 Hz), 7.18 (2H, d, J = 8.7 Hz), 7.42 (2H, d, J = 8.7 Hz), 7.94 (2H, d, J = 8.2 Hz), 8.16 (2H, d, J = 8.2 Hz), 8.25 (1H, dd, J = 2.5 Hz, 8.8 Hz), 8.54 (1H, d, J = 2.5 Hz), 10.66 (1H, s), 12.70 (1H, brs). |
| 799 | —H | —$CH_3$ | (DMSO-$d_6$) 2.99 (3H, s), 4.09 (2H, s), 6.67 (2H, d, J = 9.0 Hz), 6.96 (3H, d, J = 9.0 Hz), 7.93 (2H, d, J = 8.2 Hz), 8.16 (2H, d, J = 8.2 Hz), 8.12-8.20 (1H, m), 8.46 (1H, d, J = 2.3 Hz), 10.59 (1H, s), 12.58 (1H, brs). |
| 800 | —H | —$C_2H_5$ | (DMSO-$d_6$) 1.13 (3H, t, J = 7.1 Hz) 3.38 (2H, q, J = 7.1 Hz), 4.00 (2H, s), 6.65 (1H, d, J = 8.9 Hz), 6.73 (1H, d, J = 8.9 Hz), 6.92-6.97 (3H, m), 7.93 (2H, d, J = 8.1 Hz), 8.15-8.18 (3H, m), 8.46 (1H, s), 10.59 (1H, s). |
| 801 | —$OCH_3$ | —$CH_3$ | (DMSO-$d_6$) 3.01 (3H, s), 3.67 (3H, s), 4.12 (2H, s), 6.20 (1H, dd, J = 8.7 Hz, 2.6 Hz), 6.39 (1H, d, J = 2.5 Hz), 6.83-6.95 (2H, m), 7.93 (2H, d, J = 8.3 Hz), 8.09-8.17 (3H, m), 8.38 (1H, d, J = 2.6 Hz), 10.56 (1H, s), 12.58 (1H, brs). |
| 802 | —$OCH_2$ | —$C_2H_5$ | (DMSO-$d_6$) 1.15 (3H, t, J = 7.1 Hz), 3.43 (2H, q, J = 7.1 Hz), 3.66 (3H, s), 4.06 (2H, s), 6.14 (1H, dd, J = 8.7 Hz, 2.6 Hz), 6.31 (1H, d, J = 2.8 Hz), 6.88-6.92 (2H, m), 7.93 (2H, d, J = 8.4 Hz), 8.09-8.17 (3H, m), 8.39 (1H, d, J = 2.5 Hz), 10.55 (1H, s), 12.59 (1H, brs). |
| 803 | —$CH_3$ | —Ac | (DMSO-$d_6$) 1.84 (3H, s), 2.11 (3H, s), 4.23 (2H, s), 7.05-7.10 (2H, m), 7.23 (1H, dd, J = 2.4 Hz, 8.5 Hz), 7.33 (1H, d, J = 2.4 Hz), 7.86 (1H, d, J = 8.3 Hz), 7.91 (2H, d, J = 8.3 Hz), 8.14 (2H, d, J = 8.3 Hz), 8.20 (1H, dd, J = 2.7 Hz, 8.9 Hz), 8.45 (1H, d, J = 2.7 Hz), 10.61 (1H, s), 12.67 (1H, brs). |
| 804 | —$CH_3$ | —$CH_3$ | (DMSO-$d_6$) 2.01 (3H, s), 2.97 (3H, s), 4.06 (2H, s), 6.49 (1H, dd, J = 8.8 Hz, 3.1 Hz), 6.57 (1H, d, J = 2.9 Hz), 6.85 (1H, d, J = 8.8 Hz), 6.91 (1H, d, J = 8.9 Hz), 7.91 (2H, d, J = 8.3 Hz), 8.04-8.23 (3H, m), 8.41 (1H, d, J = 2.6 Hz), 10.56 (1H, s), 12.11-12.98 (1H, m). |
| 805 | —F | —Ac | ($CDCl_3$) 1.96 (3H, s), 4.32 (2H, s), 7.09-7.31 (4H, m), 7.75 (2H, d, J = 8.4 Hz), 8.02 (2H, d, J = 8.3 Hz), 8.20 (1H, d, J = 2.6 Hz), 8.40 (1H, dd, J = 8.9 Hz, 2.6 Hz), 8.44 (1H, s). |
| 806 | —F | —$CH_3$ | ($CDCl_3$ + DMSO-$d_6$) 3.08 (3H, s), 4.02 (2H, s), 6.47-6.52 (2H, m), 6.92 (1H, d, J = 8.7 Hz), 7.06 (1H, t, J = 9.0 Hz), 7.73 (2H, d, J = 8.4 Hz), 8.11 (2H, d, J = 8.4 Hz), 8.26 (1H, dd, J = 8.7 Hz, 2.5 Hz), 8.39 (1H, d, J = 2.5 Hz), 9.76 (1H, s). |
| 807 | —F | —$C_2H_5$ | ($CDCl_3$ + DMSO-$d_6$) 1.23 (3H, t, J = 7.1 Hz), 3.45 (2H, q, J = 7.1 Hz), 3.97 (2H, s), 6.39-6.48 (2H, m), 6.91 (1H, d, J = 8.7 Hz), 7.04 (1H, t, J = 9.1 Hz), 7.73 (2H, d, J = 7.9 Hz), 8.12 (2H, d, J = 7.9 Hz), 8.25 (1H, d, J = 9.1 Hz), 8.42 (1H, d, J = 2.5 Hz), 9.92 (1H, s). |
| 808 | —F | —$(CH_2)_2CH_3$ | ($CDCl_3$ + DMSO-$d_6$) 0.96 (3H, t, J = 7.2 Hz), 1.61-1.72 (2H, m), 3.33 (2H, t, J = 7.6 Hz), 3.99 (2H, s), 6.37-6.48 (2H, m), 6.93 (1H, d, J = 8.8 Hz), 7.04 (1H, t, J = 9.1 Hz), 7.73 (2H, d, J = 8.1 Hz), 8.09 (2H, d, J = 8.1 Hz), 8.26 (1H, dd, J = 8.9 Hz), 2.6 Hz), 8.36 (1H, d, J = 2.5 Hz), 9.45 (1H, s). |

TABLE 110

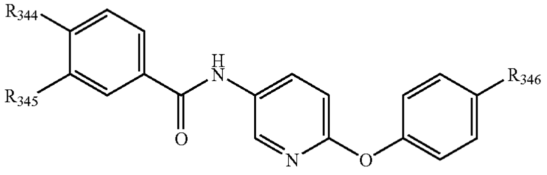

| Reference Example No. | $R_{344}$ | $R_{345}$ | $R_{346}$ | $^1H$ NMR (solvent) δ ppm |
|---|---|---|---|---|
| 809 | —Cl | —Cl | —N(Ac)$(CH_2)_2$COOH | ($DMSO-d_6$) 1.71 (3H, s), 2.39 (2H, t, J = 7.5 Hz), 3.78 (2H, t, J = 7.5 Hz), 7.08 (1H, d, J = 8.8 Hz), 7.14 (2H, d, J = 8.6 Hz), 7.31 (2H, d, J = 8.6 Hz), 7.80 (1H, d, J = 8.4 Hz), 7.91 (1H, dd, J = 2.1 Hz, 8.4 Hz), 8.15-8.21 (2H, m), 8.49 (1H, d, J = 2.5 Hz), 10.55 (1H, s), 12.20 (1H, brs) |
| 810 | —$CF_3$ | —H | —N(Ac)$(CH_2)_2$COOH | ($DMSO-d_6$) 1.71 (3H, s), 2.40 (2H, t, J = 7.3 Hz), 3.78 (2H, t, J = 7.3 Hz), 7.09 (1H, d, J = 8.7 Hz), 7.14 (2H, d, S = 8.1 Hz), 7.31 (2H, d, J = 8.1 Hz), 7.90 (2H, d, J = 8.1 Hz), 8.12 (2H, d, J = 8.1 Hz), 8.21 (1H, d, J = 8.7 Hz), 8.52 (1H, s), 10.63 (1H, s), 12.25 (1H, brs). |
| 811 | —Cl | —Cl | —$CH(CH_3)CH_2$COOH | ($CDCl_3$– $CD_3OD$) 1.26 (3H, d, J = 7.0 Hz), 2.42-2.61 (2H, m), 3.17-3.28 (1H, m), 6.84 (1H, d, J = 8.9 Hz), 6.98 (2H, d, J = 8.5 Hz), 7.20 (2H, d, J = 8.5 Hz), 7.50 (1H, d, J = 8.4 Hz), 7.73 (1H, dd, J = 8.5 Hz, 2.1 Hz), 8.01 (1H, d, J = 2.1 Hz), 8.14 (1H, d, J = 2.7 Hz), 8.26 (1H, dd, J = 8.9 Hz, 2.7 Hz). |
| 812 | —$CF_3$ | —H | —$CH(CH_3)CH_2$COOH | ($CDCl_3$– $CD_3OD$) 1.28 (3H, d, J = 7.0 Hz), 2.44-2.61 (2H, m), 3.18-3.29 (1H, m), 6.88 (1H, d, J = 8.9 Hz), 7.00 (2H, d, J = 8.5 Hz), 7.20 (2H, d, J = 8.5 Hz), 7.70 (2H, d, J = 8.2 Hz), 7.99 (2H, d, J = 8.2 Hz), 8.17 (1H, d, J = 2.6 Hz), 8.28 (1H, dd, J = 8.9 Hz, 2.6 Hz). |
| 813 | —$CF_3$ | —H | —CH═CHCOOH trans | ($DMSO-d_6$) 6.49 (1H, d, J = 16.0 Hz), 7.15 (3H, d, J = 8.8 Hz), 7.61 (1H, d, J = 16.0 Hz), 7.74 (2H, d, J = 8.8 Hz), 7.94 (2H, d, J = 8.3 Hz), 8.17 (2H, d, J = 8.3 Hz), 8.26 (1H, dd, J = 8.8 Hz, 2.7 Hz), 8.55 (1H, d, J = 2.7 Hz), 10.67 (1H, s), 12.36 (1H, s). |
| 814 | —$CF_3$ | —H | 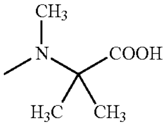 | ($CDCl_3$) 1.34 (6 H, s), 2.79 (3H, s), 6.98 (1H, d, J = 8.9 Hz), 7.10 (2H, d, J = 8.9 Hz), 7.21 (2H, d, J = 9.1 Hz), 7.76 (2H, d, J = 8.2 Hz), 8.01 (2H, d, J = 8.1 Hz), 8.10 (1H, brs), 8.24 (1H, dd, J = 8.7 Hz, 2.6 Hz), 8.31 (1H, d, J = 2.3 Hz). |

TABLE 111

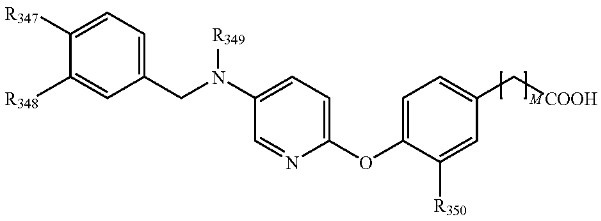

| Reference Example No. | $R_{347}$ | $R_{348}$ | $R_{349}$ | $R_{350}$ | M | $^1H$ NMR (solvent) δ ppm |
|---|---|---|---|---|---|---|
| 815 | —Cl | —Cl | —H | —F | 0 | ($DMSO-d_6$) 4.29 (2H, d, J = 5.6 Hz), 6.46 (1H, t, J = 5.9 Hz), 6.94 (1H, d, J = 8.7 Hz), 7.15 (1H, dd, J = 8.7 Hz, 3.0 Hz), 7.20 (1H, d, J = 8.3 Hz), |

TABLE 111-continued

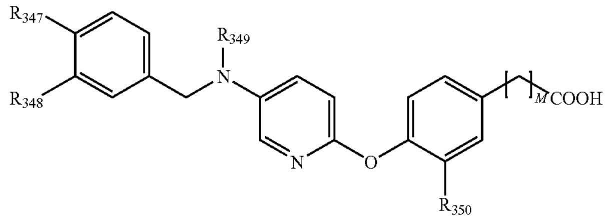

| Reference Example No. | $R_{347}$ | $R_{348}$ | $R_{349}$ | $R_{350}$ | M | $^1H$ NMR (solvent) δ ppm |
|---|---|---|---|---|---|---|
| | | | | | | 7.36 (1H, dd, J = 8.3 Hz, 1.8 Hz), 7.47 (1H, d, J = 2.8 Hz), 7.59 (1H, d, J = 8.3 Hz), 7.63 (1H, d, J = 2.0 Hz), 7.72-7.77 (2H, m). |
| 816 | $-CF_3$ | —H | —H | —F | 0 | (DMSO-$d_6$) 4.37 (2H, d, J = 5.3 Hz), 6.47 (1H, brs), 6.89 (1H, d, J = 8.7 Hz), 7.06-7.12 (1H, m), 7.13 (1H, dd, J = 8.7 Hz, 3.0 Hz), 7.45 (1H, d, J = 3.0 Hz), 7.58 (2H, d, J = 8.1 Hz), 7.65-7.69 (2H, m), 7.70 (2H, d, J = 8.1 Hz). |
| 817 | $-CF_3$ | —H | $-CH_3$ | —H | 0 | (DMSO-$d_6$) 3.03 (3H, s), 4.66 (2H, s), 6.82 (2H, d, J = 8.7 Hz), 6.87 (1H, d, J = 8.9 Hz), 7.29 (1H, dd, J = 8.9 Hz, 3.3 Hz), 7.45 (2H, d, J = 8.1 Hz), 7.68-7.72 (3H, m), 7.82 (2H, d, J = 8.7 Hz). |
| 818 | $-CF_3$ | —H | $-C_2H_5$ | —H | 0 | (DMSO-$d_6$) 1.13 (3H, t, J = 7.1 Hz), 3.49 (2H, q, J = 7.1 Hz), 4.61 (2H, s), 6.81 (2H, d, J = 8.6 Hz), 6.84 (1H, d, J = 8.9 Hz), 7.22 (1H, dd, J = 8.9 Hz, 3.3 Hz), 7.47 (2H, d, J = 8.1 Hz), 7.62 (1H, d, J = 3.3 Hz), 7.70 (2H, d, J = 8.3 Hz), 7.80 (2H, d, J = 8.7 Hz). |
| 819 | —Cl | —Cl | $-CH_3$ | $-OCH_3$ | 2 | ($CDCl_3$) 2.66 (2H, t, J = 7.7 Hz), 2.93 (2H, t, J = 7.7 Hz), 2.95 (3H, s), 3.75 (3H, s), 4.35 (2H, s), 6.68-6.88 (3H, m), 6.90-7.00 (1H, m), 7.00-7.17 (2H, m), 7.31 (1H, d, J = 2.0 Hz), 7.37 (1H, d, J = 8.2 Hz), 7.65 (1H, d, J = 3.0 Hz), 8.21 (1H, brs). |
| 820 | $-CF_3$ | —H | $-CH_3$ | $-OCH_3$ | 2 | (DMSO-$d_6$) 2.41-2.62 (2H, m), 2.69-2.85 (2H, m), 2.96 (3H, s), 3.64 (3H, s), 4.58 (2H, s), 6.70-6.79 (2H, m), 6.88 (1H, d, J = 8.0 Hz), 6.95 (1H, d, J = 1.8 Hz), 7.25 (1H, dd, J = 9.2 Hz, 3.2 Hz), 7.42 (2H, d, J = 8.0 Hz), 7.52 (1H, d, J = 3.2 Hz), 7.67 (2H, d, J = 8.0 Hz), 11.64-12.51 (1H, m). |
| 821 | —Cl | —Cl | $-CH_3$ | $-OC_2H_5$ | 2 | (DMSO-$d_6$) 1.03 (3H, t, J = 7.0 Hz), 2.53 (2H, t, J = 7.6 Hz), 2.78 (2H, t J = 7.6 Hz), 3.89 (2H, q, J = 7.0 Hz), 4.49 (2H, s), 6.70-6.80 (2H, m), 6.88 (1H, d, J = 8.0 Hz), 6.92 (1H, d, J = 1.9 Hz), 7.19 (1H, dd, J = 8.3 Hz, 2.0 Hz), 7.26 (1H, dd, J = 9.0 Hz, 3.2 Hz), 7.45 (1H, dd, J = 2.0 Hz), 7.52 (1H, d, J = 3.2 Hz), 7.56 (1H, d, J = 8.3 Hz), 11.81-12.30 (1H, m). |
| 822 | —Cl | —Cl | $-CH_3$ | —F | 2 | (DMSO-$d_6$) 2.55 (2H, t, J = 7.6 Hz), 2.80 (2H, t, J = 7.6 Hz), 2.96 (3H, s), 4.50 (2H, s), 6.92 (1H, d, J = 8.9 Hz), 7.00-7.22 (4H, m), 7.22-7.38 (1H, m), 7.38-7.40 (1H, m), 7.40-7.55 (2H, m), 12.10 (1H, brs). |
| 823 | —Cl | —Cl | $-C_2H_5$ | —F | 2 | ($CDCl_3$) 1.17 (3H, t, J = 7.0 Hz), 2.66 (2H, t, J = 7.7 Hz), 2.93 (2H, t, J = 7.7 Hz), 3.40 (2H, q, J = 7.0 Hz), 4.36 (2H, s), 6.72-6.86 (1H, m), 6.90-7.15 (5 H, m), 727-7.35 (1H, m), 7.36 (1H, d, J = 8.2 Hz), 7.59 (1H, d, J = 3.2 Hz). |

TABLE 112

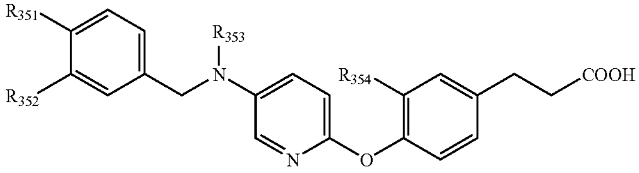

| Reference Example No. | $R_{351}$ | $R_{352}$ | $R_{353}$ | $R_{354}$ | $^1H$ NMR (solvent) δ ppm |
|---|---|---|---|---|---|
| 824 | —$CF_3$ | —H | —$CH_3$ | —H | ($DMSO-d_6$) 2.50-2.54 (2H, m), 2.79 (2H, t, J = 7.6 Hz), 3.02 (3H, s), 4.64 (2H, s), 6.86 (1H, d, J = 8.9 Hz), 6.89 (2H, d, J = 8.4 Hz), 7.19 (2H, d, J = 8.7 Hz), 7.29 (1H, dd, J = 8.9 Hz, 3.3 Hz), 7.44 (2H, d, J = 7.9 Hz), 7.69 (2H, d, J = 7.9 Hz), 7.64 (1H, d, J = 3.1 Hz). |
| 825 | —$CF_3$ | —H | —$CH_3$ | —$OC_2H_5$ | ($DMSO-d_6$) 1.03 (3H, t, J = 7.0 Hz), 2.47-2.59 (2H, m), 2.71-2.83 (2H, m), 2.97 (3H, s), 3.89 (2H, q, J = 7.0 Hz), 4.59 (2H, s), 6.69-6.79 (2H, m), 6.88 (1H, d, J = 8.0 Hz), 6.91 (1H, d, J = 1.9 Hz), 7.26 (1H, dd, J = 9.0 Hz, 3.1 Hz), 7.41 (2H, d, J = 8.0 Hz), 7.52 (1H, d, J = 3.1 Hz), 7.66 (2H, d, J = 8.0 Hz), 11.85-12.31 (1H, m), |
| 826 | —$CF_3$ | —H | —$CH_3$ | —F | ($CDCl_3$) 2.67 (2H, t, J = 7.7 Hz), 2.94 (2H, t, J = 7.7 Hz), 3.00 (3H, s), 4.49 (2H, s), 6.86 (1H, d, J = 8.9 Hz), 6.90-7.16 (4H, m), 7.33 (2H, d, J = 8.1 Hz), 7.57 (2H, d, J = 8.1 Hz), 7.64 (1H, d, J = 3.1 Hz). |
| 827 | —$CF_3$ | —H | —$C_2H_5$ | —H | ($DMSO-d_6$) 1.11 (3H, t, J = 7.0 Hz), 2.42-2.57 (2H, m), 2.71-2.82 (2H, m), 3.47 (2H, q, J = 7.0 Hz), 4.58 (2H, s), 6.82 (1H, d, J = 8.9 Hz), 6.84-6.91 (2H, m), 7.13-7.21 (2H, m), 7.20 (1H, dd, J = 8.9 Hz, 3.1 Hz), 7.45 (2H, d, J = 8.1 Hz), 7.57 (1H, d, J = 3.1 Hz), 7.68 (2H, d, J = 8.1 Hz), 12.06 (1H, brs). |
| 828 | —Cl | —Cl | —$C_2H_5$ | —$OCH_3$ | ($CDCl_3$) 1.16 (3H, t, J = 7.1 Hz), 2.55-2.78 (2H, m), 2.94 (2H, t, J = 7.7 Hz), 3.39 (2H, q, J = 7.1 Hz), 3.77 (3H, s), 4.35 (2H, s), 6.70-6.88 (3H, m), 6.92-7.13 (3H, m), 7.32 (1H, d, J = 2.0 Hz), 7.36 (1H, d, J = 8.2 Hz), 7.59 (1H, d, J = 3.1 Hz). |
| 829 | —$CF_3$ | —H | —$C_2H_5$ | —$OCH_3$ | ($DMSO-d_6$) 1.09 (3H, t, J = 7.0 Hz), 2.48-2.61 (2H, m), 2.72-2.86 (2H, m), 3.40 (2H, q, J = 7.0 Hz), 3.64 (3H, s), 4.54 (2H, s), 6.73 (1H, d, J = 9.0 Hz), 6.74 (1H, dd, J = 8.0 Hz, 1.9 Hz), 6.87 (1H, d, J = 8.0 Hz), 6.95 (1H, d, J = 1.9 Hz), 7.18 (2H, dd, J = 9.0 Hz, 3.2 Hz), 7.39-7.49 (3H, m), 7.62-7.71 (2H, m), 11.90-12.31 (1H, m). |
| 830 | —Cl | —Cl | —$C_2H_5$ | —$OC_2H_5$ | ($DMSO-d_6$) 0.95-1.11 (6 H, m), 2.41-2.57 (2H, m), 2.77 (2H, t, J = 7.7 Hz), 3.29-3.47 (2H, m), 3.88 (2H, q, J = 7.0 Hz), 4.44 (2H, s), 6.73 (1H, dd, J = 8.0 Hz, 1.9 Hz), 6.74 (1H, d, J = 9.0 Hz), 6.88 (1H, d, J = 8.0 Hz), 6.91 (1H, d, J = 1.9 Hz), 7.15-7.24 (2H, m), 7.41-7.48 (2H, m), 7.55 (1H, d, J = 8.2 Hz), 11.60-12.50 (1H, m). |
| 831 | —$CF_3$ | —H | —$C_2H_5$ | —$OC_2H_5$ | ($DMSO-d_6$) 1.02 (3H, t, J = 7.0 Hz), 1.08 (3H, t, J = 7.0 Hz), 2.46-2.59 (2H, m), 2.71-2.83 (2H, m), 3.43 (2H, q, J = 7.0 Hz), 3.89 (2H, q, J = 7.0 Hz), 6.69-6.78 (2H, m), 6.87 (1H, d, J = 8.0 Hz), 6.91 (1H, d, J = 1.8 Hz), 7.19 (1H, dd, J = 9.0 Hz, 3.2 Hz), 7.39-7.49 (3H, m), 7.61-7.69 (2H, m), 11.92-12.22 (1H, m). |
| 832 | —$CF_3$ | —H | —$C_2H_5$ | —F | ($CDCl_3$) 1.19 (3H, t, J = 7.1 Hz), 2.67 (2H, t, J = 7.7 Hz), 2.93 (2H, t, J = 7.7 Hz), 3.43 (2H, q, J = 7.1 Hz), 4.48 (2H, s), 6.83 (1H, d, J = 9.0 Hz), 6.90-7.20 (4H, m), 7.34 (2H, d, J = 8.2 Hz), 7.50-7.65 (3H, m) |

TABLE 113

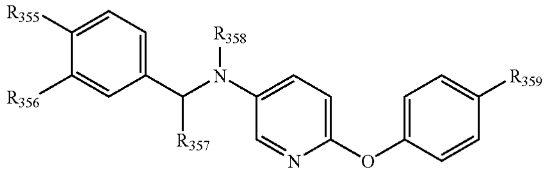

| Reference Example No. | $R_{355}$ | $R_{356}$ | $R_{357}$ | $R_{358}$ | $R_{359}$ | Form | [1]NMR (solvent) δ ppm |
|---|---|---|---|---|---|---|---|
| 833 | —$CF_3$ | —H | —$CH_3$ | —H | —COOH | free | (DMSO-$d_6$) 1.45 (3H, d, J = 6.8 Hz), 4.61 (1H, dt, J = 6.8 Hz, 6,8 Hz), 6.85 (1H, d, J = 8.6 Hz), 6.97 (2H, d, J = 8,7 Hz), 7.04 (1H, dd, J = 8.7 Hz, 3.0 Hz), 7.51 (1H, d, J = 3.0 Hz), 7.62 (2H, d, J = 8.3 Hz), 7.70 (2H, d, J = 8.3 Hz), 7.89 (2H, d, J = 8.9 Hz), 12.79 (1H, brs). |
| 834 | —$CF_3$ | —H | —$CH_3$ | —$CH_3$ | —COOH | free | (DMSO-$d_6$) 1.54 (3H, d, J = 6.8 Hz), 2.73 (3H, s), 5.23 (1H, q, J = 6.8 Hz), 7.00 (1H, d, J = 8.9 Hz), 7.05 (2H, d, J = 8.7 Hz), 7.46 (1H, dd, J = 9.1 Hz, 3.3 Hz), 7.54 (2H, d, J = 8.1 Hz), 7.72 (2H, d, J = 8.4 Hz), 7.84 (1H, d, J = 3.3 Hz), 7.93 (2H, d, J = 8.6 Hz) |
| 835 | —$CF_3$ | —H | —H | —$CH_3$ | 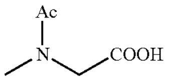 | dihydro-chloride | (DMSO-$d_6$) 1.81 (3H, s), 3.05 (3H, s), 4.22 (2H, s), 4.67 (2H, s), 6.95 (1H, d, J = 8.7 Hz), 7.04 (2H, d, J = 8.6 Hz), 7.28-7.40 (1H, m), 7.35 (2H, d, J = 8.6 Hz), 7.45 (2H, d, J = 8.1 Hz), 7.62-7.80 (1H, m), 7.70 (2H, d, J = 8.1 Hz). |
| 836 | —Cl | —Cl | —H | —$CH_3$ | 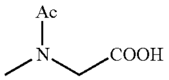 | dihydro-chloride | ($CDCl_3$) 1.81 (3H, s), 3.02 (3H, s), 4.23 (2H, s), 4.57 (2H, s), 6.95 (1H, d, J = 8.8 Hz), 7.04 (2H, d, J = 8.7 Hz), 7.22 (1H, dd, J = 8.2 Hz, 2.0 Hz), 7.32-7.40 (1H, m), 7.35 (2H, d, J = 8.7 Hz), 7.51 (1H, d, J = 2.0 Hz), 7.59 (1H, d, J = 8.2 Hz), 7.71 (1H, d, J = 3.0 Hz). |
| 837 | —$CF_3$ | —H | —H | —$(CH_2)_2OCH_3$ | —$(CH_2)_2COOH$ | free | (DMSO-$d_6$) 2.43-2.57 (2H, m), 2.71-2.82 (2H, m), 3.25 (3H, s), 3.48-3.58 (2H, m), 3.59-3.68 (2H, m), 4.66 (2H, s), 6.80 (1H, d, J = 8.9 Hz), 6.83-6.90 (2H, m), 7.11-7.25 (3H, m), 7.44 (2H, d, J = 8.0 Hz), 7.56 (1H, d, J = 3.1 Hz), 7.67 (2H, d, J = 8.0 Hz), 12.09 (1H, brs). |

TABLE 114

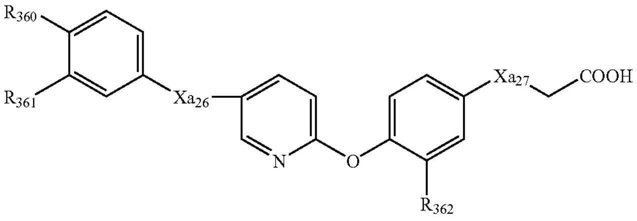

| Reference Example No. | $R_{360}$ | $R_{361}$ | $R_{362}$ | $Xa_{26}$ | $Xa_{27}$ | $^1$H NMR (solvent) δ ppm or MS |
|---|---|---|---|---|---|---|
| 838 | —Cl | —Cl | —$OCH_3$ | —CH=CH— (trans) | —$CH_2$— | $^1$H NMR (DMSO-$d_6$) 2.57-2.63 (2H, m), 2.83-2.88 (2H, m), 3.68 (3H, s), 6.84 (1H, dd, J = 8.1 Hz, 1.7 Hz), 6.98-7.05 (3H, m), 7.20 (1H, d, |

TABLE 114-continued

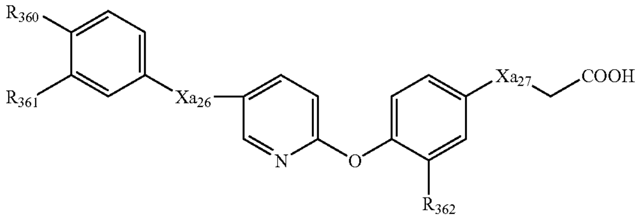

| Reference Example No. | $R_{360}$ | $R_{361}$ | $R_{362}$ | $Xa_{26}$ | $Xa_{27}$ | $^1H$ NMR (solvent) δ ppm or MS |
|---|---|---|---|---|---|---|
| | | | | | | J = 16.5 Hz), 7.36 (1H, d, J = 16.5 Hz), 7.54-7.65 (2H, m), 7.87 (1H, d, J = 1.8 Hz), 8.07-8.11 (1H, m), 8.22 (1H, d, J = 2.1 Hz), 12.20 (1H, brs). |
| 839 | $—CF_3$ | —H | $—OCH_3$ | —CH═CH— (trans) | $—CH_2—$ | $^1H$ NMR (DMSO-$d_6$) 2.58-2.63 (2H, m), 2.83-2.89 (2H, m), 3.68 (3H, s), 6.82-6.86 (1H, m), 6.99-7.06 (3H, m), 7.31 (1H, d, J = 16.5 Hz), 7.41 (1H, d, J = 16.5 Hz), 7.71-7.81 (4H, m), 8.15 (1H, dd, J = 8.7 Hz, 2.5 Hz), 8.27 (1H, d, J = 2.1 Hz), 12.18 (1H, brs). |
| 840 | $—CF_3$ | —H | $—OCH_3$ | —CO— | $—CH_2—$ | $^1H$ NMR (DMSO-$d_6$) 2.57-2.63 (2H, m), 2.83-2.89 (2H, m), 3.70 (3H, s), 6.86 (1H, dd, J = 8.1 Hz, 2.0 Hz), 7.06-7.15 (3H, m), 7.90-7.97 (4H, m), 8.18-8.22 (1H, m), 8.50 (1H, dd, J = 2.5 Hz, 0.7 Hz), 12.19 (1H, brs). |
| 841 | $—CF_3$ | —H | $—CH_3$ | —CO— | $—N(C_2H_5)—$ | $^1H$ NMR ($CDCl_3$) 1.23 (3H, t, J = 7.1 Hz), 2.12 (3H, s), 3.46 (2H, q, J = 7.1 Hz), 4.04 (2H, s), 5.77 (1H, brs), 6.55-6.59 (2H, m), 6.97 (2H, d, J = 8.7 Hz), 7.73-7.89 (4H, m), 8.17-8.21 (1H, m), 8.58 (1H, d, J = 2.3 Hz). |
| 842 | —Cl | —Cl | —H | —NHCONH— | none | MS 431 (M+) |

TABLE 115

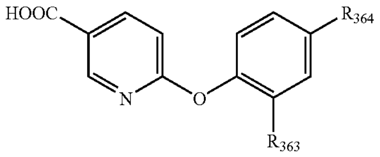

| Reference Example No. | $R_{363}$ | $R_{364}$ | Form | $^1H$ NMR (solvent) δ ppm |
|---|---|---|---|---|
| 843 | —H | 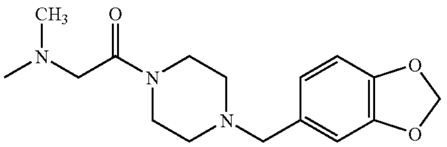 | hydro-chloride | (DMSO-$d_6$) 2.94 (3H, s), 3.10-3.59 (7H, m), 4.02-4.39 (5H, m), 6.07 (2H, s), 6.68 (2H, d, J = 9.1 Hz), 6.74-7.06 (5H, m), 7.25 (1H, brs), 8.23 (1H, dd, J = 8.7 Hz, 2.3 Hz), 8.65 (1H, d, J = 2.3 Hz), 11.23 (1H, brs). |
| 844 | —H | $—NO_2$ | free | ($CDCl_3$) 7.13 (1H, d, J = 8.5 Hz), 7.35 (2H, d, J = 9.1 Hz), 8.33 (2H, d, J = 9.1 Hz), 8.41 (1H, dd, J = 8.5 Hz, 2.5 Hz), 8.89 (1H, d, J = 2.5 Hz). |
| 845 | —H | 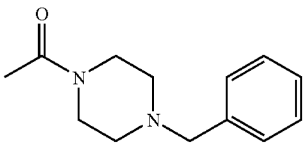 | free | (DMSO-$d_6$) 2.47 (4H, brs), 3.31-3.53 (6H, m), 7.16 (1H, d, J = 8.6 Hz), 7.23-7.34 (7H, m), 7.45-7.48 (2H, m), 8.31 (1H, dd, J = 8.6 Hz, 2.4 Hz), 8.68 (1H, d, J = 2.4 Hz), 13.20 (1H, brs). |

TABLE 115-continued

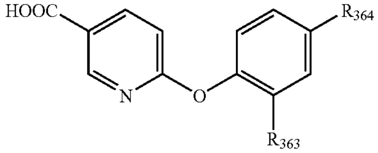

| Reference Example No. | $R_{363}$ | $R_{364}$ | Form | $^1$H NMR (solvent) δ ppm |
|---|---|---|---|---|
| 846 | —H | 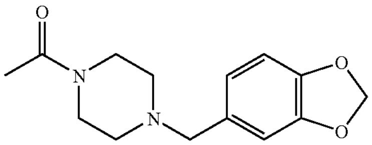 | free | ($DMSO-d_6$) 3.36-3.55 (8H, m), 3.58 (2H, s), 6.00 (2H, s), 6.78-6.92 (3H, m), 7.17 (1H, d, J = 8.6 Hz), 7.26 (2H, d, J = 8.6 Hz), 7.48 (2H, d, J = 8.4 Hz), 8.31 (1H, dd, J = 2.3 Hz, 8.6 Hz), 8.68 (1H, d, J = 2.2 Hz). |
| 847 | —H | 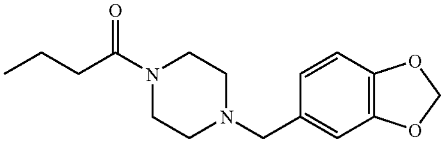 | free | ($DMSO-d_6$) 2.50 (4H, brs), 2.63-2.68 (2H, m), 2.81-2.86 (2H, m), 3.48-3.61 (6H, m), 6.01 (2H, s), 6.81-6.90 (2H, m), 6.96 (1H, s), 7.06-7.10 (3H, m), 7.30 (2H, d, J = 8.6 Hz), 8.25-8.33 (1H, m), 8.66 (1H, d, J = 2.7 Hz), 12.58 (1H, brs). |
| 848 | —$CH_3$ | —$NO_2$ | free | ($DMSO-d_6$) 2.22 (3H, s), 7.28 (1H, dd, J = 8.6 Hz, 0.7 Hz), 7.40 (1H, d, J = 8.9 Hz), 8.14 (1H, dd, J = 8.9 Hz, 2.8 Hz), 8.28 (1H, d, J = 2.6 Hz), 8.36 (1H, dd, J = 8.6 Hz, 2.3 Hz), 8.65 (1H, dd, J = 2.3 Hz, 0.7 Hz). |

TABLE 116

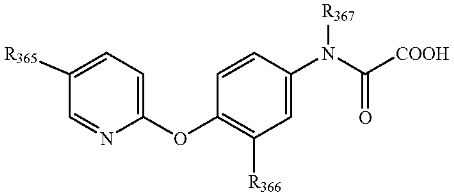

| Reference Example No. | $R_{365}$ | $R_{366}$ | $R_{367}$ | $^1$H NMR (solvent) δ ppm |
|---|---|---|---|---|
| 849 | —$NO_2$ | —$CH_3$ | —H | ($DMSO-d_6$) 2.06 (3H, s), 7.14 (1H, d, J = 8.6 Hz), 7.26 (1H, d, J = 9.1 Hz), 7.64 (1H, dd, J = 8.7 Hz, 2.5 Hz), 7.74 (1H, d, J = 2.5 Hz), 8.62 (1H, dd, J = 9.1 Hz, 3.0 Hz), 9.02 (1H, d, J = 2.8 Hz), 10.75 (1H, brs). |
| 850 | —$NO_2$ | —$CH_3$ | —$CH_3$ | ($DMSO-d_6$) 2.09 (3H, s), 3.26 (3H, s), 7.20-7.36 (4H, m), 8.64 (1H, dd, J = 9.1 Hz, 2.8 Hz), 9.03 (1H, d, J = 2.6 Hz). |
| 851 | 4-$CF_3$PhNHCO— | —$CH_3$ | —H | ($DMSO-d_6$) 2.08 (3H, s), 7.11 (1H, d, J = 8.7 Hz), 7.16 (1H, d, J = 8.7 Hz), 7.64 (1H, dd, J = 8.7 Hz, 2.5 Hz), 7.72-7.75 (3H, m), 7.98 (2H, d, J = 8.6 Hz), 8.37 (1H, dd, J = 8.7 Hz, 2.5 Hz), 8.69 (1H, d, J = 2.5 Hz), 10.62 (1H, brs), 10.74 (1H, brs). |
| 852 | 4-$CF_3$PhO$CH_2$— | —H | —H | ($DMSO-d_6$) 5.17 (2H, s), 7.06 (1H, d, J = 8.4 Hz), 7.13 (2H, d, J = 8.9 Hz), 7.21 (2H, d, J = 8.6 Hz), 7.67 (2H, d, J = 8.4 Hz), 7.79 (2H, d, J = 9.1 Hz), 7.95 (1H, dd, J = 8.4 Hz, 2.5 Hz), 8.25 (1H, d, J = 2.0 Hz), 10.78 (1H, brs). |

TABLE 116-continued

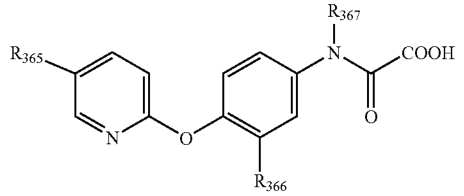

| Reference Example No. | $R_{365}$ | $R_{366}$ | $R_{367}$ | $^1H$ NMR (solvent) δ ppm |
|---|---|---|---|---|
| 853 | $4-CF_3PhOCH_2$— | —$CH_3$ | —H | ($CDCl_3$) 2.18 (3H, s), 5.05 (2H, s), 7.01-7.08 (5H, m), 7.51-7.58 (4H, m), 7.83-7.87 (1H, m), 8.20 (1H, d, J = 2.1 Hz), 9.02 (1H, brs). |
| 854 | $4-CF_3PhOCH_2$— | —$CH_3$ | —$CH_3$ | (DMSO-$d_6$) 2.09 (3H, s), 3.25 (3H, s), 5.17 (2H, s), 7.10 (1H, d, J = 8.4 Hz), 7.11 (1H, d, J = 8.4 Hz), 7.17-7.23 (3H, m), 7.32 (1H, d, J = 2.3 Hz), 7.67 (2H, d, J = 8.7 Hz), 7.98 (1H, dd, J = 8.4 Hz, 2.3 Hz), 8.24 (1H, d, J = 2.3 Hz). |

TABLE 117

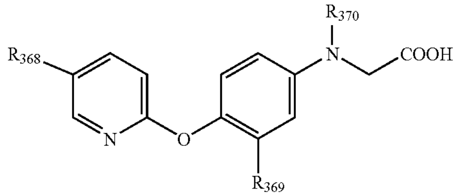

| Reference Example No. | $R_{368}$ | $R_{369}$ | $R_{370}$ | $^1H$ NMR (solvent) δ ppm |
|---|---|---|---|---|
| 855 | $3,4-Cl_2PhSO_2NH$— | —F | —$CH_3$ | (DMSO-$d_6$) 2.96 (3H, s), 4.11 (2H, s), 6.43 (1H, dd, J = 8.9 Hz, 2.1 Hz), 6.58 (1H, dd, J = 14.4 Hz, 3.0 Hz), 6.97-7.02 (2H, m), 7.53 (1H, dd, J = 8.9 Hz, 2.8 Hz), 7.63 (1H, dd, J = 8.4 Hz, 2.1 Hz), 7.77 (1H, d, J = 2.5 Hz), 7.86 (1H, d, J = 8.6 Hz), 7.88 (1H, d, J = 2.1 Hz), 10.40 (1H, s), 12.61 (1H, brs). |
| 856 | $3,4-Cl_2PhNHCO$— | —$OCH_3$ | —$C_2H_5$ | ($CDCl_3$) 1.26 (3H, t, J = 7.1 Hz), 3.45 (2H, q, J = 7.1 Hz), 3.69 (3H, s), 4.08 (2H, s), 6.24 (1H, dd, J = 8.7 Hz, 2.8 Hz), 6.31 (1H, d, J = 2.6 Hz), 6.95 (1H, d, J = 8.7 Hz), 7.00 (1H, d, J = 8.7 Hz), 7.29-7.50 (1H, m), 7.55 (1H, dd, J = 8.9 Hz, 2.5 Hz), 7.88 (1H, d, J = 8.24 (1H, dd, J = 8.7 Hz, 2.5 Hz), 8.56 (1H, brs), 8.73 (1H, d, J = 2.0 Hz). |

Reference Example 857

Production of 3-{4-[5-(3,4-dichlorobenzylmethylamino)-pyridin-2-yloxy]phenyl}propionic acid To a solution of ethyl 3-{4-[5-(3,4-dichlorobenzylamino) pyridin-2-yloxy]phenyl}propionate (1.63 g, 3.7 mmol) in ethanol (30 mL) were added 37% aqueous formaldehyde (2.0 mL, 22 mmol) and acetic acid (0.21 mL, 3.7 mmol), and the resulting solution was stirred at room temperature for 1 hour. To this solution was then added sodium cyanoborohydride (0.46 g, 7.3 mmol) at 0° C., and the resulting solution was stirred at the same temperature for 1 hour. To this solution was added water and extracted with ethyl acetate. The ethyl acetate layer was washed with water, and then dried over anhydrous magnesium sulfate. The solvent was evaporated, and the residue was purified by silica gel column chromatography (n-hexane:ethyl acetate=5:1), to thereby yield 1.55 g of ethyl 3-{4-[5-(3,4-dichlorobenzylmethylamino)-pyridin-2-yloxy]phenyl}propionate. This product was dissolved in ethanol (40 mL), and to the resulting solution was added 10% aqueous sodium hydroxide (2.7 mL, 6.7 mmol) and stirred at room temperature for 2 hours. The resulting solution was then acidified by adding 10% hydrochloric acid, and extracted with ethyl acetate. The ethyl acetate layer was washed with water, dried over anhydrous magnesium sulfate, and evaporated, to thereby yield 1.44 g of the title compound.

Appearance: Colorless oil $^1$H NMR (DMSO-$d_6$) δ 2.38-2.60 (2H, m), 2.78 (2H, t, J=7.6 Hz), 4.52 (2H, s), 6.81-6.92 (3H, m), 7.12-7.23 (3H, m), 7.28 (1H, dd, J=8.9 Hz, 3.3 Hz), 7.48 (1H, d, J=1.9 Hz), 7.57 (1H, d, J=8.2 Hz), 7.63 (1H, d, J=3.3 Hz), 11.70-12.40 (1H, m).

The following compound was produced in the same manner as in Reference Example 857.

Reference Example 858

3-(4-{5-[(3,4-Dichlorobenzyl)ethylamino]pyridin-2-yloxy}phenyl)propionic acid $^1$H NMR (DMSO-$d_6$) δ 1.09 (3H, t, J=6.9 Hz), 2.37-2.59 (2H, m), 2.64-2.83 (2H, m), 3.45 (2H, q, J=6.9 Hz), 4.48 (2H, s), 6.82 (1H, d, J=8.9 Hz), 6.85-6.92 (2H, m), 7.12-7.25 (4H, m), 7.48 (1H, d, J=1.8 Hz), 7.54-7.61 (2H, m), 11.77-12.38 (1H, m).

Reference Example 859

Production of N-[2-(4-formylphenoxy)-5-pyridyl]-3,4-dichlorobenzamide

To a solution of 4-[(5-amino-2-pyridyl)oxy]benzaldehyde ethylene acetal (5.27 g, 20.4 mmol) and triethylamine (3.41 mL, 24.5 mmol) in THF (80 mL) was added dropwise a solution of 3,4-dichlorobenzoyl chloride (4.49 g, 21.4 mmol) in THF (30 mL) under ice cooling. The resulting solution was stirred for 2 hours at the same temperature. The reaction solution was concentrated under reduced pressure, to the residue, 80% acetic acid (55 mL) was added, and the mixture was heated at 80° C. with stirring for 1 hour. The reaction solution was concentrated under reduced pressure and to the residue was added water, and extracted with ethyl acetate. The ethyl acetate layer was washed with a saturated sodium bicarbonate solution and brine, dried over anhydrous magnesium sulfate, and evaporated. The obtained solid was recrystallized from isopropanol, to thereby yield 5.63 g of the title compound.

Appearance: Pale yellow powder $^1$H NMR ($CDCl_3$) δ 7.05 (1H, d, J=8.7 Hz), 7.24 (2H, d, J=8.7 Hz), 7.57 (1H, d, J=8.4 Hz), 7.70 (1H, dd, J=8.4 Hz, 2.1 Hz), 7.82-7.93 (3H, m), 7.97 (1H, d, J=2.1 Hz), 8.25 (1H, dd, J=8.7 Hz, 2.7 Hz), 8.29 (1H, d, J=2.7 Hz), 9.96 (1H, s).

Reference Example 860

Production of ethyl{4-[5-(3,4-dichlorobenzoylamino)-pyridin-2-yloxy]benzylamino}acetate A solution of N-[2-(4-formylphenoxy)-5-pyridyl]-3,4-dichlorobenzamide (1.00 g, 2.58 mmol), glycine ethyl ester hydrochloride (0.400 g, 2.84 mmol) and sodium acetate (0.230 g, 2.84 mmol) in methanol (20 mL) was stirred for 30 minutes at 60° C. The reaction solution was cooled with ice, and then sodium cyanoborohydride (0.180 g, 2.84 mmol) was added. The resulting solution was stirred at the same temperature for 1 hour. To the reaction solution was added 5 M hydrochloric acid (2 mL) and concentrated under reduced pressure. To the residue was added a saturated sodium bicarbonate solution, and extracted with dichloromethane. The dichloromethane layer was washed with brine, dried over anhydrous sodium sulfate, and evaporated. The residue was purified by silica gel column chromatography (n-hexane: ethyl acetate=1:2), to thereby yield 0.752 g of the title compound.

Appearance: Yellow oil $^1$H NMR ($CDCl_3$) δ 1.27 (3H, t, J=7.1 Hz), 3.43 (2H, s), 3.81 (2H, s), 4.2.0 (2H, q, J=7.1 Hz), 6.95 (1H, d, J=8.8 Hz), 7.09 (2H, d, J=8.5 Hz), 7.36 (2H, d, J=8.5 Hz), 7.57 (1H, d, J=8.3 Hz), 7.71 (1H, dd, J=2.1 Hz, 8.3 Hz), 7.84 (1H, s), 7.98 (1H, d, J=2.1 Hz), 8.18 (1H, dd, J=2.7 Hz, 8.8 Hz), 8.24 (1H, d, J=2.7 Hz).

Reference Example 861

Production of (acetyl{4-[5-(3,4-dichlorobenzoylamino)-pyridin-2-yloxy]benzyl}amino)acetic acid To a solution of ethyl{4-[5-(3,4-dichloro-benzoylamino) pyridin-2-yloxy]benzylamino}acetate (0.811 g, 1.59 mmol) in dichloromethane (5 mL) were added triethylamine (0.332 mL, 2.39 mmol) and acetyl chloride (0.136 mL, 1.91 mmol) at room temperature. The resulting solution was stirred for 1 hour at the same temperature. To the reaction solution was added water, and extracted with dichloromethane. The dichloromethane layer was washed with brine, dried over anhydrous sodium sulfate, and evaporated, to thereby yield 0.785 g of residue. This residue was dissolved in ethanol (5 mL). To the resulting solution was added 5 M aqueous sodium hydroxide (0.350 mL, 1.75 mmol) at room temperature and stirred at the same temperature for 14 hours. To the resulting reaction solution were added 5 M hydrochloric acid (0.400 mL) and water, and extracted with dichloromethane. The dichloromethane layer was washed with brine, dried over anhydrous sodium sulfate, and evaporated, to thereby yield 0.776 g of the title compound.

Appearance: White amorphous powder $^1$H NMR (DMSO-$d_6$ at 375 K) δ 2.10 (3H, s), 4.02 (2H, s), 4.60 (2H, s), 7.03 (1H, d, J=8.8 Hz), 7.11 (2H, d, J=8.2 Hz), 7.32 (2H, d, J=8.2 Hz), 7.7.8 (1H, d, J=8.4 Hz), 7.97 (1H, dd, J=2.1 Hz, 8.4 Hz), 8.10-8.30 (2H, m), 8.53 (1H, d, J=2.6 Hz), 10.23 (1H, s).

Reference Example 862

Production of 1-(4-piperonylpiperazin-1-yl)-2-{methyl-[3-methyl-4-(5-nitropyridin-2-yloxy)phenyl]amino}-ethanone To a solution of {methyl[3-methyl-4-(5-nitropyridin-2-yloxy)phenyl]amino}acetic acid (0.93 g, 2.9 mmol) in DMF (40 mL) were added 1-ethyl-3-(3-dimethylaminopropyl)carbodiimide hydrochloride (0.67 g, 3.5 mmol), 1-hydroxybenzotriazole monohydrate (0.54 g, 3.5 mmol), and 1-piperonylpiperazine (0.68 g, 3.08 mmol). The reaction mixture was stirred for 15 hours at room temperature under a nitrogen atmosphere. To the resulting solution was added water and extracted with ethyl acetate. The ethyl acetate layer was washed with water and then dried over anhydrous magnesium sulfate. The solvent was evaporated, and the residue was purified by silica gel column chromatography (n-hexane: ethyl acetate=2:1→dichloromethane methanol=100:1), to thereby yield 1.2 g of the title compound.

Appearance: Yellow powder

Melting point: 142-143° C.

The following compounds were produced in the same manner as in Reference Example 862.

TABLE 118

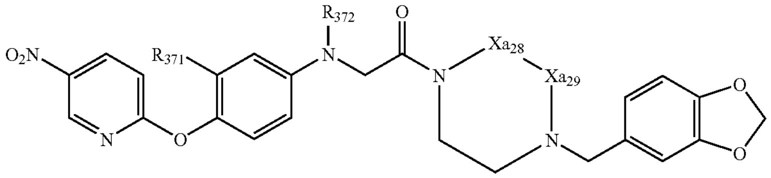

| Reference Example No. | $R_{371}$ | $R_{372}$ | $Xa_{28}$ | $Xa_{29}$ | $^1H$ NMR ($CDCl_3$) δ ppm |
|---|---|---|---|---|---|
| 863 | $-CH_3$ | $-CH_3$ | $-CH_2-$ | —CO— | 2.09 (3H, s), 3.04 (3H, s), 3.22-3.39 (2H, m), 3.60-3.90 (2H, m), 4.11 (2H, s), 4.19-4.40 (2H, m), 4.53 (2H, s), 5.95 (2H, s), 6.51-6.62 (2H, m), 6.68-6.80 (3H, m), 6.92 (1H, d, J = 8.6 Hz), 6.94 (1H, d, J = 9.0 Hz), 8.42 (1H, dd, J = 9.0 Hz, 2.6 Hz), 9.04 (1H, d, J = 2.6 Hz). |
| 864 | $-OCH_3$ | $-C_2H_5$ | $-CH_2-$ | —CO— | 1.21 (3H, t, J = 6.7 Hz), 3.20-3.33 (2H, m), 3.46 (2H, q, J = 6.7 Hz), 3.71 (3H, s), 3.65-3.85 (2H, m), 4.07 (2H, s), 4.29 (2H, s), 4.52 (2H, s), 5.96 (2H, s), 6.23 (1H, dd, J = 8.7 Hz, 2.6 Hz), 6.39 (1H, d, J = 2.6 Hz), 6.65-6.85 (3H, m), 6.97 (2H, d, J = 8.7 Hz), 8.41 (1H, dd, J = 9.0 Hz, 2.8 Hz), 9.02 (1H, d, J = 2.8 Hz). |
| 865 | —H | $-CH_3$ | $-CH_2-$ | $-CH(CH_3)-$ | 1.12-1.16 (3H, m), 2.08-2.16 (1H, m), 2.46-2.53 (1H, m), 2.71-2.73 (1H, m), 2.85-3.48 (6H, m), 3.54-3.59 (1H, m), 3.84-4.19 (4H, m), 5.94 (2H, s), 6.68-6.74 (4H, m), 6.85 (1H, brs), 6.94 (1H, d, J = 9.1 Hz), 7.01 (2H, d, J = 8.9 Hz), 8.41 (1H, dd, J = 9.1 Hz, 2.8 Hz), 9.05 (1H, d, J = 2.8 Hz). |
| 866 | —H | $-C_2H_5$ | $-CH_2-$ | $-CH(CH_3)-$ | 1.13-1.28 (6H, m), 2.08-2.16 (1H, m), 2.47-2.50 (1H, m), 2.71-2.75 (1H, m), 2.86-3.35 (3H, m), 3.41-3.49 (2H, m), 3.58-3.62 (1H, m), 3.85-4.16 (4H, m), 5.94 (2H, s), 6.67 (2H, d, J = 9.1 Hz), 6.74 (2H, brs), 6.85 (1H, brs), 6.94 (1H, d, J = 9.1 Hz), 6.99 (2H, d, J = 9.1 Hz), 8.41 (1H, dd, J = 9.1 Hz, 3.0 Hz), 9.05 (1H, d, J = 2.5 Hz). |
| 867 | —H | $-CH_3$ | $-CH(CH_3)-$ | $-CH_2-$ | 1.29-1.40 (3H, m), 1.96-2.06 (1H, m), 2.17 (1H, brs), 2.65-2.70 (1H, m), 2.81-2.86 (1H, m), 2.96-3.06 (4H, m), 3.32-3.49 (3H, m), 3.97-4.71 (3H, m), 5.95 (2H, s), 6.70 (2H, d, J = 9.2 Hz), 6.74-6.75 (2H, m), 6.87 (1H, brs), 6.94 (1H, dd, J = 9.1 Hz, 0.5 Hz), 7.01 (2H, d, J = 9.2 Hz), 8.41 (1H, dd, J = 9.1 Hz, 2.8 Hz), 9.05 (1H, dd, J = 2.8 Hz, 0.5 Hz). |
| 868 | —H | $-C_2H_5$ | $-CH(CH_3)-$ | $-CH_2-$ | 1.20 (3H, t, J = 7.1 Hz), 1.26-1.40 (3H, m), 1.98-2.05 (1H, m), 2.16-2.17 (1H, m), 2.65-2.69 (1H, m), 2.81-2.85 (1H, m), 3.02-3.56 (6H, m), 4.03-4.71 (3H, m), 5.94 (2H, s), 6.66 (2H, d, J = 9.2 H), 6.74-6.75 (2H, m), 6.87 (1H, brs), 6.94 (1H, dd, J = 9.1 Hz, 0.7 Hz), 6.99 (2H, d, J = 9.1 Hz), 8.41 (1H, dd, J = 9.1 Hz, 2.8 Hz), 9.05 (1H, dd, J = 2.8 Hz, 0.7 Hz). |

TABLE 119

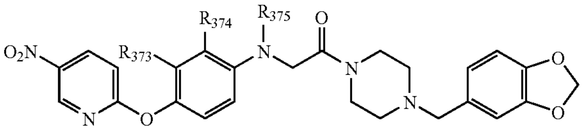

| Reference Example No. | $R_{373}$ | $R_{374}$ | $R_{375}$ | $^1H$ NMR (solvent) δ ppm or MS |
|---|---|---|---|---|
| 869 | —$COOCH_3$ | —H | —$C_2H_5$ | MS 577 ($M^+$). |
| 870 | —$OCH_3$ | —H | —H | $^1H$ NMR (DMSO-$d_6$) 2.32-2.40 (4H, m), 3.42 (2H, s), 3.50 (4H, brs), 3.63 (3H, s), 3.92 (2H, d, J = 4.6 Hz), 5.65 (1H, t, J = 4.8 Hz), 5.99 (2H, s), 6.22 (1H, dd, J = 8.6 Hz, 2.5 Hz), 6.51 (1H, d, J = 2.5 Hz), 6.76 (1H, dd, J = 7.9 Hz, 1.5 Hz), 6.84-6.91 (3H, m), 7.07 (1H, dd, J = 9.1 Hz, 0.5 Hz), 8.54 (1H, dd, J = 9.1 Hz, 2.8 Hz), 9.00 (1H, dd, J = 2.8 Hz, 0.5 Hz). |
| 871 | —$OCH_3$ | —H | —$CH_3$ | $^1H$ NMR ($CDCl_3$) 2.35-2.52 (4H, m), 3.07 (3H, s), 3.44 (2H, s), 3.41-3.55 (2H, m), 3.56-3.70 (2H, m), 3.73 (3H, s), 5.95 (2H, s), 6.24 (1H, dd, J = 8.8 Hz, 2.8 Hz), 6.35 (1H, d, J = 2.8 Hz), 6.64-6.79 (2H, m), 6.85 (1H, s), 6.89-7.04 (2H, m), 8.41 (1H, dd, J = 9.1 Hz, 2.8 Hz), 9.03 (1H, d, J = 2.8 Hz). |
| 872 | —$OCH_3$ | —H | —$C_2H_5$ | $^1H$ NMR ($CDCl_3$) 1.22 (3H, t, J = 7.0 Hz), 2.33-2.52 (4H, m), 3.49-3.58 (6H, m), 3.59-3.69 (2H, m), 3.72 (3H, s), 4.06 (2H, s), 5.95 (2H, s), 6.22 (1H, dd, J = 8.8 Hz, 2.7 Hz), 6.33 (1H, d, J = 2.7 Hz), 6.69-6.79 (2H, m), 6.85 (1H, s), 6.95 (1H, d, J = 9.1 Hz), 6.96 (1H, d, J = 8.8 Hz), 8.41 (1H, dd, J = 9.1 Hz, 2.8 Hz), 9.04 (1H, d, J = 2.8 Hz). |
| 873 | —$CH_3$ | —H | —H | $^1H$ NMR ($CDCl_3$) 2.08 (3H, s), 2.43-2.48 (4H, m), 3.45-3.48 (4H, m), 3.67-3.71 (2H, m), 3.86 (2H, d, J = 4.1 Hz), 4.93 (1H, t, J = 4.1 Hz), 5.96 (2H, s), 6.47-6.52 (2H, m), 6.71-6.78 (2H, m), 6.86-6.96 (3H, m), 8.44 (1H, dd, J = 9.1 Hz, 2.8 Hz), 9.05 (1H, d, J = 2.8 Hz). |

TABLE 119-continued

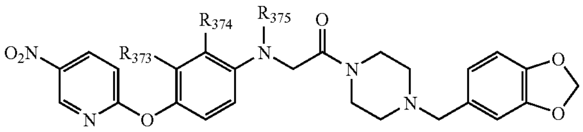

| Reference Example No. | $R_{373}$ | $R_{374}$ | $R_{375}$ | $^1H$ NMR (solvent) δ ppm or MS |
|---|---|---|---|---|
| 874 | —$CH_3$ | —H | —Ac | $^1H$ NMR ($CDCl_3$) 1.98 (3H, s), 2.16 (3H, s), 2.32-2.51 (4H, m), 3.35-3.48 (4H, m), 3.53-3.69 (2H, m), 4.46 (2H, s), 5.95 (2H, s), 6.65-6.79 (2H, m), 6.85 (1H, s), 7.08 (2H, d, J = 8.7 Hz), 7.27-7.34 (1H, m), 7.35-7.42 (1H, m), 8.51 (1H, dd, J = 9.0 Hz, 2.8 Hz), 9.02 (1H, dd, J = 2.8 Hz, 0.3 Hz). |
| 875 | —$CH_3$ | —H | —$C_2H_5$ | $^1H$ NMR ($CDCl_3$) 1.20 (3H, t, J = 7.1 Hz), 2.08 (3H, s), 2.37-2.55 (4H, m), 3.37-3.72 (8H, m), 4.05 (2H, s), 5.95 (2H, s), 6.42-6.58 (2H, m), 6.63-6.79 (2H, m), 6.81-6.99 (3H, m), 8.42 (1H, dd, J = 9.1 Hz, 2.8 Hz), 9.05 (1H, d, J = 2.8 Hz). |
| 876 | —$CH_3$ | —H | 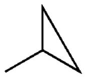 | $^1H$ NMR ($CDCl_3$) 0.64-0.69 (2H, m), 0.80-0.87 (2H, m), 2.09 (3H, s), 2.41-2.49 (4H, m), 2.76-2.84 (1H, m), 3.44 (2H, s), 3.49-3.52 (2H, m), 3.60-3.64 (2H, m), 4.18 (2H, s), 5.95 (2H, s), 6.71-6.93 (7H, m), 8.39-8.44 (1H, m), 9.05-9.06 (1H, m). |
| 877 | —$CH_3$ | —$CH_3$ | —$CH_3$ | $^1H$ NMR ($CDCl_3$) 2.05 (3H, s), 2.28 (3H, s), 2.37-2.43 (4H, m), 2.72 (3H, s), 3.42 (2H, s), 3.52-3.56 (2H, m), 3.62-3.65 (2H, m), 3.77 (2H, s), 5.95 (2H, s), 6.71-6.77 (2H, m), 6.85-6.90 (2H, m), 6.97-7.06 (2H, m), 8.45 (1H, dd, J = 9.1 Hz, 3.0 Hz), 9.04 (1H, dd, J = 3.0 Hz, 0.5 Hz). |

TABLE 120

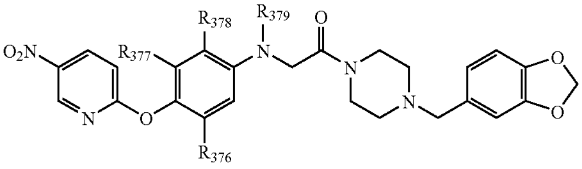

| Reference Example No. | $R_{376}$ | $R_{377}$ | $R_{378}$ | $R_{379}$ | $^1$H NMR (solvent) δ ppm or MS |
|---|---|---|---|---|---|
| 878 | —$CH_3$ | —H | —$CH_3$ | —$C_2H_5$ | MS 547 ($M^+$) |
| 879 | —F | —H | —H | —H | $^1$H NMR ($CDCl_3$) 2.44-2.49 (4H, m), 3.43-3.45 (2H, m), 3.45 (2H, s), 3.68-3.71 (2H, m), 3.84 (2H, d, J = 4.1 Hz), 5.12 (1H, brs), 5.96 (2H, s), 6.40-6.45 (2H, m), 6.71-6.80 (2H, m), 6.85 (1H, brs), 7.02 (1H, t, J = 8.5 Hz), 7.05 (1H, dd, J = 9.1 Hz, 0.5 Hz), 8.46 (1H, dd, J = 9.1 Hz, 2.8 Hz), 9.02 (1H, dd, J = 2.8 Hz, 0.7 Hz). |
| 880 | —F | —H | —H | —$CH_3$ | $^1$H NMR ($CDCl_3$) 2.44 (4H, brs), 3.06 (3H, s), 3.45 (2H, s), 3.45-3.47 (2H, m), 3.62-3.64 (2H, m), 4.11 (2H, s), 5.95 (2H, s), 6.40-6.51 (2H, m), 6.71-6.78 (2H, m), 6.85 (1H, brs), 7.04 (1H, d, J = 9.1 Hz), 7.05 (1H, t, J = 8.9 Hz), 8.46 (1H, dd, J = 9.1 Hz, 2.8 Hz), 9.02 (1H, d, J = 2.3 Hz) |
| 881 | —F | —H | —H | —$C_2H_5$ | $^1$H NMR ($CDCl_3$) 1.22 (3H, t, J = 7.2 Hz), 2.45 (4H, brs), 3.40-3.49 (4H, m), 3.45 (2H, s), 3.65 (2H, brs), 4.05 (2H, s), 5.95 (2H, s), 6.37-6.46 (2H, m), 6.74-6.75 (2H, m), 6.86 (1H, brs), 6.99-7.06 (2H, m), 8.45 (1H, dd, J = 9.1 Hz, 2.8 Hz), 9.03 (1H, d, J = 2.5 Hz). |
| 882 | —F | —H | —H | allyl | $^1$H NMR ($CDCl_3$) 2.46 (4H, brs), 3.45 (2H, s), 3.48 (2H, brs), 3.65 (2H, brs), 4.00 (2H, d, J = 5.0 Hz), 4.07 (2H, s), 5.19-5.29 (2H, m), 5.82-5.94 (1H, m), 5.95 (2H, s), 6.37-6.47 (2H, m), 6.71-6.78 (2H, m), 6.86-6.87 (1H, m), 6.98-7.05 (2H, m), 8.45 (1H, dd, J = 9.1 Hz, 2.8 Hz), 9.02 (1H, dd, J = 2.8 Hz, 0.5 Hz) |

TABLE 120-continued

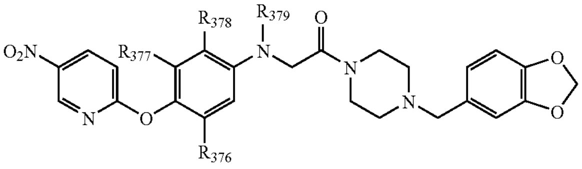

| Reference Example No. | $R_{376}$ | $R_{377}$ | $R_{378}$ | $R_{379}$ | $^1$H NMR (solvent) δ ppm or MS |
|---|---|---|---|---|---|
| 883 | —F | —H | —F | —$CH_3$ | $^1$H NMR ($CDCl_3$) 2.33-2.49 (4H, m), 2.99 (3H, s), 3.43 (2H, s), 3.37-3.50 (2H, m), 3.51-3.68 (2H, m), 4.10 (2H, s), 5.95 (2H, s), 6.69-6.78 (2H, m), 6.81 (1H, dd, J = 8.2 Hz, 12.1 Hz), 6.85 (1H, d, J = 0.96 Hz), 6.90 (1H, dd, J = 7.1 Hz, 12.8 Hz), 7.09 (1H, d, J = 9.1 Hz), 8.49 (1H, dd, J = 2.8 Hz, 9.0 Hz), 9.01 (1H, d, J = 2.8 Hz). |
| 884 | —F | —H | —F | —$C_2H_5$ | $^1$H NMR ($CDCl_3$) 1.17 (3H, t, J = 7.1 Hz), 2.30-2.52 (4H, m), 3.35 (2H, q, J = 7.1 Hz), 3.37-3.70 (6H, m), 4.04 (2H, s), 5.95 (2H, s), 6.68-6.78 (2H, m), 6.82 (1H, dd, J = 8.0 Hz, 12.1 Hz), 6.83-6.88 (1H, m), 6.91 (1H, dd, J = 7.2 Hz, 12.5 Hz), 7.09 (1H, d, J = 9.0 Hz), 8.49 (1H, dd, J = 2.8 Hz, 9.0 Hz), 9.02 (1H, d, J = 2.8 Hz). |
| 885 | —F | —F | —H | —$CH_3$ | $^1$H NMR ($CDCl_3$) 2.20-2.45 (4H, m), 2.91 (3H, s), 3.34-3.53 (6H, m), 4.31 (2H, s), 5.98 (2H, s), 6.47 (2H, d, J = 11.8 Hz), 6.70-6.79 (1H, m), 6.80-6.91 (2H, m), 7.42 (1H, d, J = 9.1 Hz), 8.64 (1H, dd, J = 2.8 Hz, 9.1 Hz), 9.05 (1H, d, J = 2.8 Hz). |
| 886 | —$CH_3$ | —H | —$CH_3$ | —$CH_3$ | MS 533 ($M^+$) |
| 887 | —$CF_3$ | —H | —H | —$C_2H_5$ | MS 587 ($M^+$) |
| 888 | —$CF_3$ | —H | —H | —$CH_3$ | MS 573 ($M^+$) |
| 889 | —H | —F | —F | —$CH_3$ | $^1$H NMR ($CDCl_3$) 2.30-2.52 (4H, m), 3.01 (3H, s), 3.43 (2H, s), 3.38-3.71 (4H, m), 4.10 (2H, s), 5.95 (2H, s), 6.65-6.81 (3H, m), 6.82-6.96 (2H, m), 7.10 (1H, d, J = 9.1 Hz), 8.49 (1H, dd, J = 2.8 Hz, 9.1 Hz), 9.01 (1H, d, J = 2.8 Hz). |

TABLE 121

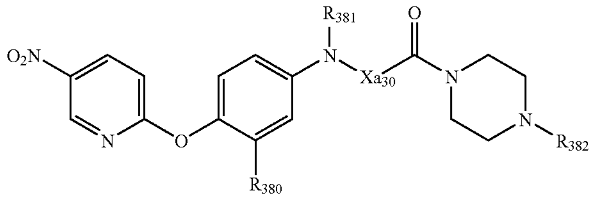

| Reference Example No. | $R_{380}$ | $R_{381}$ | $Xa_{30}$ | $R_{382}$ | mp (° C.) or $^1$H NMR ($CDCl_3$) δ ppm |
|---|---|---|---|---|---|
| 890 | —$CH_3$ | —$CH_3$ | —$CH_2$— | benzyl | $^1$H NMR 2.12 (3H, s), 2.40-2.55 (4H, m), 3.04 (3H, s), 3.45-3.55 (2H, m), 3.54 (2H, s), 3.60-3.70 (2H, m), 4.10 (2H, s), 6.50-6.61 (2H, m), 6.91 (1H, d, J = 8.5 Hz), 6.92 (1H, d, J = 9.1 Hz), 7.22-7.40 (5H, m), 8.42 (1H, dd, J = 9.1 Hz, 2.8 Hz), 9.05 (1H, d, J = 2.8 Hz). |
| 891 | —$CH_3$ | —$C_2H_5$ | —$CH_2$— | benzyl | mp 134-136 |
| 892 | —H | —$CH_3$ | —$CH_2CH_2$— | piperonyl | $^1$H NMR 2.23-2.41 (4H, m), 2.56-2.61 (2H, m), 2.97 (3H, s), 3.39-3.42 (4H, m), 3.60-3.64 (2H, m), 3.71-3.76 (2H, m), 5.94 (2H, s), 6.72-6.76 (5H, m), 6.83 (1H, brs), 6.97 (1H, d, J = 9.1 Hz), 7.02 (1H, d, J = 9.1 Hz), 8.43 (1H, dd, J = 9.1 Hz, 2.8 Hz), 9.04 (1H, d, J = 2.8 Hz). |
| 893 | —$CH_3$ | —$CH_3$ | —$CH(CH_3)$— | piperonyl | $^1$H NMR 1.31 (3H, d, J = 6.6 Hz), 2.11 (3H, s), 2.17-2.49 (4H, m), 2.78 (3H, s), 3.31-3.56 (3H, m), 3.39 (2H, s), 3.77(1H, brs), 4.57 (1H, q, J = 6.6 Hz), 5.94 (2H, s), 6.60-6.63 (2H, m), 6.68-6.75 (2H, m), 6.83 (1H, brs), 6.93-6.98 (2H, m), 8.44 (1H, dd, J = 9.1 Hz, 2.8 Hz), 9.05 (1H, d, J = 2.8 Hz). |
| 894 | —H | —$CH_3$ | —$CH(CH_3)$— | piperonyl | $^1$H NMR 1.32 (3H, d, J = 6.6 Hz), 2.19-2.50 (4H, m), 2.80 (3H, s), 3.30-3.56 (3H, m), 3.32 (2H, s), 3.78 (1H, brs), 4.58 (1H, q, J = 6.6 Hz), 5.93 (2H, s), 6.68-6.82 (3H, m), 6.77 (2H, d, J ’2 9.1 Hz), 6.98 (1H, dd, J = 8.6 Hz, 0.5 Hz), 7.04 (2H, d, J = 9.2 Hz), 8.44 (1H, dd, J = 9.1 Hz, 2.8 Hz), 9.05 (1H, dd, J = 2.8 Hz, 0.5 Hz). |
| 895 | —$CH_3$ | —H | —CO— | piperonyl | $^1$H NMR 2.15 (3H, s), 2.49-2.55 (4H, m), 3.45 (2H, s), 3.71-3.75 (2H, m), 4.25-4.28 (2H, m), 5.96 (2H, s), 6.75 (2H, brs), 6.86 (1H, brs), 7.04 (1H, d, J = 9.1 Hz), 7.06 (1H, d, J = 8.6 Hz), 7.49 (1H, dd, J = 8.7 Hz, 2.6 Hz), 7.61 (1H, d, J = 2.5 Hz), 8.48 (1H, dd, J = 9.1 Hz, 2.8 Hz), 9.02 (1H, d, J = 2.8 Hz), 9.23 (1H, brs). |
| 896 | —$CH_3$ | —$CH_3$ | —CO— | piperonyl | $^1$H NMR 2.15 (3H, s), 2.25-2.33 (4H, m), 3.33-3.42 (9H, m), 5.93 (2H, s), 6.66-6.79 (3H, m,) 7.04-7.21 (4H, m), 8.51 (1H, dd, J = 9.1 Hz, 2.8 Hz), 8.99 (1H, dd, J = 2.8 Hz, 0.5 Hz). |

TABLE 122
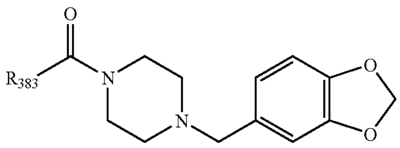
| Reference Example No. | $R_{383}$ | $^1$H NMR ($CDCl_3$) δ ppm or MS |
|---|---|---|
| 897 | 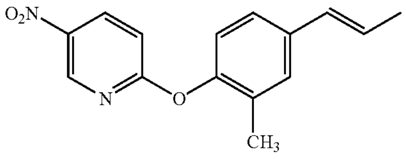 | MS 502 ($M^+$) |
| 898 | 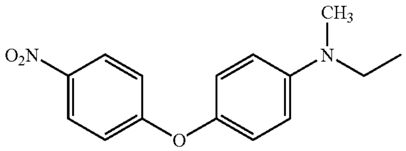 | $^1$H NMR 2.44 (4H, brs), 3.07 (3H, s), 3.44 (2H, s), 3.47-3.51 (2H, m), 3.62-3.66 (2H, m), 4.12 (2H, s), 5.95 (2H, s), 6.67-6.75 (4H, m), 6.86 (1H, s), 6.93-6.99 (4H, m), 8.16 (2H, d, J = 9.2 Hz). |
| 899 | 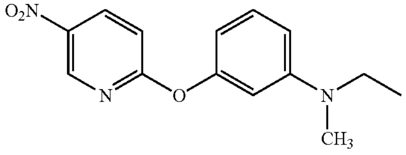 | $^1$H NMR 2.42 (4H, t, J = 4.9 Hz), 3.04 (3H, s), 3.42 (2H, s), 3.44 (2H, t, J = 4.9 Hz), 3.62 (2H, t, J = 4.9 Hz), 4.11 (2H, s), 5.95 (2H, s), 6.42-6.44 (1H, m), 6.50-6.51 (1H, m), 6.54-6.58 (1H, m), 6.70-6.77 (2H, m), 6.84 (1H, m), 6.96 (1H, d, J = 9.1 Hz), 7.24-7.30 (1H, m), 8.43 (1H, dd, J = 9.1 Hz, 2.8 Hz), 9.08 (1H, d, J = 2.8 Hz). |
| 900 | 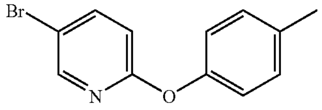 | $^1$H NMR 2.44 (4H, brs), 3.44 (2H, s), 3.55 (2H, brs), 3.73 (2H, brs), 5.95 (2H, s), 6.74 (2H, s), 6.85 (1H, s), 6.86 (1H, d, J = 8.6 Hz), 7.14 (2H, d, J = 8.6 Hz), 7.46 (2H, d, J = 8.6 Hz), 7.79 (1H, dd, J = 8.7 Hz, 2.5 Hz), 8.22 (1H, d, J = 2.5 Hz). |
| 901 | 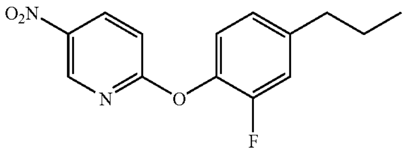 | MS 508 ($M^+$) |
| 902 | 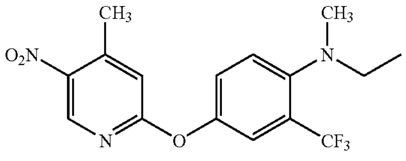 | MS 587 ($M^+$) |
| 903 | 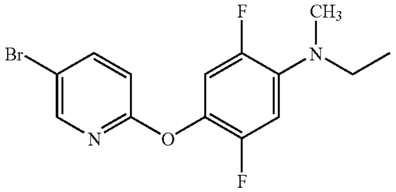 | $^1$H NMR 2.31-2.50 (4H, m), 2.96 (3H, s), 3.42 (2H, s), 3.40-3.52 (2H, m), 3.53-3.67 (2H, m), 4.05 (2H, s), 5.95 (2H, s), 6.65-6.95 (6H, m), 7.77 (1H, dd, J = 2.5 Hz, 8.7 Hz), 8.16 (1H, dd, J = 0.5 Hz, 2.5 Hz). |

TABLE 123

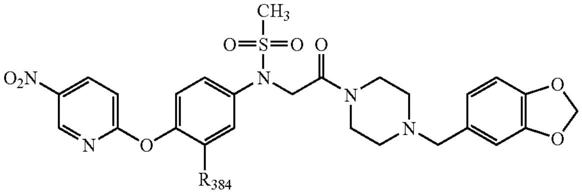

| Reference Example No. | $R_{384}$ | $^1H$ NMR ($CDCl_3$) δ ppm |
|---|---|---|
| 904 | —H | 2.29-2.34 (4H, m), 3.15 (3H, s), 3.34-3.43 (6H, m), 4.63 (2H, s), 5.98 (2H, s), 6.72-6.76 (1H, m), 6.83-6.86 (2H, m), 7.27 (2H, d, J = 8.9 Hz), 7.31 (1H, d, J = 9.3 Hz), 7.54 (2H, d, J = 8.9 Hz), 8.64 (1H, dd, J = 9.2 Hz, 2.8 Hz), 9.05 (1H, d, J = 2.8 Hz). |
| 905 | —$CH_3$ | 2.15 (3H, s), 2.42-2.43 (4H, m), 3.22 (3H, s), 3.39-3.41 (2H, m), 3.43 (2H, s), 3.61-3.63 (2H, m), 4.56 (2H, s), 5.94 (2H, s), 6.70-6.77 (2H, m), 6.84 (1H, brs), 7.06 (1H, d, J = 8.2 Hz), 7.07 (1H, d, J = 9.1 Hz), 7.48-7.52 (2H, m), 8.49 (1H, dd, J = 9.1 Hz, 2.8 Hz), 9.01 (1H, d, J = 2.8 Hz). |
| 906 | —$OCH_3$ | 2.42-2.46 (4H, m), 3.24 (3H, s), 3.40 (2H, brs), 3.43 (2H, s), 3.63 (2H, brs), 3.74 (3H, s), 4.58 (2H, s), 5.94 (2H, s), 6.70-6.77 (2H, m), 6.84 (1H, s), 7.06-7.14 (2H, m), 7.23-7.28 (1H, m), 7.32 (1H, d, J = 2.3 Hz), 8.47 (1H, dd, J = 9.1 Hz, 2.8 Hz), 8.98 (1H, d, J = 2.8 Hz). |

TABLE 124

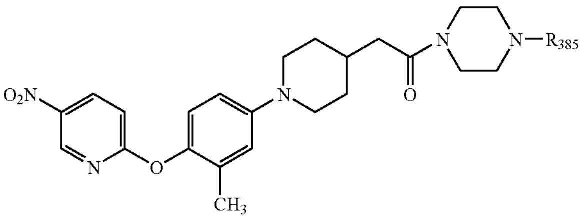

| Reference Example No. | $R_{385}$ | $^1H$ NMR ($CDCl_3$) δ ppm |
|---|---|---|
| 907 | piperonyl | 1.33-1.46 (2H, m), 1.86-2.00 (3H, m), 2.10 (3H, s), 2.29 (2H, d, J = 6.8 Hz), 2.39-2.43 (4H, m), |

TABLE 124-continued

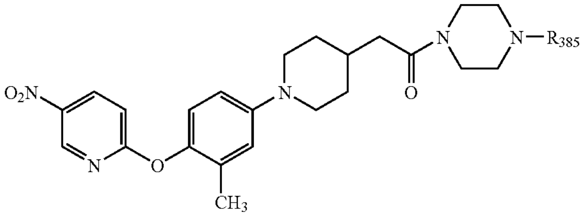

| Reference Example No. | $R_{385}$ | $^1H$ NMR ($CDCl_3$) δ ppm |
|---|---|---|
| | | 2.75 (2H, t, J = 12.2 Hz), 3.40-3.48 (4H, m), 3.62-3.66 (4H, m), 5.94 (2H, s), 6.73-6.85 (5H, m), 6.91-6.96 (2H, m), 8.43 (1H, dd, J = 9.1 Hz, 3.0 Hz), 9.04 (1H, d, J = 2.8 Hz). |
| 908 | benzyl | 1.35-1.46 (2H, m), 1.86-2.00 (3H, m), 2.10 (3H, s), 2.29 (2H, d, J = 6.8 Hz), 2.41-2.45 (4H, m), 2.75 (2H, t, J = 12.2 Hz), 3.47-3.53 (4H, m), 3.61-3.65 (4H, m), 6.79-6.96 (4H, m), 7.24-7.33 (5H, m), 8.43 (1H, dd, J = 9.1 Hz, 2.8 Hz), 9.05 (1H, d, J = 2.8 Hz). |

Reference Example 909

Production of (4-benzylpiperazin-1-yl){4-[methyl(5-nitropyridin-2-yl)amino]phenyl}methanone To a solution of 4-[methyl-(5-nitropyridin-2-yl)amino]benzoic acid (0.800 g, 2.93 mmol) and 1-benzylpiperazine (0.542 g, 3.08 mmol) in DMF (15 mL) were added triethylamine (1.02 mL, 7.32 mmol) and diethyl cyanophosphonate (0.593 mL, 3.52 mmol), and the resulting solution was stirred for 3 hours. To the resulting reaction solution was added water and extracted with ethyl-acetate. The ethyl acetate layer was washed with brine, dried over anhydrous sodium sulfate, evaporated, and the residue was purified by silica gel column chromatography (ethyl acetate), to thereby yield 1.25 g of the title compound.

Appearance: Yellow amorphous powder $^1H$ NMR ($CDCl_3$) δ 2.25-2.65 (4H, m), 3.49 (2H, brs), 3.56 (2H, s), 3.57 (3H, s), 3.81 (2H, brs), 6.43 (1H, d, J=9.5 Hz), 7.25-7.35 (7H, m), 7.53 (2H, d, J=8.4 Hz), 8.06 (1H, dd, J=2.8 Hz, 9.5 Hz), 9.12 (1H, d, J=2.8 Hz).

The following compounds were produced in the same manner as in Reference Example 909.

TABLE 125

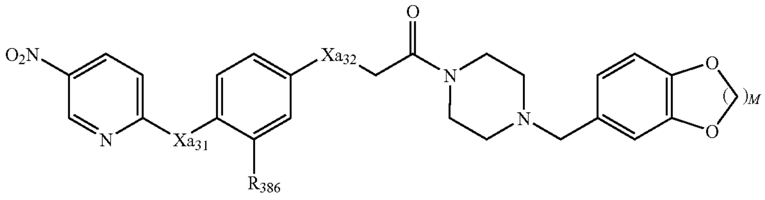

| Reference Example No. | $Xa_{31}$ | $R_{386}$ | $Xa_{32}$ | M | $^1H$ NMR (DMSO-$d_6$) δ ppm |
|---|---|---|---|---|---|
| 910 | —NH— | —H | —$CH_2$— | 1 | 2.20-2.30 (4H, m), 2.59 (2H, t, J = 7.3 Hz), 2.78 (2H, t, J = 7.3 Hz), 3.35 (2H, s), 3.36-3.45 (4H, m), 5.98 (2H, s), 6.72 (1H, dd, J = 1.3 Hz, 7.9 Hz), 6.80-6.90 (3H, m), 7.21 (2H, d, J = 8.4 Hz), 7.57 (2H, d, J = 8.4 Hz), 8.26 (1H, dd, J = 2.9 Hz, 9.3 Hz), 9.01 (1H, d, J = 2.9 Hz), 10.06 (1H, s). |

TABLE 125-continued

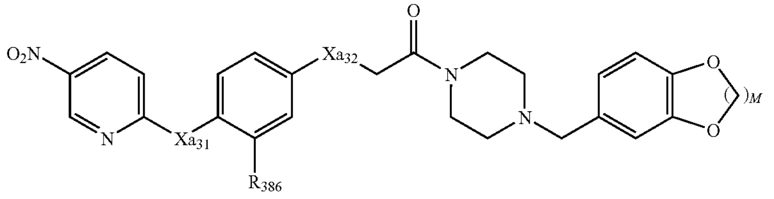

| Reference Example No. | $Xa_{31}$ | $R_{386}$ | $Xa_{32}$ | M | $^1H$ NMR (DMSO-$d_6$) δ ppm |
|---|---|---|---|---|---|
| 911 | —O— | —H | —NH— | 1 | 2.32 (2H, brs), 2.39 (2H, brs), 3.41 (2H, s), 3.50 (4H, brs), 3.91 (2H, d, J = 5.2 Hz); 5.68 (1H, t, J = 5.2 Hz), 5.99 (2H, s), 6.70 (2H, d, J = 8.9 Hz), 6.74-6.77 (1H, m), 6.83-6.88 (2H, m), 6.94 (2H, d, J = 8.9 Hz), 7.11 (1H, d, J = 9.1 Hz), 8.56 (1H, dd, J = 2.9 Hz, 9.1 Hz), 9.02 (1H, d, J = 2.9 Hz). |
| 912 | —O— | —$OCH_3$ | —NH— | 2 | 2.48 (2H, brs), 2.49 (2H, brs), 3.39 (2H, s), 3.50 (4H, brs), 3.63 (3H, s), 3.92 (2H, d, J = 4.8 Hz), 4.22 (4H, s), 5.65 (1H, brt), 6.22 (1H, dd, J = 8.6 Hz, 2.5 Hz), 6.51 (1H, d, J = 2.5 Hz), 6.73-6.81 (3H, m), 6.89 (1H, d, J = 8.6 Hz), 7.07 (1H, d, J = 9.1 Hz), 8.54 (1H, dd, J = 9.1 Hz, 2.8 Hz), 9.00 (1H, d, J = 2.8 Hz). |

Reference Example 913

Production of N-[4-(5-nitropyridin-2-yloxy)phenyl]-N-[2-(4-piperonylpiperazin-1-yl)-2-oxoethyl]acetamide To a solution of ethyl{acetyl[4-(5-nitropyridin-2-yloxy)phenyl]amino}acetate (2.30 g, 6.40 mmol) in ethanol (50 mL) was added 5 M aqueous sodium hydroxide (1.92 mL, 9.60 mmol), and the resulting solution was stirred at room temperature for 30 minutes. To this reaction solution were added 5 M hydrochloric acid (2 mL) and water, and extracted with ethyl acetate. The ethyl acetate layer was washed with brine, dried over anhydrous sodium sulfate, evaporated, and the obtained residue was purified by silica gel column chromatography (n-hexane:ethyl acetate=1:1), to thereby yield 1.68 g of an oil. To a solution of this oil in DMF (10 mL) were added 1-piperonylpiperazine (1.29 g, 5.86 mmol), triethylamine (1.85 mL, 13.3 mmol) and diethyl cyanophosphonate (1.07 mL, 6.36 mmol), and the resulting solution was stirred for 1 hour at room temperature. To this reaction solution was added water and extracted with ethyl acetate. The ethyl acetate layer was washed with brine, dried over anhydrous sodium sulfate, evaporated, and the residue was purified by silica gel column chromatography (dichloromethane:methanol=30:1), to thereby yield 2.21 g of the title compound.

Appearance: Yellow amorphous powder $^1H$ NMR ($CDCl_3$) δ 1.98 (3H, s), 2.40-2.50 (4H, m), 3.40-3.45 (4H, m), 3.62 (2H, brs), 4.48 (2H, s), 5.94 (2H, s), 6.70-6.76 (2H, m), 6.85 (1H, s), 7.09 (1H, d, J=9.1 Hz), 7.20 (2H, d, J=8.7 Hz), 7.51 (2H, d, J=8.7 Hz), 8.51 (1H, dd, J=2.8 Hz, 9.1 Hz), 9.04 (1H, d, J=2.8 Hz).

The following compounds were produced in the same manner as in Reference Example 913.

TABLE 126

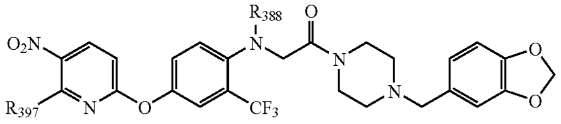

| Reference Example No. | $R_{387}$ | $R_{388}$ | MS ($M^+$) |
|---|---|---|---|
| 914 | —$CH_3$ | —$CH_3$ | 587 |
| 915 | —H | —$C_2H_5$ | 587 |

Reference Example 916

Production of 3-[3-methoxy-4-(5-nitropyridin-2-yloxy)phenyl]-1-(4-piperonylpiperazin-1-yl)propan-1-one 3-[3-methoxy-4-(5-nitropyridin-2-yloxy)phenyl]propionic acid (3.18 g, 10 mmol) was dissolved in dichloromethane (30 mL). To the resulting solution were added thionyl chloride (0.88 mL, 12 mmol) and DMF (1 drop), and refluxed for 2 hours. The reaction solution was concentrated under reduced pressure, and the residue was dissolved in dichloromethane (20 mL). To the resulting solution were added triethylamine (1.67 mL, 12 mmol) and a solution of 1-piperonylpiperazine (2.20 g, 10 mmol) in dichloromethane (30 mL) under ice cooling, and the resulting solution was stirred for 1 hour at 0° C. The resulting reaction solution was washed with water and brine. The organic layer was dried over anhydrous magnesium sulfate, and evaporated. The residue was recrystallized from ethyl acetate, to thereby yield 4.95 g of the title compound.

Appearance: Pale yellow powder $^1H$ NMR ($CDCl_3$) δ 2.33-2.42 (4H, m), 2.63-2.69 (2H, m), 2.97-3.03 (2H, m), 3.42 (4H, brs), 3.62-3.66 (2H, m), 3.74 (3H, s), 5.95 (2H, s), 6.73-6.75 (2H, m), 6.85-6.90 (3H, m), 7.04 (1H, d, J=9.1 Hz), 7.06 (1H, d, J=7.9 Hz), 8.45 (1H, dd, J=9.1 Hz, 2.8 Hz), 9.01 (1H, d, J=2.8 Hz).

The following compound was produced in the same manner as in Reference Example 916.

Reference Example 917

6-Chloro-N-(4-trifluoromethylphenyl)nicotinamide $^1$H NMR (DMSO-$d_6$) δ7.74 (1H, d, J=8.4 Hz), 7.76 (2H, d, J=8.7 Hz), 8.00 (2H, d, J=8.7 Hz), 8.38 (1H, dd, J=8.7 Hz, 2.5 Hz), 8.97 (1H, d, J=2.5 Hz), 10.80 (1H, brs).

Reference Example 918

Production of 3-{3-methoxy-4-[methyl(5-nitropyridin-2-yl)amino]phenyl}-1-(4-piperonylpiperazin-1-yl)propan-1-one To a solution of ethyl 3-{3-methoxy-4-[methyl-(5-nitropyridin-2-yl)amino]phenyl}propionate (3.85 g, 11 mmol) in ethanol (80 mL) was added 2 N aqueous sodium hydroxide (6.4 mL, 13 mmol), and the resulting solution was stirred at room temperature for 2.5 hours. To the resulting reaction solution was added 6 N hydrochloric acid (2.2 mL, 13 mmol), and the solvent was removed under reduced pressure. To the residue were added THF (80 mL) and N,N'carbonyldiimidazole (2.08 g, 13 mmol), and the resulting solution was stirred at room temperature for 3 hours. To the resulting reaction solution were added 1-piperonylpiperazine (2.60 g, 12 mmol) and DMF (40 mL), and stirred at room temperature for 21 hours. The solvent was evaporated under reduced pressure, and the residue was extracted with ethyl acetate. The ethyl acetate layer was washed with a saturated sodium bicarbonate solution, dried over anhydrous magnesium sulfate, evaporated, and the residue was purified by silica gel column chromatography (ethyl acetate), to thereby yield 4.59 g of the title compound.

Appearance: Yellow powder $^1$H NMR ($CDCl_3$) δ 2.36-2.43 (4H, m), 2.64-2.70 (2H, m), 2.99-3.05 (2H, m), 3.42-3.46 (7H, m), 3.63-3.67 (2H, m), 3.77 (3H, s), 5.95 (2H, s), 6.12 (1H, brd, J=9.1 Hz), 6.70-6.77 (2H, m), 6.85-6.90 (3H, m), 7.12 (1H, d, J=8.1 Hz), 7.97-8.01 (1H, m), 9.11 (1H, d, J=2.6 Hz).

Reference Example 919

Production of 5-{methyl[2-oxo-2-(4-piperonylpiperazin-1-yl)ethyl]amino}-2-(5-nitropyridin-2-yloxy)-benzonitrile To a solution of t-butyl 2-((3-cyano-4-(5-nitropyridin-2-yloxy)phenyl)(methyl)amino)acetate (1.2 g, 3.1 mmol) in dichloromethane (12 mL) was added trifluoroacetic acid (12 mL), and the resulting reaction solution was stirred at room temperature for 5 hours. The solvent was evaporated, and water was added to the residue, and extracted with ethyl acetate. The ethyl acetate layer was dried over anhydrous magnesium sulfate, and evaporated, to thereby yield crude 2-((3-cyano-4-(5-nitropyridin-2-yloxy)phenyl)(methyl) amino)-acetic acid. To a solution of this compound in DMF (24 mL) were added 1-ethyl-3-(3-dimethylaminopropyl)-carbodiimide hydrochloride (659 mg, 3.4 mmol), 1-hydroxybenzotriazole monohydrate (526 mg, 3.4 mmol) and 1-piperonylpiperazine (757 mg, 3.4 mmol), and the resulting reaction solution was stirred for 8 hours at room temperature. Water was added to the reaction solution and extracted with ethyl acetate. The ethyl acetate layer was then washed with, in order, saturated aqueous sodium bicarbonate solution, water and brine. The ethyl acetate layer was dried over anhydrous magnesium sulfate, and evaporated. The residue was purified by silica gel chromatography (ethyl acetate), to thereby yield 412 g of the title compound.

Appearance: Yellow amorphous powder $^1$H NMR ($CDCl_3$) δ 2.40-2.55 (4H, m), 3.09 (3H, s), 3.45-3.50 (4H, m), 3.55-3.70 (2H, m), 4.14 (2H, s), 5.95 (2H, s), 6.70-6.80 (2H, m), 6.80-6.95 (3H, m), 7.10-7.20 (2H, m), 8.50 (1H, dd, J=9.1 Hz, 2.8 Hz), 8.99 (1H, d, J=2.8 Hz).

Reference Example 920

Production of 2-{(2,3-difluoro-4-t-butoxycarbonylamino)phenoxy}-5-nitropyridine

To a solution of {2,3-difluoro-4-(5-nitropyridin-2-yloxy)}benzoic acid (1.22 g, 4.1 mmol) in t-butanol (50 mL) were added diphenylphosphorylazide (0.98 mL, 4.5 mmol) and triethylamine (0.63 mL, 4.5 mmol), and the resulting solution was refluxed for 4 hours under a nitrogen atmosphere. After cooling, water was added to the reaction solution and extracted with ethyl acetate. The ethyl acetate layer was washed with water, dried over anhydrous magnesium sulfate, and evaporated. The residue was purified by silica gel column chromatography (n-hexane:ethyl acetate=6:1), to thereby yield 1.2 g of the title compound.

Appearance: White powder $^1$H NMR ($CDCl_3$) δ 1.54 (9H, s), 6.59-6.78 (1H, m), 6.90-7.04 (1H, m), 7.13 (1H, d, J=9.0 Hz), 7.84-8.02 (1H, m), 8.51 (1H, dd, J=2.8 Hz, 9.0 Hz), 8.99 (1H, d, J=2.8 Hz).

Reference Example 921

Production of 3,4-dichloro-N-[3-fluoro-4-(4-formylphenoxy)phenyl]benzamide 3,4-Dichloro-N-[4-(4-[1,3]dioxsolane-2-ylphenoxy)-3-fluorophenyl]benzamide (17.4 g, 38.9 mmol) was added to 80% acetic acid, and the resulting solution was stirred for 1.5 hours at 80° C. The reaction solution was concentrated under reduced pressure, wherein the obtained residue was recrystallized from 80% ethanol to thereby yield 12.8 g of the title compound.

Appearance: Pale yellow powder $^1$H NMR (DMSO-$d_6$) δ 7.13 (2H, d, J=8.6 Hz), 3.40 (1H, t, J=9.0 Hz), 7.63 (1H, d, J=9.0 Hz), 7.85 (1H, d, J=8.4 Hz), 7.90-8.00 (4H, m), 8.22 (1H, d, J=1.9 Hz), 9.93 (1H, s), 10.67 (1H, s).

Reference Example 922

Production of N-[6-(4-aminophenoxy)pyridin-3-yl]-3,4-dichlorobenzamide dihydrochloride t-Butyl{4-[5-(3,4-dichlorobenzoylamino)-pyridin-2-yloxy]phenyl}carbamate (4.31 g, 9.09 mmol) was dissolved in a mixed solution of chloroform-methanol-ethyl acetate. The resulting solution was concentrated to a volume of about 20 mL. To the residue solution was added a solution of 4 N hydrogen chloride in ethyl acetate (70 mL), and left to cool for 2 hours at room temperature. The precipitated white powder was filtered, and washed with ethyl acetate, to thereby yield 4.04 g of the title compound.

Appearance: White powder $^1$H NMR (DMSO-$d_6$) δ 5.20 (2H, brs), 7.14 (1H, d, J=8.5 Hz), 7.25 (2H, d, J=8.9 Hz), 7.42 (2H, d, J=8.9 Hz), 7.84 (1H, d, J=8.5 Hz), 7.97 (1H, dd, J=8.5 Hz, 2.0 Hz), 8.24 (1H, dd, J=8.5 Hz, 2.6 Hz), 8.25 (1H, d, J=2.0 Hz), 8.51 (1H, d, J=2.6 Hz), 10.65 (1H, s).

The following compounds were produced in the same manner as in Reference Example 922.

TABLE 127

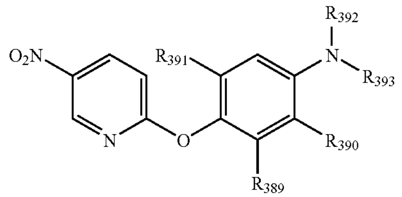

| Reference Example No. | $R_{389}$ | $R_{390}$ | $R_{391}$ | $R_{392}$ | $R_{393}$ | $^1$H NMR ($CDCl_3$) δ ppm or MS |
|---|---|---|---|---|---|---|
| 923 | —F | —H | —F | —H | —$CH_3$ | $^1$H NMR 2.83 (3H, d, J = 5.2 Hz), 3.90-4.05 (1H, m), 6.18-6.27 (2H, m), 7.15 (1H, d, J = 9.0 Hz), 8.49 (1H, dd, J = 2.8 Hz, 9.0 Hz), 9.02 (1H, d, J = 2.8 Hz). |
| 924 | —F | —F | —H | —H | —$CH_3$ | $^1$H NMR 2.92 (3H, d, J = 3.8 Hz), 3.90-4.16 (1H, m), 6.46 (1H, td, J = 22 Hz, 8.8 Hz), 6.89 (1H, td, J = 2.4 Hz, 7.8 Hz), 7.08 (1H, d, J = 9.0 Hz), 8.49 (1H, dd, J = 2.8 Hz, 9.0 Hz), 9.02 (1H, d, J = 28 Hz). |
| 925 | —$COOCH_3$ | —H | —H | —$CH_2COOH$ | —$C_2H_5$ | MS 375($M^+$) |

Reference Example 926

Production of 4-(tetrahydropyran-2-yloxy)benzylamine

To a solution of lithium aluminum hydride (2.66 g, 70 mmol) in THF (2.00 mL) was added dropwise under ice cooling a solution of 4-(tetrahydropyran-2-yloxy)benzonitrile in THF (70 mL). The resulting solution was then refluxed for 1 hour. The resulting reaction solution was again cooled with ice, and then to the solution was added dropwise, in order, water (2.66 mL), 1 N aqueous sodium hydroxide (2.66 mL) and water (7.98 mL). Insoluble matter was removed by filtration. The filtrate was concentrated under reduced pressure, after which the residue was purified by silica gel column chromatography (chloroform methanol 7:1), to thereby yield 11.41 g of the title compound.

Appearance: Colorless oil $^1$H NMR ($CDCl_3$) δ 1.56 (2H, s), 1.45-1.78 (3H, m), 1.78-2.12 (3H, m), 3.53-3.66 (1H, m), 3.80 (2H, s), 3.84-3.99 (1H, m), 5.41 (1H, t, J=3.2 Hz), 7.02 (2H, d, J=8.7 Hz), 7.22 (2H, d, J=8.7 Hz).

Reference Example 927

Production of 4-(2-fluoro-4-nitrophenoxy)phenylamine hydrochloride

N-[4-(2-fluoro-4-nitrophenoxy)phenyl]-acetamide (1.00 g, 3.45 mmol) was added to 6 M hydrochloric acid (10 mL), and the resulting solution was refluxed for 2 hours. The resulting reaction solution was concentrated under reduced pressure, to thereby yield 0.910 g of the title compound.

Appearance: Pale yellow powder $^1$H-NMR (DMSO-$d_6$) δ 3.40-4.00 (2H, m), 7.18 (1H, t, J=8.7 Hz), 7.24 (2H, d, J=8.9 Hz), 7.32 (2H, d, J=8.9 Hz), 8.10 (1H, ddd, J=1.4 Hz, 2.6 Hz, 8.9 Hz), 8.35 (1H, dd, J=2.6 Hz, 10.8 Hz).

Reference Example 928

Production of {4-[5-(3,4-dichlorobenzoylamino)pyridin-2-yloxy]phenyl}carbamate phenyl ester To a suspension of N-[6-(4-aminophenoxy)pyridin-3-yl]-3,4-dichlorobenzamide dihydrochloride (700 mg, 1.57 mmol) in THF (20 mL) was added triethylamine (1.1 mL, 7.89 mmol). To the resulting solution was then added dropwise phenyl chlorocarbonate (0.39 mL, 3.14 mmol) under ice cooling. The resulting reaction solution was stirred for 1 hour at room temperature. Water was added to the residue, and extracted with ethyl acetate. The ethyl acetate layer was washed with a saturated sodium bicarbonate solution and brine. The ethyl acetate layer was dried over anhydrous magnesium sulfate, and evaporated, whereupon the residue solidified into a powder. The powder was filtered, and washed with diethyl ether, to thereby yield 470 mg of the title compound.

Appearance: White powder $^1$H NMR (DMSO-$d_6$) δ 7.04 (1H, d, J=8.9 Hz), 7.11 (2H, d, J=8.9 Hz), 7.19-7.31 (3H, m), 7.38-7.49 (2H, m), 7.53 (2H, d, J=8.0 Hz), 7.84 (1H, d, J=8.4 Hz), 7.95 (1H, dd, J=8.4 Hz, 2.0 Hz), 8.18 (1H, dd, J=8.9 Hz, 2.2 Hz), 8.22 (1H, d, J=2.0 Hz), 8.47 (1H, d, J=2.2 Hz), 10.26 (1H, s), 10.54 (1H, s).

The following compounds were produced in the same manner as in Reference Example 928.

TABLE 128

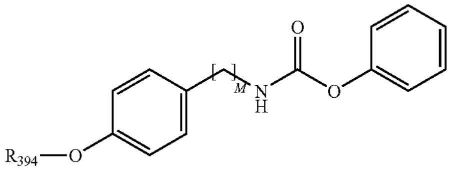

| Reference Example No. | $R_{394}$ | M | $^1$H NMR (solvent) δ ppm |
|---|---|---|---|
| 929 | 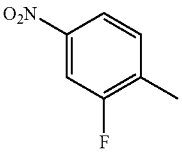 | 0 | (DMSO-$d_6$) 7.08 (1H, t, J = 8.7 Hz), 7.15-7.30 (5H, m), 7.35-7.50 (2H, m), 7.60 (2H, d, J = 8.9 Hz), 8.07 (1H, dd, J = 1.1 Hz, 9.0 Hz), 8.31 (1H, dd, J = 2.6 Hz, 10.9 Hz), 10.36 (1H, s). |
| 930 | 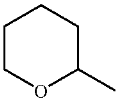 | 0 | ($CDCl_3$) 1.50-1.80 (3H, m), 1.80-2.15 (3H, m), 3.55-3.67 (1H, m), 3.85-4.00 (1H, m), 5.37 (1H, t, J = 3.3 Hz), 6.83 (1H, brs), 7.03 (2H, d, J = 9.1 Hz) 7.14-7.30 (3H, m); 7.30-7.47 (4H, m). |
| 931 | 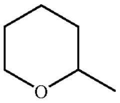 | 1 | ($CDCl_3$) 1.50-1.79 (3H, m), 1.79-2.15 (3H, m), 3.55-3.60 (1H, m), 3.82-4.00 (1H, m), 3.39 (2H, d, J = 6.0 Hz), 5.26 (1H, brs), 5.42 (1H, t, J = 3.1 Hz), 7.05 (2H, d, J = 8.7 Hz), 7.27 (2H, d, J = 8.7 Hz), 7.10-7.40 (5H, m). |

Reference Example 932

Production of 4-piperonylpiperazine-1-carboxylic acid 4-(2-fluoro-4-nitrophenoxy)phenyl]amide To a solution of [4-(2-fluoro-4-nitrophenoxy)phenyl]carbamate phenyl ester (0.700 g, 1.90 mmol) in DMF (15 mL) was added 1-piperonylpiperazine (0.460 g, 2.09 mmol), and the resulting solution was stirred for 2 hours at room temperature water was added to the resulting reaction solution, and extracted with ethyl acetate. The ethyl acetate layer was washed with brine. The ethyl acetate layer was dried over anhydrous sodium sulfate, and evaporated, to thereby yield 0.939 g of the title compound.

Appearance: Yellow oil $^1$H NMR (DMSO-$d_6$) δ 2.30-2.40 (4H, m), 3.35-3.50 (6H, m), 6.00 (2H, s), 6.70-6.90 (2H, m), 7.00-7.15 (2H, m), 7.55 (2H, d, J=9.1 Hz), 8.05-8.10 (1H, m), 8.30 (1H, dd, J=2.8 Hz, 10.9 Hz), 9.31 (1H, s).

The following compounds were produced in the same manner as in Reference Example 932.

Reference Example 933

Ethyl 3-(4-{5-[3-(3,4-dichlorophenyl)-3-ethylureido]-pyridin-2-yloxy}phenyl)propionate

MS 501 ($M^+$).

TABLE 129

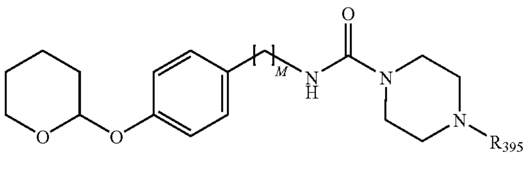

| Reference Example No. | $R_{395}$ | M | $^1$H NMR ($CDCl_3$) δ ppm |
|---|---|---|---|
| 934 | benzyl | 0 | 1.50-1.87 (3H, m), 1.87-2.15 (3H, m), 2.48 (4H, t, J = 5.1 Hz), 3.48 (4H, t, J = 5.1 Hz), 3.54 (2H, s), 3.50-3.65 (1H, m), 3.85-4.00 (1H, m), 5.34 (1H, t, J = 3.2 Hz), 6.21 (1H, brs), 6.98 (2H, d, J = 8.9 Hz), 7.22 (2H, d, J = 8.9 Hz), 7.25-7.38 (5H, m). |
| 935 | piperonyl | 1 | 1.48-1.77 (3H, m), 1.77-2.11 (3H, m), 2.40 (4H, t, J = 5.0 Hz), 3.36 (4H, t, J = 5.0 Hz), 3.41 (2H, s), 3.50-1.67 (1H, m), 3.81-3.96 (1H, m), 4.34 (2H, d, J = 5.1 Hz), 4.61 (1H, t, J =5.1 Hz), 5.40 (1H, t, J = 3.2 Hz), 5.94 (2H, s), 6.74 (2H, s), 6.84 (1H, s), 7.00 (2H, d, J = 8.6 Hz), 7.22 (2H, d, J = 8.6 Hz). |

Reference Example 936

Production of 4-piperonylpiperazine-1-carboxylic acid 4-hydroxybenzylamide

To a solution of 4-piperonylpiperazine-1-carboxylic acid 4-(tetrahydropyran-2-yloxy)benzylamide (1.1 g, 2.43 mmol) in methanol (50 mL) was added p-toluenesulfonic acid monohydrate (1.0 g, 5.26 mmol), and the resulting solution was stirred for 1 hour at room temperature. The resulting reaction solution was concentrated under reduced pressure. Water was added to the residue, and extracted with ethyl acetate. The ethyl acetate layer was washed with a saturated sodium bicarbonate solution and brine. The ethyl acetate layer was dried over anhydrous magnesium sulfate, and evaporated, to thereby yield 330 mg of the title compound.

Appearance: White powder $^1$H NMR ($CDCl_3$) δ 2.41 (4H, t, J=5.0 Hz), 3.37 (4H, t, J=5.0 Hz), 3.42 (2H, s), 4.32 (2H, d, J=5.2 Hz), 4.68 (1H, t, J=5.2 Hz), 5.94 (2H, s), 6.15 (1H, brs), 6.70-6.80 (2H, m), 6.75 (2H, d, J=8.6 Hz), 6.84 (1H, s), 7.13 (2H, d, J=8.6 Hz).

The following compound was produced in the same manner as in Reference Example 936.

Reference Example 937

4-Benzylpiperazine-1-carboxylic acid (4-hydroxyphenyl)methylamide hydrochloride $^1$H NMR (DMSO-$d_6$) δ 2.69-2.91 (2H, m), 3.03 (3H, s), 2.92-3.23 (4H, m), 3.68 (2H, d, J=13.7 Hz), 4.26 (2H, s), 6.75 (2H, d, J=8.7 Hz), 6.98 (2H, d, J=8.7 Hz), 7.45 (3H, brs), 7.54 (2H, brs), 9.52 (1H, s).

Reference Example 938

Production of 3,4-dichloro-N-{6-[4-(3-hydroxypropyl)-phenoxy]pyridin-3-yl}benzamide To 2-{4-[3-(t-butyldimethylsilanyloxy)propyl]phenoxy}-5-nitropyridine (950 mg, 1.8 mmol) were added acetic acid (10 mL) and water (5 mL), and the resulting solution was stirred for 1 hour at room temperature. The resulting reaction solution was concentrated under reduced pressure. Water was added to the residue, and extracted with ethyl acetate. The ethyl acetate layer was washed with a saturated sodium bicarbonate solution and brine. The ethyl acetate layer was dried over anhydrous magnesium sulfate, and evaporated. The residue was recrystallized from ethyl acetate, to thereby yield 520 mg of the title compound.

Appearance: White prisms $^1$H NMR (DMSO-$d_6$) δ 1.70-1.78 (2H, m), 2.59-2.65 (2H, m), 3.32-3.47 (2H, m), 4.46-4.49 (1H, m), 7.00-7.05 (3H, m), 7.23 (2H, d, J=8.2 Hz), 7.84 (1H, d, J=8.2 Hz), 7.95 (1H, dd, J=8.3 Hz, 2.0 Hz), 8.16-8.22 (2H, m), 8.48 (1H, d, J=2.6 Hz), 10.54 (1H, s).

The following compound was produced in the same manner as in Reference Example 938.

Reference Example 939

3,4-Dichloro-N-{6-[4-(2-hydroxyethyl)phenoxy]pyridin-3-yl}benzamide $^1$H NMR (DMSO-$d_6$) δ 2.73 (2H, t, J=6.9 Hz), 3.59-3.66 (2H, m), 4.65 (1H, t, J=5.3 Hz), 7.00-7.06 (3H, m), 7.25 (2H, d, J=8.3 Hz), 7.84 (1H, d, J=8.3 Hz), 7.95 (1H, dd, J=8.3 Hz, 2.0 Hz), 8.16-8.23 (2H, m), 8.47 (1H, d, J=2.6 Hz), 10.54 (1H, s).

Reference Example 940

Production of 3,4-dichloro-N-{6-[4-(5-hydroxypentyl)-phenoxy]pyridin-3-yl}benzamide To a solution of ethyl 5-{4-[5-(3,4-dichloro-benzoylamino)pyridin-2-yloxy]phenyl}pentanoate (8.79 g, 18.0 mmol) in THF (140 mL) was added sodium borohydride (3.14 g, 144 mmol), and the resulting solution was refluxed for 3 hours under a nitrogen atmosphere. The resulting reaction solution was cooled with ice, and treated with 1 N hydrochloric acid. The resulting solution was extracted with ethyl acetate. The ethyl acetate layer was washed with a saturated sodium bicarbonate solution and brine. The ethyl acetate layer was dried over anhydrous magnesium sulfate, and evaporated. The residue was purified by silica gel column chromatography (n-hexane:ethyl acetate=1:2), to thereby yield 7.07 g of the title compound.

Appearance: White powder $^1$H NMR ($CDCl_3$) δ 1.25-1.75 (7H, m), 2.62 (2H, t, J=7.6 Hz), 3.65 (2H, t, J=6.6 Hz), 6.92 (1H, d, J=8.5 Hz), 7.02 (2H, d, J=8.5 Hz), 7.19 (2H, d, J=8.5 Hz), 7.56 (1H, d, J=8.5 Hz), 7.69 (1H, dd, J=8.5 Hz, 2.0 Hz), 7.93 (1H, s), 7.97 (1H, d, J=2.0 Hz), 8.15 (1H, dd, J=8.5 Hz, 2.5 Hz), 8.22 (1H, d, J=2.5 Hz).

The following compounds were produced in the same manner as in Reference Example 940.

TABLE 130

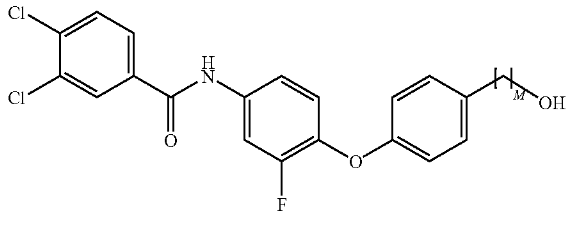

| Reference Example No. | M | mp (° C.) |
|---|---|---|
| 941 | 1 | 162-163 |
| 942 | 2 | 104-105 |
| 943 | 3 | 111-113 |
| 944 | 4 | 102-104 |

TABLE 131

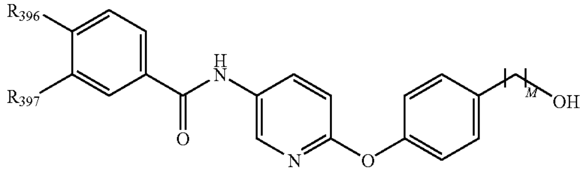

| Reference Example No. | $R_{396}$ | $R_{397}$ | M | $^1$H NMR (DMSO-$d_6$) δ ppm |
|---|---|---|---|---|
| 945 | —Cl | —Cl | 1 | 4.49 (2H, d, J = 5.6 Hz), 5.17 (1H, brs), 7.03-7.08 (3H, m), 7.35 (2H, d, J = 8.6 Hz), 7.84 (1H, d, J = 8.6 Hz), 7.93-7.97 (1H, m), 8.17-8.22 (2H, m), 8.47 (1H, d, J = 2.6 Hz), 10.53 (1H, s). |
| 946 | —$CF_3$ | —H | 1 | 4.50 (2H, d, J = 5.7 Hz), 5.18 (1H, t, J = 5.7 Hz), 7.04-7.09 (3H, m), 7.35 (2H, d, J = 8.4 Hz), 7.93 (2H, d, J = 8.4 Hz), 8.15-8.24 (3H, m), 8.50 (1H, d, J = 2.7 Hz), 10.61 (1H, s). |
| 947 | —Cl | —Cl | 4 | 1.35-1.70 (4H, m), 2.59 (2H, t, J = 7.5 Hz), 3.42 (2H, q, J = 6.0 Hz), 4.37 (1H, t, J = 5.5 Hz), 7.02 (2H, d, J = 8.2 Hz), 7.04 (1H, d, J = 8.6 Hz), 7.22 (2H, d, J = 8.2 Hz), 7.84 (1H, d, J = 8.2 Hz), 7.94 (1H, dd, J = 8.2 Hz, 2.0 Hz), 8.18 (1H, dd, J = 8.9 Hz, 2.6 Hz), 8.22 (1H, d, J = 2.0 Hz), 8.47 (1H, d, J = 2.6 Hz), 10.53 (1H, s). |

Reference Example 948

Production of 4-cyano-N-[6-(4-hydroxymethylphenoxy)-pyridin-3-yl]benzamide

A suspension of 4-[5-(4-cyanobenzoylamino)-pyridin-2-yloxy]benzoic acid (1.80 g, 5.01 mmol) in THF (20 mL) was cooled with ice-common salt, and to the solution was added triethylamine (0.77 mL, 5.51 mmol), and then ethyl chlorformate (0.53 mL, 5.51 mmol). The resulting solution was stirred at room temperature. Thirty minutes later, the reaction solution was filtered and insoluble matter was removed. The resulting filtrate was poured while stirring under ice cooling into an aqueous solution of sodium borohydride (0.95 g, 25.05 mmol) in 80% methanol (40 mL). After stirring for 30 minutes at room temperature, water (200 mL) was added to the reaction solution. The obtained mixture was extracted with ethyl acetate (200 mL). The ethyl acetate layer was washed with brine, dried over anhydrous sodium sulfate, and evaporated under reduced pressure. The residue was recrystallized from a mixed solution of ethyl acetate-n-hexane, to thereby yield 1.26 g of the title compound.

Appearance: Slightly yellow powder $^1$H NMR (DMSO-$d_6$) δ 4.50 (2H, d, J=5.3 Hz), 5.19 (1H, t, J=5.6 Hz), 7.04-7.09 (3H, m), 7.35 (2H, d, J=8.6 Hz), 8.04 (2H, d, J=8.9 Hz), 8.12 (2H, d, J=8.6 Hz), 8.21 (1H, dd, J=8.9 Hz, 2.6 Hz), 8.49 (1H, d, J=2.3 Hz), 11.63 (1H, s).

The following compounds were produced in the same manner as in Reference Example 948.

Reference Example 949

4-Chloro-N-[6-(4-hydroxymethylphenoxy)pyridin-3-yl]benzamide $^1$H NMR (DMSO-$d_6$) δ 4.50 (2H, d, J=5.3 Hz), 5.18 (1H, t, J=5.6 Hz), 7.03-7.08 (3H, m), 7.35 (2H, d, J=8.6 Hz), 7.63 (2H, d, J=8.6 Hz), 8.00 (2H, d, J=8.6 Hz), 8.20 (1H, dd, J=8.9 Hz, 2.6 Hz), 8.48 (1H, d, J=2.3 Hz), 10.46 (1H, s).

TABLE 132

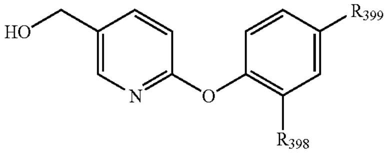

| Reference Example No. | $R_{398}$ | $R_{399}$ | $^1$H NMR ($CDC1_3$) δ ppm |
|---|---|---|---|
| 950 | —H | —$NO_2$ | 4.71 (2H, s), 7.05 (1H, d, J = 8.4 Hz), 7.25 (2H, d, J = 8.9 Hz), 7.83 (1H, dd, J = 8.3 Hz, 2.3 Hz), 8.19 (1H, d, J = 2.5 Hz), 8.27 (2H, d, J = 8.9 Hz). |
| 951 | —$CH_3$ | —$NO_2$ | 2.30 (4H, brs), 4.67 (2H, s), 7.02 (1H, d, J = 8.41 Hz,), 7.12 (1H, d, J = 8.90 Hz), 7.80 (1H, dd, J = 8.41 Hz, 2.47 Hz), 8.05-8.17 (3H, m). |

TABLE 132-continued

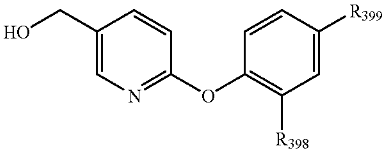

| Reference Example No. | $R_{398}$ | $R_{399}$ | $^1$H NMR ($CDCl_3$) δ ppm |
|---|---|---|---|
| 952 | —H | 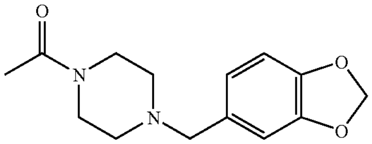 | 2.45 (4H, brs), 3.45 (2H, s), 3.57 (2H, brs), 3.69 (2H, brs), 4.67 (2H, s), 5.95 (2H, s), 6.74-6.77 (2H, m), 6.85 (1H, s), 6.94 (1H, d, J = 8.4 Hz), 7.14 (2H, d, J 8.4 Hz), 7.44 (2H, d, J = 8.4 Hz), 7.76 (1H, dd, J = 2.5 Hz, 8.4 Hz), 8.16 (1H, d, J = 2.5 Hz). |
| 953 | —H | 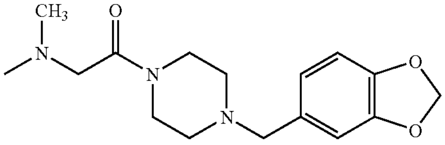 | 1.96 (1H, brs), 2.40-2.44 (4H, m), 3.02 (3H, s), 3.43 (2H, brs), 3.47-3.49 (2H, m), 3.62 (2H, brs), 4.07 (2H, s), 4.62 (2H, s), 5.94 (2H, s), 6.68-6.77 (4H, m), 6.81 (1H, d, J = 8.6 Hz), 6.85 (1H, brs), 6.99 (2H, d, J = 9.2 Hz), 7.66 (1H, dd, J = 8.4 Hz, 2.5 Hz), 8.13 (1H, d, J = 2.5 Hz). |
| 954 | —H | 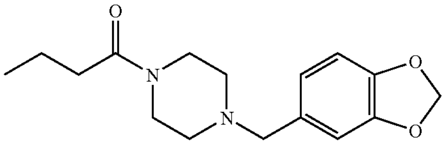 | 1.75-2.01 (1H, m), 2.22-2.50 (4H, m), 2.51-2.70 (2H, m), 2.88-3.07 (2H, m), 3.30-3.51 (4H, m), 3.52-3.78 (2H, m), 4.67 (2H, s), 5.96 (2H, s), 6.69-6.81 (2H, m), 6.83-6.88 (1H, m), 6.91 (1H, d, J = 8.4 Hz), 7.01-7.11 (2H, m), 7.19-7.29 (2H, m), 7.74 (1H, dd, J = 2.5 Hz, 8.4 Hz), 8.16 (1H, dd, J = 0.5 Hz, 2.5 Hz). |

Reference Example 955

Production of 2-[4-(1-bromoethyl)phenoxy]-5-nitropyridine 2-(4-ethylphenoxy)-5-nitropyridine (7.33 g, 30 mmol) was dissolved in carbon tetrachloride (100 mL), and to the resulting solution were added N-bromosuccimide (5.34 g, 30 mmol) and benzoyl peroxide (0.73 g, 3 mmol). This solution was refluxed overnight under a nitrogen atmosphere. The reaction solution was allowed to cool, after which insoluble matter was removed by filtration. The resulting filtrate was washed with a saturated sodium bicarbonate solution and brine. The organic layer was dried over anhydrous magnesium sulfate, and evaporated. The residue was purified by silica gel column chromatography (n-hexane:ethyl acetate=10:1), to thereby yield 1.34 g of the title compound.

Appearance: White powder $^1$H NMR ($CDCl_3$) δ 2.08 (3H, d, J=6.9 Hz), 5.26 (1H, q, J=6.9 Hz), 7.05 (1H, d, J=9.1 Hz), 7.15 (2H, d, J=8.6 Hz), 7.53 (2H, d, J=8.7 Hz), 8.49 (1H, dd, J=9.1 Hz, 2.8 Hz), 9.04 (1H, d, J=2.8 Hz).

Reference Example 956

Production of N-[6-(4-chloromethylphenoxy)pyridin-3-yl]-4-trifluoromethylbenzamide To a solution of N-[6-(4-hydroxymethylphenoxy)pyridin-3-yl]-4-trifluoromethylbenzamide (3.06 g, 7.9 mmol) in dichloromethane (90 mL) was added thionyl chloride (1.7 mL, 23.3 mmol), and the resulting solution was stirred for 4 hours at room temperature. To the residue was added a saturated sodium bicarbonate solution, and extracted with ethyl acetate. The ethyl acetate layer was washed with a saturated sodium bicarbonate solution and brine, dried over anhydrous magnesium sulfate, and evaporated. The residue was washed with diethyl ether, to thereby yield 2.95 g of the title compound.

Appearance: White powder $^1$H NMR ($CDCl_3$) δ 4.61 (2H, s), 7.00 (1H, d, J=8.9 Hz), 7.11-7.14 (2H, m), 7.41-7.44 (2H, m), 7.77 (2H, d, J=8.4 Hz), 7.89 (1H, brs), 8.00 (2H, d, J=8.4 Hz), 8.22-8.28 (2H, m).

The following compounds were produced in the same manner as in Reference Example 956.

Reference Example 957

3,4-Dichloro-N-[4-(4-chloromethylphenoxy)-3-fluorophenyl]benzamide $^1$H NMR ($CDCl_3$) δ 4.58 (2H, s), 6.95 (2H, d, J=8.6 Hz), 7.10 (1H, t, J=8.6 Hz), 7.20-7.30 (1H, m), 7.30-7.40 (3H, m), 7.59 (1H, d, J=8.3 Hz), 7.65-7.78 (2H, m), 7.96 (1H, d, J=2.1 Hz).

TABLE 133

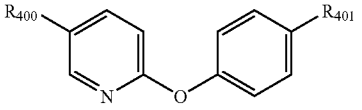

| Reference Example No. | $R_{400}$ | $R_{401}$ | $^1$H NMR ($CDCl_3$) δ ppm |
|---|---|---|---|
| 958 | —$NO_2$ | $CH_2Cl$ | 4.63 (2H, s), 7.06 (1H, d, J = 8.9 Hz), 7.16 (2H, dd, J = 6.6 Hz, 2.0 Hz), 7.47 (2H, d, J = 8.3 Hz), 8.47-8.51 (1H, m), 9.04 (1H, d, J = 2.6 Hz) |
| 959 | 3,4-$Cl_2$PhCONH— | —$CH_2Cl$ | 4.59 (2H, s), 6.95 (1H, d, J = 8.9 Hz), 7.10 (2H, d, J = 8.6 Hz), 7.40 (2H, d, J = 8.6 Hz), 7.54 (1H, d, J = 8.2 Hz), 7.71-7.75 (1H, m), 7.99 (1H, d, J = 2.3 Hz), 8.18-8.22 (2H, m), 8.30 (1H, d, J = 2.6 Hz). |
| 960 | 4-CNPhCONH— | —$CH_2Cl$ | 4.60 (2H, s), 6.99 (1H, d, J = 8.9 Hz), 7.12 (2H, d, J = 8.6 Hz), 7.42 (2H, d, J = 8.6 Hz), 7.79 (2H, d, J = 8.3 Hz), 7.97-8.00 (3H, m), 8.21 (1H, dd, J = 8.9 Hz, 2.6 Hz), 8.27 (1H, d, J = 2.6 Hz). |
| 961 | 4-ClPhCONH— | —$CH_2Cl$ | 4.61 (2H, s), 6.99 (1H, d, J = 9.6 Hz), 7.12 (2H, d, J = 8.3 Hz), 7.42 (2H, d, J = 8.3 Hz), 7.48 (2H, d, J = 8.3 Hz), 7.75 (1H, brs), 7.85 (2H, d, J = 8.3 Hz), 8.20-8.25 (2H, m). |
| 962 | —$CH_2Cl$ | 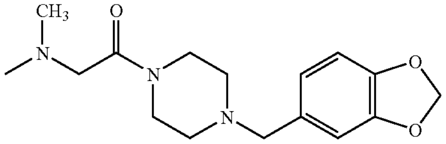 | 2.41-2.45 (4H, m), 3.03 (3H, s), 3.43 (2H, brs), 3.49 (2H, brs), 3.63 (2H, brs), 4.08 (2H, s), 4.54 (2H, s), 5.94 (2H, s), 6.70 (2H, d, J = 9.2 Hz), 6.73-6.77 (2H, m), 6.82 (1H, d, J = 8.6 Hz), 6.85 (1H, brs), 7.00 (2H, d, J = 9.2 Hz), 7.67 (1H, dd, J = 8.6 Hz, 2.5 Hz), 8.15 (1H, d, J = 2.5 Hz). |

(CNPh means a cyanophenyl group. Hereinafter CNPh indicates the same meaning.)

Reference Example 963

Production of 3,4-dichloro-N-{6-[4-(5-chloropentyl)-phenoxy]pyridin-3-yl}benzamide hydrochloride To 3,4-dichloro-N-{6-[4-(5-hydroxypentyl)-phenoxy]pyridin-3-yl}benzamide (6.83 g, 15.34 mmol) was added thionyl chloride (35 mL). The resulting solution was stirred for 20 minutes at room temperature, followed by stirring for 1 hour at 50° C. Excess thionyl chloride was evaporated, after which to the resulting residue was added ethyl acetate (100 mL). The obtained white powder was filtered, and washed with ethyl acetate, to thereby yield 6.98 g of the title compound.

Appearance: White powder $^1$H NMR (DMSO-$d_6$) δ 1.33-1.50 (2H, m), 1.50-1.68 (2H, m), 1.68-1.85 (2H, m), 2.59 (2H, t, J=7.6 Hz), 3.64 (2H, t, J=6.6 Hz), 7.02 (2H, d, J=8.5 Hz), 7.03 (1H, d, J=9.0 Hz), 7.23 (2H, d, J=8.5 Hz), 7.83 (1H, d, J=8.5 Hz), 7.97 (1H, dd, J=8.5 Hz, 2.0 Hz), 8.20 (1H, dd, J=9.0 Hz, 2.5 Hz), 8.25 (1H, d, J=2.0 Hz), 8.50 (1H, d, J=2.5 Hz), 10.63 (1H, s).

The following compounds were produced in the same manner as in Reference Example 963.

TABLE 134

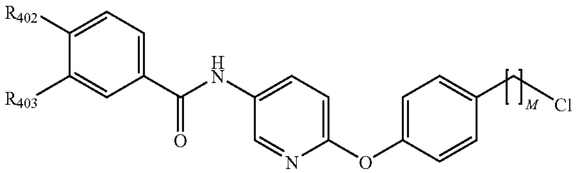

| Reference Example No. | $R_{402}$ | $R_{403}$ | M | Form | $^1$H NMR (solvent) δ ppm |
|---|---|---|---|---|---|
| 964 | —Cl | —Cl | 2 | free | ($CDCl_3$) 3.04-3.10 (2H, m), 3.69-3.75 (2H, m), 6.95 (1H, d, J = 8.6 Hz), 7.06-7.09 (2H, m), 7.24 (2H, d, J = 8.2 Hz), 7.56 (1H, d, J = 8.2 Hz), 7.69 (1H, dd, J = 8.2 Hz, 2.0 Hz), 7.93 (1H, brs), 7.97 (1H, d, J = 2.0 Hz), 8.15-8.19 (1H, m), 8.24 (1H, d, J = 2.6 Hz). |

TABLE 134-continued

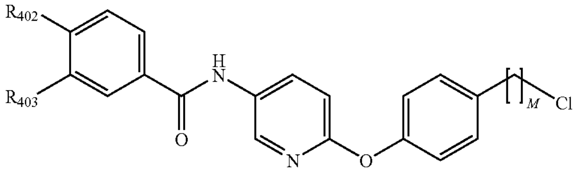

| Reference Example No. | $R_{402}$ | $R_{403}$ | M | Form | $^1$H NMR (solvent) δ ppm |
|---|---|---|---|---|---|
| 965 | —Cl | —Cl | 3 | free | ($CDCl_3$) 2.04-2.12 (2H, m), 2.76-2.81 (2H, m), 3.53-3.58 (2H, m), 6.94 (1H, d, J = 8.9 Hz), 7.04-7.07 (2H, m), 7.20-7.26 (2H, m), 7.56 (1H, d, J = 8.1 Hz), 7.70 (1H, dd, J = 8.4 Hz, 2.2 Hz), 7.90 (1H, brs), 7.97 (1H, d, J = 2.2 Hz), 8.14-8.18 (1H, m), 8.24 (1H, d, J = 2.7 Hz). |
| 966 | —$CF_3$ | —H | 3 | free | ($CDCl_3$) 2.04-2.14 (2H, m), 2.75-2.81 (2H, m), 3.53-3.57 (2H, m), 6.93 (1H, d, J = 8.7 Hz), 7.03-7.07 (2H, m), 7.20-7.23 (2H, m), 7.73 (2H, d, J = 8.2 Hz), 7.97 (2H, d, J = 8.2 Hz), 8.09 (1H, brs), 8.16-8.21 (1H, m), 8.25 (1H, d, J = 2.6 Hz). |
| 967 | —Cl | —Cl | 4 | hydrochloride | (DMSO-$d_6$) 1.60-1.85 (4H, m), 2.62 (2H, t, J = 6.3 Hz), 3.68 (2H, t, J = 6.3 Hz), 7.03 (2H, d, J = 8.5 Hz), 7.04 (1H, d, J = 9.0 Hz), 7.24 (2H, d, J = 8.5 Hz), 7.83 (1H, d, J = 8.6 Hz), 7.97 (1H, dd, J = 8.6 Hz, 2.0 Hz), 8.20 (1H, dd, J = 9.0 Hz, 2.7 Hz), 8.25 (1H, d, J = 2.2 Hz), 8.50 (1H, d, J = 2.7 Hz), 10.64 (1H, s). |

Reference Example 968

Production of N-{6-[4-(2-bromoacetyl)phenoxy]pyridin-3-yl}-3,4-dichlorobenzamide N-[6-(4-acetylphenoxy)pyridin-3-yl}-3,4-dichlorobenzamide (4.0 g, 10 mmol) was dissolved in chloroform (200 mL). To the resulting solution was added copper bromide (5.76 g, 25 mmol), and refluxed overnight. The resulting reaction solution was filtered, and the filtrate was washed with saturated sodium thiosulfate solution and brine. The organic layer was dried over anhydrous magnesium sulfate, and evaporated. To the filtered product from the earlier step was added ethyl acetate, and washed with saturated sodium thiosulfate water and brine. The organic layer was dried over anhydrous magnesium sulfate, and evaporated. The residues were combined for purification by silica gel column chromatography (n-hexane:ethyl acetate=3:1), to thereby yield 1.86 g of the title compound.

Appearance: White powder $^1$H NMR ($CDCl_3$) δ 4.43 (2H, s), 7.06 (1H, d, J=8.7 Hz), 7.21 (2H, d, J=8.9 Hz), 7.57 (1H, d, J=8.4 Hz), 7.72 (1H, dd, J=8.4 Hz, 2.0 Hz), 7.99 (1H, d, J=2.0 Hz), 8.03 (2H, d, J=8.9 Hz), 8.09 (1H, brs), 8.27 (1H, dd, J=8.7 Hz, 2.8 Hz), 8.32 (1H, d, J=2.2 Hz).

The following compound was produced in the same manner as in Reference Example 968.

Reference Example 969

N-{4-[4-(2-Bromoacetyl)phenoxy]-3-fluorophenyl}-3,4-dichlorobenzamide $^1$H NMR (DMSO-$D_6$) δ 4.88 (2H, s), 7.06 (2H, d, J=8.9 Hz), 7.30-7.50 (1H, m), 7.60-7.70 (1H, m), 7.80-8.20 (5H, m), 8.22 (1H, d, J=2.0 Hz), 10.67 (1H, brs).

Reference Example 970

Production of 4'-[4-(3-bromopropyl)phenoxy]-3,4-dichloro-3'-fluorobenzanilide To a suspension of 3,4-dichloro-3'-fluoro-4'-[4-(3-hydroxypropyl)phenoxy]benzanilide (2.32 g, 5.34 mmol) in dichloromethane (46 mL) were added carbon tetrabromide (2.13 g, 6.41 mmol) and triphenylphosphine (1.54 g, 5.88 mmol), and the resulting solution was stirred for 12 hours at room temperature. The reaction solution was concentrated under reduced pressure, and the residue was purified by silica gel column chromatography (n-hexane:ethyl acetate=5:1), to thereby yield 2.41 g of the title compound.

Appearance: White powder $^1$H NMR ($CDCl_3$) δ 2.08-2.11 (2H, m), 2.73 (2H, t, J=7.3 Hz), 3.38 (2H, t, J=6.5 Hz), 6.88 (2H, d, J=8.5 Hz), 7.02 (1H, dd, J=9.0 Hz, 8.0 Hz), 7.13 (2H, d, J=8.5 Hz), 7.17-7.28 (1H, m), 7.54 (1H, d, J=8.3 Hz), 7.60-7.74 (2H, m), 7.85 (1H, brs), 7.93 (1H, d, J=2.0 Hz).

The following compounds were produced in the same manner as in Reference Example 970.

TABLE 135

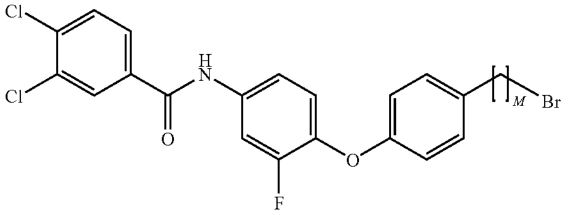

| Reference Example No. | M | $^1$H NMR ($CDCl_3$) δ ppm |
|---|---|---|
| 971 | 2 | 3.13 (2H, t, J = 7.5 Hz), 3.55 (2H, t, J = 7.5 Hz), 6.91 (2H, d, J = 6.6 Hz), 7.08 (1H, t, J = 8.7 Hz), 7.15 (2H, d, J = 6.6 Hz), 7.18-7.25 (1H, m), 7.56 (1H, d, J = 8.3 Hz), 7.65-7.75 (2H, m), 7.90-8.00 (2H, m). |
| 972 | 4 | 1.67-1.79 (2H, m), 1.81-1.94 (2H, m), 2.60 (2H, t, J = 7.5 Hz), 3.40 (2H, t, J = 6.6 Hz), 6.88 (2H, d, J = 8.6 Hz), 7.02 (1H, dd, J = 9.0 Hz, 8.0 Hz), 7.11 (2H, d, J = 8.6 Hz), 7.14-7.21 (1H, m), 7.55 (1H, d, J = 8.3 Hz), 7.60-7.73 (2H, m), 7.78 (1H, brs), 7.93 (1H, d, J = 1.9 Hz). |

Reference Example 973

Production of t-butyl 4-[4-(5-nitropyridin-2-yloxy) benzyl]piperazine-1-carboxylate To a solution of 2-(4-chloromethylphenoxy)-5-nitropyridine (12.32 g, 47 mmol) in DMF (120 mL) were added triethylamine (19.4 mL, 140 mmol) and t-butyl piperazine-1-carboxylate 11.27 g, 61 mmol), and the resulting solution was stirred for 3 hours at 50° C. Water was added to the residue, and extracted with ethyl acetate. The ethyl acetate layer was washed with water and brine. The ethyl acetate layer was dried over anhydrous magnesium sulfate, and evaporated. The residue was purified by silica gel column chromatography (n-hexane:ethyl acetate=1:1), to thereby yield 11.26 g of the title compound.

Appearance: Yellow powder $^1$H NMR ($CDCl_3$) δ 1.46 (9H, s), 2.40-2.44 (4H, m), 3.43-3.46 (4H, m), 3.54 (2H, s), 7.04 (1H, d, J=8.9 Hz), 7.09-7.14 (2H, m), 7.38-7.44 (2H, m), 8.48 (1H, dd, J=8.9 Hz, 2.8 Hz), 9.05 (1H, d, J=2.8 Hz).

The following compound was produced in the same manner as in Reference Example 973.

Reference Example 974

4-{1-[4-(5-Nitropyridin-2-yloxy)phenyl] ethyl}morpholine $^1$H NMR ($CDCl_3$) δ 1.38 (3H, d, J=6.8 Hz), 2.36-2.54 (4H, m), 3.37 (1H, q, J=6.8 Hz), 3.69-3.72 (4H, m), 7.02 (1H, dd, J=9.1 Hz, 0.5 Hz), 7.11 (2H, d, J=8.6 Hz), 7.40 (2H, d, J=8.5 Hz), 8.47 (1H, dd, J=9.1 Hz, 2.8 Hz), 9.06 (1H, dd, J=2.8 Hz, 0.5 Hz).

Reference Example 975

Production of methanesulfonic acid 6-(4-nitrophenoxy)-pyridin-3-ylmethyl ester

[6-(4-nitrophenoxy)pyridin-3-yl]methanol (6.1 g, 24.8 mmol) was dissolved in dichloromethane (150 mL), and to the resulting solution was added triethylamine (4.15 mL, 29.8 mmol) under ice cooling. To the resulting solution was added dropwise methanesulfonic acid chloride (2.11 mL, 27.3 mmol), and then stirred under a nitrogen atmosphere for 30 minutes at 0° C. The reaction solution was washed with a saturated sodium bicarbonate solution and brine. The organic layer was dried over anhydrous magnesium sulfate, and evaporated. To the residue was added a mixed solvent (50 mL) of n-hexane ethyl acetate=1:1. The precipitated crystals were removed by suction filtration, to thereby yield 7.9 g of the title compound.

Appearance: White powder $^1$H NMR ($CDCl_3$) δ 3.04 (3H, s), 5.23 (2H, s), 7.09 (1H, d, J=8.4 Hz), 7.29 (2H, d, J=9.1 Hz), 7.88 (1H, dd, J=8.4 Hz, 2.5 Hz), 8.23 (1H, d, J=2.3 Hz), 8.28 (2H, d, J=9.1 Hz).

The following compounds were produced in the same manner as in Reference Example 975.

TABLE 136

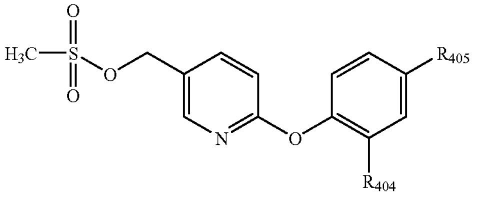

| Reference Example No. | $R_{404}$ | $R_{405}$ | $^1$H NMR ($CDCl_3$) δ ppm |
|---|---|---|---|
| 976 | —$CH_3$ | —$NO_2$ | 2.29 (3H, s), 3.03 (3H, s), 5.22 (2H, s), 7.08 (1H, dd, J = 8.4 Hz, 0.5 Hz), 7.18 (1H, d, J = 8.9 Hz), 7.86 (1H, dd, J = 8.4 Hz, 2.5 Hz), 8.11 (1H, dd, J = 8.9 Hz, 2.8 Hz), 8.17 (1H, dd, J = 2.5 Hz, 0.5 Hz), 8.19 (1H, d, J = 2.8 Hz). |
| 977 | —H | 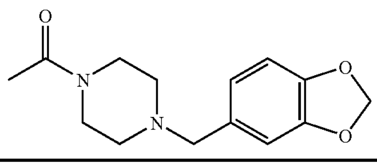 | 2.65 (4H, brs), 3.01 (3H, s), 3.65-3.75 (6H, m), 5.22 (2H, s), 5.97 (2H, s), 6.79 (2H, s), 6.92 (1H, s), 7.00 (1H, d, J = 8.4 Hz), 7.18 (2H, d, J = 8.6 Hz), 7.47 (2H, d, J = 8.7 Hz), 7.81 (1H, dd, J = 2.5 Hz, 8.4 Hz), 8.20 (1H, d, J = 2.0 Hz). |

Reference Example 978

Production of 2-(4-nitrophenoxy)-5-(4-trifluoromethyl-phenoxymethyl)pyridine

Methanesulfonic acid 6-(4-nitrophenoxy)-pyridin-3-ylmethyl ester (4.86 g, 15 mmol) was dissolved in DMF (250 mL), and to the resulting solution were added 4-hydroxybenzotrifluoride (2.92 g, 18 mmol) and potassium carbonate (3.11 g, 22.5 mmol). The resulting solution was stirred under a nitrogen atmosphere for 1 hour at 50° C. The reaction solution was concentrated under reduced pressure. To the residue was added ethyl acetate, and washed with a saturated sodium bicarbonate solution and brine. The organic layer was dried over anhydrous magnesium sulfate, and evaporated. The residue was purified by silica gel column chromatography (dichloromethane methanol=80:1), to thereby yield 5.8 g of the title compound.

Appearance: Pale yellow powder $^1$H NMR ($CDCl_3$) δ 5.09 (2H, s), 7.02-7.10 (3H, m), 7.26-7.31 (2H, m), 7.56-7.59 (2H, m), 7.88 (1H, dd, J=8.4 Hz, 2.5 Hz), 8.25-8.31 (3H, m).

The following compound was produced in the same manner as in Reference Example 978.

Reference Example 979

2-(2-Methyl-4-nitrophenoxy)-5-(4-trifluoromethyl-phenoxymethyl)pyridine $^1$H NMR ($CDCl_3$) δ 2.31 (3H, s), 5.07 (2H, s), 7.03 (2H, d, J=8.6 Hz), 7.08 (1H, d, J=8.4 Hz), 7.17 (1H, d, J=8.9 Hz), 7.57 (2H, d, J=8.4 Hz), 7.87 (1H, dd, J=8.4 Hz, 2.5 Hz), 8.10 (1H, dd, J=8.9 Hz, 2.8 Hz), 8.18 (1H, d, J=2.6 Hz), 8.21 (1H, d, J=2.5 Hz).

Example 1

Production of N-{6-[4-(4-benzylpiperazine-1-carbonyl)-phenoxy]pyridin-3-yl}-4-trifluoromethylbenzamide To a solution of 4-[5-(4-trifluoromethyl-benzoylamino)pyridin-2-yloxy]benzoic acid (1.19 g, 2.3 mmol) in DMF (30 mL) were added 1-ethyl-3-(3-dimethylaminopropyl)carbodiimide hydrochloride (530 mg, 2.8 mmol), 1-hydroxybenzotriazole monohydrate (370 mg, 2.7 mmol) and benzylpiperazine (0.475 mL, 2.7 mmol) under ice cooling. The resulting solution was stirred for 1 day gradually warming up to room temperature. To the residue was added a saturated sodium bicarbonate solution and extracted with ethyl acetate. The ethyl acetate layer was washed with a saturated sodium bicarbonate solution and brine, dried over anhydrous magnesium sulfate, and evaporated. The residue was purified by silica gel column chromatography (methanol:chloroform=1:19), to thereby yield 800 mg of the title compound.

Appearance: White needles $^1$H NMR ($CDCl_3$) δ 2.46 (4H, brs), 3.55 (2H, s), 3.72 (4H, brs), 6.96 (1H, d, J=8.9 Hz), 7.10-7.13 (2H, m), 7.28-7.40 (7H, m), 7.74 (2H, d, J=8.3 Hz), 8.02 (2H, d, J=8.3 Hz), 8.16-8.21 (1H, m), 8.32 (1H, d, J=2.6 Hz), 8.53 (1H, brs).

The following compounds were produced in the same manner as in Example 1.

TABLE 137

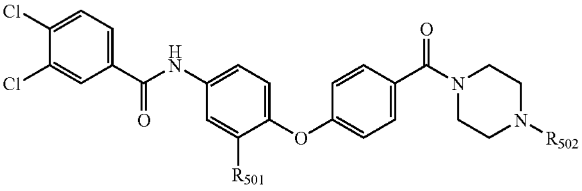

| Example No. | $R_{501}$ | $R_{502}$ | Form | mp (° C.) |
|---|---|---|---|---|
| 2 | —H | —$CH_3$ | hydrochloride | 175-176 |
| 3 | —H | benzyl | hydrochloride | 187-189 |
| 4 | —H | piperonyl | free | 182-183 |
| 5 | —H | —$COOC(CH_3)_3$ | free | 217-220 |
| 6 | —H | -Ac | free | 152-154 |
| 7 | —H | —$(CH_2)_2OH$ | hydrochloride | 153-155 |
| 8 | —F | benzyl | free | 172-173 |
| 9 | —F | piperonyl | free | 170-171 |

TABLE 138

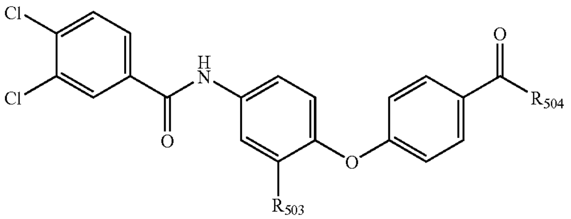

| Example No. | $R_{503}$ | $R_{504}$ | Form | mp (° C.) |
|---|---|---|---|---|
| 10 | —H | morpholino | free | 189-192 |
| 11 | —F | morpholino | free | 203-204 |
| 12 | —F | 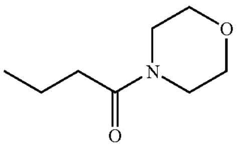 | free | 210-211 |

TABLE 138-continued

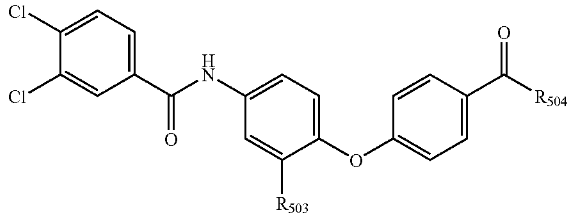

| Example No. | $R_{503}$ | $R_{504}$ | Form | mp (° C.) |
|---|---|---|---|---|
| 13 | —F | 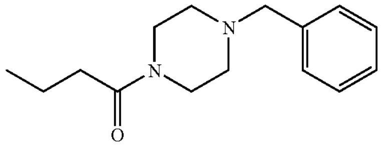 | hydrochloride | 233-235 |
| 14 | —F | 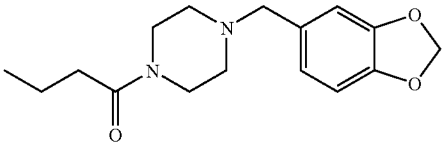 | hydrochloride | 247-249 |
| 15 | —H | 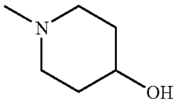 | free | 174-175 |
| 16 | —H | 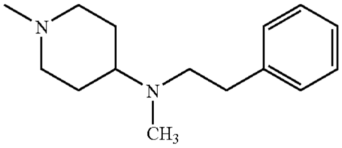 | hydrochloride | 213-216 |

TABLE 139

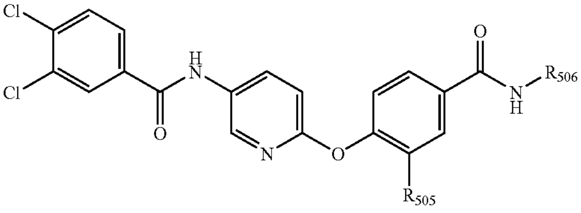

| Example No. | $R_{505}$ | $R_{506}$ | $^1$H NMR (DMSO-$d_6$) δ ppm |
|---|---|---|---|
| 17 | —$CH_3$ | —NHAc | 1.92 (3H, s), 2.17 (3H, s), 7.13 (1H, d, J = 8.2 Hz), 7.14 (1H, d, J = 8.9 Hz), 7.74 (1H, dd, J = 8.2 Hz, 2.2 Hz), 7.84 (1H, d, J = 8.2 Hz), 7.84 (1H, d, J = 2.2 Hz), 7.95 (1H, dd, J = 8.2 Hz, 2.2 Hz), 8.22 (1H, d, J = 2.2 Hz), 8.23 (1H, dd, J = 8.9 Hz, 2.6 Hz), 8.46 (1H, d, J = 2.6 Hz), 9.89 (1H, s), 10.24 (1H, s), 10.57 (1H, s). |
| 18 | —H | cyclopropyl | 0.51-0.60 (2H, m), 0.66-0.74 (2H, m), 2.80-2.89 (1H, m), 7.10-7.20 (3H, m), 7.81-7.89 (3H, m), 7.95 (1H, dd, J = 8.4 Hz, 2.1 Hz), 8.19-8.28 (2H, m), 8.42 (1H, brd), 8.52 (1H, d, J = 2.7 Hz), 10.59 (1H, s). |

TABLE 139-continued

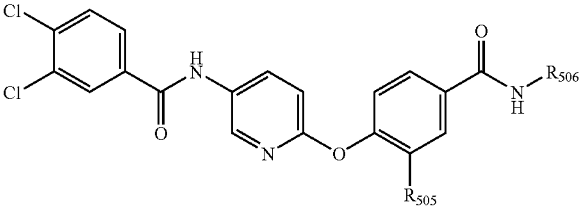

| Example No. | $R_{505}$ | $R_{506}$ | $^1$H NMR (DMSO-$d_6$) δ ppm |
|---|---|---|---|
| 19 | —H | cyclohexyl | 1.06-1.19 (1H, m), 1.21-1.36 (4H, m), 1.55-1.65 (1H, m), 1.69-1.78 (2H, m), 1.78-1.87 (2H, m), 3.69-3.80 (1H, m), 7.10-7.20 (3H, m), 7.85 (1H, d, J = 8.4 Hz), 7.86-7.92 (2H, m), 7.95 (1H, dd, J = 8.4 Hz, 2.1 Hz), 8.17 (1H, brd), 8.20-8.29 (2H, m), 8.52 (1H, d, J = 2.7 Hz), 10.58 (1H, s). |
| 20 | —H | cyclopentyl | 1.46-1.60 (4H, m), 1.63-1.76 (2H, m), 1.82-1.94 (2H, m), 4.17-4.28 (1H, m), 7.10-7.20 (3H, m), 7.85 (1H, d, J = 8.4 Hz), 7.87-7.92 (2H, m), 7.95 (1H, dd, J = 8.4 Hz, 2.1 Hz), 8.19-8.28 (3H, m), 8.52 (1H, d, J = 2.6 Hz), 10.58 (1H, s). |

TABLE 139-continued

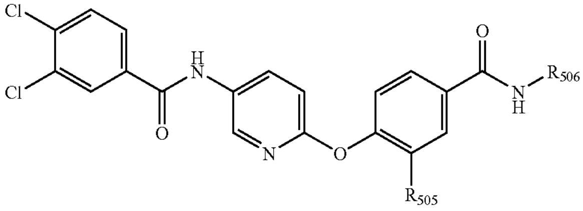

| Example No. | $R_{505}$ | $R_{506}$ | $^1$H NMR (DMSO-$d_6$) δ ppm |
|---|---|---|---|
| 21 | —H | cycloheptyl | 1.36-1.71 (10H, m), 1.80-1.90 (2H, m), 3.88-4.00 (1H, m), 7.10-7.20 (3H, m), 7.85 (1H, d, J = 8.4 Hz), 7.86-7.92 (2H, m), 7.95 (1H, dd, J = 8.4 Hz, 2.1 Hz), 8.17-8.28 (3H, m), 8.51 (1H, d, J = 2.6 Hz), 10.58 (1H, s). |
| 22 | —H | cyclododecanyl | 1.20-1.57 (20H, m), 1.61-1.63 (2H, m), 4.08-4.21 (1H, m), 7.10-7.21 (3H, m), 7.85 (1H, d, J = 8.4 Hz), 7.88-7.92 (2H, m), 7.95 (1H, dd, J = 8.4 Hz, 2.1 Hz), 8.09 (1H, brd), 8.20-8.29 (2H, m), 8.51 (1H, d, J = 2.7 Hz), 10.58 (1H, s). |
| 23 | —H | cyclooctyl | 1.44-1.65 (8H, m), 1.65-1.80 (6H, m), 3.98-4.09 (1H, m), 7.10-7.20 (3H, m), 7.85 (1H, d, J = 8.4 Hz), 7.88-7.92 (2H, m), |

TABLE 139-continued

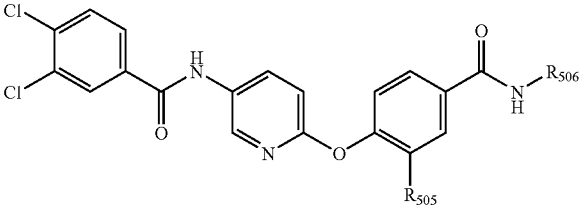

| Example No. | $R_{505}$ | $R_{506}$ | $^1$H NMR (DMSO-$d_6$) δ ppm |
|---|---|---|---|
| | | | 7.95 (1H, dd, J = 8.4 Hz, 2.1 Hz), 8.17-8.27 (3H, m), 8.51 (1H, d, J = 2.7 Hz), 10.58 (1H, s). |
| 24 | —H | cyclopropyl-methyl | 0.19-0.26 (2H, m), 0.38-0.47 (2H, m), 0.99-1.09 (1H, m), 3.12-3.19 (2H, m), 7.12-7.21 (3H, m), 7.85 (1H, d, J = 8.4 Hz), 7.89-7.94 (2H, m), 7.95 (1H, dd, J = 8.4 Hz, 2.1 Hz), 8.21-8.29 (2H, m), 8.53 (1H, d, J = 2.8 Hz), 8.54 (1H, brt), 10.60 (1H, s). |
| 25 | —H | $—(CH_2)_2NHAc$ | 1.81 (3H, s), 3.15-3.24 (2H, m), 3.24-3.33 (2H, m), 7.10-7.20 (3H, m), 7.80-8.00 (5H, m), 8.20-8.26 (2H, m), 8.48 (1H, brt), 8.52 (1H, d, J = 2.6 Hz), 10.59 (1H, s). |

TABLE 140

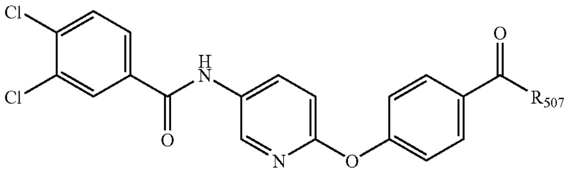

| Example No. | $R_{507}$ | Form | $^1$H NMR (solvent) δ ppm or MS |
|---|---|---|---|
| 26 | morpholino | hydro-chloride | $^1$H NMR (DMSO-$d_6$) 3.50-3.65 (8 H, m), 7.13-7.19 (3 H, m), 7.47 (2 H, d, J = 8.6 Hz), 7.84 (1 H, d, J = 8.2 Hz), 7.97 (1 H, dd, J = 8.3 Hz, 2.0 Hz), 8.23-8.27 (2 H, m), 8.54 (1 H, d, J = 2.6 Hz), 10.63 (1 H, s). |
| 27 | 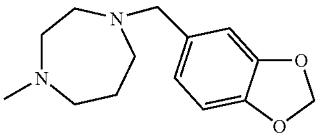 | free | $^1$H NMR ($CDCl_3$) 1.81-1.95 (2 H, m), 2.59-2.77 (4 H, m), 3.51-3.57 (4 H, m), 3.75 (2 H, brs), 5.94 (2 H, s), 6.71-6.75 (2 H, m), 6.83-6.93 (2 H, m), 7.05-7.10 (2 H, m), 7.32-7.37 (2 H, m), 7.54 (1 H, d, J = 8.2 Hz), 7.79 (1 H, dd, J = 8.3 Hz, 2.0 Hz), 8.06-8.10 (2 H, m), 8.30 (1 H, s), 8.96 (1 H, s). |
| 28 | 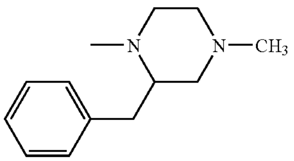 | free | MS 574 ($M^+$) |
| 29 | 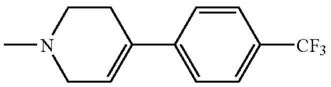 | free | MS 611 ($M^+$) |
| 30 | $—NH(CH_2)_2OCH_3$ | free | $^1$H NMR (DMSO-$d_6$) 3.32 (3 H, s), 3.39-3.48 (4 H, m), 7.15-7.20 (3 H, m), 7.85 (1 H, d, J = 8.3 Hz), 7.86-7.92 (2 H, m), 7.95 (1 H, dd, J = 8.4 Hz, 2.1 Hz), 8.20-8.26 (2 H, m), 8.50 (1 H, brt), 8.52 (1 H, d, J = 2.5 Hz), 10.59 (1 H, s). |

TABLE 140-continued

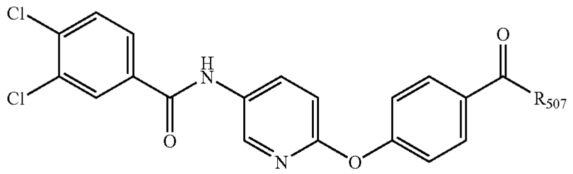

| Example No. | $R_{507}$ | Form | $^1H$ NMR (solvent) δ ppm or MS |
|---|---|---|---|
| 31 | 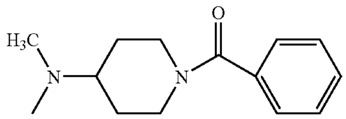 | free | MS 601 ($M^+$ − 1) |
| 32 | 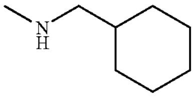 | free | $^1H$ NMR (DMSO-$d_6$) 0.86-0.99 (2 H, m), 1.10-1.27 (3 H, m), 1.50-1.65 (2 H, m), 1.65-1.78 (4 H, m), 3.06-3.15 (2 H, m), 7.11-7.22 (3 H, m), 7.85 (1 H, d, J = 8.4 Hz), 7.88-7.92 (2 H, m), 7.95 (1 H, dd, J = 8.4 Hz, 2.1 Hz), 8.20-8.28 (2 H, m), 8.40 (1 H, brt), 8.52 (1 H, d, J = 2.7 Hz), 10.58 (1 H, s). |
| 33 | $-NH(CH_2)_2OPh$ | free | $^1H$ NMR (DMSO-$d_6$) 3.63 (2 H, t, J = 5.8 Hz), 4.12 (2 H, t, J = 5.9 Hz), 6.90-7.01 (3 H, m), 7.13-7.24 (3 H, m), 7.26-7.35 (2 H, m), 7.85 (1 H, d, J = 8.4 Hz), 7.90-8.00 (3 H, m), 8.20-8.30 (2 H, m), 8.52 (1 H, d, J = 2.6 Hz), 8.69 (1 H, brt), 10.59 (1 H, s). |
| 34 | 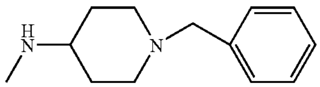 | free | MS 574 ($M^+$) |
| 35 | 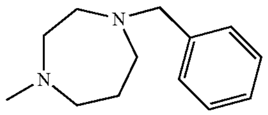 | free | $^1H$ NMR ($CDCl_3$) 1.80-1.96 (2 H, m), 2.61-2.79 (4 H, m), 3.45-3.57 (2 H, m), 3.62-3.67 (2 H, m), 3.75-3.77 (2 H, m), 6.94 (1 H, d, J = 8.6 Hz), 7.08-7.13 (2 H, m), 7.24-7.41 (7 H, m), 7.56 (1 H, d, J = 8.6 Hz), 7.76 (1 H, dd, J = 8.6 Hz, 2.0 Hz), 8.04 (1 H, d, J = 2.0 Hz), 8.07-8.14 (1 H, m), 8.29 (1 H, d, J = 2.0 Hz), 8.39 (1 H, s). |

TABLE 141

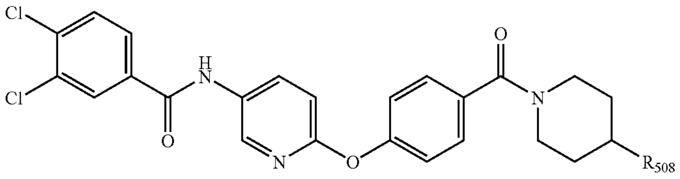

| Example No. | $R_{508}$ | Property |
|---|---|---|
| 36 | 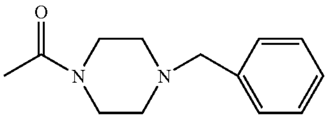 | mp 221-224° C. |
| 37 | 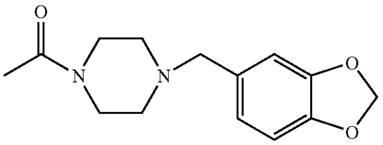 | mp 228-230° C. |

TABLE 141-continued

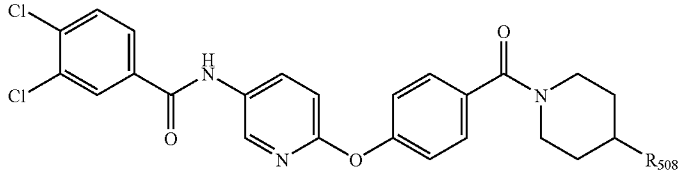

| Example No. | $R_{508}$ | Property |
|---|---|---|
| 38 | 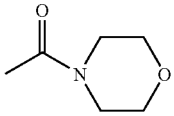 | mp 193-194° C. |
| 39 | —$N(CH_3)COOC(CH_3)_3$ | $^1H$ NMR ($CDCl_3$) δ 1.47 (9 H, s), 1.45-1.81 (4 H, m), 2.73 (3 H, s), 2.90 (2 H, brs), 4.10 (2 H, brs), 4.75 (1 H, brs), 6.95 (1 H, d, J = 8.7 Hz), 7.11 (2 H, d, J = 8.7 Hz), 7.39 (2 H, d, J = 8.7 Hz), 7.55 (1 H, d, J = 8.2 Hz), 7.77 (1 H, dd, J = 8.2 Hz, 2.0 Hz), 8.05 (1 H, d, J = 2.0 Hz), 8.14 (1 H, dd, J = 8.7 Hz, 2.6 Hz), 8.30 (1 H, d, J = 2.6 Hz), 8.77 (1 H, s). |
| 40 | —OPh | MS 560 ($M^+$ − 1) |
| 41 | 4-$CF_3$OPhO— | MS 629 ($M^+$) |
| 42 | 4-$CF_3$OPhO— | MS 644 ($M^+$ − 1) |
| 43 | 4-CNPhO— | MS 586 ($M^+$) |
| 44 | —$C_2H_5$ | MS 496 ($M^+$ − 1) |
| 45 | —$COOC_2H_5$ | $^1H$ NMR ($CDCl_3$) δ 1.27 (3 H, t, J = 7.0 Hz), 1.73 (2 H, brs), 1.95 (2 H, brs), 2.58 (1 H, m), 3.08 (2 H, brs), 3.86 (1 H, brs), 4.16 (2 H, q, J = 7.0 Hz), 4.50 (1 H, brs), 6.97 (1 H, d, J = 9.0 Hz), 7.12 (2 H, d, J = 8.5 Hz), 7.40 (2 H, d, J = 8.5 Hz), 7.57 (1 H, d, J = 8.5 Hz), 7.75 (1 H, dd, J = 8.5 Hz, 2.0 Hz), 8.03 (1 H, d, J = 2.0 Hz), 8.16 (1 H, dd, J = 9.0 Hz, 3.0 Hz), 8.30 (1 H, d, J = 3.0 Hz), 8.34 (1 H, brs). |
| 46 | —$(CH_2)_2N(CH_3)$Ph | MS 602 ($M^+$) |
| 47 | 2-FPh$CH_2$O— | MS 592 ($M^+$ − 1) |
| 48 | Ph$CH_2$O— | MS 574 ($M^+$ − 1) |
| 49 | cyclohexyl | MS 550 ($M^+$ − 1) |
| 50 | 4-ClPh- | MS 580 ($M^+$ + 1) |
| 51 | -Ph | MS 544 ($M^+$ − 1) |
| 52 | —$CHPh_2$ | MS 635 ($M^+$) |
| 53 | 2-$NH_2$PhCO— | MS 587 ($M^+$ − 1) |
| 54 | 4-$CH_3$OPhCONH— | MS 617 ($M^+$ − 1) |
| 55 | —NHCOPh | MS 587 ($M^+$ − 1) |
| 56 | 4-$CF_3$Ph$CH_2$O— | mp 186-187° C. |
| 57 | 4-ClPh$CH_2$O— | mp 176-177° C. |

TABLE 142

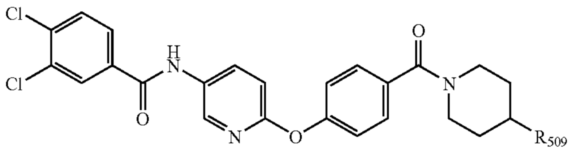

| Example No. | $R_{509}$ | MS |
|---|---|---|
| 58 | 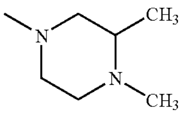 | 580 ($M^+$ − 1) |
| 59 | 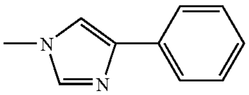 | 610 ($M^+$ − 1) |

TABLE 142-continued

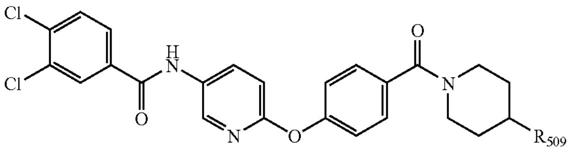

| Example No. | $R_{509}$ | MS |
|---|---|---|
| 60 | 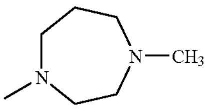 | 580 ($M^+$ − 1) |
| 61 | 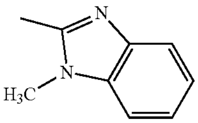 | 598 ($M^+$ − 1) |

TABLE 142-continued

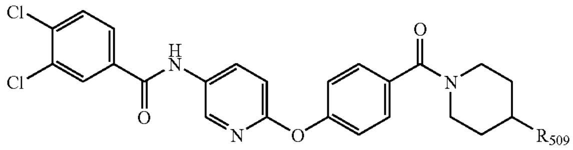

| Example No. | $R_{509}$ | MS |
|---|---|---|
| 62 | 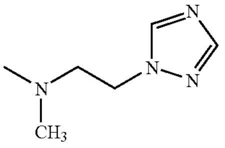 | 592 ($M^+ - 1$) |
| 63 | $Ph(CH_2)_2N(CH_3)$— | 600 ($M^+ - 2$) |
| 64 | $Ph_2CH(CH_2)_2N(CH_3)$— | 691 ($M^+ - 1$) |
| 65 | $4\text{-}CH_3SPh(CH_2)_2N(CH_3)$— | 648 ($M^+$) |
| 66 | 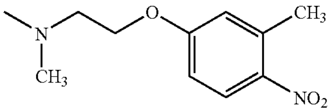 | 678 ($M^+ + H$) |
| 67 | 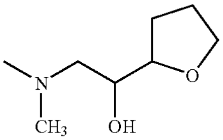 | 613 ($M^+ + H$) |
| 68 | $4\text{-}CH_3OPh(CH_2)_4N(CH_3)$— | 660 ($M^+$) |
| 69 | $4\text{-}CH_3Ph(CH_2)_2N(CH_3)$— | 617 ($M^+ + H$) |
| 70 | $PhO(CH_2)_2N(CH_3)$— | 618 ($M^+$) |
| 71 | $PhN(CH_3)(CH_2)_2N(CH_3)$— | 631 ($M^+$) |
| 72 | 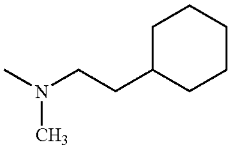 | 608 ($M^+$) |
| 73 | —$O(CH_2)_2Ph$ | 588 ($M^+ - 1$) |
| 74 | 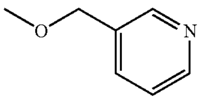 | 575 ($M^+ - 1$) |

TABLE 142-continued

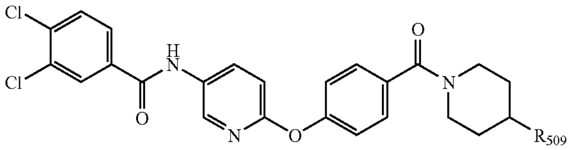

| Example No. | $R_{509}$ | MS |
|---|---|---|
| 75 | 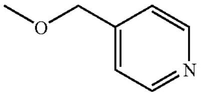 | 576 ($M^+$) |
| 76 | $4\text{-}ClPhCH_2$— | 594 ($M^+ + 1$) |
| 77 | $4\text{-}CF_3PhNH$— | 644 ($M^+$) |

TABLE 143

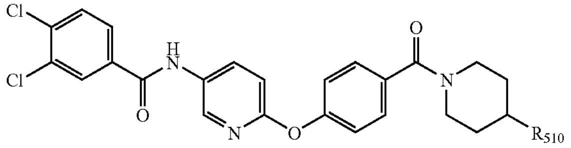

| Example No. | $R_{510}$ | MS |
|---|---|---|
| 78 | 4-CH3PhO$(CH_2)_2N(CH_3)$— | 633 ($M^+ + H$) |
| 79 | $Ph(CH_2)_3N(CH_3)$— | 616 ($M^+$) |
| 80 | 2-phenylmorpholino | 630 ($M^+$) |
| 81 | $4\text{-}CH_3PhCH_2$— | 572 ($M^+ - 1$) |
| 82 | morpholino | 554 ($M^+$) |
| 83 | $4\text{-}CH_3OPhCH_2O$— | 606 ($M^+ + H$) |
| 84 | $3\text{-}ClPhCH_2O$— | 608 ($M^+ - 1$) |
| 85 | $2\text{-}ClPhCH_2O$— | 608 ($M^+ - 1$) |
| 86 | $3,4\text{-}Cl_2PhCH_2O$— | 644 ($M^+ + 1$) |
| 87 | $3\text{-}CH_3OPhCH_2O$— | 604 ($M^+ - 1$) |
| 88 | $3,5\text{-}(CH_3O)_2PhCH_2O$— | 634 ($M^+ - 1$) |
| 89 | $4\text{-}CH_3PhCH_2O$— | 588 ($M^+ - 1$) |
| 90 | $3\text{-}CH_3PhCH_2O$— | 588 ($M^+ - 1$) |
| 91 | $2\text{-}CH_3PhCH_2O$— | 588 ($M^+ - 1$) |
| 92 | $3,4\text{-}(CH_3)_2PhCH_2O$— | 602 ($M^+ - 1$) |
| 93 | $4\text{-}FPhCH_2O$— | 592 ($M^+ - 1$) |
| 94 | $3\text{-}FPhCH_2O$— | 592 ($M^+ - 1$) |
| 95 | $3,5\text{-}F_2PhCH_2O$— | 610 ($M^+ - 1$) |
| 96 | $2\text{-}CF_3PhCH_2O$— | 642 ($M^+ - 1$) |
| 97 | $4\text{-}CF_3OPhCH_2O$— | 658 ($M^+ - 1$) |
| 98 | $3\text{-}CF_3OPhCH_2O$— | 658 ($M^+ - 1$) |
| 99 | $2\text{-}CF_3OPhCH_2O$— | 658 ($M^+ - 1$) |
| 100 | 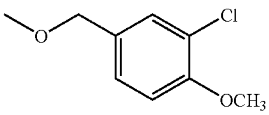 | 638 ($M^+ - 1$) |

TABLE 144

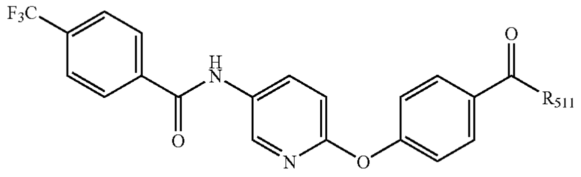

| Example No. | $R_{511}$ | mp (° C.) or $^1$H NMR ($CDCl_3$) δ ppm |
|---|---|---|
| 101 | 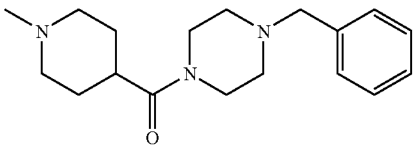 | mp 218-220 |
| 102 | 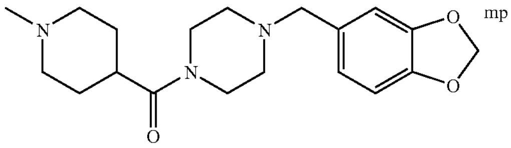 | mp 227-231 |
| 103 | 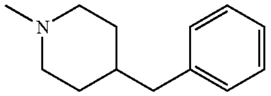 | $^1$H NMR 1.09-1.30 (1 H, m), 1.60-1.87 (4 H, m), 2.55-2.95 (4 H, m), 3.80 (1 H, brs), 4.59 (1 H, brs), 6.92 (1 H, d, J = 8.7 Hz), 7.05-7.35 (9 H, m), 7.71 (2 H, d, J = 8.6 Hz), 8.04 (2 H, d, J = 8.1 Hz), 8.14 (1 H, dd, J = 8.9 Hz, 2.6 Hz), 8.34 (1 H, d, J = 2.6 Hz), 8.99 (1 H, s). |
| 104 | 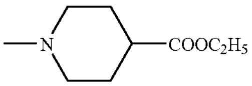 | $^1$H NMR 1.27 (3 H, t, J = 7.0 Hz), 1.74 (2 H, brs), 1.95 (2 H, brs), 2.58 (1 H, m), 3.08 (2 H, brs), 3.92 (1 H, brs), 4.17 (2 H, q, J = 7.0 Hz), 4.51 (1 H, brs), 7.01 (1 H, d, J = 9.0 Hz), 7.16 (2 H, d, J = 8.5 Hz), 7.44 (2 H, d, J = 8.5 Hz), 7.78 (2 H, d, J = 8.0 Hz), 7.88 (1 H, brs), 8.01 (2 H, d, J = 8.0 Hz), 8.24 (1 H, dd, J = 9.0 Hz, 3.0 Hz), 8.32 (1 H, d, J = 3.0 Hz) |
| 105 | 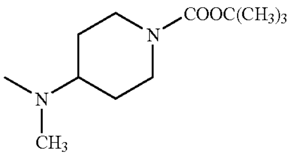 | $^1$H NMR 1.46 (9 H, s), 1.50-1.90 (4 H, m), 2.35-3.00 (2 H, m), 2.89 (3 H, s), 4.10-4.70 (3 H, m), 6.99 (1 H, d, J = 8.7 Hz), 7.14 (2 H, d, J = 8.3 Hz), 7.40 (2 H, d, J = 8.3 Hz), 7.76 (2 H, d, J = 8.1 Hz), 8.03 (2 H, d, J = 8.1 Hz), 8.22 (1 H, dd, J = 8.7 Hz, 2.6 Hz), 8.33 (1 H, d, J = 2.6 Hz), 8.34 (1 H, brs). |

TABLE 145

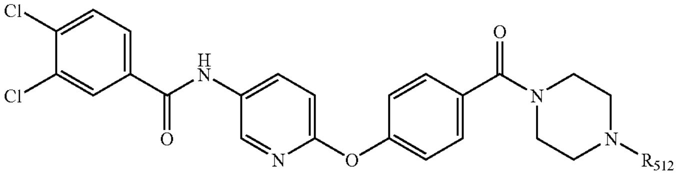

| Example No. | $R_{512}$ | $^1$H NMR ($CDCl_3$) δ ppm or MS |
|---|---|---|
| 106 | 4-$CH_3$OPhCH(Ph)- | MS 665 ($M^+$ − 1) |
| 107 | 4-$CH_3$OPhCOCH$_2$— | $^1$H NMR 2.63 (4 H, brs), 3.65 (4 H, brs), 3.82 (2 H, s), 3.88 (3 H, s), 6.92-6.98 (3 H, m), 7.12 (2 H, d, J = 8.7 Hz), 7.41 (2 H, d, J = 8.7 Hz), 7.56 (1 H, d, J = 8.2 Hz), 7.75 (1 H, dd, J = 8.2 Hz, 2.1 Hz), 7.97 (2 H, d, J = 8.9 Hz), 8.03 (1 H, d, J = 2.0 Hz), 8.16 (1 H, dd, J = 8.9 Hz, 2.8 Hz), 8.30 (1 H, d, J = 2.8 Hz), 8.39 (1 H, s). |

TABLE 145-continued

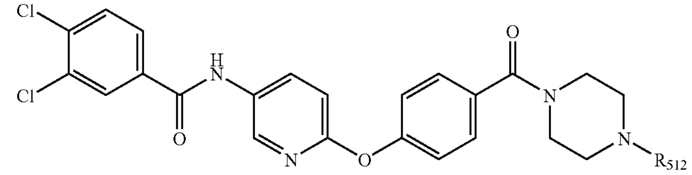

| Example No. | $R_{512}$ | $^1H$ NMR ($CDCl_3$) δ ppm or MS |
|---|---|---|
| 108 | 4-ClPh$COCH_2$— | $^1H$ NMR 2.63 (4 H, brs), 3.66 (4 H, brs), 3.83 (2 H, s), 6.97 (1 H, d, J = 8.7 Hz), 7.13 (2 H, d, J = 8.6 Hz), 7.39-7.47 (4 H, m), 7.56 (1 H, d, J = 8.4 Hz), 7.74 (1 H, dd, J = 8.2 Hz, 2.1 Hz), 7.94 (2 H, d, J = 8.6 Hz), 8.02 (1 H, d, J = 2.0 Hz), 8.16 (1 H, dd, J = 8.7 Hz, 2.8 Hz), 8.30 (1 H, d, J = 2.8 Hz), 8.37 (1 H s). |
| 109 | 3-pyridyl | $^1H$ NMR 3.20 (4 H, brs), 3.78 (4 H, brs), 6.93 (1 H, d, J = 8.7 Hz), 7.11 (2 H, d, J = 8.6 Hz), 7.19-7.21 (2 H, m), 7.39 (2 H, d, J = 8.6 Hz), 7.46 (1 H, d, J = 8.4 Hz), 7.76 (1 H, dd, J = 8.4 Hz, 2.0 Hz), 8.03 (1 H, d, J = 2.0 Hz), 8.11-8.25 (3 H, m), 8.36 (1 H, d, J = 2.5 Hz), 9.81 (1 H, s). |
| 110 | —$CH_2$CONHPh | MS 603 ($M^+$) |
| 111 | 2-pyridyl | MS 547 ($M^+$) |
| 112 | 4-pyridyl | MS 547 ($M^+$) |
| 113 | 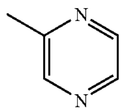 | MS 548 ($M^+$) |
| 114 | 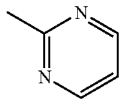 | MS 548 ($M^+$) |
| 115 | —$(CH_2)_4$Ph | MS 603 ($M^+$ + H) |
| 116 | —$CH(C_2H_5)_2$ | MS 540 ($M^+$) |
| 117 | —$CH(CH_3)_2$ | MS 511 ($M^+$ − 1) |
| 118 | —$(CH_2)_2N(CH_3)_2$ | MS 540 ($M^+$ − 1) |

TABLE 146

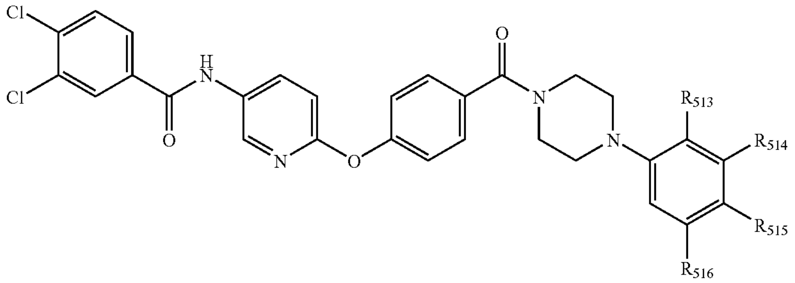

| Example No. | $R_{513}$ | $R_{514}$ | $R_{515}$ | $R_{516}$ | MS ($M^+$) |
|---|---|---|---|---|---|
| 119 | —F | —H | —H | —H | 564 |
| 120 | —Cl | —H | —H | —H | 582 |
| 121 | —$CF_3$ | —H | —H | —H | 614 |
| 122 | —$OCH_3$ | —H | —H | —H | 576 |
| 123 | —$CH_3$ | —H | —H | —H | 560 |
| 124 | —H | —$CF_3$ | —H | —H | 614 |
| 125 | —H | —Cl | —H | —H | 582 |
| 126 | —H | —$OCH_3$ | —H | —H | 576 |
| 127 | —H | —$CH_3$ | —H | —H | 560 |
| 128 | —H | —H | —CN | —H | 571 |
| 129 | —H | —H | —$OCF_3$ | —H | 630 |

TABLE 146-continued

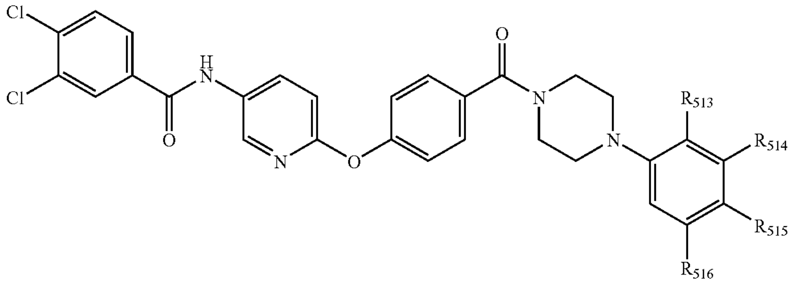

| Example No. | $R_{513}$ | $R_{514}$ | $R_{515}$ | $R_{516}$ | MS ($M^+$) |
|---|---|---|---|---|---|
| 130 | —H | —H | $—CO_2C(CH_3)_3$ | —H | 646 |
| 131 | —H | —H | —F | —H | 564 |
| 132 | —H | —H | —Cl | —H | 580 |
| 133 | —H | —H | $—OCH_3$ | —H | 576 |
| 134 | —H | —H | $—CH_3$ | —H | 560 |
| 135 | —H | —H | $—CF_3$ | —H | 614 |
| 136 | —H | —H | -Ph | —H | 622 |
| 137 | —Cl | —Cl | —H | —H | 616 |
| 138 | $—CH_3$ | $—CH_3$ | —H | —H | 574 |
| 139 | —H | $—CH_3$ | $—CH_3$ | —H | 574 |
| 140 | —F | —H | —F | —H | 582 |
| 141 | $—OCH_3$ | —H | —H | —Cl | 612 |

TABLE 147

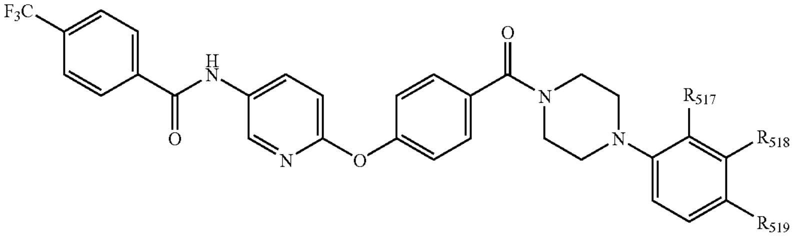

| Example No. | $R_{517}$ | $R_{518}$ | $R_{519}$ | mp (° C.) or $^1$H NMR ($CDCl_3$) δ ppm |
|---|---|---|---|---|
| 142 | —H | —H | —H | $^1$H NMR 3.20 (4 H, brs), 3.79 (4 H, brs), 6.89-6.96 (3 H, m), 7.00 (1 H, d, J = 8.9 Hz), 7.14-7.19 (2 H, m), 7.27-7.33 (2 H, m), 7.43-7.48 (2 H, m), 7.76 (2 H, d, J = 8.1 Hz), 8.02 (2 H, d, J = 8.1 Hz), 8.23 (1 H, dd, J = 8.9 Hz, 2.7 Hz), 8.31-8.34 (2 H, m). |
| 143 | —F | —H | —H | mp 193-194 |
| 144 | —Cl | —H | —H | $^1$H NMR 3.07 (4 H, brs), 3.82 (4 H, brs), 7.00-7.06 (3 H, m), 7.18 (2 H, d, J = 8.4 Hz), 7.22-7.26 (1 H, m), 7.38-7.41 (1 H, m), 7.48 (2 H, d, J = 8.6 Hz), 7.77 (2 H, d, J = 8.1 Hz), 8.04 (2 H, d, J = 8.1 Hz), 8.24 (1 H, dd, J = 8.9 Hz, 2.4 Hz), 8.30 (1 H, brs), 8.35 (1 H, d, J = 2.4 Hz). |
| 145 | —H | —Cl | —H | $^1$H NMR 3.19 (4 H, brs), 3.76 (4 H, brs), 6.77-6.81 (1 H, m), 6.86-6.88 (2 H, m), 6.99 (1 H, d, J = 8.9 Hz), 7.13-7.22 (3 H, m), 7.40-7.45 (2 H, m), 7.73 (2 H, d, J = 8.4 Hz), 8.02 (2 H, d, J = 8.4 Hz), 8.21 (1 H, dd, J = 8.9 Hz, 2.7 Hz), 8.34 (1 H, d, J = 2.7 Hz), 8.56 (1 H, s). |
| 146 | —H | $—CH_3$ | —H | $^1$H NMR 2.31 (3 H, s), 3.15 (4 H, brs), 3.74 (4 H, brs), 6.71-6.73 (3 H, m), 6.97 (1 H, d, J = 8.9 Hz), 7.11-7.18 (3 H, m), 7.42 (2 H, d, J = 8.1 Hz), 7.72 (2 H, d, J = 8.1 Hz), 8.01 (2 H, d, J = 8.1 Hz), 8.18-8.21 (1 H, m), 8.34 (1 H, brs), 8.54 (1 H, brs). |
| 147 | —H | $—OCH_3$ | —H | $^1$H NMR 3.07 (4 H, brs), 3.73 (4 H, brs), 3.88 (3 H, s), 6.88-7.08 (5 H, m), 7.13-7.17 (2 H, m), 7.42-7.47 (2 H, m), 7.75 (2 H, d, J = 8.4 Hz), 8.03 (2 H, d, J = 7.8 Hz), 8.21 (1 H, dd, J = 8.9 Hz, 2.4 Hz), 8.34 (1 H, d, J = 2.4 Hz), 8.45 (1 H, brs). |
| 148 | —H | $—CF_3$ | —H | mp 174-177 |
| 149 | —H | —H | —OH | mp 241-242 |

TABLE 147-continued

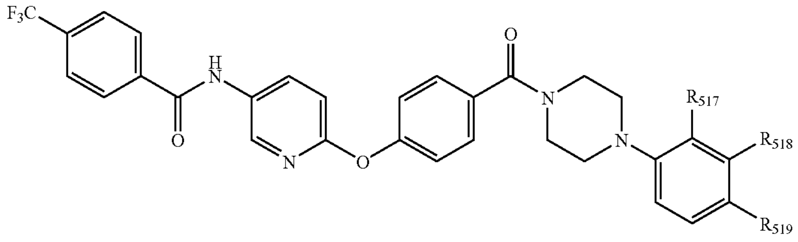

| Example No. | $R_{517}$ | $R_{518}$ | $R_{519}$ | mp (° C.) or $^1H$ NMR ($CDCl_3$) δ ppm |
|---|---|---|---|---|
| 150 | —H | —H | —$OCH_3$ | $^1H$ NMR 3.06 (4 H, brs), 3.63-3.91 (7 H, m), 6.83-6.93 (4 H, m), 6.99 (1 H, d, J = 8.6 Hz), 7.15 (2 H, d, J = 8.4 Hz), 7.44 (2 H, d, J = 8.4 Hz), 7.75 (2 H, d, J = 8.4 Hz), 8.02 (2 H, d, J = 8.1 Hz), 8.22 (1 H, dd, J = 8.9 Hz, 2.4 Hz), 8.33 (1 H, d, J = 2.4 Hz), 8.40 (1 H, brs). |
| 151 | —H | —H | —CN | $^1H$ NMR 3.23 (4 H, brs), 3.79 (4 H, brs), 7.01 (1 H, d, J = 8.9 Hz), 7.12-7.19 (5 H, m), 7.33-7.39 (1 H, m), 7.43-7.48 (2 H, m), 7.74 (2 H, d, J = 8.4 Hz), 8.02 (2 H, d, J = 8.4 Hz), 8.23 (1 H, dd, J = 8.9 Hz, 2.7 Hz), 8.35 (1 H, d, J = 2.7 Hz), 8.47 (1 H, s). |

TABLE 148

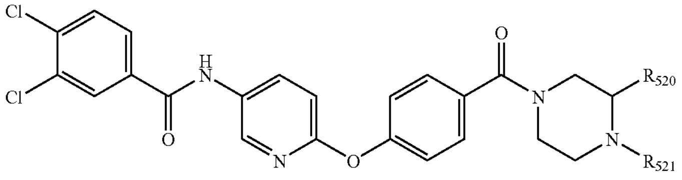

| Example No. | $R_{520}$ | $R_{521}$ | $^1H$ NMR (solvent) δ ppm or MS |
|---|---|---|---|
| 152 | —H | piperonyl | $^1H$ NMR ($CDCl_3$) 2.38-2.45 (4 H, m), 3.45 (2 H, s), 3.49-3.74 (4 H, m), 5.95 (2 H, s), 6.74 (2 H, s), 6.85 (1 H, s), 6.97 (1 H, d, J = 8.6 Hz), 7.10 (2 H, d, J = 8.9 Hz), 7.41 (2 H, d, J = 8.9 Hz), 7.58 (1 H, d, J = 8.3 Hz), 7.74 (1 H, dd, J = 8.3 Hz, 2.0 Hz), 8.02 (1 H, d, J = 2.3 Hz), 8.13-8.20 (2 H, m), 8.29 (1 H, d, J = 2.6 Hz). |
| 153 | —H | —$COOCH(CH_3)_3$ | $^1H$ NMR (DMSO-$d_6$) 1.41 (9 H, s), 3.39-3.50 (8 H, m), 7.13-7.19 (3 H, m), 7.45-7.48 (2 H, m), 7.84 (1 H, d, J = 8.4 Hz), 7.95 (1 H, dd, J = 8.4 Hz, 2.1 Hz), 8.21-8.26 (2 H, m), 8.52 (1 H, d, J = 2.3 Hz), 10.58 (1 H, s). |
| 154 | —H | 2-naphthylmethyl | MS 611 ($M^+$ + 1) |
| 155 | —H | 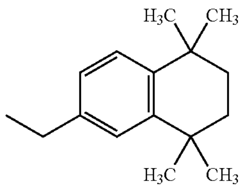 | MS 671 ($M^+$ + 1) |
| 156 | —H | 1-naphthylmethyl | MS 611 ($M^+$ + 1) |
| 157 | —$CH_3$ | 3,4-$(CH_3O)_2PhCH_2$— | MS 633 ($M^+$ + 1) |
| 158 | —H | 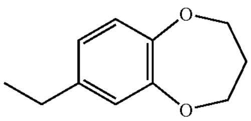 | MS 631 ($M^+$ − 1) |
| 159 | —H | —$CH(CH_3)Ph$ | MS 573 ($M^+$ − 1) |

TABLE 148-continued
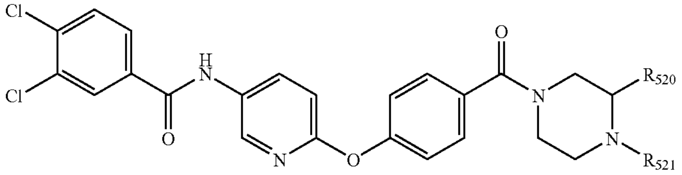
| Example No. | $R_{520}$ | $R_{521}$ | $^1H$ NMR (solvent) δ ppm or MS |
|---|---|---|---|
| 160 | —H | 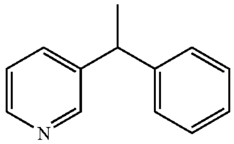 | MS 637 ($M^+$) |
| 161 | —H | $(4\text{-}FPh)_2CH$— | MS 671 ($M^+ - 1$) |
| 162 | —H | $-(CH_2)_3CH_3$ | MS 526 ($M^+$) |
| 163 | —H | $-(CH_2)_3Ph$ | MS 588 ($M^+$) |
| 164 | —H | cyclopentyl | MS 538 ($M^+$) |
| 165 | —H | cycloheptyl | MS 565 ($M^+ - 1$) |
TABLE 149
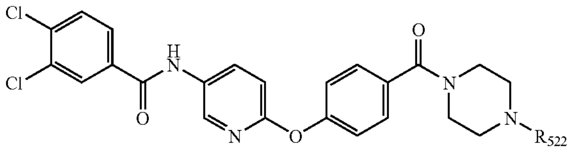
| Example No. | $R_{522}$ | MS |
|---|---|---|
| 166 | 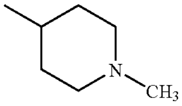 | 567 ($M^+$) |
| 167 | 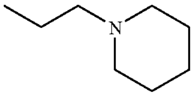 | 581 ($M^+$) |
| 168 | 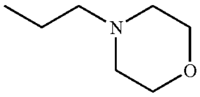 | 583 ($M^+$) |
| 169 | 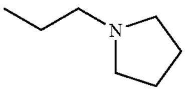 | 567 ($M^+$) |
TABLE 149-continued
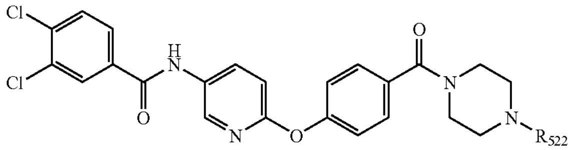
| Example No. | $R_{522}$ | MS |
|---|---|---|
| 170 | 4-pyridylmethyl | 561 ($M^+$) |
| 171 | 2-pyridylmethyl | 562 ($M^+ + H$) |
| 172 | 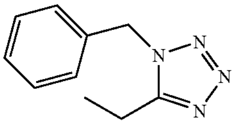 | 643 ($M^+ + H$) |
| 173 | 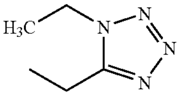 | 580 ($M^+$) |
| 174 | 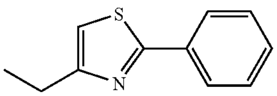 | 643 ($M^+$) |

TABLE 150

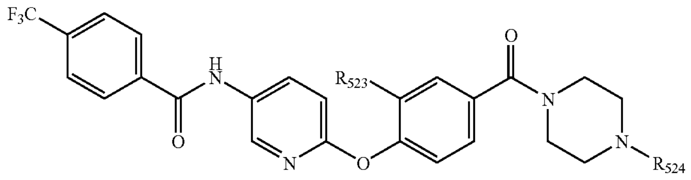

| Example No. | $R_{523}$ | $R_{524}$ | mp (° C.) or $^1$H NMR (solvent) δ ppm |
|---|---|---|---|
| 175 | —H | 3-pyridyl | $^1$H NMR ($CDCl_3$) 3.21 (4 H, brs), 3.78 (4 H, brs), 6.98 (1 H, d, J = 8.7 Hz), 7.13-7.21 (4 H, m), 7.41-7.44 (2 H, m), 7.70 (2 H, d, J = 8.1 Hz), 8.02 (2 H, d, J = 8.1 Hz), 8.12-8.14 (1 H, m), 8.20-8.27 (2 H, m), 8.35 (1 H, d, J = 2.6 Hz), 8.99 (1 H, s). |
| 176 | —H | 2-pyridyl | mp 222-224 |
| 177 | —F | 3-pyridyl | $^1$H NMR ($CDCl_3$) 3.21 (4 H, brs), 3.79 (4 H, brs), 7.05 (1 H, d, J = 8.4 Hz), 7.20-7.30 (5 H, m), 7.71 (2 H, d, J = 8.2 Hz), 8.00 (2 H, d, J = 8.2 Hz), 8.14 (1 H, brs), 8.21-8.25 (3 H, m), 8.78 (1 H, s). |
| 178 | —H | 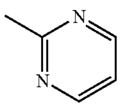 | mp 205-206 |
| 179 | —H | 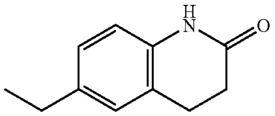 | $^1$H NMR (DMSO-$d_6$) 2.38 (4 H, brs), 2.43 (2 H, t, J = 7.5 Hz), 2.86 (2 H, t, J = 7.5 Hz), 3.41 (2 H, s), 3.45 (4 H, brs), 6.80 (1 H, d, J = 7.9 Hz), 7.06 (1 H, d, J = 7.9 Hz), 7.10 (1 H, s), 7.15 (1 H, d, J = 8.8 Hz), 7.17 (2 H, d, J = 8.4 Hz), 7.44 (2 H, d, J = 8.4 Hz), 7.94 (2 H, d, J = 8.0 Hz), 8.17 (2 H, d, J = 8.0 Hz), 8.26 (1 H, dd, J = 8.8 Hz, 2.6 Hz), 8.54 (1 H, d, J = 2.6 Hz), 10.06 (1 H, s), 10.68 (1 H, s). |
| 180 | —H | 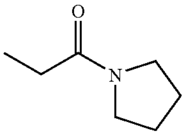 | $^1$H NMR ($CDCl_3$) 1.71-2.05 (4 H, m), 2.58 (4 H, brs), 3.16 (2 H, s), 3.36-3.53 (4 H, m), 3.55 (2 H, brs), 3.74 (2 H, brs), 7.00 (1 H, d, J = 8.9 Hz), 7.14 (2 H, d, J = 8.6 Hz), 7.42 (2 H, d, J = 8.6 Hz), 7.76 (2 H, d, J = 8.1 Hz), 8.04 (2 H, d, J = 8.1 Hz), 8.26 (1 H, dd, J = 8.9 Hz, 2.6 Hz), 8.34 (1 H, d, J = 2.6 Hz), 8.50 (1 H, s). |
| 181 | —H | $—COOC(CH_3)_3$ | $^1$H NMR ($CDCl_3$) 1.48 (9 H, s), 3.45 (4 H, brs), 3.58 (4 H, brs), 6.99 (1 H, d, J = 8.7 Hz), 7.15 (2 H, d, J = 8.7 Hz), 7.41 (2 H, d, J = 8.7 Hz), 7.74 (2 H, d, J = 8.2 Hz), 8.02 (2 H, d, J = 8.2 Hz), 8.21 (1 H, dd, J = 8.7 Hz, 2.6 Hz), 8.33 (1 H, d, J = 2.6 Hz), 8.43 (1 H, brs). |
| 182 | —H | $—CH_2COOC_2H_5$ | $^1$H NMR ($CDCl_3$) 1.28 (3 H, t, J = 7.1 Hz), 2.61 (4 H, brs), 3.26 (2 H, s), 3.57 (2 H, brs), 3.78 (2 H, brs), 4.19 (2 H, q, J = 7.1 Hz), 6.97 (1 H, d, J = 8.7 Hz), 7.12 (2 H, d, J = 8.7 Hz), 7.40 (2 H, d, J = 8.7 Hz), 7.74 (2 H, d, J = 8.1 Hz), 8.03 (2 H, d, J = 8.1 Hz), 8.19 (1 H, dd, J = 8.7 Hz, 2.6 Hz), 8.33 (1 H, d, J = 2.6 Hz), 8.61 (1 H, brs). |
| 183 | —H | $—CH_2CONHNHCOOC(CH_3)_3$ | $^1$H NMR ($CDCl_3$) 1.46 (9 H, s), 2.60 (4 H, brs), 3.17 (2 H, s), 3.67 (4 H, brs), 6.48 (1 H, brs), 7.00 (1 H, d, J = 8.7 Hz), 7.14 (2 H, d, J = 8.5 Hz), 7.41 (2 H, d, J = 8.5 Hz), 7.75 (2 H, d, J = 8.1 Hz), 8.02 (2 H, d, J = 8.1 Hz), 8.24 (1 H, dd, J = 8.7 Hz, 2.6 Hz), 8.33 (1 H, d, J = 2.6 Hz), 8.53 (2 H, s). |

TABLE 151

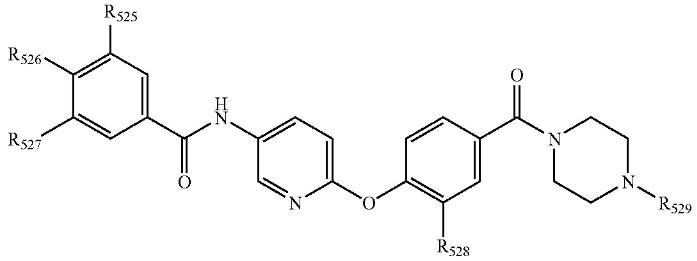

| Example No. | $R_{525}$ | $R_{526}$ | $R_{527}$ | $R_{528}$ | $R_{529}$ | Form | mp (° C.) or $^1$H NMR (solvent) δ ppm |
|---|---|---|---|---|---|---|---|
| 184 | —Cl | —Cl | —H | —F | 3-pyridyl | free | $^1$H NMR (CDCl) 3.21 (4 H, brs), 3.79 (4 H, brs), 7.02 (1 H, d, J = 8.7 Hz), 7.18-7.28 (5 H, m), 7.49 (1 H, d, J = 8.2 Hz), 7.74 (1 H, dd, J = 8.2 Hz, 1.7 Hz), 8.00 (1 H, d, J = 1.7 Hz), 8.13 (1 H, brs), 8.17-8.21 (1 H, m), 8.26 (2 H, d, J = 2.3 Hz), 9.33 (1 H, brs). |
| 185 | —H | —Cl | —H | —H | 4-CNPhCH$_2$— | free | mp 199-201 |
| 186 | —OCF$_3$ | —H | —H | —H | 3-pyridyl-methyl | free | $^1$H NMR (CDCl$_3$) 2.43-2.55 (4 H, m), 3.43-3.71 (6 H, m), 6.90 (1 H, d, J = 8.7 Hz), 7.05-7.08 (2 H, m), 7.25-7.46 (5 H, m), 7.66-7.69 (1 H, m), 7.82-7.88 (2 H, m), 8.15 (1 H, dd, J = 8.9 Hz, 2.8 Hz), 8.36 (1 H, d, J = 2.5 Hz), 8.48 (1 H, dd, J = 4.8 Hz, 1.7 Hz), 8.51 (1 H, d, J = 1.7 Hz), 9.84 (1 H, s). |
| 187 | —CF$_3$ | —H | —H | —H | 4-CNPhCH$_2$— | free | mp 193-197 |
| 188 | —F | —H | —CF$_3$ | —H | 4-CNPhCH$_2$— | oxalate | mp 136-139 |
| 189 | —CH$_3$ | —CH$_3$ | —H | —H | —COOC(CH$_3$)$_3$ | free | $^1$H NMR (CDCl$_3$) 1.48 (9 H, s), 2.34 (6 H, s), 3.46 (4 H, brs), 3.60 (4 H, brs), 6.99 (1 H, d, J = 8.7 Hz), 7.14-7.17 (2 H, m), 7.23-7.26 (1 H, m), 7.42-7.47 (2 H, m), 7.61 (1 H, dd, J = 7.8 Hz, 2.0 Hz), 7.67 (1 H, d, J = 2.0 Hz), 7.93 (1 H, brs), 8.25-8.31 (2 H, m). |

TABLE 152

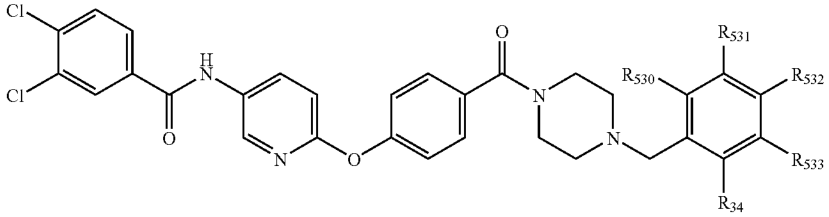

| Example No. | $R_{530}$ | $R_{531}$ | $R_{532}$ | $R_{533}$ | $R_{534}$ | MS |
|---|---|---|---|---|---|---|
| 190 | —Cl | —H | —H | —H | —H | 594 (M$^+$) |
| 191 | —OCH$_3$ | —H | —H | —H | —H | 590 (M$^+$) |
| 192 | —CH$_3$ | —H | —H | —H | —H | 574 (M$^+$) |
| 193 | —F | —H | —H | —H | —H | 578 (M$^+$) |
| 194 | —NO$_2$ | —H | —H | —H | —H | 603 (M$^+$ − 2) |
| 195 | —CF$_3$ | —H | —H | —H | —H | 628 (M$^+$) |
| 196 | —OCF$_3$ | —H | —H | —H | —H | 645 (M$^+$ + 1) |
| 197 | —H | —Cl | —H | —H | —H | 595 (M$^+$ + 1) |
| 198 | —H | —F | —H | —H | —H | 579 (M$^+$ + 1) |
| 199 | —H | —NO$_2$ | —H | —H | —H | 605 (M$^+$) |
| 200 | —H | —CF$_3$ | —H | —H | —H | 628 (M$^+$) |

TABLE 152-continued

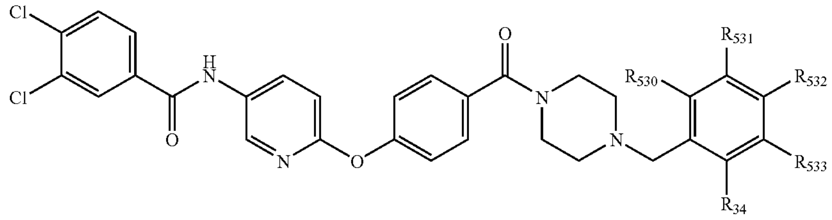

| Example No. | $R_{530}$ | $R_{531}$ | $R_{532}$ | $R_{533}$ | $R_{534}$ | MS |
|---|---|---|---|---|---|---|
| 201 | —H | —$OCF_3$ | —H | —H | —H | 644 ($M^+$) |
| 202 | —H | —$COOCH_3$ | —H | —H | —H | 618 ($M^+$) |
| 203 | —H | —H | —Cl | —H | —H | 594 ($M^+$) |
| 204 | —H | —H | —F | —H | —H | 578 ($M^+$) |
| 205 | —H | —H | —$NO_2$ | —H | —H | 605 ($M^+$) |
| 206 | —H | —H | —$COOCH_3$ | —H | —H | 618 ($M^+$) |
| 207 | —H | —H | -Ph | —H | —H | 636 ($M^+$) |
| 208 | —H | —H | —$C_2H_5$ | —H | —H | 588 ($M^+$) |
| 209 | —Cl | —Cl | —H | —H | —H | 630 ($M^+$) |
| 210 | —Cl | —H | —Cl | —H | —H | 630 ($M^+$) |
| 211 | —H | —F | —H | —F | —H | 596 ($M^+$) |
| 212 | —H | —$OCH_3$ | —H | —$OCH_3$ | —H | 622 ($M^+ + 2$) |
| 213 | —F | —H | —F | —H | —H | 596 ($M^+$) |
| 214 | —H | —Cl | —Cl | —H | —H | 630 ($M^+$) |
| 215 | —F | —H | —H | —H | —F | 596 ($M^+$) |
| 216 | —Cl | —H | —H | —H | —Cl | 630 ($M^+$) |
| 217 | —F | —H | —H | —F | —H | 596 ($M^+$) |
| 218 | —Cl | —H | —H | —Cl | —H | 629 ($M^+ + 1$) |
| 219 | —H | —Cl | —$OCH_3$ | —H | —H | 624 ($M^+$) |

TABLE 153

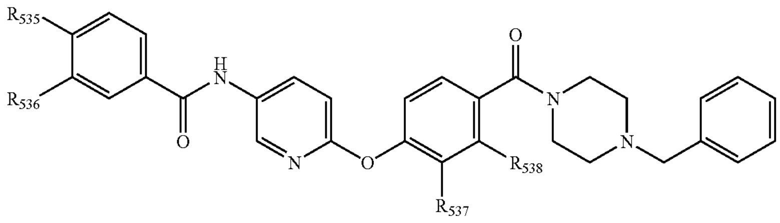

| Example No. | $R_{535}$ | $R_{536}$ | $R_{537}$ | $R_{538}$ | mp (° C.) or $^1$H NMR ($CDCl_3$) δ ppm |
|---|---|---|---|---|---|
| 220 | —Cl | —Cl | —H | —H | mp 164-166 |
| 221 | —Cl | —Cl | —F | —H | $^1$H NMR 2.46 (4 H, brs), 3.39-3.82 (6 H, m), 7.00 (1 H, d, J = 8.9 Hz), 7.13-7.33 (8 H, m), 7.52 (1 H, d, J = 8.4 Hz), 7.72 (1 H, dd, J = 8.4 Hz, 2.0 Hz), 8.00 (1 H, d, J = 2.0 Hz), 8.15 (1 H, dd, J = 8.9 Hz, 2.6 Hz), 8.23 (1 H, d, J = 2.6 Hz), 8.61 (1 H, brs). |
| 222 | —$CF_3$ | —H | —F | —H | $^1$H NMR 2.44 (4 H, brs), 3.42-3.78 (6 H, m), 6.97 (1 H, d, J = 8.7 Hz), 7.09-7.36 (8 H, m), 7.66 (2 H, d, J = 8.1 Hz), 7.96 (2 H, d, J = 8.1 Hz), 8.16 (1 H, dd, J = 8.7 Hz, 2.5 Hz), 8.26 (1 H, d, J = 2.5 Hz), 9.04 (1 H, brs). |
| 223 | —Cl | —Cl | —Cl | —H | $^1$H NMR 2.47 (4 H, brs), 3.42-3.83 (6 H, m), 7.00 (1 H, d, J = 8.9 Hz), 7.17 (1 H, d, J = 8.2 Hz), 7.25-7.33 (6 H, m), 7.46 (1 H, d, J = 1.8 Hz), 7.53 (1 H, d, J = 8.4 Hz), 7.74 (1 H, dd, J = 8.4 Hz, 2.1 Hz), 8.01 (1 H, d, J = 2.1 Hz), 8.17 (1 H, dd, J = 8.9 Hz, 2.6 Hz), 8.25 (1 H, d, J = 2.6 Hz), 8.64 (1 H, brs). |
| 224 | —$CF_3$ | —H | —Cl | —H | $^1$H NMR 2.47 (4 H, brs), 3.42-3.82 (6 H, m), 7.02 (1 H, d, J = 8.9 Hz), 7.19 (1 H, d, J = 8.4 Hz), 7.27-7.33 (6 H, m), 7.47 (1 H, d, J = 1.8 Hz), 7.73 (2 H, d, J = 8.4 Hz), 8.00 (2 H, d, J = 7.9 Hz), 8.20-8.26 (2 H, m), 8.46 (1 H, brs). |
| 225 | —Cl | —Cl | —$CH_3$ | —H | $^1$H NMR 2.15 (3 H, s), 2.45 (4 H, brs), 3.46-3.75 (6 H, m), 6.85 (1 H, d, J = 8.9 Hz), 6.95 (1 H, d, J = 8.4 Hz), 7.13-7.33 (7 H, m), 7.50 (1 H, d, J = 8.6 Hz), 7.75 (1 H, dd, J = 8.4 Hz, 2.2 Hz), 8.03 (1 H, d, J = 2.2 Hz), 8.08 (1 H, dd, J = 8.9 Hz, 3.0 Hz), 8.27 (1 H, d, J = 3.0 Hz), 9.06 (1 H, s). |

TABLE 153-continued

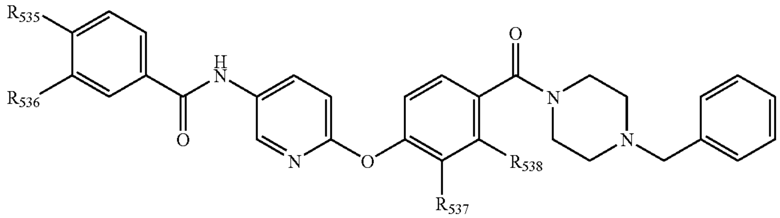

| Example No. | $R_{535}$ | $R_{536}$ | $R_{537}$ | $R_{538}$ | mp (° C.) or $^1$H NMR ($CDCl_3$) δ ppm |
|---|---|---|---|---|---|
| 226 | —$CF_3$ | —H | —$CH_3$ | —H | $^1$H NMR 2.17 (3 H, s), 2.44 (4 H, brs), 3.40-3.82 (6 H, m), 6.88 (1 H, d, J = 8.9 Hz), 6.98 (1 H, d, J = 8.1 Hz), 7.14-7.18 (1 H, m), 7.23-7.33 (6 H, m), 7.70 (2 H, d, J = 8.4 Hz), 8.01 (2 H, d, J = 8.1 Hz), 8.15 (1 H, dd, J = 8.9 Hz, 2.7 Hz), 8.30 (1 H, d, J = 2.7 Hz), 8.90 (1 H, brs). |
| 227 | —Cl | —Cl | —$OCH_3$ | —H | mp 197-199 |
| 228 | —$CF_3$ | —H | —$OCH_3$ | —H | mp 152-154 |
| 229 | —Cl | —Cl | —H | —$CH_3$ | mp 182-183 |
| 230 | —$CF_3$ | —H | —H | —$CH_3$ | mp 188-190 |
| 231 | —Cl | —Cl | —H | —$OCH_3$ | mp 196-198 |
| 232 | —$CF_3$ | —H | —H | —$OCH_3$ | $^1$H NMR 2.32-2.50 (4 H, m), 3.30 (2 H, brs), 3.53 (2 H, s), 3.70-3.81 (5 H, m), 6.61-6.65 (2 H, m), 6.91 (1 H, d, J = 8.9 Hz), 7.11-7.15 (1 H, m), 7.26-7.36 (5 H, m), 7.72 (2 H, d, J = 8.4 Hz), 8.05-8.13 (3 H, m), 8.36 (1 H, d, J = 2.4 Hz), 9.07 (1 H, s). |

TABLE 154

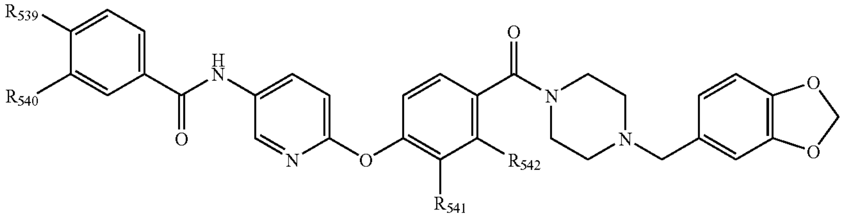

| Example No. | $R_{539}$ | $R_{540}$ | $R_{541}$ | $R_{542}$ | Form | mp (° C.) or $^1$H NMR (solvent) δ ppm |
|---|---|---|---|---|---|---|
| 233 | —$CF_3$ | —H | —H | —H | hydro-chloride | $^1$H NMR (DMSO-$d_6$) 2.90-3.70 (6 H, m), 3.80-4.60 (2 H, m), 4.24 (2 H, brs), 6.07 (2 H, s), 6.98 (1 H, d, J = 8.0 Hz), 7.05 (1 H, dd, J = 8.0 Hz, 1.5 Hz), 7.16 (1 H, d, J = 8.7 Hz), 7.20 (2 H, d, J = 8.6 Hz), 7.27 (1 H, s), 7.52 (2 H, d, J = 8.6 Hz), 7.93 (2 H, d, J = 8.3 Hz), 8.21 (2 H, d, J = 8.3 Hz), 8.30 (1 H, dd, J = 8.7 Hz, 2.6 Hz), 8.60 (1 H, d, J = 2.6 Hz), 10.80 (1 H, s). |
| 234 | —Cl | —Cl | —F | —H | free | $^1$H NMR ($CDCl_3$) 2.42 (4 H, brs), 3.37-3.79 (6 H, m), 5.94 (2 H, s), 6.70-6.77 (2 H, m), 6.84 (1 H, brs), 6.96 (1 H, d, J = 8.7 Hz), 7.10-7.22 (3 H, m), 7.47 (1 H, d, J = 8.2 Hz), 7.72 (1 H, dd, J = 8.2 Hz, 2.0 Hz), 7.99 (1 H, d, J = 2.0 Hz), 8.12 (1 H, dd, J = 8.9 Hz, 2.6 Hz), 8.25 (1 H, d, J = 2.6 Hz), 9.14 (1 H, brs). |
| 235 | —$CF_3$ | —H | —F | —H | free | $^1$H NMR ($CDCl_3$) 2.41 (4 H, brs), 3.37-3.79 (6 H, m), 5.94 (2 H, s), 6.69-6.76 (2 H, m), 6.84 (1 H, s), 6.99 (1 H, d, J = 8.9 Hz), 7.10-7.26 (3 H, m), 7.67 (2 H, d, J = 8.1 Hz), 7.97 (2 H, d, J = 8.1 Hz), 8.17 (1 H, dd, J = 8.9 Hz, 2.5 Hz), 8.26 (1 H, d, J = 2.5 Hz), 8.89 (1 H, brs). |
| 236 | —Cl | —Cl | —Cl | —H | free | $^1$H NMR ($CDCl_3$) 2.45 (4 H, brs), 3.38-3.81 (6 H, m), 5.95 (2 H, s), 6.71-6.78 (2 H, m), 6.85 (1 H, s), 7.01 (1 H, d, J = 8.7 Hz), 7.17-7.30 (2 H, m), 7.45-7.47 (1 H, m), 7.54 (1 H, d, J = 8.4 Hz), 7.70-7.74 (1 H, m), 8.00 (1 H, d, J = 1.8 Hz), 8.17 (1 H, dd, J = 8.9 Hz, 2.6 Hz), 8.24 (1 H, d, J = 2.6 Hz), 8.48 (1 H, s). |
| 237 | —$CF_3$ | —H | —Cl | —H | free | $^1$H NMR ($CDCl_3$) 2.45 (4 H, brs), 3.40-3.81 (6 H, m), 5.95 (2 H, s), 6.71-6.77 (2 H, m), 6.85 (1 H, s), |

TABLE 154-continued

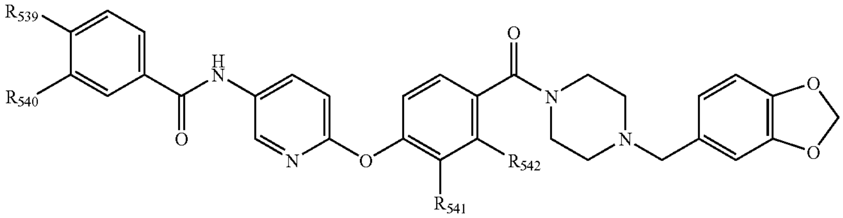

| Example No. | $R_{539}$ | $R_{540}$ | $R_{541}$ | $R_{542}$ | Form | mp (° C.) or ¹H NMR (solvent) δ ppm |
|---|---|---|---|---|---|---|
| | | | | | | 7.03 (1 H, d, J = 8.6 Hz), 7.20 (1 H, d, J = 8.2 Hz), 7.28-7.31 (1 H, m), 7.48 (1 H, d, J = 2.0 Hz), 7.74 (2 H, d, J = 8.4 Hz), 8.00 (2 H, d, J = 8.2 Hz), 8.21-8.26 (2 H, m), 8.34 (1 H, brs). |
| 238 | —$CF_3$ | —H | —$CH_3$ | —H | free | ¹H NMR ($CDCl_3$) 2.16 (3 H, s), 2.42 (4 H, brs), 3.44-3.70 (6 H, m), 5.94 (2 H, s), 6.70-6.77 (2 H, m), 6.85-6.89 (2 H, m), 6.97 (1 H, d, J = 8.4 Hz), 7.14-7.23 (2 H, m), 7.69 (2 H, d, J = 8.1 Hz), 8.01 (2 H, d, J = 8.1 Hz), 8.13-8.17 (1 H, m), 8.30 (1 H, d, J = 2.7 Hz), 8.97 (1 H, brs). |
| 239 | —Cl | —Cl | —$OCH_3$ | —H | free | mp 194-196 |
| 240 | —$CF_3$ | —H | —$OCH_3$ | —H | free | mp 134-136 |
| 241 | —$CF_3$ | —H | —H | —$Ch_3$ | free | mp 199-201 |
| 242 | —$CF_3$ | —H | —H | —$OCH_3$ | free | mp 192-193 |

TABLE 155

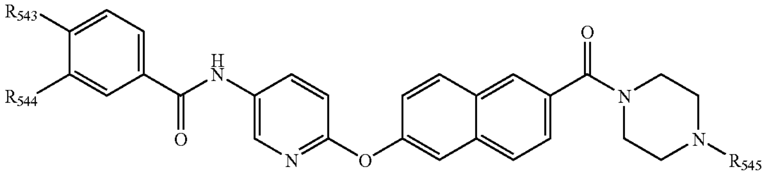

| Example No. | $R_{543}$ | $R_{544}$ | $R_{545}$ | ¹H NMR ($CDCl_3$) δppm |
|---|---|---|---|---|
| 243 | —Cl | —Cl | benzyl | 2.39-2.62(4 H, m), 3.42-3.91(6 H, m), 6.94(1 H, d, J = 8.9 Hz), 7.28-7.33(6 H, m), 7.41(1 H, dd, J = 8.4 Hz, 1.6 Hz), 7.50-7.53(2 H, m), 7.72-7.75(2 H, m), 7.81-7.84(2 H, m), 8.02(1 H, d, J = 2.1 Hz), 8.14(1 H, dd, J = 8.9 Hz, 2.7 Hz), 8.28(1 H, d, J = 2.7 Hz), 8.66(1 H, s). |
| 244 | —Cl | —Cl | piperonyl | 2.41-2.74(4 H, m), 3.42-3.91(6 H, m), 5.94(2 H, s), 6.73(2 H, brs), 6.84(1 H, brs), 6.97(1 H, d, J = 8.9 Hz), 7.29-7.33(1 H, m), 7.42(1 H, d, J = 8.2 Hz), 7.52-7.57(2 H, m), 7.71-7.85(4 H, m), 8.02(1 H, d, J = 2.0 Hz), 8.18(1 H, dd, J = 8.9 Hz, 2.8 Hz), 8.28(1 H, d, J = 2.8 Hz), 8.48(1 H, brs). |
| 245 | —Cl | —Cl | 3-pyridyl | 3.25(4 H, brs), 3.82(4 H, brs), 7.01(1 H, d, J = 8.7 Hz), 7.21-7.22(2 H, m), 7.35(1 H, dd, J = 8.9 Hz, 2.3 Hz), 7.47-7.50(1 H, m), 7.52-7.56(2 H, m), 7.74(1 H, dd, J = 8.2 Hz, 2.0 Hz), 7.80(1 H, d, J = 8.6 Hz), 7.86-7.91(2 H, m), 8.01(1 H, d, J = 2.0 Hz), 8.13-8.15(1 H, m), 8.18-8.22(1 H, m), 8.29-8.31(2 H, m), 8.42(1 H, brs). |
| 246 | —$CF_3$ | —H | benzyl | 2.35-2.58(4 H, m), 3.37-3.87(6 H, m), 6.96(1 H, d, J = 8.9 Hz), 7.28-7.34(6 H, m), 7.41(1 H, dd, J = 8.4 Hz, 1.5 Hz), 7.52(1 H, d, J = 2.0 Hz), 7.64-7.76(3 H, m), 7.83(2 H, d, J = 9.1 Hz), 8.00(2 H, d, J = 8.2 Hz), 8.19(1 H, dd, J = 8.9 Hz, 2.6 Hz), 8.30(1 H, d, J = 2.6 Hz), 8.68(1 H, brs). |
| 247 | —$CF_3$ | —H | piperonyl | 2.30-2.58(4 H, m), 3.35-3.87(6 H, m), 5.94(2 H, s), 6.70-6.177(2 H, m), 6.85(1 H, brs), 6.95(1 H, d, J = 8.7 Hz), 7.31(1 H, dd, J = 8.9 Hz, 2.1 Hz), 7.39(1 H, d, J = 8.4 Hz), 7.51(1 H, brs), 7.66-7.83(5 H, m), 7.99(2 H, d, J = 8.1 Hz), 8.17(1 H, dd, J = 8.7 Hz, 2.3 Hz), 8.30(1 H, brs), 8.89(1 H, brs). |

TABLE 155-continued

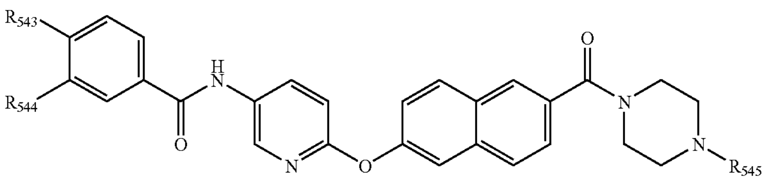

| Example No. | $R_{543}$ | $R_{544}$ | $R_{545}$ | $^1H$ NMR ($CDCl_3$) δppm |
|---|---|---|---|---|
| 248 | —$CF_3$ | —H | 3-pyridyl | 3.22(4 H, brs), 3.79(4 H, brs), 6.99(1 H, d, J = 8.7 Hz), 7.17-7.23(2 H, m), 7.33(1 H, dd, J = 8.9 Hz, 2.3 Hz), 7.45(1 H, dd, J = 8.4 Hz, 1.5 Hz), 7.54(1 H, d, J = 2.3 Hz), 7.66(2 H, d, J = 8.4 Hz), 7.76-7.86(3 H, m), 7.99(2 H, d, J = 8.1 Hz), 8.13(1 H, brs), 8.21-8.25(1 H, m), 8.28(1 H, brs), 8.33(1 H, d, J = 2.5 Hz), 9.13(1 H, s). |

TABLE 156

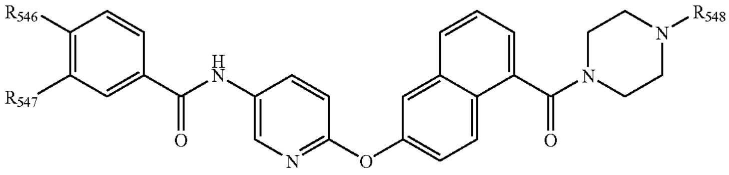

| Example No. | $R_{546}$ | $R_{547}$ | $R_{548}$ | $^1H$ NMR ($CDCl_3$) δppm |
|---|---|---|---|---|
| 249 | —Cl | —Cl | benzyl | 2.27-2.34(2 H, m), 2.58-2.61(2 H, m), 3.20-3.29(2 H, m), 3.53(2 H, s), 3.90-3.99(2 H, m), 6.91(1 H, d, J = 8.7 Hz), 7.29-7.32(7 H, m), 7.39-7.45(1 H, m), 7.53-7.56(2 H, m), 7.71-7.81(3 H, m), 8.00-8.04(2 H, m), 8.25(1 H, d, J = 2.6 Hz), 8.47(1 H, s). |
| 250 | —Cl | —Cl | piperonyl | 2.25-2.31(2 H, m), 2.55-2.59(2 H, m), 3.22(2 H, brs), 3.44(2 H, s), 3.86-4.01(2 H, m), 5.94(2 H, s), 6.69-6.76(2 H, m), 6.84-6.91(2 H, m), 7.25-7.29(2 H, m), 7.38-7.44(1 H, m), 7.52-7.55(2 H, m), 7.71-7.80(3 H, m), 7.97-8.03(2 H, m), 8.24(1 H, d, J = 2.8 Hz), 8.60(1 H, s). |
| 251 | —$CF_3$ | —H | benzyl | 2.27-2.34(2 H, m), 2.57-2.61(2 H, m), 3.23-3.25(2 H, m), 3.53(2 H, s), 3.89-3.98(2 H, m), 6.96(1 H, d, J = 8.7 Hz), 7.27-7.31(7 H, m), 7.40-7.45(1 H, m), 7.55(1 H, d, J = 2.3 Hz), 7.72-7.83 (4 H, m), 8.00(2 H, d, J = 8.1 Hz), 8.12(1 H, dd, J = 8.9 Hz, 2.8 Hz), 8.30(1 H, d, J = 2.6 Hz), 8.40(1 H, brs). |
| 252 | —$CF_3$ | —H | piperonyl | 2.25-2.31(2 H, m), 2.55-2.58(2 H, m), 3.23(2 H, m), 3.43(2 H, s), 3.85-4.00(4 H, m), 5.94(2 H, s), 6.70-6.76(2 H, m), 6.84(1 H, s), 6.96(1 H, d, J = 8.9 Hz), 7.28-7.31(2 H, m), 7.40-7.46(1 H, m), 7.55(1 H, d, J = 2.5 Hz), 7.72-7.83(4 H, m), 8.00(2 H, d, J = 7.9 Hz), 8.12(1 H, dd, J = 8.9 Hz, 2.6 Hz), 8.30(1 H, d, J = 2.6 Hz), 8.44(1 H, brs). |

TABLE 157

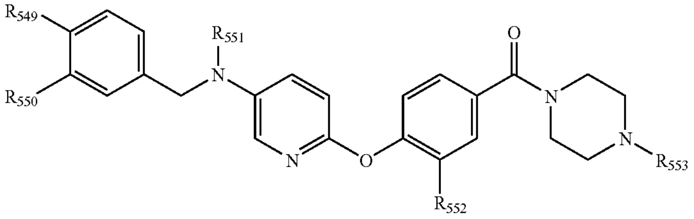

| Example No. | $R_{549}$ | $R_{550}$ | $R_{551}$ | $R_{552}$ | $R_{553}$ | Form | $^1$H NMR (solvent) δppm |
|---|---|---|---|---|---|---|---|
| 253 | —$CF_3$ | —H | —$CH_3$ | —H | 3-pyridyl | free | ($CDCl_3$) 3.06(3 H, s), 3.22(4 H, brs), 3.81(4 H, brs), 4.55(2 H, s), 6.87(1 H, d, J = 8.9 Hz), 7.09(2 H, d, J = 8.7 Hz), 7.14(1 H, dd, J = 8.9 Hz, 3.3 Hz), 7.19-7.21(2 H, m), 7.35(2 H, d, J = 7.9 Hz), 7.44(2 H, d, J = 8.7 Hz), 7.60(2 H, d, J = 8.1 Hz), 7.74(1 H, d, J = 3.0 Hz), 8.14-8.17(1 H, m), 8.31-8.33(1 H, m). |
| 254 | —$CF_3$ | —H | —H | —F | benzyl | free | ($CDCl_3$) 2.46(4 H, brs), 3.54(6 H, brs), 4.11(1 H, brs), 4.38(2 H, brs), 6.85(1 H, d, J = 8.7 Hz), 7.01(1 H, dd, J = 8.7 Hz, 3.1 Hz), 7.16-7.25(3 H, m), 7.28-7.33(5 H, m), 7.46(2 H, d, J = 8.1 Hz), 7.52(1 H, d, J = 2.6 Hz), 7.60(2 H, d, J = 8.1 Hz). |
| 255 | —$CF_3$ | —H | —$CH_3$ | —H | piperonyl | hydro-chloride | (DMSO-$d_6$) 2.49-2.52(2 H, m), 3.06(5 H, brs), 3.35(4 H, brs), 4.22(2 H, brs), 4.68(2 H, brs), 6.07(2 H, s), 6.94-7.05(5 H, m), 7.23(1 H, brs), 7.32(1 H, dd, J = 8.9 Hz, 3.3 Hz), 7.43-7.46(4 H, m), 7.69-7.72(3 H, m), 11.23(1 H, brs). |
| 256 | —Cl | —Cl | —H | —F | benzyl | free | ($CDCl_3$) 2.47(4 H, brs), 3.49-3.68(6 H, m), 4.29(2 H, s), 6.86(1 H, d, J = 8.7 Hz), 7.01(1 H, dd, J = 8.7 Hz, 3.0 Hz), 7.17-7.22(4 H, m), 7.32(5 H, brs), 7.41(1 H, d, J = 8.3 Hz), 7.45(1 H, d, J = 1.8 Hz), 7.51(1 H, d, J = 3.0 Hz). |
| 257 | —$CF_3$ | —H | —$CH_3$ | —H | 4-$CH_3OPhCH_2$— | hydro-chloride | (DMSO-$d_6$) 2.49-2.52(2 H, m), 3.06(5 H, brs), 3.32-3.38(4 H, m), 3.78(3 H, s), 4.27(2 H, d, J = 4.1 Hz), 4.68(2 H, brs), 6.96(1 H, d, J = 8.9 Hz), 7.00-7.05(4 H, m), 7.32(1 H, dd, J = 8.9 Hz, 3.3 Hz), 7.43-7.49(6 H, m), 7.68-7.72(3 H, m), 10.72(1 H, brs). |
| 258 | —$CF_3$ | —H | —$CH_3$ | —H | 4-pyridyl-methyl | hydro-chloride | (DMSO-$d_6$) 2.49-2.52(2 H, m), 3.05-3.44(9H, m), 4.26(2 H, brs), 4.68(2 H, brs), 6.96(1 H, d, J = 8.9 Hz), 7.03(2 H, d, J = 8.7 Hz), 7.32(1 H, dd, J = 8.9 Hz, 3.3 Hz), 7.42-7.47(4 H, m), 7.68-7.72(5 H, m), 8.71(2 H, dd, J = 4.6 Hz, 1.5 Hz). |

TABLE 158

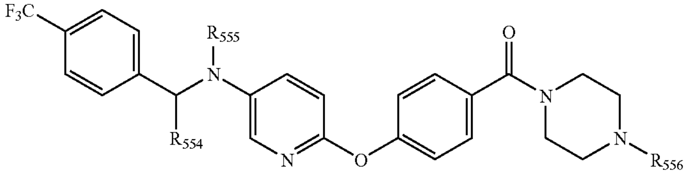

| Example No. | $R_{554}$ | $R_{555}$ | $R_{556}$ | Form | $^1$H NMR (solvent) δppm |
|---|---|---|---|---|---|
| 259 | —$CH_3$ | —H | benzyl | hydro-chloride | (DMSO-$d_6$) 1.44(3 H, d, J = 6.8 Hz), 2.44-2.52(2 H, m), 3.08-3.15(2 H, m), 3.30-3.38(4 H, |

TABLE 158-continued

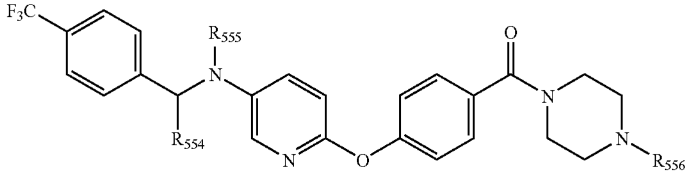

| Example No. | $R_{554}$ | $R_{555}$ | $R_{556}$ | Form | $^1$H NMR (solvent) δppm |
|---|---|---|---|---|---|
| | | | | | m), 4.33(2 H, brs), 4.55-4.62(1 H, m), 6.51(1 H, d, J = 6.3 Hz), 6.82(1 H, d, J = 8.7 Hz), 6.97(2 H, d, J = 8.7 Hz), 7.04(1 H, dd, J = 8.7 Hz, 3.0 Hz), 7.41(2 H, d, J = 8.6 Hz), 7.45-7.47(4 H, m), 7.57(2 H, brs), 7.61(2 H, d, J = 8.3 Hz), 7.69(2 H, d, J = 8.4 Hz), 10.99(1 H, brs). |
| 260 | —$CH_3$ | —$CH_3$ | benzyl | free | ($CDCl_3$) 1.58(3 H, d, J = 6.9 Hz), 2.46(4 H, brs), 2.72(3 H, s), 3.46-3.53(6 H, m), 4.97(1 H, q, J = 6.9 Hz), 6.86(1 H, d, J = 8.9 Hz), 7.07(2 H, d, J = 8.6 Hz), 7.23(1 H, dd, J = 8.9 Hz, 3.3 Hz), 7.27-7.36(5 H, m), 7.40(2 H, d, J = 8.6 Hz), 7.43(2 H, d, J = 7.3 Hz), 7.60(2 H, d, J = 8.3 Hz), 7.82(1 H, d, J = 3.3 Hz). |
| 261 | —$CH_3$ | —$CH_3$ | piperonyl | free | ($CDCl_3$) 1.58(3 H, d, J = 6.9 Hz), 2.43(4 H, brs), 2.72(3 H, s), 3.44(2 H, s), 3.48-3.68(4 H, m), 4.97(1 H, q, J = 6.9 Hz), 5.95(2 H, s), 6.74(2 H, brs), 6.85(1 H, brs), 6.87(1 H, d, J = 9.1 Hz), 7.07(2 H, d, J = 8.7 Hz), 7.23(1 H, dd, J = 8.9 Hz, 3.3 Hz), 7.40(2 H, d, J = 8.6 Hz), 7.43(2 H, d, J = 7.9 Hz), 7.60(2 H, d, J = 8.3 Hz), 7.82(1 H, d, J = 3.1 Hz). |
| 262 | —$CH_3$ | —H | piperonyl | hydro-chloride | (DMSO-$d_6$) 1.44(3 H, d, J = 6.8 Hz), 2.49-2.52(2 H, m), 3.01-3.06(2 H, m), 3.29-3.45(4 H, m), 4.23(2 H, brs), 4.58-4.62(1 H, m), 6.07(2 H, s), 6.51(1 H, d, J = 6.6 Hz), 6.82(1 H, d, J = 8.7 Hz), 6.96-6.99(4 H, m), 7.04(1 H, dd, J = 8.7 Hz, 3.0 Hz), 7.20(1 H, brs), 7.41(2 H, d, J = 8.6 Hz), 7.46(1 H, d, J = 3.0 Hz), 7.61(2 H, d, J = 8.3 Hz), 7.69(2 H, d, J = 8.4 Hz), 10.99(1 H, brs). |
| 263 | —H | —$C_2H_5$ | benzyl | hydro-chloride | (DMSO-$d_6$) 1.14(3 H, d, J = 6.9 Hz), 2.50-2.51(2 H, m), 3.11(2 H, brs), 3.35(4 H, brs), 3.51(2 H, q, J = 6.9 Hz), 4.33(2 H, brs), 4.63(2 H, brs), 6.94(1 H, d, J = 8.9 Hz), 7.03(2 H, d, J = 8.6 Hz), 7.25(1 H, dd, J = 8.9 Hz, 3.3 Hz), 7.42-7.48(7 H, m), 7.57(2 H, brs), 7.62(1 H, d, J = 3.1 Hz), 7.70(2 H, d, J = 8.1 Hz), 11.03(1 H, brs). |
| 264 | —H | —$C_2H_5$ | piperonyl | hydro-chloride | (DMSO-$d_6$) 1.14(3 H, d, J = 6.9 Hz), 2.50-2.51(2 H, m), 3.06(2 H, brs), 3.36(4 H, brs), 3.52(2 H, q, J = 6.9 Hz), 4.22(2 H,brs), 4.64(2 H, brs), 6.07(2 H, s), 6.94(1 H, d, J = 8.9 Hz), 6.99(2 H, brs), 7.03(2 H, d, J = 8.6 Hz), 7.23(1 H, brs), 7.25(1 H, dd, J = 8.9 Hz, 3.3 Hz), 7.42-7.49(4 H, m), 7.62(1 H, d, J = 3.1 Hz), 7.71(2 H, d, J = 8.1 Hz), 11.29(1 H, brs). |

TABLE 159

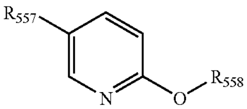

| Example No. | $R_{557}$ | $R_{558}$ | $^1$H NMR (solvent) δppm |
|---|---|---|---|
| 265 | 3,4-$Cl_2$PhCONH— | 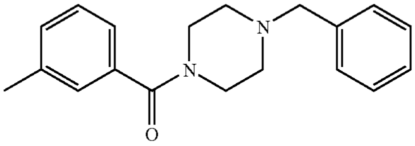 | ($CDCl_3$) 2.39-2.49(4 H, m), 3.39-3.79(6 H, m), 6.87(1 H, d, J = 8.9 Hz), 7.06-7.15(3 H, m), 7.27-7.37(6 H, m), 7.51(1 H, d, J = 8.4 Hz), 7.74-7.78(1 H, m), 8.01-8.05(2 H, m), 8.28(1 H, d, J = 2.6 Hz), 9.10(1 H, brs). |

TABLE 159-continued

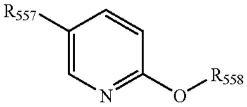

| Example No. | $R_{557}$ | $R_{558}$ | $^1H$ NMR (solvent) δppm |
|---|---|---|---|
| 266 | 3,4-$Cl_2$PhCONH— | 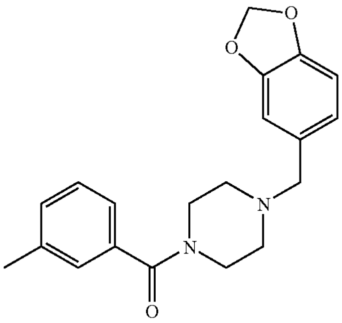 | ($CDCl_3$) 2.37-2.48(4 H, m), 3.43-3.75(6 H, m), 5.94(2 H, s), 6.70-6.77(2 H, m), 6.84(1 H, brs), 6.92(1 H, d, J = 8.9 Hz), 7.09-7.17(3 H, m), 7.34-7.40(1 H, m), 7.55(1 H, d, J = 8.4 Hz), 7.73-7.77(1 H, m), 8.04(1 H, d, J = 2.1 Hz), 8.09(1 H, dd, J = 8.9 Hz, 2.8 Hz), 8.28(1 H, d, J = 2.8 Hz), 8.63(1 H, brs). |
| 267 | 4-$CF_3PhCH_2N(CH_3)$— | 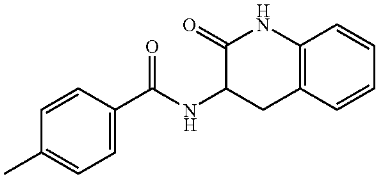 | (DMSO-$d_6$) 3.03-3.13(5 H, m), 4.69-4.75(3 H, m), 6.88-6.98(3 H, m), 7.06(2 H, d, J = 8.6 Hz), 7.16-7.23(2 H, m), 7.33(1 H, dd, J = 9.1 Hz, 3.1 Hz), 7.46(2 H, d, J = 8.3 Hz), 7.69-7.73(3 H, m), 7.91(2 H, d, J = 8.7 Hz), 8.61(1 H, d, J = 8.1 Hz), 10.35(1 H, brs). |
| 268 | 4-$CF_3PhCH_2N(CH_3)$— | 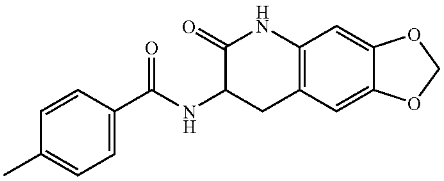 | (DMSO-$d_6$) 2.89-3.06(2 H, m), 3.06(3 H, s), 4.61-4.72(3 H, m), 5.96(2 H, s), 6.50(1 H, s), 6.84(1 H, s), 6.97(1 H, d, J = 8.9 Hz), 7.06(2 H, d, J = 8.7 Hz), 7.33(1 H, dd, J = 8.9 Hz, 3.3 Hz), 7.46(2 H, d, J = 8.1 Hz), 7.69-7.73(3 H, m), 7.89(2 H, d, J = 8.7 Hz), 8.56(1 H, d, J = 8.3 Hz), 10.15(1 H, brs). |
| 269 | 3,4-$Cl_2$PhCONH— | 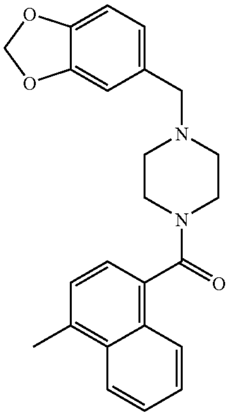 | ($CDCl_3$) 2.28-2.30(2 H, m), 2.58-2.60(2 H, m), 3.25-3.29(2 H, m), 3.44(2 H, s), 3.92-3.98(2 H, m), 5.94(2 H, s), 6.73(2 H, s), 6.84(1 H, s), 6.96(1 H, d, J = 8.7 Hz), 7.14(1 H, d, J =═0 7.8 Hz), 7.37(1 H d, J = 7.8 Hz), 7.50-7.59(3 H, m), 7.73(1 H, dd, J = 8.2 Hz, 2.1 Hz), 7.83(1 H, dd, J = 7.6 Hz, 3.0 Hz), 8.03(1 H, d, J = 2.1 Hz), 8.06-8.13(2 H, m), 8.17(1 H, s), 8.24(1 H, d, J = 3.0 Hz). |

TABLE 160

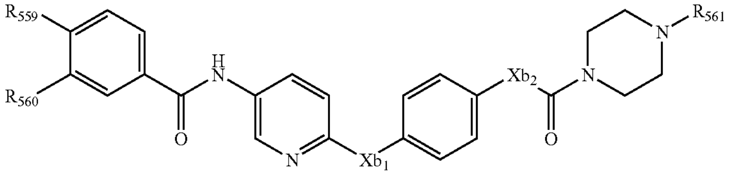

| Example No. | $R_{559}$ | $R_{560}$ | $Xb_1$ | $Xb_2$ | $R_{561}$ | Form | mp (° C.) or $^1$H NMR (DMSO-$d_6$) δppm |
|---|---|---|---|---|---|---|---|
| 270 | —Cl | —Cl | —O— | 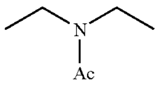 | piperonyl | free | $^1$H NMR (at 375 K) 2.00(3 H, brs), 2.30-2.38(4 H, m), 3.34-3.43(6 H, m), 4.12(2 H, s), 4.51(2 H, brs), 5.91(2 H, s), 6.73(1 H, d, J = 7.9 Hz), 6.77(1 H, d, J = 7.9 Hz), 6.81(1 H, s), 6.98(1 H, d, J = 8.8 Hz), 7.05(2 H, d, J = 8.2 Hz), 7.26(2 H, d, J = 8.2 Hz), 7.73(1 H, d, J = 8.4 Hz), 7.91(1 H, dd, J = 2.1 Hz, 8.4 Hz), 8.12-8.18(3 H, m), 8.48(1 H, d, J = 2.6 Hz), 10.17(1 H, s). |
| 271 | —Cl | —Cl | —O— | 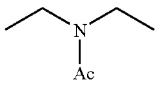 | benzyl | free | $^1$H NMR (at 375 K) 2.00(3 H, brs), 2.33-2.40(4 H, m), 3.38-3.42(4 H, m), 3.49-3.53(2 H, m), 4.13(2 H, s), 4.51(2 H, brs), 698(1 H, d, J = 8.8 Hz), 7.02-7.10(2 H, m), 7.16-7.30(7 H, m), 7.73(1 H, d, J = 8.4 Hz), 7.91(1 H, dd, J = 8.4 Hz, 2.1 Hz), 8.11-8.17(2 H, m), 8.48(1 H, d, J = 2.5 Hz), 10.17(1 H, s). |
| 272 | —$CF_3$ | —H | —O— | —CH═CH— (trans) | benzyl | free | $^1$H NMR 2.39(4 H, brs), 3.52(2 H, s), 3.58(2 H, brs), 3.71(2 H, brs), 7.13(1 H, d, J = 8.9 Hz), 7.14(2 H, d, J = 8.7 Hz), 7.24(1 H, d, J = 15.3 Hz), 7.18-7.41(5 H, m), 7.50(1 H, d, J = 15.3 Hz), 7.76(2 H, d, J = 8.7 Hz), 7.94(2 H, d, J = 8.3 Hz), 8.17(2 H, d, J = 8.3 Hz), 8.25(1 H, dd, J = 8.9 Hz, 2.7 Hz), 8.54(1 H, d, J = 2.7 Hz), 10.66(1 H, s). |
| 273 | —$CF_3$ | —H | —O— | —CH═CH— (trans) | piperonyl | free | $^1$H NMR 2.37(4 H, brs), 3.42(2 H, s), 3.58(2 H, brs), 3.70(2 H, brs), 5.99(2 H, s), 6.76(1 H, dd,J = 8.0 Hz, 2.4Hz), 6.85(1 H, d, J = 8.0 Hz), 6.88(1 H, d, J = 1.5 Hz), 7.13(1 H, d, J = 8.9 Hz), 7.14(2 H, d, J = 8.7 Hz), 7.20(1 H, d, J = 15.4 Hz), 7.50(1 H, d, J = 15.4 Hz), 7.76(2 H, d, J = 8.7 Hz), 7.94(2 H, d, J = 8.2 Hz), 8.17(2 H, d, J = 8.2 Hz), 8.25(1 H, dd, J = 8.9 Hz, 2.6 Hz), 8.54 (1 H, d, J = 2.6 Hz), 10.65(1 H, s). |
| 274 | —$CF_3$ | —H | —N($CH_3$)— | none | piperonyl | dihydro-chloride | $^1$H NMR 2.98-3.12(2 H, m), 3.12-3.36(2 H, m), 3.50(3 H, s), 3.71-4.68(6 H, m), 6.06(2 H, s), 6.93-7.06(3 H, m), 7.26(1 H, s), 7.42(2 H, d, J = 8.3 Hz), 7.53(2 H, d, J = 8.3 Hz), 7.92(2 H, d, J = 8.3 Hz), 8.12(1 H, d, J = 9.2 Hz), 8.20(2 H, d, J = 8.3 Hz), 8.67(1 H, s), 10.79(1 H, s), 11.47(1 H, brs). |
| 275 | —$CF_3$ | —H | —N($CH_3$)— | none | benzyl | free | mp 213-214 |

TABLE 161

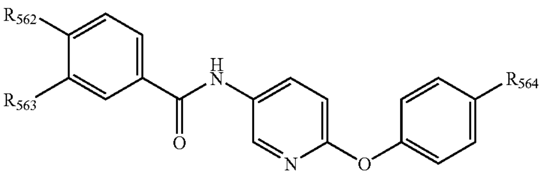

| Example No. | $R_{562}$ | $R_{563}$ | $R_{564}$ | mp (° C.) or $^1$H NMR ($CDCl_3$) δppm |
|---|---|---|---|---|
| 276 | —Cl | —Cl | 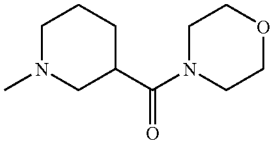 | $^1$H NMR 1.62-1.80(2 H, m), 1.82-1.87(2 H, m), 2.71(1 H, dt, J = 3 Hz, 11.0 Hz), 2.84(1 H, brs), 2.94(1 H, t, J = 11.0 Hz), 3.55-3.70(10 H, m), 6.89(1 H, d, J = 9.0 Hz), 6.93(2 H, dd, J = 7.0 Hz, 2.0 Hz), 7.02(2 H, dd, J = 7.0 Hz, 2.0 Hz), 7.56(1 H, d, J = 8.0 Hz), 7.71(1 H, dd, J = 9.0 Hz, 2.0 Hz), 7.99(1 H, d, J = 2.0 Hz), 2.0 Hz), 7.99(1 H, d, J = 2.0 Hz), 8.10(1 H, s), 8.15(1 H, dd, J = 9.0 Hz, 2.5 Hz), 8.25(1 H, d, J = 2.5 Hz). |
| 277 | —Cl | —Cl | 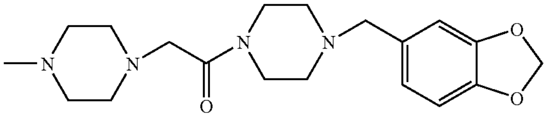 | $^1$H NMR 2.38-2.42(4 H, m), 2.62-2.67(4 H, m), 3.14-3.17(4 H, m), 3.22(2 H, s), 3.42(2 H, s), 3.61-3.63(4 H, m), 5.95(2 H, s), 6.70-6.75(2 H, m), 7.03(2 H, d, J = 8.0 Hz), 7.55(1 H, d, J = 8.0 Hz), 7.70(1 H, brs), 7.73(2 H, d, J = 8.0 Hz), 8.01(1 H, s), 8.15(1 H, brd, J = 9.0 Hz), 8.27(1 H, d, J = 2.5 Hz). |
| 278 | —Cl | —Cl | 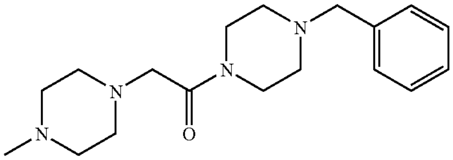 | $^1$H NMR 2.40-2.45(4 H, m), 2.60-2.64(4 H, m), 3.13(4 H, brs), 3.20(2 H, brs), 3.48(2 H, brs), 3.62(4 H, brs), 6.85-6.91(3 H, m), 7.01(2 H, d, J = 8.0 Hz), 7.26-7.32(5 H, m), 7.52(1 H, d, J = 8.5 Hz), 7.70(1 H, brs), 7.74(1 H, dd, J = 8.5 Hz, 2.0 Hz), 8.03(1 H, d, J = 2.0 Hz), 8.15(1 H, brd, J = 9.0, Hz), 8.29(1 H, d, J = 2.5 Hz). |
| 279 | —H | —$CF_3$ | 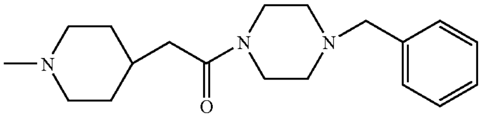 | mp 180-183 |
| 280 | —H | —$CF_3$ | 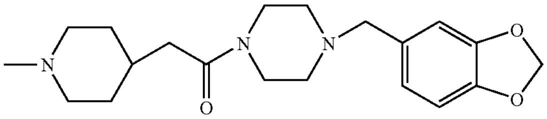 | mp 197-199 |
| 281 | —H | —$CF_3$ | 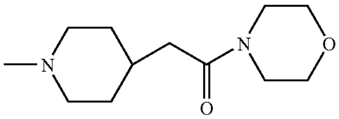 | mp 133-135 |

TABLE 162
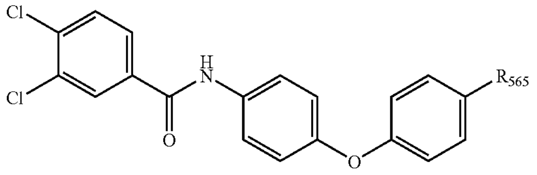
| Example No. | $R_{565}$ | Form | mp (° C.) |
|---|---|---|---|
| 282 | 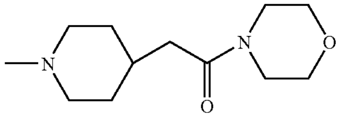 | free | 108-110 |
| 283 | 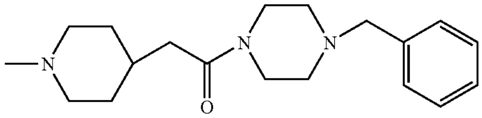 | free | 136-138 |
| 284 | 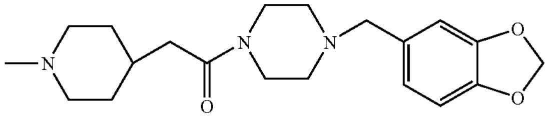 | free | 133-136 |
| 285 | 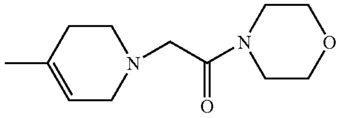 | free | 147-151 |
| 286 | 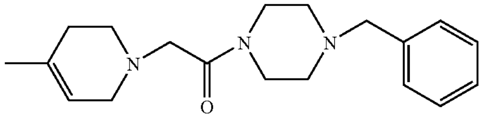 | dihydrochloride | 180-183 |
| 287 | 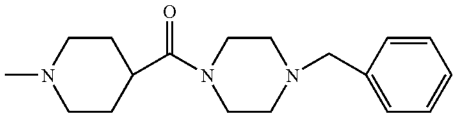 | free | 111-113 |
| 288 | 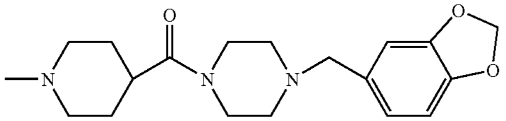 | free | 111-113 |
| 289 | 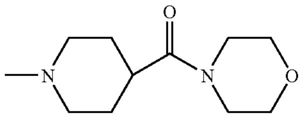 | free | 246-249 |
| 290 | 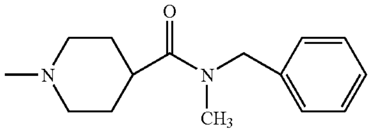 | free | 148-151 |
| 291 | 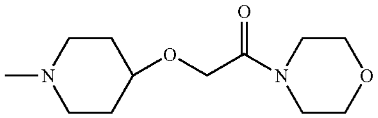 | free | 120-121 |

TABLE 163
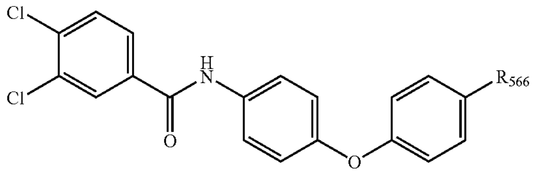
| Example No. | $R_{566}$ | Form | mp (° C.) |
|---|---|---|---|
| 292 | 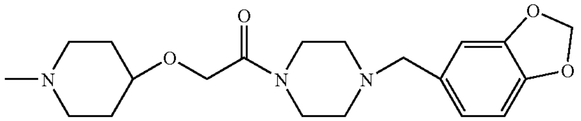 | free | 83-86 |
| 293 | 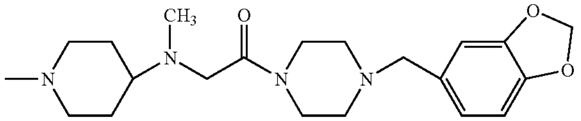 | free | 130-133 |
| 294 | 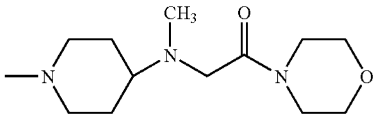 | free | 145-146 |
| 295 | 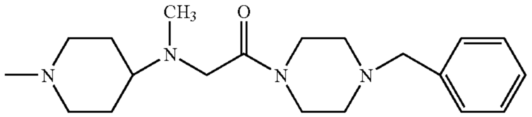 | trihydro-chloride | 180-185 |
| 296 | 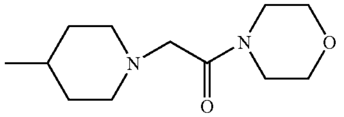 | free | 184-186 |
| 297 | 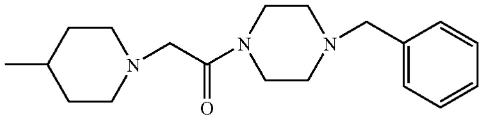 | free | 173-176 |
| 298 | 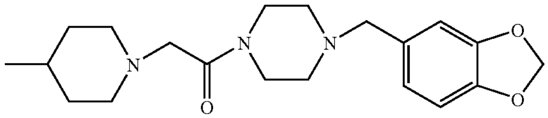 | free | 181-183 |
| 299 | 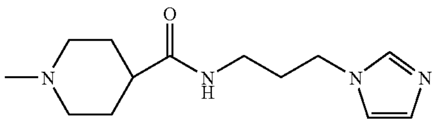 | free | 166-170 |

TABLE 164
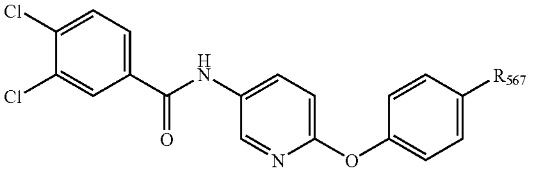
| Example No. | $R_{567}$ | mp (° C.) |
|---|---|---|
| 300 | 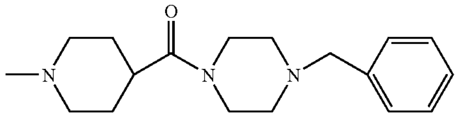 | 102-104 |
| 301 | 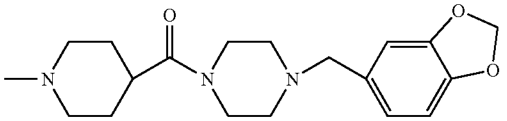 | 106-109 |
| 302 | 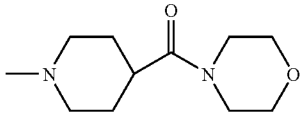 | 261-264 |
| 303 | 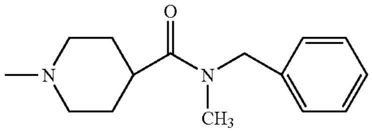 | 173-175 |
| 304 | 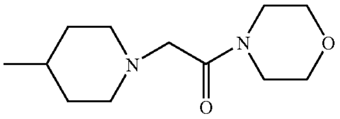 | 164-166 |
| 305 | 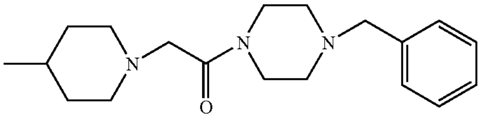 | 158-160 |
| 306 | 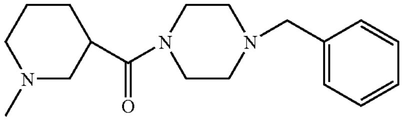 | 174-176 |
| 307 | 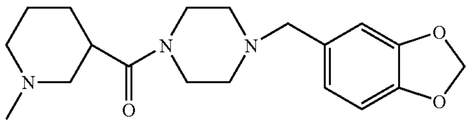 | 206-207 |
| 308 | 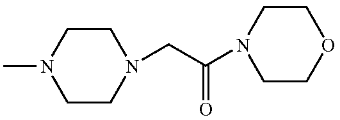 | 165-166 |
| 309 | 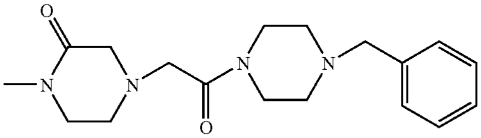 | 164-167 |

TABLE 164-continued
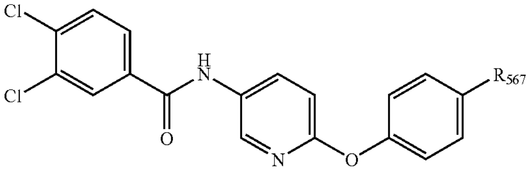
| Example No. | $R_{567}$ | mp (° C.) |
|---|---|---|
| 310 | 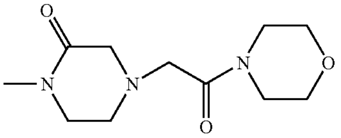 | 188-190 |
| 311 | 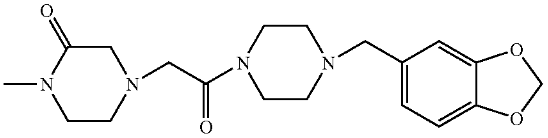 | 130-132 |
TABLE 165
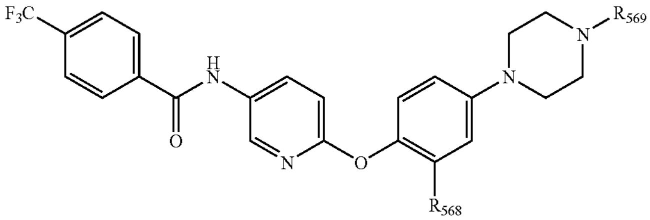
| Example No. | $R_{568}$ | $R_{569}$ | mp (° C.) or $^{1}H$ NMR ($CDCl_3$) δppm |
|---|---|---|---|
| 312 | —H | 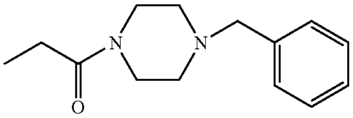 | mp 166-167 |
| 313 | —H | 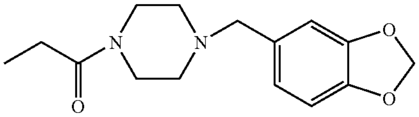 | mp 157-158 |
| 314 | —H | 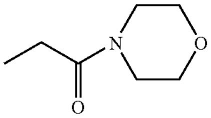 | mp 218-219 |
| 315 | 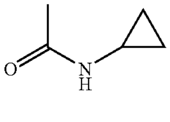 | benzyl | $^{1}H$ NMR 0.25-0.31(2 H, m), 0.61-0.69(2 H, m), 2.67-2.73(1 H, m), 2.86(4 H, brs), 3.18(4 H, brs), 3.83(2 H, s), 6.80-6.92(3 H, m), 7.16-7.62(8 H, m), 8.11(2 H, d, J = 8.1 Hz), 8.39(1 H, dd, J = 8.9 Hz, 2.6 Hz), 8.45(1 H, d, J = 2.5 Hz), 10.23(1 H, s), 10.93(1 H, brs). |
| 316 | —CONHPh | benzyl | $^{1}H$ NMR 3.07(4 H, brs), 3.26(4 H, brs), 3.98(2 H, s), 6.83-7.59(14 H, m), 7.65(2 H, d, J = 8.3 Hz), 8.06(2 H, d, J = 8.1 Hz), 8.37(1 H, d, J = 2.6 Hz), 8.49(1 H, dd, J = 8.9 Hz, 2.6 Hz), 9.30(1 H, s), 9.71(1 H, brs). |

TABLE 165-continued

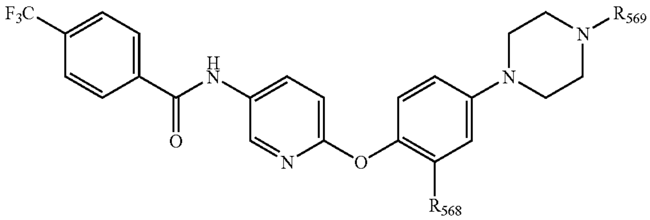

| Example No. | $R_{568}$ | $R_{569}$ | mp (° C.) or $^1$H NMR ($CDCl_3$) δppm |
|---|---|---|---|
| 317 | 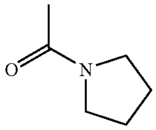 | benzyl | $^1$H NMR 1.87(4 H, brs), 2.72(4 H, brs), 3.19(4 H, brs), 3.40(4 H, brs), 3.69(2 H, s), 6.58(1 H, d, J = 8.7 Hz), 6.80(1 H, s), 6.92(1 H, d, J = 9.2 Hz), 7.02(1 H, d, J = 8.9 Hz), 7.26-7.34(5 H, m), 7.57(2 H, d, J = 7.9 Hz), 7.90(1 H, d, J = 7.1 Hz), 8.05(2 H, d, J = 8.1 Hz), 8.40(1 H, s), 9.73(1 H, s). |

TABLE 166

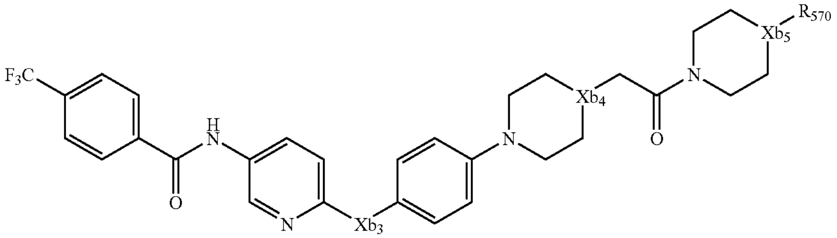

| Example No. | $Xb_3$ | $Xb_4$ | $Xb_5$ | $R_{570}$ | mp (° C.) or $^1$H NMR ($CDCl_3$) δppm |
|---|---|---|---|---|---|
| 318 | —O— | 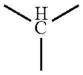 | 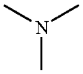 | benzyl | mp 162-163 |
| 319 | —O— | 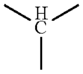 | 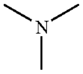 | piperonyl | mp 136-137 |
| 320 | —O— | 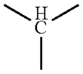 | —O— | none | mp 176-177 |
| 321 | —N($CH_3$)— | 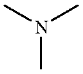 | 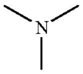 | 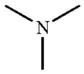 | $^1$H NMR 2.43(4 H, brs), 2.67(4 H, t, J = 4.8 Hz), 3.22(4 H, t, J = 4.8 Hz), 3.24(2 H, s), 3.42(3 H, s), 3.52(2 H, s), 3.63(4 H, brs), 6.46 (1 H, d, J = 9.1 Hz), 6.95(2 H, d, J = 8.9 Hz), 7.15(2 H, d, J = 8.9 Hz), 7.20-7.40(5 H, m), 7.65-7.80(2 H, m), 7.74(2 H, d, J = 8.2 Hz), 7.98(2 H, d, J = 8.2 Hz), 8.26(1 H, d, J = 2.5 Hz). |
| 322 | —N($CH_3$)— | 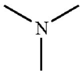 | 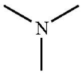 | piperonyl | $^1$H NMR 2.41(4 H, brs), 2.67(4 H, t, J = 4.8 Hz), 3.22(4 H, t, J = 5.1 Hz), 3.24(2 H, s), 3.42(5 H, s), 3.62(4 H, t, J = 4.5 Hz), 5.94(2 H, s), 6.46(1 H, d, J = 9.1 Hz), 6.74(2 H, s), 6.85(1 H, s), 6.95(2 H, d, J = 8.9 Hz), 7.15(2 H, d, J = 8.9 Hz), 7.65-7.75(1 H, m), 7.74(2 H, d, J = 8.1 Hz), 7.83(1 H, brs), 7.99(2 H, d, J = 8.1 Hz), 8.26(1 H,d, J = 2.5 Hz). |

TABLE 166-continued

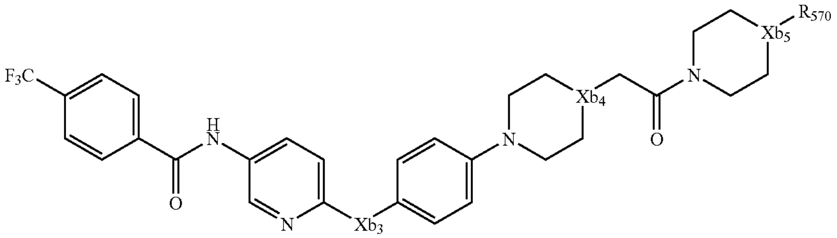

| Example No. | $Xb_3$ | $Xb_4$ | $Xb_5$ | $R_{570}$ | mp (° C.) or $^1H$ NMR ($CDCl_3$) δppm |
|---|---|---|---|---|---|
| 323 | —N(CH$_3$)— | 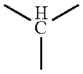 | 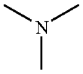 | benzyl | $^1H$ NMR 1.31-1.52(2 H, m), 1.88(2 H, d, J = 12.3 Hz), 1.88-2.15(1 H, m), 2.29(2 H, d, J = 6.7 Hz), 2.44(4 H, t, J = 5.1 Hz), 2.76(2 H, t, J = 11.2 Hz), 3.42(3 H, s), 3.49(2 H, t, J = 4.9 Hz), 3.53(2 H, s), 3.59-3.78(4 H, m), 6.47(1 H, d, J = 9.1 Hz), 6.96(2 H, d, J = 8.9 Hz), 7.13 (2 H, d, J = 8.9 Hz), 7.20-7.41(5 H, m), 7.61-7.78(2 H, m), 7.75(2 H, d, J = 8.1 Hz), 7.98 (2 H, d, J = 8.1 Hz), 8.25(1 H, d, J = 2.3 Hz). |
| 324 | —N(CH$_3$)— | 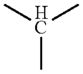 | 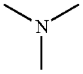 | piperonyl | $^1H$ NMR 1.30-1.51(2 H, m), 1.88(2 H, d, J = 2.9 Hz), 1.98-2.11(1 H, m), 2.29(2 H, d, J = 6.7 Hz), 2.41(4 H, m), 2.76(2 H, t, J = 11.2 Hz), 3.42(3 H, s), 3.43(2 H, s), 3.49(2 H, t, J = 4.8 Hz), 3.55-3.78(4 H, m), 5.95(2 H, s), 6.47(1 H, d, J = 9.0 Hz), 6.74(2 H, s), 6.86(1 H, s), 6.96(2 H, d, J = 8.9 Hz), 7.13(2 H, d, J = 8.9 Hz), 7.70(1 H, brs), 7.71(1 H, dd, J = 9.0 Hz, 2.7 Hz), 7.75(2 H, d, J = 8.2 Hz), 7.99(2 H, d, J = 8.2 Hz), 8.26(1 H, d, J = 2.7 Hz). |

TABLE 167

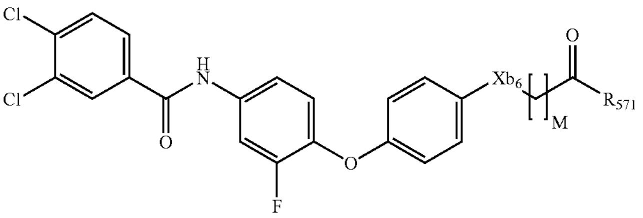

| Example No. | $Xb_6$ | M | $R_{571}$ | Form | δmp (° C.) or $^1H$ NMR |
|---|---|---|---|---|---|
| 325 | —N(Ac)— | 1 | 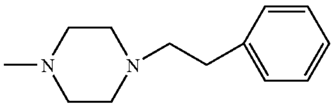 | hydro-chloride | mp 214-216 |
| 326 | —N(Ac)— | 1 | 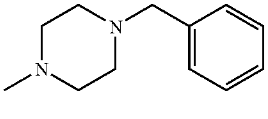 | free | $^1H$ NMR (DMSO-d$_6$) δ 1.77(3 H,s), 2.25-2.34(4 H, m), 3.30-3.50(6 H, m), 4.40 (2 H, s), 6.97(2 H, d, J = 8.8 Hz), 7.22-7.35(6 H, m), 7.36(2 H, d, J = 8.8 Hz), 7.53-7.59(1 H, m), 7.84(1 H, d, J = 8.3 Hz), 7.89-7.95(2 H, m), 8.20(1 H, d, J = 2.2 Hz), 10.61(1 H, s). |
| 327 | none | 1 | 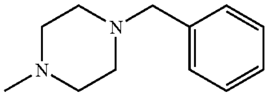 | free | mp 178-179 |
| 328 | none | 1 | morpholino | free | mp 196-198 |

TABLE 167-continued
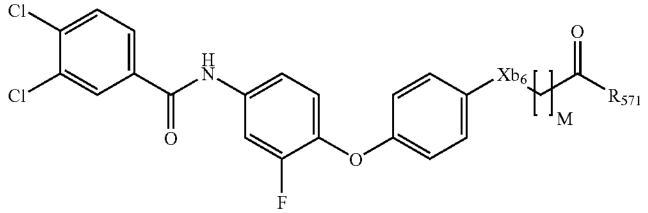
| Example No. | $Xb_6$ | M | $R_{571}$ | Form | δmp (° C.) or $^1$H NMR |
|---|---|---|---|---|---|
| 329 | none | 1 | 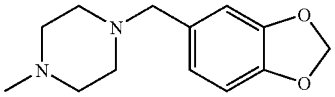 | free | mp 197-198 |
| 330 | none | 3 | morpholino | free | mp 144-146 |
| 331 | none | 3 | 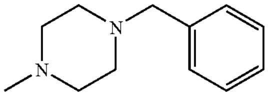 | hydro-chloride | mp 194-196 |
| 332 | none | 3 | 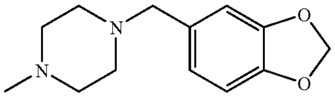 | hydro-chloride | mp 205-206 |
| 333 | —S— | 1 | 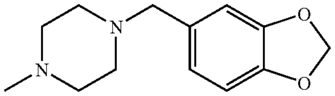 | free | $^1$H NMR ($CDCl_3$) δ 2.35-2.45(4 H, m), 3.42(2 H, s), 3.42-3.48(2 H, m), 3.58(2 H, brs), 3.65(2 H, s), 5.94(2 H, s), 6.72-6.75(2 H, m), 6.84(1 H, d, J = 1.1 Hz), 6.89(2 H, d, J = 8.8 Hz), 7.00-7.10(1 H, m), 7.19-7.25(1 H, m), 7.42(2 H, d, J = 8.8 Hz), 7.58(1 H, d, J = 8.3 Hz), 7.65-7.76(2 H, m), 7.98(1 H, s), 7.99(1 H, s). |
| 334 | —SO— | 1 | 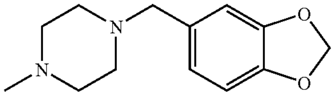 | free | mp 133-135 |
| 335 | —$SO_2$— | 1 | 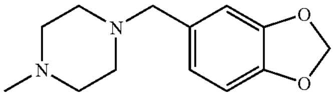 | free | mp 125-128 |
| 336 | CH═CH— (trans) | 0 | 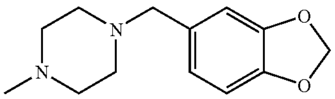 | free | mp 169-171 |
TABLE 168
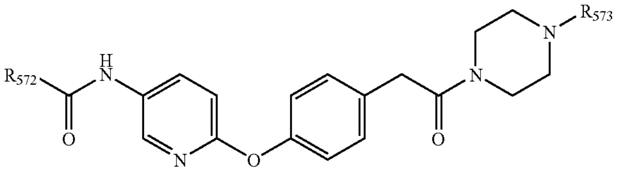
| Example No. | $R_{572}$ | $R_{573}$ | $^1$H NMR (solvent) δppm |
|---|---|---|---|
| 337 | 4-$CF_3$Ph- | benzyl | ($CDCl_3$) 2.30-2.34(2 H, m), 2.39-2.43(2 H, m), 3.46-3.49(4 H, m), 3.62-3.66(2 H, m), 3.69(2 H, s), 6.94(1 H, d, J = 8.7 Hz), 7.03-7.08(2 H, m), |

TABLE 168-continued

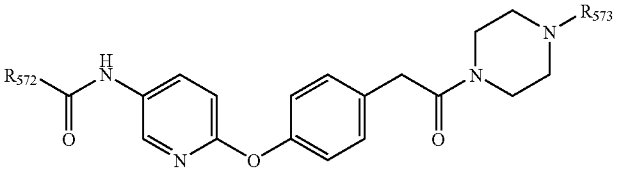

| Example No. | $R_{572}$ | $R_{573}$ | $^1$H NMR (solvent) δppm |
|---|---|---|---|
| | | | 7.19-7.35(7 H, m), 7.75(2 H, d, J = 8.2 Hz), 8.00(2 H, d, J = 8.2 Hz), 8.21(1 H, dd, J = 8.7 Hz, 2.8 Hz), 8.26(1 H, s), 8.29(1 H, d, J = 2.8 Hz). |
| 338 | 4-$CF_3$Ph- | piperonyl | ($CDCl_3$) 2.28-2.32(2 H, m), 2.36-2.39(2 H, m), 3.39(2 H, s), 3.45-3.49(2 H, m), 3.60-3.64(2 H, m), 3.68(2 H, s), 5.94(2 H, s), 6.69-6.76(2 H, m), 6.83(1 H, brs), 6.92(1 H, d, J = 8.7 Hz), 7.01-7.06(2 H, m), 7.17-7.22(2 H, m), 7.72(2 H, d, J = 8.4 Hz), 8.00(2 H, d, J = 8.1 Hz), 8.17-8.21(1 H, m), 8.29(1 H, d, J = 2.6 Hz), 8.49(1 H, brs). |
| 339 | 3,4-$Cl_2$Ph- | benzyl | ($CDCl_3$) 2.31-2.34(2 H, m), 2.38-2.42(2 H, m), 3.46-3.50(4 H, m), 3.62-3.65(2 H, m), 3.69(2 H, s), 6.90(1 H, d, J = 8.9 Hz), 7.00-7.05(2 H, m), 7.17-7.23(2 H, m), 7.28-7.35(5 H, m), 7.54(1 H, d, J = 8.2 Hz), 7.73(1 H, dd, J = 8.4 Hz, 2.1 Hz), 7.99(1 H, d, J = 2.1 Hz), 8.12-8.17(1 H, m), 8.28(1 H, d, J = 2.8 Hz), 8.44(1 H, brs). |
| 340 | 3,4-$Cl_2$Ph- | 3-pyridyl | ($CDCl_3$) 3.02-3.06(2 H, m), 3.13-3.17(2 H, m), 3.63-3.67(2 H, m), 3.76-3.82(4 H, m), 6.91(1 H, d, J = 8.9 Hz), 7.02-7.07(2 H, m), 7.17-7.24(4 H, m), 7.52(1 H, d, J = 8.4 Hz), 7.73-7.76(1 H, m), 8.01(1 H, d, J = 2.0 Hz), 8.11-8.13(1 H, m), 8.18(1 H,dd, J = 8.9 Hz, 2.8 Hz), 8.23-8.25(2 H, m), 8.95(1 H, brs). |
| 341 | 3,4-$Cl_2$Ph- | piperonyl | ($CDCl_3$) 2.28-2.39(4 H, m), 3.39(2 H, s), 3.46-3.49(2 H, m), 3.60-3.64(2 H, m), 3.69(2 H, s) 5.94(2 H, s), 6.69-6.76(2 H, m), 6.82-6.83(1 H, m), 6.89(1 H, d, J = 8.9 Hz), 6.99-7.04(2 H, m), 7.15-7.21(2 H, m), 7.53(1 H, d, J = 8.4 Hz), 7.71-7.75(1 H, m), 7.99(1 H, d, J = 2.1 Hz), 8.14(1 H, dd, J = 8.9 Hz, 2.6 Hz), 8.28(1 H, d, J = 2.6 Hz), 8.56(1 H, s). |
| 342 | 3,4-$Cl_2$PhNH— | piperonyl | (DMSO-$d_6$) 2.20-2.35(4 H, m), 3.38(2 H, s), 3.40-3.55(4 H, m), 3.69(2 H, s), 5.98(2 H, s), 6.70-6.76(1 H, m), 6.76-6.86(2 H, m), 6.97-7.00(3 H, m), 7.02-7.24(2 H, m), 7.35(1 H, dd, J = 8.8 Hz, 2.5 Hz), 7.52(1 H, d, J = 8.8 Hz), 7.86(1 H, d, J = 2.5 Hz), 7.98(1 H, dd, J = 8.8 Hz, 2.8 Hz), 8.19(1 H, d, J = 2.6 Hz), 8.89(1 H, s), 9.08(1 H, s). |

TABLE 169

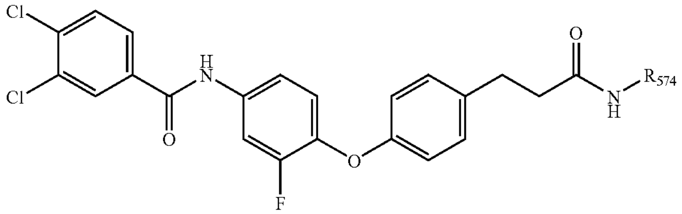

| Example No. | $R_{574}$ | $^1$H NMR (DMSO-$d_6$) δppm or MS |
|---|---|---|
| 343 | —H | $^1$H NMR 2.33(2 H, t, J = 7.7 Hz), 2.77(2 H, t, J = 7.7 Hz), 6.75(1 H, brs), 6.87(2 H, d, J = 8.6 Hz), 7.15-7.23(3 H, m), 7.28(1 H, brs), 7.54(1 H, d, J = 8.7 Hz), 7.85(1 H, d, J = 8.4 Hz), 7.89(1 H, dd, J = 13.2 Hz, 2.4 Hz), 7.94(1 H, dd, J = 8.4 Hz, 2.0 Hz), 8.21(1 H, d, J = 2.0 Hz), 10.57(1 H, s). |
| 344 | —$CH_3$ | MS 460($M^+$) |

TABLE 169-continued

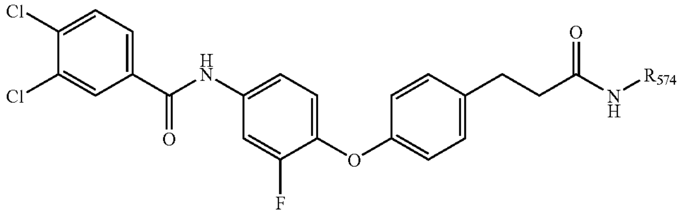

| Example No. | $R_{574}$ | $^1H$ NMR (DMSO-$d_6$) δppm or MS |
|---|---|---|
| 345 | —$C_2H_5$ | $^1H$ NMR 0.97(3 H, t, J = 7.2 Hz), 2.32(2 H, t, J = 7.8 Hz), 2.77(2 H, t, J = 7.8 Hz), 3.00-3.08(2 H, m), 6.87(2 H, d, J = 8.6 Hz), 7.14-7.21(3 H, m), 7.54(1 H, d, J = 9.8 Hz), 7.78(1 H, brt), 7.85(1 H, d, J = 8.4 Hz), 7.89(1 H, dd, J = 13.2 Hz, 2.3 Hz), 7.94(1 H, dd, J = 8.4 Hz, 2.1 Hz), 8.21(1 H, d, J = 2.1 Hz), 10.57(1 H, s). |
| 346 | —$CH(CH_3)_2$ | $^1H$ NMR 1.00(6 H, d, J = 6.6 Hz), 2.30(2 H, t, J = 7.7 Hz), 2.77(2 H, t, J = 7.7 Hz), 3.75-3.86(1 H, m), 6.87(2 H, d, J = 8.6 Hz), 7.13-7.20(3 H, m), 7.54(1 H, d, J = 8.9 Hz), 7.65(1 H, brd), 7.85(1 H, d, J = 8.4 Hz), 7.89(1 H, dd, J = 13.1 Hz, 2.5 Hz), 7.94(1 H, dd, J = 8.4 Hz, 2.1 Hz), 8.22(1 H, d, J = 2.1 Hz), 10.58(1 H, s). |
| 347 | —$CH_2CH(CH_3)_2$ | $^1H$ NMR 0.78(6 H, d, J = 6.7 Hz), 1.56-1.68(1 H, m), 2.36(2 H, t, J = 7.6 Hz), 2.78(2 H, t, J = 7.6 Hz), 2.81-2.87(2 H, m), 6.87(2 H, d, J = 8.6 Hz), 7.10-7.22(3 H, m), 7.54(1 H, d, J = 8.9 Hz), 7.77(1 H, brt), 7.85(1 H, d, J = 8.4 Hz), 7.89(1 H, dd, J = 13.2 Hz, 2.4 Hz), 7.94(1 H, dd, J = 8.4 Hz, 2.1 Hz), 8.21(1 H, d, J = 2.1 Hz), 10.57(1 H, s). |
| 348 | —$(CH_2)_3CH_3$ | $^1H$ NMR 0.84(3 H, t, J = 7.3 Hz), 1.15-1.27(2 H, m), 1.27-1.38(2 H, m), 2.33(2 H, t, J = 7.7 Hz), 2.77(2 H, t, J = 7.7 Hz), 2.97-3.05(2 H, m), 6.87(2 H, d, J = 8.6 Hz), 7.11-7.21(3 H, m), 7.50-7.58(1 H, m), 7.74(1 H, brt), 7.85(1 H, d, J = 8.4 Hz), 7.89 (1 H, dd, J = 13.2 Hz, 2.4Hz), 7.94(1 H, dd, J = 8.4 Hz, 2.1 Hz), 8.21(1 H, d, J = 2.1 Hz), 10.57(1 H, s). |
| 349 | cyclopropyl | $^1H$ NMR 0.26-0.37(2 H, m), 0.51-0.63(2 H, m), 2.29(2 H, t, J = 7.7 Hz), 2.53-2.61(1 H, m), 2.76(2 H, t, J = 7.7 Hz), 6.87(2 H, d, J = 8.6 Hz), 7.10-7.23(3 H, m), 7.54(1 H, d, J = 8.6 Hz), 7.80-8.00(4 H, m), 8.21(1 H, d, J = 2.1 Hz), 10.57(1 H, s). |
| 350 | cyclopentyl | $^1H$ NMR 1.21-1.34(2 H, m), 1.41-1.51(2 H, m), 1.51-1.63(2 H, m), 1.68-1.80(2 H, m), 2.31(2 H, t, J = 7.7 Hz), 2.76(2 H, t, J = 7.7 Hz), 3.90-3.99(1 H, m), 6.87(2 H, d, J = 8.6 Hz), 7.14-7.21(3 H, m), 7.50-7.57(1 H, m), 7.72(1 H, brd), 7.85(1 H, d, J = 8.4 Hz), 7.89(1 H, dd, J = 13.2 Hz, 2.4 Hz), 7.94(1 H, dd, J = 8.4 Hz, 2.1 Hz), 8.22(1 H, d, J = 2.1 Hz), 10.58(1 H, s). |
| 351 | cyclohexyl | $^1H$ NMR 1.00-1.15(3 H, m), 1.15-1.28(2 H, m), 1.48-1.58(1 H, m), 1.58-1.70(4 H, m), 2.31(2 H, t, J = 7.6 Hz), 2.77(2 H, t, J = 7.6 Hz), 3.44-3.53(1 H, m), 6.87(2 H, d, J = 8.6 Hz), 7.11-7.23(3 H, m), 7.50-7.57(1 H, m), 7.62(1 H, brd), 7.85(1 H, d, J = 8.4 Hz), 7.89(1 H, dd, J = 13.2 Hz, 2.4 Hz), 7.94(1 H, dd, J = 8.4 Hz, 2.1 Hz), 8.21(1 H, d, J = 2.1 Hz), 10.57(1 H, s). |

TABLE 170

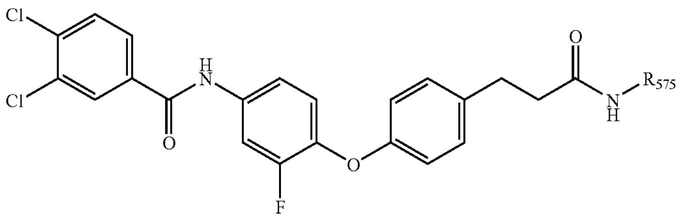

| Example No. | $R_{575}$ | $^1H$ NMR (DMSO-$d_6$) δ ppm |
|---|---|---|
| 352 | cycloheptyl | 1.28-1.40 (4 H, m), 1.40-1.61 (6 H, m), 1.63-1.77 (2 H, m), 2.31 (2 H, t, J = 7.6 Hz), 2.76 (2 H, t, J = 7.6 Hz), 3.64-3.74 (1 H, m), 6.87 (2 H, d, J = 8.6 Hz), 7.11-7.23 (3 H, m), 7.54 (1 H, d, J = 9.1 Hz), 7.67 (1 H, brd), 7.85 (1 H, d, J = 8.4 Hz), 7.89 (1 H, dd, J = 13.2 Hz, 2.4 Hz), 7.94 (1 H, dd, J = 8.4 Hz, 2.1 Hz), 8.21 (1 H, d, J = 2.1 Hz), 10.57 (1 H, s). |

TABLE 170-continued

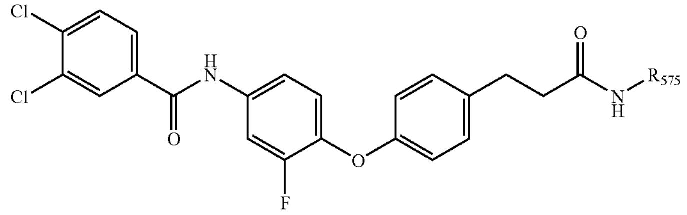

| Example No. | $R_{575}$ | $^1H$ NMR (DMSO-$d_6$) δ ppm |
|---|---|---|
| 353 | cyclooctyl | 1.30-1.65 (14 H, m), 2.31 (2 H, t, J = 7.6 Hz), 2.76 (2 H, t, J = 7.6 Hz), 3.69-3.80 (1 H, m), 6.87 (2 H, d, J = 8.6 Hz), 7.10-7.22 (3 H, m), 7.54 (1 H, d, J = 8.9 Hz), 7.65 (1 H, brd), 7.85 (1 H, d, J = 8.4 Hz), 7.89 (1 H, dd, J = 13.2 Hz, 2.3 Hz), 7.94 (1 H, dd, J = 8.4 Hz, 2.0 Hz), 8.21 (1 H, d, J = 2.0 Hz), 10.57 (1 H, s). |
| 354 | cyclododecanyl | 1.10-1.41 (20 H, m), 1.41-1.54 (2 H, m), 2.32 (2 H, t, J = 7.5 Hz), 2.77 (2 H, t, J = 7.5 Hz), 3.79-3.88 (1 H, m), 6.86 (2 H, d, J = 8.6 Hz), 7.10-7.21 (3 H, m), 7.48-7.57 (2 H, m), 7.85 (1 H, d, J = 8.4 Hz), 7.89 (1 H, dd, J = 13.1 Hz, 2.5 Hz), 7.94 (1 H, dd, J = 8.4 Hz, 2.1 Hz), 8.21 (1 H, d, J = 2.1 Hz), 10.58 (1 H, s). |
| 355 | cyclopropylmethyl | 0.06-0.16 (2 H, m), 0.28-0.42 (2 H, m), 0.78-0.90 (1 H, m), 2.35 (2 H, t, J = 7.7 Hz), 2.78 (2 H, t, J = 7.7 Hz), 2.84-2.97 (2 H, m), 6.87 (2 H, d, J = 8.5 Hz), 7.12-7.27 (3 H, m), 7.54 (1 H, d, J = 8.8 Hz), 7.85 (1 H, d, J = 8.4 Hz), 7.87 (1 H, brt), 7.89 (1 H, dd, J = 13.2 Hz, 2.3 Hz), 7.94 (1 H, dd, J = 8.4 Hz, 2.0 Hz), 8.21 (1 H, d, J = 2.0 Hz), 10.57 (1 H, s). |
| 356 | cyclohexylmethyl | 0.71-0.86 (2 H, m), 1.03-1.20 (3 H, m), 1.22-1.34 (1 H, m), 1.50-1.69 (5 H, m), 2.35 (2 H, t, J = 7.6 Hz), 2.78 (2 H, t, J = 7.6 Hz), 2.80-2.90 (2 H, m), 6.86 (2 H, d, J = 8.6 Hz), 7.12-7.23 (3 H, m), 7.54 (1 H, d, J = 8.9 Hz), 7.73 (1 H, brt), 7.85 (1 H, d, J = 8.4 Hz), 7.89 (1 H, dd, J = 13.2 Hz, 2.4 Hz), 7.94 (1 H, dd, J = 8.4 Hz, 2.1 Hz), 8.21 (1 H, d, J = 2.1 Hz), 10.57 (1 H, s). |
| 357 | piperonyl | 2.41 (2 H, t, J = 7.6 Hz), 2.81 (2 H, t, J = 7.6 Hz), 4.15 (2 H, d, J = 5.9 Hz), 5.96 (2 H, s), 6.63 (1 H, d, J = 8.0 Hz), 6.74 (1 H, d, J = 1.4 Hz), 6.80 (1 H, d, J = 8.0 Hz), 6.87 (2 H, d, J = 8.8 Hz), 7.14-7.23 (3 H, m), 7.54 (1 H, d, J = 9.8 Hz), 7.85 (1 H, d, J = 8.4 Hz), 7.89 (1 H, dd, J = 13.2 Hz, 2.4 Hz), 7.94 (1 H, dd, J = 8.4 Hz, 2.1 Hz), 8.22 (1 H, d, J = 2.1 Hz), 8.25 (1 H, brt), 8.40-8.46 (2 H, m), 10.58 (1 H, s). |
| 358 | —CH($CH_3$)Ph | 1.30 (3 H, d, J = 7.0 Hz), 2.40 (2 H, t, J = 7.5 Hz), 2.78 (2 H, t, J = 7.5 Hz), 3.86-3.96 (1 H, m), 6.82-6.99 (2 H, m), 7.12-7.24 (6 H, m), 7.24-7.31 (2 H, m), 7.55 (1 H, dd, J = 8.9 Hz, 1.2 Hz), 7.85 (1 H, d, J = 8.4 Hz), 7.90 (1 H, dd, J = 13.2 Hz, 2.5 Hz), 7.94 (1 H, dd, J = 8.4 Hz, 2.1 Hz), 8.22 (1 H, d, J = 2.1 Hz), 8.24 (1 H, brd), 10.59 (1 H, s). |

TABLE 171

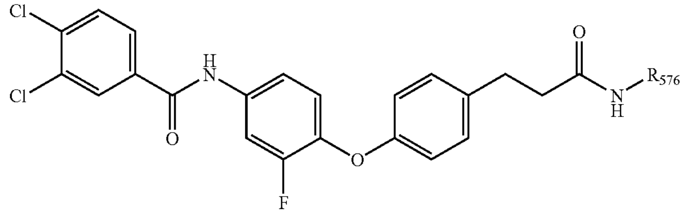

| Example No. | $R_{576}$ | $^1H$ NMR (DMSO-$d_6$) δ ppm or MS |
|---|---|---|
| 359 | 2-pyridylmethyl | MS 537($M^+$) |
| 360 | 3-pyridylmethyl | $^1H$ NMR 2.44 (2 H, t, J = 7.6 Hz), 2.82 (2 H, t, J = 7.6 Hz), 4.27 (2 H, d, J = 5.9 Hz), 6.86 (2 H, dd, J = 6.7 Hz, 1.9 Hz), 7.14-7.22 (3 H, m), 7.25-7.32 (1 H, m), 7.46-7.58 (2 H, m), 7.85 (1 H, d, J = 8.4 Hz), 7.90 (1 H, dd, J = 13.2 Hz, 2.5 Hz), 7.94 (1 H, dd, J = 8.4 Hz, 2.1 Hz), 8.22 (1 H, d, J = 2.1 Hz), 8.38 (1 H, brt), 8.40-8.46 (2 H, m), 10.58 (1 H, s). |

TABLE 171-continued

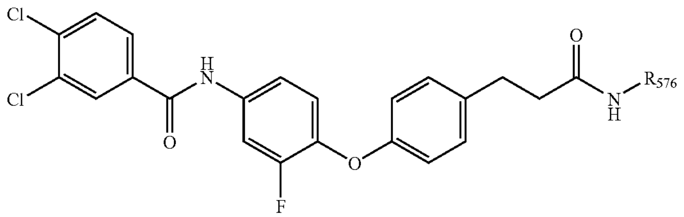

| Example No. | $R_{576}$ | $^1H$ NMR (DMSO-$d_6$) δ ppm or MS |
|---|---|---|
| 361 | 4-pyridylmethyl | MS 537($M^+$) |
| 362 | —$(CH_2)_2NHAc$ | $^1H$ NMR 1.78 (3 H, s), 2.34 (2 H, t, J = 7.8 Hz), 2.78 (2 H, t, J = 7.8 Hz), 2.96-3.10 (4 H, m), 6.83-6.91 (2 H, m), 7.14-7.23 (3 H, m), 7.54 (1 H, dd, J = 8.9 Hz, 1.3 Hz), 7.80-7.98 (5 H, m), 8.21 (1 H, d, J = 2.1 Hz), 10.58 (1 H, s). |
| 363 | —$CH(CH_3)(CH_2)_4CH_3$ | $^1H$ NMR 0.84 (3 H, t, J = 7.0 Hz), 0.96 (3 H, d, J = 6.6 Hz), 1.08-1.34 (8 H, m), 2.32 (2 H, t, J = 7.2 Hz), 2.77 (2 H, t, J = 7.2 Hz), 3.65-3.76 (1 H, m), 6.82-6.89 (2 H, m), 7.12-7.21 (3 H, m), 7.50-7.60 (2 H, m), 7.85 (1 H, d, J = 8.4 Hz), 7.89 (1 H, dd, J = 13.2 Hz, 2.5 Hz), 7.94 (1 H, dd, J = 8.3 Hz, 2.1 Hz), 8.21 (1 H, d, J = 2.1 Hz), 10.58 (1 H, s). |
| 364 | —$(CH_2)_2OCH_3$ | $^1H$ NMR 2.35 (2 H, t, J = 7.7 Hz), 2.77 (2 H, t, J = 7.7 Hz), 3.13-3.22 (2 H, m), 3.22 (3 H, s), 3.29 (2 H, t, J = 5.8 Hz), 6.82-6.92 (2 H, m), 7.13-7.23 (3 H, m), 7.54 (1 H, d, J = 8.9 Hz), 7.85 (1 H, d, J = 8.4 Hz), 7.85-7.92 (2 H, m), 7.94 (1 H, dd, J = 8.4 Hz, 2.0 Hz), 8.21 (1 H, d, J = 2.0 Hz), 10.57 (1 H, s). |
| 365 | 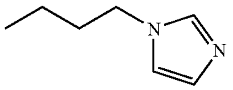 | MS 554($M^+$) |
| 366 | 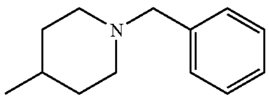 | MS 619($M^+$) |

TABLE 172

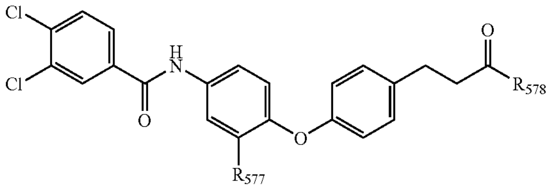

| Example No. | $R_{577}$ | $R_{578}$ | mp (° C.) or MS |
|---|---|---|---|
| 367 | —H | morpholino | mp 160-162 |
| 368 | —F | morpholino | mp 150-151 |
| 369 | —F | 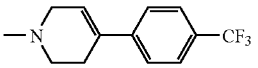 | MS 657 ($M^+$ + H) |

TABLE 172-continued

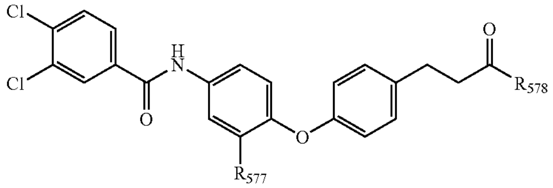

| Example No. | $R_{577}$ | $R_{578}$ | mp (° C.) or MS |
|---|---|---|---|
| 370 | —F | 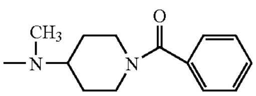 | MS 646 ($M^+$ − 1) |
| 371 | —F | 4-$CH_3OPh(CH_2)_2N(C_2H_5)$— | MS 608 ($M^+$) |
| 372 | —F | 4-$CH_3OPhCH_2N(C_2H_5)$— | MS 594 ($M^+$) |
| 373 | —F | 3,4-$(CH_3O)_2PhCH_2N(CH_2CH_2CH_3)$— | MS 638 ($M^+$) |

TABLE 173

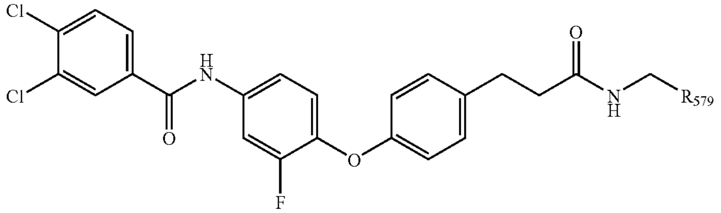

| Example No. | $R_{579}$ | $^1H$ NMR (DMSO-$d_6$) δ ppm |
|---|---|---|
| 374 | Ph- | 2.39-2.49 (2 H, m), 2.78-2.88 (2 H, m), 4.18-4.30 (2 H, m), 6.87 (2 H, d, J = 8.6 Hz), 7.02-7.33 (8 H, m), 7.55 (1 H, d, J = 8.9 Hz), 7.85 (1 H, d, J = 8.4 Hz), 7.90 (1 H, dd, J = 13.2 Hz, 2.4 Hz), 7.94 (1 H, dd, J = 8.4 Hz, 2.0 Hz), 8.22 (1 H, d, J = 2.0 Hz), 8.32 (1 H, brt), 10.58 (1 H, s). |
| 375 | 4-FPh- | 2.43 (2 H, t, J = 7.6 Hz), 2.82 (2 H, t, J = 7.6 Hz), 4.22 (2 H, d, J = 5.9 Hz), 6.87 (2 H, d, J = 8.6 Hz), 7.04-7.12 (2 H, m), 7.12-7.24 (5 H, m), 7.55 (1 H, d, J = 9.0 Hz), 7.85 (1 H, d, J = 8.4 Hz), 7.90 (1 H, dd, J = 13.2 Hz, 2.4 Hz), 7.94 (1 H, dd, J = 8.4 Hz, 2.1 Hz), 8.22 (1 H, d, J = 2.1 Hz), 8.32 (1 H, brt), 10.58 (1 H, s). |
| 376 | 3,4-$(CH_3O)_2$Ph- | 2.42 (2 H, t, J = 7.6 Hz), 2.82 (2 H, t, J = 7.6 Hz), 3.70 (3 H, s), 3.71 (3 H, s), 4.18 (2 H, d, J = 5.8 Hz), 6.67 (1 H, d, J = 8.4 Hz), 6.77-6.90 (4 H, m), 7.15-7.23 (3 H, m), 7.55 (1 H, d, J = 9.0 Hz), 7.85 (1 H, d, J = 8.4 Hz), 7.89 (1 H, dd, J = 13.2 Hz, 2.4 Hz), 7.94 (1 H, dd, J = 8.4 Hz, 2.1 Hz), 8.21 (1 H, d, J = 2.0 Hz), 8.25 (1 H, brt), 10.58 (1 H, s). |
| 377 | 2-ClPh- | 2.48 (2 H, t, J = 7.5 Hz), 2.83 (2 H, t, J = 7.5 Hz), 4.30 (2 H, d, J = 5.9 Hz), 6.88 (2 H, d, J = 8.6 Hz), 7.08-7.15 (1 H, m), 7.15-7.32 (5 H, m), 7.38-7.46 (1 H, m), 7.51-7.59 (1 H, m), 7.85 (1 H, d, J = 8.4 Hz), 7.90 (1 H, dd, J = 13.2 Hz, 2.4 Hz), 7.94 (1 H, dd, J = 8.4 Hz, 2.1 Hz), 8.22 (1 H, d, J = 2.0 Hz), 8.34 (1 H, brt), 10.58 (1 H, s). |
| 378 | 3-ClPh- | 2.45 (2 H, t, J = 7.5 Hz), 2.83 (2 H, t, J = 7.5 Hz), 4.25 (2 H, d, J = 6.0 Hz), 6.87 (2 H, d, J = 8.6 Hz), 7.07-7.12 (1 H, m), 7.12-7.21 (3 H, m), 7.21-7.25 (1 H, m), 7.25-7.33 (2 H, m), 7.55 (1 H, d, J = 9.0 Hz), 7.85 (1 H, d, J = 8.4 Hz), 7.90 (1 H, dd, J = 13.2 Hz, 2.4 Hz), 7.94 (1 H, dd, J = 8.4 Hz, 2.1 Hz), 8.22 (1 H, d, J = 2.1 Hz), 8.37 (1 H, brt), 10.58 (1 H, s). |
| 379 | 4-ClPh- | 2.44 (2 H, t, J = 7.5 Hz), 2.82 (2 H, t, J = 7.5 Hz), 4.22 (2 H, d, J = 6.0 Hz), 6.87 (2 H, d, J = 8.6 Hz), 7.14 (2 H, d, J = 8.4 Hz), 7.16-7.22 (3 H, m), 7.29-7.34 (2 H, m), 7.55 (1 H, d, J = 8.1 Hz), 7.85 (1 H, d, J = 8.4 Hz), 7.90 (1 H, dd, J = 13.2 Hz, 2.5 Hz), 7.94 (1 H, dd, J = 8.4 Hz, 2.1 Hz), 8.21 (1 H, d, J = 2.1 Hz), 8.34 (1 H, brt), 10.58 (1 H, s). |
| 380 | 2-$CH_3$Ph- | 2.21 (3 H, s), 2.44 (2 H, t, J = 7.5 Hz), 2.82 (2 H, t, J = 7.5 Hz), 4.21 (2 H, d, J = 5.7 Hz), 6.87 (2 H, d, J = 8.6 Hz), 7.00-7.07 (1 H, m), 7.07-7.23 (6 H, m), 7.55 (1 H, d, J = 9.0 Hz), 7.85 (1 H, d, J = 8.4 Hz), 7.90 (1 H, dd, J = 13.2 Hz, 2.4 Hz), 7.94 (1 H, dd, J = 8.4 Hz, 2.1 Hz), 8.16 (1 H, brt), 8.22 (1 H, d, J = 2.1 Hz), 10.58 (1 H, s). |
| 381 | 4-$CH_3$OPh- | 2.41 (2 H, t, J = 7.6 Hz), 2.81 (2 H, t, J = 7.6 Hz), 3.71 (3 H, s), 4.17 (2 H, d, J = 5.8 Hz), 6.80-6.91 (4 H, m), 7.07 (2 H, d, J = 8.5 Hz), 7.13-7.25 (3 H, m), 7.55 (1 H, d, J = 8.5 Hz), 7.85 (1 H, d, J = 8.4 Hz), 7.90 (1 H, dd, J = 13.2 Hz, 2.4 Hz), 7.94 (1 H, dd, J = 8.4 Hz, 2.1 Hz), 8.21 (1 H, d, J = 2.1 Hz), 8.24 (1 H, brt), 10.58 (1 H, s). |

TABLE 174

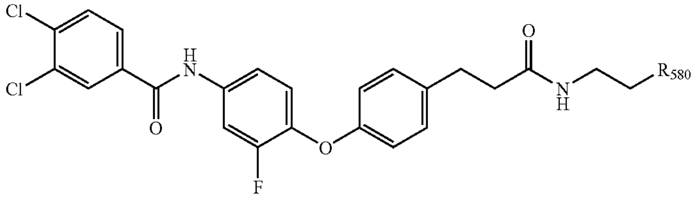

| Example No. | $R_{580}$ | $^1H$ NMR (DMSO-$d_6$) δ ppm |
|---|---|---|
| 382 | Ph- | 2.33 (2 H, t, J = 7.7 Hz), 2.66 (2 H, t, J = 7.3 Hz), 2.77 (2 H, t, J = 7.7 Hz), 3.20-3.29 (2 H, m), 6.87 (2 H, d, J = 8.6 Hz), |

TABLE 174-continued

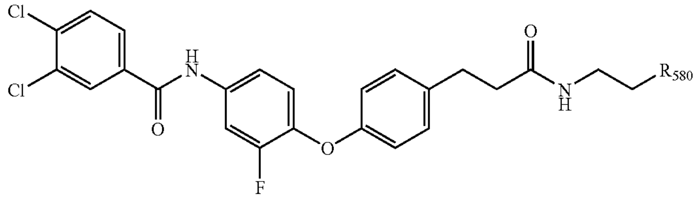

| Example No. | $R_{580}$ | $^1H$ NMR (DMSO-$d_6$) δ ppm |
|---|---|---|
| | | 7.12-7.22 (6 H, m), 7.23-7.30 (2 H, m), 7.54 (1 H, dd, J = 8.9 Hz, 1.1 Hz), 7.85 (1 H, d, J = 8.4 Hz), 7.85-7.91 (2 H, m), 7.94 (1 H, dd, J = 8.4 Hz, 2.1 Hz), 8.21 (1 H, d, J = 2.1 Hz), 10.57 (1 H, s). |
| 383 | 4-FPh- | 2.33 (2 H, t, J = 7.7 Hz), 2.65 (2 H, t, J = 7.2 Hz), 2.76 (2 H, t, J = 7.7 Hz), 3.30-3.37 (2 H, m), 6.87 (2 H, d, J = 8.5 Hz), 7.04-7.11 (2 H, m), 7.13-7.22 (5 H, m), 7.54 (1 H, d, J = 9.1 Hz), 7.85 (1 H, d, J = 8.4 Hz), 7.80-7.92 (2 H, m), 7.94 (1 H, dd, J = 8.4 Hz, 2.0 Hz), 8.21 (1 H, d, J = 2.0 Hz), 10.58 (1 H, s). |
| 384 | 4-ClPh- | 2.32 (2 H, t, J = 7.6 Hz), 2.66 (2 H, t, J = 7.1 Hz), 2.76 (2 H, t, J = 7.6 Hz), 3.18-3.27 (2 H, m), 6.87 (2 H, d, J = 8.5 Hz), 7.10-7.22 (5 H, m), 7.31 (2 H, d, J = 8.3 Hz), 7.54 (1 H, d, J = 8.9 Hz), 7.84 (1 H, d, J = 8.4 Hz), 7.85-7.92 (2 H, m), 7.94 (1 H, dd, J = 8.4 Hz, 2.0 Hz), 8.21 (1 H, d, J = 2.0 Hz), 10.57 (1 H, s). |
| 385 | 3-$CH_3$OPh- | 2.33 (2 H, t, J = 7.7 Hz), 2.64 (2 H, t, J = 7.3 Hz), 2.78 (2 H, t, J = 7.7 Hz), 3.18-3.27 (2 H, m), 3.72 (3 H, s), 6.70-6.78 (3 H, m), 6.87 (2 H, d, J = 8.6 Hz), 7.12-7.23 (4 H, m), 7.54 (1 H, dd, J = 8.9 Hz, 1.2 Hz), 7.85 (1 H, d, J = 8.4 Hz), 7.85-7.92 (2 H, m), 7.94 (1 H, dd, J = 8.4 Hz, 2.1 Hz), 8.21 (1 H, d, J = 2.0 Hz), 10.57 (1 H, s). |
| 386 | 4-$CH_3$OPh- | 2.33 (2 H, t, J = 7.6 Hz), 2.59 (2 H, t, J = 7.2 Hz), 2.77 (2 H, t, J = 7.6 Hz), 3.16-3.24 (2 H, m), 3.71 (3 H, s), 6.83 (2 H, d, J = 8.5 Hz), 6.87 (2 H, d, J = 8.5 Hz), 7.07 (2 H, d, J = 8.4 Hz), 7.13-7.23 (3 H, m), 7.54 (1 H, d, J = 8.5 Hz), 7.80-7.98 (4 H, m), 8.21 (1 H, d, J = 1.8 Hz), 10.57 (1 H, s). |
| 387 | PhO— | 2.38 (2 H, t, J = 7.7 Hz), 2.79 (2 H, t, J = 7.7 Hz), 3.38-3.43 (2 H, m), 3.94 (2 H, t, J = 5.7 Hz), 6.79-6.85 (2 H, m), 6.89-6.96 (3 H, m), 7.12-7.20 (3 H, m), 7.23-7.31 (2 H, m), 7.50-7.57 (1 H, m), 7.85 (1 H, d, J = 8.4 Hz), 7.89 (1 H, dd, J = 13.2 Hz, 2.4 Hz), 8.10 (1 h, brt), 8.22 (1 H, d, J = 2.1 Hz), 10.58 (1 H, s). |
| 388 | Ph$CH_2$— | 1.60-1.70 (2 H, m), 2.36 (2 H, t, J = 7.4 Hz), 2.49-2.55 (2 H, m), 2.79 (2 H, t, J = 7.4 Hz), 3.00-3.08 (2 H, m), 6.83-6.90 (2 H, m), 7.10-7.21 (6 H, m), 7.21-7.29 (2 H, m), 7.53 (1 H, d, J = 8.9 Hz), 7.89-7.92 (3 H, m), 8.21 (1 H, d, J = 2.1 Hz), 10.57 (1 H, s). |

TABLE 175

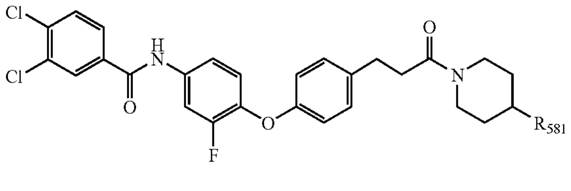

| Example No. | $R_{581}$ | MS |
|---|---|---|
| 389 | —$CHPh_2$ | 681 ($M^+$ + 1) |
| 390 | —NHCOPh | 633 ($M^+$) |
| 391 | —$O(CH_2)_2Ph$ | 634 ($M^+$) |
| 392 | —$(CH_2)_2N(CH_3)Ph$ | 647 ($M^+$) |
| 393 | 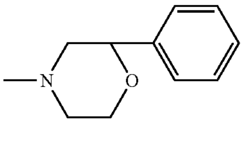 | 675 ($M^+$) |

TABLE 175-continued

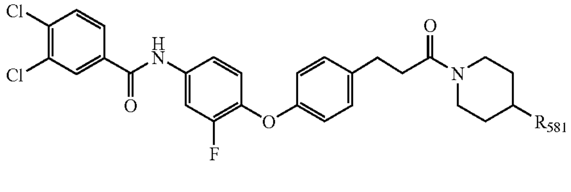

| Example No. | $R_{581}$ | MS |
|---|---|---|
| 394 | morpholino | 599 ($M^+$) |
| 395 | 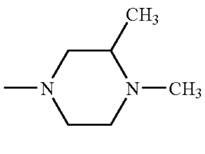 | 626 ($M^+$) |
| 396 | cyclohexyl | 596 ($M^+$) |

TABLE 175-continued

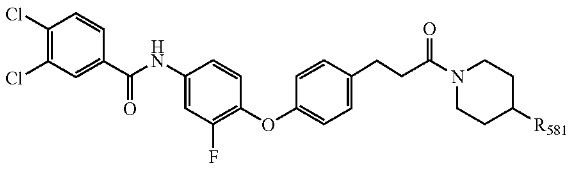

| Example No. | $R_{581}$ | MS |
|---|---|---|
| 397 | 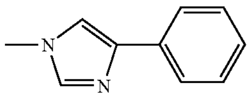 | 656 ($M^+$) |
| 398 | 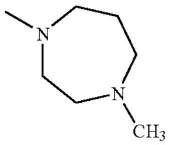 | 626 ($M^+$) |
| 399 | 4-$CH_3$OPhCONH— | 664 ($M^+$ + 1) |

TABLE 175-continued

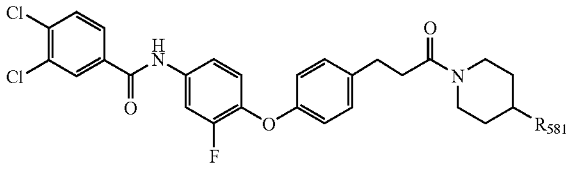

| Example No. | $R_{581}$ | MS |
|---|---|---|
| 400 | 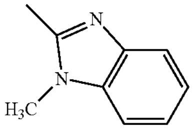 | 644 ($M^+$) |
| 401 | 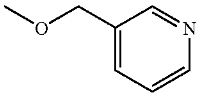 | 620 ($M^+$ − 1) |
| 402 | 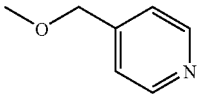 | 623 ($M^+$ + 2) |

TABLE 176

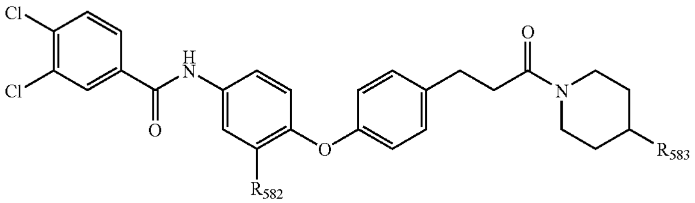

| Example No. | $R_{582}$ | $R_{583}$ | Property |
|---|---|---|---|
| 403 | —H | 4-$CF_3$OPhNH— | mp 91-95° C. |
| 404 | —F | 4-$CF_3$OPhNH— | mp 145-147° C. |
| 405 | —H | 4-$CF_3$PhO— | mp 118-121° C. |
| 406 | —H | 4-$CF_3$OPhO— | mp 126-127° C. |
| 407 | —F | 4-$CF_3$PhO— | mp 129-134° C. |
| 408 | —H | 4-CNPhO— | mp 148-149° C. |
| 409 | —F | 4-CNPhO— | mp 147-150° C. |
| 410 | —F | 4-$CF_3$OPhO— | $^1$H NMR ($CDCl_3$) δ 1.69-1.85 (4 H, m), 2.62 (2 H, t, J = 7.5 Hz), 2.90 (2 H, t, J = 7.5 Hz), 3.36 (1 H, m), 3.57-3.67 (3 H, m), 4.47 (1 H, m), 6.85-6.90 (4 H, m), 7.00 (1 H, t, J = 8.5 Hz), 7.10 (2 H, d, J = 8.5 Hz), 7.13 (2 H, d, J = 8.5 Hz), 7.30 (1 H, brd, J = 8.5 Hz), 7.52 (1 H, d, J = 8.5 Hz), 7.69-7.75 (2 H, m), 7.98 (1 H, d, J = 2.0 Hz), 8.80 (1 H, s). |
| 411 | —F | PhO— | MS 606 ($M^+$) |
| 412 | —F | 4-ClPh$CH_2$— | MS 638 ($M^+$) |
| 413 | —F | 4-$CH_3$Ph$CH_2$— | MS 618 ($M^+$) |
| 414 | —F | 4-ClPh- | MS 626 ($M^+$) |
| 415 | —F | Ph- | MS 590 ($M^+$) |
| 416 | —F | 2-$NH_2$PhCO— | MS 633 ($M^+$) |

TABLE 177

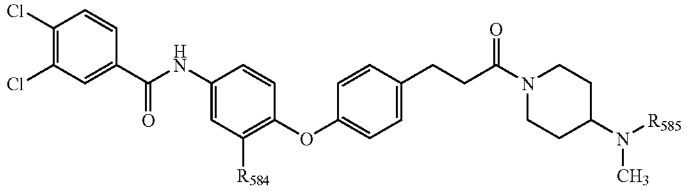

| Example No. | $R_{584}$ | $R_{585}$ | Form | mp (° C.) or MS |
|---|---|---|---|---|
| 417 | —F | —H | free | MS 543 ($M^+$) |
| 418 | —F | —$(CH_2)_2$OPh | free | MS 664 ($M^+$ + H) |
| 419 | —F | —$(CH_2)_2$Ph | free | MS 648 ($M^+$ + H) |
| 420 | —F | —$(CH_2)_2N(C_2H_5)_2$ | free | MS 643 ($M^+$ + H) |
| 421 | —H | —$(CH_2)_2$Ph | fumarate | mp 148-151 |
| 422 | —F | —$(CH_2)_3$Ph | free | MS 661 ($M^+$) |
| 423 | —F | —$(CH_2)_2CHPh_2$ | free | MS 737 ($M^+$) |
| 424 | —F | 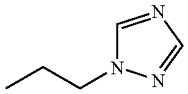 | free | MS 638 ($M^+$) |
| 425 | —F | 4-$CH_3$SPh$(CH_2)_2$— | free | MS 692 ($M^+$ − 1) |
| 426 | —F | 4-$CH_3$PhO$(CH_2)_2$— | free | MS 678 ($M^+$ + H) |
| 427 | —F | 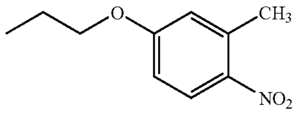 | free | MS 723 ($M^+$ + H) |
| 428 | —F | 4-$CH_3$OPh$(CH_2)_4$— | free | MS 705 ($M^+$) |
| 429 | —F | 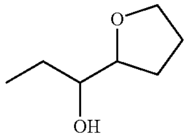 | free | MS 658 ($M^+$ + H) |
| 430 | —F | 4-$CH_3$Ph$(CH_2)_2$— | free | MS 661 ($M^+$) |
| 431 | —F | —$(CH_2)_2N(CH_3)$Ph | free | MS 676 ($M^+$) |
| 432 | —F | 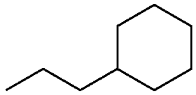 | free | MS 653 ($M^+$) |

TABLE 178

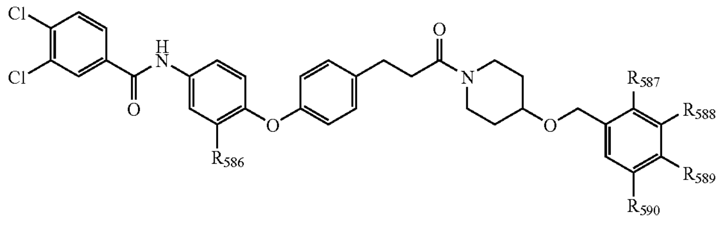

| Example No. | $R_{586}$ | $R_{587}$ | $R_{588}$ | $R_{589}$ | $R_{590}$ | mp (° C.) or MS |
|---|---|---|---|---|---|---|
| 433 | —H | —H | —H | —$CF_3$ | —H | mp 124-126 |
| 434 | —F | —H | —H | —$CF_3$ | —H | mp 132-134 |
| 435 | —F | —H | —H | —Cl | —H | MS 654 ($M^+$) |
| 436 | —F | —F | —H | —H | —H | MS 638 ($M^+$) |
| 437 | —F | —H | —H | —H | —H | MS 620 ($M^+$) |
| 438 | —F | —H | —H | —$OCH_3$ | —H | MS 651 ($M^+$ + H) |
| 439 | —F | —H | —Cl | —H | —H | MS 656 ($M^+$) |
| 440 | —F | —Cl | —H | —H | —H | MS 654 (M) |

TABLE 178-continued

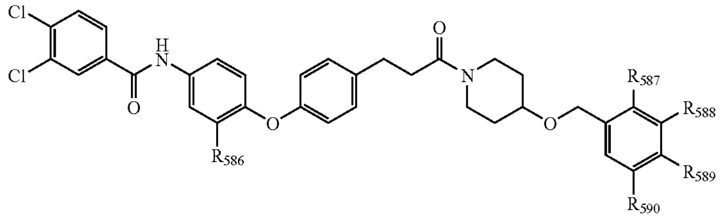

| Example No. | $R_{586}$ | $R_{587}$ | $R_{588}$ | $R_{589}$ | $R_{590}$ | mp (° C.) or MS |
|---|---|---|---|---|---|---|
| 441 | —F | —H | —Cl | —Cl | —H | MS 690 ($M^+$) |
| 442 | —F | —H | —$OCH_3$ | —H | —H | MS 650 ($M^+$) |
| 443 | —F | —H | —$OCH_3$ | —H | —$OCH_3$ | MS 680 ($M^+$) |
| 444 | —F | —H | —H | —$CH_3$ | —H | MS 635 ($M^+$ + H) |
| 445 | —F | —H | —$CH_3$ | —H | —H | MS 636 ($M^+$ + 2) |
| 446 | —F | —$CH_3$ | —H | —H | —H | MS 635 ($M^+$ + H) |
| 447 | —F | —H | —$CH_3$ | —$CH_3$ | —H | MS 648 ($M^+$) |
| 448 | —F | —H | —H | —F | —H | MS 638 ($M^+$) |
| 449 | —F | —H | —F | —H | —H | MS 638 ($M^+$) |
| 450 | —F | —H | —F | —H | —F | MS 656 ($M^+$) |
| 451 | —F | —$CF_3$ | —H | —H | —H | MS 688 ($M^+$) |
| 452 | —F | —H | —H | —$OCF_3$ | —H | MS 705 ($M^+$ + H) |
| 453 | —F | —H | —$OCF_3$ | —H | —H | MS 704 ($M^+$) |
| 454 | —F | —$OCF_3$ | —H | —H | —H | MS 704 ($M^+$) |
| 455 | —F | —H | —Cl | —$OCH_3$ | —H | MS 685 ($M^+$ + H) |

TABLE 179

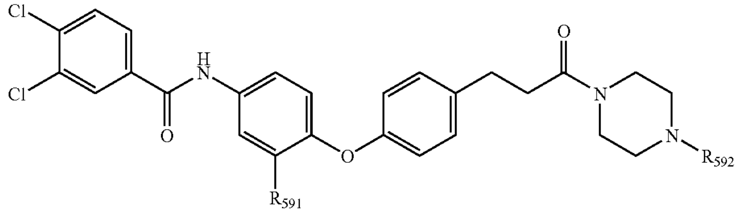

| Example No. | $R_{591}$ | $R_{592}$ | Property |
|---|---|---|---|
| 456 | —H | —$CH_2CONHPh$ | $^1H$ NMR ($CDCl_3$) δ 2.45 (2 H, brt, J = 5.0 Hz), 2.55 (2 H, brt, J = 5.0 Hz), 2.63 (2 H, t, J = 7.5 Hz), 2.96 (2 H, t, J = 7.5 Hz), 3.11 (2 H, s), 3.47 (2 H, brs), 3.70 (2 H, brs), 6.93 (2 H, d, J = 8.5 Hz), 6.98 (2 H, d, J = 8.5 Hz), 7.13 (1 H, t, J = 8.5 Hz), 7.15 (2 H, d, J = 8.5 Hz), 7.34 (2 H, t, J = 8.5 Hz), 7.52-7.59 (5 H, m), 7.73 (1 H, dd, J = 8.5 Hz, 2.0 Hz), 7.99 (1 H, d, J = 2.0 Hz), 8.28 (1 H, s), 8.92 (1 H, s). |
| 457 | —F | —$CH_2CONHPh$ | $^1H$ NMR ($CDCl_3$) δ 2.39 (2 H, brs), 2.51 (2 H, brs), 2.61 (2 H, t, J = 7.5 Hz), 2.93 (2 H, t, J = 7.5 Hz), 3.08 (2 H, s), 3.43 (2 H, brs), 3.67 (2 H, brs), 6.88 (2 H, d, J = 8.5 Hz), 7.03 (1 H, t, J = 8.5 Hz), 7.11-7.15 (3 H, m), 7.30-7.35 (3 H, m), 7.51-7.54 (3 H, m), 7.70 (1 H, dd, J = 9.0 Hz, 2.0 Hz), 7.74 (1 H, dd, J = 8.5 Hz, 2.0 Hz), 8.00 (1 H, d, J = 2.0 Hz), 8.74 (1 H, s), 8.93 (1 H, s). |
| 458 | —F | —$(CH_2)_3Ph$ | MS 633 ($M^+$) |
| 459 | —F | —$(CH_2)_4Ph$ | MS 647 ($M^+$) |
| 460 | —F | —$CH(C_2H_5)_2$ | MS 586 ($M^+$ + 1) |
| 461 | —F | —$CH(CH_3)_2$ | MS 556 ($M^+$ − 1) |
| 462 | —F | —$(CH_2)_3CH_3$ | MS 571 ($M^+$) |
| 463 | —F | —$(CH_2)_2N(CH_3)_2$ | MS 585 ($M^+$ − 1) |
| 464 | —F | —$COOC(CH_3)_3$ | mp 155-157° C. |
| 465 | —F | —$CH_2COPh$ | MS 633 ($M^+$) |
| 466 | —H | 3-pyridyl | mp 153-155° C. |
| 467 | —F | 3-pyridyl | mp 183-185° C. |
| 468 | —F | 2-pyridyl | MS 591 ($M^+$ − 1) |
| 469 | —F | 4-pyridyl | MS 592 ($M^+$) |

TABLE 179-continued
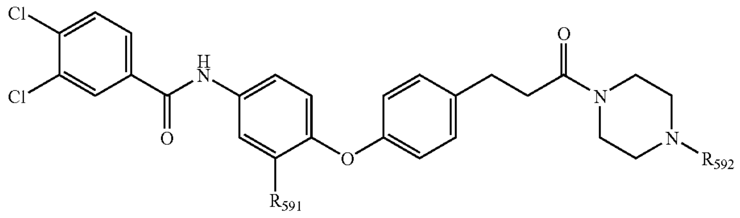
| Example No. | $R_{591}$ | $R_{592}$ | Property |
|---|---|---|---|
| 470 | —F | 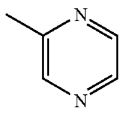 | MS 593 ($M^+$) |
| 471 | —F | 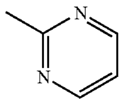 | MS 593 ($M^+$) |
TABLE 180
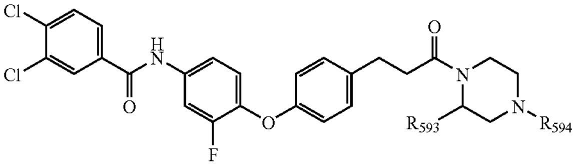
| Example No. | $R_{593}$ | $R_{594}$ | MS |
|---|---|---|---|
| 472 | —$CH_3$ | benzyl | 619 ($M^+$) |
| 473 | 2-pyridylmethyl | —H | 606 ($M^+$) |
| 474 | 3-pyridylmethyl | —H | 606 ($M^+$) |
| 475 | 4-pyridylmethyl | —H | 605 ($M^+$ − 1) |
| 476 | cyclopentyl | —H | 583 ($M^+$) |
| 477 | cycloheptyl | —H | 611 ($M^+$) |
| 478 | 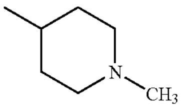 | —H | 612 ($M^+$) |
| 479 | 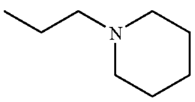 | —H | 627 ($M^+$ + H) |
| 480 | 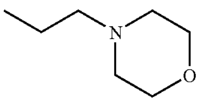 | —H | 628 ($M^+$) |
TABLE 180-continued
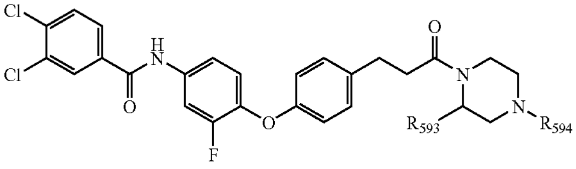
| Example No. | $R_{593}$ | $R_{594}$ | MS |
|---|---|---|---|
| 481 | 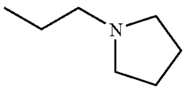 | —H | 612 ($M^+$) |
| 482 | 2-quinolylmethyl | —H | 657 ($M^+$ + H) |
| 483 | 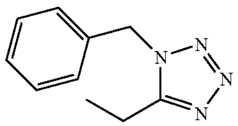 | —H | 686 ($M^+$ − 1) |
| 484 | 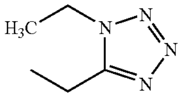 | —H | 625 ($M^+$) |
| 485 | 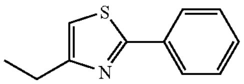 | —H | 688 ($M^+$) |

TABLE 181

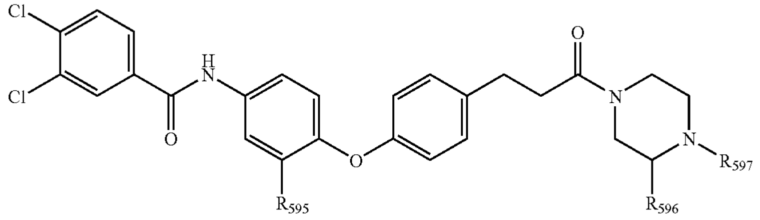

| Example No. | $R_{595}$ | $R_{596}$ | $R_{597}$ | Form | mp (° C.) or MS |
|---|---|---|---|---|---|
| 486 | —H | —H | $—COOC(CH_3)_3$ | free | mp 188-189 |
| 487 | —H | —H | $—CH_3$ | free | mp 189-191 |
| 488 | —H | —H | benzyl | fumarate | mp 190-192 |
| 489 | —F | —H | $—(CH_2)_2Ph$ | hydrochloride | mp 191-200 |
| 490 | —F | —H | piperonyl | hydrochloride | mp 226-228 |
| 491 | —F | —H | 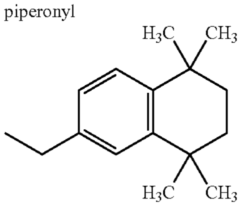 | free | MS 714 ($M^+ - 1$) |
| 492 | —F | —H | 1-naphthylmethyl | free | MS 655 ($M^+$) |
| 493 | —F | $—CH_3$ | $3,4-(CH_3O)_2PhCH_2—$ | free | MS 679 ($M^+$) |
| 494 | —F | —H | 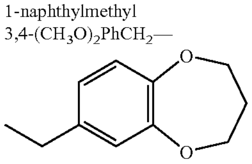 | free | MS 678 ($M^+ + 1$) |
| 495 | —F | —H | $—CH(CH_3)Ph$ | free | MS 619 ($M^+$) |
| 496 | —F | —H | 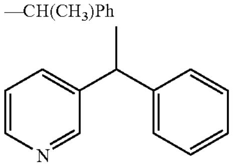 | free | MS 682 ($M^+$) |
| 497 | —F | —H | $(4-FPh)_2CH—$ | free | MS 717 ($M^+$) |
| 498 | —F | —H | $4-CH_3OPhCH(Ph)—$ | free | MS 711 ($M^+$) |

TABLE 182

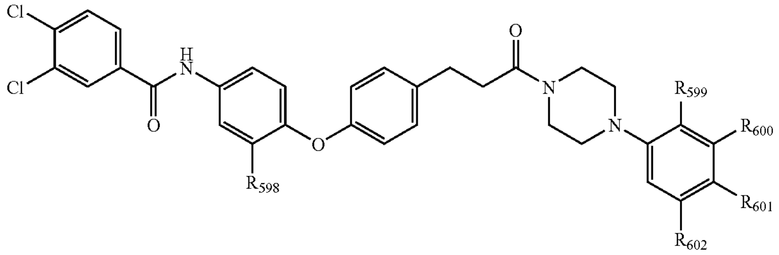

| Example No. | $R_{598}$ | $R_{599}$ | $R_{600}$ | $R_{601}$ | $R_{602}$ | Form | mp (° C.) or MS |
|---|---|---|---|---|---|---|---|
| 499 | —F | —H | —H | $—OCF_3$ | —H | hydrochloride | mp 118-121 |
| 500 | —F | —H | —H | —CN | —H | free | mp 190-192 |
| 501 | —F | —H | —H | $—OCF_3$ | —H | hydrochloride | mp 148-149 |
| 502 | —H | —H | —H | —CN | —H | free | mp 186-188 |
| 503 | —F | $—CF_3$ | —H | —H | —H | free | MS 659 ($M^+$) |
| 504 | —F | —H | $—CF_3$ | —H | —H | free | MS 659 ($M^+$) |
| 505 | —F | —H | —H | $—COOC(CH_3)_3$ | —H | free | MS 691 ($M^+$) |
| 506 | —F | —H | —H | —F | —H | free | MS 609 ($M^+$) |
| 507 | —F | $—OCH_3$ | —H | —H | —H | free | MS 621 ($M^+$) |
| 508 | —F | —Cl | —H | —H | —H | free | MS 625 ($M^+$) |
| 509 | —F | —H | —H | —Cl | —H | free | MS 627 ($M^+$) |
| 510 | —F | —H | —Cl | —H | —H | free | MS 625 ($M^+$) |
| 511 | —F | —Cl | —Cl | —H | —H | free | MS 661 ($M^+$) |

TABLE 182-continued

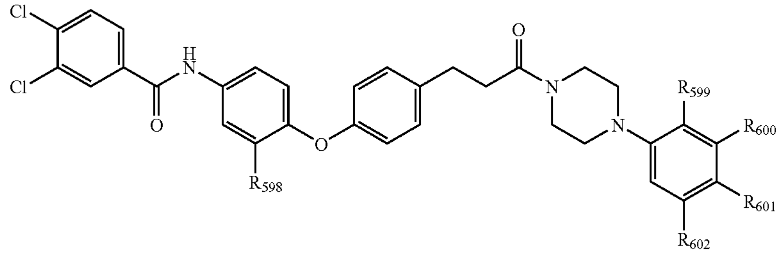

| Example No. | $R_{598}$ | $R_{599}$ | $R_{600}$ | $R_{601}$ | $R_{602}$ | Form | mp (° C.) or MS |
|---|---|---|---|---|---|---|---|
| 512 | —F | —H | —H | —$OCH_3$ | —H | free | MS 621 ($M^+$) |
| 513 | —F | —H | —$OCH_3$ | —H | —H | free | MS 621 ($M^+$) |
| 514 | —F | —H | —H | —$CH_3$ | —H | free | MS 605 ($M^+$) |
| 515 | —F | —H | —$CH_3$ | —H | —H | free | MS 605 ($M^+$) |
| 516 | —F | —$CH_3$ | —H | —H | —H | free | MS 605 ($M^+$) |
| 517 | —F | —$CH_3$ | —$CH_3$ | —H | —H | free | MS 619 ($M^+$) |
| 518 | —F | —H | —$CH_3$ | —$CH_3$ | —H | free | MS 619 ($M^+$) |
| 519 | —F | —H | —H | —$CF_3$ | —H | free | MS 659 ($M^+$) |
| 520 | —F | —H | —H | —Ph | —H | free | MS 667 ($M^+$) |
| 521 | —F | —F | —H | —H | —H | free | MS 609 ($M^+$) |
| 522 | —F | —F | —H | —F | —H | free | MS 627 ($M^+$) |
| 523 | —F | —$OCH_3$ | —H | —H | —Cl | free | MS 657 ($M^+$) |

TABLE 183

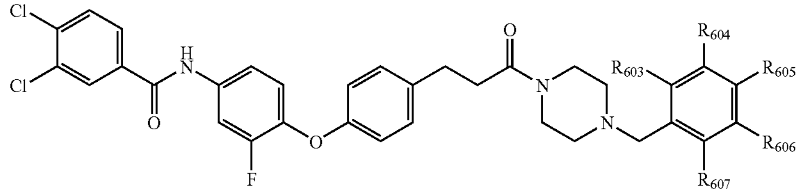

| Example No. | $R_{603}$ | $R_{604}$ | $R_{605}$ | $R_{606}$ | $R_{607}$ | Form | mp (° C.) or MS |
|---|---|---|---|---|---|---|---|
| 524 | —H | —H | —H | —H | —H | fumarate | mp 168-170 |
| 525 | —H | —H | —Cl | —H | —H | free | MS 638 ($M^+$ − 1) |
| 526 | —H | —Cl | —H | —H | —H | free | MS 639 ($M^+$) |
| 527 | —Cl | —H | —H | —H | —H | free | MS 641 ($M^+$ + 2) |
| 528 | —Cl | —Cl | —H | —H | —H | free | MS 675 ($M^+$ + 2) |
| 529 | —Cl | —H | —Cl | —H | —H | free | MS 673 ($M^+$) |
| 530 | —Cl | —H | —H | —Cl | —H | free | MS 673 ($M^+$) |
| 531 | —H | —Cl | —Cl | —H | —H | free | MS 676 ($M^+$ + 3) |
| 532 | —H | —$OCH_3$ | —H | —H | —H | free | MS 635 ($M^+$) |
| 533 | —$OCH_3$ | —H | —H | —H | —H | free | MS 635 ($M^+$) |
| 534 | —H | —$OCH_3$ | —H | —$OCH_3$ | —H | free | MS 665 ($M^+$) |
| 535 | —H | —$CH_3$ | —H | —H | —H | free | MS 619 ($M^+$) |
| 536 | —$CH_3$ | —H | —H | —H | —H | free | MS 619 ($M^+$) |
| 537 | —H | —$CH_3$ | —$CH_3$ | —H | —H | free | MS 633 ($M^+$) |
| 538 | —H | —H | —F | —H | —H | free | MS 623 ($M^+$) |
| 539 | —H | —F | —H | —H | —H | free | MS 623 ($M^+$) |
| 540 | —F | —H | —H | —H | —H | free | MS 623 ($M^+$) |
| 541 | —F | —H | —F | —H | —H | free | MS 641 ($M^+$) |
| 542 | —F | —H | —H | —H | —F | free | MS 641 ($M^+$) |
| 543 | —H | —H | —$NO_2$ | —H | —H | free | MS 650 ($M^+$) |
| 544 | —H | —$NO_2$ | —H | —H | —H | free | MS 650 ($M^+$) |
| 545 | —$NO_2$ | —H | —H | —H | —H | free | MS 650 ($M^+$) |
| 546 | —H | —$CF_3$ | —H | —H | —H | free | MS 673 ($M^+$) |
| 547 | —H | —H | —CN | —H | —H | free | MS 630 ($M^+$) |
| 548 | —H | —$OCF_3$ | —H | —H | —H | free | MS 689 ($M^+$) |
| 549 | —H | —H | —$COOCH_3$ | —H | —H | free | MS 664 ($M^+$ + 1) |
| 550 | —H | —H | —$C(CH_3)_3$ | —H | —H | free | MS 661 ($M^+$) |
| 551 | —H | —H | —$OCH_2Ph$ | —H | —H | free | MS 710 ($M^+$ − 1) |
| 552 | —H | —H | —Ph | —H | —H | free | MS 681 ($M^+$) |
| 553 | —Cl | —H | —H | —H | —Cl | free | MS 675 ($M^+$ + 2) |
| 554 | —F | —H | —H | —H | —H | free | MS 641 ($M^+$) |
| 555 | —H | —F | —H | —H | —H | free | MS 641 ($M^+$) |
| 556 | —H | —H | —$CF_3$ | —H | —H | free | MS 674 ($M^+$ + 1) |

TABLE 183-continued

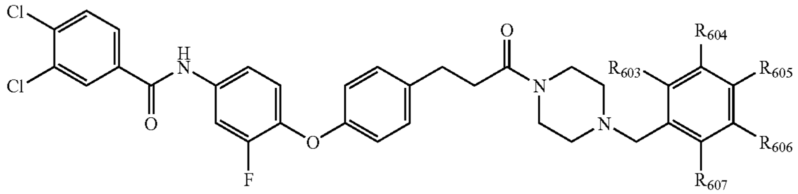

| Example No. | $R_{603}$ | $R_{604}$ | $R_{605}$ | $R_{606}$ | $R_{607}$ | Form | mp (° C.) or MS |
|---|---|---|---|---|---|---|---|
| 557 | —H | —H | —$OCF_3$ | —H | —H | free | MS 689 ($M^+$) |
| 558 | —$OCF_3$ | —H | —H | —H | —H | free | MS 689 ($M^+$) |
| 559 | —H | —$COOCH_3$ | —H | —H | —H | free | MS 663 ($M^+$) |
| 560 | —H | —H | —$C_2H_5$ | —H | —H | free | MS 633 ($M^+$) |
| 561 | —H | —H | —$CH(CH_3)_2$ | —H | —H | free | MS 647 ($M^+$) |
| 562 | —H | —Cl | —$OCH_3$ | —H | —H | free | MS 669 ($M^+$) |

TABLE 184

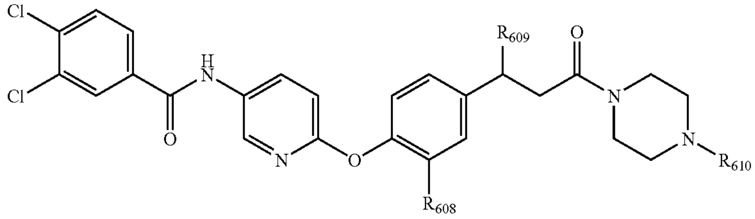

| Example No. | $R_{608}$ | $R_{609}$ | $R_{610}$ | Form | mp (° C.) or $^1$H NMR (solvent) δ ppm |
|---|---|---|---|---|---|
| 563 | —H | —$CH_3$ | piperonyl | free | mp 147-149 |
| 564 | —H | —H | piperonyl | free | mp 138-140 |
| 565 | —H | —$CH_3$ | benzyl | free | mp 150-152 |
| 566 | —H | —H | benzyl | free | $^1$H NMR ($CDCl_3$) 2.34-2.42 (4 H, m), 2.58-2.64 (2 H, m), 2.91-2.96 (2 H, m), 3.40-3.43 (2 H, m), 3.51 (2 H, s), 3.60-3.64 (2 H, m), 6.93 (1 H, d, J = 8.9 Hz), 7.01-7.04 (2 H, m), 7.20 (2 H, d, J = 8.6 Hz), 7.27-7.33 (5 H, m), 7.56 (1 H, d, J = 8.3 Hz), 7.71-7.75 (1 H, m), 8.00 (1 H, d, J = 2.0 Hz), 8.16-8.27 (3 H, m). |
| 567 | —$OCH_3$ | —H | piperonyl | free | mp 142.0-144.5 |
| 568 | —F | —H | piperonyl | free | mp 156.5-157.5 |
| 569 | —H | —H | —$COOC(CH_3)_3$ | free | $^1$H NMR ($CDCl_3$) 1.46 (9 H, s), 2.62-2.67 (2 H, m), 2.96-3.01 (2 H, m), 3.33-3.39 (6 H, m), 3.57-3.60 (2 H, m), 6.94-6.97 (1 H, m), 7.05 (2 H, d, J = 8.4 Hz), 7.23 (2 H, d, J = 8.4 Hz), 7.57 (1 H, d, J = 8.1 Hz), 7.71-7.75 (1 H, m), 8.00 (1 H, d, J = 2.2 Hz), 8.13 (1 H, brs), 8.21-8.24 (2 H, m). |
| 570 | —$OC_2H_5$ | —H | piperonyl | oxalate | $^1$H NMR (DMSO-$d_6$) 1.06 (3 H, t, J = 6.9 Hz), 2.39-2.86 (8 H, m), 3.40-3.60 (4 H, m), 3.65 (2 H, s), 3.70-5.20 (4 H, m), 6.00 (2 H, s), 6.76-6.84 (2 H, m), 6.85-7.02 (5 H, m), 7.82 (1 H, d, J = 8.4 Hz), 7.92 (1 H, m), 8.03 (1 H, m), 8.20 (1 H, d, J = 2.0 Hz), 8.35 (1 H, d, J = 2.5 Hz), 10.47 (1 H, s). |

TABLE 185

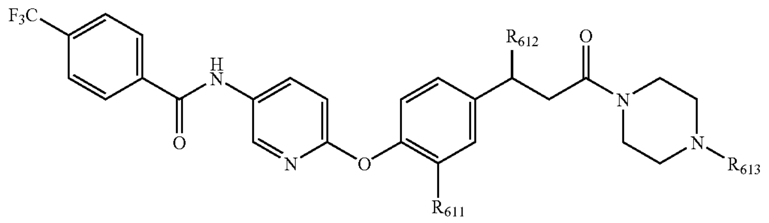

| Example No. | $R_{611}$ | $R_{612}$ | $R_{613}$ | Form | mp (° C.) or $^1$H NMR ($CDCl_3$) δppm |
|---|---|---|---|---|---|
| 571 | —H | —$CH_3$ | piperonyl | hydro-chloride | mp 218-220 |
| 572 | —H | —$CH_3$ | benzyl | free | mp 142-144 |
| 573 | —$OCH_3$ | —H | benzyl | free | $^1$H NMR 2.34-2.40 (4H, m), 2.58-2.63 (2H, m), 2.89-2.94 (2H, m), 3.39-3.42 (2H, m), 3.50 (2H, s), 3.58-3.61 (2H, m), 3.70 (3H, s), 6.75-6.80 (2H, m), 6.91 (1H, d, J = 8.7 Hz), 7.00 (1H, d, J = 7.9 Hz), 7.24-7.35 (5H, m), 7.69 (2H, d, J = 8.1 Hz), 7.98 (2H, d, J = 8.1 Hz), 8.14-8.18 (1H, m), 8.23 (1H, d, J = 2.3 Hz), 8.59 (1H, s). |
| 574 | —$OCH_3$ | —H | piperonyl | free | $^1$H NMR 2.31-2.37 (4H, m), 2.57-2.63 (2H, m), 2.88-2.94 (2H, m), 3.37-3.41 (4H, m), 3.57-3.60 (2H, m), 3.70 (3H, s), 5.93 (2H, s), 6.69-6.80 (4H, m), 6.84 (1H, brs), 6.90 (1H, d, J = 8.9 Hz), 7.00 (1H, d, J = 7.9 Hz), 7.69 (2H, d, J = 8.1 Hz), 7.98 (2H, d, J = 8.1 Hz), 8.14-8.19 (1H, m), 8.24 (1H, d, J = 2.5 Hz), 8.67 (1H, s). |
| 575 | —F | —H | piperonyl | free | mp 170.5-171.0 |
| 576 | —H | —H | —$COOC(CH_3)_3$ | free | $^1$H NMR 1.46 (9H, s), 2.66 (2H, t, J = 6.5 Hz), 2.97 (2H, t, J = 6.5 Hz), 3.25-3.48 (6H, m), 3.51-3.65 (2H, m), 6.95 (1H, d, J = 9.7 Hz), 7.04 (2H, d, J = 8.4 Hz), 7.22 (2H, d, J = 8.4 Hz), 7.75 (2H, d, J = 8.2 Hz), 8.01 (2H, d, J = 8.2 Hz), 8.18-8.33 (3H, m). |
| 577 | —$OC_2H_5$ | —H | piperonyl | hydro-chloride | mp 147.5-149.0 |

TABLE 186

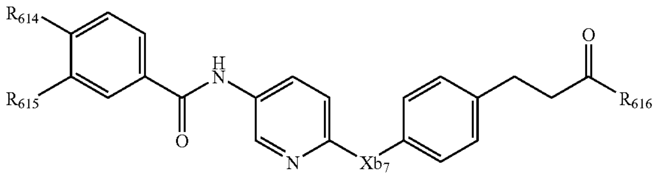

| Example No. | $R_{614}$ | $R_{615}$ | $R_{616}$ | $Xb_7$ | Form | mp (° C.) or $^1$H NMR |
|---|---|---|---|---|---|---|
| 578 | —Cl | —Cl | morpholino | —O— | free | $^1$H NMR ($CDCl_3$) δ 2.60-2.66 (2H, m), 2.96-3.02 (2H, m), 3.37-3.41 (2H, m), 3.55-3.64 (6H, m), 6.96 (1H, d, J = 8.4 Hz), 7.06 (2H, d, J = 8.6 Hz), 7.23-7.26 (2H, m), 7.58 (1H, d, J = 8.4 Hz), 7.70-7.74 (1H, m), 7.86 (1H, brs), 7.99 (1H, d, J = 1.9 Hz), 8.19-8.25 (2H, m). |

TABLE 186-continued
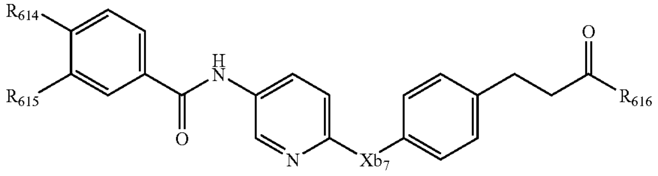
| Example No. | $R_{614}$ | $R_{615}$ | $R_{616}$ | $Xb_7$ | Form | mp (° C.) or $^1H$ NMR |
|---|---|---|---|---|---|---|
| 579 | —Cl | —Cl | 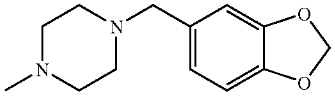 | —NH— | free | mp 141-142 |
| 580 | —Cl | —Cl | 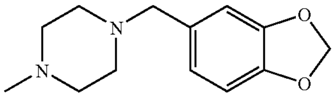 | —S— | free | mp 169-170 |
| 581 | —Cl | —Cl | 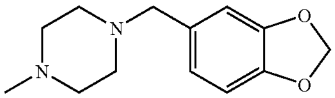 | —$SO_2$— | free | mp 154-156 |
| 582 | —$CF_3$ | —H | 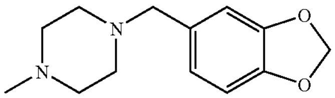 | —N($CH_3$)— | free | mp 175-176 |
| 583 | —Cl | —Cl | 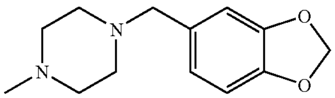 | —N($CH_2$Ph)— | free | mp 171-173 |
| 584 | —Cl | —Cl | 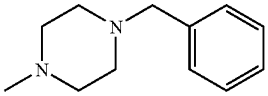 | —N($CH_2$Ph)— | free | mp 144-146 |
| 585 | —Cl | —Cl | 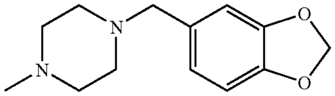 | —CO— | free | mp 129-132 |
| 586 | —Cl | —Cl | 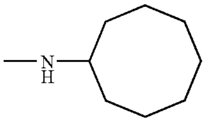 | —O— | free | mp 208-210 |
| 587 | —Cl | —Cl | —NH($CH_2$)$_2$OPh | —O— | free | mp 129-132 |
| 588 | —Cl | —Cl | 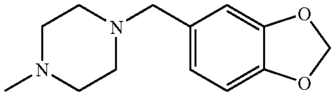 | —SO— | oxalate | mp 128-130 |

TABLE 187

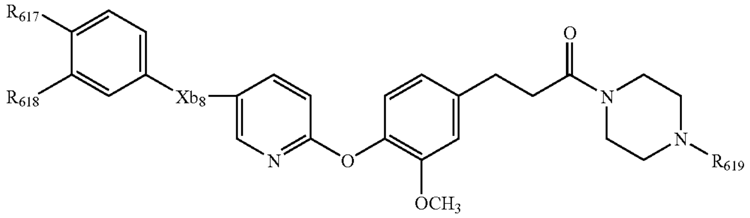

| Example No. | $R_{617}$ | $R_{618}$ | $Xb_8$ | $R_{619}$ | $^1H$ NMR ($CDCl_3$) δppm |
|---|---|---|---|---|---|
| 589 | —Cl | —Cl | —CH═CH— (trans) | piperonyl | 2.33-2.42 (4H, m), 2.62-2.68 (2H, m), 2.96-3.01 (2H, m), 3.40-3.44 (4H, m), 3.62-3.66 (2H, m), 3.76 (3H, s), 5.95 (2H, s), 6.71-6.77 (2H, m), 6.82-7.07 (7H, m), 7.28-7.32 (1H, m), 7.38-7.46 (1H, m), 7.57 (1H, d, J = 2.0 Hz), 7.83-7.87 (1H, m), 8.19 (1H, d, J = 2.3 Hz). |
| 590 | —$CF_3$ | —H | —CH═CH— (trans) | piperonyl | 2.33-2.42 (4H, m), 2.62-2.68 (2H, m), 2.96-3.02 (2H, m), 3.40-3.43 (4H, m), 3.63-3.66 (2H, m), 3.76 (3H, s), 5.94 (2H, s) 6.71-6.79 (2H, m), 6.82-6.89 (3H, m), 6.95 (1H, d, J = 8.7 Hz), 7.00 (1H, d, J = 16.5 Hz), 7.05-7.14 (2H, m), 7.55-7.62 (4H, m), 7.86-7.90 (1H, m), 8.22 (1H, d, J = 2.3 Hz). |
| 591 | —$CF_3$ | —H | —CO— | benzyl | 2.38-2.43 (4H, m), 2.63-2.68 (2H, m), 2.97-3.02 (2H, m), 3.43 (2H, brs), 3.51 (2H, s), 3.65 (2H, brs), 3.76 (3H, s), 6.84-6.89 (2H, m), 7.04-7.09 (2H, m), 7.27-7.31 (5H, m), 7.73-7.88 (4H, m), 8.19-8.22 (1H, m), 8.55 (1H, brs). |
| 592 | —$CF_3$ | —H | —CO— | piperonyl | 2.35-2.39 (4H, m), 2.62-2.68 (2H, m), 2.96-3.02 (2H, m), 3.41-3.44 (4H, m), 3.62-3.65 (2H, m), 3.76 (3H, s), 5.95 (2H, s), 6.74-6.89 (5H, m), 7.04-7.09 (2H, m), 7.73-7.88 (4H, m), 8.19-8.22 (1H, m), 8.55 (1H, brs). |
| 593 | —$CF_3$ | —H | —CO— | 3-pyridyl | 2.69-2.75 (2H, m), 3.01-3.06 (2H, m), 3.14-3.20 (4H, m), 3.59-3.62 (2H, m), 3.77 (3H, s), 3.80-3.84 (2H, m), 6.86-6.92 (2H, m), 7.04-7.11 (2H, m), 7.18-7.20 (2H, m), 7.75 (2H, d, J = 8.4 Hz), 7.87 (2H, d, J = 8.1 Hz), 8.15 (1H, t, J = 3.0 Hz), 8.20 (1H, dd, J = 8.7 Hz, 2.3 Hz), 8.30 (1H, t, J = 1.8 Hz), 8.53 (1H, d, J = 2.3 Hz). |

TABLE 188

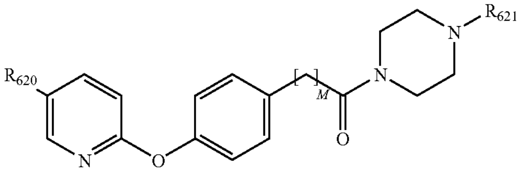

| Example No. | $R_{620}$ | $R_{621}$ | M | $^1H$ NMR (solvent) δppm |
|---|---|---|---|---|
| 594 | 3,4-$Cl_2$PhNHCON($C_2H_5$)— | 4-pyridyl-methyl | 2 | ($CDCl_3$) 1.16 (3H, t, J = 7.1 Hz), 2.35-2.45 (4H, m), 2.62-2.67 (2H, m), 2.97-3.03 (2H, m), 3.42-3.46 (2H, m), 3.51 (2H, s), 3.64-3.68 (2H, m), 3.73 (2H, q, J = 7.1 Hz), 6.07 (1H, d, J = 5.0 Hz), 7.04 (1H, d, J = 8.7 Hz), 7.09-7.14 (3H, m), 7.25-7.30 (5H, m), 7.52 (1H, d, J = 2.6 Hz), 7.61 (1H, dd, J = 8.7 Hz, 2.6 Hz), 8.11 (1H, d, J = 2.6 Hz), 8.54 (2H, d, 4 = 5.9 Hz). |
| 595 | 4-$CF_3$PhNHCON($C_2H_5$)— | piperonyl | 2 | ($CDCl_3$) 1.18 (3H, t, J = 7.1 Hz), 2.32-2.41 (4H, m), 2.61-2.67 (2H, m), 2.97 3.03 (2H, m), 3.39-3.43 (4H, m), 3.61- |

TABLE 188-continued

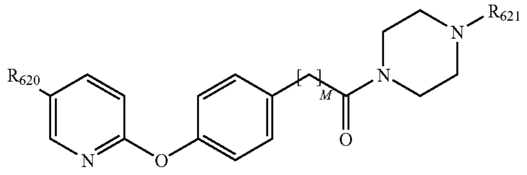

| Example No. | $R_{620}$ | $R_{621}$ | M | $^1$H NMR (solvent) δppm |
|---|---|---|---|---|
| | | | | 3.65 (2H, m), 3.75 (2H, q, J = 7.1 Hz), 5.94 (2H, s), 6.15 (1H, brs), 6.72 6.76 (2H, m), 6.83 (1H, d, J = 0.7 Hz), 7.05 (1H, dd, J = 8.7 Hz, 0.5 Hz), 7.11 (2H, d, J = 8.6 Hz), 7.29 (2H, d, J = 8.6 Hz), 7.40 (2H, d, J = 8.6 Hz), 7.49 (2H, d, 4 = 8.7 Hz), 7.63 (1H, dd, J = 8.7 Hz, 2.8 Hz), 8.14 (1H, dd, J = 2.8 Hz, 0.5 Hz). |
| 596 | 4-$CF_3$PhNHCON($C_2H_5$)— | 4-pyridyl-methyl | 2 | ($CDCl_3$) 1.18 (3H, t, J = 7.1 Hz), 2.35-2.45 (4H, m), 2.62-2.68 (2H, m), 2.98-3.03 (2H, m), 3.42-3.46 (2H, m), 3.51 (2H, s), 3.66 (2H, t, J = 5.0 Hz), 3.75 (2H, q, J = 7.1 Hz), 6.18 (1H, brs), 7.05 (1H, dd, J = 8.7 Hz, 0.5 Hz), 7.11 (2H, d, J = 8.4 Hz), 7.25-7.31 (4H, m), 7.40 (2H, d, J = 8.7 Hz), 7.49 (2H, d, J = 8.7 Hz), 7.63 (1H, dd, J = 8.7 Hz, 2.8 Hz), 8.13 (1H, dd, J = 2.6 Hz, 0.5 Hz), 8.53-8.55 (2H, m). |
| 597 | 4-$CF_3$PhNHCON($C_2H_5$)— | 2-pyridyl | 2 | ($CDCl_3$) 1.17 (3H, t, J = 7.1 Hz), 2.68-2.74 (2H, m), 3.02-3.07 (2H, m), 3.46-3.53 (6H, m), 3.70-3.78 (4H, m), 6.12 (1H, brs), 6.62-6.67 (2H, m), 7.04 (1H, d, J = 8.7 Hz), 7.12 (2H, d, J = 8.6 Hz), 7.31 (2H, d, J = 8.6 Hz), 7.40 (2H, d, J = 8.7 Hz), 7.45-7.52 (3H, m), 7.60 (1H, dd, J = 8.7 Hz, 2.6 Hz), 8.07 (1H, d, J = 2.5 Hz), 8.16-8.19 (1H, m). |

TABLE 189

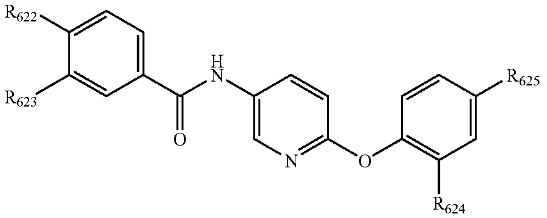

| Example No. | $R_{622}$ | $R_{623}$ | $R_{624}$ | $R_{625}$ | mp (° C.) or $^1$H NMR ($CDCl_3$) δppm |
|---|---|---|---|---|---|
| 598 | —Cl | —Cl | —H | 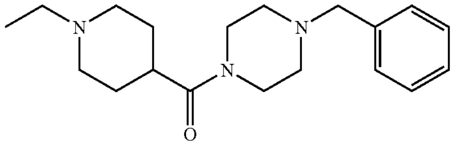 | mp 169-171 |
| 599 | —Cl | —Cl | —H | 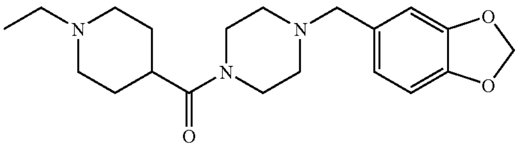 | mp 158-160 |

TABLE 189-continued

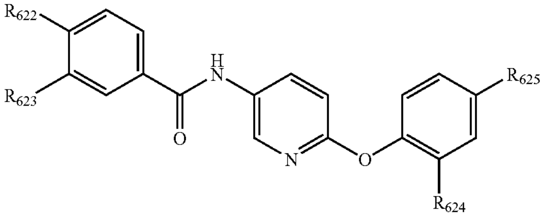

| Example No. | $R_{622}$ | $R_{623}$ | $R_{624}$ | $R_{625}$ | mp (° C.) or $^1$H NMR ($CDCl_3$) δppm |
|---|---|---|---|---|---|
| 600 | —Cl | —Cl | —H | 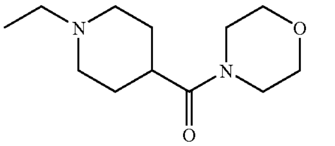 | mp 183-186 |
| 601 | —$CF_3$ | —H | —F | 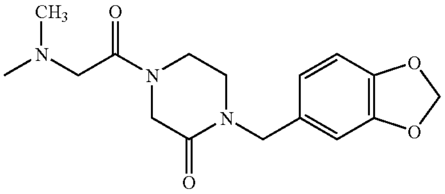 | $^1$H NMR 3.00 (3H, s), 3.20-3.36 (2H, m), 3.57-3.80 (2H, m), 4.07 (2H, s), 4.14-4.34 (2H, m), 4.51 (2H, s), 5.94 (2H, s), 6.32-6.50 (2H, m), 6.65-6.80 (3H, m), 6.92 (1H, d, J = 9.4 Hz), 7.02 (1H, t, J = 8.8 Hz), 7.71 (2H, d, J = 8.1 Hz), 7.98 (2H, d, J = 8.1 Hz), 8.10-8.20 (1H, m), 8.18 (1H, s), 8.30 (1H, s). |
| 602 | —$CF_3$ | —H | —H | 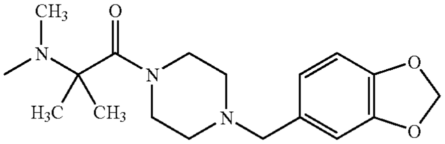 | $^1$H NMR 1.45 (6H, s), 2.14 (2H, brs), 2.33 (2H, brs), 2.87 (3H, s), 3.32 (2H, s), 3.63 (2H, brs), 3.92 (2H, brs), 5.93 (2H, s), 6.68-6.75 (2H, m), 6.82 (1H, d, J = 1.0 Hz), 6.92 (2H, d, J = 9.2 Hz), 6.93 (1H, d, J = 9.1 Hz), 7.00 (2H, d, J = 9.2 Hz), 7.77 (2H, d, J = 8.1 Hz), 7.81 (1H, s), 8.00 (2H, d, J = 8.1 Hz), 8.19 (1H, dd, J = 8.7 Hz, 2.8 Hz), 8.26 (1H, d, J = 2.1 Hz). |
| 603 | —$CF_3$ | —H | —$OCH_3$ | 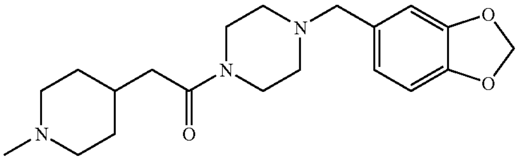 | $^1$H NMR 1.33-1.45 (2H, m), 1.82-1.96 (3H, m), 2.28 (2H, d, J = 6.8 Hz), 2.39-2.41 (4H, m), 2.72 (2H, t, J = 10.1 Hz), 3.43 (2H, s), 3.48 (2H, brs), 3.57-3.62 (4H, m), 3.72 (3H, s), 5.95 (2H, s), 6.48 (1H, dd, J = 8.7 Hz, 2.5 Hz), 6.56 (1H, d, J = 2.5 Hz), 6.71-6.77 (2H, m), 6.86 (2H, d, J = 8.6 Hz), 6.97 (1H, d, J = 8.6 Hz), 7.70 (2H, d, J = 8.4 Hz), 8.00 (2H, d, J = 8.1 Hz), 8.13 (1H, dd, J = 8.7 Hz, 2.6 Hz), 8.22 (1H, d, J = 2.5 Hz), 8.40 (1H, s). |

TABLE 190

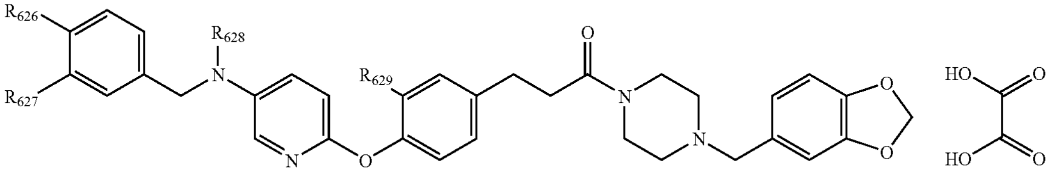

| Example No. | $R_{626}$ | $R_{627}$ | $R_{628}$ | $R_{629}$ | mp (° C.) or $^1$H NMR (DMSO-$d_6$) δppm |
|---|---|---|---|---|---|
| 604 | —$CF_3$ | —H | —$CH_3$ | —$OC_2H_5$ | $^1$H NMR 1.03 (3H, t, J = 6.9 Hz), 2.52-2.68 (6H, m), 3.89 (2H, q, J = 6.9 Hz), 4.00-5.90 (4H, m), 6.01 (2H, |

TABLE 190-continued

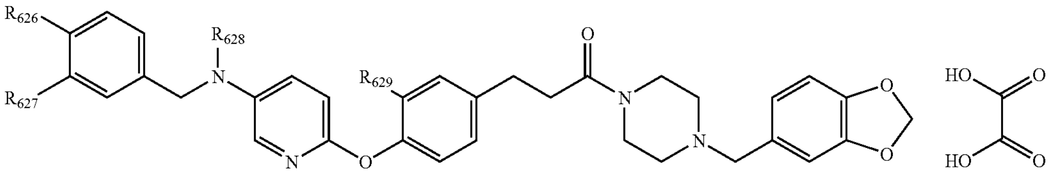

| Example No. | $R_{626}$ | $R_{627}$ | $R_{628}$ | $R_{629}$ | mp (° C.) or $^1$H NMR (DMSO-$d_6$) δppm |
|---|---|---|---|---|---|
| | | | | | s), 6.74 (1H, dd, J = 8.0 Hz, 1.8 Hz), 6.76 (1H, d, J = 8.9 Hz), 6.82 (1H, dd, J = 8.0 Hz, 1.3 Hz), 6.84-6.97 (4H, m), 7.26 (1H, dd, J = 9.0 Hz, 3.1 Hz), 7.41 (2H, d, J = 8.0 Hz), 7.50 (1H, d, J = 3.1 Hz), 7.65 (2H, d, J = 8.0 Hz). |
| 605 | —$CF_3$ | —H | —$C_2H_5$ | —$OC_2H_5$ | $^1$H NMR 1.02 (3H, t, J = 6.9 Hz), 1.08 (3H, t, J = 6.9 Hz), 2.53-2.84 (8H, m), 3.43 (2H, q, J = 6.9 Hz), 3.46-3.62 (4H, m), 3.72 (2H, s), 3.88 (2H, q, J = 6.9 Hz), 4.30-5.90 (4H, m), 6.01 (2H, s), 6.69-6.78 (2H, m), 6.82 (1H, dd, J = 8.0 Hz, 1.4 Hz), 6.83-6.97 (4H, m), 7.19 (1H, dd, J = 9.0 Hz, 3.1 Hz), 7.37-7.48 (3H, m), 7.65 (2H, d, J = 8.1 Hz). |
| 606 | —Cl | —Cl | —$CH_3$ | —H | $^1$H NMR 2.48-2.67 (6H, m), 2.68-2.82 (2H, m) 2.98 (3H, s) 3.37-3.62 (4H, m), 3.70 (2H, s), 4.50-5.90 (4H, m), 6.01 (2H, s), 6.78-6.95 (6H, m), 7.13-7.23 (3H, m), 7.28 (1H, dd, J = 9.0 Hz, 3.3 Hz), 7.48 (1H, d, J = 2.0 Hz), 7.57 (1H, d, J = 8.3 Hz), 7.61 (1H, d, J = 3.1 Hz). |
| 607 | —Cl | —Cl | —$C_2H_5$ | —H | $^1$H NMR 1.09 (3H, t, J = 6.9 Hz), 2.48-2.66 (6H, m), 2.69-2.82 (2H, m), 3.35-3.59 (6H, m), 3.67 (2H, s), 4.00-5.90 (4H, m), 6.00 (2H, s), 6.76-6.94 (6H, m), 7.13-7.25 (4H, m), 7.47 (1H, d, J = 1.9 Hz), 7.52-7.61 (2H, m). |
| 608 | —$CF_3$ | —H | —$CH_3$ | —F | $^1$H NMR 2.50-2.72 (6H, m), 2.72-2.88 (2H, m), 2.98 (3H, s), 3.32-3.61 (4H, m) 3.70 (2H, brs), 4.67 (2H, s), 6.00 (2H, s), 6.80 (1H, dd, J = 7.9 Hz, 1.4 Hz), 6.85-6.95 (3H, m), 6.98-7.11 (2H, m) 7.11-7.22 (1H, m), 7.29 (1H, dd, J = 9.0 Hz, 3.1 Hz), 7.41 (2H, d, J = 8.0 Hz), 7.50 (1H, d, J = 3.1 Hz), 7.66 (2H, d, J = 8.0 Hz). |
| 609 | —Cl | —Cl | —$C_2H_5$ | —F | $^1$H NMR 1.00-1.20 (3H, m), 2.46-2.72 (6H, m), 2.72-2.89 (2H, m), 3.29-3.61 (6H, m), 3.71 (2H, brs), 4.46 (2H, s), 6.01 (2H, s), 6.81 (1H, dd, J = 8.0 Hz, 1.4 Hz), 6.85-6.95 (3H, m), 6.98-7.11 (2H, m), 7.13-7.28 (3H, m), 7.45 (1H, d, J = 3.1 Hz), 7.46 (1H, d, J = 1.9 Hz), 7.56 (1H, d, J = 8.3 Hz). |
| 610 | —Cl | —Cl | —$CH_3$ | —$OC_2H_5$ | $^1$H NMR 1.02 (3H, t, J = 6.9 Hz), 2.42-2.81 (8H, m), 2.94 (3H, s), 3.00-4.30 (10H, m), 4.49 (2H, s), 6.00 (2H, s), 6.71-6.83 (3H, m), 6.84-6.95 (4H, m), 7.18 (1H, dd, J = 8.3 Hz, 2.0 Hz), 7.26 (1H, dd, J = 9.0 Hz, 3.2 Hz), 7.44 (1H, d, J = 2.0 Hz), 7.50 (1H, d, J = 3.0 Hz), 7.55 (1H, d, J = 8.3 Hz). |
| 611 | —Cl | —Cl | —$C_2H_5$ | —$OC_2H_5$ | $^1$H NMR 1.01 (3H, t, J = 7.0 Hz), 1.06 (3H, t, J = 7.0 Hz), 2.40-2.83 (8H, m), 2.90-4.50 (14H, m), 6.00 (2H, s), 6.70-6.82 (3H, m), 6.84-6.95 (4H, m), 7.15-7.24 (2H, m), 7.39-7.48 (2H, m), 7.55 (1H, d, J = 8.3 Hz). |
| 612 | —Cl | —Cl | —$C_2H_5$ | —$OCH_3$ | mp 91.0-96.5 dec |
| 613 | —$CF_3$ | —H | —$C_2H_5$ | —F | mp 104-107 |

TABLE 191

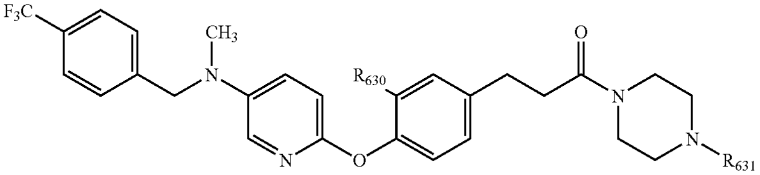

| Example No. | $R_{630}$ | $R_{631}$ | Form | $^1$H NMR (solvent) δppm |
|---|---|---|---|---|
| 614 | —H | piperonyl | free | ($CDCl_3$) 2.30-2.34 (2H, m), 2.36-2.40 (2H, m), 2.56-2.62 (2H, m), 2.91-2.96 (2H, m), |

TABLE 191-continued

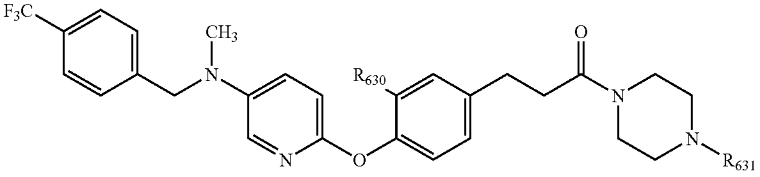

| Example No. | $R_{630}$ | $R_{631}$ | Form | $^1$H NMR (solvent) δppm |
|---|---|---|---|---|
| | | | | 3.01 (3H, s), 3.37-3.40 (4H, m), 3.60-3.64 (2H, m), 4.50 (2H, s), 5.94 (2H, s), 6.72-6.73 (2H, m), 6.80 (1H, d, J = 8.9 Hz), 6.84 (1H, brs), 6.98 (2H, d, J = 8.6 Hz), 7.11 (1H, dd, J = 8.9 Hz, 3.3 Hz), 7.18 (2H, d, J = 8.4 Hz), 7.34 (2H, d, J = 7.9 Hz), 7.58 (2H, d, J = 8.3 Hz), 7.70 (1H, d, J = 3.3 Hz). |
| 615 | —H | 3-pyridyl | free | ($CDCl_3$) 2.63-2.69 (2H, m), 2.95-3.01 (5H, m), 3.08-3.18 (4H, m), 3.54-3.58 (2H, m), 3.78-3.81 (2H, m), 4.50 (2H, s), 6.79 (1H, d, J = 8.9 Hz), 6.99 (2H, d, J = 8.6 Hz), 7.10 (1H, dd, 4 = 8.9 Hz, 3.1 Hz), 7.17-7.22 (4H, m), 7.34 (2H, d, 4 = 8.1 Hz), 7.58 (2H, d, J = 7.9 Hz), 7.67 (1H, d, J = 2.8 Hz), 8.12-8.14 (1H, m), 8.29-8.30 (1H, m). |
| 616 | —H | 4-pyridylmethyl | free | ($CDCl_3$) 2.33 (2H, t, J = 5.0 Hz), 2.41 (2H, t, J = 5.1 Hz), 2.57-2.63 (2H, m), 2.92-2.97 (2H, m), 3.02 (3H, s), 3.41 (2H, t, J = 5.0 Hz), 3.50 (2H, s), 3.65 (2H, t, J = 5.1 Hz), 4.51 (2H, s), 6.80 (1H, d, J = 8.9 Hz), 6.98 (2H, d, J = 8.4 Hz), 7.11 (1H, dd, J = 8.9 Hz, 3.1 Hz), 7.18 (2H, d, J = 8.4 Hz), 7.27 (2H, d, J = 5.6 Hz), 7.34 (2H, d, J = 8.3 Hz), 7.58 (2H, d, J = 8.3 Hz), 7.69 (1H, d, J = 3.1 Hz), 8.55 (2H, d, J = 5.8 Hz). |
| 617 | —H | benzyl | hydrochloride | (DMSO-$d_6$) 2.64-2.69 (2H, m), 2.75-2.81 (2H, m), 2.92-3.02 (5H, m), 3.23-3.32 (2H, m), 3.41-3.51 (2H, m), 4.02-4.08 (1H, m), 4.31 (2H, brs), 4.43-4.48 (1H, m) 4.64 (2H, brs), 6.86 (1H, d, J = 9.1 Hz), 6.90 (2H, d, J = 8.6 Hz), 7.20 (2H, d, J = 8.4 Hz), 7.29 (1H, dd, J = 9.1 Hz, 3.1 Hz), 7.42-7.47 (5H, m), 7.56-7.57 (2H, m), 7.62 (1H, d, J = 3.1 Hz), 7.69 (2H, d, J = 8.1 Hz), 11.08 (1H, brs). |
| 618 | —$OCH_3$ | piperonyl | hydrochloride | (DMSO-$d_6$) 2.59-3.09 (6H, m), 2.97 (3H, s), 3.16-3.61 (4H, m), 3.65 (3H, s), 3.97-4.13 (1H, m), 4.14-4.28 (2H, m), 4.38-4.51 (1H, m), 4.58 (2H, s), 6.06 (2H, s), 6.72-6.80 (2H, m), 6.89 (1H, d, J = 8.0 Hz), 6.93-7.03 (3H, m), 7.18 (1H, s), 7.26 (1H, dd, J = 9.0 Hz, 3.2 Hz), 7.42 (2H, d, J = 8.0 Hz), 7.49 (1H, d, J = 3.1 Hz), 7.67 (2H, d, J = 8.0 Hz), 10.81 (1H, brs). |

TABLE 192

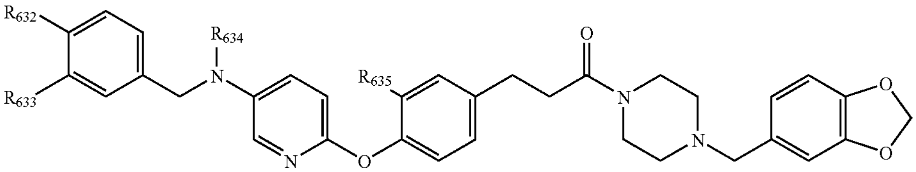

| Example No. | $R_{632}$ | $R_{633}$ | $R_{634}$ | $R_{635}$ | Form | $^1$H NMR (DMSO-$d_6$) δppm |
|---|---|---|---|---|---|---|
| 619 | —$CF_3$ | —H | —$C_2H_5$ | —H | TsOH salt | 1.11 (3H, t, J = 6.9 Hz), 2.28 (3H, s), 2.54-3.02 (7H, m), 3.17-3.48 (3H, m), 3.47 (2H, q, J = 6.9 Hz), 3.97-4.12 (1H, m), 4.15-4.31 (2H, m), 4.38-4.52 (1H, m), 4.58 (2H, s), 6.07 (2H, s), 6.78- |

TABLE 192-continued

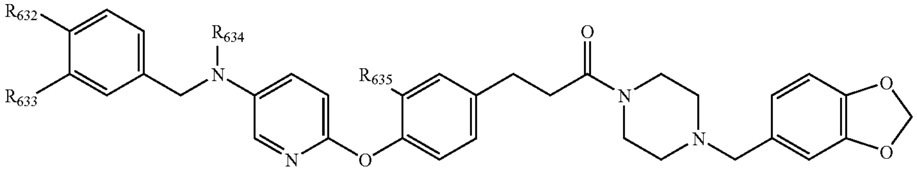

| Example No. | $R_{632}$ | $R_{633}$ | $R_{634}$ | $R_{635}$ | Form | $^1$H NMR (DMSO-$d_6$) δppm |
|---|---|---|---|---|---|---|
| | | | | | | 7.26 (11H, m), 7.39-7.49 (4H, m), 7.53 (1H, d, J = 3.1 Hz), 7.68 (2H, d, J = 8.2 Hz), 9.45-9.69 (1H, m). |
| 620 | —$CF_3$ | —H | —$(CH_2)_2OCH_3$ | —H | TsOH salt | 2.27 (3H, s), 2.52-3.03 (7H, m), 3.24 (3H, s), 3.17-3.70 (10H, m), 3.95-4.13 (1H, m), 4.15-4.32 (2H, m), 4.36-4.54 (1H, m), 4.66 (2H, s), 6.07 (2H, s), 6.80 (1H, d, J = 8.9 Hz), 6.83-7.07 (5H, m), 7.10 (2H, d, J = 7.8 Hz), 7.13 7.26 (3H, m), 7.37-7.49 (4H, m), 7.52 (1H, d, J = 3.1 Hz), 7.67 (2H, d, J = 8.1 Hz), 9.46-9.69 (1H, m). |
| 621 | —Cl | —Cl | —$CH_3$ | —$OCH_3$ | hydro-chloride | 2.60-3.15 (7H, m), 2.94 (3H, s), 3.15-3.38 (2H, m), 3.38-3.60 (1H, m), 3.65 (3H, s), 4.07 (1H, d, J = 15.7 Hz), 4.20 (2H, brs), 4.38-4.60 (1H, m), 4.48 (2H, s), 6.06 (2H, s), 6.73-6.81 (2H, m), 6.90 (1H, d, J = 8.0 Hz), 6.93-7.05 (3H, m), 7.16-7.24 (2H, m), 7.29 (1H, dd, J = 8.9 Hz, 3.2 Hz), 7.47 (1H, d, J = 1.9 Hz), 7.50 (1H, d, J = 3.1 Hz), 7.56 (1H, d, J = 8.2 Hz), 11.10 (1H, brs). |
| 622 | —Cl | —Cl | —$CH_3$ | —F | hydro-chloride | 2.58-3.17 (7H, m), 2.96 (3H, s), 3.18-3.38 (2H, m), 3.38-3.70 (1H, m), 4.00-4.18 (1H, m), 4.20 (2H, brs), 4.33 4.60 (1H, m), 4.50 (2H, s), 6.06 (2H, s), 6.92 (1H, d, J = 9.0 Hz), 6.95-7.14 (4H, m), 7.16-7.25 (3H, m), 7.31 (1H, dd, J = 9.0 Hz, 3.1 Hz), 7.47 (1H, d, J = 1.9 Hz), 7.51 (1H, d, J = 3.1 Hz), 7.56 (1H, d, J = 8.2 Hz), 11.10 (1H, brs). |
| 623 | —$CF_3$ | —H | —$C_2H_5$ | —$OCH_3$ | hydro-chloride | 1.09 (3H, t, J = 6.9 Hz), 2.58-3.11 (8H, m), 3.15-3.58 (4H, m), 3.64 (3H, s), 3.94-4.12 (1H, m), 4.14-4.28 (2H, m), 4.36-4.50 (1H, m), 4.54 (2H, s), 6.69-6.79 (2H, m), 6.88 (1H, d, J = 8.0 Hz), 6.92-7.02 (3H, m), 7.12-7.24 (2H, m), 7.37-7.49 (3H, m), 7.67 (2H, d, J = 8.1 Hz), 10.77 (1H, brs). |

(TsOH means a p-toluenesulfonic acid. Hereinafter TsOH indicates the same meaning)

TABLE 193

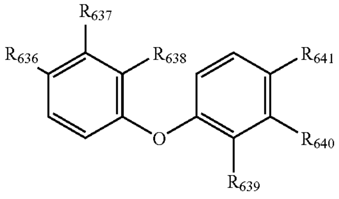

| Example No. | $R_{636}$ | $R_{637}$ | $R_{638}$ | $R_{639}$ | $R_{640}$ | $R_{641}$ | Form | mp (° C.) or $^1$H NMR |
|---|---|---|---|---|---|---|---|---|
| 624 | $Ya_2$ | —H | —H | $Ya_1$ | —H | —H | hydrochloride | $^1$H NMR (DMSO-$d_6$) δ 2.56-2.72 (2H, m), 2.73-2.94 (3H, m), 2.96-3.10 (1H, m), 3.12-3.52 (4H, m), 3.91-4.07 (1H, m), 4.10-4.26 (2H, m), 4.33 4.48 (1H, m), 6.05 (2H, s), 6.82 (1H, d, J = 8.2 Hz), 6.89-7.02 (4H, m), 7.09 (1H, t, J = 7.6 Hz), 7.14-7.25 (2H, |

TABLE 193-continued
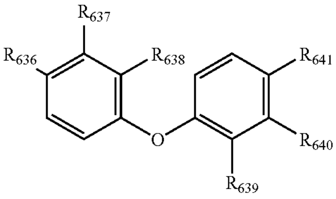
| Example No. | $R_{636}$ | $R_{637}$ | $R_{638}$ | $R_{639}$ | $R_{640}$ | $R_{641}$ | Form | mp (° C.) or $^1H$ NMR |
|---|---|---|---|---|---|---|---|---|
| | | | | | | | | m), 7.35 (1H, d, J = 7.6 Hz), 7.74 (2H, d, J = 9.0 Hz), 7.81 (1H, d, J = 8.4 Hz), 7.94 (1H, dd, J = 8.4 Hz, 2.1 Hz), 8.22 (1H, d, J = 2.1 Hz), 10.45 (1H, s), 11.15 (1H, brs). |
| 625 | $Ya_2$ | —H | —H | —H | $Ya_1$ | —H | oxalate | mp 134-143 |
| 626 | —H | —H | $Ya_2$ | —H | —H | $Ya_1$ | fumarate | mp 123-126 |
| 627 | —H | $Ya_2$ | —H | —H | —H | $Ya_1$ | hydrochloride | mp 141-153 |
In the above-mentioned Table, $Ya_1$ means a group of
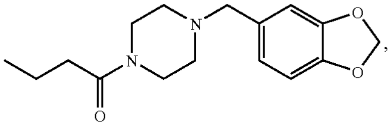
and $Ya_2$ means a group of
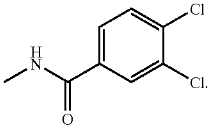
TABLE 194
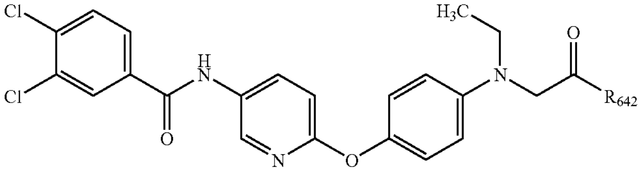
| Example No. | $R_{642}$ | MS ($M^+$ + H) |
|---|---|---|
| 628 | 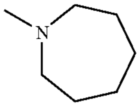 | 540 |
| 629 | 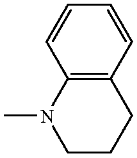 | 574 |
| 630 | morpholino | 528 |
| 631 | 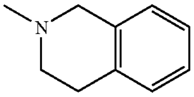 | 574 |

TABLE 194-continued
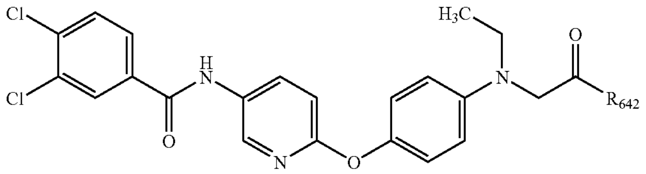
| Example No. | $R_{642}$ | MS ($M^+ + H$) |
|---|---|---|
| 632 | 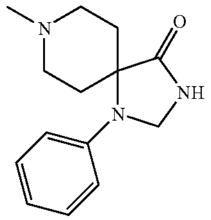 | 673 |
| 633 | 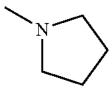 | 513 |
| 634 | 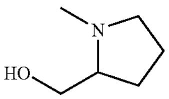 | 543 |
| 635 | 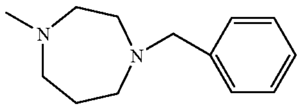 | 632 |
| 636 | 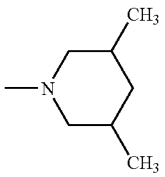 | 555 |
| 637 | 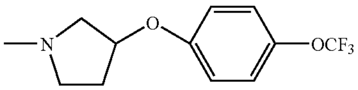 | 689 |
| 638 | 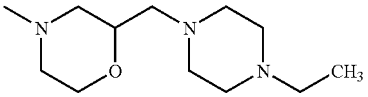 | 655 |
| 639 | 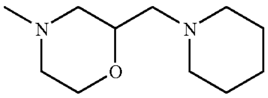 | 626 |

TABLE 195

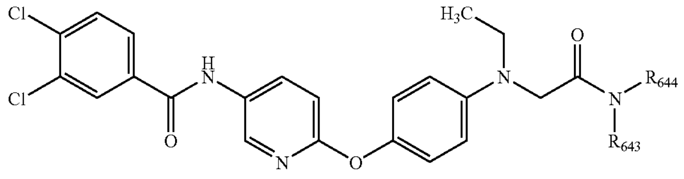

| Example No. | $R_{643}$ | $R_{644}$ | MS ($M^+ + H$) |
|---|---|---|---|
| 640 | $—CH_3$ | cyclohexyl | 554 |
| 641 | —H | cyclohexyl | 540 |
| 642 | $—C_2H_5$ | —Ph | 562 |
| 643 | $—CH_3$ | $4\text{-}CH_3Ph—$ | 562 |
| 644 | —H | cycloheptyl | 554 |
| 645 | —H | cyclooctyl | 569 |
| 646 | —H | benzyl | 548 |
| 647 | —H | $2\text{-}ClPhCH_2—$ | 584 |
| 648 | —H | $3\text{-}ClPhCH_2—$ | 584 |
| 649 | —H | $4\text{-}ClPhCH_2—$ | 584 |
| 650 | $—CH_3$ | $Ph(CH_2)_2—$ | 577 |
| 651 | $—CH_3$ | $3,4\text{-}(CH_3O)_2PhCH_2—$ | 623 |
| 652 | $—CH_3$ | benzyl | 562 |
| 653 | $—C_2H_5$ | benzyl | 576 |
| 654 | —H | $PhOCH_2CH(CH_3)—$ | 593 |
| 655 | $—C_2H_5$ | cyclohexyl | 569 |
| 656 | —H | $—C_2H_5$ | 486 |
| 657 | —H | $-(CH_2)_2CH_3$ | 500 |
| 658 | —H | $-(CH_2)_2OCH_3$ | 516 |
| 659 | $—C_2H_5$ | cyclohexylmethyl | 583 |
| 660 | —H | $4\text{-}CH_3OPhCH_2—$ | 578 |
| 661 | —H | $4\text{-}CH_3OPh(CH_2)_2—$ | 593 |
| 662 | —H | $4\text{-}CF_3OPhCH_2—$ | 632 |
| 663 | —H | $4\text{-}CF_3OPh—$ | 618 |
| 664 | —H | $4\text{-}ClPh(CH_2)_2—$ | 598 |
| 665 | —H | piperonyl | 592 |
| 666 | —H | $—(CH_2)_2OPh$ | 579 |
| 667 | —H | cyclopentyl | 527 |
| 668 | —H | cyclohexylmethyl | 554 |
| 669 | —H | 4-hydroxycyclohexan-1-yl | 556 |
| 670 | —H | $4\text{-}FPhCH_2—$ | 566 |
| 671 | —H | $—CH(CH_3)Ph$ | 562 |
| 672 | —H | $—(CH_2)_3Ph$ | 576 |
| 673 | —H | —Ph | 534 |
| 674 | —H | $4\text{-}CH_3OPh—$ | 564 |
| 675 | —H | $—(CH_2)_2Ph$ | 562 |
| 676 | —H | 3-PhOPh— | 627 |
| 677 | —H | 4-PhOPh— | 627 |
| 678 | —H | $2\text{-}CH_3OPh(CH_2)_2—$ | 593 |
| 679 | —H | $2\text{-}FPh(CH_2)_2—$ | 580 |

TABLE 196

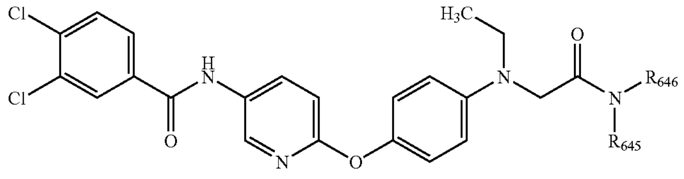

| Example No. | $R_{645}$ | $R_{646}$ | MS ($M^+ + H$) |
|---|---|---|---|
| 680 | —H | 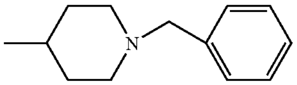 | 632 |
| 681 | —H | $—CH(CH_3)_2$ | 501 |

TABLE 196-continued

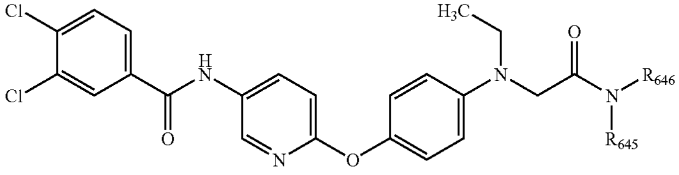

| Example No. | $R_{645}$ | $R_{646}$ | MS ($M^+ + H$) |
|---|---|---|---|
| 682 | $—CH_3$ | 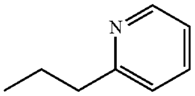 | 578 |
| 683 | $—(CH_2)_2OH$ | $—(CH_2)_2OH$ | 547 |
| 684 | $—CH_3$ | $—(CH_2)_2N(CH_3)_2$ | 544 |
| 685 | —H | $—(CH_2)_3CH_3$ | 515 |
| 686 | —H | cyclopropyl | 499 |
| 687 | —H | 2-pyridylmethyl | 550 |
| 688 | —H | 3-pyridylmethyl | 550 |
| 689 | —H | $—CH_2CH(CH_3)_2$ | 515 |
| 690 | —H | cyclopropylmethyl | 513 |
| 691 | —H | 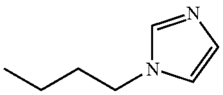 | 567 |
| 692 | —H | 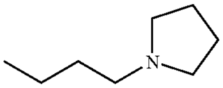 | 570 |
| 693 | —H | 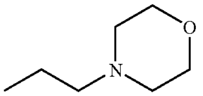 | 572 |

TABLE 197

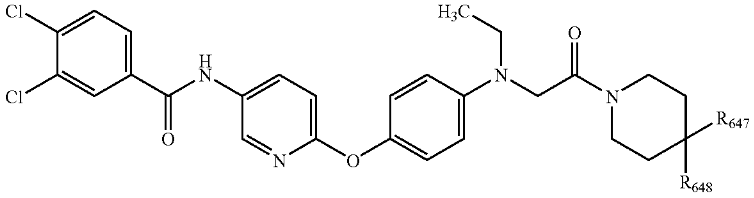

| Example No. | $R_{647}$ | $R_{648}$ | $^1H$ NMR or MS |
|---|---|---|---|
| 694 | —H | $4-CF_3OPhO—$ | MS 702 ($M^+ + H$) |
| 695 | —H | benzyl | MS 617 ($M^+ + H$) |
| 696 | —OH | 4-ClPh— | MS 654 ($M^+ + H$) |
| 697 | —H | —H | MS 526 ($M^+ + H$) |
| 698 | —H | —Ph | MS 602 ($M^+ + H$) |
| 699 | —H | piperonyl | $^1H$ NMR ($CDCl_3$) δ 1.11-1.16 (5H, m), 1.65-1.71 (3H, m), 2.48 (2H, d, J = 6.4 Hz), 2.54-2.58 (1H, m), 2.95-3.04 (1H, m), 3.35 (2H, q, J = 7.1 Hz), 3.84-3.89 (1H, m), 4.01 (2H, s), 4.52-4.57 (1H, m), 5.93 (2H, s), 6.56 6.63 (4H, m), 6.73 (1H, d, J = 7.8 Hz), 6.79 (1H, d, J = 8.7 Hz), 6.92 (2H, d, J = 9.1 Hz), 7.52 (1H, d, J = 8.4 Hz), 7.72 (1H, dd, J = 8.4 Hz, 2.0 Hz), 7.99 (1H, d, J = 2.0 Hz), 8.04 (1H, dd, J = 8.9 Hz, 2.8 Hz), 8.26 (1H, d, J = 2.5 Hz), 8.56 (1H, brs). |

TABLE 197-continued

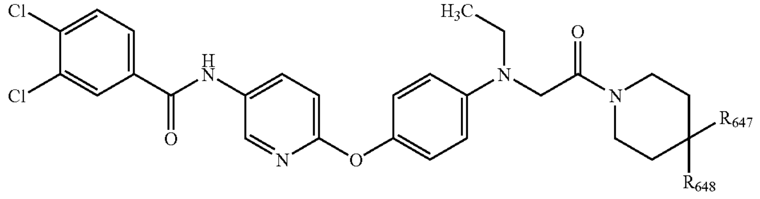

| Example No. | $R_{647}$ | $R_{648}$ | $^1H$ NMR or MS |
|---|---|---|---|
| 700 | —H | 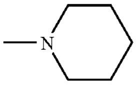 | MS 610 ($M^+$ + H) |
| 701 | —H | 4-$CH_3$OPhCONH— | MS 676 ($M^+$ + H) |
| 702 | —H | —N($CH_3$)$CH_2$Ph | MS 646 ($M^+$ + H) |
| 703 | —H | 4-$CH_3$PhO ($CH_2$)$_2$N($CH_3$)— | MS 690 ($M^+$ + H) |
| 704 | —OH | —Ph | MS 619 ($M^+$ + H) |
| 705 | —H | 4-CNPhO— | MS 644 ($M^+$ + H) |
| 706 | —H | 2-ClPh$CH_2$— | MS 653 ($M^+$ + H) |
| 707 | —$CH_2$($CH_2$)$_3$$CH_2$— | MS 595 ($M^+$ + H) | |

TABLE 198

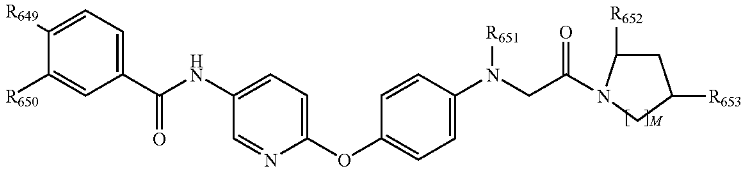

| Example No. | $R_{649}$ | $R_{650}$ | $R_{651}$ | $R_{652}$ | $R_{653}$ | M | $^1H$ NMR (solvent) δppm |
|---|---|---|---|---|---|---|---|
| 708 | —Cl | —Cl | —$CH_3$ | —$CONH_2$ | —H | 1 | (DMSO-$d_6$) 1.79-2.02 (4H, m), 2.96 (3H, s), 3.37-3.67 (3H, m), 4.19 (2H, s), 6.61-6.70 (2H, m), 6.89-6.95 (3H, m), 7.83 (1H, d, J = 8.4 Hz), 7.94 (1H, dd, J = 8.4 Hz, 2.0 Hz), 8.13 (1H, dd, J = 8.9 Hz, 2.6 Hz), 8.22 (1H, d, J = 2.0 Hz), 8.43 (1H, d, J = 2.6 Hz), 10.51 (1H, s). |
| 709 | —Cl | —Cl | —$CH_3$ | —H | benzyl | 2 | ($CDCl_3$) 1.18-1.26 (2H, m), 1.57 (3H, brs), 1.58-1.74 (2H, m), 2.49-2.58 (2H, m), 3.83 (1H, d, J = 13.5 Hz), 4.08 (2H, s), 4.56 (1H, d, J = 13.5 Hz), 6.40 (1H, d, J = 8.9 Hz), 6.67 (2H, d, J = 9.1 Hz), 6.98 (2H, d, J = 9.1 Hz), 7.12-7.32 (5H, m), 7.56 (1H, d, J = 8.4 Hz), 7.71 (1H, dd, J = 8.4 Hz, 2.1 Hz), 7.98 (1H, d, J = 2.1 Hz), 8.03-8.10 (2H, m), 8.24 (1H, d, J = 2.6 Hz). |
| 710 | —$CF_3$ | —H | —$C_2H_5$ | —H | piperonyl | 2 | ($CDCl_3$) 1.12-1.17 (5H, m), 1.64-1.71 (3H, m), 2.48 (2H, d, J = 6.6 Hz), 2.53-2.58 (1H, m), 2.94-3.03 (1H, m), 3.37 (2H, q, J = 7.1 Hz), 3.84-3.89 (1H, m), 4.01 (2H, s), 4.53-4.58 (1H, m), 5.93 (2H, s), 6.56-6.63 (4H, m), 6.73 (1H, d, J = 7.8 Hz), 6.82 (1H, d, J = 8.9 Hz), 6.95 (2H, d, J = 9.1 Hz), 7.72 (2H, d, J = 8.3 Hz), 7.99 (2H, d, J = 8.1 Hz), 8.10 (1H, dd, J = 8.9 Hz, 2.8 Hz), 8.27 (1H, d, J = 2.6 Hz), 8.37 (1H, brs). |
| 711 | —Cl | —Cl | —$CH_3$ | —H | piperonyl | 2 | ($CDCl_3$) 1.03-1.17 (2H, m), 1.64-1.74 (3H, m), 2.46-2.57 (3H, m), 2.97-3.04 (4H, m), 3.80-3.85 (1H, m), 4.07 (2H, s), 4.51-4.55 (1H, m), 5.92 (2H, s), 6.56 6.63 (4H, m), 6.73 (1H, d, J = 7.8 Hz), 6.79 (1H, d, J = 8.9 Hz), 6.94 (2H, d, J = 8.9 Hz), 7.52 (1H, d, J = 8.4 Hz), 7.71 |

TABLE 198-continued

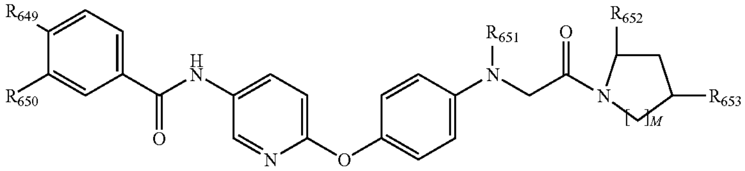

| Example No. | $R_{649}$ | $R_{650}$ | $R_{651}$ | $R_{652}$ | $R_{653}$ | M | $^1$H NMR (solvent) δppm |
|---|---|---|---|---|---|---|---|
| | | | | | | | (1H, dd, J = 8.4 Hz, 2.1 Hz), 7.98 (1H, d, J = 2.1 Hz), 8.04 (1H, d, J = 8.9 Hz), 8.25 (1H, d, J = 2.3 Hz), 8.49 (1H, brs). |
| 712 | —$CF_3$ | —H | —$CH_3$ | —H | piperonyl | 2 | ($CDCl_3$) 1.09-1.17 (2H, m), 1.67-1.70 (3H, m), 2.47-2.52 (3H, m), 2.94-3.03 (4H, m), 3.80-3.85 (1H, m), 4.06 (2H, s), 4.50-4.55 (1H, m), 5.92 (2H, s), 6.55-6.65 (4H, m), 6.73 (1H, d, J = 7.9 Hz), 6.81 (1H, d, J = 8.9 Hz), 6.95 (2H, d, J = 8.9 Hz), 7.70 (2H, d, J = 8.1 Hz), 7.99 (2H, d, J = 8.1 Hz), 8.09 (1H, dd, J = 8.9 Hz, 2.1 Hz), 8.26 (1H, d, J = 2.6 Hz), 8.48 (1H, brs). |

TABLE 199

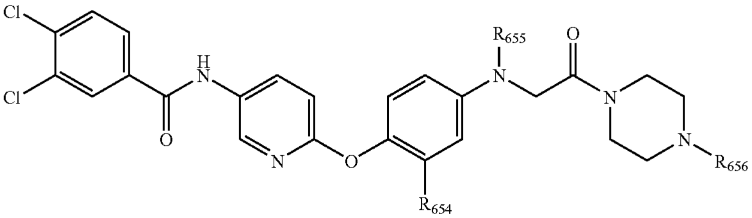

| Example No. | $R_{654}$ | $R_{655}$ | $R_{656}$ | $^1$H NMR (solvent) δppm |
|---|---|---|---|---|
| 713 | —$OCH_3$ | —$CH_3$ | 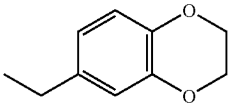 | ($CDCl_3$) 2.38-2.43 (4H, m), 2.95 (3H, s), 3.40 (2H, s), 3.47.-3.58 (4H, m), 3.63 (3H, s), 4.05 (2H, s), 4.24 (4H, s), 6.12 (1H, dd, J = 8.7 Hz, 2.6 Hz), 6.21 (1H, d, J = 2.6 Hz), 6.74-6.87 (5H, m), 7.44 (1H, d, J = 8.4 Hz), 7.69 (1H, dd, J = 8.4 Hz, 2.0 Hz), 7.96 (1H, d, J = 2.0 Hz), 8.02 (1H, dd, J = 8.9 Hz, 2.6 Hz), 8.19 (1H, d, J = 2.6 Hz), 9.00 (1H, s). |
| 714 | —F | —$CH_3$ | 3-furylmethyl | (DMSO-$d_6$) 2.32 (2H, brs), 2.41 (2H, brs), 2.93 (3H, s), 3.37 (2H, s), 3.44 (4H, brs), 4.29 (2H, s), 6.40-6.44 (2H, m), 6.56 (1H, dd, J = 14.5 Hz, 2.8 Hz), 7.01-7.08 (2H, m), 7.58 (1H, s), 7.62 (1H, s), 7.84 (1H, d, J = 8.4 Hz), 7.94 (1H, dd, J = 8.4 Hz, 2.0 Hz), 8.16 (1H, dd, J = 8.9 Hz, 2.8 Hz), 8.22 (1H, d, J = 2.0 Hz), 8.39 (1H, d, J = 2.6 Hz), 10.53 (1H, s). |
| 715 | —F | —$CH_3$ | 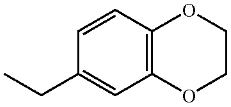 | (DMSO-$d_6$) 2.30 (2H, brs), 2.39 (2H, brs), 2.93 (3H, s), 3.38 (2H, s), 3.44 (4H, brs), 4.22 (4H, s), 4.28 (2H, s), 6.41 (1H, dd, J = 8.6 Hz, 2.2. Hz), 6.56 (1H, dd, J = 14.4 Hz, 2.8 Hz), 6.76-6.81 (3H, m), 7.01-7.08 (2H, m), 7.84 (1H, d, J = 8.4 Hz), 7.94 (1H, dd, J = 8.4 Hz, 2.0 Hz), 8.16 (1H, dd, J = 8.9 Hz, 2.8 Hz), 8.22 (1H, d, J = 2.0 Hz), 8.39 (1H, d, J = 2.5 Hz), 10.53 (1H, s). |
| 716 | —H | —$CH_3$ | 3-furylmethyl | ($CDCl_3$) 2.42 (4H, brs), 2.97 (3H, s), 3.40 (2H, s), 3.50 (2H, brs), 3.61 (2H, brs), 4.07 (2H, s), 6.38 (1H, d, J = 1.5 Hz), 6.63 (2H, d, J = 9.1 Hz), 6.80 (1H, d, J = 8.9 Hz), 6.95 (2H, d, J = 9.1 Hz), 7.34 (1H, |

TABLE 199-continued

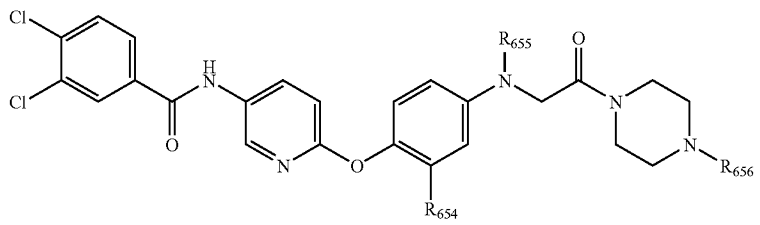

| Example No. | $R_{654}$ | $R_{655}$ | $R_{656}$ | $^1$H NMR (solvent) δppm |
|---|---|---|---|---|
| | | | | s), 7.40 (1H, t, J = 1.5 Hz), 7.52 (1H, d, J = 8.4 Hz), 7.70 (1H, dd, J = 8.4 Hz, 2.0 Hz), 7.97 (1H, d, J = 2.0 Hz), 8.04 (1H, dd, J = 8.9 Hz, 2.6 Hz), 8.24 (1H, d, J = 2.6 Hz), 8.42 (1H, s). |
| 717 | —$OCH_3$ | —$CH_3$ | 3-furylmethyl | ($CDCl_3$) 2.40-2.44 (4H, m), 2.96 (3H, s), 3.39 (2H, s), 3.49-3.63 (4H, m), 3.63 (3H, s), 4.06 (2H, s), 6.12 (1H, dd, J = 8.7 Hz, 2.6 Hz) 6.22 (1H, d, J = 2.5 Hz), 6.38 (1H, s), 6.76 (1H, d, J = 8.7 Hz), 6.86 (1H, d, J = 8.7 Hz), 7.33-7.47 (3H, m), 7.69 (1H, dd, J = 8.4 Hz, 2.0 Hz), 7.96-8.04 (2H, m), 8.20 (1H, d, J = 2.3 Hz), 8.92 (1H, s). |

TABLE 200

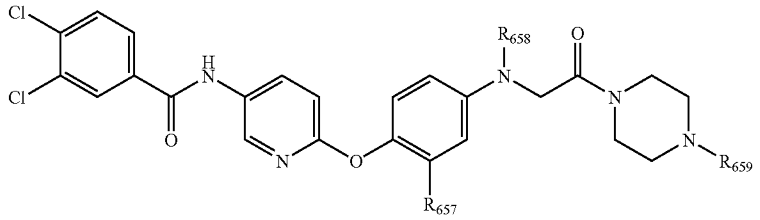

| Example No. | $R_{657}$ | $R_{658}$ | $R_{659}$ | Property |
|---|---|---|---|---|
| 718 | —$CH_3$ | —$CH_3$ | 3-furylmethyl | mp 116.5-118.0° C. |
| 719 | —H | —$C_2H_5$ | 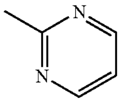 | MS 606($M^+$ + H) |
| 720 | —H | —$C_2H_5$ | 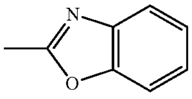 | MS 645($M^+$ + H) |
| 721 | —H | —$C_2H_5$ | 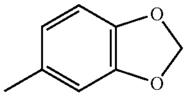 | $^1$H NMR ($CDCl_3$) δ 1.16 (3 H, t, J = 7.1 Hz), 3.04 (4 H, brs), 3.40 (2 H, q, J = 7.1 Hz), 3.66-3.76 (4 H, m), 4.07 (2 H, s), 5.91 (2 H, s), 6.36 (1 H, dd, J = 8.4 Hz, 2.5 Hz), 6.55 (1 H, d, J = 2.3 Hz), 6.66 (2 H, d, J = 9.1 Hz), 6.73 (1 H, d, J = 8.4 Hz), 6.83 (1 H, d, J = 8.9 Hz), 6.96 (2 H, d, J = 8.9 Hz), 7.54 (1 H, d, J = 8.4 Hz), 7.71 (1 H, dd, J = 8.4 Hz, 2.1 Hz), 7.98 (1 H, d, J = 2.1 Hz), 8.07 (1 H, dd, J = 8.9 Hz, 2.6 Hz), 8.22 (1 H, brs), 8.24 (1 H, d, J = 2.5 Hz). |

TABLE 200-continued

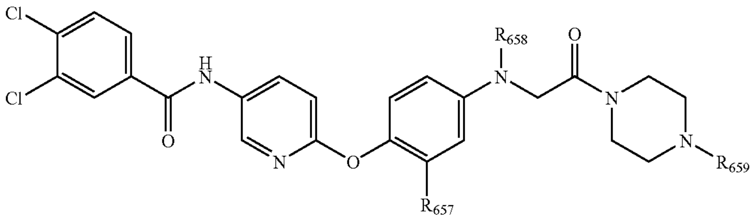

| Example No. | $R_{657}$ | $R_{658}$ | $R_{659}$ | Property |
|---|---|---|---|---|
| 722 | —H | $—CH_3$ | 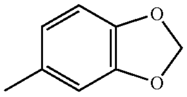 | $^1$H NMR ($CDCl_3$) δ 3.00-3.03 (7 H, m), 3.64 (2 H, brs), 3.75 (2 H, brs), 4.12 (2 H, s), 5.91 (2 H, s), 6.36 (1 H, dd, J = 8.4 Hz, 2.5 Hz), 6.55 (1 H, d, J = 2.3 Hz), 6.68 (2 H, d, J = 9.1 Hz), 6.73 (1 H, d, J = 8.4 Hz), 6.83 (1 H, d, J = 8.9 Hz), 6.98 (2 H, d, J = 9.1 Hz), 7.54 (1 H, d, J = 8.4 Hz), 7.71 (1 H, dd, J = 8.4 Hz, 2.1 Hz), 7.98 (1 H, d, J = 2.1 Hz), 8.07 (1 H, dd, J = 8.9 Hz, 2.8 Hz), 8.22 (1 H, brs), 8.23 (1 H, d, J = 3.0 Hz). |
| 723 | —H | $—C_2H_5$ | 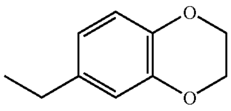 | $^1$H NMR (DMSO-$d_6$) δ 1.11 (3 H, t, J = 7.1 Hz), 2.31 (2 H, brs), 2.38 (2 H, brs), 3.22-3.58 (8 H, m), 4.16 (2 H, s), 4.21 (4 H, s), 6.56 (2 H, d, J = 9.0 Hz), 6.71-6.85 (3 H, m), 6.90 (2 H, d, J = 9.0 Hz), 6.93 (1 H, d, J = 8.9 Hz), 7.83 (1 H, d, J = 8.4 Hz), 7.95 (1 H, dd, J = 8.4 Hz, 2.0 Hz), 8.12 (1 H, dd, J = 8.9 Hz, 2.6 Hz), 8.22 (1 H, d, J = 2.0 Hz), 8.43 (1 H, d, J = 2.6 Hz), 10.51 (1 H, s). |
| 724 | —H | $—C_2H_5$ | 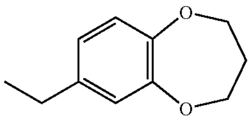 | $^1$H NMR ($CDCl_3$) δ 1.13 (3 H, t, J = 7.0 Hz, 2.10-2.25 (2 H, m), 2.42 (4 H, brs), 3.34 (2 H, q, J = 7.0 Hz), 3.42 (2 H, s), 3.50 (2 H, brs), 3.61 (2 H, brs), 4.01 (2 H, s), 4.11-4.31 (4 H, m), 6.59 (2 H, d, J = 9.2 Hz), 6.79 (1 H, d, J = 8.9 Hz), 6.82-6.98 (5 H, m), 7.51 (1 H, d, J = 8.4 Hz), 7.70 (1 H, dd, J = 8.4 Hz, 2.0 Hz), 7.98 (1 H, d, J = 2.8 Hz), 8.03 (1 H, dd, J = 8.9 Hz, 2.8 Hz), 8.24 (1 H, d, J = 2.8 Hz), 8.54 (1 H, s). |

TABLE 201

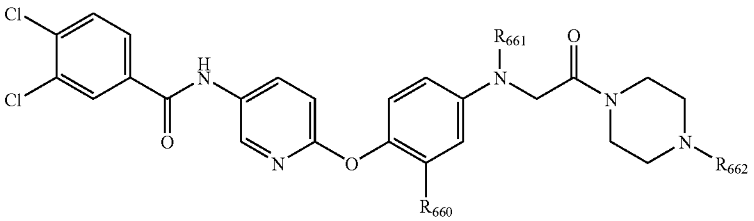

| Example No. | $R_{660}$ | $R_{661}$ | $R_{662}$ | mp (° C.) or $^1$H NMR (solvent) δ ppm |
|---|---|---|---|---|
| 725 | $—CH_3$ | —Ac | piperonyl | mp 216-217 |
| 726 | $—CH_3$ | —Ac | benzyl | $^1$H NMR (DMSO-$d_6$) 1.82 (3 H, s), 2.09 (3 H, s), 2.28-2.36 (4 H, m), 3.35-3.50 (6 H, m), 4.44 (2 H, s), 7.05-7.10 (2 H, m), 7.20-7.32 (7 H, m, 7.82 (1 H, d, J = 8.5 Hz), 7.92 (1 H, dd, J = 1.9 Hz, 8.5 Hz), 8.15-8.20 (2 H, m), 8.42 (1 H, d, J = 2.5 Hz), 10.53 (1 H, s). |
| 727 | —H | $—C_2H_5$ | 3-pyridyl | $^1$H NMR (DMSO-$d_6$) 1.13 (3 H, t, J = 7.1 Hz), 3.21 (2 H, brs), 3.29 (2 H, brs), 3.37 (2 H, q, J = 7.1 Hz), 3.51-3.78 (4 H, m), 4.26 (2 H, s), 6.60 (2 H, d, J = 9.0 Hz), 6.92 (2 H, d, J = 9.0 Hz), 6.94 (1 H, d, J = 8.9 Hz), 7.23 (1 H, dd, J = 8.5 Hz, 4.6 Hz), 7.36 (1 H, dd, J = 8.5 Hz, 1.6 Hz), 7.83 (1 H, d, J = 8.5 Hz), 7.94 (1 H, dd, J = 8.5 Hz, 2.0 Hz), 8.03 (1 H, d, J = 4.6 Hz), 8.12 (1 H, dd, J = 8.9 Hz, 2.8 Hz), |

TABLE 201-continued

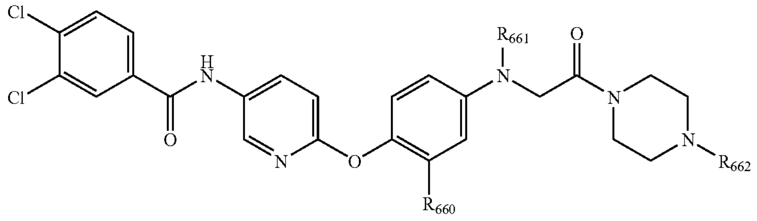

| Example No. | $R_{660}$ | $R_{661}$ | $R_{662}$ | mp (° C.) or $^1$H NMR (solvent) δ ppm |
|---|---|---|---|---|
| | | | | 8.22 (1 H, d, J = 2.0 Hz), 8.34 (1 H, d, J = 2.8 Hz), 8.43 (1 H, d, J = 2.8 Hz), 10.51 (1 H, s). |
| 728 | —F | —$C_2H_5$ | piperonyl | mp 149-151 |
| 729 | —F | —$CH_3$ | piperonyl | mp 199-201 |
| 730 | —F | —Ac | piperonyl | mp 233-235 |
| 731 | —$OCH_3$ | —$CH_3$ | piperonyl | $^1$H NMR ($CDCl_3$) 2.41-2.43 (4 H, m), 3.02 (3 H, s), 3.42 (2 H, s), 3.49-3.62 (4 H, m), 3.72 (3 H, s), 4.08 (2 H, s), 5.95 (2 H, s), 6.21 (1 H, dd, J = 8.7 Hz, 2.6 Hz), 6.32 (1 H, d, J = 2.8 Hz), 6.73-6.77 (2 H, m), 6.84 (2 H, t, J = 4.5 Hz), 6.95 (1 H, d, J = 8.7 Hz), 7.54 (1 H, d, J = 8.4 Hz), 7.70 (1 H, dd, J = 8.2 Hz, 2.0 Hz), 7.97 (2 H, d, J = 2.0 Hz), 8.05-8.09 (1 H, m), 8.19 (1 H, d, J = 2.5 Hz). |
| 732 | —H | —$CH_3$ | 3-pyridylmetyl | $^1$H NMR ($CDCl_3$) 2.40-2.42 (4 H, m), 2.93 (3 H, s), 3.44 (2 H, s), 3.48-3.58 (4 H, m), 4.06 (2 H, s), 6.58 (2 H, d, J = 9.1 Hz), 6.74 (1 H, d, J = 8.9 Hz), 6.90 (2 H, d, J = 9.1 Hz), 7.25-7.30 (1 H, m), 7.43 (1 H, d, J = 8.4 Hz), 7.66-7.73 (2 H, m), 7.97 (1 H, d, J = 2.0 Hz), 8.03 (1 H, dd, J = 8.9 Hz, 2.6 Hz), 8.25 (1 H, d, J = 2.5 Hz), 8.47-8.51 (2 H, m), 9.59 (1 H, s). |
| 733 | —H | —$CH_3$ | 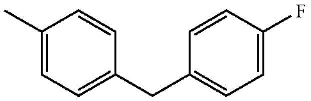 | $^1$H NMR (DMSO-$d_6$) 2.96 (3 H, s), 3.07-3.15 (4 H, m), 3.59 (4 H, brs), 3.83 (2 H, s), 4.31 (2 H, s), 6.66 (2 H, d, J = 9.1 Hz), 6.88-6.95 (5 H, m, 7.05-7.13 (4 H, m), 7.20-7.24 (2 H, m), 7.83 (1 H, d, J = 8.4 Hz), 7.95 (1 H, dd, J = 8.4 Hz, 2.0 Hz), 8.12 (1 H, dd, J = 8.9 Hz, 2.8 Hz), 8.22 (1 H, d, J = 2.0 Hz), 8.43 (1 H, d, J = 2.5 Hz), 10.50 (1 H, s). |

TABLE 202

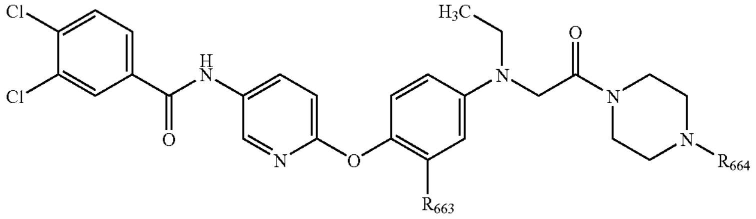

| Example No. | $R_{663}$ | $R_{664}$ | MS or $^1$H NMR |
|---|---|---|---|
| 734 | —H | —$CHPh_2$ | MS 694($M^+$ + H) |
| 735 | —H | 3-$CH_3$OPh- | MS 634($M^+$ + H) |
| 736 | —H | 4-$CH_3$OPh- | MS 634($M^+$ + H) |
| 737 | —H | 3,4- $(CH_3)_2$Ph- | MS 632($M^+$ + H) |
| 738 | —H | 2,3-$Cl_2$Ph- | MS 673($M^+$ + H) |
| 739 | —H | 2,4-$F_2$Ph- | MS 640($M^+$ + H) |
| 740 | —H | 2-$CH_3$OPh- | MS 634($M^+$ + H) |
| 741 | —H | 3-$CF_3$Ph- | MS 671($M^+$ + H) |
| 742 | —H | 2-ClPh- | MS 639($M^+$ + H) |
| 743 | —H | 4-$CF_3$Ph- | MS 671($M^+$ + H) |
| 744 | —H | -Ph | MS 604($M^+$ + H) |
| 745 | —H | 2-pyridylmethyl | MS 619($M^+$ + H) |
| 746 | —H | 2-pyridyl | MS 605($M^+$ + H) |
| 747 | —H | —$(CH_2)_3$Ph | MS 646($M^+$ + H) |

TABLE 202-continued

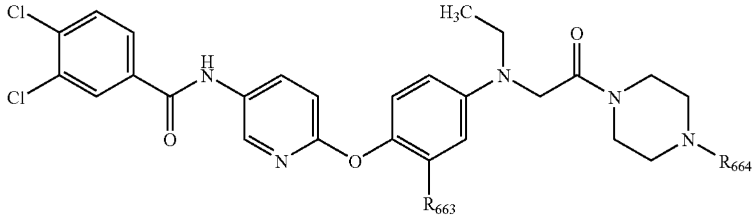

| Example No. | $R_{663}$ | $R_{664}$ | MS or $^1$H NMR |
|---|---|---|---|
| 748 | —H | $—(CH_2)_4Ph$ | MS 660($M^+$ + H) |
| 749 | —H | $—(CH_2)_2N(CH_3)_2$ | MS 599($M^+$ + H) |
| 750 | —H | cyclopentyl | MS 596($M^+$ + H) |
| 751 | —H | 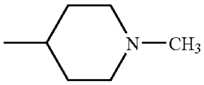 | MS 625($M^+$ + H) |
| 752 | —H | 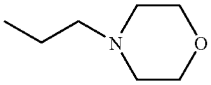 | MS 641($M^+$ + H) |
| 753 | —H | $—CH(CH_3)Ph$ | MS 634($M^+$ + H) |
| 754 | —H | $—(CH_2)_2Ph$ | MS 632($M^+$ + H) |
| 755 | —H | $—CH_2CONHPh$ | MS 661($M^+$ + H) |
| 756 | —H | $—(CH_2)_3N(CH_3)_2$ | MS 613($M^+$ + H) |
| 757 | —H | 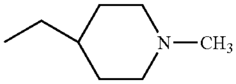 | MS 639($M^+$ + H) |
| 758 | —H | $—CH_3$ | MS 542($M^+$ + H) |
| 759 | $—OCH_3$ | —H | $^1$H NMR ($CDCl_3$) δ 1.26 (3 H, t, J = 6.9 Hz), 2.70 (1 H, brs), 2.82-2.87 (4 H, m), 3.33 (2 H, q, J = 6.9 Hz), 3.49-3.57 (4 H, m), 3.62 (3 H, s), 4.00 (2 H, s), 6.09 (1 H, d, J = 8.7 Hz), 6.20 (1 H, s), 6.73 (1 H, d, J = 8.7 Hz), 6.83 (1 H, d, J = 8.6 Hz), 7.42 (1 H, d, J = 8.3 Hz), 7.70 (1 H, d, J = 7.4 Hz), 7.97-8.03 (2 H, m), 8.23 (1 H, s), 9.26 (1 H, brs). |

TABLE 203

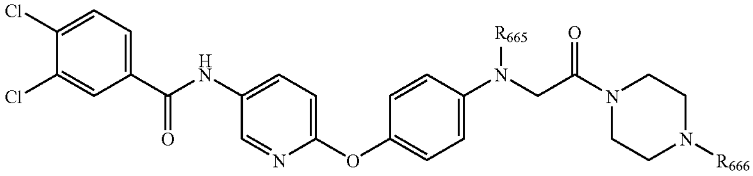

| Example No. | $R_{665}$ | $R_{666}$ | Form | $^1$H NMR (DMSO-$d_6$) δ ppm |
|---|---|---|---|---|
| 760 | —Ac | piperonyl | hydro-chloride | 1.84 (3 H, s), 2.83-3.14 (2 H, m), 3.23-3.32 (2 H, m), 4.02 (1 H, d, J = 13.6 Hz), 4.18-4.27 (2 H, m), 4.40 (1 H, d, J = 13.6 Hz), 4.50-4.60 (2 H, m), 6.07 (2 H, s), 6.96-7.03 (2 H, m), 7.10-7.25 (4 H, m), 7.43 (2 H, d, J = 8.8 Hz), 7.85 (1 H, d, J = 8.4 Hz), 7.98 (1 H, dd, J = 2.0 Hz, 8.4 Hz), 8.24 (1 H, dd, J = 2.6 Hz, 8.9 Hz), 8.26 (1 H, d, J = 2.0 Hz), 8.54 (1 H, d, J = 2.6 Hz), 10.69 (1 H, s), 11.07 (1 H, brs). |
| 761 | —Ac | benzyl | hydro-chloride | 1.84 (3 H, s), 2.90-3.17 (2 H, m), 3.23-3.35 (2 H, m), 4.03 (1 H, d, J = 14.4 Hz), 4.28-4.43 (3 H, m), 4.50-4.62 (2 H, m), 7.13 (1 H, d, J = 8.8 Hz), 7.17 (2 H, d, J = 8.8 Hz), 7.40-7.50 (5 H, m), 7.58-7.62 (2 H, m), 7.85 (1 H, d, J = 8.4 Hz), 8.00 (1 H, dd, J = 2.0 Hz, 8.4 Hz), |

TABLE 203-continued

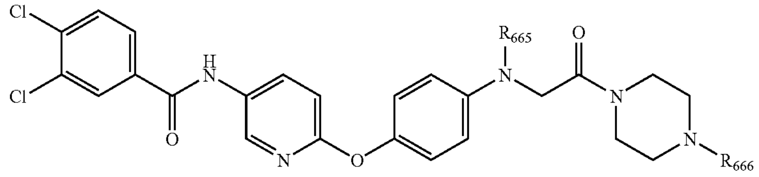

| Example No. | $R_{665}$ | $R_{666}$ | Form | $^1$H NMR (DMSO-$d_6$) δ ppm |
|---|---|---|---|---|
| | | | | 8.20-8.29 (2 H, m), 8.54 (1 H, d, J = 2.6 Hz), 10.70 (1 H, s), 11.21 (1 H, brs). |
| 762 | —$C_2H_5$ | 3-furylmethyl | trihydro-chloride | 1.11 (3 H, t, J = 7.1 Hz), 2.75-3.30 (3 H, m), 3.30-3.50 (2 H, m), 3.40 (2 H, q, J = 7.1 Hz), 3.51-3.72 (1 H, m), 3.95-4.15 (1 H, m), 4.22 (2 H, s), 4.30-4.62 (3 H, m), 6.80-6.85 (1 H, m), 6.89 (2 H, d, J = 8.9 Hz), 7.00 (1 H, d, J = 8.9 Hz), 7.0 1 (2 H, d, J = 8.9 Hz), 7.70-7.80 (1 H, m), 7.84 (1 H, d, J = 8.5 Hz), 7.88 (1 H, s), 7.99 (1 H, dd, J = 8.5 Hz, 2.0 Hz), 8.19 (1 H, dd, J = 8.9 Hz, 2.7 Hz), 8.27 (1 H, d, J = 2.0 Hz), 8.50 (1 H, d, J = 2.7 Hz), 10.69 (1 H, s). |
| 763 | —$C_2H_5$ | 4-pyridylmethyl | tetrahydro-chloride | 1.11 (3 H, t, J = 7.0 Hz), 3.00-3.60 (6 H, m), 3.41 (2 H, q, J = 7.0 Hz), 3.90 (2 H, brs), 4.42 (2 H, brs), 4.63 (2 H, brs), 6.82 (2 H, d, J = 8.8 Hz), 6.98 (3 H, d, J = 8.8 Hz), 7.84 (1 H, d, J = 8.4 Hz), 7.98 (1 H, dd, J = 8.4 Hz, 2.0 Hz), 8.17 (1 H, dd, J = 8.9 Hz, 2.6 Hz), 8.22-8.39 (3 H, m), 8.49 (1 H, d, J = 2.5 Hz), 8.99 (2 H, d, J = 6.2 Hz), 10.67 (1 H, s). |
| 764 | —$CH_3$ | 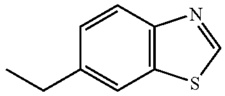 | dihydro-chloride | 2.94 (3 H, s), 2.80-3.22 (3 H, m), 3.22-3.70 (3 H, m), 3.95-4.60 (6 H, m), 6.68 (2 H, d, J = 9.1 Hz), 6.92 (2 H, d, J = 9.1 Hz), 6.95 (1 H, d, J = 8.9 Hz), 7.79 (1 H, dd, J = 8.4 Hz, 1.6 Hz), 7.84 (1 H, d, J = 8.4 Hz), 7.96 (1 H, dd, J = 8.4 Hz, 2.0 Hz), 8.14 (1 H, dd, J = 8.9 Hz, 2.3 Hz), 8.20 (1 H, d, J = 8.4 Hz), 8.24 (1 H, d, J = 2.0 Hz), 8.40 (1 H, d, J = 1.6 Hz), 8.44 (1 H, d, J = 2.3 Hz), 9.51 (1 H, s), 10.57 (1 H, s). |

TABLE 204

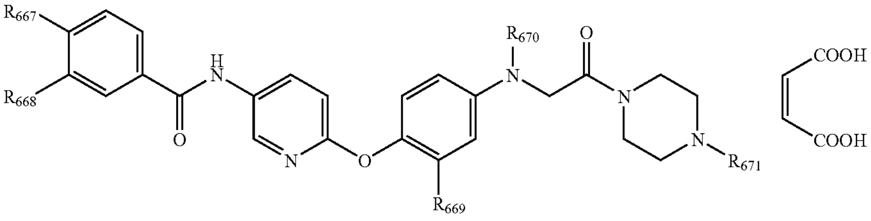

| Example No. | $R_{667}$ | $R_{668}$ | $R_{669}$ | $R_{670}$ | $R_{671}$ | mp (° C.) or $^1$H NMR (solvent) δ ppm |
|---|---|---|---|---|---|---|
| 765 | —Cl | —Cl | —H | —$CH_3$ | piperonyl | mp 198-200 |
| 766 | —Cl | —Cl | —H | —$C_2H_5$ | benzyl | $^1$H NMR (DMSO-$d_6$) 1.12 (3 H, t, J = 7.1 Hz), 2.98 (4 H, brs), 3.34 (2 H, q, J = 7.1 Hz), 3.20-3.50 (2 H, m), 3.67 (2 H, brs), 4.10 (2 H, brs), 4.23 (2 H, s), 6.11 (2 H, s), 6.59 (2 H, d, J = 9.2 Hz), 6.91 (2 H, d, J = 9.2 Hz), 6.94 (1 H, d, J = 8.9 Hz), 7.45 (5 H, s), 7.84 (1 H, d, J = 8.4 Hz), 7.94 (1 H, dd, J = 8.4 Hz, 2.6 Hz), 8.12 (1 H, dd, J = 8.9 Hz, 2.6 Hz), 8.22 (1 H, d, J = 2.0 Hz), 8.43 (1 H, d, J = 2.6 Hz), 10.51 (1 H, s). |

TABLE 204-continued

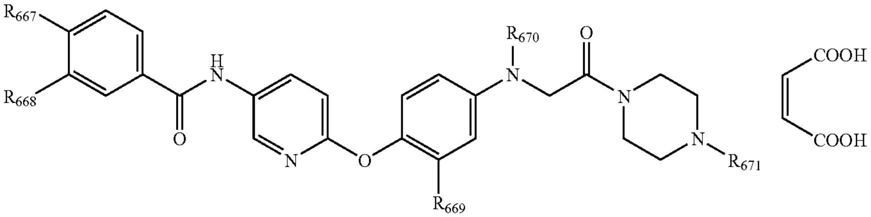

| Example No. | $R_{667}$ | $R_{668}$ | $R_{669}$ | $R_{670}$ | $R_{671}$ | mp (° C.) or $^1$H NMR (solvent) δ ppm |
|---|---|---|---|---|---|---|
| 767 | —Cl | —Cl | —H | —$CH_3$ | 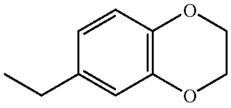 | $^1$H NMR (DMSO-$d_6$) 2.94 (3 H, s), 3.05 (4 H, brs), 3.40 (2 H, brs), 3.63 (2 H, brs), 4.04 (2 H, brs), 4.26 (4 H, s), 4.31 (2 H, brs), 6.09 (2 H, s), 6.65 (2 H, d, J = 9.1 Hz), 6.82-7.06 (6 H, m), 7.84 (1 H, d, J = 8.4 Hz), 7.94 (1 H, dd, J = 8.4 Hz, 2.0 Hz), 8.12 (1 H, dd, J = 8.8 Hz, 2.5 Hz), 8.22 (1 H, d, J = 2.0 Hz), 8.43 (1 H, d, J = 2.5 Hz), 10.51 (1 H, s). |
| 768 | —Cl | —Cl | —$OCH_3$ | —$C_2H_5$ | piperonyl | mp 172-177 |
| 769 | —$CF_3$ | —H | —H | —$C_2H_5$ | benzyl | $^1$H NMR ($CDCl_3$ + $CD_3OD$) 1.13 (3 H, t, J = 6.9 Hz), 3.08 (4 H, brs), 3.36 (2 H, q, J = 6.9 Hz), 3.85 (4 H, brs), 4.09 (2 H, s), 4.18 (2 H, s), 6.31 (2 H, s), 6.73 (2 H, d, J = 8.9 Hz), 6.87 (1 H, d, J = 9.2 Hz), 6.98 (2 H, d, J = 8.9 Hz), 7.40-7.44 (5 H, m), 7.73 (2 H, d, J = 8.4 Hz), 8.07 (2 H, d, J = 8.3 Hz), 8.27 (2 H, d, J = 7.4 Hz), 9.63 (1 H, s). |
| 770 | —$CF_3$ | —H | —H | —$CH_3$ | 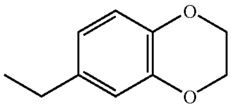 | $^1$H NMR (DMSO-$d_6$) 2.94 (3 H, s), 2.95 (4 H, brs), 3.33 (4 H, brs), 4.03 (2 H, brs), 4.26 (4 H, s), 4.31 (2 H, brs), 6.09 (2 H, s), 6.65 (2 H, d, J = 9.2 Hz), 6.85-7.03 (6 H, m, 7.93 (2 H, d, J = 8.2 Hz), 8.14 (1 H, dd, J = 8.9 Hz, 2.5 Hz), 8.16 (2 H, d, J = 8.2 Hz), 8.45 (1 H, d, J = 2.5 Hz), 10.59 (1 H, s). |

TABLE 205

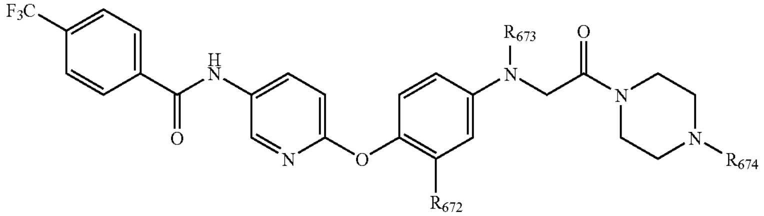

| Example No. | $R_{672}$ | $R_{673}$ | $R_{674}$ | mp (° C.) or $^1$H NMR (solvent) δ ppm |
|---|---|---|---|---|
| 771 | —H | —Ac | benzyl | mp 161-162 |
| 772 | —$CH_3$ | —Ac | piperonyl | $^1$H NMR (DMSO-$d_6$) 1.82 (3 H, s), 2.10 (3 H, s), 2.23-2.36 (4 H, m), 3.33-3.45 (6 H, m), 4.44 (2 H, s), 5.96 (2 H, s), 6.72 (1 H, d, J = 8.0 Hz), 6.82 (1 H, d, J = 8.0 Hz), 6.84 (1 H, s), 7.02-7.10 (2 H, m), 7.23 (1 H, d, J = 8.6 Hz), 7.33 (1 H, s), 7.91 (2 H, d, J = 8.4 Hz), 8.14 (2 H, d, J = 8.4 Hz), 8.20 (1 H, d, J = 8.6 Hz), 8.45 (1 H, s), 10.60 (1 H, s). |
| 773 | —$CH_3$ | —Ac | benzyl | $^1$H NMR (DMSO-$d_6$) 1.82 (3 H, s), 2.10 (3 H, s), 2.30-2.37 (4 H, m), 3.35-3.45 (4 H, m), 3.47 (2 H, s), 4.44 (2 H, s), 7.03-7.10 (2 H, m), 7.20-7.35 (7 H, m), 7.91 (2 H, d, J = 8.4 Hz), 8.14 (2 H, |

TABLE 205-continued

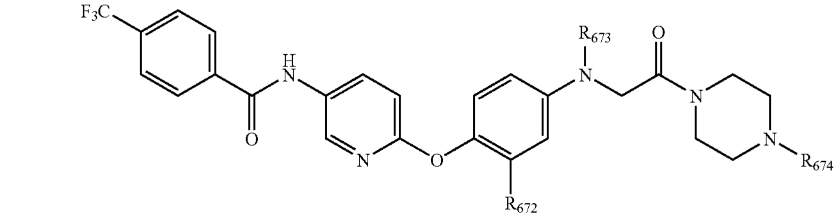

| Example No. | $R_{672}$ | $R_{673}$ | $R_{674}$ | mp (° C.) or $^1$H NMR (solvent) δ ppm |
|---|---|---|---|---|
| | | | | d, J = 8.4 Hz), 8.21 (1 H, dd, J = 2.5 Hz, 8.9 Hz), 8.45 (1 H, d, J = 2.5 Hz), 10.60 (1 H, s). |
| 774 | —H | —$C_2H_5$ | piperonyl | mp 178-180 |
| 775 | —F | —$C_2H_5$ | piperonyl | mp 170-172 |
| 776 | —F | —$CH_3$ | piperonyl | mp 220-221 |
| 777 | —$OCH_3$ | —$CH_3$ | piperonyl | $^1$H NMR ($CDCl_3$) 2.38-2.42 (4 H, m), 2.96 (3 H, s), 3.41 (2 H, s), 3.47-3.58 (4 H, m), 3.64 (3 H, s), 4.05 (2 H, s), 5.94 (2 H, s), 6.13 (1 H, dd, J = 8.9 Hz, 2.8 Hz), 6.24 (1 H, d, J = 2.8 Hz), 6.70-6.89 (5 H, m), 7.64 (2 H, d, J = 8.3 Hz), 7.96 (2 H, d, J = 8.1 Hz), 8.06 (1 H, dd, J = 8.9 Hz, 2.6 Hz), 8.20 (1 H, d, J = 2.6 Hz), 8.93 (1 H, s). |
| 778 | —$OCH_3$ | —$CH_3$ | 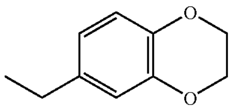 | $^1$H NMR ($CDCl_3$) 2.38-2.42 (4 H, m), 2.96 (3 H, s), 3.40 (2 H, s), 3.47-3.57 (4 H, m), 3.98 (3 H, s), 4.05 (2 H, s), 4.24 (4 H, s), 6.13 (1 H, dd, J = 8.9 Hz, 2.8 Hz), 6.23 (1 H, d, J = 2.6 Hz), 6.73-6.88 (5 H, m), 7.63 (2 H, d, J = 8.3 Hz), 7.97 (2 H, d, J = 8.1 Hz), 8.07 (1 H, dd, J = 8.9 Hz, 2.6 Hz), 8.20 (1 H, d, J = 2.5 Hz), 9.11 (1 H, s). |
| 779 | —F | —$CH_3$ | 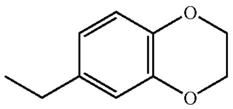 | $^1$H NMR (DMSO-$d_6$) 2.30 (2 H, brs), 2.39 (2 H, brs), 2.93 (3 H, s), 3.38 (2 H, s), 3.44 (4 H, brs), 4.22 (4 H, s), 4.28 (2 H, s), 6.40-6.43 (1 H, m), 6.56 (1 H, dd, J = 14.2 Hz, 2.6 Hz), 6.73-6.81 (3 H, m), 7.02-7.08 (2 H, m), 7.93 (2 H, d, J = 8.6 Hz), 8.14-8.21 (3 H, m), 8.49 (1 H, d, J = 2.6 Hz), 10.61 (1 H, s). |
| 780 | —F | —$CH_3$ | 3-furylmethyl | $^1$H NMR (DMSO-$d_6$) 2.32 (2 H, s), 2.41 (2 H, s), 2.93 (3 H, s), 3.37 (2 H, s), 3.44 (4 H, brs), 4.29 (2 H, s), 6.40-6.44 (2 H, m), 6.55 (1 H, dd, J = 14.5 Hz, 2.8 Hz), 7.02-7.08 (2 H, m), 7.58-7.62 (2 H, m), 7.93 (2 H, d, J = 8.4 Hz), 8.14-8.21 (3 H, m), 8.41 (1 H, d, J = 2.6 Hz), 10.61 (1 H, s). |

TABLE 206

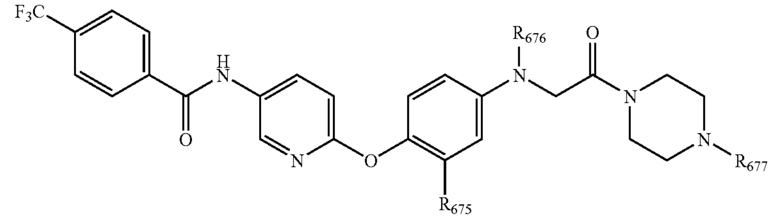

| Example No. | $R_{675}$ | $R_{676}$ | $R_{677}$ | mp (° C.) or $^1$H NMR (solvent) δ ppm |
|---|---|---|---|---|
| 781 | —$OCH_3$ | —$C_2H_5$ | 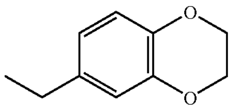 | $^1$H NMR ($CDCl_3$) 1.16 (3 H, t, J = 6.9 Hz), 2.38-2.43 (4 H, m), 3.33-3.62 (8 H, m), 3.66 (3 H, s), 4.02 (2 H, s), 4.26 (4 H, s), 6.14 (1 H, dd, J = 8.7 Hz, 2.6 Hz), 6.25 (1 H, d, J = 2.6 Hz), 6.75-6.90 (5 H, m), 7.66 (2 H, d, J = 8.3 Hz), 8.01 (2 H, d, J = 8.3 Hz), 8.09 (1 H, dd, J = 9.1 Hz, 2.8 Hz), 8.26 (1 H, d, J = 2.6 Hz), 9.19 (1 H, s). |
| 782 | —F | —Ac | piperonyl | $^1$H NMR (DMSO-$d_6$) 1.88 (3 H, s), 2.33 (4 H, brs), 3.40 (2 H, s), 3.40 (4 H, brs), 4.50 (2 H, s), |

TABLE 206-continued

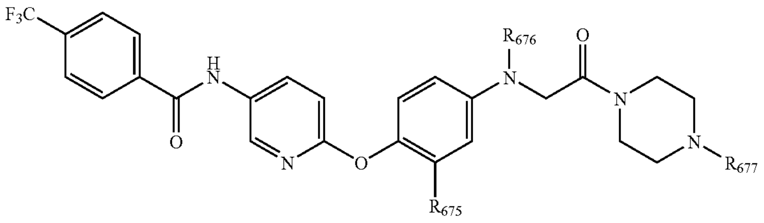

| Example No. | $R_{675}$ | $R_{676}$ | $R_{677}$ | mp (° C.) or $^1$H NMR (solvent) δ ppm |
|---|---|---|---|---|
| | | | | 5.99 (2 H, s), 6.73-6.76 (1 H, m), 6.83-6.86 (2 H, m), 7.21 (1 H, d, J = 8.9 Hz), 7.32-7.49 (3 H, m), 7.94 (2 H, d, J = 8.3 Hz), 8.16 (2 H, d, J = 8.1 Hz), 8.25 (1 H, dd, J = 8.9 Hz, 2.6 Hz), 8.46 (1 H, d, J = 2.6 Hz), 10.66 (1 H, s). |
| 783 | —H | —$CH_3$ | 3-furylmethyl | $^1$H NMR ($CDCl_3$) 2.44 (4 H, brs), 2.99 (3 H, s), 3.40 (2 H, s), 3.50 (2 H, t, J = 4.9 Hz), 3.62 (2 H, t, J = 4.9 Hz), 4.07 (2 H, s), 6.38 (1 H, d, J = 1.0 Hz), 6.67 (2 H, d, J = 9.1 Hz), 6.84 (1 H, d, J = 8.8 Hz), 6.98 (2 H, d, J = 9.1 Hz), 7.34 (1 H, s), 7.40 (1 H, t, J = 1.6 Hz), 7.73 (2 H, d, J = 8.2 Hz), 7.99 (2 H, d, J = 8.2 Hz), 8.11 (1 H, dd, J = 8.8 Hz, 2.6 Hz), 8.24 (1 H, s), 8.25 (1 H, d, J = 2.6 Hz). |
| 784 | —$OCH_3$ | —$C_2H_5$ | 3-furylmethyl | mp 174-176 |
| 785 | —$OCH_3$ | —$CH_3$ | 3-furylmethyl | mp 160-164 |
| 786 | —$CH_3$ | —$CH_3$ | —COOC $(CH_3)_3$ | $^1$H NMR ($CDCl_3$) 1.47 (9 H, s), 2.12 (3 H, s), 3.01 (3 H, s), 3.30-3.71 (8 H, m), 4.09 (2 H, s), 6.44-6.66 (2 H, m), 6.83 (1 H, d, J = 8.9 Hz), 6.93 (1 H, d, J = 8.4 Hz), 7.75 (2 H, d, J = 8.1 Hz), 7.94 (1 H, s), 7.99 (2 H, d, J = 8.1 Hz), 8.15 (1 H, d, J = 9.2 Hz), 8.22 (1 H, s). |
| 787 | —H | —$C_2H_5$ | 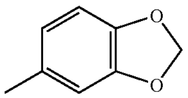 | $^1$H NMR ($CDCl_3$) 1.18 (3 H, t, J = 7.1 Hz), 3.03 (4 H, brs), 3.43 (2 H, q, J = 7.1 Hz), 3.67-3.77 (4 H, m), 4.08 (2 H, s), 5.91 (2 H, s), 6.36 (1 H, dd, J = 8.4 Hz, 2.3 Hz), 6.55 (1 H, d, J = 2.5 Hz), 6.68-6.75 (3 H, m), 6.87 (1 H, d, J = 8.7 Hz), 7.00 (2 H, d, J = 8.9 Hz), 7.75 (2 H, d, J = 8.4 Hz), 7.98 (1 H, brs), 7.99 (2 H, d, J = 8.3 Hz), 8.13 (1 H, dd, J = 8.7 Hz, 2.6 Hz), 8.25 (1 H, d, J = 2.6 Hz) |

TABLE 207

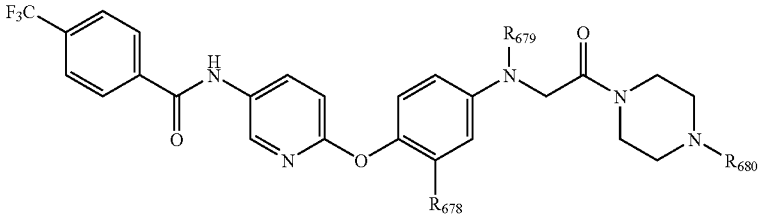

| Example No. | $R_{678}$ | $R_{679}$ | $R_{680}$ | Form | mp (° C.) or $^1$H NMR (solvent) δ ppm |
|---|---|---|---|---|---|
| 788 | —F | —$(CH_2)_2CH_3$ | piperonyl | free | $^1$H NMR ($CDCl_3$) 0.94 (3 H, t, J = 7.3 Hz), 1.58-1.69 (2 H, m), 2.45 (4 H, brs), 3.29 (2 H, t, J = 7.6 Hz), 3.45 (2 H, s), 3.49 (2 H, brs), 3.64 (2 H, brs), 4.05 (2 H, s), 5.95 (2 H, s), 6.34-6.44 (2 H, m), 6.75 (2 H, s), 6.86 (1 H, s), 6.96 (1 H, d, J = 8.9 Hz), 7.03 (1 H, t, J = 9.1 Hz), 7.76 (2 H, d, J = 8.2 Hz), 7.86 (1 H, brs), 8.00 (2 H, d, J = 8.1 Hz), 8.16-8.22 (2 H, m). |

TABLE 207-continued

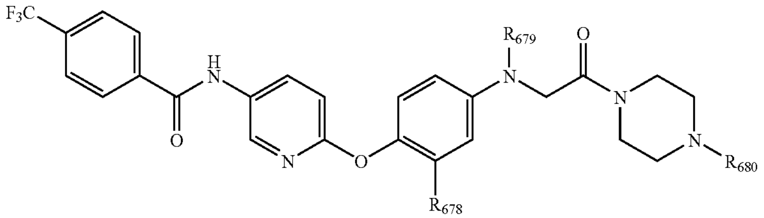

| Example No. | $R_{678}$ | $R_{679}$ | $R_{680}$ | Form | mp (° C.) or $^1$H NMR (solvent) δ ppm |
|---|---|---|---|---|---|
| 789 | —H | —$CH_3$ | 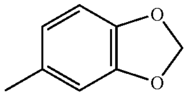 | free | $^1$H NMR ($CDCl_3$) 3.02 (7 H, brs), 3.64 (2 H, brs), 3.75 (2 H, brs), 4.12 (2 H, s), 5.91 (2 H, s), 6.36 (1 H, dd, J = 8.4 Hz, 2.5 Hz), 6.55 (1 H, d, J = 2.5 Hz), 6.70 (2 H, d, J = 9.1 Hz), 6.73 (1 H, d, J = 8.3 Hz), 6.85 (1 H, d, J = 8.9 Hz), 6.99 (2 H, d, J = 9.2 Hz), 7.73 (2 H, d, J = 8.3 Hz), 7.98 (2 H, d, J = 8.3 Hz), 8.12 (1 H, dd, J = 9.1 Hz, 2.8 Hz), 8.15 (1 H, brs), 8.24 (1 H, d, J = 2.5 Hz). |
| 790 | —$OCH_3$ | —$CH_3$ | 4- (4-FPhCO)Ph- | free | $^1$H NMR ($CDCl_3$) 3.03 (3 H, s), 3.39 (4 H, brs), 3.70 (3 H, s), 3.71-3.79 (4 H, m), 4.14 (2 H, s), 6.23 (1 H, dd, J = 8.9 Hz, 2.8 Hz), 6.36 (1 H, d, J = 2.6 Hz), 6.81-6.96 (4 H, m), 7.09-7.17 (2 H, m), 7.68 (2 H, d, J = 8.4 Hz), 7.72-7.78 (4 H, m), 7.99 (2 H, d, J = 8.3 Hz), 8.09 (1 H, dd, J = 8.9 Hz, 2.8 Hz), 8.21 (1 H, d, J = 2.6 Hz), 8.53 (1 H, s). |
| 791 | —$OCH_3$ | —$C_2H_5$ | 4- (4-FPhCO)Ph- | free | $^1$H NMR ($CDCl_3$) 1.17 (3 H, t, J = 6.9 Hz), 3.37-3.42 (6 H, m), 3.67 (3 H, s), 3.71-3.76 (4 H, m), 4.08 (2 H, s), 6.19 (1 H, dd, J = 8.9 Hz, 2.8 Hz), 6.33 (1 H, d, J = 2.6 Hz), 6.77-6.92 (4 H, m), 7.09-7.15 (2 H, m), 7.64 (2 H, d, J = 8.3 Hz), 7.71-7.77 (4 H, m), 7.98 (2 H, d, J = 8.1 Hz), 8.07 (1 H, dd, J = 8.9 Hz, 2.6 Hz), 8.23 (1 H, d, J = 2.6 Hz), 8.83 (1 H, s). |
| 792 | —$CH_3$ | —$CH_3$ | 3-furylmethyl | hydro-chloride | mp 158.5-161.0 |

TABLE 208

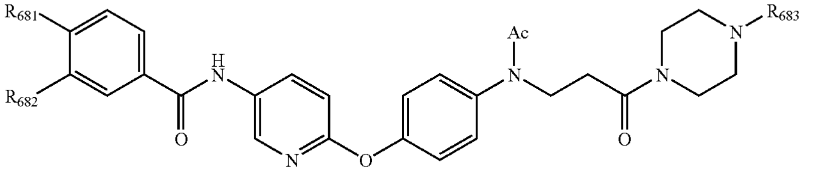

HCl

| Example No. | $R_{681}$ | $R_{682}$ | $R_{683}$ | $^1$H NMR (DMSO-$d_6$) δ ppm |
|---|---|---|---|---|
| 793 | —Cl | —Cl | piperonyl | 1.74 (3 H, s), 2.19-2.34 (4 H, m), 2.54 (2 H, t, J = 7.7 Hz), 3.32-3.46 (6 H, m), 3.76 (2 H, t, J = 7.7 Hz), 5.96 (2 H, s), 6.72 (1 H, d, J = 7.9 Hz), 6.77-6.85 (2 H, m), 7.11 (1 H, d, J = 8.8 Hz), 7.17 (2 H, d, J = 8.6 Hz), 7.31 (2 H, d, J = 8.6 Hz), 7.83 (1 H, d, J = 8.4 Hz), 7.93 (1 H, dd, J = 8.4 Hz, 2.1 Hz), 8.17-8.25 (2 H, m, 8.51 (1 H, d, J = 2.4 Hz), 10.57 (1 H, s). |
| 794 | —Cl | —Cl | benzyl | 1.74 (3 H, s), 2.25-2.37 (4 H, m), 2.54 (2 H, t, J = 7.7 Hz), 3.36-3.42 (4 H, m), 3.46 (2 H, s), 3.76 (2 H, t, J = 7.7 Hz), 7.11 (1 H, d, J = 8.8 Hz), 7.16 (2 H, d, J = 8.6 Hz), 7.20-7.31 (5 H, m), 7.34 (2 H, d, J = 8.6 Hz), 7.83 (1 H, d, J = 8.4 Hz), 7.93 (1 H, dd, J = 8.4 Hz, 2.1 Hz), 8.19-8.25 (2 H, m), 8.51 (1 H, d, J = 2.5 Hz), 10.57 (1 H, s). |

TABLE 208-continued

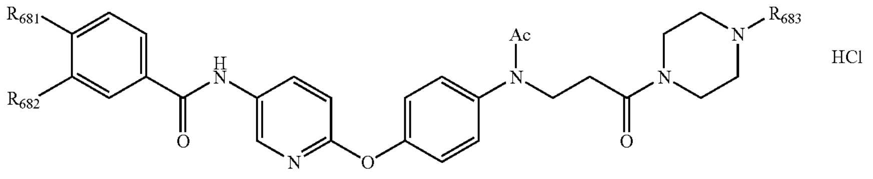

| Example No. | $R_{681}$ | $R_{682}$ | $R_{683}$ | $^1$H NMR (DMSO-$d_6$) δ ppm |
|---|---|---|---|---|
| 795 | —$CF_3$ | —H | piperonyl | 1.74 (3 H, s), 2.20-2.35 (4 H, m), 2.54 (2 H, t, J = 7.7 Hz), 3.34-3.42 (6 H, m), 3.76 (2 H, t, J = 7.7 Hz), 5.96 (2 H, s), 6.72 (1 H, d, J = 7.8 Hz), 6.78-6.86 (2 H, m), 7.12 (1 H, d, J = 8.8 Hz), 7.17 (2 H, d, J = 8.5 Hz), 7.35 (2 H, d, J = 8.5 Hz), 7.92 (2 H, d, J = 8.2 Hz), 8.15 (2 H, d, J = 8.2 Hz), 8.24 (1 H, dd, J = 8.8 Hz, 2.5 Hz), 8.54 (1 H, d, J = 2.5 Hz), 10.65 (1 H, s). |
| 796 | —$CF_3$ | —H | benzyl | 1.74 (3 H, s), 2.18-2.36 (4 H, m), 2.54 (2 H, t, J = 7.7 Hz), 3.35-3.45 (4 H, m), 3.46 (2 H, s), 3.76 (2 H, t, J = 7.7 Hz), 7.12 (1 H, d, J = 8.8 Hz), 7.17 (2 H, d, J = 8.6 Hz), 7.20-7.33 (5 H, m), 7.34 (2 H, d, J = 8.6 Hz), 7.92 (2 H, d, J = 8.3 Hz), 8.15 (2 H, d, J = 8.3 Hz), 8.24 (1 H, dd, J = 8.8 Hz, 2.5 Hz), 8.54 (1 H, d, J = 2.5 Hz), 10.65 (1 H, s). |

TABLE 209

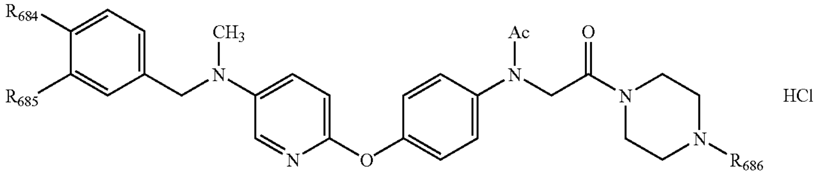

| Example No. | $R_{684}$ | $R_{685}$ | $R_{686}$ | $^1$H NMR (DMSO-$d_6$) δ ppm |
|---|---|---|---|---|
| 797 | —Cl | —Cl | benzyl | 1.80 (3 H, s), 3.02 (3 H, s), 2.70-3.40 (5 H, m), 3.41-3.68 (1 H, m), 3.88-4.10 (1 H, m), 4.32 (2 H, brs), 4.25-4.50 (1 H, m), 4.50 (2 H, d, J = 3.8 Hz), 4.57 (2 H, s), 6.94 (1 H, d, J = 8.9 Hz), 7.02 (2 H, d, J = 8.7 Hz), 7.22 (1 H, dd, J = 8.2 Hz, 2.0 Hz), 7.34 (1 H, dd, J = 8.9 Hz, 3.2 Hz), 7.36 (2 H, d, J = 8.7 Hz), 7.42-7.49 (3 H, m), 7.50 (1 H, d, J = 2.0 Hz), 7.55-7.64 (1 H, m), 7.62 (2 H, d, J = 8.2 Hz), 7.66 (1 H, d, J = 6.1 Hz). |
| 798 | —Cl | —Cl | piperonyl | 1.81 (3 H, s), 2.75-3.40 (5 H, m), 3.02 (3 H, s), 3.43-3.67 (1 H, m), 3.90-4.10 (1 H, m), 4.22 (2 H, brs), 4.30-4.50 (1 H, m), 4.50 (2 H, d, J = 4.6 Hz), 4.57 (2 H, s), 6.07 (2 H, s), 6.94 (2 H, d, J = 8.8 Hz), 6.97-7.07 (1 H, m), 7.02 (2 H, d, J = 8.9 Hz), 7.22 (1 H, dd, J = 8.3 Hz, 1.8 Hz), 7.24 (1 H, s), 7.34 (1 H, dd, J = 8.8 Hz, 3.0 Hz), 7.36 (2 H, d, J = 8.9 Hz), 7.50 (1 H, d, J = 1.8 Hz), 7.60 (1 H, d, J = 8.3 Hz), 7.67 (1 H, d, J = 3.0 Hz). |
| 799 | —$CF_3$ | —H | benzyl | 1.80 (3 H, s), 3.05 (3 H, s), 2.70-3.40 (5 H, m), 3.41-3.68 (1 H, m), 3.90-4.08 (1 H, m), 4.22-4.45 (1 H, m), 4.32 (2 H, brs), 4.50 (2 H, d, J = 3.5 Hz), 4.67 (2 H, s), 6.94 (1 H, d, J = 8.9 Hz), 7.02 (2 H, d, J = 8.8 Hz), 7.34 (1 H, dd, J = 8.9 Hz, 3.3 Hz), 7.36 (2 H, d, J = 8.8 Hz), 7.39-7.50 (5 H, m), 7.54-7.64 (2 H, m), 7.67 (1 H, d, J = 3.3 Hz), 7.70 (2 H, d, J = 8.1 Hz). |
| 800 | —$CF_3$ | —H | piperonyl | 1.80 (3 H, s), 2.70-3.40 (5 H, m), 3.05 (3 H, s), 3.43-3.65 (1 H, m), 3.90-4.09 (1 H, m), 4.22 (2 H, s), 4.29-4.48 (1 H, m), 4.50 (2 H, d, J = 4.8 Hz), 4.67 (2 H, s), 6.07 (2 H, s), 6.94 (1 H, d, J = 8.9 Hz), 7.00 (2 H, d, J = 7.0 Hz), 7.02 (2 H, d, J = 8.8 Hz), 7.24 (1 H, d, J = 1.1 Hz), 7.35 (1 H, dd, J = 8.9 Hz, 2.3 Hz), 7.36 (2 H, d, J = 8.8 Hz), 7.45 (2 H, d, J = 8.1 Hz), 7.67 (1 H, d, J = 3.3 Hz), 7.70 (2 H, d, J = 8.1 Hz). |

TABLE 210

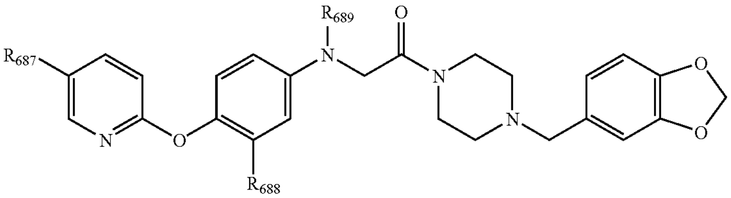

| Example No. | $R_{687}$ | $R_{688}$ | $R_{689}$ | $^1H$ NMR ($CDCl_3$) δ ppm |
|---|---|---|---|---|
| 801 | 4-$CF_3$PhCO— | —$CH_3$ | —$C_2H_5$ | 1.19 (3 H, t, J = 7.1 Hz), 2.11 (3 H, s), 2.42-2.45 (4 H, m), 3.39-3.53 (6 H, m), 3.63-3.66 (2 H, m), 4.04 (2 H, s), 5.95 (2 H, s), 6.50-6.54 (2 H, m), 6.71-6.77 (2 H, m), 6.85 (1 H, s), 6.90-6.95 (2 H, m), 7.75 (2 H, d, J = 8.2 Hz), 7.87 (2 H, d, J = 8.1 Hz), 8.17 (1 H, dd, J = 8.7 Hz, 2.5 Hz), 8.59 (1 H, d, J = 2.0 Hz). |
| 802 | 3,4-$Cl_2$PhNHCO— | —$OCH_3$ | —$C_2H_5$ | 1.19 (5 H, t, J = 7.1 Hz), 2.42 (4 H, brs), 3.42 (2 H, q, J = 7.1 Hz), 3.43 (2 H, s), 3.51 (2 H, s), 3.62 (2 H, brs), 3.68 (3 H, s), 4.04 (2 H, s), 5.95 (2 H, s), 6.17 (1 H, dd, J = 8.7 Hz, 2.6 Hz), 6.28 (1 H, d, J = 2.6 Hz), 6.73-6.74 (2 H, m), 6.85 (1 H, brs), 6.88 (1 H, d, J = 8.6 Hz), 6.90 (1 H, d, J = 8.7 Hz), 7.37 (1 H, d, J = 8.7 Hz), 7.47 (1 H, dd, J = 8.7 Hz, 2.5 Hz), 7.86 (1 H, d, J = 2.5 Hz), 8.11 (1 H, dd, J = 8.6 Hz, 2.5 Hz), 8.31 (1 H, brs), 8.58 (1 H, d, J = 2.3 Hz). |
| 803 | 4-$CF_3$PhNHCO— | —$OCH_3$ | —$C_2H_5$ | 1.19 (3 H, t, J = 7.1 Hz), 2.42 (4 H, brs), 3.38-3.47 (4 H, m), 3.51 (2 H, brs), 3.62 (2 H, brs), 3.68 (3 H, s), 4.05 (2 H, s), 5.94 (2 H, s), 6.17 (1 H, dd, J = 8.7 Hz, 2.8 Hz), 6.29 (1 H, d, J = 2.8 Hz), 6.73-6.74 (2 H, m), 6.84 (1 H, brs), 6.89 (1 H, d, J = 8.7 Hz), 6.91 (1 H, d, J = 8.7 Hz), 7.58 (2 H, d, J = 8.7 Hz), 7.76 (2 H, d, J = 8.7 Hz), 8.13 (1 H, dd, J = 8.7 Hz, 2.5 Hz), 8.44 (1 H, brs), 8.64 (1 H, d, J = 2.5 Hz). |
| 804 | 3,4-$Cl_2$PhNHCONH— | —$CONHCH_3$ | —$C_2H_5$ | 1.07 (3 H, t, J = 7.0 Hz), 2.30-2.45 (4 H, m), 2.85 (3 H, d, J = 4.9 Hz), 3.33 (2 H, q, J = 7.0 Hz), 3.38 (2 H, s), 3.38-3.50 (2 H, m), 3.50-3.65 (2 H, m), 4.01 (2 H, s), 5.95 (2 H, s), 6.55-6.65 (1 H, m), 6.69-6.84 (5 H, m), 7.14 (1 H, d, J = 3.1 Hz), 7.25-7.35 (2 H, m), 7.35-7.45 (1 H, m), 7.65 (1 H, d, J = 1.5 Hz), 7.72 (1 H, d, J = 2.6 Hz), 7.84 (1 H, dd, J = 8.9 Hz, 2.7 Hz), 8.02 (1 H, s), 8.61 (1 H, s). |
| 805 | 4-$CF_3$Ph$CH_2$— | —H | —$CH_3$ | 2.42 (4 H, t, J = 5.1 Hz), 3.02 (3 H, s), 3.43 (2 H, s), 3.48 (2 H, brs), 3.63 (2 H, brs), 3.95 (2 H, s), 4.06 (2 H, s), 5.94 (2 H, s), 6.70 (2 H, d, J = 9.0 Hz), 6.73 (2 H, s), 6.74 (1 H, d, J = 10.0 Hz), 6.84 (1 H, s), 7.00 (2 H, d, J = 9.0 Hz), 7.27 (2 H, d, J = 8.1 Hz), 7.38 (1 H, dd, J = 8.4 Hz, 2.5 Hz), 7.54 (2 H, d, J = 8.1 Hz), 8.03 (1 H, d, J = 2.5 Hz). |

TABLE 211

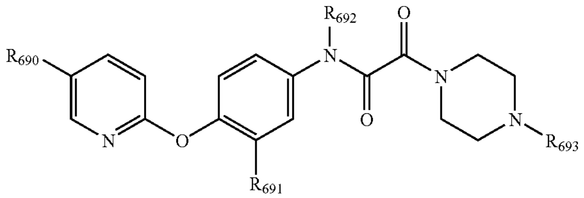

| Example No. | $R_{690}$ | $R_{691}$ | $R_{692}$ | $R_{693}$ | $^1$H NMR (solvent) δ ppm |
|---|---|---|---|---|---|
| 806 | 4-$CF_3$PhNHCO— | —$CH_3$ | —H | piperonyl | ($CDCl_3$) 2.17 (3 H, s), 2.49-2.54 (4 H, m), 3.45 (2 H, s), 3.71-3.75 (2 H, m), 4.26 (2 H, brs), 5.96 (2 H, s), 6.75 (2 H, brs), 6.86 (1 H, brs), 7.02 (1 H, d, J = 8.7 Hz), 7.06 (1 H, d, J = 8.7 Hz), 7.47 (1 H, dd, J = 8.7 Hz, 2.5 Hz), 7.58 (1 H, d, J = 2.3 Hz), 7.63 (2 H, d, J = 8.4 Hz), 7.75 (2 H, d, J = 8.3 Hz), 7.84 (1 H, brs), 8.22 (1 H, dd, J = 8.7 Hz, 2.6 Hz), 8.64 (1 H, d, J = 2.5 Hz), 9.20 (1 H, brs). |
| 807 | 4-$CF_3$PhO$CH_2$— | —H | —H | piperonyl | ($CDCl_3$) 2.51-2.54 (4 H, m), 3.45 (2 H, s), 3.71-3.75 (2 H, m), 4.27-4.29 (2 H, m), 5.05 (2 H, s), 5.95 (2 H, s), 6.85 (2 H, brs), 6.86 (1 H, brs), 6.96 (1 H, d, J = 8.4 Hz), 7.02 (2 H, d, J = 8.6 Hz), 7.14 (2 H, d, J = 8.9 Hz), 7.56 (2 H, d, J = 8.6 Hz), 7.64 (2 H, d, J = 8.9 Hz), 7.78 (1 H, dd, J = 8.4 Hz, 2.3 Hz), 8.22 (1 H, d, J = 2.3 Hz), 9.21 (1 H, brs). |
| 808 | 4-$CF_3$PhO$CH_2$— | —H | —H | 4-pyridylmethyl | ($CDCl_3$) 2.52-2.58 (4 H, m), 3.55 (2 H, s), 3.74-3.77 (2 H, m), 4.29-4.32 (2 H, m), 5.04 (2 H, s), 6.96 (1 H, d, J = 8.4 Hz), 7.02 (2 H, d, J = 8.4 Hz), 7.15 (2 H, d, J = 8.9 Hz), 7.26-7.30 (2 H, m), 7.56 (2 H, d, J = 8.6 Hz), 7.64 (2 H, d, J = 9.1 Hz), 7.78 (1 H, dd, J = 8.6 Hz, 2.5 Hz), 8.22 (1 H, d, J = 2.0 Hz), 8.56-8.58 (2 H, m), 9.24 (1 H, brs). |
| 809 | 4-$CF_3$PhO$CH_2$— | —$CH_3$ | —$CH_3$ | piperonyl | a mixture of the rotational isomers (DMSO-$d_6$) 2.07-2.43 (7 H, m), 3.24-3.57 (11 H, m), 5.17 (2 H, brs), 5.95-5.99 (2 H, m), 6.66-6.89 (3 H, m), 7.07-7.12 (2 H, m), 7.16-7.37 (4 H, m), 7.66 (2 H, d, J = 8.4 Hz), 7.85-8.00 (1 H, m), 8.22 (1 H, d, J = 2.0 Hz). |
| 810 | 4-$CF_3$PhO$CH_2$— | —$CH_3$ | —$CH_3$ | 3,4-$(CH_3O)_2$Ph$CH_2$— | a mixture of the rotational isomers (DMSO-$d_6$) 2.07-2.43 (7 H, m), 3.26-3.75 (15 H, m), 5.17 (2 H, brs), 6.70-6.91 (3 H, m), 7.07-7.12 (2 H, m), 7.16-7.37 (4 H, m), 7.66 (2 H, d, J = 8.9 Hz), 7.95-8.00 (1 H, m), 8.22 (1 H, d, J = 2.0 Hz). |

TABLE 212

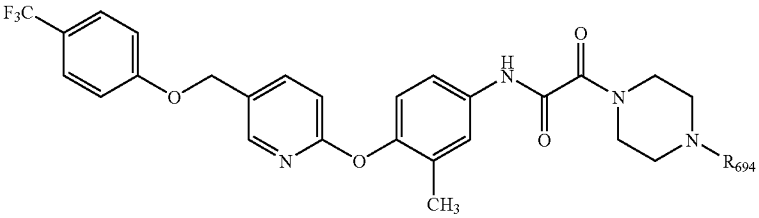

| Example No. | $R_{694}$ | $^1$H NMR ($CDCl_3$) δ ppm |
|---|---|---|
| 811 | piperonyl | 2.18 (3 H, s), 2.49-2.54 (4 H, m), 3.45 (2 H, s), 3.70-3.74 (2 H, m), 4.23-4.27 (2 H, m), 5.03 (2 H, s), 5.95 (2 H, s), 6.71 |

TABLE 212-continued

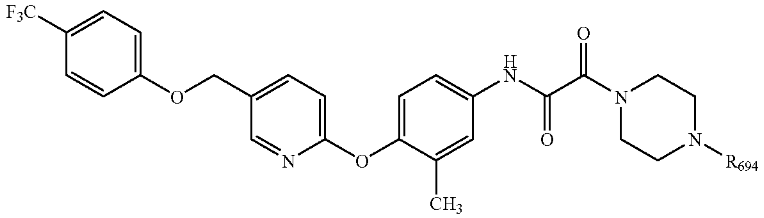

| Example No. | $R_{694}$ | $^1H$ NMR ($CDCl_3$) δ ppm |
|---|---|---|
| | | 6.78 (2 H, m), 6.86 (1 H, brs), 6.92 (1 H, d, J = 8.6 Hz), 7.00-7.06 (3 H, m), 7.44 (1 H, dd, J = 8.7 Hz, 2.6 Hz), 7.54-7.58 (3 H, m), 7.77 (1 H, dd, J = 8.6 Hz, 2.5 Hz), 8.20 (1 H, d, J = 2.3 Hz), 9.20 (1 H, brs). |
| 812 | 3,4- $(CH_3O)_2PhCH_2$— | 2.18 (3 H, s), 2.50-2.55 (4 H, m), 3.48 (2 H, s), 3.71-3.75 (2 H, m), 3.88 (3 H, s), 3.90 (3 H, s), 4.24-4.28 (2 H, m), 5.03 (2 H, s), 6.79-6.86 (2 H, m), 6.88 (1 H, brs), 6.93 (1 H, d, J = 8.4 Hz), 7.00-7.06 (3 H, m), 7.44 (1 H, dd, J = 8.6 Hz, 2.6 Hz), 7.54-7.58 (3 H, m), 7.77 (1 H, dd, J = 8.4 Hz, 2.5 Hz), 8.20 (1 H, d, J = 2.5 Hz), 9.19 (1 H, brs). |
| 813 | 4-pyridylmethyl | 2.18 (3 H, s), 2.52-2.58 (4 H, m), 3.55 (2 H, s), 3.73-3.77 (2 H, m), 4.27-4.31 (2 H, m), 5.03 (2 H, s), 6.93 (1 H, d, J = 8.4 Hz), 7.00-7.06 (3 H, m), 7.28 (2 H, d, J = 5.9 Hz), 7.44 (1 H, dd, J = 8.7 Hz, 2.6 Hz), 7.54-7.57 (3 H, m), 7.77 (1 H, dd, J = 8.4 Hz, 2.3 Hz), 8.19 (1 H, d, J = 2.1 Hz), 8.56 (2 H, d, J = 5.9 Hz), 9.23 (1 H, brs). |

TABLE 213

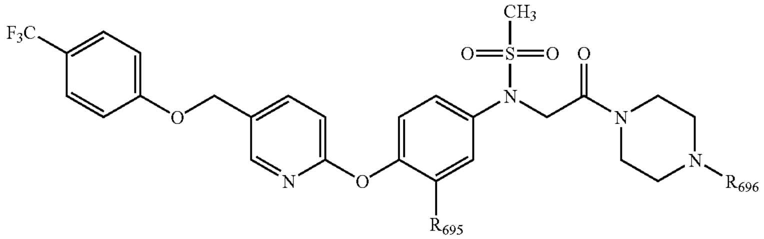

| Example No. | $R_{695}$ | $R_{696}$ | $^1H$ NMR ($CDCl_3$) δ ppm |
|---|---|---|---|
| 814 | —H | piperonyl | 2.42 (4 H, brs), 3.21 (3 H, s), 3.37 (2 H, brs), 3.42 (2 H, s), 3.62 (2 H, brs), 4.54 (2 H, s), 5.06 (2 H, s), 5.94 (2 H, s), 6.70-6.77 (2 H, m), 6.83 (1 H, brs), 6.98-7.04 (3 H, m), 7.14 (2 H, d, J = 8.7 Hz), 7.56 (2 H, d, J = 8.7 Hz), 7.62 (2 H, d, J = 8.9 Hz), 7.81 (1 H, dd, J = 8.4 Hz, 2.3 Hz), 8.23 (1 H, d, J = 2.1 Hz). |
| 815 | —H | 4-pyridylmethyl | 2.48 (4 H, brs), 3.21 (3 H, s), 3.41 (2 H, brs), 3.53 (2 H, s), 3.65 (2 H, brs), 4.55 (2 H, s), 5.06 (2 H, s), 7.01 (1 H, d, J = 8.2 Hz), 7.03 (2 H, d, J = 8.4 Hz), 7.14 (2 H, d, J = 8.9 Hz), 7.26-7.28 (2 H, m), 7.57 (2 H, d, J = 8.7 Hz), 7.62 (2 H, d, J = 8.7 Hz), 7.81 (1 H, dd, J = 8.4 Hz, 2.3 Hz), 8.23 (1 H, d, J = 2.1 Hz), 8.56 (2 H, d, J = 5.6 Hz). |
| 816 | —$CH_3$ | piperonyl | 2.18 (3 H, s), 2.41-2.44 (4 H, m), 3.22 (3 H, s), 3.36-3.39 (2 H, m), 3.43 (2 H, s), 3.60-3.64 (2 H, m), 4.54 (2 H, s), 5.05 (2 H, s), 5.94 (2 H, s), 6.73-6.74 (2 H, m), 6.84 (1 H, brs), 6.97 (1 H, d, J = 8. 4 Hz), 7.02 (1 H, d, J = 8.6 Hz), 7.04 (2 H, d, J = 8.6 Hz), 7.45 (1 H, dd, J = 8.6 Hz, 2.6 Hz), 7.49 (1 H, d, J = 2.5 Hz), 7.56 (2 H, d, J = 8.4 Hz), 7.80 (1 H, dd, J = 8.6 Hz, 2.5 Hz), 8.20 (1 H, d, J = 2.0 Hz). |
| 817 | —$CH_3$ | 3,4- $(CH_3O)_2PhCH_2$— | 2.18 (3 H, s), 2.44 (4 H, brs), 3.22 (3 H, s), 3.38-3.40 (2 H, m), 3.46 (2 H, s), 3.63-3.65 (2 H, m), 3.87 (3 H, s), 3.89 (3 H, s), 4.55 (2 H, s), 5.04 (2 H, s), 6.81 (2 H, brs), 6.87 (1 H, brs), 6.98 (1 H, d, J = 8.6 Hz), 7.02 (1 H, d, J = 8.4 Hz), 7.04 (2 H, d, J = 8.4 Hz), 7.45 (1 H, dd, J = 8.6 Hz, 2.6 Hz), 7.49 (1 H, d, J = 2.6 Hz), 7.56 (2 H, d, J = 8.4 Hz), 7.80 (1 H, dd, J = 8.4 Hz, 2.5 Hz), 8.20 (1 H, d, J = 2.3 Hz). |

TABLE 214
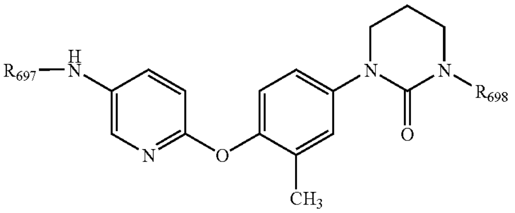
| Example No. | $R_{697}$ | $R_{698}$ | mp (° C.) |
|---|---|---|---|
| 818 | 4-$CF_3$PhCO— | 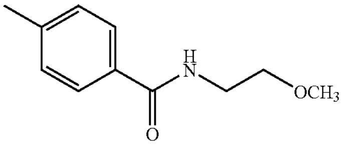 | 207.0-209.0 |
| 819 | 4-$CF_3$PhCO— | 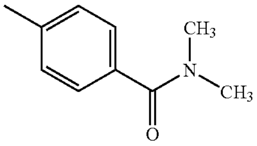 | 237.0-238.0 |
| 820 | 3,4-$Cl_2$Ph$SO_2$— | 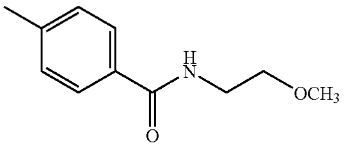 | 115.0-116.0 |
| 821 | 3,4-$Cl_2$PhNHCO— | —$CH_2$CONHPh | 147.0-148.0 |
| 822 | 3,4-$Cl_2$PhNHCO— | 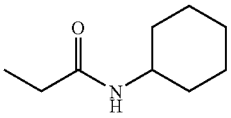 | 207.0-208.0 |
TABLE 215
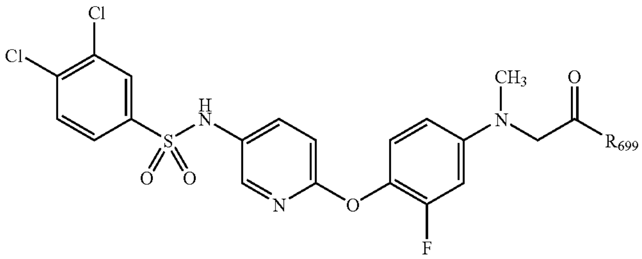
| Example No. | $R_{699}$ | $^1$H NMR or MS |
|---|---|---|
| 823 | 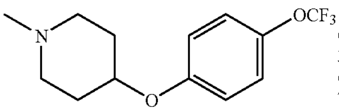 | $^1$H NMR (DMSO-$d_6$) δ 1.40-1.80 (2 H, m), 1.80-2.10 (2 H, m), 2.93 (3 H, s), 3.15-3.50 (2 H, m), 3.60-3.90 (2 H, 3 m), 4.31 (2 H, s), 4.60-4.70 (1 H, m), 6.35-6.45 (1 H, m), 6.54 (1 H, dd, J = 14.4 Hz, 2.6 Hz), 6.96-7.11 (4 H, m), 7.27-7.31 (2 H, m), 7.52 (1 H, dd, J = 8.7 Hz, 2.7 Hz), 7.63 (1 H, dd, J = 8.5 Hz, 2.1 Hz), 7.76 (1 H, d, J = 2.7 Hz), 7.84-7.88 (2 H, m), 10.39 (1 H, brs). |
| 824 | 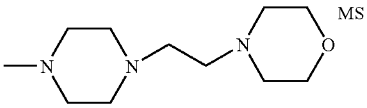 | MS 682 ($M^+$ + H) |

TABLE 215-continued
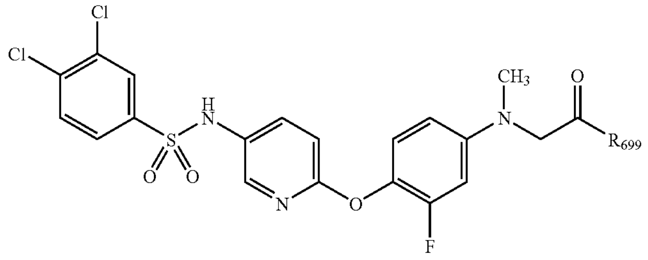
| Example No. | $R_{699}$ | $^1H$ NMR or MS |
| --- | --- | --- |
| 825 | 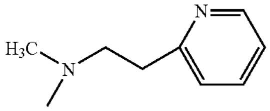 | MS 618 ($M^+$ + H) |
| 826 | $—N[CH_2CH(CH_3)_2]_2$ | MS 611 ($M^+$ + H) |
| 827 | 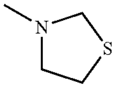 | MS 571 ($M^+$ + H) |
| 828 | 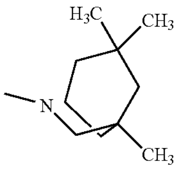 | MS 635 ($M^+$ + H) |
| 829 | $—N[(CH_2)_3N(CH_3)_2]_2$ | MS 669 ($M^+$ + H) |
| 830 | 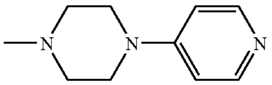 | MS 645 ($M^+$ + H) |
| 831 | 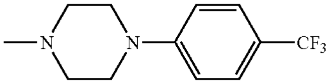 | MS 712 ($M^+$ + H) |
| 832 | 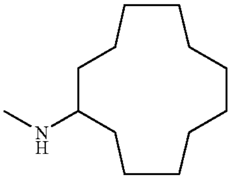 | MS 665 ($M^+$ + H) |
| 833 | 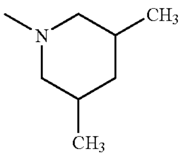 | MS 595 ($M^+$ + H) |
| 834 | 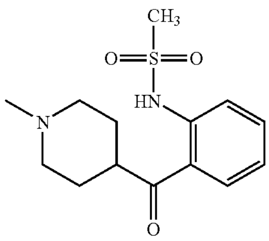 | MS 764 ($M^+$ + H) |

TABLE 216
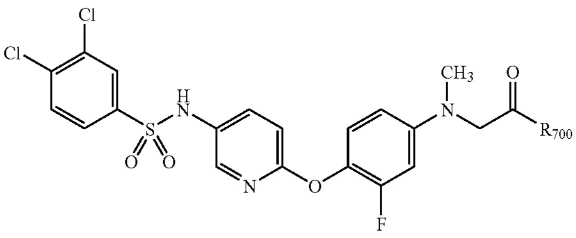
| Example No. | $R_{699}$ | MS ($M^+$ + H) |
|---|---|---|
| 835 | 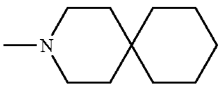 | 635 |
| 836 | 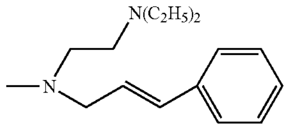 | 714 |
| 837 | 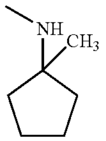 | 581 |
| 838 | 4-$CF_3OPhCH_2NH$— | 673 |
| 839 | 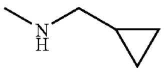 | 553 |
| 840 | —$NH(CH_2)_5OH$ | 585 |
| 841 | —$NHCH(CH_3)COOCH_3$ | 585 |
| 842 | 3,5-$F_2PhCH_2N(C_2H_5)$— | 653 |
| 843 | 4-$CH_3PhNHCOCH_2N(CH_3)$— | 660 |
| 844 | 3,4-$(CH_3O)_2PhCH_2N(C_2H_5)$— | 677 |
| 845 | 4-$CH_3PhCH_2N(C_2H_5)$— | 631 |
| 846 | 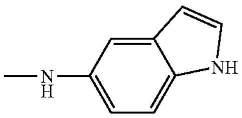 | 614 |
| 847 | 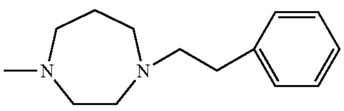 | 686 |
| 848 | 3,4-$Cl_2Ph$- | 714 |
| 849 | 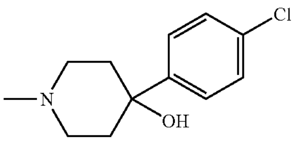 | 695 |
TABLE 216-continued
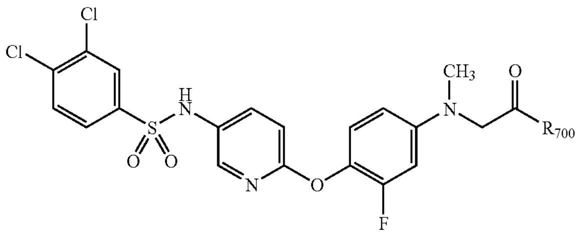
| Example No. | $R_{699}$ | MS ($M^+$ + H) |
|---|---|---|
| 850 | 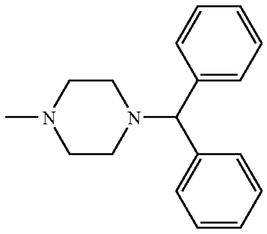 | 734 |
| 851 | —$N(CH_2Ph)CH_2CH_2CN$ | 642 |
| 852 | —$N(C_2H_5)CH(CH_3)_2$ | 569 |
| 853 | —$NHC(CH_3)_2CH_2Ph$ | 631 |
| 854 | 3-CNPhNH— | 600 |
| 855 | 3,5-$F_2PhNH$— | 611 |
TABLE 217
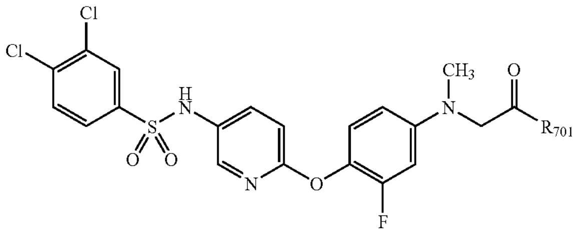
| Example No. | $R_{701}$ | MS ($M^+$ + H) |
|---|---|---|
| 856 | 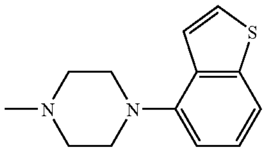 | 700 |
| 857 | 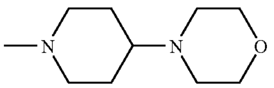 | 652 |
| 858 | 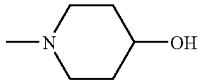 | 583 |
| 859 | 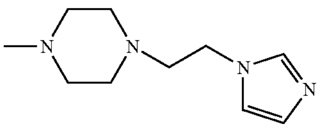 | 662 |

TABLE 217-continued
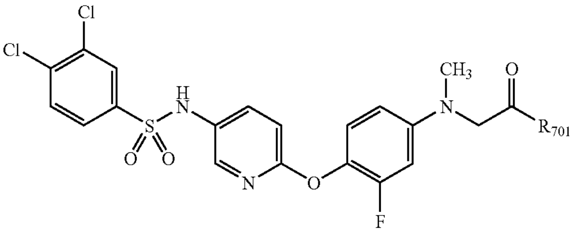
| Example No. | $R_{701}$ | MS ($M^+$ + H) |
|---|---|---|
| 860 | 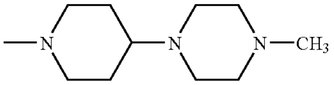 | 665 |
| 861 | 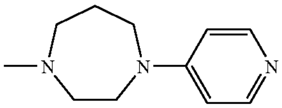 | 659 |
| 862 | 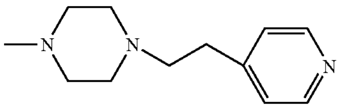 | 673 |
| 863 | 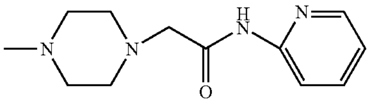 | 702 |
| 864 | 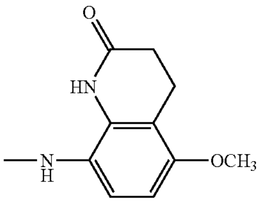 | 674 |
| 865 | 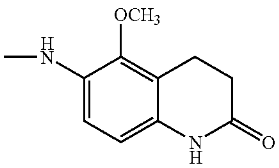 | 674 |
| 866 | 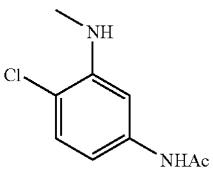 | 666 |
TABLE 218
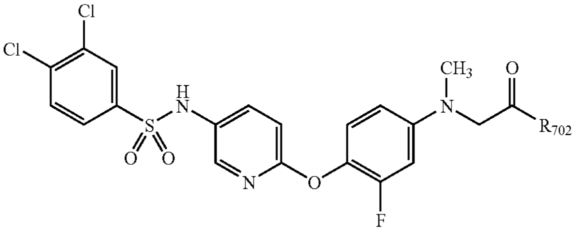
| Example No. | $R_{702}$ | MS ($M^+$ + H) |
|---|---|---|
| 867 | 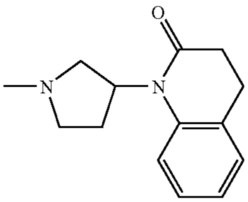 | 698 |
| 868 | 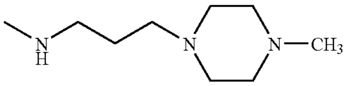 | 639 |
| 869 | 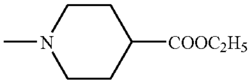 | 639 |
| 870 | 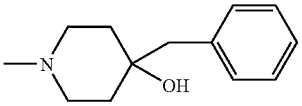 | 673 |
| 871 | 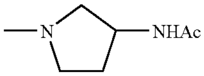 | 610 |
| 872 | 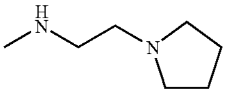 | 596 |
| 873 | 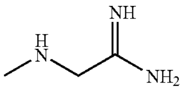 | 555 |
| 874 | 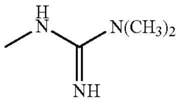 | 569 |
| 875 | 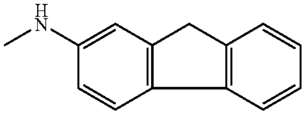 | 663 |
| 876 | 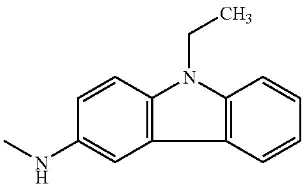 | 692 |

TABLE 219
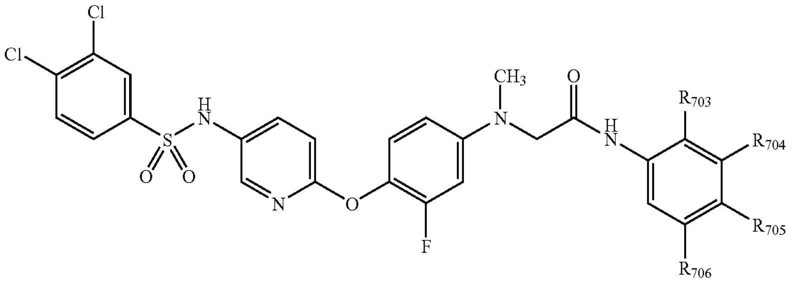
| Example No. | $R_{703}$ | $R_{704}$ | $R_{705}$ | $R_{706}$ | MS ($M^+ + H$) |
|---|---|---|---|---|---|
| 877 | —H | —H | $—OCF_3$ | —H | 659 |
| 878 | —H | —H | $—CH_3$ | —H | 589 |
| 879 | $—OCH_3$ | $—OCH_3$ | —H | —H | 635 |
| 880 | —H | —H | $—SCH_3$ | —H | 621 |
| 881 | $—CH(CH_3)_2$ | —H | —H | —H | 617 |
| 882 | —H | —H | cyclohexyl | —H | 657 |
| 883 | —NHPh | —H | —Cl | —H | 702 |
| 884 | 4-ClPhNH— | —H | —H | $—COOC_2H_5$ | 774 |
| 885 | —H | —H | $—O(CH_2)_2N(C_2H_5)_2$ | —H | 690 |
| 886 | —H | —H | 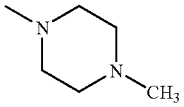 | —H | 673 |
| 887 | —H | —H | 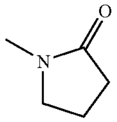 | —H | 658 |
| 888 | —H | —H | $—NHSO_2CH_3$ | —H | 668 |
| 889 | —H | —H | $—(CH_2)OH$ | —H | 619 |
| 890 | —H | —H | $—(CH_2)_4CH_3$ | —H | 645 |
| 891 | —H | —H | benzyl | —H | 665 |
| 892 | —H | —H | —SPh | —H | 683 |
| 893 | —H | —H | 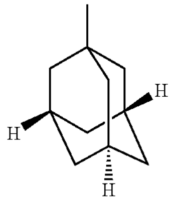 | —H | 709 |
TABLE 220
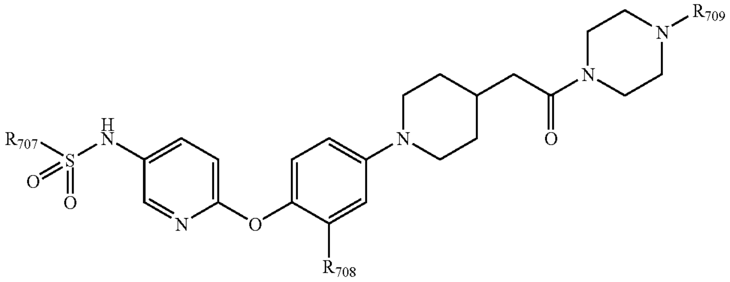
| Example No. | $R_{707}$ | $R_{708}$ | $R_{709}$ | $^1H$ NMR ($CDCl_3$) δ ppm |
|---|---|---|---|---|
| 894 | $4-CF_3Ph-$ | $—CH_3$ | piperonyl | 1.34-1.42 (2 H, m), 1.80-1.98 (3 H, m), 2.03 (3 H, s), 2.29 (2 H, d, J = 6.6 Hz), 2.41 (4 H, brs), |

TABLE 220-continued

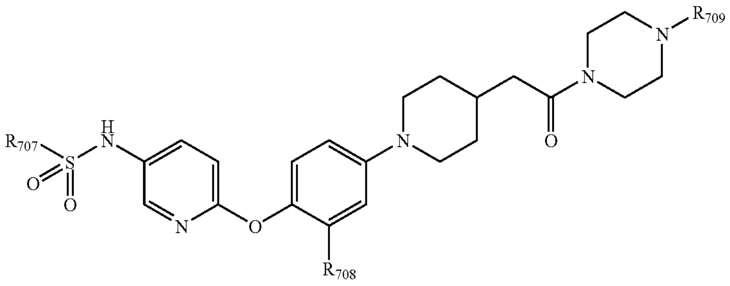

| Example No. | $R_{707}$ | $R_{708}$ | $R_{709}$ | $^1H$ NMR ($CDCl_3$) δ ppm |
|---|---|---|---|---|
| | | | | 2.65 (2 H, t, J = 12.0 Hz), 3.43 (2 H, s), 3.49-3.65 (6 H, m), 5.94 (2 H, s), 6.69-6.87 (8 H, m), 7.56 (1 H, dd, J = 8.9 Hz, 2.8 Hz), 7.68 (2 H, d, J = 8.6 Hz), 7.76-7.85 (3 H, m). |
| 895 | 3,4-$Cl_2$Ph- | —$CH_3$ | piperonyl | 1.34-1.39 (2 H, m), 1.79-1.98 (3 H, m), 2.04 (3 H, s), 2.29 (2 H, d, J = 6.6 Hz), 2.41 (4 H, brs), 2.64 (2 H, t, J = 11.9 Hz), 3.43 (2 H, s), 3.49-3.65 (6 H, m), 5.94 (2 H, s), 6.70-6.88 (7 H, m), 7.45-7.50 (3 H, m), 7.55 (1 H, dd, J = 8.9 Hz, 2.8 Hz), 7.78-7.82 (2 H, m). |
| 896 | 4-$CF_3$Ph- | —$CH_3$ | benzyl | 1.34-1.43 (2 H, m), 1.80-2.01 (3 H, m), 2.03 (3 H, s), 2.29 (2 H, d, J = 6.6 Hz), 2.43 (4 H, brs), 2.65 (2 H, t, J = 12.0 Hz), 3.49-3.65 (8 H, m), 6.70-6.76 (3 H, m), 6.86 (1 H, d, J = 8.7 Hz), 7.26-7.32 (6 H, m), 7.55 (1 H, dd, J = 8.7 Hz, 2.6 Hz), 7.68 (2 H, d, J = 8.6 Hz), 7.76 (1 H, d, J = 2.8 Hz), 7.84 (2 H, d, J = 8.4 Hz). |
| 897 | 3,4-$Cl_2$Ph- | —$CH_3$ | benzyl | 1.27-1.39 (2 H, m), 1.79-2.01 (3 H, m), 2.04 (3 H, s), 2.29 (2 H, d, J = 6.8 Hz), 2.43 (4 H, brs), 2.64 (2 H, t, J = 11.9 Hz), 3.53-3.66 (8 H, m), 6.69-6.76 (3 H, m), 6.86 (1 H, d, J = 8.7 Hz), 7.29-7.32 (6 H, m), 7.44-7.50 (2 H, m), 7.55 (1 H, dd, J = 8.7 Hz, 2.6 Hz), 7.79-7.82 (2 H, m). |
| 898 | 4-$CF_3$Ph- | —H | 3,4-$Cl_2$Ph- | 1.34-1.46 (2 H, m), 1.83-2.02 (3 H, m), 2.34 (2 H, d, J = 6.8 Hz), 2.67 (2 H, t, J = 12.0 Hz), 3.15-3.17 (4 H, m), 3.55-3.65 (4 H, m), 3.78-3.80 (2 H, m), 6.72-6.97 (7 H, m), 7.26-7.31 (2 H, m), 7.56 (1 H, dd, J = 8.9 Hz, 2.8 Hz), 7.70 (2 H, d, J = 8.24 Hz), 7.78-7.86 (3 H, m). |
| 899 | 4-$CF_3$Ph- | —H | 3,4-$CF_3$Ph- | 1.35-1.47 (2 H, m), 1.83-2.02 (3 H, m), 2.36 (2 H, d, J = 6.8 Hz), 2.67 (2 H, t, J = 12.0 Hz), 3.28-3.30 (4 H, m), 3.57 (2 H, d, J = 12.2 Hz), 3.68 (2 H, brs), 3.82 (2 H, brs), 6.76 (1 H, d, J = 8.7 Hz), 6.87-6.96 (7 H, m), 7.50 (2 H, d, J = 8.6 Hz), 7.56 (1 H, dd, J = 8.9 Hz, 2.8 Hz), 7.69 (2 H, d, J = 8.4 Hz), 7.80-7.86 (3 H, m). |
| 900 | 3,4-$Cl_2$Ph- | —H | 4-$CF_3$Ph- | 1.34-1.47 (2 H, m), 1.83-2.02 (3 H, m), 2.35 (2 H, d, J = 6.8 Hz), 2.68 (2 H, t, J = 12.0 Hz), 3.29-3.31 (4 H, m), 3.58 (2 H, d, J = 12.2 Hz), 3.68 (2 H, brs), 3.83 (2 H, brs), 6.79 (1 H, d, J = 8.7 Hz), 6.88-6.98 (7 H, m), 7.50-7.59 (5 H, m), 7.79 (1 H, d, J = 2.8 Hz), 7.83-7.84 (1 H, m). |

TABLE 221

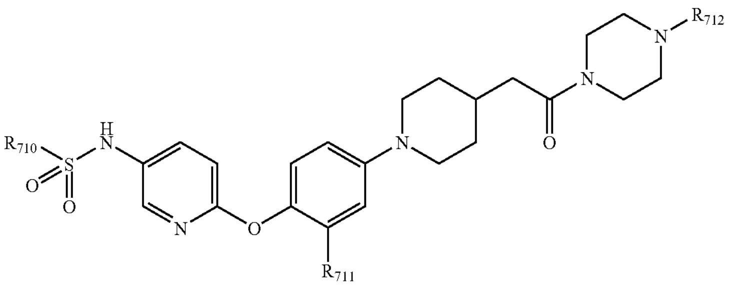

| Example No. | $R_{710}$ | $R_{711}$ | $R_{712}$ | $^1$H NMR ($CDCl_3$) δ ppm |
|---|---|---|---|---|
| 901 | 3,4-$Cl_2$Ph- | —H | 3,4-$Cl_2$Ph- | 1.34-1.46 (2 H, m), 1.82-2.02 (3 H, m), 2.35 (2 H, d, J = 6.6 Hz), 2.66 (2 H, t, J = 12.0 Hz), 3.16-3.17 (4 H, m), 3.57 (2 H, d, J = 12.2 Hz), 3.65 (2 H, brs), 3.80 (2 H, brs), 6.72-6.78 (2 H, m), 6.87-6.97 (6 H, m), 7.29 (1 H, d, J = 8.9 Hz), 7.49 (2 H, s), 7.57 (1 H, dd, J = 8.7 Hz, 2.6 Hz), 7.81-7.84 (2 H, m). |
| 902 | 4-$CF_3$Ph- | —$CH_3$ | 3,4-$Cl_2$Ph- | 1.34-1.46 (2 H, m), 1.82-2.01 (3 H, m), 2.03 (3 H, s), 2.35 (2 H, d, J = 6.8 Hz), 2.67 (2 H, t, J = 12.0 Hz), 3.15-3.17 (4 H, m), 3.58 (2 H, d, J = 12.2 Hz), 3.65 (2 H, brs), 3.79 (2 H, brs), 6.70-6.76 (4 H, m), 6.86 (1 H, d, J = 8.6 Hz), 6.96 (1 H, d, J = 2.8 Hz), 7.29 (1 H, d, J = 8.7 Hz), 7.53-7.57 (1 H, m), 7.68 (2 H, d, J = 8.2 Hz), 7.77 (1 H, d, J = 2.5 Hz), 7.84 (2 H, d, J = 8.2 Hz), 8.05 (1 H, s). |
| 903 | 4-$CF_3$Ph- | —H | piperonyl | 1.27-1.41 (2 H, m), 1.83-2.05 (3 H, m), 2.29 (2 H, d, J = 6.8 Hz), 2.40-2.44 (4 H, m), 2.66-2.75 (2 H, m), 3.44-3.56 (4 H, m), 3.65-3.74 (4 H, m), 5.95 (2 H, s), 6.75-6.99 (8 H, m), 7.57 (1 H, dd, J = 8.9 Hz, 2.8 Hz), 7.71-7.74 (4 H, m), 7.85 (2 H, d, J = = 8.2 Hz). |
| 904 | 3,4-$Cl_2$Ph- | —H | benzyl | 1.31-1.40 (2 H, m), 1.80-2.05 (3 H, m), 2.29 (2 H, d, J = 6.8 Hz), 2.62-2.71 (2 H, m), 3.53-3.58 (6 H, m), 3.66 (2 H, brs), 6.79 (1 H, d, J = 8.7 Hz), 6.88-6.98 (4 H, m), 7.31 (5 H, brs), 7.50 (2 H, s), 7.56 (1 H, dd, J = 8.9 Hz, 2.8 Hz), 7.77-7.84 (3 H, m). |
| 905 | 4-$CF_3$Ph- | —H | benzyl | 1.30-1.43 (2 H, m), 1.80-2.04 (3 H, m), 2.28 (2 H, d, J = 6.8 Hz), 2.42-2.46 (4 H, m), 2.62-2.70 (2 H, m), 3.47-3.58 (6 H, m), 3.66 (2 H, brs), 6.78 (1 H, d, J = 8.7 Hz), 6.87-6.97 (4 H, m), 7.26-7.32 (6 H, m), 7.56 (1 H, dd, J = 8.9 Hz, 2.8 Hz), 7.68-7.77 (3 H, m), 7.83-7.86 (2 H, m). |
| 906 | 3,4-$Cl_2$Ph- | —H | piperonyl | 1.33-1.39 (2 H, m), 1.79-2.00 (3 H, m) 2.30 (2 H, d, J = 6.8 Hz), 2.42-2.44 (4 H, m), 2.65 (2 H, t, J = 10.4 Hz), 3.43 (2 H, s), 3.49-3.57 (4 H, m), 3.65 (2 H, brs), 5.94 (2 H, s), 6.74-6.77 (3 H, m), 6.84-6.97 (5 H, m), 7.49-7.59 (3 H, m), 7.81-7.85 (3 H, m). |
| 907 | 4-$CF_3$Ph- | —$OCH_3$ | piperonyl | 1.33-1.44 (2 H, m), 1.82-1.95 (3 H, m), 2.29 (2 H, d), J = 6.8 Hz), 2.41 (4 H, brs), 2.70 (2 H, t, J = 12.2 Hz), 3.43-3.64 (8 H, m), 3.67 (3 H, s), 5.94 (2 H, s), 6.46 (1 H, dd, J = 8.7 Hz, 2.6 Hz), 6.54 (1 H, d, J = 2.5 Hz, 6.70-6.78 (4 H, m), 6.85 (1 H, s), 6.92 (1 H, d, J = 8.6 Hz), 7.55 (1 H, dd, J = 8.7 Hz, 2.6 Hz), 7.67 (2 H, d, J = 8.4 Hz), 7.74 (1 H, d, J = 2.6 Hz), 7.84 (2 H, d, J = 8.2 Hz). |

TABLE 222

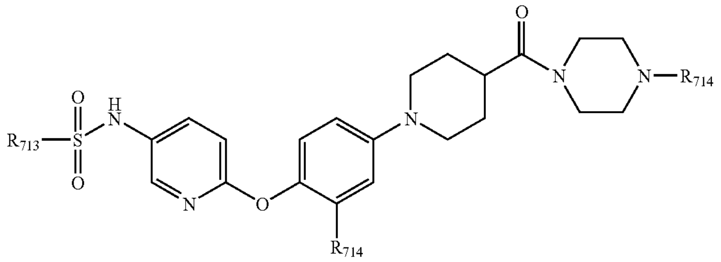

| Example No. | $R_{713}$ | $R_{714}$ | $R_{715}$ | $^1$H NMR ($CDCl_3$) δ ppm |
|---|---|---|---|---|
| 908 | 3,4-$Cl_2$Ph- | —H | benzyl | 1.76-1.99 (4 H, m), 2.45-2.73 (7 H, m), 3.53 (4 H, brs), 3.66 (4 H, brs), 6.75 (1 H, d, J = 8.7 Hz), 6.87-6.97 (4 H, m), 7.29-7.59 (9H, m), 7.83 (2 H, d, J = 2.0 Hz). |
| 909 | 4-$CF_3$Ph- | —H | benzyl | 1.77-1.99 (4 H, m), 2.45 (4 H, brs), 2.53-2.76 (3 H, m), 3.54 (4 H, brs), 3.65-3.69 (4 H, m), 6.81 (1 H, d, J = 8.7 Hz), 6.90-6.99 (4 H, m), 7.28-7.34 (6 H, m), 7.57 (1 H, dd, J = 8.9 Hz, 2.8 Hz), 7.71-7.75 (3 H, m), 7.85 (2 H, d, J = 8.2 Hz). |
| 910 | 4-$CF_3$Ph- | —$CH_3$ | piperonyl | 1.75-1.96 (4 H, m), 2.04 (3 H, s), 2.44 (4 H, brs), 2.53-2.73 (3 H, m), 3.43 (2 H, s), 3.53 (2 H, brs), 3.63 (4 H, brs), 5.94 (2 H, s), 6.70-6.89 (8 H, m), 7.56 (1 H, dd, J = 8.9 Hz, 2.8 Hz), 7.67 (2 H, d, J = 8.6 Hz), 7.78 (1 H, d, J = 2.6 Hz), 7.84 (2 H, d, J = 8.2 Hz). |
| 911 | 4-$CF_3$Ph- | —$CH_3$ | benzyl | 1.75-2.02 (4 H, m), 2.03 (3 H, s), 2.45 (4 H, brs), 2.55-2.72 (3 H, m), 3.53 (4 H, brs), 3.66 (4 H, brs), 6.72-6.77 (3 H, m), 6.87 (1 H, d, J = 8.6 Hz), 7.25-7.31 (6 H, m), 7.56 (1 H, dd, J = 8.7 Hz, 2.6 Hz), 7.66 (2 H, d, J = 8.2 Hz), 7.78-7.86 (3 H, m). |
| 912 | 3,4-$Cl_2$Ph- | —$CH_3$ | piperonyl | 1.76-1.98 (4 H, m), 2.04 (3 H, s), 2.44 (4 H, brs), 2.54-2.72 (3 H, m), 3.43 (2 H, s), 3.54 (2 H, brs), 3.63-3.67 (4 H, m), 5.94 (2 H, s), 6.70-6.89 (8 H, m), 7.44-7.59 (3 H, m), 7.80 (2 H, J = 2.0 Hz). |
| 913 | 3,4-$Cl_2$Ph- | —$CH_3$ | benzyl | 1.77-1.97 (4 H, m), 2.07 (3 H, s), 2.45 (4 H, brs), 2.53-2.75 (3 H, m), 3.54 (4 H, brs), 3.66 (4 H, brs), 6.75-6.81 (3 H, m), 6.90 (1 H, d, J = 8.6 Hz), 7.26-7.33 (6 H, m), 7.51-7.58 (3 H, m), 7.72 (1 H, d, J = 2.6 Hz), 7.79 (1 H, s). |
| 914 | 3,4-$Cl_2$Ph- | —H | piperonyl | 1.76-1.99 (4 H, m), 2.44 (4 H, brs), 2.54-2.74 (3 H, m), 3.43 (2 H, s), 3.54 (2 H, brs), 3.63-3.67 (4 H, m), 5.94 (2 H, s), 6.74-6.98 (8 H, m), 7.45-7.59 (3 H, m), 7.81-7.84 (3 H, m). |
| 915 | 4-$CF_3$Ph- | —H | piperonyl | 1.76-1.80 (2 H, m), 1.91-1.95 (2 H, m), 2.43 (4 H, brs), 2.59-2.73 (3 H, m), 3.43 (2 H, s), 3.54 (2 H, brs), 3.62 (4 H, brs), 5.94 (2 H, s), 6.72-6.75 (3 H, m), 6.84-6.96 (5 H, m), 7.57 (1 H, dd, J = 8.7 Hz, 2.8 Hz), 7.66 (2 H, d, J = 8.4 Hz), 7.82-7.87 (4 H, m). |

TABLE 223

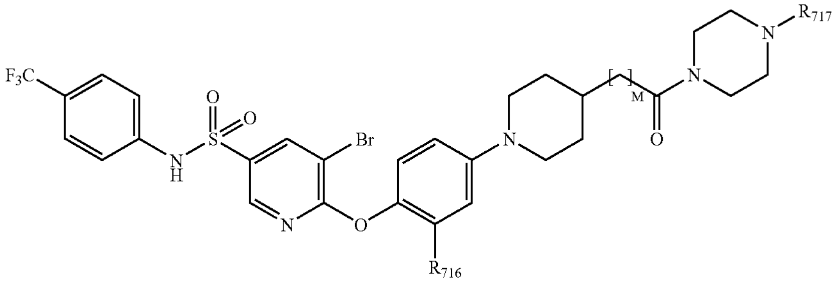

| Example No. | $R_{716}$ | $R_{717}$ | M | $^1$H NMR ($CDCl_3$) δ ppm |
|---|---|---|---|---|
| 916 | —H | piperonyl | 1 | 1.31-1.45 (2 H, m), 1.82-2.02 (3 H, m), 2.33 (2 H, d, J = 6.8 Hz), 2.43 (4 H, brs), 2.69 (2 H, t, J = 12.0 Hz), |

TABLE 223-continued

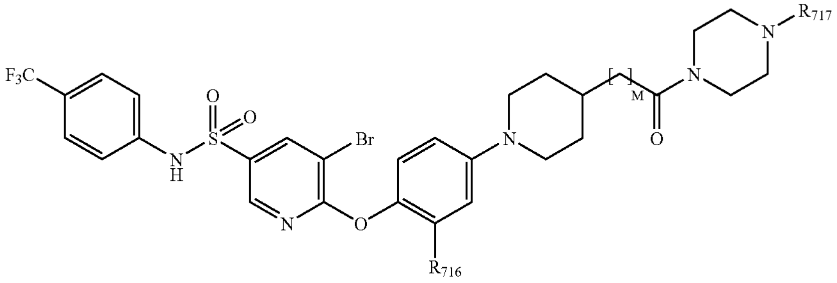

| Example No. | $R_{716}$ | $R_{717}$ | M | $^1H$ NMR ($CDCl_3$) δ ppm |
|---|---|---|---|---|
| | | | | 3.43 (2 H, s), 3.51-3.67 (6 H, m), 5.93 (2 H, s), 6.73-6.99 (8 H, m), 7.28 (2 H, d, J = 8.6 Hz), 7.50 (2 H, d, J = 8.6 Hz), 8.28 (1 H, d, J = 2.1 Hz), 8.43 (1 H, d, J = 2.1 Hz). |
| 917 | —H | benzyl | 1 | 1.34-1.44 (2 H, m), 1.82-2.00 (3 H, m), 2.32 (2 H, d, J = 6.8 Hz), 2.43-2.47 (4 H, m), 2.69 (2 H, t, J = 12.0 Hz), 3.51-3.67 (8 H, m), 6.88 (2 H, d, J = 9.2 Hz), 6.98 (2 H, d, J = 9.2 Hz), 7.25-7.32 (8 H, m), 7.50 (2 H, d, J = 8.6 Hz), 8.28 (1 H, d, J = 2.3 Hz), 8.43 (1 H, d, J = 2.1 Hz). |
| 918 | —$CH_3$ | piperonyl | 1 | 1.31-1.45 (2 H, m), 1.82-2.00 (3 H, m), 2.02 (3 H, s), 2.33 (2 H, d, J = 6.8 Hz), 2.43 (4 H, brs), 2.68 (2 H, t, J = 11.9 Hz), 3.41-3.67 (8 H, m), 5.92 (2 H, s), 6.73-6.92 (7 H, m), 7.25-7.30 (2 H, m), 7.50 (2 H, d, J = 8.6 Hz), 8.30 (1 H, d, J = 2.3 Hz), 8.41 (1 H, d, J = 2.3 Hz). |
| 919 | —$CH_3$ | benzyl | 1 | 1.37-1.40 (2 H, m), 1.83-2.01 (3 H, m), 2.03 (3 H, s), 2.31 (2 H, d, J = 6.9 Hz), 2.43-2.47 (4 H, m), 2.70 (2 H, t, J = 12.0 Hz), 3.51-3.67 (8 H, m), 6.74-6.80 (2 H, m), 6.91 (1 H, d, J = 8.6 Hz), 7.24-7.33 (8 H, m), 7.52 (2 H, d, J = 8.4 Hz), 8.29 (1 H, d, J = 2.1 Hz), 8.42 (1 H, d, J = 2.3 Hz). |
| 920 | —H | piperonyl | 0 | 1.79-2.03 (4 H, m), 2.45 (4 H, brs), 2.57-2.76 (3 H, m), 3.44 (2 H, s), 3.55 (2 H, brs), 3.66 (4 H, brs), 5.94 (2 H, s), 6.72-6.78 (2 H, m), 6.85-7.00 (6 H, m), 7.28 (2 H, d, J = 8.6 Hz), 7.50 (2 H, d, J = 8.6 Hz), 8.28 (1 H, d, J = 2.1 Hz), 8.42 (1 H, d, J = 2.1 Hz). |

TABLE 224

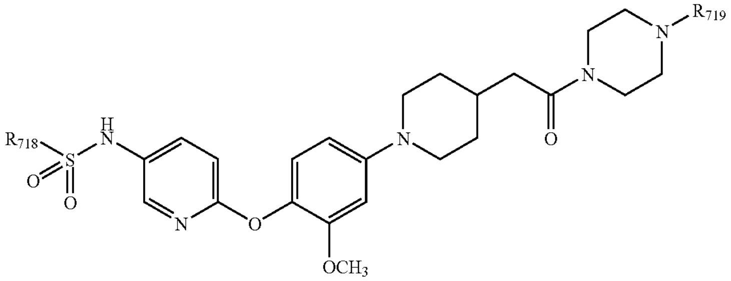

| Example No. | $R_{718}$ | $R_{719}$ | $^1H$ NMR ($CDCl_3$) δ ppm |
|---|---|---|---|
| 921 | 3,4-$Cl_2$Ph- | piperonyl | 1.37-1.44 (2 H, m), 1.81-2.02 (3 H, m), 2.30 (2 H, d, J = 6.8 Hz), 2.42 (4 H, brs), 2.69 (2 H, t, J = 11.9 Hz), 3.43 (2 H, s), 3.43-3.65 (6 H, m), 3.68 (3 H, s), 5.94 (2 H, s), 6.46 (1 H, dd, J = 8.7 Hz, 2.5 Hz), 6.54 (1 H, d, J = 2.3 Hz), 6.73-6.76 (3 H, m), 6.85 (1 H, s), 6.93 (1 H, d, J = 8.6 Hz), 7.44-7.57 (3 H, m), 7.79-7.83 (3 H, m). |
| 922 | 4-$CF_3$Ph- | benzyl | 1.37-1.44 (2 H, m), 1.81-2.02 (3 H, m), 2.29 (2 H, d, J = 6.8 Hz), 2.42-2.46 (4 H, m), 2.69 (2 H, t, J = 12.0 Hz), 3.48-3.63 (8 H, m), 3.67 (3 H, s), 6.46 (1 H, dd, J = 8.7 Hz, 2.6 Hz), 6.54 (1 H, d, J = 2.6 Hz), 6.75 (1 H, d, J = 8.9 Hz), 6.92 (1 H, d, J = 8.7 Hz), 7.26-7.36 (6 H, m), 7.54 (1 H, dd, J = 8.7 Hz, 2.8 Hz), 7.67 (2 H, d, J = 8.6 Hz), 7.75 (1 H, d, J = 2.8 Hz), 7.83 (2 H, d, J = 8.1 Hz). |

TABLE 224-continued

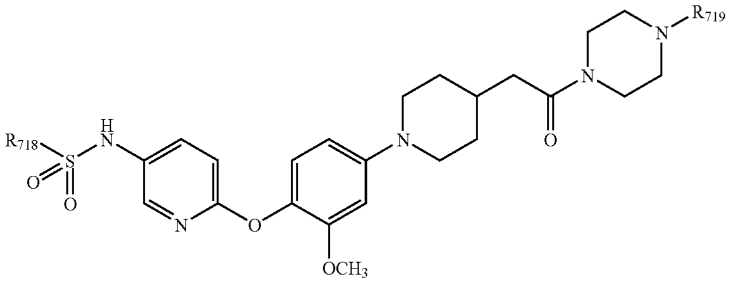

| Example No. | $R_{718}$ | $R_{719}$ | $^1$H NMR ($CDCl_3$) δ ppm |
|---|---|---|---|
| 923 | 3,4-$Cl_2$Ph- | benzyl | 1.37-1.44 (2 H, m), 1.81-2.02 (3 H, m), 2.30 (2 H, d, J = 6.8 Hz), 2.42-2.46 (4 H, m), 2.69 (2 H, t, J = 11.9 Hz), 3.50-3.66 (8 H, m), 3.67 (3 H, s), 6.45 (1 H, dd, J = 8.7 Hz, 2.5 Hz), 6.54 (1 H, d, J = 2.5 Hz), 6.74 (1 H, d, J = 8.7 Hz), 6.93 (1 H, d, J = 8.6 Hz), 7.26-7.32 (5 H, m), 7.43-7.56 (3 H, m), 7.79-7.83 (3 H, m). |

TABLE 225

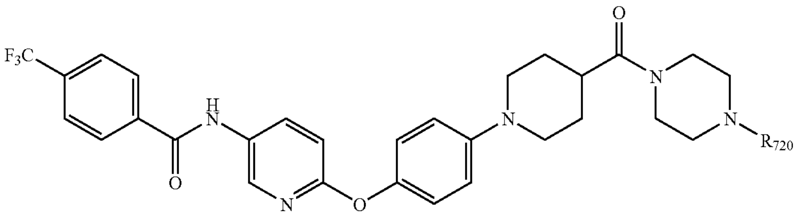

| Example No. | $R_{720}$ | $^1$H NMR ($CDCl_3$) δ ppm |
|---|---|---|
| 924 | benzyl | 1.63-1.77 (2 H, m), 1.81-1.98 (2 H, m), 2.44 (4 H, brs), 2.53-2.72 (3 H, m), 3.53 (4 H, brs), 3.65-3.69 (4 H, m), 6.90-7.04 (5 H, m), 7.26-7.33 (5 H, m), 7.74 (2 H, d, J = 8.2 Hz), 7.99 (2 H, d, J = 8.2 Hz), 8.14-8.19 (2 H, m), 8.27 (1 H, d, J = 2.6 Hz). |
| 925 | piperonyl | 1.64-1.77 (2 H, m), 1.89-1.97 (2 H, m), 2.39-2.41 (4 H, m), 2.56-2.75 (3 H, m), 3.43 (2 H, s), 3.52-3.69 (6 H, m), 5.94 (2 H, s), 6.70-6.77 (2 H, m), 6.85-7.04 (6 H, m), 7.74 (2 H, d, J = 8.2 Hz), 7.99 (2 H, d, J = 8.2 Hz), 8.14-8.18 (2 H, m), 8.27 (1 H, d, J = 2.5 Hz). |

The following compounds were made in the same manner as in Reference Example 918.

TABLE 226

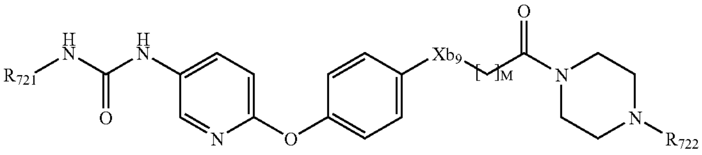

| Example No. | $R_{721}$ | $Xb_9$ | $R_{722}$ | M | $^1$H NMR ($CDCl_3$) δ ppm |
|---|---|---|---|---|---|
| 926 | 4-$CF_3$Ph- | $—CH_2—$ | benzyl | 1 | 2.38-2.44 (4 H, m), 2.63-2.68 (2 H, m), 2.89-2.95 (2 H, m), 3.45-3.49 (2 H, m), 3.52 (2 H, s), 3.64-3.68 (2 H, m), 6.85 (1 H, d, J = 8.9 Hz), 6.93-6.98 (2 H, m), 7.08-7.13 (2 H, m), 7.28-7.36 (5 H, m), 7.44-7.51 (4 H, m), 7.96 (1 H, d, J = 2.5 Hz), 8.00-8.04 (1 H, m), 8.14 (1 H, s), 8.18 (1 H, s). |
| 927 | 3,4-$Cl_2$Ph- | $—CH(CH_3)—$ | piperonyl | 0 | 1.47 (3 H, d, J = 6.8 Hz), 2.00-2.15 (1 H, m), 2.25-2.50 (3 H, m), 3.36 (2 H, s), 3.36-3.80 (4 H, m), 3.98 (1 H, q, J = 6.8 Hz), |

TABLE 226-continued

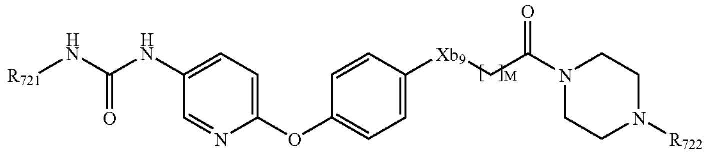

| Example No. | $R_{721}$ | $Xb_9$ | $R_{722}$ | M | $^1H$ NMR ($CDCl_3$) δ ppm |
|---|---|---|---|---|---|
| | | | | | 5.93 (2 H, s), 6.65-6.75 (2 H, m), 6.79 (1 H, d, J = 1.2 Hz), 6.89 (1 H, d, J = 8.8 Hz), 7.02-7.06 (2 H, m), 7.16-7.33 (4 H, m), 7.57 (1 H, d, J = 2.4 Hz), 7.91 (1 H, d, J = 2.7 Hz), 8.00 (1 H, brs), 8.05-8.10 (2 H, m). |
| 928 | 3,4-$Cl_2$Ph- | —$C(CH_3)_2$— | piperonyl | 0 | 1.55 (6 H, s), 1.80-2.15 (2 H, m), 2.20-2.55 (2 H, m), 2.95-3.20 (2 H, m), 3.31 (2 H, s), 3.50-3.90 (2 H, m), 5.91 (2 H, s), 6.60-6.72 (2 H, m), 6.76 (1 H, d, J = 1.3 Hz), 6.90 (1 H, d, J = 8.9 Hz), 7.07-7.33 (6 H, m), 7.58 (1 H, d, J = 2.4 Hz), 7.88 (1 H, d, J = 2.7 Hz), 8.09-8.11 (2 H, m), 8.17 (1 H, dd, J = 8.9 Hz, 2.8 Hz). |

TABLE 227

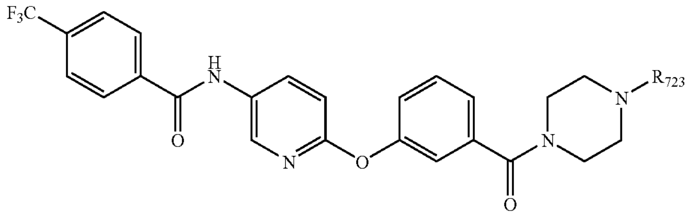

| Example No. | $R_{723}$ | $^1H$ NMR ($CDCl_3$) δ ppm |
|---|---|---|
| 929 | benzyl | 2.33-2.55 (4 H, m), 3.36-3.79 (6 H, m), 6.89 (1 H, d, J = 8.7 Hz), 7.07-7.15 (3 H, m), 7.24-7.38 (6 H, m), 7.67-7.70 (2 H, m), 8.00 (2 H, d, J = 7.9 Hz), 8.09-8.13 (1 H, m), 8.32 (1 H, d, J = 2.3 Hz), 9.05 (1 H, brs). |
| 930 | piperonyl | 2.36-2.44 (4 H, m), 3.37-3.76 (6 H, m), 5.93 (2 H, s), 6.69-6.75 (2 H, m), 6.83 (1 H, brs), 6.86 (1 H, d, J = 8.7 Hz), 7.04-7.06 (2 H, m), 7.10-7.14 (1 H, m), 7.27-7.36 (1 H, m), 7.65 (2 H, d, J = 8.4 Hz), 7.99 (2 H, d, J = 8.1 Hz), 8.07-8.12 (1 H, m), 8.34 (1 H, d, J = 2.6 Hz), 9.41 (1 H, s). |

TABLE 228

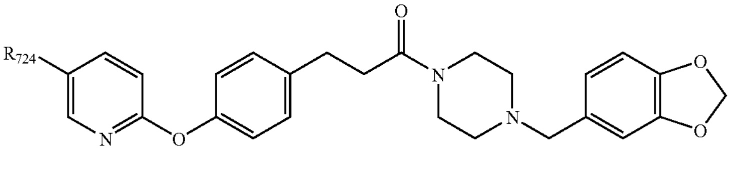

| Example No. | $R_{724}$ | $^1H$ NMR ($CDCl_3$) δ ppm |
|---|---|---|
| 931 | 4-$CF_3PhCH_2N(SO_2CH_3)$— | 2.31-2.41 (4 H, m), 2.58-2.64 (2 H, m), 2.94-2.97 (2 H, m), 2.99 (3 H, s), 3.38-3.41 (4 H, m), 3.60-3.65 (2 H, m), 4.85 (2 H, s), 5.94 (2 H, s), 6.65-6.75 (2 H, m), 6.83-6.87 (2 H, m), 6.95-7.05 (2 H, m), 7.20-7.30 (2 H, m), 7.38-7.41 (2 H, m), 7.52 (1 H, dd, J = 8.8 Hz, 2.8 Hz), 7.54-7.57 (2 H, m), 8.04 (1 H, d, J = 2.3 Hz). |
| 932 | 3,4-$Cl_2PhCH_2N(SO_2CH_3)$— | 2.25-2.45 (4 H, m), 2.59-2.65 (2 H, m), 2.94-3.05 (5 H, m), 3.30-3.45 (4 H, m), 3.55-3.70 (2 H, m), 4.74 (2 H, s), 5.95 (2 H, s), 6.65-6.80 (2 H, m), 6.84-6.89 (2 H, m), 7.02-7.15 (3 H, m), 7.23-7.30 (3 H, m), 7.30-7.40 (2 H, m), 8.03 (1 H, d, J = 2.7 Hz). |
| 933 | 3,4-$Cl_2PhCH_2NHCO$— | 2.25-2.45 (4 H, m), 2.59-2.65 (2 H, m), 2.94-3.00 (2 H, m), 3.37-3.41 (4 H, m), 3.59-3.65 (2 H, m), 4.58 (2 H, d, J =5.9 Hz), |

TABLE 228-continued

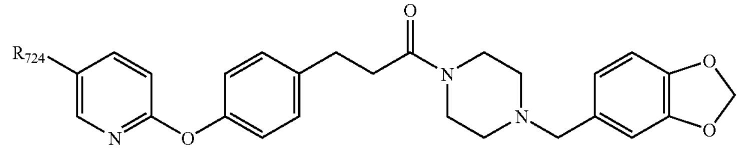

| Example No. | $R_{724}$ | $^1H$ NMR ($CDCl_3$) δ ppm |
|---|---|---|
| | | 5.94 (2 H, s), 6.50-6.65 (1 H, m), 6.65-6.80 (2 H, m), 6.84 (1 H, s), 6.94 (1 H, d, J = 8.6 Hz), 7.03-7.06 (2 H, m), 7.17 (1 H, dd, J = 8.2 Hz, 2.0 Hz), 7.22-7.26 (2 H, m), 7.38-7.42 (2 H, m), 8.14 (1 H, dd, J = 8.6 Hz, 2.5 Hz), 8.57 (1 H, d, J. 2.3 Hz). |
| 934 | 3,4-$Cl_2$PhNHCON($C_2H_5$)— | 1.17 (3 H, t, J = 7.1 Hz), 2.32-2.42 (4 H, m), 2.61-2.67 (2 H, m), 2.97-3.03 (2 H, m), 3.39-3.43 (4 H, m), 3.61-3.65 (2 H, m), 3.74 (2 H, q, J = 7.1 Hz), 5.94 (2 H, s), 6.00 (1 H, brs), 6.70-6.85 (3 H, m), 7.05 (1 H, d, J = 8.7 Hz), 7.09-7.13 (3 H, m), 7.26-7.31 (3 H, m), 7.52 (1 H, d, J = 2.5 Hz), 7.61 (1 H, dd, J = 8.7 Hz, 2.8 Hz), 8.12 (1 H, d, J = 2.4 Hz). |
| 935 | 3,4-$Cl_2$PhN($CH_3$)— | 2.25-2.45 (4 H, m), 2.59-2.65 (2 H, m), 2.95-3.00 (2 H, m), 3.25 (3 H, s), 3.38-3.42 (4 H, m), 3.61-3.65 (2 H, m), 5.94 (2 H, s), 6.55-6.65 (1 H, m), 6.65-6.80 (2 H, m), 6.80-6.85 (2 H, m), 6.89-6.93 (1 H, m), 7.06-7.10 (2 H, m), 7.20-7.27 (3 H, m), 7.45-7.50 (1 H, m), 8.01 (1 H, d, J = 2.4 Hz). |
| 936 | 3,4-$Cl_2$PhNH— | 2.31-2.41 (4 H, m), 2.59-2.65 (2 H, m), 2.94-3.00 (2 H, m), 3.37-3.41 (4 H, m), 3.61-3.65 (2 H, m), 5.61 (1 H, brs), 5.94 (2 H, s), 6.69-6.80 (3 H, m), 6.84 (1 H, s), 6.90 (1 H, d, J = 8.7 Hz), 6.96 (1 H, d, J = 2.7 Hz), 7.04-7.07 (2 H, m), 7.21-7.25 (3 H, m), 7.49 (1 H, dd, J = 8.7 Hz, 2.9 Hz), 8.00 (1 H, d, J = 2.8 Hz). |
| 937 | 4-$CF_3PhCH_2$NHCO— | 2.31-2.40 (4 H, m), 2.59-2.65 (2 H, m), 2.95-3.01 (2 H, m), 3.38-3.41 (4 H, m), 3.60-3.64 (2 H, m), 4.70 (2 H, d, J =5.8 Hz), 5.94 (2 H, s), 6.35-6.50 (1 H, m), 6.70-6.77 (2 H, m), 6.84 (1 H, s), 6.95 (1 H, d, J = 8.6 Hz), 7.03-7.07 (2 H, m), 7.23-7.26 (2 H, m), 7.44-7.47 (2 H, m), 7.59-7.62 (2 H, m), 8.14 (1 H, dd, J = 8.6 Hz, 2.5 Hz), 8.57 (1 H, d, J = 2.4 Hz). |
| 938 | 3,4-$Cl_2$PhN($C_2H_5$)CONH— | 1.17 (3 H, t, J = 7.1 Hz), 2.30-2.40 (4 H, m), 2.57-2.63 (2 H, m), 2.92-2.98 (2 H, m), 3.37-3.40 (4 H, m), 3.60-3.64 (2 H, m), 3.77 (2 H, q, J = 7.1 Hz), 5.94 (2 H, s), 6.65-6.80 (2 H, m), 6.81-6.85 (2 H, m), 6.98-7.00 (2 H, m), 7.17-7.21 (3 H, m), 7.45 (1 H, d, J = 2.4 Hz), 7.57 (1 H, d, J = 8.5 Hz), 7.85-7.91 (2 H, m). |

TABLE 229

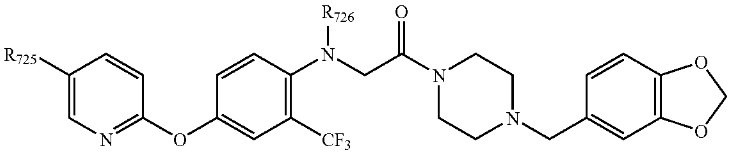

| Example No. | $R_{725}$ | $R_{726}$ | $^1H$ NMR ($CDCl_3$) δ ppm |
|---|---|---|---|
| 939 | 3,4-$Cl_2$PhNHCO— | —$CH_3$ | 2.30-2.50 (4 H, m), 2.78 (3 H, s), 3.42 (2 H, s), 3.50-3.65 (4 H, m), 3.82 (2 H, s), 5.95 (2 H, s), 6.65-6.75 (2 H, m), 6.85 (1 H, s), 7.05 (1 H, d, J = 8.6 Hz), 7.26-7.30 (1 H, m), 7.39-7.43 (2 H, m), 7.49-7.53 (2 H, m), 7.88 (1 H, d, J = 2.4 Hz), 8.24 (1 H, dd, J = 8.6 Hz, 2.5 Hz), 8.31 (1 H, brs), 8.66 (1 H, d, J = 2.4 Hz). |
| 940 | 4-$CF_3$PhNHCO— | —$CH_3$ | 2.30-2.45 (4 H, m), 2.78 (3 H, s), 3.41 (2 H, s), 3.55-3.59 (4 H, m), 3.82 (2 H, s), 5.94 (2 H, s), 6.65-6.80 (2 H, m), 6.85 (1 H, s), 7.05 (1 H, d, J = 8.6 Hz), 7.26-7.30 (1 H, m), 7.41 (1 H, d, J = 2.8 Hz), 7.51 (1 H; d, J = 8.8 Hz), 7.59-7.63 (2 H, m), 7.77-7.80 (2 H, m), 8.26 (1 H, dd, J = 8.6 Hz, 2.5 Hz), 8.54 (1 H, brs), 8.66 (1 H, d, J = 2.2 Hz). |
| 941 | 3,4-$Cl_2PhCH_2$NHCO— | —$CH_3$ | 2.30-2.45 (4 H, m), 2.80 (3 H, s), 3.42 (2 H, s), 3.50-3.65 (4 H, m), 3.81 (2 H, s), 4.59 (2 H, d, J = 5.9 Hz), 5.95 (2 H, s), 6.50-6.60 (1 H, m), 6.65- |

TABLE 229-continued

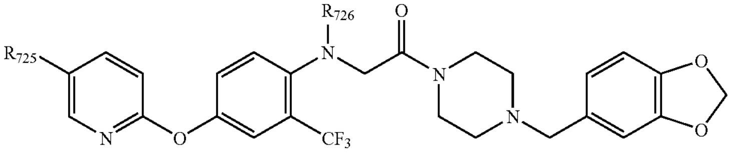

| Example No. | $R_{725}$ | $R_{726}$ | $^1H$ NMR ($CDCl_3$) δ ppm |
|---|---|---|---|
| | | | 6.80 (2 H, m), 6.85 (1 H, s), 7.01 (1 H, d, J = 8.6 Hz), 7.18 (1 H, dd, J = 8.2 Hz, 2.0 Hz), 7.30 (1 H, dd, J = 8.8 Hz, 2.7 Hz), 7.39-7.43 (3 H, m), 7.54 (1 H, d, J = 8.8 Hz), 8.18 (1 H, dd, J = 8.6 Hz, 2.5 Hz), 8.56 (1 H, d, J = 2.4 Hz). |
| 942 | 4-$CF_3PhCH_2NHCO$— | —$CH_3$ | 2.30-2.45 (4 H, m), 2.80 (3 H, s), 3.42 (2 H, s), 3.50-3.65 (4 H, m), 3.81 (2 H, s), 4.70 (2 H, d, J = 5.9 Hz), 5.94 (2 H, s), 6.50-6.65 (1 H, m), 6.70-6.80 (2 H, m), 6.85 (1 H, s), 7.00 (1 H, d, J = 8.6 Hz), 7.29 (1 H, dd, J = 8.8 Hz, 2.7 Hz), 7.39-7.62 (6 H, m), 8.18 (1 H, dd, J = 8.6 Hz, 2.5 Hz), 8.57 (1 H, d, J = 2.4 Hz). |
| 943 | 3,4-$Cl_2PhN(CH_3)$— | —$C_2H_5$ | 1.02 (3 H, t, J = 7.1 Hz), 2.35-2.40 (4 H, m), 3.22 (2 H, q, J = 7.1 Hz), 3.27 (3 H, s), 3.40 (2 H, s), 3.45-3.60 (4 H, m), 3.85 (2 H, s), 5.94 (2 H, s), 6.64 (1 H, dd, J = 8.9 Hz, 2.9 Hz), 6.65-6.75 (2 H, m), 6.84 (1 H, s), 6.90 (1 H, d, J = 2.8 Hz), 6.96 (1 H, d, J = 8.7 Hz), 7.22-7.26 (1 H, m), 7.26-7.35 (1 H, m), 7.42 (1 H, d, J = 2.8 Hz), 7.50 (1 H, dd, J = 8.7 Hz, 2.9 Hz), 7.66 (1 H, d, J = 8.8 Hz), 8.00 (1 H, d, J = 2.6 Hz). |

TABLE 230

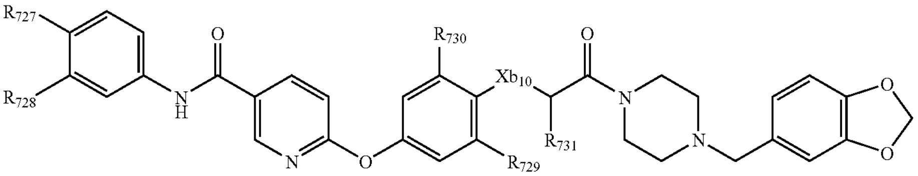

| Example No. | $R_{727}$ | $R_{728}$ | $R_{729}$ | $R_{730}$ | $R_{731}$ | $Xb_{10}$ | $^1H$ NMR ($CDCl_3$) δ ppm |
|---|---|---|---|---|---|---|---|
| 944 | —Cl | —Cl | —$CH_3$ | —$CH_3$ | —H | —$N(CH_3)$— | 2.30 (6 H, s), 2.32-2.45 (4 H, m), 2.83 (3 H, s), 3.30-3.45 (4 H, m), 3.55-3.70 (2 H, m), 3.83 (2 H, s), 5.94 (2 H, s), 6.69-6.76 (4 H, m), 6.83 (1 H, s), 6.96 (1 H, d, J = 8.6 Hz), 7.40 (1 H, d, J = 8.7 Hz), 7.50 (1 H, dd, J 8.8 Hz, 2.5 Hz), 7.87 (1 H, d, J = 2.4 Hz), 8.19 (1 H, dd, J = 8.6 Hz, 2.5 Hz), 8.3 1 (1 H, brs), 8.68 (1 H, d, J = 2.2 Hz). |
| 945 | —$CF_3$ | —H | —$CH_3$ | —$CH_3$ | —H | —$N(CH_3)$— | 2.30-2.45 (10 H, m), 2.86 (3 H, s), 3.30-3.45 (4 H, m), 3.55-3.70 (2 H, m), 3.84 (2 H, s), 5.94 (2 H, s), 6.65-6.78 (4 H, m), 6.84 (1 H, s), 6.99 (1 H, d, J = 8.6 Hz), 7.60-7.65 (2 H, m), 7.70-7.78 (2 H, m), 8.07 (1 H, brs), 8.21 (1 H, dd, J = 8.6 Hz, 2.6 Hz), 8.70 (1 H, d, J = 2.5 Hz). |
| 946 | —$CF_3$ | —H | —H | —H | —H | —$CH(CH_3)$— | 1.30-1.36 (3 H, m), 2.10-2.40 (4 H, m), 2.47-2.67 (2 H, m), 3.25-3.45 (5 H, m), 3.50-3.65 (2 H, m), 5.93 (2 H, s), 6.65-6.75 (2 H, m), 6.83 (1 H, d, J = 0.9 Hz), 7.01 (1 H, dd, J = 8.6 Hz, 0.6 Hz), 7.06-7.15 (2 H, m), 7.25-7.30 (2 H, m), 7.60-7.64 (2 H, m), 7.74-7.78 (2 H, m), 8.14 (1 H, brs), 8.22 (1 H, dd, J = 8.6 Hz, 2.6 Hz), 8.67-8.68 (1 H, m). |
| 947 | —$CF_3$ | —H | —H | —H | —$CH_3$ | —$CH_2$— | 1.14-1.17 (3 H, m), 1.95-2.10 (1 H, m), 2.15-2.45 (3 H, m), 2.55-2.70 (1 H, m), 3.45-3.70 (2 H, m), 5.92-5.94 (2 H, m), |

TABLE 230-continued

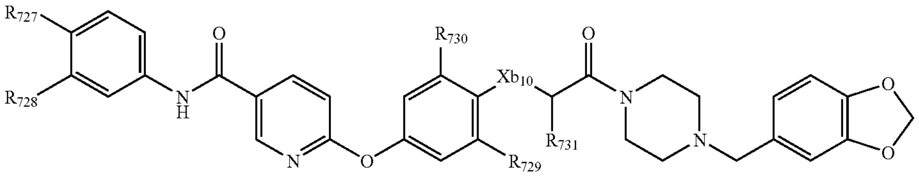

| Example No. | $R_{727}$ | $R_{728}$ | $R_{729}$ | $R_{730}$ | $R_{731}$ | $Xb_{10}$ | $^1H$ NMR ($CDCl_3$) δ ppm |
|---|---|---|---|---|---|---|---|
| | | | | | | | 6.65-6.85 (3 H, m), 6.95-7.06 (3 H, m), 7.10-7.30 (2 H, m), 7.59-7.63 (2 H, m), 7.75-7.79 (2 H, m), 8.24 (1 H, dd, J = 8.6 Hz, 2.6 Hz), 8.40 (1 H, brs), 8.71 (1 H, d, J = 2.4 Hz). |

TABLE 231

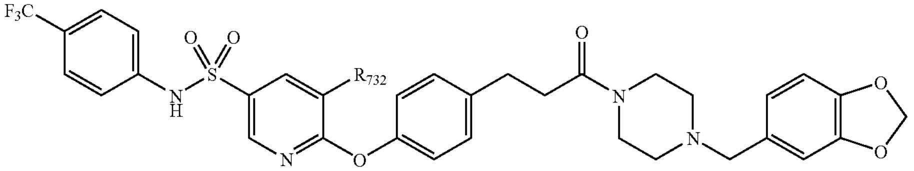

| Example No. | $R_{732}$ | $^1H$ NMR (DMSO-$d_6$) δ ppm |
|---|---|---|
| 948 | —Br | 2.20-2.35 (4 H, m), 2.59-2.65 (2 H, m), 2.79-2.85 (2 H, m), 3.20-3.60 (6 H, m), 5.99 (2 H, s), 6.73-6.77 (1 H, m), 6.83-6.86 (2 H, m), 7.07-7.10 (2 H, m), 7.27-7.34 (4 H, m), 7.62-7.65 (2 H, m), 8.44-8.48 (2 H, m), 10.90 (1 H, brs). |
| 949 | —H | 2.20-2.35 (4 H, m), 2.59-2.65 (2 H, m), 2.78-2.84 (2 H, m), 3.38-3.44 (6 H, m), 5.98 (2 H, s), 6.72-6.76 (1 H, m), 6.82-6.86 (2 H, m), 7.04-7.08 (2 H, m), 7.17 (1 H, d, J = 8.8 Hz), 7.26-7.33 (4 H, m), 7.61-7.65 (2 H, m), 8.17 (1 H, dd, J = 8.7 Hz, 2.6 Hz), 8.55 (1 H, d, J = 2.6 Hz), 10.98 (1 H, brs). |

Example 950

Production of 3,4-dichloro-N-{6-[4-(4-phenethylpiperazine-1-carbonyl)phenoxy]pyridin-3-yl}benzamide To a solution of ethyl 4-(5-aminopyridin-2-yloxy)benzoate (690 mg, 2.7 mmol) in THF (10 mL) were added triethylamine (0.73 mL, 5.3 mmol) and 3,4-dichlorobenzoyl chloride (570 mg, 2.7 mmol) under ice cooling, and the resulting solution was stirred for 1 hour under ice cooling. This reaction solution was concentrated under reduced pressure, and to the residue was added ethyl acetate. The resulting solution was washed with water, 1 N hydrochloric acid and brine, and then dried over anhydrous magnesium sulfate. The solvent was evaporated, and the residue was washed, when hot, with n-hexane:dichloromethane=1:2. The product was dissolved in THF (20 mL). To the residue was added 1 N aqueous sodium hydroxide (2.9 mL, 2.9 mmol), and this solution was stirred for 5 hours at 100° C. THF was evaporated, and the aqueous layer was made to have a pH of 3 with 1 N hydrochloric acid. Precipitated matter was collected by filtration, and dried. The resulting product was dissolved in bMF (10 mL), and 1-phenethylpiperazine (200 mg, 1.1 mmol), 1-ethyl-3-(3-dimethylaminopropyl)carbodiimide hydrochloride (240 mg, 1.3 mmol) and 1-hydroxybenzotriazole monohydrate (170 mg, 1.3 mmol) were added to the solution. The resulting solution was stirred for 1 day at room temperature. This reaction solution was concentrated under reduced pressure, and to the residue was added chloroform. The resulting solution was washed with water, and then dried over anhydrous magnesium sulfate. The solvent was evaporated, and the residue was purified by silica gel column chromatography (methanol:chloroform=1:99), to thereby yield 310 mg of the title compound.

Appearance: White Powder $^1H$ NMR ($CDCl_3$) δ 2.54 (4H, brs), 2.62-2.68 (2H, m), 2.79-2.85 (2H, m), 3.60-3.73 (4H, m), 6.95 (1H, d, J=8.9 Hz), 7.09-7.23 (5H, m), 7.27-7.33 (2H, m), 7.37-7.41 (2H, m), 7.55 (1H, d, J=8.3 Hz), 7.74-7.78 (1H, m), 8.04 (1H, d, J=2.0 Hz), 8.11-8.15 (1H, m), 8.31 (1H, d, J=2.6 Hz), 8.57 (1H, brs).

The following compounds were produced in the same manner as in Example 950.

TABLE 232

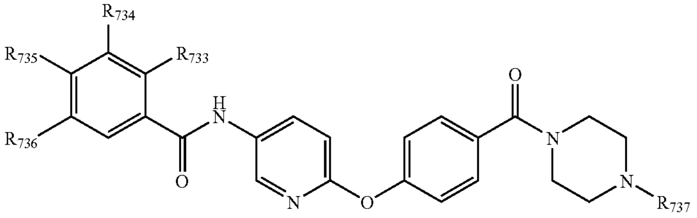

| Example No. | $R_{733}$ | $R_{734}$ | $R_{735}$ | $R_{736}$ | $R_{737}$ | MS ($M^+ + H$) |
|---|---|---|---|---|---|---|
| 951 | $-CH_3$ | —F | —H | —H | 4-CNPhCH$_2$— | 550 |
| 952 | —H | —F | —F | —H | 4-CNPhCH$_2$— | 554 |
| 953 | —H | —Cl | —H | —Cl | 4-CNPhCH$_2$— | 586 |
| 954 | —H | $-OCF_3$ | —H | —H | 4-CNPhCH$_2$— | 602 |
| 955 | $-CH_3$ | —F | —H | —H | 2-pyridylmethyl | 526 |
| 956 | —H | $-CH_3$ | $-CH_3$ | —H | 2-pyridylmethyl | 522 |
| 957 | —H | —F | —F | —H | 2-pyridylmethyl | 530 |
| 958 | —H | —Cl | —H | —Cl | 2-pyridylmethyl | 530 |
| 959 | —H | $-CF_3$ | —H | —H | 2-pyridylmethyl | 562 |
| 960 | —H | —H | —Cl | —H | 2-pyridylmethyl | 528 |
| 961 | —H | $-CF_3$ | —H | —F | 2-pyridylmethyl | 580 |
| 962 | —H | $-OCF_3$ | —H | —H | 2-pyridylmethyl | 578 |
| 963 | $-CH_3$ | —F | —H | —H | 3-pyridylmethyl | 526 |
| 964 | —H | $-CH_3$ | $-CH_3$ | —H | 3-pyridylmethyl | 522 |
| 965 | —H | —F | —F | —H | 3-pyridylmethyl | 530 |
| 966 | —H | —Cl | —H | —Cl | 3-pyridylmethyl | 562 |
| 967 | —H | $-CF_3$ | —H | —H | 3-pyridylmethyl | 562 |
| 968 | —H | —H | —Cl | —H | 3-pyridylmethyl | 528 |
| 969 | —H | $-CF_3$ | —H | —F | 3-pyridylmethyl | 580 |
| 970 | $-CH_3$ | —F | —H | —H | 4-pyridylmethyl | 526 |
| 971 | —H | $-CH_3$ | $-CH_3$ | —H | 4-pyridylmethyl | 522 |
| 972 | —H | —F | —F | —H | 4-pyridylmethyl | 530 |
| 973 | —H | —Cl | —H | —Cl | 4-pyridylmethyl | 562 |
| 974 | —H | $-CF_3$ | —H | —H | 4-pyridylmethyl | 562 |
| 975 | —H | —H | —Cl | —H | 4-pyridylmethyl | 528 |
| 976 | —H | $-CF_3$ | —H | —F | 4-pyridylmethyl | 580 |
| 977 | —H | $-OCF_3$ | —H | —H | 4-pyridylmethyl | 578 |
| 978 | $-CH_3$ | —F | —H | —H | piperonyl | 569 |
| 979 | —H | $-CH_3$ | $-CH_3$ | —H | piperonyl | 565 |
| 980 | —H | —F | —F | —H | piperonyl | 573 |
| 981 | —H | —Cl | —H | —Cl | piperonyl | 605 |
| 982 | —H | $-CF_3$ | —H | —H | piperonyl | 605 |
| 983 | —H | $-CF_3$ | —H | —F | piperonyl | 623 |

TABLE 233

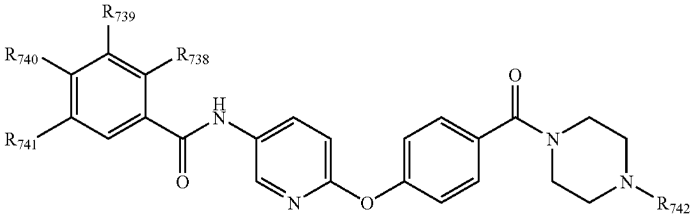

| Example No. | $R_{738}$ | $R_{739}$ | $R_{740}$ | $R_{741}$ | $R_{742}$ | MS ($M^+ + H$) |
|---|---|---|---|---|---|---|
| 984 | —H | $-OCF_3$ | —H | —H | piperonyl | 621 |
| 985 | —H | $-CH_3$ | $-CH_3$ | —H | benzyl | 521 |
| 986 | —H | —F | —F | —H | benzyl | 529 |
| 987 | $-CH_3$ | —F | —H | —H | 4-AcNHPhCH$_2$— | 582 |
| 988 | —H | $-CH_3$ | $-CH_3$ | —H | 4-ACNHPhCH$_2$— | 578 |
| 989 | —H | —F | —F | —H | 4-AcNHPhCH$_2$— | 586 |
| 990 | —H | —Cl | —H | —Cl | 4-AcNHPhCH$_2$— | 618 |
| 991 | —H | $-CF_3$ | —H | —H | 4-AcNHPhCH$_2$— | 618 |
| 992 | —H | —H | —Cl | —H | 4-AcNHPhCH$_2$— | 584 |
| 993 | —H | $-CF_3$ | —H | —F | 4-AcNHPhCH$_2$— | 636 |
| 994 | —H | $-OCF_3$ | —H | —H | 4-AcNHPhCH$_2$— | 634 |
| 995 | $-CH_3$ | —F | —H | —H | 2,3-$(CH_3)_2$PhCH$_2$— | 553 |
| 996 | —H | $-CH_3$ | $-CH_3$ | —H | 2,3-$(CH_3)_2$PhCH$_2$— | 549 |

TABLE 233-continued

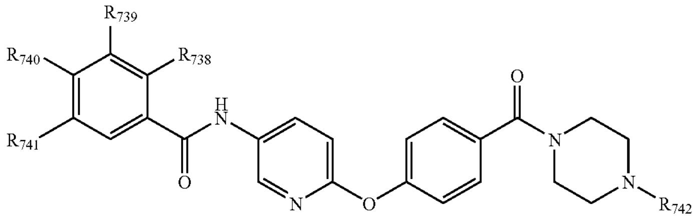

| Example No. | $R_{738}$ | $R_{739}$ | $R_{740}$ | $R_{741}$ | $R_{742}$ | MS ($M^+$ + H) |
|---|---|---|---|---|---|---|
| 997 | —H | —F | —F | —H | 2,3-$(CH_3)_2PhCH_2$— | 557 |
| 998 | —H | —Cl | —H | —Cl | 2,3-$(CH_3)_2PhCH_2$— | 589 |
| 999 | —H | —$CF_3$ | —H | —H | 2,3-$(CH_3)_2PhCH_2$— | 589 |
| 1000 | —H | —H | —Cl | —H | 2,3-$(CH_3)_2PhCH_2$— | 555 |
| 1001 | —H | —$CF_3$ | —H | —F | 2,3-$(CH_3)_2PhCH_2$— | 607 |
| 1002 | —H | —$OCF_3$ | —H | —H | 2,3-$(CH_3)_2PhCH_2$— | 605 |
| 1003 | —$CH_3$ | —F | —H | —H | 3-furylmethyl | 515 |
| 1004 | —H | —$CH_3$ | —$CH_3$ | —H | 3-furylmethyl | 511 |
| 1005 | —H | —F | —F | —H | 3-furylmethyl | 519 |
| 1006 | —H | —Cl | —H | —Cl | 3-furylmethyl | 551 |
| 1007 | —H | —$CF_3$ | —H | —H | 3-furylmethyl | 551 |
| 1008 | —H | —H | —Cl | —H | 3-furylmethyl | 517 |
| 1009 | —H | —Cl | —Cl | —H | 3-furylmethyl | 551 |
| 1010 | —H | —$CF_3$ | —H | —F | 3-furylmethyl | 569 |
| 1011 | —H | —$OCF_3$ | —H | —H | 3-furylmethyl | 567 |
| 1012 | —$CH_3$ | —F | —H | —H | 3-pyridyl | 512 |
| 1013 | —H | —$CH_3$ | —$CH_3$ | —H | 3-pyridyl | 508 |
| 1014 | —H | —F | —F | —H | 3-pyridyl | 516 |
| 1015 | —H | —Cl | —H | —Cl | 3-pyridyl | 548 |
| 1016 | —H | —$CF_3$ | —H | —H | 3-pyridyl | 548 |
| 1017 | —H | —$CF_3$ | —H | —F | 3-pyridyl | 566 |
| 1018 | —H | —$OCF_3$ | —H | —H | 3-pyridyl | 564 |

TABLE 234

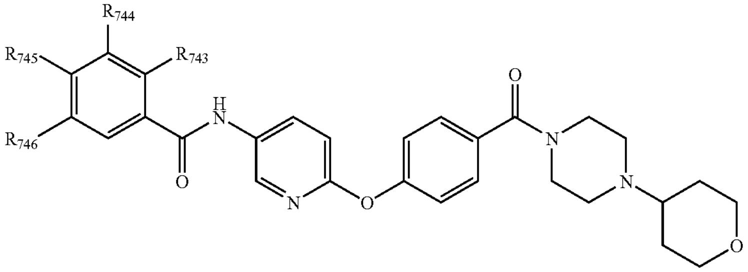

| Example No. | $R_{743}$ | $R_{744}$ | $R_{745}$ | $R_{746}$ | MS ($M^+$ + H) |
|---|---|---|---|---|---|
| 1019 | —$CH_3$ | —F | —H | —H | 519 |
| 1020 | —H | —$CH_3$ | —$CH_3$ | —H | 515 |
| 1021 | —H | —F | —F | —H | 523 |
| 1022 | —H | —Cl | —H | —Cl | 555 |
| 1023 | —H | —$CF_3$ | —H | —H | 555 |
| 1024 | —H | —H | —Cl | —H | 521 |
| 1025 | —H | —Cl | —Cl | —H | 555 |
| 1026 | —H | —$CF_3$ | —H | —F | 573 |
| 1027 | —H | —$OCF_3$ | —H | —H | 571 |

TABLE 235

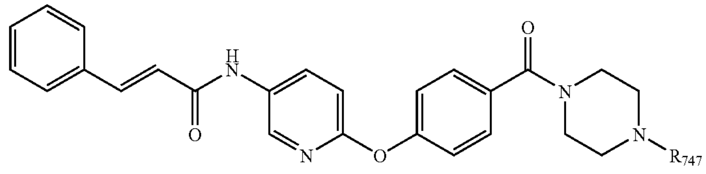

| Example No. | $R_{747}$ | MS ($M^+$ + H) |
|---|---|---|
| 1028 | 4-CNPh$CH_2$— | 544 |
| 1029 | 2-pyridylmethyl | 520 |
| 1030 | 3-pyridylmethyl | 520 |
| 1031 | 4-pyridylmethyl | 520 |
| 1032 | 4-AcNHPh$CH_2$— | 576 |
| 1033 | 2,3-$(CH_3)_2$Ph$CH_2$— | 547 |
| 1034 | 3-furylmethyl | 509 |
| 1035 | 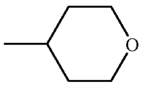 | 513 |

Example 1036

Production of 2-{3-methyl-4-[5-(4-trifluoromethyl-benzoyl)pyridin-2-yloxy]phenylamino}-1-(4-piperonylpiperazin-1-yl)ethanone To a solution of 2-chloro-5-(4-trifluoromethylbenzoyl)pyridine (1.00 g, 3.5 mmol) in DMF (30 mL) were added N-(4-hydroxy-3-methylphenyl)glycine ethyl ester (0.81 g, 3.9 mmol), cesium carbonate (1.71 g, 5.2 mmol) and copper (I) iodide (200 mg, 1.05 mmol), and the resulting solution was stirred for 3.5 hours at 60° C. under an argon atmosphere. The resulting reaction solution was filtered and concentrated. To the residue was added water and extracted with ethyl acetate. The ethyl acetate layer was washed with water and then dried over anhydrous magnesium sulfate. The solvent was evaporated, and the residue was purified by silica gel column chromatography (n-hexane:ethyl acetate=3:1), to thereby yield 1.20 g of a yellow oil. The yellow oil was dissolved in THF (23 mL), and to the solution was added 1 M aqueous sodium hydroxide (3.9 mL, 3.9 mmol). The resulting solution was stirred for 3 hours at room temperature. This reaction solution was cooled with ice, and made to have a pH of 1 with 6 M hydrochloric acid. The resulting solution was extracted with ethyl acetate, and the ethyl acetate layer was washed with water and then dried over anhydrous magnesium sulfate. The solvent was evaporated under reduced pressure, to thereby yield 1.04 g of a yellow oil. This yellow oil was dissolved in DMF (20 mL), and to the resulting solution were added 1-piperonylpiperazine (530 mg, 2.4 mmol), 1-ethyl-3-(3-dimethylaminopropyl)carbodiimide hydrochloride (560 mg, 2.9 mmol) and 1-hydroxybenzotriazole monohydrate (390 mg, 2.6 mmol), and the resulting solution was stirred for 15 hours at room temperature. The reaction solution was concentrated under reduced pressure, and to the residue was added water, and extracted with ethyl acetate. The ethyl acetate layer was washed with water, dried over anhydrous magnesium sulfate, evaporated, and the residue was purified by silica gel column chromatography (n-hexane:ethyl acetate=1:2→ethyl acetate), to thereby yield 280 mg of a yellow oil. To this oil was added diethyl ether and left to stand. Precipitated matter, was collected by filtration, to thereby yield 220 mg of the title compound.

Appearance: Yellow powder $^1$H NMR ($CDCl_3$) δ 2.11 (3H, s), 2.43-2.48 (4H, m), 3.45-3.48 (4H, m), 3.67-3.71 (2H, m), 3.86 (2H, d, J=4.1 Hz), 4.90 (1H, t, J=4.1 Hz), 5.96 (2H, s), 6.49-6.53 (2H, m), 6.71-6.78 (2H, m), 6.86-6.97 (3H, m), 7.75 (2H, d, J=8.1 Hz), 7.87 (2H, d, J=8.1 Hz), 8.18 (1H, dd, J=8.7 Hz, 2.5 Hz), 8.58 (1H, d, J=2.1 Hz).

The following compound was produced in the same manner as in Example 1036.

Example 1037

6-(4-{[2-(4-Piperonylpiperazin-1-yl)-2-oxoethyl]methylamino}-2,5-difluorophenoxy)-N-(4-trifluoromethylphenyl)nicotinamide hydrobromide Melting point: 224.5-226.0° C.

Example 1038

Production of N-(6-{2-methyl-4-[methyl-(2-oxo-2-piperazin-1-ylethyl)amino]phenoxy}pyridin-3-yl)-3,4-dichlorobenzamide To a solution of methyl{4-[5-(3,4-dichlorobenzoylamino)-pyridin-2-yloxy]-3-methylphenyl}aminoacetic acid (1.59 g, 3.5 mmol) in DMF (60 mL) were added 1-ethyl-3-(3-dimethylaminopropyl)carbodiimide hydrochloride (0.79 g, 4.1 mmol), 1-hydroxybenzotriazole monohydrate (0.63 g, 4.1 mmol), and 1-t-butyloxycarbonylpiperazine (0.68 g, 3.6 mmol). The resulting solution was stirred for 15 hours at room temperature under a nitrogen atmosphere. Water was added to the solution, and extracted with ethyl acetate. The ethyl acetate layer was washed with a saturated sodium bicarbonate solution and then the ethyl acetate layer was dried over anhydrous magnesium sulfate. The solvent was evaporated, and the residue was purified by silica gel column chromatography (n-hexane:ethyl acetate=2:1→3:2), to thereby yield an amide product. This amide product was dissolved in THF (20 mL). To the solution was then added 10% hydrochloric acid (10 mL), and the resulting solution was stirred for 14 hours at room temperature. To this reaction solution was added a saturated sodium bicarbonate solution to make the solution neutral, and extracted with ethyl acetate. The ethyl acetate layer was dried over anhydrous magnesium sulfate, evaporated, and the residue was purified by silica gel column chromatography (dichloromethane:methanol=50:1→20:1), to thereby yield 0.38 g of the title compound.

Appearance: Colorless amorphous powder $^1$H NMR ($CDCl_3$) δ 2.10 (3H, s), 2.75-2.94 (4H, m), 2.99 (3H, s), 3.40-3.70 (4H, m), 4.08 (2H, s), 6.46-6.59 (2H, m), 6.79 (1H, d, J=8.9 Hz), 6.89 (1H, d, J=8.6 Hz), 7.55 (1H, d, J=8.4 Hz), 7.71 (1H, dd, J=8.4 Hz, 2.1 Hz), 7.98 (1H, d, J=2.1 Hz), 8.03-8.14 (2H, m), 8.23 (1H, d, J=2.6 Hz).

Example 1039

Production of N-(6-{4-[3-(4-piperonylpiperazin-1-yl)-3-oxopropyl]phenoxy}pyridin-3-yl)-4-trifluoromethylbenzamide To a solution of 3-[4-(5-aminopyridin-2-yloxy)phenyl]-1-(4-piperonylpiperazin-1-yl)propan-1-one trihydrochloride (200 mg, 0.35 mmol) in THF (4 mL) were added triethylamine (0.243 mL, 1.8 mmol) and 4-trifluoromethylbenzoyl chloride (0.055 mL, 0.37 mmol), and the resulting solution was stirred for 1 hour at room temperature. Water was added to the residue, and extracted with ethyl acetate. The ethyl acetate layer was washed with water and brine, dried over anhydrous magnesium sulfate, evaporated, and the residue was recrystallized from diethyl ether, to thereby yield 170 mg of the title compound.

Appearance: White powder

Melting point: 140-141° C.

$^1$H NMR ($CDCl_3$) δ 2.32-2.40 (4H, m), 2.59-2.65 (2H, m), 2.93-2.99 (2H, m), 3.41 (4H, brs), 3.60-3.64 (2H, m), 5.94 (2H, s), 6.71-6.77 (2H, m), 6.85 (1H, s), 6.96 (1H, d, J=8.9 Hz), 7.05 (2H, d, J=8.4 Hz), 7.22 (2H, d, J=8.4 Hz), 7.76 (2H, d, J=8.4 Hz), 8.01 (2H, d, J=8.4 Hz), 8.11-8.14 (1H, m), 8.23 (1H, dd, J=8.9 Hz, 2.7 Hz), 8.28 (1H, d, J=2.7 Hz).

A crude titled product (77.4 g) obtained using the same procedures was recrystallized from ethyl acetate (400 mL), to thereby yield 49.66 g of the title compound.

Appearance: White powder; Melting point: 142-144° C.

The following compounds were produced in the same manner as in Example 1039.

TABLE 236

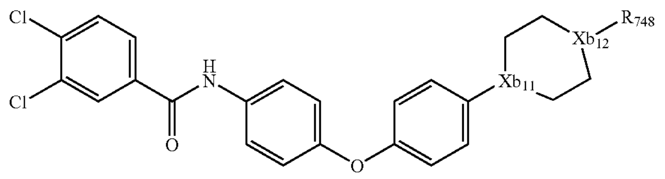

| Example No. | $Xb_{11}$ | $Xb_{12}$ | $R_{748}$ | mp (° C.) or $^1$H NMR |
|---|---|---|---|---|
| 1040 | 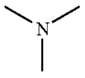 | 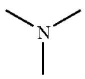 | —$COOC(CH_3)_3$ | mp 197-199 |
| 1041 | 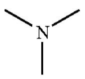 | 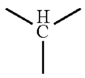 | —$OCH_2OCH_3$ | mp 152-154 |
| 1042 | 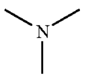 | 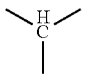 | —$COOC_2H_5$ | mp 189-190 |
| 1043 | 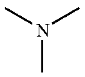 | 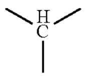 | —$N(CH_3)COOC(CH_3)_3$ | mp 146-147 |
| 1044 | 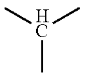 | 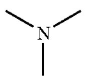 | —$COOC(CH_3)_3$ | mp 192-193 |
| 1045 | 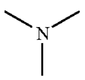 | 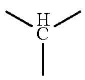 | —$OCH_2COOC_2H_5$ | $^1$H NMR ($CDCl_3$) δ 1.30 (3 H, t, J = 7.0 Hz), 1.75-1.81 (2 H, m), 2.03 (2 H, brs), 2.85-2.90 (2 H, m), 3.45-3.49 (2 H, m), 3.56 (1 H, m), 4.15 (2 H, s), 4.23 (2 H, q, J = 7.0 Hz), 6.90-6.95 (6 H, m), 7.50-7.53 (3 H, m), 7.69 (1 H, dd, J = 8.5 Hz, 2.0 Hz), 7.95 (1 H, d, J = 2.0 Hz), 8.04 (1 H, brs). |

TABLE 237

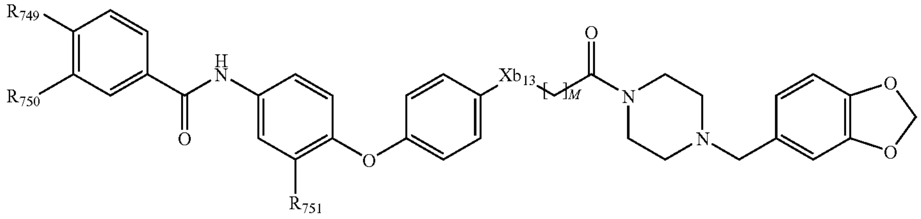

| Example No. | $R_{749}$ | $R_{750}$ | $R_{751}$ | $Xb_{13}$ | M | Form | mp (° C.) or $^1$H NMR |
|---|---|---|---|---|---|---|---|
| 1046 | —Cl | —Cl | —F | —N(Ac)— | 1 | free | $^1$H NMR (DMSO-$d_6$) δ 1.78 (3 H, s), 2.22-2.38 (4 H, m), 3.30-3.50 (6 H, m), 4.41 (2 H, s), 5.98 (2 H, s), 6.74 (1 H, d, J = 8.1 Hz), 6.80-6.86 (2 H, m), 6.98 (2 H, d, J = 8.8 Hz), 7.29 (1 H, t, J = 9.2 Hz), 7.38 (2 H, d, J = 8.8 Hz), 7.58 (1 H, d, J = 9.2 Hz), 7.84 (1 H, d, J 8.4 Hz), 7.90-7.96 (2 H, m), 8.21 (1 H, d, J = 1.8 Hz), 10.61 (1 H, s). |
| 1047 | —Cl | —Cl | —F | —NH— | 0 | free | mp 224-228 |
| 1048 | —Cl | —Cl | —F | —NH— | 1 | dihydrochloride | mp 174-178 |
| 1049 | —$CF_3$ | —H | —H | —N($CH_3$)— | 1 | free | $^1$H NMR (ODC$l_3$) δ 2.45 (4 H, brs), 3.03 (3 H, s), 3.46 (2 H, s), 3.52 (2 H, brs), 3.64 (2 H, brs), 4.08 (2 H, s), 5.95 (2 H, s), 6.67 (2 H, d, J = 9.1 Hz), 6.74-6.78 (2 H, m), 6.87 (1 H, s), 6.92-6.97 (4 H, m), 7.52 (2 H, d, J = 8.9 Hz), 7.74-7.81 (3 H, m), 7.98 (2 H, d, J = 8.2 Hz). |
| 1050 | —Cl | —Cl | —H | —N($CH_3$)— | 1 | free | $^1$H NMR ($CDCl_3$) δ 2.49 (4 H, brs), 3.02 (3 H, s), 3.50 (2 H, s), 3.55 (2 H, brs), 3.66 (2 H, brs), 4.08 (2 H, s), 5.96 (2 H, s), 6.67 (2 H, d, J = 9.1 Hz), 6.74-6.78 (2 H, m), 6.88-6.96 (5 H, m), 7.50 (2 H, d, J = 8.9 Hz), 7.56 (1 H, d, J = 8.4 Hz), 7.70 (1 H, dd, J = 8.4 Hz, 2.1 Hz), 7.83 (1 H, s), 7.97 (1 H, d, J = 2.1 Hz). |
| 1051 | —Cl | —Cl | —F | —O— | 1 | hydrochloride | $^1$H NMR (DMSO-$d_6$) δ 2.83-2.95 (1 H, m), 2.97-3.12 (2 H, m), 3.23-3.56 (3 H, m), 3.95-4.06 (1 H, m), 4.18-4.29 (2 H, m), 4.33-4.44 (1 H, m), 4.75-4.92 (2 H, m), 6.07 (2 H, s), 6.90-6.96 (4 H, m), 6.97-7.04 (2 H, m), 7.11 (1 H, t, J = 9.1 Hz), 7.15-7.22 (1 H, m), 7.52 (1 H, d, J = 9.1 Hz), 7.84 (1 H, d, J = 8.4 Hz), 7.88 (1 H, d, J = 13.3 Hz), 7.94 (1 H, dd, J = 8.4 Hz, 1.9 Hz), 8.23 (1 H, d, J = 1.9 Hz), 10.60 (1 H, s), 11.10 (1 H, brs). |

TABLE 238

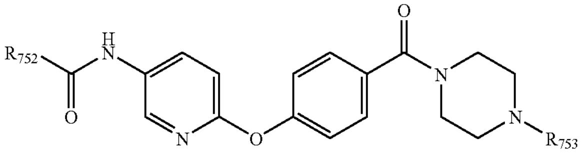

| Example No. | $R_{752}$ | $R_{753}$ | mp (° C.) or $^1$H NMR ($CDCl_3$) δ ppm |
|---|---|---|---|
| 1052 | 4-ClPh- | benzyl | mp 187-190 |
| 1053 | 3-ClPh- | benzyl | $^1$H NMR 2.38 (4 H, brs), 3.34-3.71 (6 H, m), 6.86 (1 H, d, J = 8.8 Hz), 7.00-7.05 (2 H, m), 7.19-7.36 (8 H, m), |

TABLE 238-continued

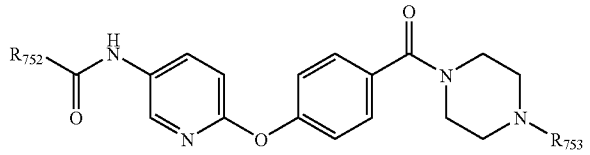

| Example No. | $R_{752}$ | $R_{753}$ | mp (° C.) or $^1$H NMR ($CDCl_3$) δ ppm |
|---|---|---|---|
| | | | 7.43-7.47 (1 H, m), 7.69-7.73 (1 H, m), 7.83 (1 H, t, J = 1.8 Hz), 8.08 (1 H, dd, J = 8.8 Hz, 2.8 Hz), 8.24 (1 H, d, J = 2.6 Hz), 8.5 1 (1 H, brs). |
| 1054 | 4-$CH_3$Ph- | 4-$CH_3$OPh$CH_2$— | $^1$H NMR 2.32-2.50 (7 H, m), 3.44-3.79 (9 H, m), 6.84-6.92 (3 H, m), 7.06-7.11 (2 H, m), 7.20-7.23 (4 H, m), 7.34-7.39 (2 H, m), 7.79 (2 H, d, J = 8.3 Hz), 8.16-8.21 (1 H, m), 8.35 (1 H, d, J = 2.8 Hz), 8.76 (1 H, brs). |
| 1055 | 2-naphthyl | 4-$CH_3$OPh$CH_2$— | $^1$H NMR 2.41 (4 H, bra), 3.46-3.80 (6 H, m), 3.81 (3 H, s), 6.83-6.90 (2 H, m), 6.95 (1 H, d, J = 8.7 Hz), 7.10 (2 H, d, J = 8.7 Hz), 7.22 (2 H, d, J = 8.6 Hz), 7.38 (2 H, d, J = 8.7 Hz), 7.52-7.63 (2 H, m), 7.88-7.97 (4 H, m), 8.27 (1 H, dd, J = 8.7 Hz, 2.8 Hz), 8.41-8.43 (2 H, m), 8.80 (1 H, brs). |
| 1056 | 4-ClPh- | 4-$CH_3$OPh$CH_2$— | $^1$H NMR 2.43 (4 H, brs), 3.48-3.77 (6 H, m), 3.80 (3 H, s), 6.83-6.89 (2 H, m), 6.96 (1 H, d, J = 8.9 Hz), 7.10-7.15 (2 H, m), 7.22 (2 H, d, J = 8.6 Hz), 7.38-7.48 (4 H, m), 7.82-7.87 (2 H, m), 8.17-8.21 (2 H, m), 8.30 (1 H, d, J = 2.6 Hz). |
| 1057 | 3-ClPh- | 4-$CH_3$OPh$CH_2$— | $^1$H NMR 2.41 (4 H, brs), 3.46-3.76 (6 H, m), 3.79 (3 H, s), 6.83-6.89 (3 H, m), 7.05 (2 H, d, J = 8.4 Hz), 7.21 (2 H, d, J = 8.6 Hz), 7.31-7.48 (4 H, m), 7.77 (1 H, d, J = 7.8 Hz), 7.90 (1 H, s), 8.08-8.12 (1 H, m), 8.35 (1 H, d, J = 2.5 Hz), 9.26 (1 H, brs). |
| 1058 | 4-$CF_3$OPh- | benzyl | mp 152-153 |
| 1059 | 2,4-$Cl_2$Ph- | benzyl | mp 196-197 |
| 1060 | 2,3-$F_2$Ph- | benzyl | mp 172-175 |
| 1061 | 4-ClPh- | piperonyl | $^1$H NMR 2.45 (4 H, brs), 3.45 (2 H, s), 3.45-3.75 (4 H, m), 5.95 (2 H, s), 6.74-6.77 (2 H, m), 6.86 (1 H, a), 6.99 (1 H, d, J = 8.9 Hz), 7.14 (2 H, d, 4 8.7 Hz), 7.42-7.51 (4 H, m), 7.84 (2 H, d, J = 8.7 Hz), 7.91 (1 H, brs), 8.22 (1 H, dd, J = 8.7 Hz, 2.8 Hz), 8.29 (1 H, d, 2.1 Hz) |
| 1062 | 4-ClPh- | 3-pyridyl | $^1$H NMR 3.24 (4 H, brs), 3.49-3.82 (4 H, m), 7.02 (1 H, d, J = 8.7 Hz), 7.16-7.24 (4 H, m), 7.48 (2 H, d, J = 8.9 Hz), 7.49 (2 H, d, J = 8.7 Hz), 7.85 (2 H, d, J = 8.7 Hz), 8.04 (1 H, brs), 8.15-8.17 (1 H, m), 8.24 (1 H, dd, J = 8.7 Hz, 2.8 Hz), 8.31-8.32 (2 H, m). |

TABLE 239

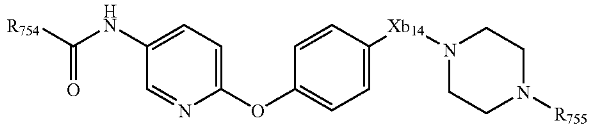

| Example No. | $R_{754}$ | $R_{755}$ | $Xb_{14}$ | Form | Property |
|---|---|---|---|---|---|
| 1063 | 3-$CF_3$OPh- | benzyl | —CO— | maleate | mp 155-157° C. |
| 1064 | 3,5-$Cl_2$Ph- | benzyl | —CO— | dihydrochloride | $^1$H NMR (DMSO-$d_6$) δ 3.15-3.54 (8 H, m), 4.36 (2 H, s), 7.15-7.22 (3 H, m), 7.47-7.60 (7 H, m), 7.90-7.91 (1 H, m), 8.00 (1 H, s), 8.01 (1 H, s), 8.22-8.27 (1 H, m), 8.54 (1 H, d, J = 2.2 Hz), 10.69 (1 H, s). |
| 1065 | PhCH═CH— (trans) | benzyl | —CO— | free | MS 518($M^+$) |
| 1066 | PhCH═CH— (trans) | piperonyl | —CO— | free | $^1$H NMR ($CDCl_3$) δ 2.45 (4 H, brs), 3.44 (2 H, s), 3.52 (2 H, brs), 3.76 (2 H, brs), 5.95 (2 H, s), 6.60 (1 H, d, J = 15.5 Hz), 6.74-6.77 (2 H, m), 6.85 (1 H, s), 6.95 (1 H, d, J = |

TABLE 239-continued

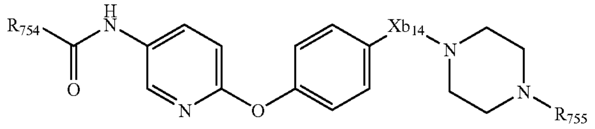

| Example No. | $R_{754}$ | $R_{755}$ | $Xb_{14}$ | Form | Property |
|---|---|---|---|---|---|
| | | | | | 8.7 Hz), 7.12 (2 H, d, J = 8.6 Hz), 7.38-7.45 (511, m), 7.53-7.56 (211, m), 7.74 (1 H, brs), 7.77 (1 H, d, J = 15.5 Hz), 8.21 (1 H, d, J = 8.4 Hz), 8.25 (1 H, d, J = 2.5 Hz). |
| 1067 | PhCH═CH— (trans) | 3-pyridyl | —CO— | free | $^1$H NMR ($CDCl_3$) δ 3.20 (4 H, brs), 3.79 (4 H, brs), 6.67 (1 H, d, J = 15.7 Hz), 6.92 (1 H, d, J = 8.7 Hz), 7.10-7.21 (4 H, m), 7.33-7.46 (7 H, m), 7.73 (1 H, d, J = 15.7 Hz), 8.11-8.31 (4 H, m), 9.30 (1 H, s). |
| 1068 | 3,4-$Cl_2$Ph- | benzyl | —$SO_2$— | hydrochloride | mp 253-256° C. |
| 1069 | 4-$CF_3$Ph- | benzyl | —$SO_2$— | hydrochloride | mp 249-251° C. |

TABLE 240

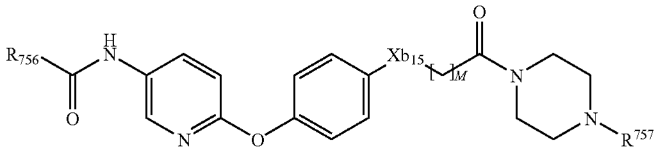

| Example No. | $R_{756}$ | $R_{757}$ | $Xb_{15}$ | M | $^1$H NMR (solvent) δ ppm |
|---|---|---|---|---|---|
| 1070 | 3,4- | benzyl | —CH(OH)— | 0 | ($CDCl_3$) 1.95-2.15 (1 H, m), 2.15-2.40 (3 H, m), 3.42 (2 H, s), 3.49 (4 H, brs), 5.42 (1 H, d, J = 6.6 Hz), 5.61 (1 H, d, J = 6.6 Hz), 7.08 (1 H, d, J = 8.9 Hz), 7.09 (2 H, d, J = 8.6 Hz), 7.15-7.43 (5 H, m), 7.38 (2 H, d, J = 8.6 Hz), 7.85 (1 H, d, J = 8.4 Hz), 7.95 (1 H, dd, J = 8.4 Hz, 2.0 Hz), 8.20 (1 H, dd, J = 8.9 Hz, 2.7 Hz), 8.23 (1 H, d, J = 2.3 Hz), 8.50 (1 H, d, J = 2.7 Hz), 10.57 (1 H, s). |
| 1071 | 4-$CF_3$Ph- | benzyl | —CH(OH)— | 0 | ($CDCl_3$) 1.90-2.05 (1 H, m), 2.22-2.57 (3 H, m), 3.10-3.40 (2 H, m), 3.44 (2 H, s), 3.58-. 3.85 (2 H, m), 4.75 (1 H, d, J = 6.4 Hz), 5.21 (1 H, d, J 6.4 Hz), 6.96 (1 H, d, J = 8.9 Hz), 7.12 (2 H, d, J = 8.6 Hz), 7.20-7.38 (5 H, m), 7.32 (2 H, d, J = 8.6 Hz), 7.78 (2 H, d, J = 8.1 Hz), 7.92 (1 H, brs), 8.00 (2 H, d, J = 8.1 Hz), 8.22 (1 H, dd, J = 8.9 Hz, 2.5 Hz), 8.29 (1 H, d, J = 2.5 Hz). |
| 1072 | 4-$CF_3$Ph- | piperonyl | —O— | 1 | (DMSO-$d_6$) 2.32 (2 H, brs), 2.40 (2 H, brs), 3.41 (2 H, s), 3.46 (4 H, brs), 4.81 (2 H, s), 5.99 (2 H, s), 6.73-6.88 (3 H, m), 6.94 (2 H, d, J = 9.2 Hz), 7.02 (1 H, d, J = 8.7 Hz), 7.05 (2 H, d, J = 9.2 Hz), 7.93 (2 H, d, J = 8.4 Hz), 8.16 (2 H, d, J = 8.4 Hz), 8.19 (1 H, dd, J = 8.7 Hz, 2.7 Hz), 8.47 (1 H, d, J = 2.7 Hz), 10.60 (1 H, s). |
| 1073 | 4-$CF_3$Ph- | benzyl | —O— | 1 | ($CDCl_3$) 2.35-2.53 (4 H, m), 3.51 (2 H, s), 3.56 (2 H, t, J = 5.0 Hz), 3.62 (2 H, t, J = 5.0 Hz), 4.64 (2 H, s), 6.90 (1 H, d, J = 8.8 Hz), 6.92 (2 H, d, J = 9.0 Hz), 7.04 (2 H, d, J = 9.0 Hz), 7.21-7.41 (5 H, m), 7.73 (2 H, d, J = 8.1 Hz), 8.00 (2 H, d, J = 8.1 Hz), 8.18 (1 H, dd, J = 8.8 Hz, 2.6 Hz), 8.27 (1 H, d, J = 2.6 Hz), 8.32 (1 H, brs). |
| 1074 | 3-ClPh- | piperonyl | none | 2 | ($CDCl_3$) 2.31-2.38 (4 H, m), 2.58-2.64 (2 H, m), 2.90-2.96 (2 H, m), 3.37-3.40 (4 H, m), 3.59-3.62 (2 H, m), 5.94 (2 H, s), 6.70- |

TABLE 240-continued

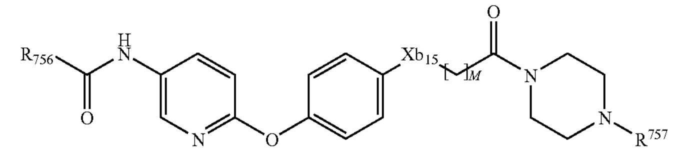

| Example No. | $R_{756}$ | $R_{757}$ | $Xb_{15}$ | M | $^1$H NMR (solvent) δ ppm |
|---|---|---|---|---|---|
| | | | | | 6.77 (2 H, m), 6.84 (1 H, a), 6.92 (1 H, d, J = 8.9 Hz), 7.03 (2 H, d, J = 8.4 Hz), 7.20 (2 H, d, J = 8.4 Hz), 7.38-7.44 (1 H, m), 7.50-7.54 (1 H, m), 7.77 (1 H, d, J = 7.8 Hz), 7.87-7.88 (1 H, m), 8.21 (1 H, dd, J = 8.9 Hz, 2.7 Hz), 8.28 (1 H, d, J = 2.7 Hz), 8.36 (1 H, s). |

TABLE 241

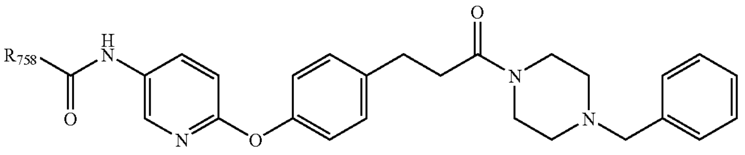

| Example No. | $R_{758}$ | mp (° C.) or $^1$H NMR |
|---|---|---|
| 1075 | 3-ClPh- | $^1$H NMR ($CDCl_3$) δ 2.33-2.38 (4 H, m), 2.55-2.61 (2 H, m), 2.86-2.91 (2 H, m), 3.37-3.41 (2 H, m), 3.49 (2 H, s), 3.56-3.60 (2 H, m), 6.87 (1 H, d, J = 8.9 Hz), 6.97-7.01 (2 H, m), 7.14 (2 H, d, J = 8.6 Hz), 7.25-7.37 (6 H, m), 7.45-7.48 (1 H, m), 7.75-7.79 (1 H, m), 7.87 (1 H, t, J = 1.8 Hz), 8.18 (1 H, dd, J = 8.9 Hz, 2.8 Hz), 8.32 (1 H, d, J = 2.8 Hz), 9.06 (1 H, brs). |
| 1076 | 4-ClPh- | mp 136-139 |
| 1077 | 2-ClPh- | $^1$H NMR ($CDCl_3$) δ 2.32-2.41 (4 H, m), 2.56-2.61 (2 H, m), 2.90-2.96 (2 H, m), 3.37-3.41 (2 H, m), 3.50 (2 H, s), 3.58-3.61 (2 H, m), 6.92 (1.H, d, J = 8.7 Hz), 7.03 (2 H, d, J = 8.4 Hz), 7.19-7.43 (10 H, m), 7.69-7.72 (1 H, m), 8.21-8.27 (3 H, m). |
| 1078 | Ph- | $^1$H NMR ($CDCl_3$) δ 2.36 (4 H, brs), 2.56-2.61 (2 H, m), 2.89-2.95 (2 H, m), 3.36-3.41 (2 H, m), 3.49 (2 H, s), 3.58-3.62 (2 H, m), 6.99 (1 H, d, J = 8.7 Hz), 7.01 (2 H, d, J = 8.1 Hz), 7.18 (2 H, d, J = 8.1 Hz), 7.26-7.55 (8 H, m), 7.87 (2 H, d, J = 6.6 Hz), 8.20 (1 H, d, J = 8.7 Hz), 8.28 (1 H, brs), 8.50 (1 H, brs). |
| 1079 | 4-CNPh- | $^1$H NMR ($CDCl_3$) δ 2.33-2.41 (4 H, m, 2.56-2.62 (2 H, m), 2.87 2.92 (2 H, m), 3.38-3.42 (2 H, m), 3.50 (2 H, s), 3.56-3.60 (2 H, m), 6.91 (1 H, d, J = 8.9 Hz), 6.98-7.01 (2 H, m), 7.14-7.19 (2 H, m), 7.25-7.35 (5 H, m), 7.71-7.75 (2 H, m), 7.99-8.02 (2 H, m), 8.17-8.29 (2 H, m), 8.75-8.97 (1 H, m). |
| 1080 | 3-$CH_3$OPh- | $^1$H NMR ($CDCl_3$) δ 2.33-2.41 (4 H, m), 2.56-2.62 (2 H, m), 2.90 2.95 (2 H, m), 3.38-3.42 (2 H, m), 3.51 (2 H, s), 3.60-3.63 (2 H, m), 3.83 (3 H, s), 6.90 (1 H, d, J = 8.7 Hz), 7.00-7.09 (3 H, m), 7.18 (2 H, d, J = 8.6 Hz), 7.26-7.44 (8 H, m), 8.19-8.23 (1 H, m), 8.29 (1 H, d, J = 2.8 Hz), 8.48 (1 H, brs). |
| 1081 | 4-$CH_3$Ph- | $^1$H NMR ($CDCl_3$) δ 2.33-2.40 (7 H, m), 2.56-2.62 (2 H, m), 2.90-2.95 (2 H, m), 3.38-3.41 (2 H, m), 3.49 (2 H, s), 3.59-3.62 (2 H, m), 6.89 (1 H, d, J 8.7 Hz), 7.01 (2 H,d, J = 8.6 Hz), 7.16-7.32 (9 H, m), 7.78 (2 H, d, J = 8.2 Hz), 8.18-8.22 (1 H, m), 8.27 (1 H, d, J = 2.6 Hz), 8.33-8.44 (1 H, m). |
| 1082 | 2-$CH_3$Ph- | $^1$H NMR ($CDCl_3$) δ 2.32-2.40 (4 H, m), 2.48 (3 H, s), 2.55-2.60 (2 H, m), 2.89-2.95 (2 H, m), 3.37-3.40 (2 H, m), 3.50 (2 H, s), 3.57-3.60 (2 H, m), 6.89-6.92 (1 H, m), 7.00-7.05 (2 H, m), 7.18-7.47 (10 H, m), 7.45 (1 H, d, J = 2.2 Hz), 8.04 (1 H, brs), 8.23-8.25 (2 H, m). |
| 1083 | 4-$CH_3$OPh- | $^1$H NMR ($CDCl_3$) δ 2.31-2.38 (4 H, m), 2.54-2.60 (2 H, m), 2.87-2.93 (2 H, m); 3.37-3.40 (2 H, m), 3.48 (2 H, s), 3.58-3.61 (2 H, m), 3.82 (3 H, s), 6.84-6.90 (3 H, m), 6.99 (2 H, d, J = 8.4 Hz), 7.15 (2 H, d, J = 8.6 Hz), 7.25-7.32 (5 H, m), 7.85 (2 H, d, J = 8.9 Hz), 8.17 (1 H, dd, J = 8.9 Hz, 2.7 Hz), 8.28 (1 H, d, J = 2.7 Hz), 8.73 (1 H, brs). |
| 1084 | 2-$CH_3$OPh- | $^1$H NMR ($CDCl_3$) δ 2.33-2.42 (4 H, m), 2.58-2.64 (2 H, m), 2.93-2.99 (2 H, m), 3.38-3.42 (2 H, m), 3.49 (2 H, s), 3.61-3.65 (2 H, m), 8.23-8.29 (3 H, m), 9.76 (1 H, s). |
| 1085 | 2-naphthyl | mp 156-159 |
| 1086 | 4-$CF_3$Ph- | $^1$H NMR (DMSO-$d_6$) δ 2.30-2.32 (4 H, m), 2.59-2.65 (2 H, m), 2.79-2.84 (2 H, m), 3.44-3.47 (6 H, m), 7.02 (2 H, d, J = 8.6 Hz), 7.05 (1 H, d, |

TABLE 241-continued

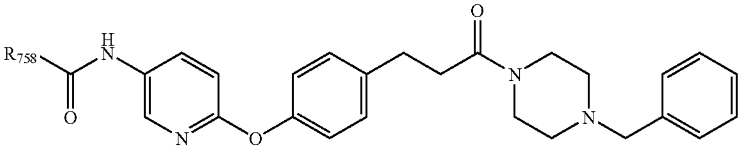

| Example No. | $R_{758}$ | mp (° C.) or $^1$H NMR |
|---|---|---|
| | | J = 9.1 Hz), 7.25-7.35 (7 H, m), 7.93 (2 H, d, J = 8.3 Hz), 8.16 (2 H, d, J = 8.3 Hz), 8.21 (1 H, dd, J = 8.9 Hz, 2.6 Hz), 8.49 (1 H, d, J = 2.6 Hz), 10.62 (1 H, brs). |

TABLE 242

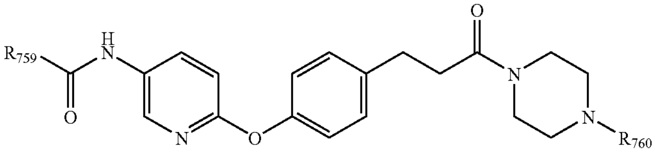

| Example No. | $R_{759}$ | $R_{760}$ | Form | mp (° C.) or $^1$H NMR |
|---|---|---|---|---|
| 1087 | 4-$CF_3$OPh- | benzyl | maleate | mp 144-146 |
| 1088 | 3-$CF_3$OPh- | benzyl | maleate | mp 125-128 |
| 1089 | 4-$CF_3$OPh- | piperonyl | free | mp 187-190 |
| 1090 | 2-$CF_3$OPh- | piperonyl | free | $^1$H NMR ($CDCl_3$) δ 2.31-2.39 (4 H, m), 2.57-2.63 (2 H, m), 2.91-2.97 (2 H, m), 3.37-3.40 (4 H, m), 3.58-3.62 (2 H, m), 5.93 (2 H, s), 6.70-6.76 (2 H, m), 6.84 (1 H, s), 6.93 (1 H, d, J = 8.9 Hz), 7.03-7.07 (2 H, m), 7.19-7.23 (2 H, m), 7.32-7.36 (1 H, m), 7.40-7.46 (1 H, m), 7.53-7.59 (1 H, m), 7.99-8.03 (1 H, m), 8.20 (1 H, dd, J = 8.9 Hz, 2.7 Hz), 8.27 (1 H, d, J = 2.7 Hz), 8.55 (1 H, brs). |
| 1091 | 3-$CF_3$OPh- | piperonyl | free | $^1$H NMR ($CDCl_3$) δ 2.30-2.36 (4 H, m), 2.55-2.61 (2 H, m), 2.86-2.92 (2 H, m), 3.37 3.40 (4 H, m), 3.56-3.60 (2 H, m), 5.93 (2 H, s), 6.69-6.76 (2 H, m), 6.83 (1 H, s), 6.88-6.92 (1 H, m), 6.98-7.02 (2 H, m), 7.14-7.18 (2 H, m), 7.36-7.40 (1 H, m), 7.44-7.52 (1 H, m), 7.78-7.85 (2 H, m), 8.19 (1 H, dd, J = 8.9 Hz, 2.7 Hz), 8.29-8.31 (1 H, m), 8.78-8.92 (1 H, m). |
| 1092 | 3,5-$Cl_2$Ph- | piperonyl | dihydro-chloride | $^1$H NMR (DMSO-$d_6$) δ 2.69-3.33 (10 H, m), 3.99-4.11 (1 H, m), 4.23 (2 H, s), 4.44-4.49 (1 H, m), 6.07 (2 H, s), 6.97-7.07 (5 H, m), 7.20-7.30 (3 H, m), 7.89-8.00 (1 H, m), 8.00 (2 H, d, J = 1.8 Hz), 8.19 (1 H, dd, J = 8.9 Hz, 2.6 Hz), 8.48 (1 H, d, J = 2.3 Hz), 10.64 (1 H, s). |
| 1093 | PhCH═CH— (trans) | piperonyl | free | $^1$H NMR ($CDCl_3$) δ 2.05-3.38 (9 H, m), 3.69-4.71 (5 H, m), 5.96 (2 H, s), 6.72-6.79 (2 H, m), 6.95-7.05 (4 H, m), 7.13-7.23 (3 H, m), 7.35-7.37 (3 H, m), 7.51-7.5.4 (2 H, m), 7.70-7.76 (1 H, m), 8.41 (1 H, d, J 2.3 Hz), 8.50 (1 H, d, J = 8.7 Hz), 8.95 (1 H, brs). |
| 1094 | 2-naphthyl | piperonyl | free | $^1$H NMR ($CDCl_3$) δ 2.28-2.34 (4 H, m), 2.55-2.61 (2 H, m), 2.89-2.95 (2 H, m), 3.38 (4 H, brs), 3.58 (2 H, brs), 5.92 (2 H, s), 6.69-6.76 (2 H, m), 6.83 (1 H, s), 6.92 (1 H, d, J = 8.6 Hz), 7.02 (2 H, d, J = 8.4 Hz), 7.18 (2 H, d, J = 8.4 Hz), 7.51-7.61 (2 H, m), 7.86-7.94 (4 H, m), 8.27 (1 H, dd, J = 8.6 Hz, 2.7 Hz), 8.33-8.38 (2 H, m), 8.55 (1 H, brs). |
| 1095 | 4-ClPh- | piperonyl | free | $^1$H NMR ($CDCl_3$) δ 2.31-2.41 (4 H, m), 2.59-2.65 (2 H, m), 2.94-3.00 (2 H, m), 3.38-3.41 (4 H, m), 3.63 (2 H, brs), 5.94 (2 H, s), 6.71-6.77 (2 H, m), 6.85 (1 H, s), 6.95 (1 H, d, J = 8.9 Hz), 7.05 (2 H, d, J = 8.4 Hz), 7.23 (2 H, d, J = 8.4 Hz), 7.48 (2 H, d, J = 8.6 Hz), 7.82-7.89 (3 H, m), 8.19-8.25 (2 H, m). |

TABLE 243

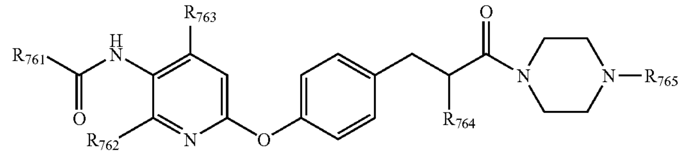

| Example No. | $R_{761}$ | $R_{762}$ | $R_{763}$ | $R_{764}$ | $R_{765}$ | $^1$H NMR ($CDCl_3$) δ ppm |
|---|---|---|---|---|---|---|
| 1096 | 4-$CF_3$Ph- | —H | —H | —OH | —$COOC(CH_3)_3$ | 1.44 (9 H, s), 2.82-3.00 (2 H, m), 3.00-3.80 (9 H, m), 4.60 (1 H, t, J = 6.5 Hz), 6.97 (1 H, d, J = 8.8 Hz), 7.06 (2 H, d, J = 8.6 Hz), 7.24 (2 H, d, J = 8.6 Hz), 7.75 (2 H, d, J = 8.1 Hz), 8.00 (2 H, d, J = 8.1 Hz), 8.07 (1 H, brs), 8.18 (1 H, d, J = 2.6 Hz), 8.27 (1 H, dd, J = 8.8 Hz, 2.6 Hz). |
| 1097 | 4-$CF_3$Ph- | —H | —$CH_3$ | —H | piperonyl | 2.32 (3 H, s), 2.32-2.40 (4 H, m), 2.59-2.64 (2 H, m), 2.93-2.98 (2 H, m), 3.30-3.45 (4 H, m), 3.55-3.70 (2 H, m), 5.94 (2 H, s), 6.65-6.75 (2 H, m), 6.82-6.84 (2 H, m), 7.03-7.07 (2 H, m), 7.20-7.24 (2 H, m), 7.72 (1 H, brs), 7.75-7.79 (2 H, m), 8.00-8.04 (2 H, m), 8.30 (1 H, s). |
| 1098 | 4-$CF_3$Ph- | —$CH_3$ | —H | —H | piperonyl | 2.31-2.40 (4 H, m), 2.47 (3 H, s), 2.59-2.65 (2 H, m), 2.94-3.00 (2 H, m), 3.38-3.41 (4 H, m), 3.60-3. 65 (2 H, m), 5.94 (2 H, s), 6.68-6.77 (3 H, m), 6.84 (1 H, s), 7.04-7.08 (2 H, m), 7.20-7.24 (2 H, m), 7.63 (1 H, brs), 7.77-7.80 (2 H, m), 7.99-8.11 (3 H, m). |
| 1099 | 3,4-$Cl_2$Ph- | —$CH_3$ | —H | —H | piperonyl | 2.25-2.40 (4 H, m), 2.45 (3 H, s), 2.58-2.64 (2 H, m), 2.92-2.98 (2 H, m), 3.38-3.41 (4 H, m), 3.60-3.64 (2 H, m), 5.94 (2 H, s), 6.66-6.76 (3 H, m), 6.84 (1 H, s), 7.03-7.07 (2 H, m), 7.18-7.22 (2 H, m), 7.59 (1 H, d, J = 8.3 Hz), 7.67 (1 H, brs), 7.72 (1 H, dd, J = 8.4 Hz, 2.0 Hz), 7.98-8.02 (2 H, m). |
| 1100 | 3,4-$Cl_2$Ph- | —H | —$CH_3$ | —H | piperonyl | 2.31 (3 H, s), 2.31-2.40 (4 H, m), 2.58-2.64 (2 H, m), 2.92-2.98 (2 H, m), 3.37-3.41 (4 H, m), 3.60-3.64 (2 H, m), 5.94 (2 H, s), 6.65-6.75 (2 H, m), 6.80-6.84 (2 H, m), 7.03-7.06 (2 H, m), 7.20-7.24 (2 H, m), 7.58 (1 H, d, J = 8.3 Hz), 7.64 (1 H, brs), 7.73 (1 H, dd, J = 8.3 Hz, 1.8 Hz), 8.01 (1 H, d, J = 1.9 Hz), 8.26 (1 H, s). |

TABLE 244

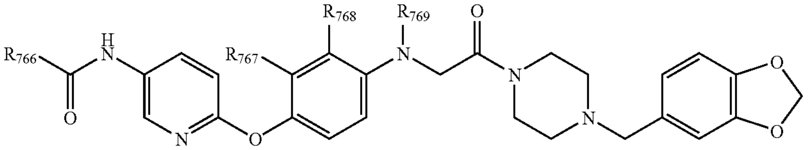

| Example No. | $R_{766}$ | $R_{767}$ | $R_{768}$ | $R_{769}$ | mp (° C.) or $^1$H NMR (solvent) δ ppm |
|---|---|---|---|---|---|
| 1101 | 4-$CF_3$Ph- | —H | —H | —Ac | mp 189-191 |
| 1102 | 3,4-$Cl_2$Ph- | —H | —H | —$COC_2H_5$ | mp 204-206 |
| 1103 | 3,4-$Cl_2$Ph- | —H | —H | —H | mp 188-189 |

TABLE 244-continued

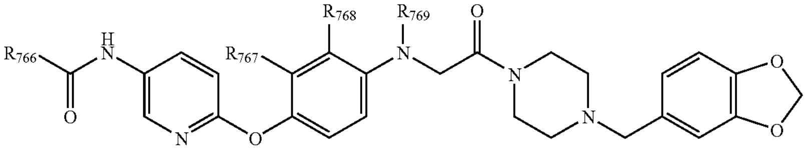

| Example No. | $R_{766}$ | $R_{767}$ | $R_{768}$ | $R_{769}$ | mp (° C.) or $^1$H NMR (solvent) δ ppm |
|---|---|---|---|---|---|
| 1104 | 3,4-$Cl_2$Ph- | —H | —H | 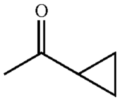 | $^1$H NMR (DMSO-$d_6$) 0.60-0.70 (2 H, m), 0.75-0.80 (2 H, m), 1.42 (1 H, m), 2.25-2.35 (4 H, m), 3.35-3.45 (6 H, m), 4.49 (2 H, s), 5.98 (2 H, s), 6.74 (1 H, d, J = 7.9 Hz), 6.84 (1 H, d, J = 7.9 Hz), 6.86 (1 H, s), 7.12 (1 H, d, J = 8.8 Hz), 7.18 (2 H, d, J = 8.6 Hz), 7.47 (2 H, d, J = 8.6 Hz), 7.84 (1 H, d, J = 8.4 Hz), 7.95 (1 H, dd, J = 8.4 Hz, 2.0 Hz), 8.20-8.23 (2 H, m), 8.5 1 (1 H, d, J = 2.5 Hz), 10.58 (1 H, s). |
| 1105 | 4-$CF_3$Ph- | —H | —H | —$CH_3$ | H NMR (DMSO-$d_6$) 2.31-2.39 (4 H, m), 2.94 (3 H, s), 3.31 (2 H, s), 3.42 (4 H, brs), 4.24 (2 H, s), 5.99 (2 H, s), 6.64 (2 H, d, J = 9.1 Hz), 6.76 (1 H, dd, J = 7.9 Hz, 1.2 Hz), 6.84-6.96 (5 H, m), 7.93 (2 H, d, J = 8.3 Hz), 8.13 (1 H, s), 8.16 (2 H, d, J = 8.6 Hz), 8.45 (1 H, d, J = 2.5 Hz), 10.58 (1 H, s). |
| 1106 | 3,4-$Cl_2$Ph- | —H | —H | 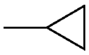 | $^1$H NMR ($CDCl_3$) 0.57-0.62 (2 H, m), 0.75-0.82 (2 H, m), 2.37-2.49 (4 H, m), 2.70-2.74 (1 H, m), 3.45 (2 H, s), 3.49-3.59 (4 H, m), 4.17 (2 H, s), 5.95 (2 H, s), 6.74-6.94 (8 H, m), 7.49 (1 H, d, J = 8.2 Hz), 7.67-7.71 (1 H, m), 7.95 (1 H, d, J = 2.1 Hz), 8.00 (1 H, dd, J = 8.9 Hz, 2.6 Hz), 8.24 (1 H, d, J 2.6 Hz), 8.59 (1 H, brs). |
| 1107 | 4-$CF_3$Ph- | —H | —H | 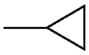 | $^1$H NMR ($CDCl_3$) 0.57-0.62 (2 H, m), 0.74-0.81 (2 H, m), 2.35-2.47 (4 H, m), 2.66-2.74 (1 H, m), 3.44 (2 H, s), 3.47-3.57 (4 H, m), 4.16 (2 H, s), 5.94 (2 H, s), 6.70-6.94 (8 H, m), 7.66 (2 H, d, J = 8.2 Hz), 7.95 (2 H, d, J = 8.0 Hz), 8.04 (1 H, dd, J = 8.9 Hz, 2.6 Hz), 8.25 (1 H, d, J = 2.6 Hz), 8.80 (1 H, s). |
| 1108 | 4-$CF_3$Ph- | —$CH_3$ | —$CH_3$ | —$CH_3$ | $^1$H NMR ($CDCl_3$) 2.09 (3 H, s), 2.26 (3 H, s), 2.39 (4 H, brs), 2.67 (3 H, s), 3.41 (2 H, s), 3.53 3.63 (4 H, m), 3.74 (2 H, s), 5.94 (2 H, s), 6.71-6.77 (2 H, m), 6.85-6.90 (3 H, m), 6.98 (1 H, d, J = 8.7 Hz), 7.75 (2 H, d, J = 8.2 Hz), 7.98-8.01 (3 H, m), 8.18 (1 H, dd, J = 8.9 Hz, 2.8 Hz), 8.25 (1 H, d, J = 2.3 Hz). |
| 1109 | 3,4-$Cl_2$Ph- | —$CH_3$ | —$CH_3$ | —$CH_3$ | $^1$H NMR ($CDCl_3$) 2.09 (3 H, s), 2.25 (3 H, s), 2.37-2.40 (4 H, m), 2.66 (3 H, s), 3.41 (2 H, s), 3.53-3.63 (4 H, m), 3.73 (2 H, s), 5.94 (2 H, s), 6.70-6.77 (2 H, m), 6.84-6.89 (3 H, m), 6.96 (1 H, d, J = 8.7 Hz), 7.56 (1 H, d, J = 8.2 Hz), 7.70-7.74 (1 H, m), 7.99 (1 H, d, J = 2.0 Hz), 8.10-8.16 (2 H, m), 8.24 (1 H, d, J = 2.8 Hz). |

TABLE 245

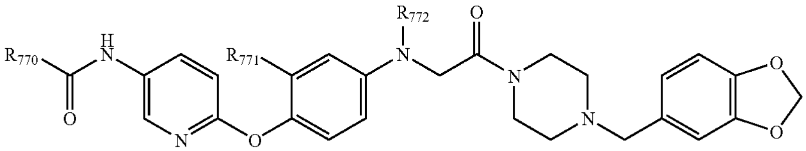

| Example No. | $R_{770}$ | $R_{771}$ | $R_{772}$ | Form | mp (° C.) or $^1$H NMR (solvent) δ ppm |
|---|---|---|---|---|---|
| 1110 | 4-$CF_3$Ph- | —$OCH_3$ | —$C_2H_5$ | free | mp 142.6-146.5 |
| 1111 | 4-$CF_3$Ph- | —$CH_3$ | —$C_2H_5$ | hydrochloride | mp 173-175 dec |
| 1112 | 3,4-$Cl_2$Ph- | —$CH_3$ | —$C_2H_5$ | hydrochloride | mp 168.5-171.0 |
| 1113 | 2,3-$Cl_2$Ph- | —$CH_3$ | —$CH_3$ | free | $^1$H NMR ($CDCl_3$) 2.12 (3H, s), 2.41-2.45 (4H, m), 3.01 (3H, s), 3.43 |

TABLE 245-continued

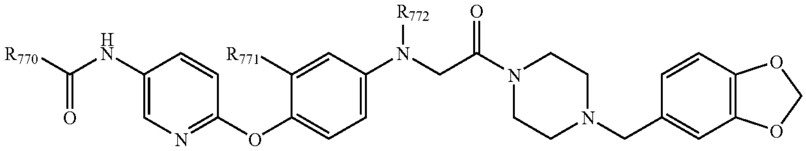

| Example No. | $R_{770}$ | $R_{771}$ | $R_{772}$ | Form | mp (° C.) or $^1$H NMR (solvent) δ ppm |
|---|---|---|---|---|---|
| | | | | | (2H, s), 3.50 (2H, s), 3.63 (2H, brs), 4.07 (2H, s), 5.95 (2H, s), 6.52-6.58 (2H, m), 6.71-6.77 (2H, m), 6.81-6.93 (3H, m), 7.32 (1H, t, J = 7.8 Hz), 7.56-7.61 (2H, m), 7.68 (1H, brs), 8.16 (1H, dd, J = 8.7 Hz, 2.8 Hz), 8.20 (1H, d, J = 2.2 Hz). |
| 1114 | 3,4-$Cl_2$Ph- | —$OCH_3$ | —H | free | $^1$H NMR (DMSO-$d_6$) 2.32-2.40 (4H, m), 3.42 (2H, s), 3.51 (4H, brs), 3.63 (3H, s), 3.91 (2H, d, J = 4.8 Hz), 5.54 (1H, t, J = 4.8 Hz), 5.99 (2H, s), 6.21 (1H, dd, J = 8.6 Hz, 2.5 Hz), 6.50 (1H, d, J = 2.5 Hz), 6.76 (1H, dd, J = 7.9 Hz, 1.5 Hz), 6.82-6.88 (4H, m), 7.82 (1H, d, J = 8.4 Hz), 7.94 (1H, dd, J = 8.4 Hz, 2.0 Hz), 8.07 (1H, dd, J = 8.9 Hz, 2.6 Hz), 8.21 (1H, d, J = 2.2 Hz), 8.37 (1H, d, J = 2.5 Hz), 10.44 (1H, s). |
| 1115 | 4-$CF_3$Ph- | —$OCH_3$ | —H | free | $^1$H NMR ($CDCl_3$) 2.32-2.40 (4H, m), 3.42 (2H, s), 3.50 (4H, brs), 3.63 (3H, s), 3.91 (2H, d, J = 4.6 Hz), 5.55 (1H, brt), 5.99 (2H, s), 6.20 (1H, dd, J = 8.6 Hz, 2.5 Hz), 6.49 (1H, d, J = 2.3 Hz), 6.74-6.88 (5H, m), 7.92 (2H, d, J = 8.4 Hz), 8.07-8.17 (3H, m), 8.38 (1H, d, J = 2.3 Hz), 10.53 (1H, s). |
| 1116 | 4-$CF_3$Ph- | —$CH_3$ | 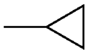 | free | $^1$H NMR ($CDCl_3$) 0.59-0.64 (2H, m), 0.76-0.82 (2H, m), 2.08 (3H, s), 2.37-2.47 (4H, m), 2.69-2.77 (1H, m), 3.44 (2H, s), 3.48-3.59 (4H, m), 4.16 (2H, s), 5.94 (2H, s), 6.67-6.77 (5H, m), 6.86 (2H, d, J = 8.6 Hz), 7.70 (2H, d, J = 8.2 Hz), 7.97 (2H, d, J = 8.1 Hz), 8.08 (1H, dd, J = 8.9 Hz, 2.8 Hz), 8.23 (1H, d, J = 2.8 Hz), 8.39 (1H, brs). |
| 1117 | 3,4-$Cl_2$Ph- | —$CH_3$ | 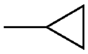 | free | $^1$H NMR ($CDCl_3$) 0.59-0.65 (2H, m), 0.76-0.83 (2H, m), 2.08 (3H, s), 2.38-2.48 (4H, m), 2.71-2.78 (1H, m), 3.44 (2H, s), 3.49-3.59 (4H, m), 4.17 (2H, s), 5.95 (2H, s), 6.67-6.77 (5H, m), 6.85-6.88 (2H, m), 7.53 (1H, d, J = 8.2 Hz), 7.68-7.72 (1H, m), 7.96 (1H, d, J = 2.0 Hz), 8.02-8.07 (1H, m), 8.22-8.26 (2H, m). |
| 1118 | 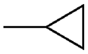 | —$CH_3$ | —$CH_3$ | free | $^1$H NMR ($CDCl_3$) 0.83-0.85 (2H, m), 1.07-1.08 (2H, m), 1.46-1.63 (1H, m), 2.10 (3H, s), 2.41-2.44 (4H, m), 3.00 (3H, s), 3.43 (2H, s), 3.47-3.49 (2H, m), 3.63 (2H, brs), 4.06 (2H, s), 5.94 (2H, s), 6.51-6.55 (2H, m), 6.70-6.77 (3H, m), 6.85 (1H, brs), 6.89 (1H, d, J = 8.4 Hz), 7.44-7.64 (1H, m), 8.01-8.04 (1H, m), 8.08 (1H, d, J = 2.3 Hz). |

TABLE 246

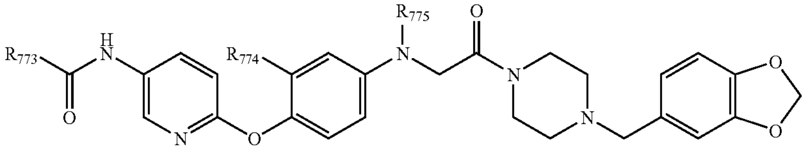

| Example No. | $R_{773}$ | $R_{774}$ | $R_{775}$ | Form | $^1$H NMR (solvent) δ ppm |
|---|---|---|---|---|---|
| 1119 | 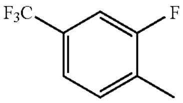 | —$CH_3$ | —$CH_3$ | hydrochloride | (DMSO-$d_6$) 2.01 (3H, s), 2.80-3.18 (3H, m), 2.93 (3H, s), 3.35 (2H, s), 3.38-3.62 (1H, m), 3.95-4.50 (4H, m), 4.27 (2H, s), 6.08 (2H, s), 6.49 (1H, dd, J = 8.7 Hz, 2.7 Hz), 6.58 (1H, d, J = 2.7 Hz), 6.83 (1H, d, J = 8.7 Hz), 6.92 (1H, d, J = 8.9 Hz), 7.02 (2H, s), 7.21 (1H, s), 7.74 (1H, d, J = 8.4 Hz), 7.90 (1H, d, J = 8.4 Hz), 7.88-7.95 (1H, m), 8.11 (1H, dd, J = 8.9 Hz, 2.7 Hz), 8.36 (1H, d, J = 2.7 Hz), 10.71 (1H, s). |
| 1120 | 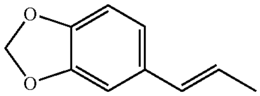 | —$CH_3$ | —$CH_3$ | free | ($CDCl_3$) 2.11 (3H, s), 2.42 (4H, brs), 3.00 (3H, s), 3.43 (2H, s), 3.47-3.49 (2H, m), 3.63 (2H, brs), 4.07 (2H, s), 5.95 (2H, s), 6.01 (2H, s), 6.37 (1H, d, J = 15.2 Hz), 6.52-6.56 (2H, m), 6.74-6.85 (5H, m), 6.91 (1H, d, J = 8.6 Hz), 7.00-7.02 (2H, m), 7.49 (1H, brs), 7.65 (1H, d, J = 15.3 Hz), 8.16-8.17 (2H, m). |
| 1121 | 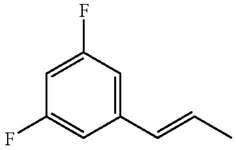 | —$CH_3$ | —$CH_3$ | free | ($CDCl_3$) 2.09 (3H, s), 2.42-2.43 (4H, m), 3.00 (3H, s), 3.43 (2H, s), 3.47-3.50 (2H, m), 3.63 (2H, brs), 4.08 (2H, s), 5.95 (2H, s), 6.49-6.61 (3H, m), 6.70-6.91 (6H, m), 7.01-7.03 (2H, m), 7.63 (1H, d, J = 15.3 Hz), 7.98 (1H, brs), 8.16-8.19 (2H, m). |
| 1122 | 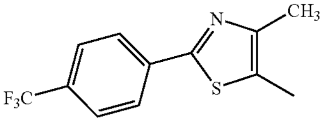 | —$CH_3$ | —$CH_3$ | free | ($CDCl_3$) 2.17 (3H, s), 2.43 (4H, brs), 2.82 (3H, s), 3.01 (3H, s), 3.44 (2H, s), 3.50 (2H, brs), 3.63 (2H, brs), 4.08 (2H, s), 5.95 (2H, s), 6.53-6.57 (2H, m), 6.74 (2H, brs), 6.81 (1H, d, J = 8.9 Hz), 6.85 (1H, s), 6.92 (1H, d, J = 8.6 Hz), 7.52 (1H, brs), 7.73 (2H, d, J = 8.3 Hz), 8.04-8.09 (3H, m), 8.18 (1H, d, J = 2.8 Hz). |
| 1123 | 4-$CF_3$Ph- | —F | allyl | free | ($CDCl_3$) 2.45 (4H, brs), 3.45 (2H, s), 3.45 (2H, brs), 3.64 (2H, brs), 3.99 (2H, d, J = 5.1 Hz), 4.05 (2H, s), 5.18-5.28 (2H, m), 5.83-5.93 (1H, m), 5.95 (2H, s), 6.36-6.47 (2H, m), 6.75 (2H, s), 6.86-6.87 (1H, m), 6.96 (1H, d, J = 9.1 Hz), 7.03 (1H, t, J = 8.9 Hz), 7.75-7.78 (3H, m), 7.99 (2H, d, J = 8.1 Hz), 8.15-8.22 (2H, m). |
| 1124 | 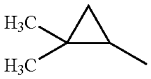 | —$CH_3$ | —$CH_3$ | free | ($CDCl_3$) 0.83-0.87 (1H, m), 1.19-1.22 (7H, m), 1.37-1.42 (1H, m), 2.10 (3H, s), 2.41-2.44 (4H, m), 3.00 (3H, s), 3.43 (2H, s), 3.48 (2H, brs), 3.63 (2H, brs), 4.06 (2H, s), 5.94 (2H, s), 6.51-6.56 (2H, m), 6.70-6.77 (3H, m), 6.85-6.91 (2H, m), 7.40 (1H, brs), 8.05-8.06 (2H, m). |

TABLE 247

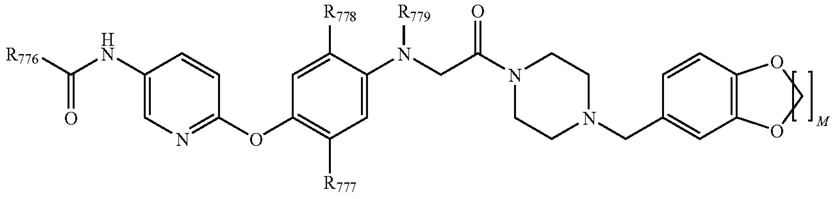

| Example No. | $R_{776}$ | $R_{777}$ | $R_{778}$ | $R_{779}$ | M | mp (° C.) or $^1$H NMR |
|---|---|---|---|---|---|---|
| 1125 | 4-$CF_3$Ph- | —F | —F | —$CH_3$ | 1 | mp 160.0-161.5 |
| 1126 | 3,4-$Cl_2$Ph- | —F | —F | —$CH_3$ | 1 | mp 207-209 |
| 1127 | 4-$CF_3$Ph- | —F | —F | —$C_2H_5$ | 1 | $^1$H NMR (DMSO-$d_6$) δ 1.07 (3H, t, J = 7.0 Hz), 2.20-2.41 (4H, m), 3.20-3.30 (2H, m), 3.39 (2H, s), 3.39-3.52 (4H, m), 4.11 (2H, s), 5.97 (2H, s), 6.71-6.76 (1H, m), 6.78-6.88 (3H, m), 7.09-7.19 (2H, m), 7.92 (2H, d, J = 8.4 Hz), 8.15 (2H, d, J = 8.4 Hz), 8.20 (1H, dd, J = 2.7 Hz, 9.0 Hz), 8.42 (1H, d, J = 2.7 Hz). |
| 1128 | 3,4-$Cl_2$Ph- | —$CH_3$ | —$CH_3$ | —$C_2H_5$ | 1 | $^1$H NMR (DMSO-$d_6$) δ 0.95 (3H, t, J = 7.0 Hz), 2.01 (3H, s), 2.19 (3H, s), 2.20-2.40 (4H, m), 3.00 (2H, q, J = 7.0 Hz), 3.30-3.55 (6H, m), 3.79 (2H, s), 5.98 (2H, s), 6.74 (1H, dd, J = 7.9 Hz, 1.4 Hz), 6.82-6.86 (3H, m), 6.97 (1H, d, J = 8.9 Hz), 7.05 (1H, s), 7.84 (1H, d, J = 8.4 Hz), 7.94 (1H, dd, J = 8.4 Hz, 2.0 Hz), 8.15 (1H, dd, J = 8.9 Hz, 2.7 Hz), 8.21 (1H, d, J = 2.0 Hz), 8.42 (1H, d, J = 2.6 Hz), 10.51 (1H, brs). |
| 1129 | 4-$CF_3$Ph- | —$CH_3$ | —$CH_3$ | —$C_2H_5$ | 1 | $^1$H NMR (DMSO-$d_6$) δ 0.95 (3H, t, J = 7.0 Hz), 2.02 (3H, s), 2.19 (3H, s), 2.20-2.40 (4H, m), 3.00 (2H, q, J = 7.0 Hz), 3.30-3.60 (6H, m), 3.79 (2H, s), 5.98 (2H, s), 6.74 (1H, d, J = 7.9 Hz), 6.82-6.85 (3H, m), 6.98 (1H, d, J = 8.6 Hz), 7.05 (1H, s), 7.91-7.95 (2H, m), 8.14-8.20 (3H, m), 8.44 (1H, d, J = 1.8 Hz), 10.59 (1H, brs). |
| 1130 | 4-$CF_3$Ph- | —$OCH_3$ | —H | —H | 2 | $^1$H NMR ($CDCl_3$) δ 2.44 (4H, brs), 3.43 (4H, brs), 3.49 (2H, s), 3.66 (3H, s), 3.83 (2H, brs), 4.25 (4H, s), 4.67 (1H, brs), 6.10 (1H, dd, J = 8.6 Hz, 2.5 Hz), 6.23 (1H, d, J = 2.5 Hz), 6.75-6.96 (5H, m), 7.67 (2H, d, J = 8.3 Hz), 7.96 (2H, d, J = 8.1 Hz), 8.10 (1H, dd, J = 8.9 Hz, 2.6 Hz), 8.20-8.24 (1H, m), 8.56 (1H, s). |

TABLE 248

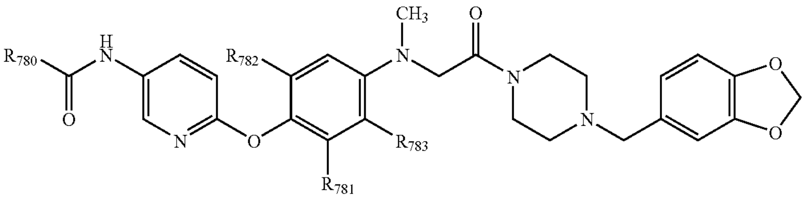

| Example No. | $R_{780}$ | $R_{781}$ | $R_{782}$ | $R_{783}$ | mp (° C.) or $^1$H NMR (solvent) δ ppm |
|---|---|---|---|---|---|
| 1131 | 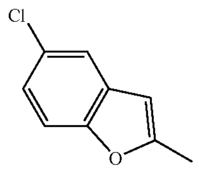 | —$CH_3$ | —H | —H | $^1$H NMR ($CDCl_3$) 2.13 (3H, s), 2.43 (4H, t, J = 4.8 Hz), 3.02 (3H, s), 3.44 (2H, s), 3.50 (2H, brs), 3.64 (2H, brs), 4.08 (2H, s), 5.94 (2H, s), 6.53-6.58 (2H, m), 6.74 (2H, brs), 6.83 (1H, d, J = 8.9 Hz), 6.85 (1H, s), 6.93 (1H, d, J = 8.4 Hz), 7.42 (1H, dd, J = 8.9 Hz, 2.0 Hz), 7.50 (1H, d, J = 8.9 Hz), 7.53 (1H, s), 7.69 (1H, d, J = 1.8 Hz), 8.19 (1H, dd, J = 8.9 Hz, 2.8 Hz), 8.26 (1H, brs), 8.31 (1H, d, J = 2.6 Hz). |
| 1132 | 3,4-$Cl_2$Ph- | —F | —F | —H | mp 203.5-204.5 |

TABLE 248-continued

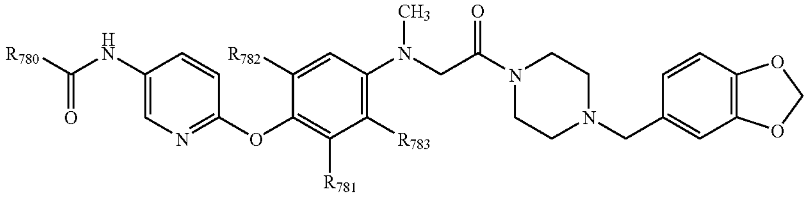

| Example No. | $R_{780}$ | $R_{781}$ | $R_{782}$ | $R_{783}$ | mp (° C.) or $^1$H NMR (solvent) δ ppm |
|---|---|---|---|---|---|
| 1133 | 4-$CF_3$Ph- | —F | —F | —H | mp 230.0-231.5 |
| 1134 | 4-ClPh- | —$CH_3$ | —H | —H | $^1$H NMR ($CDCl_3$) 2.08 (3H, s), 2.42 (4H, brs), 2.97 (3H, s), 3.43 (2H, s), 3.49 (2H, brs), 3.60 (2H, brs), 4.05 (2H, s), 5.94 (2H, s), 6.48-6.52 (2H, m), 6.74-6.89 (5H, m), 7.41 (2H, d, J = 8.6 Hz), 7.80 (2H, d, J = 8.4 Hz), 8.08 (1H, dd, J = 8.9 Hz, 2.8 Hz), 8.21 (1H, d, J = 2.6 Hz), 8.29 (1H, s). |
| 1135 | 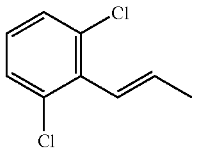 | —$CH_3$ | —H | —H | $^1$H NMR ($CDCl_3$) 2.11 (3H, s), 2.43-2.44 (4H, m), 3.00 (3H, s), 3.43 (2H, s), 3.47-3.49 (2H, m), 3.63 (2H, brs), 4.07 (2H, s), 5.95 (2H, s), 6.51-6.57 (2H, m), 6.69-6.93 (6H, m), 7.19 (1H, dd, J = 8.7 Hz, 7.5 Hz), 7.35-7.38 (2H, m), 7.55 (1H, brs), 7.86 (1H, d, J = 15.8 Hz), 8.17-8.20 (2H, m). |
| 1136 | 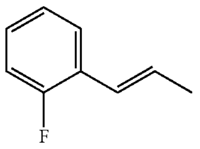 | —$CH_3$ | —H | —H | $^1$H NMR ($CDCl_3$) 2.10 (3H, s), 2.43 (4H, brs), 3.00 (3H, s), 3.43 (2H, s), 3.50 (2H, brs), 3.64 (2H, brs), 4.07 (2H, s), 5.95 (2H, s), 6.50-6.56 (2H, m), 6.67-6.92 (6H, m), 7.07-7.19 (2H, m), 7.31-7.36 (1H, m), 7.47-7.52 (1H, m), 7.73 (1H, brs), 7.80 (1H, d, J = 15.7 Hz), 8.14-8.20 (2H, m). |
| 1137 | 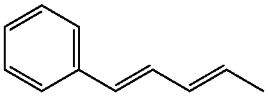 | —$CH_3$ | —H | —H | $^1$H NMR ($CDCl_3$) 2.11 (3H, s), 2.41-2.44 (4H, m), 3.00 (3H, s), 3.43 (2H, s), 3.47-3.49 (2H, m), 3.63 (2H, brs), 4.06 (2H, s), 5.94 (2H, s), 6.09 (1H, d, J = 14.7 Hz), 6.51-6.56 (2H, m), 6.70-6.96 (7H, m), 7.30-7.55 (7H, m), 8.14 (1H, d, J = 2.5 Hz), 8.14 (1H, brs). |
| 1138 | 4-$CF_3$Ph- | —F | —H | —F | mp 169.0-170.0 |
| 1139 | 3,4-$Cl_2$Ph- | —F | —H | —F | mp 138.0-139.0 |

TABLE 249

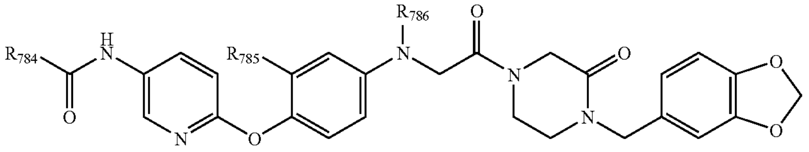

| Example No. | $R_{784}$ | $R_{785}$ | $R_{786}$ | $^1$H NMR (solvent) δ ppm |
|---|---|---|---|---|
| 1140 | 3,4-$Cl_2$Ph- | —$CH_3$ | —$CH_3$ | (DMSO-$d_6$) 2.00 (3H, s), 2.93 (3H, s), 3.23 (1H, brs), 3.36 (1H, brs), 3.63 (1H, brs), 3.72 (1H, brs), 4.07 (1H, s), 4.27 (1H, s), 4.29 (2H, s), 4.47 (2H, s), 5.99 (2H, s), 6.43-6.63 (2H, m), 6.77 (1H, dd, J = 8.0 Hz, 1.5 Hz), 6.77-6.88 (2H, m), 6.82 (1H, d, J = 8.8 Hz), 6.90 (1H, d, J = 8.6 Hz), 7.83 (1H, d, J = 8.4 Hz), 7.94 (1H, dd, J = 8.4 Hz, 2.0 Hz), 8.12 (1H, dd, J = 8.8 Hz, 2.6 Hz), 8.21 (1H, d, J = 2.0 Hz), 8.40 (1H, d, J = 2.6 Hz), 10.48 (1H, s). |

TABLE 249-continued

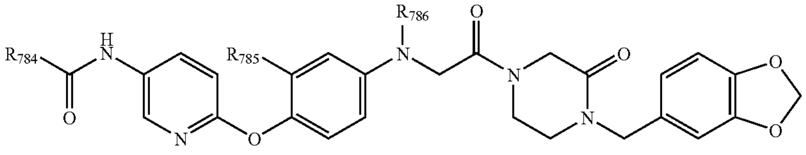

| Example No. | $R_{784}$ | $R_{785}$ | $R_{786}$ | $^1$H NMR (solvent) δ ppm |
|---|---|---|---|---|
| 1141 | 4-$CF_3$Ph- | —$CH_3$ | —$CH_3$ | ($CDCl_3$) 2.10 (3H, s), 2.90-3.06 (3H, m), 3.20-3.34 (2H, m), 3.62-3.84 (2H, m), 4.08 (2H, s), 4.20-4.33 (2H, m), 4.52 (2H, s), 5.95 (2H, s), 6.53 (1H, dd, J = 8.6 Hz, 3.0 Hz), 6.58 (1H, d, J = 3.0 Hz), 6.67-6.79 (3H, m), 6.82 (1H, d, J = 8.9 Hz), 6.91 (1H, d, J = 8.1 Hz), 7.74 (2H, d, J = 8.2 Hz), 7.99 (2H, d, J = 8.2 Hz), 8.10 (1H, s), 8.15 (1H, dd, J = 9.2 Hz, 2.3 Hz), 8.22 (1H, d, J = 2.3 Hz). |
| 1142 | 3,4-$Cl_2$Ph- | —$OCH_3$ | —$C_2H_5$ | ($CDCl_3$) 1.17 (3H, t, J = 6.4 Hz), 3.17-3.30 (2H, m), 3.32-3.52 (2H, m), 3.70 (3H, s), 3.62-3.86 (2H, m), 4.03 (2H, s), 4.29 (2H, s), 4.50 (2H, s), 5.95 (2H, s), 6.22 (1H, d, J = 8.9 Hz), 6.37 (1H, s), 6.70 (1H, d, J = 8.2 Hz), 6.75 (1H, s), 6.76 (1H, d, J = 8.9 Hz), 6.86 (1H, d, J = 8.9 Hz), 6.94 (1H, d, J = 8.7 Hz), 7.54 (1H, d, J = 8.4 Hz), 7.70 (1H, dd, J = 8.4 Hz, 2.0 Hz), 7.98 (1H, d, J = 2.0 Hz), 8.08 (1H, s), 8.08 (1H, dd, J = 8.9 Hz, 2.3 Hz), 8.20 (1H, d, J = 2.3 Hz). |
| 1143 | 4-$CF_3$Ph- | —$OCH_3$ | —$C_2H_5$ | ($CDCl_3$) 1.18 (3H, t, J = 6.7 Hz), 3.16-3.33 (2H, m), 3.33-3.50 (2H, m), 3.72 (2H, s), 3.62-3.85 (3H, m), 4.04 (2H, s), 4.29 (2H, s), 4.50 (2H, s), 5.95 (2H, s), 6.23 (1H, dd, J = 8.7 Hz, 2.8 Hz), 6.38 (1H, s), 6.71 (1H, d, J = 8.1 Hz), 6.76 (1H, s), 6.76 (1H, d, J = 8.7 Hz), 6.88 (1H, d, J = 8.7 Hz), 6.95 (1H, d, J = 8.7 Hz), 7.74 (2H, d, J = 8.0 Hz), 7.99 (2H, d, J = 8.0 Hz), 8.03 (1H, s), 8.13 (1H, dd, J = 8.7 Hz, 2.4 Hz), 8.21 (1H, d, J = 2.4 Hz). |

TABLE 250

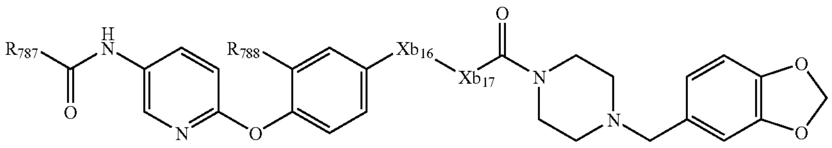

| Example No. | $R_{787}$ | $R_{788}$ | $Xb_{16}$ | $Xb_{17}$ | Form | $^1$H NMR (solvent) δ ppm |
|---|---|---|---|---|---|---|
| 1144 | 4-$CF_3$Ph- | —H | —N($CH_3$)— | —CH($CH_3$)— | free | ($CDCl_3$) 1.30 (3H, d, J = 6.3 Hz), 2.16-2.48 (4H, m), 2.77 (3H, s), 3.26-3.56 (3H, m), 3.39 (2H, s), 3.78 (1H, brs), 4.56 (1H, q, J = 6.6 Hz), 5.92 (2H, s), 6.68-6.77 (4H, m), 6.82 (1H, s), 6.91 (1H, d, J = 8.9 Hz), 7.04 (2H, d, J = 9.1 Hz), 7.76 (2H, d, J = 8.2 Hz), 7.90 (1H, brs), 7.99 (2H, d, J = 8.1 Hz), 8.17 (1H, dd, J = 8.9 Hz, 2.6 Hz), 8.25 (1H, d, J = 2.6 Hz). |
| 1145 | 4-$CF_3$Ph- | —$CH_3$ | —N($CH_3$)— | —CH($CH_3$)— | free | ($CDCl_3$) 1.29 (3H, d, J = 6.6 Hz), 2.14 (3H, s), 2.14-2.22 (1H, m), 2.29-2.35 (2H, m), 2.48 (1H, brs), 2.76 (3H, s), 3.26-3.56 (3H, m), 3.39 (2H, s), 3.78 (1H, brs), 4.57 (1H, q, J = 6.6 Hz), 5.93 (2H, s), 6.58-6.62 (2H, m), 6.68-6.75 (2H, m), 6.83 (1H, brs), 6.86 (1H, d, J = 8.9 Hz), 6.95 (1H, d, J = 9.2 Hz), 7.76 (2H, d, J = 8.3 Hz), 7.90 (1H, brs), 7.99 (2H, d, J = 8.3 Hz), 8.16 (1H, dd, J = 8.9 Hz, 2.8 Hz), 8.23 (1H, d, J = 2.5 Hz). |
| 1146 | 3,4-$Cl_2$Ph- | —H | —$CH_2$— | —NH— | hydrochloride | (DMSO-$d_6$) 2.78-3.10 (2H, m), 3.10-3.35 (4H, m), 4.00-4.19 (2H, m), 4.18-4.32 (4H, m), 6.07 (2H, s), |

TABLE 250-continued

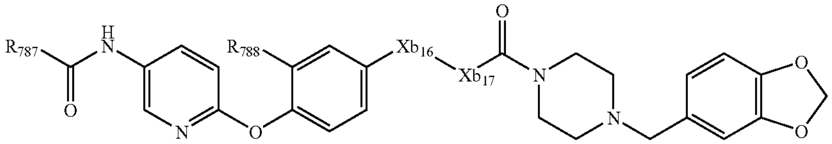

| Example No. | $R_{787}$ | $R_{788}$ | $Xb_{16}$ | $Xb_{17}$ | Form | $^1$H NMR (solvent) δ ppm |
|---|---|---|---|---|---|---|
| | | | | | | 6.95-7.10 (3H, m), 7.06 (2H, d, J = 8.6 Hz), 7.23 (1H, s), 7.30 (2H, d, J = 8.6 Hz), 7.39 (1H, t, J = 5.5 Hz), 7.84 (1H, d, J = 8.4 Hz), 7.97 (1H, dd, J = 8.4 Hz, 2.0 Hz), 8.19 (1H, dd, J = 8.7 Hz, 2.6 Hz), 8.25 (1H, d, J = 2.0 Hz), 8.48 (1H, d, J = 2.6 Hz), 10.62 (1H, s). |
| 1147 | 4-$CF_3$Ph- | —H | —$CH_2$— | —NH— | hydrochloride | (DMSO-$d_6$) 2.80-3.05 (2H, m), 3.11-3.38 (4H, m), 4.00-4.35 (4H, m), 4.24 (2H, s), 6.07 (2H, s), 6.98 (1H, d, J = 8.7 Hz), 6.92-7.10 (2H, m), 7.06 (2H, d, J = 8.6 Hz), 7.24 (1H, d, J = 1.3 Hz), 7.30 (2H, d, J = 8.6 Hz), 7.35-7.45 (1H, m), 7.93 (2H, d, J = 8.3 Hz), 8.19 (2H, d, J = 8.3 Hz), 8.22 (1H, dd, J = 8.7 Hz, 2.5 Hz), 8.51 (1H, d, J = 2.5 Hz), 10.70 (1H, s). |

TABLE 251

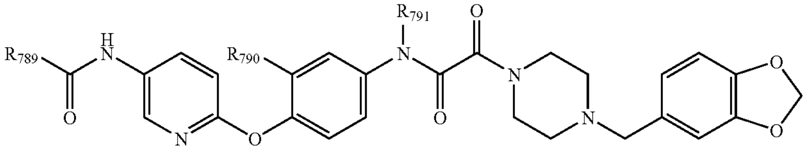

| Example No. | $R_{789}$ | $R_{790}$ | $R_{791}$ | $^1$H NMR (solvent) δ ppm |
|---|---|---|---|---|
| 1148 | 4-$CF_3$Ph- | —$CH_3$ | —H | ($CDCl_3$) 2.17 (3H, s), 2.50-2.55 (4H, m), 3.46 (2H, s), 3.71-3.74 (2H, m), 4.26 (2H, brs), 5.95 (2H, s), 6.74-6.75 (2H, m), 6.86 (1H, brs), 6.91-6.95 (1H, m), 7.04 (1H, d, J = 8.7 Hz), 7.43 (1H, dd, J = 8.7 Hz, 2.5 Hz), 7.56 (1H, d, J = 2.3 Hz), 7.76 (2H, d, J = 8.4 Hz), 7.94 (1H, brs), 7.99 (2H, d, J = 8.1 Hz), 8.20-8.23 (2H, m), 9.17 (1H, brs). |
| 1149 | 3,4-$Cl_2$Ph- | —$CH_3$ | —H | ($CDCl_3$) 2.18 (3H, s), 2.50-2.56 (4H, m), 3.47 (2H, s), 3.72-3.75 (2H, m), 4.25-4.29 (2H, m), 5.96 (2H, s), 6.75 (2H, m), 6.86 (1H, brs), 6.93 (1H, d, J = 8.7 Hz), 7.04 (1H, d, J = 8.7 Hz), 7.44 (1H, dd, J = 8.7 Hz, 2.6 Hz), 7.56-7.57 (1H, m), 7.58 (1H, d, J = 8.3 Hz), 7.70 (1H, brs), 7.71 (1H, dd, J = 8.3 Hz, 2.1 Hz), 7.98 (1H, d, J = 2.1 Hz), 8.15-8.47 (1H, m), 10.54 (1H, brs). |
| 1150 | 3,4-$Cl_2$Ph- | —$CH_3$ | —$CH_3$ | (DMSO-$d_6$) 2.10-2.49 (7H, m), 3.26-3.57 (9H, m), 5.96-5.99 (2H, m), 6.69-6.89 (3H, m), 7.05-7.11 (2H, m), 7.16-7.28 (1H, m), 7.30-7.37 (1H, m), 7.84 (1H, d, J = 8.4 Hz), 7.94 (1H, dd, J = 8.4 Hz, 2.0 Hz), 8.18-8.22 (2H, m), 8.42-8.47 (1H, m), 10.54 (1H, brs). |
| 1151 | 4-$CF_3$Ph- | —$CH_3$ | —$CH_3$ | (DMSO-$d_6$) 2.10-2.46 (7H, m), 3.26-3.57 (9H, m), 5.96-6.00 (2H, m), 6.69-6.89 (3H, m), 7.06-7.12 (2H, m), 7.17-7.29 (1H, m), 7.31-7.37 (3H, m), 7.94 (1H, d, J = 8.6 Hz), 8.16 (2H, d, J = 8.6 Hz), 8.21-8.25 (2H, m), 8.45-8.49 (1H, m), 10.61 (1H, brs). |
| 1152 | 4-$CF_3$Ph- | —H | —$SO_2CH_3$ | ($CDCl_3$) 2.45 (4H, brs), 3.19 (3H, s), 3.39 (2H, brs), 3.46 (2H, s), 3.62 (2H, brs), 4.52 (2H, s), 5.94 (2H, s), 6.74 (2H, brs), 6.84 (1H, brs), 7.00 (1H, d, J = 8.7 Hz), 7.10 (2H, d, J = 8.7 Hz), 7.57 (2H, d, J = 8.7 Hz), 7.75 (2H, d, J = 8.1 Hz), 8.00 (2H, d, J = 8.1 Hz), 8.15-8.24 (2H, m), 8.31 (1H, brs). |
| 1153 | 3,4-$Cl_2$Ph- | —$CH_3$ | —$SO_2CH_3$ | ($CDCl_3$) 2.16 (3H, s), 2.46 (4H, brs), 3.20 (3H, s), 3.40 (2H, brs), 3.47 (2H, s), 3.63 (2H, brs), 4.52 (2H, s), 5.94 (2H, s), 6.70-6.77 (2H, m), 6.83 (1H, brs), 6.95 (1H, d, J = 9.1 Hz), 6.99 (1H, d, J = 8.7 Hz), 7.38-7.57 (3H, m), |

TABLE 251-continued

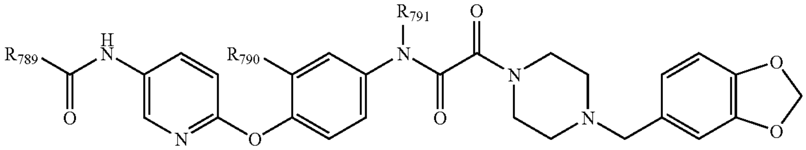

| Example No. | $R_{789}$ | $R_{790}$ | $R_{791}$ | $^1H$ NMR (solvent) δ ppm |
|---|---|---|---|---|
| | | | | 7.71 (1H, dd, J = 8.4 Hz, 2.0 Hz), 7.97 (1H, d, J = 2.0 Hz), 8.11 (1H, brs), 8.17 (1H, dd, J = 8.9 Hz, 2.6 Hz), 8.25 (1H, d, J = 2.6 Hz). |
| 1154 | 4-$CF_3$Ph- | —$CH_3$ | —$SO_2CH_3$ | ($CDCl_3$) 2.18 (3H, s), 2.42-2.46 (4H, m), 3.21 (3H, s), 3.39-3.40 (2H, m), 3.44 (2H, s), 3.62 (2H, brs), 4.53 (2H, s), 5.94 (2H, s), 6.70-6.77 (2H, m), 6.84 (1H, brs), 6.96-7.03 (2H, m), 7.41-7.46 (2H, m), 7.76 (2H, d, J = 8.2 Hz), 7.98-8.01 (3H, m), 8.21 (1H, dd, J = 8.7 Hz, 2.8 Hz), 8.26 (1H, d, J = 2.3 Hz). |
| 1155 | 3,4-$Cl_2$Ph- | —H | —$SO_2CH_3$ | ($CDCl_3$) 2.41-2.45 (4H, m), 3.19 (3H, s), 3.38 (2H, brs), 3.44 (2H, s), 3.61 (2H, brs), 4.52 (2H, s), 5.94 (2H, s), 6.72-6.74 (2H, m), 6.83 (1H, brs), 6.98 (1H, d, J = 8.7 Hz), 7.09 (2H, d, J = 8.7 Hz), 7.55 (1H, d, J = 8.4 Hz), 7.56 (2H, d, J = 8.7 Hz), 7.72 (1H, dd, J = 8.4 Hz, 2.1 Hz), 7.98 (1H, d, J = 2.1 Hz), 8.18 (1H, dd, J = 8.7 Hz, 2.8 Hz), 8.27 (1H, brs), 8.30 (1H, d, J = 2.1 Hz). |

TABLE 252

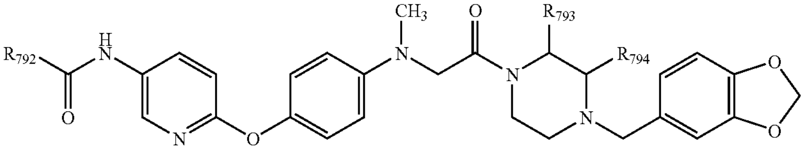

| Example No. | $R_{792}$ | $R_{793}$ | $R_{794}$ | $^1H$ NMR ($CDCl_3$) δ ppm |
|---|---|---|---|---|
| 1156 | 4-$CF_3$Ph- | —H | —$CH_3$ | 1.21 (3H, t, J = 6.8 Hz), 2.05-2.14 (1H, m), 2.44-2.51 (1H, m), 2.70-2.74 (1H, m), 2.83-3.32 (6H, m), 3.55-3.59 (1H, m), 3.84-4.08 (4H, m), 5.94 (2H, s), 6.66 (2H, d, J = 8.9 Hz), 6.74 (2H, brs), 6.81-6.85 (2H, m), 6.97 (2H, d, J = 8.4 Hz), 7.72 (2H, d, J = 8.3 Hz), 7.98 (2H, d, J = 8.3 Hz), 8.11 (1H, d, J = 9.1 Hz), 8.25 (1H, d, J = 2.5 Hz), 8.31 (1H, brs). |
| 1157 | 4-$CF_3$Ph- | —$CH_3$ | —H | 1.26-1.39 (3H, m), 1.99-2.04 (1H, m), 2.13-2.17 (1H, m), 2.64-2.67 (1H, m), 2.79-2.83 (1H, m), 2.98 (4H, brs), 3.31-3.53 (3H, m), 3.97-4.66 (3H, m), 5.95 (2H, s), 6.64 (2H, d, J = 9.1 Hz), 6.74 (2H, brs), 6.82 (1H, d, J = 8.9 Hz), 6.87 (1H, brs), 6.96 (2H, d, J = 9.1 Hz), 7.71 (2H, d, J = 7.9 Hz), 7.98 (2H, d, J = 8.3 Hz), 8.10 (1H, dd, J = 8.9 Hz, 2.5 Hz), 8.25 (1H, d, J = 2.5 Hz), 8.40 (1H, brs). |
| 1158 | 3,4-$Cl_2$Ph- | —H | —$CH_3$ | 1.21 (3H, t, J = 6.8 Hz), 2.07-2.14 (1H, m), 2.43-2.52 (1H, m), 2.70 (1H, brs), 2.83-3.32 (6H, m), 3.55-3.60 (1H, m), 3.83-4.08 (4H, m), 5.94 (2H, s), 6.64 (2H, d, J = 9.1 Hz), 6.74 (2H, brs), 6.81 (1H, d, J = 8.9 Hz), 6.85 (1H, brs), 6.96 (2H, d, J = 8.7 Hz), 7.53 (1H, d, J = 8.4 Hz), 7.71 (1H, dd, J = 8.3 Hz, 2.1 Hz), 7.98 (1H, d, J = 2.0 Hz), 8.05 (1H, dd, J = 8.9 Hz, 2.6 Hz), 8.24 (1H, d, J = 2.5 Hz), 8.31 (1H, brs). |
| 1159 | 3,4-$Cl_2$Ph- | —$CH_3$ | —H | 1.26-1.39 (3H, m), 1.99-2.17 (2H, m), 2.64-2.68 (1H, m), 2.79-2.84 (1H, m), 2.99 (4H, brs), 3.31-3.54 (3H, m), 4.01-4.68 (3H, m), 5.95 (2H, s), 6.64 (2H, d, J = 9.1 Hz), 6.74 (2H, brs), 6.81 (1H, d, J = 8.9 Hz), 6.87 (1H, brs), 6.96 (2H, d, J = 8.9 Hz), 7.53 (1H, d, J = 8.4 Hz), 7.71 (1H, dd, J = 8.4 Hz, 2.0 Hz), 7.98 (1H, d, J = 2.0 Hz), 8.06 (1H, dd, J = 8.9 Hz, 2.5 Hz), 8.24 (1H, d, J = 2.3 Hz), 8.26 (1H, brs). |

TABLE 253

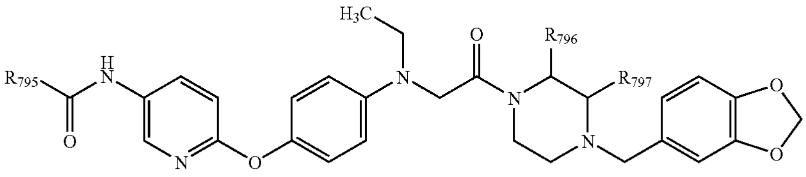

| Example No. | $R_{795}$ | $R_{796}$ | $R_{797}$ | $^1H$ NMR ($CDCl_3$) δ ppm |
|---|---|---|---|---|
| 1160 | 3,4-$Cl_2$Ph- | —H | —$CH_3$ | 1.16-1.19 (6H, m), 2.04-2.14 (1H, m), 2.43-2.52 (1H, m), 2.66-2.74 (1H, m), 2.83-3.36 (5H, m), 3.59-3.63 (1H, m), 3.84-4.08 (4H, m), 5.94 (2H, s), 6.59 (2H, d, J = 8.9 Hz), 6.74 (2H, brs), 6.79 (1H, d, J = 8.9 Hz), 6.85 (1H, brs), 6.92 (2H, d, J = 8.9 Hz), 7.50 (1H, d, J = 8.4 Hz), 7.71 (1H, dd, J = 8.4 Hz, 2.1 Hz), 7.98 (1H, d, J = 2.0 Hz), 8.03 (1H, dd, J = 8.9 Hz, 2.6 Hz), 8.25 (1H, d, J = 2.3 Hz), 8.64 (1H, brs). |
| 1161 | 4-$CF_3$Ph- | —H | —$CH_3$ | 1.09-1.15 (6H, m), 2.04-2.13 (1H, m), 2.43-2.51 (1H, m), 2.66-2.74 (1H, m), 2.83-3.38 (5H, m), 3.58-3.63 (1H, m), 3.84-4.08 (4H, m), 5.94 (2H, s), 6.61 (2H, d, J = 8.9 Hz), 6.74 (2H, brs), 6.81 (1H, d, J = 8.9 Hz), 6.85 (1H, brs), 6.94 (2H, d, J = 8.3 Hz), 7.71 (2H, d, J = 7.8 Hz), 7.99 (2H, d, J = 8.1 Hz), 8.10 (1H, d, J = 9.1 Hz), 8.26 (1H, d, J = 2.5 Hz), 8.50 (1H, brs). |
| 1162 | 3,4-$Cl_2$Ph- | —$CH_3$ | —H | 1.15 (3H, t, J = 7.1 Hz), 1.26-1.43 (3H, m), 2.00 (1H, brs), 2.13 (1H, brs), 2.64-2.68 (1H, m), 2.79-2.83 (1H, m), 3.02-4.68 (9H, m), 5.95 (2H, s), 6.61 (2H, d, J = 9.1 Hz), 6.74 (2H, brs), 6.81 (1H, d, J = 8.7 Hz), 6.87 (1H, brs), 6.94 (2H, d, J = 8.9 Hz), 7.53 (1H, d, J = 8.4 Hz), 7.71 (1H, dd, J = 8.4 Hz, 2.1 Hz), 7.99 (1H, d, J = 2.0 Hz), 8.06 (1H, d, J = 8.9 Hz), 8.25 (1H, d, J = 2.6 Hz), 8.32 (1H, brs). |
| 1163 | 4-$CF_3$Ph- | —$CH_3$ | —H | 1.15 (3H, t, J = 6.9 Hz), 1.26-1.39 (3H, m), 1.99 (1H, brs), 2.13 (1H, brs), 2.63-2.67 (1H, m), 2.79-2.83 (1H, m), 3.00-4.67 (9H, m), 5.95 (2H, s), 6.61 (2H, d, J = 8.4 Hz), 6.74 (2H, brs), 6.82 (1H, d, J = 8.7 Hz), 6.87 (1H, brs), 6.95 (2H, d, J = 8.9 Hz), 7.71 (2H, d, J = 7.9 Hz), 7.99 (2H, d, J = 8.1 Hz), 8.10 (1H, d, J = 8.3 Hz), 8.27 (1H, d, J = 2.5 Hz), 8.38 (1H, brs). |

TABLE 254

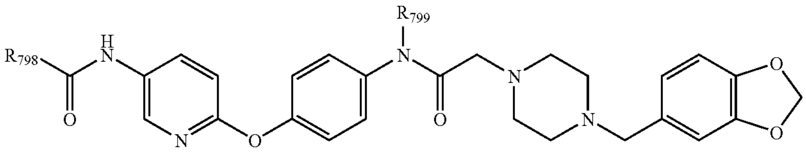

| Example No. | $R_{798}$ | $R_{799}$ | $^1H$ NMR ($CDCl_3$) δ ppm |
|---|---|---|---|
| 1164 | 4-$CF_3$Ph— | —H | 2.52 (4H, brs), 2.64 (4H, brs), 3.12 (2H, s), 3.45 (2H, brs), 5.94 (2H, s), 6.75 (2H, brs), 6.86 (1H, brs), 6.95 (1H, d, J = 8.7 Hz), 7.11 (2H, d, J = 8.9 Hz), 7.60 (2H, d, J = 8.9 Hz), 7.76 (2H, d, J = 8.3 Hz), 7.98 (1H, brs), 8.00 (2H, d, J = 8.3 Hz), 8.21 (1H, dd, J = 8.9 Hz, 2.8 Hz), 8.26 (1H, d, J = 2.5 Hz), 9.16 (1H, brs). |
| 1165 | 3,4-$Cl_2$Ph- | —H | 2.52 (4H, brs), 2.62-2.64 (4H, m), 3.12 (2H, s), 3.45 (2H, brs), 5.95 (2H, s), 6.75 (2H, brs), 6.86 (1H, brs), 6.94 (1H, d, J = 8.7 Hz), 7.10 (2H, d, J = 8.9 Hz), 7.57 (1H, d, J = 8.4 Hz), 7.59 (2H, d, J = 8.9 Hz), 7.72 (1H, dd, J = 8.4 Hz, 2.1 Hz), 7.99 (2H, brs), 8.17 (1H, dd, J = 8.9 Hz, 2.8 Hz), 8.25 (1H, d, J = 2.8 Hz), 9.17 (1H, brs). |
| 1166 | 3,4-$Cl_2$Ph- | —$CH_3$ | 2.44 (8H, brs), 2.95 (2H, s), 3.26 (3H, s), 3.39 (2H, s), 5.92 (2H, s), 6.71 (2H, brs), 6.81 (1H, brs), 7.02 (1H, d, J = 8.7 Hz), 7.14-7.22 (4H, m), 7.58 (1H, d, J = 8.4 Hz), 7.77 (1H, dd, J = 8.4 Hz, 2.1 Hz), 8.05 (1H, d, J = 2.1 Hz), 8.27 (1H, dd, J = 8.7 Hz, 2.6 Hz), 8.32 (1H, d, J = 2.6 Hz), 8.33 (1H, brs). |
| 1167 | 4-$CF_3$Ph- | —$CH_3$ | 2.50 (8H, brs), 2.95 (2H, s), 3.24 (3H, s), 3.47 (2H, s), 5.92 (2H, s), 6.72 (2H, brs), 6.81 (1H, brs), 7.02 (1H, d, J = 8.7 Hz), 7.13-7.21 (4H, m), 7.74 (2H, d, J = 8.4 Hz), 8.05 (2H, d, J = 8.1 Hz), 8.30 (1H, dd, J = 8.9 Hz, 2.5 Hz), 8.35 (1H, d, J = 2.3 Hz), 8.61 (1H, brs). |

TABLE 255

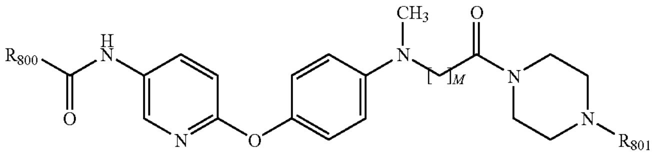

| Example No. | $R_{800}$ | $R_{801}$ | M | Form | $^1$H NMR (solvent) δ ppm |
|---|---|---|---|---|---|
| 1168 | 3,4-$Cl_2$Ph- | piperonyl | 2 | hydrochloride | (DMSO-$d_6$) 2.60-2.61 (2H, m), 2.75-3.08 (6H, m), 3.22-3.60 (5H, m), 4.03 (1H, d, J = 13.9 Hz), 4.20 (2H, d, J = 4.3 Hz), 4.46 (1H, d, J = 13.9 Hz), 6.06 (2H, s), 6.73 (2H, d, J = 8.9 Hz), 6.93-6.99 (5H, m), 7.20 (1H, brs), 7.83 (1H, d, J = 8.4 Hz), 7.96 (1H, dd, J = 8.4 Hz, 2.1 Hz), 8.14 (1H, dd, J = 8.9 Hz, 2.6 Hz), 8.23 (1H, d, J = 2.0 Hz), 8.45 (1H, d, J = 2.6 Hz), 10.57 (1H, brs), 11.00 (1H, brs). |
| 1169 | 4-$CF_3$Ph- | piperonyl | 2 | hydrochloride | (DMSO-$d_6$) 2.60-2.62 (2H, m), 2.88-3.08 (6H, m), 3.23-3.60 (5H, m), 4.01-4.06 (1H, m), 4.20-4.21 (2H, m), 4.43-4.49 (1H, m), 6.07 (2H, s), 6.73 (2H, d, J = 8.6 Hz), 6.94-6.99 (5H, m), 7.20 (1H, brs), 7.93 (2H, d, J = 8.2 Hz), 8.14-8.19 (3H, m), 8.47 (1H, d, J = 2.5 Hz), 10.64 (1H, brs), 11.00 (1H, brs). |
| 1170 | 4-$CF_3$Ph- | benzyl | 0 | free | ($CDCl_3$) 2.25 (4H, t, J = 4.9 Hz), 3.19 (3H, s), 3.23 (4H, t, J = 4.9 Hz), 3.43 (2H, s), 6.95 (1H, d, J = 8.7 Hz), 7.08 (4H, s), 7.20-7.32 (5H, m), 7.75 (2H, d, J = 8.0 Hz), 8.02 (2H, d, J = 8.0 Hz), 8.24 (1H, dd, J = 8.7 Hz, 2.5 Hz), 8.31 (1H, d, J = 2.5 Hz), 8.34 (1H, s). |
| 1171 | 3,4-$Cl_2$Ph- | benzyl | 0 | hydrochloride | (DMSO-$d_6$) 2.70-3.00 (2H, m), 3.14 (3H, s), 2.95-3.30 (4H, m), 3.72 (2H, d, J = 13.7 Hz), 4.29 (2H, s), 7.08 (1H, d, J = 8.7 Hz), 7.11 (2H, d, J = 8.9 Hz), 7.23 (2H, d, J = 8.9 Hz), 7.39-7.48 (3H, m), 7.51-7.60 (2H, m), 7.84 (1H, d, J = 8.5 Hz), 7.97 (1H, dd, J = 8.5 Hz, 2.0 Hz), 8.22 (1H, dd, J = 8.7 Hz, 2.6 Hz), 8.25 (1H, d, J = 20 Hz), 8.53 (1H, d, J = 2.6 Hz), 10.67 (1H, s). |

TABLE 256

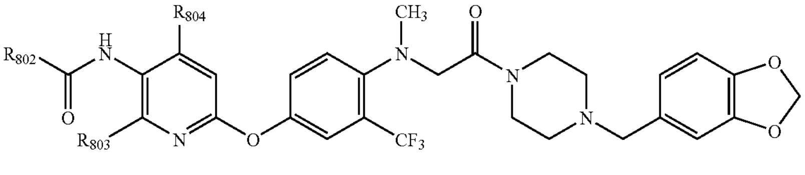

| Example No. | $R_{802}$ | $R_{803}$ | $R_{804}$ | $^1$H NMR ($CDCl_3$) δ ppm |
|---|---|---|---|---|
| 1172 | 3,4-$Cl_2$Ph- | —H | —$CH_3$ | 2.34 (3H, s), 2.34-2.50 (4H, m), 2.78 (3H, s), 3.42 (2H, s), 3.50-3.70 (4H, m), 3.80 (2H, s), 5.95 (2H, s), 6.70-6.80 (2H, m), 6.85-6.89 (2H, m), 7.26-7.35 (1H, m), 7.40 (1H, d, J = 2.8 Hz), 7.51 (1H, d, J = 8.9 Hz), 7.57-7.61 (2H, m), 7.74 (1H, dd, J = 8.3 Hz, 2.0 Hz), 8.01 (1H, d, J = 2.0 Hz), 8.29 (1H, s). |
| 1173 | 4-$CF_3$Ph- | —H | —$CH_3$ | 2.36 (3H, s), 2.36-2.50 (4H, m), 2.79 (3H, s), 3.42 (2H, s), 3.50-3.65 (4H, m), 3.80 (2H, s), 5.94 (2H, s), 6.70-6.75 (2H, m), 6.85-6.90 (2H, m), 7.30 (1H, dd, J = 8.8 Hz, 2.7 Hz), 7.40 (1H, d, J = 2.8 Hz), 7.51 (1H, d, J = 8.8 Hz), 7.68 (1H, brs), 7.76-7.80 (2H, m), 8.01-8.04 (2H, m), 8.34 (1H, s). |

TABLE 256-continued

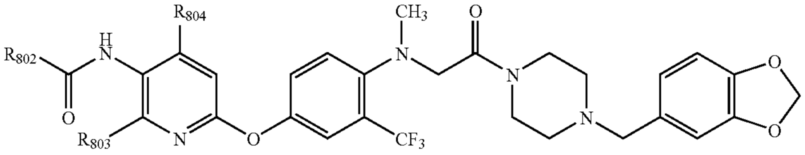

| Example No. | $R_{802}$ | $R_{803}$ | $R_{804}$ | $^1H$ NMR ($CDCl_3$) δ ppm |
|---|---|---|---|---|
| 1174 | 3,4-$Cl_2$Ph- | —$CH_3$ | —H | 2.30-2.44 (4H, m), 2.44 (3H, s), 2.79 (3H, s), 3.42 (2H, s), 3.50-3.65 (4H, m), 3.80 (2H, s), 5.95 (2H, s), 6.65-6.81 (3H, m), 6.85 (1H, s), 7.29 (1H, dd, J = 8.8 Hz, 2.8 Hz), 7.41 (1H, d, J = 2.7 Hz), 7.49 (1H, d, J = 8.8 Hz), 7.59 (1H, d, J = 8.3 Hz), 7.67 (1H, brs), 7.72 (1H, dd, J = 8.3 Hz, 2.1 Hz), 8.00 (1H, d, J = 2.0 Hz), 8.09 (1H, d, J = 8.7 Hz). |
| 1175 | 4-$CF_3$Ph- | —$CH_3$ | —H | 2.35-2.45 (4H, m), 2.45 (3H, s), 2.79 (3H, s), 3.42 (2H, s), 3.50-3.65 (4H, m), 3.80 (2H, s), 5.95 (2H, s), 6.65-6.82 (2H, m), 6.85 (1H, s), 7.30 (1H, dd, J = 8.8 Hz, 2.8 Hz), 7.41 (1H, d, J = 2.8 Hz), 7.50 (1H, d, J = 8.8 Hz), 7.72 (1H, brs), 7.77-7.80 (2H, m), 8.00-8.03 (2H, m), 8.15 (1H, d, J = 8.6 Hz). |

TABLE 257

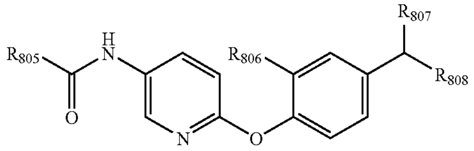

| Example No. | $R_{805}$ | $R_{806}$ | $R_{807}$ | $R_{808}$ | Form | $^1H$ NMR (DMSO-$d_6$) δ ppm |
|---|---|---|---|---|---|---|
| 1176 | 3,4-$Cl_2$Ph- | —H | —H | 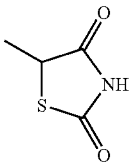 | free | 3.14 (1H, dd, J = 14.0 Hz, 9.4 Hz), 3.40 (1H, dd, J = 14.0 Hz, 4.5 Hz), 4.93 (1H, dd, J = 9.4 Hz, 4.5 Hz), 7.07 (1H, d, J = 8.9 Hz), 7.07 (2H, d, J = 8.4 Hz), 7.29 (2H, d, J = 8.4 Hz), 7.84 (1H, d, J = 8.4 Hz), 7.95 (1H, dd, J = 8.4 Hz, 2.0 Hz), 8.20 (1H, dd, J = 8.9 Hz, 2.5 Hz), 8.22 (1H, d, J = 2.0 Hz), 8.48 (1H, d, J = 2.5 Hz), 10.56 (1H, s), 12.06 (1H, s). |
| 1177 | 4-$CF_3$OPh- | —$CH_3$ | —H | 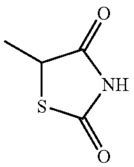 | hydrochloride | 2.09 (3H, s), 3.09 (1H, dd, J = 14.3 Hz, 9.6 Hz), 3.40 (1H, dd, J = 14.3 Hz, 4.3 Hz), 4.93 (1H, dd, J = 9.6 Hz, 4.3 Hz), 6.99 (1H, d, J = 8.1 Hz), 7.02 (1H, d, J = 8.9 Hz), 7.12 (1H, d, J = 8.1 Hz), 7.20 (1H, s), 7.55 (2H, d, J = 8.8 Hz), 8.10 (2H, d, J = 8.8 Hz), 8.20 (1H, dd, J = 8.9 Hz, 2.6 Hz), 8.44 (1H, d, J = 2.6 Hz), 10.54 (1H, s), 12.10 (1H, s). |
| 1178 | 3,4-$Cl_2$Ph- | —H | —$CH_3$ | morpholino | hydrochloride | 1.70 (3H, d, J = 6.9 Hz), 2.94-3.01 (2H, m), 3.63-4.02 (6H, m), 4.50 (1H, t, J = 6.6 Hz), 7.13 (1H, d, J = 9.1 Hz), 7.23 (2H, d, J = 8.7 Hz), 7.64 (2H, d, J = 8.7 Hz), 7.85 (1H, d, J = 8.4 Hz), 7.96 (1H, dd, J = 8.4 Hz, 2.2 Hz), 8.23 (1H, dd, J = 8.9 Hz, 2.6 Hz), 8.24 (1H, d, J = 2.1 Hz), 8.54 (1H, d, J = 2.1 Hz), 10.63 (1H, brs), 10.89 (1H, brs). |
| 1179 | 4-$CF_3$Ph- | —H | —$CH_3$ | morpholino | hydrochloride | 1.72 (3H, d, J = 6.6 Hz), 2.92 (2H, brs), 3.35 (2H, brs), 3.69-3.99 (4H, m), 4.49 (1H, brs), 7.14 (1H, d, J = 8.7 Hz), 7.22 (2H, d, J = 8.3 Hz), 7.69 (2H, d, J = 8.3 Hz), 7.94 (2H, d, J = 8.3 Hz), 8.20 (2H, d, J = 8.1 Hz), 8.28 (1H, d, J = 8.9 Hz), 8.58 (1H, brs), 10.77 (1H, brs), 11.47 (1H, brs). |

TABLE 257-continued
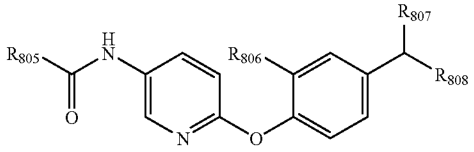
| Example No. | $R_{805}$ | $R_{806}$ | $R_{807}$ | $R_{808}$ | Form | $^1$H NMR (DMSO-$d_6$) δ ppm |
|---|---|---|---|---|---|---|
| 1180 | Ph- | —H | —$CH_3$ | morpholino | hydrochloride | 1.70 (3H, d, J = 6.8 Hz), 2.94 (2H, brs), 3.38-3.43 (2H, m), 3.62-4.02 (4H, m), 4.50 (1H, t, J = 6.6 Hz), 7.12 (1H, d, J = 8.7 Hz), 7.22 (2H, d, J = 8.6 Hz), 7.52-7.65 (5H, m), 7.96-8.00 (2H, m), 8.26 (1H, dd, J = 8.7 Hz, 2.8 Hz), 8.56 (1H, d, J = 2.8 Hz), 10.47 (1H, brs), 10.91 (1H, brs). |
TABLE 258
| Example No. | Chemical stracture | mp (° C.) |
|---|---|---|
| 1181 | 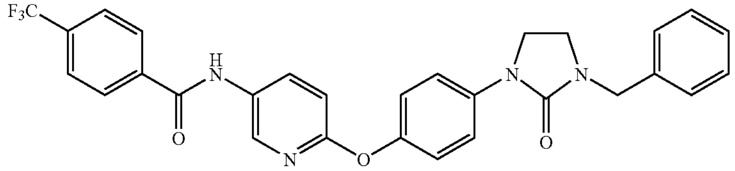 | 203.0-204.0 |
| 1182 | 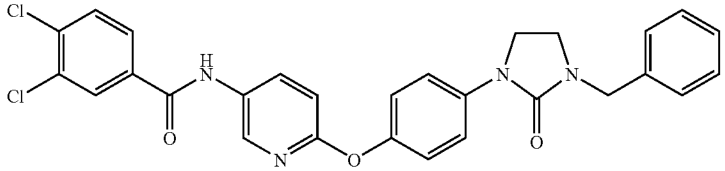 | 186.0-187.0 |
| 1183 | 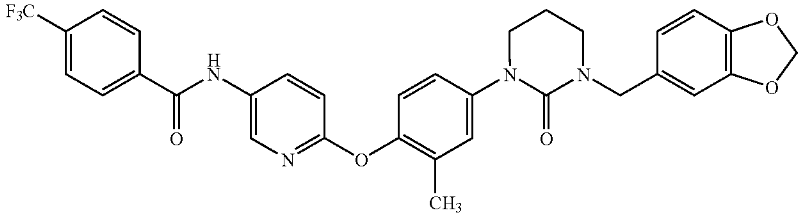 | 165.0-166.0 |
| 1184 | 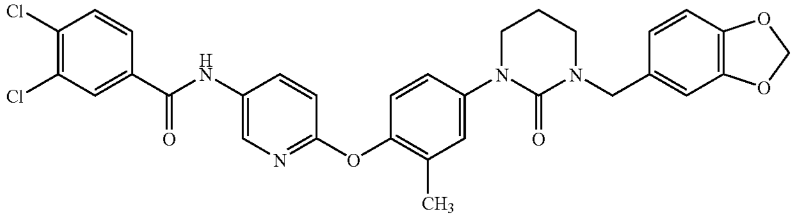 | 122.0-124.0 |
| 1185 | 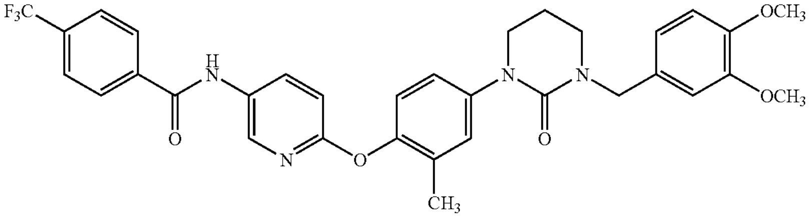 | 155.0-157.0 |

TABLE 258-continued

| Example No. | Chemical structure | mp (° C.) |
|---|---|---|
| 1186 | 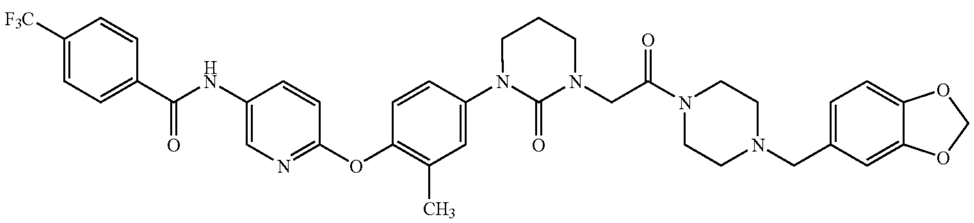 | 182.0-183.5 |
| 1187 | 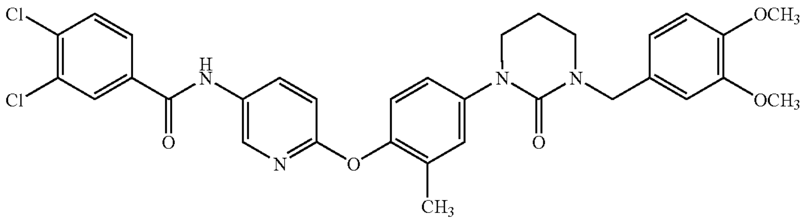 | 117.0-118.0 |
| 1188 | 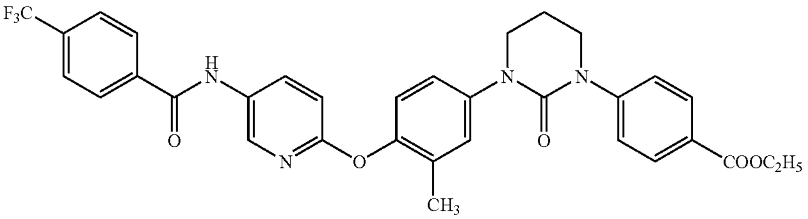 | 160.0-161.0 |

TABLE 259

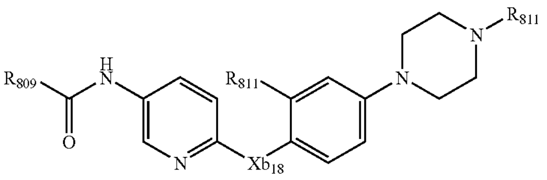

| Example No. | $R_{809}$ | $R_{810}$ | $R_{811}$ | $Xb_{18}$ | $^1H$ NMR ($CDCl_3$) δ ppm |
|---|---|---|---|---|---|
| 1189 | 4-$CF_3$Ph- | —$COOCH_3$ | benzyl | —O— | 2.62 (4H, brs), 3.23 (4H, brs), 3.58 (2H, s), 3.67 (3H, s), 6.95 (1H, d, J = 9.7 Hz), 7.06-7.14 (2H, m), 7.26-7.36 (5H, m), 7.49 (1H, d, J = 2.3 Hz), 7.74 (2H, d, J = 8.3 Hz), 7.87 (1H, s), 7.98 (2H, d, J = 8.1 Hz), 8.16-8.18 (2H, m). |
| 1190 | 3,4-$Cl_2$Ph- | —H | —$COOC(CH_3)_3$ | —O— | 1.49 (9H, s), 3.11 (4H, t, J = 4.8 Hz), 3.58 (4H, t, J = 4.8 Hz), 6.92 (1H, d, J = 9.0 Hz), 6.96 (2H, d, J = 8.5 Hz), 7.06 (2H, d, J = 8.5 Hz), 7.58 (1H, d, J = 8.5 Hz), 7.70 (1H, dd, J = 8.5 Hz, 2.0 Hz), 7.74 (1H, brs), 7.98 (1H, d, J = 2.0 Hz), 8.15 (1H, brd, J = 9.0 Hz), 8.24 (1H, d, J = 2.5 Hz). |
| 1191 | 4-$CF_3$Ph- | —H | —$COOC(CH_3)_3$ | —O— | 1.49 (2H, s), 3.11 (4H, t, J = 5.0 Hz), 3.58 (4H, t, J = 5.0 Hz), 6.93 (1H, d, J = 9.0 Hz), 6.96 (2H, d, J = 9.0 Hz), 7.06 (2H, d, J = 9.0 Hz), 7.77 (2H, d, J = 8.0 Hz), 7.82 (2H, brs), 7.99 (2H, d, J = 8.0 Hz), 8.19 (1H, dd, J = 9.0 Hz, 2.5 Hz), 8.25 (1H, d, J = 2.5 Hz). |
| 1192 | 4-$CF_3$Ph- | —H | —$CH_2COOC_2H_5$ | —$N(CH_3)$— | 1.30 (3H, t, J = 7.1 Hz), 2.77 (4H, t, J = 5.0 Hz), 3.28 (4H, t, J = 5.0 Hz), 3.29 (2H, s), 3.42 (3H, s), 4.22 (2H, |

TABLE 259-continued

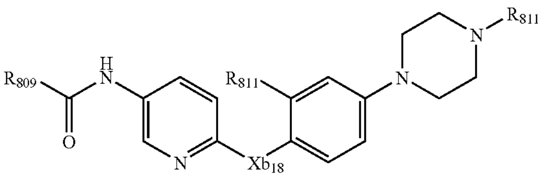

| Example No. | $R_{809}$ | $R_{810}$ | $R_{811}$ | $Xb_{18}$ | $^1H$ NMR ($CDCl_3$) δ ppm |
|---|---|---|---|---|---|
| | | | | | q, J = 7.1 Hz), 6.47 (1H, d, J = 9.2 Hz), 6.96 (2H, d, J = 9.0 Hz), 7.15 (2H, d, J = 9.0 Hz), 7.69 (1H, brs), 7.70 (1H, d, J = 2.5 Hz), 7.74 (2H, d, J = 8.1 Hz), 7.98 (2H, d, J = 8.1 Hz), 8.26 (1H, d, J = 2.5 Hz). |

TABLE 260

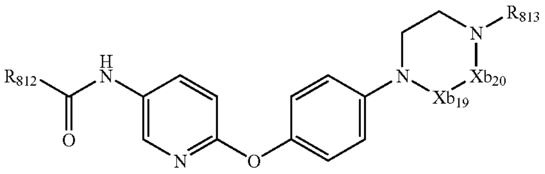

| Example No. | $R_{812}$ | $R_{813}$ | $Xb_{19}$ | $Xb_{20}$ | $^1H$ NMR (solvent) δ ppm |
|---|---|---|---|---|---|
| 1193 | 3,4-$Cl_2$Ph- | —$COOC(CH_3)_3$ | —CO— | —$CH_2$— | ($CDCl_3$) 1.51 (9 H, s), 3.75 (2 H, m), 3.79 (2 H, m), 4.26 (2 H, s), 6.98 (1 H, d, J = 8.8 Hz), 7.14 (2 H, dd, J = 6.9 Hz, 2.1 Hz), 7.28 (2 H, dd, J = 6.9 Hz, 2.1 Hz), 7.58 (1 H, d, J = 8.3 Hz), 7.72 (1 H, dd, J = 8.3 Hz, 2.1 Hz), 7.99 (1 H, d, J = 2.1 Hz), 8.13 (1 H, dd, J = 8.8 Hz, 2.7 Hz), 8.29 (1 H, d, J = 2.7 Hz). |
| 1194 | 3,4-$Cl_2$Ph- | piperonyl | —$CH_2$— | —CO— | (DMSO-$d_6$) 3.22-3.50 (4 H, m), 3.84 (2 H, s), 4.50 (2 H, s), 6.00 (2 H, s), 6.77 (1 H, dd, J = 8.0 Hz, 1.4 Hz), 6.84 (1 H, d, J = 1.4 Hz), 6.87 (1 H, d, J = 8.0 Hz), 6.98 (2 H, d, J = 8.6 Hz), 6.97-7.06 (3 H, m), 7.84 (1 H, d, J = 8.4 Hz), 7.94 (1 H, dd, J = 8.4 Hz, 2.0 Hz), 8.15 (1 H, dd, J = 8.9 Hz, 2.8 Hz), 8.22 (1 H, d, J = 2.0 Hz), 8.44 (1 H, d, J = 2.3 Hz), 10.51 (1 H, s). |
| 1195 | 4-$CF_3$Ph- | piperonyl | —$CH_2$— | —CO— | (DMSO-$d_6$) 3.27-3.40 (2 H, m), 3.40-3.50 (2 H, m), 3.85 (2 H, s), 4.50 (2 H, s), 6.00 (2 H, s), 6.77 (1 H, dd, J = 7.9 Hz, 1.5 Hz), 6.84 (1 H, d, J = 1.5 Hz), 6.88 (1 H, d, J = 7.9 Hz), 6.95-7.07 (5 H, m), 7.93 (2 H, d, J = 8.1 Hz), 8.16 (2 H, d, J = 8.1 Hz), 8.17 (1 H, dd, J = 8.8 Hz, 2.5 Hz), 8.46 (1 H, d, J = 2.5 Hz), 10.60 (1 H, s). |

TABLE 261

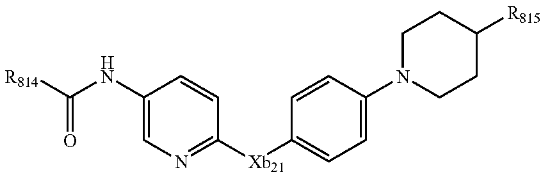

| Example No. | $R_{814}$ | $R_{815}$ | $Xb_{21}$ | $^1$H NMR ($CDCl_3$) δ ppm |
|---|---|---|---|---|
| 1196 | 3,4-$Cl_2$Ph- | —$COOC_2H_5$ | —O— | 1.28 (3 H, t, J = 7.0 Hz), 1.88-1.93 (2 H, m), 2.03 (2 H, brd, J = 10.0 Hz), 2.42 (1 H, m), 2.78 (1 H, t, J = 10.5 Hz), 3.59 (2 H, dt, J = 12.5 Hz, 3.5 Hz), 4.16 (2 H, q, J = 7.0 Hz), 6.90 (1 H, d, J = 9.0 Hz), 6.95 (2 H, d, J = 9.0 Hz), 7.03 (2 H, d, J = 9.0 Hz), 7.58 (1 H, d, J = 8.5 Hz), 7.70 (1 H, brs), 7.71 (1 H, dd, J = 8.5 Hz, 2.0 Hz), 7.98 (1 H, d, J = 2.0 Hz), 8.14 (1 H, dd, J = 9.0 Hz, 2.5 Hz), 8.24 (1 H, d, J = 2.5 Hz). |
| 1197 | 3,4-$Cl_2$Ph- | —$CH_2COOC_2H_5$ | —O— | 1.27 (3 H, t, J = 7.0 Hz), 1.40-1.46 (2 H, m), 1.82 (2 H, brd, J = 13.0 Hz), 1.90 (1 H, m), 2.27 (2 H, d, J = 7.0 Hz), 2.69 (2 H, brt, J = 13.0 Hz), 3.57 (2 H, brd, J = 12.0 Hz), 4.15 (2 H, q, J = 7.0 Hz), 6.83 (1 H, d, J = 9.0 Hz), 6.90 (2 H, d, J = 9.0 Hz), 6.97 (2 H, d, J = 9.0 Hz), 7.49 (1 H, d, J = 8.5 Hz), 7.68 (1 H, dd, J = 8.5 Hz, 2.0 Hz), 7.95 (1 H, d, J = 2.0 Hz), 8.10 (1 H, dd, J = 9.0 Hz, 2.5 Hz), 8.21 (1 H, d, J = 2.5 Hz), 8.48 (1 H, brs). |
| 1198 | 4-$CF_3$Ph- | —$CH_2COOC_2H_5$ | —N($CH_3$)— | 1.28 (3 H, t, J = 7.1 Hz), 1.46 (2 H, qd, J = 12.2 Hz, 3.4 Hz), 1.86 (2 H, d, J = 13.5 Hz), 1.85-2.10 (1 H, m), 2.30 (2 H, d, J = 7.1 Hz), 2.76 (2 H, td, J = 12.2 Hz, 2.2 Hz), 3.42 (3 H, s), 3.68 (2 H, d, J = 12.2 Hz), 4.16 (2 H, q, J = 7.1 Hz), 6.46 (1 H, d, J = 9.0 Hz), 6.96 (2 H, d, J = 8.9 Hz), 7.13 (2 H, d, J = 8.9 Hz), 7.72 (1 H, dd, J = 9.0 Hz, 2.5 Hz), 7.73 (1 H, d, J = 2.5 Hz), 7.74 (2 H, d, J = 8.2 Hz), 7.98 (2 H, d, J = 8.2 Hz), 8.26 (1 H, d, J = 2.5 Hz). |
| 1199 | 4-$CF_3$Ph- | —$CH_2COOC_2H_5$ | —O— | 1.28 (3 H, t, J = 7.0 Hz), 1.44 (2 H, dq, J = 3.5 Hz, 12.0 Hz), 1.84 (2 H, brd, J = 13.0 Hz), 1.93 (1 H, m), 2.29 (2 H, d, J = 7.0 Hz), 2.73 (2 H, dt, J = 2.5 Hz, 12.0 Hz), 3.61 (2 H, brd, J = 12.0 Hz), 4.15 (2 H, q, J = 7.0 Hz), 6.91 (1 H, d, J = 9.0 Hz), 6.96 (2 H, d, J = 9.0 Hz), 7.04 (2 H, d, J = 9.0 Hz), 7.74 (1 H, brs), 7.77 (2 H, d, J = 8.5 Hz), 7.99 (2 H, d, J = 8.5 Hz), 8.18 (1 H, dd, J = 9.0 Hz, 2.5 Hz), 8.25 (1 H, d, J = 2.5 Hz). |
| 1200 | 4-$CF_3$Ph- | —$COOC_2H_5$ | —O— | 1.26 (3 H, t, J = 7.1 Hz), 1.77-1.98 (4 H, m), 2.35-2.43 (1 H, m), 2.68-2.76 (2 H, m), 3.51-3.55 (2 H, m), 4.14 (2 H, q, J = 7.1 Hz), 6.78 (1 H, d, J = 8.9 Hz), 6.85-6.95 (4 H, m), 7.61 (2 H, d, J = 8.2 Hz), 7.93 (2 H, d, J = 8.1 Hz), 8.09 (1 H, dd, J = 8.9 Hz, 2.6 Hz), 8.25 (1 H, d, J = 2.6 Hz), 9.00 (1 H, s). |

TABLE 262

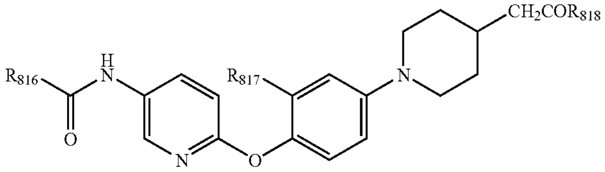

| Example No. | $R_{816}$ | $R_{817}$ | $R_{818}$ | $^1$H NMR ($CDCl_3$) δ ppm |
|---|---|---|---|---|
| 1201 | 4-$CF_3$Ph- | —$CH_3$ | 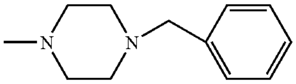 | 1.34-1.43 (2 H, m), 1.80-1.98 (3 H, m), 2.10 (3 H, s), 2.26 (2 H, d, J = 6.8 Hz), 2.38-2.44 (4 H, m), 2.66 (2 H, t, J = 12.2 Hz), 3.46-3.63 (8 H, m), 6.72-6.81 (3 H, m), 6.90 (1 H, d, J = 8.6 Hz), 7.26-7.33 (5 H, m), 7.70 (2 H, d, J = 8.2 Hz), 8.00 (2 H, d, J = 8.1 Hz), 8.15 (1 H, dd, J = 8.9 Hz, 2.8 Hz), 8.25 (1 H, d, J = 2.5 Hz), 8.60 (1 H, s). |
| 1202 | 4-$CF_3$Ph- | —$CH_3$ | 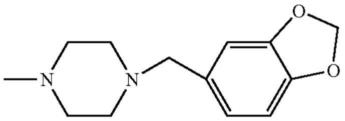 | 1.31-1.43 (2 H, m), 1.79-1.98 (3 H, m), 2.11 (3 H, s), 2.26 (2 H, d, J = 6.8 Hz), 2.36-2.39 (4 H, m), 2.66 (2 H, t, J = 12.0 Hz), 3.42 (2 H, s), 3.45-3.61 (6 H, m), 6.70-6.92 (7 H, m), 7.70 (2 H, d, J = 8.2 Hz), 7.99 (2 H, d, J = 8.1 Hz), 8.15 (1 H, dd, J = 8.9 Hz, 2.8 Hz), 8.25 (1 H, d, J = 2.5 Hz), 8.55 (1 H, s). |
| 1203 | 3,4-$Cl_2$Ph- | —$CH_3$ | 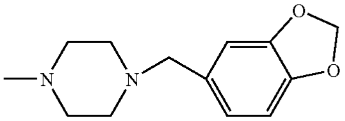 | 1.29-1.41 (2 H, m), 1.77-1.98 (3 H, m), 2.09 (3 H, s), 2.26 (2 H, d, J = 6.8 Hz), 2.34-2.40 (4 H, m), 2.62 (2 H, t, J = 12.0 Hz), 3.41 (2 H, s), 3.46-3.60 (6 H, m), 6.70-6.90 (7 H, m), 7.49 (1 H, d, J = 8.4 Hz), 7.73 (1 H, dd, J = 8.2 Hz, 2.0 Hz), 7.99 (1 H, d, J = 2.0 Hz), 8.12 (1 H, dd, J = 8.9 Hz, 2.6 Hz), 8.25 (1 H, d, J = 2.6 Hz), 8.99 (1 H, s). |
| 1204 | 3,4-$Cl_2$Ph- | —$CH_3$ | 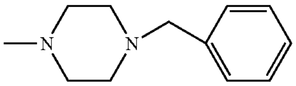 | 1.29-1.41 (2 H, m), 1.77-1.98 (3 H, m), 2.09 (3 H, s), 2.26 (2 H, d, J = 6.8 Hz), 2.37-2.44 (4 H, m), 2.63 (2 H, t, J = 11.9 Hz), 3.48-3.63 (8 H, m), 6.70-6.78 (2 H, m), 6.88 (1 H, d, J = 8.6 Hz), 7.26-7.33 (6 H, m), 7.48 (1 H, d, J = 8.4 Hz), 7.72 (1 H, dd, J = 8.4 Hz, 2.1 Hz), 7.99 (1 H, d, J = 2.1 Hz), 8.12 (1 H, dd, J = 8.9 Hz, 2.6 Hz), 8.26 (1 H, d, J = 2.6 Hz), 9.03 (1 H, s). |
| 1205 | 4-$CF_3$Ph- | —$OCH_3$ | —$OC_2H_5$ | 1.27 (3 H, t, J = 7.1 Hz), 1.39-1.42 (2 H, m), 1.80-1.85 (3 H, m), 2.28 (2 H, d, J = 6.9 Hz), 2.70 (3 H, t, J = 10.1 Hz), 3.56 (2 H, d, J = 12.2 Hz), 3.66 (3 H, s), 4.14 (2 H, q, J = 7.3 Hz), 6.43 (1 H, dd, J = 8.7 Hz, 2.5 Hz), 6.51 (1 H, d, J = 2.5 Hz), 6.78 (1 H, d, J = 8.9 Hz), 6.90 (1 H, d, J = 8.7 Hz), 7.63 (2 H, d, J = 8.6 Hz), 7.96 (2 H, d, J = 8.2 Hz), 8.08 (1 H, dd, J = 8.9 Hz, 2.6 Hz), 8.18 (1 H, d, J = 2.6 Hz), 8.95 (1 H, s). |

TABLE 263

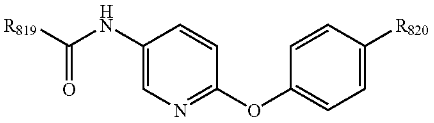

| Example | $R_{819}$ | $R_{820}$ | mp (° C.) or $^1$H NMR (solvent) δppm |
|---|---|---|---|
| 1206 | 3,4-$Cl_2$Ph- | morpholino | $^1$H NMR (DMSO-$d_6$) 3.07-3.10(4 H, m), 3.73-3.77(4 H, m), 6.96-7.04(5 H, m), 7.83(1 H, d, J = 8.2 Hz), 7.94(1 H, dd, J = 8.2 Hz, 2.0 Hz), |

TABLE 263-continued

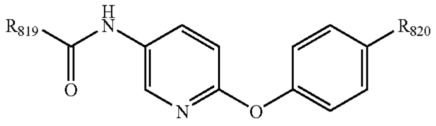

| Example | $R_{819}$ | $R_{820}$ | mp (° C.) or $^1$H NMR (solvent) δppm |
|---|---|---|---|
| | | | 8.15(1 H, dd, J = 8.9 Hz, 2.6 Hz), 8.22(1 H, d, J = 2.0 Hz), 8.45(1 H, d, J = 2.6 Hz), 8.;22(1 H, d, J = 2.0 Hz), 8.45(1 H, d, J = 2.6 Hz), 10.51(1 H, brs). |
| 1207 | 3,4-$Cl_2$Ph- | 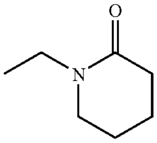 | $^1$H NMR ($CDCl_3$) 1.72-1.90(4 H, m), 2.40-2.53(2 H, m), 3.20-3.32(2 H, m), 4.58(2 H, s), 6.95(1 H, d, J = 8.9 Hz), 7.08(2 H, d, J = 8.6 Hz), 7.27(2 H, d, J = 8.6 Hz), 7.58(1 H, d, J = 8.6 Hz), 7.73(1 H, dd, J = 8.6 Hz, 2.0 Hz), 8.01(1 H, d, J = 2.0 Hz), 8.11(1 H, s), 8.19(1 H, dd, J = 8.9 Hz, 2.3 Hz), 8.28(1 H, d, J = 2.3 Hz). |
| 1208 | 4-$CF_3$Ph- | —NHCONHPh | mp 240.0-240.5 |
| 1209 | 3,4-$Cl_2$Ph- | 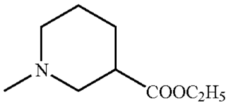 | $^1$H NMR ($CDCl_3$) 1.28(3 H, t, J = 7.0 Hz), 1.60-1.70(2 H, m), 1.83(1 H, m), 2.03(1 H, m), 2.69(1 H, m), 2.82(1 H, brt, J = 12.0 Hz), 3.03(1 H, dd, J = 12.0 Hz, 10.0 Hz),3.42(1 H, brd, J = 12.0 Hz), 3.65(1 H, brd, J = 12.0 Hz), 41.7(2 H, q, J = 7.0 Hz), 6.90(1 H, d, J = 9.0 Hz), 6.97(2 H, d, J = 9.0 Hz), 7.03(2 H, d, J = 9.0 Hz), 7.58(1 H, d, J = 8.5 Hz), 7.70(1 H, dd, J = 8.5 Hz, 2.0 Hz), 7.75(1 H, s), 7.97(1 H, d, J = 2.0 Hz), 8.14(1 H, brd, J = 9.0 Hz), 8.23(1 H, d, J = 2.5 Hz). |
| 1210 | 3,4-$Cl_2$Ph- | 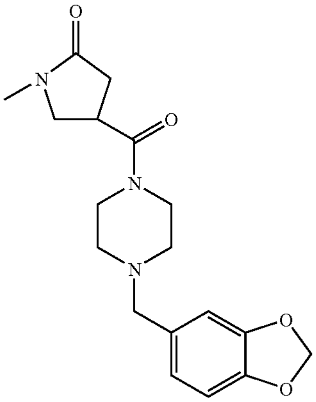 | $^1$H NMR (DMSO-$d_6$) 2.33-2.38(4 H, m), 2.65-2.83(2 H, m), 3.41(2 H, s), 3.45-3.57(4 H, m), 3.65-3.75(1 H, m), 3.91-4.08(2 H, m), 6.00(2 H, s), 6.76(1 H, dd, J = 1.5 Hz, 8.1 Hz), 6.84-6.88(2 H, m), 7.07(1 H, d, J = 8.9 Hz), 7.14(2 H, d, J = 8.9 Hz), 7.67(2 H, d, J = 9.1 Hz), 7.85(1 H, d, J = 8.4 Hz), 7.95(1 H, dd, J = 2.0 Hz, 8.4 Hz), 8.19(1 H, dd, J = 2.6 Hz, 8.9 Hz), 8.23(1 H, d, J = 2.1 Hz), 8.47(1 H, d, J = 2.6 Hz), 10.56(1 H, s). |
| 1211 | 4-$CF_3$Ph- | 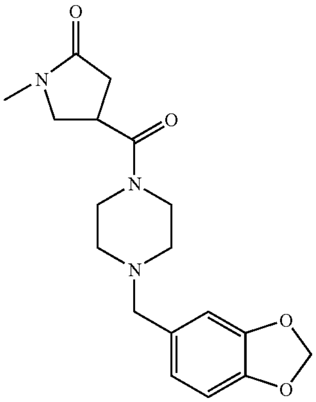 | $^1$H NMR (DMSO-$d_6$) 2.33-2.38(4 H, m), 2.65-2.83(2 H, m), 3.41(2 H, s), 3.51(4 H, brs), 3.65-3.75(1 H, m), 3.91-4.08(2 H, m), 5.99(2 H, s), 6.76(1 H, dd, J = 1.3 Hz, 7.9 Hz), 6.84-6.88(2 H, m), ), 7.08(1 H, d, J = 8.9 Hz), 7.15(2 H, d, J = 6.9 Hz), 7.68(2 H, d, J = 6.9 Hz), 7.94(2 H, d, J = 8.6 Hz), 8.17(2 H, d, J = 8.1 Hz), 8.23(1 H, dd, J = 2.6 Hz, 8.9 Hz), 8.50(1 H, d, J = 2.6 Hz), 10.64(1 H, s). |

TABLE 264

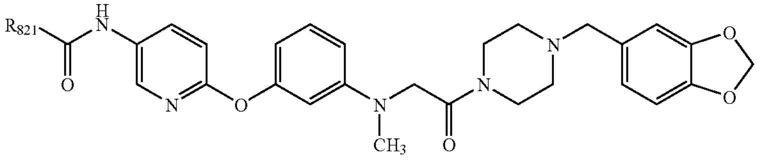

| Example No. | $R_{821}$ | $^1$H NMR (DMSO-$d_6$) δ ppm |
|---|---|---|
| 1212 | 3,4-$Cl_2$Ph- | 2.25-2.33 (4 H, m), 2.92 (3 H, s), 3.36 (2 H, s), 3.42 (4 H, brs), 4.23 (2 H, s), 5.98 (2 H, s), 6.29-6.32 (2 H, m), 6.42-6.45 (1 H, m), 6.70-6.74 (1 H, m), 6.80-6.84 (2 H, m), 6.97 (1 H, d, J = 8.9 Hz), 7.11-7.17 (1 H, m), 7.84 (1 H, d, J = 8.4 Hz), 7.95 (1 H, dd, J = 8.4 Hz, 2.0 Hz), 8.16-8.22 (2 H, m), 8.52 (1 H, d, J = 2.5 Hz), 10.55 (1 H, s). |
| 1213 | 4-$CF_3$Ph- | 2.26-2.33 (4 H, m), 2.92 (3 H, s), 3.37-3.41 (6 H, m), 4.23 (2 H, s), 5.98 (2 H, s), 6.29-6.34 (2 H, m), 6.42-6.45 (1 H, m), 6.70-6.74 (1 H, m), 6.80-6.84 (2 H, m), 6.98 (1 H, d, J = 8.9 Hz), 7.11-7.17 (1 H, m), 7.93 (2 H, d, J = 8.3 Hz), 8.16 (2 H, d, J = 8.1 Hz), 8.21 (1 H, dd, J = 8.9 Hz, 2.6 Hz), 8.54 (1 H, d, J = 2.3 Hz), 10.63 (1 H, s). |

TABLE 265

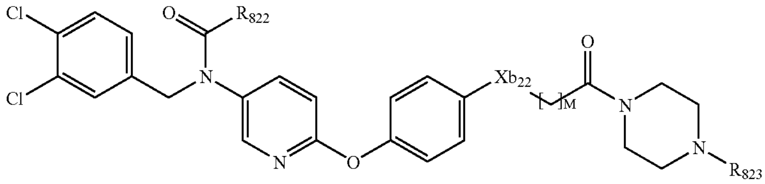

| Example No. | $R_{822}$ | $R_{823}$ | $Xb_{22}$ | M | Form | $^1$H NMR (solvent) δ ppm |
|---|---|---|---|---|---|---|
| 1214 | —$CH_3$ | piperonyl | —N($CH_3$)— | 1 | free | ($CDCl_3$) 1.90 (3 H, s), 2.41-2.45 (4 H, m), 3.03 (3 H, s), 3.43 (2 H, s), 3.49( 2 H, brs), 3.63 (2 H, brs), 4.09 (2 H, s), 4.77 (2 H, s), 5.95 (2 H, s), 6.70 (2 H, d, J = 9.1 Hz), 6.74-6.75 (2 H, m), 6.81-6.85 (2 H, m), 7.00 (2 H, d, J = 9.1 Hz), 7.04 (1 H, dd, J = 8.4 Hz, 2.1 Hz), 7.24 (1 H, dd, J = 8.7 Hz, 2.87 Hz), 7.31 (1 H, d, J = 2.1 Hz), 7.35 (1 H, d, J = 8.1 Hz), 7.83 (1 H, d, J = 2.6 Hz). |
| 1215 | —$C_2H_5$ | piperonyl | —N($CH_3$)— | 1 | free | ($CDCl_3$) 1.08 (3 H, t, J = 7.4 Hz), 2.07 (2 H, q, J = 7.4 Hz), 2.41-2.45 (4 H, m), 3.03 (3 H, s), 3.43 (2 H, s), 3.48 (2 H, brs), 3.63 (2 H, brs), 4.09 (2 H, s), 4.77 (2 H, s), 5.95 (2 H, s), 6.70 (2 H, d, J = 9.2 Hz), 6.73-6.74 (2 H, m), 6.82 (1 H, d, J = 8.7 Hz), 6.85 (1 H, brs), 7.00 (2 H, d, J = 9.1 Hz), 7.04 (1 H, dd, J = 8.3 Hz, 2.0 Hz), 7.22 (1 H, dd, J = 8.7 Hz, 2.8 Hz), 7.30 (1 H, d, J = 2.0 Hz), 7.34 (1 H, d, J = 8.3 Hz), 7.82 (1 H, d, J = 2.5 Hz). |
| 1216 | —$CH_3$ | benzyl | none | 0 | hydro-chloride | (DMSO-$d_6$) 1.87 (3 H, s), 3.14 (2 H, brs), 3.37 (6 H, brs), 4.35 (2 H, s), 4.85 (2 H, s), 7.13 (1 H, d, J = 8.9 Hz), 7.22 (2 H, d, J = 8.4 Hz), 7.41-7.58 (10 H, m), 7.80 (1 H, dd, J = 8.9 Hz, 2.6 Hz), 8.03 (1 H, d, J = 2.6 Hz), 10.88 (1 H, brs). |

Example 1217

Production of 1H-indole-2-carboxylic acid {6-[4-(2,4-dioxothiazolidine-5-ylmethyl)-2-methylphenoxy]pyridin-3-yl}amide To a solution of 5-[4-(5-aminopyridin-2-yloxy)-3-methylbenzyl]thiazolidine-2,4-dione (150 mg, 0.46 mmol) in DMF (5 mL) were added indole-2-carboxylic acid (74 mg, 0.46 mmol), 1-hydroxybenzotriazole monohydrate (70 mg, 0.46 mmol) and 1-ethyl-3-(3-dimethylaminopropyl)carbodiimide hydrochloride (110 mg, 0.57 mmol), and the resulting solution was stirred for 5 days at room temperature. This reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, evaporated, and the residue was then purified by silica gel column chromatography (chloroform:methanol=30:1). To the obtained powdery substance was added ethanol, the resulting solution was filtered and the filtrate was washed with ethanol, to thereby yield 100 mg of the title compound.

Appearance: White powder $^{1}H$ NMR (DMSO-$d_6$) δ 2.10 (3H, s), 3.09 (1H, dd, J=14.2 Hz, 9.7 Hz), 3.40 (1H, dd, J=14.2 Hz, 4.2 Hz), 4.94 (1H, dd, J=9.7 Hz, 4.2 Hz), 6.99 (1H, d, J=8.2 Hz), 7.04 (1H, d, J=8.9 Hz), 7.05-7.16 (2H, m), 7.20 (1H, s), 7.24 (1H, dd, J=7.0 Hz, 1.0 Hz), 7.39 (1H, d, J=1.6 Hz), 7.46 (1H, d, J=8.2 Hz), 7.68 (1H, d, J=7.7 Hz), 8.21 (1H, dd, J=8.9 Hz, 2.8 Hz), 8.49 (1H, d, J=2.8 Hz), 10.37 (1H, s), 11.80 (1H, s), 12.09 (1H, s).

The following compounds were produced in the same manner as in Example 1217.

TABLE 266

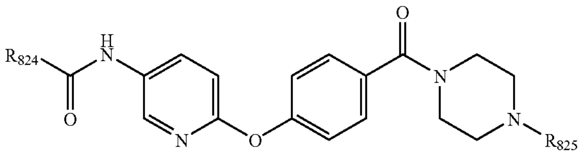

| Example No. | $R_{824}$ | $R_{825}$ | Form | $^{1}H$ NMR (solvent) δ ppm |
|---|---|---|---|---|
| 1218 | 3,4-$(CH_3)_2$Ph- | 4-$CH_3OPhCH_2$— | free | ($CDCl_3$) 2.34 (6 H, s), 2.45 (4 H, brs), 3.45 (2 H, s), 3.47-3.79 (4 H, m), 3.81 (3 H, s), 6.83-6.89 (2 H, m), 6.97 (1 H, d, J = 8.9 Hz), 7.11-7.16 (2 H, m), 7.21-7.26 (3 H, m), 7.41-7.46 (2 H, m), 7.59-7.62 (1 H, m), 7.67 (1 H, d, J = 1.9 Hz), 7.92 (1 H, brs), 8.23-8.30 (1 H, m), 8.31 (1 H, d, J = 2.4 Hz). |
| 1219 | 2-$(CH_3)_2$NPh- | benzyl | trihydro-chloride | (DMSO-$d_6$) 3.07 (6 H, s), 3.17-3.48 (8 H, m), 4.35 (2 H, s), 7.16-7.21 (3 H, m), 7.41-7.54 (6 H, m), 7.59-7.70 (4 H, m), 7.92 (1 H, d, J = 7.1 Hz), 8.27 (1 H, dd, J = 2.8 Hz, 8.7 Hz), 8.55 (1 H, d, J = 2.1 Hz), 11.30 (1 H, s). |
| 1220 | 3,5-$(CH_3)_2$Ph- | benzyl | hydro-chloride | (DMSO-$d_6$) 2.36 (6 H, s), 3.00-3.20 (2 H, m), 3.20-3.40 (2 H, m), 3.47 (2 H, brs), 4.40 (2 H, brs), 4.33 (2 H, s), 7.13 (1 H, d, J = 8.9 Hz), 7.19 (2 H, d, J = 8.6 Hz), 7.24 (1 H, s), 7.40-7.70 (7 H, m), 7.51 (2 H, d, J = 8.6 Hz), 8.26 (1 H, dd, J = 8.9 Hz, 2.6 Hz), 8.56 (1 H, d, J = 2.6 Hz), 10.41 (1 H, s). |
| 1221 | 2,3-$(CH_3O)_2$Ph- | benzyl | hydro-chloride | (DMSO-$d_6$) 3.00-3.65 (6 H, m), 3.80 (3 H, s), 3.86 (3 H, s), 4.20 (2 H, brs), 4.33 (2 H, brs), 7.09-7.25 (6 H, m), 7.40-7.80 (7 H, m), 8.23 (1 H, dd, J = 8.9 Hz, 2.3 Hz), 8.52 (1 H, d, J = 2.3 Hz), 10.43 (1 H, s). |
| 1222 | 4-$(CH_3)_2$NPh- | benzyl | free | ($CDCl_3$) 2.48 (4 H, brs), 3.06 (6 H, s), 3.55 (2 H, s), 3.70 (4 H, brs), 6.71 (2 H, d, J = 9.0 Hz), 6.96 (1 H, d, J = 9.6 Hz), 7.13 (2 H, d, J = 8.7 Hz), 7.20-7.38 (5 H, m), 7.43 (2 H, d, J = 8.7 Hz), 7.71 (1 H, brs), 7.78 (2 H, d, J = 9.0 Hz), 8.20-8.30 (2 H, m). |
| 1223 | 1-naphthyl | benzyl | free | (DMSO-$d_6$) 2.41 (4 H, brs), 3.51 (4 H, brs), 3.52 (2 H, s), 7.17 (3 H, d, J = 8.7 Hz), 7.21-7.38 (5 H, m), 7.44 (2 H, d, J = 8.7 Hz), 7.55-7.69 (3 H, m), 7.80 (1 H, d, J = 6.4 Hz), 7.98-8.06 (1 H, m), 8.10 (1 H, d, J = 8.1 Hz), 8.18-8.27 (1 H, m), 8.32 (1 H, dd, J = 8.7 Hz, 2.6 Hz), 8.58 (1 H, d, J = 2.6 Hz), 10.76 (1 H, s). |

TABLE 267
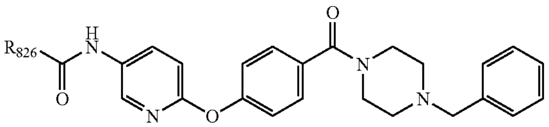
| Example No. | $R_{826}$ | Form | mp (° C.) |
|---|---|---|---|
| 1224 | 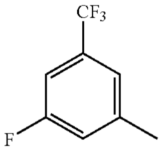 | maleate | 172-175 |
| 1225 | 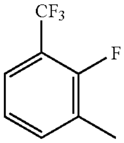 | maleate | 143-146 |
| 1226 | 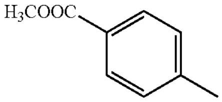 | free | 187-189 |
TABLE 267-continued
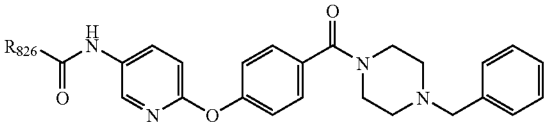
| Example No. | $R_{826}$ | Form | mp (° C.) |
|---|---|---|---|
| 1227 | 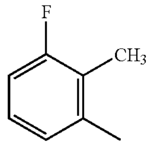 | free | 191-192 |
| 1228 | 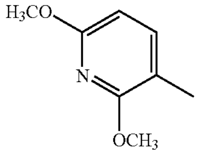 | maleate | 180-182 |
| 1229 | 2,5-$(CF_3)_2$Ph- | dihydro-chloride | 152-156 |
| 1230 | 2,5-$F_2$Ph- | maleate | 182-184 |
| 1231 | 2,3-$Cl_2$Ph- | free | 195-196 |
| 1232 | 3-PhOPh- | free | 171-172 |
| 1233 | 3-$CF_3$Ph- | dihydro-chloride | 146-146 |
TABLE 268
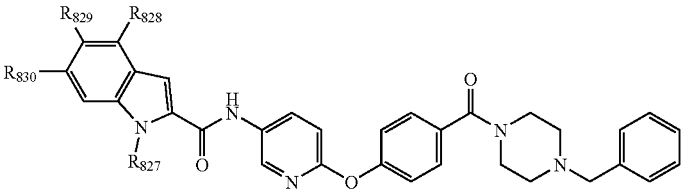
| Example No. | $R_{827}$ | $R_{828}$ | $R_{829}$ | $R_{830}$ | MS ($M^+$ + H) |
|---|---|---|---|---|---|
| 1234 | —H | —H | —H | —H | 532 |
| 1235 | —H | —H | —$OCH_3$ | —H | 562 |
| 1236 | —H | —H | —Cl | —H | 566 |
| 1237 | —H | —H | —F | —H | 550 |
| 1238 | —$CH_3$ | —H | —H | —H | 546 |
| 1239 | —H | —H | —Br | —H | 612 |
| 1240 | —H | —H | —$CH_3$ | —H | 546 |
| 1241 | —H | —H | —$OCF_3$ | —H | 616 |
| 1242 | —H | —$OCH_3$ | —H | —H | 562 |
| 1243 | —H | —Cl | —H | —H | 566 |
| 1244 | —H | —H | —H | —$OCH_3$ | 562 |
| 1245 | —H | —Cl | —H | —Cl | 600 |
| 1246 | —H | —H | —H | —Cl | 566 |
| 1247 | —H | —H | —$OCH_3$ | —$OCH_3$ | 592 |

TABLE 269

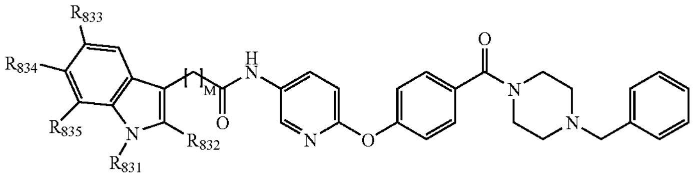

| Example No. | $R_{831}$ | $R_{832}$ | $R_{833}$ | $R_{834}$ | $R_{835}$ | M | MS ($M^+$ + H) |
|---|---|---|---|---|---|---|---|
| 1248 | —H | —H | —H | —H | —H | 0 | 532 |
| 1249 | —H | —H | —H | —H | —H | 2 | 560 |
| 1250 | —H | —H | —H | —H | —H | 1 | 546 |
| 1251 | —H | —H | —Cl | —H | —H | 1 | 580 |
| 1252 | —H | —$CH_3$ | —H | —H | —H | 1 | 560 |
| 1253 | —H | —$CH_3$ | —$CH_3$ | —H | —H | 1 | 574 |
| 1254 | —H | —$CH_3$ | —$OCH_3$ | —H | —H | 1 | 590 |
| 1255 | —H | —$CH_3$ | —F | —H | —H | 1 | 578 |
| 1256 | —H | —$CH_3$ | —$C(CH_3)_3$ | —H | —H | 1 | 616 |
| 1257 | —H | —$CH_3$ | —$CH_3$ | —H | —$CH_3$ | 1 | 588 |
| 1258 | —H | —$CH_3$ | —Br | —H | —F | 1 | 658 |
| 1259 | —H | —$CH_3$ | —H | —H | —F | 1 | 578 |
| 1260 | —H | —$CH_3$ | —$C_2H_5$ | —H | —H | 1 | 588 |
| 1261 | —H | —H | —F | —H | —H | 1 | 564 |
| 1262 | —H | —H | —H | —F | —H | 1 | 564 |
| 1263 | —$CH_3$ | —H | —H | —H | —H | 1 | 560 |
| 1264 | —H | —H | —$OCH_3$ | —H | —H | 1 | 576 |
| 1265 | —H | —H | —H | —H | —$CH_3$ | 1 | 560 |
| 1266 | —H | —H | —$CH_3$ | —H | —H | 1 | 560 |
| 1267 | —H | —H | —Br | —H | —H | 1 | 626 |

TABLE 270

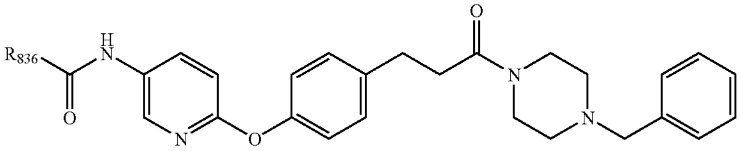

| Example No. | $R_{836}$ | $^1H$ NMR (solvent) δ ppm |
|---|---|---|
| 1268 | 3-CNPh- | ($CDCl_3$) 2.37-2.44 (4 H, m), 2.57-2.63 (2 H, m), 2.88-2.95 (2 H, m), 3.42-3.45 (2 H, m), 3.55 (2 H, s), 3.60-3.64 (2 H, m), 6.90 (1 H, d, J = 8.9 Hz), 7.00 (2 H, d, J = 8.6 Hz), 7.16 (2 H, d, J = 8.6 Hz), 7.25-7.31 (5 H, m), 7.54-7.76 (1 H, m) 7.76-7.80 (1 H, m), 8.19-8.26 (3 H, m), 8.37 (1 H, d, J = 2.6 Hz), 9.41 (1 H, brs). |
| 1269 | 2-CNPh- | ($CDCl_3$) 2.35-2.45 (4 H, m), 2.60-2.66 (2 H, m), 2.95-3.01 (2 H, m), 3.40-3.44 (2 H, m), 3.52 (2 H, s), 3.63-3.67 (2 H, m), 7.05-7.13 (3 H, m), 7.23-7.32 (8 H, m), 7.69-7.80 (3 H, m), 7.93-7.96 (2 H, m), 8.23 (1 H, d, J = 2.5 Hz). |
| 1270 | 3-$N(CH_3)_2$Ph- | ($CDCl_3$) 2.35-2.44 (4 H, m), 2.57-2.62 (2 H, m), 2.91-2.98 (8 H, m), 3.39-3.43 (2 H, m), 3.53 (2 H, s), 3.62-3.65 (2 H, m), 6.84-6.92 (2 H, m), 7.02 (2 H, d, J = 8.6 Hz), 7.11 (1 H, d, J = 7.9 Hz), 7.19 (2 H, d, J = 8.6 Hz), 7.25-7.35 (7 H, m), 8.22-8.37 (3 H, m). |
| 1271 | 3-$CH_3$Ph- | ($CDCl_3$) 2.36-2.46 (7 H, m), 2.57-2.63 (2 H, m), 2.91-2.97 (2 H, m), 3.40-3.44 (2 H, m), 3.56 (2 H, s), 3.62-3.66 (2 H, m), 6.91 (1 H, d, J = 8.9 Hz), 7.00-7.05 (2 H, m), 7.19 (2 H, d, J = 8.6 Hz), 7.25-7.35 (7 H, m), 7.66-7.71 (2 H, m), 8.23-8.31 (2 H, m), 8.43 (1 H, brs). |
| 1272 | 3,4-$(CH_3)_2$Ph- | ($CDCl_3$) 2.31 (3 H, s), 2.32 (3 H, s), 2.36-2.46 (4 H, m), 2.58-2.64 (2 H, m), 2.92-2.98 (2 H, m), 3.41-3.44 (2 H, m), 3.56 (2 H, s), 3.63-3.67 (2 H, m), 6.90-6.94 (1 H, m), 7.03 (2 H, d, J = 8.4 Hz), 7.19-7.37 (8 H, m), 7.58-7.73 (2 H, m), 8.21-8.28 (3 H, m). |
| 1273 | 2-FPh- | (DMSO-$d_6$) 2.28-2.31 (4 H, m), 2.59-2.64 (2 H, m), 2.78-2.84 (2 H, m), 3.44-3.47 (6 H, m), 7.01 (2 H, d, J = 8.4 Hz), 7.02-7.05 (1 H, m), 7.26 (2 H, d, J = 8.4 Hz), 7.31-7.40 (7 H, m), 7.51-7.61 (1 H, m), 7.64-7.72 (1 H, m), 8.18 (1 H, dd, J = 8.9 Hz, 2.6 Hz), 8.45 (1 H, d, J = 2.5 Hz), 10.54 (1 H, brs). |
| 1274 | 3-FPh- | (DMSO-$d_6$) 2.30 (4 H, brs), 2.62 (2 H, brs), 2.81 (2 H, brs), 3.47 (6 H, brs), 7.03 (3 H, brs), 7.25-7.30 (7 H, m), 7.47 (1 H, brs), 7.60 (1 H, d, J = 6.1 Hz), 7.77-7.81 (2 H, m), 8.20 (1 H, d, J = 7.6 Hz), 8.49 (1 H, brs), 10.46 (1 H, brs). |
| 1275 | 4-FPh- | (DMSO-$d_6$) 2.28-2.30 (4 H, m), 2.58-2.64 (2 H, m), 2.77-2.83 (2 H, m), 3.43-3.46 (6 H, m), 7.00 (2 H, d, J = 8.6 Hz), 7.02 (1 H, d, J = 8.7 Hz), |

TABLE 270-continued

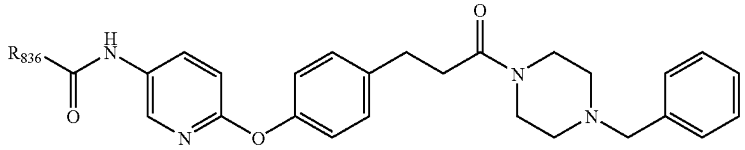

| Example No. | $R_{836}$ | $^1$H NMR (solvent) δ ppm |
|---|---|---|
| | | 7.25 (2 H, d, J = 8.6 Hz), 7.29-7.40 (7 H, m), 8.01-8.06 (2 H, m), 8.18 (1 H, dd, J = 8.7 Hz, 2.6 Hz), 8.46 (1 H, d, J = 2.5 Hz), 10.39 (1 H, brs). |
| 1276 | 4-AcPh- | (DMSO-$d_6$) 2.28-2.32 (4 H, m), 2.59-2.65 (5 H, m), 2.79-2.84 (2 H, m), 3.44-3.47 (6 H, m), 6.99-7.06 (3 H, m), 7.27-7.36 (7 H, m), 8.09 (4 H, brs), 8.21 (1 H, dd, J = 8.9 Hz, 2.8 Hz), 8.50 (1 H, d, J = 2.6 Hz), 10.56 (1 H, brs). |
| 1277 | 3,4-$F_2$Ph- | (DMSO-$d_6$) 2.28-2.32 (4 H, m), 2.59-2.65 (2 H, m), 2.79-2.84 (2 H, m), 3.44-3.47 (6 H, m), 7.01 (2 H, d, J = 8.4 Hz), 7.04 (1 H, d, J = 8.7 Hz), 7.27 (2 H, d, J = 8.4 Hz), 7.31-7.36 (5 H, m), 7.59-7.69 (1 H, m), 7.85-7.89 (1 H, m), 8.00-8.07 (1 H, m), 8.18 (1 H, dd, J = 8.9 Hz, 2.6 Hz), 8.46 (1 H, d, J = 2.5 Hz), 10.46 (1 H, brs). |

TABLE 271

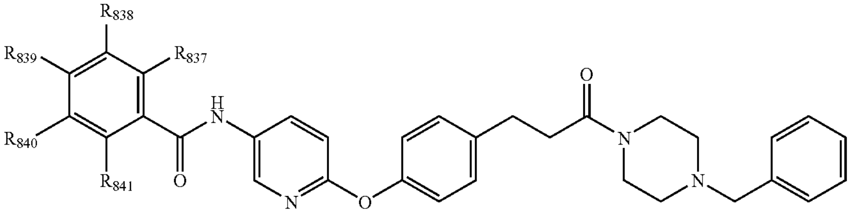

| Example No. | $R_{837}$ | $R_{838}$ | $R_{839}$ | $R_{840}$ | $R_{841}$ | $^1$H NMR (solvent) δ ppm or MS |
|---|---|---|---|---|---|---|
| 1278 | —H | —F | —H | —F | —H | $^1$H NMR (DMSO-$d_6$) 2.29-2.32 (4 H, m), 2.59-2.65 (2 H, m), 2.79-2.85 (2 H, m), 3.44-3.48 (6 H, m), 7.00-7.06 (3 H, m), 7.25-7.36 (7 H, m), 7.51-7.59 (1 H, m), 7.67-7.71 (2 H, m), 8.19 (1 H, dd, J = 8.7 Hz, 2.6 Hz), 8.48 (1 H, d, J = 2.5 Hz), 10.51 (1 H, brs). |
| 1279 | —H | —H | —$SO_2NH_2$ | —H | —H | $^1$H NMR (DMSO-$d_6$) 2.25-2.35 (4 H, m), 2.60-2.66 (2 H, m), 2.74-2.85 (2 H, m), 3.31 (2 H, s), 3.40-3.50 (4 H, m), 7.00-7.06 (3 H, m), 7.25-7.34 (7 H, m), 7.53 (2 H, s), 7.97 (2 H, d, J = 8.6 Hz), 8.12 (2 H, d, J = 8.6 Hz), 8.21 (1 H, dd, J = 8.9 Hz, 2.7 Hz), 8.49 (1 H, d, J = 2.7 Hz), 10.56 (1 H, s). |
| 1280 | —H | —H | —NHAc | —H | —H | MS 576 ($M^+$ − 1) |
| 1281 | —F | —H | —$CF_3$ | —H | —H | MS 607 ($M^+$ + H) |
| 1282 | —$COOC_2H_5$ | —H | —H | —H | —H | MS 593 ($M^+$ + 1) |
| 1283 | —Cl | —Cl | —H | —H | —H | MS 590 ($M^+$ + 2) |
| 1284 | —H | —H | —$COOCH_3$ | —H | —H | MS 579 ($M^+$ + H) |
| 1285 | —$OCH_3$ | —H | —$OCH_3$ | —H | —H | MS 580 ($M^+$) |
| 1286 | —Cl | —H | —Cl | —H | —H | MS 589 ($M^+$) |
| 1287 | —$CH_3$ | —H | —$CH_3$ | —H | —H | MS 548 ($M^+$) |
| 1288 | —F | —H | —F | —H | —H | MS 557 ($M^+$ + H) |
| 1289 | —H | —$OCH_3$ | —$OCH_3$ | —H | —H | MS 580 ($M^+$) |
| 1290 | —$CF_3$ | —H | —H | —H | —H | MS 589 ($M^+$ + 1) |
| 1291 | —H | —$CF_3$ | —H | —H | —H | MS 588 ($M^+$) |
| 1292 | —H | —$COOCH_3$ | —H | —H | —H | MS 579 ($M^+$ + 1) |
| 1293 | —F | —H | —H | —H | —F | MS 557 ($M^+$ + 1) |
| 1294 | —F | —F | —H | —H | —H | MS 557 ($M^+$ + H) |
| 1295 | —$CF_3$ | —H | —H | —$CF_3$ | —H | MS 656 ($M^+$) |
| 1296 | —H | —F | —H | —$CF_3$ | —H | MS 606 ($M^+$) |
| 1297 | —F | —$CF_3$ | —H | —H | —H | MS 607 ($M^+$ + H) |
| 1298 | —F | —H | —H | —$CF_3$ | —H | MS 607 ($M^+$ + 1) |
| 1299 | —$CH_3$ | —H | —H | —$CH_3$ | —H | MS 549 ($M^+$ + 1) |

TABLE 271-continued

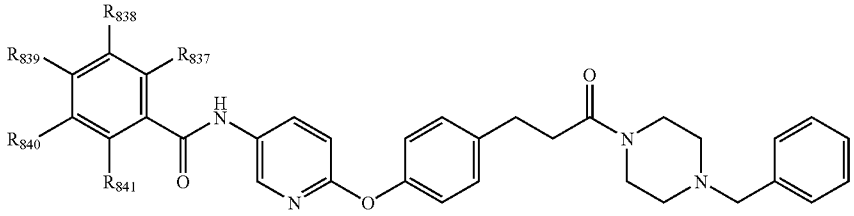

| Example No. | $R_{837}$ | $R_{838}$ | $R_{839}$ | $R_{840}$ | $R_{841}$ | $^1$H NMR (solvent) δ ppm or MS |
|---|---|---|---|---|---|---|
| 1300 | —F | —H | —H | —F | —H | MS 557 ($M^+$ + H) |
| 1301 | —Cl | —H | —F | —H | —H | MS 572 ($M^+$) |
| 1302 | —H | —OAc | —H | —H | —H | MS 579 ($M^+$ + 1) |
| 1303 | —$OCF_3$ | —H | —H | —H | —H | MS 604 ($M^+$) |

TABLE 272

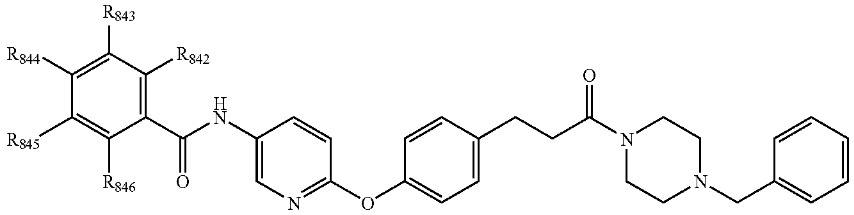

| Example No. | $R_{842}$ | $R_{843}$ | $R_{844}$ | $R_{845}$ | $R_{846}$ | $^1$H NMR or MS |
|---|---|---|---|---|---|---|
| 1304 | —H | —$CF_3$ | —F | —H | —H | MS 607 ($M^+$ + 1) |
| 1305 | —$OCH_3$ | —H | —H | —$OCH_3$ | —H | MS 580 ($M^+$) |
| 1306 | —Cl | —H | —H | —Cl | —H | MS 590 ($M^+$ + 1) |
| 1307 | —$CH_3$ | —H | —H | —F | —H | MS 552 ($M^+$) |
| 1308 | —$N(CH_3)_2$ | —H | —H | —H | —H | MS 564 ($M^+$ + H) |
| 1309 | —$OCH_3$ | —H | —H | —H | —$OCH_3$ | MS 581 ($M^+$ + H) |
| 1310 | —H | —OPh | —H | —H | —H | MS 613 ($M^+$ + H) |
| 1311 | —H | —$OCH_3$ | —H | —$OCH_3$ | —H | MS 581 ($M^+$ + H) |
| 1312 | —H | —Cl | —H | —Cl | —H | MS 589 ($M^+$ + H) |
| 1313 | —H | —$CH_3$ | —H | —$CH_3$ | —H | MS 549 ($M^+$ + H) |
| 1314 | —$OCH_3$ | —$OCH_3$ | —H | —H | —H | MS 581 ($M^+$ + H) |
| 1315 | —$CH_3$ | —$CH_3$ | —H | —H | —H | MS 549 ($M^+$ + H) |
| 1316 | —$CH_3$ | —F | —H | —H | —H | MS 553 ($M^+$ + H) |
| 1317 | —H | —H | —$N(CH_3)_2$ | —H | —H | MS 564 ($M^+$ + H) |
| 1318 | —H | —$CF_3$ | —H | —$CF_3$ | —H | MS 656 ($M^+$) |
| 1319 | —Cl | —H | —H | —$CF_3$ | —H | MS 622 ($M^+$) |
| 1320 | —H | —$CH_3$ | —NHAc | —H | —H | MS 591 ($M^+$) |
| 1321 | —H | —Cl | —NHAc | —H | —H | MS 611 ($M^+$) |
| 1322 | —H | —$OCH_3$ | —NHAc | —H | —H | MS 607 ($M^+$) |
| 1323 | —H | —NHAc | —$CH_3$ | —H | —H | MS 591 ($M^+$) |
| 1324 | —H | —NHAc | —Cl | —H | —H | MS 611 ($M^+$) |
| 1325 | —H | —NHAc | —$OCH_3$ | —H | —H | MS 607 ($M^+$) |
| 1326 | —H | —NHAc | —F | —H | —H | MS 595 ($M^+$) |
| 1327 | —H | —$CH_3$ | —NHCOPh | —H | —H | MS 653 ($M^+$) |
| 1328 | —H | —Cl | —NHCOPh | —H | —H | MS 673 ($M^+$) |
| 1329 | —H | —$OCH_3$ | —NHCOPh | —H | —H | MS 669 ($M^+$) |
| 1330 | —H | —NHCOPh | —$CH_3$ | —H | —H | MS 653 ($M^+$) |
| 1331 | —H | —NHCOPh | —Cl | —H | —H | MS 673 ($M^+$) |
| 1332 | —H | —NHCOPh | —$OCH_3$ | —H | —H | MS 669 ($M^+$) |
| 1333 | —H | —NHCOPh | —F | —H | —H | MS 657 ($M^+$) |
| 1334 | —COOH | —H | —Cl | —Cl | —H | $^1$H NMR (DMSO-$d_6$) δ 2.42 (4 H, brs), 2.62 (2 H, t, J = 7.1 Hz), 2.81 (2 H, t, J = 7.1 Hz), 3.33 (1 H, brs), 3.47 (4 H, brs), 3.60 (2 H, s), 7.00 (2 H, d, J = 8.6 Hz), 7.02 (1 H, d, J = 4.7 Hz), 7.26 (2 H, d, J = 8.6 Hz), 7.28-7.38 (5 H, m), 7.94 (1 H, s), 8.05 (1 H, s), 8.10 (1 H, dd, J = 8.7 Hz, 2.8 Hz), 8.36 (1 H, d, J = 2.8 Hz), 10.68 (1 H, s). |

TABLE 273

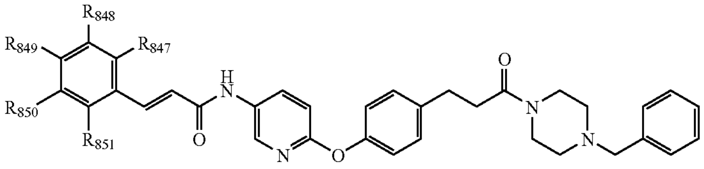

| Example No. | $R_{847}$ | $R_{848}$ | $R_{849}$ | $R_{850}$ | $R_{851}$ | MS |
|---|---|---|---|---|---|---|
| 1335 | —H | —H | —H | —H | —H | 546 ($M^+$) |
| 1336 | —H | —$OCH_3$ | —H | —H | —H | 577 ($M^+$ + H) |
| 1337 | —Cl | —H | —H | —H | —H | 581 ($M^+$ + H) |
| 1338 | —H | —Cl | —H | —H | —H | 581 ($M^+$ + H) |
| 1339 | —H | —H | —Cl | —H | —H | 581 ($M^+$ + H) |
| 1340 | —F | —H | —H | —H | —H | 565 ($M^+$ + H) |
| 1341 | —H | —F | —H | —H | —H | 565 ($M^+$ + H) |
| 1342 | —H | —H | —F | —H | —H | 565 ($M^+$ + H) |
| 1343 | —H | —H | —$N(CH_3)_2$ | —H | —H | 590 ($M^+$ + 1) |
| 1344 | —H | —$OCH_3$ | —$OCH_3$ | —H | —H | 606 ($M^+$) |
| 1345 | —Cl | —H | —H | —H | —Cl | 615 ($M^+$ + 1) |
| 1346 | —H | —Cl | —Cl | —H | —H | 615 ($M^+$ + H) |
| 1347 | —F | —H | —H | —H | —F | 583 ($M^+$ + H) |
| 1348 | —H | —F | —H | —F | —H | 583 ($M^+$ + H) |
| 1349 | —H | —$OCH_2O$— | | —H | —H | 591 ($M^+$ + H) |
| 1350 | —H | —$OCH_3$ | —H | —$OCH_3$ | —H | 607 ($M^+$ + H) |
| 1351 | —H | —H | —$CH_3$ | —H | —H | 561 ($M^+$ + H) |
| 1352 | —H | —$CF_3$ | —H | —H | —H | 615 ($M^+$ + H) |
| 1353 | —H | —H | —$OCH_3$ | —H | —H | 577 ($M^+$ + 1) |
| 1354 | —$OCH_3$ | —$OCH_3$ | —H | —H | —H | 606 ($M^+$) |
| 1355 | —$OCH_3$ | —H | —H | —$OCH_3$ | —H | 607 ($M^+$ + 1) |
| 1356 | —H | —$OCH_3$ | —$OCH_3$ | —$OCH_3$ | —H | 637 ($M^+$ + 1) |

TABLE 274

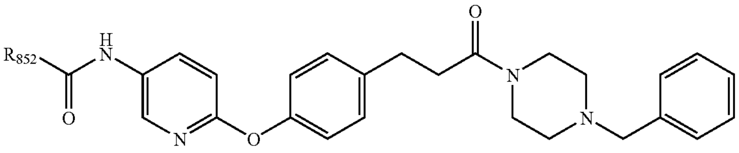

| Example No. | $R_{852}$ | $^1H$ NMR (solvent) δ ppm |
|---|---|---|
| 1357 | 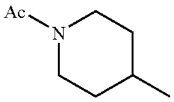 | ($CDCl_3$) 1.68-1.86 (2 H, m), 1.91-2.03 (2 H, m), 2.12 (3 H, s), 2.34-2.40 (2 H, m), 2.40-2.46 (2 H, m), 2.48-2.56 (1 H, m), 2.62 (2 H, t, J = 7.9 Hz), 2.66-2.75 (1 H, m), 2.96 (2 H, t, J = 7.9 Hz), 3.08-3.18 (1 H, m), 3.38-3.45 (2 H, m), 3.51 (2 H, s), 3.59-3.69 (2 H, m), 3.88-3.97 (1 H, m), 4.59-4.69 (1 H, m), 6.89 (1 H, d, J = 9.7 Hz), 7.02 (2 H, d, J = 8.4 Hz), 7.22 (2 H, d, J = 8.4 Hz), 7.25-7.31 (1 H, m), 7.31-7.38 (4 H, m), 7.54 (1 H, brs), 8.08-8.16 (2 H, m). |
| 1358 | 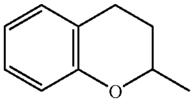 | ($CDCl_3$) 2.05-2.18 (1 H, m), 2.32-2.40 (2 H, m), 2.40-2.47 (2 H, m), 2.49-2.56 (1 H, m), 2.63 (2 H, t, J = 7.9 Hz), 2.80-2.90 (1 H, m), 2.90-3.02 (3 H, m), 3.36-3.46 (2 H, m), 3.51 (2 H, s), 3.60-3.70 (2 H, m), 4.64-4.70 (1 H, m), 6.88-7.02 (3 H, m), 7.04 (2 H, d, J = 8.4 Hz), 7.09-7.15 (1 H, m), 7.15-7.22 (1 H, m), 7.22-7.25 (1 H, m), 7.25-7.30 (2 H, m), 7.30-7.38 (4 H, m), 8.14 (1 H, dd, J = 8.8, 2.8 Hz), 8.25 (1 H, d, J = 2.8 Hz), 8.54 (1 H, brs). |
| 1359 | —$CH_2OCH_3$ | ($CDCl_3$) 2.30-2.38 (2 H, m), 2.38-2.45 (2 H, m), 2.62 (2 H, t, J = 7.9 Hz), 2.96 (2 H, t, J = 7.9 Hz), 3.35-3.43 (2 H, m), 3.50 (2 H, s), 3.52 (3 H, s), 3.58-3.68 (2 H, m), 4.04 (2 H, s), 6.90 (1 H, d, J = 8.8 Hz), 7.03 (2 H, d, J = 8.4 Hz), 7.22 (2 H, d, J = 8.4 Hz), 7.25-7.29 (1 H, m), 7.29-7.37 (4 H, m), 8.14 (1 H, dd, J = 8.8, 2.8 Hz), 8.18-8.25 (2 H, m). |
| 1360 | —$CH_3$ | ($CDCl_3$) 2.18 (3 H, s), 2.32-2.39 (2 H, m), 2.39-2.45 (2 H, m), 2.61 (2 H, t, J = 7.9 Hz), 2.95 (2 H, t, J = 7.9 Hz), 3.36-3.44 (2 H, m), 3.50 (2 H, s), 3.60-3.68 (2 H, m), 6.85-6.92 (1 H, m), 7.02 (2 H, d, J = 8.4 Hz), 7.21 (2 H, d, J = 8.4 Hz), 7.25-7.30 (1 H, m), 7.30-7.35 (4 H, m), 7.38 (1 H, brs), 8.06-8.15 (2 H, m). |
| 1361 | —$C(CH_3)_3$ | ($CDCl_3$) 1.32 (9 H, s), 2.32-2.38 (2 H, m), 2.38-2.44 (2 H, m), 2.62 (2 H, t, J = 7.9 Hz), 2.96 (2 H, t, J = 7.9 Hz), 3.37-3.43 (2 H, m), 3.50 (2 H, s), 3.60-3.69 (2 H, m), 6.87 (1 H, d, J = 9.8 Hz), |

TABLE 274-continued

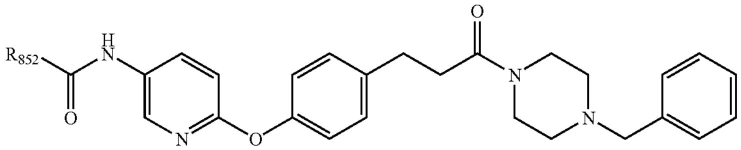

| Example No. | $R_{852}$ | $^1$H NMR (solvent) δ ppm |
|---|---|---|
| | | 7.02 (2 H, d, J = 8.4 Hz), 7.22 (2 H, d, J = 8.4 Hz), 7.25-7.30 (1 H, m), 7.30-7.37 (5 H, m), 8.07-8.15 (2 H, m). |
| 1362 | $—(CH_2)_2OPh$ | ($DMSO-d_6$) 2.23-2.33 (4 H, m), 2.56-2.67 (2 H, m), 2.73-2.86 (4 H, m), 3.37-3.50 (6 H, m), 4.26 (2 H, t, J = 6.0 Hz), 6.90-6.96 (3 H, m), 6.96-7.02 (3 H, m), 7.20-7.35 (9 H, m), 8.07 (1 H, dd, J = 8.8, 2.7 Hz), 8.33 (1 H, d, J = 2.7 Hz), 10.23 (1 H, s). |
| 1363 | $3-CH_3OPhOCH_2—$ | ($DMSO-d_6$) 2.23-2.34 (4 H, m), 2.58-2.68 (2 H, m), 2.76-2.85 (2 H, m), 3.38-3.50 (6 H, m), 3.74 (3 H, s), 4.68 (2 H, s), 6.51-6.62 (3 H, m), 6.95-7.04 (3 H, m), 7.18-7.28 (4 H, m), 7.28-7.37 (4 H, m), 8.09 (1 H, dd, J = 8.9, 2.7 Hz), 8.36 (1 H, d, J = 2.7 Hz), 10.22 (1 H, s). |
| 1364 | $3-CH_3PhOCH_2—$ | ($DMSO-d_6$) 2.23-2.34 (7 H, m), 2.56-2.66 (2 H, m), 2.74-2.84 (2 H, m), 3.37-3.50 (6 H, m), 4.67 (2 H, s), 6.75-6.81 (2 H, m), 6.81-6.88 (1 H, m), 6.96-7.03 (3 H, m), 7.14-7.21 (1 H, m), 7.21-7.28 (3 H, m), 7.28-7.36 (4 H, m), 8.09 (1 H, dd, J = 8.9, 2.7 Hz), 8.36 (1 H, d, J = 2.7 Hz), 10.21 (1 H, s). |
| 1365 | $4-CH_3PhOCH_2—$ | ($DMSO-d_6$) 2.23 (3 H, s), 2.26-2.32 (4 H, m), 2.57-2.65 (2 H, m), 2.73-2.83 (2 H, m), 3.36-3.50 (6 H, m), 4.65 (2 H, s), 6.90 (2 H, d, J = 8.5 Hz), 6.95-7.02 (3 H, m), 7.11 (2 H, d, J = 8.5 Hz), 7.20-7.29 (3 H, m), 7.29-7.35 (4 H, m), 8.08 (1 H, dd, J = 8.9, 2.7 Hz), 8.36 (1 H, d, J = 2.7 Hz), 10.21 (1 H, s). |

TABLE 275

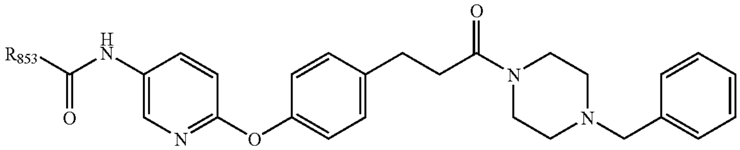

| Example No. | $R_{853}$ | $^1$H NMR ($DMSO-d_6$) δ ppm or MS |
|---|---|---|
| 1366 | $PhOCH_2—$ | $^1$H NMR 2.23-2.34 (4 H, m), 2.57-2.65 (2 H, m), 2.76-2.85 (2 H, m), 3.38-3.50 (6 H, m), 4.70 (2 H, s), 6.92-7.05 (6 H, m), 7.20-7.27 (3 H, m), 7.27-7.38 (6 H, m), 8.09 (1 H, dd, J = 8.9, 2.7 Hz), 8.36 (1 H, d, J = 2.7 Hz), 10.24 (1 H, s). |
| 1367 | $4-CH_3PhCH_2—$ | $^1$H NMR 2.21-2.32 (7 H, m), 2.56-2.65 (2 H, m), 2.73-2.82 (2 H, m), 3.37-3.49 (6 H, m), 3.58 (2 H, s), 6.92-7.00 (3 H, m), 7.09-7.16 (2 H, m), 7.19-7.21 (2 H, m), 7.21-7.27 (3 H, m), 7.27-7.35 (4 H, m), 8.04 (1 H, dd, J = 8.9, 2.7 Hz), 8.30 (1 H, d, J = 2.7 Hz), 10.27 (1 H, s). |
| 1368 | $4-ClPhCH_2—$ | $^1$H NMR 2.21-2.32 (4 H, m), 2.55-2.65 (2 H, m), 2.73-2.82 (2 H, m), 3.38-3.49 (6 H, m), 3.66 (2 H, s), 6.93-7.00 (3 H, m), 7.20-7.26 (3 H, m), 7.26-7.35 (6 H, m), 7.35-7.42 (2 H, m), 8.04 (1 H, dd, J = 8.9, 2.7 Hz), 8.30 (1 H, d, J = 2.7 Hz), 10.33 (1 H, s). |
| 1369 | $4-CH_3OPhCH_2—$ | $^1$H NMR 2.22-2.33 (4 H, m), 2.56-2.65 (2 H, m), 2.75-2.83 (2 H, m), 3.38-3.50 (6 H, m), 3.56 (2 H, s), 3.73 (3 H, s), 6.84-6.90 (2 H, m), 6.92-7.00 (3 H, m), 7.19-7.28 (5 H, m), 7.28-7.36 (4 H, m), 8.04 (1 H, dd, J = 8.9, 2.7 Hz), 8.30 (1 H, d, J = 2.7 Hz), 10.25 (1 H, s). |
| 1370 | $4-FPhCH_2—$ | $^1$H NMR 2.23-2.32 (4 H, m), 2.56-2.65 (2 H, m), 2.75-2.84 (2 H, m), 3.39-3.50 (6 H, m), 3.64 (2 H, s), 6.93-7.00 (3 H, m), 7.11-7.19 (2 H, m), 7.21-7.29 (3 H, m), 7.29-7.40 (6 H, m), 8.04 (1 H, dd, J = 8.9, 2.7 Hz), 8.30 (1 H, d, J = 2.7 Hz), 10.31 (1 H, s). |
| 1371 | benzyl | $^1$H NMR 2.22-2.33 (4 H, m), 2.56-2.67 (2 H, m), 2.72-2.84 (2 H, m), 3.37-3.50 (6 H, m), 3.64 (2 H, s), 6.90-7.00 (3 H, m), 7.20-7.29 (4 H, m), 7.29-7.38 (8 H, m), 8.05 (1 H, dd, J = 8.8, 2.7 Hz), 8.31 (1 H, d, J = 2.7 Hz), 10.32 (1 H, s). |
| 1372 | $—(CH_2)_3Ph$ | MS 563 ($M^+ + 1$) |

TABLE 275-continued

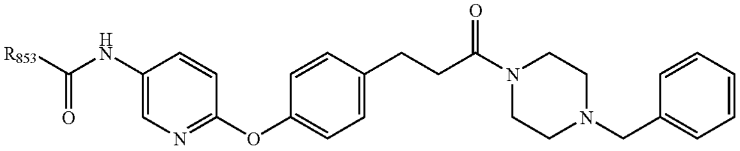

| Example No. | $R_{853}$ | $^1H$ NMR (DMSO-$d_6$) δ ppm or MS |
|---|---|---|
| 1373 | $—(CH_2)_2CH_3$ | MS 487 ($M^+$ + 1) |
| 1374 | $—CH(CH_3)_2$ | MS 486 ($M^+$) |
| 1375 | cyclopentyl | MS 512 ($M^+$) |
| 1376 | 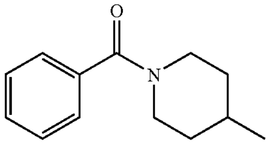 | MS 630 ($M^+$) |
| 1377 | $—(CH_2)_2Ph$ | MS 549 ($M^+$ + H) |
| 1378 | 2-furyl | MS 511 ($M^+$ + H) |
| 1379 | 2-thienyl | MS 527 ($M^+$ + H) |
| 1380 | 2-thenyl | MS 541 ($M^+$ + H) |
| 1381 | cyclohexyl | MS 527 ($M^+$ + H) |
| 1382 | cycloheptyl | MS 541 ($M^+$ + H) |
| 1383 | cyclopentylmethyl | MS 527 ($M^+$ + H) |
| 1384 | cyclohexylmethyl | MS 541 ($M^+$ + H) |
| 1385 | 2-$Ch_3OPhOCH_2$— | MS 581 ($M^+$ + 1) |

TABLE 276

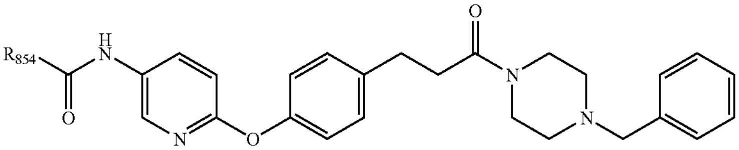

| Example No. | $R_{854}$ | MS |
|---|---|---|
| 1386 | 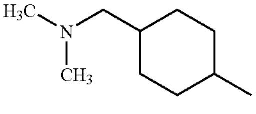 | 584 ($M^+$ + 1) |
| 1387 | 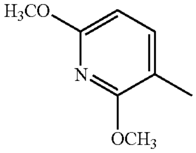 | 582 ($M^+$ + 1) |
| 1388 | 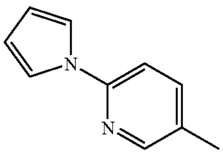 | 587 ($M^+$ + H) |
| 1389 | 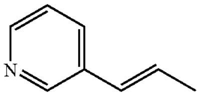 | 547 ($M^+$) |

TABLE 276-continued
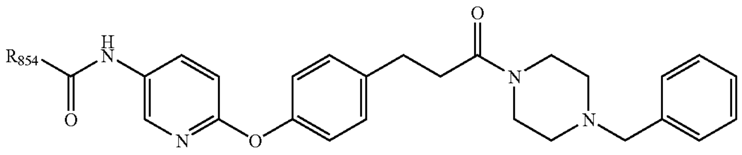
| Example No. | $R_{854}$ | MS |
|---|---|---|
| 1390 | 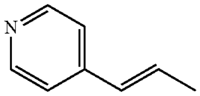 | 547 ($M^+$) |
| 1391 | 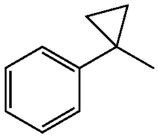 | 561 ($M^+ + 1$) |
| 1392 | 2-$CH_3$PhO$CH_2$— | 565 ($M^+ + H$) |
| 1393 | 2-ClPhO$CH_2$— | 585 ($M^+$) |
| 1394 | 3-ClPhO$CH_2$— | 585 ($M^+ + H$) |
| 1395 | 4-CNPhO$CH_2$— | 575 ($M^+$) |
| 1396 | 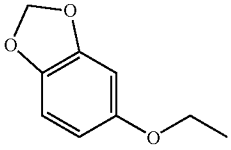 | 595 ($M^+ + H$) |
| 1397 | 3,4,5-$(CH_3O)_3$PhO$CH_2$— | 641 ($M^+ + 1$) |
| 1398 | 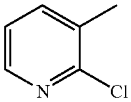 | 556 ($M^+ + 1$) |
| 1399 | 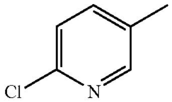 | 556 ($M^+ + H$) |
| 1400 | 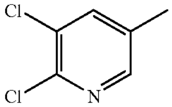 | 590 ($M^+ + H$) |
| 1401 | 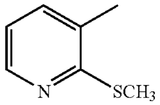 | 567 ($M^+$) |
| 1402 | 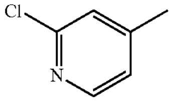 | 556 ($M^+$) |

TABLE 277
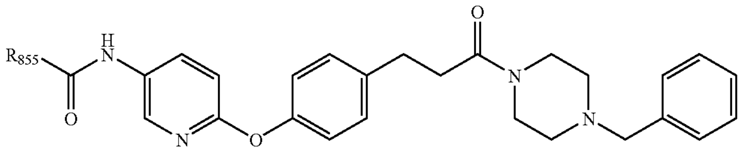
| Example No. | $R_{855}$ | MS |
|---|---|---|
| 1403 | 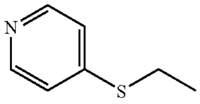 | 566 ($M^+ - 1$) |
| 1404 | 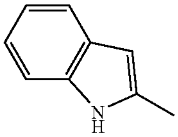 | 559 ($M^+$) |
| 1405 | 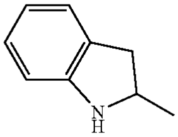 | 562 ($M^+ + H$) |
| 1406 | 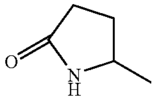 | 528 ($M^+ + 1$) |
| 1407 | 2-quinolyl | 571 ($M^+$) |
| 1408 | 3-quinolyl | 572 ($M^+ + H$) |
| 1409 | 4-quinolyl | 571 ($M^+$) |
| 1410 | 6-quinolyl | 571 ($M^+$) |
| 1411 | 1-isoquinolyl | 571 ($M^+$) |
| 1412 | 3-isoquinolyl | 572 ($M^+ + H$) |
| 1413 | 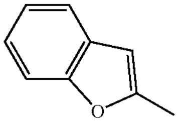 | 560 ($M^+$) |
| 1414 | 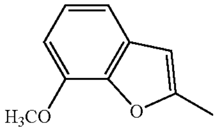 | 590 ($M^+$) |
| 1415 | 3,4-$Cl_2PhCH_2$— | 603 ($M^+ + H$) |
| 1416 | 2-$CH_3OPhCH_2$— | 564 ($M^+$) |
| 1417 | —$CH(CH_2Ph)NHAc$ | 605 ($M^+$) |
| 1418 | 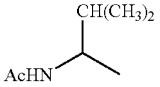 | 557 ($M^+$) |
| 1419 | —$CH_2NHAc$ | 515 ($M^+$) |
| 1420 | —$CH(CH_3)NHAc$ | 529 ($M^+$) |
| 1421 | —$CH(CH_2Ph)NHCOPh$ | 667 ($M^+$) |
| 1422 | 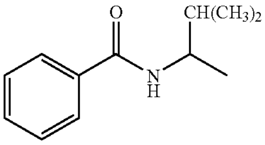 | 619 ($M^+$) |
| 1423 | —$CH_2NHCOPh$ | 577 ($M^+$) |

TABLE 278

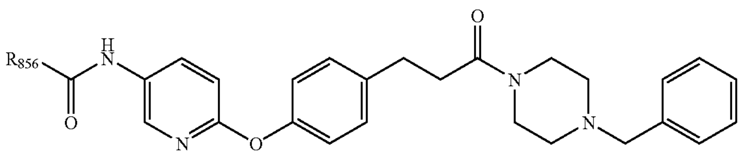

| Example No. | $R_{856}$ | MS |
|---|---|---|
| 1424 | —$CH(CH_3)NHCOPh$ | 591 ($M^+$) |
| 1425 | 2-pyridyl | 522 ($M^+ + H$) |
| 1426 | 3-pyridyl | 522 ($M^+ + H$) |
| 1427 | 4-pyridyl | 522 ($M^+ + H$) |
| 1428 | 1-naphthyl | 571 ($M^+ + H$) |
| 1429 | 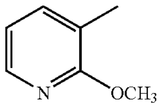 | 551 ($M^+$) |
| 1430 | 2-pyrrolyl | 509 ($M^+$) |
| 1431 | 3-pyridylmethyl | 536 ($M^+ + H$) |
| 1432 | 3-furyl | 510 ($M^+$) |
| 1433 | 3-thienyl | 526 ($M^+$) |
| 1434 | 3-thenyl | 541 ($M^+ + H$) |
| 1435 | 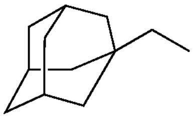 | 592 ($M^+$) |
| 1436 | 3-$CH_3PhCH_2$— | 549 ($M^+ + H$) |
| 1437 | 3-$ClPhCH_2$— | 569 ($M^+ + H$) |
| 1438 | 2-$FPhCH_2$— | 553 ($M^+ + H$) |
| 1439 | 3-$FPhCH_2$— | 553 ($M^+ + H$) |
| 1440 | 2,5-$(CH_3O)_2PhCH_2$— | 594 ($M^+$) |
| 1441 | 2,4-$Cl_2PhCH_2$— | 603 ($M^+ + H$) |
| 1442 | 2,6-$Cl_2PhCH_2$— | 602 ($M^+$) |
| 1443 | 3,4,5-$(CH_3O)_3PhCH_2$— | 624 ($M^+$) |
| 1444 | $CH(OCH_3)Ph$ | 564 ($M^+$) |
| 1445 | 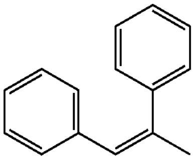 | 622 ($M^+$) |
| 1446 | 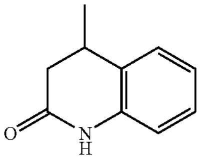 | 588 ($M^+ + H$) |
| 1447 | 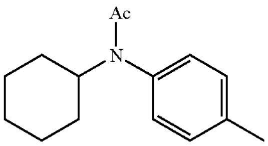 | 659 ($M^+$) |
| 1448 | 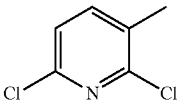 | 589 ($M^+$) |

TABLE 279
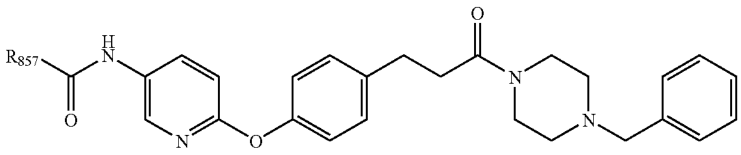
| Example No. | $R_{857}$ | MS |
|---|---|---|
| 1449 | 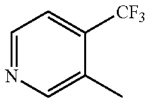 | 589 ($M^+$) |
| 1450 | 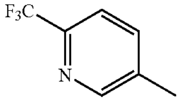 | 590 ($M^+ + H$) |
| 1451 | 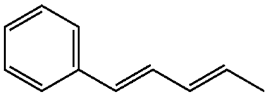 | 573 ($M^+ + H$) |
| 1452 | 4-$CH_3OPhO(CH_2)_2$— | 595 ($M^+ + H$) |
| 1453 | 4-$CH_3OPh(CH_2)_2$— | 579 ($M^+ + H$) |
| 1454 | 3,4,5-$(CH_3O)_3Ph(CH_2)_2$— | 638 ($M^+$) |
| 1455 | 2,4-$Cl_2PhOCH_2$— | 618 ($M^+$) |
| 1456 | $PhSCH_2$— | 567 ($M^+ + H$) |
| 1457 | —$(CH_2)_2COPh$ | 577 ($M^+ + H$) |
| 1458 | 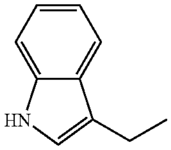 | 573 ($M^+$) |
| 1459 | 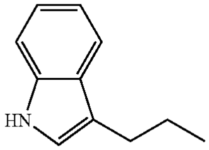 | 588 ($M^+ + H$) |
| 1460 | 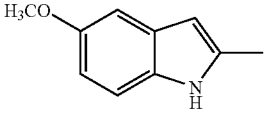 | 590 ($M^+ + H$) |
| 1461 | 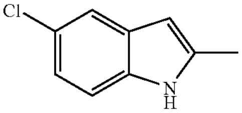 | 594 ($M^+ + H$) |
| 1462 | 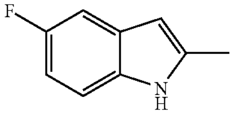 | 578 ($M^+ + H$) |
| 1463 | 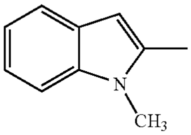 | 573 ($M^+$) |
| 1464 | 4—$CH_3OPh(CH_2)_3$— | 593 ($M^+ + H$) |

TABLE 279-continued

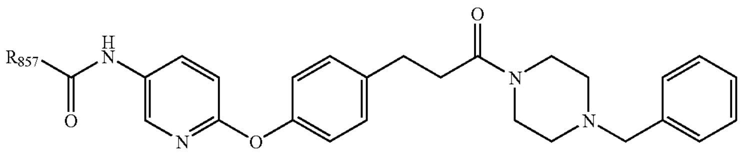

| Example No. | $R_{857}$ | MS |
|---|---|---|
| 1465 | 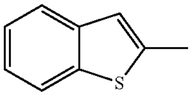 | 576 ($M^+$) |

TABLE 280

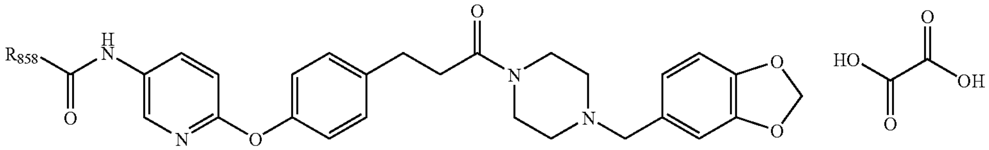

| Example No. | $R_{858}$ | mp (° C.) or $^1H$ NMR (DMSO-$d_6$) δ ppm |
|---|---|---|
| 1466 | 2,5-$F_2$Ph- | mp 173-176 |
| 1467 | 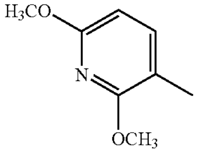 | mp 181-182 |
| 1468 | 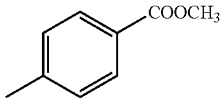 | mp 199-201 |
| 1469 | 2,3-$Cl_2$Ph- | mp 149-151 |
| 1470 | 2,4-$Cl_2$Ph- | $^1H$ NMR 2.54 (4 H, brs), 2.64 (2 H, t, J = 7.5 Hz), 2.81 (2 H, t, J = 7.5 Hz), 3.51 (4 H, brs), 3.65 (2 H, brs), 6.01 (2 H, s), 6.81 (1 H, d, J = 8.0 Hz), 6.89 (1 H, d, J = 8.0 Hz), 6.92 (1 H, s), 7.01 (2 H, d, J = 8.5 Hz), 7.04 (1 H, d, J = 9.0 Hz), 7.26 (2 H, d, J = 8.5 Hz), 7.57 (1 H, dd, J = 8.5 Hz, 2.0 Hz), 7.65 (1 H, d, J = 8.5 Hz), 7.78 (1 H, d, J = 2.0 Hz), 8.15 (1 H, dd, J = 9.0 Hz, 2.5 Hz), 8.41 (1 H, d, J = 2.5 Hz), 10.69 (1 H, s). |
| 1471 | 2,5-$(CF_3)_2$Ph- | $^1H$ NMR 2.54 (4 H, brs), 2.64 (2 H, t, J = 7.5 Hz), 2.81 (2 H, t, J = 7.5 Hz), 3.49 (4 H, brs), 3.59 (2 H, brs), 6.00 (2 H, s), 6.79 (1 H, d, J = 8.0 Hz), 6.88 (1 H, d, J = 8.0 Hz), 6.90 (1 H, s), 7.02 (2 H, d, J = 8.5 Hz), 7.05 (1 H, d, J = 9.0 Hz), 7.27 (2 H, d, J = 8.5 Hz), 8.12-8.14 (3 H, m), 8.21 (1 H, s), 8.37 (1 H, d, J = 2.5 Hz), 10.84 (1 H, s). |
| 1472 | 3-$CF_3$Ph- | $^1H$ NMR 2.54 (4 H, brs), 2.64 (2 H, t, J = 7.5 Hz), 2.82 (2 H, t, J = 7.5 Hz), 3.51 (4 H, brs), 3.63 (2 H, brs), 6.01 (2 H, s), 6.81 (1 H, d, J = 8.0 Hz), 6.89 (1 H, d, J = 8.0 Hz), 6.92 (1 H, s), 7.02 (2 H, d, J = 8.5 Hz), 7.05 (1 H, d, J = 9.0 Hz), 7.27 (2 H, d, J = 8.5 Hz), 7.80 (1 H, t, J = 8.0 Hz), 7.99 (1 H, d, J = 8.0 Hz), 8.19 (1 H, dd, J = 9.0 Hz, 2.5 Hz), 8.27 (1 H, d, J = 8.0 Hz), 8.30 (1 H, s), 8.48 (1 H, d, J = 2.5 Hz), 10.61 (1 H, s). |
| 1473 | 2,3-$F_2$Ph- | $^1H$ NMR 2.54 (4 H, brs), 2.64 (2 H, t, J = 7.5 Hz), 2.81 (2 H, t, J = 7.5 Hz), 3.51 (4 H, brs), 3.62 (2 H, brs), 6.01 (2 H, s), 6.80 (1 H, d, J = 8.0 Hz), 6.89 (1 H, d, J = 8.0 Hz), 6.92 (1 H, s), 7.02 (2 H, d, J = 8.5 Hz), 7.04 (1 H, d, J = 9.0 Hz), 7.26 (2 H, d, J = 8.5 Hz), 7.36 (1 H, m), 7.50 (1 H, m), 7.60 (1 H, m), 8.16 (1 H, dd, J = 9.0 Hz, 2.5 Hz), 8.43 (1 H, d, J = 2.5 Hz), 10.67 (1 H, s). |

TABLE 281

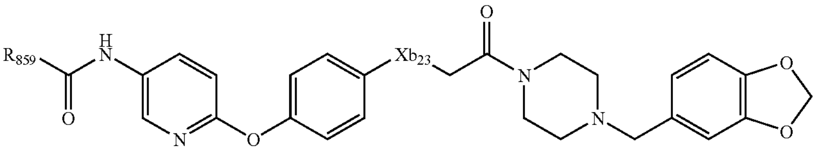

| Example No. | $R_{859}$ | $Xb_{23}$ | Form | mp (° C.) or $^1$H NMR (solvent) δ ppm |
|---|---|---|---|---|
| 1474 | 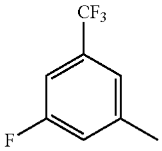 | —N(Ac)— | free | mp 142-144 |
| 1475 | 3,4-$F_2$Ph- | —$CH_2$— | free | $^1$H NMR ($CDCl_3$) 2.31-2.40 (4 H, m), 2.59-2.65 (2 H, m), 2.92-2.98 (2 H, m), 3.38-3.41 (4 H, m), 3.60-3.64 (2 H, m), 5.94 (2 H, s), 6.70-6.77 (2 H, m), 6.84 (1 H, s), 6.94 (1 H, d, J = 8.9 Hz), 7.01-7.07 (2 H, m), 7.19-7.24 (2 H, m), 7.29-7.33 (1 H, m), 7.62-7.68 (1 H, m), 7.74-7.81 (1 H, m), 8.01 (1 H, brs), 8.16-8.20 (1 H, m), 8.24 (1 H, d, J = 2.2 Hz). |
| 1476 | 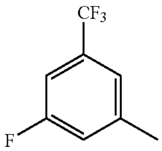 | —$CH_2$— | hydro-chloride | $^1$H NMR (DMSO-$d_6$) 2.60-2.98 (6 H, m), 3.01-3.15 (1 H, m), 3.26 (2 H, t, J = 15.0 Hz), 3.46-3.59 (1 H, m), 4.00-4.11 (1 H, m), 4.15-4.27 (2 H, m), 4.30-4.51 (1 H, m), 6.05 (2 H, s), 6.97 (1 H, d, J = 7.9 Hz), 6.98-7.09 (4 H, m), 7.20-7.31 (3 H, m), 7.97 (1 H, d, J = 8.4 Hz), 8.11-8.23 (3 H, m), 8.50 (1 H, d, J = 2.7 Hz), 10.78 (1 H, s), 11.38 (1 H, brs). |
| 1477 | 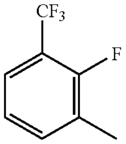 | —$CH_2$— | hydro-chloride | $^1$H NMR (DMSO-$d_6$) 2.60-2.99 (6 H, m), 3.01-3.17 (1 H, m), 3.25 (2 H, t, J = 15.0 Hz), 3.48-3.60 (1 H, m), 4.00-4.12 (1 H, m), 4.15-4.28 (2 H, m), 4.39-4.51 (1 H, m), 6.05 (2 H, s), 6.96 (1 H, d, J = 8.8 Hz), 6.99-7.08 (4 H, m), 7.19-7.31 (3 H, m), 7.55 (1 H, t, J = 7.8 Hz), 7.90-8.04 (2 H, m), 8.16 (1 H, dd, J = 8.8 Hz, 2.7 Hz), 8.43 (1 H, d, J = 2.7 Hz), 10.82 (1 H, s), 11.44 (1 H, brs). |
| 1478 | 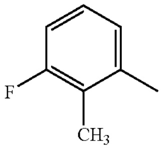 | —$CH_2$— | hydro-chloride | mp 213-215 |
| 1479 | 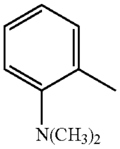 | —$CH_2$— | trihydro-chloride | $^1$H NMR (DMSO-$d_6$) 2.69-3.40 (15 H, m), 3.99-4.49 (5 H, m), 6.07 (2 H, s), 6.97-7.09 (5 H, m), 7.21-7.30 (3 H, m), 7.43-7.47 (1 H, m), 7.65-7.70 (2 H, m), 7.91 (1 H, d, J = 9.4 Hz), 8.21 (1 H, dd, J = 8.9 Hz, 2.6 Hz), 8.48 (1 H, d, J = 2.1 Hz), 11.23 (1 H, s). |
| 1480 | 3-PhOPh- | —$CH_2$— | hydro-chloride | $^1$H NMR (DMSO$d_6$) 2.60-3.09 (7 H, m), 3.18-3.31 (2 H, m), 3.38-3.50 (1 H, m), 4.08 (1 H, d, J = 14.0 Hz), 4.22 (2 H, brs), 4.45 (1 H, d, J = 14.0 Hz), 6.07 (2 H, s), 6.90-7.08 (7 H, m), 7.15-7.26 (5 H, m), 7.44 (2 H, t, J = 7.9 Hz), 7.56 (1 H, t, J = 7.9 Hz), 7.61 (1 H, s), 7.79 (1 H, d, J = 7.6 Hz), 8.19 (1 H, dd, J = 8.9 Hz, 2.6 Hz), 8.45 (1 H, d, J = 2.6 Hz), 10.45 (1 H, s), 10.90-11.20 (1 H, m). |

TABLE 282

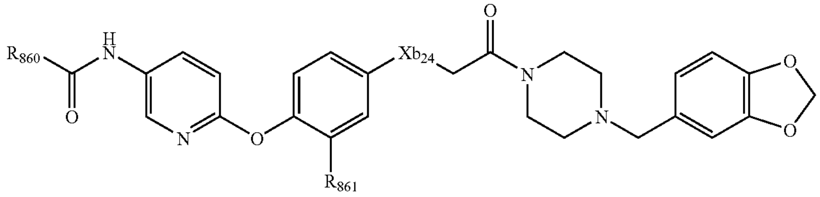

| Example No. | $R_{860}$ | $R_{861}$ | $Xb_{24}$ | Form | mp (° C.) or $^1$H NMR (solvent) δ ppm |
|---|---|---|---|---|---|
| 1481 | 1-naphthyl | —H | —$CH_2$— | hydro-chloride | $^1$H NMR (DMSO-$d_6$) 2.50-3.60 (10 H, m), 4.00-4.20 (1 H, m), 4.22 (2 H, s), 4.35-4.51 (1 H, m), 6.07 (2 H, s), 6.91-7.08 (2 H, m), 7.04 (2 H, d, J = 8.6 Hz), 7.08 (1 H, d, J = 8.9 Hz), 7.21 (1 H, s), 7.39 (2 H, d, J = 8.6 Hz), 7.55-7.67 (3 H, m), 7.79 (1 H, d, J = 7.1 Hz), 7.98-8.05 (1 H, m), 8.10 (1 H, d, J = 8.2 Hz), 8.16-8.22 (1 H, m), 8.26 (1 H, dd, J = 8.9 Hz, 2.5 Hz), 8.54 (1 H, d, J = 2.5 Hz), 10.72 (1 H, s) |
| 1482 | 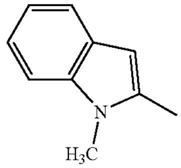 | —$CH_3$ | —N($CH_3$)— | free | $^1$H NMR ($CDCl_3$) 2.13 (3 H, s), 2.43 (4 H, t, J = 4.8 Hz), 3.01 (3 H, s), 3.44 (2 H, s), 3.45-3.56 (2 H, m), 3.56-3.70 (2 H, m), 4.08 (2 H, s), 4.09 (3 H, s), 5.95 (2 H, s), 6.51-6.60 (2 H, m), 6.72-6.76 (2 H, m), 6.82 (1 H, d, J = 8.9 Hz), 6.85 (1 H, s), 6.92 (1 H, d, J = 8.4 Hz), 7.04 (1 H, s), 7.14-7.23 (1 H, m), 7.28-7.40 (1 H, m), 7.42 (1 H, d, J = 7.9 Hz), 7.67 (1 H, d, J = 7.9 Hz), 7.94 (1 H, s), 8.14 (1 H, dd, J = 8.9 Hz, 2.8 Hz), 8.22 (1 H, d, J = 2.8 Hz). |
| 1483 | 3,5-($CH_3$)$_2$Ph- | —H | —$CH_2$— | hydro-chloride | H NMR (DMSO-$d_6$) 2.36 (6 H, s), 2.60-3.60 (10 H, m), 4.00-4.60 (2 H, m), 4.29 (2 H, s), 6.07 (2 H, s), 6.85-7.10 (5 H, m), 7.22 (2 H, s), 7.27 (2 H, d, J = 8.5 Hz), 7.57 (2 H, s), 8.19 (1 H, dd, J = 8.9 Hz, 2.7 Hz), 8.48 (1 H, d, J = 2.7 Hz), 10.34 (1 H, s). |
| 1484 | 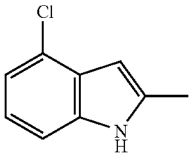 | —$CH_3$ | —N($CH_3$)— | free | mp 143-144 |
| 1485 | 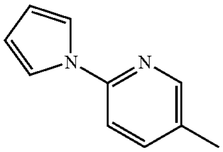 | —$CH_3$ | —N($CH_3$)— | free | mp 163-165 |
| 1486 | 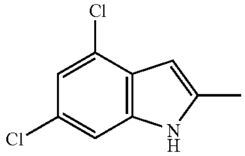 | —$CH_3$ | —N($CH_3$)— | free | mp 224-227 dec |

TABLE 282-continued

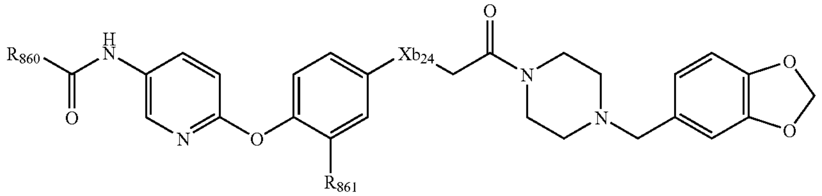

| Example No. | $R_{860}$ | $R_{861}$ | $Xb_{24}$ | Form | mp (° C.) or $^1$H NMR (solvent) δ ppm |
|---|---|---|---|---|---|
| 1487 | 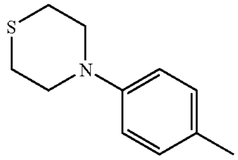 | —$CH_3$ | —N($CH_3$)— | free | mp 131-134 |

TABLE 283

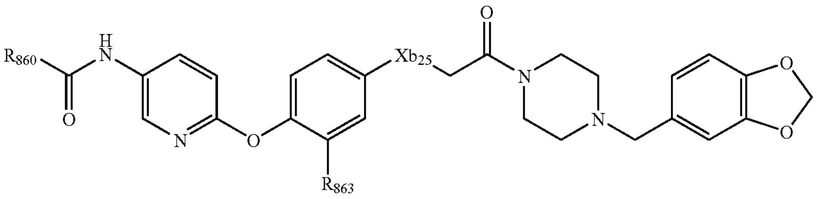

| Example No. | $R_{862}$ | $R_{863}$ | $Xb_{25}$ | Form | $^1$H NMR (solvent) δ ppm |
|---|---|---|---|---|---|
| 1488 | 2,3-($CH_3O$)$_2$Ph- | —H | —$CH_2$— | hydro-chloride | (DMSO-$d_6$) 3.80 (3 H, s), 3.86 (3 H, s), 2.60-3.60 (10 H, m), 4.00-4.20 (1 H, m), 4.22 (2 H, s), 4.40-4.55 (1 H, m), 6.07 (2 H, s), 6.90-7.30 (11 H, m), 8.18 (1 H, dd, J = 8.8 Hz, 2.6 Hz), 8.45 (1 H, d, J = 2.6 Hz), 10.37 (1 H, s). |
| 1489 | 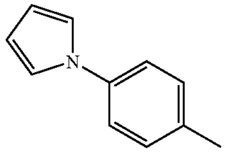 | —$CH_3$ | —N($CH_3$)— | free | ($CDCl_3$) 2.12 (3 H, s), 2.35-2.50 (4 H, m), 3.01 (3 H, s), 3.43 (2 H, s), 3.45-3.55 (2 H, m), 3.57-3.70 (2 H, m), 4.07 (2 H, s) 5.95 (2 H, s), 6.40 (2 H, t, J = 2.2 Hz), 6.50-6.59 (2 H, m), 6.74 (2 H, s), 6.81 (1 H, d, J = 8.9 Hz), 6.85 (1 H, s), 6.92 (1 H, d, J = 8.6 Hz), 7.17 (2 H, t, J = 2.2 Hz), 7.49 (2 H, d, J = 8.8 Hz), 7.90 (1 H, brs), 7.95 (2 H, d, J = 8.8 Hz), 8.15 (1 H, dd, J = 8.9 Hz, 2.3 Hz), 8.22 (1 H, d, J = 2.3 Hz). |
| 1490 | 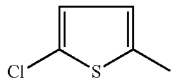 | —$CH_3$ | —N($CH_3$)— | free | ($CDCl_3$) 2.04 (3 H, s), 2.39-2.46 (4 H, m), 2.94 (3 H, s), 3.43-3.51 (4 H, m), 3.59-3.63 (2 H, m), 4.05 (2 H, s), 5.94 (2 H, s), 6.41-6.48 (2 H, m), 6.67-6.84 (6 H, m), 7.44 (1 H, d, J = 4.1 Hz), 8.01 (1 H, dd, J = 8.9 Hz, 2.6 Hz), 8.17 (1 H, d, J = 2.6 Hz), 8.82 (1 H, brs). |
| 1491 | 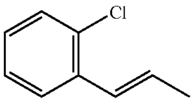 | —$CH_3$ | —N($CH_3$)— | maleate | (DMSO-$d_6$) 2.01 (3 H, s), 2.50 (4 H, brs), 2.93 (3 H, s), 3.33 (4 H, brs), 4.03 (2 H, s), 4.29 (2 H, s), 6.06 (2 H, s), 6.10 (2 H, s), 6.48 (1 H, dd, J = 8.9 Hz, 2.8 Hz), 6.56 (1 H, s), 6.81-7.01 (6 H, m), 7.43-7.53 (2 H, m), 7.57 ( 1 H, dd, J = 5.9 Hz, 3.6 Hz), 7.77 (1 H, dd, J = 5.8 Hz, 3.6 Hz), 7.88 (1 H, d, J = 15.7 Hz), 8.11 (1 H, dd, J = 8.7 Hz, 2.5 Hz), 8.36 (1 H, d, J = 2.6 Hz), 10.42 (1 H, s). |
| 1492 | 4-($CH_3$)$_2$NPh- | —H | —$CH_2$— | free | ($CDCl_3$) 2.33 (2 H, t, J = 5.0 Hz), 2.39 (2 H, t, J = 5.0 Hz), 2.61 (2 H, t, J = 7.5 Hz), 2.97 (2 H, t, J = 7.5 Hz), 3.05 (6 H, s), |

TABLE 283-continued

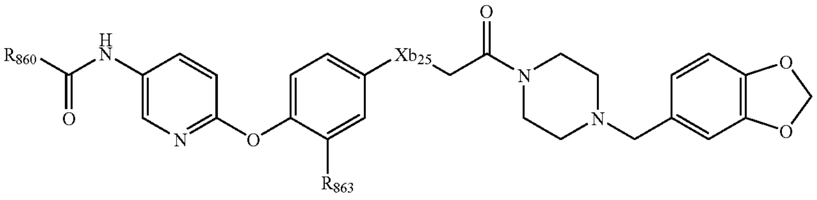

| Example No. | $R_{862}$ | $R_{863}$ | $Xb_{25}$ | Form | $^1$H NMR (solvent) δ ppm |
|---|---|---|---|---|---|
| | | | | | 3.32-3.45 (2 H, m), 3.41 (2 H, s), 3.63 (2 H, t, J = 5.0 Hz), 5.94 (2 H, s), 6.70 (2 H, d, J = 9.0 Hz), 6.74 (2 H, s), 6.85 (1 H, s), 6.92 (1 H, d, J = 9.0 Hz), 7.04 (2 H, d, J = 8.6 Hz), 7.22 (2 H, d, J = 8.6 Hz), 7.72 (1 H, s), 7.78 (2 H, d, J = 9.0 Hz), 8.21 (1 H, d, J = 2.8 Hz), 8.23 (1 H, dd, J = 8.6 Hz, 2.8 Hz). |
| 1493 | 2,4-$Cl_2$PhO$CH_2$— | —$CH_3$ | —N($CH_3$)— | free | ($CDCl_3$) 2.11 (3 H, s), 2.42 (4 H, brs), 3.00 (3 H, s), 3.43 (2 H, s), 3.49 (2 H, brs), 3.63 (2 H, brs), 4.07 (2 H, s), 4.62 (2 H, s), 5.94 (2 H, s), 6.54 (1 H, dd, J = 11.1 Hz, 2.3 Hz), 6.74-6.92 (6 H, m), 7.24 (1 H, dd, J = 8.7 Hz, 2.5 Hz), 7.43 (1 H, d, J = 2.5 Hz), 8.06 (1 H, dd, J = 8.9 Hz, 2.8 Hz), 8.23 (1 H, d, J = 2.6 Hz), 8.55 (1 H, s). |

TABLE 284

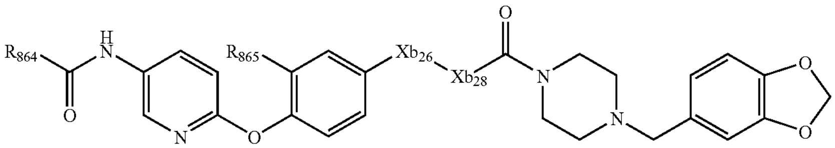

| Example No. | $R_{864}$ | $R_{865}$ | $Xb_{26}$ | $Xb_{27}$ | Form | mp (° C.) or $^1$H NMR (solvent) δ ppm |
|---|---|---|---|---|---|---|
| 1494 | 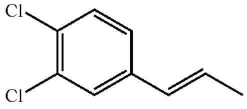 | —$CH_3$ | —N($CH_3$)— | —$CH_2$— | free | $^1$H NMR ($CDCl_3$) 2.10 (3 H, s), 2.45 (4 H, brs), 3.01 (3 H, s), 3.45 (2 H, s), 3.51 (2 H, brs), 3.64 (2 H, brs), 4.08 (2 H, s), 5.95 (2 H, s), 6.51-6.59 (3 H, m), 6.75-6.92 (5 H, m), 7.33 (1 H, d, J = 8.3 Hz), 7.45 (1 H, d, J = 8.4 Hz), 7.61-7.76 (3 H, m), 8.16 (1 H, d, J = 8.9 Hz), 8.18 (1 H, s). |
| 1495 | 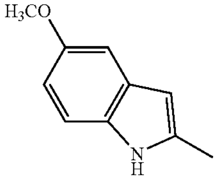 | —$CH_3$ | —N($CH_3$)— | —$CH_2$— | free | $^1$H NMR ($CDCl_3$) 2.09 (3 H, s), 2.34-2.48 (4 H, m), 2.98 (3 H, s), 3.42 (2 H, s), 3.40-3.55 (2 H, m), 3.55-3.70 (2 H, m), 3.84 (3 H, s), 4.06 (2 H, s), 5.94 (2 H, s), 6.46-6.55 (2 H, m), 6.67-6.76 (2 H, m), 6.77 (1 H, d, J = 8.9 Hz), 6.85 (1 H, s), 6.89 (1 H, d, J = 8.5 Hz), 6.93-6.98 (1 H, m), 6.97 (1 H, dd, J = 8.9 Hz, 2.3 Hz), 7.04 (1 H, d, J = 2.3 Hz), 7.30 (1 H, d, J = 8.9 Hz), 8.11 (1 H, dd, J = 8.9 Hz, 2.5 Hz), 8.22 (1 H, s), 8.25 (1 H, d, J = 2.5 Hz), 9.45 (1 H, s). |

TABLE 284-continued

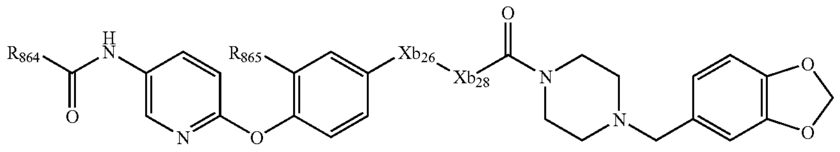

| Example No. | $R_{864}$ | $R_{865}$ | $Xb_{26}$ | $Xb_{27}$ | Form | mp (° C.) or $^1$H NMR (solvent) δ ppm |
|---|---|---|---|---|---|---|
| 1496 | 3,4-$(CH_3)_2$Ph- | —H | —$CH_2$— | —$CH_2$— | free | $^1$H NMR ($CDCl_3$) 2.31-2.38 (10 H, m), 2.57-2.63 (2 H, m), 2.91-2.97 (2 H, m), 3.37-3.40 (4 H, m), 3.59-3.63 (2 H, m), 5.93 (2 H, s), 6.70-6.77 (2 H, m), 6.84 (1 H, s), 6.91 (1 H, d, J = 8.9 Hz), 7.00-7.05 (2 H, m), 7.17-7.22 (3 H, m), 7.60 (1 H, dd, J = 7.8 Hz, 1.9 Hz), 7.66 (1 H, d, J = 1.9 Hz), 8.16-8.26 (3 H, m). |
| 1497 | 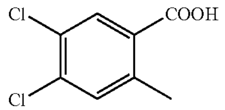 | —H | —$CH_2$— | —$CH_2$— | free | $^1$H NMR (DMSO-$d_6$) 2.41 (4 H, brs), 2.62 (2 H, t, J = 7.5 Hz), 2.81 (2 H, t, J = 7.5 Hz), 3.32 (1 H, brs), 3.47 (4 H, brs), 3.52 (2 H, s), 6.00 (2 H, s), 6.78 (1 H, d, J = 8.0 Hz), 6.87 (1 H, d, J = 8.0 Hz), 6.88 (1 H, d, J = 2.0 Hz), 7.00 (2 H, d, J = 8.5 Hz), 7.03 (1 H, d, J = 8.9 Hz), 7.26 (2 H, d, J = 8.5 Hz), 7.94 (1 H, s), 8.05 (1 H, s), 8.10 (1 H, dd, J = 8.9 Hz, 2.6 Hz), 8.36 (1 H, d, J = 2.6 Hz), 10.72 (1 H, s). |
| 1498 | 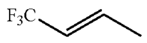 | —$CH_3$ | —N($CH_3$)— | —$CH_2$— | hydro-chloride | mp 145.0-148.0 |
| 1499 | 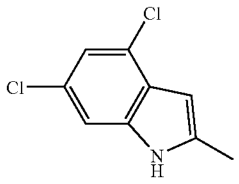 | —$CH_3$ | —N($CH_3$)— | —CO— | free | mp 269.0-272.0 |

TABLE 285

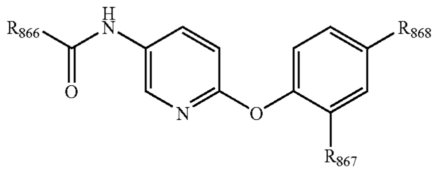

| Example No. | $R_{866}$ | $R_{867}$ | $R_{868}$ | Form | $^1$H NMR (solvent) δ ppm |
|---|---|---|---|---|---|
| 1500 | 3,4-$Cl_2$Ph- | —$CH_3$ | 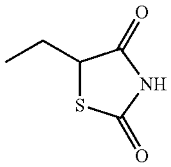 | hydro-chloride | (DMSO-$d_6$) 2.08 (3 H, s), 3.09 (1 H, dd, J = 14.2 Hz, 9.7 Hz), 3.40 (1 H, dd, J = 14.2 Hz, 4.2 Hz), 4.93 (1 H, dd, J = 9.7 Hz, 4.2 Hz), 7.00 (1 H, d, J = 8.3 Hz), 7.02 (1 H, d, J = 8.9 Hz), 7.11 (1 H, dd, J = 8.3 Hz, 2.0 Hz), 7.20 (1 H, d, J = 2.0 Hz), 7.83 (1 H, d, J = 8.4 Hz), 7.95 (1 H, dd, J = 8.4 Hz, 2.0 Hz), 8.18 (1 H, dd, J = 8.9 Hz, 2.5 Hz), 8.23 (1 H, d, J = 2.0 Hz), 8.44 (1 H, d, J = 2.5 Hz), 10.57 (1 H, s), 12.08 (1 H, s). |

TABLE 285-continued

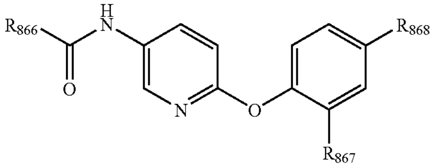

| Example No. | $R_{866}$ | $R_{867}$ | $R_{868}$ | Form | $^1H$ NMR (solvent) δ ppm |
|---|---|---|---|---|---|
| 1501 | 4-$CF_3$Ph- | —$CH_3$ | 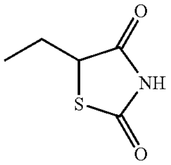 | free | (DMSO-$d_6$) 2.09 (3 H, s), 3.09 (1 H, dd, J = 14.1 Hz, 9.6 Hz), 3.40 (1 H, dd, J = 14.1 Hz, 4.3 Hz), 4.93 (1 H, dd, J = 9.6 Hz, 4.3 Hz), 6.99 (1 H, d, J = 8.2 Hz), 7.03 (1 H, d, J = 8.9 Hz), 7.12 (1 H, dd, J = 8.2 Hz, 2.0 Hz), 7.20 (1 H, d, J = 2.0 Hz), 7.93 (2 H, d, J = 8.2 Hz), 8.16 (2 H, d, J = 8.2 Hz), 8.20 (1 H, dd, J = 8.9 Hz, 2.5 Hz), 8.45 (1 H, d, J = 2.5 Hz), 10.60 (1 H, s), 12.07 (1 H, s). |
| 1502 | 3-$CF_3$Ph- | —H | 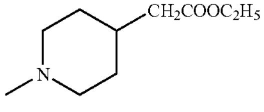 | free | ($CDCl_3$) 1.28 (3 H, t, J = 7.0 Hz), 1.46 (2 H, dq, J = 4.0 Hz, 12.5 Hz), 1.85 (2 H, brd, J = 12.5 Hz), 1.93 (1 H, m), 2.73 (2 H, dt, J = 2.5 Hz, 12.0 Hz), Hz), 3.61 (2 H, brd, J = 12.0 Hz), 4.15 (2 H, q, J = 7.0 Hz), 6.90 (1 H, d, J = 9.0 Hz), 6.96 (2 H, d, J = 9.0 Hz), 7.03 (2 H, d, J = 9.0 Hz), 7.65 (1 H, t, J = 8.0 Hz), 7.83 (1 H, d, J = 8.0 Hz), 7.86 (1 H, brs), 8.07 (1 H, d, J = 8.0 Hz), 8.14 (1 H, brs), 8.18 (1 H, dd, J = 9.0 Hz, 2.5 Hz), 8.27 (1 H, d, J = 2.5 Hz). |

Example 1503

Production of N-[6-(4-{[2-(4-piperonylpiperazin-1-yl)-2-oxoethyl]methylamino}-2-methylphenoxy)pyridin-3-yl]-4-trifluoromethylbenzamide To a suspension of 1-(4-piperonylpiperazin-1-yl)-2-{methyl-[3-methyl-4-(5-nitropyridin-2-yloxy)phenyl]amino}ethanone (2.65 g, 5.10 mmol) in ethyl acetate (50 mL) was added 5% platinum-carbon (0.20 g) under a nitrogen atmosphere, and the resulting mixture was stirred for 11 hours under a hydrogen atmosphere. The platinum-carbon was separated off by filtration using Celite. To a solution of the resulting filtrate in ethyl acetate was added triethylamine (0.78 mL, 5.61 mmol) under ice cooling, and then to the resulting solution was added 4-(trifluoromethyl)benzoyl chloride (0.80 mL, 5.36 mmol). This reaction solution was stirred for 16 hours, and then added a saturated sodium bicarbonate solution. The resulting solution was stirred at room temperature, and after 20 minutes, extracted with ethyl acetate. The ethyl acetate layer was washed with water, and then dried over anhydrous magnesium sulfate. The solvent was evaporated, and the residue was recrystallized from acetone-diethyl ether, to thereby yield 3.03 g of the title compound.

Appearance: Pale yellow powder

Melting point: 153.0-154.5° C.; $^1H$ NMR ($CDCl_3$) δ 2.12 (3H, s), 2.31-2.52 (4H, m), 3.01 (3H, s), 3.38-3.72 (6H, m), 4.07 (2H, s), 5.95 (2H, s), 6.49-6.61 (2H, m), 6.69-6.78 (2H, m), 6.79-6.88 (2H, m), 6.92 (1H, d, J=8.6 Hz), 7.76 (2H, d, J=8.3 Hz), 7.81-7.90 (1H, m), 7.99 (2H, d, J=8.3 Hz), 8.13 (1H, dd, J=8.8 Hz, 2.6 Hz), 8.23 (1H, d, J=2.6 Hz).

A crude titled product (5.00 g, 7.6 mmol) obtained using the same procedures was recrystallized from ethanol (15 mL), to thereby yield 3.90 g of the title compound.

Appearance: Pale yellow powder

Melting point: 156-158° C.

The following compounds were produced in the same manner as in Example 1503.

Example 1504

N-{6-[2-methyl-4-(2-oxo-3-piperonylimidazolidin-1-yl)phenoxy]pyridin-3-yl}-4-trifluoromethylbenzamide mp 188.0-189.0° C.

TABLE 286

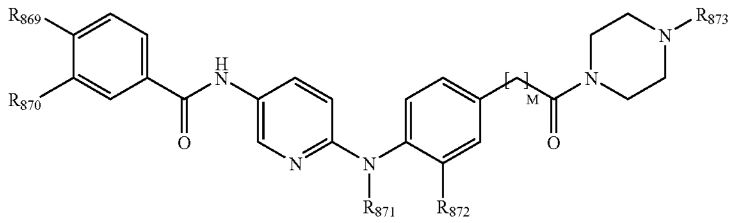

| Example No. | $R_{869}$ | $R_{870}$ | $R_{871}$ | $R_{872}$ | $R_{873}$ | M | Form | mp (° C.) or $^1$H NMR (solvent) δ ppm |
|---|---|---|---|---|---|---|---|---|
| 1505 | —Cl | —Cl | cyclopentyl | —H | piperonyl | 2 | oxalate | mp 135-139 |
| 1506 | —Cl | —Cl | —$(CH_2)_2CH_3$ | —H | piperonyl | 2 | free | $^1$H NMR (DMSO-$d_6$) 0.86 (3 H, t, J = 7.5 Hz), 1.56 (2 H, q, J = 7.5 Hz), 2.27 (2 H, brs), 2.64 (2 H, t, J = 7.4 Hz), 2.83 (2 H, t, J = 7.4 Hz), 3.37-3.48 (6 H, m), 3.84 (2 H, t, J = 7.5 Hz), 5.98 (2 H, s), 6.36 (1 H, d, J = 9.1 Hz), 6.74 (1 H, d, J = 7.9 Hz), 6.83 (1 H, d, J = 7.9 Hz), 6.86 (1 H, s), 7.16 (2 H, d, J = 8.2 Hz), 7.30 (2 H, d, J = 8.2 Hz), 7.70 (1 H, dd, 9.1 Hz, 2.6 Hz), 7.81 (1 H, d, J = 8.4 Hz), 7.93 (1 H, dd, J = 8.4 Hz, 1.9 Hz), 8.19 (1 H, d, J = 1.9 Hz), 8.43 (1 H, d, J = 2.6 Hz), 10.27 (1 H, s). |
| 1507 | —Cl | —Cl | —$CH_3$ | —$OCH_3$ | piperonyl | 2 | free | $^1$H NMR ($CDCl_3$) 2.34-2.41 (4 H, m), 2.62-2.68 (2 H, m), 2.95-3.01 (2 H, m), 3.34 (3 H, s), 3.38-3.45 (4 H, m), 3.62-3.65 (2 H, m), 3.75 (3 H, s), 5.94 (2 H, s), 6.25 (1 H, d, J = 9.2 Hz), 6.70-6.84 (5 H, m), 7.12 (1 H, d, J = 7.6 Hz), 7.53 (1 H, d, J = 8.2 Hz), 7.67-7.72 (2 H, m), 7.97 (2 H, d, J = 2.0 Hz), 8.24 (1 H, d, J = 2.5 Hz). |
| 1508 | —$CF_3$ | —H | —$CH_3$ | —$OCH_3$ | piperonyl | 2 | free | $^1$H NMR ($CDCl_3$) 2.36-2.37 (4 H, m), 2.62-2.67 (2 H, m), 2.94-2.99 (2 H, m), 3.28-3.45 (7 H, m), 3.60-3.64 (2 H, m), 3.74 (3 H, s), 5.93 (2 H, s), 6.25 (1 H, d, J = 9.1 Hz), 6.70-6.84 (5 H, m), 7.11 (1 H, d, J = 7.6 Hz), 7.67-7.75 (3 H, m), 7.97 (2 H, d, J = 7.9 Hz), 8.16-8.32 (2 H, m). |
| 1509 | —Cl | —Cl | —$CH_3$ | —H | benzyl | 0 | oxalate | mp 228-230 |

TABLE 287

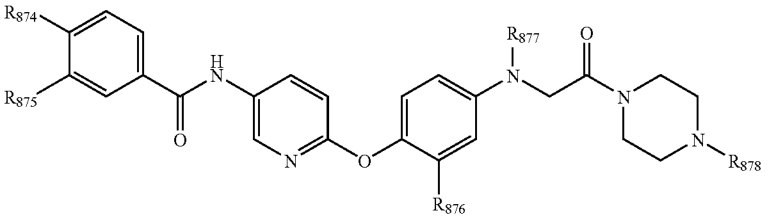

| Example No. | $R_{874}$ | $R_{875}$ | $R_{876}$ | $R_{877}$ | $R_{878}$ | Form | mp (° C.) or $^1$H NMR (solvent) δ ppm |
|---|---|---|---|---|---|---|---|
| 1510 | —Cl | —Cl | —H | 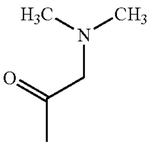 | piperonyl | dioxalate | $^1$H NMR (DMSO-$d_6$) 2.36-2.50 (4 H, m), 2.73 (6 H, s), 3.42-3.56 (6 H, m), 3.94 (2 H, s), 4.56 (2 H, s), 5.98 (2 H, s), 6.76 (1 H, d, J = 8.0 Hz), 6.85 (1 H, d, J = 8.0 Hz), 6.88 (1 H, s), 7.13 (1 H, d, J = 8.9 Hz), 7.23 (2 H, d; J = 8.8 Hz), 7.45 (2 H, d, J = 8.8 Hz), 7.83 (1 H, d, J = 8.4 Hz), 7.93 (1 H, dd, J = 8.4 Hz, 2.0 Hz), 8.20-8.25 (2 H, m), 8.52 (1 H, d, J = 2.7 Hz), 10.63 (1 H, s). |
| 1511 | —$CF_3$ | —H | —$CH_3$ | —H | piperonyl | free | $^1$H NMR ($CDCl_3$) 2.11 (3 H, s), 2.42-2.48 (4 H, m), 3.45-3.48 (4 H, m), 3.66-3.70 (2 H, m), 3.86 (2 H, s), 4.83 (1 H, brs), 5.96 (2 H, s), 6.46-6.52 (2 H, m), 6.71-6.78 (2 H, m), 6.83-6.91 (3 H, m), 7.75-7.82 (3 H, m), 7.99 (2 H, d, J = 8.1 Hz), 8.16 (1 H, dd, J = 8.9 Hz, 2.8 Hz), 8.22 (1 H, d, J = 2.8 Hz). |
| 1512 | —Cl | —Cl | —$CH_3$ | —$CH_3$ | piperonyl | hydro-chloride | mp 183-185 dec |
| 1513 | —$CF_3$ | —H | —$CH_3$ | —$C_2H_5$ | benzyl | maleate | mp 165-167 |
| 1514 | —Cl | —Cl | —$CH_3$ | —$C_2H_5$ | benzyl | free | mp 102-105 |
| 1515 | —$CF_3$ | —H | —$CH_3$ | —$CH_3$ | benzyl | free | mp 110-111 |
| 1516 | —Cl | —Cl | —$CH_3$ | —$CH_3$ | benzyl | free | mp 111-113 |

TABLE 288

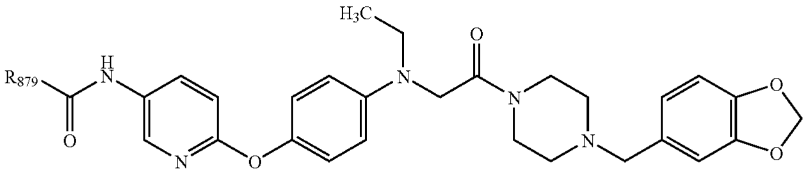

| Example No. | $R_{879}$ | Form | mp (° C.) or MS |
|---|---|---|---|
| 1517 | 3,4-$Cl_2$Ph- | maleate | mp 203-205 |
| 1518 | 3-PhOPh- | free | MS 686 ($M^+$ + H) |
| 1519 | 3,5-$Cl_2$Ph- | free | MS 662 ($M^+$ + H) |
| 1520 | 3,5-$(CH_3)_2$Ph- | free | MS 622 ($M^+$ + H) |
| 1521 | 2,3-$(CH_3)_2$Ph- | free | MS 622 ($M^+$ + H) |
| 1522 | 2,3-$Cl_2$Ph- | free | MS 662 ($M^+$ + H) |
| 1523 | 1-naphthyl | free | MS 644 ($M^+$ + H) |
| 1524 | 2,4-$(CH_3)_2$Ph- | free | MS 622 ($M^+$ + H) |
| 1525 | 3,4-$(CH_3)_2$Ph- | free | MS 622 ($M^+$ + H) |
| 1526 | 3,4-$F_2$Ph- | free | MS 630 ($M^+$ + H) |
| 1527 | 3-$CF_3$Ph- | free | MS 663 ($M^+$ + H) |
| 1528 | 3-$CF_3$OPh- | free | MS 678 ($M^+$ + H) |
| 1529 | 4-$CF_3$OPh- | free | MS 678 ($M^+$ + H) |
| 1530 | 3-ClPhO$CH_2$— | free | MS 658 ($M^+$ + H) |

TABLE 288-continued

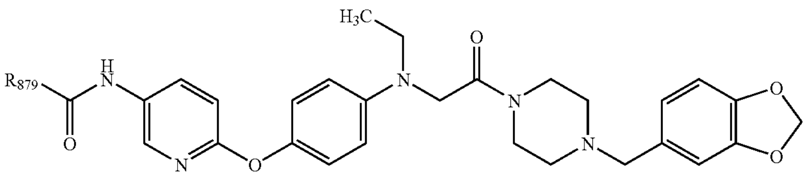

| Example No. | $R_{879}$ | Form | mp (° C.) or MS |
|---|---|---|---|
| 1531 | 2-quinolyl | free | MS 645 ($M^+$ + H) |
| 1532 | 4-quinolyl | free | MS 645 ($M^+$ + H) |
| 1533 | 1-isoquinolyl | free | MS 645 ($M^+$ + H) |
| 1534 | 3-isoquinolyl | free | MS 645 ($M^+$ + H) |
| 1535 | 3,4-$Cl_2PhCH_2$— | free | MS 676 ($M^+$ + H) |
| 1536 | 2,4-$Cl_2PhCH_2$— | free | MS 676 ($M^+$ + H) |
| 1537 | 3,5-$(CF_3)_2$Ph- | free | MS 731 ($M^+$ + H) |
| 1538 | 2,4-$Cl_2PhOCH_2$— | free | MS 691 ($M^+$ + H) |
| 1539 | 4-$CH_3$OPh- | free | MS 624 ($M^+$ + H) |
| 1540 | 4-$CH_3PhCH_2$— | free | MS 622 ($M^+$ + H) |
| 1541 | $PhOCH_2$— | free | MS 624 ($M^+$ + H) |
| 1542 | 3-pyridyl | free | MS 595 ($M^+$ + H) |
| 1543 | —$CH(CH_3)_2$ | free | MS 560 ($M^+$ + H) |
| 1544 | cyclopentyl | free | MS 586 ($M^+$ + H) |
| 1545 | cyclohexyl | free | MS 600 ($M^+$ + H) |
| 1546 | cycloheptyl | free | MS 614 ($M^+$ + H) |
| 1547 | cycloheptylmethyl | free | MS 628 ($M^+$ + H) |
| 1548 | 3-$CH_3$Ph- | free | MS 608 ($M^+$ + H) |
| 1549 | 3-$(CH_3)_2$NPh- | free | MS 637 ($M^+$ + H) |
| 1550 | 4-$(CH_3)_2$NPh- | free | MS 637 ($M^+$ + H) |
| 1551 | 2,5-$(CH_3)_2$Ph- | free | MS 622 ($M^+$ + H) |
| 1552 | —$CH(CH_3)$Ph | free | MS 622 ($M^+$ + H) |
| 1553 | —$C(CH_3)_3$ | free | MS 574 ($M^+$ + H) |

TABLE 289

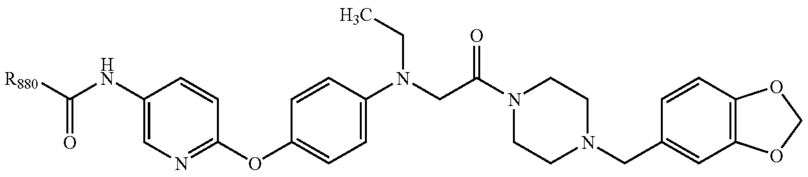

| Example No. | $R_{880}$ | MS ($M^+$ + H) |
|---|---|---|
| 1554 | 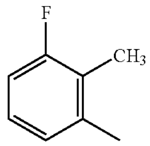 | 626 |
| 1555 | 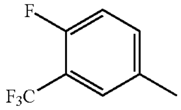 | 681 |
| 1556 | 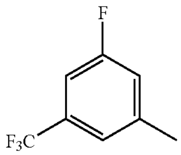 | 681 |

TABLE 289-continued
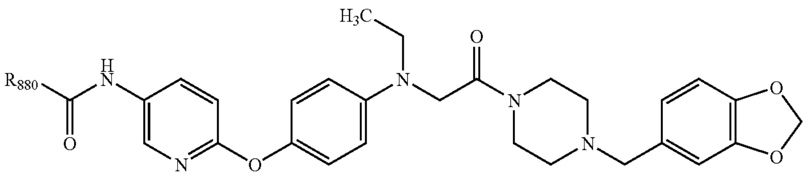
| Example No. | $R_{880}$ | MS ($M^+ + H$) |
|---|---|---|
| 1557 | 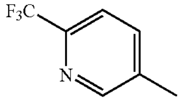 | 663 |
| 1558 | 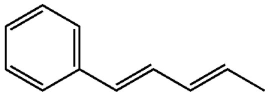 | 646 |
| 1559 | 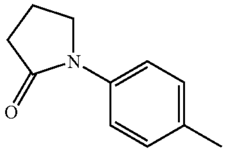 | 677 |
| 1560 | 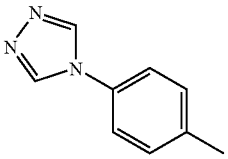 | 661 |
| 1561 | 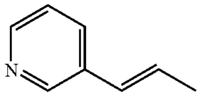 | 621 |
| 1562 | 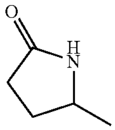 | 601 |
| 1563 | 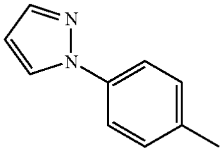 | 660 |
| 1564 | 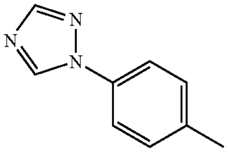 | 661 |
| 1565 | 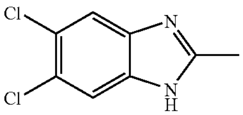 | 702 |

TABLE 290
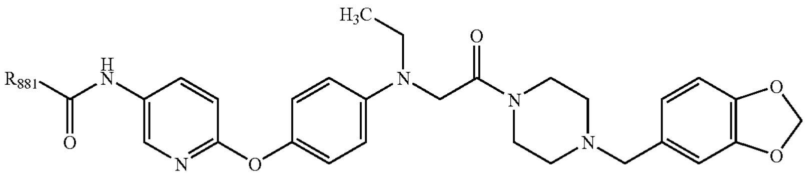
| Example No. | $R_{881}$ | MS ($M^+$ + H) |
|---|---|---|
| 1566 | 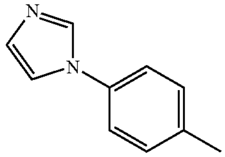 | 660 |
| 1567 | 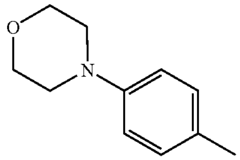 | 679 |
| 1568 | 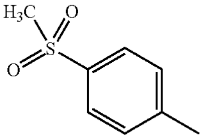 | 672 |
| 1569 | 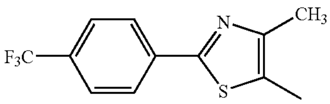 | 759 |
| 1570 | 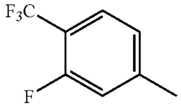 | 680 |
| 1571 | 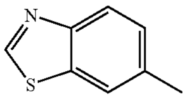 | 651 |
| 1572 | 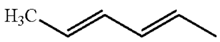 | 584 |
| 1573 | 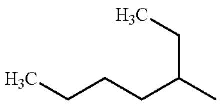 | 616 |
| 1574 | 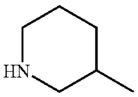 | 601 |
| 1575 | 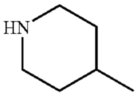 | 601 |

TABLE 290-continued
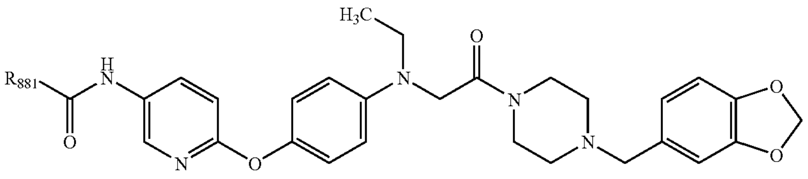
| Example No. | $R_{881}$ | MS ($M^+ + H$) |
|---|---|---|
| 1576 | 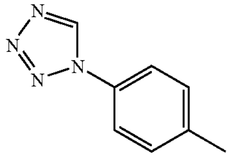 | 662 |
| 1577 | 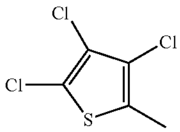 | 704 |
| 1578 | 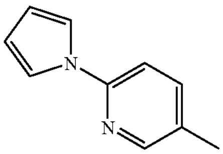 | 660 |
TABLE 291
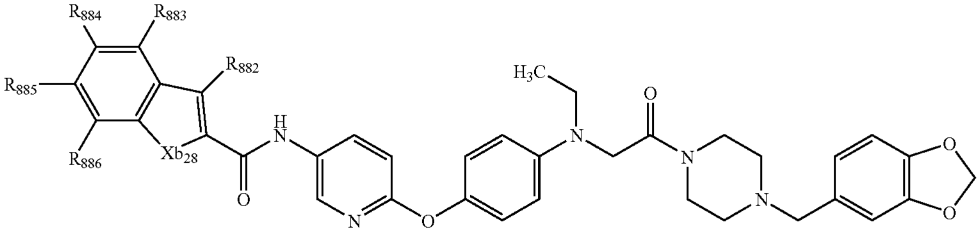
| Example No. | $Xb_{28}$ | $R_{882}$ | $R_{883}$ | $R_{884}$ | $R_{885}$ | $R_{886}$ | MS ($M^+ + H$) |
|---|---|---|---|---|---|---|---|
| 1579 | —NH— | —H | —H | —H | —H | —H | 634 |
| 1580 | —O— | —H | —H | —H | —H | —H | 634 |
| 1581 | —O— | —H | —H | —H | —H | —$OCH_3$ | 664 |
| 1582 | —NH— | —H | —H | —$OCH_3$ | —H | —H | 663 |
| 1583 | —NH— | —H | —H | —Cl | —H | —H | 667 |
| 1584 | —NH— | —H | —H | —F | —H | —H | 651 |
| 1585 | —N($CH_3$)— | —H | —H | —H | —H | —H | 647 |
| 1586 | —S— | —H | —H | —H | —H | —H | 650 |
| 1587 | —NH— | —H | —H | —Br | —H | —H | 711 |
| 1588 | —NH— | —H | —H | —$CH_3$ | —H | —H | 648 |
| 1589 | —NH— | —H | —H | —$OCF_3$ | —H | —H | 717 |
| 1590 | —NH— | —H | —$OCH_3$ | —H | —H | —H | 664 |
| 1591 | —NH— | —H | —Cl | —H | —H | —H | 667 |
| 1592 | —NH— | —H | —H | —H | —$OCH_3$ | —H | 663 |
| 1593 | —NH— | —H | —Cl | —H | —Cl | —H | 701 |
| 1594 | —NH— | —H | —H | —H | —Cl | —H | 667 |
| 1595 | —NH— | —H | —H | —$OCH_3$ | —$OCH_3$ | —H | 693 |
| 1596 | —O— | —$CH_3$ | —H | —H | —H | —H | 648 |
| 1597 | —O— | —H | —H | —$OCH_3$ | —H | —H | 664 |
| 1598 | —O— | —H | —H | —Cl | —H | —H | 668 |

TABLE 292

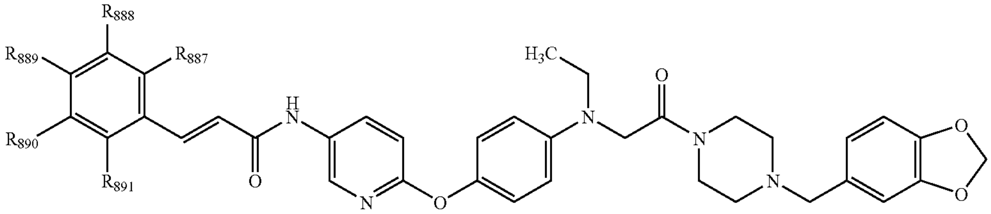

| Example No. | $R_{887}$ | $R_{888}$ | $R_{889}$ | $R_{890}$ | $R_{891}$ | MS ($M^+$ + H) |
|---|---|---|---|---|---|---|
| 1599 | —H | —$OCH_3$ | —H | —H | —H | 650 |
| 1600 | —H | —H | —$OCH_3$ | —H | —H | 650 |
| 1601 | —H | —Cl | —H | —H | —H | 654 |
| 1602 | —F | —H | —H | —H | —H | 638 |
| 1603 | —H | —F | —H | —H | —H | 638 |
| 1604 | —$OCH_3$ | —$OCH_3$ | —H | —H | —H | 680 |
| 1605 | —$OCH_3$ | —H | —H | —$OCH_3$ | —H | 680 |
| 1606 | —H | —$OCH_3$ | —$OCH_3$ | —H | —H | 680 |
| 1607 | —Cl | —H | —H | —H | —Cl | 688 |
| 1608 | —H | —Cl | —Cl | —H | —H | 688 |
| 1609 | —F | —H | —H | —H | —F | 656 |
| 1610 | —H | —F | —H | —F | —H | 656 |
| 1611 | —H | —$OCH_2O$— | | —H | —H | 664 |
| 1612 | —H | —$OCH_3$ | —$OCH_3$ | —$OCH_3$ | —H | 711 |
| 1613 | —H | —$OCH_3$ | —H | —$OCH_3$ | —H | 681 |
| 1614 | —H | —$CF_3$ | —H | —H | —H | 689 |

Example 1615

Production of 3,4-dichloro-N-[6-(2-fluoro-4-{methyl [2-oxo-2-(4-piperonylpiperazin-1-yl)ethyl] amino}phenoxy)pyridin-3-yl]benzenesulfonamide To a solution of 2-{[4-(5-aminopyridin-2-yloxy)-3-fluorophenyl]methylamino}-1-(4-piperonylpiperazin-1-yl)ethanone (15.85 g, 1.9 mmol) in dichloromethane (150 mL) were added 3,4-dichlorobenzenesulfonyl chloride (12.92 g, 1.9 mmol) and pyridine (11 mL, 12.4 mmol), and the resulting solution was stirred for 1 hour at room temperature. Water was added to the reaction solution, and extracted with ethyl acetate. The organic layer was washed with water and brine, and then dried over anhydrous magnesium sulfate. The solvent was evaporated under reduced pressure, and the residue was purified by silica gel column chromatography (ethyl acetate), and recrystallized from ethanol, to thereby yield 5.6 g of the title compound.

Appearance: White powder; Melting point: 185.6-187.0° C.;

$^1$H NMR ($CDCl_3$) δ 2.45 (4H, t, J=4.6 Hz), 3.01 (3H, s), 3.44 (2H, s), 3.47 (2H, brs), 3.64 (2H, brs), 4.07 (2H, s), 5.95 (2H, s), 6.33-6.44 (2H, m), 6.71-6.78 (2H, m), 6.84-6.87 (2H, m), 6.98 (1H, t, J=9.1 Hz), 7.47 (1H, dd, J=8.4 Hz, 2.0 Hz), 7.51 (2H, dd, J=8.4 Hz, 2.8 Hz), 7.68 (1H, d, J=2.1 Hz), 7.83 (1H, d, J=1.8 Hz); MS 701 ($M^+$).

The following compounds were produced in the same manner as in Example 1615.

TABLE 293

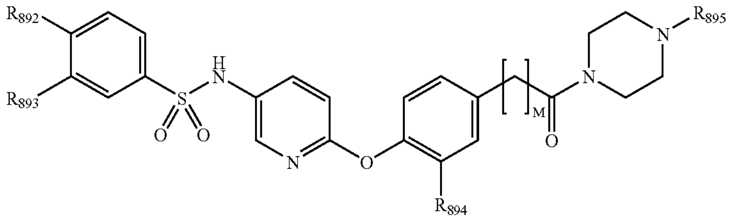

| Example No. | $R_{892}$ | $R_{893}$ | $R_{894}$ | $R_{895}$ | M | $^1$H NMR (solvent) δppm |
|---|---|---|---|---|---|---|
| 1616 | —$CH_3$ | —H | —H | benzyl | 2 | ($CDCl_3$) 2.29-2.37(2 H, m), 2.37-2.45(5 H, m), 2.61(2 H, t, J = 7.9 Hz), 2.95(2 H, t, J = 7.9 Hz), 3.35-3.42(2 H, m), 3.50(2 H, s), 3.59-3.68(2 H, m), 6.58(1 H, brs), 6.83(1 H, d, J = 8.8 Hz), 7.00(2 H, d, J = 8.4 Hz), 7.18-7.38(9 H, m), .755-7.63(3 H, m), 7.68(1 H, d, J = 2.8 Hz). |
| 1617 | —$CF_3$ | —H | —H | benzyl | 0 | ($CDCl_3$) 2.46(4 H, brs), 3.54(2 H, s), 3.54(2 H, brs), 3.79(2 H, brs), 6.88(1 H, d, J = 8.7 Hz), 7.10(2 H, d, J = 8.6 Hz), 7.28-7.33(5 H, m), 7.42(2 H, d, J = 8.6 Hz), 7.59(1 H, dd, J = 8.7 |

TABLE 293-continued

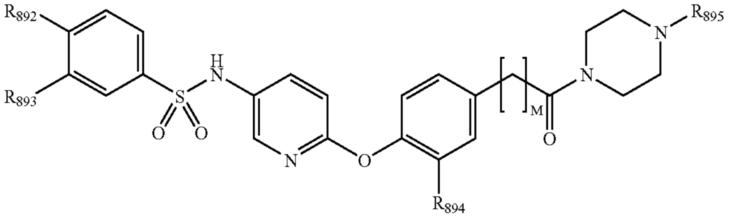

| Example No. | $R_{892}$ | $R_{893}$ | $R_{894}$ | $R_{895}$ | M | $^1$H NMR (solvent) δppm |
|---|---|---|---|---|---|---|
| | | | | | | Hz, 2.8 Hz), 7.73(2 H, d, J = 8.4 Hz), 7.74(1 H, s), 7.86(2 H, d, J = 8.4 Hz). |
| 1618 | —$CF_3$ | —H | —$CH_3$ | piperonyl | 2 | (DMSO-$d_6$) 1.96(3 H, s), 2.20-2.40(4 H, m), 2.56-2.62(2 H, m), 2.73-2.78(2 H, m), 3.32(2 H, s), 3.37-3.43(4 H, m), 5.99(2 H, s), 6.74(1 H, dd, J = 7.9 Hz, 1.3 Hz), 6.82-6.93(4 H, m), 7.05(1 H, dd, J = 8.2 Hz, 1.9 Hz), 7.12(1 H, s), 7.52(1 H, dd, J = 8.8 Hz, 2.7 Hz), 7.73(1 H, d, J = 2.7 Hz), 7.89-7.98(4 H, m), 10.45(1 H, brs). |
| 1619 | —Cl | —Cl | —$OCH_3$ | piperonyl | 2 | (DMSO-$d_6$) 2.20-2.40(4 H, m), 2.58-2.64(2 H, m), 2.75-2.81(2 H, m), 3.37-3.43(6 H, m), 3.60(3 H, s), 5.97(2 H, s), 6.70-7.00(7 H, m), 7.47(1 H, dd, J = 8.8 Hz, 2.8 Hz), 7.61(1 H, dd, J = 8.5 Hz, 2.1 Hz), 7.68(1 H, d, J = 2.6 Hz), 7.82-7.86(2 H, m), 10.32(1 H, brs). |
| 1620 | —$CF_3$ | —H | —$OCH_3$ | piperonyl | 2 | (DMSO-$d_6$) 2.20-2.40(4 H, m), 2.55-2.70(2 H, m), 2.75-2.85(2 H, m), 3.30-3.50(6 H, m), 3.58(3 H, s), 5.97(2 H, s), 6.71-7.00(7 H, m), 7.47(1 H, dd, J = 8.8 Hz, 2.7 Hz), 7.67(1 H, d, J = 2.7 Hz), 7.87-7.98(4 H, m), 10.40(1 H, brs). |
| 1621 | —Cl | —Cl | —$CH_3$ | piperonyl | 2 | (DMSO-$d_6$) 1.97(3 H, s), 2.20-2.35(4 H, m), 2.56-2.62(2 H, m), 2.73-2.79(2 H, m), 3.37-3.50(6 H, m), 5.98(2 H, s), 6.72-6.76(1 H, m), 6.82-6.94(4 H, m), 7.00-7.13(2 H, m), 7.52(1 H, dd, J = 8.8 Hz, 2.8 Hz), 7.62(1 H, dd, J = 8.4 Hz, 2.1 Hz), 7.72(1 H, d, J = 2.6 Hz), 7.83(1 H, d, J = 2.1 Hz), 7.85(1 H, d, J = 8.5 Hz), 10.36(1 H, brs). |
| 1622 | —$CF_3$ | —H | —F | piperonyl | 2 | (DMSO-$d_6$) 2.20-2.35(4 H, m), 2.60-2.66(2 H, m), 2.78-2.84(2 H, m), 3.39(2 H, s), 3.42-3.50(4 H, m), 5.99(2 H, s), 6.72-6.76(1 H, m), 6.83-6.86(2 H, m), 7.03-7.24(4 H, m), 7.55(1 H, dd, J = 8.8 Hz, 2.7 Hz), 7.75(1 H, d, J = 2.7 Hz), 7.90-7.99(4 H, m), 10.52(1 H, brs). |

TABLE 294

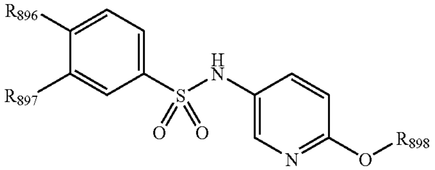

| Example No. | $R_{896}$ | $R_{897}$ | $R_{898}$ | mp (° C.) or $^1$H NMR (solvent) δppm |
|---|---|---|---|---|
| 1623 | —$CF_3$ | —H | 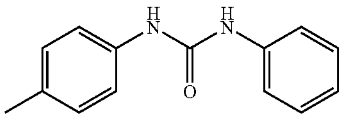 | mp 208.0-209.0 |

TABLE 294-continued

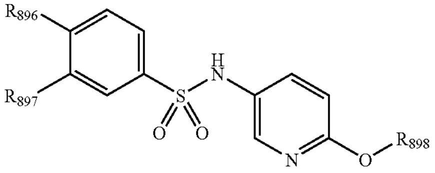

| Example No. | $R_{896}$ | $R_{897}$ | $R_{898}$ | mp (° C.) or $^1$H NMR (solvent) δppm |
|---|---|---|---|---|
| 1624 | —Cl | —Cl | 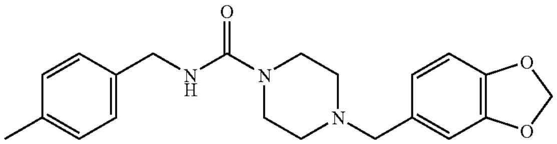 | $^1$H NMR ($CDCl_3$) 1.70(1 H, brs), 2.42(4 H, t, J = 5.1 Hz), 3.39(4 H, t, J = 5.1 Hz), 3.43(2 H, s), 4.38(2 H, d, J = 5.4 Hz), 4.80(1 H, t, J = 5.4 Hz), 5.94(2 H, s), 6.73(2 H, s), 6.84(1 H, s), 6.86(1 H, d, J = 8.5 Hz), 7.00(2 H, d, J = 8.6 Hz), 7.27(2 H, d, J = 8.6 Hz), 7.51(2 H, d, J = 2.5 Hz), 7.58(1 H, dd, J = 8.7 Hz, 2.7 Hz), 7.73(1 H, dd, J = 2.7 Hz, 0.7 Hz), 7.83(1 H, t, J = 2.5 Hz). |
| 1625 | —Cl | —Cl | 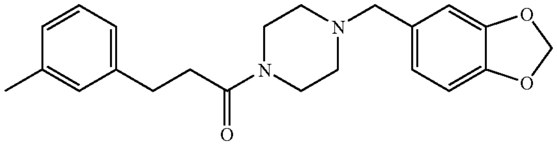 | $^1$H NMR (DMSO-$d_6$) 2.20-2.35(4 H, m), 2.56-2.62(2 H, m), 2.77-2.82(2 H, m), 3.30-3.50(6 H, m), 5.98(2 H, s), 6.70-6.80(1 H, m), 6.82-6.90(3 H, m), 6.93-6.97(2 H, m), 7.05-7.10(1 H, m), 7.24-7.35(1 H, m), 7.54(1 H, dd, J = 8.8 Hz, 2.8 Hz), 7.64(1 H, dd, J = 8.5 Hz, 2.0 Hz), 7.80(1 H, d, J = 2.8 Hz), 7.86(1 H, d, J = 8.4 Hz), 7.89(1 H, d, J = 2.0 Hz), 10.43(1 H, brs). |
| 1626 | —$CF_3$ | —H | 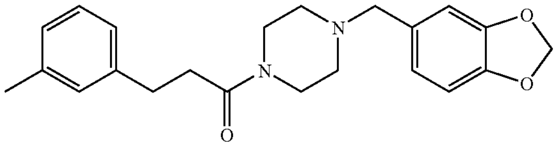 | $^1$H NMR (DMSO-$d_6$) 2.20-2.30(4 H, m), 2.55-2.61(2 H, m), 2.76-2.82(2 H, m), 3.30-3.40(6 H, m), 5.98(2 H, s), 6.70-6.80(1 H, m), 6.82-6.95(5 H, m), 7.05(1 H, d, J = 7.7 Hz), 7.23-7.30(1 H, m), 7.54(1 H, dd, J = 8.8 Hz, 2.8 Hz), 7.80(1 H, d, J = 2.8 Hz), 7.90-7.99(4 H, m), 10.52(1 H, brs). |
| 1627 | —Cl | —Cl | 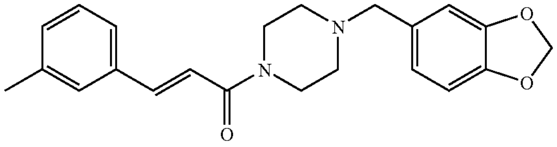 | $^1$H NMR (DMSO-$d_6$) 2.25-2.45(4 H, m), 3.42(2 H, s), 3.50-3.75(4 H, m), 5.99(2 H, s), 6.75-6.80(1 H, m), 6.83-6.88(2 H, m), 7.00(1 H, d, J = 8.8 Hz), 7.05-7.10(1 H, m), 7.25-7.29(1 H, m), 7.35-7.65(6 H, m), 7.80(1 H, d, J = 2.7 Hz), 7.86(1 H, d, J = 8.4 Hz), 7.90(1 H, d, J = 2.1 Hz), 10.44 (1 H, brs). |

TABLE 295

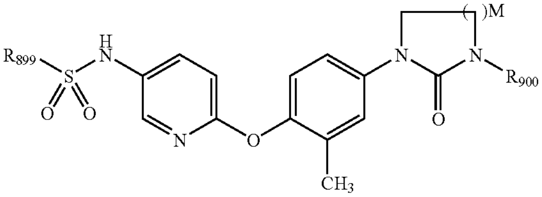

| Example No. | $R_{899}$ | $R_{900}$ | M | mp (° C.) or $^1$H NMR (DMSO-$d_6$) δppm |
|---|---|---|---|---|
| 1628 | 4-$CF_3$Ph- | piperonyl | 2 | $^1$H NMR 1.89-2.06(5 H, m), 3.17-3.31(2 H, m), 3.52-3.71(2 H, m), 4.39(2 H, s), 5.98(2 H, m), 6.75(1 H, dd, J = 1.2 Hz, 7.9 Hz), 6.83(1 H, d, J = 1.2 Hz), 6.86(1 H, d, J = 7.9 |

TABLE 295-continued

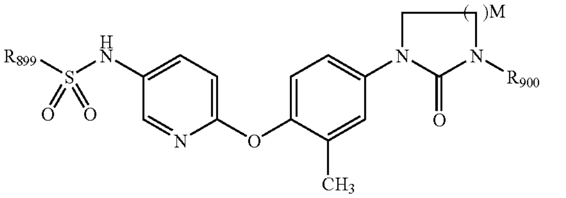

| Example No. | $R_{899}$ | $R_{900}$ | M | mp (° C.) or $^1$H NMR (DMSO-$d_6$) δppm |
|---|---|---|---|---|
| | | | | Hz), 6.92(1 H, d, J = 8.6 Hz), 6.95(1 H, d, J = 8.8 Hz), 7.09(1 H, dd, J = 2.5 Hz, 8.6 Hz), 7.18(1 H, d, J = 2.5 Hz), 7.53(1 H, dd, J = 2.8 Hz, 8.8 Hz), 7.75(1, d, J = 2.8 Hz), 7.90(2 H, d, J = 8.4 Hz), 7.96(2 H, d, J = 8.4 Hz), 10.47(1 H, s). |
| 1629 | 3,4-$Cl_2$Ph- | piperonyl | 2 | $^1$H NMR (1.89-2.09(5 H, m), 3.19-3.33(2 H, m), 3.50-3.71(2 H, m), 4.39(2 H, s), 5.98(2 H, s), 6.73-6.78(1 H, m), 6.83(1 H, d, J = 1.3 Hz), 6.86(1 H, d, J = 7.9 Hz), 6.93(1 H, d, J = 8.6 Hz), 6.97(1 H, d, J = 8.8 Hz), 7.10(1 H, d, J = 2.4 Hz, 8.6 Hz), 7.19(1 H, d, J = 2.4 Hz), 7.53(1 H, dd, J = 2.7 Hz, 8.8 Hz), 7.62(1 H, dd, J = 2.1 Hz, 8.4 Hz), 7.75(1 H, d, J = 2.7 Hz), 7.83(1 H, d, J = 2.1 Hz), 7.85(1 H, d, J = 8.4 Hz), 10.37(1 H, s). |
| 1630 | 4-$CF_3$Ph- | piperonyl | 1 | mp 163.0-164.0 |
| 1631 | 3,4-$Cl_2$Ph- | piperonyl | 1 | mp 190.5-191.0 |
| 1632 | 4-$CF_3$Ph- | 3,4-$(CH_3O)_2PhCH_2$— | 2 | mp 141.0-143.0 |
| 1633 | 3,4-$Cl_2$Ph- | 3,4-$(CH_3O)_2PhCH_2$— | 2 | mp 135.0-136.0 |
| 1634 | 3,4-$Cl_2$Ph- | 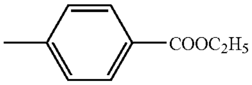 | 2 | mp 181.0-183.0 |

TABLE 296

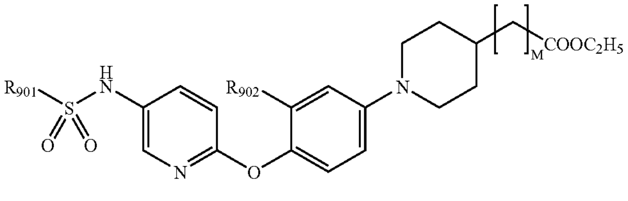

| Example | $R_{901}$ | $R_{902}$ | M | $^1$H NMR ($CDCl_3$) δppm |
|---|---|---|---|---|
| 1635 | 3,4-$Cl_2$Ph- | —$CH_3$ | 0 | 1.27(3 H, t, J = 7.1 Hz), 1.84-2.05(4 H, m), 2.06(3 H, s), 2.40-2.48(1 H, m), 2.71-2.81(2 H, m), 3.56-3.61(2 H, m), 4.16(2 H, q, J = 7.1 Hz), 6.74-6.79(3 H, m), 6.89(1 H, d, J = 8.6 Hz), 7.47-7.57(4 H, m), 7.76-7.79(2 H, m). |
| 1636 | 4-$CF_3$Ph- | —$CH_3$ | 0 | 1.27(3 H, t, J = 7.1 Hz), 1.84-2.00(4 H, m), 2.03(3 H, s), 2.42-2.51(1 H, m), 2.70-2.79(2 H, m), 3.55-3.60(2 H, m), 4.16(2 H, q, J = 7.1 Hz), 6.68-6.78(3 H, m), 6.87(1 H, d, J = 8.6 Hz), 7.55(1 H, dd, J = 8.7 Hz, 2.6 Hz), 7.67(2 H, d, J = 8.2 Hz), 7.79-7.84(3 H, m), 8.10(1 H, s). |
| 1637 | 3,4-$Cl_2$Ph- | —H | 1 | 1.27(3 H, t, J = 7.1 Hz), 1.39-1.48(2 H, m), 1.81-1.92(3 H, m), 2.29(2 H, d, J = 6.9 Hz), 2.71(2 H, dd, J = 12.2 Hz, 9.9 Hz), 3.59(2 H, d, J = 12.4 Hz), 4.15(2 H, q, J = 7.3 Hz), 6.78(1 H, d, J = 8.7 Hz), 6.90-6.98(4 H, m), 7.50(2 H, d, J = 1.2 Hz), 7.55(1 H, dd, J = 8.7 Hz, 2.6 Hz), 7.78-7.81(3 H, m). |
| 1638 | 4-$CF_3$Ph- | —H | 1 | 1.27(3 H, t, J = 7.1 Hz), 1.36-1.48(2 H, m), 1.81-1.92(3 H, m), 2.29(2 H, d, J = 6.9 Hz), 2.70(2 H, dd, J = 12.2 Hz, 9.9 Hz), 3.59(2 H, d, J = 12.2 Hz), 4.15(2 H, q, J = 7.3 Hz), 6.75(1 H, d, J = 8.9 Hz), 6.89-6.97(4 H, m), 7.55(1 H, dd, J = 8.7 Hz, 2.6 Hz), 7.68(2 H, d, J = 8.7 Hz), 7.79-7.85(4 H, m). |
| 1639 | 4-$CF_3$Ph- | —$OCH_3$ | 1 | 1.27(3 H, t, J = 7.1 Hz), 1.30-1.48(2 H, m), 1.82-2.05(3 H, m), 2.29(2 H, d, J = 6.9 Hz), 2.69-2.77(2 H, m), 3.60(2 H, d, J = 12.2 Hz), 3.68(3 H, s), 4.15(2 H, q, J = 7.1 Hz), 6.48(1 H, dd, J = 8.6 Hz, 2.5 Hz), 6.56(1 H, d, J = 2.6 Hz), |

TABLE 296-continued

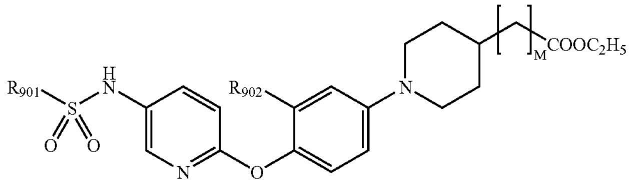

| Example | $R_{901}$ | $R_{902}$ | M | $^1H$ NMR ($CDCl_3$) δppm |
|---|---|---|---|---|
| | | | | 6.76(1 H, d, J = 8.7 Hz), 6.94(1 H, d, J = 8.7 Hz), 7.54(1 H, dd, J = 8.7 Hz, 2.8 z), 7.66-7.73(4 H, m), 7.83(2 H, d, J = 8.2 Hz). |
| 1640 | 3,4-$Cl_2$Ph- | —$OCH_3$ | 1 | 1.28(3 H, t, J = 7.1 Hz), 1.30-1.48(2 H, m), 1.82-2.05(3 H, m), 2.29(2 H, d, J = 6.9 Hz), 2.73(2 H, t, J = 12.0 Hz), 3.60(2 H, d, J = 12.2 Hz), 3.69(3 H, s), 4.16(2 H, q, J = 7.1 Hz), 5.29(2 H, s), 6.48(1 H, dd, J = 8.7 Hz, 2.6 Hz), 6.56(1 H, d, J = 2.6 Hz), 6.77(1 H, d, J = 8.7 Hz), 6.94(1 H, d, J = 8.6 Hz), 7.46-7.75(3 H, m), 7.79-7.80(3 H, m). |
| 1641 | 4-$CF_3$Ph- | —H | 0 | 1.27(3 H, t, J = 7.1 Hz), 1.81-1.94(2 H, m), 2.00-2.05(2 H, m), 2.40-2.54(1 H, m), 2.71-2.82(2 H, m), 3.56-3.60(2 H, m), 4.16(2 H, q, J = 7.1 Hz), 6.78(1 H, d, J = 8.9 Hz), 6.90-6.99(5 H, m), 7.56(1 H, dd, J = 8.9 Hz, 2.8 z), 7.70(2 H, d, J = 8.4 Hz), 7.77(1 H, d, J = 2.8 Hz), 7.84(2 H, d, J = 8.2 Hz). |
| 1642 | 3,4-$Cl_2$Ph- | —H | 0 | 1.27(3 H, t, J = 7.3 Hz), 1.89-1.94(2 H, m), 2.01-2.05(2 H, m), 2.38-2.54(1 H, m), 2.72-2.82(2 H, m), 3.56-3.61(2 H, m), 4.16(2 H, q, J = 7.1 Hz), 6.80(1 H, d, J = 8.7 Hz), 6.91-7.00(4 H, m), 7.26(1 H, brs), 7.51-7.58(3 H, m), 7.77(1 H, d, J = 2.8 Hz), 7.82(1 H, s). |

TABLE 297

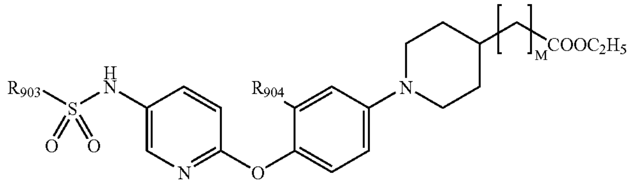

| Example No. | $R_{903}$ | $R_{904}$ | M | $^1H$ NMR ($CDCl_3$) δppm |
|---|---|---|---|---|
| 1643 | 4-$CF_3$Ph- | —$CH_3$ | 1 | 1.27(3 H, t, J = 7.1 Hz), 1.38-1.43(2 H, m), 1.80-2.01(3 H, m), 2.02(3 H, s), 2.29(2 H, d, J = 6.9 Hz), 2.69(2 H, t, J = 12.0 Hz), 3.58(2 H, d, J = 12.0 Hz), 4.15(2 H, q, J = 7.3 Hz), 6.67-6.87(4 H, m), 7.53-7.68(3 H, m), 7.79-7.84(4 H, m). |
| 1644 | 3,4-$Cl_2$Ph- | —$CH_3$ | 1 | 1.27(3 H, t, J = 7.1 Hz), 1.30-1.48(2 H, m), 1.80-2.04(3 H, m), 2.05(3 H, s), 2.29(2 H, d, J = 6.9 Hz), 2.69(2 H, t, J = 12.0 Hz), 3.58(2 H, d, J = 12.0 Hz), 4.15(2 H, q, J = 7.1 Hz), 6.71-6.79(3 H, m), 6.88(1 H, d, J = 8.6 Hz), 7.49-7.57(4 H, m), 7.77(2 H, d, J = 2.8 Hz). |

TABLE 298

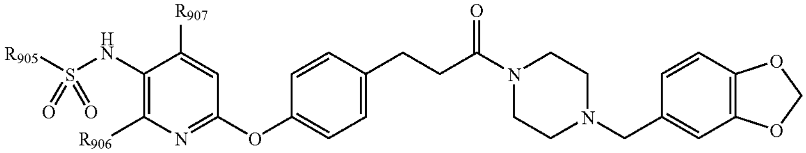

| Example No. | $R_{905}$ | $R_{906}$ | $R_{907}$ | Form | mp (° C.) |
|---|---|---|---|---|---|
| 1645 | 4-$CF_3$Ph- | —H | —$CH_3$ | hydrochloride | 189.0-191.0 |
| 1646 | 3,4-$Cl_2$Ph- | —H | —$CH_3$ | free | 180.0-182.0 |
| 1647 | 4-$CF_3$Ph- | —$CH_3$ | —H | free | 129.5-131.0 |
| 1648 | 3,4-$Cl_2$Ph- | —$CH_3$ | —H | free | 129.0-130.0 |

TABLE 299

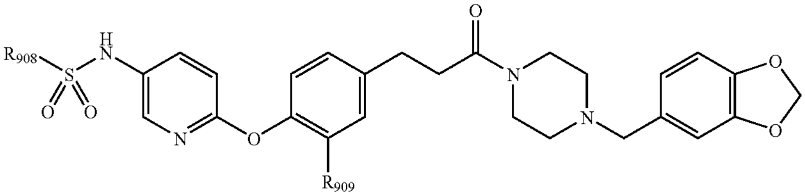

| Example No. | $R_{908}$ | $R_{909}$ | $^1H$ NMR (DMSO-$d_6$) δppm |
|---|---|---|---|
| 1649 | 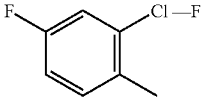 | —F | 2.20-2.35(4 H, m), 2.60-2.66(2 H, m), 2.77-2.83(2 H, m), 3.39(2 H, s), 3.39-3.50(4 H, m), 5.99(2 H, s), 6.65-6.76(1 H, m), 6.83-6.86(2 H, m), 7.01-7.25(4 H, m), 7.30-7.40(1 H, m), 7.55(1 H, dd, J = 8.8 Hz, 2.8 Hz), 7.72(1 H, dd, J = 8.7 Hz, 2.6 Hz), 7.78(1 H, d, J = 2.3 Hz), 8.00-8.05(1 H, m), 10.65(1 H, brs). |
| 1650 | 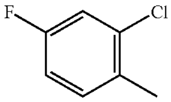 | $—CH_3$ | 1.94(3 H, s), 2.20-2.35(4 H, m), 2.56-2.61(2 H, m), 2.72-2.78(2 H, m), 3.38(2 H, s), 3.38-3.50(4 H, m), 5.98(2 H, s), 6.72-6.75(1 H, m), 6.82-6.91(4 H, m), 7.03-7.12(2 H m), 7.30-7.45(1 H, m), 7.52(1 H, dd, J = 8.8 Hz, 2.2 Hz), 7.71(1 H, dd, J = 8.7 Hz, 2.1 Hz), 7.78(1 H, d, J = 2.7 Hz), 7.98-8.04(1 H, m), 10.58(1 H, brs). |
| 1651 | 3,4-$Cl_2$Ph- | —H | 2.20-2.35(4 H, m), 2.57-2.63(2 H, m), 2.76-2.82(2 H, m), 3.39(2 H, s), 3.39-3.43(4 H, m), 5.99(2 H, s), 6.70-6.76(1 H, m), 6.82-6.86(2 H, m), 6.93-6.98(3 H, m), 7.22-7.26(2 H, m), 7.51-7.55(1 H, m), 7.63(1 H, dd, J = 8.5 Hz, 2.0 Hz), 7.79(1 H, d, J = 2.7 Hz), 7.86(1 H, d, J = 8.5 Hz), 7.88(1 H, d, J = 2.1 Hz), 10.41(1 H, brs). |
| 1652 | 4-$CF_3$Ph- | —H | 2.20-2.35(4 H, m), 2.57-2.63(2 H, m), 2.76-2.82(2 H, m), 3.32(2 H, s), 3.32-3.50(4 H, m), 5.98(2 H, s), 6.70-6.76(1 H, m), 6.82-6.86(2 H, m), 6.92-6.98(3 H, m), 7.22-7.25(2 H, m), 7.52(1 H, dd, J = 8.8 Hz, 2.8 Hz), 7.78(1 H, d, J = 2.7 Hz), 7.90-7.99(4 H, m), 10.50(1 H, brs). |
| 1653 | 3,4-$Cl_2$Ph- | —F | 2.20-2.35(4 H, m), 2.60-2.66(2 H, m), 2.78-2.84(2 H, m), 3.39(2 H, s), 3.42-3.50(4 H, m), 5.99(2 H, s), 6.70-6.7(1 H, m), 6.82-6.86(2 H, m), 7.04-7.30(4 H, m), 7.55(1 H, dd, J = 8.8 Hz, 2.8 Hz), 7.63(1 H, dd, J = 8.5 Hz, 2.2 Hz), 7.75(1 H, d, J = 2.6 Hz), 7.85(1 H, d, J = 8.5 Hz), 7.88(1 H, d, J = 2.1 Hz), 10.43(1 H, brs). |

TABLE 300

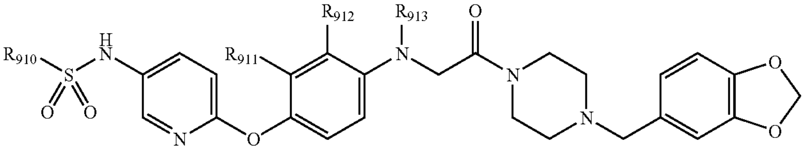

| Example No. | $R_{910}$ | $R_{911}$ | $R_{912}$ | $R_{913}$ | mp (° C.) or $^1H$ NMR (solvent) δppm |
|---|---|---|---|---|---|
| 1654 | 4-$CF_3$Ph- | —F | —H | $—CH_3$ | mp 186.0-188.0 |
| 1655 | 3,4-$Cl_2$Ph- | —F | —H | $—C_2H_5$ | mp 157.3-160.1 |
| 1656 | 4-$CF_3$Ph- | —F | —H | $—C_2H_5$ | mp 173.0-176.8 |
| 1657 | 4-$CF_3$Ph- | $—OCH_3$ | —H | $—C_2H_5$ | mp 179.0-181.0 |
| 1658 | 3,4-$Cl_2$Ph- | $—OCH_3$ | —H | $—C_2H_5$ | mp 175.0-176.0 |
| 1659 | 4-$CF_3$Ph- | $—CH_3$ | —H | $—CH_3$ | mp 170.0-172.0 |
| 1660 | 3,4-$Cl_2$Ph- | $—CH_3$ | —H | $—CH_3$ | mp 170.0-173.0 |
| 1661 | 3,4-$Cl_2$Ph- | —H | —H | $—CH_3$ | mp 135.0-137.0 |
| 1662 | 4-$CF_3$Ph- | —H | —H | $—CH_3$ | mp 189.0-190.0 |
| 1663 | 4-$CF_3$Ph- | —F | —F | $—CH_3$ | mp 159.5-160.0 |
| 1664 | 3,4-$Cl_2$Ph- | —F | —F | $—CH_3$ | mp 136.0-137.0 |
| 1665 | Ph- | —H | —H | $—CH_3$ | $^1H$ NMR ($CDCl_3$) 2.41-2.45(4 H, m), 3.01(3 H, s), 3.43(2 H, s), 3.47-3.49(2 H, m), 3.63(2 H, brs), 4.07(2 H, s), 5.95(2 H, s), 6.63(1 H, brs), 6.66(2 H, d, J = 9.1 Hz), 6.71-6.77(3 H, m), 6.85(1 H, brs), 6.93(2 H, d, J = 9.1 Hz), 7.42-7.59(4 H, m), 7.68-7.73(3 H, m). |
| 1666 | $—(CH_2)_3CH_3$ | —H | —H | $—CH_3$ | $^1H$ NMR ($CDCl_3$) 0.93(3 H, t, J = 7.3 Hz), 1.36-1.50(2 H, m), 1.75-1.87(2 H, m), 2.41- |

TABLE 300-continued

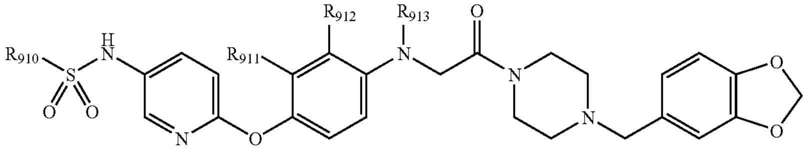

| Example No. | $R_{910}$ | $R_{911}$ | $R_{912}$ | $R_{913}$ | mp (° C.) or $^1$H NMR (solvent) δppm |
|---|---|---|---|---|---|
| | | | | | 2.45(4 H, m), 3.01-3.06(5 H, m), 3.44(2 H, s), 3.47-3.49(2 H, m), 3.63(2 H, brs), 4.09(2 H, s), 5.95(2 H, s), 6.37(1 H, brs), 6.69(2 H, d, J = 9.1 Hz), 6.72-6.77(2 H, m), 6.82-6.96(2 H, m), 6.99(2 H, d, J = 9.1 Hz), 7.65(1 H, dd, J = 8.7 Hz, 2.8 H), 8.00(1 H, d, J = 2.8 Hz). |
| 1667 | 4-$CH_3$Ph- | —H | —H | —$CH_3$ | $^1$H NMR ($CDCl_3$) 2.39(3 H, s), 2.41-2.44(4 H, m), 3.01(3 H, s), 3.43(2 H, s), 3.47-3.49(2 H, m), 3.62(2 H, brs), 4.07(2 H, s), 5.95(2 H, s), 6.46-6.51(1 H, m), 6.66(2 H, d, J = 8.9 Hz), 6.70-6.77(3 H, m), 6.85(1 H, brs), 6.94(2 H, d, J = 8.9 Hz), 7.23(2 H, d, J = 8.1 Hz), 7.50(1 H, dd, J = 8.2 Hz, 2.8 Hz), 7.58(2 H, d, J = 8.4 Hz), 7.66(1 H, d, J = 2.6 Hz). |
| 1668 | 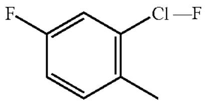 | —F | —H | —$CH_3$ | $^1$H NMR (DMSO-$d_6$) 2.25-2.45(4 H, m), 2.91(3 H, s), 3.42(6 H, brs), 4.26(2 H, s), 5.99(2 H, s), 6.30-6.40(1 H, m), 6.45-6.55(1 H, m), 6.74-6.77(1 H, m), 6.83-7.05(4 H, m), 7.30-7.45(1 H, m), 7.51(1 H, dd, J = 8.9 Hz, 2.8 Hz), 7.71(1 H, dd, J = 8.7 Hz, 2.5 Hz), 7.79(1 H, d, J = 2.7 Hz), 8.02(1 H, dd, J = 8.9 Hz, 5.9 Hz), 10.60(1 H, brs). |
| 1669 | 3,4-$Cl_2$Ph- | —$COOCH_3$ | —H | —$C_2H_5$ | $^1$H NMR (DMSO-$d_6$) 1.11(3 H, t, J = 7.0 Hz), 2.20-2.5(4 H, m), 3.30-3.50(11 H, m), 4.22(2 H, s), 5.99(2 H, s), 6.75-7.00(7 H, m), 7.45-7.55(1 H, m), 7.60-7.70(2 H, m), 7.83-7.87(2 H, m), 10.31(1 H, brs). |

TABLE 301

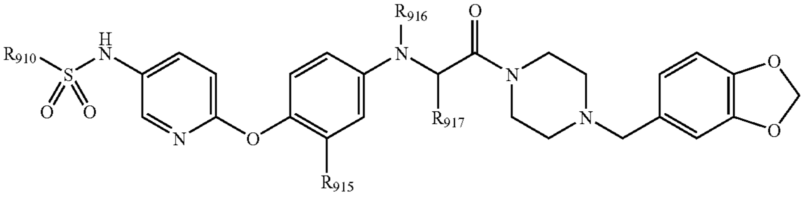

| Example No. | $R_{914}$ | $R_{915}$ | $R_{916}$ | $R_{917}$ | $^1$H NMR (solvent) δppm |
|---|---|---|---|---|---|
| 1670 | 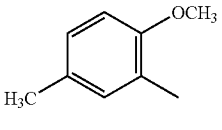 | —F | —$CH_3$ | —H | (DMSO-$d_6$) 2.23(3 H, s), 2.25-2.45(4 H, m), 2.91(3 H, s), 3.41(6 H, brs), 3.83(3 H, s), 4.25(2 H, s), 5.99(2 H, s), 6.30-6.40(1 H, m), 6.45-6.55(1 H, m), 6.75-6.77(1 H, m), 6.83-6.99(4 H, m), 7.07(1 H, d, J = 8.5 Hz), 7.30-7.40(1 H, m), 7.48(1 H, d, J = 1.9 Hz), 7.51(1 H, dd, J = 8.8 Hz, 2.7 Hz), 7.74(1 H, d, J = 2.6 Hz), 9.85(1 H, brs). |
| 1671 | 3,4-$Cl_2$Ph- | —$CH_3$ | —$CH_3$ | —$CH_3$ | ($CDCl_3$) 1.28(3 H, d, J = 6.6 Hz), 2.05(3 H, s), 2.08-2.21(1 H, m), 2.33(2 H, brs), 2.50(1 H, brs), 2.75(3 H, s), 3.29-3.57(3 H, m), 3.38(2 H, s), 3.77(1 H, brs), 4.55(1 H, q, J = 6.6 Hz), 5.94(2 H, s), 6.56-6.59(2 H, m), 6.68-6.75(2 H, m), 6.79-6.82(2 H, m), 6.89-6.93(1 H, m), 7.51-7.52(2 H, m), 7.57(1 H, dd, J = 8.9 Hz, 2.8 Hz), 7.71(1 H, dd, J = 2.8 Hz, 0.5 Hz), 7.79(1 H, dd, J = 1.7 Hz, 0.8 Hz). |
| 1672 | 4-$CF_3$Ph- | —$CH_3$ | —$CH_3$ | —$CH_3$ | ($CDCl_3$) 1.28(3 H, d, J = 6.4 Hz), 2.07(3 H, s), 2.17-2.20(1 H, m), 2.33-2.36(2 H, m), 2.47-2.49(1 H, m), 2.75(3 H, s), 3.28- |

TABLE 301-continued

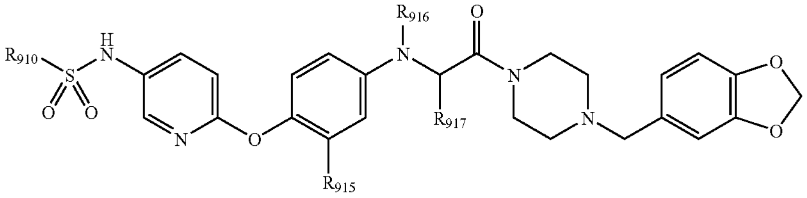

| Example No. | $R_{914}$ | $R_{915}$ | $R_{916}$ | $R_{917}$ | $^1H$ NMR (solvent) δppm |
|---|---|---|---|---|---|
| | | | | | 3.30(1 H, m), 3.38(2 H, s), 3.38-3.50(1 H, m), 3.52-3.56(1 H, m), 3.77-3.82(1 H, m), 4.55(1 H, q, J = 6.6 Hz), 5.94(2 H, s), 6.55-6.59(2 H, m), 6.68-6.75(2 H, m), 6.78-6.82(2 H, m), 6.89-6.92(1 H, m), 7.57(1 H, dd, J = 8.7 Hz, 2.8 Hz), 7.70(1 H, dd, J = 2.8 Hz, 0.5 Hz), 7.73(2 H, d, J = 8.3 Hz), 7.85(2 H, d, J = 8.3 Hz). |
| 1673 | 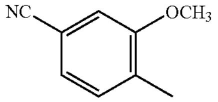 | —F | —$CH_3$ | —H | ($DMSO-d_6$) 2.20-2.50(4 H, m), 2.91(3 H, s), 3.35-3.50(6 H, m), 4.26(2 H, s), 5.99(2 H, s), 6.20-6.30(1 H, m), 6.45-6.55(1 H, m), 6.75-6.80(1 H, m), 6.84-7.01(4 H, m), 7.52(1 H, dd, J = 8.8 Hz, 2.7 Hz), 7.79(1 H, d, J = 2.8 Hz), 7.97(1 H, dd, J = 8.2 Hz, 1.5 Hz), 8.09(1 H, d, J = 8.2 Hz), 8.29(1 H, d, J = 1.5 Hz), 10.80(1 H, brs). |
| 1674 | 4-PhOPh- | —F | —$CH_3$ | —H | ($DMSO-d_6$) 2.20-2.45(4 H, m), 2.92(3 H, s), 3.35-3.50(6 H, m), 4.26(2 H, s), 5.99(2 H, s), 6.35-6.45(1 H, m), 6.45-6.60(1 H, m), 6.76(1 H, d, J = 7.9 Hz), 6.83-6.87(2 H, m), 6.93-7.14(6 H, m), 7.20-7.30(1 H, m), 7.43-7.55(3 H, m), 7.68-7.74(3 H, m), 10.17(1 H, brs). |
| 1675 | 3,4-$Cl_2$Ph- | —$CF_3$ | —$C_2H_5$ | —H | ($DMSO-d_6$) 1.11(3 H, t, J = 6.9 Hz), 2.25-2.45(4 H, m), 3.35-3.55(8 H, m), 4.27(2 H, s), 5.99(2 H, s), 6.67-6.88(5 H, m), 6.94-7.05(2 H, m), 7.52(1 H, dd, J = 8.8 Hz, 2.8 Hz), 7.63(1 H, dd, J = 8.4 Hz, 2.2 Hz), 7.75(1 H, d, J = 2.7 Hz), 7.83-7.87(2 H, m), 10.38(1 H, brs). |

TABLE 302

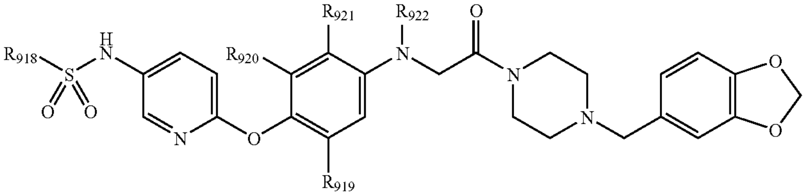

| Example No. | $R_{918}$ | $R_{919}$ | $R_{920}$ | $R_{921}$ | $R_{922}$ | Form | Property |
|---|---|---|---|---|---|---|---|
| 1676 | 4-$CF_3$Ph- | —F | —F | —H | —$CH_3$ | free | mp 199.0-200.0° C. |
| 1677 | 3,4-$Cl_2$Ph- | —F | —F | —H | —$CH_3$ | free | mp 198.0-199.0° C. |
| 1678 | 4-$CF_3$Ph- | —F | —H | —F | —$CH_3$ | free | mp 176.0-177.0° C. |
| 1679 | 3,4-$Cl_2$Ph- | —F | —H | —F | —$CH_3$ | free | mp 115.0-116.0° C. |
| 1680 | 4-$CF_3$Ph- | —F | —H | —F | —$C_2H_5$ | free | mp 173.0-174.0° C. |
| 1681 | 3,4-$Cl_2$Ph- | —F | —H | —F | —$C_2H_5$ | free | mp 156.0-157.0° C. |
| 1682 | 3,4-$Cl_2$Ph- | —$CH_3$ | —H | —$CH_3$ | —$C_2H_5$ | hydro-chloride | $^1H$ NMR ($DMSO-d_6$) δ 0.95(3 H, t, J = 7.0 Hz), 1.97(3 H, s), 2.28(3 H, s), 2.70-4.40(14 H, m), 6.07(2 H, s), 6.86(1 H, brs), 6.93-7.10(3 H, m), 7.20-7.40(2 H, m), 7.56(1 H, dd, J = 8.8 Hz, 2.7 Hz), 7.66(1 H, dd, J = 8.5 Hz, 2.1 Hz), 7.78(1 H, d, J = 2.6 Hz), 7.85-7.88(2 H, m), 10.55(1 H, brs), 11.47(1 H, brs). |
| 1683 | 4-$CF_3$Ph- | —$CH_3$ | —H | —$CH_3$ | —$C_2H_5$ | free | $^1H$ NMR ($DMSO-d_6$) δ 0.92(3 H, t, J = 7.0 Hz), 1.91(3 H, s), 2.16(3 H, |

TABLE 302-continued

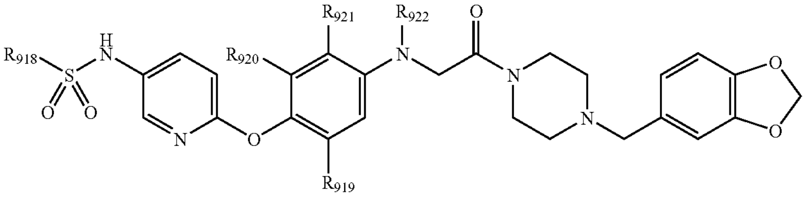

| Example No. | $R_{918}$ | $R_{919}$ | $R_{920}$ | $R_{921}$ | $R_{922}$ | Form | Property |
|---|---|---|---|---|---|---|---|
| | | | | | | | s), 2.20-2.40(4 H, m), 2.98(2 H, q, J = 7.0 Hz), 3.30-3.50(6 H, m), 3.77(2 H, s), 5.98(2 H, s), 6.72-6.76(2 H, m), 6.82-6.90(3 H, m), 7.01(1 H, s), 7.51(1 H, dd, J = 8.8 Hz, 2.8 Hz), 7.75(1 H, d, J = 2.7 Hz), 7.89-7.99(4 H, m), 10.45(1 H, brs). |
| 1684 | 3,4-$Cl_2$Ph- | —F | —H | —H | —H | hydro-chloride | $^1$H NMR (DMSO-$d_6$) δ 2.75-3.65(7 H, m), 3.85-4.55(6 H, m), 6.08(2 H, s), 6.47-6.50(1 H, m), 6.59(1 H, dd, J = 13.5 Hz, 2.6 Hz), 6.92-7.01(4 H, m), 7.20(1 H, s), 7.52(1 H, dd, J = 8.7 Hz, 2.6 Hz), 7.64(1 H, dd, J = 8.4 Hz, 2.1 Hz), 7.76(1 H, d, J = 2.5 Hz), 7.86(1 H, d, J = 8.6 Hz), 7.89(1 H, d, J = 2.2 Hz), 10.45(1 H, s), 10.90(1 H, brs). |
| 1685 | 4-$CH_3$OPh- | —H | —H | —H | —$CH_3$ | free | MS 646($M^+$ + H) |
| 1686 | 1-naphthyl | —H | —H | —H | —$CH_3$ | free | MS 666($M^+$ + H) |
| 1687 | 2-naphthyl | —H | —H | —H | —$CH_3$ | free | MS 666($M^+$ + H) |
| 1688 | 2-$CH_3$Ph- | —H | —H | —H | —$CH_3$ | free | MS 630($M^+$ + H) |
| 1689 | 4-FPh- | —H | —H | —H | —$CH_3$ | free | MS 634($M^+$ + H) |
| 1690 | 2-$CF_3$Ph- | —H | —H | —H | —$CH_3$ | free | MS 684($M^+$ + H) |
| 1691 | 2-ClPh- | —H | —H | —H | —$CH_3$ | free | MS 650($M^+$ + H) |

TABLE 303

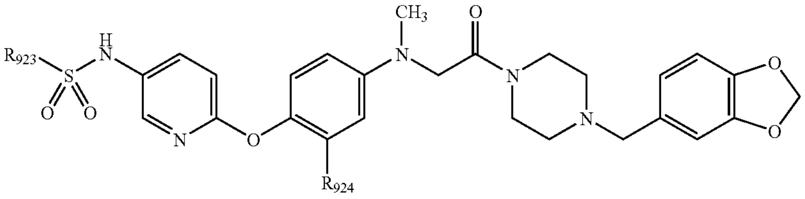

| Example No. | $R_{923}$ | $R_{924}$ | MS ($M^+$ + H) |
|---|---|---|---|
| 1692 | 2-thienyl | —H | 622 |
| 1693 | 2-$CF_3$OPh- | —H | 700 |
| 1694 | 3-$CF_3$OPh- | —H | 700 |
| 1695 | 3-$CH_3$OPh- | —H | 646 |
| 1696 | 3-FPh- | —H | 634 |
| 1697 | 2,3-$Cl_2$Ph- | —H | 684 |
| 1698 | 3-$CF_3$Ph- | —H | 684 |
| 1699 | 4-$CF_3$OPh- | —H | 700 |
| 1700 | 4-biphenylyl | —H | 692 |
| 1701 | 3,4-$(CH_3O)_2$Ph- | —H | 676 |
| 1702 | 2,5-$(CH_3O)_2$Ph- | —H | 676 |
| 1703 | 3-$CH_3$Ph- | —H | 630 |
| 1704 | 2,5-$Cl_2$Ph- | —H | 684 |
| 1705 | 3-ClPh- | —H | 650 |
| 1706 | 2,4-$Cl_2$Ph- | —H | 684 |
| 1707 | 2,3,4-$Cl_3$Ph- | —H | 720 |
| 1708 | —$C_2H_5$ | —H | 568 |
| 1709 | 2,6-$Cl_2$Ph- | —H | 684 |
| 1710 | 4-$CH_3$OOPh- | —F | 664 |
| 1711 | 4-ClPh- | —F | 668 |
| 1712 | 1-naphthyl | —F | 684 |
| 1713 | 2-naphthyl | —F | 684 |

TABLE 303-continued

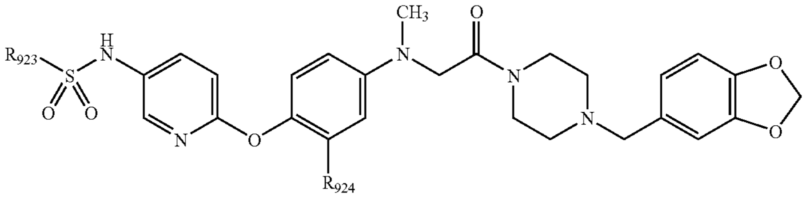

| Example No. | $R_{923}$ | $R_{924}$ | MS ($M^+$ + H) |
|---|---|---|---|
| 1714 | 2-$CH_3$Ph- | —F | 648 |
| 1715 | 4-FPh- | —F | 652 |
| 1716 | 2-$CF_3$Ph- | —F | 702 |
| 1717 | 2-thienyl | —F | 640 |
| 1718 | 2-ClPh- | —F | 668 |
| 1719 | 2-$CF_3$OPh- | —F | 718 |
| 1720 | 3-$CF_3$OPh- | —F | 718 |
| 1721 | 2-CNPh- | —F | 660 |
| 1722 | 3-$CH_3$OPh- | —F | 664 |
| 1723 | 3-FPh- | —F | 652 |
| 1724 | 2,3-$Cl_2$Ph- | —F | 702 |
| 1725 | 3-$CF_3$Ph- | —F | 702 |
| 1726 | 4-$CF_3$OPh- | —F | 718 |
| 1727 | 4-biphenylyl | —F | 710 |
| 1728 | 3,4-$(CH_3O)_2$Ph- | —F | 694 |
| 1729 | 2,5-$(CH_3O)_2$Ph- | —F | 694 |

TABLE 304

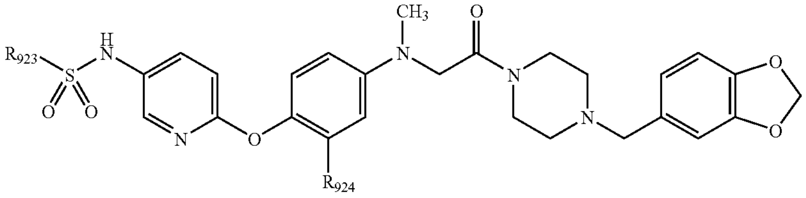

| Example No. | $R_{925}$ | $R_{926}$ | MS ($M^+$ + H) |
|---|---|---|---|
| 1730 | 3-$CH_3$Ph- | —F | 648 |
| 1731 | 2,5-$Cl_2$Ph- | —F | 702 |
| 1732 | 3-ClPh- | —F | 668 |
| 1733 | 2,4-$Cl_2$Ph- | —F | 702 |
| 1734 | —$CH_3$ | —F | 572 |
| 1735 | 2,3,4-$Cl_3$Ph- | —F | 738 |
| 1736 | —$(CH_2)_3CH_3$ | —F | 614 |
| 1737 | —$C_2H_5$ | —F | 586 |
| 1738 | 2,6-$Cl_2$Ph- | —F | 702 |
| 1739 | 4-$CH_3$OPh- | —$CH_3$ | 660 |
| 1740 | 4-ClPh- | —$CH_3$ | 664 |
| 1741 | 1-naphthyl | —$CH_3$ | 680 |
| 1742 | 2-naphthyl | —$CH_3$ | 680 |
| 1743 | 2-$CH_3$Ph- | —$CH_3$ | 644 |
| 1744 | 4-FPh- | —$CH_3$ | 648 |
| 1745 | 2-$CF_3$Ph- | —$CH_3$ | 698 |
| 1746 | 2-thienyl | —$CH_3$ | 636 |
| 1747 | 2-ClPh- | —$CH_3$ | 664 |
| 1748 | 2-$CF_3$OPh- | —$CH_3$ | 714 |
| 1749 | 2-CNPh- | —$CH_3$ | 656 |
| 1750 | 3-$CH_3$OPh- | —$CH_3$ | 660 |
| 1751 | 3-FPh- | —$CH_3$ | 648 |
| 1752 | 2,3-$Cl_2$Ph- | —$CH_3$ | 698 |
| 1753 | 3-$CF_3$Ph- | —$CH_3$ | 698 |
| 1754 | 4-$CF_3$OPh- | —$CH_3$ | 714 |
| 1755 | 4-biphenylyl | —$CH_3$ | 706 |
| 1756 | 3,4-$(CH_3O)_2$Ph- | —$CH_3$ | 690 |
| 1757 | 2,5-$(CH_3O)_2$Ph- | —$CH_3$ | 690 |
| 1758 | 3-$CH_3$Ph- | —$CH_3$ | 644 |
| 1759 | 2,5-$Cl_2$Ph- | —$CH_3$ | 698 |
| 1760 | 3-ClPh- | —$CH_3$ | 664 |
| 1761 | 2,4-$Cl_2$Ph- | —$CH_3$ | 698 |

TABLE 304-continued

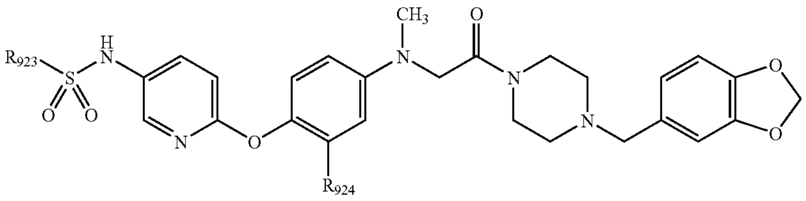

| Example No. | $R_{925}$ | $R_{926}$ | MS ($M^+$ + H) |
|---|---|---|---|
| 1762 | —$CH_3$ | —$CH_3$ | 568 |
| 1763 | 2,3,4-$Cl_3$Ph- | —$CH_3$ | 734 |
| 1764 | —$(CH_2)_3CH_3$ | —$CH_3$ | 610 |
| 1765 | —$C_2H_5$ | —$CH_3$ | 582 |
| 1766 | 2,6-$Cl_2$Ph- | —$CH_3$ | 698 |
| 1767 | 2,4,5-$Cl_3$Ph- | —H | 719 |

TABLE 305

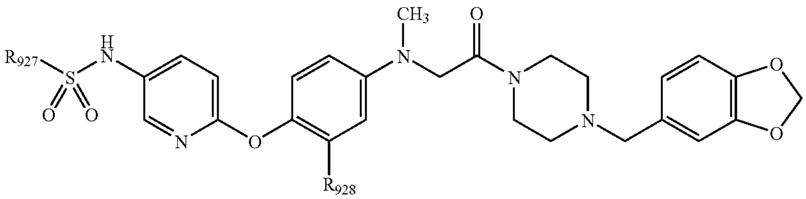

| Example No. | $R_{927}$ | $R_{928}$ | MS ($M^+$ + H) |
|---|---|---|---|
| 1768 | 2,4,6-$(CH_3)_3$Ph- | —H | 658 |
| 1769 | 4-$C_2H_5$Ph- | —H | 644 |
| 1770 | 2,5-$(CH_3)_2$Ph- | —H | 644 |
| 1771 | 2-FPh- | —H | 634 |
| 1772 | 2,4,6-$(CH_3)_3$Ph- | —F | 676 |
| 1773 | 4-$CH_3$Ph- | —F | 648 |
| 1774 | 4-$C_2H_5$Ph- | —F | 662 |
| 1775 | 2,5-$(CH_3)_2$Ph- | —F | 662 |
| 1776 | 2-FPh- | —F | 652 |
| 1777 | 2,4,5-$Cl_3$Ph- | —$CH_3$ | 732 |
| 1778 | 2,4,6-$(CH_3)_3$Ph- | —$CH_3$ | 672 |
| 1779 | 4-$CH_3$Ph- | —$CH_3$ | 644 |
| 1780 | 4-$C_2H_5$Ph- | —$CH_3$ | 658 |
| 1781 | 2,5-$(CH_3)_2$Ph- | —$CH_3$ | 658 |
| 1782 | 2-FPh- | —$CH_3$ | 648 |
| 1783 | 4-BrPh- | —H | 696 |
| 1784 | —$CH(CH_3)_2$ | —H | 582 |
| 1785 | 8-quinolyl | —H | 667 |
| 1786 | 3-CNPh- | —H | 641 |
| 1787 | 4-PhOPh- | —H | 708 |
| 1788 | 3-BrPh- | —H | 696 |
| 1789 | 4-CNPh- | —H | 641 |
| 1790 | 2,4-$F_2$Ph- | —H | 652 |
| 1791 | 4-BrPh- | —F | 714 |
| 1792 | —$CH(CH_3)_2$ | —F | 600 |
| 1793 | 8-quinolyl | —F | 685 |
| 1794 | 3-CNPh- | —F | 659 |
| 1795 | 4-CNPh- | —F | 659 |
| 1796 | 2,4-$F_2$Ph- | —F | 670 |
| 1797 | 4-BrPh- | —$CH_3$ | 710 |
| 1798 | —$CH(CH_3)_2$ | —$CH_3$ | 596 |
| 1799 | 8-quinolyl | —$CH_3$ | 681 |
| 1800 | 3-CNPh- | —$CH_3$ | 655 |
| 1801 | 3-BrPh- | —$CH_3$ | 710 |
| 1802 | 4-CNPh- | —$CH_3$ | 655 |
| 1803 | 2,4-$F_2$ph- | —$CH_3$ | 666 |
| 1804 | 2,4,6-$Cl_3$Ph- | —H | 720 |
| 1805 | 2,4,6-$Cl_3$Ph- | —F | 738 |

TABLE 306
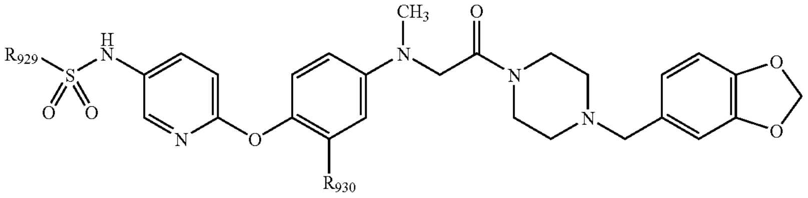
| Example No. | $R_{929}$ | $R_{930}$ | MS ($M^+$ + H) |
|---|---|---|---|
| 1806 | 2,4,5-$Cl_3$Ph- | —F | 738 |
| 1807 | 2,4,6-$Cl_3$Ph- | —$CH_3$ | 734 |
| 1808 | Ph- | —F | 634 |
| 1809 | Ph- | —$CH_3$ | 630 |
| 1810 | 2,5-$F_2$Ph- | —F | 670 |
| 1811 | 2,5-$F_2$Ph- | —$CH_3$ | 666 |
| 1812 | 2,6-$F_2$Ph- | —$CH_3$ | 666 |
| 1813 | 3,4-$F_2$Ph- | —$CH_3$ | 666 |
| 1814 | 2,6-$F_2$Ph- | —H | 652 |
| 1815 | 3,4-$F_2$Ph- | —H | 652 |
| 1816 | 2,6-$F_2$Ph- | —F | 670 |
| 1817 | 3,4-$F_2$Ph- | —F | 670 |
| 1818 | —$CH_3$ | —H | 554 |
| 1819 | 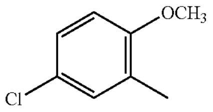 | —H | 680 |
| 1820 | 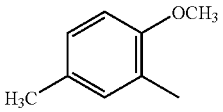 | —H | 660 |
| 1821 | 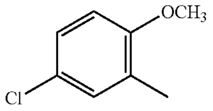 | —F | 698 |
| 1822 | 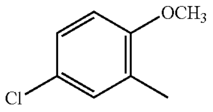 | —$CH_3$ | 694 |
| 1823 | 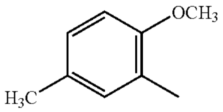 | —$CH_3$ | 674 |
| 1824 | 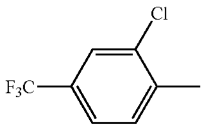 | —H | 718 |
| 1825 | 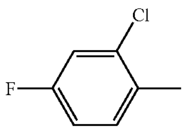 | —H | 668 |
| 1826 | 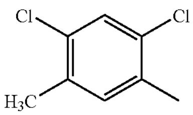 | —H | 698 |

TABLE 306-continued
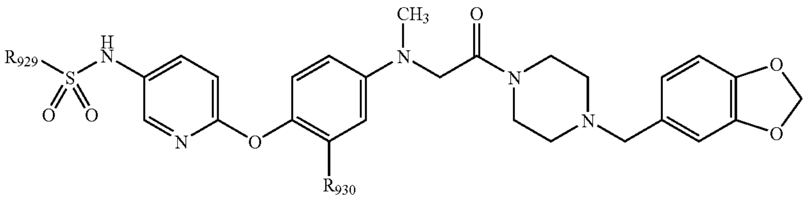
| Example No. | $R_{929}$ | $R_{930}$ | MS ($M^+$ + H) |
|---|---|---|---|
| 1827 | 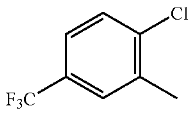 | —H | 718 |
TABLE 307
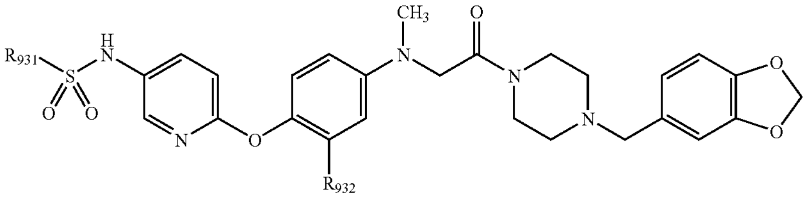
| Example No. | $R_{931}$ | $R_{932}$ | MS ($M^+$ + H) |
|---|---|---|---|
| 1828 | 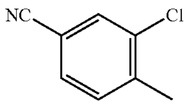 | —H | 675 |
| 1829 | 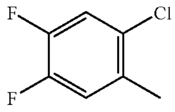 | —H | 686 |
| 1830 | 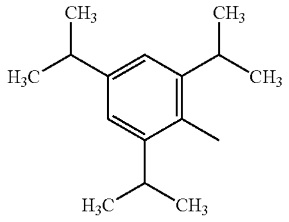 | —H | 742 |
| 1831 | 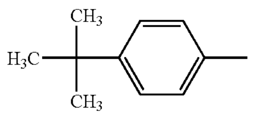 | —H | 672 |
| 1832 | 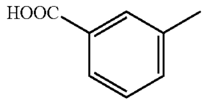 | —H | 660 |
| 1833 | 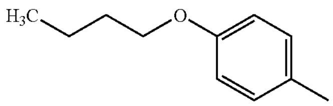 | —H | 688 |

TABLE 307-continued
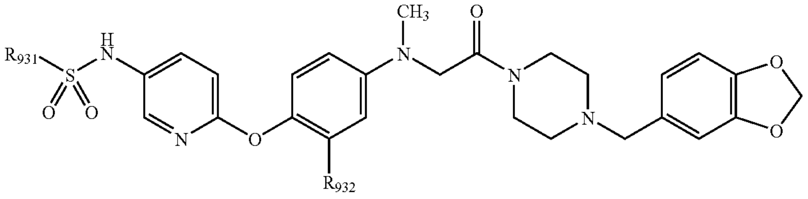
| Example No. | $R_{931}$ | $R_{932}$ | MS ($M^+$ + H) |
|---|---|---|---|
| 1834 | 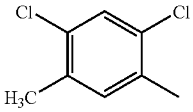 | —F | 716 |
| 1835 | 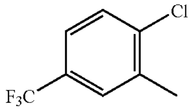 | —F | 736 |
| 1836 | 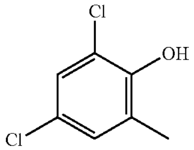 | —F | 718 |
| 1837 | 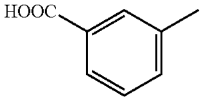 | —F | 678 |
| 1838 | 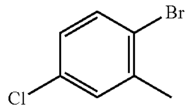 | —F | 747 |
| 1839 | 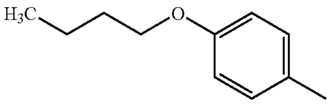 | —F | 706 |
| 1840 | 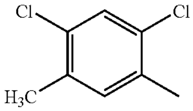 | $—CH_3$ | 712 |
TABLE 308
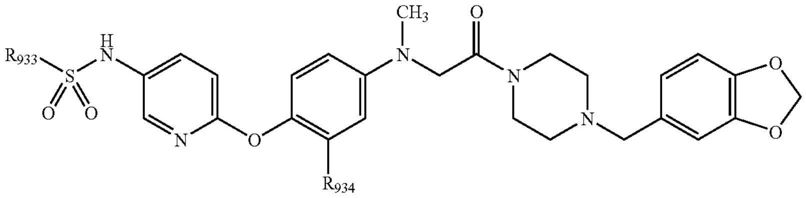
| Example No. | $R_{933}$ | $R_{934}$ | MS ($M^+$ + H) |
|---|---|---|---|
| 1841 | 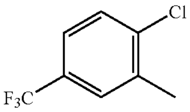 | $—CH_3$ | 732 |

TABLE 308-continued
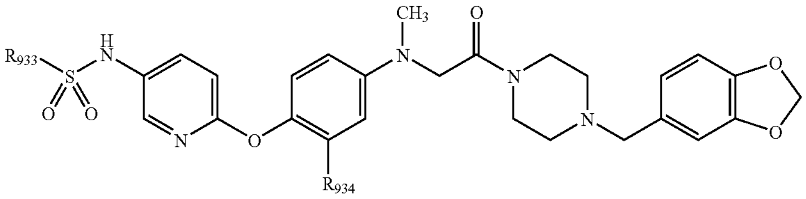
| Example No. | $R_{933}$ | $R_{934}$ | MS ($M^+$ + H) |
|---|---|---|---|
| 1842 | 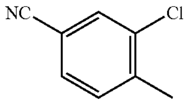 | —$CH_3$ | 689 |
| 1843 | 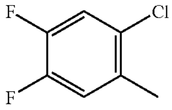 | —$CH_3$ | 700 |
| 1844 | 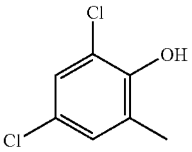 | —$CH_3$ | 714 |
| 1845 | 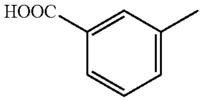 | —$CH_3$ | 674 |
| 1846 | 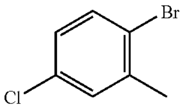 | —$CH_3$ | 743 |
| 1847 | 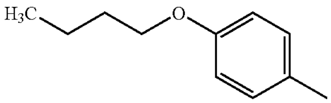 | —$CH_3$ | 702 |
| 1848 | 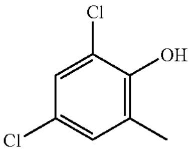 | —H | 700 |
| 1849 | 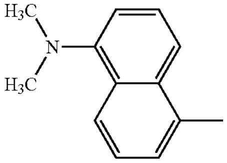 | —H | 709 |
| 1850 | 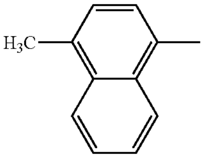 | —H | 680 |

TABLE 308-continued
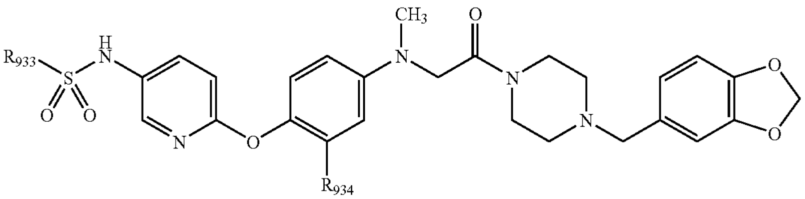
| Example No. | $R_{933}$ | $R_{934}$ | MS ($M^+$ + H) |
|---|---|---|---|
| 1851 | 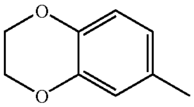 | —H | 674 |
| 1852 | 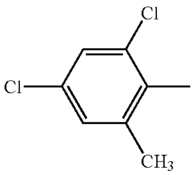 | —H | 698 |
TABLE 309
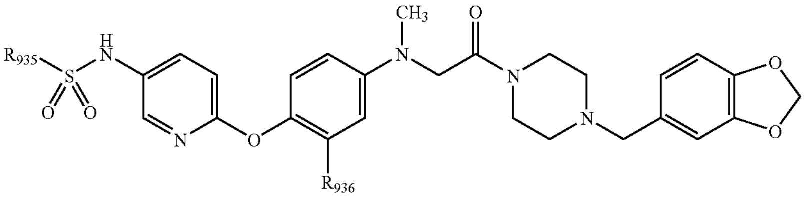
| Example No. | $R_{935}$ | $R_{936}$ | MS ($M^+$ + H) |
|---|---|---|---|
| 1853 | 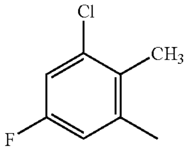 | —H | 682 |
| 1854 | 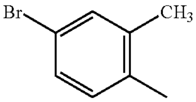 | —H | 710 |
| 1855 | 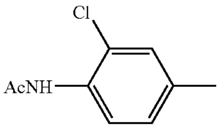 | —H | 707 |
| 1856 | 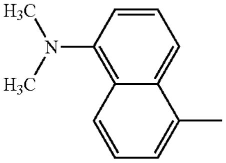 | —F | 727 |

TABLE 309-continued
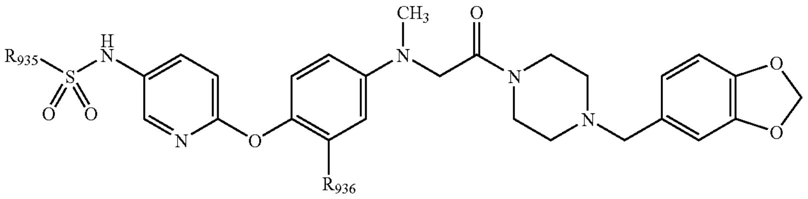
| Example No. | $R_{935}$ | $R_{936}$ | MS ($M^+ + H$) |
|---|---|---|---|
| 1857 | 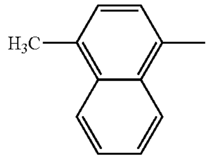 | —F | 698 |
| 1858 | 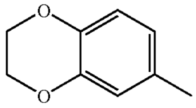 | —F | 692 |
| 1859 | 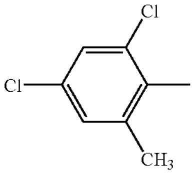 | —F | 716 |
| 1860 | 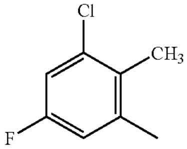 | —F | 700 |
| 1861 | 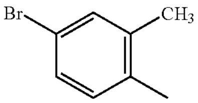 | —F | 728 |
| 1862 | 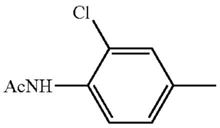 | —F | 725 |
| 1863 | 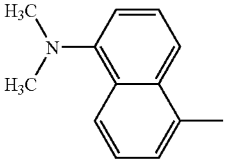 | —$CH_3$ | 723 |

TABLE 310
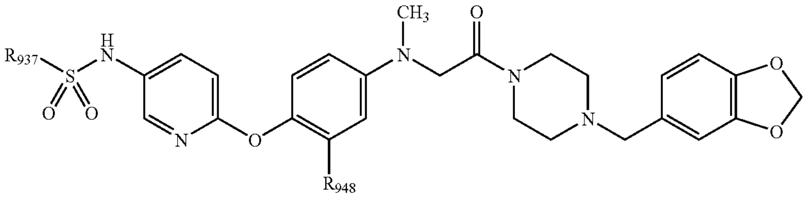
| Example No. | $R_{937}$ | $R_{938}$ | MS ($M^+$ + H) |
|---|---|---|---|
| 1864 | 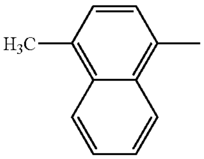 | —$CH_3$ | 694 |
| 1865 | 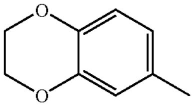 | —$CH_3$ | 688 |
| 1866 | 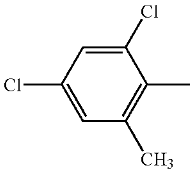 | —$CH_3$ | 712 |
| 1867 | 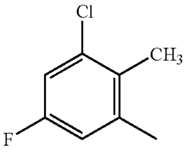 | —$CH_3$ | 696 |
| 1868 | 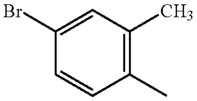 | —$CH_3$ | 724 |
| 1869 | 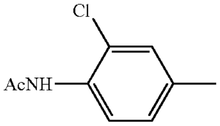 | —$CH_3$ | 721 |
| 1870 | 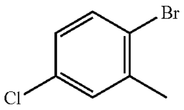 | —H | 730 |
| 1871 | 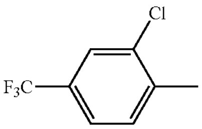 | —F | 736 |
| 1872 | 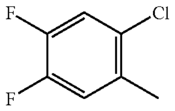 | —F | 704 |

TABLE 310-continued
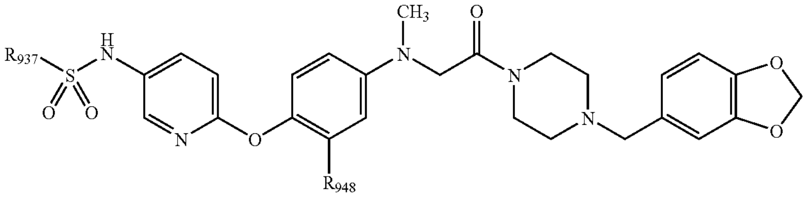
| Example No. | $R_{937}$ | $R_{938}$ | MS ($M^+$ + H) |
|---|---|---|---|
| 1873 | 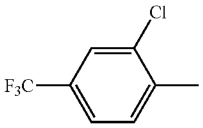 | —$CH_3$ | 732 |
| 1874 | 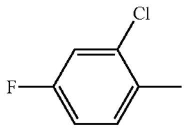 | —$CH_3$ | 682 |
| 1875 | 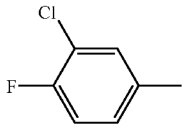 | —H | 668 |
TABLE 311
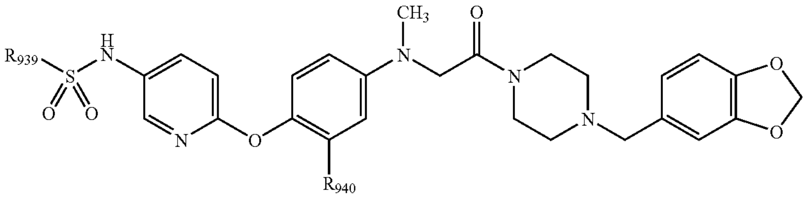
| Example No. | $R_{939}$ | $R_{940}$ | MS ($M^+$ + H) |
|---|---|---|---|
| 1876 | 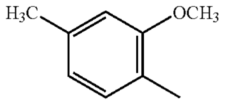 | —H | 660 |
| 1877 | 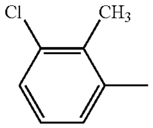 | —H | 664 |
| 1878 | 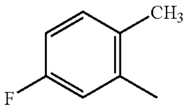 | —H | 648 |
| 1879 | 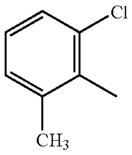 | —H | 664 |

TABLE 311-continued
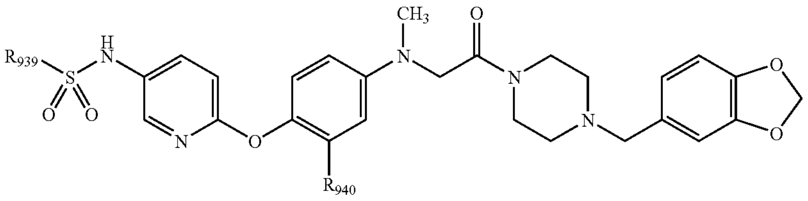
| Example No. | $R_{939}$ | $R_{940}$ | MS ($M^+$ + H) |
|---|---|---|---|
| 1880 | 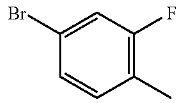 | —H | 714 |
| 1881 | 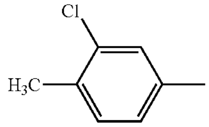 | —H | 664 |
| 1882 | 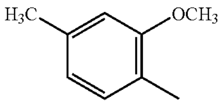 | —F | 678 |
| 1883 | 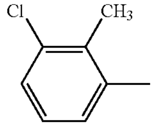 | —F | 682 |
| 1884 | 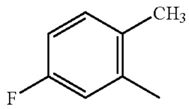 | —F | 666 |
| 1885 | 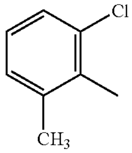 | —F | 682 |
| 1886 | 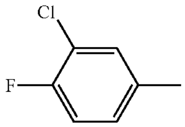 | —F | 686 |
| 1887 | 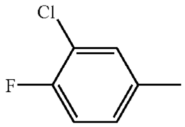 | —$CH_3$ | 682 |
| 1888 | 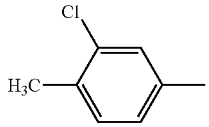 | —F | 682 |

TABLE 312
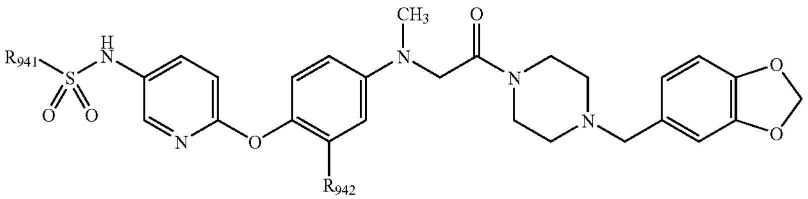
| Example No. | $R_{941}$ | $R_{942}$ | MS ($M^+ + H$) |
|---|---|---|---|
| 1889 | 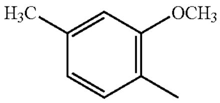 | —$CH_3$ | 674 |
| 1890 | 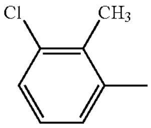 | —$CH_3$ | 678 |
| 1891 | 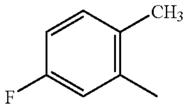 | —$CH_3$ | 662 |
| 1892 | 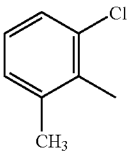 | —$CH_3$ | 678 |
| 1893 | 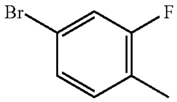 | —$CH_3$ | 728 |
| 1894 | 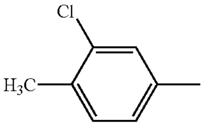 | —$CH_3$ | 678 |
| 1895 | 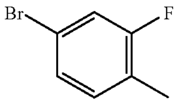 | —F | 732 |
| 1896 | 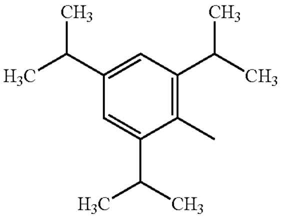 | —F | 760 |

TABLE 312-continued
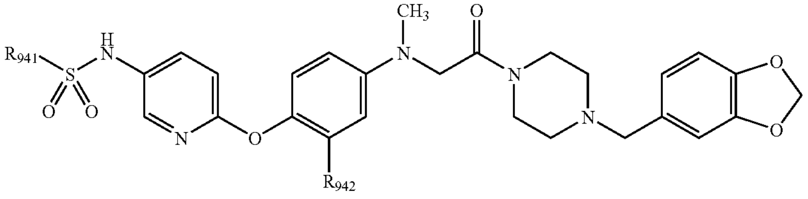
| Example No. | $R_{941}$ | $R_{942}$ | MS ($M^+$ + H) |
|---|---|---|---|
| 1897 | 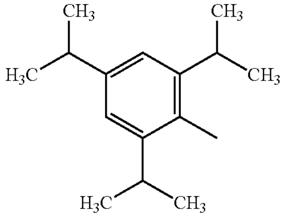 | —$CH_3$ | 756 |
| 1898 | 3-BrPh- | —F | 714 |
| 1899 | 4-PhOPh- | —$CH_3$ | 722 |
| 1900 | 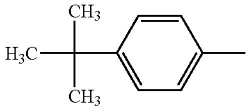 | —F | 690 |
| 1901 | 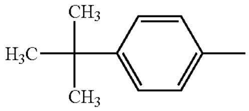 | —$CH_3$ | 686 |
TABLE 313
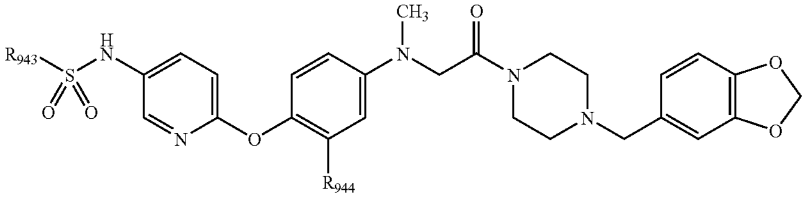
| Example No. | $R_{943}$ | $R_{944}$ | MS ($M^+$ + H) |
|---|---|---|---|
| 1902 | 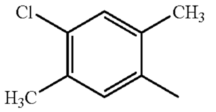 | —H | 678 |
| 1903 | 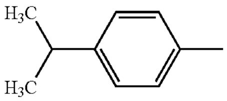 | —H | 658 |
| 1904 | 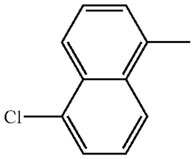 | —H | 700 |

TABLE 313-continued
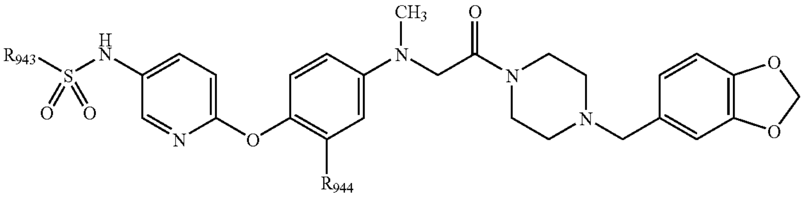
| Example No. | $R_{943}$ | $R_{944}$ | MS ($M^+$ + H) |
|---|---|---|---|
| 1905 | 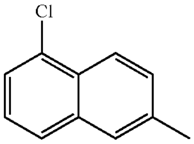 | —H | 700 |
| 1906 | 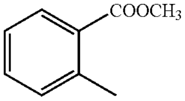 | —H | 674 |
| 1907 | 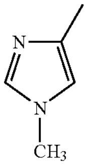 | —H | 620 |
| 1908 | 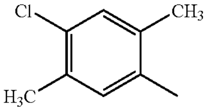 | —F | 696 |
| 1909 | 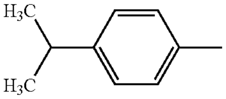 | —F | 676 |
| 1910 | 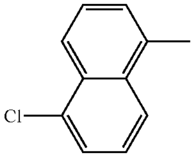 | —F | 718 |
| 1911 | 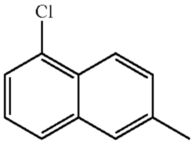 | —F | 718 |
| 1912 | 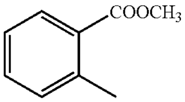 | —F | 692 |
| 1913 | 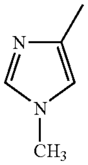 | —F | 638 |

TABLE 314
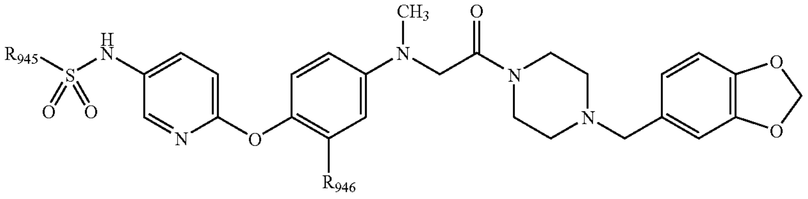
| Example No. | $R_{945}$ | $R_{946}$ | MS ($M^+ + H$) |
|---|---|---|---|
| 1914 | 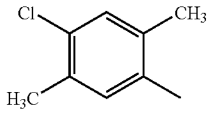 | —$CH_3$ | 692 |
| 1915 | 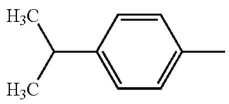 | —$CH_3$ | 672 |
| 1916 | 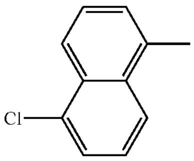 | —$CH_3$ | 714 |
| 1917 | 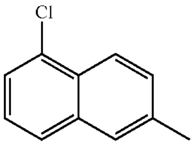 | —$CH_3$ | 714 |
| 1918 | 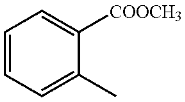 | —$CH_3$ | 688 |
| 1919 | 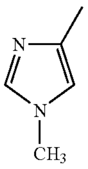 | —$CH_3$ | 634 |
| 1920 | 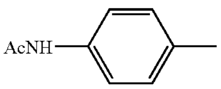 | —H | 673 |
| 1921 | vinyl | —H | 566 |
| 1922 | —$(CH_2)_3Cl$ | —H | 616 |
| 1923 | cyclohexylmethyl | —H | 636 |
| 1924 | 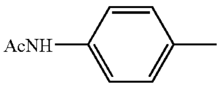 | —F | 691 |
| 1925 | vinyl | —F | 584 |
| 1926 | —$(CH_2)_3Cl$ | —F | 634 |
| 1927 | cyclohexylmethyl | —F | 654 |
| 1928 | 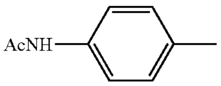 | —$CH_3$ | 687 |
| 1929 | vinyl | —$CH_3$ | 580 |

TABLE 314-continued
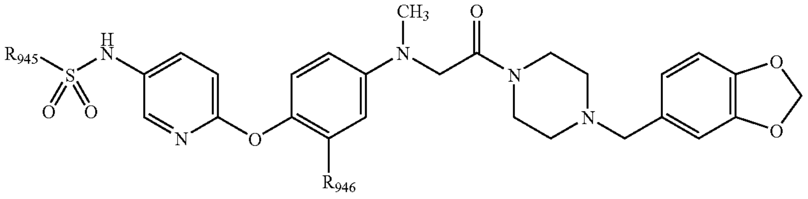
| Example No. | $R_{945}$ | $R_{946}$ | MS ($M^+$ + H) |
|---|---|---|---|
| 1930 | $-(CH_2)_3Cl$ | $-CH_3$ | 630 |
| 1931 | cyclohexylmethyl | $-CH_3$ | 650 |
| 1932 | 2-BrPh- | —H | 696 |
| 1933 | 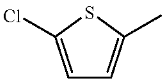 | —H | 656 |
TABLE 315
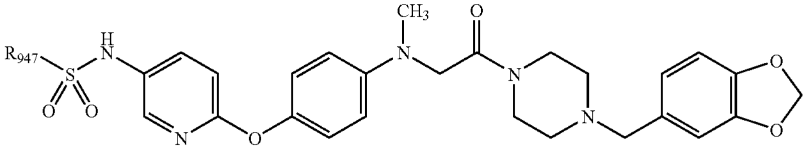
| Example No. | $R_{947}$ | MS ($M^+$ + H) |
|---|---|---|
| 1934 | 3,5-$Cl_2$Ph | 684 |
| 1935 | 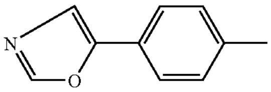 | 683 |
| 1936 | 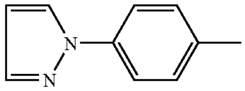 | 682 |
| 1937 | 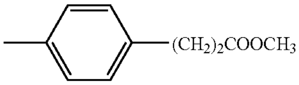 | 702 |
| 1938 | 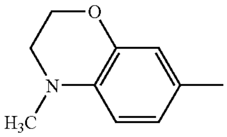 | 687 |
| 1939 | 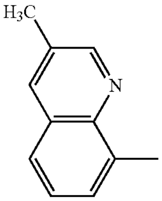 | 681 |
| 1940 | 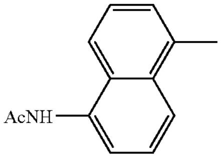 | 723 |

TABLE 315-continued
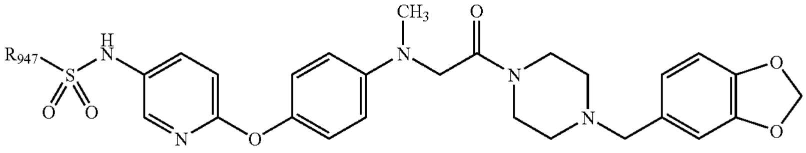
| Example No. | $R_{947}$ | MS ($M^+$ + H) |
|---|---|---|
| 1941 | 5-isoquinolyl | 667 |
| 1942 | $—CH_2CF_3$ | 622 |
| 1943 | 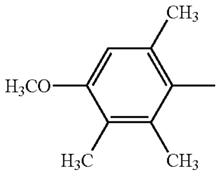 | 688 |
| 1944 | 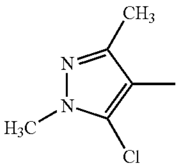 | 668 |
| 1945 | 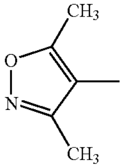 | 635 |
| 1946 | 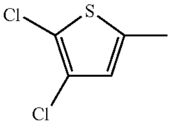 | 690 |
| 1947 | 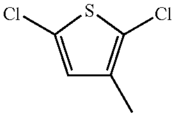 | 690 |
TABLE 316
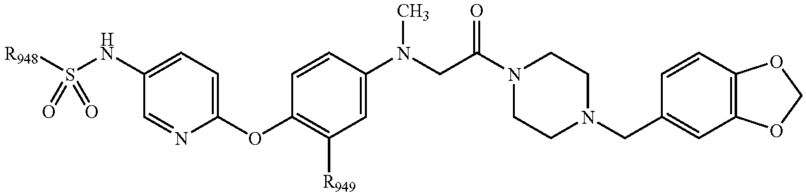
| Example No. | $R_{948}$ | $R_{949}$ | MS ($M^+$ + H) |
|---|---|---|---|
| 1948 | $—CH_2Cl$ | —H | 588 |
| 1949 | 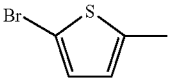 | —H | 702 |

TABLE 316-continued
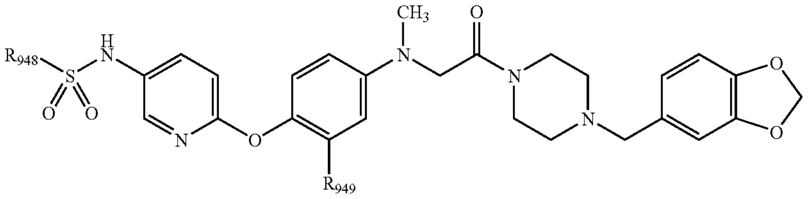
| Example No. | $R_{948}$ | $R_{949}$ | MS ($M^+ + H$) |
|---|---|---|---|
| 1950 | 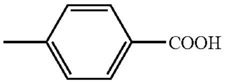 | —H | 660 |
| 1951 | 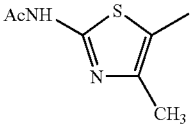 | —H | 694 |
| 1952 | 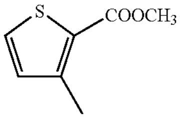 | —H | 680 |
| 1953 | 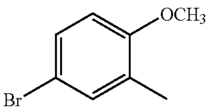 | —H | 726 |
| 1954 | benzyl | —H | 630 |
| 1955 | PhCH═CH— | —H | 642 |
| 1956 | —$(CH_2)_2CH_3$ | —H | 582 |
| 1957 | 2-BrPh- | —F | 714 |
| 1958 | 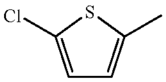 | —F | 674 |
| 1959 | 3,5-$Cl_2$Ph | —F | 702 |
| 1960 | 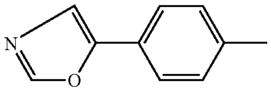 | —F | 701 |
| 1961 | 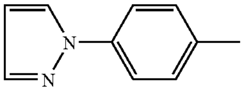 | —F | 700 |
| 1962 | 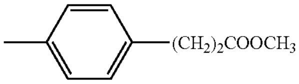 | —F | 720 |
| 1963 | 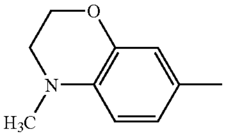 | —F | 705 |

TABLE 316-continued
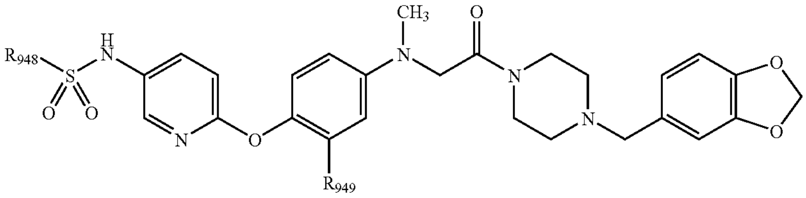
| Example No. | $R_{948}$ | $R_{949}$ | MS ($M^+$ + H) |
|---|---|---|---|
| 1964 | 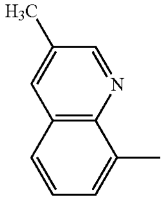 | —F | 699 |
| 1965 | 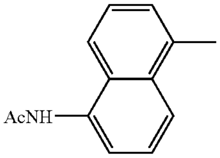 | —F | 741 |
TABLE 317
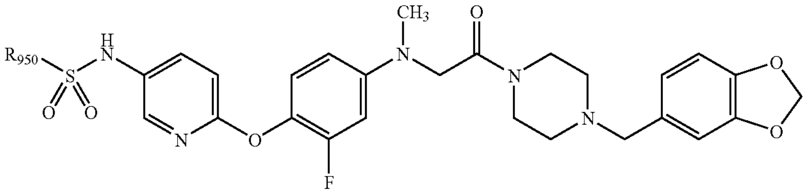
| Example No. | $R_{950}$ | MS ($M^+$ + H) |
|---|---|---|
| 1966 | 5-isoquinolyl | 685 |
| 1967 | $—CH_2CF_3$ | 640 |
| 1968 | 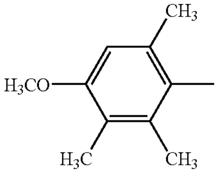 | 706 |
| 1969 | 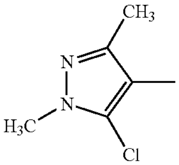 | 686 |
| 1970 | 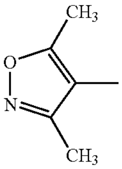 | 653 |

TABLE 317-continued
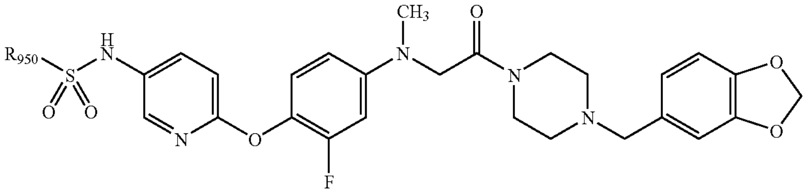
| Example No. | $R_{950}$ | MS ($M^+ + H$) |
|---|---|---|
| 1971 | 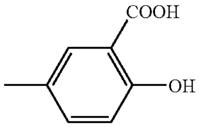 | 694 |
| 1972 | 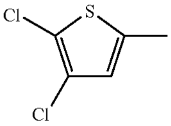 | 708 |
| 1973 | 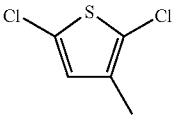 | 708 |
| 1974 | $-CH_2Cl$ | 606 |
| 1975 | 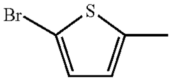 | 720 |
| 1976 | 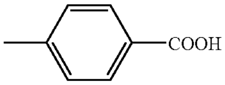 | 678 |
| 1977 | 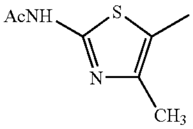 | 712 |
| 1978 | 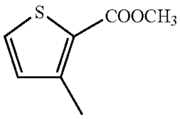 | 698 |
| 1979 | 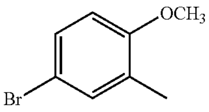 | 744 |
| 1980 | benzyl | 648 |
| 1981 | PhCH═CH— | 660 |

TABLE 318
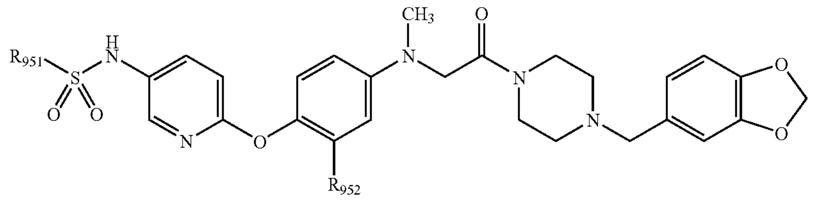
| Example No. | $R_{951}$ | $R_{952}$ | MS ($M^+ + H$) |
|---|---|---|---|
| 1982 | $-(CH_2)_2CH_3$ | —F | 600 |
| 1983 | 2-BrPh- | $-CH_3$ | 710 |
| 1984 | 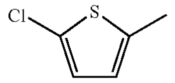 | $-CH_3$ | 670 |
| 1985 | 3,5-$Cl_2$Ph | $-CH_3$ | 698 |
| 1986 | 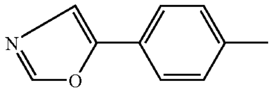 | $-CH_3$ | 697 |
| 1987 | 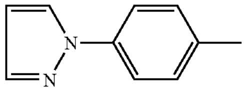 | $-CH_3$ | 696 |
| 1988 | 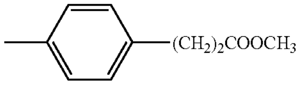 | $-CH_3$ | 716 |
| 1989 | 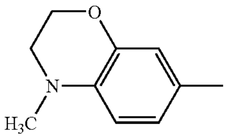 | $-CH_3$ | 701 |
| 1990 | 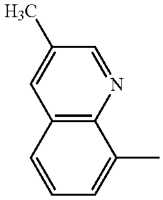 | $-CH_3$ | 695 |
| 1991 | 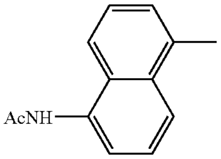 | $-CH_3$ | 737 |
| 1992 | 5-isoquinolyl | $-CH_3$ | 681 |
| 1993 | $-CH_2CF_3$ | $-CH_3$ | 636 |
| 1994 | 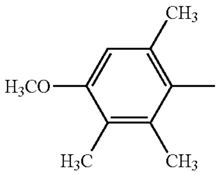 | $-CH_3$ | 702 |

TABLE 318-continued
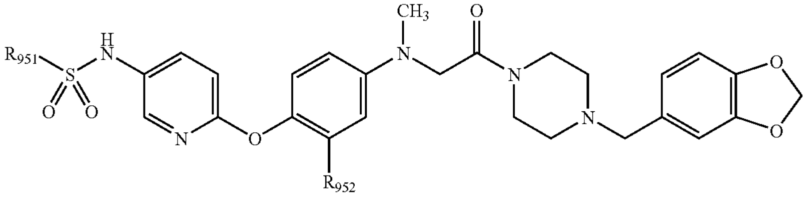
| Example No. | $R_{951}$ | $R_{952}$ | MS ($M^+$ + H) |
|---|---|---|---|
| 1995 | 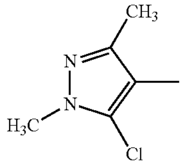 | —$CH_3$ | 682 |
| 1996 | 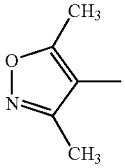 | —$CH_3$ | 649 |
TABLE 319
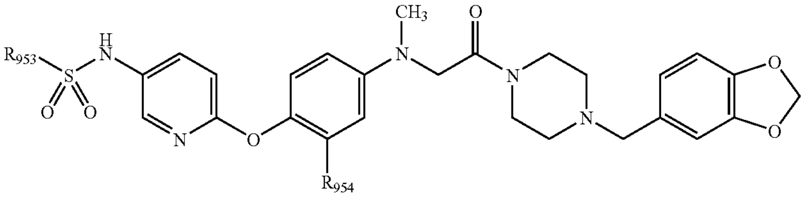
| Example No. | $R_{953}$ | $R_{954}$ | MS ($M^+$ + H) |
|---|---|---|---|
| 1997 | 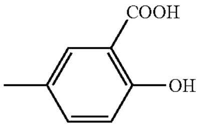 | —$CH_3$ | 690 |
| 1998 | 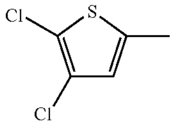 | —$CH_3$ | 704 |
| 1999 | 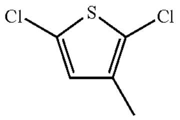 | —$CH_3$ | 704 |
| 2000 | —$CH_2Cl$ | —$CH_3$ | 602 |
| 2001 | 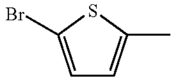 | —$CH_3$ | 716 |
| 2002 | 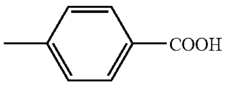 | —$CH_3$ | 674 |

TABLE 319-continued

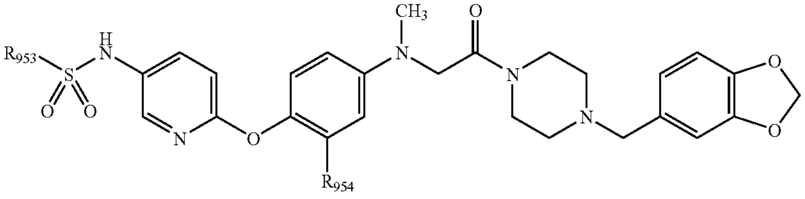

| Example No. | $R_{953}$ | $R_{954}$ | MS ($M^+$ + H) |
|---|---|---|---|
| 2003 | 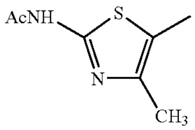 | —$CH_3$ | 708 |
| 2004 | 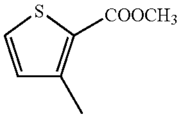 | —$CH_3$ | 694 |
| 2005 | 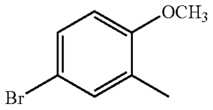 | —$CH_3$ | 740 |
| 2006 | benzyl | —$CH_3$ | 644 |
| 2007 | —$CHCl_2$ | —$CH_3$ | 636 |
| 2008 | PhCH═CH— | —$CH_3$ | 656 |
| 2009 | —$(CH_2)_2CH_3$ | —$CH_3$ | 596 |
| 2010 | 2,3,4-$F_3$Ph- | —H | 670 |
| 2011 | 2,3,4-$F_3$Ph- | —F | 688 |
| 2012 | 2,3,4-$F_3$Ph- | —$CH_3$ | 684 |

TABLE 320

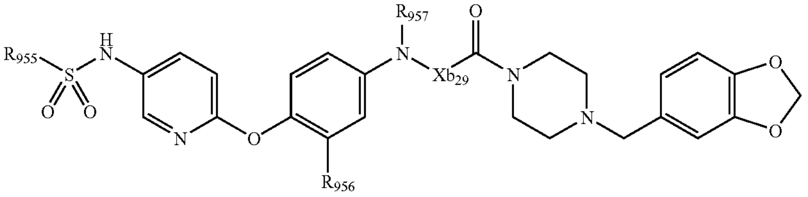

| Example No. | $R_{955}$ | $R_{956}$ | $R_{957}$ | $Xb_{29}$ | $^1$H NMR (solvent) δppm |
|---|---|---|---|---|---|
| 2013 | 3,4-$Cl_2$Ph- | —$CH_3$ | —H | —CO— | ($CDCl_3$) 2.12 (3 H, s), 2.50-2.52 (4 H, m), 3.45 (2 H, s), 3.72 (2 H, brs), 4.24 (2 H, brs), 5.95 (2 H, s), 6.71-6.78 (2 H, m), 6.85-6.89 (2 H, m), 7.00 (1 H, d, J = 8.6 Hz), 7.42 (1 H, dd, J = 8.6 Hz, 2.5 Hz), 7.52-7.55 (3 H, m), 7.60 (1 H, dd, J = 8.7 Hz, 2.8 Hz), 7.70 (1 H, d, J = 2.6 Hz), 7.79 (1 H, brs), 9.17 (1 H, brs). |
| 2014 | 4-$CF_3$Ph- | —$CH_3$ | —H | —CO— | ($CDCl_3$) 2.10 (3 H, s), 2.50-2.54 (4 H, m), 3.45 (2 H, s), 3.70-3.73 (2 H, m), 4.23 (2 H, brs), 5.95 (2 H, s), 6.71-6.78 (2 H, m), 6.83-6.87 (2 H, m), 6.99 (1 H, d, J = 8.6 Hz), 7.42(1 H, dd, J = 8.6 Hz, 2.6 Hz), 7.54 (1 H, d, J = 2.5 Hz), 7.60 (1 H, dd, J = 8.7 Hz, 3.3 Hz), 7.70 (1 H, d, J = 3.3 Hz), 7.72 (2 H, d, J = 8.9 Hz), 7.85(2 H, d, J = 8.3 Hz), 9.18 (1 H, brs). |
| 2015 | 3,4-$Cl_2$Ph- | —$CH_3$ | —$CH_3$ | —CO— | ($CDCl_3$) 2.12 (3 H, brs), 2.20-2.50 (4 H, m), 3.27-3.46 (9 H, m), 5.95-5.96 (2 H, m), 6.66-6.77 (3 H, m), 6.85-7.04 (2 H, m), 7.08-7.22 (2 H, m), 7.51-7.53 (2 H, m), 7.55-7.72 (2 H, m), 7.78-7.80 (1 H, m). |

TABLE 320-continued

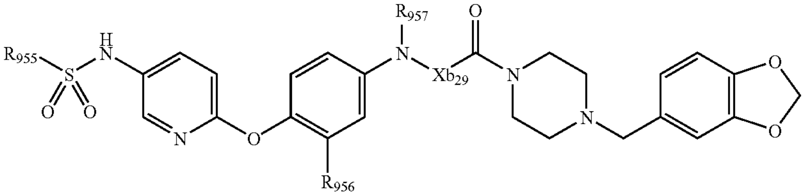

| Example No. | $R_{955}$ | $R_{956}$ | $R_{957}$ | $Xb_{29}$ | $^1$H NMR (solvent) δppm |
|---|---|---|---|---|---|
| 2016 | 4-$CF_3$Ph- | —$CH_3$ | —$CH_3$ | —CO— | (DMSO-$d_6$) 2.11 (3 H, s), 2.19-2.51 (4 H, m), 3.28-3.71 (9 H, m), 5.96 (2 H, s), 6.65-6.78 (3 H, m), 6.85-7.04 (2 H, m), 7.08-7.22 (2 H, m), 7.57-7.65 (1 H, m), 7.70-7.73 (3 H, m), 7.84-7.87 (2 H, m). |
| 2017 | 3,4-$Cl_2$Ph- | —H | —$SO_2CH_3$ | —$CH_2$— | ($CDCl_3$) 2.42 (4 H, brs), 3.20 (3 H, s), 3.37-3.39 (2 H, m), 3.42 (2 H, s), 3.61 (2 H, brs), 4.54 (2 H, s), 5.95 (2 H, s), 6.70-6.77 (2 H, m), 6.83 (1 H, brs), 6.93 (1 H, d, J = 8.6 Hz), 7.08 (2 H, d, J = 8.9 Hz), 7.53-7.54 (2 H, m), 7.58-7.63 (3 H, m), 7.77 (1 H, d, J = 2.6 Hz), 7.88 (1 H, d, J = 1.0 Hz). |
| 2018 | 4-$CF_3$Ph- | —H | —$SO_2CH_3$ | —$CH_2$— | ($CDCl_3$) 2.42 (4 H, brs), 3.19 (3 H, s), 3.37 (2 H, brs), 3.42 (2 H, s), 3.61 (2 H, brs), 4.53 (2 H, s), 5.95 (2 H, s), 6.73-6.77 (2 H, m), 6.83 (1 H, brs), 6.92 (1 H, d, J = 8.7 Hz), 7.08(2 H, d, J = 8.7 Hz), 7.59 (2 H, d, J = 8.7 Hz), 7.61 (1 H, dd, J = 8.7 Hz, 2.8 Hz), 7.73-7.76 (3 H, m), 7.87 (2 H, d, J = 8.6 Hz). |
| 2019 | 3,4-$Cl_2$Ph- | —$CH_3$ | —$SO_2CH_3$ | —$CH_2$— | ($CDCl_3$) 2.12 (3 H, s), 2.42 (4 H, brs), 3.21 (3 H, s), 3.83 (2 H, brs), 3.42 (2 H, s), 3.61 (2 H, brs), 4.53 (2 H, s), 5.95 (2 H, s), 6.70-6.77 (2 H, m), 6.83 (1 H, brs), 6.91 (1 H, d, J = 8.7 Hz), 6.98 (1 H, d, J = 8.4 Hz), 7.40-7.50 (2 H, m), 7.53-7.56 (2 H, m), 7.60 (1 H, dd, J = 8.7 Hz, 2.8 Hz), 7.71 (1 H, d, J = 2.3 Hz), 7.80 (1 H, dd, J = 1.7 Hz, 0.8 Hz). |

TABLE 321

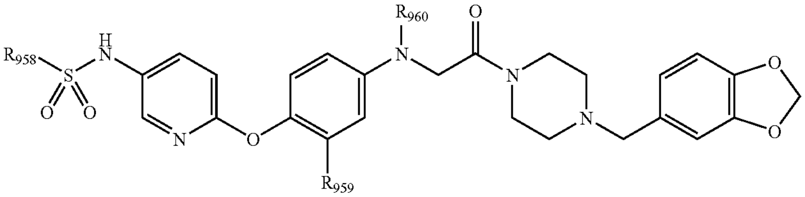

| Example No. | $R_{958}$ | $R_{959}$ | $R_{960}$ | $^1$H NMR (solvent) δ ppm |
|---|---|---|---|---|
| 2020 | 4-$CF_3$Ph- | —$CH_3$ | —$SO_2CH_3$ | ($CDCl_3$) 2.10 (3 H, s), 2.40-2.42 (4 H, m), 3.20 (3 H, s), 3.37 (2 H, brs), 3.42 (2 H, s), 3.60 (2 H, brs), 4.53 (2 H, s), 5.94 (2 H, s), 6.69-6.76 (2 H, m), 6.83 (1 H, brs), 6.87 (1 H, d, J = 8.7 Hz), 6.96 (1 H, d, J = 8.4 Hz), 7.40 (1 H, d, J = 8.6 Hz), 7.44 (1 H, brs), 7.59 (1 H, dd, J = 8.7 Hz, 2.8 Hz), 7.72 (2 H, d, J = 8.2 Hz), 7.73 (1 H, d, J = 2.8 Hz), 7.86 (2 H, d, J = 8.2 Hz). |
| 2021 | 4-$CF_3$Ph- | —$CF_3$ | —$C_2H_5$ | (DMSO-$d_6$) 1.11 (3 H, t, J = 6.9 Hz), 2.25-2.45 (4 H, m), 3.35-3.55 (8 H, m), 4.26 (2 H, s), 5.99 (2 H, s), 6.67-7.04 (7 H, m), 7.52 (1 H, dd, J = 8.8 Hz, 2.8 Hz), 7.74 (1 H, d, J = 2.6 Hz), 7.88-7.98 (4 H, m), 10.48 (1 H, brs). |
| 2022 | 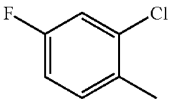 | —$CF_3$ | —$C_2H_5$ | (DMSO-$d_6$) 1.11 (3 H, t, J = 6.9 Hz), 2.25-2.45 (4 H, m), 3.35-3.55 (8 H, m), 4.26 (2 H, s), 5.99 (2 H, s), 6.67-7.03 (7 H, m), 7.30-7.45 (1 H, m), 7.52 (1 H, dd, J = 8.8 Hz, 2.6 Hz), 7.71 (1 H, dd, J = 8.7 Hz, 2.5 Hz), 7.79 (1 H, d, J = 2.7 Hz), 7.99-8.05 (1 H, m), 10.61 (1 H, brs). |

TABLE 321-continued

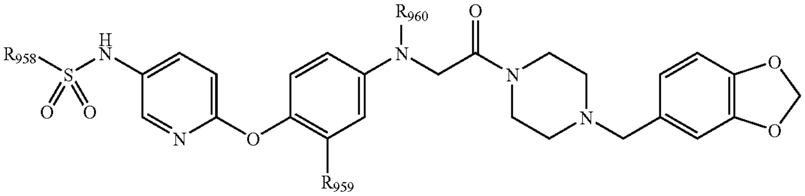

| Example No. | $R_{958}$ | $R_{959}$ | $R_{960}$ | $^1H$ NMR (solvent) δ ppm |
|---|---|---|---|---|
| 2023 | 3,4-$Cl_2$Ph- | —$CF_3$ | —$CH_3$ | ($DMSO-d_6$) 2.20-2.45 (4 H, m), 2.97 (3 H, s), 3.40-3.55 (6 H, m), 4.34 (2 H, s), 5.99 (2 H, s), 6.70-6.80 (2 H, m), 6.83-6.88 (3 H, m), 6.97 (1 H, d, J = 8.8 Hz), 7.03-7.07 (1 H, m), 7.52 (1 H, dd, J = 8.8 Hz, 2.8 Hz), 7.63 (1 H, dd, J = 8.6 Hz, 2.2 Hz), 7.75 (1 H, d, J = 2.7 Hz), 7.83-7.87 (2 H, m), 10.39 (1 H, brs). |
| 2024 | 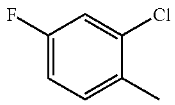 | —$CF_3$ | —$CH_3$ | ($DMSO-d_6$) 2.25-2.50 (4 H, m), 2.97 (3 H, s), 3.35-3.55 (6 H, m), 4.34 (2 H, s), 5.99 (2 H, s), 6.74-7.05 (7 H, m), 7.30-7.45 (1 H, m), 7.52 (1 H, dd, J = 8.8 Hz, 2.7 Hz), 7.71 (1 H, dd, J = 8.7 Hz, 2.5 Hz), 7.80 (1 H, d, J = 2.7 Hz), 8.00-8.06 (1 H, m), 10.61 (1 H, brs). |
| 2025 | 3,4-$Cl_2$Ph- | —CN | —$CH_3$ | ($DMSO-d_6$) 2.25-2.50 (4 H, m), 2.94 (3 H, s), 3.35-3.50 (6 H, m), 4.33 (2 H, s), 5.99 (2 H, s), 6.74-7.11 (7 H, m), 7.50-7.65 (2 H, m), 7.78 (1 H, d, J = 2.6 Hz), 7.83 (1 H, d, J = 8.5 Hz), 7.89 (1 H, d, J = 1.5 Hz), 10.45 (1 H, brs). |
| 2026 | 4-$CF_3$Ph- | —$OCH_3$ | —$SO_2CH_3$ | ($CDCl_3$) 2.43 (4 H, brs), 3.20 (3 H, s), 3.38 (2 H, brs), 3.43 (2 H, s), 3.61 (2 H, brs), 3.68 (3 H, s), 4.54 (2 H, s), 5.94 (2 H, s), 6.73-6.76 (2 H, m), 6.80-6.90 (2 H, m), 7.04 (1 H, d, J = 8.4 Hz), 7.15-7.19 (1 H, m), 7.24-7.26 (1 H, m), 7.57 (1 H, dd, J = 8.7 Hz, 2.8 Hz), 7.70-7.72 (4 H, m), 7.85 (2 H, d, J = 8.2 Hz). |
| 2027 | 3,4-$Cl_2$Ph- | —$OCH_3$ | —$SO_3CH_3$ | ($CDCl_3$) 2.43 (4 H, brs), 3.21 (3 H, s), 3.37 (2 H, brs), 3.43 (2 H, s), 3.61 (2 H, brs), 3.71 (3 H, s), 4.54 (2 H, s), 5.95 (2 H, s), 6.73-6.77 (2 H, m), 6.83 (1 H, s), 6.92 (1 H, d, J = 8.7 Hz), 7.06 (1 H, d, J = 8.6 Hz), 7.18 (1 H, dd, J = 8.4 Hz, 2.3 Hz), 7.25 (2 H, s), 7.52 (2 H, s), 7.57 (1 H, dd, J = 8.7 Hz, 2.8 Hz), 7.70 (1 H, d, J = 2.6 Hz), 7.81 (1 H, s). |

TABLE 322

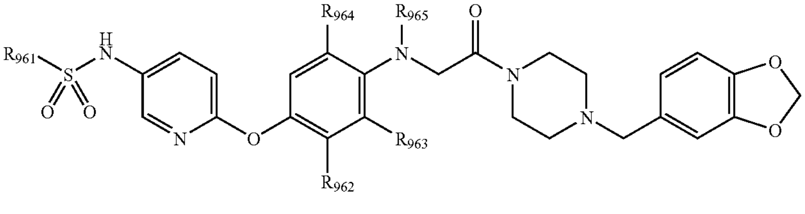

| Example No. | $R_{961}$ | $R_{962}$ | $R_{963}$ | $R_{964}$ | $R_{965}$ | $^1H$ NMR ($DMSO-d_6$) δ ppm |
|---|---|---|---|---|---|---|
| 2028 | 3,4-$Cl_2$Ph- | —$CH_3$ | —H | —$CH_3$ | —$CH_3$ | 1.93 (3 H, s), 2.16 (3 H, s), 2.20-2.40 (4 H, m), 2.63 (3 H, s), 3.39 (2 H, s), 3.39-3.50 (4 H, m), 3.74 (2 H, s), 5.99 (2 H, s), 6.72-6.92 (5 H, m), 6.98 (1 H, s), 7.51 (1 H, dd, J = 8.8 Hz, 2.4 Hz), 7.63 (1 H, dd, J = 8.5 Hz, 1.4 Hz), 7.73 (1 H, d, J = 2.6 Hz), 7.82-7.87 (2 H, m), 10.35 (1 H, brs). |

TABLE 322-continued

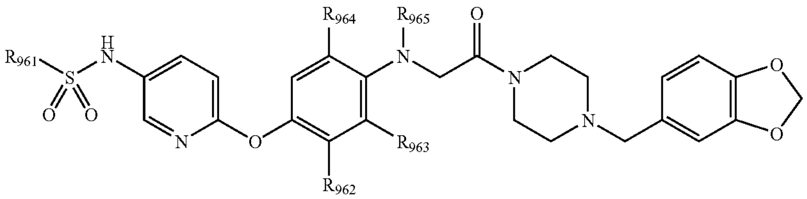

| Example No. | $R_{961}$ | $R_{962}$ | $R_{963}$ | $R_{964}$ | $R_{965}$ | $^1H$ NMR ($DMSO-d_6$) δ ppm |
|---|---|---|---|---|---|---|
| 2029 | 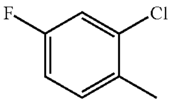 | $-CH_3$ | —H | $-CH_3$ | $-CH_3$ | 1.90 (3 H, s), 2.15 (3 H, s), 2.25-2.40 (4 H, m), 2.62 (3 H, s), 3.38 (2 H, s), 3.38-3.50 (4 H, m), 3.73 (2 H,s ), 5.98 (2 H, s), 6.72-6.76 (2 H, m), 6.82-6.88 (3 H, m), 6.97 (1 H, s), 7.30-7.45 (1 H, m), 7.51 (1 H, dd, J = 8.8 Hz, 2.7 Hz), 7.72 (1 H, dd, J = 8.7 Hz, 2.6 Hz), 7.78 (1 H, d, J = 2.8 Hz), 7.98-8.04 (1 H, m ), 10.56 (1 H, brs). |
| 2030 | 3,4-$Cl_2$Ph- | —H | $-CF_3$ | —H | $-C_2H_5$ | 0.92 (3 H, t, J = 7.1 Hz), 2.20-2.40 (4 H, m), 3.11 (2 H, q, J = 7.1 Hz), 3.35-3.50 (6 H, m), 3.83 (2 H, s), 5.98 (2 H, s), 6.70-6.90 (3 H, m), 7.05 (1 H, d, J = 8.8 Hz), 7.32-7.36 (2 H, m), 7.56-7.75 (3 H, m), 7.81-7.91 (3 H, m), 10.48 (1 H, brs). |

Example 2031

N-{4-[4-(4-benzenesulfonylpiperazin-1-yl)phenoxy]phenyl}-3,4-dichlorobenzamide

Melting point: 191-192° C.

The following compounds were produced in the same manner as in Reference Example 292.

TABLE 323

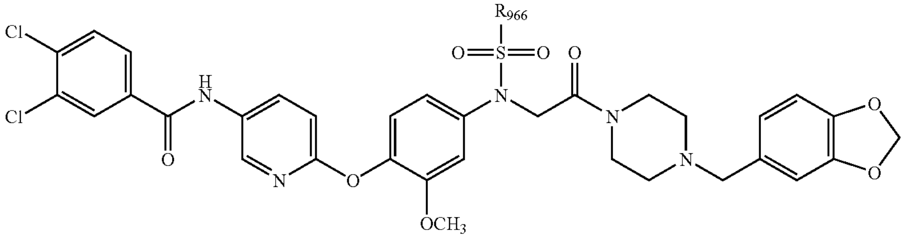

| Example No. | $R_{966}$ | $^1H$ NMR ($CDCl_3$) δ ppm |
|---|---|---|
| 2032 | $-CH_3$ | 2.41 (4H, brs), 3.20 (3H, s), 3.36 (2H, brs), 3.42 (2H, s), 3.59 (2H, brs), 3.66 (3H, s), 4.50 (2H, s), 5.94 (2H, s), 6.70-6.76 (2H, m), 6.83 (1H, s), 6.93 (1H, d, J = 8.7 Hz), 6.99-7.04 (2H, m), 7.13 (1H, dd, J = 8.4 Hz, 2.1 Hz), 7.51 (1H, d, J = 2.3 Hz), 7.69 (1H, dd, J = 8.4 Hz, 2.1 Hz), 7.95 (1H, d, J = 2.1 Hz), 8.12 (1H, dd, J = 8.7 Hz, 2.6 Hz), 8.23 (1H, d, J = 2.6 Hz), 8.53 (1H, s). |
| 2033 | $-C_2H_5$ | 1.37 (3H, t, J = 7.4 Hz), 2.42 (4H, brs), 3.38-3.46 (6H, m), 3.60 (2H, brs), 3.71 (3H, s), 4.53 (2H, s), 5.94 (2H, s), 6.70-6.77 (2H, m), 6.84 (1H, s), 6.97 (1H, d, J = 8.7 Hz), 7.06 (1H, d, J = 8.6 Hz), 7.14-7.18 (1H, m), 7.26 (1H, s), 7.55 (1H, d, J = 8.4 Hz), 7.71 (1H, dd, J = 8.4 Hz, 2.1 Hz), 7.98 (1H, d, J = 2.1 Hz), 8.16-8.23 (3H, m). |

Example 2034

Production of t-butyl 4-{4-[5-(3,4-dichlorobenzoylamino)pyridin-2-yloxy]phenylcarbamoyl}piperidine-1-carboxylate To a solution of N-[6-(4-aminophenoxy)pyridin-3-yl]-3,4-dichlorobenzamide dihydrochloride (1.0 g, 2.24 mmol) in DMF (15 mL) were added, piperidine-1,4-dicarboxylic acid mono-t-butyl ester (510 mg, 2.22 mmol), triethylamine (0.94 mL, 6.74 mmol), 1-hydroxybenzotriazole monohydrate (350 mg, 2.29 mmol) and 1-ethyl-3-(3-dimethylaminopropyl)carbodiimide hydrochloride (514 mg, 2.68 mmol) under ice cooling. The resulting solution was then stirred under ice cooling for 1 hour, and at room temperature for 17 hours. This reaction solution was concentrated under reduced pressure. The residue was diluted with water and ethyl acetate, whereupon a white powder was precipitated. The white powder was filtered, then washed with water, and subsequently washed with ethyl acetate, to thereby yield 1.04 g of the title compound.

Appearance: White powder $^1H$ NMR ($DMSO-d_6$) δ 1.41 (9H, s), 1.35-1.50 (2H, m), 1.70-1.85 (2H, m), 2.40-2.60 (1H, m), 2.65-2.90 (2H, m), 3.90-4.11 (2H, m), 7.03 (1H, d, J=8.9 Hz), 7.06 (2H, d, J=8.9 Hz), 7.62 (2H, d, J=8.9 Hz), 7.84 (1H, d, J=8.5 Hz), 7.94 (1H, dd, J=8.5 Hz, 2.0 Hz), 8.17 (1H, dd, J=8.9 Hz, 2.6 Hz), 8.22 (1H, d, J=2.0 Hz), 8.46 (1H, d, J=2.6 Hz), 9.96 (1H, s), 10.54 (1H, s).

The following compound was produced in the same manner as in Example 2034.

Example 2035

3,4-Dichloro-N-(6-{4-[2-(2,4-dioxothiazolidine-5-yl)-acetylamino]phenoxy}pyridin-3-yl)benzamide $^1$H NMR (DMSO-$d_6$) δ 3.07 (1H, dd, J=16.5 Hz, 8.9 Hz), 3.24 (1H, dd, J=16.5 Hz, 4.0 Hz), 4.73 (1H, dd, J=9.0 Hz, 4.0 Hz), 7.04 (1H, d, J=8.9 Hz), 7.08 (2H, d, J=8.9 Hz), 7.58 (2H, d, J=8.9 Hz), 7.84 (1H, d, J=8.2 Hz), 7.94 (1H, dd, J=8.2 Hz, 2.0 Hz), 8.18 (1H, dd, J=8.9 Hz, 2.6 Hz), 8.22 (1H, d, J=2.0 Hz), 8.46 (1H, d, J=2.6 Hz), 10.21 (1H, s), 10.53 (1H, s), 12.00 (1H, s).

Example 2036

Production of 3,4-dichloro-N-(6-{4-[4-piperonylpiperazin-1-ylmethyl]phenoxy}pyridin-3-yl)benzamide To a solution of 3,4-dichloro-N-[6-(4-piperazin-1-ylmethylphenoxy)pyridin-3-yl]benzamide (300 mg, 0.66 mmol) in DMF (10 mL) were added piperonylic acid (120 mg, 0.72 mmol), 1-ethyl-3-(3-dimethylaminopropyl)carbodiimide hydrochloride (140 mg, 0.73 mmol) and 1-hydroxybenzotriazole monohydrate (100 mg, 0.74 mmol) under ice cooling. The resulting reaction solution was stirred overnight at room temperature. To the residue was added a saturated sodium bicarbonate solution, and extracted with ethyl acetate. The ethyl acetate layer was washed with a saturated sodium bicarbonate solution and brine. The ethyl acetate layer was dried over anhydrous magnesium sulfate, and evaporated, to thereby yield 110 mg of the title compound.

Appearance: White powder $^1$H NMR ($CDCl_3$) δ 2.46 (4H, brs), 3.53 (2H, s), 3.60 (4H, brs), 5.99 (2H, s), 6.79 (1H, d, J=7.9 Hz), 6.85-6.96 (3H, m), 7.08 (2H, d, J=8.6 Hz), 7.33 (2H, d, J=8.3 Hz), 7.54 (1H, d, J=8.3 Hz), 7.69-7.73 (1H, m), 7.99 (1H, d, J=2.3 Hz), 8.16-8.21 (1H, m), 8.27-8.30 (2H, m).

The following compounds were produced in the same manner as in Example 2036.

TABLE 324

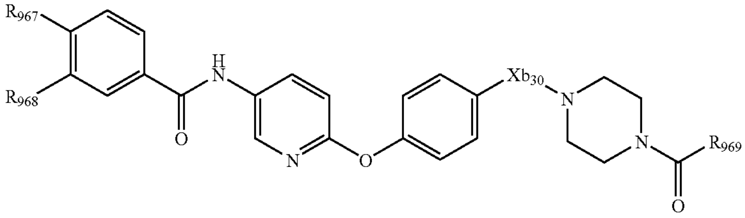

| Example No. | $R_{967}$ | $R_{968}$ | $Xb_{30}$ | $R_{969}$ | mp (° C.) or $^1$H NMR (solvent) δ ppm |
|---|---|---|---|---|---|
| 2037 | —$CF_3$ | —H | —CO— | 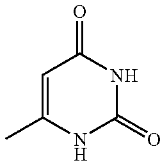 | $^1$H NMR (DMSO-$d_6$) 3.52 (4 H, brs), 3.60 (4 H, brs), 5.57 (1 H, s), 7.17 (1 H, d, J = 8.9 Hz), 7.20 (2 H, d, J = 8.9 Hz), 7.51 (2 H, d, J = 8.4 Hz), 7.95 (2 H, d, J = 8.1 Hz), 8.17 (2 H, d, J = 8.1 Hz), 8.27 (1 H, dd, J = 8.9 Hz, 2.6 Hz), 8.55 (1 H, d, J = 2.6 Hz), 10.69 (1 H, brs), 11.18 (1 H, brs), 11.32 (1 H, brs). |
| 2038 | —Cl | —Cl | —$CH_2$— | 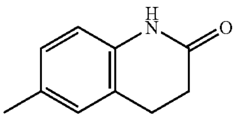 | mp 250-251 |
| 2039 | —$CF_3$ | —H | —$CH_2$— | 2-CNPh- | mp 189-192 |
| 2040 | —$CF_3$ | —H | —$CH_2$— | 4-pyridyl | mp 122-124 |
| 2041 | —$CF_3$ | —H | —$CH_2$— | 3-pyridyl | mp 167-168 |
| 2042 | —$CF_3$ | —H | —$CH_2$— | 2-pyridyl | mp 189-191 |
| 2043 | —$CF_3$ | —H | —$CH_2$— | 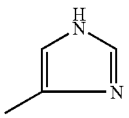 | $^1$H NMR (DMSO-$d_6$) 2.45 (4 H, brs), 3.36 (2 H, s), 3.54-4.18 (4 H, m), 7.09 (3 H, d, J = 8.9 Hz), 7.36 (2 H, d, J = 8.4 Hz), 7.59 (1 H, brs), 7.72 (1 H, s), 7.94 (2 H, d, J = 8.4 Hz), 8.18 (2 H, d, J = 8.4 Hz), 8.24 (1 H, dd, J = 8.9 Hz, 2.6 Hz), 8.53 (1 H, d, J = 2.6 Hz), 10.67 (1 H, s), 12.48 (1 H, brs). |

TABLE 324-continued

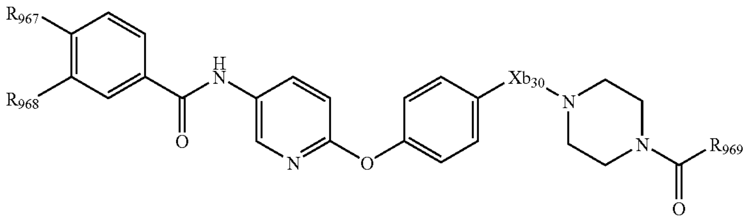

| Example No. | $R_{967}$ | $R_{968}$ | $Xb_{30}$ | $R_{969}$ | mp (° C.) or $^1$H NMR (solvent) δ ppm |
|---|---|---|---|---|---|
| 2044 | —$CF_3$ | —H | —$CH_2$— | 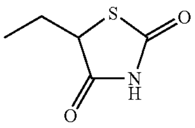 | $^1$H NMR ($CDCl_3$ + $CD_3OD$) 2.98-3.15 (5 H, m), 3.34-3.47 (1 H, m), 3.61-3.76 (4 H, m), 4.18 (2 H, s), 4.57 (1 H, dd, J = 10.2 Hz, 3.1 Hz), 7.04 (1 H, d, J = 8.7 Hz), 7.19 (2 H, d, J = 8.6 Hz), 7.49 (2 H, d, J = 8.6 Hz), 7.79 (2 H, d, J = 8.3 Hz), 8.11 (2 H, d, J = 8.1 Hz ), 8.25 (1 H, dd, J = 8.9 Hz, 2.8 Hz), 8.52 (1 H, d, J = 2.3 Hz). |
| 2045 | —$CF_3$ | —H | —$(CH_2)_3$— | 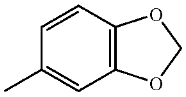 | $^1$H NMR ($CDCl_3$) 1.81-1.89 (2 H, m), 2.40-2.45 (6 H, m), 2.62-2.68 (2 H, m), 3.61 (4 H, brs), 5.98 (2 H, s), 6.76-6.93 (4 H, m), 7.03 (2 H, d, J = 8.4 Hz), 7.19 (2 H, d, J = 8.4 Hz), 7.68 (2 H, d, J = 8.4 Hz), 7.99 (2 H, d, J = 8.3 Hz), 8.18-8.23 (1 H, m), 8.30 (1 H, d, J = 2.6 Hz ), 8.73 (1 H, s). |
| 2046 | —$CF_3$ | —H | —$(CH_2)_3$— | 3,4-$(CH_3O)_2$Ph- | $^1$H NMR ($CDCl_3$) 1.78-1.89 (2 H, m), 2.39-2.45 (6 H, m), 2.63-2.68 (2 H, m), 3.62 (4 H, brs), 3.85 (3 H, s), 3.89 (3 H, s), 6.82-6.85 (1 H, m), 6.91-6.95 (3 H, m), 7.01-7.06 (2 H, m), 7.18-7.23 (2 H, m), 7.70 (2 H, d, J = 8.2 Hz), 7.99 (2 H, d, J = 8.2 Hz), 8.20-8.24 (1 H, m), 8.29 (1 H, d, J = 2.6 Hz), 8.51 (1 H, brs). |

TABLE 325

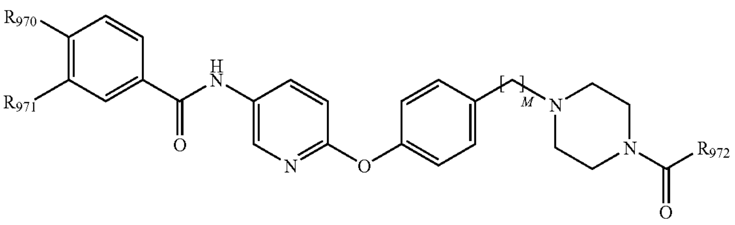

| Example No. | $R_{970}$ | $R_{971}$ | $R_{972}$ | M | Form | $^1$H NMR (solvent) δ ppm |
|---|---|---|---|---|---|---|
| 2047 | —$CF_3$ | —H | 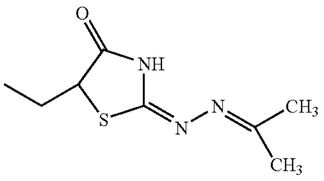 | 1 | free | (DMSO-$d_6$) 1.94 (6 H, s), 2.49-2.51 (4 H, m), 2.76-2.93 (1 H, m), 3.17-3.51 (7 H, m), 4.20 (1 H, dd, J = 10.4 Hz, 3.0 Hz), 7.09-7.13 (3 H, m), 7.42 (2 H, brs), 7.94 (2 H, d, J = 8.4 Hz), 8.16-8.26 (3 H, m), 8.54 (1 H, d, J = 2.5 Hz), 10.67 (1 H, s), 11.68 (1 H, brs). |

TABLE 325-continued

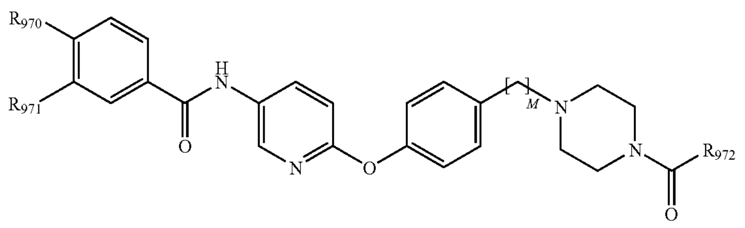

| Example No. | $R_{970}$ | $R_{971}$ | $R_{972}$ | M | Form | $^1$H NMR (solvent) δ ppm |
|---|---|---|---|---|---|---|
| 2048 | —$CF_3$ | —H | 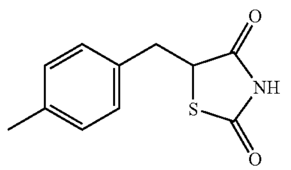 | 1 | free | ($CDCl_3$ + $CD_3OD$) 2.46-2.59 (4 H, m), 3.16 (1 H, dd, J = 14.2 Hz, 9.4 Hz), 3.32 (4 H, brs), 3.51 (1 H, dd, J = 14.0 Hz, 3.8 Hz), 3.79 (2 H, brs), 4.50 (1 H, dd, J = 9.4 Hz, 4.0 Hz), 6.93 (1 H, d, J = 8.9 Hz), 7.06 (2 H, d, J = 8.4 Hz), 7.26-7.46 (6 H, m), 7.72 (2 H, d, J = 8.3 Hz), 8.05 (2 H, d, J = 8.1 Hz), 8.27 (1 H, d, J = 2.1 Hz), 8.33 (1 H, dd, J = 8.9 Hz, 2.8 Hz). |
| 2049 | —$CF_3$ | —H | 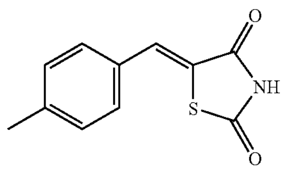 | 1 | free | (DMSO-$d_6$) 2.49-2.52 (4 H, m), 3.34-3.40 (4 H, m), 3.57 (2 H, s), 7.06-7.10 (3 H, m), 7.36 (2 H, d, J = 8.6 Hz), 7.54 (2 H, d, J = 8.1 Hz), 7.67 (2 H, d, J = 8.4 Hz), 7.79 (1 H, s), 7.94 (2 H, d, J = 8.6 Hz), 8.15-8.25 (3 H, m), 8.51 (1 H, d, J = 2.8 Hz), 10.64 (1 H, s). |
| 2050 | —$CF_3$ | —H | 4-pyridyl | 3 | hydro-chloride | (DMSO-$d_6$) 2.04 (2 H, brs), 2.63-2.69 (2 H, m), 3.10-3.59 (9 H, m), 4.54 (1 H, brs), 7.05-7.08 (3 H, m), 7.28 (2 H, d, J = 8.2 Hz), 7.45 (2 H, d, J = 4.9 Hz), 7.94 (2 H, d, J = 8.2 Hz), 8.18-8.26 (3 H, m), 8.53 (1 H, d, J = 2.3 Hz), 8.70 (2 H, d, J = 5.4 Hz), 10.72 (1 H, s), 11.27 (1 H, brs). |
| 2051 | —Cl | —Cl | 3,4-$F_2$Ph- | 1 | free | ($CDCl_3$) 2.46 (4 H, brs), 3.47-3.72 (6 H, m), 6.91 (1 H, d, J = 8.9 Hz), 7.05-7.33 (7 H, m), 7.50 (1 H, d, J = 8.4 Hz), 7.71 (1 H, dd, J = 8.4 Hz, 2.1 Hz), 7.97 (1 H, d, J = 2.1 Hz), 8.14-8.18 (1 H, m), 8.28 (1 H, d, J = 2.6 Hz), 8.68 (1 H, s). |

TABLE 326

| Example No. | Chemical stracture | mp (° C.) or $^1$H NMR |
|---|---|---|
| 2052 | 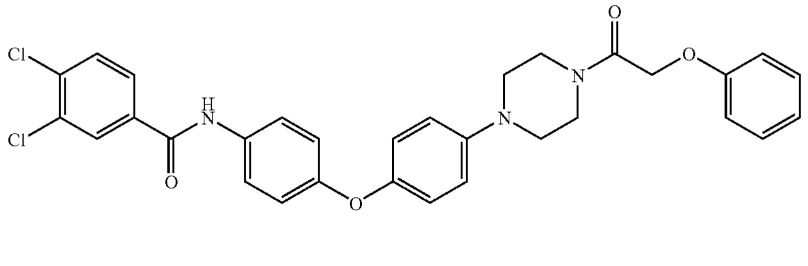 | mp 171-173 |

TABLE 326-continued

| Example No. | Chemical stracture | mp (° C.) or $^1$H NMR |
|---|---|---|
| 2053 | 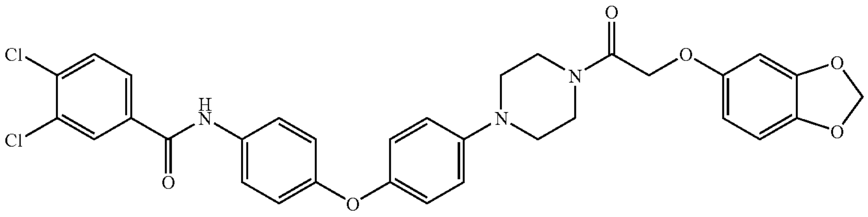 | mp 116-118 |
| 2054 | 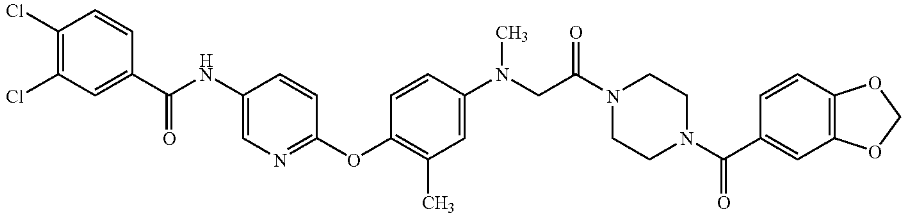 | mp 133-135 |
| 2055 | 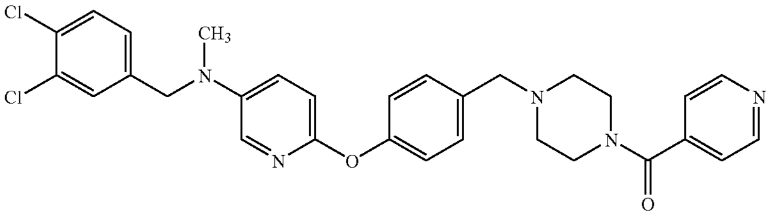 | $^1$H NMR ($CDCl_3$) δ 2.39 (2 H, brs), 2.55 (2 H, brs), 3.00 (3 H, s), 3.35 (2 H, brs), 3.51 (2 H, s), 3.79 (2 H, brs), 4.40 (2 H, s), 6.82 (1 H, d, J = 8.9 Hz), 6.99-7.13 (4 H, m), 7.25-7.29 (5 H, m), 7.32 (1 H, d, J = 1.8 Hz), 7.39 (1 H, d, J = 3.3 Hz), 8.68-8.70 (2 H, m). |

Example 2056

Production of N-{6-[4-(4-chloroacetylpiperazino)phenoxy]-3-pyridyl}-4-(trifluoromethyl)benzamide To a solution of N-[6-(4-piperazinophenoxy)-3-pyridyl]-4-(trifluoromethyl)benzamide (885 mg, 2.00 mmol) in DMF (20 mL) were added triethylamine (0.418 mL, 3.00 mmol) and chloroacetyl chloride (0.191 g, 2.40 mmol), and the resulting reaction solution was stirred for 10 minutes at room temperature. To this reaction solution was added ethyl acetate. The resulting solution was washed with water, and then dried over anhydrous magnesium sulfate. The solvent was evaporated, to thereby yield 1.00 g of the title compound.

Appearance: White powder $^1$H NMR ($CDCl_3$) δ 3.17 (2H, t, J=5.0 Hz), 3.22 (2H, t, J=5.0 Hz), 3.70 (2H, t, J=5.0 Hz), 3.80 (2H, t, J=5.0 Hz), 6.95 (1H, d, J=9.0 Hz), 6.97 (2H, d, J=9.0 Hz), 7.08 (2H, d, J=9.0 Hz), 7.77 (1H, brs), 7.78 (2H, d, J=8.0 Hz), 7.99 (2H, d, J=8.0 Hz), 8.20 (1H, dd, J=9.0 Hz, 2.5 Hz), 8.26 (1H, d, J=2.5 Hz).

The following compounds were produced in the same manner as in Example 2056.

TABLE 327

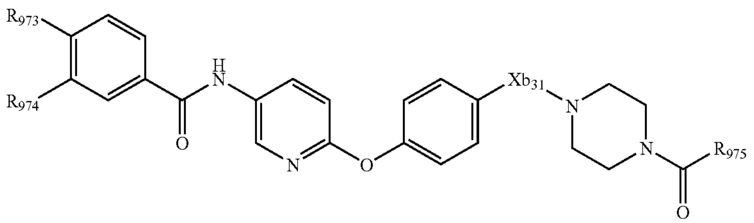

| Example No. | $R_{973}$ | $R_{974}$ | $Xb_{31}$ | $R_{975}$ | mp (° C.) or $^1$H NMR (solvent) δ ppm |
|---|---|---|---|---|---|
| 2057 | —$CF_3$ | —H | —CO— | 4-CNPh- | $^1$H NMR (DMSO-$d_6$) 3.29-3.69 (8 H, m), 7.14-7.20 (3 H, m), 7.49 (2 H, d, J = 8.6 Hz), 7.63 (2 H, d, J = 8.1 Hz), 7.93-7.95 (4 H, m), 8.17 (2 H, d, J = 8.1 Hz), 8.27 (1 H, dd, J = 8.9 Hz, 2.4 Hz), 8.55 (1 H, d, J = 2.4 Hz), 10.66 (1 H, s). |

TABLE 327-continued

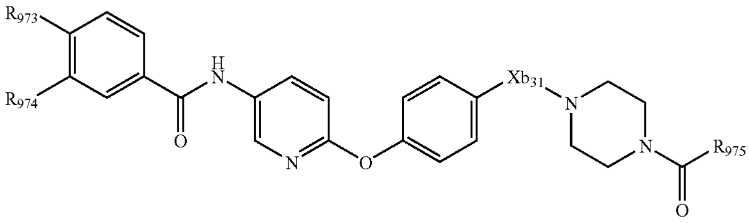

| Example No. | $R_{973}$ | $R_{974}$ | $Xb_{31}$ | $R_{975}$ | mp (° C.) or $^1$H NMR (solvent) δ ppm |
|---|---|---|---|---|---|
| 2058 | —$CF_3$ | —H | —CO— | —$CH_3$ | $^1$H NMR ($CDCl_3$) 2.13 (3 H, s), 3.35-3.90 (8 H, m), 7.02 (1 H, d, J = 8.8 Hz), 7.17 (2 H, d, J = 8.6 Hz), 7.44 (2 H, d, J = 8.6 Hz), 7.75 (2 H, d, J = 8.1 Hz), 8.02 (2 H, d, J = 8.1 Hz), 8.25 (1 H, dd, J = 8.8 Hz, 2.5 Hz), 8.33 (1 H, d, J = 2.5 Hz), 8.38 (1 H, brs). |
| 2059 | —Cl | —Cl | —$CH_2$— | -Ph | $^1$H NMR ($CDCl_3$) 2.08-2.55 (4 H, m), 3.43-3.45 (2 H, m), 3.55 (2 H, s), 3.79-3.81 (2 H, m), 6.96 (1 H, d, J = 8.9 Hz), 7.07-7.12 (2 H, m), 7.33-7.46 (7 H, m), 7.57 (1 H, d, J = 8.6 Hz), 7.69-7.73 (1 H, m), 7.94-7.99 (2 H, m), 8.17-8.21 (1 H, m), 8.27 (1 H, d, J = 2.6 Hz). |
| 2060 | —Cl | —Cl | —$CH_2$— | 4-CNPh- | $^1$H NMR ($CDCl_3$) 2.44 (2 H, brs), 2.58 (2 H, brs), 3.39 (2 H, brs), 3.56 (2 H, s), 3.81 (2 H, brs), 6.96 (1 H, d, J = 8.9 Hz), 7.08-7.12 (2 H, m), 7.34 (2 H, d, J = 8.4 Hz), 7.48-7.51 (2 H, m), 7.57 (1 H, d, J = 8.4 Hz), 7.69-7.77 (3 H, m), 7.95 (1 H, brs), 7.98 (1 H, d, J = 2.0 Hz), 8.14-8.21 (1 H, m), 8.27 (1 H, d, J = 2.3 Hz), |
| 2061 | —$CF_3$ | —H | —$CH_2$— | 4-CNPh- | mp 167-168 |
| 2062 | —$CF_3$ | —H | —$CH_2$— | -Ph | $^1$H NMR ($CDCl_3$) 2.41-2.53 (4 H, m), 3.43 (2 H, brs), 3.53 (2 H, s), 3.78 (2 H, brs), 6.95 (1 H, d, J = 8.9 Hz), 7.06-7.11 (2 H, m), 7.33-7.41 (7 H, m), 7.71 (2 H, d, J = 8.4 Hz), 7.99 (2 H, d, J = 8.4 Hz), 8.23 (1 H, dd, J = 8.9 Hz, 2.7 Hz), 8.31 (1 H, d, J = 2.7 Hz), 8.39 (1 H, s). |
| 2063 | —$CF_3$ | —H | —$CH_2$— | 3,4-$F_2$Ph- | mp 130-133 |
| 2064 | —$CF_3$ | —H | —$CH_2$— | 3-CNPh- | $^1$H NMR ($CDCl_3$) 2.43 (2 H, brs), 2.56 (2 H, brs), 3.39 (2 H, brs), 3.55 (2 H, s), 3.79 (2 H, brs), 6.97 (1 H, d, J = 8.9 Hz), 7.07-7.12 (2 H, m), 7.32-7.37 (2 H, m), 7.50-7.77 (6 H, m), 8.00 (2 H, d, J = 8.1 Hz), 8.07 (1 H, brs), 8.23 (1 H, dd, J = 8.9 Hz, 2.7 Hz), 8.28 (1 H, d, J = 2.7 Hz). |
| 2065 | —$CF_3$ | —H | —$CH_2$— | 4-$CH_3$Ph- | mp 193-194 |
| 2066 | —$CF_3$ | —H | —$CH_2$— | 4-ClPh- | mp 176-178 |
| 2067 | —$CF_3$ | —H | —$CH_2$— | 4-$CH_3$OPh- | mp 190-191 |

TABLE 328

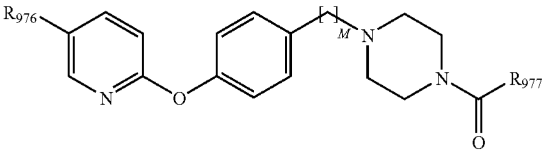

| Example No. | $R_{976}$ | $R_{977}$ | M | $^1$H NMR ($CDCl_3$) δ ppm |
|---|---|---|---|---|
| 2068 | 3,4-$Cl_2PhCH_2N(CH_3)$— | -Ph | 1 | 2.38 (2 H, brs), 2.53 (2 H, brs), 2.99 (3 H, s), 3.42 (2 H, brs), 3.50 (2 H, s), 3.79 (2 H, brs), 4.39 (2 H, s), 6.81 (1 H, d, J = 8.9 Hz), 6.99-7.12 (4 H, m), 7.26-7.39 (9 H, m), 7.69 (1 H, d, J = 3.1 Hz). |
| 2069 | 3,4-$Cl_2PhCH_2N(CH_3)$— | 4-CNPh- | 1 | 2.39 (2 H, brs), 2.55 (2 H, brs), 3.01 (3 H, s), 3.35 (2 H, brs), 3.51 (2 H, s), 3.79 (2 H, brs), 4.40 (2 H, s), 6.82 (1 H, d, J = 8.9 Hz), 6.99-7.13 (4 H, m), 7.25-7.33 (3 H, m), 7.39 (1 H, d, J = 8.1 Hz), 7.48-7.52 (2 H, m), 7.69-7.73 (3 H, m). |

TABLE 328-continued

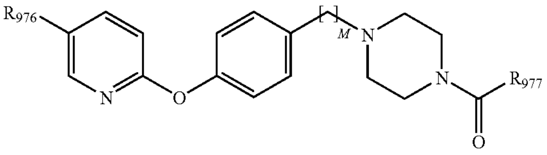

| Example No. | $R_{976}$ | $R_{977}$ | M | $^1$H NMR ($CDCl_3$) δ ppm |
|---|---|---|---|---|
| 2070 | 3,4-$Cl_2PhCH_2N(CH_3)$— | 4-ClPh | 1 | 2.34-2.59 (4 H, m), 3.00 (3 H, s), 3.36 (2 H, brs), 3.52 (2 H, s), 3.83 (2 H, brs), 4.40 (2 H, s), 6.82 (1 H, d, J = 8.9 Hz), 6.98-7.13 (4 H, m), 7.25-7.41 (8 H, m), 7.70 (1 H, d, J = 3.3 Hz). |
| 2071 | 3,4-$Cl_2PhCH_2N(CH_3)$— | 3,4-$F_2$Ph- | 1 | 2.33-2.57 (4 H, m), 3.00 (3 H, s), 3.37-3.51 (4 H, m), 3.75 (2 H, brs), 4.40 (2 H, s), 6.82 (1 H, d, J = 8.9 Hz), 7.00-7.32 (10 H, m), 7.39 (1 H, d, J = 8.1 Hz), 7.69 (1 H, d, J = 3.1 Hz). |
| 2072 | 4-$CF_3$PhCONH— | -Ph | 3 | 1.78-1.89 (2 H, m), 2.39-2.49 (6 H, m), 2.66 (2 H, t, J = 7.6 Hz), 3.44 (2 H, brs), 3.79 (2 H, brs), 6.94 (1 H, d, J = 8.7 Hz), 7.02-7.07 (2 H, m), 7.18-7.23 (2 H, m), 7.35-7.42 (5 H, m), 7.72 (2 H, d, J = 8.2 Hz), 7.99 (2 H, d, J = 8.1 Hz), 8.19-8.29 (3 H, m). |
| 2073 | 4-$CF_3$PhCONH— | 4-CNPh- | 3 | 1.79-1.90 (2 H, m), 2.41-2.69 (8 H, m), 3.39 (2 H, brs), 3.81 (2 H, brs), 6.95 (1 H, d, J = 8.9 Hz), 7.02-7.07 (2 H, m), 7.18-7.23 (2 H, m), 7.49 (2 H, d, J = 7.9 Hz), 7.69-7.77 (4 H, m), 8.00 (2 H, d, J = 8.1 Hz), 8.06 (1 H, brs), 8.21 (1 H, dd, J = 8.9 Hz, 2.6 Hz), 8.28 (1 H, d, J = 2.6 Hz). |
| 2074 | 4-$CF_3$PhCONH— | 3,4-$F_2$Ph- | 3 | 1.81-1.87 (2 H, m), 2.41-2.69 (8 H, m), 3.47-3.76 (4 H, m), 6.95 (1 H, d, J = 8.7 Hz), 7.02-7.07 (2 H, m), 7.11-7.28 (5 H, m), 7.75 (2 H, d, J = 8.4 Hz), 7.99-8.06 (3 H, m), 8.19-8.23 (1 H, m), 8.28 (1 H, d, J = 2.6 Hz). |

TABLE 329

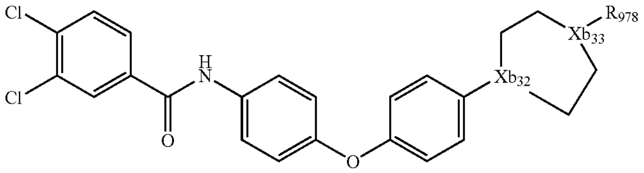

| Example No. | $Xb_{32}$ | $Xb_{33}$ | $R_{978}$ | mp (° C.) or $^1$H NMR (solvent) δ ppm |
|---|---|---|---|---|
| 2075 | 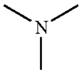 | 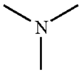 | —COPh | mp 136-138 |
| 2076 | 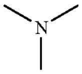 | 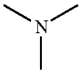 | 4-$CH_3$OPhCO— | mp 161-162 |
| 2077 | 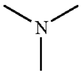 | 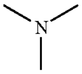 | 4-$CF_3$PhCO— | mp 143-144 |
| 2078 | 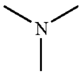 | 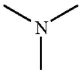 | 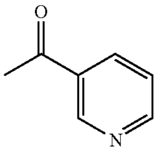 | mp 163-165 |

TABLE 329-continued

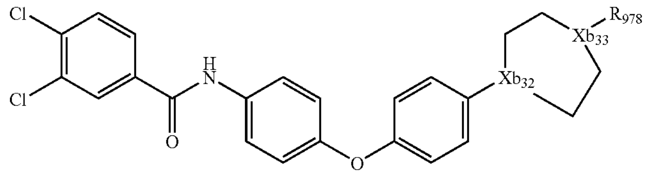

| Example No. | $Xb_{32}$ | $Xb_{33}$ | $R_{978}$ | mp (° C.) or $^1H$ NMR (solvent) δ ppm |
|---|---|---|---|---|
| 2079 | 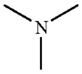 | 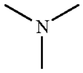 | 4-ClPhCO— | mp 147-151 |
| 2080 | 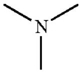 | 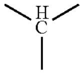 | —$N(CH_3)COPh$ | mp 231-232 |
| 2081 | 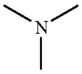 | 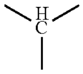 | —$N(CH_3)COCH_2Cl$ | $^1H$ NMR ($CDCl_3$) 1.70-1.76 (2 H, m), 1.80-1.90 (2 H, m), 2.80-2.88 (2 H, m), 2.98 (3 H, s), 3.56-3.68 (2 H, m), 4.10 (2 H, s), 4.57 (1 H, m), 6.94-6.99 (6 H, m), 7.53-7.58 (3 H, m), 7.69-7.71 (2 H, m), 7.97 (1 H, d, J = 2.0 Hz). |
| 2082 | 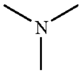 | 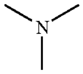 | —$COCH_2Cl$ | $^1H$ NMR (DMSO-$d_6$) 3.08 (2 H, m), 3.14 (2 H, m), 3.61 (4 H, m), 4.44 (2 H, s), 6.93-7.02 (6 H, m), 7.71 (2 H, d, J = 9.0 Hz), 7.82 (1 H, d, J = 8.5 Hz), 7.93 (1 H, dd, J = 8.5 Hz, 2.0 Hz), 8.21 (1 H, d, J = 2.0 Hz), 10.39 (1 H, s). |
| 2083 | 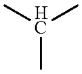 | 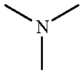 | —$COCH_2Cl$ | $^1H$ NMR ($CDCl_3$) 1.66 (1 H, m), 1.74 (1 H, m), 1.91-1.98 (2 H, m), 2.72-2.77 (2 H, m), 3.24 (1 H, m), 3.99 (1 H, brd, J = 13.0 Hz), 4.11 (2 H, s), 4.73 (1 H, brd, J = 13.0 Hz), 6.96 (2 H, d, J = 8.5 Hz), 7.02 (2 H, d, J = 9.0 Hz), 7.15 (2 H, d, J = 8.5 Hz), 7.56-7.79 (3 H, m), 7.71 (1 H, dd, J = 8.5 Hz, 2.0 Hz), 7.90 (1 H, brs), 7.98 (1 H, d, J = 2.0 Hz). |

TABLE 330

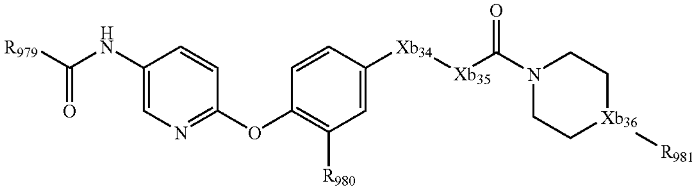

| Example No. | $R_{979}$ | $R_{980}$ | $Xb_{34}$ | $Xb_{35}$ | $Xb_{36}$ | $R_{981}$ | mp (° C.) or MS |
|---|---|---|---|---|---|---|---|
| 2084 | 3,4-$Cl_2Ph$- | —H | none | none | 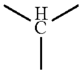 | —$N(CH_3)COCH_2Ph$ | MS 616 ($M^+$) |
| 2085 | 4-$CF_3Ph$- | —$CH_3$ | —$N(CH_3)$— | —$CH_2$— | 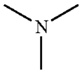 | 4-CNPhCO— | mp 131-132 |
| 2086 | 4-$CF_3Ph$- | —$CH_3$ | —$N(CH_3)$— | —$CH_2$— | 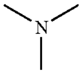 | 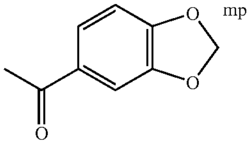 | mp 143-145 |

TABLE 331

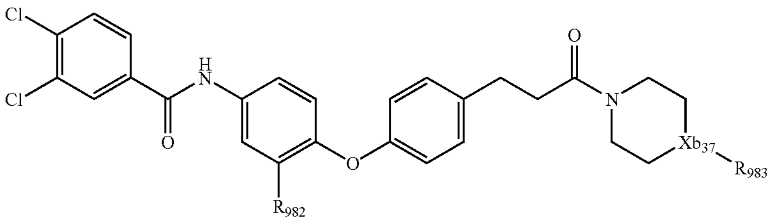

| Example No. | $R_{982}$ | $Xb_{37}$ | $R_{983}$ | Property |
|---|---|---|---|---|
| 2087 | —H | 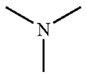 | —Ac | mp 138-140° C. |
| 2088 | —F | 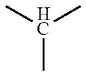 | —N($CH_3$)$COCH_2$Ph | MS 661 ($M^+$) |
| 2089 | —H | 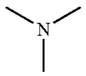 | —$COCH_2Cl$ | $^1$H NMR ($CDCl_3$) δ 2.62 (2 H, t, J = 7.6 Hz), 2.95 (2 H, t, J = 7.6 Hz), 3.31-3.73 (8 H, m), 4.05 (2 H, s), 6.91 (2 H, d, J = 8.5 Hz), 6.97 (2 H, d, J = 8.9 Hz), 7.15 (2 H, d, J = 8.5 Hz), 7.49-7.60 (3 H, m), 7.68 (1 H, dd, J = 8.3 Hz, 2.1 Hz), 7.91 (1 H, brs), 7.95 (1 H, d, J = 2.1 Hz). |

TABLE 332

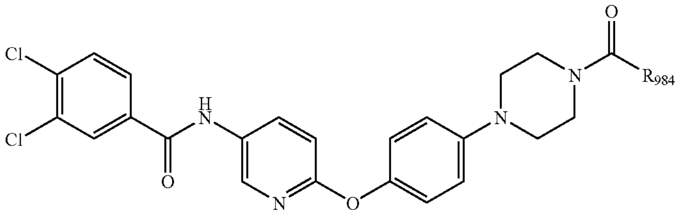

| Example No. | $R_{984}$ | mp (° C.) |
|---|---|---|
| 2090 | 2-pyridyl | 217-218 |
| 2091 | 3-pyridyl | 191-192 |
| 2092 | 4-pyridyl | 204-205 |

TABLE 333

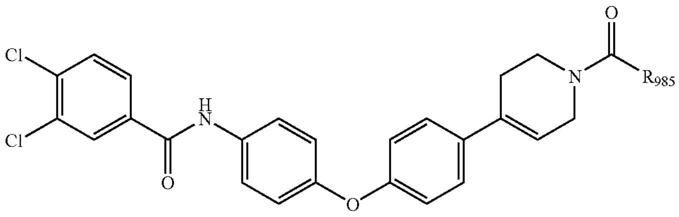

| Example No. | $R_{985}$ | mp (° C) or $^1$H NMR ($CDCl_3$) δ ppm |
|---|---|---|
| 2093 | -Ph | mp 185-186 |
| 2094 | —$CH_2Cl$ | a mixture of the rotational isomers $^1$H NMR 2.57 (0.4 H, brs), 2.65 (0.6 H, brs), 3.74 (0.6 H, t, J = 6.0 Hz), 3.85 (0.4 H, t, J = 6.0 Hz), 4.13 (0.8 H, s), 4.15 (1.2 H, s), 4.22 (1.2 H, m), 4.25 (0.8 H, m), 5.89 (0.4 H, brs), 6.04 (0.6 H, brs), 6.98 (2 H, d, J = 8.5 Hz), 7.04 (2 H, d, J = 9.0 Hz), 7.34 (2 H, dd, J = 8.5 Hz, 4.0 Hz), 7.56-7.60 (3 H, m ), 7.71 (1 H, dd, J = 8.5 Hz, 2.0 Hz), 7.89 (1 H, brs), 7.89 (1 H, d, J = 2.0 Hz). |

Example 2095

Production of 1-{4-[4-(3,4-dichlorobenzoylamino)-phenoxy]phenyl}-4-benzoyloxypiperidine To a solution of 1-{4-[4-(3,4-dichlorobenzoylamino)phenoxy]phenyl}-4-hydroxypiperidine (200 mg, 0.44 mmol) in dichloromethane (8 mL) were added with triethylamine (0.091 mL, 0.65 mmol), benzoyl chloride (74 mg, 0.53 mmol) and 4-(dimethylamino)pyridine (3 mg, 0.025 mmol), and the resulting solution was stirred for 2.5 days at room temperature. This reaction solution was purified by silica gel column chromatography (methanol:dichloromethane=7:93), to thereby yield 80 mg of the title compound.

Appearance: White powder

Melting point: 188-190° C.

Example 2096

Production of 3,4-dichloro-N-(6-{4-[[2-oxo-2-(4-piperonylpiperazin-1-yl)ethyl](2,2,2-trifluoroacetyl)amino]phenoxy}pyridin-3-yl)benzamide To a solution of 3,4-dichloro-N-(6-{4-[2-oxo-2-(4-piperonylpiperazin-1-yl)ethylamino]phenoxy}pyridin-3-yl)benzamide (0.152 g, 0.239 mmol) in THF (5 mL) were added triethylamine (0.0500 mL, 0.359 mmol) and trifluoroacetic anhydride (0.0410 mL, 0.2.87 mmol), and the resulting solution was stirred for 6 hours. Water was added to the resulting reaction solution, and extracted with ethyl acetate. The ethyl acetate layer was washed with brine, dried over anhydrous magnesium sulfate, and evaporated. The residue was purified by silica gel column chromatography (dichloromethane: methanol=20:1) to yield a solid. This solid was recrystallized from methanol, to thereby yield 28.8 mg of the title compound.

Appearance: White powder

Melting point: 211-213° C.

The following compound was produced in the same manner as in Example 2096.

Example 2097

N-[6-(4-Acetyl[2-oxo-2-(4-piperonylpiperazin-1-yl)ethyl]amino}-2-methoxyphenoxy)pyridin-3-yl]-3,4-dichlorobenzamide $^1$H NMR ($CDCl_3$) δ 1.90 (3H, s), 2.28 (2H, brs), 2.38 (2H, brs), 3.37 (4H, brs), 3.49 (2H, brs), 3.67 (3H, s), 4.43 (2H, s), 5.93 (2H, s), 6.68-6.75 (2H, m), 6.82 (1H, s), 6.91-6.97 (2H, m), 7.07-7.10 (2H, m), 7.53 (1H, d, J=8.4 Hz), 7.76 (1H, dd, J=8.4 Hz, 2.0 Hz), 8.05 (1H, d, J=2.0 Hz), 8.20 (1H, dd, J=8.9 Hz, 2.8 Hz), 8.37 (1H, d, J=2.6 Hz), 9.26 (1H, s).

Example 2098

Production of N-[6-(benzoyl{4-[3-oxo-3-(4-piperonylpiperazin-1-yl)propyl]phenyl}amino)pyridin-3-yl]-3,4-dichlorobenzamide monooxalate To a solution of 3,4-dichloro-N-(6-{4-[3-oxo-3-(4-piperonylpiperazin-1-yl)propyl]phenylamino}-pyridin-3-yl)benzamide (250 mg, 0.395 mmol) in THF (5 mL) were added triethylamine (0.132 mL, 0.949 mmol) and benzoyl chloride (0.0550 mL, 0.474 mmol), and the resulting solution was stirred for 7 hours at room temperature. Water was added to the resulting reaction solution, and extracted with ethyl acetate. The ethyl acetate layer was washed with brine, dried over anhydrous magnesium sulfate, and evaporated. The residue was purified by silica gel column chromatography (dichloromethane:methanol 10:1) to yield 0.300 g of a free form. To this free form were added isopropanol (5 mL) and oxalic acid dihydrate (100 mg, 0.793 mmol), and the resulting solution was dissolved under heat. The solvent was evaporated, and the resulting solid was recrystallized from isopropanol, to thereby yield 80.0 mg of the title compound.

Appearance: Yellow powder

Melting point: 140-143° C.

The following compound was produced in the same manner as in Example 2098.

Example 2099

N-[6-(Acetyl{4-[3-oxo-3-(4-piperonylpiperazin-1-yl)propyl]phenyl}amino)pyridin-3-yl]-3,4-dichlorobenzamide Melting point: 150-165° C.

$^1$H NMR (DMSO-$d_6$) δ 1.98 (3H, s), 2.62-2.98 (7H, m), 3.04 (1H, t, J=12.1 Hz), 3.26 (2H, t, J=14.7 Hz), 3.35-3.50 (2H, m), 4.06 (1H, d, J=13.8 Hz), 4.13-4.26 (2H, m), 4.44 (1H, d, J=13.8 Hz), 6.07 (2H, s), 6.95-7.02 (2H, m), 7.20-7.24 (3H, m), 7.28 (2H, d, J=8.3 Hz), 7.52 (1H, d, J=8.9 Hz), 7.85 (1H, d, J=8.4 Hz), 7.96 (1H, dd, J=2.0 Hz, 8.4 Hz), 8.23-8.26 (2H, m), 8.77 (1H, s), 10.77 (1H, s), 11.10 (1H, brs).

Example 2100

Production of 6-{4-[3-(4-piperonylpiperazin-1-yl)-3-oxopropyl]phenoxy}-N-(3,4-dichlorophenyl)nicotinamide To a solution of 6-{4-[3-(4-piperonylpiperazin-1-yl)-3-oxopropyl]phenoxy}nicotinic acid (1.23 g, 2.5 mmol) in THF (35 mL) was added N,N'-carbonyldiimidazole (540 mg, 3.3 mmol), and the resulting solution was stirred for 30 minutes at room temperature. The resulting reaction solution was concentrated under reduced pressure, and to the residue was added 3,4-dichloroaniline (4.07 g, 25 mmol). The resulting solution was stirred for 3 days at room temperature. The solvent was evaporated under reduced pressure. The residue was purified by silica gel column chromatography (ethyl acetate), and the resulting product was recrystallized from diethyl ether, to thereby yield 510 mg of the title compound.

Appearance: White powder $^1$H NMR ($CDCl_3$) δ 2.33 (4H, brs), 2.59-2.65 (2H, m), 2.91-2.97 (2H, m), 3.40 (4H, brs), 3.59 (2H, s), 5.94 (2H, s), 6.70-6.76 (2H, m), 6.83 (1H, s), 6.96-7.06 (3H, m), 7.20-7.26 (2H, m), 7.40 (1H, d, J=8.6 Hz), 7.50-7.54 (1H, m), 7.86 (1H, d, J=1.8 Hz), 8.18-8.22 (1H, m), 8.44 (1H, brs), 8.66 (1H, brs).

The following compounds were produced in the same manner as in Example 2100.

TABLE 334

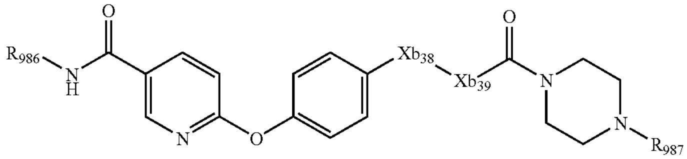

| Example No. | $R_{986}$ | $Xb_{38}$ | $Xb_{39}$ | $R_{987}$ | mp (° C.) or $^1$H NMR ($CDCl_3$) δ ppm |
|---|---|---|---|---|---|
| 2101 | 3,4-$Cl_2$Ph- | none | none | benzyl | mp 206-207 |
| 2102 | 4-$CF_3$Ph- | none | none | benzyl | $^1$H NMR 2.44 (4H, brs), 3.53-3.70 (6H, m), 6.93 (1H, d, J = 8.4 Hz), 7.11-7.14 (2H, m), 7.27-7.40 (7H, m), 7.56 (2H, d, J = 8.9 Hz), 7.83 (2H, d, J = 8.4 Hz), 8.23-8.27 (1H, m), 8.71 (1H, d, J = 2.4 Hz), 9.39 (1H, brs). |
| 2103 | 4-$CF_3$Ph- | —N($CH_3$)— | —$CH_2$— | piperonyl | $^1$H NMR 2.42 (4H, brs), 3.03 (3H, s), 3.43-3.52 (4H, m), 3.60 (2H, brs), 4.10 (2H, s), 5.95 (2H, s), 6.66-6.77 (4H, m), 6.85 (1H, brs), 6.89 (1H, d, J = 8.6 Hz), 6.98 (2H, d, J = 6.6 Hz), 7.60 (2H, d, J = 8.4 Hz), 7.76 (2H, d, J = 8.4 Hz), 8.14 (1H, dd, J = 8.6 Hz, 2.6 Hz), 8.33 (1H, brs), 8.63 (1H, brs). |
| 2104 | 3,4-$Cl_2$Ph- | —N($CH_3$)— | —$CH_2$— | piperonyl | $^1$H NMR 2.42-2.44 (4H, m), 3.05 (3H, s), 3.44 (2H, brs), 3.47-3.57 (2H, m), 3.63 (2H, brs), 4.11 (2H, s), 5.95 (2H, s), 6.68-6.74 (4H, m), 6.85 (1H, brs), 6.92 (1H, d, J = 8.9 Hz), 7.00 (2H, d, J = 8.7 Hz), 7.42-7.44 (2H, m), 7.80-7.86 (1H, m), 7.87 (1H, d, J = 2.1 Hz), 8.13 (1H, dd, J = 8.7 Hz, 2.6 Hz), 8.63 (1H, d, J = 2.1 Hz). |
| 2105 | 4-$CF_3$Ph- | none | none | piperonyl | $^1$H NMR 2.71 (4H, brs), 3.46-3.92 (6H, m), 5.91 (2H, s), 6.65-6.73 (2H, m), 6.81 (1H, d, J = 1.5 Hz), 7.01 (1H, d, J = 9.1 Hz), 7.14 (2H, d, J = 8.7 Hz), 7.43 (2H, d, J = 8.7 Hz), 7.60 (2H, d, J = 8.6 Hz), 7.82 (2H, d, J = 8.6 Hz), 8.29 (1H, dd, J = 2.6 Hz, 8.6 Hz), 8.71 (1H, d, J = 2.1 Hz), 8.87 (1H, brs). |

Example 2106

Production of (4-benzylpiperazin-1-yl){4-[5-(3,4-dichlorophenylsulfanyl)pyridin-2-yloxy]phenyl}methanone To a solution of [4-(5-aminopyridin-2-yloxy)phenyl](4-benzylpiperazin-1-yl)methanone (0.73 g, 1.88 mmol) in concentrated sulfuric acid (0.38 mL)-water (1.1 mL) were added dropwise a solution of sodium nitrate (0.13 g, 1.88 mmol) in water (0.6 mL) under ice cooling. The reaction mixture was stirred for 10 minutes. This reaction mixture was added to a solution of 3,4-dichlorobenzenethiol (0.24 mL, 1.88 mmol) in 2 N aqueous sodium hydroxide (2 mL) under cooling with ice. Water was added to the resulting reaction solution, and extracted with dichloromethane. The dichloromethane layer was dried over anhydrous magnesium sulfate, and evaporated. The residue was purified by silica gel chromatography (dichloromethane:methanol=80:1), to thereby yield 0.1 g of the title compound.

Appearance: Yellow oil $^1$H NMR ($CDCl_3$) δ 2.49 (4H, brs), 3.56 (2H, s), 3.56 (2H, brs), 3.78 (2H, brs), 6.99 (1H, d, J=8.9 Hz), 7.20 (2H, d, J=8.7 Hz), 7.25-7.39 (5H, m), 7.46 (1H, dd, J=8.2 Hz, 2.0 Hz), 7.47 (2H, d, J=8.7 Hz), 7.56 (1H, d, J=8.2 Hz), 7.76 (1H, d, J=2.0 Hz), 7.86 (1H, dd, J=8.9 Hz, 2.5 Hz), 8.50 (1H, d, J=2.5 Hz).

The following compound was produced in the same manner as in Example 2106.

Example 2107

2-({4-[5-(3,4-Dichlorophenylsulfanyl)pyridin-2-yloxy]-3-methoxyphenyl}ethylamino)-1-(4-piperonylpiperazin-1-yl)ethanone $^1$H NMR ($CDCl_3$) δ 1.20 (3H, t, J=7.0 Hz), 2.43 (4H, t, J=4.9 Hz), 3.43 (2H, s), 3.35-3.50 (2H, m), 3.49-3.60 (2H, m), 3.60-3.70 (2H, m), 3.73 (3H, s), 4.05 (2H, s), 5.95 (2H, s), 6.22 (1H, dd, J=8.9 Hz, 2.7 Hz), 6.35 (1H, d, J=2.7 Hz), 6.70-6.76 (2H, m), 6.85 (1H, s), 6.90 (1H, d, J=9.0 Hz), 6.98 (1H, d, J=8.8 Hz), 7.46 (1H, dd, J=8.2 Hz, 2.0 Hz), 7.55 (1H, d, J=8.2 Hz), 7.75 (1H, d, J=2.0 Hz), 7.78 (1H, dd, J=9.0 Hz, 2.5 Hz), 8.49 (1H, d, J=2.5 Hz).

Example 2108

Production of 1-(6-{4-[3-(4-piperonylpiperazin-1-yl)-3-oxopropyl]phenoxy}pyridin-3-yl)-3-(3,4-dichlorophenyl)urea To a solution of 3-[4-(5-aminopyridin-2-yloxy)phenyl]-1-(4-piperonylpiperazin-1-yl)propane-1-one (600 mg, 1.3 mmol) in toluene (20 mL) were added ethyldiisopropylamine (0.454 mL, 2.6 mmol) and 3,4-dichlorophenylisocyanate (270 mg, 1.4 mmol), and the resulting solution was stirred for 1 day under reflux. The reaction solution was evaporated under reduced pressure. The residue was purified by silica gel column chromatography (methanol:chloroform=1:19), and then recrystallized from ethyl acetate to thereby yield 280 mg of the title compound.

Appearance: Pale yellow powder $^1$H NMR ($CDCl_3$) δ 2.37-2.39 (4H, m), 2.61-2.67 (2H, m), 2.89-2.94 (2H, m), 3.41-3.47 (4H, m), 3.61-3.65 (2H, m), 5.94 (2H, s), 6.69-6.83 (4H, m), 6.95 (2H, d, J=8.4 Hz), 7.10-7.26 (4H, m), 7.49 (1H, d, J=2.3 Hz), 7.93-7.96 (2H, m), 8.1-5 (1H, s), 8.21 (1H, s).

The following compounds were produced in the same manner as in Example 2108.

(285 mg, 1.29 mmol), and the resulting solution was stirred for 17 hours at room temperature. This reaction solution was concentrated under reduced pressure. Water was added to the residue, and extracted with ethyl acetate. The ethyl acetate layer was washed with brine, dried over anhydrous magnesium sulfate, and evaporated. The residue was then purified by silica gel column chromatography (dichloromethane: methanol=25:1). The obtained residue was dissolved in a mixed solvent of ethanol-ethyl acetate. To the resulting solution was added a solution of 4 N hydrogen chloride in ethyl acetate to bring the pH to 3. The precipitated white powder

TABLE 335

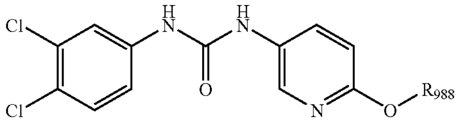

| Example No. | $R_{988}$ | $^1$H NMR (solvent) δ ppm |
|---|---|---|
| 2109 | 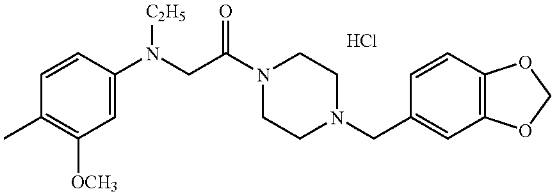 | (DMSO-$d_6$) 1.13 (3H, t, J = 6.9 Hz), 2.20-2.60 (1H, m), 2.75-3.20 (2H, m), 3.20-3.65 (7H, m), 3.64 (3H, s), 4.05-4.52 (4H, m), 6.07 (2H, brs), 6.10 (1H, dd, J = 8.8 Hz, 2.7 Hz), 6.27 (1H, brs), 6.80 (1H, d, J = 8.6 Hz), 6.84 (1H, d, J = 8.6 Hz), 7.01 (2H, brs), 7.19 (1H, brs), 7.33 (1H, dd, J = 8.9 Hz, 2.6 Hz), 7.51 (1H, d, J = 8.9 Hz), 7.85 (1H, dd, J = 8.9 Hz, 2.6 Hz), 7.86 (1H, d, J = 2.6 Hz), 8.07 (1H, d, J = 2.6 Hz), 8.94 (1H, s), 9.28 (1H, s). |
| 2110 | 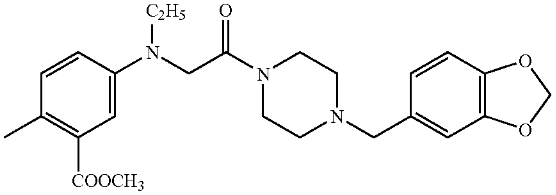 | ($CDCl_3$) 1.14 (3H, t, J = 7.0 Hz), 2.35-2.55 (4H, m), 3.38 (2H, q, J = 7.0 Hz), 3.44 (2H, s), 3.45-3.55 (2H, m), 3.60 (3H, s), 3.60-3.75 (2H, m), 4.02 (2H, s), 5.95 (2H, s), 6.60-6.80 (4H, m), 6.85 (1H, s), 6.92 (1H, d, J = 8.9 Hz), 7.00-7.15 (2H, m), 7.22 (1H, d, J = 8.7 Hz), 7.45 (1H, d, J = 2.3 Hz), 7.75-7.85 (2H, m), 7.95 (1H, s), 7.97 (1H, s). |
| 2111 | 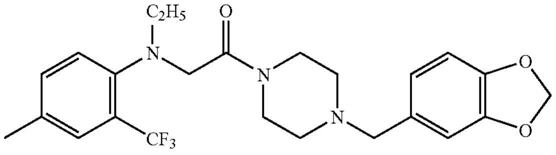 | ($CDCl_3$) 1.09 (3H, t, J = 7.1 Hz), 2.35-2.45 (4H, m), 3.10 (2H, q, J = 7.1 Hz), 3.43 (2H, s), 3.55-3.65 (4H, m), 3.85 (2H, s), 5.95 (2H, s), 6.70-6.80 (2H, m), 6.85 (1H, s), 6.90 (1H, d, J = 8.8 Hz), 7.05-7.35 (4H, m), 7.46 (1H, d, J = 8.8 Hz), 7.53 (1H, d, J = 2.4 Hz), 7.79 (1H, brs), 7.85 (1H, brs), 7.93 (1H, d, J = 2.6 Hz), 7.99 (1H, dd, J = 8.8 Hz, 2.8 Hz). |
| 2112 | 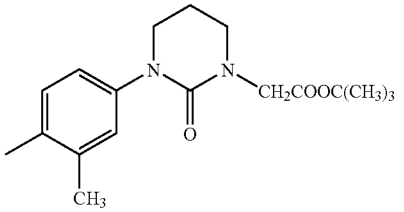 | ($CDCl_3$) 1.44 (9H, s), 1.96 (3H, s), 2.10-2.30 (2H, m), 3.42-3.61 (2H, m), 3.62-3.78 (2H, m), 4.04 (2H, s), 6.58 (1H, d, J = 8.8 Hz), 6.60 (1H, d, J = 8.5 Hz), 6.91 (1H, dd, J = 2.6 Hz, 8.5 Hz), 7.00 (1H, d, J = 2.6 Hz), 7.31 (1H, d, J = 8.8 Hz), 7.36 (1H, dd, J = 2.3 Hz, 8.8 Hz), 7.69 (1H, d, J = 2.3 Hz), 7.79 (1H, dd, J = 2.8 Hz, 8.8 Hz), 7.91 (1H, d, J = 2.8 Hz), 7.93 (1H, s), 8.05 (1H, s). |

Example 2113

Production of 4-piperonylpiperazine-1-carboxylic acid {(4-[5-(3,4-dichlorobenzoylamino)pyridin-2-yloxy]phenyl}amide hydrochloride To a solution of {4-[5-(3,4-dichlorobenzoyl-amino)pyridin-2-yloxy]phenyl}-carbamic acid phenyl ester (320 mg, 0.65 mmol) in DMF (4 mL) was added 1-piperonylpiperazine was then filtered off and washed with ethanol, to thereby yield 330 mg of the title compound.

Appearance: White powder $^1$H NMR (DMSO-$d_6$) δ 2.85-3.09 (2H, m), 3.20-3.50 (4H, m), 4.12-4.38 (4H, m), 6.08 (2H, s), 7.02 (2H, d, J=9.0 Hz), 6.93-7.12 (3H, m), 7.28 (1H, d, J=1.5 Hz), 7.49 (2H, d, J=9.0 Hz), 7.83 (1H, d, J=8.5 Hz), 7.97 (1H, dd, J=8.5 Hz, 2.0 Hz), 8.19 (1H, dd, J=8.8 Hz, 2.6 Hz), 8.25 (1H, d, J=2.0 Hz), 8.50 (1H, d, J=2.6 Hz), 8.92 (1H, s), 10.63 (1H, s)

The following compound was produced in the same manner as in Example 2113.

Example 2114

4-Benzylpiperazine-1-carboxylic acid {4-[5-(3,4-dichlorobenzoylamino)pyridin-2-yloxy]phenyl}amide hydrochloride $^1$H NMR (DMSO-d$_6$) δ 2.90-3.20 (2H, m), 3.22-3.45 (4H, m), 4.27 (2H, d, J=13.6 Hz), 4.35 (2H, d, J=5.0 Hz), 7.02 (1H, d, J=8.9 Hz), 7.03 (2H, d, J=8.9 Hz), 7.41-7.52 (3H, m), 7.48 (2H, d, J=8.9 Hz), 7.55-7.69 (2H, m), 7.84 (1H, d, J=8.4 Hz), 7.97 (1H, dd, J=8.4 Hz, 2.0 Hz), 8.19 (1H, dd, J=8.9 Hz, 2.6 Hz), 8.25 (1H, d, J=2.0 Hz), 8.49 (1H, d, J=2.6 Hz), 8.90 (1H, s), 10.62 (1H, s).

Example 2115

Production of 2-[(4-{5-[(3,4-dichlorobenzylidene)-amino]pyridin-2-yloxy}phenyl)methylamino]-1-(4-piperonylpiperazin-1-yl)ethanone 2-{[(4-(5-aminopyridin-2-yloxy)phenyl]methylamino}-1-(4-piperonylpiperazin-1-yl)ethanone (7.80 g, 16.4 mmol) was dissolved in methanol (400 mL), and to the resulting solution was added 3,4-dichlorobenzaldehyde (2.87 g, 16.4 mmol). This solution was refluxed for 16 hours. The resulting reaction solution was concentrated under reduced pressure, to thereby yield 10.4 g of the title compound.

Appearance: Brown oil $^1$H NMR (CDCl$_3$) δ 2.44 (4H, brs), 3.03 (3H, s), 3.44-3.45 (2H, m), 3.50 (2H, brs), 3.63 (2H, brs), 4.09 (2H, s), 5.94 (2H, s), 6.65-6.77 (4H, m), 6.84-6.88 (2H, m), 7.03 (2H, d, J=9.1 Hz), 7.54 (1H, d, J=8.3 Hz), 7.58 (1H, dd, J=8.9 Hz, 2.8 Hz), 7.70 (1H, dd, J=8.4 Hz, 2.0 Hz), 8.00 (1H, d, J=2.0 Hz), 8.10 (1H, d, J=2.8 Hz), 8.39 (1H, s).

The following compounds were produced in the same manner as in Example 2115.

TABLE 336

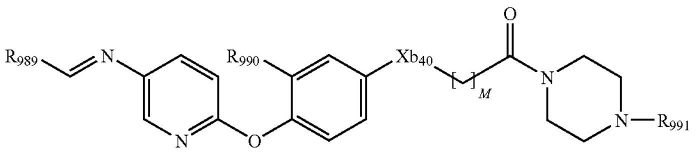

| Example No. | $R_{989}$ | $R_{990}$ | $R_{991}$ | $Xb_{40}$ | M | $^1$H NMR (solvent) δ ppm |
|---|---|---|---|---|---|---|
| 2116 | 3,4-$Cl_2$Ph | —H | benzyl | none | 0 | (DMSO-d$_6$) 2.41 (4 H, brs), 3.34-3.51 (6 H, m), 7.19 (1 H, d, J = 8.7 Hz), 7.20 (2 H, d, J = 7.9 Hz), 7.29-7.33 (5 H, m), 7.45 (2 H, d, J = 7.9 Hz), 7.81 (1 H, d, J = 8.3 Hz), 7.91-7.96 (2 H, m), 8.15 (1 H, brs), 8.18 (1 H, d, J = 2.6 Hz), 8.75 (1 H, s). |
| 2117 | 3,4-$Cl_2$Ph | —H | benzyl | none | 2 | (DMSO-d$_6$) 2.30 (4 H, brs), 2.60-2.62 (2 H, m), 2.79-2.85 (2 H, m), 3.44-3.48 (6 H, m), 7.05 (2 H, d, J = 8.4 Hz), 7.09 (1 H, d, J = 8.7 Hz), 7.25-7.36 (7 H, m), 7.81 (1 H, d, J = 8.2 Hz), 7.88-7.93 (2 H, m), 8.13-8.14 (2 H, m), 8.74 (1 H, s). |
| 2118 | 4-$CF_3$Ph- | —H | benzyl | none | 0 | (CDCl$_3$) 2.47 (4 H, brs), 3.55 (2 H, brs), 3.55 (2 H, s), 3.79 (2 H, brs), 7.00 (1 H, d, J = 8.7 Hz), 7.18 (2 H, d, J = 8.6 Hz), 7.22-7.40 (5 H, m), 7.47 (2 H, d, J = 8.6 Hz), 7.67 (1 H, dd, J = 8.7 Hz, 2.6 Hz), 7.74 (2 H, d, J = 8.1 Hz), 8.03 (2 H, d, J = 8.1 Hz), 8.14 (1 H, d, J = 2.6 Hz), 8.54 (1 H, s). |
| 2119 | 4-$CF_3$Ph- | —H | piperonyl | —N($CH_3$)— | 1 | (CDCl$_3$) 2.45 (4 H, brs), 3.04 (3 H, s), 3.45-3.51 (4 H, m), 3.65 (2 H, s), 4.09 (2 H, s), 5.95 (2 H, s), 6.71-6.74 (4 H, m), 6.86-6.89 (2 H, m), 7.04 (2 H, d, J = 9.1 Hz), 7.61 (1 H, dd, J = 8.7 Hz, 2.6 Hz), 7.73 (2 H, d, J = 8.3 Hz), 8.01 (2 H, d, J = 8.4 Hz), 8.14 (1 H, d, J = 2.6 Hz), 8.53 (1 H, s). |
| 2120 | 4-$CF_3$Ph- | —F | benzyl | none | 0 | (CDCl$_3$) 2.49 (4 H, brs), 3.43-3.75 (6 H, m), 7.07 (1 H, d, J = 8.6 Hz), 7.29-7.34 (8 H, m), 7.69 (1 H, dd, J = 8.7 Hz, 2.8 Hz), 7.74 (2 H, d, J = 8.3 Hz), 8.02 (2 H, d, J = 8.3 Hz), 8.05 (1 H, d, J = 2.6 Hz), 8.53 (1 H, s). |
| 2121 | 3,4-$Cl_2$Ph | —H | piperonyl | —N($CH_3$)— | 2 | (CDCl$_3$) 2.34-2.41 (4 H, m), 2.55-2.61 (2 H, m), 2.95 (3 H, s), 3.41 (4 H, brs), 3.61-3.65 (2 H, m), 3.68-3.76 (2 H, m), 5.94 (2 H, s), 6.70-6.77 (4 H, m), 6.84 (1 H, d, J = 1.0 Hz), 6.89 (1 H, dd, J = 8.7 Hz, 0.5 Hz), 7.04 (2 H, d, J = 9.2 Hz), 7.55 (1 H, d, J = 8.3 Hz), 7.60 (1 H, dd, J = 8.7 Hz, 2.8 Hz), 7.71 (1 H, dd, J = 8.3 Hz, 2.0 Hz), 8.01 (1 H, d, J = 1.8 Hz), 8.11 (1 H, dd, J = 2.8 Hz, 0.5 Hz), 8.40 (1 H, brs). |

TABLE 336-continued

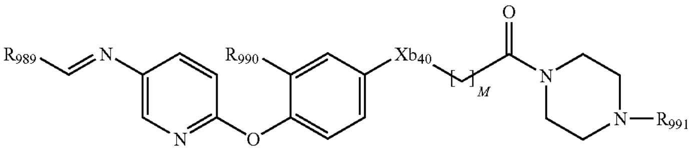

| Example No. | $R_{989}$ | $R_{990}$ | $R_{991}$ | $Xb_{40}$ | M | $^1$H NMR (solvent) δ ppm |
|---|---|---|---|---|---|---|
| 2122 | 4-$CF_3$Ph | —H | piperonyl | —N($CH_3$)— | 2 | ($CDCl_3$) 2.34-2.41 (4 H, m), 2.55-2.61 (2 H, m), 2.95 (3 H, s), 3.39-3.42 (4 H, m), 3.61-3.64 (2 H, m), 3.68-3.76 (2 H, m), 5.94 (2 H, s), 6.70-6.77 (4 H, m), 6.84 (1 H, d, J = 0.8 Hz), 6.90 (1 H, dd, J = 8.7 Hz, 0.7 Hz), 7.05 (2 H, d, J = 9.2 Hz), 7.63 (1 H, dd, J = 8.7 Hz, 2.8 Hz), 7.73 (2 H, d, J = 8.3 Hz), 8.01 (2 H, d, J = 8.6 Hz), 8.13 (1 H, dd, J = 2.8 Hz, 0.7 Hz), 8.53 (1 H, brs). |

TABLE 337

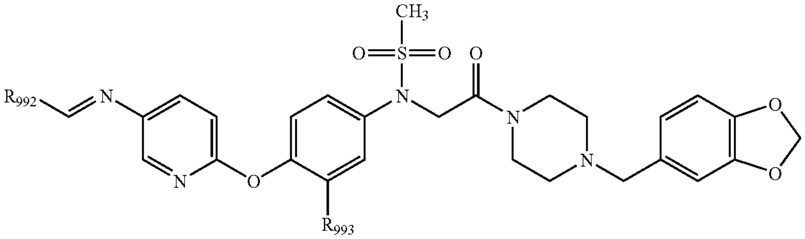

| Example No. | $R_{992}$ | $R_{993}$ | $^1$H NMR ($CDCl_3$) δ ppm |
|---|---|---|---|
| 2123 | 3,4-$Cl_2$Ph- | —H | 2.43 (4 H, brs), 3.22 (3 H, s), 3.38 (2 H, brs), 3.43 (2 H, s), 3.62 (2 H, brs), 4.55 (2 H, s), 5.95 (2 H, s), 6.74 (2 H, brs), 6.84 (1 H, brs), 7.01 (1 H, d, J = 8.6 Hz), 7.15 (2 H, d, J = 8.7 Hz), 7.57 (1 H, d, J = 8.3 Hz), 7.61-7.68 (3 H, m), 7.72 (1 H, dd, J = 8.3 Hz, 1.8 Hz), 8.03 (1 H, d, J = 1.8 Hz), 8.11 (1 H, d, J = 2.8 Hz), 8.42 (1 H, brs). |
| 2124 | 3,4-$Cl_2$Ph- | —$CH_3$ | 2.20 (3 H, s), 2.42-2.43 (4 H, m), 3.23 (3 H, s), 3.38 (2 H, brs), 3.43 (2 H, s), 3.62 (2 H, brs), 4.54 (2 H, s), 5.94 (2 H, s), 6.70-6.77 (2 H, m), 6.84 (1 H, brs), 6.97 (1 H, dd, J = 8.7 Hz, 0.5 Hz), 7.05 (1 H, d, J = 8.6 Hz), 7.43-7.49 (2 H, m), 7.55 (1 H, d, J = 8.2 Hz), 7.62-7.66 (1 H, m), 7.69-7.74 (1 H, m), 8.01 (1 H, d, J = 2.0 Hz), 8.07 (1 H, d, J = 2.1 Hz), 8.40 (1 H, brs). |
| 2125 | 4-$CF_3$Ph- | —$CH_3$ | 2.20 (3 H, s), 2.41-2.43 (4 H, m), 3.23 (3 H, s), 3.38 (2 H, brs), 3.43 (2 H, s), 3.60 (2 H, brs), 4.55 (2 H, s), 5.95 (2 H, s), 6.73-6.74 (2 H, m), 6.84 (1 H, brs), 6.98 (1 H, d, J = 8.7 Hz), 7.05 (1 H, d, J = 8.4 Hz), 7.43-7.49 (2 H, m), 7.65-7.75 (3 H, m), 8.00-8.10 (3 H, m), 8.53 (1 H, brs). |
| 2126 | 4-$CF_3$Ph- | —$OCH_3$ | 2.43 (4 H, brs), 3.24 (3 H, s), 3.39 (2 H, brs), 3.43 (2 H, s), 3.63 (2 H, brs), 3.77 (3 H, s), 4.57 (2 H, s), 5.94 (2 H, s), 6.73-6.77 (2 H, m), 6.84 (1 H, s), 7.02 (1 H, d, J = 8.6 Hz), 7.13 (1 H, d, J = 8.4 Hz), 7.22 (1 H, dd, J = 8.4 Hz, 2.3 Hz), 7.30 (1 H, d, J = 2.3 Hz), 7.66 (1 H, dd, J = 8.7 Hz, 2.8 Hz), 7.73 (2 H, d, J = 8.1 Hz), 8.01 (2 H, d, J = 8.1 Hz), 8.08 (1 H, d, J = 2.5 Hz), 8.53 (1 H, s). |

TABLE 338

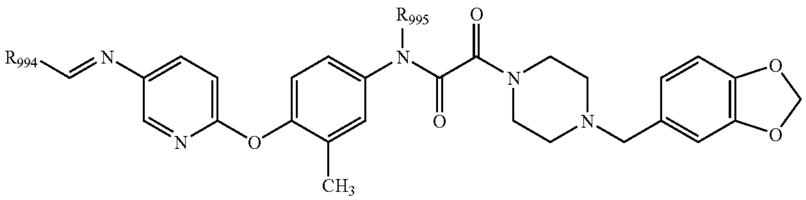

| Example No. | $R_{994}$ | $R_{995}$ | $^{1}H$ NMR (solvent) δ ppm |
|---|---|---|---|
| 2127 | 3,4-$Cl_2$Ph- | —H | ($CDCl_3$) 2.20 (3 H, s), 2.49-2.55 (4 H, m), 3.45 (2 H, s), 3.71-3.75 (2 H, m), 4.25-4.29 (2 H, m), 5.95 (2 H, s), 6.75 (2 H, brs), 6.86 (1 H, brs), 6.92 (1 H, d, J = 8.6 Hz), 7.06 (1 H, d, J = 8.6 Hz), 7.44 (1 H, dd, J = 8.6 Hz, 2.6 Hz), 7.53-7.65 (3 H, m), 7.70 (1 H, dd, J = 8.2 Hz, 2.0 Hz), 8.01 (1 H, d, J = 1.8 Hz), 8.07 (1 H, d, J = 2.8 Hz), 8.40 (1 H, brs), 9.17 (1 H, brs). |
| 2128 | 4-$CF_3$Ph- | —H | ($CDCl_3$) 2.20 (3 H, s), 2.49-2.55 (4 H, m), 3.45 (2 H, s), 3.71-3.75 (2 H, m), 4.25-4.28 (2 H, m), 5.95 (2 H, s), 6.75 (2 H, brs), 6.86 (1 H, brs), 6.93 (1 H, d, J = 8.7 Hz), 7.07 (1 H, d, J = 8.7 Hz), 7.45 (1 H, dd, J = 8.7 Hz, 2.6 Hz), 7.58 (1 H, d, J = 2.5 Hz), 7.65 (1 H, dd, J = 8.6 Hz, 2.6 Hz), 7.73 (2 H, d, J = 8.2 Hz), 8.01 (2 H, d, J = 8.1 Hz), 8.10 (1 H, d, J = 2.8 Hz), 8.53 (1 H, s), 9.19 (1 H, brs). |
| 2129 | 3,4-$Cl_2$Ph- | —$CH_3$ | a mixture of the rotational isomers (DMSO-$d_6$) 2.10-2.44 (7 H, m), 3.16-3.57 (9 H, m), 5.96-5.99 (2 H, m), 6.67-6.89 (3 H, m), 7.09-7.26 (3 H, m), 7.29-7.38 (1 H, m), 7.81 (1 H, d, J = 8.41 Hz), 7.89-7.96 (2 H, m), 8.10-8.15 (2 H, m), 8.74 (1 H, s). |
| 2130 | 4-$CF_3$Ph- | —$CH_3$ | a mixture of rotational isomers (DMSO-$d_6$) 2.11-2.44 (7 H, m), 3.18-3.57 (9 H, m), 5.96-6.00 (2 H, m), 6.67-6.90 (3 H, m), 7.09-7.27 (3 H, m), 7.29-7.38 (1 H, m), 7.90 (2 H, d, J = 8.24 Hz), 7.95-8.00 (1 H, m), 8.11-8.16 (3 H, m), 8.85 (1 H, s). |

TABLE 339

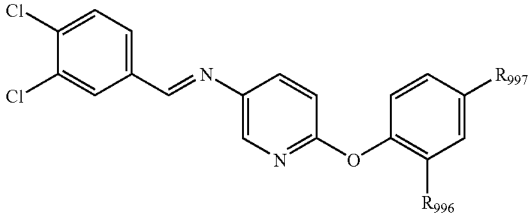

| Example No. | $R_{996}$ | $R_{997}$ | $^{1}H$ NMR ($CDCl_3$) δ ppm |
|---|---|---|---|
| 2131 | —H | 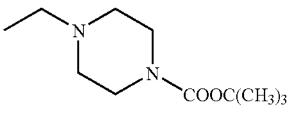 | 1.46 (9 H, s), 2.41-2.45 (4 H, m), 3.43-3.47 (4 H, m), 3.53 (2 H, s), 6.96 (1 H, d, J = 8.7 Hz), 7.08-7.14 (2 H, m), 7.36 (2 H, d, J = 8.4 Hz), 7.55 (1 H, d, J = 8.2 Hz), 7.63 (1 H, dd, J = 8.7 Hz, 2.6 Hz), 7.71 (1 H, dd, J = 2.0 Hz), 8.01 (1 H, d, J = 1.8 Hz), 8.11-8.12 (1 H, m), 8.41 (1 H, s). |
| 2132 | —$CH_3$ | 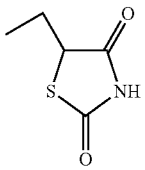 | 2.19 (3 H, s), 3.12 (1 H, dd, J = 14.0 Hz, 9.9 Hz), 3.55 (1 H, dd, J = 14.0 Hz, 3.8 Hz), 4.54 (1 H, dd, J = 9.9 Hz, 3.8 Hz), 6.95 (1 H, d, J = 8.7 Hz), 7.04 (1 H, d, J = 8.1 Hz), 7.12 (1 H, dd, J = 8.1 Hz, 2.1 Hz), 7.16 (1 H, d, J = 2.1 Hz), 7.56 (1 H, d, J = 8.4 Hz), 7.64 (1 H, dd, J = 8.7 Hz, 2.3 Hz), 7.71 (1 H, dd, J = 8.4 Hz, 1.8 Hz), 8.02 (1 H, d, J = 1.8 Hz), 8.08 (1 H, d, J = 2.3 Hz), 8.18 (1 H, brs), 8.41 (1 H, s). |

Example 2133

Production of 3-({4-[5-(3,4-dichlorobenzylamino)-pyridin-2-yloxy]phenyl}methylamino)-1-(4-piperonylpiperazin-1-yl)propane-1-one 3-[(4-{5-(3,4-dichlorobenzylidene)pyridin-2-yloxy}phenyl)methylamino]-1-(4-piperonylpiperazin-1-yl)propane-1-one (3.88 g, 6.0 mmol) was dissolved in a mixed solvent of methanol (150 mL) and THF (50 mL). To the resulting solution was slowly added sodium borohydride (1.13 g, 30.0 mmol) and that resulting solution was stirred for 13 hours at room temperature. This reaction solution was concentrated under reduced pressure. The resulting residue was diluted with ethyl acetate, and washed with a saturated sodium bicarbonate solution and brine. The organic layer was dried over anhydrous magnesium sulfate, and evaporated. The residue was then purified by silica gel column chromatography (dichloromethane:methanol=40:1), to thereby yield 3.60 g of the title compound.

Appearance: White powder $^1$H NMR ($CDCl_3$) δ 2.32-2.39 (4H, m), 2.52-2.57 (2H, m), 2.91 (3H, s), 3.36-3.40 (4H, m), 3.59-3.63 (2H, m), 3.66-3.71 (2H, m), 3.97 (1H, brs), 4.27 (2H, d, J=5.0 Hz), 5.94 (2H, s), 6.65-6.76 (5H, m), 6.83 (1H, d, J=1.0 Hz), 6.94 (1H, dd, J=8.9 Hz, 3.0 Hz), 6.97 (2H, d, J=9.2 Hz), 7.18 (1H, dd, J=8.3 Hz, 2.0 Hz), 7.40 (1H, d, J=8.4 Hz), 7.45 (1H, d, J=2.0 Hz), 7.56 (1H, d, J=2.5 Hz); MS 647 ($M^+$).

The following compounds were produced in the same manner as in Example 2133.

TABLE 340

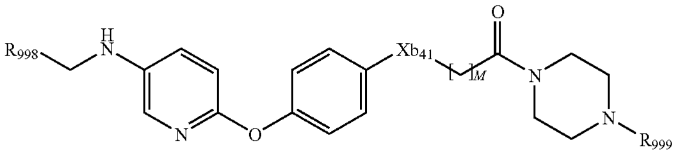

| Example No. | $R_{998}$ | $R_{999}$ | $Xb_{41}$ | M | $^1$H NMR (solvent) δ ppm |
|---|---|---|---|---|---|
| 2134 | 4-$CF_3$Ph- | piperonyl | —N($CH_3$)— | 1 | ($CDCl_3$) 2.42 (4 H, brs), 2.99 (3 H, s), 3.43-3.49 (4 H, m), 3.62 (2 H, brs), 4.04 (2 H, s), 4.37 (2 H, s), 5.95 (2 H, s), 6.67-6.75 (5 H, m), 6.86 (1 H, brs), 6.92-6.97 (3 H, m), 7.47 (2 H, d, J = 7.9 Hz), 7.58-7.61 (3 H, m). |
| 2135 | 4-$CF_3$Ph- | piperonyl | —N($CH_3$)— | 2 | ($CDCl_3$) 2.32-2.39 (4 H, m), 2.52-2.57 (2 H, m), 2.91 (3 H, s), 3.36-3.39 (4 H, m), 3.59-3.63 (2 H, m), 3.66-3.71 (2 H, m), 4.00 (1 H, brs), 4.37 (2 H, d, J = 4.3 Hz), 5.94 (2 H, s), 6.66-6.76 (5 H, m), 6.83 (1 H, d, J = 1.0 Hz), 6.95 (1 H, dd, J = 8.9 Hz, 3.0 Hz), 6.97 (2 H, d, J = 9.1 Hz), 7.46 (2 H, d, J = 8.1 Hz), 7.57-7.61 (3 H, m). |
| 2136 | 3,4-$Cl_2$Ph- | piperonyl | —N($CH_3$)— | 1 | ($CDCl_3$) 2.39-2.43 (4 H, m), 2.99 (3 H, s), 3.42 (2 H, brs), 3.46-3.50 (2 H, m), 3.60-3.62 (2 H, m), 3.97 (1 H, t, J = 5.8 Hz), 4.05 (2 H, s), 4.26 (2 H, d, J = 5.8 Hz), 5.95 (2 H, s), 6.65-6.77 (5 H, m), 6.85 (1 H, brs), 6.93 (1 H, dd, J = 8.6 Hz, 3.1 Hz), 6.96 (2 H, d, J = 9.1 Hz), 7.18 (1 H, dd, J = 8.3 Hz, 2.1 Hz), 7.40 (1 H, d, J = 8.3 Hz), 7.45 (1 H, d, J = 2.1 Hz), 7.57 (1 H, d, J = 2.8 Hz) |
| 2137 | 3,4-$Cl_2$Ph- | benzyl | none | 2 | (DMSO-$d_6$) 2.26-2.28 (4 H, m), 2.57 (2 H, t, J = 7.9 Hz), 2.76 (2 H, t, J = 7.9 Hz), 3.40-3.46 (6 H, m), 4.28 (2 H, d, J = 5.9 Hz), 6.36 (1 H, t, J = 6.1 Hz), 6.77 (1 H, d, J = 8.7 Hz), 6.85 (2 H, d, J = 8.3 Hz), 7.09 (1 H, dd, J = 8.7 Hz, 3.0 Hz), 7.17 (2 H, d, J = 8.4 Hz), 7.24-7.37 (6 H, m), 7.50 (1 H, d, J = 3.0 Hz), 7.58 (1 H, d, J = 8.3 Hz), 7.62 (1 H, d, J = 1.8 Hz). |
| 2138 | 3,4-$Cl_2$Ph- | benzyl | none | 0 | (DMSO-$d_6$) 2.38 (4 H, brs), 3.33-3.50 (6 H, m), 4.30 (2 H, d, J = 6.3 Hz), 6.47 (1 H, t, J = 6.3 Hz), 6.87 (1 H, d, J = 8.7 Hz), 6.97 (2 H, d, J = 8.6 Hz), 7.12 (1 H, dd, J = 8.7 Hz, 3.0 Hz), 7.25-7.39 (8 H, m), 7.56 (1 H, d, J = 3.0 Hz), 7.58-7.64 (2 H, m). |
| 2139 | 4-$CF_3$Ph- | benzyl | none | 0 | ($CDCl_3$) 2.45 (4 H, brs), 3.52 (2 H, brs), 3.53 (2 H, s), 3.73 (2 H, brs), 4.16 (1 H, brs), 4.41 (2 H, s), 6.80 (1 H, d, J = 8.7 Hz), 6.99 (1 H, dd, J = 8.7 Hz, 3.0 Hz), 7.03 (2 H, d, J = 8.5 Hz), 7.20-7.37 (5 H, m), 7.38 (2 H, d, J = 8.5 Hz), 7.48 (2 H, d, J = 8.1 Hz), 7.61 (2 H, d, J = 8.1 Hz), 7.64 (1 H, d, J = 3.0 Hz). |

TABLE 341

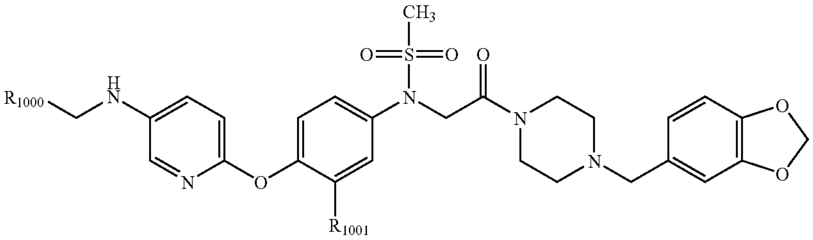

| Example No. | $R_{1000}$ | $R_{1001}$ | $^1H$ NMR ($CDCl_3$) δ ppm |
|---|---|---|---|
| 2140 | 3,4-$Cl_2$Ph- | —H | 2.41 (4 H, brs), 3.19 (3 H, s), 3.33-3.35 (2 H, m), 3.42 (2 H, s), 3.60 (2 H, brs), 4.08 (1 H, brs), 4.30 (2 H, d, J = 5.3 Hz), 4.50 (2 H, s), 5.95 (2 H, s), 6.73-6.74 (2 H, m), 6.80-6.84 (2 H, m), 6.99 (1 H, dd, J = 8.6 Hz, 3.1 Hz), 7.02 (2 H, d, J = 8.7 Hz), 7.20 (1 H, dd, J = 8.3 Hz, 2.0 Hz), 7.42 (1 H, d, J = 8.3 Hz), 7.66 (1 H, d, J = 2.1 Hz), 7.54 (2 H, d, J = 8.9 Hz), 7.60 (1 H, d, J = 2.8 Hz). |
| 2141 | 3,4-$Cl_2$Ph- | —$CH_3$ | 2.19 (3 H, s), 2.41 (4 H, brs), 3.19 (3 H, s), 3.35 (2 H, brs), 3.41 (2 H, s), 3.60 (2 H, brs), 4.07-4.15 (1 H, m), 4.27 (2 H, s), 4.50 (2 H, s), 5.93 (2 H, s), 6.69-6.78 (3 H, m), 6.83 (1 H, brs), 6.88 (1 H, d, J = 8.6 Hz), 6.98 (1 H, dd, J = 8.7 Hz, 3.0 Hz), 7.17-7.20 (1 H, m), 7.34-7.44 (4 H, m), 7.53 (1 H, d, J = 3.0 Hz). |
| 2142 | 4-$CF_3$Ph- | —$CH_3$ | 2.20 (3 H, s), 2.41 (4 H, brs), 3.19 (3 H, s), 3.35-3.37 (2 H, m), 3.41 (2 H, s), 3.60-3.62 (2 H, m), 4.15 (1 H, brs), 4.38 (2 H, s), 4.50 (2 H, s), 5.94 (2 H, s), 6.73 (2 H, brs), 6.76 (1 H, d, J = 8.7 Hz), 6.83 (1 H, brs), 6.88 (1 H, d, J = 8.6 Hz), 7.00 (1 H, dd, J = 8.7 Hz, 3.0 Hz), 7.36 (1 H, dd, J= 8.6 Hz, 2.6 Hz), 7.42 (1 H, d, J = 2.5 Hz), 7.47 (2 H, d, J = 8.1 Hz), 7.56 (1 H, d, J = 2.8 Hz), 7.59 (2 H, d, J = 8.1 Hz). |
| 2143 | 4-$CF_3$Ph- | —$OCH_3$ | 2.41 (4 H, brs), 3.21 (3 H, s), 3.36 (2 H, brs), 3.42 (2 H, s), 3.60 (2 H, brs), 3.76 (3 H, s), 4.09 (1 H, brs), 4.37 (2 H, s), 4.52 (2 H, s), 5.94 (2 H, s), 6.70-6.83 (4 H, m), 6.97-7.02 (2 H, m), 7.12-7.16 (1 H, m), 7.23-7.26 (1 H, m), 7.44-7.60 (5 H, m). |

TABLE 342

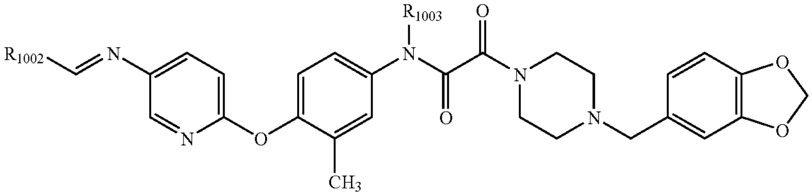

| Example No. | $R_{1002}$ | $R_{1003}$ | $^1H$ NMR (solvent) δ ppm |
|---|---|---|---|
| 2144 | 3,4-$Cl_2$Ph- | —H | ($CDCl_3$) 2.17 (3 H, s), 2.48-2.53 (4 H, m), 3.44 (2 H, s), 3.69-3.73 (2 H, m), 3.97 (1 H, brs), 4.23-4.27 (4 H, m), 5.95 (2 H, s), 6.70-6.74 (3 H, m), 6.85 (1 H, brs), 6.94 (1 H, d, J = 8.7 Hz), 6.96 (1 H, dd, J = 8.7 Hz, 3.1 Hz), 7.18 (1 H, dd, J = 8.2 Hz, 2.0 Hz), 7.36 (1 H, dd, J = 8.7 Hz, 2.5 Hz), 7.40 (1 H, d, J = 8.2 Hz), 7.45 (1 H, d, J = 2.1 Hz), 7.51 (1 H, d, J = 2.3 Hz), 7.55 (1 H, d, J = 3.0 Hz), 9.11 (1 H, brs). |
| 2145 | 4-$CF_3$Ph- | —H | ($CDCl_3$) 2.19 (3 H, s), 2.48-2.53 (4 H, m), 3.44 (2 H, s), 3.70-3.73 (2 H, m), 4.00 (1 H, brs), 4.23-4.27 (2 H, m), 4.37 (2 H, s), 5.95 (2 H, s), 6.72 (1 H, d, J = 8.7 Hz), 6.74-6.77 (2 H, m), 6.85 (1 H, brs), 6.94 (1 H, d, J = 8.7 Hz), 6.97 (1 H, dd, J = 8.7 Hz, 3.1 Hz), 7.37 (1 H, dd, J = 8.7 Hz, 2.6 Hz), 7.47 (2 H, d, J = 8.4 Hz), 7.51 (1 H, d, J = 2.5 Hz), 7.57 (1 H, d, J = 3.1 Hz), 7.60 (2 H, d, J = 8.1 Hz), 9.11 (1 H, brs). |
| 2146 | 3,4-$Cl_2$Ph- | —$CH_3$ | a mixture of the rotational isomers ($DMSO-d_6$) 2.25-2.42 (7 H, m), 3.22-3.55 (9 H, m), 4.27 (2 H, d, J = 6.27 Hz), 5.77-5.99 (2 H, m), 6.38 (1 H, t, J = 6.27 Hz), 6.65-6.90 (5 H, m), 7.06-7.14 (2 H, m), 7.22-7.28 (1 H, m), 7.32-7.36 (1 H, m), 7.46 (1 H, d, J = 2.80 Hz), 7.56-7.61 (2 H, m). |

TABLE 342-continued

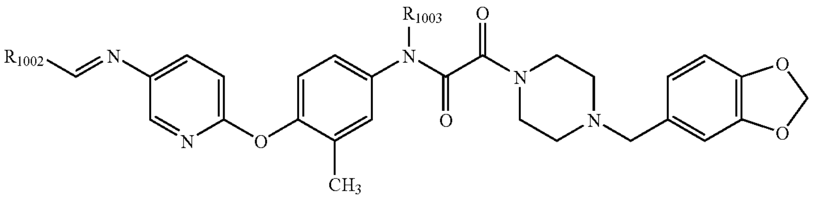

| Example No. | $R_{1002}$ | $R_{1003}$ | $^1$H NMR (solvent) δ ppm |
|---|---|---|---|
| 2147 | 4-$CF_3$Ph- | —$CH_3$ | a mixture of the rotational isomers (DMSO-$d_6$) 2.24-2.41 (7 H, m), 3.20-3.54 (9 H, m), 4.34-4.36 (2 H, m), 5.95-5.98 (2 H, m), 6.38-6.41 (1 H, m), 6.65-6.88 (5 H, m), 7.03-7.13 (2 H, m), 7.21-7.27 (1 H, m), 7.45 (1 H, d, J = 2.64 Hz), 7.55 (2 H, d, J = 7.75 Hz), 7.67 (2 H, d, J = 7.75 Hz). |

TABLE 343

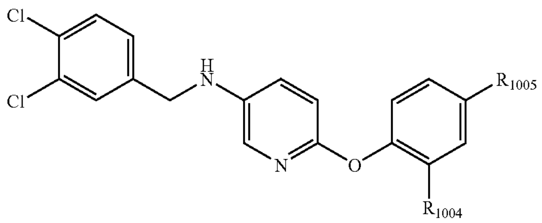

| Example No. | $R_{1004}$ | $R_{1005}$ | $^1$H NMR ($CDCl_3$) δ ppm |
|---|---|---|---|
| 2148 | —H | 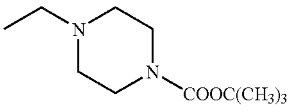 | 1.45 (9 H, s), 2.37-2.40 (4 H, m), 3.40-3.44 (4 H, m), 3.47 (2 H, s), 4.28 (2 H, s), 6.77 (1 H, d, J = 8.7 Hz), 6.95-7.01 (3 H, m), 7.17-7.21 (1 H, m), 7.26-7.29 (2 H, m), 7.41 (1 H, d, J = 8.1 Hz), 7.45 (1 H, d, J = 1.8 Hz), 7.60 (1 H, d, J = 3.0 Hz). |
| 2149 | —$CH_3$ | 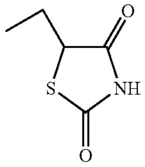 | 2.19 (3 H, s), 3.05 (1 H, dd, J = 14.0 Hz, 10.0 Hz), 3.50 (1 H, dd, J = 14.0 Hz, 3.8 Hz), 4.02 (1 H, brs), 4.27 (2 H, s), 4.49 (1 H, dd, J = 10.0 Hz, 3.8 Hz), 6.73 (1 H, d, J = 8.7 Hz), 6.99 (1 H, d, J = 8.2 Hz), 6.97 (1 H, dd, J = 8.7 Hz, 2.9 Hz), 7.02 (1 H, dd, J = 8.2 Hz, 2.0 Hz), 7.09 (1 H, d, J = 2.0 Hz), 7.18 (1 H, dd, J = 8.2 Hz, 2.0 Hz), 7.41 (1 H, d, J = 8.2 Hz), 7.45 (1 H, d, J = 2.0 Hz), 7.55 (1 H, d, J = 2.9 Hz), 8.61 (1 H, brs). |

Example 2150

Production of 1-(4-benzylpiperazin-1-yl)-3-(4-{5-(piperonylamino)pyridin-2-yloxy}phenyl)propane-1-one 3-[4-(5-aminopyridin-2-yloxy)phenyl]-1-(4-piperonylpiperazin-1-yl)propane-1-one (1.04 g, 2.5 mmol) was dissolved in methanol (25 mL). To the resulting solution was added piperonal (0.39 g, 2.63 mmol), and this solution was refluxed overnight. The resulting reaction solution was cooled with ice, and then sodium borohydride (0.28 g, 7.50 mmol) was added. The resulting solution was stirred for 2 hours at room temperature. This reaction solution was concentrated under reduced pressure. The residue was diluted with ethyl acetate, and washed with water, saturated sodium bicarbonate solution and brine. The organic layer was dried over anhydrous magnesium sulfate, and evaporated. The residue was then purified by silica gel column chromatography (ethyl acetate), to thereby yield 0.80 g of the title compound.

Appearance: Yellow oil $^1$H NMR (DMSO-$d_6$) δ 2.28 (4H, brs), 2.57 (2H, t, J=7.9 Hz), 2.76 (2H, t, J=7.9 Hz), 3.40-3.46 (6H, m), 4.15 (2H, d, J=6.1 Hz), 5.97 (2H, s), 6.21 (1H, t, J=6.1 Hz), 6.76 (1H, d, J=8.6 Hz), 6.82-6.86 (4H, m), 6.92 (1H, brs), 7.08 (1H, dd, J=8.7 Hz, 3.0 Hz), 7.17 (2H, d, J=8.4 Hz), 7.24-7.32 (5H, m), 7.51 (1H, d, J=3.0 Hz).

The following compounds were produced in the same manner as in Example 2150.

TABLE 344

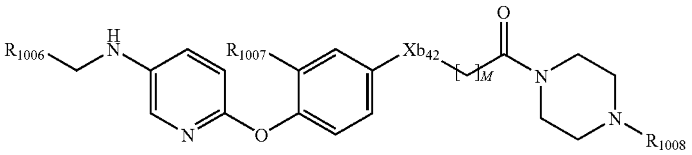

| Example No. | $R_{1006}$ | $R_{1007}$ | $R_{1008}$ | $Xb_{42}$ | M | $^1$H NMR (solvent) δ ppm |
|---|---|---|---|---|---|---|
| 2151 | 4-$CF_3$Ph- | —$CH_3$ | piperonyl | —N($C_2H_5$)— | 1 | ($CDCl_3$) 1.15 (3 H, t, J = 7.1 Hz), 2.11 (3 H, s), 2.30-2.50 (4 H, m), 3.39 (2 H, q, J = 7.1 Hz), 3.42 (2 H, s), 3.42-3.55 (2 H, m) 3.56-3.70 (2 H, m), 3.80-4.05 (1 H, m), 3.99 (2 H, s), 4.36 (2 H, s), 5.94 (2 H, s), 6.44-6.55 (2 H, m), 6.58-6.64 (1 H, m), 6.69-6.78 (2 H, m), 6.80-6.89 (2 H, m), 6.94 (1 H, dd, J = 8.8 Hz, 3.1 Hz), 7.46 (2 H, d, J = 8.0 Hz), 7.55-7.63 (3 H, m). |
| 2152 | 3,4-$Cl_2$Ph- | —$CH_3$ | piperonyl | —N($C_2H_5$)— | 1 | ($CDCl_3$) 1.15 (3 H, t, J = 7.1 Hz), 2.11 (3 H, s), 2.32-2.49 (4 H, m), 3.39 (2 H, q, J = 7.1 Hz), 3.42 (2 H, s), 3.44-3.55 (2 H, m), 3.56-3.69 (2 H, m), 3.79-3.94 (1 H, m), 3.99 (2 H, s), 4.15-4.30 (2 H, m), 5.94 (2 H, s), 6.50 (1 H, dd, J = 8.5 Hz, 3.0 Hz), 6.54 (1 H, d, J = 3.0 Hz), 6.58-6.65 (1 H, m), 6.69-6.78 (2 H, m), 6.82-6.88 (2 H, m), 6.92 (1 H, dd, J = 8.8 Hz, 3.0 Hz), 7.18 (1 H, dd, J = 8.2 Hz, 2.0 Hz), 7.40 (1 H, d, J = 8.2 Hz), 7.45 (1 H, d, J = 2.0 Hz), 7.57 (1 H, d, J = 3.0 Hz). |
| 2153 | 4-$CF_3$Ph- | —H | benzyl | none | 2 | (DMSO-$d_6$) 2.28 (4 H, brs), 2.54-2.60 (2 H, m), 2.73-2.79 (2 H, m), 3.42-3.46 (6 H, m), 4.37 (2 H, d, J = 5.9 Hz), 6.41 (1 H, t, J = 6.1 Hz), 6.77 (1 H, d, J = 8.7 Hz), 6.84 (2 H, d, J = 8.6 Hz), 7.08 (1 H, dd, J = 8.7 Hz, 3.0 Hz), 7.17 (2 H, d, J = 8.6 Hz), 7.22-7.35 (5 H, m), 7.50 (1 H, d, J = 3.0 Hz), 7.58 (2 H, d, J = 7.9 Hz), 7.69 (2 H, d, J = 7.9 Hz). |
| 2154 | 4-ClPh- | —H | benzyl | none | 2 | (DMSO-$d_6$) 2.28 (4 H, t, J = 4.8 Hz), 2.57 (2 H, t, J = 7.3 Hz), 2.76 (2 H, t, J = 7.3 Hz), 3.38-3.46 (6 H, m), 4.25 (2 H, d, J = 6.1 Hz), 6.32 (1 H, t, J = 6.1 Hz), 6.76 (1 H, d, J = 8.6 Hz), 6.84 (2 H, d, J = 8.6 Hz), 7.07 (1 H, dd, J = 8.7 Hz, 3.1 Hz), 7.17 (2 H, d, J = 8.6 Hz), 7.24-7.32 (5 H, m), 7.38 (4 H, brs), 7.50 (1 H, d, J = 3.1 Hz). |
| 2155 | 3,4-$F_2$Ph- | —H | benzyl | none | 2 | (DMSO-$d_6$) 2.26-2.28 (4 H, m), 2.57-2.60 (2 H, m), 2.73-2.79 (2 H, m), 3.37-3.46 (6 H, m), 4.25 (2 H, d, J = 5.8 Hz), 6.32 (1 H, t, J = 5.8 Hz), 6.77 (1 H, d, J = 8.6 Hz), 6.84 (2 H, d, J = 8.3 Hz), 7.08 (1 H, dd, J = 8.6 Hz, 3.0 Hz), 7.17 (2 H, d, J = 8.4 Hz), 7.22-7.43 (8 H, m), 7.50 (1 H, d, J = 3.1 Hz). |

TABLE 345

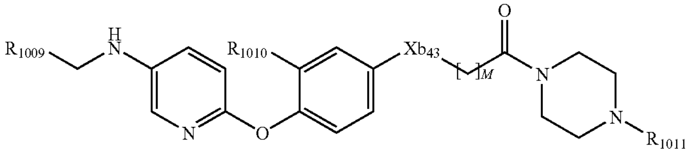

| Example No. | $R_{1009}$ | $R_{1010}$ | $R_{1011}$ | $Xb_{43}$ | M | mp (° C.) or $^1$H NMR (solvent) δ ppm |
|---|---|---|---|---|---|---|
| 2156 | 4-$CF_3$Ph- | —$CH_3$ | piperonyl | —N($CH_3$)— | 1 | $^1$H NMR ($CDCl_3$) 2.12 (3 H, s), 2.42 (4 H, t, J = 5.0 Hz), 2.98 (3 H, |

TABLE 345-continued

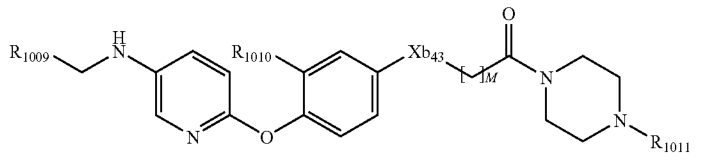

| Example No. | $R_{1009}$ | $R_{1010}$ | $R_{1011}$ | $Xb_{43}$ | M | mp (° C.) or $^1$H NMR (solvent) δ ppm |
|---|---|---|---|---|---|---|
| | | | | | | s), 3.41-3.55 (4 H, m), 3.56-3.67 (2 H, m), 3.77-3.99 (1 H, m), 4.04 (2 H, s), 4.36 (2 H, s), 5.94 (2 H, s), 6.52 (1 H, dd, J = 8.7 Hz, 3.0 Hz), 6.56 (1 H, d, J = 3.0 Hz), 6.59-6.64 (1 H, m), 6.69-6.78 (2 H, m), 6.85 (1 H, s), 6.87 (1 H, d, J = 8.7 Hz), 6.93 (1 H, dd, J = 8.8 Hz, 3.0 Hz), 7.46 (2 H, d, J = 8.0 Hz), 7.54-7.63 (3 H, m). |
| 2157 | 3,4-$Cl_2$Ph- | —$CH_3$ | piperonyl | —N($CH_3$)— | 1 | mp 132-134 |
| 2158 | 4-$CF_3$Ph- | —$CH_3$ | piperonyl | —N(Ac)— | 1 | $^1$H NMR ($CDCl_3$) 1.94 (3 H, s), 2.09 (3 H, s), 2.30-2.50 (4 H, m), 3.29-3.51 (4 H, m), 3.52-3.69 (2 H, m), 3.92-4.17 (1 H, m), 4.29-4.51 (4 H, m), 5.94 (2 H, s), 6.69-6.77 (2 H, m), 6.78 (1 H, d, J = 8.7 Hz), 6.81-6.86 (1 H, m), 6.91 (1 H, d, J = 8.5 Hz), 7.01 (1 H, dd, J = 8.7 Hz, 3.1 Hz), 7.18 (1 H, dd, J = 8.5 Hz, 2.5 Hz), 7.28 (1 H, d, J = 2.5 Hz), 7.48 (2 H, d, J = 8.1 Hz), 7.56-7.64 (3 H, m). |
| 2159 | 3,4-$Cl_2$Ph- | —$CH_3$ | piperonyl | —N(Ac)— | 1 | $^1$H NMR ($CDCl_3$) 1.95 (3 H, s), 2.07 (3 H, s), 2.30-2.51 (4 H, m), 3.29-3.50 (4 H, m), 3.51-3.71 (2 H, m), 3.92-4.18 (1 H, m), 4.29 (2 H, s), 4.42 (2 H, s), 5.94 (2 H, s), 6.69-6.78 (3 H, m), 6.82-6.87 (1 H, m), 6.91 (1 H, d, J = 8.5 Hz), 7.00 (1 H, dd, J = 8.7, 3.0 Hz), 7.14-7.23 (2 H, m), 7.26-7.31 (1 H, m), 7.41 (1 H, d, J = 8.2 Hz), 7.46 (1 H, d, J = 2.0 Hz), 7.57 (1 H, d, J = 3.0 Hz). |
| 2160 | Ph- | —H | benzyl | none | 2 | $^1$H NMR (DMSO-$d_6$) 2.27 (4 H, brs), 2.54-2.60 (2 H, m), 2.73-2.79 (2 H, m), 3.40-3.46 (6 H, m), 4.25 (2 H, d, J = 5.9 Hz), 6.28 (1 H, t, J = 5.9 Hz), 6.76 (1 H, d, J = 8.7 Hz), 6.84 (2 H, d, J = 8.4 Hz), 7.09 (1 H, dd, J = 8.7 Hz, 3.0 Hz), 7.17 (2 H, d, J = 8.7 Hz), 7.23-7.38 (10 H, m), 7.52 (1 H, d, J = 3.0 Hz). |
| 2161 | 4-$CF_3$Ph- | —$OCH_3$ | piperonyl | —N($CH_3$)— | 1 | mp 102-103 |
| 2162 | 3,4-$Cl_2$Ph- | —$OCH_3$ | piperonyl | —N($CH_3$)— | 1 | mp 145-146 |
| 2163 | 4-$CF_3$Ph- | —$OCH_3$ | piperonyl | —N($C_2H_5$)— | 1 | mp 160.0-160.5 |
| 2164 | 3,4-$Cl_2$Ph- | —$OCH_3$ | piperonyl | —N($C_2H_5$)— | 1 | mp 133-134 |
| 2165 | 3,4-$Cl_2$Ph- | —F | piperonyl | —N($CH_3$)— | 1 | mp 134-137 |

TABLE 346

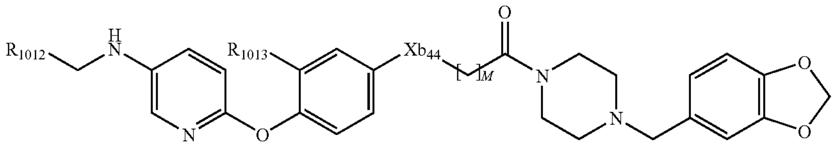

| Example No. | $R_{1012}$ | $R_{1013}$ | $Xb_{44}$ | M | mp (° C.) or $^1$H NMR ($CDCl_3$) δ ppm |
|---|---|---|---|---|---|
| 2166 | 4-$CF_3$Ph- | —$OCH_3$ | none | 2 | $^1$H NMR 2.38-2.44 (4 H, m), 2.56-2.67 (2 H, m), 2.88-2.99 (2 H, m), 3.31-3.45 (2 H, m), 3.40 (2 H, s), 3.57-3.69 (2 H, m), 3.76 (3 H, s), 3.80-4.06 (1 H, m), 4.37 (2 H, s), 5.94 (2 H, s), 6.68-6.81 (4 H, m), 6.83-6.87 (2 H, m), 6.96 (1 H, d, J = 8.0 Hz), 6.98 (1 H, dd, J = 8.7 Hz, 3.0 Hz), 7.46 (2 H, d, J = 8.0 Hz), 7.54 (1 H, d, J = 2.6 Hz), 7.59 (2 H, d, J = 8.0 Hz). |
| 2167 | 4-$CF_3$Ph- | —F | —$N(C_2H_5)$— | 1 | mp 106-107 |
| 2168 | 4-$CF_3$Ph- | —F | —$N(CH_3)$— | 1 | mp 163-164 |
| 2169 | 3,4-$Cl_2$Ph- | —F | —$N(C_2H_5)$— | 1 | mp 107.5-109.0 |
| 2170 | 4-$CF_3$Ph- | —H | —$N(SO_2CH_3)$— | 1 | $^1$H NMR 2.41 (4 H, brs), 3.18 (3 H, s), 3.35 (2 H, brs), 3.42 (2 H, s), 3.62 (2 H, brs), 4.14 (1 H, brs), 4.41 (2 H, brs), 4.50 (2 H, s), 5.94 (2 H, s), 6.70-6.76 (2 H, m), 6.80-6.83 (2 H, m), 6.98-7.04 (3 H, m), 7.47-7.56 (4 H, m), 7.60-7.63 (3 H, m). |

Example 2171

Production of 1-(4-benzylpiperazin-1-yl)-3-[4-(5-dibenzylaminopyridin-2-yloxy)phenyl]propane-1-one 3-[4-(5-aminopyridin-2-yloxy)phenyl]-1-(4-benzylpiperazin-1-yl)propane-1-one (1.0 g, 2.4 mmol) was dissolved in DMF (30 mL). To this solution were added potassium carbonate (0.73 g, 5.28 mmol), sodium iodide (0.76 g, 5.04 mmol) and benzyl bromide (0.60 mL, 5.04 mmol), and the resulting solution was stirred at room temperature overnight. This reaction solution was concentrated under reduced pressure. The residue was diluted with chloroform, and washed with water, saturated sodium bicarbonate solution and brine. The organic layer was dried over anhydrous magnesium sulfate, and evaporated. The residue was then purified by silica gel column chromatography (chloroform methanol=80:1), to thereby yield 0.67 g of the title compound.

Appearance: Yellow oil $^1$H NMR (DMSO-$d_6$) δ 2.27 (4H, brs), 2.50-2.59 (2H, m), 2.73-2.78 (2H, m), 3.37-3.45 (6H, m), 4.68 (4H, s), 6.78 (1H, d, J=8.9 Hz), 6.85 (2H, d, J=8.4 Hz), 7.17 (2H; d, J=8.6 Hz), 7.20-7.36 (16H, m), 7.54 (1H, d, J=3.1 Hz).

Example 2172

Production of 2-[(4-{5-[(3,4-dichlorobenzyl)-ethylamino]pyridin-2-yloxy}phenyl)methylamino]-1-(4-piperonylpiperazin-1-yl)ethanone 2-({4-[5-(3,4-dichlorobenzylamino)pyridin-2-yloxy]phenyl}methylamino)-1-(4-piperonylpiperazin-1-yl)ethanone (1.59 g, 2.5 mmol) was dissolved in dichloroethane (80 mL). To this solution were added acetoaldehyde (1.40 mL, 25.0 mmol) and sodium triacetyloxy borohydride (1.59 mL, 7.5 mmol) under ice cooling. To the resulting solution was added dropwise acetic acid (0.43 mL, 7.5 mmol), and this solution was stirred at room temperature for 16 hours. The resulting reaction solution was washed with a saturated sodium bicarbonate solution and brine. The organic layer was dried over anhydrous magnesium sulfate, and evaporated. The residue was then purified by silica gel column chromatography (chloroform:methanol=50:1). The obtained solid was recrystallized from ethanol, to thereby yield 0.65 g of the title compound.

Appearance: White powder $^1$H NMR ($CDCl_3$) δ 1.17 (3H, t, J=7.1 Hz), 2.41 (4H, brs), 2.99 (3H, s), 3.36-3.44 (4H, m), 3.48 (2H, brs), 3.62 (2H, brs), 4.04 (2H, s), 4.35 (2H, s), 5.95 (2H, s), 6.67-6.77 (5H, m), 6.85 (1H, brs), 6.97 (2H, d, J=9.1 Hz), 7.01 (1H, dd, J=8.9 Hz, 3.1 Hz), 7.07 (1H, dd, J=8.2 Hz, 2.0 Hz), 7.32 (1H, d, J=2.0 Hz), 7.37 (1H, d, J=8.3 Hz), 7.63 (1H, d, J=3.0 Hz); MS 661 ($M^+$).

The following compounds were produced in the same manner as in Example 2172.

TABLE 347

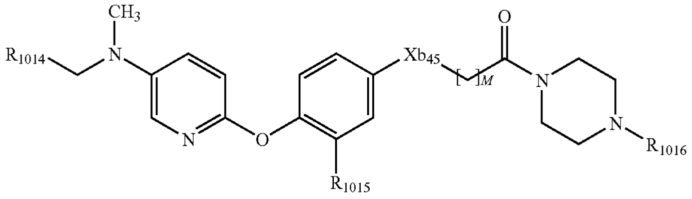

| Example No. | $R_{1014}$ | $R_{1015}$ | $R_{1016}$ | $Xb_{45}$ | M | $^1H$ NMR ($CDCl_3$) δ ppm |
|---|---|---|---|---|---|---|
| 2173 | 4-$CF_3$Ph- | —H | piperonyl | —N($CH_3$)— | 1 | 2.44 (4 H, brs), 2.99 (6 H, s), 3.39-3.62 (6 H, m), 4.04 (2 H, s), 4.48 (2 H, s), 5.95 (2 H, s), 6.62-6.78 (5 H, m), 6.86 (1 H, brs), 6.97 (2 H, d, J = 9.1 Hz), 7.08 (1 H, dd, J = 8.9 Hz, 3.1 Hz), 7.34 (2 H, d, J = 7.9 Hz), 7.57 (2 H, d, J = 8.1 Hz), 7.69 (1 H, d, J = 3.1 Hz). |
| 2174 | 3,4-$Cl_2$Ph- | —H | piperonyl | —N($CH_3$)— | 2 | 2.32-2.40 (4 H, m), 2.53-2.58 (2 H, m), 2.92 (3 H, s), 2.97 (3 H, s), 3.37-3.40 (4 H, m), 3.59-3.63 (2 H, m), 3.66-3.72 (2 H, m), 4.37 (2 H, s), 5.94 (2 H, s), 6.66-6.76 (5 H, m), 6.83 (1 H, d, J = 1.0 Hz), 6.98 (2 H, d, J = 9.1 Hz), 7.04-7.11 (2 H, m), 7.32 (1 H, d, J = 2.0 Hz), 7.38 (1 H, d, J = 8.3 Hz), 7.67 (1 H, d, J = 3.1 Hz). |
| 2175 | 4-$CF_3$Ph- | —H | piperonyl | —N($CH_3$)— | 2 | 2.32-2.39 (4 H, m), 2.52-2.57 (2 H, m), 2.92 (3 H, s), 2.99 (3 H, s), 3.36-3.40 (4 H, m), 3.59-3.63 (2 H, m), 3.66-3.72 (2 H, m), 4.48 (2 H, s), 5.94 (2 H, s), 6.67-6.76 (5 H, m), 6.83 (1 H, d, J = 1.0 Hz), 6.98 (2 H, d, J = 9.2 Hz), 7.09 (1 H, dd, J = 9.1 Hz, 3.1 Hz), 7.34 (2 H, d, J = 7.9 Hz), 7.57 (2 H, d, J = 8.1 Hz), 7.68 (1 H, d, J = 2.8 Hz). |
| 2176 | 3,4-$Cl_2$Ph- | —H | piperonyl | —N($CH_3$)— | 1 | 2.40-2.44 (4 H, m), 2.96 (3 H, s), 3.00 (3 H, s), 3.43 (2 H, brs), 3.49 (2 H, brs), 3.62 (2 H, brs), 4.05 (2 H, s), 4.36 (2 H, s), 5.95 (2 H, s), 6.67-6.77 (5 H, m), 6.85 (1 H, brs), 6.97 (2 H, d, J = 9.1 Hz), 7.06 (1 H, dd, J = 8.3 Hz, 1.7 Hz), 7.07 (1 H, dd, J = 8.9 Hz, 3.1 Hz), 7.32 (1 H, d, J = 2.0 Hz), 7.38 (1 H, d, J = 8.3 Hz), 7.69 (1 H, d, J = 3.1 Hz). |
| 2177 | 4-$CF_3$Ph- | —F | benzyl | none | 0 | 2.46 (4 H, brs), 3.02 (3 H, s), 3.54 (6 H, brs), 4.52 (2 H, s), 6.89 (1 H, d, J = 8.9 Hz), 7.14 (1 H, dd, J = 8.9 Hz, 3.1 Hz), 7.17-7.21 (2 H, m), 7.28-7.35 (8 H, m), 7.58 (2 H, d, J = 8.1 Hz), 7.62 (1 H, d, J = 2.8 Hz). |
| 2178 | 3,4-$Cl_2$Ph- | —F | benzyl | none | 0 | 2.47 (4 H, brs), 3.00 (3 H, s), 3.55-3.73 (6 H, m), 4.40 (2 H, s), 6.89 (1 H, d, J = 8.9 Hz), 7.06 (1 H, dd, J = 8.2 Hz, 1.7 Hz), 7.14 (1 H, dd, J = 8.9 Hz, 3.1 Hz), 7.17-7.22 (3 H, m), 7.28-7.33 (6 H, m), 7.39 (1 H, d, J = 8.3 Hz), 7.61 (1 H, d, J = 3.3 Hz). |

TABLE 348

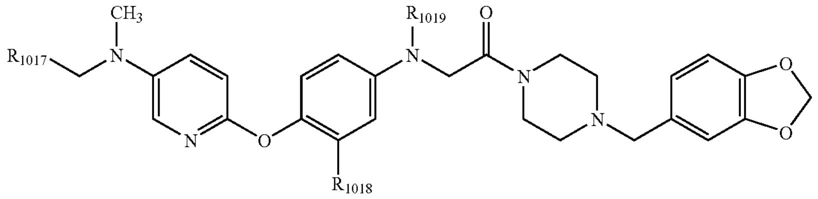

| Example No. | $R_{1017}$ | $R_{1018}$ | $R_{1019}$ | Form | mp (° C.) or $^1$H NMR (DMSO-$d_6$) δ ppm |
|---|---|---|---|---|---|
| 2179 | 4-$CF_3$Ph- | —$CH_3$ | —$C_2H_5$ | fumarate | mp 157-159 dec |
| 2180 | 3,4-$Cl_2$Ph- | —$CH_3$ | —$C_2H_5$ | fumarate | mp 148-151 dec |
| 2181 | 4-$CF_3$Ph- | —$CH_3$ | —$CH_3$ | fumarate | mp 151-154 |
| 2182 | 3,4-$Cl_2$Ph- | —$CH_3$ | —$CH_3$ | hydrochloride | mp 139-142 |
| 2183 | 4-$CF_3$Ph- | —$CH_3$ | —Ac | hydrochloride | mp 199.5-201.5 |
| 2184 | 3,4-$Cl_2$Ph- | —$CH_3$ | —Ac | hydrochloride | mp 188.5-190.0 |
| 2185 | 4-$CF_3$Ph- | —$OCH_3$ | —$CH_3$ | oxalate | $^1$H NMR 2.48-2.81 (4 H, m), 2.93 (3 H, s), 2.94 (3 H, s), 3.36-3.85 (9 H, m), 4.25 (2 H, s), 4.56 (2 H, s), 6.01 (2 H, s), 6.12 (1 H, dd, J = 8.8 Hz, 2.8 Hz), 6.29 (1 H, d, J = 2.8 Hz), 6.66 (1 H, d, J = 9.0 Hz), 6.77 (1 H, d, J = 8.8 Hz), 6.79-6.98 (3 H, m), 7.22 (1 H, dd, J = 9.0 Hz, 3.2 Hz), 7.42 (2 H, d, J = 8.1 Hz), 7.52 (1 H, d, J = 3.2 Hz), 7.67 (2 H, d, J = 8.1 Hz). |
| 2186 | 3,4-$Cl_2$Ph- | —$OCH_3$ | —$CH_3$ | hydrochloride | $^1$H NMR 2.75-3.18 (8 H, m), 3.21-3.42 (2 H, m), 3.63 (3 H, s), 3.83-4.52 (10 H, m), 6.06 (2 H, s), 6.16 (1 H, dd, J = 8.8 Hz, 2.7 Hz), 6.34 (1 H, d, J = 2.7 Hz), 6.68 (1 H, d, J = 9.0 Hz), 6.79 (1 H, d, J = 8.8 Hz), 6.94-7.06 (2 H, m), 7.16-7.24 (2 H, m), 7.27 (1 H, dd, J = 9.0 Hz, 3.2 Hz), 7.47 (1 H, d, J = 2.0 Hz), 7.53 (1 H, d, J = 3.2 Hz), 7.56 (1 H, d, J = 8.2 Hz), 10.91-11.26 (1 H, m). |
| 2187 | 4-$CF_3$Ph- | —$OCH_3$ | —$C_2H_5$ | fumarate | mp 159-162 |
| 2188 | 3,4-$Cl_2$Ph- | —$OCH_3$ | —$C_2H_5$ | fumarate | mp 154-157 |
| 2189 | 4-$CF_3$Ph- | —F | —$CH_3$ | hydrobromide | mp 211-212 |
| 2190 | 3,4-$Cl_2$Ph- | —F | —$CH_3$ | hydrobromide | mp 206.5-207.0 |
| 2191 | 4-$CF_3$Ph- | —F | —$C_2H_5$ | hydrobromide | mp 151.0-152.5 |
| 2192 | 3,4-$Cl_2$Ph- | —F | —$C_2H_5$ | hydrobromide | mp 172.5-174.5 |

TABLE 349

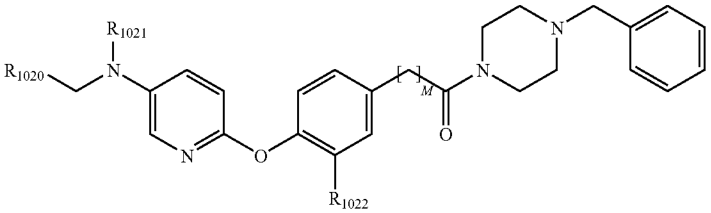

| Example No. | $R_{1020}$ | $R_{1021}$ | $R_{1022}$ | M | Form | $^1$H NMR (DMSO-$d_6$) δ ppm |
|---|---|---|---|---|---|---|
| 2193 | Ph- | —$CH_3$ | —H | 2 | dihydro-chloride | 2.50-3.07 (10 H, m), 3.22-3.31 (2 H, m), 3.45-3.50 (1 H, m), 4.03-4.08 (1 H, m), 4.30 (2 H, d, J = 3.8 Hz), 4.42-4.55 (3 H, m), 6.85-6.92 (3 H, m), 7.19-7.26 (5 H, m), 7.30-7.35 (3 H, m), 7.45-7.47 (3 H, m), 7.58-7.60 (2 H, m), 7.66 (1 H, d, J = 2.8 Hz), 11.33 (2 H, brs). |
| 2194 | 3,4-$Cl_2$Ph- | —$CH_3$ | —H | 0 | dihydro-chloride | 2.50-2.51 (2 H, m), 3.03 (3 H, s), 3.13-3.48 (6 H, m), 4.34-4.37 (2 H, m), 4.58 (2 H, s), 6.97 (1 H, d, J = 8.9 Hz), 7.04 (2 H, d, J = 8.4 Hz), 7.23 (1 H, dd, J = 8.4 Hz, 1.5 Hz), 7.34 (1 H, dd, J = 8.9 Hz, 3.1 Hz), |

TABLE 349-continued

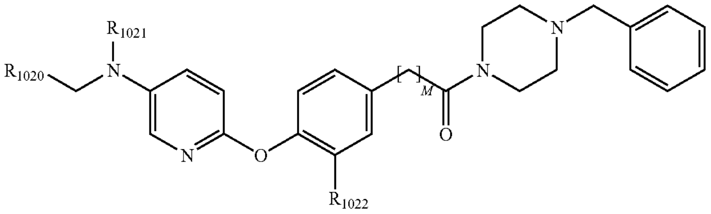

| Example No. | $R_{1020}$ | $R_{1021}$ | $R_{1022}$ | M | Form | $^1$H NMR (DMSO-$d_6$) δ ppm |
|---|---|---|---|---|---|---|
| | | | | | | 7.44-7.47 (5 H, m), 7.51 (1 H, d, J = 1.5 Hz), 7.58-7.61 (3 H, m), 7.70 (1 H, d, J = 3.3 Hz), 11.52 (2 H, brs). |
| 2195 | 4-$CF_3$Ph- | —$CH_3$ | —H | 0 | dihydro-chloride | 3.06 (3 H, s), 3.00-3.20 (2 H, m), 3.20-3.40 (2 H, m), 3.45 (2 H, brs), 4.20-4.50 (2 H, m), 4.34 (2 H, s), 4.69 (2 H, s), 6.97 (1 H, d, J = 8.9 Hz), 7.04 (2 H, d, J = 8.8 Hz), 7.33 (1 H, dd, J = 8.9 Hz, 3.1 Hz), 7.41-7.49 (7 H, m), 7.55-7.68 (2 H, m), 7.70 (1 H, d, J = 3.1 Hz), 7.71 (2 H, d, J = 8.0 Hz). |
| 2196 | 3,4-$Cl_2$Ph- | —$CH_3$ | —H | 2 | dihydro-chloride | 2.49-3.07 (10 H, m), 3.23-3.27 (2 H, m), 3.45-3.55 (1 H, m), 4.03-4.08 (1 H, m), 4.30 (2 H, d, J = 4.3 Hz), 4.42-4.47 (1 H, m), 4.54 (2 H, s), 6.87 (1 H, d, J = 9.1 Hz), 6.90 (2 H, d, J = 8.6 Hz), 7.19-7.23 (3 H, m), 7.32 (1 H, dd, J = 8.9 Hz, 3.3 Hz), 7.45-7.50 (4 H, m), 7.57-7.64 (4 H, m), 11.33 (2 H, brs). |
| 2197 | 4-$CF_3$Ph- | —$C_2H_5$ | —F | 0 | hydro-chloride | 1.21 (3 H, t, J = 6.9 Hz), 2.50-2.51 (2 H, m), 3.14-3.38 (6 H, m), 3.49 (2 H, q, J = 6.9 Hz), 4.34 (2 H, brs), 4.61 (2 H, brs), 6.98 (1 H, d, J = 8.9 Hz), 7.25-7.29 (3 H, m), 7.42-7.50 (7 H, m), 7.58 (2 H, brs), 7.69 (2 H, d, J = 8.1 Hz), 11.12 (1 H, brs). |
| 2198 | 3,4-$Cl_2$Ph- | —$C_2H_5$ | —F | 0 | hydro-chloride | 1.10 (3 H, t, J = 7.0 Hz), 2.49-2.52 (2 H, m), 3.13 (2 H, brs), 3.32-3.58 (6 H, m), 4.33 (2 H, brs), 4.50 (2 H, brs), 6.99 (1 H, d, J = 9.1 Hz), 7.20-7.31 (4 H, m), 7.42-7.57 (6 H, m), 7.58-7.60 (3 H, m), 11.14 (1 H, brs). |

TABLE 350

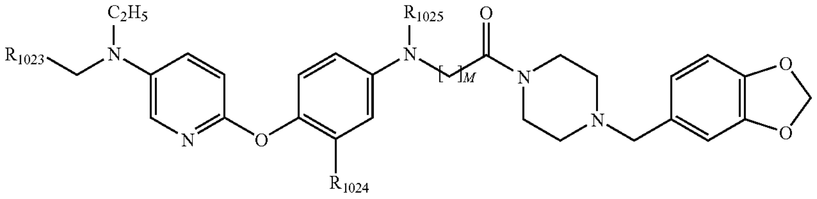

| Example No. | $R_{1023}$ | $R_{1024}$ | $R_{1025}$ | M | Form | mp (° C.) or $^1$H NMR (solvent) δ ppm |
|---|---|---|---|---|---|---|
| 2199 | 3,4-$Cl_2$Ph- | —H | —$CH_3$ | 2 | free | $^1$H NMR ($CDCl_3$) 1.17 (3 H, t, J = 7.1 Hz), 2.32-2.39 (4 H, m), 2.52-2.57 (2 H, m), 2.91 (3 H, s), 3.36-3.44 (6 H, m), 3.59-3.63 (2 H, m), 3.66-3.71 (2 H, m), 4.35 (2 H, s), 5.95 (2 H, s), 6.67-6.76 (5 H, m), 6.83 (1 H, d, J = 1.0 Hz), 6.98 (2 H, d, J = 9.1 Hz), 7.03 (1 H, dd, J = 9.1 Hz, 3.3 Hz), 7.07 (1 H, dd, J = 8.9 Hz, 2.1 Hz), 7.32 (1 H, d, J = 2.0 Hz), 7.47 (1 H, d, J = 8.3 Hz), 7.62 (1 H, d, J = 3.1 Hz). |
| 2200 | 4-$CF_3$Ph- | —H | —$CH_3$ | 2 | free | $^1$H NMR ($CDCl_3$) 1.19 (3 H, t, J = 7.1 Hz), 2.32-2.38 (4 H, m), 2.52-2.57 (2 H, m), 2.91 (3 H, s), 3.36-3.47 (6 H, m), 3.59-3.63 (2 H, m), |

TABLE 350-continued

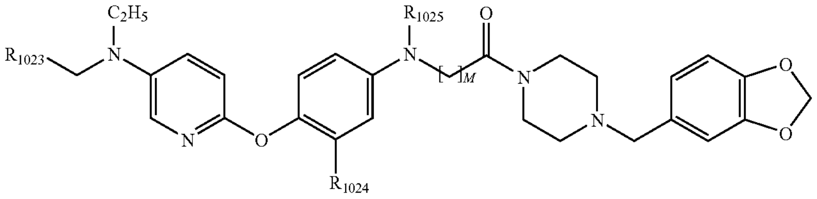

| Example No. | $R_{1023}$ | $R_{1024}$ | $R_{1025}$ | M | Form | mp (° C.) or $^1$H NMR (solvent) δ ppm |
|---|---|---|---|---|---|---|
| | | | | | | 3.66-3.71 (2 H, m), 4.47 (2 H, s), 5.94 (2 H, s), 6.67-6.76 (5 H, m), 6.83 (1 H, d, J = 1.0 Hz), 6.97 (2 H, d, J = 9.2 Hz), 7.03 (1 H, dd, J = 9.1 Hz, 3.1 Hz), 7.35 (2 H, d, J = 7.9 Hz), 7.56 (2 H, d, J = 7.9 Hz), 7.63 (1 H, d, J = 2.8 Hz). |
| 2201 | 3,4-$Cl_2$Ph- | —$CH_3$ | —$CH_3$ | 1 | hydrochloride | mp 167-170 dec |
| 2202 | 4-$CF_3$Ph- | —$CH_3$ | —Ac | 1 | hydrochloride | mp 186-189 |
| 2203 | 3,4-$Cl_2$Ph- | —$CH_3$ | —Ac | 1 | hydrochloride | mp 188.5-191.0 |
| 2204 | 4-$CF_3$Ph- | —$OCH_3$ | —$CH_3$ | 1 | oxalate | $^1$H NMR (DMSO-$d_6$) 1.08 (3 H, t, J = 7.0 Hz), 2.50-2.81 (4 H, m), 2.93 (3 H, s), 3.41 (2 H, q, J = 7.0 Hz), 3.33-3.72 (7 H, m), 3.77 (2 H, s), 4.25 (2 H, s), 4.52 (2 H, s), 6.01 (2 H, s), 6.12 (1 H, dd, J = 8.8 Hz, 2.7 Hz), 6.28 (1 H, d, J = 2.7 Hz), 6.64 (1 H, d, J = 9.0 Hz), 6.76 (1 H, d, J = 8.7 Hz), 6.80-6.94 (2 H, m), 6.97 (1 H, brs), 7.15 (1 H, dd, J = 9.0 Hz, 3.2 Hz), 7.34-7.50 (3 H, m), 7.66 (2 H, d, J = 8.1 Hz). |
| 2205 | 3,4-$Cl_2$Ph- | —$OCH_3$ | —$CH_3$ | 1 | hydrochloride | $^1$H NMR (DMSO-$d_6$) 1.06 (3 H, t, J = 6.9 Hz), 2.75-3.16 (5 H, m), 3.21-3.48 (4 H, m), 3.62 (3 H, s), 3.71-4.52 (10 H, m), 6.06 (2 H, s), 6.16 (1 H, dd, J = 8.8 Hz, 2.7 Hz), 6.34 (1 H, d, J = 2.7 Hz), 6.67 (1 H, d, J = 8.9 Hz), 6.78 (1 H, d, J = 8.8 Hz), 6.94-7.06 (2 H, m), 7.13-7.28 (3 H, m), 7.41-7.52 (2 H, m), 7.56 (1 H, d, J = 8.3 Hz), 10.83-11.19 (1 H, m). |

TABLE 351

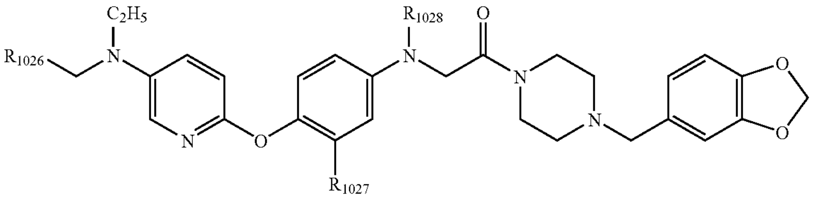

| Example No. | $R_{1026}$ | $R_{1027}$ | $R_{1028}$ | Form | mp (° C.) |
|---|---|---|---|---|---|
| 2206 | 4-$CF_3$Ph- | —$CH_3$ | —$C_2H_5$ | oxalate | 126-128 |
| 2207 | 3,4-$Cl_2$Ph- | —$CH_3$ | —$C_2H_5$ | oxalate | 111-113 |
| 2208 | 4-$CF_3$Ph- | —$CH_3$ | —$C_2H_5$ | oxalate | 120-123 |
| 2209 | 4-$CF_3$Ph- | —$OCH_3$ | —$CH_3$ | hydrobromide | 205-208 |
| 2210 | 3,4-$Cl_2$Ph- | —$OCH_3$ | —$C_2H_5$ | hydrobromide | 133-135 |
| 2211 | 4-$CF_3$Ph- | —F | —$CH_3$ | hydrobromide | 203-205 |
| 2212 | 3,4-$Cl_2$Ph- | —F | —$CH_3$ | hydrobromide | 185-188 |
| 2213 | 4-$CF_3$Ph- | —F | —$C_2H_5$ | oxalate | 121.0-122.5 |
| 2214 | 3,4-$Cl_2$Ph- | —F | —$C_2H_5$ | hydrobromide | 165.0-166.5 |

TABLE 352

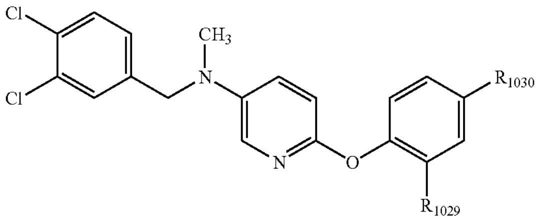

| Example No. | $R_{1029}$ | $R_{1030}$ | $^1H$ NMR ($CDCl_3$) δ ppm |
|---|---|---|---|
| 2215 | —H | 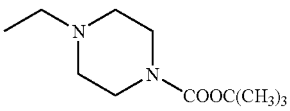 | 1.45 (9 H, s), 2.39-2.43 (4 H, m), 3.01 (3 H, s), 3.41-3.44 (4 H, m), 3.50 (2 H, s), 4.41 (2 H, s), 6.82 (1 H, d, J = 8.9 Hz), 7.01 (2 H, d, J = 8.4 Hz), 7.08-7.13 (2 H, m), 7.27-7.41 (4 H, m), 7.70 (1 H, d, J = 8.6 Hz). |
| 2216 | —$CH_3$ | 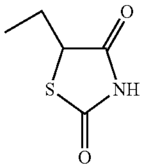 | 2.20 (3 H, s), 2.98 (3 H, s), 3.06 (1 H, dd, J = 14.0 Hz, 10.1 Hz), 3.52 (1 H, dd, J = 14.0 Hz, 3.8 Hz), 4.38 (2 H, s), 4.50 (1 H, dd, J = 10.1 Hz, 3.8 Hz), 6.77 (1 H, d, J = 8.9 Hz), 6.91 (1 H, d, J = 8.3 Hz), 7.03 (1 H, dd, J = 8.3 Hz, 2.1 Hz), 7.05-7.16 (3 H, m), 7.32 (1 H, d, J = 2.1 Hz), 7.39 (1 H, d, J = 8.3 Hz), 7.67 (1 H, d, J = 3.1 Hz). |

TABLE 353

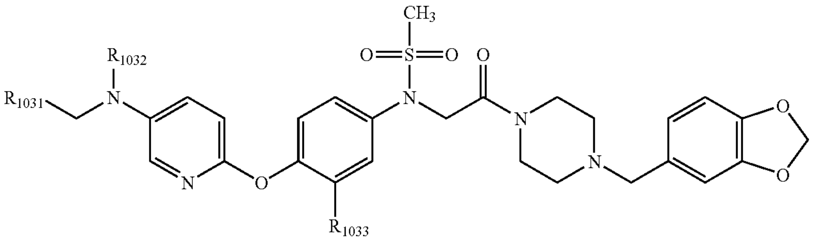

| Example No. | $R_{1031}$ | $R_{1032}$ | $R_{1033}$ | $^1H$ NMR ($CDCl_3$) δ ppm |
|---|---|---|---|---|
| 2217 | 3,4-$Cl_2$Ph- | —$CH_3$ | —H | 2.41 (4 H, brs), 3.02 (3 H, s), 3.19 (3 H, s), 3.36 (2 H, brs), 3.42 (2 H, s), 3.60 (2 H, brs), 4.41 (2 H, s), 4.51 (2 H, s), 5.95 (2 H, s), 6.73-6.77 (2 H, m), 6.84-6.87 (2 H, m), 7.03 (2 H, d, J = 8.9 Hz), 7.07 (1 H, dd, J = 8.3 Hz, 2.0 Hz), 7.12 (1 H, dd, J = 8.9 Hz, 3.1 Hz), 7.33 (1 H, d, J = 2.0 Hz), 7.40 (1 H, d, J = 8.3 Hz), 7.59 (2 H, d, J = 8.9 Hz), 7.69 (1 H, d, J = 3.1 Hz). |
| 2218 | 3,4-$Cl_2$Ph- | —$C_2H_5$ | —H | 1.21 (3 H, t, J = 7.1 Hz), 2.41 (4 H, brs), 3.18 (3 H, s), 3.36 (2 H, brs), 3.42 (2 H, s), 3.46 (2 H, q, J = 7.1 Hz), 3.60 (2 H, brs), 4.40 (2 H, s), 4.50 (2 H, s), 5.94 (2 H, s), 6.73-6.77 (2 H, m), 6.81-6.84 (2 H, m), 7.01-7.10 (4 H, m), 7.33 (1 H, d, J = 2.0 Hz), 7.39 (1 H, d, J = 8.3 Hz), 7.54 (2 H, d, J = 9.1 Hz), 7.64 (1 H, d, J = 3.0 Hz). |
| 2219 | 4-$CF_3$Ph- | —$CH_3$ | —H | 2.41 (4 H, brs), 3.05 (3 H, s), 3.19 (3 H, s), 3.34-3.36 (2 H, m), 3.42 (2 H, s), 3.60 (2 H, brs), 4.50 (2 H, s), 4.54 (2 H, s), 5.95 (2 H, s), 6.73-6.74 (2 H, m), 6.83 (1 H, brs), 6.85 (1 H, d, J = 8.9 Hz), 7.03 (2 H, d, J = 8.9 Hz), 7.13 (1 H, dd, J = 8.9 Hz, 3.3 Hz), 7.34 (2 H, d, J = 7.9 Hz), 7.54 (2 H, d, J = 8.9 Hz), 7.59 (2 H, d, J = 8.1 Hz), 7.70 (1 H, d, J = 3.1 Hz). |
| 2220 | 4-$CF_3$Ph- | —$C_2H_5$ | —H | 1.22 (3 H, t, J = 7.1 Hz), 2.41 (4 H, brs), 3.19 (3 H, s), 3.35 (2 H, brs), 3.42 (2 H, s), 3.48 (2 H, q, J = 7.1 Hz), 3.60 (2 H, brs), 4.50 (2 H, s), 4.52 (2 H, s), 5.95 (2 H, s), 6.70-6.77 (2 H, m), 6.82 (1 H, d, J = 8.7 Hz), 6.84 (1 H, brs), 7.02 (2 H, d, J = 8.9 Hz), 7.07 (1 H, dd, J = 8.9 Hz, 3.1 Hz), 7.36 (2 H, d, J = 7.9 Hz), 7.54 (2 H, d, J = 8.9 Hz), 7.58 (2 H, d, J = 8.1 Hz), 7.65 (1 H, d, J = 3.0 Hz). |

TABLE 353-continued

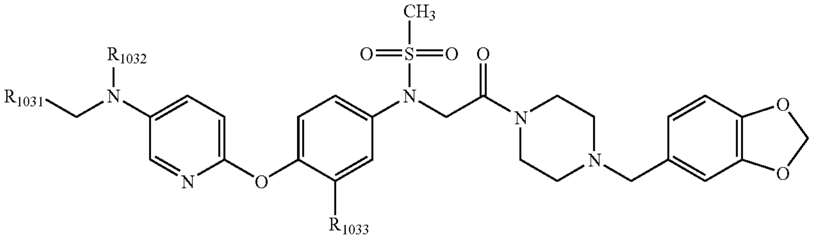

| Example No. | $R_{1031}$ | $R_{1032}$ | $R_{1033}$ | $^1H$ NMR ($CDCl_3$) δ ppm |
|---|---|---|---|---|
| 2221 | 3,4-$Cl_2$Ph- | —$CH_3$ | —$CH_3$ | 2.21 (3 H, s), 2.42 (4 H, brs), 3.00 (3 H, s), 3.21 (3 H, s), 3.34-3.38 (2 H, m), 3.42 (2 H, s), 3.59-3.62 (2 H, m), 4.39 (2 H, s), 4.51 (2 H, s), 5.95 (2 H, s), 6.73-6.77 (2 H, m), 6.80-6.83 (2 H, m), 6.91 (1 H, d, J = 8.6 Hz), 7.06 (1 H, dd, J = 8.2 Hz, 2.1 Hz), 7.12 (1 H, dd, J = 8.9 Hz, 3.1 Hz), 7.32-7.44 (4 H, m), 7.65 (1 H, d, J = 3.1 Hz). |
| 2222 | 4-$CF_3$Ph- | —$CH_3$ | —$CH_3$ | 2.21 (3 H, s), 2.42 (4 H, brs), 3.02 (3 H, s), 3.20 (3 H, s), 3.34-3.38 (2 H, m), 3.42 (2 H, s), 3.58-3.62 (2 H, m), 4.51 (4 H, brs), 5.94 (2 H, s), 6.70-6.76 (2 H, m), 6.79-6.83 (2 H, m), 6.90 (1 H, d, J = 8.6 Hz), 7.12 (1 H, dd, J = 8.9 Hz, 3.3 Hz), 7.32-7.39 (3 H, m), 7.43 (1 H, d, J = 2.5 Hz), 7.58 (2 H, d, J = 8.1 Hz), 7.66 (1 H, d, J = 3.0 Hz). |

TABLE 354

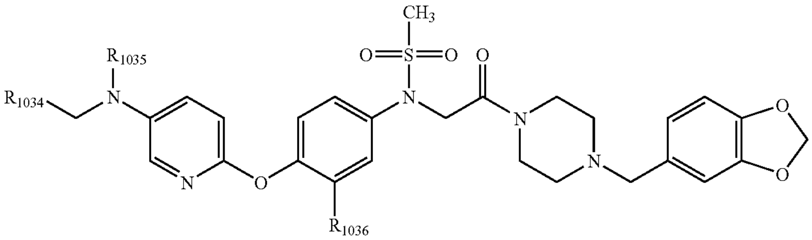

| Example No. | $R_{1034}$ | $R_{1035}$ | $R_{1036}$ | $^1H$ NMR ($CDCl_3$) δppm |
|---|---|---|---|---|
| 2223 | 3,4-$Cl_2$Ph- | —$C_2H_5$ | —$CH_3$ | 1.19(3 H, t, J = 7.1 Hz), 2.21(3 H, s), 2.41(4 H, brs), 3.20(3H, s), 3.34-3.37(2 H, m), 3.42(2 H, s), 3.43(2 H, q, J = 7.1 Hz), 3.58-3.62(2 H, m), 4.38(2 H, s), 4.50(2 H, s), 5.95(2 H, s), 6.70-6.77(2 H, m), 6.79(1 H, d, J = 8.9 Hz), 6.83(1 H, d, J = 0.8 Hz), 6.91(1 H, d, J = 8.6 Hz), 7.04-7.09(2 H, m), 7.32-7.43(4 H, m), 7.60(1 H, d, J = 3.0 Hz). |
| 2224 | 4-$CF_3$Ph- | —$C_2H_5$ | —$CH_3$ | 1.21(3 H, t, J = 7.1 Hz), 2.21(3 H, s), 2.41(4 H, brs), 3.20(3 H, s), 3.34-3.37(2 H, m), 3.42(2 H, s), 3.46(2 H, q, J = 7.1 Hz), 3.58-3.62(2 H, m), 4.50(4 H, brs), 5.94(2 H, s), 6.70-6.74(2 H, m), 6.78(1 H, d, J = 9.2 Hz), 6.83(1 H, brs), 6.90(1 H, d, J = 8.6 Hz), 7.04-7.08(1 H, m), 7.34-7.43(4 H, m), 7.57(1 H, d, J = 8.1 Hz), 7.60(1 H, d, J = 3.0 Hz). |
| 2225 | 4-$CF_3$Ph- | —$CH_3$ | —$OCH_3$ | 2.42(4 H, brs), 3.01(3 H, s), 3.21(3 H, s), 3.37(2 H, brs), 3.42(2 H, s), 3.61(2 H, brs), 3.78(3 H, s), 4.27(2 H, s), 4.53(2 H, s), 5.94(2 H, s), 6.72-6.76(2 H, m), 6.84(2 H, d, J = 8.4 Hz), 7.00(1 H, d, J = 8.4 Hz), 7.10-7.16(2 H, m), 7.24-7.26(1 H, m), 7.33(2 H, d, J = 8.1 Hz), 7.57(2 H, d, J = 7.9 Hz), 7.62(1 H, d, J = 3.0 Hz). |
| 2226 | 4-$CF_3$Ph- | —$C_2H_5$ | —$OCH_3$ | 1.20(3 H, t, J = 6.9 Hz), 2.42(4 H, brs), 3.21(3 H, s), 3.36(2 H, brs), 3.40-3.48(4 H, m), 3.61(2 H, brs), 3.77(3 H, s), 4.48(2 H, s), 4.52(2 H, s), 5.94(2 H, s), 6.73-6.76(2 H, m), 6.81-6.85(2 H, m), 6.99(1 H, d, J = 8.6 Hz), 7.07(1 H, dd, J = 9.1 Hz, 3.3 Hz), 7.14(1 H, dd, J = 8.4 Hz, 2.3 Hz), 7.24(1 H, d, J = 2.5 Hz), 7.34(2 H, d, J = 8.1 Hz), 7.54-7.57(3 H, m). |

TABLE 355

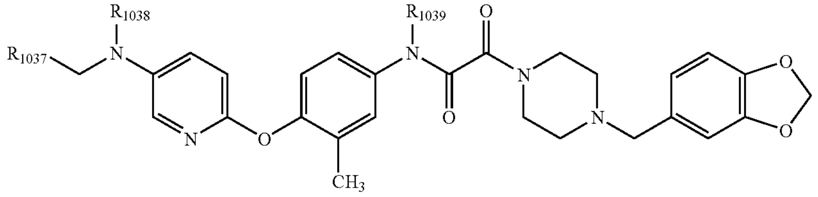

| Example No. | $R_{1037}$ | $R_{1038}$ | $R_{1039}$ | $^1H$ NMR (solvent) δppm |
|---|---|---|---|---|
| 2227 | 3,4-$Cl_2$Ph- | —$CH_3$ | —H | ($CDCl_3$) 2.20(3 H, s), 2.48-2.54(4 H, m), 2.97(3 H, s), 3.44(2 H, s), 3.70-3.73(2 H, m), 4.23-4.27(2 H, m), 4.37(2 H, s), 5.95(2 H, s), 6.73-6.77(3 H, m), 6.85(1 H, brs), 6.95(1 H, d, J = 8.6 Hz), 7.06(1 H, dd, J = 8.2 Hz, 2.0 Hz), 7.10(1 H, dd, J = 8.9 Hz, 3.1 Hz), 7.32(1 H, d, J = 2.0 Hz), 7.37(1 H, dd, J = 8.6 Hz, 2.6 Hz), 7.38(1 H, d, J = 8.2 Hz), 7.52(1 H, d, J = 2.5 Hz), 7.66(1 H, d, J = 2.8 Hz), 9.12(1 H, brs). |
| 2228 | 4-$CF_3$Ph- | —$CH_3$ | —H | ($CDCl_3$) 2.20(3 H, s), 2.48-2.54(4 H, m), 3.00(3 H, s), 3.44(2 H, s), 3.72(2 H, t, J = 5.0 Hz), 4.23-4.27(2 H, m), 4.49(2 H, s), 5.95(2 H, s), 6.73-6.77(3 H, m), 6.85(1 H, brs), 6.95(1 H, d, J = 8.7 Hz), 7.10(1 H, dd, J = 8.9 Hz, 3.3 Hz), 7.32-7.39(3 H, m), 7.52(1 H, d, J = 2.5 Hz), 7.57(2 H, d, J = 8.1 Hz), 7.67(1 H, d, J = 3.3 Hz), 9.12(1 H, brs). |
| 2229 | 3,4-$Cl_2$Ph- | —$C_2H_5$ | —H | ($CDCl_3$) 1.18(3 H, t, J = 7.1 Hz), 2.20(3 H, s), 2.48-2.53(4 H, m), 3.41(2 H, q, J = 7.1 Hz), 3.44(2 H, s), 3.70-3.73(2 H, m), 4.23-4.27(2 H, m), 4.36(2 H, s), 5.95(2 H, s), 6.72-6.77(3 H, m), 6.85(1 H, brs), 6.95(1 H, d, J = 8.6 Hz), 7.02-7.09(2 H, m), 7.32-7.39(3 H, m), 7.51(1 H, d, J = 2.6 Hz), 7.60(1 H, d, J = 3.1 Hz), 9.12(1 H, brs). |
| 2230 | 4-$CF_3$Ph- | —$C_2H_5$ | —H | ($CDCl_3$) 1.19(3 H, t, J = 7.1 Hz), 2.20(3 H, s), 2.48-2.53(4 H, m), 3.43(2 H, q, J = 7.1 Hz), 3.44(2 H, s), 3.70-3.73(2 H, m), 4.23-4.27(2 H, m), 4.48(2 H, s), 5.95(2 H, s), 6.71-6.77(3 H, m), 6.85(1 H, brs), 6.95(1 H, d, J = 8.7 Hz), 7.04(1 H, dd, J = 8.9 Hz, 3.1 Hz), 7.32-7.38(3 H, m), 7.51(1 H, d, J = 2.5 Hz), 7.56(2 H, d, J = 8.1 Hz), 7.61(1 H, d, J = 3.1 Hz), 9.11(1 H, brs). |
| 2231 | 3,4-$Cl_2$Ph- | —$C_2H_5$ | —$CH_3$ | a mixture of the rotational isomers ($DMSO-d_6$) 1.09(3 H, t, J = 6.93 Hz), 2.29-2.42(7 H, m), 3.22-3.54(11 H, m), 4.48(2 H, s), 5.97-5.99(2 H, m), 6.64-6.94(5 H, m), 7.07-7.27(4 H, m), 7.46-7.59(3 H, m). |
| 2232 | 4-$CF_3$Ph- | —$C_2H_5$ | —$CH_3$ | a mixture of the rotational isomers ($DMSO-d_6$) 1.12(3 H, t, J = 6.93 Hz), 2.07-2.42(7 H, m), 3.22-3.55(11 H, m), 4.59(2 H, s), 5.97-5.99(2 H, m), 6.65-6.94(5 H, m), 7.07-7.18(1 H, m), 7.23-7.29(2 H, m), 7.44(2 H, d, J = 8.08 Hz), 7.53(1 H, d, J = 3.13 Hz), 7.67(2 H, d, J = 8.41 Hz). |

TABLE 356

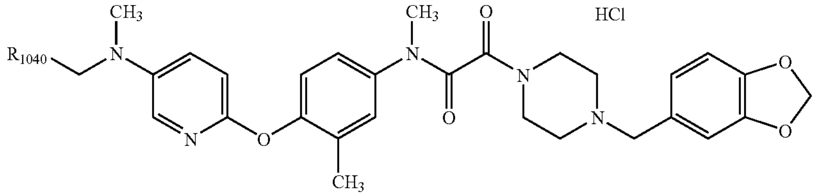

| Example No. | $R_{1040}$ | $^1H$ NMR ($DMSO-d_6$) δppm |
|---|---|---|
| 2233 | 3,4-$Cl_2$Ph- | a mixture of the rotational isomers 2.09-2.12(3 H, m), 2.66-4.53(18 H, m), 6.05-6.08(2 H, m), 6.88-6.93(2 H, m), 6.96-7.11(3 H, m), 7.19-7.25(3 H, m), 7.32-7.36(1 H, m), 7.48(1 H, d, J = 2.1 Hz), 7.55-7.60(2 H, m), 11.35(1 H, brs). |
| 2234 | 4-$CF_3$Ph- | a mixture of the rotational isomers 2.10-2.12(3 H, m), 2.66-4.64(18 H, m), 6.05-6.08(2 H, m), 6.87-6.92(2 H, m), 6.96-7.11(3 H, m), 7.18-7.25(2 H, m), 7.30-7.35(1 H, m), |

TABLE 356-continued

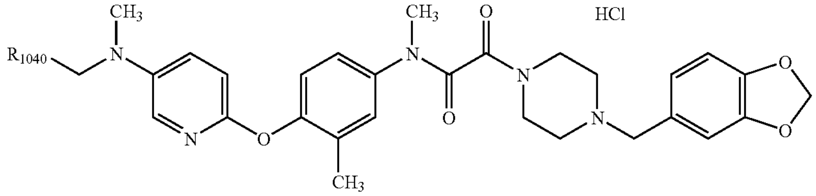

| Example No. | $R_{1040}$ | $^1H$ NMR (DMSO-$d_6$) δppm |
|---|---|---|
| | | 7.43(2 H, d, J = 8.1 Hz), 7.60-7.61(1 H, m), 7.68(2 H, d, J = 8.2 Hz), 11.27(1 H, brs). |

Example 2235

Production of (4-{5-[benzyl-(3,4-dichlorobenzyl)-amino]pyridin-2-yloxy}(4-benzylpiperazin-1-yl) methanone (4-benzylpiperazin-1-yl){4-[5-(3,4-dichlorobenzy-lamino)pyridin-2-yloxy]phenyl}methanone (1.09 g, 2.0 mmol) was dissolved in DMF (30 mL). To this solution were added potassium carbonate (0.28 g, 2.0 mmol) and benzyl bromide (0.24 mL, 2.0 mmol), and the resulting solution was stirred at room temperature for 2 hours, then subsequently stirred for 1 hour at 70° C. To the resulting solution were further added potassium carbonate (0.03 g, 0.2 mmol) and benzyl bromide (0.02 mL, 0.2 mmol), and this solution was stirred for 3 hours at 70° C. To the resulting solution were again added potassium carbonate (0.03 g, 0.2 mmol), benzyl bromide (0.02 mL, 0.2 mmol) and sodium iodide (0.15 g, 1.0 mmol), and this solution was stirred for overnight at 70° C. The resulting reaction solution was concentrated under reduced pressure. The residue was diluted with chloroform, and this solution was washed with water, saturated sodium bicarbonate solution and brine. The organic layer was dried over anhydrous magnesium sulfate, and evaporated. The residue was then purified by silica gel column chromatography (ethyl acetate), to thereby yield 0.64 g of the title compound.

Appearance: Pale yellow oil $^1H$ NMR ($CDCl_3$) δ 2.37 (4H, brs), 3.28-3.50 (6H, m), 4.71 (2H, s), 4.73 (2H, s), 6.90 (1H, d, J=8.9 Hz), 6.99 (2H, d, J=8.6 Hz), 7.22-7.37 (14H, m), 7.52 (1H, d, J=2.0 Hz), 7.58-7.61 (2H, m).

The following compounds were produced in the same manner as in Example 2235.

TABLE 357

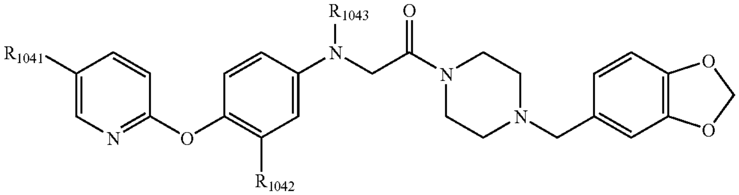

| Example No. | $R_{1041}$ | $R_{1042}$ | $R_{1043}$ | $^1H$ NMR ($CDCl_3$) δppm |
|---|---|---|---|---|
| 2236 | 3,4-$Cl_2$PhCON($CH_3$)— | —$OCH_3$ | —$C_2H_5$ | 1.19(3 H, t, J = 7.1 Hz), 2.42(4 H, t, J = 4.8 Hz), 3.30-3.55(4 H, m), 3.43(2 H, s), 3.44(3 H, s), 3.58-3.70(2 H, m), 3.67(3 H, s), 4.03(2 H, s), 5.95(2 H, s), 6.19(1 H, dd, J = 8.8 Hz, 2.8 Hz), 6.30(1 H, d, J = 2.8 Hz), 6.70-6.75(2 H, m), 6.79(1 H, d, J = 8.9 Hz), 6.85(1 H, s), 6.92(1 H, d, J = 8.8 Hz), 7.05 (1 H, dd, J = 8.1 Hz, 2.0 Hz), 7.27(1 H, d, J = 8.1 Hz), 7.35(1 H, dd, J = 8.9 Hz, 2.6 Hz), 7.41(1 H, d, J = 2.0 Hz), 7.80(1 H, d, J = 2.6 Hz). |
| 2237 | 4-$CF_3$PhCON($CH_3$)— | —$CH_3$ | —$CH_3$ | 1.97(3 H, s), 2.43(4 H, t, J = 5.0 Hz), 3.00(3 H, s), 3.44(2 H, s), 3.47(3 H, s), 3.42-3.57(2 H, m), 3.63(2 H, brs), 4.06(2 H, s), 5.95(2 H, s), 6.44-6.55(2 H, m), 6.67-6.79(3 H, m), 6.82-6.90(2 H, m), 7.40-7.47(1 H, m), 7.37(2 H, d, J = 8.1 Hz), 7.48 (2 H, d, J = 8.1 Hz), 7.81(1 H, brs). |
| 2238 | 4-$CF_3$PhCON($CH_3$)— | —$OCH_3$ | —$C_2H_5$ | 1.18(3 H, t, J = 7.1 Hz), 2.41(4 H, t, J = 4.9 Hz), 3.40(2 H, q, J = 7.1 Hz), 3.42(2 H, t, J = 3.5 Hz), 3.47(3 H, s), 3.42-3.59(2 H, m), 3.63(5 H, s), 4.02(2 H, s), 5.95(2 H, s), 6.18(1 H, dd, J = 8.7 Hz, 2.8 Hz), 6.28(1 H, d, J = 2.8 Hz), 6.69-6.78(2 H, m), 6.77(1 H, |

TABLE 357-continued

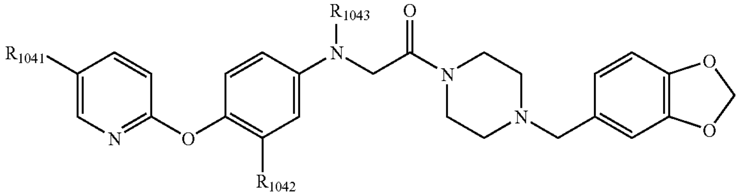

| Example No. | $R_{1041}$ | $R_{1042}$ | $R_{1043}$ | $^1$H NMR ($CDCl_3$) δppm |
|---|---|---|---|---|
| | | | | d, J = 8.8 Hz), 6.85(1 H, s), 6.90(1 H, d, J = 8.7 Hz), 7.35(1 H, d, J = 8.8 Hz), 7.38(2 H, d, J = 8.4 Hz), 7.48(2 H, d, J = 8.4 Hz), 7.79(1 H, brs). |
| 2239 | 3,4-$Cl_2$PhN($CH_3$)CO— | —$OCH_3$ | —$C_2H_5$ | 1.18(3 H, t, J = 7.1 Hz), 2.42(4 H, t, J = 5.0 Hz), 3.42(2 H, s), 3.43(2 H, q, J = 7.1 Hz), 3.45(3 H, s), 3.55(2 H, brs), 3.65(5 H, brs), 4.02(2 H, s), 5.95(2 H, s), 6.19(1 H, dd, J = 8.7 Hz, 2.8 Hz), 6.29(1 H, d, J = 2.8 Hz), 6.71-6.74(3 H, m), 6.85(1 H, brs), 6.87(1 H, dd, J = 8.6 Hz, 2.5 Hz), 6.92(1 H, d, J = 8.7 Hz), 7.20(1 H, d, J = 2.5 Hz), 7.32(1 H, d, J = 8.4 Hz), 7.64(1 H, dd, J = 8.6 Hz, 2.3 Hz), 8.05(1 H, d, J = 1.8 Hz). |
| 2240 | 3,4-$Cl_2PhSO_2N(CH_3)$— | —F | —$CH_3$ | 2.44(2 H, brs), 3.03(3 H, s), 3.19(3 H, s), 3.44(2 H, brs), 3.47(2 H, brs), 3.62(2 H, brs), 4.08(2 H, brs), 4.08(2 H, s), 5.95(2 H, s), 6.41(1 H, dd, J = 8.2 Hz, 3.1 Hz), 6.42-6.50(1 H, m), 6.70-6.79(2 H, m), 6.85(1 H, brs), 6.90(1 H, d, J = 8.7 Hz), 7.04(1 H, t, J = 7.8 Hz), 7.34(1 H, dd, J = 8.4 Hz, 2.2 Hz), 7.50(1 H, dd, J = 8.7 Hz, 2.8 Hz), 7.56(1 H, d, J = 8.4 Hz), 7.72(1 H, d, J = 2.2 Hz), 7.77(1 H, d, J = 2.8 Hz). |

TABLE 358

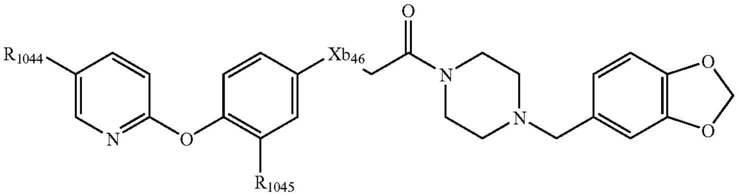

| Example No. | $R_{1044}$ | $R_{1045}$ | $Xb_{46}$ | Form | mp (° C.) or $^1$H NMR |
|---|---|---|---|---|---|
| 2241 | 4-$CF_3$PhCON($CH_3$)— | —$CH_3$ | —N($SO_2CH_3$)— | free | $^1$H NMR ($CDCl_3$) δ 2.05(3 H, s), 2.42(4 H, brs), 3.20(3 H, s), 3.34-3.37(2 H, m), 3.42(2 H, s), 3.48(3 H, s), 3.59-3.61(2 H, m), 4.52(2 H, s), 5.95(2 H, s), 6.70-6.77(2 H, m), 6.84(1 H, brs), 6.86(1 H, d, J = 8.7 Hz), 6.97(1 H, d, J = 8.1 Hz), 7.37-7.51(7 H, m), 7.79(1 H, brs). |
| 2242 | 3,4-$Cl_3$PhCON($CH_3$)— | —$CH_3$ | —N($SO_2CH_3$)— | free | $^1$H NMR ($CDCl_3$) δ 2.09(3 H, s), 2.42(4 H, brs), 3.21(3 H, s), 3.37(2 H, brs), 3.43(2 H, s), 3.46(3 H, s), 3.61(2 H, brs), 4.52(2 H, s), 5.95(2 H, s), 6.70-6.80(2 H, m), 6.84(1 H, brs), 6.89(1 H, d, J = 8.7 Hz), 6.99(1 H, d, J = 8.4 Hz), 7.09(1 H, dd, J = 8.2 Hz, 1.8 Hz), 7.29(1 H, d, J = 8.2 Hz), 7.38(1 H, d, J = 2.0 Hz), 7.42-7.46(3 H, m), 7.80(1 H, d, J = 2.5 |

TABLE 358-continued

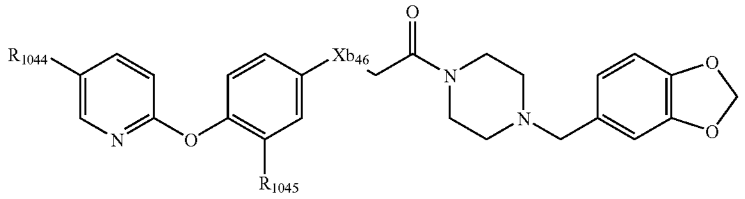

| Example No. | $R_{1044}$ | $R_{1045}$ | $Xb_{46}$ | Form | mp (° C.) or $^1H$ NMR |
|---|---|---|---|---|---|
| | | | | | Hz). |
| 2243 | 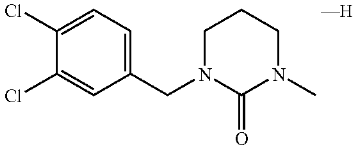 | —H | —$CH_2$— | free | mp 133.0-134.0 |
| 2244 | 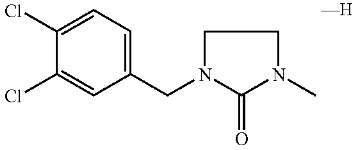 | —H | —$CH_2$— | free | mp 117.0-118.0 |
| 2245 | 4-$CF_3PhN(CH_3)SO_2$— | —H | —$CH_2$— | free | $^1H$ NMR ($CDCl_3$) δ2.33-2.41(4 H, m), 2.63(2 H, t, J = 7.3 Hz), 2.99(2 H, t, J = 7.3 Hz), 3.22(3 H, s), 3.40(4 H, brs), 3.61-3.64(2 H, m), 5.93(2 H, s), 6.69-6.76(2 H, m), 6.84(1 H, s), 6.94(1 H, d, J = 8.7 Hz), 7.06(2 H, d, J = 8.6 Hz), 7.27-7.31(4 H, m), 7.59(2 H, d, J = 8.4 Hz), 7.71(1 H, dd, J = 8.7 Hz, 2.6 Hz), 8.37(1 H, d, J = 2.6 Hz). |
| 2246 | $F_3CCH$═$CHCON(CH_3)$— | —$CH_3$ | —$N(CH_3)$— | hydro-chloride | mp 161.0-164.0 |

TABLE 359

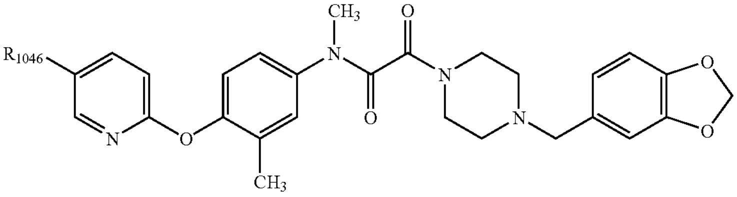

| Example No. | $R_{1046}$ | $^1H$ NMR (solvent) δppm |
|---|---|---|
| 2247 | 3,4-$Cl_2PhCON(CH_3)$— | a mixture of the rotational isomers ($DMSO-d_6$) 1.93(3 H, brs), 2.08-2.42(4 H, m), 3.21-3.56(12 H, m), 5.97-5.99(2 H, m), 6.66-6.89(3 H, m), 6.90-7.07(2 H, m), 7.13-7.32(3 H, m), 7.48-7.54(2 H, m), 7.85-7.89(2 H, m). |
| 2248 | 4-$CF_3PhCON(CH_3)$— | a mixture of the rotational isomers ($DMSO-d_6$) 1.87(3 H, brs), 2.07-2.41(4 H, m), 3.20-3.55(12 H, m), 5.97-5.99(2 H, m), 6.66-6.89(3 H, m), 6.98-7.04(2 H, m), 7.12-7.21(1 H, m), 7.24-7.30(1 H, m), 7.47(2 H, brs), 7.61-7.64(2 H, m), 7.86-7.89(2 H, m). |
| 2249 | 3,4-$Cl_2PhSO_2N(CH_3)$— | ($CDCl_3$) 2.17(3 H, s), 2.23-2.53(4 H, m), 3.21(3 H, brs), 3.32-3.82(9 H, m), 5.93-5.95(2 H, m), 6.65-6.78(3 H, m), 6.85-6.95(1 H, m0, 7.02-7.06(1 H, m), 7.07-7.18(2 H, m), 7.38-7.42(1 H, m), 7.53-7.58(2 H, m), 7.67-7.68(1 H, m), 7.78-7.80(1 H, m). |

TABLE 359-continued

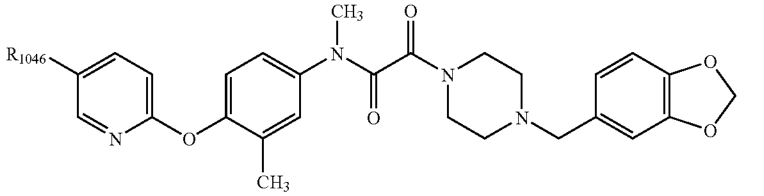

| Example No. | $R_{1046}$ | $^1$H NMR (solvent) δppm |
|---|---|---|
| 2250 | 4-$CF_3PhSO_2N(CH_3)$— | a mixture of the rotational isomers (DMSO-$d_6$) 2.07-2.43(7 H, m), 3.16-3.56(12 H, m), 6.67-6.70(2 H, m), 6.76-6.89(3 H, m), 7.05-7.36(4 H, m), 7.61-7.66(1 H, m), 7.77-7.80(2 H, m), 7.91-7.80(3 H, m). |
| 2251 | 4-$CF_3PhSO_2N(C_2H_5)$— | ($CDCl_3$) 1.13(3 H, t, J = 7.1 Hz), 2.18(3 H, s), 2.23-2.52(4 H, m), 3.32-3.66(11 H, m), 5.93-5.95(2 H, m), 6.66-6.95(4 H, m), 7.04-7.19(3 H, m), 7.46(1 H, dd, J = 8.7 Hz, 2.6 Hz), 7.73-7.80(5 H, m). |

TABLE 360

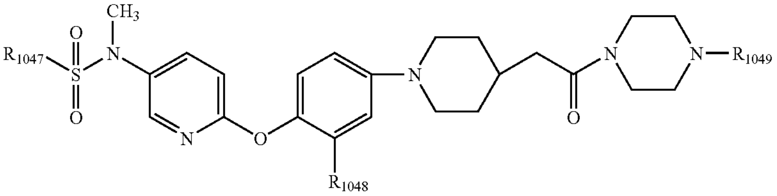

| Example No. | $R_{1047}$ | $R_{1048}$ | $R_{1049}$ | $^1$H NMR ($CDCl_3$) δppm |
|---|---|---|---|---|
| 2252 | 4-$CF_3$Ph- | —H | benzyl | 1.34-1.46(2 H, m), 1.85-2.03(3 H, m), 2.29(2 H, d, J = 6.8 Hz), 2.43(4 H, brs), 2.73(2 H, t, J = 12.0 Hz), 3.19(3 H, s), 3.47-3.65(8 H, m), 6.83(1 H, d, J = 8.7 Hz), 6.92-7.03(4 H, m), 7.26-7.33(5 H, m), 7.48(1 H, dd, J = 8.9 Hz, 2.8 Hz), 7.70-7.78(5 H, m). |
| 2253 | 3.4-$Cl_2$Ph- | —H | piperonyl | 1.33-1.46(2 H, m), 1.85-2.04(3 H, m), 2.29(2 H, d, J = 6.8 Hz), 2.39-2.42(4 H, m), 2.74(2 H, t, J = 12.2 Hz), 3.19(3 H, s), 3.43(2 H, s), 3.46-3.64(6 H, m), 5.94(2 H, s), 6.70-6.77(2 H, m), 6.83(2 H, d, J = 8.9 Hz), 6.92-7.03(4 H, m), 7.38(1 H, dd, J = 8.4 Hz, 2.1 Hz), 7.49(1 H, dd, J = 9.9 Hz, 2.8 Hz), 7.56(1 H, d, J = 8.4 Hz), 7.70(1 H, d, J = 2.1 Hz), 7.81(1 H, d, J = 2.3 Hz). |
| 2254 | 4-$CF_3$Ph- | —H | piperonyl | 1.34-1.46(4 H, m), 1.85-2.02(3 H, m), 2.28(2 H, d, J = 6.8 Hz), 2.39-2.42(4 H, m), 2.74(2 H, t, J = 12.0 Hz), 3.20(3 H, s), 3.43(2 H, s), 3.46-3.64(6H, m), 5.94(2 H, s), 6.70-6.77(2 H, m), 6.81-7.03(6 H, m), 7.49(1 H, dd, J = 8.7 Hz, 2.8 Hz), 7.71-7.78(5 H, m). |
| 2255 | 4-$CF_3$Ph- | —$OCH_3$ | benzyl | 1.31-1.42(2 H, m), 1.86-2.00(3 H, m), 2.29(2 H, d, J = 6.8 Hz), 2.42-2.45(4 H, m), 2.76(2 H, t, J = 12.0 Hz), 3.19(3 H, s), 3.49-3.69(8 H, m), 3.75(3 H, s), 6.51(1 H, dd, J = 8.7 Hz, 2.5 Hz), 6.59(1 H, d, J = 2.5 Hz), 6.83(1 H, d, J = 8.7 Hz), 6.98(1 H, d, J = 8.7 Hz), 7.26-7.33(5 H, m), 7.47(1 H, dd, J = 8.9 Hz, 2.8 Hz), 7.69-7.75(5 H, m). |
| 2256 | 3,4-$Cl_2$Ph- | —H | benzyl | 1.39-1.42(2 H, m), 1.84-2.02(3 H, m), 2.28(2 H, d, J = 6.8 Hz), 2.41-2.45(4 H, m), 2.73(2 H, t, J = 12.2 Hz), 3.19(3 H, s), 3.48-3.95(8 H, m), 6.83(1 H, d, J = 8.7 Hz), 6.92-7.03(4 H, m), 7.27-7.39(6 H, m), 7.48(1 H, dd, J = 8.7 Hz, 2.8 Hz), 7.55(1 H, d, J = 8.4 Hz), 7.70(1 H, d, J = 2.1 Hz), 7.81(1 H, d, J = 2.3 Hz). |
| 2257 | 3,4-$Cl_2$Ph- | —$OCH_3$ | benzyl | 1.34-1.42(2 H, m), 1.82-2.00(3 H, m), 2.29(2 H, d, J = 6.8 Hz), 2.41-2.45(4 H, m), 2.76(2 H, t, J = 12.2 Hz), 3.19(3 H, s), 3.49-3.65(8 H, m), 3.75(3 H, s), 6.51(1 H, dd, J = 8.7 Hz, 2.6 Hz), 6.58(1 H, d, J = 2.6 Hz), 6.84(1 H, d, J = 8.7 Hz), 6.98(1 H, d, J = 8.6 Hz), 7.26-7.39(6 H, m), 7.46(1 H, dd, J = 8.7 |

TABLE 360-continued

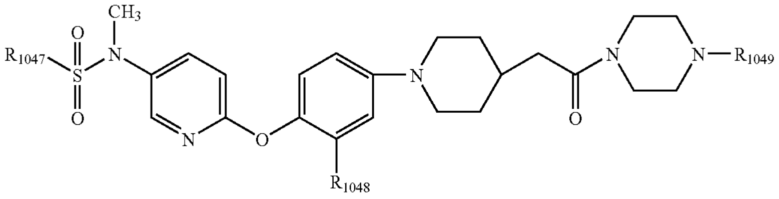

| Example No. | $R_{1047}$ | $R_{1048}$ | $R_{1049}$ | $^1H$ NMR ($CDCl_3$) δppm |
|---|---|---|---|---|
| | | | | Hz, 2.6 Hz), 7.54(1 H, d, J = 8.4 Hz), 7.69(1 H, d, J = 2.0 Hz), 7.78(1 H, d, J = 2.5 Hz). |

TABLE 361

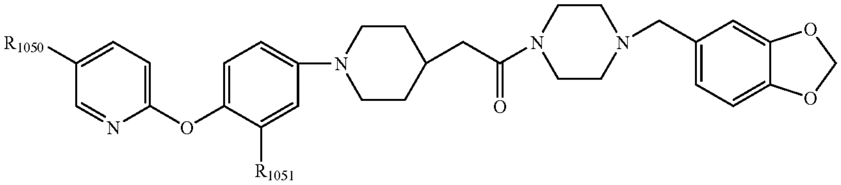

| Example No. | $R_{1050}$ | $R_{1051}$ | $^1H$ NMR ($CDCl_3$) δppm |
|---|---|---|---|
| 2258 | 4-$CF_3$PhN($CH_3$)$SO_2$— | —H | 1.34-1.46(2 H, m), 1.85-2.00(3 H, m), 2.28(2 H, d, J = 6.8 Hz), 2.39-2.43(4 H, m), 2.75(2 H, t, J = 12.2 Hz), 3.21(3 H, s), 3.43(2 H, s), 3.46-3.64(6 H, m), 5.94(2 H, s), 6.70-6.77(2 H, m), 6.85-7.02(6 H, m), 7.26-7.31(2 H, m), 7.59(2 H, d, J = 8.6 Hz), 7.67(1 H, dd, J = 8.7 Hz, 2.6 Hz), 8.39(1 H, d, J = 2.1 Hz). |
| 2259 | 4-$CF_3$Ph$SO_2$N($C_2H_5$)— | —$OCH_3$ | 1.11(3 H, t, J = 7.1 Hz), 1.30-1.42(2 H, m), 1.85-2.00(3 H, m), 2.29(2 H, d, J = 6.8 Hz), 2.39-2.44(4 H, m), 2.76(2 H, t, J = 12.2 Hz), 3.40-3.70(10 H, m), 3.75(3 H, s), 5.94(2 H, s), 6.51(1 H, dd, J = 8.7 Hz, 2.6 Hz), 6.59(1 H, d, J = 2.6 Hz), 6.74-6.87(4 H, m), 6.99(1 H, d, J = 8.7 Hz), 7.37-7.48(2 H, m), 7.54(1 H, d, J = 8.4 Hz), 7.73-7.75(2 H, m). |
| 2260 | 4-$CF_3$Ph$SO_2$N($C_2H_5$)— | —H | 1.11(3 H, t, J = 7.1 Hz), 1.35-1.47(2 H, m), 1.85-2.00(3 H, m), 2.29(2 H, d, J = 6.8 Hz), 2.40-2.42(4 H, m), 2.74(2 H, t, J = 12.0 Hz), 3.42-3.48(4 H, m), 3.57-3.64(6 H, m), 5.94(2 H, s), 6.74-6.77(2 H, m), 6.82-7.04(6 H, m), 7.41(1 H, dd, J = 8.7 Hz, 2.8 Hz), 7.72-7.94(5 H, m). |
| 2261 | 4-$CF_3$Ph$SO_2$N($CH_3$)— | —$OCH_3$ | 1.39-1.47(2 H, m), 1.86-2.00(3 H, m), 2.29(2 H, d, J = 6.8 Hz), 2.41(4 H, brs), 2.76(2 H, t, J = 12.0 Hz), 3.19(3 H, s), 3.43(2 H, s), 3.48(2 H, brs), 3.60(4 H, brs), 3.64(3 H, s), 5.93(2 H, s), 6.51(1 H, dd, J = 8.7 Hz, 2.5 Hz), 6.59(1 H, d, J = 2.5 Hz), 6.74-6.84(4 H, m), 6.98(1 H, d, J = 8.6 Hz), 7.46(1 H, dd, J = 8.7 Hz, 2.6 Hz), 7.69-7.76(5 H, m). |
| 2262 | 4-$CF_3$PhN($CH_3$)$SO_2$— | —$CH_3$ | 1.34-1.45(2 H, m), 1.85-2.01(3 H, m), 2.07(3 H, s), 2.29(2 H, d, J = 6.8 Hz), 2.41-2.43(4 H, m), 2.73(2 H, t, J = 12.0 Hz), 3.22(3 H, s), 3.43(2 H, s), 3.46-3.77(6 H, m), 5.94(2 H, s), 6.74-6.94(7 H, m), 7.29(2 H, d, J = 8.2 Hz), 7.58(2 H, d, J = 8.4 Hz), 7.68(1 H, dd, J = 8.7 Hz, 2.6 Hz), 8.38(1 H, d, J = 2.5 Hz). |
| 2263 | 3,4-$Cl_2$Ph$SO_2$N($CH_3$)— | —$CH_3$ | 1.38-1.41(2 H, m), 1.84-1.98(3 H, m), 2.11(3 H, s), 2.29(2 H, d, J = 6.8 Hz), 2.41(4 H, brs), 2.72(2 H, t, J = 12.0 Hz), 3.19(3 H, s), 3.43-3.64(8 H, m), 5.94(2 H, s), 6.74-6.85(6 H, m), 6.93(1 H, d, J = 8.6 Hz), 7.39(1 H, dd, J = 8.4 Hz, 2.1 Hz), 7.49(1 H, dd, J = 8.7 Hz, 2.8 Hz), 7.56(1 H, d, J = 8.4 Hz), 7.67(1 H, d, J = 2.0 Hz), 7.78(1 H, d, J = 2.3 Hz). |
| 2264 | 3,4-$Cl_2$Ph$SO_2$N($CH_3$)— | —$OCH_3$ | 1.39-1.47(2 H, m), 1.85-2.02(3 H, m), 2.29(2 H, d, J = 6.8 Hz), 2.39-2.44(4 H, m), 2.76(2 H, t, J = 12.2 Hz), 3.19(3 H, s), 3.43(2 H, s), 3.49(2 H, brs), 3.59-3.73(4 H, m), 3.75(3 H, s), 5.94(2 H, s), 6.51(1 H, dd, J = 8.7 Hz, 2.6 Hz), 6.59(1 H, d, J = 2.6 Hz), 6.74-6.85(4 H, m), 6.98(1 H, d, J = 8.6 Hz), 7.38(1 H, dd, |

TABLE 361-continued
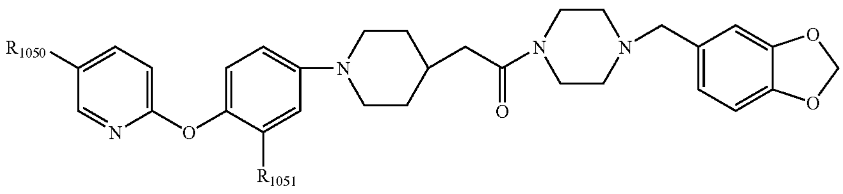
| Example No. | $R_{1050}$ | $R_{1051}$ | $^1H$ NMR ($CDCl_3$) δppm |
|---|---|---|---|
| | | | J = 8.2 Hz, 2.0 Hz), 7.46(1 H, dd, J = 8.7 Hz, 2.8 Hz), 7.55(1 H, d, J = 8.4 Hz), 7.69(1 H, d, J = 2.1 Hz), 7.78(1 H, d, J = 2.8 Hz). |
TABLE 362
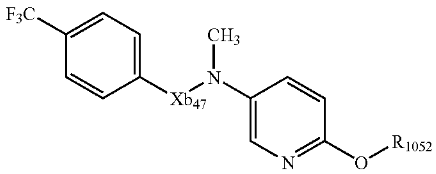
| Example No. | $Xb_{47}$ | $R_{1052}$ | $^1H$ NMR ($CDCl_3$) δppm |
|---|---|---|---|
| 2265 | —CO— | 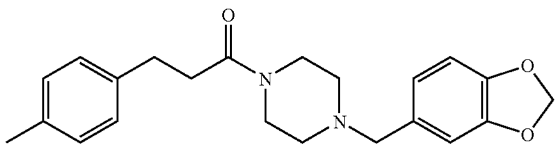 | 2.33(2 H, d, J = 5.1 Hz), 2.38(2 H, d, J = 5.1 Hz), 2.60(2 H, t, J = 5.1 Hz), 2.96(2 H, t, J = 8.0 Hz), 3.33-3.46(2 H, m), 3.40(2 H, s), 3.47(3 H, s), 3.62(2 H, t, J = 2.0 Hz), 5.94(2 H, s), 6.67-6.79(2 H, m), 6.83(1 H, d, J = 8.7 Hz), 6.84(1 H, s), 6.99(2 H, d, J = 8.4 Hz), 7.22(2 H, d, J = 8.4 Hz), 7.34-7.45(1 H, m), 7.40(2 H, d, J = 8.2 Hz), 7.50(2 H, d, J = 8.2 Hz), 7.85(1 H, brs). |
| 2266 | —CO— | 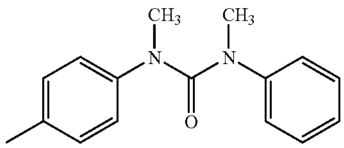 | 3.17(3 H, s), 3.21(3 H, s), 3.48(3 H, s), 6.70(1 H, d, J = 8.7 Hz), 6.72-6.84(6 H, m), 6.95(1 H, t, J = 7.4 Hz), 7.07(2 H, t, J = 7.8 Hz), 7.31-7.45(3 H, m), 7.46-7.58(2 H, m), 7.79-7.92(1 H, m). |
| 2267 | —$SO_2$— | 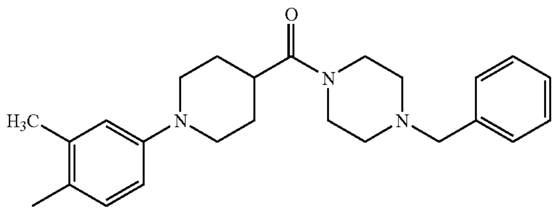 | 1.78-2.04(4 H, m), 2.11(3 H, s), 2.44 (4 H, brs), 2.53-2.76(3 H, m), 3.19(3 H, s), 3.53(4 H, brs), 3.67(4 H, brs), 6.76-6.81(3 H, m), 6.93(1 H, d, J = 8.6 Hz), 7.26-7.33(5 H, m), 7.49(1 H, dd, J = 8.9 Hz, 2.8 Hz), 7.70-7.79(5 H, m). |

TABLE 363

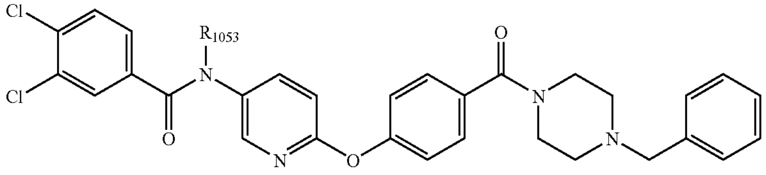

| Example No. | $R_{1053}$ | Form | $^1H$ NMR (DMSO-$d_6$) δppm |
|---|---|---|---|
| 2268 | —$CH_3$ | free | 2.39(4 H, brs), 3.32-3.51(9 H, m), 7.08(1 H, d, J = 8.7 Hz), 7.09(2 H, d, J = 8.4 Hz), 7.25-7.31(6 H, m), 7.41(2 H, d, J = 8.6 Hz), 7.55-7.58(2 H, m), 7.87(1 H, dd, J = 8.7 Hz, 2.8 Hz), 8.03(1 H, brs). |
| 2269 | benzyl | hydro-chloride | 3.12-3.43(8 H, m), 4.33(2 H, s), 5.09(2 H, s), 7.02(1 H, d, J = 8.7 Hz), 7.07(2 H, d, J = 7.8 Hz), 7.26-7.33(6 H, m), 7.45-7.48(5 H, m), 7.55-7.58(3 H, m), 7.67(1 H, brs), 7.77(1 H, d, J = 8.7 Hz), 7.85(1 H, brs), 11.09(1 H, brs). |

Example 2270

Production of 1-(t-butoxycarbonyl)-4-{4-[4-(3,4-dichlorobenzoylamino)phenoxy]phenyl}-4-hydroxypiperidine To a solution of N-[4-(4-bromophenoxy)phenyl]-3,4-dichlorobenzamide (4.94 g, 11.3 mmol) in THF (100 mL) was stirred at −85° C., and added a solution of 2.46 M n-butyl lithium hexane (9.65 mL, 23.7 mmol) dropwise over 10 minutes. Upon stirring for 20 minutes at the same temperature, crystals were precipitated. To this reaction solution was added a solution of 1-(t-butoxycarbonyl)-4-piperidone (2.48 g, 12.4 mmol) in THF (20 mL). The temperature of the solution was raised over 3 hours to −40° C., and then aqueous saturated ammonium chloride was added to the solution. The resulting reaction solution was extracted with ethyl acetate, and dried over anhydrous magnesium sulfate. The solvent was then evaporated, and the residue was purified by silica gel column chromatography (ethyl acetate:n-hexane=2:3 to 1:1), to yield 2.30 g of a white powder. These crystals were washed with ether, to thereby yield 1.80 g of the title compound.

Appearance: White powder

Melting point: 208-209° C.

Example 2271

Production of 1-(t-butoxycarbonyl)-4-(4-{4-[4-(3,4-dichlorobenzoylamino)phenoxy]phenyl}-1,2,5,6-tetrahydropyridine To a solution of 1-(t-butoxycarbonyl)-4-{4-[4-(3,4-dichlorobenzoylamino)phenoxy]phenyl}-4-hydroxypiperidine (1.56 g, 2.80 mmol) in toluene (32 mL) was added p-toluenesulfonic acid hydrate (53 mg, 0.28 mmol), and the resulting solution was refluxed for 18 hours. The resulting reaction solution was purified by silica gel column chromatography (dichloromethane methanol=20:1), to thereby yield 1.35 g of the title compound.

Appearance: White powder

Melting point: 173-174° C.

Example 2272

Production of 1-{4-[4-(3,4-dichlorobenzoylamino)-phenoxy]phenyl}-4-hydroxypiperidine To a solution of 1-{4-[4-(3,4-dichlorobenzoylamino)phenoxy]phenyl}-4-(methoxymethoxy)piperidine (5.50 g, 11.0 mmol) in ethanol (110 mL) was added 2 M hydrochloric acid (55 mL, 110 mmol), and the resulting solution was stirred for 8 hours at 60° C. To the resulting reaction solution was added potassium carbonate (16 g) at room temperature, and the solvent was evaporated under reduced pressure. Water (200 mL) was added to the residue. Precipitated crystals were collected by filtration, to thereby yield 5.0 g of the title compound.

Appearance: Pale brown powder

Melting point: 178-180° C.

Example 2273

Production of 1-(3-{4-[4-(3,4-dichlorobenzoylamino)-phenoxy]phenyl}propionyl)piperazine monohydrochloride To a solution of 1-(t-butoxycarbonyl)-4-(3-{4-[4-(3,4-dichlorobenzoylamino)phenoxy]phenyl}-propionyl)piperazine (2.40 g, 4.01 mmol) in dichloromethane (24 mL) was added trifluoroacetic acid (12 mL) under ice cooling, and the resulting solution was stirred for 3 hours at the same temperature. The solvent was evaporated. To the residue was added acetone (5 mL), and then added a saturated sodium bicarbonate solution to make the solution basic. The formed solids were collected by filtration and dried, whereby 2.00 g of a white powder free form was obtained. This free form (0.500 g) was dissolved in ethanol (10 mL) and 5 M hydrochloric acid (0.4 mL) by heating. The solvent was then evaporated, and the obtained solid was recrystallized from isopropanol, to thereby yield 0.388 g of the title compound.

Appearance: White powder

Melting point: 127-130° C.

The following compounds were produced in the same manner as in Example 2273.

TABLE 364

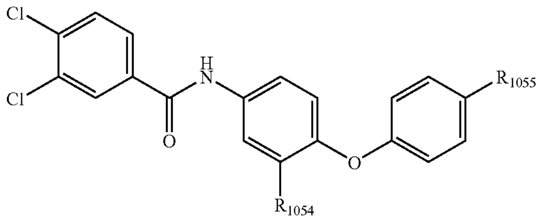

| Example No. | $R_{1054}$ | $R_{1055}$ | Form | mp (° C.) or $^1$H NMR (solvent) δppm |
|---|---|---|---|---|
| 2274 | —F | 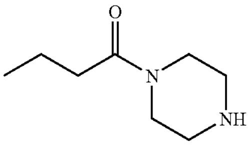 | hydro-chloride | mp 149-151 |
| 2275 | —H | 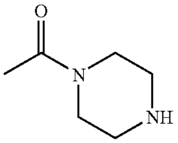 | free | mp 198-199 |
| 2276 | —H | 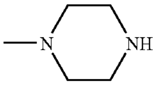 | free | mp 170-174 |
| 2277 | —H | 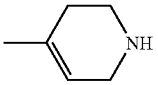 | free | $^1$H NMR ($CDCl_3$) 2.43-2.46(2 H, m), 3.11(2 H, t, J = 5.5 Hz), 3.53(2 H, q, J = 3 Hz), 6.10(1 H, m), 6.97(2 H, d, J = 8.5 Hz), 7.04(2 H, d, J = 9.0 Hz), 7.36(2 H, d, J = 8.5 Hz), 7.56-7.59(3 H, m), 7.68-7.69(2 H, m), 7.97(1 H, d, J = 2.0 Hz). |
| 2278 | —H | 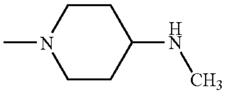 | free | $^1$H NMR (DMSO-$d_6$) 1.32-1.36(2 H, m), 1.85-1.91(2 H, m), 2.32(3 H, s), 2.45(1 H, m), 2.66-2.71(2 H, m), 3.54-3.56(2 H, m), 4.13(1 H, m), 6.89-6.97(6 H, m), 7.65-7.71(3 H, m), 7.82(1 H, d, J = 8.5 Hz), 7.93(1 H, dd, J = 8.5 Hz, 2.0 Hz), 8.21(1 H, d, J = 2.0 Hz), 10.36(1 H, s). |
| 2279 | —H | 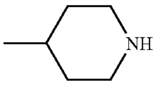 | free | $^1$H NMR ($CDCl_3$) 1.63(2 H, m), 1.83(2 H, brd, J = 14.0 Hz), 2.61(1 H, m), 2.75(2 H, dt, J = 2.5 Hz, 12.0 Hz), 3.20(2 H, brd, J = 12.0 Hz), 6.95(2 H, d, J = 8.5 Hz), 7.03(2 H, d, J = 9.0 Hz), 7.19(2 H, d, J = 8.5 Hz), 7.55(1 H, d, J = 8.0 Hz), 7.58(2 H, d, J = 8.5 Hz), 7.69(1 H, dd, J = 8.0 Hz, 2.0 Hz), 7.69(1 H, brs), 7.97(1 H, d, J = 2.0 Hz). |

TABLE 365

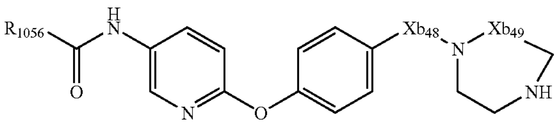

| Example No. | $R_{1056}$ | $Xb_{48}$ | $Xb_{49}$ | Form | $^1$H NMR (solvent) δppm |
|---|---|---|---|---|---|
| 2280 | 3,4-$Cl_2$Ph- | none | —CO— | trifluoro-acetate | (DMSO-$d_6$) 3.56(2 H, brs), 3.87(2 H, m), 3.92(2 H, brs), 7.14(1 H, d, J = 8.8 Hz), 7.20(2 H, dd, J = 6.7 Hz, 2.2 Hz), 7.35((2 H, dd, J = 6.7 Hz, 2.2 Hz), 7.85(1 H, d, J = 8.4 Hz), 7.95(1 H, dd, J = 8.4 Hz, 2.1 Hz), 8.22(1 H, dd, J = 8.8 Hz, 2.7 Hz), 8.23(1 H, d, J = 2.1 Hz), |

TABLE 365-continued

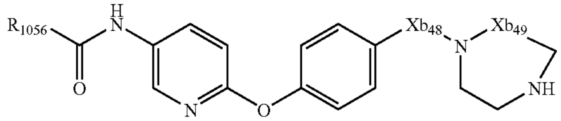

| Example No. | $R_{1056}$ | $Xb_{48}$ | $Xb_{49}$ | Form | $^1$H NMR (solvent) δppm |
|---|---|---|---|---|---|
| | | | | | 8.51(1 H, d, J = 2.7 Hz), 9.30(2 H, brs), 10.59(1 H, s). |
| 2281 | 4-$CF_3$Ph- | none | —$CH_2$— | free | ($CDCl_3$) 3.07(4 H, t, J = 5.0 Hz), 3.15(4 H, t, J = 5.0 Hz), 6.92(1 H, d, J = 9.0 Hz), 6.96(2 H, d, J = 9.0 Hz), 7.06(2 H, d, J = 9.0 Hz), 7.77(1 H, brs), 7.78(2 H, d, J = 8.0 Hz), 7.99(2 H, d, J = 8.0 Hz), 8.19(1 H, brd, J = 9.0 Hz), 8.25(1 H, d, J = 2.5 Hz). |
| 2282 | 3,4-$Cl_2$Ph- | none | —$CH_2$— | free | ($CDCl_3$) 3.18(4 H, dd, J = 5.5 Hz, 2.5 Hz), 3.16(4 H, dd, J = 5.5 Hz, 2.5 Hz), 6.90(1 H, d, J = 9.0 Hz), 6.95(2 H, d, J = 9.0 Hz), 7.05(2 H, d, J = 9.0 Hz), 7.58(1 H, d, J = 8.5 Hz), 7.71(1 H, dd, J = 8.5 Hz, 2.0 Hz), 7.88(1 H, brs), 7.98(1 H, d, J = 2.0 Hz), 8.16(1 H, dd, J = 9.0 Hz, 2.5 Hz), 8.24(1 H, d, J = 2.5 Hz). |
| 2283 | 3,4-$Cl_2$Ph- | —$CH_2$— | —$CH_2$— | free | (DMSO-$d_6$) 2.45-2.47(4 H, m), 2.88-2.92(4 H, m), 3.49(2 H, s), 7.05-7.09(3 H, m), 7.33(2 H, d, J = 8.6 Hz), 7.84(1 H, d, J = 8.6 Hz), 7.95-7.99(1 H, m), 8.18-8.25(2 H, m), 8.51(1 H, d, J = 2.6 Hz), 10.62(1 H, s). |
| 2284 | 3,4-$Cl_2$Ph- | —CO— | —$CH_2$— | free | (DMSO-$d_6$) 2.69(4 H, brs), 3.40(4 H, brs), 7.12-7.17(3 H, s), 7.41-7.44(2 H, m), 7.84(1 H, d, J = 8.4 Hz), 7.96(1 H, dd, J = 8.4 Hz, 2.2 Hz), 8.21-8.26(2 H, m), 8.52(1 H, d, J = 2.7 Hz), 10.62(1 H, brs). |
| 2285 | 4-$CF_3$Ph- | —$CH_2$— | —$CH_2$— | free | (DMSO-$d_6$) 2.44-2.46(4 H, m), 2.89-2.92(4 H, m), 3.49(2 H, s), 4.79(1 H, brs), 7.06-7.09(3 H, m), 7.33(2 H, d, J = 8.6 Hz), 7.94(2 H, d, J = 8.1 Hz), 8.16-8.25(3 H, m), 8.52(1 H, d, J = 2.7 Hz), 10.65(1 H, s). |
| 2286 | 3,4-$(CH_3)_2$Ph- | —CO— | —$CH_2$— | free | (DMSO-$d_6$) 2.29(3 H, s), 2.30(3 H, s), 2.73(4 H, brs), 3.44(4 H, brs), 7.09-7.16(3 H, m), 7.29(1 H, d, J = 7.9 Hz), 7.40-7.44(2 H, m), 7.69-7.72(1 H, m), 7.75(1 H, brs), 8.22-8.26(1 H, m), 8.53(1 H, d, J = 2.8 Hz), 10.31(1 H, s). |

TABLE 366

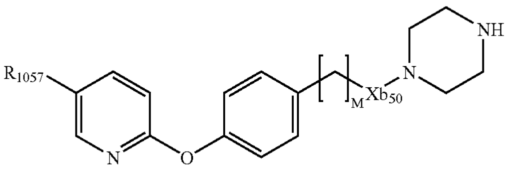

| Example No. | $R_{1057}$ | $Xb_{50}$ | M | $^1$H NMR (solvent) δppm |
|---|---|---|---|---|
| 2287 | 3,4-$Cl_2PhCH_2N(CH_3)$— | none | 1 | (DMSO-$d_6$) 2.51-2.54(4 H, m), 3.00(3 H, s), 3.06-3.08(4 H, m), 3.50(2 H, s), 4.55(2 H, s), 6.88(1 H, d, J = 8.9 Hz), 6.94(2 H, d, J = 8.4 Hz), 7.19-7.32(4 H, m), 7.49(1 H, d, J = 1.5 Hz), 7.58(1 H, d, J = 8.2 Hz), 7.64(1 H, d, J = 3.1 Hz), 8.73(1 H, brs). |
| 2288 | 4-$CF_3$PhCONH— | none | 3 | ($CDCl_3$) 1.77-1.96(6 H, m), 2.35-2.44(6 H, m), 2.61-2.66(2 H, m), 6.92(1 H, d, J = 8.6 Hz), 7.01-7.05(2 H, m), 7.17-7.23(2 H, m), 7.74(2 H, d, J = 8.4 Hz), 8.00(2 H, d, J = 8.4 Hz), 8.21(1 H, dd, J = 8.6 Hz, 2.6 Hz), 8.27-8.28(2 H, m). |

TABLE 366-continued

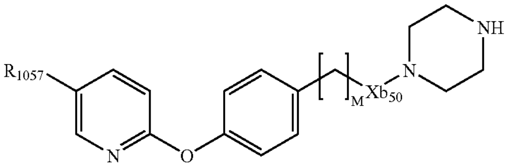

| Example No. | $R_{1057}$ | $Xb_{50}$ | M | $^1$H NMR (solvent) δppm |
|---|---|---|---|---|
| 2289 | 3,4-$Cl_2$PhCONH— | —CO— | 2 | (DMSO-$d_6$) 2.59-2.69(6 H, m), 2.79-2.85(2 H, m), 3.37-3.43(4 H, m), 4.31(1 H, brs), 7.00-7.06(3 H, m), 7.27(2 H, d, J = 8.6 Hz), 7.84(1 H, d, J = 8.4 Hz), 7.95(1 H, dd, J = 8.4 Hz, 2.1 Hz), 8.16-8.22(2 H, m), 8.46(1 H, d, J = 2.3 Hz), 10.54(1 H, s). |
| 2290 | 4-$CF_3$PhCONH— | —COCO— | 1 | ($CDCl_3$) 1.69(1 H, brs), 2.51(2 H, t, J = 5.1 Hz), 2.77(2 H, t, J = 5.1 Hz), 3.15(2 H, t, J = 5.1 Hz), 3.53(2 H, t, 5.1 Hz), 4.05(2 H, s), 6.98(1 H, d, J = 8.7 Hz), 7.11(2 H, d, J = 8.5 Hz), 7.29(2 H, d, J = 8.5 Hz), 7.76(2 H, d, J = 8.2 Hz), 7.99(2 H, d, J = 8.2 Hz), 8.01(1 H, brs), 8.21(1 H, dd, J = 8.7 Hz, 2.7 Hz), 8.25(1 H, d, J = 2.7 Hz). |

Example 2291

[3-(4-{5-[3-(3,4-Dichlorophenyl)ureido]pyridin-2-yloxy}-3-methylphenyl)-2-oxotetrahydropyrimidin-1-yl]acetic acid $^1$H NMR (DMSO-$d_6$) δ 1.87-2.15 (5H, m), 3.25-3.47 (2H, m), 3.58-3.75 (2H, m), 3.95 (2H, s), 6.82-7.00 (2H, m), 7.01-7.12 (1H, m), 7.17 (1H, d, J=2.4 Hz), 7.29-7.32 (1H, m), 7.50 (1H, d, J=8.8 Hz), 7.85 (1H, d, J=2.4 Hz), 7.89-8.02 (1H, m), 8.11 (1H, d, J=2.7 Hz), 8.95 (1H, s), 9.17 (1H, s), 12.50 (1H, s).

The following compounds were produced in the same manner as in Reference Example 922.

TABLE 367

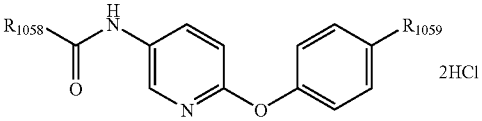

2HCl

| Example No. | $R_{1058}$ | $R_{1059}$ | $^1$H NMR (DMSO-$d_6$) δppm |
|---|---|---|---|
| 2292 | 3,4-$Cl_2$Ph- | 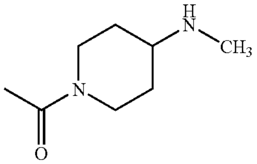 | 1.40-1.65(2 H, m), 1.95-2.18(2 H, m), 2.40-2.65(3 H, m), 3.00(2 H, brs), 3.25(1 H, brs), 3.85(1 H, brs), 4.40(1 H, brs), 7.15(1 H, d, J = 9.0 Hz), 7.19(2 H, d, J = 8.7 Hz), 7.43(2 H, d, J = 8.7 Hz), 7.84(1 H, d, J = 8.4 Hz), 7.99(1 H, dd, J = 8.4 Hz, 2.0 Hz), 8.22-8.30(2 H, m), 8.56(1 H, d, J = 2.0 Hz), 10.71(1 H, s). |
| 2293 | 3,4-$Cl_2$Ph- | 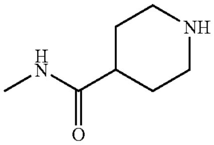 | 1.70-2.05(4 H, m), 2.60-2.80(1 H, m), 2.80-3.05(2 H, m), 3.44(2 H, d, J = 7.1 Hz), 7.03(1 H, d, J = 8.7 Hz), 7.07(2 H, d, J = 8.9 Hz), 7.65(2 H, d, J = 8.9 Hz), 7.84(1 H, d, J = 8.4 Hz), 7.98(1 H, dd, J = 8.4 Hz, 2.0 Hz), 8.20(1 H, dd, J = 8.7 Hz, 2.7 Hz), 8.26(1 H, d, J = 2.0 Hz), 8.50(1 H, d, J = 2.7 Hz), 10.22(1 H, s), 10.65(1 H, s). |
| 2294 | 4-$CF_3$Ph- | 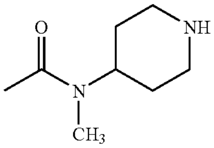 | 1.75-1.90(2 H, m), 1.95-2.30(2 H, m), 2.84(3 H, s), 2.70-3.15(2 H, m), 3.20-3.42(2 H, m), 4.55(1 H, brs), 6.51(1 H, brs), 7.16(1 H, d, J = 8.8 Hz), 7.17(2 H, d, J = 8.4 Hz), 7.47(2 H, d, J = 8.4 Hz), 7.94(2 H, d, J = 8.1 Hz), 8.22(2 H, d, J = 8.1 Hz), 8.31(1 H, dd, J = 8.8 Hz, 2.6 Hz), 8.60(1 H, d, J = 2.6 Hz), 10.84(1 H, s). |

TABLE 368

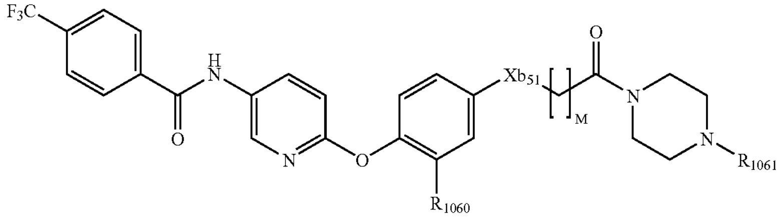

| Example No. | $R_{1060}$ | $R_{1061}$ | $Xb_{51}$ | M | Form | $^1H$ NMR (solvent) δppm |
|---|---|---|---|---|---|---|
| 2295 | —H | —H | none | 0 | dihydro-chloride | (DMSO-$d_6$) 3.16(4 H, brs), 3.75(4 H, brs), 7.16(1 H, d, J = 8.9 Hz), 7.19(2 H, d, J = 8.7 Hz), 7.53(2 H, d, J = 8.7 Hz), 7.93(2 H, d, J = 8.1 Hz), 8.21(2 H, d, J = 8.1 Hz), 8.30(1 H, dd, J = 8.9 Hz, 2.5 Hz), 8.60(1 H, d, J = 2.5 Hz), 10.81(1 H, s). |
| 2296 | —H | —H | none | 2 | dihydro-chloride | (DMSO-$d_6$) 2.68(1 H, d, J = 6.5 Hz), 2.71(1 H, d, J = 8.4 Hz), 2.82(1 H, d, J = 8.4 Hz), 2.84(1 H, d, J = 6.5 Hz), 3.04(4 H, brs), 3.70(4 H, t, J = 5.0 Hz), 7.03(2 H, d, J = 8.6 Hz), 7.05(1 H, d, J = 8.9 Hz), 7.29(2 H, d, J = 8.6 Hz), 7.41(1 H, brs), 7.92(2 H, d, J = 8.5 Hz), 8.21(2 H, d, J = 8.5 Hz), 8.25(1 H, dd, J = 8.9 Hz, 2.8 Hz), 8.54(1 H, d, J = 2.8 Hz), 10.80(1 H, s). |
| 2297 | —$CH_3$ | —H | —$N(CH_3)$— | 1 | free | ($CDCl_3$) 2.11(3 H, s), 2.74-2.96(4 H, m), 3.01(3 H, s), 3.39-3.70(4 H, m), 4.08(2 H, s), 6.54(1 H, dd, J = 8.6 Hz, 3.0 Hz), 6.57(1 H, d, J = 3.0 Hz), 6.81 (1 H, d, J = 8.9 Hz), 6.91(1 H, d, J = 8.6 Hz), 7.75(2 H, d, J = 8.2 Hz), 7.93-8.02(3 H, m), 8.13(1 H, dd, J = 8.9 Hz, 2.7 Hz), 8.24(1 H, d, J = 2.7 Hz). |
| 2298 | —H | —$CH_2CONHNH_2$ | none | 0 | trihydro-chloride | (DMSO-$d_6$) 3.42(4 H, brs), 3.75(4 H, brs), 4.21(2 H, s), 7.17(1 H, d, J = 8.8 Hz), 7.21(2 H, d, J = 8.6 Hz), 7.53 (2 H, d, J = 8.6 Hz), 7.94(2 H, d, J = 8.1 Hz), 8.22(2 H, d, J = 8.1 Hz), 8.31(1 H, dd, J = 8.8 Hz, 2.6 Hz), 8.62(1 H, d, J = 2.6 Hz), 10.87(1 H, s). |

Example 2299

Production of 1-(3-{4-[4-(3,4-dichlorobenzoylamino)-phenoxy]phenyl}propionyl)-4-piperonylpiperazine monohydrochloride To a suspension consisting of 1-(3-{4-[4-(3,4-dichlorobenzoylamino)phenoxy]phenyl}propionyl)-piperazine (0.500 g, 1.00 mmol) and diisopropyl-ethylamine (0.262 mL, 1.50<mmol) in acetonitrile (12 mL) was added piperonyl chloride (0.188 g, 1.10 mmol), and the resulting solution was heated to reflux for 1.5 hours. Water was added to this reaction solution, and extracted with ethyl acetate. The ethyl acetate layer was washed with brine, dried over anhydrous magnesium sulfate, and evaporated. The residue was purified by silica gel column chromatography (dichloromethane:methanol=30:1), to thereby yield 0.486 g of a free form. This free form was dissolved in ethanol (10 mL) and 5 M hydrochloric acid (0.3 mL) by heating. The solvent was then evaporated, and the obtained solid was recrystallized from 90% ethanol (17.5 mL), to thereby yield 0.322 g of the title compound.

Appearance: White powder

Melting point: 221-224° C.

A crude titled product (9.95 g, 14.9 mmol) obtained using the same procedures was recrystallized from 80% ethanol (350 mL), to thereby yield 9.37 g of the title compound.

Appearance: White powder

Melting point: 232-234° C.

The following compounds were produced in the same manner as in Example 2299.

TABLE 369

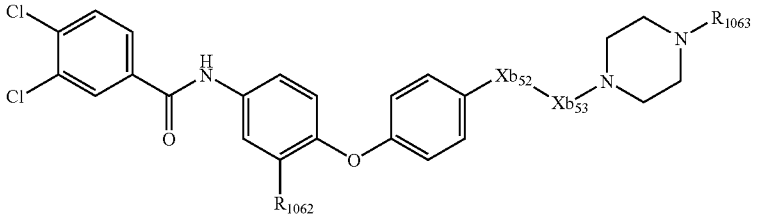

| Example No. | $R_{1062}$ | $Xb_{52}$ | $Xb_{53}$ | $R_{1063}$ | Form | mp (° C.) or $^1H$ NMR ($CDCl_3$) δppm |
|---|---|---|---|---|---|---|
| 2300 | —H | $—(CH_2)_2—$ | —CO— | $—(CH_2)_2Ph$ | hydro-chloride | mp 205-207 |
| 2301 | —H | $—(CH_2)_2—$ | —CO— | $—(CH_2)_2OH$ | hydro-chloride | mp 101-105 |
| 2302 | —H | $—(CH_2)_2—$ | —CO— | $—(CH_2)_2Ph$ | ½ fumarate | mp 156-159 |
| 2303 | —F | $—(CH_2)_2—$ | —CO— | $4-CH_3PhCH_2—$ | free | mp 105-107 |
| 2304 | —F | $—(CH_2)_2—$ | —CO— | $4-CH_3OPhCH_2—$ | free | mp 137-139 |
| 2305 | —F | $—(CH_2)_2—$ | —CO— | $2-CF_3PhCH_2—$ | free | mp 130-132 |
| 2306 | —F | $—(CH_2)_2—$ | —CO— | 2-naphthyl-methyl | hydro-chloride | mp 172-175 |
| 2307 | —H | $—(CH_2)_2—$ | —CO— | $—CH_2COOC_2H_5$ | free | $^1H$ NMR 1.25 (3H, t, J = 7.1 Hz), 2.39-2.53 (4H, m), 2.58 (2H, t, J = 7.8 Hz), 2.90 (2H, t, J = 7.8 Hz), 3.19 (2H, s), 3.36-3.48 (2H, m), 3.58-3.69 (2H, m), 4.16 (2H, q, J = 7.1 Hz), 6.89 (2H, d, J = 8.6 Hz), 6.96 (2H, d, J = 8.9 Hz), 7.12 (2H, d, J = 8.6 Hz), 7.47-7.59 (3H, m), 7.69 (1H, dd, J = 8.3 Hz, 2.1 Hz), 7.96 (1H, d, J = 2.1 Hz), 8.14 (1H, brs). |
| 2308 | —H | none | —CO— | $—(CH_2)_2Ph$ | hydro-chloride | mp 210-218 |
| 2309 | —H | none | none | $—(CH_2)_2Ph$ | free | mp 214-215 |
| 2310 | —H | none | none | benzyl | free | mp 189-190 |
| 2311 | —H | none | none | $—(CH_2)_3Cl$ | free | $^1H$ NMR 2.00 (2H, m), 2.56 (2H, t, J = 7.0 Hz), 2.62-2.64 (4H, m), 3.16-3.18 (4H, m), 3.64 (2H, t, J = 7.0 Hz), 6.92 (2H, d, J = 7.0 Hz), 6.95-6.98 (4H, m), 7.52 (2H, d, J = 9.0 Hz), 7.57 (1H, d, J = 8.0 Hz), 7.69 (1H, dd, J = 8.0 Hz, 2.0 Hz), 7.70 (1H, s), 7.96 (1H, d, J = 2.0 Hz). |
| 2312 | —H | none | none | $—CH_2COOC_2H_5$ | free | $^1H$ NMR 1.30 (3H, t, J = 7.0 Hz), 2.76 (4H, t, J = 5.0 Hz), 3.21 (4H, t, J = 5.0 Hz), 3.28 (2H, s), 4.21 (2H, q, J = 7.0 Hz), 6.91-6.98 (6H, m), 7.52 (2H, d, J = 9.0 Hz), 7.57 (1H, d, J = 8.5 Hz), 7.69 (1H, dd, J = 8.5 Hz, 2.0 Hz), 7.72 (1H, brs), 7.96 (1H, d, J = 2.0 Hz). |

TABLE 370

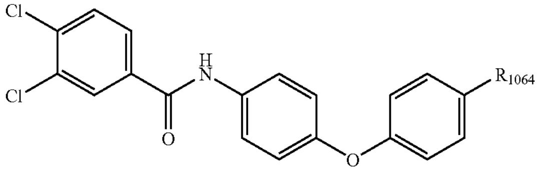

| Example No. | $R_{1064}$ | mp (° C.) or $^1H$ NMR ($CDCl_3$) δppm |
|---|---|---|
| 2313 | 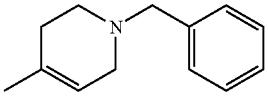 | mp 189-195 |
| 2314 | 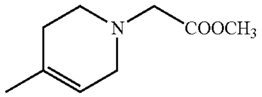 | $^1H$ NMR 2.60 (2H, brs), 2.85 (2H, m), 3.31 (2H, m), 3.39 (2H, s), 3.76 (3H, s), 6.00 (1H, brs), 6.95 (2H, d, J = 8.5 Hz), 7.03 (2H, d, J = 8.5 Hz), 7.34 (2H, d, J = 8.5 Hz), 7.57 (2H, d, J = 8.5 Hz), 7.57 (1H, brs), 7.70 (1H, d, J = 7.0 Hz), 7.75 (1H, brs), 7.97 (1H, s). |
| 2315 | 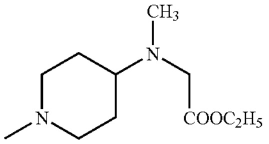 | $^1H$ NMR 1.28 (3H, t, J = 7.0 Hz), 1.60-1.70 (2H, m), 1.93-1.96 (2H, m), 2.46 (3H, s), 2.60-2.72 (3H, m), 3.37 (2H, s), 3.64-3.66 (2H, m), 4.20 (2H, q, J = 7.0 Hz), 6.93-6.98 (6H, m), 7.52 (2H, m), 7.57 (1H, d, J = 8.5 Hz), 7.68-7.70 (2H, m), 7.96 (1H, d, J = 2.0 Hz). |
| 2316 | 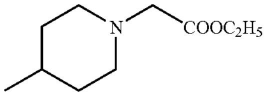 | $^1H$ NMR 1.29 (3H, t, J = 7.0 Hz), 1.81-1.88 (4H, m), 2.30 (2H, brt, J = 11.0 Hz), 2.49 (1H, m), 3.06 (2H, brd, J = 11.0 Hz), 4.21 (2H, q, J = 7.0 Hz), 6.94 (2H, d, J = 8.5 Hz), 7.01 (2H, d, J = 9.0 Hz), 7.18 (2H, d, J = 8.5 Hz), 7.55-7.68 (3H, m), 7.69 (1H, d, J = 2.0 Hz), 7.75 (1H, brs), 7.97 (1H, d, J = 2.0 Hz). |
| 2317 | 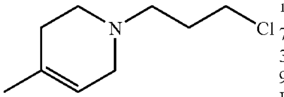 | $^1H$ NMR 2.04 (2H, m), 2.56 (2H, brs), 2.62 (2H, t, J = 7.0 Hz), 2.72 (2H, t, J = 5.5 Hz), 3.17 (2H, brs), 3.64 (2H, t, J = 6.5 Hz), 6.02 (1H, brs), 6.96 (2H, d, J = 9.0 Hz), 7.04 (2H, d, J = 9.0 Hz), 7.36 (2H, d, J = 9.0 Hz), 7.58 (3H, m), 7.70 (1H, dd, J = 8.5 Hz, 2.0 Hz), 7.77 (1H, brs), 7.98 (1H, d, J = 2.0 Hz). |

TABLE 371

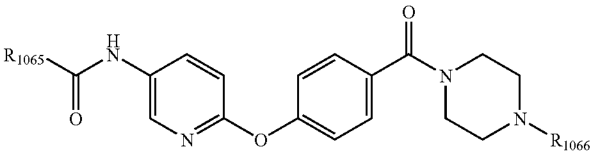

| Example No. | $R_{1065}$ | $R_{1066}$ | $^1H$ NMR (solvent) δppm |
|---|---|---|---|
| 2318 | 4-$CF_3$Ph- | —$(CH_2)_2$Ph | (DMSO-$d_6$) 2.31-2.60 (6H, m), 2.67-2.81 (2H, m), 3.51 (4H, brs), 7.16 (1H, d, J = 8.8 Hz), 7.17 (2H, d, J = 8.5 Hz), 7.10-7.33 (5H, m), 7.44 (2H, d, J = 8.5 Hz), 7.94 (2H, d, J = 8.2 Hz), 8.17 (2H, d, J = 8.2 Hz), 8.26 (1H, dd, J = 8.8 Hz, 2.6 Hz), 8.55 (1H, d, J = 2.6 Hz), 10.67 (1H, s). |
| 2319 | 3,4-$Cl_2$Ph- | 4-CNPh$CH_2$— | ($CDCl_3$) 2.46 (4H, brs), 3.59 (2H, s), 3.75 (4H, brs), 6.97 (1H, d, J = 8.9 Hz), 7.11-7.14 (2H, m), 7.40-7.43 (2H, m), 7.46 (2H, d, J = 7.8 Hz), 7.56-7.65 (3H, m), 7.72-7.76 (1H, m), 8.02 (1H, d, J = 2.2 Hz), 8.16 (1H, dd, J = 8.9 Hz, 2.7 Hz), 8.27 (1H, brs), 8.30 (1H, d, J = 2.7 Hz). |
| 2320 | 3,4-$Cl_2$Ph- | —$CH_2$COPh | ($CDCl_3$) 2.65 (4H, brs), 3.60-3.82 (4H, m), 3.89 (2H, s), 6.99 (1H, d, J = 8.7 Hz), 7.15 (2H, d, J = 8.6 Hz), 7.43-7.50 (4H, m), 7.56-7.60 (2H, m), 7.72-7.76 (1H, m), 7.97-8.02 (3H, m), 8.13-8.21 (2H, m), 8.30 (1H, d, J = 2.5 Hz). |
| 2321 | 3,4-$Cl_2$Ph- | 3,4-$(CH_3)_2$Ph$CH_2$— | ($CDCl_3$) 2.25 (3H, s), 2.26 (3H, s), 2.44 (4H, brs), 3.47 (2H, s), 3.73 (4H, brs), 6.89 (1H, d, J = 8.9 |

TABLE 371-continued

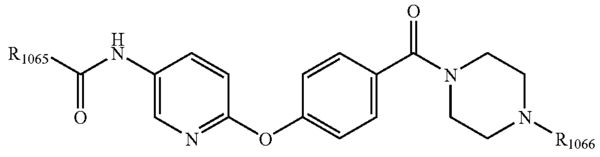

| Example No. | $R_{1065}$ | $R_{1066}$ | $^1H$ NMR (solvent) δppm |
|---|---|---|---|
| | | | Hz), 7.01-7.10 (5H m) 7.32-7.36 (2H, m), 7.51 (1H, d, J = 8.4 Hz), 7.74-7.78 (1H, m), 8.05 (1H, d, J = 8.1 Hz), 8.09 (1H, dd, J = 8.8 Hz, 2.7 Hz), 8.30 (1H, d, J = 2.7 Hz), 9.06 (1H, brs). |
| 2322 | 3,4-$Cl_2$Ph- | 4-$C(CH_3)_3$COPh$CH_2$— | ($CDCl_3$) 1.36 (9H, s), 2.48 (4H, brs), 3.58 (2H, s), 3.70 (4H, brs), 6.96 (1H, d, J = 8.7 Hz), 7.11-7.14 (2H, m), 7.39-7.43 (4H, m), 7.57 (1H, d, J = 8.4 Hz), 7.69 (2H, d, J = 8.3 Hz), 7.73-7.77 (1H, m), 8.03 (1H, d, J = 2.0 Hz), 8.15 (1H, dd, J = 8.9 Hz, 2.7 Hz), 8.30 (1H, d, J = 2.7 Hz), 8.37 (1H, brs). |
| 2323 | 3,4-$Cl_2$Ph- | 4-Ph$CH_2$OPh$CH_2$— | ($CDCl_3$) 2.45 (4H, brs), 3.49 (2H, s), 3.73 (4H, brs), 5.06 (2H, s), 6.92-6.98 (3H, m), 7.11-7.15 (2H, m), 7.23 (2H, d, J = 8.6 Hz), 7.32-7.46 (7H, m), 7.57 (1H, d, J = 8.1 Hz), 7.75 (1H, dd, J = 8.4 Hz, 2.2 Hz), 8.03 (1H, d, J = 2.2 Hz), 8.16 (1H, dd, J = 8.9 Hz, 2.7 Hz), 8.26 (1H, brs), 8.29 (1H, d, J = 2.7 Hz). |
| 2324 | 3,4-$Cl_2$Ph- | 4-$C(CH_3)_3$Ph$CH_2$— | ($CDCl_3$) 1.32 (9H, s), 2.48 (4H, brs), 3.53 (2H, s), 3.70 (4H, brs), 6.98 (1H, d, J = 8.4 Hz), 7.13 (2H, d, J = 8.6 Hz), 7.21-7.27 (2H, m), 7.36 (2H, d, J = 8.4 Hz), 7.43 (2H, d, J = 8.6 Hz), 7.59 (1H, d, J = 8.1 Hz), 7.72-7.76 (1H, m), 8.02 (1H, d, J = 2.2 Hz), 8.13 (1H brs), 8.16-8.20 (1H, m), 8.30 (1H, d, J = 2.2 Hz). |
| 2325 | 3,4-$Cl_2$Ph- | 3-$CH_3$Ph$CH_2$— | ($CDCl_3$) 2.36 (3H, s), 2.47 (4H, brs), 3.52 (2H, s), 3.74 (4H, brs), 6.97 (1H, d, J = 8.7 Hz), 7.08-7.26 (6H, m), 7.41-7.44 (2H, m), 7.58 (1H, d, J = 8.4 Hz), 7.76 (1H, dd, J = 8.4 Hz, 2.1 Hz), 8.04 (1H, d, J = 2.1 Hz), 8.14-8.19 (1H, m), 8.26 (1H, brs), 8.30 (1H, d, J = 2.2 Hz). |

TABLE 372

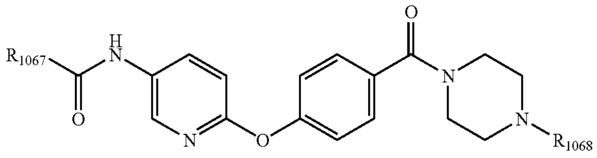

| Example No. | $R_{1067}$ | $R_{1068}$ | $^1H$ NMR ($CDCl_3$) δppm |
|---|---|---|---|
| 2326 | 3,4-$Cl_2$Ph- | 4-$CH(CH_3)_2$Ph$CH_2$— | 1.25 (6H, d, J = 7.3 Hz), 2.46 (4H, brs), 2.85-2.96 (1H, m), 3.52 (2H, s), 3.75 (4H, brs), 6.95 (1H, d, J = 8.9 Hz), 7.10-7.13 (2H, m), 7.17-7.26 (4H, m), 7.38-7.42 (2H, m), 7.57 (1H, d, J = 8.1 Hz), 7.75 (1H, dd, J = 8.4 Hz, 2.2 Hz), 8.04 (1H, d, J = 2.2 Hz), 8.14 (1H, dd, J = 8.9 Hz, 2.7 Hz), 8.30 (1H, d, J = 2.7 Hz), 8.41 (1H, brs). |
| 2327 | 3,4-$Cl_2$Ph- | 4-$CH_3$Ph$CH_2$— | 2.34 (3H, s), 2.45 (4H, brs), 3.51 (2H, s), 3.73 (4H, brs), 6.93 (1H, d, J = 8.7 Hz), 7.07-7.22 (6H, m), 7.35-7.38 (2H, m), 7.54 (1H, d, J = 8.4 Hz), 7.77 (1H, dd, J = 8.4 Hz, 2.2 Hz), 8.05 (1H, d, J = 2.2 Hz), 8.12 (1H, dd, J = 8.9 Hz, 2.7 Hz), 8.30 (1H, d, J = 2.7 Hz), 8.82 (1H, s). |
| 2328 | 3,4-$Cl_2$Ph- | 3,4-$F_2$Ph$CH_2$— | 2.45 (4H, brs), 3.49-3.73 (6H, m), 6.96 (1H, d, J = 8.7 Hz), 7.01-7.23 (5H, m), 7.39-7.42 (2H, m), 7.56 (1H, d, J = 8.4 Hz), 7.76 (1H, dd, J = 8.4 Hz, 2.1 Hz), 8.03 (1H, d, J = 2.1 Hz), 8.17 (1H, dd, J = 8.7 Hz, 2.7 Hz), 8.30 (1H, d, J = 2.7 Hz), 8.50 (1H, s). |
| 2329 | 3,4-$Cl_2$Ph- | 4-$CH_3$OPh$CH_2$— | 2.43 (4H, brs), 3.48 (2H, s), 3.73 (4H, brs), 3.81 (3H, s), 6.85-6.93 (3H, m), 7.06-7.10 (2H, m), |

TABLE 372-continued

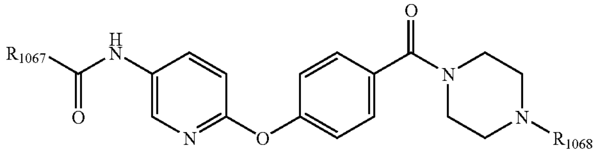

| Example No. | $R_{1067}$ | $R_{1068}$ | $^1$H NMR ($CDCl_3$) δppm |
|---|---|---|---|
| | | | 7.21-7.24 (2H, m) 7.34-7.37 (2H, m), 7.53 (1H, d, J = 8.4 Hz), 7.77 (1H, dd, J = 8.4 Hz, 2.1 Hz), 8.05 (1H, d, J = 2.1 Hz), 8.10 (1H, dd, J = 8.9 Hz, 2.7 Hz), 8.30 (1H, d, J = 2.7 Hz), 8.90 (1H, s). |
| 2330 | 4-$CF_3$Ph- | 4-$CF_3PhCH_2$— | 2.48 (4H, brs), 3.60 (2H, s), 3.70 (4H, brs), 7.00 (1H, d, J = 8.9 Hz), 7.12-7.17 (2H, m), 7.41-7.48 (4H, m), 7.60 (2H, d, J = 7.9 Hz), 7.77 (2H, d, J = 8.1 Hz), 8.02 (2H, d, J = 8.1 Hz), 8.14 (1H, brs), 8.19-8.24 (1H, m), 8.32 (1H, d, J = 2.3 Hz). |
| 2331 | 4-$CF_3$Ph- | 3,4-$(CH_3)_2PhCH_2$— | 2.25 (3H, s), 2.26 (3H, s), 2.45 (4H, brs), 3.47 (2H, s), 3.40-3.90 (4H, m), 6.98 (1H, d, J = 8.7 Hz), 6.97-7.10 (3H, m), 7.13 (2H, d, J = 8.7 Hz), 7.42 (2H, d, J = 8.7 Hz), 7.76 (2H, d, J = 8.1 Hz), 8.02 (2H, d, J = 8.1 Hz), 8.18 (1H, brs), 8.20 (1H, dd, J = 8.7 Hz, 2.5 Hz), 8.31 (1H, d, J = 2.5 Hz). |
| 2332 | 4-$CF_3$Ph- | 3-$CH_3PhCH_2$— | 2.35 (3H, s), 2.46 (4H, brs), 3.35-3.90 (4H, m), 3.50 (2H, s), 6.98 (1H, d, J = 8.9 Hz), 7.12 (2H, d, J = 8.6 Hz), 7.05-7.30 (4H, m), 7.41 (2H, d, J = 8.6 Hz), 7.76 (2H, d, J = 8.1 Hz), 8.02 (2H, d, J = 8.1 Hz), 8.19 (1H, dd, J = 8.9 Hz, 2.6 Hz), 8.28 (1H, brs), 8.31 (1H, d, J = 2.6 Hz). |
| 2333 | 4-$CF_3$Ph- | 4-$CH_3PhCH_2$— | 2.34 (3H, s), 2.44 (4H, brs), 3.50 (2H, s), 3.35-3.85 (4H, m), 6.97 (1H, d, J = 8.9 Hz), 7.12 (2H, d, J = 8.8 Hz), 7.12 (2H, d, J = 8.1 Hz), 7.20 (2H, d, J = 8.1 Hz), 7.40 (2H, d, J = 8.8 Hz), 7.75 (2H, d, J = 8.1 Hz), 8.02 (2H, d, J = 8.1 Hz), 8.18 (1H, dd, J = 8.9 Hz, 2.5 Hz), 8.32 (1H, d, J = 2.5 Hz), 8.38 (1H, s). |

TABLE 373

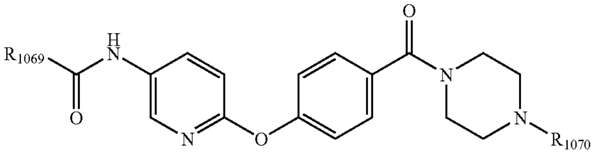

| Example No. | $R_{1069}$ | $R_{1070}$ | $^1$H NMR ($CDCl_3$) δppm |
|---|---|---|---|
| 2334 | 3,4-$Cl_2$Ph- | 3-$CH_3OPhCH_2$— | 2.47 (4H, brs), 3.46-3.82 (6H, m), 3.86 (3H, s), 6.80-6.84 (1H, m), 6.88-6.92 (2H, m) 6.95 (1H, d, J = 8.8 Hz), 7.10-7.13 (2H, m), 7.23 (1H, d, J = 8.1 Hz), 7.38-7.41 (2H, m), 7.56 (1H, d, J = 8.3 Hz), 7.73-7.77 (1H, m), 8.04 (1H, d, J = 2.1 Hz), 8.12-8.16 (1H, m), 8.29 (1H, d, J = 2.7 Hz), 8.44 (1H, brs). |
| 2335 | 3,4-$Cl_2$Ph- | 2-quinolylmethyl | 2.58 (4H, brs), 3.58-3.76 (4H, m), 3.88 (2H, s), 6.94 (1H, d, J = 8.8 Hz), 7.11 (2H, d, J = 8.4 Hz), 7.40 (2H, d, J = 8.6 Hz), 7.51-7.57 (2H, m), 7.62 (1H, d, J = 8.4 Hz), 7.68-7.84 (3H, m), 8.04 (1H, d, J = 2.1 Hz), 8.07 (1H, d, J = 8.6 Hz), 8.12-8.17 (2H, m), 8.29 (1H, d, J = 2.5 Hz), 8.65 (1H, brs). |
| 2336 | 3,4-$Cl_2$Ph- | 4-$CF_3PhCH_2$— | 2.47 (4H, brs), 3.44-3.85 (6H, m), 6.98 (1H, d, J = 8.9 Hz), 7.11-7.16 (2H, m), 7.39-7.48 (4H, m), 7.56-7.61 (3H, m), 7.75 (1H, dd, J = 8.4 Hz, 2.1 Hz), 8.02 (1H, d, J = 2.1 Hz), 8.14-8.18 (1H, m), 8.24 (1H, brs), 8.30 (1H, d, J = 2.6 Hz). |
| 2337 | 3,4-$Cl_2$Ph- | 4-$CF_3OPhCH_2$— | 2.46 (4H, brs), 3.46-3.84 (6H, m), 6.96 (1H, d, J = 8.9 Hz), 7.10-7.20 (4H, m), 7.34-7.41 (4H, m), 7.56 (1H, d, J = 8.4 Hz), 7.76 (1H, dd, J = 8.4 Hz, 2.1 Hz), 8.03 (1H, d, J = 2.1 Hz), 8.11-8.16 (1H, m), 8.30 (1H, d, J = 2.5 Hz), 8.49 (1H, brs). |

TABLE 373-continued

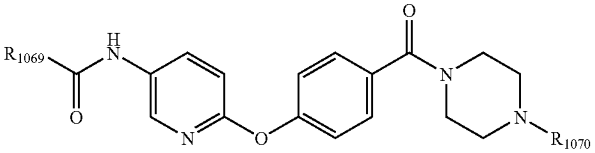

| Example No. | $R_{1069}$ | $R_{1070}$ | $^1H$ NMR ($CDCl_3$) δppm |
|---|---|---|---|
| 2338 | 3,4-$Cl_2$Ph- | PhO$(CH_2)_2$— | 2.60 (4H, brs), 2.85 (2H, t, J = 5.4 Hz), 3.53-3.75 (4H, m), 4.12 (2H, t, J = 5.4 Hz), 6.88-6.99 (4H, m), 7.06-7.13 (2H, m), 7.25-7.37 (4H, m), 7.51 (1H, d, J = 8.4 Hz), 7.77 (1H, dd, J = 8.4 Hz, 2.1 Hz), 8.05 (1H, d, J = 2.1 Hz), 8.07-8.12 (1H, m), 8.32 (1H, d, J = 2.6 Hz), 9.10 (1H, brs). |
| 2339 | 4-$CF_3$Ph- | 4-CNPh$CH_2$— | 2.45 (4H, brs), 3.58 (2H, s), 3.63 (4H, brs), 6.98 (1H, d, J = 8.8 Hz), 7.13 (2H, d, J = 8.7 Hz), 7.41 (2H, d, J = 8.7 Hz), 7.46 (2H, d, J = 8.1 Hz), 7.62 (2H, d, J = 8.1 Hz), 7.75 (2H, d, J = 8.1 Hz), 8.01 (2H, d, J = 8.1 Hz), 8.20 (1H, dd, J = 8.8 Hz, 2.6 Hz), 8.28 (1H, brs), 8.33 (1H, d, J = 2.6 Hz). |
| 2340 | 4-$CF_3$Ph- | 3,4-$F_2$Ph$CH_2$— | 2.44 (4H, brs), 3.48 (2H, s), 3.64 (4H, brs), 6.98 (1H, d, J = 8.9 Hz), 6.97-7.25 (3H, m), 7.12 (2H, d, J = 8.7 Hz), 7.41 (2H, d, J = 8.7 Hz), 7.75 (2H, d, J = 8.0 Hz), 8.01 (2H, d, J = 8.0 Hz), 8.19 (1H, dd, J = 8.9 Hz, 2.3 Hz), 8.30 (1H, brs), 8.32 (1H, d, J = 2.3 Hz). |
| 2341 | 4-$CF_3$Ph- | 4-$CH_3$OPh$CH_2$— | 2.43 (4H, brs), 3.48 (2H, s), 3.60 (4H, brs), 3.80 (3H, s), 6.86 (2H, d, J = 8.7 Hz), 6.96 (1H, d, J = 8.7 Hz), 7.11 (2H, d, J = 8.7 Hz), 7.22 (2H, d, J = 8.7 Hz), 7.38 (2H, d, J = 8.7 Hz), 7.74 (2H, d, J = 8.1 Hz), 8.02 (2H, d, J = 8.1 Hz), 8.17 (1H, dd, J = 8.7 Hz, 2.4 Hz), 8.32 (1H, d, J = 2.4 Hz), 8.52 (1H, s). |

TABLE 374

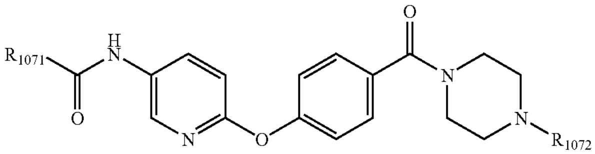

| Example No. | $R_{1071}$ | $R_{1072}$ | mp (° C.) or $^1H$ NMR ($CDCl_3$) δppm |
|---|---|---|---|
| 2342 | 3,4-$(CH_3)_2$Ph- | 4-CNPh$CH_2$— | $^1H$ NMR 2.33 (6H, s), 2.45 (4H, brs), 3.58 (2H, s), 3.64 (4H, brs), 6.97 (1H, d, J = 8.7 Hz), 7.11-7.16 (2H, m), 7.24 (1H, d, J = 7.6 Hz), 7.41-7.47 (4H, m), 7.58-7.67 (4H, m), 7.94 (1H, brs), 8.24 (1H, dd, J = 8.7 Hz, 2.7 Hz), 8.31 (1H, d, J = 2.7 Hz). |
| 2343 | 3,4-$(CH_3)_2$Ph- | 3,4-$F_2$Ph$CH_2$— | $^1H$ NMR 2.34 (6H, s), 2.45 (4H, brs), 3.48 (2H, s), 3.65 (4H, brs), 6.98 (1H, d, J = 8.9 Hz), 7.03-7.23 (6H, m), 7.41-7.46 (2H, m), 7.59-7.62 (1H, m), 7.67 (1H, d, J = 1.8 Hz), 7.95 (1H, brs), 8.26 (1H, dd, J = 8.9 Hz, 2.7 Hz), 8.31 (1H, d, J = 2.7 Hz). |
| 2344 | 4-$CF_3$Ph- | 3-$CH_3$OPh$CH_2$— | mp 118-120 |
| 2345 | 4-$CF_3$Ph- | 2-quinolylmethyl | $^1H$ NMR 2.56 (4H, brs), 3.43-3.81 (4H, m), 3.87 (2H, s), 6.94 (1H, d, J = 8.9 Hz), 7.08-7.13 (2H, m), 7.35-7.40 (2H, m), 7.51-7.57 (1H, m), 7.61 (1H, d, J = 8.4 Hz), 7.68-7.74 (3H, m), 7.81-7.84 (1H, m), 8.01-8.20 (5H, m), 8.33 (1H, d, J = 2.7 Hz), 8.94 (1H, s). |
| 2346 | 4-$CF_3$Ph- | PhO$(CH_2)_2$— | mp 161-162 |

TABLE 374-continued

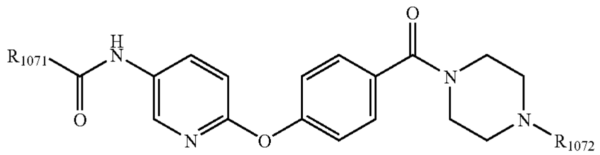

| Example No. | $R_{1071}$ | $R_{1072}$ | mp (° C.) or $^1$H NMR ($CDCl_3$) δppm |
|---|---|---|---|
| 2347 | 4-$CF_3$Ph- | 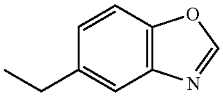 | $^1$H NMR 2.48 (4H, brs), 3.55 (2H, brs), 3.66 (2H, s), 3.75 (2H, brs), 6.97 (1H, d, J = 8.7 Hz), 7.12 (2H, d, J = 8.4 Hz), 7.32-7.43 (1H, m), 7.41 (2H, d, J = 8.4 Hz), 7.55 (1H, d, J = 8.4 Hz), 7.70-7.80 (1H, m), 7.75 (2H, d, J = 8.1 Hz), 8.02 (2H, d, J = 8.1 Hz), 8.10 (1H, s), 8.20 (1H, dd, J = 8.7 Hz, 2.6 Hz), 8.32 (1H, d, J = 2.6 Hz), 8.41 (1H, s). |

TABLE 375

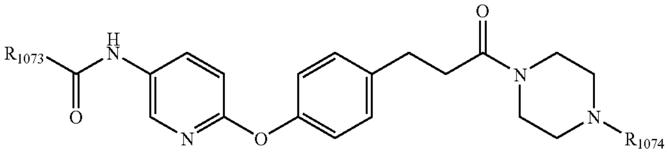

| Example No. | $R_{1073}$ | $R_{1074}$ | $^1$H NMR ($CDCl_3$) δppm |
|---|---|---|---|
| 2348 | 3,4-$Cl_2$Ph- | 2,6-$F_2PhCH_2$— | 2.42 (4H, brs), 2.54-2.60 (2H, m), 2.83-2.88 (2H, m), 3.38-3.42 (2H, m), 3.55-3.58 (2H, m), 3.69 (2H, s), 6.85-6.98 (5H, m), 7.12 (2H, d, J = 8.6 Hz), 7.19-7.31 (1H, m), 7.48 (1H, d, J = 8.4 Hz), 7.74 (1H, dd, J = 8.4 Hz, 2.1 Hz), 7.99 (1H, d, J = 2.1 Hz), 8.14-8.18 (1H, m), 8.30 (1H, d, J = 2.8 Hz), 9.19 (1H, brs). |
| 2349 | 3,4-$Cl_2$Ph- | 4-$CF_3PhCH_2$— | 2.33-2.41 (4H, m), 2.59-2.65 (2H, m), 2.92-2.97 (2H, m), 3.40-3.44 (2H, m), 3.55 (2H, s), 3.61-3.64 (2H, m), 6.93 (1H, d, J = 8.8 Hz), 7.02-7.06 (2H, m), 7.20 (2H, d, J = 8.6 Hz), 7.44 (2H, d, J = 8.4 Hz), 7.54-7.60 (3H, m), 7.74 (1H, dd, J = 8.4 Hz, 2.2 Hz), 8.01 (1H, d, J = 2.2 Hz), 8.17-8.21 (1H, m), 8.28 (1H, d, J = 2.6 Hz), 8.44 (1H, brs). |
| 2350 | 4-$CF_3$Ph- | 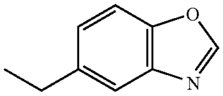 | 2.28 (2H, t, J = 4.9 Hz), 2.43 (2H, t, J = 4.9 Hz), 2.61 (2H, t, J = 7.5 Hz), 2.96 (2H, t, J = 7.5 Hz), 3.30 (2H, t, J = 4.9 Hz), 3.59 (2H, s), 3.63 (2H, t, J = 4.9 Hz), 6.96 (1H, d, J = 8.3 Hz), 7.04 (2H, d, J = 8.5 Hz), 7.21 (2H, d, J = 8.5 Hz), 7.36 (1H, dd, J = 8.5 Hz, 1.5 Hz), 7.53 (1H, d, J = 8.4 Hz), 7.73 (1H, brs), 7.75 (2H, d, J = 8.3 Hz), 8.01 (1H, s), 8.02 (2H, d, J = 8.3 Hz), 8.25 (1H, s), 8.27 (1H, dd, J = 8.3 Hz, 2.6 Hz), 8.58 (1H, s). |
| 2351 | 3,4-$Cl_2$Ph- | 3,4-$F_2PhCH_2$— | 2.31-2.40 (4H, m), 2.60-2.65 (2H, m), 2.93-2.99 (2H, m), 3.39-3.45 (4H, m), 3.61-3.65 (2H, m), 6.95 (1H, d, J = 8.8 Hz), 7.03-7.24 (7H, m), 7.57 (1H, d, J = 8.3 Hz), 7.73 (1H, dd, J = 8.4 Hz, 2.1 Hz), 8.00 (1H, d, J = 2.1 Hz), 8.10 (1H, brs), 8.16-8.20 (1H, m), 8.26 (1H, d, J = 2.3 Hz). |
| 2352 | 3,4-$Cl_2$Ph- | 3,5-$F_2PhCH_2$— | 2.32-2.38 (4H, m), 2.58-2.64 (2H, m), 2.89-2.94 (2H, m), 3.40-3.46 (4H, m), 3.59-3.62 (2H, m), 6.66-6.74 (1H, m), 6.85-7.03 (5H, m), 7.17 (2H, d, J = 8.6 Hz), 7.52 (1H, d, J = 8.2 Hz), 7.71-7.75 (1H, m), 7.99 (1H, d, J = 2.0 Hz), 8.16-8.20 (1H, m), 8.28 (1H, d, J = 2.6 Hz), 8.77 (1H, brs). |

TABLE 376

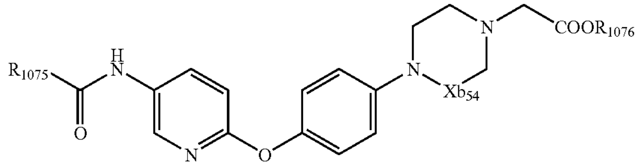

| Example No. | $R_{1075}$ | $Xb_{54}$ | $R_{1076}$ | $^1$H NMR ($CDCl_3$) δppm |
|---|---|---|---|---|
| 2353 | 3,4-$Cl_2$Ph- | —CO— | —$CH_3$ | 3.03 (2H, t, J = 5.2 Hz), 3.39 (2H, s), 3.51 (2H, s), 3.76 (2H, t, J = 5.2 Hz), 3.77 (3H, s), 6.98 (1H, d, J = 8.9 Hz), 7.15 (2H, dd, J = 8.8 Hz, 2.1 Hz), 7.30 (2H, dd, J = 8.8 Hz, 2.1 Hz), 7.59 (1H, d, J = 8.4 Hz), 7.72 (1H, dd, J = 8.4 Hz, 2.1 Hz), 7.99 (1H, d, J = 2.1 Hz), 8.15 (1H, dd, J = 8.9 Hz, 2.7 Hz), 8.29 (1H, d, J = 2.7 Hz). |
| 2354 | 3,4-$Cl_2$Ph- | —$CH_2$— | —$CH_3$ | 2.75 (4H, t, J = 5.0 Hz), 3.23 (4H, t, J = 5.0 Hz), 3.30 (2H, s), 3.75 (3H, s), 6.90 (1H, d, J = 9.0 Hz), 6.95 (2H, d, J = 9.0 Hz), 7.04 (2H, d, J = 9.0 Hz), 7.58 (1H, d, J = 8.5 Hz), 7.70 (1H, dd, J = 8.5 Hz, 2.0 Hz), 7.76 (1H, brs), 7.98 (1H, d, J = 2.0 Hz), 8.15 (1H, dd, J = 9.0 Hz, 3.0 Hz), 8.23 (1H, d, J = 3.0 Hz). |
| 2355 | 3,4-$Cl_2$Ph- | —$CH_2$— | —$C_2H_5$ | 1.31 (3H, t, J = 7.0 Hz), 2.75 (4H, t, J = 5.0 Hz), 3.23 (4H, t, J = 5.0 Hz), 3.28 (2H, s), 4.21 (2H, q, J = 7.0 Hz), 6.90 (1H, d, J = 9.0 Hz), 6.95 (2H, d, J = 9.0 Hz), 7.04 (2H, d, J = 9.0 Hz), 7.57 (1H, d, J = 8.5 Hz), 7.71 (1H, dd, J = 8.5 Hz, 2.0 Hz), 7.88 (1H, brs), 7.98 (1H, d, J = 2.0 Hz), 8.15 (1H, dd, J = 9.0 Hz, 2.5 Hz), 8.24 (1H, d, J = 2.5 Hz). |
| 2356 | 4-$CF_3$Ph- | —$CH_2$— | —$CH_3$ | 2.75 (4H, t, J = 5.0 Hz), 3.24 (4H, t, J = 5.0 Hz), 3.30 (2H, s), 3.75 (3H, s), 6.92 (1H, d, J = 9.0 Hz), 6.96 (2H, d, J = 9.0 Hz), 7.06 (2H, d, J = 9.0 Hz), 7.74 (1H, brs), 7.78 (2H, d, J = 8.0 Hz), 7.99 (2H, d, J = 8.0 Hz), 8.19 (1H, dd, J = 9.0 Hz, 2.5 Hz), 8.25 (1H, d, J = 2.5 Hz). |

Example 2357

Production of 3,4-dichloro-N-[6-(4-{4-[(3,4-difluorobenzyl)methylamino]piperidine-1-carbonyl}phenoxy)pyridin-3-yl]benzamide 3,4-dichloro-N-{6-[4-(4-methylamino-piperidine-1-carbonyl)phenoxy]pyridin-3-yl}benzamide dihydrochloride (114 mg, 0.2 mmol) was dissolved in DMF (3 mL). To the resulting solution were added 4-bromomethyl-1,2-difluorobenzene (31 μl, 0.24 mmol) and potassium carbonate (111 mg, 0.8 mmol), and this solution was stirred for 4 hours at room temperature. The resulting reaction solution was concentrated under reduced pressure. The residue was diluted with ethyl acetate and washed with water and brine. The organic layer was dried over anhydrous magnesium sulfate, and evaporated. This residue was purified by silica gel column chromatography (chloroform:methanol=50:1), to thereby yield 60 mg of the title compound.

Appearance: White powder $^1$H NMR ($CDCl_3$) δ 1.64 (4H, brs), 1.84 (2H, brs), 2.20 (3H, s), 2.65-2.90 (3H, m), 3.54 (2H, s), 6.95-7.08 (4H, m), 7.13 (2H, d, J=9.3 Hz), 7.41 (2H, d, J=9.2 Hz), 7.57 (1H, d, J=8.4 Hz), 7.75 (1H, dd, J=8.4 Hz, 2.0 Hz), 8.03 (1H, d, J=2.0 Hz), 8.15 (1H, dd, J=8.9 Hz, 2.8 Hz), 8.30 (1H, brs), 8.31 (1H, d, J=2.2 Hz).

The following compounds were produced in the same manner as in Example 2357.

TABLE 377

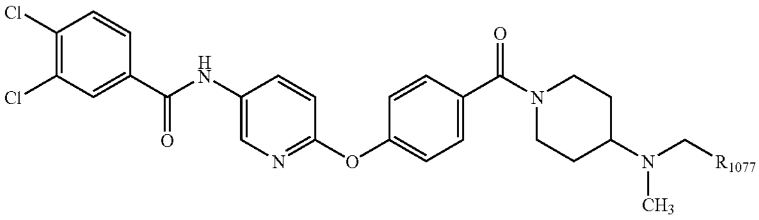

| Example No. | $R_{1077}$ | $^1$H NMR ($CDCl_3$) δppm |
|---|---|---|
| 2358 | 2,4-$F_2$Ph- | 1.66 (4H, brs), 1.91 (2H, brs), 2.25 (3H, s), 2.73-3.08 (3H, m), 3.63 (2H, s), 6.75-6.89 (3H, m), 6.97 (1H, d, J = 8.7 Hz), 7.13 (2H, d, J = 9.2 Hz), 7.42 (2H, d, J = 9.2 Hz), 7.57 (1H, d, J = 8.3 Hz), |

TABLE 377-continued

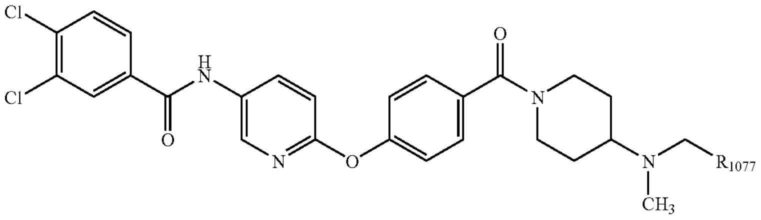

| Example No. | $R_{1077}$ | $^1H$ NMR ($CDCl_3$) δppm |
|---|---|---|
| | | 7.76 (1H, dd, J = 8.3 Hz, 2.1 Hz), 8.04 (1H, d, J = 2.1 Hz), 8.16 (1H, dd, J = 8.9 Hz, 2.8 Hz), 8.31 (1H, d, J = 2.3 Hz), 8.37 (1H, brs). |
| 2359 | 2,5-$F_2$Ph- | 1.72 (4H, brs), 1.88 (2H, brs), 2.25 (3H, s), 2.67-2.96 (3H, m), 3.62 (2H, s), 6.85-7.02 (3H, m), 7.09-7.23 (3H, m), 7.39 (2H, d, J = 8.9 Hz), 7.55 (1H, d, J = 8.3 Hz), 7.77 (1H, dd, J = 8.4 Hz, 2.1 Hz), 8.05 (1H, d, J = 2.1 Hz), 8.12 (1H, dd, J = 8.9 Hz, 2.8 Hz), 8.31 (1H, d, J = 2.6 Hz), 8.66 (1H, brs). |
| 2360 | 4-$CH(CH_3)_2$Ph- | 1.25 (6H, d, J = 6.9 Hz), 1.57-2.21 (7H, m), 2.66-3.07 (4H, m), 3.56 (2H, s), 3.90 (1H, brs), 4.66 (1H, brs), 6.90 (1H, d, J = 8.9 Hz), 7.04-7.10 (2H, m), 7.16-7.25 (4H, m), 7.31-7.36 (2H, m), 7.50 (1H, d, J = 8.4 Hz), 7.77 (1H, dd, J = 8.4 Hz, 2.1 Hz), 8.06-8.10 (2H, m), 8.33 (1H, d, J = 2.5 Hz), 9.37 (1H, s). |
| 2361 | 4-$C(CH_3)_3$Ph- | 1.32 (9H, s), 1.58 (2H, brs), 1.89 (2H, brs), 2.22 (3H, s), 2.62-3.10 (3H, m), 3.57 (2H, s), 3.92 (1H, brs), 4.69 (1H, brs), 6.92 (1H, d, J = 8.6 Hz), 7.06-7.11 (2H, m), 7.22-7.25 (2H, m), 7.32-7.37 (4H, m), 7.53 (1H, d, J = 8.6 Hz), 7.78 (1H, dd, J = 8.4 Hz, 2.2 Hz), 8.07 (1H, d, J = 2.2 Hz), 8.11 (1H, d, J = 2.7 Hz), 8.32 (1H, d, J = 2.7 Hz), 9.07 (1H, brs). |

TABLE 378

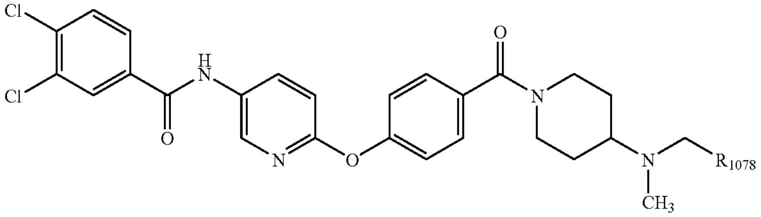

| Example No. | $R_{1078}$ | $^1H$ NMR ($CDCl_3$) δppm |
|---|---|---|
| 2362 | 4-CNPh- | 1.54 (1H, brs), 1.86 (3H, brs), 2.20 (3H, s), 2.64-3.04 (3H, m), 3.64 (2H, s), 3.91 (1H, brs), 4.69 (1H, brs), 6.91 (1H, d, J = 8.9 Hz), 7.05-7.10 (2H, m), 7.32-7.37 (2H, m), 7.45 (2H, d, J = 8.4 Hz), 7.50 (1H, d, J = 8.4 Hz), 7.59-7.62 (2H, m), 7.75-7.79 (1H, m), 8.05 (1H, d, J = 2.0 Hz), 8.10 (1H, dd, J = 8.9 Hz, 2.7 Hz), 8.35 (1H, d, J = 2.7 Hz), 9.31 (1H, brs). |
| 2363 | Ph- | 1.55 (2H, brs), 1.87 (2H, brs), 2.22 (3H, s), 2.61-2.80 (2H, m), 2.90 (1H, brs), 3.60 (2H, s), 3.93 (1H, brs), 4.72 (1H, brs), 6.98 (1H, d, J = 8.9 Hz), 7.14 (2H, d, J = 8.7 Hz), 7.18-7.37 (5H, m), 7.43 (2H, d, J = 8.7 Hz), 7.58 (1H, d, J = 8.4 Hz), 7.75 (1H, dd, J = 8.4 Hz, 2.0 Hz), 8.02 (1H, d, J = 2.0 Hz), 8.16 (1H, dd, J = 8.9 Hz, 2.4 Hz), 8.19 (1H, brs), 8.30 (1H, d, J = 2.4 Hz). |
| 2364 | 2-ClPh- | 1.50 (2H, brs), 1.90 (2H, brs), 2.26 (3H, s), 2.68-2.85 (2H, m), 2.98 (1H, brs), 3.70 (2H, s), 3.95 (1H, brs), 4.75 (1H brs), 6.98 (1H, d, J = 8.7 Hz), 7.14 (2H, d, J = 8.5 Hz), 7.15-7.30 (2H, m), 7.34 (1H, dd, J = 7.2 Hz, 2.0 Hz), 7.43 (2H, d, J = 8.5 Hz), 7.47 (1H, dd, J = 7.2 Hz, 2.0 Hz), 7.58 (1H, d, J = 8.4 Hz), 7.75 (1H, dd, J = 8.4 Hz, 2.0 Hz), 8.04 (1H, d, J = 2.0 Hz), 8.16 (1H, dd, J = 8.7 Hz, 2.8 Hz), 8.31 (1H, d, J = 2.8 Hz), 8.32 (1H, brs). |
| 2365 | 3-ClPh- | 1.50 (2H, brs), 1.87 (2H, brs), 2.21 (3H, s), 2.55-3.20 (3H, m), 3.57 (2H, s), 3.95 (1H, brs), 4.70 (1H, brs), 6.99 (1H, d, J = 8.8 Hz), 7.14 (2H, d, J = 8.7 Hz), 7.15-7.28 (3H, m), 7.33 (1H, brs), 7.44 (2H, d, J = 8.7 Hz), 7.59 (1H, d, J = 8.4 Hz), 7.74 (1H, dd, J = 8.4 Hz, 2.0 Hz), 8 02 (1H, d, J = 2.0 Hz), 8.09 (1H, brs), 8.17 (1H, dd, J = 8.8 Hz, 2.8 Hz), 8.30 (1H, d, J = 2.8 Hz). |
| 2366 | 3,4-$Cl_2$Ph- | 1.50 (2H, brs), 1.85 (2H, brs), 2.20 (3H, s), 2.60-3.15 (3H, m), 3.54 (2H, s), 3.95 (1H, brs), 4.70 (1H, brs), 6.97 (1H, d, J = 8.9 Hz), 7.13 (2H, d, J = 8.6 Hz), 7.10-7.19 (1H, m), 7.36 (1H, s), 7.41 (2H, d, J = 8.6 Hz), 7.35- |

TABLE 378-continued

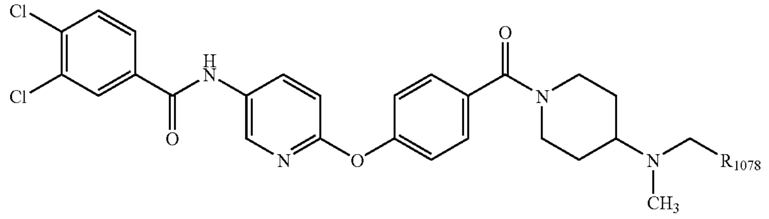

| Example No. | $R_{1078}$ | $^1H$ NMR ($CDCl_3$) δppm |
|---|---|---|
| | | 7.47 (1H, m), 7.57 (1H, d, J = 8.4 Hz), 7.75 (1H, dd, J = 8.4 Hz, 2.1 Hz), 8.03 (1H, d, J = 2.1 Hz), 8.14 (1H, dd, J = 8.9 Hz, 2.5 Hz), 8.30 (1H, d, J = 2.5 Hz), 8.40 (1H, s). |
| 2367 | 2,3-$Cl_2$Ph- | 1.60 (2H, brs), 1.90 (2H, brs), 2.26 (3H, s), 2.65-3.20 (3H, m), 3.72 (2H, s), 3.90 (1H, brs), 4.72 (1H, brs), 6.97 (1H, d, J = 8.8 Hz), 7.13 (2H, d, J = 8.6 Hz), 7.20 (1H, d, J = 8.0 Hz), 7.36 (1H, dd, J = 8.0 Hz, 1.5 Hz), 7.42 (2H, d, J = 8.6 Hz), 7.37-7.46 (1H, m), 7.57 (1H, d, J = 8.2 Hz), 7.75 (1H, dd, J = 8.4 Hz, 2.0 Hz), 8.04 (1H, d, J = 2.0 Hz), 8.14 (1H, dd, J = 8.8 Hz, 2.7 Hz), 8.30 (1H, d, J = 2.7 Hz), 8.38 (1H, brs). |
| 2368 | 2-FPh- | 1.55 (2H, brs), 1.85 (2H, brs), 2.25 (3H, s), 2.50-3.20 (3H, m), 3.65 (2H, s), 3.95 (1H, brs), 4.70 (1H, brs), 6.97 (1H, d, J = 8.8 Hz), 6.95-7.17 (2H, m), 7.13 (2H, d, J = 8.7 Hz), 7.18-7.29 (1H, m), 7.32-7.45 (1H, m), 7.42 (2H, d, J = 8.7 Hz), 7.57 (1H, d, J = 8 2 Hz), 7.75 (1H, dd, J = 8.2 Hz, 2.1 Hz), 8.04 (1H, d, J = 2.1 Hz), 8.14 (1H, dd, J = 8.8 Hz, 2.5 Hz), 8.30 (1H, d, J = 2.5 Hz), 8.34 (1H, brs). |
| 2369 | 2-$CH_3$Ph- | 1.67 (4H, brs), 1.89 (2H, brs), 2.19 (3H, s), 2.36 (3H, s), 2.67-2.96 (3H, m), 3.57 (2H, s), 6.96 (1H, d, J = 8.7 Hz), 7.07-7.26 (6H, m), 7.41 (2H, d, J = 8.1 Hz), 7.57 (1H, d, J = 8.4 Hz), 7.77 (1H, dd, J = 8.4 Hz, 2.0 Hz), 8.05 (1H, d, J = 2.0 Hz), 8.14 (1H, dd, J = 8.9 Hz, 2.6 Hz), 8.31 (1H, d, J = 2.6 Hz), 8.51 (1H brs). |

TABLE 379

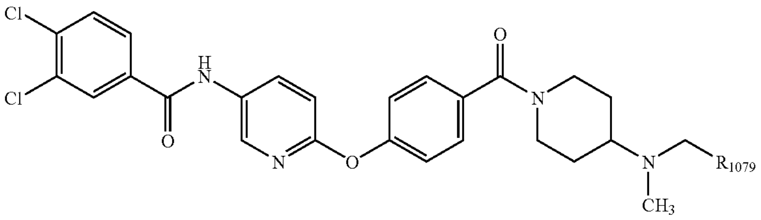

| Example No. | $R_{1079}$ | Form | $^1H$ NMR (solvent) δppm |
|---|---|---|---|
| 2370 | 3,5-$(CH_3O)_2$Ph- | hydro-chloride | (DMSO-$d_6$) 1.67-1.93 (2H, m), 2.08-2.30 (2H, m), 2.61 (3H, d, J = 4.8 Hz), 2.95 (1H, brs), 3.31-3.75 (4H, m), 3.77 (6H, s), 4.02-4.18 (1H, m), 4.31-4.45 (1H, m), 6.57 (1H, t, J = 2.0 Hz), 6.83 (2H, d, J = 2.0 Hz), 7.16 (1H, d, J = 8.7 Hz), 7.20 (2H, d, J = 8.6 Hz), 7.49 (2H, d, J = 8.6 Hz), 7.85 (1H, d, J = 8.4 Hz), 7.97 (1H, dd, J = 8.4 Hz, 2.1 Hz), 8.24 (1H, d, J = 2.1 Hz), 8.24 (1H, dd, J = 8.7 Hz, 2.6 Hz), 8.55 (1H, d, J = 2.6 Hz), 10.64 (1H, brs). |
| 2371 | 3-$CH_3$OPh- | free | ($CDCl_3$) 1.60 (2H, brs), 1.87 (2H, brs), 2.23 (3H, s), 2.52-3.20 (3H, m), 3.58 (2H, s), 3.81 (3H, s), 3.95 (1H, brs), 4.70 (1H, brs), 6.75-6.90 (3H, m), 6.97 (1H, d, J = 8.9 Hz), 7.13 (2H, d, J = 8.6 Hz), 7.21 (1H, d, J = 8.0 Hz), 7.41 (2H, d, J = 8.6 Hz), 7.57 (1H, d, J = 8.4 Hz), 7.75 (1H, dd, J = 8.4 Hz, 2.0 Hz), 8.04 (1H, d, J = 2.0 Hz), 8.14 (1H, dd, J = 8.9 Hz, 2.6 Hz), 8.30 (1H, d, J = 2.6 Hz), 8.36 (1H, brs). |
| 2372 | 3-$CH_3$Ph- | free | ($CDCl_3$) 1.61 (4H, brs), 1.88 (2H, brs), 2.22 (3H, s), 2.35 (3H, s), 2.68-3.01 (3H, m), 3.56 (2H, s), 6.98 (1H, d, J = 8.9 Hz), 7.06-7.29 (6H, m), 7.42 (2H, d, J = 8.6 Hz), 7.58 (1H, d, J = 8.2 Hz), 7.76 (1H, dd, J = 8.3 Hz, 2.0 Hz), 8.04 (1H, d, J = 2.0 Hz), 8.16 (1H, dd, J = 8.9 Hz, 2.6 Hz), 8.31 (1H, d, J = 2.3 Hz), 8.38 (1H, brs). |
| 2373 | 3,5-$F_2$Ph- | free | ($CDCl_3$) 1.42-1.96 (4H, m), 2.21 (3H, s), 2.65-3.10 (3H, m), 3.56 (2H, s), 3.90 (1H, brs), 4.68 (1H, brs), 6.64-6.70 (1H, m), 6.85-6.92 (3H, m), 7.04-7.09 (2H, m), 7.31- |

TABLE 379-continued

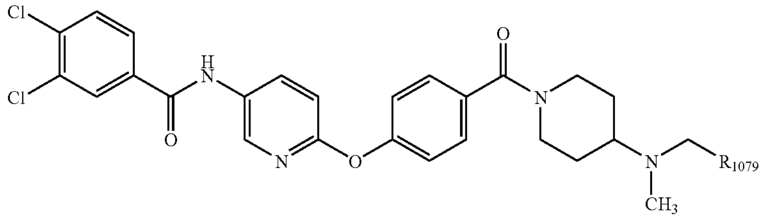

| Example No. | $R_{1079}$ | Form | $^1H$ NMR (solvent) δppm |
|---|---|---|---|
| | | | 7.36 (2H, m), 7.50 (1H, d, J = 8.4 Hz), 7.74-7.79 (1H, m), 8.05-8.10 (2H, m), 8.33 (1H, d, J = 2.5 Hz), 9.30 (1H, brs). |
| 2374 | 3,4-$(CH_3)_2$Ph- | free | ($CDCl_3$) 1.59 (4H, brs), 1.90-1.98 (2H, m), 2.22 (3H, s), 2.25 (3H, s), 2.26 (3H, s), 2.67-2.97 (3H, m), 3.59 (2H, s), 6.99 (1H, d, J = 8.7 Hz), 7.05-7.10 (3H, m), 7.15 (2H, d, J = 9.4 Hz), 7.44 (2H, d, J = 9.4 Hz), 7.59 (1H, d, J = 8.3 Hz), 7.74 (1H, dd, J = 8.3 Hz, 2.2 Hz), 8.02 (1H, d, J = 2.0 Hz), 8.03 (1H, brs), 8.18 (1H, dd, J = 8.7 Hz, 2.8 Hz), 8.31 (1H, d, J = 2.8 Hz). |
| 2375 | 3-FPh- | free | ($CDCl_3$) 1.59-1.85 (6H, m), 2.22 (3H, s), 2.67-2.99 (3H, m), 3.59 (2H, s), 6.94-6.97 (2H, m), 7.05-7.13 (5H, m), 7.39 (2H, d, J = 8.4 Hz), 7.56 (1H, d, J = 8.4 Hz), 7.77 (1H, dd, J = 8.4 Hz, 2.0 Hz), 8.05 (1H, d, J = 2.0 Hz), 8.13 (1H, dd, J = 8.7 Hz, 2.6 Hz), 8.31 (1H, d, J = 2.5 Hz), 8.63 (1H, brs). |
| 2376 | 2,6-$F_2$Ph- | free | ($CDCl_3$) 1.65 (4H, brs), 1.81-1.91 (2H, m), 2.28 (3H, s), 2.69-3.03 (3H, m), 3.69 (2H, s), 6.83-6.92 (3H, m), 6.99 (1H, d, J = 8.9 Hz), 7.15 (2H, d, J = 9.2 Hz), 7.44 (2H, d, J = 9.2 Hz), 7.59 (1H, d, J = 8.4 Hz), 7.75 (1H, dd, J = 8.4 Hz, 2.2 Hz), 8.03 (1H, d, J = 2.2 Hz), 8.17 (1H, brs), 8.18 (1H, dd, J = 8.7 Hz, 2.8 Hz), 8.31 (1H, d, J = 2.6 Hz). |

TABLE 380

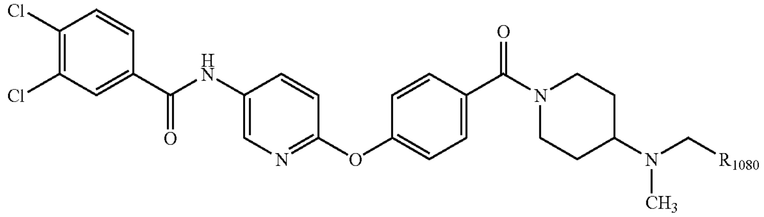

| Example No. | $R_{1080}$ | mp (° C.) or MS |
|---|---|---|
| 2377 | 4-$CF_3$OPh- | mp 180-181 |
| 2378 | 2-$NO_2$Ph- | MS 634 ($M^+$ + H) |
| 2379 | 3-$NO_2$Ph- | MS 634 ($M^+$ + H) |
| 2380 | 4-$NO_2$Ph- | MS 634 ($M^+$ + H) |
| 2381 | 2-$CF_3$Ph- | MS 657 ($M^+$ + H) |
| 2382 | 3-$CF_3$Ph- | MS 657 ($M^+$ + H) |
| 2383 | 4-$CF_3$Ph- | MS 657 ($M^+$ + H) |
| 2384 | 2-$CF_3$OPh- | MS 673 ($M^+$ + H) |
| 2385 | 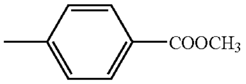 | MS 647 ($M^+$ + H) |
| 2386 | 4-biphenylyl | MS 665 ($M^+$ + H) |
| 2387 | 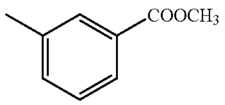 | MS 647 ($M^+$ + H) |

TABLE 380-continued

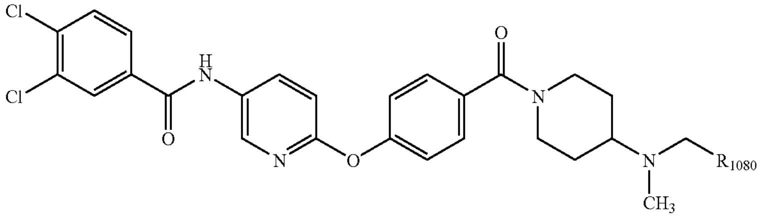

| Example No. | $R_{1080}$ | mp (° C.) or MS |
|---|---|---|
| 2388 | 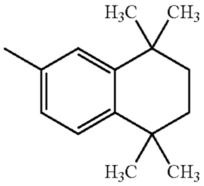 | MS 699 ($M^+$ + H) |
| 2389 | 2-pyridyl | MS 590 ($M^+$ + H) |
| 2390 | 2-quinolyl | MS 640 ($M^+$ + H) |
| 2391 | 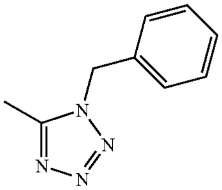 | MS 671 ($M^+$ + H) |
| 2392 | 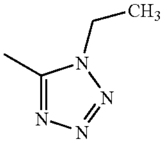 | MS 609 ($M^+$ + H) |
| 2393 | 2,4-$Cl_2$Ph- | MS 657 ($M^+$ + H) |
| 2394 | 2,5-$Cl_2$Ph- | MS 657 ($M^+$ + H) |
| 2395 | 2,6-$Cl_2$Ph- | MS 657 ($M^+$ + H) |

TABLE 381

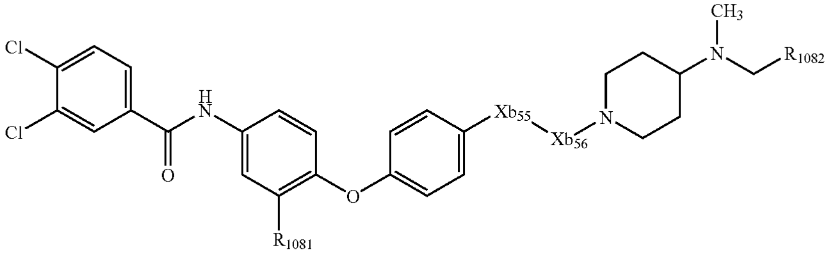

| Example No. | $R_{1081}$ | $Xb_{55}$ | $Xb_{56}$ | $R_{1082}$ | mp (° C.) or MS |
|---|---|---|---|---|---|
| 2396 | —H | none | none | Ph- | mp 155-158 |
| 2397 | —F | —$(CH_2)_2$— | —CO— | Ph- | MS 634 ($M^+$ + H) |
| 2398 | —F | —$(CH_2)_2$— | —CO— | 2-ClPh- | MS 668 ($M^+$ + 1) |
| 2399 | —F | —$(CH_2)_2$— | —CO— | 3-ClPh- | MS 668 ($M^+$ + H) |
| 2400 | —F | —$(CH_2)_2$— | —CO— | 4-ClPh- | MS 668 ($M^+$ + H) |
| 2401 | —F | —$(CH_2)_2$— | —CO— | 2,3-$Cl_2$Ph- | MS 702 ($M^+$ + 1) |
| 2402 | —F | —$(CH_2)_2$— | —CO— | 2,4-$Cl_2$Ph- | MS 701 ($M^+$) |
| 2403 | —F | —$(CH_2)_2$— | —CO— | 2,5-$Cl_2$Ph- | MS 702 ($M^+$ + 1) |
| 2404 | —F | —$(CH_2)_2$— | —CO— | 2,6-$Cl_2$Ph- | MS 702 ($M^+$ + H) |
| 2405 | —F | —$(CH_2)_2$— | —CO— | 3,4-$Cl_2$Ph- | MS 703 ($M^+$) |
| 2406 | —F | —$(CH_2)_2$— | —CO— | 3-pyridyl | MS 634 ($M^+$) |

TABLE 381-continued

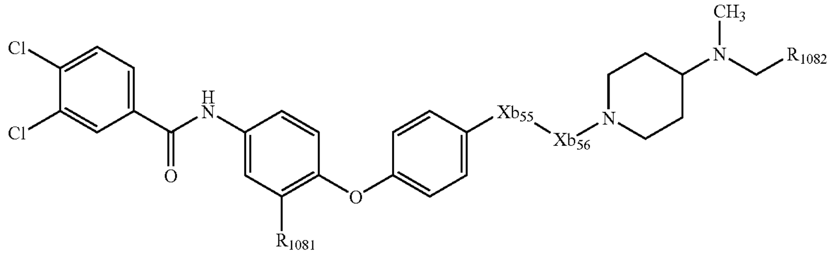

| Example No. | $R_{1081}$ | $Xb_{55}$ | $Xb_{56}$ | $R_{1082}$ | mp (° C.) or MS |
|---|---|---|---|---|---|
| 2407 | —F | —$(CH_2)_2$— | —CO— | 2-quinolyl | MS 685 ($M^+$ + H) |
| 2408 | —F | —$(CH_2)_2$— | —CO— | 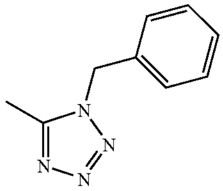 | MS 716 ($M^+$ + H) |
| 2409 | —F | —$(CH_2)_2$— | —CO— | 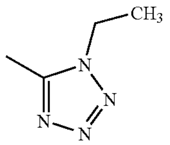 | MS 654 ($M^+$ + H) |
| 2410 | —F | —$(CH_2)_2$— | —CO— | 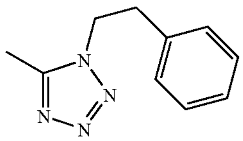 | MS 730 ($M^+$ + H) |
| 2411 | —F | —$(CH_2)_2$— | —CO— | 3-$CH_3$OPh- | MS 662 ($M^+$ − 1) |
| 2412 | —F | —$(CH_2)_2$— | —CO— | 3,5-$(CH_3O)_2$Ph- | MS 693 ($M^+$) |
| 2413 | —F | —$(CH_2)_2$— | —CO— | 2-$CH_3$Ph- | MS 648 ($M^+$ + H) |
| 2414 | —F | —$(CH_2)_2$— | —CO— | 3-$CH_3$Ph- | MS 648 ($M^+$ + H) |
| 2415 | —F | —$(CH_2)_2$— | —CO— | 4-$CH_3$Ph- | MS 648 ($M^+$ + H) |
| 2416 | —F | —$(CH_2)_2$— | —CO— | 3,4-$(CH_3)_2$Ph- | MS 662 ($M^+$ + 1) |
| 2417 | —F | —$(CH_2)_2$— | —CO— | 2-FPh- | MS 652 ($M^+$ + H) |
| 2418 | —F | —$(CH_2)_2$— | —CO— | 3-FPh- | MS 652 ($M^+$ + H) |
| 2419 | —F | —$(CH_2)_2$— | —CO— | 4-FPh- | MS 652 ($M^+$ + 1) |
| 2420 | —F | —$(CH_2)_2$— | —CO— | 2,4-$F_2$Ph- | MS 670 ($M^+$ + H) |
| 2421 | —F | —$(CH_2)_2$— | —CO— | 2,5-$F_2$Ph- | MS 670 ($M^+$ + H) |
| 2422 | —F | —$(CH_2)_2$— | —CO— | 2,6-$F_2$Ph- | MS 671 ($M^+$ + 2) |
| 2423 | —F | —$(CH_2)_2$— | —CO— | 3,4-$F_2$Ph- | MS 670 ($M^+$ + H) |
| 2424 | —F | —$(CH_2)_2$— | —CO— | 3,5-$F_2$Ph- | MS 670 ($M^+$ + H) |

TABLE 382

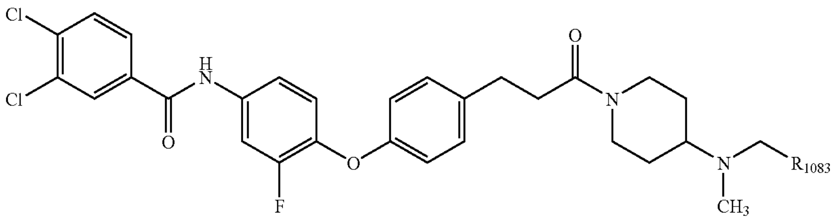

| Example No. | $R_{1083}$ | MS |
|---|---|---|
| 2425 | 2-$NO_2$Ph- | 679 ($M^+$ + H) |
| 2426 | 3-$NO_2$Ph- | 678 ($M^+$) |
| 2427 | 4-$NO_2$Ph- | 679 ($M^+$ + H) |

TABLE 382-continued

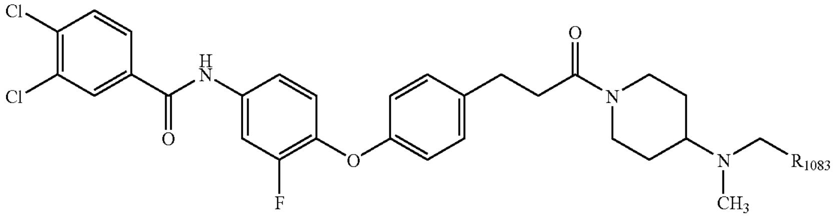

| Example No. | $R_{1083}$ | MS |
|---|---|---|
| 2428 | 2-$CF_3$Ph- | 701 ($M^+$ ) |
| 2429 | 3-$CF_3$Ph- | 702 ($M^+$ + H) |
| 2430 | 4-$CF_3$Ph- | 701 ($M^+$) |
| 2431 | 4-CNPh- | 659 ($M^+$ + H) |
| 2432 | 2-$CF_3$OPh- | 718 ($M^+$ + H) |
| 2433 | 3-$CF_3$OPh- | 718 ($M^+$ + H) |
| 2434 | 4-$CF_3$OPh- | 718 ($M^+$ + H) |
| 2435 | 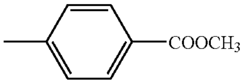 | 692 ($M^+$ + H) |
| 2436 | 4-biphenylyl | 710 ($M^+$ + H) |
| 2437 | 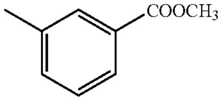 | 692 ($M^+$ + H) |
| 2438 | 4-$C_2H_5$Ph- | 662 ($M^+$ + H) |
| 2439 | 4-$CH(CH_3)_2$Ph- | 676 ($M^+$ + H) |
| 2440 | 4-$C(CH_3)_3$Ph- | 690 ($M^+$ + H) |
| 2441 | 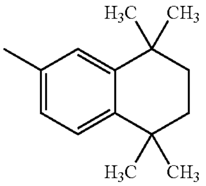 | 744 ($M^+$ + H) |
| 2442 | 2-naphthyl | 684 ($M^+$ + H) |
| 2443 | 2-pyridyl | 635 ($M^+$ + H) |

Example 2444

Production of 1-(4-piperonylpiperazin-1-yl)-2-{4-[5-(4-trifluoromethylphenoxymethyl)pyridin-2-yloxy]-phenylamino}ethanone 4-[5-(4-trifluoromethylphenoxymethyl)pyridin-2-yloxy] phenylamine (4.50 g, 12.5 mmol) was dissolved in DMF (150 mL). To the resulting solution were added potassium carbonate (2.60 g, 18.8 mmol) and sodium iodide (1.87 g, 12.5 mmol), and then to this solution was added 2-chloro-1-(4-piperonylpiperazin-1-yl)ethanone (4.21 g, 12.5 mmol). The resulting solution was stirred for 11 hours under a nitrogen atmosphere at 80° C. The resulting reaction solution was concentrated under reduced pressure. To the residue was added ethyl acetate and washed with a saturated sodium bicarbonate solution and brine. The organic layer was dried over anhydrous magnesium sulfate, and evaporated. The residue was purified by silica gel column chromatography (dichloromethane:methanol=80:1), to thereby yield 5.2 g of the title compound.

Appearance: White powder $^1$H NMR ($CDCl_3$) δ 2.44-2.46 (4H, m), 3.43-3.47 (4H, m), 3.69 (2H, t, J=5.0 Hz), 3.86 (2H, s), 4.91 (1H, brs), 5.02 (2H, s), 5.94 (2H, s), 6.64 (2H, d, J=8.9 Hz), 6.74-6.75 (2H, m), 6.85-6.89 (2H, m), 6.96-7.03 (4H, m), 7.55 (2H, d, J=8.4 Hz), 7.72 (1H, dd, J=8.4 Hz, 2.5 Hz), 8.22 (1H, d, J=2.0 Hz).

Example 2445

Production of N-{6-[4-(4-thiazole-2-ylmethylpiperazine-1-carbonyl)phenoxy]pyridin-3-yl}-4-trifluoromethyl-benzamide To a suspension of N-{6-[4-(piperazine-1-carbonyl)phenoxy]pyridin-3-yl}-4-trifluoromethyl-benzamide dihydrochloride (400 mg, 0.74 mmol) in 1,2-dichloroethane (20 mL) were added 2-formylthiazole (125 mg, 1.10 mmol) and triethylamine (0.21 mL, 1.50 mmol). After the resulting solution was stirred at room temperature for 30 minutes, sodium triacetyloxy borohydride (312 mg, 1.47 mmol) was added under ice cooling. The reaction mixture was stirred at the same temperature for 30 minutes and at room temperature for 1 hour. Acetic acid (0.085 mL, 1.48 mmol) was added to the reaction mixture, and stirred at room temperature for 17 hours. The reaction mixture was poured into ice water, and extracted with chloroform. The chloroform layer was washed with a saturated sodium bicarbonate solution and brine, and dried over anhydrous magnesium sulfate. A significant part of the solvent was evaporated. The white precipitate was then filtered off and washed with ethyl acetate, to thereby yield 293 mg of the title compound.

Appearance: White powder $^1$H NMR (DMSO-$d_6$) δ 2.55 (4H, brs), 3.55 (4H, brs), 3.90 (2H, s), 7.15 (1H, d, J=8.7 Hz), 7.16 (2H, d, J=8.6 Hz), 7.45 (2H, d, J=8.6 Hz), 7.68 (1H, d, J=3.2 Hz), 7.73 (1H, d, J=3.2 Hz), 7.94 (2H, d, J=8.1 Hz), 8.17 (2H, d, J=8.1 Hz), 8.26 (1H, dd, J=8.7 Hz, 2.3 Hz), 8.55 (1H, d, J=2.3 Hz), 10.68 (1H, s).

The following compounds were produced in the same manner as in Example 2445.

TABLE 383

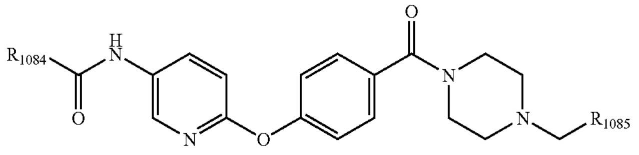

| Example No. | $R_{1084}$ | $R_{1085}$ | $^1$H NMR (solvent) δppm |
|---|---|---|---|
| 2446 | 3,4-$Cl_2$Ph- | 3,4-$(CH_3)_2$Ph- | ($CDCl_3$) 2.27 (3H, s), 2.29 (3H, s), 2.42 (4H, brs), 3.49 (2H, s), 3.70 (4H, brs), 6.90 (1H, d, J = 8.9 Hz), 7.05-7.10 (5H, m), 7.34-7.36. (2H, m), 7.50 (1H, d, J = 8.4 Hz), 7.75-7.79 (1H, m), 8.00-8.14 (2H, m), 8.33 (1H, d, J = 2.7 Hz), 9.30 (1H, brs). |
| 2447 | 4-$CF_3$Ph- | 2-FPh- | ($CDCl_3$) 2.50 (4H, brs), 3.55 (2H, brs), 3.70 (2H, brs), 3.62 (2H, s), 6.98 (1H, d, J = 8.8 Hz), 6.95-7.17 (2H, m), 7.12 (2H, d, J = 8.7 Hz), 7.20-7.41 (2H, m), 7.40 (2H, d, J = 8.7 Hz), 7.76 (2H, d, J = 8.2 Hz), 8.02 (2H, d, J = 8.2 Hz), 8.19 (1H, dd, J = 8.8 Hz, 2.8 Hz), 8.31 (1H, s), 8.32 (1H, d, J = 2.8 Hz). |
| 2448 | 4-$CF_3$Ph- | 3-pyridyl | ($CDCl_3$) 2.46 (4H, brs), 3.55 (2H, s), 3.58-3.73 (4H, m), 6.97 (1H, d, J = 8.7 Hz), 7.10-7.15 (2H, m), 7.25-7.30 (1H, m), 7.38-7.43 (2H, m), 7.65-7.69 (1H, m), 7.74 (2H, d, J = 8.1 Hz), 8.03 (2H, d, J = 8.1 Hz), 8.19-8.23 (1H, m), 8.32 (1H, d, J = 2.3 Hz), 8.51-8.53 (1H, m), 8.54 (1H, d, J = 1.5 Hz), 8.62 (1H, brs). |
| 2449 | 4-$CF_3$Ph- | cyclohexyl | (DMSO-$d_6$) 0.60-1.90 (11H, m), 2.10 (2H, d, J = 7.2 Hz), 2.34 (4H, brs), 3.50 (4H, brs), 7.15 (1H, d, J = 8.8 Hz), 7.16 (2H, d, J = 8.7 Hz), 7.43 (2H, d, J = 8.7 Hz), 7.94 (2H, d, J = 8.1 Hz), 8.17 (2H, d, J = 8.1 Hz), 8.26 (1H, dd, J = 8.8 Hz, 2.7 Hz), 8.55 (1H, d, J = 2.7 Hz), 10.66 (1H, s). |
| 2450 | 4-$CF_3$Ph- | 3-furyl | ($CDCl_3$) 2.46 (4H, brs), 3.42 (2H, s), 3.40-3.90 (4H, m), 6.39 (1H, brs), 6.98 (1H, d, J = 8.9 Hz), 7.13 (2H, d, J = 8.7 Hz), 7.34 (1H, brs), 7.33-7.42 (1H, m), 7.41 (2H, d, J = 8.7 Hz), 7.76 (2H, d, J = 8.1 Hz), 8.02 (2H, d, J = 8.1 Hz), 8.20 (1H, dd, J = 8.9 Hz, 2.5 Hz), 8.29 (1H, s), 8.32 (1H, d, J = 2.5 Hz). |
| 2451 | 4-$CF_3$Ph- | 4-pyridyl | ($CDCl_3$) 2.45 (4H, brs), 3.41-3.81 (6H, m), 6.95 (1H, d, J = 8.9 Hz), 7.08-7.13 (2H, m), 7.28 (2H, d, J = 5.9 Hz), 7.35-7.40 (2H, m), 7.70 (2H, d, J = 8.4 Hz), 8.02 (2H, d, J = 8.4 Hz), 8.21 (1H, dd, J = 8.9 Hz, 2.7 Hz), 8.33 (1H, d, J = 2.7 Hz), 8.53-8.55 (2H, m), 9.02 (1H, s). |
| 2452 | 4-$CF_3$Ph- | 2-furyl | ($CDCl_3$) 2.50 (4H, brs), 3.59 (2H, s), 3.73 (4H, brs), 6.23 (1H, d, J = 3.0 Hz), 6.33 (1H, dd, J = 3.0 Hz, 2.0 Hz), 6.99 (1H, d, J = 8.9 Hz), 7.13 (2H, d, J = 8.8 Hz), 7.41 (2H, d, J = 8.8 Hz), 7.35-7.48 (1H, m), 7.76 (2H, d, J = 8.1 Hz), 8.02 (2H, d, J = 8.1 Hz), 8.20 (1H, dd, J = 8.9 Hz, 2.5 Hz), 8.24 (1H, brs), 8.32 (1H, d, J = 2.5 Hz) |
| 2453 | 4-$CF_3$Ph- | 4-$NO_2$Ph- | ($CDCl_3$) 2.48 (4H, brs), 3.63 (2H, s), 3.73 (4H, brs), 7.00 (1H, d, J = 8.8 Hz), 7.14 (2H, d, J = 8.7 Hz), 7.43 (2H, d, J = 8.7 Hz), 7.53 (2H, d, J = 8.4 Hz), 7.76 (2H, d, J = 8.0 Hz), 8.01 (2H, d, J = 8.0 Hz), 8.15 (1H, brs), 8.20 (2H, d, J = 8.4 Hz), 8.21 (1H, dd, J = 8.8 Hz, 2.5 Hz), 8.32 (1H, d, J = 2.5 Hz). |

TABLE 384

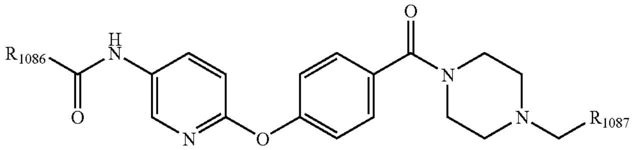

| Example No. | $R_{1086}$ | $R_{1087}$ | mp (° C.) or $^1$H NMR (solvent) δ ppm |
|---|---|---|---|
| 2454 | 4-$CF_3$Ph- | 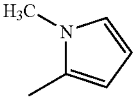 | $^1$H NMR ($CDCl_3$) 2.43(4 H, brs), 3.46(2 H, s), 3.55(4 H, brs), 3.65 (3 H, s), 5.95-6.08(2 H, m), 6.61(1 H, t, J = 2.2 Hz), 6.98(1 H, d, J = 8.9 Hz), 7.13(2 H, d, J = 8.8 Hz), 7.41(2 H, d, J = 8.8 Hz), 7.76(2 H, d, J = 8.1 Hz), 8.02(2 H, d, J = 8.1 Hz), 8.20(1 H, dd, J = 8.9 Hz, 2.5 Hz), 8.25(1 H, brs), 8.31(1 H, d, J = 2.5 Hz). |
| 2455 | 4-$CF_3$Ph- | 2-pyridyl | mp 175-176 |
| 2456 | 4-$CF_3$Ph- | 4-OHPh- | $^1$H NMR (DMSO-$d_6$) 2.36(4 H, brs), 3.32(2 H, s), 3.49(4 H, brs), 6.70(2 H, d, J = 8.4 Hz), 7.09(2 H, d, J = 8.4 Hz), 7.15(1 H, d, J = 8.9 Hz), 7.16(2 H, d, J = 8.6 Hz), 7.43(2 H, d, J = 8.6 Hz), 7.94(2 H, d, J = 8.0 Hz), 8.17(2 H, d, J = 8.0 Hz), 8.26(1 H, dd, J = 8.9 Hz, 2.5 Hz), 8.54(1 H, d, J = 2.5 Hz), 9.27(1 H, s), 10.66(1 H, s). |
| 2457 | 4-$CF_3$Ph- | 2-OHPh- | $^1$H NMR ($CDCl_3$) 2.59(4 H, brs), 3.68(4 H, brs), 3.75(2 H, s), 6.72-6.88(2 H, m), 6.92-7.10(1 H, m), 7.01(1 H, d, J = 8.8 Hz), 7.15(2 H, d, J = 8.8 Hz), 7.10-7.25(1 H, m), 7.44(2 H, d, J = 8.8 Hz), 7.76(2 H, d, J = 8.1 Hz), 8.01(2 H, d, J = 8.1 Hz), 8.12(1 H, brs), 8.22(1 H, dd, J = 8.8 Hz, 2.3 Hz), 8.31(1 H, d, J = 2.3 Hz). |
| 2458 | 4-$CF_3$Ph- | 4-AcNHPh- | $^1$H NMR (DMSO-$d_6$) 2.02(3 H, s), 2.38(4 H, brs), 3.45(2 H, s), 3.45 (4 H, brs), 7.15(1 H, d, J = 8.9 Hz), 7.16(2 H, d, J = 8.6 Hz), 7.22(2 H, d, J = 8.4 Hz), 7.44(2 H, d, J = 8.6 Hz), 7.52(2 H, d, J = 8.4 Hz), 7.94(2 H, d, J = 8.1 Hz), 8.17(2 H, d, J = 8.1 Hz), 8.26(1 H, dd, J = 8.9 Hz, 2.6 Hz), 8.54(1 H, d, J = 2.6 Hz), 9.90(1 H, s), 10.66(1 H, s). |
| 2459 | 4-$CF_3$Ph- | 2,3-$(CH_3)_2$Ph- | $^1$H NMR ($CDCl_3$) 2.25(3 H, s), 2.28(3 H, s), 2.42(4 H, brs), 3.47(2 H, s), 3.67(4 H, brs), 6.95(1 H, d, J = 8.7 Hz), 6.95-7.12(3 H, m), 7.10 (2 H, d, J = 8.6 Hz), 7.38(2 H, d, J = 8.6 Hz), 7.73(2 H, d, J = 8.1 Hz), 8.00(2 H, d, J = 8.1 Hz), 8.17(1 H, dd, J = 8.7 Hz, 2.7 Hz), 8.30 (1 H, d, J = 2.7 Hz), 8.43(1 H, s). |
| 2460 | 4-$CF_3$Ph- | 3-thienyl | $^1$H NMR ($CDCl_3$) 2.45(4 H, brs), 3.55(2 H, brs), 3.56(2 H, s), 3.72 (2 H, brs), 6.97(1 H, d, J = 8.9 Hz), 7.05(1 H, dd, J = 5.0 Hz, 1.1 Hz), 7.08-7.17(1 H, m), 7.12(2 H, d, J = 8.7 Hz), 7.29(1 H, dd, J = 5.0 Hz, 3.0 Hz), 7.39(2 H, d, J = 8.7 Hz), 7.75(2 H, d, J = 8.1 Hz), 8.02(2 H, d, J = 8.1 Hz), 8.19(1 H, dd, J = 8.9 Hz, 2.8 Hz), 8.32(1 H, d, J = 2.8 Hz), 8.41(1 H, brs). |
| 2461 | 3,4-$Cl_2$Ph- | 3-pyridyl | $^1$H NMR ($CDCl_3$) 2.46(4 H, brs), 3.46(2 H, s), 3.55-3.80(4 H, m), 6.96(1 H, d, J = 8.9 Hz), 7.12(2 H, d, J = 8.4 Hz), 7.26-7.30(1 H, m), 7.40(2 H, d, J = 8.4 Hz), 7.56(1 H, d, J = 8.4 Hz), 7.65-7.78(2 H, m), 8.04(1 H, d, J = 2.2 Hz), 8.16(1 H, dd, J = 8.9 Hz, 2.7 Hz), 8.29(1 H, d, J = 2.2 Hz), 8.51-8.56(2 H, m), 8.61(1 H, brs). |

TABLE 385

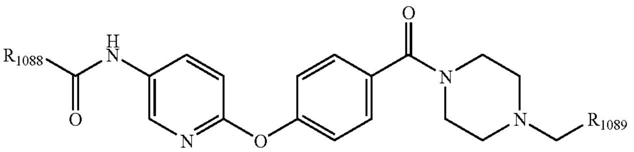

| Example No. | $R_{1088}$ | $R_{1089}$ | Form | $^1$H NMR (solvent) δ ppm |
|---|---|---|---|---|
| 2462 | 4-$CF_3$Ph- | cyclopropyl | free | ($CDCl_3$) 0.11(2 H, dd, J = 10.5 Hz, 4.5 Hz), 0.54(2 H, dd, J = 12.5 Hz, 6.5 Hz), 0.77-0.93(1 H, m), 2.29(2 H, d, J = 6.5 Hz), 2.52(4 H, brs), 3.55(2 H, brs), 3.75(2 H, brs), 6.98(1 H, d, J = 8.9 Hz), 7.14(2 H, d, |

TABLE 385-continued

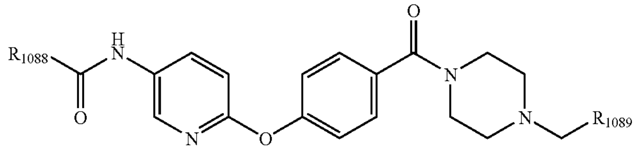

| Example No. | $R_{1088}$ | $R_{1089}$ | Form | $^1$H NMR (solvent) δ ppm |
|---|---|---|---|---|
| | | | | J = 8.7 Hz), 7.42(2 H, d, J = 8.7 Hz), 7.76(2 H, d, J = 8.1 Hz), 8.03(2 H, d, J = 8.1 Hz), 8.20 (1 H, dd, J = 8.9 Hz, 2.5 Hz), 8.33(1 H, d, J = 2.5 Hz), 8.36 (1 H, brs). |
| 2463 | 4-$CF_3$Ph- | 3-OHPh- | hydro-chloride | ($DMSO-d_6$) 2.90-3.70(6 H, m), 3.90-4.20(2 H, m), 4.24 (2 H, d, J = 3.9 Hz), 6.86(1 H, dd, J = 8.1 Hz, 1.7 Hz), 6.97 (1 H, brs), 7.01(1 H, d, 4 7.7 Hz), 7.16(1 H, d, J = 8.9 Hz), 7.20(2 H, d, J = 8.6 Hz), 7.25(1 H, t, J = 7.7 Hz), 7.52 (2 H, d, J = 8.6 Hz), 7.94(2 H, d, J = 8.1 Hz), 8.20(2 H, d, J = 8.1 Hz), 8.29(1 H, dd, J = 8.9 Hz, 2.5 Hz), 8.58(1 H, d, J = 2.5 Hz), 10.77(1 H, s). |
| 2464 | 4-$CF_3$Ph- | —$C(CH_3)_3$ | free | ($CDCl_3$) 0.88(9 H, s), 2.09(2 H, s), 2.52(4 H, brs), 3.49(2 H, brs), 3.68(2 H,brs), 6.97(1 H, d, J = 8.8 Hz), 7.12(2 H, d, J = 8.5 Hz), 7.39(2 H, d, J = 8.5 Hz), 7.75(2 H, d, J = 8.1 Hz), 8.03(2 H, d, J = 8.1 Hz), 8.19(1 H, dd, J = 8.8 Hz, 2.5 Hz), 8.33(1 H, d, J = 2.5 Hz), 8.47(1 H, s). |
| 2465 | 4-$CF_3$Ph- | 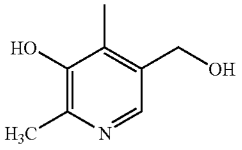 | free | ($CDCl_3$) 2.42(3 H, s), 2.59(4 H, brs), 3.48-3.76(4 H, m), 3.91(2 H, s), 4.56(2 H, s), 7.00(1 H, d, J = 8.9 Hz), 7.13(2 H, d, J = 8.7 Hz), 7.39(2 H, d, J = 8.6 Hz), 7.71(2 H, d, J = 8.3 Hz), 7.79(1 H, s), 8.00(2 H, d, J = 8.1 Hz), 8.22-8.29(2 H, m), 8.81(1 H, brs). |
| 2466 | 4-$CF_3$Ph- | 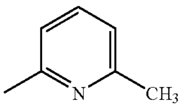 | free | ($CDCl_3$) 2.55(3 H, s), 2.35-2.70(4 H, m), 3.66(2 H, s), 3.40-3.95(4 H, m), 6.98(1 H, d, J = 8.7 Hz), 7.05(1 H, d, J = 7.6 Hz), 7.12(2 H, d, J = 8.5 Hz), 7.22(1 H, d, J = 7.6 Hz), 7.42(2 H, d, J = 8.5 Hz), 7.56(1 H, t, J = 7.6 Hz), 7.75 (2 H, d, J = 8.2 Hz), 8.02(2 H, d, J = 8.2 Hz), 8.21(1 H, dd, J = 8.7 Hz, 2.8 Hz), 8.31(1 H, d, J = 2.8 Hz), 8.38(1 H, s). |
| 2467 | 3,4-$Cl_2$Ph- | 4-AcNHPh- | free | ($DMSO-d_6$) 2.02(3 H, s), 2.38(4 H, brs), 3.44(2 H, s), 3.55 (4 H, brs), 7.14(1 H, d, J = 8.8 Hz), 7.16(2 H, d, J = 8.7 Hz), 7.21(2 H, d, J = 8.4 Hz), 7.43(2 H, d, J = 8.7 Hz), 7.52 (2 H, d, J = 8.4 Hz), 7.84(1 H, d, J = 8.4 Hz), 7.95(1 H, dd, J = 8.4 Hz, 2.0 Hz), 8.22(1 H, d, J = 2.0 Hz), 8.23(1 H, dd, J = 8.8 Hz, 2.6 Hz), 8.51(1 H, d, J = 2.6 Hz), 9.90(1 H, s), 10.59(1 H, s). |

TABLE 386

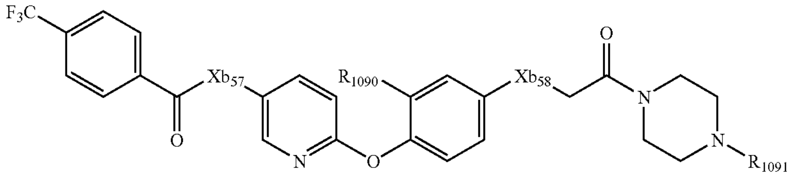

| Example No. | $Xb_{57}$ | $R_{1090}$ | $R_{1091}$ | $Xb_{58}$ | Form | $^1H$ NMR (solvent) δ ppm |
|---|---|---|---|---|---|---|
| 2468 | —NH— | —H | 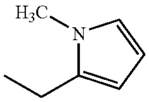 | —$CH_2$— | trihydro-cloride | (DMSO-$d_6$) 2.60-3.20(7 H, m), 3.22-3.60(3 H, m), 3.71(3 H, s), 4.10(1 H, d, J = 13.2 Hz), 4.30 (2 H, d, J = 4.8 Hz), 4.48(1 H, d, J = 13.2 Hz), 6.05(1 H, t, J = 2.5 Hz), 6.32(1 H, dd, J = 3.6 Hz, 1.9 Hz), 6.87(1 H, t, J = 2.5 Hz), 7.04(2 H, d, J = 8.4 Hz), 7.06 (1 H, d, J = 8.8 Hz), 7.29(2 H, d, J = 8.4 Hz), 7.93(2 H, d, J = 8.5 Hz), 8.19(2 H, d, J = 8.5 Hz), 8.22 (1 H, dd, J = 8.8 Hz, 2.6 Hz), 8.51(1 H, d, J = 2.6 Hz), 10.70(1 H, s). |
| 2469 | —NH— | —H | 3-furylmethyl | —$CH_2$— | free | ($CDCl_3$) 2.25-2.45(4 H, m), 2.60(2 H, t, J = 7.7 Hz), 2.93(2 H, t, J = 7.7 Hz), 3.37 (2 H, s), 3.40(2 H, t, J 5.0 Hz), 3.60 (2 H, t, J = 5.0 Hz), 6.37 (1 H, d, J = 1.5 Hz), 6.93(1 H, d, J = 8.8 Hz), 7.02(2 H, d, J = 8.6 Hz), 7.19(2 H, d, J = 8.6 Hz), 7.33(1 H, s), 7.39(1 H, t, J = 1.5 Hz), 7.73(2 H, d, J = 8.1 Hz), 8.01(2 H, d, J = 8.1 Hz), 8.21(1 H, dd, J = 8.8 Hz, 2.6 Hz), 8.28(1 H, d, J = 2.6 Hz), 8.46(1 H, s). |
| 2470 | —NH— | —H | furfuryl | —$CH_2$— | free | ($CDCl_3$) 2.31-2.52(4 H, m), 2.60(2 H, t, J = 7.2 Hz), 2.93(2 H, t, J = 7.2 Hz), 3.43 (2 H, t, J = 5.0 Hz), 3.55(2 H, s), 3.63 (2 H, t, J = 5.0 Hz), 6.21(1 H, d, J = 2.6 Hz), 6.32(1 H, d, J = 3.0 Hz), 6.94(1 H, d, J = 8.9 Hz), 7.02(2 H, d, J = 8.5 Hz), 7.19(2 H, d, J = 8.5 Hz), 7.38(1 H, d, J = 2.8 Hz), 7.74(2 H, d, J = 8.0 Hz), 8.00 (2 H, d, J = 8.0 Hz), 8.21(1 H, dd, J = 8.9 Hz, 2.5 Hz), 8.28(1 H, d, J = 2.5 Hz), 8.35(1 H, s). |
| 2471 | none | —$CH_3$ | piperonyl | —N($CH_3$)— | free | ($CDCl_3$) 2.12(3 H, s), 2.42-2.45(4 H, m), 3.03(3 H, s), 3.44(2 H, s), 3.47-3.52(2 H, m), 3.62-3.65(2 H, m), 4.09(2 H, s), 5.95 (2 H, s), 6.54-6.59(2 H, m), 6.71-6.77 (2 H, m), 6.85(1 H, s), 6.92-6.96(2 H, m), 7.75(2 H, d, J = 8.4 Hz), 7.87(2 H, d, J = 8.1 Hz), 8.17(1 H, dd, J = 8.6 Hz, 2.5 Hz), 8.58(1 H d J = 2.1 Hz). |

TABLE 387

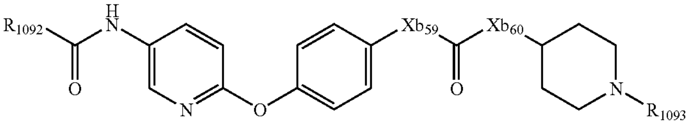

| Example No. | $R_{1092}$ | $Xb_{59}$ | $Xb_{60}$ | $R_{1093}$ | $^1$H NMR (DMSO-$d_6$) δ ppm |
|---|---|---|---|---|---|
| 2472 | 3,4-$Cl_2$Ph- | —NH— | none | benzyl | 1.55-1.82(4 H, m) 1.96(2 H, t, J = 10.5 Hz), 2.21-2.40(1 H, m), 2.87(2 H, d, J = 10.5 Hz), 3.47(2 H, s), 7.02(1 H, d, J = 8.9 Hz), 7.05(2 H, d, J = 9.1 Hz), 7.18-7.42(5 H, m), 7.62(2 H, d, J = 9.1 Hz, 7.84(1 H, d, J = 8.4 Hz), 7.94(1 H, dd, J = 8.4 Hz, 2.0 Hz), 8.17(1 H, dd, J = 8.9 Hz, 2.6 Hz), 8.22(1 H, d, J = 2.0 Hz), 8.46(1 H, d, J = 2.6 Hz), 9.89(1 H, s), 10.53(1 H, s). |
| 2473 | 3,4-$Cl_2$Ph- | —NH— | none | 3-furylmethyl | 1.55-1.85(4 H, m), 1.85-2.07(2 H, m), 2.18-2.40(1 H, m), 2.80-3.00(2 H, m), 3.32(2 H, s), 6.44(1 H, s), 7.02(1 H, d, J = 8.9 Hz), 7.05(2 H, d, J = 8.9 Hz), 7.57(1 H, s) 7.57-7.66(1 H, m), 7.62(2 H, d, J = 8.9 Hz), 7.84(1 H, d, J = 8.4 Hz), 7.94(1 H, dd, J = 8.4 Hz, 2.0 Hz), 8.17(1 H, dd, J = 8.9 Hz, 2.6 Hz), 8.22(1 H, d, J = 2.0 Hz), 8.45(1 H, d, J = 2.6 Hz), 9.89(1 H, s), 10.54(1 H, s). |
| 2474 | 4-$CF_3$Ph- | none | —N($CH_3$)— | benzyl | 1.50-2.30(6 H, m), 2.84(5 H, brs), 3.44(2 H, brs), 4.27(1 H, brs), 7.16(3 H, d, J = 8.6 Hz), 7.18-7.39(5 H, m), 7.41(2 H, d, J = 8.5 Hz), 7.95(2 H, d, J = 8.1 Hz), 8.17(2 H, d, J = 8.1 Hz), 8.27(1 H, dd, J = 8.9 Hz, 2.5 Hz), 8.56 (1 H, d, J = 2.5 Hz), 10.68(1 H, s). |
| 2475 | 4-$CF_3$Ph- | none | —N($CH_3$)— | 3-furylmethyl | 1.50-2.20(6 H, m), 2.83(3 H, s), 2.72-3.02(2 H, m), 3.30(2 H, d, J = 3.5 Hz), 4.28(1 H, brs), 6.41(1 H, s), 7.15(1 H, d, J = 8.8 Hz), 7.16(2 H, d, J = 8.4 Hz), 7.41(2 H, d, J = 8.4 Hz), 7.53 (1 H, s), 7.60(1 H, s), 7.95(2 H, d, J = 8.1 Hz), 8.17(2 H, d, J = 8.1 Hz), 8.27(1 H, dd, J = 8.8 Hz, 2.5 Hz), 8.55(1 H, d, J = 2.5 Hz), 10.68 (1 H, s). |

TABLE 388

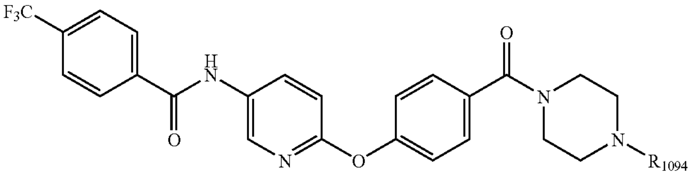

| Example No. | $R_{1094}$ | $^1$H NMR ($CDCl_3$) δ ppm |
|---|---|---|
| 2476 | cyclohexyl | 1.00-1.40(5 H, m), 1.52-1.70(1 H, m), 1.70-1.92(4 H, m), 2.21-2.40(1 H, m), 2.57 (4 H, brs), 3.52(2 H, brs),3.73(2 H, brs), 6.98(1 H, d, J = 8.9 Hz), 7.13(2 H, d, J = 8.8 Hz), 7.41(2 H, d, J = 8.8 Hz), 7.76(2 H, d, J = 8.2 Hz), 8.03(2 H, d, J = 8.2 Hz), 8.19 (1 H, dd, J = 8.9 Hz, 2.5 Hz), 8.33(1 H, d, J = 2.5 Hz), 8.36(1 H, brs). |

TABLE 388-continued

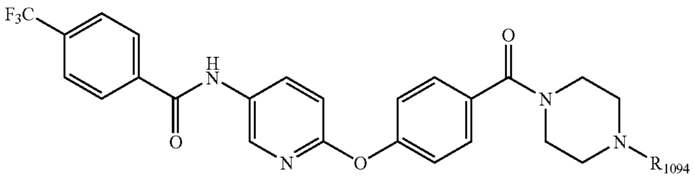

| Example No. | $R_{1094}$ | $^1H$ NMR ($CDCl_3$) δ ppm |
| --- | --- | --- |
| 2477 | 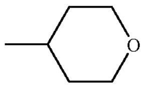 | 1.40-1.85(4 H, m), 2.38-2.60(1 H, m), 2.57(4 H, brs), 3.38(2 H, t, J = 11.0 Hz), 3.72 (4 H, brs), 4.03(2 H, dd, J = 11.0 Hz, 3.5 Hz), 7.00(1 H, d, J = 8.7 Hz), 7.15(2 H, d, J = 8.7 Hz), 7.43(2 H, d, J = 8.7 Hz), 7.77(2 H, d, J = 8.5 Hz), 8.02(2 H, d, J = 8.5 Hz), 8.16(1 H, brs), 8.21(1 H, dd, J = 8.7 Hz, 2.5 Hz), 8.32(1 H, d, J = 2.5 Hz). |
| 2478 | cyclopropyl | 0.33-0.58(4 H, m), 1.45-1.72(1 H, m), 2.62(4 H, brs), 3.49(2 H, brs), 3.68(2 H, brs), 7.00(1 H, d, J = 8.9 Hz), 7.15(2 H, d, J = 8.4 Hz), 7.43(2 H, d, J = 8.4 Hz), 7.77(2 H, d, J = 8.4 Hz), 8.02(2 H, d, J = 8.4 Hz), 8.21(1 H, s), 8.21(1 H, dd, J = 8.9 Hz, 2.6 Hz), 8.33(1 H, d, J = 2.6 Hz). |

TABLE 389

| Example No. | Chemical structure | $^1H$ NMR (solvent) δ ppm |
| --- | --- | --- |
| 2479 | 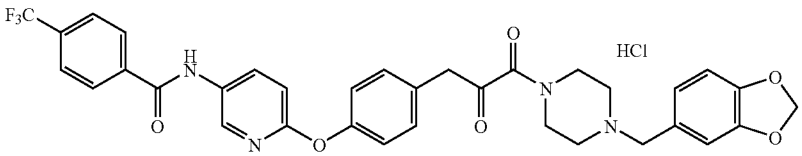 | ($DMSO-d_6$) 2.77-3.10(2 H, m), 3.17-3.63(4 H, m), 3.71-3.89(1 H, m), 4.18(2 H, s), 4.24(2 H, s), 4.27-4.44(1 H, m), 6.07(2 H, s), 6.92-7.06(2 H, m), 7.09(3 H, d, J = 8.6 Hz), 7.22(1 H, s), 7.28(2 H, d, J = 8.6 Hz), 7.92(2 H, d, J = 8.0 Hz), 8.18(2 H, d, J = 8.0 Hz), 8.24(1 H, dd, J = 8.8 Hz, 2.5 Hz), 8.53(1 H, d, J = 2.5 Hz), 10.69(1 H, s). |
| 2480 | 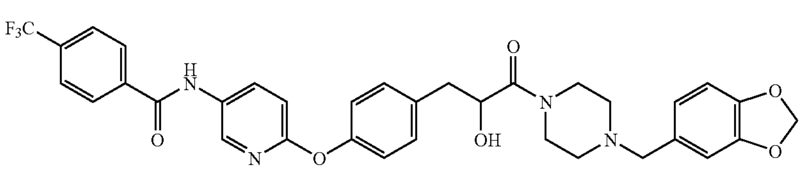 | ($CDCl_3$) 2.25-2.52(4 H, m), 2.77-2.95 (2 H, m), 3.12-3.29(1 H, m), 3.29-3.46 (1 H, m), 3.41(2 H, s), 3.43-3.59(1 H, m), 3.65-3.84(2 H, m), 5.30(1 H, brs), 5.92 (2 H, s), 6.73(2 H, s), 6.84(1 H, s), 6.95 (1 H, d, J = 9.0 Hz), 7.05(2 H, d, J = 8.4 Hz), 7.23(2 H, d, J = 8.4 Hz), 7.75(2 H, d, J = 8.1 Hz), 7.98(2 H, d, J = 8.1 Hz), 8.03(1 H, brs), 8.20(1 H, dd, J = 9.0 Hz, 2.5 Hz), 8.22(1 H, s). |
| 2481 | 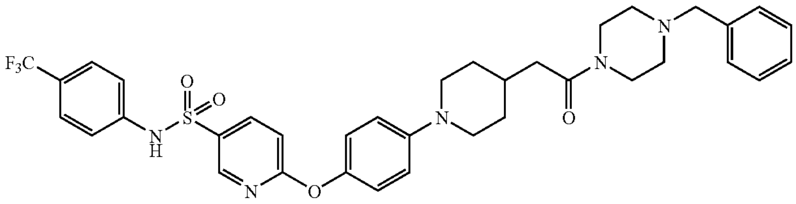 | ($CDCl_3$) 1.32-1.44(2 H, m), 1.83-2.02 (3 H, m), 2.30(2 H, d, J = 6.8 Hz), 2.42-2.47(4 H, m), 2.69(2 H, t, J = 12.0 Hz), 3.48-3.66(8 H, m), 6.86-6.99(6 H, m), 7.25-7.32(7 H, m), 7.50(2 H, d, J = 8.6 Hz), 7.98(1 H, dd, J = 8.7 Hz, 2.6 Hz), 8.59(1 H, d, J = 2.0 Hz). |

Example 2482

Production of N-(6-{4-[4-((1S,2S)-2-hydroxy-cyclohexyl)piperazine-1-carbonyl]phenoxy}pyridin-3-yl)-4-trifluoromethylbenzamide To a solution of N-{6-[4-(piperazine-1-carbonyl)phenoxy]-pyridin-3-yl}-4-trifluoromethyl-benzamide (430 mg, 0.91 mmol) in methanol was added 1,2-epoxycyclohexane (180 mg, 1.83 mmol), and the resulting solution was stirred for 1 day under reflux. The resulting reaction solution was concentrated under reduced pressure. The residue was purified by silica gel column chromatography (chloroform: methanol=35:1), and then ethyl acetate was added. The precipitated white powder was filtered off and washed with ethyl acetate, to thereby yield 284 mg of the title compound.

Appearance: White powder $^1$H NMR ($CDCl_3$) δ 1.03-1.38 (4H, m), 1.42-1.88 (3H, m), 2.06-2.35 (2H, m), 2.31 (2H, brs), 2.74 (2H, brs), 3.30-4.00 (6H, m), 7.00 (1H, d, J=8.9 Hz), 7.15 (2H, d, J=8.7 Hz), 7.43 (2H, d, J=8.7 Hz), 7.77 (2H, d, J=8.1 Hz), 8.02 (2H, d, J=8.1 Hz), 8.21 (1H, brs), 8.22 (1H, dd, J=8.9 Hz, 2.7 Hz), 8.33 (1H, d, J=2.7 Hz).

Example 2483

Production of 3,4-dichloro-N-[6-({4-[3-oxo-3-(4-piperonylpiperazin-1-yl)propyl]phenyl}methylamino)-pyridin-3-yl]benzamide dioxalate To a solution of 3,4-dichloro-N-(6-{4-[3-oxo-3-(4-piperonylpiperazin-1-yl)propyl]phenylamino}pyridin-3-yl)benzamide (250 mg, 0.395 mmol) in methanol (3 mL) were added acetic acid (0.500 mL) and 37% aqueous formaldehyde (0.640 mL, 7.89 mmol), and the resulting solution was stirred for 30 minutes at 50° C. To the reaction solution was added sodium cyanoborohydride (0.160 g, 2.55 mmol) at room temperature, and stirred for 8 hours at 50° C. Water was added to the reaction solution and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=10:1), to yield a free form. This free form was dissolved in isopropanol (5 mL) and oxalic acid dihydrate (7.0 mg, 0.555 mmol) by heating. The solvent was evaporated, and the resulting solid was recrystallized from isopropanol, to thereby yield 0.193 g of the title compound.

Appearance: Pale yellow powder

Melting point: 127-129° C.

The following compound was produced in the same manner as in Example 2483.

Example 2484

2-(Ethyl{4-[5-(4-trifluoromethylphenoxymethyl)pyridin-2-yloxy]phenyl}amino)-1-(4-piperonylpiperazin-1-yl)ethanone $^1$H NMR ($CDCl_3$) δ 1.18 (3H, t, j 7.1 Hz), 2.41-2.44 (4H, m), 3.39-3.47 (4H, m), 3.51 (2H, brs), 3.64 (2H, brs), 4.03 (2H, s), 5.03 (2H, s), 5.94 (2H, s), 6.68 (2H, d, J=19.1 Hz), 6.73-6.74 (2H, m), 6.85-6.88 (2H, m), 6.99 (2H, d, J=9.1 Hz), 7.01 (2H, d, J=8.4 Hz), 7.55 (2H, d, J=8.7 Hz), 7.71 (1H, dd, J=8.6° Hz, 2.5 Hz), 8.22 (1H, d, J=2.3 Hz).

Example 2485

Production of 3,4-dichloro-N-[6-(4-thiomorpholine-4-ylmethylphenoxy)pyridin-3-yl]benzamide monohydrochloride 3,4-dichloro-N-[6-(4-chloromethylphenoxy)-pyridin-3-yl]benzamide (0.61 g, 1.5 mmol) was dissolved in DMF (5 mL). To the resulting solution were added triethylamine (0.84 mL, 6.0 mmol) and thiomorpholine (0.15 mL, 1.5 mmol), and this solution was stirred overnight at 40° C. The resulting reaction solution was concentrated under reduced pressure. To the residue was added ethyl acetate and washed with a saturated sodium bicarbonate solution and brine. The organic layer was dried over anhydrous magnesium sulfate and evaporated. This residue was purified by silica gel column chromatography (chloroform:methanol=80:1). The obtained solid (0.56 g, 1.18 mmol) was dissolved in ethyl acetate (50 mL), and a solution of 4 N hydrogen chloride in ethyl acetate (0.295 mL, 1.18 mmol) was added, and this solution was stirred for 1 hour at room temperature. The precipitated crystals were collected by suction filtration, and recrystallized from methanol, to thereby yield 0.38 g of the title compound.

Appearance: White powder $^1$H NMR (DMSO-$d_6$) δ 2.80-2.83 (2H, m), 3.09-3.17 (4H, m), 3.61 (2H, m), 4.35 (2H, s), 7.14 (1H, d, J=8.9 Hz), 7.21 (2H, d, J=8.3 Hz), 7.60 (2H, d, J=8.3 Hz), 7.85 (1H, d, J=8.6 Hz), 7.96 (1H, dd, J=8.3 Hz, 2.0 Hz), 8.23 (1H, dd, J=8.9 Hz, 2.6 Hz), 8.24 (1H, d, J=2.0 Hz), 8.53 (1H, d, J=2.6 Hz), 10.45 (1H, brs), 10.62 (1H, brs).

The following compounds were produced in the same manner as in Example 2485.

Example 2486

3,4-Dichloro-N-(4-{4-[1-(3-imidazole-1-ylpropyl)-1,2,3,6-tetrahydropyridine-4-yl]phenoxy}phenyl)-benzamide Melting point: 169-171° C.

TABLE 390

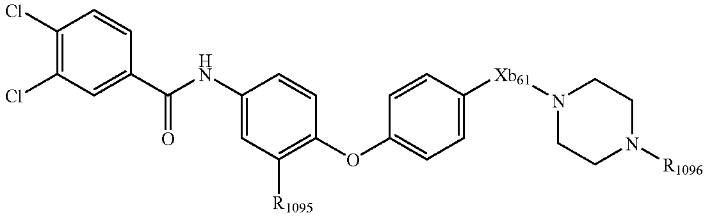

| Example No. | $R_{1095}$ | $Xb_{61}$ | $R_{1096}$ | Form | mp (° C.) |
|---|---|---|---|---|---|
| 2487 | —F | —$CH_2$— | benzyl | dihydro-chloride | 178-179 |
| 2488 | —F | —$CH_2$— | piperonyl | dihydro-chloride | 192-195 |

TABLE 390-continued

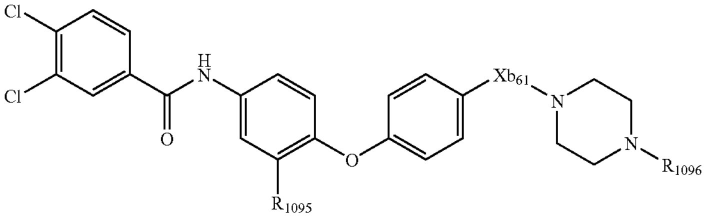

| Example No. | $R_{1095}$ | $Xb_{61}$ | $R_{1096}$ | Form | mp (° C.) |
|---|---|---|---|---|---|
| 2489 | —F | $-(CH_2)_2-$ | benzyl | dihydro-chloride | 208-210 |
| 2490 | —F | $-(CH_2)_2-$ | piperonyl | dihydro-chloride | 202-205 |
| 2491 | —F | $-(CH_2)_3-$ | benzyl | dihydro-chloride | 260-262 |
| 2492 | —F | $-(CH_2)_3-$ | piperonyl | dihydro-chloride | 258-260 |
| 2493 | —F | $-(CH_2)_4-$ | benzyl | dihydro-chloride | 245-248 |
| 2494 | —F | $-(CH_2)_4-$ | piperonyl | dihydro-chloride | 256-258 |
| 2495 | —H | none | 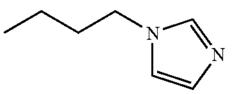 | free | 172-173 |
| 2496 | —H | none | 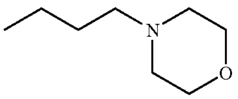 | free | 131-134 |

TABLE 391

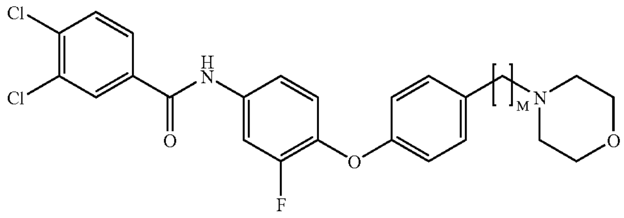

| Example No. | M | Form | mp (° C.) |
|---|---|---|---|
| 2497 | 1 | hydrochloride | 165-168 |
| 2498 | 2 | free | 143-144 |
| 2499 | 3 | oxalate | 173-175 |
| 2500 | 4 | hydrochloride | 226-228 |

TABLE 392

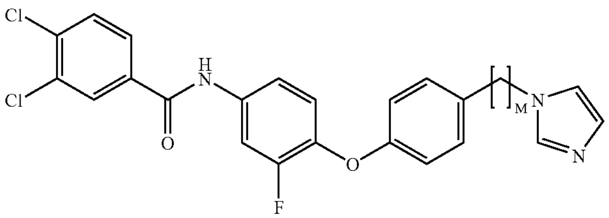

| Example No. | M | mp (° C.) |
|---|---|---|
| 2501 | 1 | 183-185 |
| 2502 | 4 | 141-143 |

TABLE 393

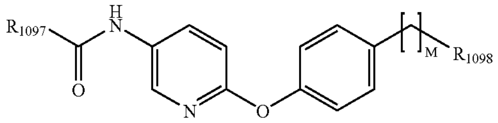

| Example No. | $R_{1097}$ | $R_{1098}$ | M | Form | $^1$H NMR (solvent) δ ppm |
|---|---|---|---|---|---|
| 2503 | 3,4-$Cl_2$Ph- | piperidino | 1 | free | ($CDCl_3$) 1.42-1.58(6 H, m), 2.36-2.38(4 H, m), 3.44(2 H, s), 6.86(1 H, d, J = 8.9 Hz), 6.99(2 H, dd, J 6.6 Hz, 2.0 Hz), 7.26 7.31(2 H, m), 7;47(1 H, d, J = 8.3 Hz), 7.67(1 H, dd, J = 8.3 Hz, 2.0 Hz), 7.94(1 H, d, J = 2.3 Hz), 8.10(1 H, dd, J = 8.9 Hz, 2.6 Hz), 8.21(1 H, d, J = 2.6 Hz), 8.69(1 H, brs). |
| 2504 | 3,4-$Cl_2$Ph- | piperidino | 3 | dihydro-chloride | ($DMSO-d_6$) 1.67-1.77(6 H, m), 1.99-2.10 (2 H, m), 2.61-3.05 (6 H, m), 3.40-3.43(2 H, m), 6.01(1 H, brs), 7.04-7.08(3 H, m), 7.28(9 H d, J = 8.6 Hz), 7.84(1 H, d, J = 8.4 Hz), 7.96-8.00 (1 H, m), 8.198.23(1 H, m), 8.26(1 H, d, J = 1.9 Hz), 8.51 (1 H, d, J = 2.7 Hz), 10.24(1 H, brs), 10.67(1 H, s). |
| 2505 | 3,4-$Cl_2$Ph- | piperidino | 4 | free | ($CDCl_3$) 1.40-1.50(2 H, m), 1.50-1.75(8 H, m), 2.25-2.50 (6 H, m), 2.63(2 H, t, J = 7.0 Hz), 6.93(1 H, d, J = 9.0 Hz), 7.03(2 H, d, J = 8.5 Hz), 7.19(2 H, d, J = 8.5 Hz), 7.58(1 H, d, J = 8.5 Hz), 7.71(1 H, dd, J = 8.5 Hz, 2.0 Hz) 7 82(1 H, s), 7.98(1 H, d, J = 2.0 Hz), 8.16(1 H, dd, J = 9.0 Hz, 3.0 Hz), 8.25(1 H, d, J = 3.0 Hz). |
| 2506 | 3,4-$Cl_2$Ph- | piperidino | 5 | free | ($CDCl_3$) 1.20-1.80(12 H, m), 2.31(2 H, t, J = 7.8 Hz), 2.40 (4 H, brs), 2.61(2 H, t, J = 7.8 Hz), 6.94(1 H, d, J = 8.8 Hz), 7.04(2 H, d, J = 8.4 Hz), 7.20(2 H, d, J = 8.4 Hz), 7.58(1 H, d, J = 8.2 Hz), 7.72(1 H, s), 7.71(1 H, dd, J = 8.2 Hz, 2.0 Hz), 7.98(1 H, d, J = 2.3 Hz), 8.16(1 H, dd, J = 8.8 Hz, 2.8 Hz), 8.24(1 H, d, J = 2.8 Hz). |
| 2507 | 4-$CF_3$Ph- | morpholino | 1 | free | ($DMSO-d_6$) 2.37(4 H, t, J = 4.6 Hz), 3.46 (2 H, s), 3.59(4 H, t, J = 4.6 Hz), 7.07(3 H, d, J = 8.6 Hz), 7.33(2 H, d, J = 8.6 Hz), 7.93(2 H, d, J = 8.6 Hz), 8.15-8.24(3 H, m), 8.51(1 H, d, J = 2.6 Hz), 10.63(1 H, s). |
| 2508 | 3,4-$Cl_2$Ph- | morpholino | 1 | free | ($CDCl_3$) 2.56(4 H, t, J = 4.6 Hz), 3.60(2 H, s), 3.82(4 H, t, J = 4 6 Hz), 7.05(1 H, d, J = 8.6 Hz), 7.18(2 H, dd, J = 6.6 Hz, 2.0 Hz), 7.45(2 H, d, J = 8.6 Hz), 7.67(1 H, d, J = 8.6 Hz), 7.80(1 H, dd, J = 8.3 Hz, 2.0 Hz), 7.99(1 H, brs), 8.07(1 H, d, J = 2.0 Hz), 8.25-8.29(1 H, m), 8.35(1 H, d, J = 2.6 Hz). |
| 2509 | 3,4-$Cl_2$Ph- | morpholino | 2 | free | ($CDCl_3$) 2.54-2.85(8 H, m), 3.74-3.78(4 H, m), 6.95(1 H, d, J = 8.9 Hz) 7 04-7.07(2 H, m), 7.22-7.26(2 H, m), 7.58-1 H, d, J = 8.6 Hz), 7.68-7.72(1 H, m), 7.79(1 H, brs), 7.98(1 H, d, J = 2.0 Hz), 8.17(1 H, dd, J = 8.9 Hz, 2.6 Hz), 8.24(1 H, d, J = 2.6 Hz). |
| 2510 | 3,4-$Cl_2$Ph- | morpholino | 3 | free | ($CDCl_3$) 1.78-1.83(2 H, m), 2.34-2.45(6 H, m), 2.60-2.66 (2 H, m), 3.70-3.73(4 H, m), 6.88(1 H, d, J = 8.6 Hz), 7.00 (2 H, d, J = 8.6 Hz), 7.18(2 H, d, J = 8.6 Hz), 7.51(1 H, d, J = 8.6 Hz), 7.667.70(1 H, m), 7.94(1 H, d, J = 2.2 Hz), 8.108.14(1 H, m), 8.22(1 H, d, J = 2.7 Hz), 8.40(1 H, brs). |

TABLE 394

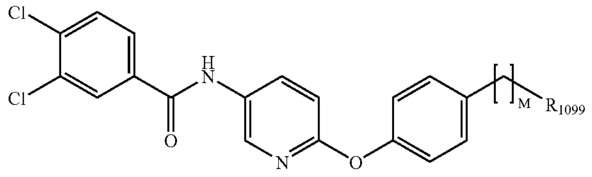

| Example No. | $R_{1099}$ | M | Form | $^1H$ NMR (solvent) δ ppm |
|---|---|---|---|---|
| 2511 | morpholino | 4 | dihydro-chloride | ($DMSO-d_6$) 1.55-1.90(4 H, m), 2.63(2 H, t, J = 7.2 Hz), 2.90-3.20(4 H, m), 3.30-3.50(2 H, m), 3.79(2 H, t, J = 11.2 Hz), 3.93(2 H, s), 7.04(2 H, d, J = 8.2 Hz), 7.05(1 H, d, J = 9 0 Hz), 7.26(2 H, d, J = 8.2 Hz), 7.84(1 H, d, J = 8.2 Hz), 7198(1 H, dd, J = 8.2 Hz, 2.0 Hz), 8.20(1 H dd J = 9.0 Hz, 2.7 Hz), 8.25(1 H, d, J = 2.0 Hz), 8.50(1 H, d, J = 2.7 Hz), 10.65(1 H, s). |
| 2512 | morpholino | 5 | free | ($CDCl_3$) 1.30-1.45(2 H, m), 1.45-1.75(4 H, m), 2.33(2 H, t, J = 7.2 Hz), 2.44(4 H, t, J = 4.6 Hz), 2.62(2 H, t, J = 7.7 Hz), 3.72(4 H, t, J = 4.6 Hz), 6.94(1 H, d, 4 9.0 Hz), 7.04(2 H, d, J = 8.5 Hz), 7.20(2 H, d, J = 8.5 Hz) 7.58(1 H, d, J = 8.2 Hz), 7.65-7.75(2 H, m), 7.98(1 H, d, J = 2.0 Hz), 8.16 (1 H, dd, J = 9.0 Hz, 2.6 Hz), 8.24(1 H, d, J = 2.6 Hz). |
| 2513 | 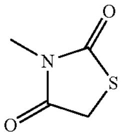 | 3 | free | ($CDCl_3$) 1.97-2.03(2 H, m), 2.67(2 H, t, 4 7.6 Hz), 3.68-3.73(2 H, m), 3.88(2 H, s), 6.95(1 H, d, J = 8.9 Hz), 7.05(2 H, d, J = 8.6 Hz), 7.21(2 H, d, J = 8.6 Hz) 7.56(1 H, d, J = 8.3 Hz), 7.69-7.74(2 H, m), 7.98(1 H, d, J = 2.3 Hz), 8.14-8.18(1 H, m), 8.23(1 H, d, J = 3.0 Hz). |
| 2514 | 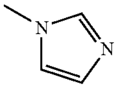 | 1 | free | ($DMSO-d_6$) 5.20(2 H, s), 6.91(1 H, s), 7.07(1 H, d, J = 8.6 Hz), 7.10(2 H, d, J = 8.6 Hz), 7.22(1 H, s), 7.31(2 H, d, J = 8.6 Hz), 7.77(1 H, s), 7.84 (1 H, d, J = 8.6 Hz), 7.94(1 H, dd, J = 8.6 Hz, 2.0 Hz), 8.19(1 H, dd, J = 8.6 Hz, 2.3 Hz), 8.22(1 H, d, J = 2.0 Hz), 8.46(1 H, d, J = 2.3 Hz), 10.57 (1 H, s). |
| 2515 | 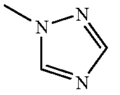 | 1 | hydro-chloride | ($DMSO-d_6$) 5.48(2 H, s), 7.09(1 H, d, J = 8.5 Hz), 7.12(2 H, d, J = 8.6 Hz), 7.38(2 H, d, J = 8.6 Hz), 7.83(1 H, d, J = 8.5 Hz), 7.98(1 H, dd J = 8.5 Hz, 2.0 Hz), 8.23(1 H, dd, J = 8.5 Hz, 2.3 Hz), 8.26(1 H, s), 8.26(1 H, d, J = 2.0 Hz), 8.51(1 H, d, J = 2.3 Hz), 9.05(1 H, s), 10.70(1 H, s). |
| 2516 | 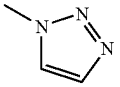 | 1 | free | ($DMSO-d_6$) 5.63(2 H, d, J = 8.6 Hz), 7.09(1 H, d, J = 8.6 Hz), 7.11(2 H, d, J = 8.6 Hz), 7.36(2 H, d, J = 8.6 Hz), 7.76(1 H, d, J = 1.0 Hz), 7.84(1 H, d, J = 8.3 Hz), 7.94(1 H, dd, J = 8.3 Hz, 2.0 Hz), 8.20(1 H, dd, J = 8.6 Hz, 2.6 Hz) 8.23(2 H, s), 8.46(1 H, d, J = 2.6 Hz), 10.55(1 H, s). |
| 2517 | 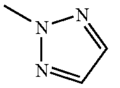 | 1 | hydro-chloride | ($DMSO-d_6$) 5.66(2 H, s), 7.09(1 H, d, J = 8.6 Hz, 7.10(2 H, d, J = 8.6 Hz), 7.32(2 H, d, J = 8.6 Hz), 7.83(2 H, s), 7.83(1 H, d, J = 8.5 Hz), 7.96 (1 H, dd, J = 8.5 Hz, 2.0 Hz), 8.21(1 H, dd, J = 8.5 Hz, 2.3 Hz), 8.23(1 H, d, J = 2.0 Hz), 8.47(1 H, d, J = 2.3 Hz), 10.61(1 H, s). |
| 2518 | 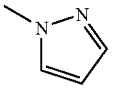 | 1 | hydro-chloride | ($DMSO-d_6$) 5.34(2 H, s), 6.28(1 H, t, J = 2.0 Hz), 7.06(1 H, d, J = 9.0 Hz), 7.07(2 H, d, J = 8.6 Hz), 7.26(2 H, d, J = 8.6 Hz), 7.47(1 H, d, J = 2.0 Hz), 7.83(1 H, d, J = 8.6 Hz), 7.85(1 H, d, J = 2.0 Hz), 7.96(1 H, dd, J = 8.6 Hz, 2.0 Hz), 8.20(1 H, dd, J = 9.0 Hz, 2.6 Hz), 8.23(1 H, d, J = 2.0 Hz), 8.47(1 H, d, J = 2.6 Hz), 10.61(1 H, s). |
| 2519 | 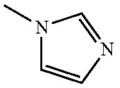 | 2 | free | ($CDCl_3$) 3.04(2 H, t, J = 7.0 Hz), 4.17(2 H, t, J = 7.0 Hz), 6.87(1 H, t, J = 1.3 Hz), 6.94(1 H, d, J = 8.7 Hz), 7.02(1 H, brs), 7.05(4 H, s), 7.30(1 H, brs), 7.56(1 H, d, J = 8.3 Hz), 7.75(1 H, dd, J = 8.3 Hz, 2.1 Hz), 8.03(1 H, d, J = 2.1 Hz), 8.17(1 H, dd, J = 8.7 Hz, 2.3 Hz), 8.23(1 H, d, J = 2.3 Hz), 8.6 1(1 H, brs). |

TABLE 395

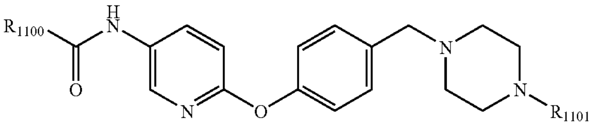

| Example No. | $R_{1100}$ | $R_{1101}$ | $^1$H NMR (solvent) δ ppm |
|---|---|---|---|
| 2520 | 4-ClPh- | piperonyl | ($CDCl_3$) 2.48(8 H, brs), 3.42(2 H, s),3.50(2 H, s), 5.93(2 H, s), 6.74 (2 H, s), 6.85(1 H, s), 6.94(1 H, d, J = 8.6 Hz), 7.07(2 H, d, J = 8.6 Hz), 7.33(2 H, d, J = 8.6 Hz), 7.49(2 H, d, J = 8.6 Hz), 7.73(1 H, brs), 7.82(2 H, d, J = 8.6 Hz), 8.18-8.24(2 H, m). |
| 2521 | 4-CNPh- | piperonyl | ($CDCl_3$) 2.48(8 H, brs), 3.42(2 H, s), 3.51(2 H, s), 5.93(2 H, s), 6.73-6.74(2 H, m), 6.85(1 H, s), 6.96(1 H, d, J = 8.9 Hz), 7.07(2 H, d, J = 8.6 Hz), 7.34(2 H, d, J = 8.6 Hz), 7.79-7.82(3 H, m), 7.99(2 H, d, J = 8.2 Hz), 8.19(1 H, dd, J = 8.9 Hz, 2.6 Hz), 8.26(1 H, d, J = 2.6 Hz). |
| 2522 | 3,4-$Cl_2$Ph- | benzyl | ($CDCl_3$) 2.51(8 H, brs), 3.52(2 H, s), 3.53(2 H, s), 6.95(1 H, d, J = 8.9 Hz), 7.07(2 H, d, J = 8.2 Hz), 7.26-7.36(7 H, m), 7.59(1 H, d, J = 8.6 Hz), 7.69-7.73(2 H, ml), 7.99(1 H, d, J = 2.0 Hz), 8.18(1 H, dd, J = 8.9 Hz, 2.6 Hz), 8.25(1 H, d, J = 2.6 Hz). |
| 2523 | 3,4-$Cl_2$Ph- | $—COOC(CH_3)_3$ | ($CDCl_3$) 1.46(9 H, s), 2.40(4 H, t, J = 5.0 Hz), 3.43(4 H, t, J = 5.0 Hz), 3.50(2 H, s), 6.95(1 H, d, J = 8.9 Hz), 7.08(2 H, d, J = 8.6 Hz), 7.34 (2 H, d, J = 8.6 Hz), 7.57(1 H, d, J = 8.3 Hz), 7.70-7.74(1 H, m), 8.00 (1 H, d, J = 2.0 Hz), 8.07(1 H, brs), 8.17-8.21(1 H, m), 8.27(1 H, d, J = 2.6 Hz). |
| 2524 | 3,4-$Cl_2$Ph- | $—C_2H_5$ | ($CDCl_3$) 1.08(3 H, t, J = 7.3 Hz), 2.38-2.49(10 H, m), 3.48(2 H, s), 6.88(1 H, d, J = 8.9 Hz), 7.01(2 H, d, J = 8.3 Hz), 7.30(2 H, d, J = 8.6 Hz), 7.49(1 H, d, J = 8.3 Hz), 7.66-7.70(1 H, m), 7.95(1 H, d, J = 2.0 Hz), 8.13(1 H, dd, J = 8.9 Hz, 2.6 Hz), 8.23(1 H, d, J = 2.6 Hz), 8.58 (1 H, brs). |
| 2525 | 3,4-$Cl_2$Ph- | -Ph | ($CDCl_3$) 2.64(4 H, t, J = 5.0 Hz), 3.22(4 H, t, J = 5.0 Hz), 3.57(2 H, s), 6.83-6.88(1 H, m), 6.92-6.99(3 H, m), 7.10(2 H, d, J = 8.6 Hz), 7.23-7.29(2 H, m), 7.39(2 H, d, J = 8.6 Hz), 7.59(1 H, d, J = 8.6 Hz), 7.71(1 H, dd, J = 8.3 Hz, 2.0 Hz), 7.76(1 H, s), 7.99(1 H, d, J = 2.0 Hz), 8.19(1 H, dd, J = 8.6 Hz, 2.6 Hz), 8.26(1 H, d, J = 2.6 Hz). |
| 2526 | 4-$CF_3$Ph- | $—COOC(CH_3)_3$ | (DMSO-$d_6$) 1.40(9 H, s), 2.32-2.36(4 H, m), 3.30-3.35(4 H, m), 3.49 (2 H, s), 7.06-7.09(3 H, m), 7.32-7.36(2 H, m), 7.94(2 H, d, J = 8.4 Hz), 8.18(2 H, d, J = 8.1 Hz), 8.24(1 H, dd, J = 8.9 Hz, 2.7 Hz), 8.52 (1 H, d, J = 2.7 Hz), 10.64(1 H, s). |
| 2527 | 3,4-$Cl_2$Ph | $—CH_3$ | ($CDCl_3$) 2.27(3 H, s), 2.45(8 H, brs), 3.47(2 H, s), 6.87(1 H, d, J = 8.9 Hz), 6.99-7.03(2 H, m), 7.27-7.31(2 H, m), 7.48(1 H, dd, J = 8.3 Hz, 2.6 Hz), 7.68(1 H, dd, J = 8.6 Hz, 2.0 Hz), 7.94(1 H, d, J = 2.0 Hz), 8.12(1 H, dd, J = 8.9 Hz, 2.6 Hz), 8.23(1 H, d, J = 2.6 Hz), 8.76(1 H, brs). |
| 2528 | 3,4-$Cl_2$Ph- | piperonyl | ($CDCl_3$) 2.47(8 H, brs), 3.42(2 H, s), 3.49(2 H, s), 5.93(2 H, s), 6.73 (2 H, d, J = 0.7 Hz), 6.84(1 H, s), 6.91(1 H, d, J = 8.9 Hz), 7.04(2 H, d, J = 8.6 Hz), 7.31(2 H, d, J = 8.6 Hz), 7.53(1 H, d, J = 8.2 Hz), 7.70 (1 H, dd, J = 8.3 Hz, 2.0 Hz), 7.97(1 H, d, J = 2.3 Hz), 8.138.18(1 H, m), 8.24(2 H, d, J = 2.6 Hz). |

TABLE 396

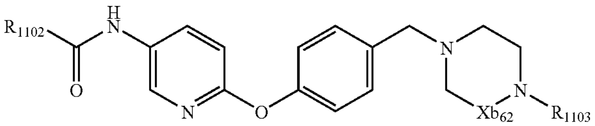

| Example No. | $R_{1102}$ | $Xb_{62}$ | $R_{1103}$ | Form | $^1$H NMR (solvent) δ ppm |
|---|---|---|---|---|---|
| 2529 | 3,4-$Cl_2$Ph- | $—(CH_2)_2—$ | piperonyl | free | ($CDCl_3$) 1.97-2.01(2 H, m), 2.85-2.90(8 H, m), 3.68(2 H, s), 3.75(2 H, s), 5;95(2 H, s), 6.74-6.84(2 H, m), 6.94-6.97(2 H, m), 7.08(2 H, d, J = 8.6 Hz), 7.41(2 H, d, J = 8.6 Hz),. 7.57(1 H, d, J = 8.6 Hz), |

TABLE 396-continued

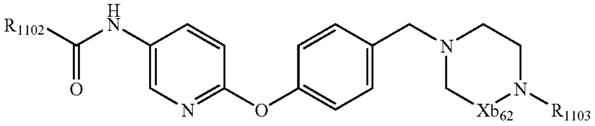

| Example No. | $R_{1102}$ | $Xb_{62}$ | $R_{1103}$ | Form | $^1$H NMR (solvent) δ ppm |
|---|---|---|---|---|---|
| | | | | | 7.75(1 H, dd, J = 8.6 Hz, 2.3 Hz), 8.01-8.02(2 H, m), 8.20(1 H, dd, J = 8.9 Hz, 2.6 Hz), 8.31(1 H, d, J = 2.6 Hz). |
| 2530 | 3,4-$Cl_2$Ph- | —$(CH_2)_2$— | benzyl | trihydro-chloride | (DMSO-$d_6$) 2.25(2 H, brs), 3.38 (4 H, brs), 3.78(4 H, brs), 4.38 (4 H, s), 7.127.22(3 H, m), 7.46-7.48(3 H, m), 7.62-7.67 (4 H, m), 7.84(1 H, d, J = 8.6 Hz), 7.98 (1 H, dd, J = 8.6 Hz, 2.0 Hz), 8.22-8.27(2 H, m), 8.55 (1 H, d, J = 2.6 Hz), 10.68(1 H, s). |
| 2531 | 3,4-$Cl_2$Ph- | —CO— | benzyl | free | ($CDCl_3$) 2.66(2 H, t, J 5.9 Hz), 3.22-3.25(4 H, m), 3.55(2 H, s), 4.60(2 H, s), 6.95(1 H, d, J = 8.9 Hz), 7.08(2 H, d, J = 8.6 Hz), 7.23-7.35(7 H, m), 7.56(1 H, d, J = 8.3 Hz, 7.72(1 H, dd, J = 2.0 Hz, 8.6 Hz), 8.00(1 H, d, J = 2.0 Hz), 8.10(1 H, s), 8.18(1 H, dd, J = 2.6 Hz, 8.6 Hz), 8.28 (1 H, d, J = 2.6 Hz). |
| 2532 | 4-$CF_3$Ph- | —$CH_2$— | 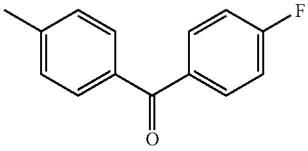 | free | ($CDCl_3$) 2.6 1(4 H, brs), 3.38(4 H, brs), 3.55(2 H, s), 6.85-6.94(3 H, m), 7.06-7.14 (4 H, m), 7.36(2 H, d, J = 8.3 Hz), 7.64(2 H, d, J = 8.3 Hz), 7.70-7.75(4 H, m), 7.99 (2 H, t, J = 8.3 Hz), 8.24(1 H, dd, J = 8.7 Hz, 2.5 Hz), 8.40(1 H, d, J = 2.6 Hz), 9.19 (1 H, s). |
| 2533 | 4-$CF_3$Ph- | —$CH_2$— | 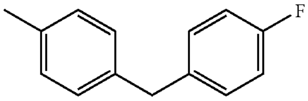 | free | ($CDCl_3$) 2.58-2.62(4 H, m), 3.14-3.17(4 H, m), 3.54(2 H, s), 3.86(2 H, s), 6.83-7.14 (11 H, m), 7.36(2 H, d, J = 8.4 Hz), 7.71 (2 H, d, J = 8.3 Hz), 7.96(2 H, d, J = 8.1 Hz), 8.15-8.26(3 H, m). |

TABLE 397

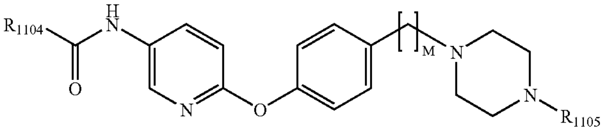

| Example No. | $R_{1104}$ | $R_{1105}$ | M | $^1$H NMR ($CDCl_3$) δ ppm |
|---|---|---|---|---|
| 2534 | 3,4-$Cl_2$Ph- | —$CH_3$ | 2 | 2.30(3 H, s), 2.50-2.81(12 H, m), 6.86(1 H, d, J = 8.6 Hz), 6.98 (2 H, d, J = 8.6 Hz), 7.18(2 H, d, J = 8.3 Hz), 7.47(1 H, d, J = 8.3 Hz), 7.67(1 H, dd, J = 8.3 Hz, 2.0 Hz), 7.94(1 H, d, J = 2.0 Hz), 8.11(1 H, dd, J = 8.9 Hz, 2.6 Hz), 8.21(1 H, d, J = 2.6 Hz), 8.66 (1 H, brs). |
| 2535 | 3,4-$Cl_2$Ph- | piperonyl | 2 | 2.51-2.83(12 H, m), 3.43(2 H, s), 5.93(2 H, s), 6.74 (2 H, d, J = 1.0 Hz), 6.86-7.03(4 H, m), 7.20(2 H, d, J = 8.3 Hz), 7.53(1 H, d, J = 8.6 Hz), 7.68-7.72 (1 H, m), 7.97(1 H, d, J = 2.0 Hz), 8.15(1 H, dd, J = 8.9 Hz, 2.6 Hz), 8.23(2 H, d, J = 2.6 Hz). |
| 2536 | 3,4-$Cl_2$Ph- | —$CH_3$ | 3 | 1.78-1.84(2 H, m), 2.29(3 H, s), 2.36-2.48(10 H, m), 2.59-2.65 (2 H, m), 6.89(1 H, d, J = 8.4 Hz), 7.00(2 H, d, J = 8.4 Hz), 7.18 (2 H, d, J = 8.4 Hz), 7.52(1 H, d, J = 8.6 Hz), 7.67-7.71(1 H,m), 7.96(1 H, d, J = 2.2 Hz), 8.11-8.15(1 H, m), |

| | | | | |
|---|---|---|---|---|
| | | | | 8.23(1 H, d, J = 2.7 Hz), 8.31(1 H, brs). |
| 2537 | 3,4-$Cl_2$Ph- | piperonyl | 3 | 1.78-1.84(2 H, m), 2.36-2.47(10 H, m), 2.60-2.65 (2 H, m), 3.41 (2 H, s), 5.93(2 H, s), 6.73(2 H, d, J = 0.8 Hz), 6.85(1 H, s), 6.91 (1 H, d, J = 8.9 Hz), 7.02(2 H, d, J = 8.4 Hz), 7.19(2 H, d, J = 8.6 Hz), 7.55(1 H, d, J = 8.1 Hz), 7.68-7.71(1 H, m), 7.96-7.97(2 H, m), 8.14-8.17(1 H, m), 8.23(1 H, d, J = 2.7 Hz). |
| 2538 | 4-$CF_3$Ph- | —$COOC(CH_3)_3$— | 3 | 1.46(9 H,.s), 1.78-1.89(2 H, m), 2.36-2.42(6 H, m), 2.62-2.68 (2 H, m), 3.42-3.45(4 H, m), 6.94(1 H, d, J = 8.9 Hz), 7.01-7.06 (2 H, m), 7.18-7.23(2 H, m), 7.76(2 H, d, J = 8.2 Hz), 7.99-8.03 (3 H, m), 8.22(1 H, dd, J = 8.9 Hz, 2.6 Hz), 8.28(1 H, d, J = 2.6 Hz). |
| 2539 | 3,4-$Cl_2$Ph- | —$CH_3$ | 4 | 1.50-1.80(4 H, m), 2.32(3 H, s), 2.38(2 H, t, J = 7.3 Hz), 2.30-2.70(8 H, m), 2.64(2 H, t, J = 7.3 Hz), 6.94(1 H, d, J = 8.8 Hz), 7.03(2 H, d, J = 8.2 Hz), 7.19(2 H, d, J = 8.2 Hz), 7.58(1 H, d, J = 8.2 Hz), 7.72(1 H, dd, J = 8.2 Hz, 2.0 Hz), 7.84(1 H, s), 8.00(1 H, d, J = 2.0 Hz), 8.18(1 H, dd, J = 8.8 Hz, 2.6 Hz), 8.26 (1 H, d, J = 2.6 Hz). |
| 2540 | 3,4-$Cl_2$Ph- | benzyl | 4 | 1.45-1.75(4 H, m), 2.36(2 H, t, J = 7.5 Hz), 2.30-2.65(8 H, m), 2.62(2 H, t, J = 7.7 Hz), 3.51(2 H, s), 6.92(1 H, d, J = 8.6 Hz), 7.03(2 H, d, J = 8.6 Hz), 7.19(2 H, d, J = 8.6 Hz), 7.15-7.40(5 H, m), 7.57(1 H, d, J = 8.2 Hz), 7.71(1 H, dd, J = 8.2 Hz, 2.0 Hz), 7.85(1 H, s), 7.98(1 H, d, 4 2.0 Hz), 8.16(1 H, dd, J = 8.6 Hz, 2.5 Hz), 8.24(1 H, d, J = 2.5 Hz). |
| 2541 | 3,4-$Cl_2$Ph- | benzyl | 5 | 1.25-1.45(2 H, m), 1.45-1.75(4 H, m), 2.34(2 H, t, J = 7.7 Hz), 2.30-2.70(8 H, m), 2.61(2 H, t, J = 7.7 Hz), 3.51(2 H, s), 6.93(1 H, d, J = 8.7 Hz), 7.03(2 H, d, J = 8.6 Hz), 7.19(2 H, d, J = 8.6 Hz), 7.20-7.40(5 H, m), 7.58(1 H, d, J = 8.3 Hz), 7.70(1 H, dd, J = 8.3 Hz, 2.0 Hz), 7.71(1 H, d, J = 2.0 Hz), 7.98(1 H, d, J = 2.0 Hz), 8.16(1 H, dd, J = 8.7 Hz, 2.6 Hz), 8.24(1 H, d, J = 2.6 Hz). |

TABLE 398

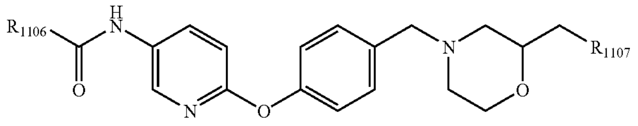

| Example No. | $R_{1106}$ | $R_{1107}$ | Form | $^1H$ NMR (DMSO-$d_6$) δ ppm |
|---|---|---|---|---|
| 2542 | 3,4-$Cl_2$Ph- | —H | hydro-chloride | 1.12(3 H, d, J = 6.3 Hz), 2.75-3.03(2 H, m), 3.24-3.39(2 H, m), 378-3.98(3 H, m), 4.31(2 H, brs) 7.13(1 H, d, J = 8.6 Hz), 7.20 (2 H, d, J = 8.3 Hz), 7.63(2 H, d, J = 8.3 Hz), 7.84(1 H, d, J = 8.2 Hz), 7.98(1 H, dd, J = 8.2 Hz, 2.6 Hz), 8.24(1 H, dd, J = 8.9 Hz, 2.6 Hz), 8.25(1 H, d, J = 2.0 Hz), 8.55(1 H, d, J = 2.6 Hz), 10.67(1 H, brs), 11.10(1 H, brs). |
| 2543 | 3,4-$Cl_2$Ph- | —$O(CH_2)_3CH_3$ | hydro-chloride | 0.87(3 H, t, J = 7.3 Hz), 1.22-1.36(2 H, m), 1.41-1.51(2 H, m), 2.90-3.07(2 H, m), 3.23-3.50(611, m), 3.80-3.88(1 H, m), 3.99-4.02(2 H, m), 4.35(2 H, brs), 7.13(1 H, d, J = 8.9 Hz), 7.21 (2 H, d, J = 8.6 Hz), 7.63(2 H, d, J = 8.3 Hz), 7.84(1 H, d, J = 8.6 Hz), 7.97(1 H, dd, J = 8.3 Hz, 2.0 Hz), 8.24(1 H, dd, J = 8.9 Hz, 2.6 Hz), 8.25(1 H, d, J = 2.0 Hz), 8.54(1 H, d, J = 2.6 Hz), 10.66(1 H, brs), 11.17(1 H, brs). |
| 2544 | 3,4-$Cl_2$Ph- | piperidino | dihydro-chloride | 1.38-1.77(6 H, m), 2.92-3.10(5 H, m), 3.22-3.33(4 H, m), 3.47-3.51(1 H, m), 3.97-4.06(2 H, m), 4.27-4.55(3 H, m), 7.13 (1 H, d, J = 8.9 Hz), 7.21(2 H, d, J = 8.6 Hz), 7.67(2 H, d, J = 8.6 Hz), 7.84(1 H, d, J = 8.6 Hz), 7.99(1 H, dd, J = 8.2 Hz, 2.0 Hz), 8.26(1 H, dd, J = 8.6 Hz, 3.0 Hz), 8.28(1 H, d, J = 2.3 Hz), 8.57(1 H, d, J = 2.6 Hz), 10.27(1 H, brs), 10.74(1 H, brs), 11.91 (1 H, brs). |

TABLE 398-continued

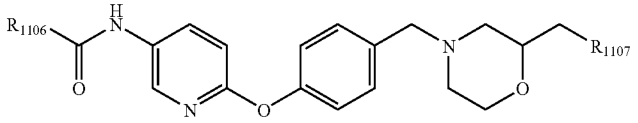

| Example No. | $R_{1106}$ | $R_{1107}$ | Form | $^1$H NMR (DMSO-$d_6$) δ ppm |
|---|---|---|---|---|
| 2545 | 4-$CF_3$Ph- | —H | hydro-chloride | 1.12(3 H, d, J = 6.1 Hz), 2.68-2.80(1 H, m), 2.983.06(1 H, m), 3.24-3.28(2 H, m), 3.80-3.90(3 H, m), 4.31(2 H, brs), 7.14(1 H, d, J = 8.7 Hz), 7.21(2 H, d, J = 8.4 Hz), 7.64(2 H, d, J = 8.1 Hz), 7.93(2 H, d, J = 8.4 Hz), 8.19(2 H, d, J = 8.2 Hz), 8.27(1 H, dd, J = 8.9 Hz, 2.6 Hz), 8.57(1 H, d, J = 2.6 Hz), 10.75(1 H, brs), 11.19(1 H, brs). |
| 2546 | 4-$CF_3$Ph- | —OCH | hydro-chloride | 2.92-3.12(2 H, m), 3.26(3 H, s), 3.34-3.47 (4 H, m), 3.80-4.02 (3 H, m), 4.34(2 H, brs), 7.14(1 H, d, J = 8.9 Hz), 7.21(2 H, d, J = 8.6 Hz), 7.63(2 H, d, J = 8.2 Hz), 7.94(2 H, d, J = 8.4 Hz), 8.18 (2 H, d, J = 8.1 Hz), 8.27(1 H, dd, J 8.7 Hz, 2.6 Hz), 8.57(1 H, d, J = 2.6 Hz), 10.73(1 H, brs), 11.13(1 H, brs). |
| 2547 | 3,4-$Cl_2$Ph- | —$OCH_3$ | hydro-chloride | 2.92-3.11(2 H, m), 3.26(3 H, s), 3.31-3.52 (4 H, m), 3.79-3.87 (1 H, m), 3.95-4.04 (2 H, m), 4.34(2 H, brs), 7.14(1 H, d, J = 8.9 Hz), 7.21(2 H, d, J = 8.6 Hz), 7.62(2 H, d, J = 8.6 Hz), 7.84(1 H, d, J = 8.4 Hz), 7.97(1 H, dd, J = 8.4 Hz, 2.2 Hz), 8.24-8.26(2 H, m), 8.54(1 H, d, J = 2.6 Hz), 10.66(1 H, brs), 11.02(1 H, brs). |

TABLE 399

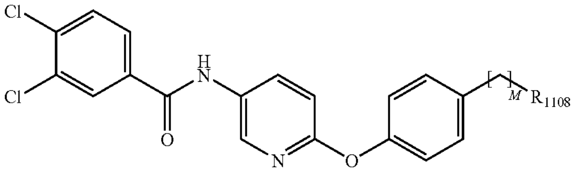

| Example No. | $R_{1108}$ | M | Form | $^1$H NMR (solvent) δppm |
|---|---|---|---|---|
| 2548 | 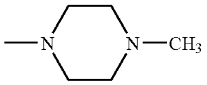 | 5 | free | ($CDCl_3$) 1.30-1.45 (2H, m), 1.45-1.75 (4H, m), 2.30 (3H, s), 2.25-2.40 (2H, m), 2.49 (8H, brs), 2.62 (2H, t, J = 7.5 Hz), 6.94 (1H, d, J = 8.9 Hz), 7.04 (2H, d, J = 8.6 Hz), 7.20 (2H, d, J = 8.6 Hz), 7.59 (1H, d, J = 8.2 Hz), 7.65-7.75 (2H, m), 7.98 (1H, d, J = 2.0 Hz), 8.17 (1H, dd, J = 8.9 Hz, 3.0 Hz), 8.24 (1H, d, J = 3.0 Hz). |
| 2549 | 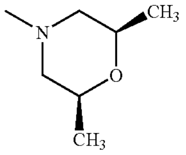 | 1 | hydro-chloride | (DMSO-$d_6$) 1.13 (6H, d, J = 6.6 Hz), 2.66-2.76 (2H, m), 3.25-3.34 (2H, m), 3.91-3.99 (2H, m), 4.30 (2H, s), 7.14 (1H, d, J = 8.6 Hz), 7.21 (2H, d, J = 8.6 Hz), 7.62 (2H, d, J = 8.3 Hz), 7.85 (1H, d, J = 8.6 Hz), 7.97 (1H, dd, J = 8.6 Hz, 2.0 Hz), 8.24 (.1H, dd, J = 8.6 Hz, 3.0 Hz), 8.25 (1H, d, J = 2.3 Hz), 8.55 (1H, d, J = 2.6 Hz), 10.65 (1H, brs), 10.96 (1H, brs). |
| 2550 | 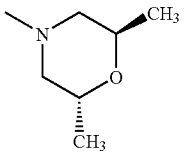 | 1 | hydro-chloride | (DMSO-$d_6$) 1.11 (3H, d, J = 6.3 Hz), 1.40 (3H, d, J = 6.9 Hz), 2.67-2.75 (1H, m), 3.10 (2H, m), 3.25-3.33 (1H, m), 4.02-4.32 (4H, m), 7.14 (1H, d, J = 8.9 Hz), 7.21 (2H, d, J = 8.3 Hz), 7.65 (2H, d, J = 8.6 Hz), 7.85 (1H, d, J = 8.2 Hz), 7.97 (1H, dd, J = 8.6 Hz, 2.0 Hz), 8.21-8.26 (2H, m), 8.54 (1H, d, J = 2.3 Hz), 10.46 (1H, brs), 10.64 (1H, brs). |

Example 2551

Production of 1-(3-{4-[4-(3,4-dichlorobenzoylamino)-phenoxy]phenyl}propionyl)-4-[2-(morpholino)acetyl]-piperazine To a solution of 1-chloroacetyl-4-(3-{4-[4-(3,4-dichlorobenzoylamino)phenoxy]phenyl}propionyl)-piperazine (0.515 g, 0.896 mmol) and diisopropylethylamine (0.234 mL, 1.34 mmol) in acetonitrile (11 mL) was added morpholine (0.117 mL, 1.34 mmol), and the resulting solution was refluxed for 1 hour. This reaction solution was concentrated under reduced pressure. To the residue was added a saturated sodium bicarbonate solution, and extracted with chloroform. The chloroform layer was dried over anhydrous magnesium sulfate, and evaporated. The obtained solid was recrystallized from water-containing acetone, to thereby yield 0.441 g of the title compound.

Appearance: White powder

Melting point: 187-190° C.

The following compounds were produced in the same manner as in Example 2551.

TABLE 400

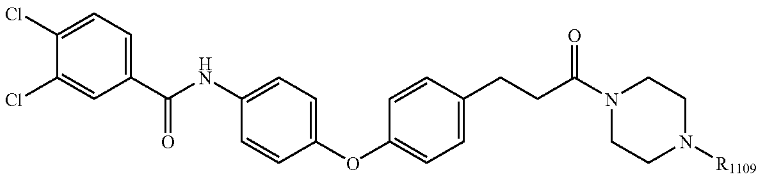

| Example No. | $R_{1109}$ | Form | mp (° C.) or $^1$H NMR |
|---|---|---|---|
| 2552 | —$COCH_2N(C_2H_5)_2$ | 3/2 oxalate | mp 107-118 |
| 2553 | —$COCH_2NHCH_2Ph$ | hydrochloride | mp 199-202 |
| 2554 | —$COCH_2N(C_2H_5)CH_2Ph$ | fumarate | $^1$H NMR (DMSO-$d_6$) δ 0.99 (3H, t, J = 7.1 Hz), 2.56-2.70 (2H, m), 2.73 2.86 (2H, m), 3.09-3.50 (12H, m), 3.59 (2H, s), 6.61 (2H, s), 6.91 (2H, d, J = 8.0 Hz), 6.98 (2H, d, J = 9.0 Hz), 7.14-7.37 (7H, m), 7.74 (2H, d, J = 9.0 Hz), 7.81 (1H, d, J = 8.4 Hz), 7.92 (1H, dd, J = 8.4 Hz, 2.1 Hz), 8.20 (1H, d, J = 2.1 Hz), 10.39 (1H, s), 13.09 (2H, brs). |
| 2555 | 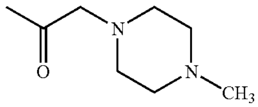 | dihydrochloride | mp 173-176 |
| 2556 | —$COCH_2N(C_2H_5)Ph$ | free | mp 140-143 |

TABLE 401

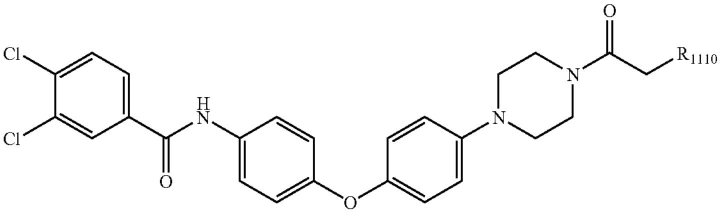

| Example No. | $R_{1110}$ | mp (° C.) |
|---|---|---|
| 2557 | 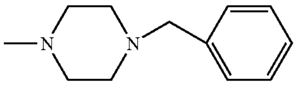 | 206-210 |
| 2558 | 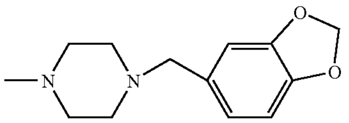 | 154-156 |

TABLE 401-continued
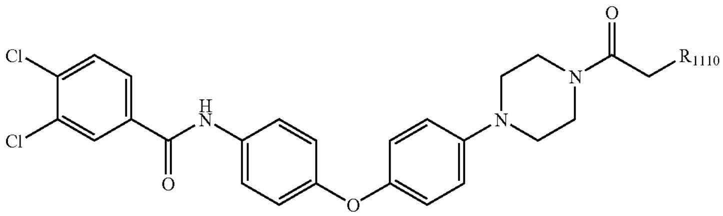
| Example No. | $R_{1110}$ | mp (° C.) |
|---|---|---|
| 2559 | morpholino | 177-178 |
| 2560 | 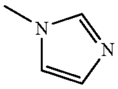 | 204-206 |
| 2561 | —$N(CH_3)CH_2Ph$ | 182-184 |
TABLE 402
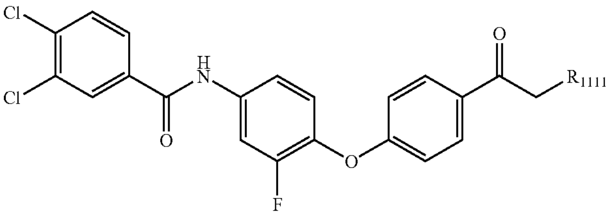
| Example No. | $R_{1111}$ | mp (° C.) |
|---|---|---|
| 2562 | 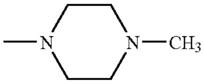 | 151-152 |
| 2563 | morpholino | 177-178 |
| 2564 | 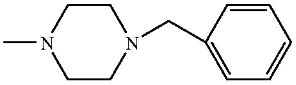 | 146-147 |
TABLE 403
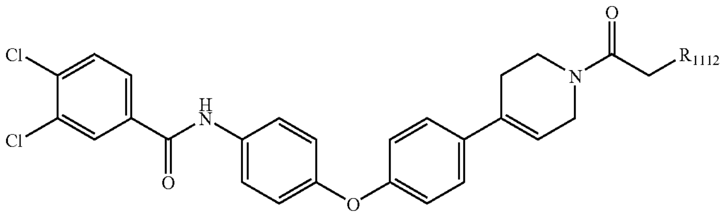
| Example No. | $R_{1112}$ | mp (° C.) |
|---|---|---|
| 2565 | morpholino | 195-197 |
| 2566 | 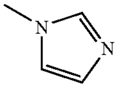 | 146-148 |

TABLE 403-continued
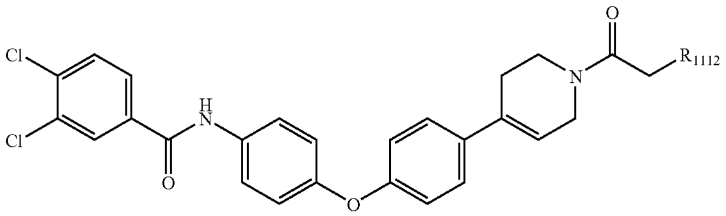
| Example No. | $R_{1112}$ | mp (° C.) |
|---|---|---|
| 2567 | 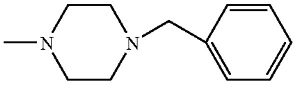 | 173-176 |
| 2568 | 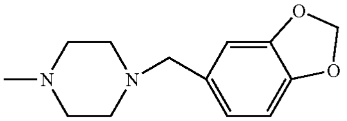 | 150-153 |
TABLE 404
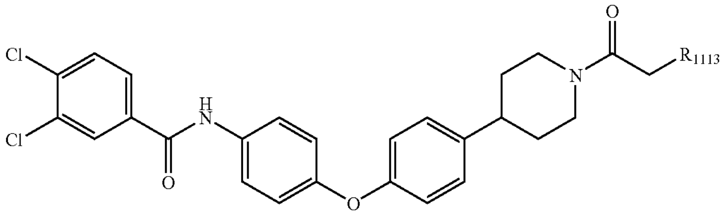
| Example No. | $R_{1113}$ | Form | mp (° C.) |
|---|---|---|---|
| 2569 | 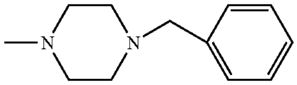 | dihydrochloride | 152-155 |
| 2570 | 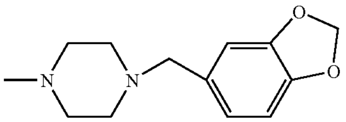 | dihydrochloride | 181-185 |
| 2571 | morpholino | hydrochloride | 146-150 |
TABLE 405
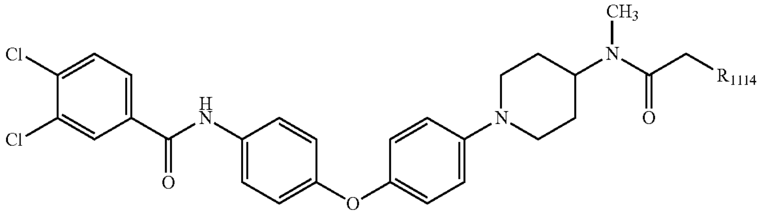
| Example No. | $R_{1114}$ | mp (° C.) |
|---|---|---|
| 2572 | morpholino | 157-160 |
| 2573 | 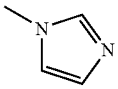 | 241-243 |

TABLE 405-continued
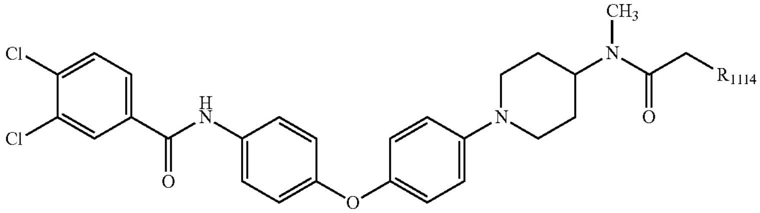
| Example No. | $R_{1114}$ | mp (° C.) |
|---|---|---|
| 2574 | 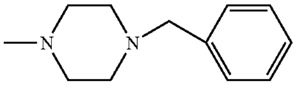 | 193-196 |
| 2575 | 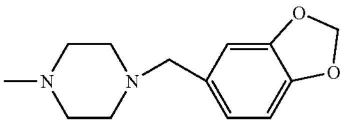 | 180-182 |
TABLE 406
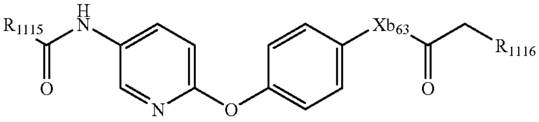
| Example No. | $R_{1115}$ | $Xb_{63}$ | $R_{1116}$ | mp (° C.) or $^1$H NMR |
|---|---|---|---|---|
| 2576 | 3,4-$Cl_2$Ph— | none | morpholino | $^1$H NMR (DMSO-$d_6$) δ 2.50-2.53 (4H, m), 3.55-3.61 (4H, m), 3.82 (2H, s), 7.20 (1H, d, J = 8.7 Hz), 7.21 (2H, d, J = 8.1 Hz), 7.85 (1H, d, J = 8.4 Hz), 7.96 (1H, dd, J = 8.4 Hz, 1.2 Hz), 8.06 (2H, d, J = 8.4 Hz), 8.23 (1H, d, J = 1.5 Hz), 8.27 (1H, dd, J = 8.9 Hz, 2.8 Hz), 8.55 (1H, d, J = 2.8 Hz), 10.61 (1H, brs). |
| 2577 | 4-$CF_3$Ph— | 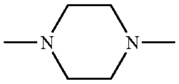 | 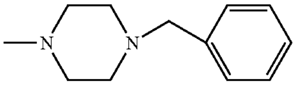 | mp 179-181 |
| 2578 | 4-$CF_3$Ph— | 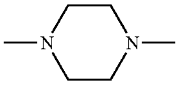 | 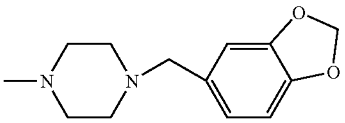 | mp 172-174 |
| 2579 | 4-$CF_3$Ph— | 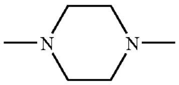 | morpholino | mp 144-146 |
| 2580 | 4-$CF_3$Ph— | 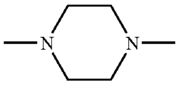 | —N($CH_3$)$CH_2$Ph | mp 188-190 |
| 2581 | 4-$CF_3$Ph— | 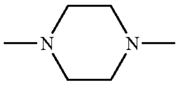 | 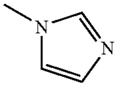 | mp 192-193 |

The following compound was produced in the same manner as in Reference Example 860.

Example 2582

1-{4-[5-(3,4-Dichlorobenzoylamino)pyridin-2-yloxy]benzyl}piperazine-4-carboxylic acid ethyl ester Appearance: Pale yellow oil $^1$H NMR ($CDCl_3$) δ 1.25 (3H, t, J=7.0 Hz), 1.76 (2H, m), 1.77 (2H, m), 2.03 (2H, t, J=11.5 Hz), 2.28 (1H, m), 2.87 (2H, brd, J=11.5 Hz), 3.48 (2H, s), 4.13 (2H, q, J=7.0 Hz), 6.94 (1H, d, J=9.0 Hz), 7.06 (2H, d, J=8.5 Hz), 7.33 (2H, d, J=9.0 Hz), 7.57 (1H, d, J=8.5 Hz), 7.70 (1H, dd, J=8.5 Hz, 2.0 Hz), 7.88 (1H, brs), 7.97 (1H, d, J=2.0 Hz), 8.17 (1H, dd, J=9.0 Hz, 3.0 Hz), 8.24 (1H, d, J=3.0 Hz).

Example 2583

Production of 3,4-dichloro-N-{6-[4-(2,4-dioxo-3,4-dihydro-2H-pyrimidin-1-ylmethyl)phenoxy]pyridin-3-yl}benzamide To uracil (200 mg, 1.8 mmol) was added hexamethyldisilazane (5 mL), and the resulting solution was stirred for 5.5 hours at 150° C. Insoluble matter was removed by filtration, and the filtrate was concentrated under reduced pressure. The residue was dissolved in a solution of acetonitrile (10 mL)-THF (5 mL), and to this solution were added 3,4-dichloro-N-[6-(4-chloromethylphenoxy)pyridin-3-yl]benzamide (500 mg, 1.2 mmol) and tin tetrachloride (3 drops). The resulting solution was refluxed for 2.5 hours. To this reaction solution was added methanol (1 mL), and the resulting solution was stirred for 30 minutes at room temperature. The resulting reaction solution was concentrated under reduced pressure, and the residue was purified by silica gel column chromatography (methanol:chloroform=1:99→3:97), to thereby yield 20 mg of the title compound.

Appearance: White powder $^1$H NMR (DMSO-$d_6$) δ 4.88 (2H, s), 5.61 (1H, dd, J=7.9 Hz, 2.3 Hz), 7.07-7.13 (3H, m), 7.35 (2H, d, J=8.6 Hz), 7.79-7.85 (2H, m), 7.95 (1H, dd, J=8.6 Hz, 2.0 Hz), 8.18 (1H, d, J=2.6 Hz), 8.22 (1H, d, J=2.0 Hz), 8.47 (1H, d, J=2.6 Hz), 10.55 (1H, s), 11.33 (1H, s);

MS: m/z 482 ($M^+$).

Example 2584

Production of N-{6-[4-(4-benzyl-2-oxopiperazin-1-ylmethyl)phenoxy]pyridin-3-yl}-3,4-dichlorobenzamide dihydrochloride To a solution of 4-benzylpiperazin-2-one (0.56 g, 2.95 mmol) in DMF (10 mL) was added 60% sodium hydride (0.12 g, 2.95 mmol), and this solution was stirred at room temperature for 30 minutes. 2-(4-chloromethylphenoxy)-5-nitropyridine (0.78 g, 2.95 mmol) was added to the reaction mixture, and the mixture was stirred for 1 hour at room temperature. To this mixture was added brine (50 mL), and extracted with ethyl acetate (50 mL). The ethyl acetate layer was washed with brine, dried over anhydrous magnesium sulfate, and evaporated under reduced pressure. The remaining oil was dissolved in ethyl acetate (5 mL), and to the resulting solution was added iron powder (0.33 g, 5.89 mmol). This solution was stirred for 2 hours at room temperature. The resulting reaction solution was concentrated under reduced pressure, and a saturated sodium bicarbonate solution (50 mL) was added to the residue. The obtained mixture was extracted with ethyl acetate (50 mL). The ethyl acetate layer was washed with brine, dried over anhydrous sodium sulfate, and evaporated. The remaining oil was dissolved in THF (10 mL). To the resulting solution were added triethylamine (0.21 mL, 1.47 mmol) and 3,4-dichlorobenzoyl chloride (0.31 mL, 1.47 mmol), and this solution was stirred at room temperature for 2 hours. A saturated sodium bicarbonate solution (50 mL) was added to the solution, and extracted with ethyl acetate (50 mL). The ethyl acetate layer was washed with brine, dried over anhydrous magnesium sulfate, and evaporated under reduced pressure. The residue was purified by silica gel column chromatography (chloroform:methanol=40:1). The obtained oil was dissolved in ethyl acetate (5 mL), and to the resulting solution was added a solution of 4 N hydrogen chloride in ethyl acetate (1.5 mL, 6 mmol). The formed white powder was collected by suction filtration, to thereby yield 0.045 g of the title compound.

Appearance: White powder $^1$H NMR (DMSO-$d_6$) δ 3.54 (4H, m), 3.86 (2H, brs), 4.42 (2H, s), 4.59 (2H, brs), 7.06-7.12 (3H, m), 7.34 (2H, d, J=8.6 Hz), 7.48-7.51 (3H, m), 7.57-7.60 (2H, m), 7.84 (1H, d, J=8.6 Hz), 7.97 (1H, dd, J=2.0 Hz, 8.3 Hz), 8.18-8.24 (2H, m), 8.49 (1H, d, J=2.6 Hz), 10.61 (1H, s).

The following compound was produced in the same manner as in Reference Example 656.

Example 2585

2-({4-[5-(3,4-Dichlorophenylamino)pyridin-2-yloxy]-2-trifluoromethylphenyl}ethylamino)-1-(4-piperonylpiperazin-1-yl)ethanone $^1$H NMR ($CDCl_3$) δ 1.02 (3H, t, J=7.1 Hz), 2.30-2.45 (4H, m), 3.22 (2H, q, J=7.1 Hz), 3.40 (2H, s), 3.45-3.65 (4H, m), 3.85 (2H, s), 5.57 (1H, brs), 5.94 (2H, s), 6.65-6.80 (3H, m), 6.85 (1H, s), 6.95 (1H, d, J=8.7 Hz), 7.00 (1H, d, J=2.7 Hz), 7.29-7.31 (2H, m), 7.39 (1H, d, J=2.7 Hz), 7.53 (1H, dd, J=8.7 Hz, 2.9 Hz), 7.64 (1H, d, J=8.8 Hz), 7.99 (1H, d, J=2.7 Hz).

The following compounds were produced in the same manner as in Reference Example 658.

TABLE 407

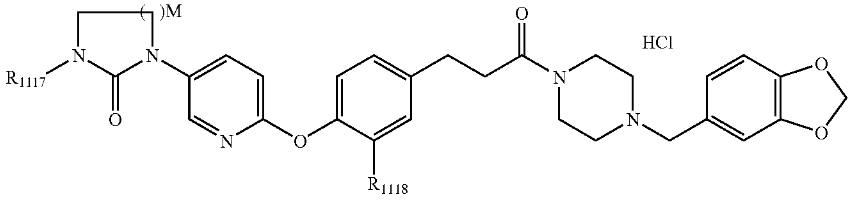

| Example No. | $R_{1117}$ | $R_{1118}$ | M | mp (° C.) or $^1$H NMR (DMSO-$d_6$) δ ppm |
|---|---|---|---|---|
| 2586 | 4-$CF_3$Ph- | —H | 2 | $^1$H NMR 2.14-2.30 (2H, m), 2.62-3.12 (7H, m), 3.20-3.58 (3H, m), 3.77 (2H, t, J = 5.9 Hz), 3.81-4.15 (3H, m), 4.16-4.32 (2H, m), 4.49-4.57 (1H, m), 6.08 (2H, s), 6.96-7.09 (5H, m), 7.21 (1H, |

TABLE 407-continued

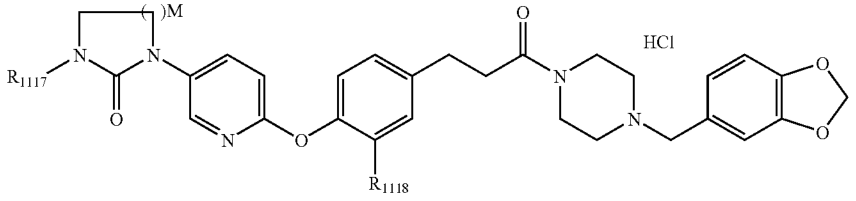

| Example No. | $R_{1117}$ | $R_{1118}$ | M | mp (° C.) or $^1$H NMR (DMSO-$d_6$) δ ppm |
|---|---|---|---|---|
| | | | | s), 7.29 (2H, d, J = 8.5 Hz), 7.58 (2H, d, J = 8.5 Hz), 7.70 (2H, d, J = 8.8 Hz), 7.86 (1H, dd, J = 2.8 Hz, 8.8 Hz), 8.13 (1H, d, J = 2.8 Hz), 10.78-11.01 (1H, m). |
| 2587 | 3,4-$Cl_2$Ph- | —H | 2 | mp 182.0-183.0 |
| 2588 | 3-$CF_3$Ph- | —H | 1 | mp 200.0-203.0 |
| 2589 | 4-$CF_3$Ph- | —$OCH_3$ | 1 | mp 153.0-154.0 |
| 2590 | 3,4-$Cl_2$Ph- | —$OCH_3$ | 1 | mp 169.0-171.0 |
| 2591 | 4-$CF_3$Ph- | —$OCH_3$ | 2 | mp 134.0-136.0 |
| 2592 | 3,4-$Cl_2$Ph- | —$OCH_3$ | 2 | mp 130.0-132.0 |

TABLE 408

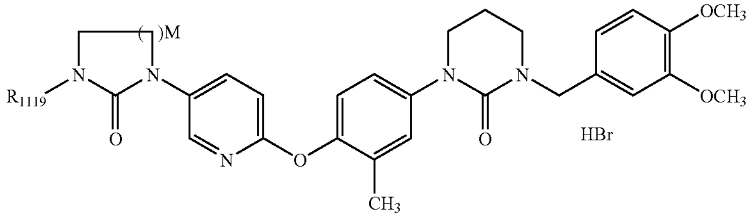

| Example No. | $R_{1119}$ | M | mp (° C.) or $^1$H NMR (DMSO-$d_6$) δ ppm |
|---|---|---|---|
| 2593 | 4-$CF_3$Ph- | 1 | $^1$H NMR 1.90-2.06 (2H, m), 2.07 (3H, s), 3.18-3.32 (2H, m), 3.55-3.70 (2H, m), 3.73 (3H, s), 3.74 (3H, s), 3.91-4.12 (4H, m), 4.43 (2H, s), 4.49-4.93 (1H, m), 6.81 (1H, dd, J = 1.8 Hz, 8.1 Hz), 6.88 (1H, d, J = 1.8 Hz), 6.92 (1H, d, J = 8.1 Hz), 6.97 (1H, d, J = 8.5 Hz), 7.06 (1H, d, J = 9.0 Hz), 7.12 (1H, dd, J = 2.4 Hz, 8.5 Hz), 7.21 (1H, d, J = 2.4 Hz), 7.71 (2H, d, J = 8.9 Hz), 7.83 (2H, d, J = 8.9 Hz), 8.19 (1H, dd, J = 2.9 Hz, 9.0 Hz), 8.27 (1H, d, J = 2.9 Hz). |
| 2594 | 3,4-$Cl_2$Ph- | 1 | mp 146.0-148.0 |
| 2595 | 3,4-$Cl_2$Ph- | 2 | $^1$H NMR 1.91-2.11 (5H, m), 2.12-2.24 (2H, m), 3.19-3.32 (2H, m), 3.58-3.83 (10H, m), 3.85-4.22 (3H, m), 4.42 (2H, s), 6.81 (1H, dd, J = 1.8 Hz, 8.1 Hz), 6.87 (1H, d, J = 1.8 Hz), 6.91 (1H, d, J = 8.1 Hz), 6.94-7.02 (2H, m), 7.12 (1H, dd, J = 2.5 Hz, 8.6 Hz), 7.21 (1H, d, J = 2.5 Hz), 7.35 (1H, dd, J = 2.5 Hz, 8.8 Hz), 7.57 (1H, d, J = 8.8 Hz), 7.66 (1H, d, J = 2.5 Hz), 7.82 (1H, dd, J = 2.5 Hz, 8.8 Hz), 8.07 (1H, d, J = 2.5 Hz). |

Example 2596

Production of 3-(4-{5-[4-(3,4-dichlorophenyl)piperazin-1-yl]pyridin-2-yloxy}phenyl)-1-(4-pipeonylpiperazin-1-yl)propane-1-one To a solution of 3-[4-(5-bromopyridin-2-yloxy)phenyl]-1-(4-piperonylpiperazin-1-yl)propane-1-one (359 mg, 0.69 mmol) and 1-(3,4-dichlorophenyl)-piperazine (206 mg, 0.89 mmol) in toluene (16 mL) were added with $Pd_2(dba)_3$ (25 mg, 0.027 mmol), Xantphos (32 mg, 0.055 mmol) and sodium t-butoxide (99 mg, 1.03 mmol), and the resulting solution was refluxed under an argon atmosphere for 3 hours. The solution was left to cool, water was added to this reaction mixture. The resulting solution was extracted with dichloromethane, dried over anhydrous magnesium sulfate, and evaporated under reduced pressure. The residue was purified by silica gel column chromatography (dichloromethane methanol=30:1), to thereby yield 236 mg of the title compound.

Appearance: Pale yellow powder $^1$H NMR ($CDCl_3$) δ 2.31-2.40 (4H, m), 2.58-2.64 (2H, m), 2.92-2.98 (2H, m), 3.23-3.38 (8H, m), 3.41 (4H, brs), 3.63 (2H, t, J=4.9 Hz), 5.94 (2H, s), 6.72-6.73 (2H, m), 6.78 (1H, dd, J=8.9 Hz, 2.8 Hz), 6.84-6.90 (2H, m), 6.99-7.06 (3H, m), 7.19-7.24 (3H, m), 7.32 (1H, dd, J=9.4 Hz, 3.1 Hz), 7.88 (1H, d, J=3.0 Hz). Tris(dibenzylideneacetone)dipalladium is abbreviated to $Pd_2(dba)_3$. Hereinafter, the same. 4,5-bis(diphenylphosphino)-9,9-dimethylxanthene is abbreviated to Xantphos. Hereinafter the same.

The following compounds were produced in the same manner as in Example 2596.

TABLE 409

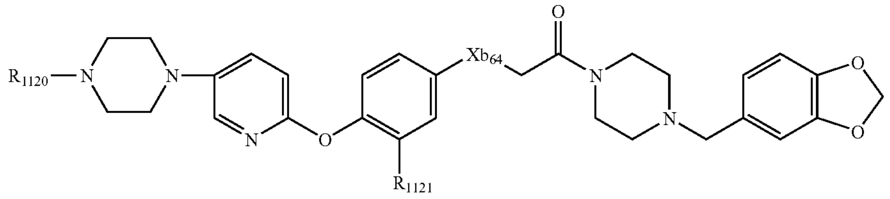

| Example No. | $R_{1120}$ | $R_{1121}$ | $Xb_{64}$ | $^1H$ NMR ($CDCl_3$) δppm |
|---|---|---|---|---|
| 2597 | 4-$CF_3PhCH_2$— | —H | —$CH_2$— | 2.31-2.38 (4H, m), 2.60-2.64 (6H, m), 2.95 (2H, t, J = 7.3 Hz), 3.11-3.15 (4H, m), 3.40 (4H, brs), 3.61 (4H, brs), 5.93 (2H, s), 6.73 (2H, s), 6.83 (2H, d, J = 9.1 Hz), 6.99 (2H, d, J = 8.4 Hz), 7.19 (2H, d, J = 8.4 Hz), 7.29 (1H, dd, J = 8.9 Hz, 3.1 Hz), 7.47 (2H, d, J = 8.2 Hz), 7.58 (2H, d, J = 8.1 Hz), 7.83 (1H, d, J = 3.0 Hz). |
| 2598 | 3,4-$Cl_2Ph$— | —$CH_3$ | —N($CH_3$)— | 2.13 (3H, s), 2.40-2.44 (4H, m), 3.00 (3H, s), 3.18-3.38 (8H, m), 3.43 (2H, s), 3.49 (2H, brs), 3.63 (2H, brs), 4.06 (2H, s), 5.94 (2H, s), 6.52-6.57 (2H, m), 6.69-6.91 (6H, m), 7.00 (1H, d, J = 3.0 Hz), 7.26-7.32 (2H, m), 7.86 (1H, d, J = 2.8 Hz). |
| 2599 | 4-$CF_3Ph$— | —$CH_3$ | —N($CH_3$)— | 2.13 (3H, s), 2.41-2.44 (4H, m), 3.00 (3H, s), 3.20-3.24 (4H, m), 3.34-3.43 (6H, m), 3.49 (2H, brs), 3.63 (2H, brs), 4.06 (2H, s), 5.94 (2H, s), 6.52-6.58 (2H, m), 6.70-6.77 (3H, m), 6.85-6.98 (4H, m), 7.31 (1H, dd, J = 9.1 Hz, 3.1 Hz), 7.50 (2H, d, J = 8.6 Hz), 7.87 (1H, d, J = 2.6 Hz). |
| 2600 | 4-$CF_3Ph$— | —H | —$CH_2$— | 2.31-2.40 (4H, m), 2.61 (2H, t, J = 7.3 Hz), 2.96 (2H, t, J = 7.3 Hz), 3.23-3.27 (4H, m), 3.38-3.45 (8H, m), 3.63 (2H, t, J = 4.8 Hz), 5.94 (2H, s), 6.70-6.76 (2H, m), 6.84-7.06 (6H, m), 7.19-7.26 (2H, m), 7.36 (1H, dd, J = 8.9 Hz, 3.1 Hz), 7.51 (2H, d, J = 8.9 Hz), 7.89 (1H, d, J = 3.0 Hz). |

The following compounds were produced in the same manner as in Reference Example 659.

TABLE 410

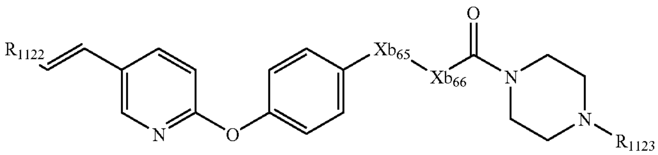

| Example No. | $R_{1122}$ | $Xb_{65}$ | $Xb_{66}$ | $R_{1123}$ | $^1H$ NMR ($CDCl_3$) δppm |
|---|---|---|---|---|---|
| 2601 | 4-$CF_3Ph$— | —N($CH_3$)— | —$CH_2$— | piperonyl | 2.41-2.44 (4H, m), 3.03 (3H, s), 3.43 (2H, s), 3.47-3.50 (2H, m), 3.61-3.65 (2H, m), 4.09 (2H, s), 5.93 (2H, s), 6.68-6.77 (4H, m), 6.83-6.86 (2H, m) 6.99 (1H, d, J = 16.5 Hz), 7.00-7.06 (2H, m), 7.10 (1H, d, J = 16.5 Hz), 7.54-7.61 (4H, m), 7.84 (1H, dd, J = 8.6 Hz, 2.5 Hz), 8.26 (1H, d, J = 2.5 Hz). |
| 2602 | 3,4-$Cl_2Ph$— | —N($CH_3$)— | —$CH_2$— | piperonyl | 2.42-2.45 (4H, m), 3.04 (3H, s), 3.44 (2H, s), 3.48-3.52 (2H, m), 3.62-3.66 (2H, m), 4.09 (2H, s), 5.95 (2H, s), 6.68-6.86 (6H, m), 6.94 (1H, d, J = 17.3 Hz), 6.99-7.04 (3H, m), 7.31 (1H, dd, J = 8.4 Hz, 2.0 Hz), 7.42 (1H, d, J = 8.4 Hz), 7.57 (1H, d, J = 2.0 Hz), 7.82 (1H, d, J = 8.4 Hz), 8.24 (1H, brs). |
| 2603 | 4-$CF_3Ph$— | —$CH_2$— | —$CH_2$— | piperonyl | 2.32-2.41 (4H, m), 2.60-2.66 (2H, m), 2.96-3.01 (2H, m), 3.39-3.43 (4H, m), 3.62-3.66 (2H, m), 5.95 (2H, s), 6.70-6.77 (2H, m), 6.84-6.85 (1H, m), 6.93 (1H, d, J = 8.6 Hz), 7.00-7.09 (3H, m), |

TABLE 410-continued

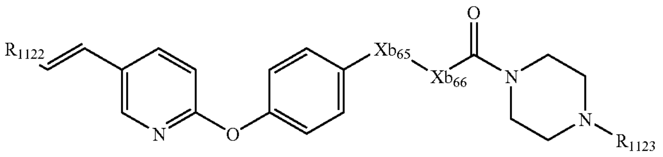

| Example No. | $R_{1122}$ | $Xb_{65}$ | $Xb_{66}$ | $R_{1123}$ | $^1H$ NMR ($CDCl_3$) δppm |
|---|---|---|---|---|---|
| | | | | | 7.12 (1H, d, J = 16.5 Hz), 7.23-7.27 (2H, m), 7.56-7.64 (4H, m), 7.90 (1H, dd, J = 8.7 Hz, 2.6 Hz), 8.27 (1H, d, J = 2.6 Hz). |
| 2604 | 4-$CF_3$Ph— | none | none | benzyl | 2.47 (4H, brs), 3.55-3.77 (6H, m), 6.97 (1H, d, J = 8.6 Hz), 7.05 (1H, d, J = 16.3 Hz), 7.10-7.27 (3H, m), 7.28-7.34 (5H, m), 7.45-7.50 (2H, m), 7.57-7.64 (4H, m), 7.93 (1H, dd, J = 8.6 Hz, 2.4 Hz), 8.29 (1H, d, J = 2.4 Hz). |
| 2605 | 3,4-$Cl_2$Ph— | none | none | benzyl | 2.52 (4H, brs), 3.49-3.90 (6H, m), 6.89-6.98 (2H, m), 7.03 (1H, d, J = 16.5 Hz), 7.15-7.20 (2H, m), 7.30-7.50 (9H, m), 7.58 (1H, d, J = 2.1 Hz), 7.90 (1H, dd, J = 8.7 Hz, 2.5 Hz), 8.26 (1H, d, J = 2.5 Hz). |

TABLE 411

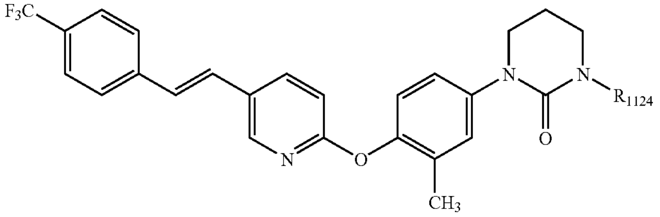

| Example No. | $R_{1124}$ | Form | $^1H$ NMR (solvent) δppm |
|---|---|---|---|
| 2606 | piperonyl | hydrobromide | (DMSO-$d_6$) 1.89-2.06 (2H, m), 2.06 (3H, s), 3.18-3.35 (2H, m), 3.57-3.71 (2H, m), 4.40 (2H, s), 4.42-4.80 (1H, m, 5.99 (2H, s), 6.77 (1H, dd, J = 1.6 Hz, 7.9 Hz), 6.84 (1H, d, J = 1.6 Hz), 6.87 (1H, d, J = 7.9 Hz), 7.01 (1H, d, J = 8.6 Hz), 7.07 (1H, d, J = 8.6 Hz), 7.13 (1H, dd, J = 2.5 Hz, 8.6 Hz), 7.23 (1H, d, J = 2.5 Hz), 7.32 (1H, d, J = 16.5 Hz), 7.42 (1H, d, J = 16.5 Hz), 7.72 (2H, d, J = 8.5 Hz), 7.79 (2H, d, J = 8.5 Hz), 8.19 (1H, dd, J = 2.4 Hz, 8.6 Hz), 8.30 (1H, d, J = 2.4 Hz). |
| 2607 | 3,4-$(CH_3O)_2PhCH_2$— | free | ($CDCl_3$) 1.99-2.14 (2H, m), 2.18 (3H, s), 3.22-3.38 (2H, m), 3.63-3.79 (2H, m), 3.89 (3H, s), 3.90 (3H, s), 4.57 (2H, s), 6.76-6.95 (4H, m), 6.97-7.20 (4H, m), 7.51-7.67 (4H, m), 7.88 (1H, dd, J = 2.5 Hz, 8.6 Hz), 8.27 (1H, d, J = 2.5 Hz). |

Example 2608

Production of 1-(3,4-dimethoxybenzyl)-3-{3-methyl-4-[5-(4-trifluoromethylphenylethynyl)pyridin-2-yloxy]phenyl}tetrahydropyrimidin-2-one To a solution of 1-[4-(5-bromopyridin-2-yloxy)-3-methylphenyl]-3-(3,4-dimethoxybenzyl)tetrahydropyrimidin-2-one (0.3 g, 0.59 mmol) in N-methylpyrrolidone (10 mL) were added bis(triphenylphosphine)palladium dichloride (20 mg, 0.03 mmol), copper iodide (11 mg, 0.059 mmol), 4-ethynyl-α,α,α-trifluorotoluene (0.14 mL, 0.88 mmol) and triethylamine (0.14 mL, 10 mmol) under a nitrogen atmosphere. The resulting solution was stirred for 3 hours at 110 to 120° C. After being left to cool, water was added to the reaction solution. The resulting solution was extracted with ethyl acetate. The ethyl acetate layer was washed with water and dried over anhydrous magnesium sulfate. The solvent was then evaporated, and the residue was purified by silica gel chromatography (n-hexane:ethyl acetate=4:1→1:1), to thereby yield 0.28 g of the title compound.

Appearance: Pale brown amorphous powder $^1H$ NMR ($CDCl_3$) δ 1.97-2.15 (2H, m), 2.16 (3H, s), 3.31 (2H, t, J=6.0 Hz), 3.72 (2H, t, J=6.0 Hz), 3.88 (3H, s), 3.89

(3H, s), 4.57 (2H, s), 6.72-6.95 (5H, m), 7.04 (1H, d, J=8.6 Hz), 7.17 (1H, dd, J=2.6 Hz, 8.6 Hz), 7.55-7.68 (4H, m), 7.78 (1H, dd, J=2.3 Hz, 8.6 Hz), 8.36 (1H, d, J=2.3 Hz).

Example 2609

Production of 3-(3-methyl-4-{5-[2-oxo-2-(4-trifluoromethylphenyl)ethyl]pyridin-2-yloxy}phenyl)-1-piperonyltetrahydropyrimidin-2-one hydrobromide To a solution of 3-[4-(5-bromopyridin-2-yloxy)-3-methylphenyl]-1-piperonyltetrahydropyrimidin-2-one (0.11 g, 0.22 mmol) in toluene (10 mL) were added $Pd_2(dba)_3$ (10 mg, 0.01 mmol) and Xantphos (15 mg, 0.03 mmol) under a nitrogen atmosphere. The resulting solution was stirred for 5 minutes, and then 4'-(trifluoromethyl)acetophenone (63 mg, 0.33 mmol) and potassium bis(trimethylsilyl)amide (66 mg, 0.33 mmol) were added to the reaction % solution. The resulting solution was stirred at 70 to 80° C. for 30 minutes, and left to cool. Water was added to the reaction solution, and extracted with ethyl acetate. The ethyl acetate layer was dried over anhydrous magnesium sulfate, and evaporated. The residue was purified by silica gel column chromatography (n-hexane: ethyl acetate=2:1→1:1), to yield 50 mg of a free form. To this free form was added an equivalent amount of hydrobromic acid, to thereby yield 50 mg of the title compound.

Appearance: Colorless amorphous powder $^1H$ NMR (DMSO-$d_6$) δ 1.85-2.10 (2H, m), 2.06 (3H, s), 3.14-3.47 (2H, m), 3.50-3.76 (2H, m), 4.40 (2H, s), 4.49 (2H, s), 4.70-5.40 (1H, m), 5.98 (2H, s), 6.70-6.80 (1H, m), 6.81-6.90 (2H, m), 6.90-7.04 (2H, m), 7.12 (1H, d, J=2.2 Hz, 8.6 Hz), 7.18-7.26 (1H, m), 7.72 (1H, dd, J=2.2 Hz, 8.5 Hz), 7.93 (2H, d, J=8.2 Hz), 7.95-8.02 (1H, m), 8.24 (2H, d, J=8.2 Hz).

The following compounds were produced in the same manner as in Example 2609.

TABLE 412

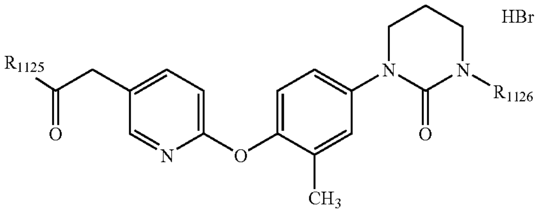

| Example No. | $R_{1125}$ | $R_{1126}$ | $^1H$ NMR ($CDCl_3$) δppm |
|---|---|---|---|
| 2610 | 3,4-$Cl_2$Ph— | piperonyl | 1.82-2.10 (2H, m), 2.07 (3H, s), 3.12-3.32 (2H, m), 3.53-3.72 (2H, m), 4.40 (2H, s), 4.45 (2H, s), 4.80-5.40 (1H, m), 5.99 (2H, s), 6.71-6.80 (1H, m), 6.81-6.90 (2H, m), 6.98 (2H, dd, J = 2.4 Hz, 8.5 Hz), 7.12 (1H, dd, J = 2.4 Hz, 8.5 Hz), 7.21 (1H, d, J = 2.4 Hz), 7.70 (1H, dd, J = 2.2Hz, 8.4 Hz), 7.84 (1H, d, J = 8.4 Hz), 7.96 (1H, d, J = 2.2 Hz), 8.00 (1H, dd, J = 2.0 Hz, 8.4 Hz), 8.25 (1H, d, J = 2.0 Hz). |
| 2611 | 4-$CF_3$Ph— | 3,4-$(CH_3O)_2$Ph— | 1.87-2.11 (5H, m), 3.15-3.32 (2H, m), 3.43-3.71 (3H, m), 3.74 (3H, s), 3.75 (3H, s), 4.44 (2H, s), 4.51 (2H, s), 6.78-6.86 (1H, m), 6.87-6.91 (1H, m), 6.93 (1H, d, J = 8.5 Hz), 6.99 (1H, d, J = 8.5 Hz), 7.00 (1H, d, J = 8.5 Hz), 7.14 (1H, dd, J = 2.4 Hz, 8.5 Hz), 7.19-7.25 (1H, m), 7.73 (1H, dd J = 2.4 Hz, 8.5 Hz), 7.94 (1H, d, J = 8.3 Hz), 7.97-8.01 (1H, m), 8.25 (1H, d, J = 8.3 Hz). |

TABLE 413

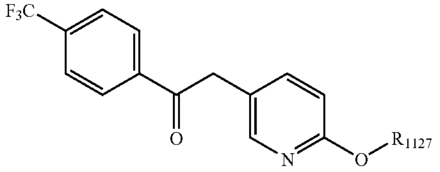

| Example No. | $R_{1127}$ | mp (° C.) or $^1H$ NMR (solvent) δppm |
|---|---|---|
| 2612 | 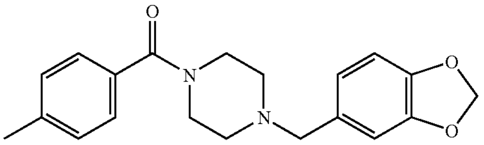 | $^1H$ NMR ($CDCl_3$) 2.44 (4H, brs), 3.44 (2H, s), 3.54 (2H, brs), 3.73 (2H, brs), 4.29 (2H, s), 5.94 (2H, s), 6.74 (2H, s), 6.85 (1H, s), 6.94 (1H, d, J = 8.4 Hz), 7.16 (2H, d, J = 8.6 Hz), 7.45 (2H, d, J = 8.6 Hz), 7.63 (1H, dd, J = 8.4 Hz, 2.5 Hz), 7.76 (2H, d, J = 8.1 Hz), 8.07 (1H, d, J = 2.5 Hz), 8.11 (2H, d, J = 8.1 Hz). |

TABLE 413-continued

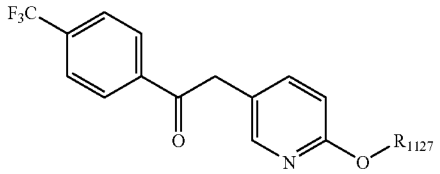

| Example No. | $R_{1127}$ | | mp (° C.) or $^1$H NMR (solvent) δppm |
|---|---|---|---|
| 2613 | 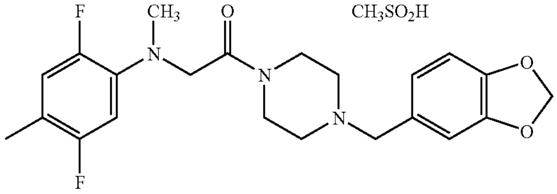 | $CH_3SO_2H$ | $^1$H NMR (DMSO-$d_6$) 2.31 (3H, s), 2.76-3.45 (9H, m), 3.69-4.57 (8H, m), 6.07 (2H, s), 6.81-7.22 (6H, m), 7.74 (1H, dd, J = 2.2 Hz, 8.4 Hz), 7.89-8.00 (2H, m), 8.24 (1H, d, J = 8.4 Hz), 9.49-9.79 (1H, m). |
| 2614 | 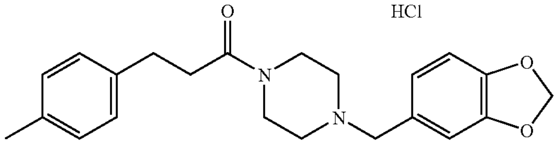 | HCl | mp 164.0-166.0 |

The following compounds were produced in the same manner as in Reference Example 111.

TABLE 414

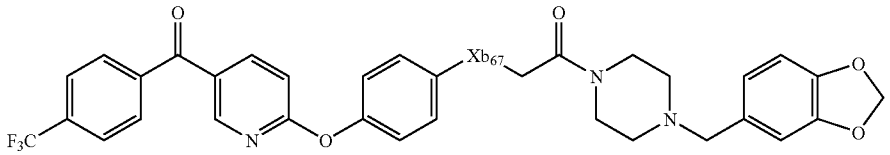

| Example No. | $Xb_{67}$ | $^1$H NMR (solvent) δppm |
|---|---|---|
| 2615 | —$N(CH_3)$— | 2.42-2.45 (4H, m), 3.05 (3H, s), 3.44 (2H, s), 3.47-3.51 (2H, m), 3.62-3.65 (2H, m), 4.11 (2H, s), 5.95 (2H, s), 6.69-6.77 (4H, m), 6.85 (1H, s), 6.97 (1H, d, J = 8.7 Hz), 7.01-7.07 (2H, m), 7.75 (2H, d, J = 8.4 Hz), 7.87 (2H, d, J = 8.1 Hz), 8.17 (1H, dd, J = 8.7 Hz, 2.3 Hz), 8.58 (1H, d, J = 2.3 Hz). |
| 2616 | —$CH_2$— | 2.32-2.41 (4H, m), 2.61-2.67 (2H, m), 2.97-3.03 (2H, m), 3.41-3.43 (4H, m), 3.62-3.66 (2H, m), 5.95 (2H, s), 6.70-6.77 (2H, m), 6.84 (1H, s), 7.03-7.13 (3H, m), 7.28-7.32 (2H, m), 7.76 (2H, d, J = 8.1 Hz), 7.88 (2H, d, J = 8.1 Hz), 8.22 (1H, dd, J = 8.6 Hz, 2.4 Hz), 8.58 (1H, d, J = 2.4 Hz). |

TABLE 415

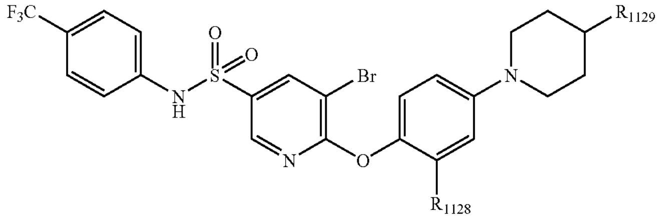

| Example No. | $R_{1128}$ | $R_{1129}$ | $^1$H NMR ($CDCl_3$) δppm |
|---|---|---|---|
| 2617 | —H | —$CH_2COOC_2H_5$ | 1.27 (3H, t, J = 7.1 Hz), 1.34-1.48 (2H, m), 1.81-1.99 (3H, m), 2.29 (2H, d, J = 6.9 Hz), 2.73 (2H, t, J = 12.2 Hz), 3.63 (2H, d, J = 12.2 Hz), 4.15 (2H, q, J = 7.3 Hz), 6.91- |

TABLE 415-continued

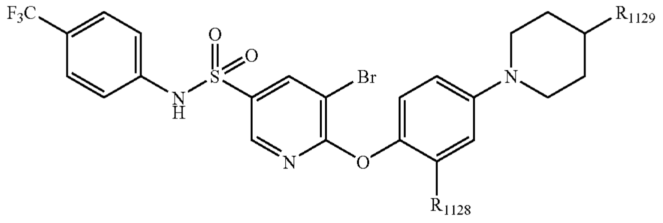

| Example No. | $R_{1128}$ | $R_{1129}$ | $^1$H NMR ($CDCl_3$) δppm |
|---|---|---|---|
| | | | 7.01 (4H, m), 7.18-7.26 (3H, m), 7.54 (2H, d, J = 8.9 Hz), 8.26 (1H, d, J = 2.3 Hz), 8.43 (1H, d, J = 2.3 Hz). |
| 2618 | —$CH_3$ | —$CH_2COOC_2H_5$ | 1.28 (3H, t, J = 7.1 Hz), 1.30-1.39 (2H, m), 1.80-1.96 (3H, m), 2.07 (3H, s), 2.29 (2H, d, J = 6.9 Hz), 2.70 (2H, t, J = 12.0 Hz), 3.61 (2H, d, J = 12.4 Hz), 4.17 (2H, q, J = 7.3 Hz), 6.74-6.78 (2H, m), 6.92 (1H, d, J = 8.6 Hz), 7.20-7.26 (3H, m), 7.52 (2H, d, J = 8.4 Hz), 8.28 (1H, d, J = 2.3 Hz), 8.41 (1H, d, J = 2.3 Hz). |
| 2619 | —H | —$COOC_2H_5$ | 1.27 (3H, t, J = 7.1 Hz), 1.92-2.00 (2H, m), 2.01-2.05 (2H, m), 2.38-2.47 (1H, m), 2.74-2.84 (2H, m), 3.59-3.63 (2H, m), 4.15 (2H, q, J = 7.1 Hz), 6.93-7.02 (4H, m), 7.17-7.26 (3H, m), 7.54 (2H, d, J = 8.4 Hz), 8.26 (1H, d, J = 2.3 Hz), 8.43 (1H, d, J = 2.3 Hz). |

TABLE 416

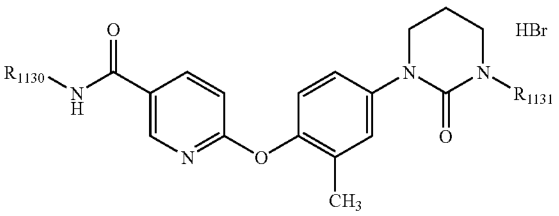

| Example No. | $R_{1130}$ | $R_{1131}$ | mp (° C.) or $^1$H NMR (DMSO-$d_6$) δppm |
|---|---|---|---|
| 2620 | 4-$CF_3$Ph- | piperonyl | mp 129.0-130.5 |
| 2621 | 4-$CF_3$Ph- | 3,4-$(CH_3O)_2PhCH_2$— | mp 130.0-132.0 |
| 2622 | 3,4-$Cl_2$Ph- | 3,4-$(CH_3O)_2PhCH_2$— | $^1$H NMR 1.85-2.14(5 H, m), 3.13-3.33( 2 H, m), 3.58-3.71(2 H, m), 3.73(3 H, s), 3.74(3 H, s), 4.12-4.78(3 H, m), 6.73-6.94(3 H, m), 7.04(1 H, d, J = 8.6 Hz), 7.11-7.20(2 H, m), 7.25(1 H, d, J = 2.4 Hz), 7.61(1 H, d, J = 8.8 Hz), 7.71(1 H, dd, J = 2.4 Hz, 8.8 Hz), 8.11(1 H, d, J = 2.4 Hz), 8.34(1 H, dd J = 2.4 Hz, 8.8 Hz), 8.66(1 H, d, J = 2.4 Hz), 10.53(1 H, s). |

Example 2623

Production of 2-[4-(3-{4-[4-(3,4-dichlorobenzoylamino)-phenoxy]phenyl}propionyl)piperazin-1-yl] acetic acid hydrochloride To a solution of ethyl 2-[4-(3-{4-[4-(3,4-dichlorobenzoylamino)phenoxy]phenyl}propionyl)piperazin-1-yl]acetate (0.493° g, 0.843 mmol) in THF (5 mL) and ethanol (5 mL) were added 5 M aqueous sodium hydroxide (0.253 mL, 1.27 mmol) and water (1 mL), and the resulting solution was refluxed for 1 hour. This reaction solution was concentrated under reduced pressure, and the residue was dissolved in 50% aqueous ethanol. To the resulting solution was added 5 M hydrochloric acid (0.253 mL, 1.27 mmol), and the obtained solid was collected by filtration. To this solid was dissolved in ethanol (10 mL) and 5 M hydrochloric acid (0.3 mL) by heating. The solvent was then evaporated, and the obtained solid was recrystallized from ethanol-diethyl ether, to thereby yield 0.381 g of the title compound.

Appearance: White powder

Melting point: 215-218° C.

The following compounds were produced in the same manner as in Example 2623.

TABLE 417

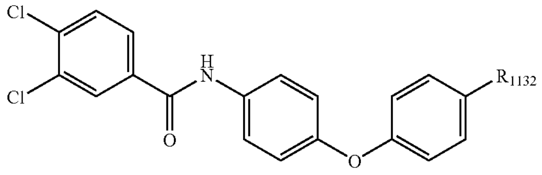

| Example No. | $R_{1132}$ | $^1$H NMR (solvent) δppm |
|---|---|---|
| 2624 | 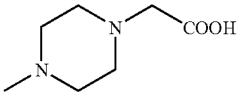 | (DMSO-$d_6$) 2.71-2.73(4 H, m), 3.12-3.14(4 H, m), 3.21(2 H, s), 6.91-6.98(6 H, m), 7.71(2 H, dd, J = 7.0 Hz, 2.0 Hz), 7.82(1 H, d, J = 8.0 Hz), 7.93(1 H, dd, J = 8.0 Hz, 2.0 Hz), 8.21(1 H, d, J = 2.0 Hz), 10.38(1 H, s). |
| 2625 | 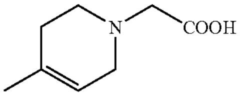 | ($CDCl_3$) 2.68(2 H, m), 3.05(2 H, m), 3.35(2 H, s), 3.49(2 H, m), 6.00(1 H, m), 6.98(2 H, d, J = 8.5 Hz), 7.05(2 H, d, J = 8.5 Hz), 7.35(2 H, d, J = 8.5 Hz), 7.58(2 H, d, J = 8.5 Hz), 7.58(1 H, brs), 7.77(2 H, m), 7.97(1 H, s). |
| 2626 | 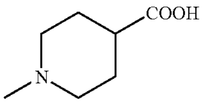 | (DMSO-$d_6$) 1.60-1.70(2 H, m), 1.85-1.90(2 H, m), 2.50(1 H, m), 2.65-2.73(2 H, m), 3.55(2 H, brd, J = 12.5 Hz), 6.90-6.98(6 H, m), 7.71(2 H, d, J = 9.0 Hz), 7.81(1 H, d, J = 8.5 Hz), 7.93(1 H, dd, J = 8.5 Hz, 2.0 Hz), 8.21(1 H, d, J = 2.0 Hz), 10.37(1 H, s), 12.20(1 H, brs). |
| 2627 | 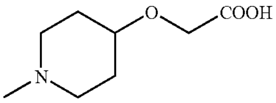 | (DMSO-$d_6$) 1.51-1.58(2 H, m), 1.90-1.95(2 H, m), 2.78-2.82(2 H, m), 3.43(2 H, m), 3.52(1 H, m), 3.92(2 H, s), 6.89-6.98(6 H, m), 7.70(2 H, d, J = 9.0 Hz), 7.82(1 H, d, J = 8.5 Hz), 7.93(1 H, dd, J = 8.5 Hz, 2.0 Hz), 8.21(1 H, d, J = 2.0 Hz), 10.40(1 H, s). |
| 2628 | 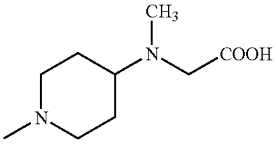 | (DMSO-$d_6$) 1.59-1.66(2 H, m), 1.94-1.97(2 H, m), 2.54(3 H, s), 3.62(2 H, t, J = 11.0 Hz), 2.98(1 H, m), 3.29(2 H, s), 3.67-3.70(2 H, m), 6.90-6.99(6 H, m), 7.71(2 H, d, J = 9.0 Hz), 7.82(1 H, d, J = 8.5 Hz), 7.93(1 H, dd, J = 8.5 Hz, 2.0 Hz), 8.21(1 H, d, J = 2.0 Hz), 10.39(1 H, s). |
| 2629 | 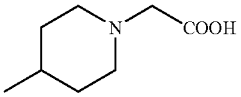 | ($CDCl_3$) 1.80-1.83(4 H, m), 2.61-2.65(3 H, m), 3.24(2 H, s), 3.25(2 H, brd, J = 11.0 Hz), 6.94(2 H, d, J = 8.5 Hz), 7.03(2 H, d, J = 9.0 Hz), 7.25(2 H, d, J = 8.5 Hz), 7.76(2 H, d, J = 9.0 Hz), 7.83(1 H, d, J = 8.5 Hz), 7.94(1 H, dd, J = 8.5 Hz, 2.0 Hz), 8.21(1 H, d, J = 2.0 Hz), 10.41(1 H, s). |

TABLE 418

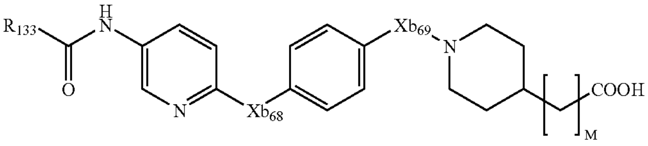

| Example No. | $R_{1133}$ | $Xb_{68}$ | $Xb_{69}$ | M | $^1$H NMR (DMSO-$d_6$) δppm |
|---|---|---|---|---|---|
| 2630 | 4-$CF_3$Ph- | —N($CH_3$)— | none | 1 | 1.20-1.45(2 H, m), 1.70-1.95(3 H, m), 2.20(2 H, d, J = 6.6 Hz), 2.67(2 H, t, J = 12.4 Hz), 3.32(3 H, s), 3.67(2 H, d, J = 12.4 Hz), 6.42(1 H, d, J = 9.1 Hz), 6.99(2 H, d, J = 8.9 Hz), 7.11(2 H, d, J = 8.9 Hz), 7.73(1 H, dd, J = 9.1 Hz, 2.3 Hz), 7.90(2 H, d, J = 8.2 Hz), 8.15(2 H, d, J = 8.2 Hz), 8.46(1 H, d, J = 2.3 Hz), 10.33(1 H, s). |
| 2631 | 3.4-$Cl_2$Ph- | —O— | —$CH_2$— | 0 | 1.57(2 H, brs), 1.81(2 H, brs), 2.00(2 H, brs), 2.23(1 H, brs), 2.77(2 H, brs), 3.44(2 H, brs), 7.05(1 H, d, J = 9.0 Hz), 7.07(2 H, d, J = 8.5 Hz), 7.35(2 H, d, J = 8.5 Hz), 7.84(1 H, d, J = 8.5 Hz), 7.95(1 H, d, J = 8.5 Hz), 8.20(1 H, dd, J = 9.0 Hz, 3.0 Hz), 8.22(1 H, d, J = 2.0 Hz), 8.49(1 H, d, J = 3.0 Hz), 10.56(1 H, s), 12.15(1 H, brs). |

TABLE 418-continued

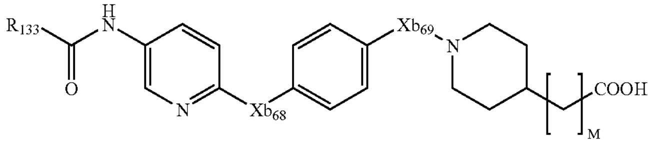

| Example No. | $R_{1133}$ | $Xb_{68}$ | $Xb_{69}$ | M | $^1H$ NMR (DMSO-$d_6$) δppm |
|---|---|---|---|---|---|
| 2632 | 3,4-$Cl_2$Ph- | —O— | —CO— | 0 | 1.52(2 H, m), 1.86(2 H, brs), 2.52(1 H, m), 3.10(2 H, brs), 3.65(1 H, brs), 4.31(1 H, brs), 7.15(1 H, d, J = 9.0 Hz), 7.16(2 H, d, J = 8.5 Hz), 7.43(2 H, d, J = 8.5 Hz), 7.84(2 H, d, J = 8.5 Hz), 7.95(1 H, dd, J = 8.5 Hz, 2.0 Hz), 8.23(1 H, d, J = 2.0 Hz), 8.24(1 H, dd, J = 9.0 Hz, 3.0 Hz), 8.52(1 H, d, J = 3.0 Hz), 10.60(1 H, s). |
| 2633 | 4-$CF_3$Ph- | —O— | —CO— | 0 | 1.52(2 H, m), 1.86(2 H, brs), 2.54(1 H, m), 3.05(2 H, brs), 3.63(1 H, brs), 4.31(1 H, brs), 7.15(1 H, d, J = 9.0 Hz), 7.16(2 H, d, J = 8.5 Hz), 7.44(2 H, d, J = 8.5 Hz), 7.94(2 H, d, J = 8.5 Hz), 8.17(2 H, d, J = 8.5 Hz), 8.27(1 H, dd, J = 9.0 Hz, 2.5 Hz), 8.55(1 H, d, J = 2.5 Hz), 10.67(1 H, s). |
| 2634 | 3,4-$Cl_2$Ph- | —O— | none | 0 | 1.63-1.71(2 H, m), 1.92(2 H, brd, J = 10.0 Hz), 2.74(2 H, t, J = 11.5 Hz), 3.58(2 H, brd, J = 12.5 Hz), 6.96( 1 H, d J = 9.0 Hz), 6.98(4 H, s), 7.83(1 H, d,J = 8.5 Hz), 7.94(1 H, dd, J = 8.5 Hz, 2.0 Hz), 8.14(1 H, dd, J = 9.0 Hz, 2.5 Hz), 8.21(1 H, d, J = 2.0 Hz), 8.44(1 H, d, J = 2.5 Hz), 10.50(1 H, s), 12.20(1 H, brs). |
| 2635 | 3,4-$Cl_2$Ph- | —O— | none | 1 | 1.31-1.34(2 H, m), 1.77(2 H, brd, J = 11.5 Hz), 2.20(2 H, t, J = 6.5 Hz), 2.64(2 H, brt, J = 10.5 Hz), 3.61(2 H, brd, J = 12.5 Hz), 6.96(1 H, d, J = 9.0 Hz), 6.96(4 H, s), 7.83 (1 H, d, J = 8.5 Hz), 7.94(1 H, dd, J = 8.5 Hz, 2.0 Hz), 8.14(1 H, dd, J = 9.0 Hz, 2.5 Hz), 8.21(1 H, d, J = 2.0 Hz), 8.44(1 H, d, J = 2.5 Hz), 10.50(1 H, s), 12.06(1 H, brs). |

TABLE 419

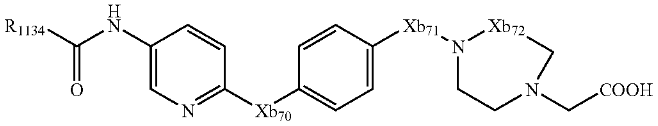

| Example No. | $R_{1134}$ | $Xb_{70}$ | $Xb_{71}$ | $Xb_{72}$ | $^1H$ NMR (DMSO-$d_6$) δppm |
|---|---|---|---|---|---|
| 2636 | 4-$CF_3$Ph- | —O— | —CO— | —$CH_2$— | 3.30(4 H, brs), 3.77(4 H, brs), 3.99(2 H, s), 7.17(1 H, d, J = 8.8 Hz), 7.21(2 H, d, J = 8.6 Hz), 7.51(2 H, d, J = 8.6 Hz), 7.94(2 H, d, J = 8.0 Hz), 8.20(2 H, d, J = 8.0 Hz), 8.29(1 H, dd, J = 8.8 Hz, 2.6 Hz), 8.59(1 H, d, J = 2.6 Hz), 10.79(1 H, s). |
| 2637 | 3,4-$Cl_2$Ph- | —O— | none | —$CH_2$— | 2.71(4 H, t, J = 5.0 Hz), 3.13(2 H, s), 3.14(4 H, t, J = 5.0 Hz), 6.96-7.00(5 H, m), 7.82(1 H, d, J = 8.5 Hz), 7.96(1 H, dd, J = 8.5 Hz, 2.0 Hz), 8.16(1 H, dd, J = 9.0 Hz, 2.5 Hz), 8.24(1 H, d, J = 2.0 Hz), 8.37(1 H, s), 8.46(1 H, d, J = 2.5 Hz), 10.62(1 H, brs). |
| 2638 | 4-$CF_3$Ph- | —N($CH_3$)— | none | —$CH_2$— | 2.64(4 H, brs), 2.95(2 H, s), 3.15(4 H, brs), 3.33(3 H, s), 6.42(1 H, d, J = 9.1 Hz), 6.99(2 H, d, J = 8.9 Hz), 7.13(2 H, d, J = 8.9 Hz), 7.75(1 H, dd, J = 9.1 Hz, 2.5 Hz), 7.89(2 H, d, J = 8.2 Hz), 8.17(2 H, d, J = 8.2 Hz), 8.49(1 H, d, J = 2.5 Hz), 10.46(1 H, s). |
| 2639 | 4-$CF_3$Ph- | —O— | none | —$CH_2$— | 2.72(4 H, t, J = 5.0 Hz), 3.15(4 H, t, J = 5.0 Hz), 3.20(2 H, s), 6.96-7.01(5 H, |

TABLE 419-continued

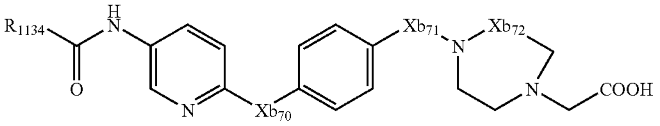

| Example No. | $R_{1134}$ | $Xb_{70}$ | $Xb_{71}$ | $Xb_{72}$ | $^1H$ NMR (DMSO-$d_6$) δppm |
|---|---|---|---|---|---|
| | | | | | m), 7.93(2 H, d, J = 8.5 Hz), 8.16(2 H, d, J = 8.5 Hz), 8.18(1 H, dd, J = 8.0 Hz, 2.5 Hz), 8.46(1 H, d, J = 2.5 Hz), 10.60(1 H, s). |
| 2640 | 3,4-$Cl_2$Ph- | —O— | none | —CO— | 3.13(2 H, brs), 3.17(2 H, s), 3.48(2 H, brs), 3.71(2 H, brs), 7.12(1 H, d, J = 8.9 Hz), 7.15(2 H, dd, J = 6.8 Hz, 2.1 Hz), 7.36(2 H, dd, J = 6.8 Hz, 2.1 Hz), 7.84(1 H, d, J = 8.4 Hz), 7.95(1 H, dd, J = 8.4 Hz, 2.1 Hz), 8.22(1 H, dd, J = 8.9 Hz, 2.7 Hz), 8.23(1 H, d, J = 2.1 Hz), 8.49(1 H, d, J = 2.7 Hz), 10.58(1 H, s). |

TABLE 420

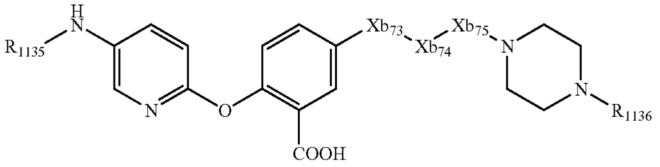

| Example No. | $R_{1135}$ | $Xb_{73}$ | $Xb_{74}$ | $Xb_{75}$ | $R_{1136}$ | $^1H$ NMR (solvent) δppm |
|---|---|---|---|---|---|---|
| 2641 | 4-$CF_3$PhCO— | none | none | none | benzyl | ($CD_3OD$) 3.47(8 H, brs), 4.43(2 H, s), 6.96 (1 H, d, J = 8.9 Hz), 7.14(1 H, d, J = 8.9 Hz), 7.30(1 H, dd, J = 8.9 Hz, 3.0 Hz), 7.51-7.59(6 H, m), 7.82(2 H, d, J = 8.3 Hz), 8.12-8.18(3 H, m), 8.36(1 H, d, J = 2.5 Hz). |
| 2642 | 3,4-$Cl_2$Ph$SO_2$— | —N($C_2H_5$)— | —$CH_2$— | —CO— | piperonyl | (DMSO-$d_6$) 1.11(3 H, t, J = 7.0 Hz), 2.20-2.45 (4 H, m), 3.30-3.55(8 H, m), 4.22(2 H, s), 5.99 (2 H, s), 6.70-7.00(7 H, m), 7.40-7.50(1 H, m), 7.55-7.60(1 H, m), 7.66(1 H, d, J = 2.7 Hz), 7.84(1 H,d, J = 8.4 Hz), 7.88(1 H, d, J = 2.1 Hz), 01.27(1 H, brs), 12.51(1 H, brs). |
| 2643 | 3,4-$Cl_2$PhNHCO— | —N($C_2H_5$)— | —$CH_2$— | —CO— | piperonyl | (DMSO-$d_6$) 1.13(3 H, t, J = 7.0 Hz), 2.20-2.50 (4 H, m), 3.30-3.60(8 H, m), 4.21(2 H, s), 5.99 (2 H, s), 6.60-7.05(7 H, m), 7.30-7.40(1 H, m), 7.47(1 H, d, J = 8.8 Hz), 7.65-7.85(1 H, m), 7.90(1 H, d, J = 2.3 Hz), 8.06(1 H, d, J = 2.6 Hz), 9.80(2 H, brs), 12.40(1 H, brs). |

TABLE 421

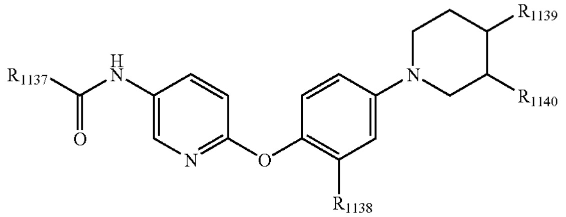

| Example No. | $R_{1137}$ | $R_{1138}$ | $R_{1139}$ | $R_{1140}$ | $^1H$ NMR (solvent) δppm |
|---|---|---|---|---|---|
| 2644 | 3,4-$Cl_2$Ph- | —H | —H | —COOH | ($CDCl_3$) 1.80(1 H, m), 1.86-1.94(3 H, m), 2.82(1 H, m), 3.14(2 H, m), 3.32 (2 H, m), 6.94(1 H, d, J = 9.0 Hz), 7.06(4 H, s), 7.57(1 H, d, J = 8.5 Hz), 7.72(1 H, d, J = 8.5 Hz), 7.93(1 H, brs), 7.99(1 H, s), 8.18(1 H, brd, J = 9.0 Hz), 8.26(1 H, d, J = 2.5 Hz). |
| 2645 | 4-$CF_3$Ph- | —H | —$CH_2$COOH | —H | ($CDCl_3$) 1.44-1.50(2 H, m), 1.90(2 H, brd, J = 13.5 Hz), 1.94(1 H, m), 2.36 (2 H, d, J = 7.0 Hz), 2.75(2 H, dt, J = 2.5 Hz, 12.0 Hz), 3.63(2 H, brd, J = 12.0 Hz), 6.92(1 H, d, J = 9.0 Hz), 6.97(2 H, d, J = 9.0 Hz), 7.04(2 H, d, J = 9.0 Hz), 7.72(1 H, s), 7.78(2 H, d, J = 8.0 Hz), 7.99(2 H, d, J = 8.0 Hz), 8.19(1 H, dd, J = 9.0 Hz, 2.5 Hz), 8.25(1 H, d, J = 2.5 Hz). |
| 2646 | 3-$CF_3$Ph- | —H | —$CH_2$COOH | —H | ($CDCl_3$) 1.46-1.49(2 H, m), 1.89(2 H, brd,J ’2 15.0 Hz), 1.95(1 H, m), 2.3692 H, d, J = 7.0 Hz), 2.74(2 H, dt, J = 2.0 Hz, 12.0 Hz), 3.63(2 H, brd, J = 12.0 Hz), 6.92(1 H, d, J = 9.0 Hz), 6.97(2 H, d, J = 9.0 Hz), 7.05 (2 H, d, J = 9.0 Hz), 7.66(1 H, t, J = 7.5 Hz), 7.73(2 H, brs), 7.84(1 H, d, J = 7.5 Hz), 8.07(1 H, d, J = 7.5 Hz), 8.14(1 H, brs), 8.17(1 H, dd, J = 9.0 Hz, 2.5 Hz), 8.27(1 H, d, J = 2.5 Hz). |
| 2647 | 4-$CF_3$Ph- | —$OCH_3$ | —$CH_2$COOH | —H | (DMSO-$d_6$) 1.31-1.36(2 H, m), 1.77-1.81(3 H, m), 2.21(2 H, d, J = 7.4 Hz), 2.68-2.75(2 H, m), 3.64(2 H, brs), 3.68(3 H, s), 6.52(1 H, brs), 6.68(1 H, brs), 6.89-6.96(2 H, m), 7.92(2 H, d, J = 8.4 Hz), 8.09-8.17(3 H, m), 8.38(1 H, d, J = 2.5 Hz), 10.54(1 H, s), 12.10(1 H, brs). |
| 2648 | 4-$CF_3$Ph- | —H | —COOH | —H | ($CDCl_3$ + $CD_3OD$) 1.82-1.96(2 H, m), 2.04-2.09(2 H, m), 2.38-2.48(1 H, m), 2.74-2.84(2 H, m), 3.52-3.61(2 H, m), 6.86(1 H, dd, J = 8.9 Hz, 0.5 Hz), 6.96-7.05(4 H, m), 7.69-7.76(2 H, m), 8.06(2 H, d, J = 8.1 Hz), 8.16(1 H, d, J = 8.1 Hz), 8.23-8.33(2 H, m). |

TABLE 422

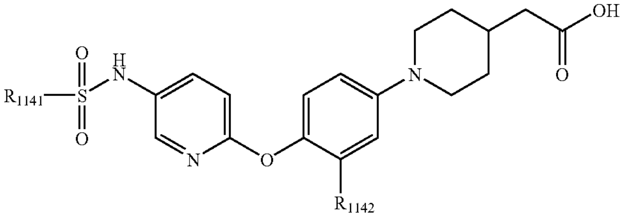

| Example No. | $R_{1141}$ | $R_{1142}$ | $^1H$ NMR (DMSO-$d_6$) δppm |
|---|---|---|---|
| 2649 | 4-$CF_3$Ph- | —$CH_3$ | 1.41(2 H, brs), 1.84-1.96(3 H, m), 1.97(3 H, s), 2.22(2 H, d, J = 6.6 Hz), 2.55-2.75(2 H, m), 3.58(2 H, d, J = 11.9 Hz), 6.72- |

TABLE 422-continued

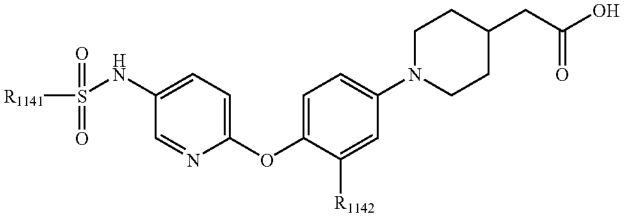

| Example No. | $R_{1141}$ | $R_{1142}$ | $^1$H NMR (DMSO-$d_6$) δppm |
|---|---|---|---|
| | | | 7.11(4 H, m), 7.52(1 H, dd, J = 8.9 Hz, 2.8 Hz), 7.74(1 H, d, J = 2.6 Hz), 7.89-7.99(4 H, m), 10.49(1 H, s), 12.14(1 H, brs). |
| 2650 | 3,4-$Cl_2$Ph- | —$CH_3$ | 1.38(2 H, brs), 1.82-1.96(3 H, m), 1.97(3 H, s), 2.22(2 H, d, J = 6.4 Hz), 2.55-2.75(2 H, m), 3.59(2 H, d, J = 11.9 Hz), 6.88-6.91(4 H, m), 7.51(1 H, dd, J = 8.7 Hz, 2.5 Hz), 7.63(1 H, dd, J = 8.4 Hz, 2.1 Hz), 7.74(1 H, d, J = 2.8 Hz), 7.83-7.87(2 H, m), 10.38(1 H, s), 12.12(1 H, brs). |
| 2651 | 3.4-$Cl_2$Ph- | —H | 1.30-1.37(2 H, m), 1.75-1.91(3 H, m), 2.20(2 H, d, J = 6.9 Hz), 2.51-2.62(2 H, m), 3.60(2 H, d, J = 12.0 Hz), 6.87-6.94(5 H, m), 7.50(1 H, dd, J = 8.7 Hz, 2.8 Hz), 7.62(1 H, dd, J = 8.6 Hz, 2.3 Hz), 7.77(1 H, d, J = 2.8 Hz), 7.84-7.89(2 H, m), 10.39(1 H, s), 12.09(1 H, brs). |
| 2652 | 4-$CF_3$Ph- | —H | 1.29-1.33(2 H, m), 1.74-1.91(3 H, m), 2.19(2 H, d, J = 6.8 Hz), 2.63-2.75(2 H, m), 3.59(2 H, d, J = 12.2 Hz), 6.86-6.93(5 H, m), 7.50(1 H, dd, J = 8.9 Hz, 2.8 Hz), 7.77(1 H, d, J = 2.6 Hz), 7.89-7.99(4 H, m), 10.47(1 H, s), 12.09(1 H, brs). |
| 2653 | 4-$CF_3$Ph- | —$OCH_3$ | 1.41(2 H, brs), 1.81-1.85(3 H, m), 2.25(2 H, d, J = 6.4 Hz), 2.55-2.79(2 H, m), 3.64(3 H, s), 3.68(2 H, brs), 6.73-6.95(4 H, m), 7.51(1 H, dd, J = 8.7 Hz, 2.5 Hz), 7.73(1 H, d, J = 2.6 Hz), 7.92-8.02(4 H, m), 10.45(1 H, s), 12.14(1 H, brs). |
| 2654 | 3,4-$Cl_2$Ph- | —$OCH_3$ | 1.42(2 H, brs), 1.79-1.91(3 H, m), 2.23(2 H, d, J = 6.6 Hz), 2.76-2.83(2 H, m), 3.63(5 H, brs), 6.63-6.98(4 H, m), 7.48(1 H, dd, J = 8.7 Hz, 2.6 Hz), 7.63(1 H, dd, J = 8.4 Hz, 2.0 Hz), 7.71(1 H, d, J = 2.8 Hz), 7.85-7.88(2 H, m), 10.36(1 H, s), 12.33(1 H, brs). |

TABLE 423

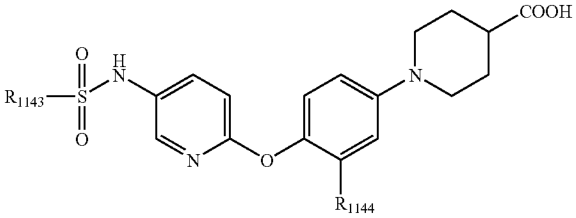

| Example No. | $R_{1143}$ | $R_{1144}$ | $^1$H NMR (DMSO-$d_6$) δppm |
|---|---|---|---|
| 2655 | 4-$CF_3$Ph- | —$CH_3$ | 1.81-1.99(4 H, m), 2.00(3 H, s), 2.41-2.44(1 H, m), 2.75(2 H, brs), 3.58(2 H, d, J = 12.2 Hz), 6.91-7.20(4 H, m), 7.53(1 H, dd, J = 8.9 Hz, 2.6 Hz), 7.75(1 H, d, J = 2.6 Hz), 7.90-7.99(4 H, m), 10.52(1 H, s), 12.41(1 H, brs). |
| 2656 | 3,4-$Cl_2$Ph- | —$CH_3$ | 1.63-1.71(2 H, m), 1.91-1.94(2 H, m), 1.95(3 H, s), 2.41-2.48(1 H, m), 2.75-2.80(2 H, m), 3.58(2 H, d, J = 12.9 Hz), 6.85-6.89(3 H, m), 7.50(1 H, dd, J = 8.7 Hz, 2.6 Hz), 7.68-7.79(2 H, m), 7.81-7.98(4 H, m), 10.43(1 H, s), 12.35(1 H, brs). |
| 2657 | 3,4-$Cl_2$Ph- | —H | 1.74(2 H, brs), 1.93-1.98(2 H, m), 2.49-2.51(2 H, m), 2.88(1 H, brs), 3.55-3.60(2 H, m), 6.90-7.01(5 H, m), 7.50-7.89(5 H, m), 10.41(1 H, s), 12.13(1 H, brs). |
| 2658 | 4-$CF_3$Ph- | —H | 1.66-1.71(2 H, m), 1.88-1.92(2 H, m), 2.34-2.42(1 H, m), 2.68-2.76(2 H, m), 3.56(2 H, d, J = 12.4 Hz), 6.85-6.92(5 H, m), 7.48(1 H, d, J = 2.8 Hz), 7.51(1 H, d, J = 2.8 Hz), 7.77-7.99(4 H, m), 10.47(1 H, s), 12.21(1 H, s). |

TABLE 424

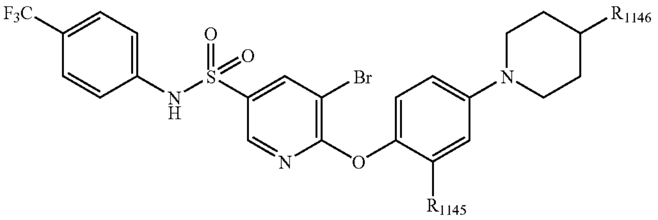

| Example No. | $R_{1145}$ | $R_{1146}$ | $^1H$ NMR (DMSO-$d_6$) δppm |
|---|---|---|---|
| 2659 | —H | —$CH_2COOH$ | 1.26-1.32(2 H, m), 1.74-1.91(3 H, m), 2.20(2 H, d, J = 6.6 Hz), 2.66(2 H, t, J = 11.0 H), 3.63(2 H, d, J = 12.5 Hz), 6.93-7.03(4 H, m), 7.13-7.35(2 H, m), 7.65(2 H, d, J = 8.6 Hz), 8.42(1 H, d, J = 2.3 Hz), 8.47(1 H, d, J = 2.3 Hz), 11.00(1 H, s), 12.07(1 H, brs). |
| 2660 | —$CH_3$ | —$CH_2COOH$ | 1.30-1.41(2 H, m), 1.80-2.00(3 H, m), 1.99(3 H, s), 2.20(2 H, d, J = 6.6 Hz), 2.68-2.76(2 H, m), 3.62(2 H, d, J = 12.2 Hz), 6.88-6.96(3 H, m), 7.33(2 H, d, J = 8.2 Hz), 7.65(2 H, d, J = 8.6 Hz), 8.44(2 H, s), 11.00(1 H, s), 12.10(1 H, brs). |
| 2661 | —H | —COOH | 1.63-1.70(2 H, m), 1.88-1.92(2 H, m), 2.41-2.45(1 H, m), 2.71-2.79(2 H, m), 3.61(2 H, d, J = 12.5 Hz), 6.93-7.00(4 H, m), 7.31(2 H, d, J = 8.6 Hz), 7.63(2 H, d, J = 8.7 Hz), 8.40-8.47(2 H, m), 10.63(1 H, s), 12.21(1 H, s). |

TABLE 425

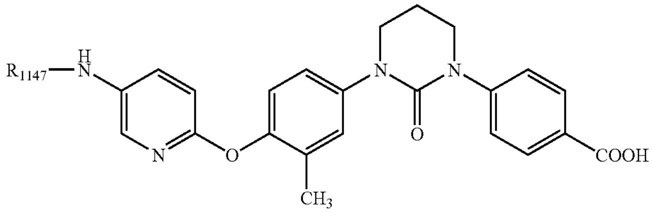

| Example No. | $R_{1147}$ | $^1H$ NMR (DMSO-$d_6$) δppm |
|---|---|---|
| 2662 | 4-$CF_3$PhCO— | 2.08(3 H, s), 2.09-2.32(2 H, m), 3.65-3.93(4 H, m), 7.01(1 H, d, J = 8.6 Hz), 7.06(1 H, d, J = 8.9 Hz), 7.19(1 H, dd, J = 2.6 Hz, 8.6 Hz), 7.29(1 H, d, J = 2.6 Hz), 7.42-7.51(2 H, m), 7.81-7.98(4 H, m), 8.10-8.18(2 H, m), 8.21(1 H, dd, J = 2.6 Hz, 8.9 Hz), 8.43(1 H, d, J = 2.6 Hz), 10.60(1 H, s), 12.60-12.91(1 H, m). |
| 2663 | 3,4-$Cl_2PhSO_2$— | 1.99(3 H, s), 2.07-2.31(2 H, m), 3.60-3.91(4 H, m), 6.97(1 H, d, J = 8.5 Hz), 6.98(1 H, d, J = 8.8 Hz), 7.16(1 H, dd, J = 2.4 Hz, 8.5 Hz), 7.25(1 H, d, J = 2.2 Hz), 7.40-7.51(2 H, m), 7.54(1 H, dd, J = 2.8 Hz, 8.8 Hz), 7.62(1 H, dd, J = 2.2 Hz, 8.5 Hz), 7.75(1 H, d, J = 2.8 Hz), 7.79-7.93(4 H, m). |

Example 2664

Production of (4-{5-[(4-trifluoromethylphenylamino)-methyl]-pyridin-2-yloxy}phenyl)(4-piperonylpiperazin-1-yl)methanone Methanesulfonic acid 6-[4-(4-piperonylpiperazine-1-carbonyl)phenoxy]pyridin-3-yl ester (0.433 g, 0.824 mmol) and 4-trifluoromethyl phenylamine (0.310 mL, 2.47 mmol) were mixed together, and the resulting mixture was stirred for 2 hours at 100° C. The formed yellow mass was stirred together with a saturated sodium bicarbonate solution, ethyl acetate and THF (20 ml of each). The organic layer was collected, washed with brine, dried over anhydrous magnesium sulfate, and evaporated under reduced pressure. The residue was purified by silica gel column chromatography (dichloromethane:methanol=50:1), to thereby yield 0.236 g of the title compound.

Appearance: Pale yellow amorphous powder $^1H$ NMR ($CDCl_3$) δ 2.44 (4H, brs), 3.45 (2H, s), 3.57 (2H, brs), 3.75 (2H, brs), 4.30-4.35 (1H, m), 4.36 (2H, s), 5.95 (2H, s), 6.63 (2H, d, J=8.7 Hz), 6.74-6.77 (2H, m), 6.85 (1H, s), 6.93 (1H, d, J=8.4 Hz), 7.15 (2H, d, J=8.4 Hz), 7.39-7.47 (4H, m), 7.71 (1H, dd, J=2.5 Hz, 8.4 Hz), 8.18 (1H, d, J=2.3 Hz).

The following compounds were produced in the same manner as in Example 2664.

TABLE 426

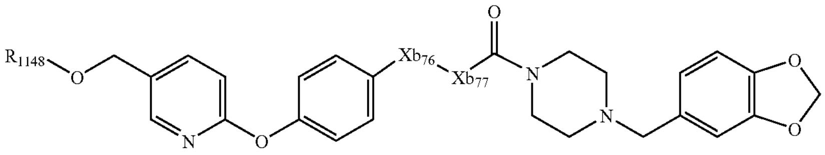

| Example No. | $R_{1148}$ | $Xb_{76}$ | $Xb_{77}$ | Form | $^1$NMR (solvent) δppm |
|---|---|---|---|---|---|
| 2665 | 3,4-$Cl_2$Ph- | —N($CH_3$)— | —$CH_2$— | free | ($CDCl_3$) 2.42-2.44(4 H, m), 3.03(3 H, s), 3.43(2 H, brs), 3.49-3.50(2 H, m), 3.63(2 H, brs), 4.08(2 H, s), 4.94(2 H, s), 5.94(2 H, s), 6.70(2 H, d, J = 9.2 Hz), 6.74(2 H, brs), 6.80(1 H, dd, J = 8.9 Hz, 2.8 Hz), 6.83-6.86(2 H, m), 7.01(2 H, d, J = 9.1 Hz), 7.05(1 H, d, J = 2.8 Hz), 7.32(1 H, d, J = 8.9 Hz), 7.86(1 H, dd, J = 8.6 Hz, 2.5 Hz), 8.19(1 H, d, J = 1.8 Hz). |
| 2666 | 4-$CF_3$Ph- | —N($CH_3$)— | —$CH_2$— | free | ($CDCl_3$) 2.41-2.44(4 H, m), 3.03(3 H, s), 3.43(2 H, brs), 3.49(2 H, brs), 3.63(2 H, brs), .408(2 H, s), 5.02(2 H, s), 5.95(2 H, s), 6.69-6.74(4 H, m), 6.85-6.88(2 H, m), 7.00-7.03(4 H, m), 7.56(2 H, d, J = 8.6 Hz), 7.72(1 H, dd, J = 8.6 Hz, 2.5 Hz), 8.22(1 H, d, J = 2.3 Hz). |
| 2667 | 4-$CF_3$Ph- | none | none | hydro-chloride | (DMSO-$d_6$) 3.10-3.42( 8 H, m), 4.24(2 H, brs), 5.20(2 H, s), 6.07(2 H, s), 6.97-7.04(2 H, m), 7.15(1 H, d, J = 8.6 Hz), 7.21-7.24(5 H, m), 7.52(2 H, d, J = 8.6 Hz), 7.68(2 H, d, J = 8.7 Hz), 8.01(1 H, dd, J = 2.5 Hz, 8.4 Hz), 8.29(1 H, d, J = 2.3 Hz), 11.00(1 H, brs). |

Example 2668

Production of 2-(methyl-{4-[5-(5-trifluoromethyl-pyridin-2-yloxymethyl)pyridin-2-yloxy]phenyl}amino)-1-(4-piperonylpiperazin-1-yl)ethanone 2-{[4-(5-hydroxymethylpyridin-2-yloxy)phenyl]methylamino}-1-(4-piperonylpiperazin-1-yl)ethanone (0.98 g, 2.0 mmol) was dissolved in DMF (30 mL). To the resulting solution was added 60% sodium hydride (60%, 88 mg, 2.2 mmol) under ice cooling, and this solution was stirred for 30 minutes at 0° C. To the reaction solution was added 2-chloro-5-(trifluoromethyl)pyridine (0.36 g, 2.0 mol), and this solution was stirred under a nitrogen atmosphere for 3 hours at 60° C. The resulting reaction solution was concentrated under reduced pressure. To the residue was added ethyl acetate, and this solution was washed with water and brine. The organic layer was dried over anhydrous magnesium sulfate, and evaporated. The residue was purified by silica gel column chromatography (n-hexane ethyl acetate=1:5), to thereby yield 0.68 g of the title compound.

Appearance: White powder $^1$H NMR ($CDCl_3$) δ 2.41-2.44 (4H, m), 3.02 (3H, s), 3.43 (2H, s), 3.48 (2H, brs), 3.63 (2H, brs), 4.08 (2H, s), 5.37 (2H, s), 5.94 (2H, s), 6.68-6.77 (4H, m), 6.81-6.84 (3H, m), 7.00 (2H, d, J=9.1 Hz), 7.72-7.79 (2H, m), 8.27 (1H, d, J=2.3 Hz), 8.44 (1H, brs).

The following compounds were produced in the same manner as in Example 2668.

TABLE 427

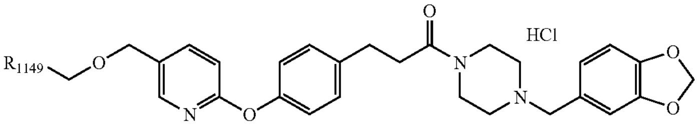

| Example No. | $R_{1149}$ | mp (° C.) |
|---|---|---|
| 2669 | 4-$CF_3$Ph- | 165.0-166.0 |
| 2670 | 3-$CF_3$Ph- | 163.0-165.0 |
| 2671 | 3,4-$Cl_2$Ph- | 160.0-161.5 |

Example 2672

3,4-dichloro-N-{6-[4-(3,5-dioxoisoxazolidine-4-ylidenemethyl)phenoxy]pyridin-3-yl}benzamide To a solution of hydroxylamine hydrochloride (500 mg, 1.0 mmol) in water (0.2 mL) were added sodium carbonate (1.05 g, 9.91 mmol) and a solution of 2-{4-[5-(3,4-dichlorobenzoylamino)pyridin-2-yloxy]benzylidene}malonic acid dimethyl ester (500 mg, 1.0 mmol) in THF (5 mL). To the resulting solution was subsequently added methanol (5 mL) and stirred for 8 hours at 60° C. The reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=30:1). To the resulting white precipitate was added ethyl acetate, filtered, and the filtrate was washed with diethyl ether, to thereby yield 105 mg of the title compound.

Appearance: White powder $^1$H NMR (DMSO-$d_6$) δ 7.12 (1H, d, J=8.9 Hz), 7.14 (2H, d, J=8.8 Hz), 7.63 (2H, d, J=8.8 Hz), 7.84 (1H, d, J=58.4 Hz), 7.95 (1H, dd, J=8.4 Hz, 2.0 Hz), 8.15 (1H, s), 8.22 (1H, dd, J=8.9 Hz, 2.6 Hz), 8.22 (1H, d, J=2.0 Hz), 8.51 (1H, d, J=2.6 Hz), 10.57 (1H, s), 11.16 (1H, s).

Example 2673

Production of 3,4-dichloro-N-{6-[4-(5-methyl-[1,2,4]oxadiazol-3-ylmethyl)phenoxy]pyridin-3-yl}benzamide monohydrochloride To 3,4-dichloro-N-{6-[4-(N-acetoxycarbamimidoylmethyl)phenoxy]pyridin-3-yl}benzamide (340 mg, 0.788 mmol) was added acetic acid (4 mL), and the resulting solution was stirred under reflux for 10 minutes. This reaction solution was concentrated under reduced pressure. To the residue was added a saturated sodium bicarbonate solution, and the resulting solution was extracted with ethyl acetate. The ethyl acetate layer was washed with brine, dried over anhydrous magnesium sulfate, and evaporated. The residue was purified by silica gel column chromatography (chloroform:methanol=40:1), and the obtained reside was dissolved in ethyl acetate (5 mL). To this solution was added a solution of 4 N hydrogen chloride in ethyl acetate until the compound no longer precipitated out. The obtained white powder was filtered, and washed with diethyl ether, to thereby yield 154 mg of the title compound.

Appearance: White powder $^1$H NMR (DMSO-$d_6$) δ 2.55 (3H, s), 4.05 (2H, s), 7.07 (1H, d, J=8.7 Hz), 7.07 (2H, d, J=8.6 Hz), 7.33 (2H, d, J=8.6 Hz), 7.83 (1H, d, J=8.4 Hz), 7.96 (1H, dd, J=8.4 Hz, 2.0 Hz), 8.21 (1H, dd, J=8.7 Hz, 2.6 Hz), 8.24 (1H, d, J=2.0 Hz), 8.48 (1H, d, J=2.6 Hz), 10.62 (1H, s).

Example 2674

Production of 1-(3-{4-[5-(3,4-dichlorobenzoylamino)-2-pyridylmethyl]phenyl}propionyl)-4-piperonylpiperazine monohydrochloride To a solution of ethyl 3-(4-{5-[bis(3,4-dichlorobenzoyl)amino]-2-pyridylmethyl}phenyl)propionate (177 mg, 0.281 mmol) in THF (5 mL) and ethanol (5 mL) were added 5 M aqueous sodium hydroxide (0.0929 mL, 0.463 mmol) and water (1 mL), and the resulting solution was refluxed for 1 hour. To this reaction solution was added 5 M hydrochloric acid (0.12 mL), and extracted with ethyl acetate. The ethyl acetate layer was washed with brine, dried over anhydrous magnesium sulfate, and evaporated. The residue was dissolved in DMF (3 mL), and to the resulting solution were then added 1-piperonylpiperazine (102 mg, 0.463 mmol), triethylamine (0.137 mL, 0.983 mmol) and diethyl cyanophosphonate (0.0703 mL, 463 mmol), and stirred for 1.5 hours at room temperature. Water was added to the resulting reaction solution, and extracted with ethyl acetate. The ethyl acetate layer was washed with a saturated sodium bicarbonate solution and brine, dried over anhydrous magnesium sulfate, and evaporated. The residue was purified by silica gel column chromatography (dichloromethane:methanol=70:1→40:1→20:1), to thereby yield 44.1 mg of a free form. This free form was dissolved in ethanol (5 mL) and 5 M hydrochloric acid (0.03 mL) by heating. The solvent was then evaporated, and the obtained solid was recrystallized from water-containing isopropanol, to thereby yield 19.6 mg of the title compound.

Appearance: Pale yellow powder

Melting point: 181-183° C.

Example 2675

Production of N-(6-{4-[4-(5-oxo-4,5-dihydro-[1,3,4]oxadiazole-2-ylmethyl)piperazine-1-carbonyl]-phenoxy}pyridin-3-yl)-4-trifluoromethylbenzamide monooxalate To a suspension of N-{6-[4-(4-hydrazinocarbonylmethylpiperazine-1-carbonyl)phenoxy]pyridin-3-yl}-4-trifluoromethylbenzamide trihydrochloride (300 mg, 0.46 mmol) in THF (7 mL) was added triethylamine (0.29 mL, 2.08 mmol), and the resulting solution was stirred for 10 minutes at room temperature. To the solution was added N,N'-carbonyldiimidazole (97 mg, 0.60 mmol) under ice cooling, and the resulting solution was stirred for 1 hour at room temperature. The reaction solution was concentrated under reduced pressure. To the residue was added a saturated sodium bicarbonate solution, and extracted with ethyl acetate. The ethyl acetate layer was dried over anhydrous magnesium sulfate, and evaporated. The residue was then purified by silica gel column chromatography (chloroform methanol=15:1). The obtained residue was dissolved in ethanol, and to the resulting solution was added oxalic acid. Ethanol was evaporated under reduced pressure, after which the solidified white substance was filtered, and washed with diethyl ether, to thereby yield 140 mg of the title compound.

Appearance: White powder $^1$H NMR (DMSO-$d_6$) δ 2.31-2.69 (4H, m), 3.53 (2H, s), 3.53 (4H, brs), 7.16 (1H, d, J=8.9 Hz), 7.17 (2H, d, J=8.5 Hz), 7.45 (2H, d, J=8.5 Hz), 7.94 (2H, d, J=8.1 Hz), 8.17 (2H, d, J=8.1 Hz), 8.26 (1H, dd, J=8.9 Hz, 2.7 Hz), 8.55 (1H, d, J=2.7 Hz), 10.67 (1H, s), 12.27 (1H, s).

Example 2676

Production of 4-(4-{4-[4-(3,4-dichlorobenzoylamino)-2-fluorophenoxy]phenyl}-4-hydroxybutyryl)morpholine To a suspension of 4-(4-{4-[4-(3,4-dichlorobenzoylamino)-2-fluorophenoxy]phenyl}-4-oxobutyryl)morpholine (1.00 g, 1.83 mmol) in THF (20 mL) and methanol (5 mL) was added sodium borohydride (0.0694 g, 1.83 mmol), and the resulting solution was stirred for 1 hour at room temperature. To this reaction solution were added water and saturated aqueous ammonium chloride, and extracted with ethyl acetate. The ethyl acetate layer was washed with brine, dried over anhydrous magnesium sulfate, evaporated, and the residue was purified by silica gel column chromatography (dichloromethane:methanol=30:1). The obtained solid was recrystallized from water-containing isopropanol, to thereby yield 0.850 g of the title compound.

Appearance: White powder

Melting point: 108-111° C.

The following compounds were produced in the same manner as in Example 2676.

TABLE 428

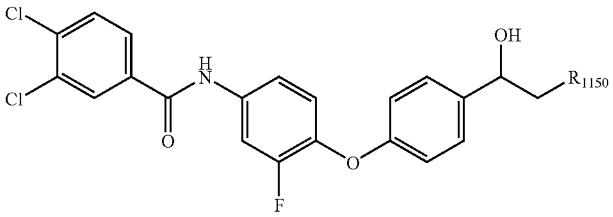

| Example No. | $R_{1150}$ | Form | mp (° C.) |
|---|---|---|---|
| 2677 | morpholino | free | 142-145 |
| 2678 | 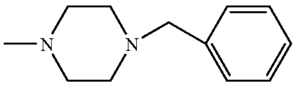 | free | 150-152 |
| 2679 | 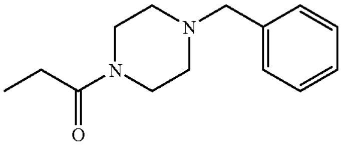 | hydro-chloride | 197-199 |
| 2680 | 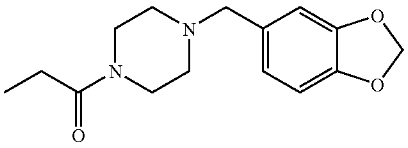 | hydro-chloride | 222-225 |

TABLE 429

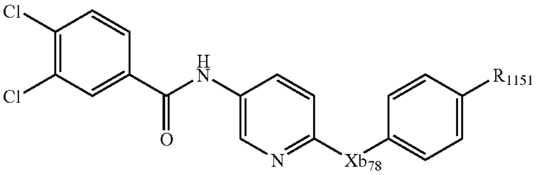

| Example No. | $Xb_{78}$ | $R_{1151}$ | Form | mp (° C.) or $^1H$ NMR |
|---|---|---|---|---|
| 2681 | —O— | 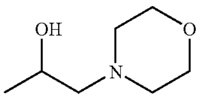 | free | $^1H$ NMR (DMSO-$d_6$) δ 2.38-2.54(6 H, m), 3.58(4 H, t, J = 4.5 Hz), 4.73-4.77(1 H, m), 5.06(1 H, d, J = 3.8 Hz), 7.04-7.07(3 H, m), 7.38(2 H, d, J = 8.4 Hz), 7.84(1 H, d, J = 8.4 Hz), 7.95(1 H, dd, J = 8.4 Hz, 1.2 Hz), 8.22(1 H, d, J = 2.0 Hz), 8.19(1 H, dd, J = 8.9 Hz, 2.8 Hz), 8.48(1 H, d, J = 2.6 Hz), 10.55(1 H, brs). |
| 2682 | —CH(OH)— | 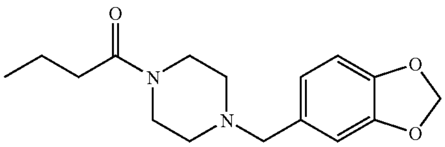 | oxalate | mp 102-108 |

TABLE 430

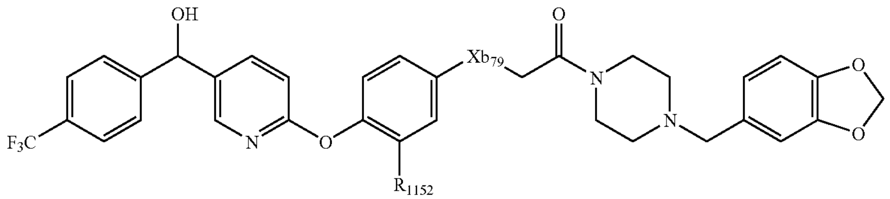

| Example No. | $R_{1152}$ | $Xb_{79}$ | $^1H$ NMR ($CDCl_3$) δppm |
|---|---|---|---|
| 2683 | —$OCH_3$ | —$CH_2$— | 2.30-2.39(4 H, m), 2.57-2.62(2 H, m), 2.90-2.95(2 H, m), 3.36-3.43(4 H, m), 3.58-3.61(2 H, m), 3.70(3 H, s), 5.83(1 H, s), 5.93(2 H, s), 6.69-6.88(6 H, m), 6.99(1 H, d, J = 8.1 Hz), 7.47-7.62(5 H, m), 8.07(1 H, d, J = 2.3 Hz). |
| 2684 | —H | N($CH_3$)— | 2.38-2.43(4 H, m), 2.99(3 H, s), 3.42-3.60(6 H, m), 4.05(2 H, s), 5.77(1 H, s), 5.94(2 H, s), 6.64-6.84(6 H, m), 6.93-6.99(2 H, m), 7.47(2 H, d, J = 8.1 Hz), 7.53-7.59(3 H, m), 8.10(1 H, d, J = 2.1 Hz). |

Example 2685

Production of {6-[4-(4-piperonylpiperazin-1-ylmethyl)phenoxy]pyridin-3-ylmethyl}-(4-trifluoromethylphenyl)amine To a suspension of lithium aluminum hydride (0.106 g, 2.80 mmol) in THF (10 mL) was added dropwise a solution of 6-[4-(4-piperonylpiperazine-1-carbonyl)-phenoxy]-N-(4-trifluoromethylphenyl)nicotinamide (0.423 g, 0.700 mmol) in THF (10 mL) under ice cooled stirring. Once the entire amount was added dropwise, the solution temperature was slowly raised, and stirred under reflux, for 2 hours. After cooling, ice water (50 mL) was added to the solution, and the mixture was extracted with ethyl acetate. The ethyl acetate layer was washed with brine, dried over anhydrous magnesium sulfate, and evaporated. The residue was purified by silica gel column chromatography (dichloromethane methanol 40:1), to thereby yield 0.125 g of the title compound.

Appearance: Pale Yellow oil

MS 576 ($M^+$)

The following compounds were produced in the same manner as in Example 2685.

Example 2686

N-[6-(2-fluoro-4-{methyl[2-(4-piperonylpiperazin-1-yl)ethyl]amino}phenoxy)pyridin-3-yl]-3,4-dichlorobenzenesulfonamide $^1H$ NMR ($CDCl_3$) δ 2.50-2.55 (10H, m), 2.92 (3H, s), 3.41-3.45 (4H, m), 5.93 (2H, s), 6.39-6.49 (2H, m), 6.73-6.74 (2H, m), 6.84-6.89 (2H, m), 6.99 (1H, t, J=9.1 Hz), 7.42-7.70 (4H, m), 7.81 (1H, brs).

Example 2687

Production of 3-(3-methyl-4-{5-[2-(4-trifluoromethyl-phenyl)ethyl]pyridin-2-yloxy}phenyl)-1-piperonyl-tetrahydropyrimidin-2-one hydrobromide To a solution of 3-(3-methyl-4-{5-[(E)-2-(4-trifluoromethylphenyl)vinyl]pyridin-2-yloxy}phenyl)-1-piperonyltetrahydropyrimidin-2-one (0.16 g, 0.27 mmol) in ethyl acetate (15 mL) was added 5% platinum-carbon (0.05 g) under a nitrogen atmosphere, and the resulting solution was then stirred under a hydrogen atmosphere for 4.5 hours at room temperature. The resulting reaction solution was filtered through Celite, and the filtrate was concentrated under reduced pressure. The residue was purified by silica gel chromatography (ethyl acetate:=n-hexane 1:4-1:2), and to the resulting product was added hydrobromide, to thereby yield 50 mg of the title compound.

Appearance: Colorless amorphous powder $^1H$ NMR (DMSO-$d_6$) δ 1.85-2.09 (5H, m), 2.77-3.02 (4H, m), 3.15-3.33 (2H, m), 3.55-3.70 (2H, m), 3.75-4.15 (1H, m), 4.40 (2H, s), 5.99 (2H, s), 6.76 (1H, dd, J=1.5 Hz, 7.8 Hz), 6.80-6.98 (4H, m), 7.10 (1H, dd, J=2.6 Hz, 8.5 Hz), 7.19 (1H, d, J=2.6 Hz), 7.44 (2H, d, J=8.1 Hz), 7.62 (2H, d, J=8.1 Hz), 7.71 (1H, dd, J=2.4 Hz, 8.4 Hz), 7.91 (1H, d, J=2.4 Hz).

The following compounds were produced in the same manner as in Reference Example 673.

TABLE 431

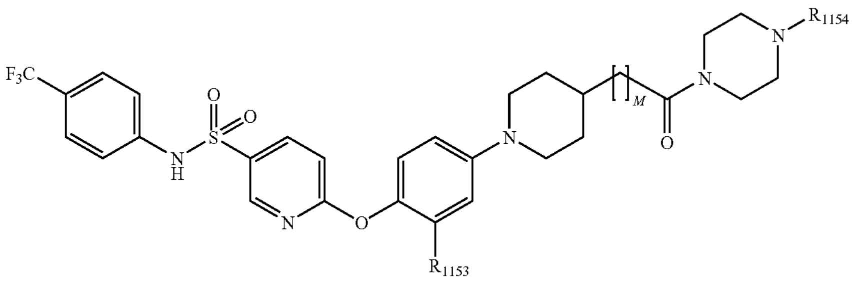

| Example No. | $R_{1153}$ | $R_{1154}$ | M | $^1$H NMR ($CDCl_3$) δ ppm |
|---|---|---|---|---|
| 2688 | —H | piperonyl | 1 | 1.31-1.45 (2H, m), 1.84-2.02 (3H, m), 2.30 (2H, d, J = 6.8 Hz), 2.41-2.43 (4H, m), 2.72 (2H, t, J = 12.2 Hz), 3.43 (2H, s), 3.44-3.65 (6H, m), 5.95 (2H, s), 6.71-6.77 (2H, m), 6.85-7.00 (6H, m), 7.21-7.26 (3H, m), 7.51 (2H, d, J = 8.6 Hz), 7.98 (1H, dd, J = 8.7 Hz, 2.6 Hz), 8.60 (1H, d, J = 2.6 Hz). |
| 2689 | —H | —H | 1 | 1.38-1.46 (2H, m), 1.84-2.00 (3H, m), 2.31 (2H, d, J = 6.8 Hz), 2.71 (2H, t, J = 12.2 Hz), 2.86-2.89 (4H, m), 3.48-3.63 (7H, m), 6.86-6.99 (5H, m), 7.23-7.29 (3H, m), 7.49 (2H, d, J = 8.4 Hz), 7.97 (1H, dd, J = 8.9 Hz, 2.6 Hz), 8.60 (1H, d, J = 2.1 Hz). |
| 2690 | —$CH_3$ | piperonyl | 1 | 1.36-1.40 (2H, m), 1.82-2.02 (3H, m), 2.03 (3H, s), 2.30 (2H, d, J = 6.8 Hz), 2.41-2.43 (4H, m), 2.68 (2H, t, J = 12.0 Hz), 3.43 (2H, s), 3.49-3.65 (6H, m), 5.94 (2H, s), 6.74-6.89 (8H, m), 7.24 (2H, d, J = 8.2 Hz), 7.49 (2H, d, J = 8.6 Hz), 7.99 (1H, dd, J = 8.7 Hz, 2.5 Hz), 8.58 (1H, d, J = 2.1 Hz). |
| 2691 | —H | piperonyl | 0 | 1.78-2.03 (4H, m), 2.46 (4H, brs), 2.55-2.77 (3H, m), 3.46 (2H, s), 3.55 (2H, brs), 3.67 (4H, brs), 5.95 (2H, s), 6.75-6.78 (2H, m), 6.85-7.01 (6H, m), 7.21-7.26 (3H, m), 7.52 (2H, d, J = 8.6 Hz), 7.98 (1H, dd, J = 8.7 Hz, 2.6 Hz), 8.60 (1H, d, J = 2.5 Hz). |

Example 2692

Production of 1-[3-(4-{1-[5-(3,4-dichlorobenzoylamino)-2-pyridyl]-1-hydroxyimino}methylphenyl)propionyl]-4-piperonylpiperazine To a solution of 1-(3-{4-[5-(3,4-dichloro-benzoylamino)pyridine-2-carbonyl]phenyl}propionyl)-4-piperonylpiperazine (0.330 g, 0.511 mmol) in pyridine (7 mL) was added hydroxylamine hydrochloride (53.3 mg, 0.767 mmol), and the resulting solution was refluxed for 0.5 hours. The reaction solution was concentrated under reduced pressure, and to the residue was added brine. This solution was extracted with dichloromethane. The dichloromethane layer was dried over anhydrous magnesium sulfate, and evaporated. The residue was purified by silica gel column chromatography (dichloromethane:methanol=15:1), whereby 0.225 g of the title compound was obtained as a mixture of the syn form and the anti form (1:1) of the oxime.

Appearance: Colorless amorphous powder $^1$H NMR ($CDCl_3$) δ 2.21-2.39 (4H, m), 2.49-2.60 (2H, m), 2.78-2.90 (2H, m), 3.29-3.44 (4H, m), 3.55 (2H, s), 5.90 (2H, s), 6.62-6.73 (2H, m), 6.80 (1H, s), 7.07 (1H, d, J=7.7 Hz), 7.12 (1H, d, J=7.7 Hz), 7.15-7.30 (2.5H, m), 7.39 (0.5H, d, J=8.4 Hz), 7.42 (0.5H, d, J=8.4 Hz), 7.45-7.51 (0.5H, m), 7.62-7.74 (1H, m), 7.94 (0.5H, d, J=2.0 Hz), 7.99 (0.5H, d, J=2.0 Hz), 8.09-8.28 (1H, m), 8.62 (0.5H, s), 8.85 (0.5H, s), 9.40 (0.5H, brs), 9.62 (0.5H, brs), 10.21 (0.5H, brs), 13.85 (0.5H, brs).

Example 2693

Production of 4-(2-oxo-3-{4-[5-(4-trifluoromethylbenzoylamino)pyridin-2-yloxy]phenyl}propionyl)-piperazine-1-carboxylic acid t-butyl ester To a solution of 4-(2-hydroxy-3-{4-[5-(4-trifluoromethylbenzoylamino)pyridin-2-yloxy]phenyl}propionyl)piperazine-1-carboxylic acid t-butyl ester (0.58 g, 0.94 mmol) in dichloromethane (4 mL) was added a Dess-Martin reagent (0.8 g, 1.89 mmol), and the resulting solution was then stirred under a nitrogen gas flow for 4 hours at room temperature. The reaction solution was concentrated under reduced pressure. To the residue was added 1 N aqueous sodium hydroxide (50 mL), and extracted with ethyl acetate. The ethyl acetate layer was washed with brine, dried over anhydrous magnesium sulfate, and evaporated. The residue was purified by silica gel chromatography (dichloromethane:methanol=50:1), to thereby yield 0.31 g of the title compound.

Appearance: Yellow powder $^1$H NMR ($CDCl_3$) δ 1.41 (9H, s), 2.99-3.22 (4H, m), 3.25-3.41 (2H, m), 3.42-3.60 (2H, m), 4.04 (2H, s), 6.97 (1H, d, J=8.9 Hz), 7.10 (2H, d, J=8.4 Hz), 7.27 (2H, d, J=8.4 Hz), 7.73 (2H, d, J=8.0 Hz), 7.99 (2H, d, J=8.0 Hz), 8.13 (1H, d, J=2.8 Hz), 8.30 (1H, dd, J=8.9 Hz, 2.8 Hz), 8.45 (1H, brs).

Example 2694

Production of 3,4-dichloro-N-{3-fluoro-4-[4-(1-hydroxy-2-morpholine-4-ylethyl)phenoxy]phenyl}benzamide 3,4-Dichloro-N-{3-fluoro-4-[4-(1-hydroxy-2-morpholine-4-ylethyl)phenoxy]phenyl}benzamide (37.4 g) was recrystallized from ethanol (700 mL) to yield 34.34 g of the title compound.

Appearance: White powder

Melting point: 175-176° C.

Example 2695

Production of N-[6-(4-{[2-(4-piperonylpiperazin-1-yl)-2-oxoethyl]ethylamino}-2-fluorophenoxy)pyridin-3-yl]-3,4-dichlorobenzenesulfonamide N-[6-(4-{2-(4-Piperonylpiperazin-1-yl)-2-oxoethyl]ethylamino}-2-fluorophenoxy)pyridin-3-yl]-3,4-dichlorobenzenesulfonamide (8.15 g) was recrystallized from ethanol (60 mL) to yield 7.78 g of the title compound.

Appearance: White powder

Melting point: 163-166° C.

Example 2696

Production of N-[6-(4-{[2-(4-piperonylpiperazin-1-yl)-2-oxoethyl]methylamino}-2-methylphenoxy)pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (5.1 g, 7.7 mmol) was recrystallized from acetone (15 mL) to yield 3.7 g of the title compound.

Appearance: White powder

Melting point: 128-131° C.

Example 2697

Production of N-{6-[4-(4-benzylpiperazine-1-carbonyl)phenoxy]pyridin-3-yl}-4-trifluoromethyl-benzamide N-{[6-[4-(4-Benzylpiperazine-1-carbonyl)-phenoxy]pyridin-3-yl}-4-trifluoromethylbenzamide (78.86 g) was recrystallized from ethanol (530 mL) to yield 96.66 g of the title compound.

Appearance: White needles

Melting point: 177.6-179.2° C.

Example 2698

Production of N-(6-{4-[4-(2-oxo-1,2,3,4-tetrahydroquinoline-6-ylmethyl)piperazine-1-carbonyl]phenoxy}-pyridin-3-yl)-4-trifluoromethylbenzamide To a solution of 4-[5-(4-trifluoromethylbenzoylamino)pyridin-2-yloxy]benzoic acid (4.30 g, 10.7 mmol) in DMF (150 mL) were added 1-(2-oxo-1,2,3,4-tetrahydroquinoline-6-ylmethyl)-piperazine (2.6 g, 10.7 mmol), 1-hydroxybenzotriazole monohydrate (1.64 g, 10.7 mmol) and 1-ethyl-3-(3-dimethylaminopropyl)carbodiimide hydrochloride (2.46 g, 12.8 mmol) under ice cooling, and the resulting solution was stirred for 1 hour under ice cooling and for 17 hours at room temperature. This reaction solution was concentrated under reduced pressure. To the residue was added a saturated sodium bicarbonate solution, and extracted with ethyl acetate. The ethyl acetate layer was washed with a saturated sodium bicarbonate solution and brine, dried over anhydrous magnesium sulfate, and evaporated. The residue was recrystallized from ethyl acetate, to thereby yield 5.24 g of the title compound.

Appearance: White powder

Melting point: 250.5-252.5° C.

Example 2699

Production of N-(6-{4-[4-(4-benzylpiperidine-1-carbonyl)piperazine-1-carbonyl]phenoxy}pyridin-3-yl)-3,4-dichlorobenzamide To a solution of 1-{4-[5-(3,4-dichlorobenzoylamino)pyridin-2-yloxy]benzoyl}piperidine-4-carboxylic acid (4.5 g, 8.8 mmol) in DMF (88 mL) were added 1-benzylpiperazine (1.83 mL, 10.5 mmol), 1-hydroxybenzotriazole monohydrate (1.61 g, 10.5 mmol) and 1-ethyl-3-(3-dimethylaminopropyl)carbodiimide hydrochloride (2.02 g, 10.5 mmol) under ice cooling, and the resulting solution was stirred overnight at room temperature. To this reaction solution was added a saturated sodium bicarbonate solution, and the resulting solution was extracted with ethyl acetate. The ethyl acetate layer was washed with a saturated sodium bicarbonate solution and brine, dried over anhydrous magnesium sulfate, and evaporated. The residue was recrystallized from isopropyl alcohol (700 mL), to thereby yield 3.2 g of the title compound.

Appearance: White powder

Melting point: 223-225° C.

Example 2700

Production of N-[6-(4-{[2-(4-benzylpiperazin-1-yl)-2-oxoethyl]methylamino}-2-methylphenoxy)pyridin-3-yl]-4-trifluoromethylbenzamide To a suspension of 1-(4-benzylpiperazin-1-yl)-2-{methyl[3-methyl-4-(5-nitropyridin-2-yloxy)phenyl]amino}ethanone (2.85 g, 6.0 mmol) in ethyl acetate (30 mL) was added 5% platinum-carbon (0.30 g) under a nitrogen atmosphere, and the resulting solution was stirred for 3 hours at 40° C. under a hydrogen atmosphere. The platinum-carbon was separated off with Celite, and the filtrate was concentrated. The residue was dissolved in THF (30 mL), and to this solution was added triethylamine (1.26 mL, 9.1 mmol) under ice cooling. To the resulting solution was then added dropwise 4-(trifluoromethyl)benzoyl chloride (1.16 mL, 7.8 mmol). This reaction solution was stirred overnight, then a saturated sodium bicarbonate solution was added, and the mixture was extracted with ethyl acetate. The ethyl acetate layer was washed with water, and then dried over anhydrous sodium sulfate. The solvent was evaporated, and the residue was purified by silica gel column chromatography (dichloromethane:methanol=20:1). The resulting product was then recrystallized from a mixed solvent consisting of diisopropyl ether-acetone, to thereby yield 1.37 g of the title compound.

Appearance: White powder

Melting point: 112-113° C.

Example 2701

Production of (4-benzylpiperazin-1-yl)(4-{5-[methyl(4-trifluoromethylbenzyl)amino]pyridin-2-yloxy}phenyl)-methanone To a solution of (4-benzylpiperazin-1-yl){4-[5-(4-trifluoromethylbenzylamino)pyridin-2-yloxy]phenyl}methanone (5.40 g, 9.88 mmol) in methanol (150 mL) were added 37% aqueous formaldehyde (2.8 mL), sodium cyanoborohydride (1.86 g, 29.6 mmol) and acetic acid (1.7 mL) under ice cooling, and the resulting solution was stirred at room temperature for 2 hours. The solvent was evaporated under reduced pressure. Water was added to the residue, and this solution was neutralized with a saturated sodium bicarbonate solution, and extracted with chloroform. The organic layer was washed with water, and then dried over anhydrous magnesium sulfate. The solvent was evaporated, and the residue was purified by silica gel column chromatography (chloroform:methanol=60:1). To the resulting product was then added a solution of 4 M hydrogen chloride in ethyl acetate until the resulting solution had a pH of 1. The precipitates were collected by filtration and recrystallized from ethanol (80 mL), to thereby yield 2.5 g of the title compound.

Appearance: White powder

Melting point: 180-183.5° C.

Example 2702

Production of 4-piperonylpiperazine-1-carboxyl 4-[5-(3,4-dichlorobenzoylamino)pyridin-2-yloxy] benzylamide hydrochloride To a solution of 4-piperonylpiperazine-1-carboxyl 4-(5-aminopyridin 2-yloxy)benzylamide (2.48 g, 5.4 mmol) in THF (50 mL) were added triethylamine (0.9 mL, 6.5 mmol) and 3,4-dichlorobenzoyl chloride (1.13 g, 5.4 mmol) under ice cooling, and the resulting solution was stirred under ice cooling for 10 minutes. Water was added to the residue, and extracted with ethyl acetate. The ethyl acetate layer was washed with water and brine, dried over anhydrous magnesium sulfate, and evaporated. The residue was purified by silica gel column chromatography (dichloromethane:methanol=25:1) to yield 2.97 g of a white powder. This white powder was dissolved in ethanol (45 mL), and to the resulting solution was added a solution of 4 M hydrogen chloride in ethyl acetate until the solution had a pH of 1. The precipitates were collected by filtration and recrystallized from 83% ethanol (36 mL), to thereby yield 2.72 g of the title compound.

Appearance: White powder

Melting point: 243.5-246.5° C.

Example 2703

Production of N-[6-(4-{4-[2-(4-piperonylpiperazin-1-yl)-2-oxoethyl]piperidin-1-yl}-2-methylphenoxy) pyridin-3-yl]-4-trifluoromethylbenzenesulfonamide N-[6-(4-{4-[2-(4-Piperonylpiperazin-1-yl)-2-oxoethyl] piperidin-1-yl}-2-methylphenoxy)pyridin-3-yl]-4-trifluoromethylbenzenesulfonamide (1.35 g) was recrystallized from ethanol (20 mL) to yield 1.23 g of the title compound.

Appearance: White powder

Melting point: 156-158° C.

Example 2704

Production of N-(6-{4-[4-(4-piperonylpiperazine-1-carbonyl)piperidin-1-yl]phenoxy}pyridin-3-yl)-3,4-dichlorobenzenesulfonamide N-(6-{4-[4-(4-Piperonylpiperidine-1-carbonyl)piperidin-1-yl]phenoxy}pyridin-3-yl)-3,4-dichlorobenzenesulfonamide (1.95 g) was recrystallized from ethanol (35 mL) to yield 1.70 g of the title compound.

Appearance: White powder

Melting point: 130-133° C.

Example 2705

Production of N-[6-(4-{[2-(4-piperonylpiperazin-1-yl)-2-oxoethyl]methylamino}-2-methylphenoxy) pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (0.86 g, 1.30 mmol) was recrystallized from a mixed solvent of acetone (3 mL) diethyl ether (4 mL) and n-hexane (1 mL) to yield 0.72 g of the title compound.

Appearance: Pale yellow powder

Melting point: 154-155° C.

Example 2706

Production of N-(6-{4-[4-(4-benzylpiperazine-1-carbonyl)piperidin-1-yl]phenoxy}pyridin-3-yl)-4-trifluoromethylbenzensulfonamide N-(6-{4-[4-(4-Benzylpiperidin-1-carbonyl)piperidin-1-yl]phenoxy}pyridin-3-yl)-4-trifluoromethylbenzensulfonamide (1.55 g) was recrystallized from ethanol (60 mL) to yield 1.41 g of the title compound.

Appearance: White powder

Melting point: 199-201° C.

Example 2707

Production of N-[6-(4-{4-[2-(4-benzylpiperazin-1-yl)-2-oxoethyl]piperidin-1-yl}-2-methylphenoxy) pyridin-3-yl]-3,4-dichlorobenzenesulfonamide To a solution of (1-{4-[5-(3,4-dichlorobenzenesulfonylamino)pyridin-2-yloxy]-3-methylphenyl}piperidine-4-yl) acetic acid (1.70 g, 3.1 mmol) and 1-benzylpiperazine (0.71 g, 4.0 mmol) in DMF (40 mL) were added triethylamine (1.08 mL, 7.8 mmol) and diethyl cyanophosphonate (0.76 g, 4.3 mmol) under ice cooling, and the resulting solution was stirred for 1 hour under ice cooling. To this reaction solution was added a saturated sodium bicarbonate solution, and extracted with ethyl acetate. The ethyl acetate layer was washed with a saturated sodium bicarbonate solution and brine, dried over anhydrous sodium sulfate, and evaporated. The residue was purified by silica gel column chromatography (dichloromethane:methanol=40:1), after which the resulting product was recrystallized from ethanol, to thereby yield 1.61 g of the title compound.

Appearance: White needles

Melting point: 151-155° C.

Example 2708

Production of N-[6-(4-{[2-(4-benzothiazole-6-ylmethylpiperazin-1-yl)-2-oxoethyl]methylamino}-phenoxy)pyridin-3-yl]-3,4-dichlorobenzamide dihydrochloride To a solution of ({4-[5-(3,4-dichlorobenzoyl-amino)pyridin-2-yloxy]phenyl}methylamino)acetic acid (1.02 g, 2.3 mmol) and 1-(benzothiazole-6-ylmethyl)-piperazine (0.58 g, 2.5 mmol) in DMF (15 mL) were added triethylamine (0.95 mL, 6.9 mmol) and diethyl cyanophosphonate (0.447 mL, 2.7 mmol) under ice cooling, and the resulting solution was stirred for 30 minutes under ice cooling and for 45 minutes at room temperature. Water was added to the solution, and extracted with ethyl acetate. The ethyl acetate layer was washed with a saturated sodium bicarbonate solution and brine, dried over anhydrous sodium sulfate, and evaporated. The residue was purified by silica gel column chromatography (dichloromethane:methanol=30:1) to obtain 1.28 g of a white powder. This white powder was dissolved in ethanol (15 mL), and to the resulting solution was added a solution of 4 M hydrogen chloride in ethyl acetate until the resulting solution had a pH of 1. The precipitates were collected by filtration and recrystallized from 85% ethanol (30 mL), to thereby yield 1.06 g of the title compound.

Appearance: White powder

Melting point: 202-223° C.

Example 2709

Production of 3,4-dichloro-N-{6-[4-({2-[4-(2,3-dihydrobenzo[1,4]dioxin-6-ylmethyl)piperazin-1-yl]-2-oxoethyl}methylamino)phenoxy]pyridin-3-yl}benzamide maleate To a solution of ({4-[5-(3,4-dichlorobenzoyl-amino)pyridin-2-yloxy]phenyl}methylamino)acetic acid (2.50 g, 5.6 mmol) in DMF (55 mL) were added 1-(2,3-dihydrobenzo[1,4]dioxin-6-ylmethyl)piperazine (1.7 g, 7.3 mmol), 1-hydroxybenzotriazole monohydrate (0.86 g, 5.6 mmol) and 1-ethyl-3-(3-dimethylaminopropyl)carbodiimide hydrochloride (1.29 g, 6.7 mmol) under ice cooling, and the resulting solution was stirred for 30 minutes under ice cooling and for 17 hours at room temperature. This reaction solution was concentrated under reduced pressure. Water was added to the residue, and extracted with ethyl acetate. The ethyl acetate layer was washed with a saturated sodium bicarbonate solution and brine, dried over anhydrous magnesium sulfate, and evaporated. The residue was dissolved in ethanol (30 mL). To the resulting solution was added maleic acid (0.32 g, 2.7 mmol), and this solution was left to stand. The precipitates were collected by filtration, to thereby yield 1.45 g of the title compound.

Appearance: Pale yellow powder

Melting point: 188-190° C.

Example 2710

Production of N-(6-{4-[4-(4-benzylpiperazine-1-carbonyl)piperidin-1-yl]phenoxy}pyridin-3-yl)-3,4-dichlorobenzenesulfonamide N-(6-{4-[4-(4-Benzylpiperazine-1-carbonyl)piperidin-1-yl]phenoxy}pyridin-3-yl)-3,4-dichlorobenzenesulfonamide (0.79 g) was recrystallized from ethanol (15 mL) to yield 0.67 g of the title compound.

Appearance: White powder

Melting point: 185-189° C.

Example 2711

Production of N-[6-(4-{[2-(4-piperonylpiperazin-1-yl)-2-oxoethyl]methylamino}-2-methylphenoxy)pyridin-3-yl]-4-pyrrole-1-ylbenzamide N-[6-(4-{[2-(4-Piperonylpiperazin-1-yl)-2-oxoethyl]methylamino}-2-methylphenoxy)pyridin-3-yl]-4-pyrrole-1-ylbenzamide (2.49 g) was recrystallized from a mixed solvent consisting of acetone (20 mL) and diethyl ether (30 mL) to yield 2.26 g of the title compound.

Appearance: Pale yellow powder

Melting point: 163.1-166.5° C.

Example 2712

Production of N-[6-(4-{[2-(4-piperonylpiperazin-1-yl)-2-oxoethyl]ethylamino}-2-fluorophenoxy)pyridin-3-yl]-4-trifluoromethylbenzenesulfonamide N-[6-(4-{[2-(4-Piperonylpiperazin-1-yl)-2-oxoethyl]ethylamino}-2-fluorophenoxy)pyridin-3-yl]-4-trifluoromethylbenzenesulfonamide (8.18 g) was recrystallized from a mixed solvent consisting of ethyl acetate (70 mL) and n-hexane (20 mL) to yield 6.93 g of the title compound.

Appearance: White powder

Melting point: 177.8-180.1° C.

Example 2713

Production of 6-(4-{4-[2-(4-piperonylpiperazin-1-yl)-2-oxoethyl]piperidin-1-yl]-2-methylphenoxy}pyridine-3-sulfonyl-(4-trifluoromethylphenyl)amide 6-(4-{4-[2-(4-Piperonylpiperazin-1-yl)-2-oxoethyl]piperidin-1-yl]-2-methylphenoxy}pyridine-3-sulfonyl-(4-trifluoromethylphenyl)amide (1.50 g) was recrystallized from ethanol (20 mL) to yield 1.40 g of the title compound.

Appearance: White powder

Melting point: 156-160° C.

Example 2714

Production of N-[6-(4-{[2-(4-piperonylpiperazin-1-yl)-2-oxoethyl]methylamino}-2-methylphenoxy)pyridin-3-yl]-4-trifluoromethylbenzamide N-[6-(4-{[2-(4-Piperonylpiperazin-1-yl)-2-oxoethyl]methylamino}-2-methylphenoxy)pyridin-3-yl]-4-trifluoromethylbenzamide (2.1 g, 3.2 mmol) was heated to dissolve in acetone (5 mL), and to the resulting solution was then added diethyl ether (10 mL), whereby recrystallization yielded 2.0 g of the title compound.

Appearance: White powder

Melting point: 113-116° C.

Example 2715

Production of 3,4-dichloro-N-{3-fluoro-4-[4-(1-hydroxy-2-morpholine-4-ylethyl)phenoxy]phenyl}benzamide 3,4-Dichloro-N-{3-fluoro-4-[4-(1-hydroxy-2-morpholine-4-ylethyl)phenoxy]phenyl}benzamide (5 g) was recrystallized from ethyl acetate-n-hexane to yield 4.73 g of the title compound.

Appearance: White powder

Melting point: 169-170° C.

Example 2716

Production of N-(6-{4-[4-(4-piperonylpiperazine-1-carbonyl)piperidine-1-carbonyl]phenoxy}pyridin-3-yl)-3,4-dichlorobenzamide To a solution of 1-{4-[5-(3,4-dichlorobenzoylamino)pyridin-2-yloxy]benzoyl}piperidine-4-carboxylic acid (7.96 g, 15.5 mmol) in DMF (160 mL) were added 1-piperonylpiperazine (3.75 g, 17.6 mmol), 1-hydroxybenzotriazole monohydrate (2.85 g, 18.6 mmol) and 1-ethyl-3-(3-dimethylaminopropyl)carbodiimide hydrochloride (3.56 g, 18.6 mmol) under ice cooling, and the resulting solution was stirred for overnight at room temperature. This reaction solution was concentrated under reduced pressure. To the residue were added water and ethyl acetate, and the resulting solution was vigorously stirred. The resulting precipitates were collected by filtration and recrystallized from a dichloromethane-methanol mixed solvent, to thereby yield 7.36 g of the title compound.

Appearance: White powder

Melting point: 236-238° C.

Example 2717

Production of N-{6-[(4-{4-[2-(4-piperonylpiperazin-1-yl)-2-oxoethyl]piperidin-1-yl}phenyl)methylamino]-pyridin-3-yl}-4-trifluoromethylbenzamide To a solution of [1-(4-{methyl[5-(4-trifluoromethylbenzoylamino)pyridin-2-yl]amino}phenyl)piperidine-4-yl]acetic acid (0.80 g, 1.6 mmol) in DMF (10 mL) were added 1-piperonylpiperazine (0.41 g, 1.9 mmol), 1-hydroxybenzotriazole monohydrate (0.24 g, 1.6 mmol) and 1-ethyl-3-(3-dimethylaminopropyl)carbodiimide hydrochloride (0.39 g, 2.0 mmol) under ice cooling, and the resulting solution was stirred for 3 hours at room temperature. This reaction solution was concentrated under reduced pressure. To the residue was added a saturated sodium bicarbonate solution, and extracted with dichloromethane. The dichloromethane layer was washed with a saturated sodium bicarbonate solution and brine, dried over anhydrous magnesium sulfate, and evaporated. The residue was purified by silica gel column chromatography (dichloromethane:methanol=20:1). The resulting product was then recrystallized from a mixed solvent consisting of 95% ethanol-dichloromethane, to thereby yield 1.05 g of the title compound.

Appearance: White powder

Melting point: 210-212° C.

Formulation Example 1

100 g of the N-[6-(4-{4-[2-(piperonyl-piperazin-1-yl)-2-oxoethyl]piperidin-1-yl}phenoxy)-pyridin-3-yl]-4-trifluoromethylbenzamide obtained in Example 319, 40 g of Avicel (Tradename, manufactured by Asahi Kasei Corporation), 30 g of cornstarch and 2 g of magnesium stearate were mixed and ground together. The resulting mixture was then formed into a sugar-coated R 10-mm-tablets using a pestle. The obtained tablets were coated with a film coating agent containing 10 g of TC-5 (Tradename, manufactured by Shin-Etsu Chemical Co., Ltd., hydroxypropylmethyl cellulose), 3 g of polyethylene glycol 6000, 40 g of castor oil and a suitable amount of ethanol, to thereby prepare a film-coated tablet.

Pharmacological Test 1

Anti-Cancer Effect (In-Vitro) on Cancer Cells

Anti-proliferative effect of test compounds on human hepatic cancer cells (HuH-7), human lung cancer cells (EBC-1), human colorectal cancer cells (HCT116), human prostatic cancer cells (22Rv1), human pancreatic cancer cells (MIA PaCa-2), human stomach cancer cells (MKN45), human breast cancer cells (ZR-75-1) was checked by a sulforhodamine B method in accordance with Skehan P et al. (J. Natl. Cancer Inst. 1990 Jul. 4; 82(13): 1107-12). Explanation will be made taking HuH-7 cells as an example.

HuH-7 cells were seeded on DMEM medium (Dulbeco's modified Eagle Medium) containing 10% fetal bovine serum of a 96-well microplate and cultured at 37° C. for 24 hours in the presence of 5% carbon dioxide gas ($CO_2$). Thereafter, a test compound was added to the wells and the cells were cultured for a further 5 days. After the cultivation, trichloro acetic acid was added to the wells so as to obtain a final concentration of 10%. The microplate was allowed to stand still at 4° C. for one hour to fix the cells on the wells. The microplate was washed with water to remove the medium and trichloroacetic acid and dried in the air. After the air-dry, the microplate was stored at 4° C. until it was stained with sulforhodamine B.

To each of the wells, a 1% aqueous acetic acid solution containing 0.4% sulforhodamine B was added and the wells were allowed to stand still at room temperature for 20 to 30 minutes. After the supernatant was removed, each well was washed with the 1% aqueous acetic acid solution and a 10 mM aqueous Tris (Tris hydroxyaminomethane) solution was add to each well and stirred. In this manner, the dye taken in the cell was eluted. Subsequently, OD (optical density) was measured at a measurement wavelength of 492 nm and a reference wavelength of 690 nm to obtain the difference (A) in OD thus measured. Furthermore, the OD of a control well (containing no cells) was measured at a measurement wavelength of 492 nm and a reference wavelength of 690 nm to obtain the difference (B) in OD. The difference (A−B) was regarded as the cell proliferation activity of each of the wells.

Anti-proliferative effect of test compounds on human chronic myelogenous leukemia cells (KU812) was determined by an MTT assay in accordance with the method described in Singh A K et al. (Cancer Lett. 1996 Oct. 1; 107(1): 109-15). To describe more specifically, KU812 cells were seeded on RPMI 1640 medium containing 10% fetal bovine serum of a 96-well microplate, cultured at 37° C. for 24 hours in the presence of a 5% carbon dioxide gas ($CO_2$). Thereafter, a test compound was added to the wells and the cells were cultured for a further 5 days. After the incubation, 10 μl of 5 mg/mL MTT (3-(4,5-dimethyl)-2,5-diphenyltetrazolium bromide) was added to the wells. After the cells were cultured for 4 hours, 100 μl of 0.01N HCl containing 10% SDS (sodium dodecyl sulfate) was added to the wells, which was further cultured overnight. Subsequently, OD was measured at a measurement wavelength of 570 nm and a reference wavelength of 690 nm to obtain the difference (A) in OD. Furthermore, OD of a control well (containing no cells) was measured at a measurement wavelength of 570 nm and a reference wavelength of 690 nm to obtain the difference (B) in OD. The difference (A−B) was regarded as the cell proliferation activity of each of the wells.

The cell proliferation activity (T) at the time a test compound was added was compared to that (C) of the control (containing no test compound) and the cell proliferation suppression activity (T/C) of the test compound was computationally obtained. Based on this, the concentration (IC50) of the test compound at which the proliferation of 50% of the cells was inhibited, that is, the concentration of the test compound providing T/C=0.5, was obtained.

TABLE 432

| Example No. | HuH-7 IC50 (nM) | EBC-1 IC50 (nM) | HCT116 IC50 (nM) | 22Rv1 IC50 (nM) | MIA PaCa-2 IC50 (nM) | MKN45 IC50 (nM) | ZR-75-1 IC50 (nM) | KU812 IC50 (nM) |
|---|---|---|---|---|---|---|---|---|
| 276 | <100 | <1000 | <1000 | <1000 | <100 | <1000 | <1000 | <100 |
| 322 | <100 | <100 | <100 | <100 | <100 | <100 | <100 | <100 |
| 582 | <100 | <100 | <100 | <1000 | <100 | <1000 | <1000 | <100 |
| 940 | <100 | <100 | <1000 | <1000 | <100 | <100 | <1000 | <100 |
| 1039 | <100 | <100 | <100 | <100 | <100 | <100 | <1000 | <100 |
| 1049 | <100 | <100 | <100 | <100 | <100 | <1000 | <100 | <100 |
| 1202 | <100 | <100 | <100 | <100 | <100 | <100 | <100 | <100 |
| 1503 | <100 | <100 | <100 | <100 | <100 | <100 | <100 | <100 |
| 2228 | <100 | <100 | <1000 | <1000 | <100 | <1000 | <1000 | <100 |

Pharmacological Test 2

Anti-Cancer Effect (In-Vitro) on Hepatic Cancer Cells HuH-7

Human hepatic cancer cells HuH-7 were transplanted into SCID mice (a group of 6 female mice). Anti-tumor effect of test compounds according to the present invention was checked. To describe more specifically, the cancer cells were cultured in advance and a cell suspension solution containing the cancer cells in a concentration of $2.5\times10^7$ cells/mL was prepared. Then, 0.2 mL of the cell suspension solution was injected into the right axillary region of each of the mice to transplant the cancer cells. In this manner, cancer-bearing mice were prepared. When the tumor grew up to a diameter of 5 mm or more, the mice were divided into groups based on tumor volume. From the following day after the grouping, a 5% gum arabic suspension solution containing a test compound was orally administrated once a day for consecutive 9 days. To a control group, a 5% gum arabic suspension solution was administrated. Next day after completion of administration, the volume of a tumor was measured. The ratio in volume of a tumor at the time of grouping relative to that measured next day after completion of administration was calculated to obtain a relative tumor volume of each group. Then, the ratio (T/C %) in relative tumor volume of a control group to a test group (administrated with a test compound) was calculated and used as an index of the effect.

Relative tumor volume=tumor volume measured on the next day of completion of administration/tumor volume measured at the time of grouping ($T/C$ %)=(an average value of relative tumor volume of test compound administration group)/(an average value of relative tumor volume of a control group)×100

TABLE 433

| Compound | Applied dose (mg/kg/day) | T/C % |
|---|---|---|
| Example 811 | 30 | <50 |
| Example 1202 | 100 | <50 |
| Example 1503 | 100 | <50 |

Pharmacological Test 3

Anti-Proliferative effect of test compounds on human renal cancer cells (Caki-2) was checked in the same manner as in Pharmacological test 1 in accordance with the sulforhodamine B method of Skehan P et al.

In addition, anti-proliferative effect of test compounds on human acute myelogenous leukemia cells (KG-1), human Burkitt's lymphoma cells (Daudi), human lymphoma cells (U937) and human multiple myeloma cells (IM-9) was checked by the MTT assay in the same manner as in Pharmacological test 1 in accordance with Singh A K et al. (Cancer Lett. 1996 Oct. 1; 107(1): 109-15).

IC50 values of human renal cancer cells (Caki-2), human acute myelogenous leukemia cells (KG-1) and human multiple myeloma, cells (IM-9) are shown in Table 434.

The cell proliferation activity of each of the test compounds on human Burkitt's lymphoma cells (Daudi) and human lymphoma cells (U937) was compared to that of a control (containing no test compounds) to obtain cell proliferation suppression activities (T/C) of each test compound. The results are shown in Table 435.

TABLE 434

| Example No. | Caki-2 IC50 (nM) | IM-9 IC50 (nM) | KG-1 IC50 (nM) |
|---|---|---|---|
| 276 | <1000 | <1000 | <100 |
| 322 | <100 | <100 | <100 |
| 582 | <1000 | <100 | <100 |
| 940 | <1000 | <100 | <100 |
| 1039 | <100 | <100 | <100 |
| 1049 | <100 | <100 | <100 |
| 1202 | <100 | <100 | <100 |
| 1503 | <100 | <100 | <100 |
| 2228 | <100 | <100 | <100 |

TABLE 435

| Example No. | Applied dose (nM) | Daudi (T/C %) | U937 (T/C %) |
|---|---|---|---|
| 322 | 10 | <70 | <70 |
| 1202 | 10 | <70 | <70 |
| 1503 | 10 | <70 | <70 |

The invention claimed is:

1. A method for treating a tumor comprising administering, to a patient in need thereof, an effective amount of a compound represented by the general formula (2) or a salt thereof:

[formula 2]

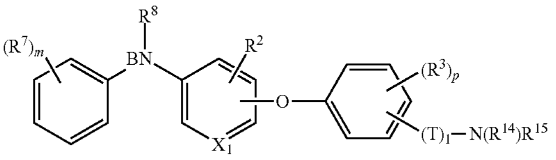

wherein $X_1$ represents a nitrogen atom or a group —CH═, $R^8$ represents a hydrogen atom, a lower alkyl group that may have a lower alkoxy group as a substituent, a lower alkanoyl group, a lower alkylsulfonyl group, or a phenyl lower alkyl group, B represents a group —CO— or a lower alkylene group, $R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have a group, as a substituent, selected from the group consisting of a lower alkyl group, a lower alkanoyl group, a benzoyl group and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group, or a 5- or 6-membered saturated or unsaturated heterocyclic group having 1 to 4 nitrogen atoms, oxygen atoms, or sulfur atoms (wherein said heterocyclic ring may be substituted by an oxo group), m represents an integer between 1 and 5, wherein when m represents 2 to 5, two to five $R^7$s may be identical or different, $R^2$ represents a hydrogen atom, a halogen atom, or a lower alkyl group, p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —$CONR^{11}R^{12}$, or a cyano group, each of $R^{11}$ and $R^{12}$, which are identical or different, represents a hydrogen atom, a lower alkyl group, a cycloalkyl group, or a phenyl group; or $R^{11}$ and $R^{12}$, together with the nitrogen atom to which they bind, may bind to each other, directly or via a nitrogen atom, a sulfur atom, or an oxygen atom to form a 5- to 7-membered saturated heterocyclic ring, T represents a lower alkylene group, a group —$N(R^{17})$—$B_3$—CO—, a group —$B_{19}$—$N(R^{18})$—CO—, a group —$B_4$—CO—, a group -Q-$B_5$—CO—, a group —$B_6$—$N(R^{19})$—$B_7$—CO—, a group —CO—$B_8$—, a group —CH(OH)—$B_9$—, a group —CO—$B_{10}$—CO—, a group —CH(OH)—$B_{11}$—CO—, a group —CO—, a group —$SO_2$—, or a group —$B_{23a}$—CO—CO—, $R^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, $B_3$ represents a lower alkylene group, $B_{19}$ represents a lower alkylene group, $R^{18}$ represents a hydrogen atom or a lower alkyl group, $B_4$ represents a lower alkenylene group, or a lower alkylene group that may have a hydroxyl group as a substituent, Q represents an oxygen atom or a group —S(O)n- (wherein n has the same meaning as described above), $B_5$ represents a lower alkylene group, $B_6$ represents a lower alkylene group, $R^{19}$ represents a hydrogen atom or a lower alkanoyl group, $B_7$ represents a lower alkylene group, $B_8$ represents a lower alkylene group, $B_9$ represents a lower alkylene group, $B_{10}$ represents a lower alkylene group, $B_{11}$ represents a lower alkylene group, $B_{23a}$ represents a lower alkylene group, I represents 0 or 1, $R^{14}$ and $R^{15}$, together with the nitrogen atom to which they bind, form a piperidinyl group or a piperazinyl group, wherein a substituent on the piperidinyl group or the piperazinyl group represents a phenyl-substituted lower alkyl group, which may have a pyridyl group on the lower alkyl group, having 1 to 2 phenyl groups that may be substituted by 1 to 3 groups, as substituent on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group;

wherein tumor is at least one tumor chosen from liver cancer, non-small-cell lung cancer, large bowel cancer, pancreatic cancer, stomach cancer, breast cancer, prostatic cancer, acute myelogenous leukemia, chronic myelogenous leukemia, multiple myeloma, and non-Hodgkin's lymphoma.

2. A method according to claim 1, for treating a tumor comprising administering, to a patient in need thereof, an effective amount of an aromatic compound selected from the group consisting of:

N-[6-(4-{[2-(4-piperonylpiperazin-1-yl)-2-oxoethyl]ethylamino}-2-methoxyphenoxy)pyridin-3-yl]-3,4-dichlorobenzamide, N-{2-[4-(1,3-benzodioxol-5-ylmethyl)piperazin-1-yl]-2-oxoethyl{-N-{4-[(5-{methyl[4-(trifluoromethyl)benzyl]amino}pyridin-2-yl)oxy]phenyl}acetamide, N-(6-{4-[3-(4-piperonylpiperazin-1-yl)-3-oxopropyl]phenoxy}pyridin-3-yl)-4-trifluoromethylbenzamide, N-[4-(4-{[2-(4-piperonylpiperazin-1-yl)-2-oxoethyl]methylamino}phenoxy)phenyl]-4-trifluoromethylbenzamide, N-[6-(4-{[2-(4-piperonylpiperazin-1-yl)-2-oxoethyl]ethylamino}-2-methoxyphenoxy)pyridin-3-yl]-4-trifluoromethylbenzamide, N-[6-(4-{[2-(4-piperonylpiperazin-1-yl)-2-oxoethyl]methylamino}-2-methylphenoxy)pyridin-3-yl]-4-trifluoromethylbenzamide, and N-[6-(4-{[4-(4-pivaloylbenzyl)piperazin-1-yl]oxomethyl}phenoxy)pyridin-3-yl]-3,4-dichlorobenzamide, or a salt thereof.

3. A method for treating a tumor comprising administering, to a patient in need thereof, an effective amount of an aromatic compound selected from the group consisting of:

3,4-dichloro-N-(6-{4-[3-(morpholin-4-ylcarbonyl)piperidin-1-yl]phenoxy}pyridin-3-yl)benzamide, N-(6-{[4-(4-{2-[4-(1,3-benzodioxol-5-ylmethyl)piperazin-1-yl]-2-oxoethyl}piperazin-1-yl)phenyl](methyl)amino}pyridin-3-yl)-4-(trifluoromethyl)benzamide, N-{6-[(4-{3-[4-(1,3-benzodioxol-5-ylmethyl)piperazin-1-yl]-3-oxopropyl}phenyl)(methyl)amino]pyridin-3-yl}-4-(trifluoromethyl)benzamide, 2-[4-(1,3-benzodioxol-5-ylmethyl)piperazin-1-yl]-N-{3-methyl-4-[(5-{[4-(trifluoromethyl)phenoxy]methyl}pyridin-2-yl)oxy]phenyl}-2-oxoacetamide, 6-{4-[{2-[4-(1,3-benzodioxol-5-ylmethyl)piperazin-1-yl]-2-oxoethyl}(methyl)amino]-3-(trifluoromethyl)phenoxy}-N-[4-(trifluoromethyl)phenyl]pyridine-3-carboxamide, N-(6-{4-[3-(4-piperonylpiperazin-1-yl)-3-oxopropyl]phenoxy}pyridin-3-yl)-4-trifluoromethylbenzamide, N-(4-{4-[{2-[4-(1,3-benzodioxol-5-ylmethyl)piperazin-1-yl]-2-oxoethyl}(methyl)amino]phenoxy}phenyl)-4-(trifluoromethyl)benzamide, N-{6-[4-(4-{2-[4-(1,3-benzodioxol-5-ylmethyl)piperazin-1-yl]-2-oxoethyl}piperidin-1-yl)-2-methylphenoxy]pyridin-3-yl}-4-(trifluoromethyl)benzamide, N-[6-(4-{[2-(4-piperonylpiperazin-1-yl)-2-oxoethyl]methylamino}-2-methylphenoxy)pyridin-3-yl]-4-trifluoromethylbenzamide, 2-[4-(1,3-benzodioxol-5-ylmethyl)piperazin-1-yl]-N-{3-methyl-4-[(5-{methyl[4-(trifluoromethyl)benzyl]amino}pyridin-2-yl)oxy]phenyl}-2-oxoacetamide, or a salt thereof;

wherein tumor is at least one tumor chosen from liver cancer, non-small-cell lung cancer, large bowel cancer, pancreatic cancer, stomach cancer, breast cancer, prostatic cancer, acute myleogenous leukemia, chronic myelogenous leukemia, multiple myeloma, and non-Hodgkin's lymphoma.

4. The method according to any one of claims 1-3, wherein the tumor is at least one solid tumor chosen from liver cancer, non-small-cell lung cancer, large bowel cancer, pancreatic cancer, stomach cancer, breast cancer, and prostatic cancer.

5. The method according to any one of claims 1-3, wherein the tumor is at least one hematological cancer chosen from acute myelogenous leukemia, chronic myelogenous leukemia, and multiple myeloma.

6. The method according to any one of claims 1-3, wherein the tumor is non-Hodgkin's lymphoma.

* * * * *